(12) United States Patent
Amans et al.

(10) Patent No.: US 10,583,139 B2
(45) Date of Patent: *Mar. 10, 2020

(54) 2,3-DISUBSTITUTED 1-ACYL-4-AMINO-1,2,3,4-TETRAHYDROQUINOLINE DERIVATIVES AND THEIR USE AS BROMODOMAIN INHIBITORS

(71) Applicant: GlaxoSmithKline Intellectual Property (No.2) Limited, Brentford, Middlesex (GB)

(72) Inventors: Dominique Amans, Middlesex (GB); Stephen John Atkinson, Stevenage (GB); Lee Andrew Harrison, Stevenage (GB); David Jonathan Hirst, Stevenage (GB); Robert Peter Law, Stevenage (GB); Matthew Lindon, Stevenage (GB); Alexander Preston, Stevenage (GB); Jonathan Thomas Seal, Stevenage (GB); Christopher Roland Wellaway, Stevenage (GB)

(*) Notice: Subject to any disclaimer, the term of this patent is extended or adjusted under 35 U.S.C. 154(b) by 0 days.

This patent is subject to a terminal disclaimer.

(21) Appl. No.: 16/016,955

(22) Filed: Jun. 25, 2018

(65) Prior Publication Data

US 2018/0303831 A1    Oct. 25, 2018

Related U.S. Application Data

(62) Division of application No. 15/466,925, filed on Mar. 23, 2017, now Pat. No. 10,034,881, which is a
(Continued)

(51) Int. Cl.
| | |
|---|---|
| A61K 31/506 | (2006.01) |
| A61K 31/497 | (2006.01) |
| C07D 401/14 | (2006.01) |
| A61K 31/4709 | (2006.01) |
| A61K 31/496 | (2006.01) |
| C07D 498/08 | (2006.01) |
| A61K 31/5377 | (2006.01) |
| A61K 31/5386 | (2006.01) |
| A61K 31/4375 | (2006.01) |
| A61K 31/4706 | (2006.01) |
| C07D 498/04 | (2006.01) |
| C07D 487/08 | (2006.01) |
| C07D 471/08 | (2006.01) |
| C07D 471/04 | (2006.01) |
| C07D 471/14 | (2006.01) |
| C07D 471/12 | (2006.01) |
| C07D 413/12 | (2006.01) |
| C07D 405/14 | (2006.01) |
| C07D 413/14 | (2006.01) |
| C07D 215/227 | (2006.01) |
| C07D 215/46 | (2006.01) |
| C07D 215/48 | (2006.01) |
| C07D 401/04 | (2006.01) |
| C07D 401/12 | (2006.01) |

(Continued)

(52) U.S. Cl.
CPC ........ *A61K 31/506* (2013.01); *A61K 31/4375* (2013.01); *A61K 31/4706* (2013.01); *A61K 31/4709* (2013.01); *A61K 31/496* (2013.01); *A61K 31/497* (2013.01); *A61K 31/5377* (2013.01); *A61K 31/5386* (2013.01); *C07D 215/227* (2013.01); *C07D 215/44* (2013.01); *C07D 215/46* (2013.01); *C07D 215/48* (2013.01); *C07D 401/04* (2013.01); *C07D 401/12* (2013.01); *C07D 401/14* (2013.01); *C07D 405/04* (2013.01); *C07D 405/14* (2013.01); *C07D 409/12* (2013.01); *C07D 409/14* (2013.01); *C07D 413/04* (2013.01); *C07D 413/12* (2013.01); *C07D 413/14* (2013.01); *C07D 417/12* (2013.01); *C07D 417/14* (2013.01); *C07D 471/04* (2013.01); *C07D 471/08* (2013.01); *C07D 487/08* (2013.01); *C07D 498/04* (2013.01); *C07D 498/08* (2013.01)

(58) Field of Classification Search
CPC .............. A61K 31/506; A61K 31/4375; A61K 31/4706; A61K 31/4709; A61K 31/496; A61K 31/497; A61K 31/5377; A61K 31/5386
USPC ........................................................ 514/496
See application file for complete search history.

(56) References Cited

U.S. PATENT DOCUMENTS 7,030,246 B2    4/2006  Bladh et al.
8,580,957 B2 *  11/2013 Demont ............... C07D 215/44
                                                                544/128
(Continued)

FOREIGN PATENT DOCUMENTS

EP    2412710 A1    2/2012
EP    2415764 A1 *  2/2012  ............. A61K 31/47
(Continued)

OTHER PUBLICATIONS

Funabashi et al. Bulletin of the Chemical Society of Japan, (1969), 42(10), p. 2885-2894.*
(Continued)

*Primary Examiner* — Yong L Chu
(74) *Attorney, Agent, or Firm* — McCarter & English, LLP; Steven G. Davis; Yun Wang

(57) ABSTRACT

The present invention relates to novel compounds, pharmaceutical compositions containing such compounds and to their use in therapy.

16 Claims, No Drawings

Related U.S. Application Data division of application No. 14/770,499, filed as application No. PCT/EP2014/054795 on Mar. 12, 2014, now Pat. No. 9,637,456.

(60) Provisional application No. 61/882,798, filed on Sep. 26, 2013, provisional application No. 61/781,583, filed on Mar. 14, 2013.

(51) Int. Cl.
| | |
|---|---|
| *C07D 405/04* | (2006.01) |
| *C07D 409/12* | (2006.01) |
| *C07D 409/14* | (2006.01) |
| *C07D 413/04* | (2006.01) |
| *C07D 417/12* | (2006.01) |
| *C07D 417/14* | (2006.01) |
| *C07D 215/44* | (2006.01) |

(56) References Cited

U.S. PATENT DOCUMENTS

| | | | | |
|---|---|---|---|---|
| 9,637,456 B2 * | 5/2017 | Amans | ................ | C07D 401/14 |
| 10,034,881 B2 * | 7/2018 | Amans | ................ | C07D 401/14 |

FOREIGN PATENT DOCUMENTS

| | | | |
|---|---|---|---|
| WO | 2003/105849 A1 | 12/2003 | |
| WO | 2004/052863 A1 | 6/2004 | |
| WO | 2004/072042 A2 | 8/2004 | |
| WO | 2005/007094 A2 | 1/2005 | |
| WO | 2011/054841 A1 | 5/2011 | |
| WO | 2011/054843 A1 | 5/2011 | |
| WO | WO-2011054848 A1 * | 5/2011 | ........... C07D 215/44 |
| WO | 2012/143413 A1 | 10/2012 | |
| WO | 2012/143415 A1 | 10/2012 | |
| WO | 2012/150234 A1 | 11/2012 | |
| WO | 2013/027168 A1 | 5/2013 | |

OTHER PUBLICATIONS

Horig et al., From bench to clinic and back: Perspective on the 1st IQPC Translational Research conference. J Transl Med. Dec. 20, 2004;2(1):44. 8 pages.

Jahagirdar et al., Oral Administration of a Novel Small Molecule BET Bromodomain Inhibitor, RVX-297, Reduces Disease Severity in a Rat Collagen-Induced Arthritis Model. 2012 ACR/ARHP Annual Meeting, Abstract 341, 3 pages (2012).

Nadeem et al., Imiquimod-induced psoriasis-like skin inflammation is suppressed by BET bromodomain inhibitor in mice through RORC/IL-17A pathway modulation. Pharmacol Res. Sep. 2015;99:248-57.

Schafer et al., Failure is an option: learning from unsuccessful proof-of-concept trials. Drug Discov Today. Nov. 2008;13(21-22):913-6.

* cited by examiner

2,3-DISUBSTITUTED 1-ACYL-4-AMINO-1,2,3,4-TETRAHYDROQUINOLINE DERIVATIVES AND THEIR USE AS BROMODOMAIN INHIBITORS

FIELD OF THE INVENTION

The present invention relates to novel compounds, pharmaceutical compositions containing such compounds and to their use in therapy.

BACKGROUND OF THE INVENTION

The genomes of eukaryotic organisms are highly organised within the nucleus of the cell. The long strands of duplex DNA are wrapped around an octomer of histone proteins (most usually comprising two copies of histones H2A, H2B, H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins recognise and bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRDT) which contain tandem bromodomains capable of binding to two acetylated lysine residues in close proximity, increasing the specificity of the interaction. Numbering from the N-terminal end of each BET protein the tandem bromodomains are typically labelled Binding Domain 1 (BD1) and Binding Domain 2 (BD2) (Chung et al, *J Med. Chem.* 2011, 54, 3827-3838).

A novel class of compounds have been found which inhibit the binding of bromodomains with its cognate acetylated proteins, more particularly a class of compounds that inhibit the binding of BET family bromodomains to acylated lysine residues, even more particularly a class of compounds that selectively inhibit the binding and function of BET family bromodomains via Binding Domain 2 (BD2). Such compounds will hereafter be referred to as "bromodomain inhibitors".

Funabashi et al describe 1,2,3,4,-tetrahydroquinolines and conduct a configuration and conformation analysis (Funabashi et al, *Bulletin of the Chemical Society of Japan,* 1969, 42, 2885-2894).

SUMMARY OF THE INVENTION

In a first aspect of the present invention, there is provided a compound of formula (I)

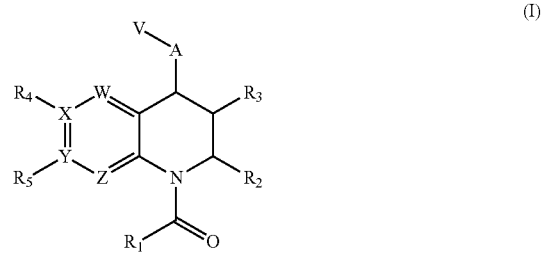

(I)

or a salt thereof, more particularly a compound of formula (I) or a pharmaceutically acceptable salt thereof.

In a second aspect of the present invention, there is provided a pharmaceutical composition comprising a compound of formula (I) or a pharmaceutically acceptable salt thereof and one or more pharmaceutically acceptable carriers, diluents or excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

DETAILED DESCRIPTION OF THE INVENTION

The present invention relates to a compound of formula (I)

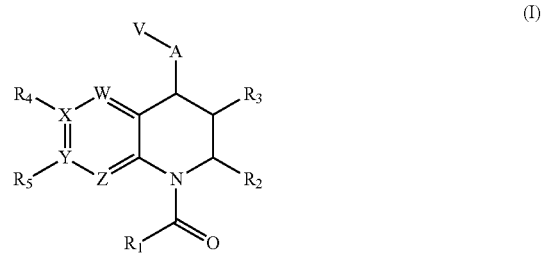

(I)

or a salt thereof
wherein
$R_1$ is $C_{1-4}$alkyl;

$R_2$ is $C_{1-4}$alkyl, $C_{3-7}$cycloalkyl, —$CH_2CF_3$, —$CH_2OCH_3$ or heterocyclyl;

$R_3$ is $C_{1-4}$alkyl, —$CH_2F$, —$CH_2OH$ or —$CH_2OC(O)CH_3$;

$R_4$ when present is H, hydroxy, halo, cyano, —$CO_2H$, —$CONH_2$, —$OSO_2CF_3$, —$C(O)N(R_8)C_{1-4}$alkyleneOH, —$C(O)N(R_8)C_{1-4}$alkyleneOCH$_3$, —$C(O)N(R_8)C_{1-4}$alkyleneNR$_6$R$_7$, —$C(O)N(R_8)C_{1-4}$alkyleneSO$_2$CH$_3$, —$C(O)N(R_8)C_{1-4}$alkyleneCN, —$C(O)NHOH$, —$C(O)NHCH(CH_2OH)_2$, —$OCH_2CH_2OH$, —B—$C_{1-6}$alkyl, —B—$C_{3-7}$cycloalkyl, —B-phenyl, —B-heterocyclyl or —B-heteroaromatic, wherein the $C_{3-7}$cycloalkyl, phenyl, heterocyclyl or heteroaromatic ring is optionally substituted by 1 or 2 substituents independently selected from =O, $C_{1-6}$alkyl, $C_{1-6}$alkoxy, halo, —$NH_2$, —$CO_2H$, —$C(O)C_{1-6}$alkyl, —$C(O)NHC_{1-6}$alkyl, cyano, —$CH_2CH_2NHCH_3$, —$CH_2CH_2OH$, —$CH_2CH_2OCH_3$, $C_{3-7}$cycloalkyl, phenyl, heterocyclyl and heteroaromatic;

$R_5$ when present is H, halo, hydroxy or $C_{1-6}$alkoxy;

A is —NH—, —O—, —S—, —SO—, —$SO_2$—, —N($C_{1-4}$alkyl)- or —NC(O)(CH$_3$)—;

B is a bond, —O—, —N($R_8$)—, S, —SO—, —$SO_2$—, —$SO_2N(R_8)$—, —$CH_2$—, —C(O)—, —$CO_2$—, —N($R_8$)C(O)—, —C(O)N($R_8$)—, —C(O)N($R_8$)CH$_2$— or —C(O)N($R_8$)CH$_2$CH$_2$—;

V is phenyl, heteroaromatic or pyridone any of which may be optionally substituted by 1, 2 or 3 substituents independently selected from $C_{1-6}$alkyl, fluorine, chlorine, $C_{1-6}$alkoxy, hydroxy, cyclopropyl, cyano, —$CO_2CH_3$, heterocyclyl, —$CO_2H$, —$CH_2NR_6R_7$, —$NR_6R_7$, —$C(O)NR_6R_7$, —$NR_6C(O)R_7$, —$CF_3$, —$NO_2$, —$CH_2OCH_3$, —$CH_2OH$—, CH(OH)CH$_3$, —$SO_2CH_3$, —$CH_2$heterocyclyl, —$OCH_2CH_2NHC(O)CH_3$, —$OCH_2CH_2OH$, —$OCH_2CH_2NH_2$, —$C(O)NH$heteroaromatic, —$C(O)NHCH_2$heterocyclyl, —$C(O)NHCH_2CH_2OH$, —$C(O)NHCH_2CH_2NH_2$, —$C(O)NHCH_2CH_2SO_2Me$, —$C(O)NHCH_2CH(OH)CH_3$, —$C(O)$heterocyclyl and —$C(O)NH$heterocyclyl, wherein the heterocyclyl ring is optionally substituted by —OH;

$R_6$, $R_7$, $R_8$, $R_9$ and $R_{10}$ are each independently selected from H and $C_{1-4}$alkyl;

W is CH or N;
X is C or N;
Y is C or N; and
Z is CH or N;

subject to the proviso that no more than 2 of W, X, Y and Z are N; and that the compound of formula (I) is not 1-(2-ethyl-3-methyl-4-(phenylamino)-3,4-dihydroquinolin-1(2H)-yl)ethanone or 1-(2-ethyl-3-methyl-4-(phenylamino)-3,4-dihydroquinolin-1(2H)-yl)propan-1-one.

In one embodiment the compound of formula (I) or a salt thereof is a racemic mixture of formula (Ia)

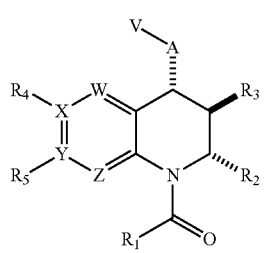

(Ia)

or a salt thereof.

In another embodiment the compound of formula (I) or a salt thereof is an enantiomer of formula (Iaa)

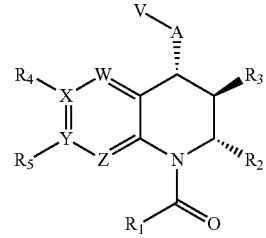

(Iaa)

or a salt thereof.

In one embodiment there is provided a compound of formula (I) or a salt thereof
wherein:
$R_1$ is $C_{1-4}$alkyl;
$R_2$ is $C_{1-4}$alkyl, $C_{3-7}$cycloalkyl, —$CH_2CF_3$ or —$CH_2OCH_3$;
$R_3$ is $C_{1-4}$alkyl;
$R_4$ when present is H, hydroxy, halo, cyano, —$CO_2H$, —$CONH_2$, —$OSO_2CF_3$, —$C(O)N(R_8)CH_2CH(R_9)OH$, —$C(O)N(R_8)CH_2CH_2OCH_3$, —$C(O)N(R_8)CH_2CH_2NHCH_3$, —$C(O)N(R_8)CH_2CH_2SO_2CH_3$, C(O)N($R_8$)CH$_2$CH$_2$CN, —B—$C_{1-6}$alkyl, —B—$C_{3-7}$cycloalkyl, —B-phenyl, —B-heterocyclyl or —B-heteroaromatic, wherein the $C_{3-7}$cycloalkyl, phenyl, heterocyclyl or heteroaromatic ring is optionally substituted by 1 or 2 substituents independently selected from =O, $C_{1-6}$alkyl, $C_{1-6}$alkoxy, halo, —$NH_2$, —$CO_2H$, —$C(O)NHC_{1-6}$alkyl, cyano, —$CH_2CH_2NHCH_3$, —$CH_2CH_2OCH_3$, $C_{3-7}$cycloalkyl, phenyl, heterocyclyl and heteroaromatic;

$R_5$ when present is H, halo, hydroxy or $C_{1-6}$alkoxy;

A is —NH—, —O—, —S—, —SO—, —$SO_2$— or —N($C_{1-4}$alkyl)-;

B is a bond, —O—, —N($R_8$)—, S, —SO—, —$SO_2$—, —$SO_2N(R_8)$—, —$CH_2$—, —C(O)—, —N($R_8$)C(O)—, —C(O)N($R_8$)—, —C(O)N($R_8$)CH$_2$— or —C(O)N($R_8$)CH$_2$CH$_2$—;

V is phenyl or heteroaromatic either of which may be optionally substituted by 1, 2 or 3 substituents independently selected from $C_{1-6}$alkyl, fluorine, chlorine, $C_{1-6}$alkoxy, hydroxy, cyclopropyl, cyano, —$CO_2CH_3$, heterocyclyl, —$CO_2H$, —$CH_2NR_6R_7$, —$NR_6R_7$, —$C(O)NR_6R_7$ and —$NR_6C(O)R_7$;

$R_6$, $R_7$, $R_8$ and $R_9$ are each independently selected from H and $C_{1-4}$alkyl;
W is CH or N;
X is C or N;
Y is C or N; and
Z is CH or N;

subject to the proviso that no more than 2 of W, X, Y and Z are N; and that the compound of formula (I) is not 1-(2-ethyl-3-methyl-4-(phenylamino)-3,4-dihydroquinolin-1(2H)-yl)ethanone or 1-(2-ethyl-3-methyl-4-(phenylamino)-3,4-dihydroquinolin-1(2H)-yl)propan-1-one.

In a further embodiment there is provided a compound of formula (I)
or a salt thereof
wherein:
$R_1$ is $C_{1-4}$alkyl;
$R_2$ is $C_{1-4}$alkyl, $C_{3-7}$cycloakyl, —$CH_2CF_3$ or —$CH_2OCH_3$;
$R_3$ is $C_{1-4}$alkyl;

R$_4$ when present is H, hydroxy, —B—C$_{1-6}$alkyl, —B—C$_{3-7}$cycloalkyl, —B-phenyl, —B-heterocyclyl or —B-heteroaromatic, wherein the C$_{3-7}$cycloalkyl, phenyl, heterocyclyl or heteroaromatic ring is optionally substituted by 1 or 2 substituents independently selected from =O, C$_{1-6}$alkyl, C$_{1-6}$alkoxy, halo, —NH$_2$, —CO$_2$H, —C(O)NHC$_{1-6}$alkyl, cyano, —CH$_2$CH$_2$NHCH$_3$, —CH$_2$CH$_2$OCH$_3$, C$_{3-7}$cycloalkyl, phenyl, heterocyclyl and heteroaromatic;

R$_5$ when present is H, halo, hydroxy or C$_{1-6}$alkoxy;

A is —NH—, —O—, —S—, —SO—, —SO$_2$— or —N(C$_{1-4}$ alkyl)-;

B is a bond, —O—, —N(R$_8$)—, —SO$_2$—, —SO$_2$NH— or —CH$_2$—;

V is phenyl or heteroaromatic either of which may be optionally substituted by 1, 2 or 3 substituents independently selected from C$_{1-6}$alkyl, fluorine, chlorine, C$_{1-6}$alkoxy, hydroxy, cyclopropyl, cyano, —CO$_2$CH$_3$, heterocyclyl, —NR$_6$R$_7$, —C(O)NR$_6$R$_7$ and —NR$_6$C(O)R$_7$;

R$_6$, R$_7$ and R$_8$ are each independently selected from H and C$_{1-4}$alkyl;

W is CH or N;
X is C or N;
Y is C or N; and
Z is CH or N;

subject to the proviso that no more than 2 of W, X, Y and Z are N; and that the compound of formula (I) is not 1-(2-ethyl-3-methyl-4-(phenylamino)-3,4-dihydroquinolin-1 (2H)-yl)ethanone or 1-(2-ethyl-3-methyl-4-(phenylamino)-3,4-dihydroquinolin-1(2H)-yl)propan-1-one.

In one embodiment R$_1$ is methyl or ethyl. In another embodiment R$_1$ is methyl.

In one embodiment R$_2$ is C$_{1-4}$alkyl, C$_{3-7}$cycloakyl, —CH$_2$CF$_3$ or —CH$_2$OCH$_3$. In another embodiment R$_2$ is methyl, ethyl or cyclopropyl. In another embodiment R$_2$ is methyl or cyclopropyl. In a further embodiment R$_2$ is cyclopropyl.

In one embodiment R$_3$ is C$_{1-4}$alkyl. In another embodiment R$_3$ is methyl.

In one embodiment R$_4$ is H, hydroxy, fluoro, cyano, —CO$_2$H, —CONH$_2$, —OSO$_2$CF$_3$, —C(O)NHCH$_2$CH$_2$OH, C(O)NHCH$_2$C(CH$_3$)OH, —C(O)NHCH$_2$CH$_2$OCH$_3$, —C(O)NHCH$_2$CH$_2$NHCH$_3$, —C(O)NHCH$_2$CH$_2$SO$_2$CH$_3$, —C(O)NHCH$_2$CH$_2$CN, —B—CH$_3$, —B—CH(CH$_3$)$_2$, —B—CH$_2$CH$_3$, —B-phenyl, —B— heterocyclyl or —B-heteroaromatic, wherein the phenyl, heterocyclyl or heteroaromatic ring is optionally substituted by 1 or 2 substituents independently selected from =O, —CH$_3$, —CH$_2$CH$_3$, —OCH$_3$, —NH$_2$, —C(O)NHCH$_3$, —CH$_2$CH$_2$NHCH$_3$, —CH$_2$CH$_2$OCH$_3$ and —CO$_2$H.

In another embodiment R$_4$ is H, hydroxy, fluoro, cyano, —CO$_2$H, —CONH$_2$, —OSO$_2$CF$_3$, —C(O)NHCH$_2$CH$_2$OH, C(O)NHCH$_2$C(CH$_3$)OH, —C(O)NHCH$_2$CH$_2$OCH$_3$, —C(O)NHCH$_2$CH$_2$NHCH$_3$, —C(O)NHCH$_2$CH$_2$SO$_2$CH$_3$, —C(O)NHCH$_2$CH$_2$CN, —B—CH$_3$, —B—CH(CH$_3$)$_2$, —B—CH$_2$CH$_3$, —B-phenyl, —B-piperidinyl, —B-morpholinyl, —B-piperazinyl, —B-2,5-diazabicyclo[2.2.2]octan-2-yl, —B-8-oxa-3-azabicyclo[3.2.1]octan-3-yl, —B-3,8-diazabicyclo[3.2.1]octan-3-yl, —B-pyrrolidinyl, —B-3,6-dihydro-2H-pyran, —B-1,2,3,6-tetrahydropyridinyl, —B-tetrahydrofuranyl, —B-tetrahydro-2H-thiopyran1,1,dioxide, —B— pyrazolyl or —B-pyridinyl wherein the phenyl, heterocyclyl or heteroaromatic ring is optionally substituted by 1 or 2 substituents independently selected from =O, —CH$_3$, —CH$_2$CH$_3$, —OCH$_3$, —NH$_2$, —C(O)NHCH$_3$, —CH$_2$CH$_2$NHCH$_3$, —CH$_2$CH$_2$OCH$_3$ and —CO$_2$H.

In another embodiment R$_4$ is H, —C(O)NHCH$_3$, —C(O)NHCH$_2$CH$_3$, —C(O)NHCH$_2$CH$_2$OCH$_3$, -morpholinyl, -piperazinyl, -3,6-dihydro-2H-pyran, -1,2,3,6-tetrahydropyridinyl, -pyrazolyl, —C(O)NH-tetrahydro-2H-pyran, —C(O)NH-pyridinyl or —C(O)NH-pyrazolyl wherein the heterocyclyl or heteroaromatic ring is optionally substituted by —CH$_2$CH$_2$OCH$_3$.

In another embodiment R$_4$ is H, —C(O)NHCH$_3$, —C(O)NHCH$_2$CH$_3$, —C(O)NHCH$_2$CH$_2$OCH$_3$,

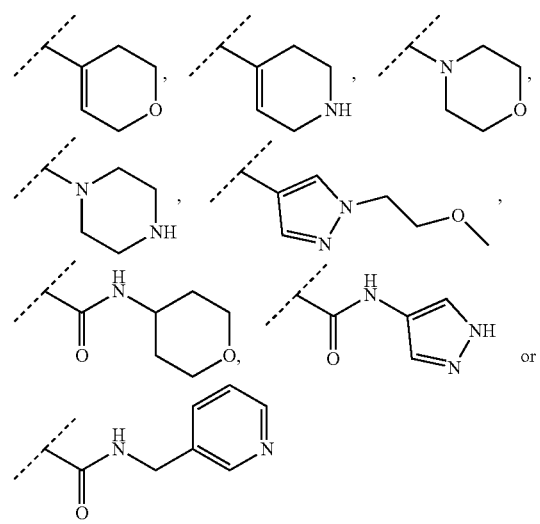

In another embodiment R$_4$ is selected from:

(i) —C(O)NHC$_{1-6}$alkyl (such as —C(O)NHCH$_3$, —C(O)NHCH$_2$CH$_3$, or C(O)NHCH(CH$_3$) 2);

(ii) —C(O)N(R$_8$)C$_{1-4}$alkyleneOH (such as —C(O)NHCH$_2$CH$_2$OH, —C(O)NHCH(CH$_3$)CH$_2$OH, C(O)NHCH$_2$C(CH$_3$)$_2$OH or C(O)NHCH$_2$CH(CH$_3$)OH);

(iii) —C(O)N(R$_8$)C$_{1-4}$alkyleneOCH$_3$ (such as —C(O)NHCH$_2$CH$_2$OCH$_3$, C(O)NHCH$_2$CH$_2$CH$_2$OCH$_3$ or C(O)NHCH$_2$CH(CH$_3$)OCH$_3$);

(iv) —C(O)NHCH(CH$_2$OH)$_2$, (v) —C(O)N(R$_8$)C$_{1-4}$alkyleneNR$_6$R$_7$ (such as C(O)NHCH$_2$CH$_2$NHCH$_3$ or C(O)NHCH$_2$CH$_2$N(CH$_3$)$_2$);

(vi) —C(O)N(R$_8$)C$_{1-4}$alkyleneSO$_2$CH$_3$, (such as C(O)NHCH$_2$CH$_2$SO$_2$CH$_3$);

(vii) —C(O)N(R$_8$)C$_{1-4}$alkyleneCN (such as —C(O)NHCH$_2$CH$_2$CN); and (viii) —B-heterocyclyl or —B-heteroaromatic in which B is —C(O)NH, —C(O)NHCH$_2$— or —C(O)NHCH$_2$CH$_2$— (such as a group selected from

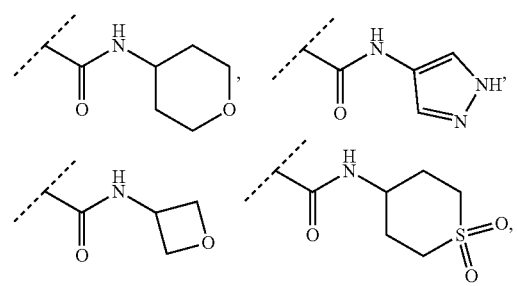

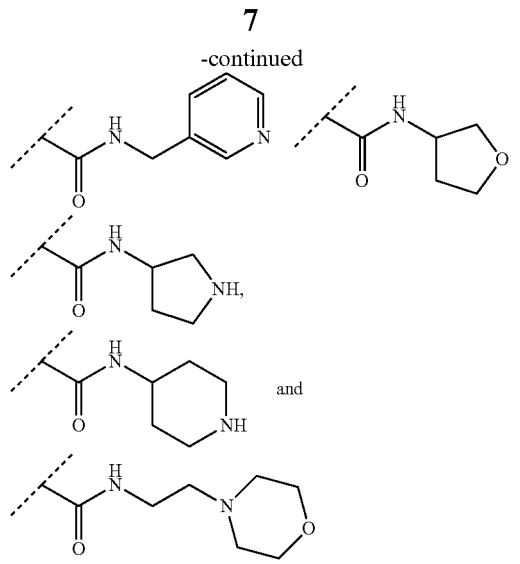

In a further embodiment $R_4$ is —C(O)NH$_2$.
In a further embodiment $R_4$ is —CO$_2$H.
In a further embodiment $R_4$ is cyano.
In a further embodiment $R_4$ is fluoro.

In one embodiment B is a bond, —O—, —NH— —C(O)NH— or —SO$_2$—. In another embodiment B is a bond. In another embodiment B is —O—. In another embodiment B is —NH—. In another embodiment B is —SO$_2$—. In a further embodiment B is —C(O)NH—.

In one embodiment $R_5$ is H, fluoro, hydroxy or —OCH$_3$. In another embodiment $R_5$ is H, fluoro or —OCH$_3$ In a further embodiment $R_5$ is H.

In one embodiment A is NH, O or N(CH$_3$). In another embodiment A is NH. In another embodiment A is O. In a further embodiment A is N(CH$_3$).

In one embodiment V is phenyl or heteroaromatic, either of which may be optionally substituted by 1 or 2 substituents independently selected from C$_{1-6}$alkyl, fluorine, chlorine, —OCH$_3$, —OCH(CH$_3$)$_2$, hydroxy, cyclopropyl, cyano, —CO$_2$H, —CH$_2$NH$_2$, —C(O)NHCH$_3$, —C(O)N(CH$_3$)$_2$, —CO$_2$CH$_3$, piperazinyl and morpholinyl.

In another embodiment V is phenyl, pyridinyl, pyrimidinyl, imidazopyridinyl, quinolinyl, thienyl, thiazolyl, oxazolyl and pyrazinyl, any of which may be optionally substituted by 1 or 2 substituents independently selected from C$_{1-6}$alkyl, fluorine, chlorine, —OCH$_3$, —OCH(CH$_3$)$_2$, hydroxy, cyclopropyl, cyano, —CH$_2$NH$_2$, —C(O)NHCH$_3$, —CO$_2$CH$_3$, piperazinyl and morpholinyl.

In another embodiment V is phenyl or pyridinyl either of which may be optionally substituted by 1 substituent selected from methyl, —OCH$_3$, fluorine, —CH$_2$NH$_2$ and cyano.

In another embodiment embodiment V is

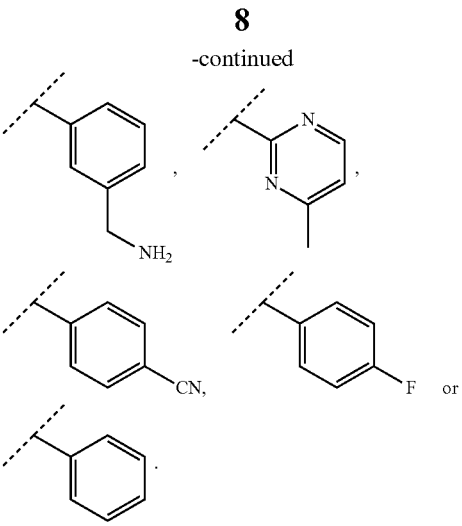

In another embodiment embodiment V is

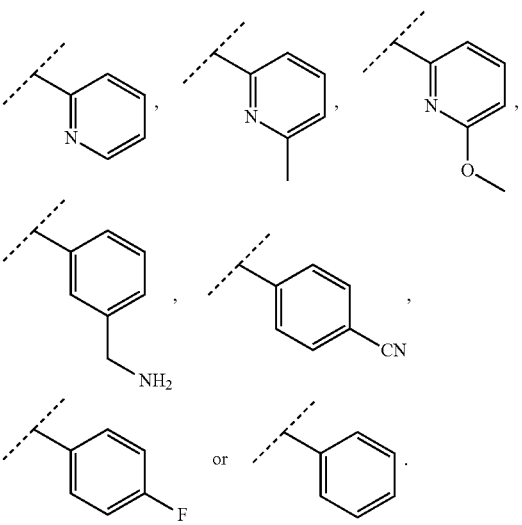

In another embodiment V is

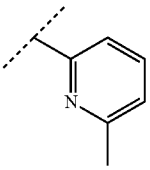

In a further embodiment V is

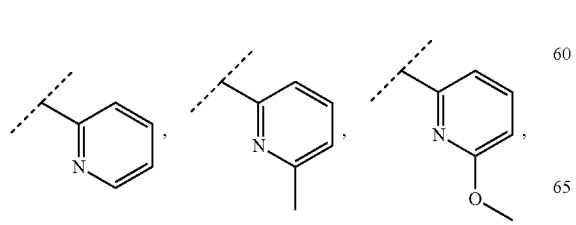

In a further embodiment V is

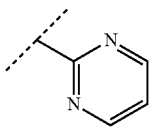

In one embodiment W is CH. In another embodiment W is N.
In one embodiment X is C. In another embodiment X is N
In one embodiment Y is C. In another embodiment Y is N.
In one embodiment Z is CH. In another embodiment Y is N.

It is to be understood that the present invention covers all combinations of substituent groups described hereinabove.

Compounds of the invention include the compounds of Examples 1 to 599 and salts thereof.

Compounds of the invention include the compounds of Examples 1 to 292 and salts thereof.

In another embodiment compounds of the invention include the compounds of Examples 1 to 290 and salts thereof. In another embodiment compounds of the invention include the compounds of Examples 293 to 599 and salts thereof.

In one embodiment, the compound of formula (I) is
rac-1-((2S,3R,4R)-2,3-dimethyl-4-(phenylamino)-3,4-dihydroquinolin-1(2H)-yl)ethanone;
rac-1-((2S,3R,4R)-2,3-dimethyl-4-((6-methylpyridin-2-yl)amino)-3,4-dihydroquinolin-1(2H)-yl)ethanone;
rac-1-((2S,3R,4R)-4-((6-methoxypyridin-2-yl)amino)-2,3-dimethyl-3,4-dihydroquinolin-1(2H)-yl)ethanone;
rac-1-((2S,3R,4R)-4-(imidazo[1,2-a]pyridin-8-ylamino)-2,3-dimethyl-3,4-dihydroquinolin-1(2H)-yl)ethanone;
rac-1-((2S,3R,4R)-4-((3-methoxyphenyl)amino)-2,3-dimethyl-3,4-dihydroquinolin-1(2H)-yl)ethanone;
rac-1-((2S,3R,4R)-2,3-dimethyl-4-((3-morpholinophenyl)amino)-3,4-dihydroquinolin-1(2H)-yl)ethanone;
rac-1-((2S,3R,4R)-2,3-dimethyl-4-(quinolin-5-ylamino)-3,4-dihydroquinolin-1(2H)-yl)ethanone;
rac-1-((2S,3R,4R)-2,3-dimethyl-4-((3-(piperazin-1-yl)phenyl)amino)-3,4-dihydroquinolin-1(2H)-yl)ethanone;
rac-1-((2S,3R,4R)-4-((4-chloro-2-methoxyphenyl)amino)-2,3-dimethyl-3,4-dihydroquinolin-1(2H)-yl)ethanone;
rac-1-((2S,3R,4R)-1-acetyl-2,3-dimethyl-1,2,3,4-tetrahydroquinolin-4-yl)amino)pyridin-2(1H)-one;
rac-1-((2S,3R,4R)-2,3-dimethyl-4-(pyridin-2-ylamino)-3,4-dihydroquinolin-1(2H)-yl)ethanone;
rac-1-((2S,3R,4R)-2,3-dimethyl-4-(thiophen-3-ylamino)-3,4-dihydroquinolin-1(2H)-yl)ethanone;
rac-1-((2S,3R,4R)-4-((4-chlorophenyl)amino)-2,3-dimethyl-3,4-dihydroquinolin-1(2H)-yl)ethanone;
rac-1-((2S,3R,4R)-2,3-dimethyl-4-((3-methylpyridin-2-yl)amino)-3,4-dihydroquinolin-1(2H)-yl)ethanone;
rac-1-((2S,3R,4R)-4-((4-methoxyphenyl)amino)-2,3-dimethyl-3,4-dihydroquinolin-1(2H)-yl)ethanone;
rac-1-((2S,3R,4R)-2,3-dimethyl-4-(m-tolylamino)-3,4-dihydroquinolin-1(2H)-yl)ethanone;
rac-1-((2S,3R,4R)-2,3-dimethyl-4-((5-methylpyridin-3-yl)amino)-3,4-dihydroquinolin-1(2H)-yl)ethanone;
rac-1-((2S,3R,4R)-2,3-dimethyl-4-(pyrimidin-2-ylamino)-3,4-dihydroquinolin-1(2H)-yl)ethanone;
rac-1-((2S,3R,4R)-2,3-dimethyl-4-((4-methylpyridin-2-yl)amino)-3,4-dihydroquinolin-1(2H)-yl)ethanone;
rac-1-((2S,3R,4R)-2,3-dimethyl-4-(p-tolylamino)-3,4-dihydroquinolin-1(2H)-yl)ethanone;
rac-1-((2S,3R,4R)-2,3-dimethyl-4-((5-methylpyridin-2-yl)amino)-3,4-dihydroquinolin-1(2H)-yl)ethanone;
rac-1-((2S,3R,4R)-4-((5-chloropyridin-3-yl)amino)-2,3-dimethyl-3,4-dihydroquinolin-1(2H)-yl)ethanone;
rac-1-((2S,3R,4R)-2,3-dimethyl-4-((2-methylpyridin-4-yl)amino)-3,4-dihydroquinolin-1(2H)-yl)ethanone;
rac-1-((2S,3R,4R)-2,3-dimethyl-4-((5-methylpyrazin-2-yl)amino)-3,4-dihydroquinolin-1(2H)-yl)ethanone;
1-((2S,3R,4R)-2-ethyl-3-methyl-4-((6-methylpyridin-2-yl)amino)-3,4-dihydroquinolin-1(2H)-yl)ethanone;
1-((2R,3S,4S)-2-ethyl-3-methyl-4-((6-methylpyridin-2-yl)amino)-3,4-dihydroquinolin-1(2H)-yl)ethanone;
rac-1-((2S,3R,4R)-2-cyclopropyl-3-methyl-4-(phenylamino)-3,4-dihydroquinolin-1(2H)-yl)ethanone;
1-((2S,3R,4R)-2-cyclopropyl-3-methyl-4-(phenylamino)-3,4-dihydroquinolin-1(2H)-yl)ethanone;
1-((2R,3S,4S)-2-cyclopropyl-3-methyl-4-(phenylamino)-3,4-dihydroquinolin-1(2H)-yl)ethanone;
rac-1-((2S,3R,4R)-2-cyclopropyl-3-methyl-4-((6-methylpyridin-2-yl)amino)-3,4-dihydroquinolin-1(2H)-yl)ethanone;
1-((2S,3R,4R)-2-cyclopropyl-3-methyl-4-((6-methylpyridin-2-yl)amino)-3,4-dihydroquinolin-1(2H)-yl)ethanone;
1-((2R,3S,4S)-2-cyclopropyl-3-methyl-4-((6-methylpyridin-2-yl)amino)-3,4-dihydroquinolin-1(2H)-yl)ethanone;
rac-4-(((2S,3R,4R)-1-acetyl-2-cyclopropyl-3-methyl-1,2,3,4-tetrahydroquinolin-4-yl)amino)benzonitrile;
rac-1-((2S,3R,4R)-2-cyclopropyl-3-methyl-4-(o-tolylamino)-3,4-dihydroquinolin-1(2H)-yl)ethanone;
rac-1-((2S,3R,4R)-2-cyclopropyl-4-((4-fluorophenyl)amino)-3-methyl-3,4-dihydroquinolin-1(2H)-yl)ethanone;
rac-3-(((2S,3R,4R)-1-acetyl-2-cyclopropyl-3-methyl-1,2,3,4-tetrahydroquinolin-4-yl)amino)benzonitrile;
rac-1-((2S,3R,4R)-2-cyclopropyl-4-((3-cyclopropylphenyl)amino)-3-methyl-3,4-dihydroquinolin-1(2H)-yl)ethanone;
rac-1-((2S,3R,4R)-2-cyclopropyl-4-((3-fluorophenyl)amino)-3-methyl-3,4-dihydroquinolin-1(2H)-yl)ethanone;
rac-1-((2S,3R,4R)-2-cyclopropyl-4-((6-methoxypyridin-2-yl)amino)-3-methyl-3,4-dihydroquinolin-1(2H)-yl)ethanone;
rac-2-(((2S,3R,4R)-1-acetyl-2-cyclopropyl-3-methyl-1,2,3,4-tetrahydroquinolin-4-yl)amino)benzonitrile;
rac-1-(((2S,3R,4R)-2-cyclopropyl-3-methyl-4-((4-methylpyrimidin-2-yl)amino)-3,4-dihydroquinolin-1(2H)-yl)ethanone;
rac-1-(((2S,3R,4R)-2-cyclopropyl-4-((3-methoxypyridin-2-yl)amino)-3-methyl-3,4-dihydroquinolin-1(2H)-yl)ethanone;
rac-1-(((2S,3R,4R)-2-cyclopropyl-4-((6-fluoropyridin-2-yl)amino)-3-methyl-3,4-dihydroquinolin-1(2H)-yl)ethanone;
rac-1-((2S,3R,4R)-2-cyclopropyl-4-((5-fluoropyridin-2-yl)amino)-3-methyl-3,4-dihydroquinolin-1(2H)-yl)ethanone;
rac-1-((2S,3R,4R)-2-cyclopropyl-4-((6-isopropoxypyridin-2-yl)amino)-3-methyl-3,4-dihydroquinolin-1(2H)-yl)ethanone;
rac-1-((2S,3R,4R)-2-cyclopropyl-4-((4-cyclopropylphenyl)amino)-3-methyl-3,4-dihydroquinolin-1(2H)-yl)ethanone;
rac-4-(((2S,3R,4R)-1-acetyl-2-cyclopropyl-3-methyl-1,2,3,4-tetrahydroquinolin-4-yl)amino)-N-methylbenzamide;

rac-6-(((2S,3R,4R)-1-acetyl-2-cyclopropyl-3-methyl-1,2,3,4-tetrahydroquinolin-4-yl)amino)nicotinonitrile;
rac-methyl 4-(((2S,3R,4R)-1-acetyl-2-cyclopropyl-3-methyl-1,2,3,4-tetrahydroquinolin-4-yl)amino)benzoate;
rac-1-((2S,3R,4R)-2-cyclopropyl-4-((6-hydroxypyridin-2-yl)amino)-3-methyl-3,4-dihydroquinolin-1(2H)-yl)ethanone;
rac-1-((2S,3R,4R)-2-cyclopropyl-3-methyl-4-((6-methylpyrazin-2-yl)amino)-3,4-dihydroquinolin-1(2H)-yl)ethanone;
rac-1-((2S,3R,4R)-2-cyclopropyl-4-((3-hydroxypyridin-2-yl)amino)-3-methyl-3,4-dihydroquinolin-1(2H)-yl)ethanone;
rac-6-(((2S,3R,4R)-1-acetyl-2-cyclopropyl-3-methyl-1,2,3,4-tetrahydroquinolin-4-yl)amino)picolinonitrile;
rac-1-((2S,3R,4R)-2-cyclobutyl-3-methyl-4-(phenylamino)-3,4-dihydroquinolin-1(2H)-yl)ethanone;
rac-1-((2S,3R,4R)-2-isopropyl-3-methyl-4-(phenylamino)-3,4-dihydroquinolin-1(2H)-yl)ethanone;
rac-1-((2S,3R,4R)-3-methyl-4-(phenylamino)-2-(2,2,2-trifluoroethyl)-3,4-dihydroquinolin-1(2H)-yl)ethanone;
rac-1-((2R,3R,4R)-2-(methoxymethyl)-3-methyl-4-(phenylamino)-3,4-dihydroquinolin-1(2H)-yl)ethanone;
rac-1-((2S,3R,4R)-2-cyclopropyl-3-methyl-4-(phenylamino)-3,4-dihydroquinolin-1(2H)-yl)propan-1-one;
rac-1-((2S,3R,4R)-2-cyclopropyl-3-methyl-4-((6-methylpyridin-2-yl)amino)-3,4-dihydroquinolin-1(2H)-yl)propan-1-one;
rac-1-((2S,3S,4R)-2-cyclopropyl-3-methyl-4-(methyl(phenyl)amino)-3,4-dihydroquinolin-1(2H)-yl)ethanone;
rac-1-((2S,3R,4R)-6-methoxy-2,3-dimethyl-4-(phenylamino)-3,4-dihydroquinolin-1(2H)-yl)ethanone;
rac-1-((2S,3R,4R)-6-hydroxy-2,3-dimethyl-4-(phenylamino)-3,4-dihydroquinolin-1(2H)-yl)ethanone;
rac-(2S,3R,4R)-1-acetyl-2,3-dimethyl-4-(phenylamino)-1,2,3,4-tetrahydroquinolin-6-yl trifluoromethanesulfonate;
rac-1-((2S,3R,4R)-2-ethyl-6-fluoro-3-methyl-4-((6-methylpyridin-2-yl)amino)-3,4-dihydroquinolin-1(2H)-yl)ethanone;
rac-4-(((2S,3R,4R)-1-acetyl-2-ethyl-6-fluoro-3-methyl-1,2,3,4-tetrahydroquinolin-4-yl)amino)benzonitrile;
rac-1-((2S,3R,4R)-2-cyclopropyl-7-fluoro-3-methyl-4-((6-methylpyridin-2-yl)amino)-3,4-dihydroquinolin-1(2H)-yl)ethanone;
rac-1-((2S,3R,4R)-2-cyclopropyl-7-methoxy-3-methyl-4-((6-methylpyridin-2-yl)amino)-3,4-dihydroquinolin-1(2H)-yl)ethanone;
rac-1-((2S,3R,4R)-2-cyclopropyl-7-hydroxy-3-methyl-4-((6-methylpyridin-2-yl)amino)-3,4-dihydroquinolin-1(2H)-yl)ethanone;
rac-(2S,3R,4R)-1-acetyl-2-cyclopropyl-3-methyl-4-((6-methylpyridin-2-yl)amino)-1,2,3,4-tetrahydroquinoline-6-carbonitrile;
rac-1-((2S,3R,4R)-2-cyclopropyl-3-methyl-4-((6-methylpyridin-2-yl)amino)-6-(methylsulfonyl)-3,4-dihydroquinolin-1(2H)-yl)ethanone;
rac-1-((2S,3R,4R)-2-cyclopropyl-6-(isopropylsulfonyl)-3-methyl-4-((6-methylpyridin-2-yl)amino)-3,4-dihydroquinolin-1(2H)-yl)ethanone;
rac-1-((2S,3R,4R)-2,3-dimethyl-4-(phenylamino)-6-(piperazin-1-yl)-3,4-dihydroquinolin-1(2H)-yl)ethanone;
rac-1-((2S,3R,4R)-2,3-dimethyl-6-morpholino-4-(phenylamino)-3,4-dihydroquinolin-1(2H)-yl)ethanone;
1-((2S,3R,4R)-2,3-dimethyl-6-morpholino-4-(phenylamino)-3,4-dihydroquinolin-1(2H)-yl)ethanone;
1-((2R,3S,4S)-2,3-dimethyl-6-morpholino-4-(phenylamino)-3,4-dihydroquinolin-1(2H)-yl)ethanone;
1-((rac-2S,3R,4R)-2,3-dimethyl-6-(3-methylpiperazin-1-yl)-4-(phenylamino)-3,4-dihydroquinolin-1(2H)-yl)ethanone;
rac-1-((2S,3R,4R)-2,3-dimethyl-6-morpholino-4-(pyridin-3-ylamino)-3,4-dihydroquinolin-1(2H)-yl)ethanone;
rac-1-((2S,3R,4R)-6-(4-aminopiperidin-1-yl)-2,3-dimethyl-4-(phenylamino)-3,4-dihydroquinolin-1(2H)-yl)ethanone;
rac-1-((2S,3R,4R)-2,3-dimethyl-4-((6-methylpyridin-2-yl)amino)-6-morpholino-3,4-dihydroquinolin-1(2H)-yl)ethanone;
rac-1-((2S,3R,4R)-2,3-dimethyl-4-(phenylamino)-6-(piperidin-4-ylamino)-3,4-dihydroquinolin-1(2H)-yl)ethanone;
1-((rac-2S,3R,4R)-2,3-dimethyl-6-(2-methylmorpholino)-4-(phenylamino)-3,4-dihydroquinolin-1(2H)-yl)ethanone;
1-((rac-2S,3R,4R)-6-(-2,5-diazabicyclo[2.2.2]octan-2-yl)-2,3-dimethyl-4-(phenylamino)-3,4-dihydroquinolin-1(2H)-yl)ethanone;
rac-1-((2S,3R,4R)-6-((1R,5S)-8-oxa-3-azabicyclo[3.2.1]octan-3-yl)-2,3-dimethyl-4-(phenylamino)-3,4-dihydroquinolin-1(2H)-yl)ethanone;
1-((rac-2S,3R,4R)-2,3-dimethyl-6-(3-methylpyrrolidin-1-yl)-4-(phenylamino)-3,4-dihydroquinolin-1(2H)-yl)ethanone;
1-((rac-2S,3R,4R)-2,3-dimethyl-6-(2-methylpyrrolidin-1-yl)-4-(phenylamino)-3,4-dihydroquinolin-1(2H)-yl)ethanone;
rac-1-((2S,3R,4R)-6-(3,8-diazabicyclo[3.2.1]octan-3-yl)-2,3-dimethyl-4-(phenylamino)-3,4-dihydroquinolin-1(2H)-yl)ethanone;
rac-6-(((2S,3R,4R)-1-acetyl-2,3-dimethyl-6-morpholino-1,2,3,4-tetrahydroquinolin-4-yl)amino)nicotinonitrile;
rac-1-((2S,3R,4R)-2-ethyl-3-methyl-6-morpholino-4-(phenylamino)-3,4-dihydroquinolin-1(2H)-yl)ethanone;
rac-1-((2S,3R,4R)-2-cyclopropyl-6-(3,6-dihydro-2H-pyran-4-yl)-3-methyl-4-((6-methylpyridin-2-yl)amino)-3,4-dihydroquinolin-1(2H)-yl)ethanone;
1-((rac-2S,3R,4R)-2-cyclopropyl-3-methyl-6-(3-methylpiperazin-1-yl)-4-((6-methylpyridin-2-yl)amino)-3,4-dihydroquinolin-1(2H)-yl)ethanone;
rac-1-((2S,3R,4R)-2-cyclopropyl-3-methyl-4-((6-methylpyridin-2-yl)amino)-6-(1,2,3,6-tetrahydropyridin-4-yl)-3,4-dihydroquinolin-1(2H)-yl)ethanone;
rac-1-((2S,3R,4R)-2-cyclopropyl-3-methyl-4-((6-methylpyridin-2-yl)amino)-6-(piperidin-4-yl)-3,4-dihydroquinolin-1(2H)-yl)ethanone;
rac-1-((2S,3R,4R)-2-cyclopropyl-3-methyl-4-((6-methylpyridin-2-yl)amino)-6-morpholino-3,4-dihydroquinolin-1(2H)-yl)ethanone;
rac-1-((2S,3R,4R)-2-cyclopropyl-3-methyl-6-morpholino-4-(phenylamino)-3,4-dihydroquinolin-1(2H)-yl)ethanone;
1-((2S,3R,4R)-2-cyclopropyl-3-methyl-6-morpholino-4-(phenylamino)-3,4-dihydroquinolin-1(2H)-yl)ethanone;
1-((2S,3R,4R)-2-cyclopropyl-3-methyl-6-morpholino-4-(phenylamino)-3,4-dihydroquinolin-1(2H)-yl)ethanone;
rac-1-((2S,3R,4R)-2-cyclopropyl-6-(3,6-dihydro-2H-pyran-4-yl)-3-methyl-4-(pyridin-2-ylamino)-3,4-dihydroquinolin-1(2H)-yl)ethanone;
rac-1-((2S,3R,4R)-2-cyclopropyl-3-methyl-4-((6-methylpyridin-2-yl)amino)-6-(tetrahydro-2H-pyran-4-yl)-3,4-dihydroquinolin-1(2H)-yl)ethanone;
rac-1-((2S,3R,4R)-2-cyclopropyl-3-methyl-4-(phenylamino)-6-(piperazin-1-yl)-3,4-dihydroquinolin-1(2H)-yl)ethanone;

rac-1-((2S,3R,4R)-2-cyclopropyl-3-methyl-4-((6-methylpyridin-2-yl)amino)-6-((tetrahydro-2H-pyran-4-yl)oxy)-3,4-dihydroquinolin-1(2H)-yl)ethanone;

rac-1-((2S,3R,4R)-2-cyclopropyl-3-methyl-6-morpholino-4-(pyridin-2-ylamino)-3,4-dihydroquinolin-1(2H)-yl)ethanone;

rac-1-((2S,3R,4R)-2-cyclopropyl-6-(1-ethyl-1H-pyrazol-4-yl)-3-methyl-4-(phenylamino)-3,4-dihydroquinolin-1(2H)-yl)ethanone;

rac-1-((2S,3R,4R)-2-cyclopropyl-3-methyl-6-(1-methyl-1H-pyrazol-4-yl)-4-(phenylamino)-3,4-dihydroquinolin-1(2H)-yl)ethanone;

rac-4-((2S,3R,4R)-1-acetyl-2-cyclopropyl-3-methyl-4-(phenylamino)-1,2,3,4-tetrahydroquinolin-6-yl)benzoic acid;

rac-1-((2S,3R,4R)-2,3-dimethyl-4-(phenylamino)-3,4-dihydro-1,5-naphthyridin-1(2H)-yl)ethanone;

rac-(6 S,7R,8R)-5-acetyl-6-cyclopropyl-7-methyl-8-(phenylamino)-5,6,7,8-tetrahydro-1,5-naphthyridin-2(1H)-one;

1-((2S,3R,4R)-2-cyclopropyl-3-methyl-4-(phenylamino)-3,4-dihydro-1,5-naphthyridin-1(2H)-yl)ethanone;

1-((2S,3R,4R)-2-cyclopropyl-3-methyl-4-(phenylamino)-3,4-dihydro-1,5-naphthyridin-1(2H)-yl)ethanone;

rac-4-((6S,7R,8R)-5-acetyl-6-cyclopropyl-7-methyl-8-(phenylamino)-5,6,7,8-tetrahydro-1,5-naphthyridin-2-yl)-N-methyl benzamide;

rac-5-((6S,7R,8R)-5-acetyl-6-cyclopropyl-7-methyl-8-(phenylamino)-5,6,7,8-tetrahydro-1,5-naphthyridin-2-yl)-N-methylpicolinamide;

rac-1-((2S,3R,4R)-2-cyclopropyl-6-(6-methoxypyridin-3-yl)-3-methyl-4-(phenylamino)-3,4-dihydro-1,5-naphthyridin-1(2H)-yl)ethanone;

rac-1-((2S,3R,4R)-2-cyclopropyl-6-(1-ethyl-1H-pyrazol-4-yl)-3-methyl-4-(phenylamino)-3,4-dihydro-1,5-naphthyridin-1(2H)-yl)ethanone;

1-((rac-2 S,3R,4R)-2-cyclopropyl-3-methyl-6-(3-methylpiperazin-1-yl)-4-(phenylamino)-3,4-dihydro-1,5-naphthyridin-1(2H)-yl)ethanone;

rac-1-((2S,3R,4R)-2-cyclopropyl-3-methyl-4-(phenylamino)-6-(piperazin-1-yl)-3,4-dihydro-1,5-naphthyridin-1(2H)-yl)ethanone;

rac-1-((2S,3R,4R)-6-(4-aminopiperidin-1-yl)-2-cyclopropyl-3-methyl-4-(phenylamino)-3,4-dihydro-1,5-naphthyridin-1(2H)-yl)ethanone;

rac-1-((2S,3R,4R)-2-cyclopropyl-3-methyl-6-morpholino-4-(phenylamino)-3,4-dihydro-1,5-naphthyridin-1(2H)-yl)ethanone;

rac-1-((2S,3R,4R)-2-cyclopropyl-6-methoxy-3-methyl-4-((6-methylpyridin-2-yl)amino)-3,4-dihydro-1,5-naphthyridin-1(2H)-yl)ethanone;

rac-1-((2S,3R,4R)-2-cyclopropyl-6-hydroxy-3-methyl-4-((6-methyl pyridin-2-yl)amino)-3,4-dihydro-5-naphthyridin-1(2H)-yl)ethanone;

rac-1-((2S,3R,4R)-2-cyclopropyl-3-methyl-4-((6-methylpyridin-2-yl)amino)-3,4-dihydro-5-naphthyridin-1(2H)-yl)ethanone;

1-((2S,3R,4R)-2-cyclopropyl-3-methyl-4-((6-methylpyridin-2-yl)amino)-3,4-dihydro-1,5-naphthyridin-1(2H)-yl)ethanone;

1-((2R,3S,4S)-2-cyclopropyl-3-methyl-4-((6-methylpyridin-2-yl)amino)-3,4-dihydro-1,5-naphthyridin-1(2H)-yl)ethanone;

rac-1-((2S,3R,4R)-2,3-dimethyl-4-(phenylamino)-3,4-dihydro-1,7-naphthyridin-1(2H)-yl)ethanone;

rac-1-((2S,3R,4R)-2-cyclopropyl-3-methyl-4-(phenylamino)-3,4-dihydro-1,7-naphthyridin-1(2H)-yl)ethanone;

rac-1-((2S,3R,4R)-2-cyclopropyl-3-methyl-4-((6-methylpyridin-2-yl)amino)-3,4-dihydro-7-naphthyridin-1(2H)-yl)ethanone;

rac-1-((2S,3R,4R)-3-methyl-4-(phenylamino)-2-propyl-3,4-dihydro-1,7-naphthyridin-1(2H)-yl)ethanone;

rac-1-((2S,3S,4R)-2-cyclopropyl-3-methyl-4-phenoxy-3,4-dihydroquinolin-1(2H)-yl)ethanone;

rac-1-((2S,3S,4R)-2-cyclopropyl-3-methyl-4-((6-methyl pyridin-2-yl)oxy)-3,4-dihydroquinolin-1(2H)-yl)ethanone;

rac-1-((2S,3R,4R)-2,3-dimethyl-4-(pyridin-2-ylamino)-3,4-dihydroquinolin-1(2H)-yl)ethanone;

rac-1-((2S,3R,4R)-2-ethyl-3-methyl-4-((6-methylpyridin-2-yl)amino)-3,4-dihydroquinolin-1(2H)-yl)ethanone;

rac-1-((2S,3R,4R)-2-cyclopropyl-3-methyl-4-((4-methyloxazol-2-yl)amino)-3,4-dihydroquinolin-1(2H)-yl)ethanone;

rac-1-((2S,3R,4R)-4-((3-(aminomethyl)phenyl)amino)-2-cyclopropyl-3-methyl-3,4-dihydroquinolin-1(2H)-yl)ethanone;

rac-4-(((2S,3R,4R)-1-acetyl-2-cyclopropyl-3-methyl-1,2,3,4-tetrahydroquinolin-4-yl)amino)-N,N-dimethylbenzamide;

rac-1-((2S,3R,4R)-4-((5-chloropyridin-2-yl)amino)-2-cyclopropyl-3-methyl-3,4-dihydroquinolin-1(2H)-yl)ethanone;

rac-4-(((2S,3R,4R)-1-acetyl-2-cyclopropyl-3-methyl-1,2,3,4-tetrahydroquinolin-4-yl)amino)benzoic acid;

rac-6-(((2S,3R,4R)-1-acetyl-2-cyclopropyl-3-methyl-1,2,3,4-tetrahydroquinolin-4-yl)amino)-2-methylnicotinonitrile;

rac-2-(((2S,3R,4R)-1-acetyl-2-cyclopropyl-3-methyl-1,2,3,4-tetrahydroquinolin-4-yl)amino)pyrimidine-5-carbonitrile;

rac-1-((2S,3R,4R)-2,3-diethyl-4-((6-methylpyridin-2-yl)amino)-3,4-dihydroquinolin-1(2H)-yl)ethanone;

rac-(2S,3R,4R)-1-acetyl-2-cyclopropyl-3-methyl-4-((6-methylpyridin-2-yl)amino)-1,2,3,4-tetrahydroquinoline-6-carboxylic acid;

rac-(2S,3R,4R)-1-acetyl-2-cyclopropyl-N,N,3-trimethyl-4-((6-methylpyridin-2-yl)amino)-1,2,3,4-tetrahydroquinoline-6-carboxamide;

rac-(2S,3R,4R)-1-acetyl-2-cyclopropyl-3-methyl-4-((6-methylpyridin-2-yl)amino)-1,2,3,4-tetrahydroquinoline-6-carboxamide;

rac-4-(((2S,3R,4R)-1-acetyl-2-cyclopropyl-3-methyl-6-(1-(2-(methylamino)ethyl)-1H-pyrazol-4-yl)-1,2,3,4-tetrahydroquinolin-4-yl)amino)benzonitrile;

rac-1-((2S,3R,4R)-2-cyclopropyl-6-(1-(2-methoxyethyl)-1H-pyrazol-4-yl)-3-methyl-4-((6-methylpyridin-2-yl)amino)-3,4-dihydroquinolin-1(2H)-yl)ethanone;

1-((2 S,3R,4R)-2-cyclopropyl-6-(1-(2-meth oxyethyl)-1H-pyrazol-4-yl)-3-methyl-4-((6-methylpyridin-2-yl)amino)-3,4-dihydroquinolin-1(2H)-yl)ethanone;

1-((2R,3S,4S)-2-cyclopropyl-6-(1-(2-methoxyethyl)-1H-pyrazol-4-yl)-3-methyl-4-((6-methylpyridin-2-yl)amino)-3,4-dihydroquinolin-1(2H)-yl)ethanone;

rac-1-((2 S,3R,4R)-2-cyclopropyl-6-(1-(2-meth oxyethyl)-1H-pyrazol-4-yl)-3-methyl-4-((5-methylpyrazin-2-yl)amino)-3,4-dihydroquinolin-1(2H)-yl)ethanone;

1-((2 S,3R,4R)-2-cyclopropyl-6-(1-(2-meth oxyethyl)-1H-pyrazol-4-yl)-3-methyl-4-((5-methylpyrazin-2-yl)amino)-3,4-dihydroquinolin-1(2H)-yl)ethanone;

1-((2R,3S,4S)-2-cyclopropyl-6-(1-(2-methoxyethyl)-1H-pyrazol-4-yl)-3-methyl-4-((5-methylpyrazin-2-yl)amino)-3,4-dihydroquinolin-1(2H)-yl)ethanone;

rac-4-(((2S,3R,4R)-1-acetyl-6-fluoro-2,3-dimethyl-1,2,3,4-tetrahydroquinolin-4-yl)amino)benzonitrile;
rac-1-((2S,3R,4R)-6-fluoro-2,3-dimethyl-4-((5-methylpyrazin-2-yl)amino)-3,4-dihydroquinolin-1(2H)-yl)ethanone;
rac-1-((2S,3R,4R)-6-fluoro-4-((5-fluoropyridin-2-yl)amino)-2,3-dimethyl-3,4-dihydroquinolin-1(2H)-yl)ethanone;
rac-5-(((2S,3R,4R)-1-acetyl-6-fluoro-2,3-dimethyl-1,2,3,4-tetrahydroquinolin-4-yl)amino)pyrazine-2-carbonitrile;
rac-6-(((2S,3R,4R)-1-acetyl-6-fluoro-2,3-dimethyl-1,2,3,4-tetrahydroquinolin-4-yl)amino)nicotinonitrile;
rac-1-((2S,3R,4R)-6-fluoro-2,3-dimethyl-4-((4-methylpyrimidin-2-yl)amino)-3,4-dihydroquinolin-1(2H)-yl)ethanone;
rac-4-(((2S,3R,4R)-1-acetyl-6-fluoro-2,3-dimethyl-1,2,3,4-tetrahydroquinolin-4-yl)amino)-N-methylbenzamide;
1-((2S,3R,4R)-2-ethyl-6-fluoro-3-methyl-4-((6-methylpyridin-2-yl)amino)-3,4-dihydroquinolin-1(2H)-yl)ethanone;
1-((2R,3S,4S)-2-ethyl-6-fluoro-3-methyl-4-((6-methylpyridin-2-yl)amino)-3,4-dihydroquinolin-1(2H)-yl)ethanone;
4-(((2S,3R,4R)-1-acetyl-2-ethyl-6-fluoro-3-methyl-1,2,3,4-tetrahydroquinolin-4-yl)amino)benzonitrile;
4-(((2R,3S,4S)-1-acetyl-2-ethyl-6-fluoro-3-methyl-1,2,3,4-tetrahydroquinolin-4-yl)amino)benzonitrile;
rac-1-((2S,3R,4R)-2-ethyl-6-fluoro-3-methyl-4-((4-methylpyrimidin-2-yl)amino)-3,4-dihydroquinolin-1(2H)-yl)ethanone;
rac-1-((2S,3R,4R)-2-ethyl-6-fluoro-4-((5-fluoropyridin-2-yl)amino)-3-methyl-3,4-dihydroquinolin-1(2H)-yl)ethanone;
rac-4-(((2S,3R,4R)-1-acetyl-2-ethyl-6-fluoro-3-methyl-1,2,3,4-tetrahydroquinolin-4-yl)amino)benzonitrile;
rac-4-(((2S,3R,4R)-1-acetyl-2-ethyl-6-fluoro-3-methyl-1,2,3,4-tetrahydroquinolin-4-yl)amino)-N-methylbenzamide;
rac-1-((2S,3R,4R)-2-ethyl-6-fluoro-4-((6-methoxypyridin-2-yl)amino)-3-methyl-3,4-dihydroquinolin-1(2H)-yl)ethanone;
rac-6-(((2S,3R,4R)-1-acetyl-2-ethyl-6-fluoro-3-methyl-1,2,3,4-tetrahydroquinolin-4-yl)amino)nicotinonitrile;
rac-5-(((2S,3R,4R)-1-acetyl-2-ethyl-6-fluoro-3-methyl-1,2,3,4-tetrahydroquinolin-4-yl)amino)pyrazine-2-carbonitrile;
rac-1-((2S,3R,4R)-2-ethyl-6-fluoro-3-methyl-4-((5-methylpyrazin-2-yl)amino)-3,4-dihydroquinolin-1(2H)-yl)ethanone;
rac-6-(((2S,3R,4R)-1-acetyl-2-cyclopropyl-6-fluoro-3-methyl-1,2,3,4-tetrahydroquinolin-4-yl)amino)nicotinonitrile;
rac-5-(((2S,3R,4R)-1-acetyl-2-cyclopropyl-6-fluoro-3-methyl-1,2,3,4-tetrahydroquinolin-4-yl)amino)pyrazine-2-carbonitrile;
rac-1-((2 S,3R,4R)-2-cyclopropyl-6-fluoro-3-methyl-4-((4-methyl pyrimidin-2-yl)amino)-3,4-dihydroquinolin-1(2H)-yl)ethanone;
rac-1-((2S,3R,4R)-2-cyclopropyl-6-fluoro-3-methyl-4-((5-methyl pyrazin-2-yl)amino)-3,4-dihydroquinolin-1(2H)-yl)ethanone;
rac-1-((2S,3R,4R)-2-cyclopropyl-6-fluoro-4-((5-fluoropyridin-2-yl)amino)-3-methyl-3,4-dihydroquinolin-1(2H)-yl)ethanone;
rac-4-(((2S,3R,4R)-1-acetyl-2-cyclopropyl-6-fluoro-3-methyl-1,2,3,4-tetrahydroquinolin-4-yl)amino)benzonitrile;
rac-1-((2S,3R,4R)-2-cyclopropyl-6-fluoro-3-methyl-4-((6-methylpyridin-2-yl)amino)-3,4-dihydroquinolin-1(2H)-yl)ethanone;
rac-4-(((2S,3R,4R)-1-acetyl-2-cyclopropyl-6-fluoro-3-methyl-1,2,3,4-tetrahydroquinolin-4-yl)amino)-N-methylbenzamide;
rac-1-((2S,3R,4R)-2-cyclopropyl-6-fluoro-4-((6-methoxypyridin-2-yl)amino)-3-methyl-3,4-dihydroquinolin-1(2H)-yl)ethanone;
rac-1-((2S,3R,4R)-2-cyclopropyl-6-fluoro-4-((6-hydroxypyridin-2-yl)amino)-3-methyl-3,4-dihydroquinolin-1(2H)-yl)ethanone;
rac-5-(((2S,3R,4R)-1-acetyl-6-(3,6-dihydro-2H-pyran-4-yl)-2,3-dimethyl-1,2,3,4-tetrahydroquinolin-4-yl)amino)pyrazine-2-carbonitrile;
rac-1-((2S,3R,4)-6-(3,6-dihydro-2H-pyran-4-yl)-2,3-dimethyl-4-((5-methylpyrazin-2-yl)amino)-3,4-dihydroquinolin-1(2H)-yl)ethanone;
rac-1-((2S,3R,4R)-6-(3,6-dihydro-2H-pyran-4-yl)-2,3-dimethyl-4-((4-methylpyrimidin-2-yl)amino)-3,4-dihydroquinolin-1(2H)-yl)ethanone;
rac-6-(((2S,3R,4R)-1-acetyl-6-(3,6-dihydro-2H-pyran-4-yl)-2,3-dimethyl-1,2,3,4-tetrahydroquinolin-4-yl)amino)nicotinonitrile;
rac-1-((2S,3R,4R)-2,3-dimethyl-4-((6-methylpyridin-2-yl)amino)-6-(tetrahydro-2H-pyran-4-yl)-3,4-dihydroquinolin-1(2H)-yl)ethanone;
rac-1-((2S,3R,4R)-2,3-dimethyl-4-((4-methylpyrimidin-2-yl)amino)-6-(tetrahydro-2H-pyran-4-yl)-3,4-dihydroquinolin-1(2H)-yl)ethanone;
rac-4-(((2S,3R,4R)-1-acetyl-2,3-dimethyl-6-(tetrahydro-2H-pyran-4-yl)-1,2,3,4-tetrahydroquinolin-4-yl)amino)-N-methylbenzamide;
rac-5-(((2S,3R,4R)-1-acetyl-2,3-dimethyl-6-(tetrahydro-2H-pyran-4-yl)-1,2,3,4-tetrahydroquinolin-4-yl)amino)pyrazine-2-carbonitrile;
rac-1-((2S,3R,4R)-2,3-dimethyl-4-((5-methylpyrazin-2-yl)amino)-6-(tetrahydro-2H-pyran-4-yl)-3,4-dihydroquinolin-1(2H)-yl)ethanone;
rac-(2S,3R,4R)-1-acetyl-2-cyclopropyl-N,3-dimethyl-4-((5-methyl pyrazin-2-yl)amino)-1,2,3,4-tetrahydroquinoline-6-carboxamide;
rac-1-((2S,3R,4R)-2-cyclopropyl-6-(3,6-dihydro-2H-pyran-4-yl)-4-((6-methoxypyridin-2-yl)amino)-3-methyl-3,4-dihydroquinolin-1(2H)-yl)ethanone;
rac-1-((2S,3R,4R)-2-cyclopropyl-6-(3,6-dihydro-2H-pyran-4-yl)-3-methyl-4-(pyrimidin-2-ylamino)-3,4-dihydroquinolin-1(2H)-yl)ethanone;
rac-4-(((2S,3R,4R)-1-acetyl-2-cyclopropyl-6-(3,6-dihydro-2H-pyran-4-yl)-3-methyl-1,2,3,4-tetrahydroquinolin-4-yl)amino)-N-methylbenzamide;
rac-1-((2S,3R,4R)-2-cyclopropyl-6-(3,6-dihydro-2H-pyran-4-yl)-3-methyl-4-((5-methylpyrazin-2-yl)amino)-3,4-dihydroquinolin-1(2H)-yl)ethanone;
rac-5-(((2S,3R,4R)-1-acetyl-2-cyclopropyl-6-(3,6-dihydro-2H-pyran-4-yl)-3-methyl-1,2,3,4-tetrahydroquinolin-4-yl)amino)pyrazine-2-carbonitrile;
rac-6-(((2S,3R,4R)-1-acetyl-2-cyclopropyl-6-(3,6-dihydro-2H-pyran-4-yl)-3-methyl-1,2,3,4-tetrahydroquinolin-4-yl)amino)nicotinonitrile;
rac-1-((2S,3R,4R)-2-cyclopropyl-6-(3,6-dihydro-2H-pyran-4-yl)-3-methyl-4-((4-methylpyrimidin-2-yl)amino)-3,4-dihydroquinolin-1(2H)-yl)ethanone;
rac-1-((2S,3R,4R)-2,3-dimethyl-4-((5-methylpyrazin-2-yl)amino)-6-(piperidin-4-yl)-3,4-dihydroquinolin-1(2H)-yl)ethanone;
rac-1-((2S,3R,4R)-4-((5-fluoropyridin-2-yl)amino)-2,3-dimethyl-6-(piperidin-4-yl)-3,4-dihydroquinolin-1(2H)-yl)ethanone;

rac-1-((2S,3R,4R)-2,3-dimethyl-4-((6-methylpyridin-2-yl)amino)-6-(piperidin-4-yl)-3,4-dihydroquinolin-1(2H)-yl)ethanone;

rac-4-(((2S,3R,4R)-1-acetyl-2,3-dimethyl-6-(piperidin-4-yl)-1,2,3,4-tetrahydroquinolin-4-yl)amino)benzonitrile;

rac-6-(((2S,3R,4R)-1-acetyl-2,3-dimethyl-6-(piperidin-4-yl)-1,2,3,4-tetrahydroquinolin-4-yl)amino)nicotinonitrile;

rac-4-(((2S,3R,4R)-1-acetyl-2,3-dimethyl-6-(piperidin-4-yl)-1,2,3,4-tetrahydroquinolin-4-yl)amino)-N-methylbenzamide;

1-((2S,3R,4R)-2-cyclopropyl-3-methyl-4-((6-methylpyridin-2-yl)amino)-6-(1,2,3,6-tetrahydropyridin-4-yl)-3,4-dihydroquinolin-1(2H)-yl)ethanone;

1-((2R,3S,4S)-2-cyclopropyl-3-methyl-4-((6-methylpyridin-2-yl)amino)-6-(1,2,3,6-tetrahydropyridin-4-yl)-3,4-dihydroquinolin-1(2H)-yl)ethanone;

rac-1-((2S,3R,4R)-2-cyclopropyl-4-((6-hydroxypyridin-2-yl)amino)-3-methyl-6-(1,2,3,6-tetrahydropyridin-4-yl)-3,4-dihydroquinolin-1(2H)-yl)ethanone;

rac-1-((2S,3R,4R)-2-cyclopropyl-4-((6-methoxypyridin-2-yl)amino)-3-methyl-6-(1,2,3,6-tetrahydropyridin-4-yl)-3,4-dihydroquinolin-1(2H)-yl)ethanone;

rac-4-(((2S,3R,4R)-1-acetyl-2-cyclopropyl-3-methyl-6-(1,2,3,6-tetrahydropyridin-4-yl)-1,2,3,4-tetrahydroquinolin-4-yl)amino)benzonitrile;

rac-4-(((2S,3R,4R)-1-acetyl-2-cyclopropyl-3-methyl-6-(1,2,3,6-tetrahydropyridin-4-yl)-1,2,3,4-tetrahydroquinolin-4-yl)amino)-N-methylbenzamide;

rac-1-((2S,3R,4R)-2-cyclopropyl-3-methyl-4-((4-methylpyrimidin-2-yl)amino)-6-(1,2,3,6-tetrahydropyridin-4-yl)-3,4-dihydroquinolin-1(2H)-yl)ethanone;

rac-4-(((2S,3R,4R)-1-acetyl-2-cyclopropyl-3-methyl-6-(piperidin-4-yl)-1,2,3,4-tetrahydroquinolin-4-yl)amino)benzonitrile;

rac-4-(((2S,3R,4R)-1-acetyl-2-cyclopropyl-3-methyl-6-(piperidin-4-yl)-1,2,3,4-tetrahydroquinolin-4-yl)amino)-N-methylbenzamide;

4-(((2S,3R,4R)-1-acetyl-2,3-dimethyl-6-morpholino-1,2,3,4-tetrahydroquinolin-4-yl)amino)benzonitrile;

1-((2S,3R,4R)-2,3-dimethyl-4-((4-methylpyrimidin-2-yl)amino)-6-morpholino-3,4-dihydroquinolin-1(2H)-yl)ethanone;

rac-4-(((2S,3R,4R)-1-acetyl-2,3-dimethyl-6-morpholino-1,2,3,4-tetrahydroquinolin-4-yl)amino)-N-methylbenzamide;

1-((2S,3R,4R)-2,3-dimethyl-4-((5-methylpyrazin-2-yl)amino)-6-morpholino-3,4-dihydroquinolin-1(2H)-yl)ethanone;

rac-1-((2S,3R,4R)-2-ethyl-3-methyl-4-((4-methylpyrimidin-2-yl)amino)-6-morpholino-3,4-dihydroquinolin-1(2H)-yl)ethanone;

rac-6-(((2S,3R,4R)-1-acetyl-2-ethyl-3-methyl-6-morpholino-1,2,3,4-tetrahydroquinolin-4-yl)amino)nicotinonitrile;

rac-1-((2S,3R,4R)-2-ethyl-3-methyl-4-((5-methylpyrazin-2-yl)amino)-6-morpholino-3,4-dihydroquinolin-1(2H)-yl)ethanone;

rac-1-((2S,3R,4R)-2-ethyl-3-methyl-4-((6-methylpyridin-2-yl)amino)-6-morpholino-3,4-dihydroquinolin-1(2H)-yl)ethanone;

rac-4-(((2S,3R,4R)-1-acetyl-2-ethyl-3-methyl-6-morpholino-1,2,3,4-tetrahydroquinolin-4-yl)amino)benzonitrile;

rac-1-((2S,3R,4R)-2-ethyl-4-((6-methoxypyridin-2-yl)amino)-3-methyl-6-morpholino-3,4-dihydroquinolin-1(2H)-yl)ethanone;

rac-1-((2S,3R,4R)-2-ethyl-4-((5-fluoropyridin-2-yl)amino)-3-methyl-6-morpholino-3,4-dihydroquinolin-1(2H)-yl)ethanone;

rac-4-(((2S,3R,4R)-1-acetyl-2-cyclopropyl-3-methyl-6-morpholino-1,2,3,4-tetrahydroquinolin-4-yl)amino)-N-methylbenzamide;

rac-1-((2S,3R,4R)-2-cyclopropyl-3-methyl-4-((4-methylpyrimidin-2-yl)amino)-6-morpholino-3,4-dihydroquinolin-1(2H)-yl)ethanone;

rac-1-((2S,3R,4R)-2-cyclopropyl-4-((6-hydroxypyridin-2-yl)amino)-3-methyl-6-morpholino-3,4-dihydroquinolin-1(2H)-yl)ethanone;

rac-1-((2S,3R,4R)-2-cyclopropyl-3-methyl-4-((5-methylpyrazin-2-yl)amino)-6-morpholino-3,4-dihydroquinolin-1(2H)-yl)ethanone;

rac-6-(((2S,3R,4R)-1-acetyl-2-cyclopropyl-3-methyl-6-morpholino-1,2,3,4-tetrahydroquinolin-4-yl)amino)nicotinonitrile;

5-(((2S,3R,4R)-1-acetyl-2,3-dimethyl-6-(piperazin-1-yl)-1,2,3,4-tetrahydroquinolin-4-yl)amino)pyrazine-2-carbonitrile;

4-(((2S,3R,4R)-1-acetyl-2,3-dimethyl-6-(piperazin-1-yl)-1,2,3,4-tetrahydroquinolin-4-yl)amino)benzonitrile;

1-((2S,3R,4R)-2,3-dimethyl-4-((4-methylpyrimidin-2-yl)amino)-6-(piperazin-1-yl)-3,4-dihydroquinolin-1(2H)-yl)ethanone;

4-(((2S,3R,4R)-1-acetyl-2,3-dimethyl-6-(piperazin-1-yl)-1,2,3,4-tetrahydroquinolin-4-yl)amino)-N-methylbenzamide;

1-((2S,3R,4R)-2,3-dimethyl-4-((5-methylpyrazin-2-yl)amino)-6-(piperazin-1-yl)-3,4-dihydroquinolin-1(2H)-yl)ethanone;

rac-1-((2S,3R,4R)-2-ethyl-3-methyl-4-((5-methylpyrazin-2-yl)amino)-6-(piperazin-1-yl)-3,4-dihydroquinolin-1(2H)-yl)ethanone;

rac-4-(((2S,3R,4R)-1-acetyl-2-ethyl-3-methyl-6-(piperazin-1-yl)-1,2,3,4-tetrahydroquinolin-4-yl)amino)benzonitrile;

rac-4-(((2S,3R,4R)-1-acetyl-2-ethyl-3-methyl-6-(piperazin-1-yl)-1,2,3,4-tetrahydroquinolin-4-yl)amino)-N-methylbenzamide;

rac-5-(((2S,3R,4R)-1-acetyl-2-ethyl-3-methyl-6-(piperazin-1-yl)-1,2,3,4-tetrahydroquinolin-4-yl)amino)pyrazine-2-carbonitrile;

rac-6-(((2S,3R,4R)-1-acetyl-2-ethyl-3-methyl-6-(piperazin-1-yl)-1,2,3,4-tetrahydroquinolin-4-yl)amino)nicotinonitrile;

4-(((rac-2S,3R,4R)-1-acetyl-2-cyclopropyl-3-methyl-6-((S)-3-methylpiperazin-1-yl)-1,2,3,4-tetrahydroquinolin-4-yl)amino)benzonitrile;

4-(((rac-2S,3R,4R)-1-acetyl-2-cyclopropyl-3-methyl-6-((R)-3-methylpiperazin-1-yl)-1,2,3,4-tetrahydroquinolin-4-yl)amino)benzonitrile;

1-((2S,3R,4R)-2-cyclopropyl-4-((6-methoxypyridin-2-yl)amino)-3-methyl-6-((S)-3-methylpiperazin-1-yl)-3,4-dihydroquinolin-1(2H)-yl)ethanone;

1-((2S,3R,4R)-2-cyclopropyl-4-((5-fluoropyridin-2-yl)amino)-3-methyl-6-((S)-3-methylpiperazin-1-yl)-3,4-dihydroquinolin-1(2H)-yl)ethanone;

1-((rac-2S,3R,4R)-2-cyclopropyl-3-methyl-6-((S)-3-methylpiperazin-1-yl)-4-((5-methylpyrazin-2-yl)amino)-3,4-dihydroquinolin-1(2H)-yl)ethanone;

4-(((rac-2S,3R,4R)-1-acetyl-2-cyclopropyl-3-methyl-6-((S)-3-methylpiperazin-1-yl)-1,2,3,4-tetrahydroquinolin-4-yl)amino)-N-methylbenzamide;

6-(((rac-2S,3R,4R)-1-acetyl-2-cyclopropyl-3-methyl-6-((S)-3-methylpiperazin-1-yl)-1,2,3,4-tetrahydroquinolin-4-yl)amino)nicotinonitrile;

rac-(2S,3R,4R)-1-acetyl-4-((5-cyanopyridin-2-yl)amino)-N,2,3-trimethyl-1,2,3,4-tetrahydroquinoline-6-carboxamide;
rac-(2S,3R,4R)-1-acetyl-N,2,3-trimethyl-4-((6-methylpyridin-2-yl)amino)-1,2,3,4-tetrahydroquinoline-6-carboxamide;
rac-(2S,3R,4R)-1-acetyl-4-((5-cyanopyrazin-2-yl)amino)-N,2,3-trimethyl-1,2,3,4-tetrahydroquinoline-6-carboxamide;
rac-(2S,3R,4R)-1-acetyl-2-ethyl-N,3-dimethyl-4-((5-methylpyrazin-2-yl)amino)-1,2,3,4-tetrahydroquinoline-6-carboxamide;
rac-(2S,3R,4R)-1-acetyl-2-ethyl-N,3-dimethyl-4-((4-methylpyrimidin-2-yl)amino)-1,2,3,4-tetrahydroquinoline-6-carboxamide;
rac-(2S,3R,4R)-1-acetyl-2-ethyl-N,3-dimethyl-4-((6-methylpyridin-2-yl)amino)-1,2,3,4-tetrahydroquinoline-6-carboxamide;
rac-(2S,3R,4R)-1-acetyl-4-((5-cyanopyrazin-2-yl)amino)-2-ethyl-N,3-dimethyl-1,2,3,4-tetrahydroquinoline-6-carboxamide;
rac-(2S,3R,4R)-1-acetyl-4-((5-cyanopyridin-2-yl)amino)-2-ethyl-N,3-dimethyl-1,2,3,4-tetrahydroquinoline-6-carboxamide;
rac-(2S,3R,4R)-1-acetyl-2-cyclopropyl-N,3-dimethyl-4-((6-methylpyridin-2-yl)amino)-1,2,3,4-tetrahydroquinoline-6-carboxamide;
(2S,3R,4R)-1-acetyl-2-cyclopropyl-N,3-dimethyl-4-((6-methylpyridin-2-yl)amino)-1,2,3,4-tetrahydroquinoline-6-carboxamide;
(2R,3S,4S)-1-acetyl-2-cyclopropyl-N,3-dimethyl-4-((6-methylpyridin-2-yl)amino)-1,2,3,4-tetrahydroquinoline-6-carboxamide;
rac-(2S,3R,4R)-1-acetyl-2-cyclopropyl-N,3-dimethyl-4-((4-methylpyrimidin-2-yl)amino)-1,2,3,4-tetrahydroquinoline-6-carboxamide;
rac-(2S,3R,4R)-1-acetyl-4-((5-cyanopyridin-2-yl)amino)-2-cyclopropyl-N,3-dimethyl-1,2,3,4-tetrahydroquinoline-6-carboxamide;
rac-(2S,3R,4R)-1-acetyl-4-((5-cyanopyrazin-2-yl)amino)-2-cyclopropyl-N,3-dimethyl-1,2,3,4-tetrahydroquinoline-6-carboxamide;
rac-(2S,3R,4R)-1-acetyl-4-((4-cyanophenyl)amino)-2-cyclopropyl-N,3-dimethyl-1,2,3,4-tetrahydroquinoline-6-carboxamide;
rac-(2S,3R,4R)-1-acetyl-2-cyclopropyl-4-((5-fluoropyridin-2-yl)amino)-N,3-dimethyl-1,2,3,4-tetrahydroquinoline-6-carboxamide;
rac-(2S,3R,4R)-1-acetyl-2-cyclopropyl-4-((6-methoxypyridin-2-yl)amino)-N,3-dimethyl-1,2,3,4-tetrahydroquinoline-6-carboxamide;
rac-(2S,3R,4R)-1-acetyl-2-cyclopropyl-N,3-dimethyl-4-((5-methylpyrazin-2-yl)amino)-1,2,3,4-tetrahydroquinoline-6-carboxamide;
(2S,3R,4R)-1-acetyl-2-cyclopropyl-3-methyl-4-((6-methylpyridin-2-yl)amino)-1,2,3,4-tetrahydroquinoline-6-carboxylic acid;
(2S,3R,4R)-1-acetyl-2-cyclopropyl-N-ethyl-3-methyl-4-((6-methylpyridin-2-yl)amino)-1,2,3,4-tetrahydroquinoline-6-carboxamide;
(2S,3R,4R)-1-acetyl-2-cyclopropyl-N-propyl-3-methyl-4-((6-methylpyridin-2-yl)amino)-1,2,3,4-tetrahydroquinoline-6-carboxamide;
1-((2S,3R,4R)-2-cyclopropyl-3-methyl-4-((6-methylpyridin-2-yl)amino)-6-(pyrrolidine-1-carbonyl)-3,4-dihydroquinolin-1(2H)-yl)ethanone;
1-((2S,3R,4R)-2-cyclopropyl-3-methyl-4-((6-methylpyridin-2-yl)amino)-6-(morpholine-4-carbonyl)-3,4-dihydroquinolin-1(2H)-yl)ethanone;
1-((2S,3R,4R)-2-cyclopropyl-3-methyl-4-((6-methylpyridin-2-yl)amino)-6-(morpholine-4-carbonyl)-3,4-dihydroquinolin-1(2H)-yl)ethanone;
(2S,3R,4R)-1-acetyl-2-cyclopropyl-3-methyl-4-((6-methylpyridin-2-yl)amino)-N-(pyridin-3-ylmethyl)-1,2,3,4-tetrahydroquinoline-6-carboxamide;
(2S,3R,4R)-1-acetyl-2-cyclopropyl-3-methyl-4-((6-methylpyridin-2-yl)amino)-N-(1H-pyrazol-4-yl)-1,2,3,4-tetrahydroquinoline-6-carboxamide;
(2S,3R,4R)-1-acetyl-2-cyclopropyl-3-methyl-4-((6-methylpyridin-2-yl)amino)-N-(2-morpholinoethyl)-1,2,3,4-tetrahydroquinoline-6-carboxamide;
(2S,3R,4R)-1-acetyl-2-cyclopropyl-N-(2-methoxyethyl)-3-methyl-4-((6-methylpyridin-2-yl)amino)-1,2,3,4-tetrahydroquinoline-6-carboxamide;
(2S,3R,4R)-1-acetyl-2-cyclopropyl-N-(2-methoxyethyl)-3-methyl-4-((6-methylpyridin-2-yl)amino)-1,2,3,4-tetrahydroquinoline-6-carboxamide;
(2S,3R,4R)-1-acetyl-2-cyclopropyl-N-(1,1-dioxidotetrahydro-2H-thiopyran-4-yl)-3-methyl-4-((6-methylpyridin-2-yl)amino)-1,2,3,4-tetrahydroquinoline-6-carboxamide;
(2S,3R,4R)-1-acetyl-2-cyclopropyl-N-(1,1-dioxidotetrahydro-2H-thiopyran-4-yl)-3-methyl-4-((6-methylpyridin-2-yl)amino)-1,2,3,4-tetrahydroquinoline-6-carboxamide;
(2S,3R,4R)-1-acetyl-2-cyclopropyl-3-methyl-4-((6-methylpyridin-2-yl)amino)-N—((S)-tetrahydrofuran-3-yl)-1,2,3,4-tetrahydroquinoline-6-carboxamide;
(2S,3R,4R)-1-acetyl-2-cyclopropyl-3-methyl-4-((6-methylpyridin-2-yl)amino)-N—((R)-tetrahydrofuran-3-yl)-1,2,3,4-tetrahydroquinoline-6-carboxamide;
(2S,3R,4R)-1-acetyl-2-cyclopropyl-3-methyl-4-((6-methylpyridin-2-yl)amino)-N-(2-(methylsulfonyl)ethyl)-1,2,3,4-tetrahydroquinoline-6-carboxamide;
(2S,3R,4R)-1-acetyl-2-cyclopropyl-N-(2-hydroxypropyl)-3-methyl-4-((6-methylpyridin-2-yl)amino)-1,2,3,4-tetrahydroquinoline-6-carboxamide;
rac-(2S,3R,4R)-1-acetyl-2,3-dimethyl-4-((6-methylpyridin-2-yl)amino)-1,2,3,4-tetrahydroquinoline-6-carboxylic acid;
rac-(2S,3R,4R)-1-acetyl-N-(2-hydroxyethyl)-2,3-dimethyl-4-((6-methylpyridin-2-yl)amino)-1,2,3,4-tetrahydroquinoline-6-carboxamide;
rac-(2S,3R,4R)-1-acetyl-N-ethyl-2,3-dimethyl-4-((6-methylpyridin-2-yl)amino)-1,2,3,4-tetrahydroquinoline-6-carboxamide;
rac-(2S,3R,4R)-1-acetyl-2,3-dimethyl-4-((6-methylpyridin-2-yl)amino)-N-(piperidin-4-yl)-1,2,3,4-tetrahydroquinoline-6-carboxamide;
rac-(2S,3R,4R)-1-acetyl-2,3-dimethyl-N-(2-(methylamino)ethyl)-4-((6-methylpyridin-2-yl)amino)-1,2,3,4-tetrahydroquinoline-6-carboxamide;
rac-(2S,3R,4R)-1-acetyl-N-(2-methoxyethyl)-2,3-dimethyl-4-((6-methylpyridin-2-yl)amino)-1,2,3,4-tetrahydroquinoline-6-carboxamide;
rac-(2S,3R,4R)-1-acetyl-N-(2-cyanoethyl)-2,3-dimethyl-4-((6-methylpyridin-2-yl)amino)-1,2,3,4-tetrahydroquinoline-6-carboxamide;
rac-(2S,3R,4R)-1-acetyl-2,3-dimethyl-4-((6-methylpyridin-2-yl)amino)-N-(2-morpholinoethyl)-1,2,3,4-tetrahydroquinoline-6-carboxamide;
rac-(2S,3R,4R)-1-acetyl-N-isopropyl-2,3-dimethyl-4-((6-methylpyridin-2-yl)amino)-1,2,3,4-tetrahydroquinoline-6-carboxamide;

rac-(2S,3R,4R)-1-acetyl-2,3-dimethyl-4-((6-methylpyridin-2-yl)amino)-N-(tetrahydro-2H-pyran-4-yl)-1,2,3,4-tetrahydroquinoline-6-carboxamide;

rac-(2S,3R,4R)-1-acetyl-N-(1,1-dioxidotetrahydro-2H-thiopyran-4-yl)-2,3-dimethyl-4-((6-methylpyridin-2-yl)amino)-1,2,3,4-tetrahydroquinoline-6-carboxamide;

rac-1-((2S,3R,4R)-2,3-dimethyl-4-((6-methylpyridin-2-yl)amino)-6-(morpholine-4-carbonyl)-3,4-dihydroquinolin-1(2H)-yl)ethanone;

(rac-2S,3R,4R)-1-acetyl-2,3-dimethyl-4-((6-methylpyridin-2-yl)amino)-N-(pyrrolidin-3-yl)-1,2,3,4-tetrahydroquinoline-6-carboxamide;

rac-(2S,3R,4R)-1-acetyl-2-ethyl-3-methyl-4-((6-methylpyridin-2-yl)amino)-1,2,3,4-tetrahydroquinoline-6-carboxylic acid;

rac-(2S,3R,4R)-1-acetyl-2-ethyl-N-(2-hydroxyethyl)-3-methyl-4-((6-methylpyridin-2-yl)amino)-1,2,3,4-tetrahydroquinoline-6-carboxamide;

rac-(2S,3R,4R)-1-acetyl-N,2-diethyl-3-methyl-4-((6-methylpyridin-2-yl)amino)-1,2,3,4-tetrahydroquinoline-6-carboxamide;

rac-(2S,3R,4R)-1-acetyl-2-ethyl-3-methyl-4-((6-methylpyridin-2-yl)amino)-N-(piperidin-4-yl)-1,2,3,4-tetrahydroquinoline-6-carboxamide;

rac-(2S,3R,4R)-1-acetyl-2-ethyl-3-methyl-N-(2-(methylamino)ethyl)-4-((6-methylpyridin-2-yl)amino)-1,2,3,4-tetrahydroquinoline-6-carboxamide;

rac-(2S,3R,4R)-1-acetyl-2-ethyl-N-(2-methoxyethyl)-3-methyl-4-((6-methylpyridin-2-yl)amino)-1,2,3,4-tetrahydroquinoline-6-carboxamide;

rac-(2S,3R,4R)-1-acetyl-N-(2-cyanoethyl)-2-ethyl-3-methyl-4-((6-methylpyridin-2-yl)amino)-1,2,3,4-tetrahydroquinoline-6-carboxamide;

rac-(2S,3R,4R)-1-acetyl-2-ethyl-3-methyl-4-((6-methylpyridin-2-yl)amino)-N-(2-morpholinoethyl)-1,2,3,4-tetrahydroquinoline-6-carboxamide;

rac-(2S,3R,4R)-1-acetyl-2-ethyl-N-isopropyl-3-methyl-4-((6-methylpyridin-2-yl)amino)-1,2,3,4-tetrahydroquinoline-6-carboxamide;

rac-(2S,3R,4R)-1-acetyl-2-ethyl-3-methyl-4-((6-methylpyridin-2-yl)amino)-N-(tetrahydro-2H-pyran-4-yl)-1,2,3,4-tetrahydroquinoline-6-carboxamide;

rac-(2S,3R,4R)-1-acetyl-N-(1,1-dioxidotetrahydro-2H-thiopyran-4-yl)-2-ethyl-3-methyl-4-((6-methylpyridin-2-yl)amino)-1,2,3,4-tetrahydroquinoline-6-carboxamide;

rac-1-((2S,3R,4R)-2-ethyl-3-methyl-4-((6-methylpyridin-2-yl)amino)-6-(morpholine-4-carbonyl)-3,4-dihydroquinolin-1(2H)-yl)ethanone;

(rac-2S,3R,4R)-1-acetyl-2-ethyl-3-methyl-4-((6-methylpyridin-2-yl)amino)-N-(pyrrolidin-3-yl)-1,2,3,4-tetrahydroquinoline-6-carboxamide;

rac-1-((2S,3R,4R)-2-cyclopropyl-3-methyl-4-((4-methylthiazol-2-yl)amino)-3,4-dihydroquinolin-1(2H)-yl)ethanone;

(2S,3R,4R)-1-acetyl-2-cyclopropyl-3-methyl-4-((4-methylpyrimidin-2-yl)amino)-1,2,3,4-tetrahydroquinoline-6-carboxamide;

(2S,3R,4R)-1-acetyl-2-cyclopropyl-3-methyl-4-((4-methylpyrimidin-2-yl)amino)-1,2,3,4-tetrahydroquinoline-6-carboxylic acid; or a salt thereof.

In another embodiment, the compound of formula (I) is (2S,3R,4R)-1-Acetyl-2-cyclopropyl-3-methyl-4-(pyrimidin-2-ylamino)-1,2,3,4-tetrahydroquinoline-6-carbonitrile;

(2S,3R,4R)-1-Acetyl-2-cyclopropyl-4-((6-(hydroxymethyl)pyridin-2-yl)amino)-3-methyl-1,2,3,4-tetrahydroquinoline-6-carbonitrile;

2-(((2S,3R,4R)-1-acetyl-6-cyano-2-cyclopropyl-3-methyl-1,2,3,4-tetrahydroquinolin-4-yl)amino)nicotinamide;

(2S,3R,4R)-1-Acetyl-4-((3-(2-aminoethoxy)phenyl)amino)-2-cyclopropyl-3-methyl-1,2,3,4-tetrahydroquinoline-6-carbonitrile;

(2S,3R,4R)-1-acetyl-4-((4-cyano-2-fluorophenyl)amino)-2-cyclopropyl-3-methyl-1,2,3,4-tetrahydroquinoline-6-carboxamide;

(2S,3R,4R)-1-acetyl-4-((4-cyanophenyl)amino)-2-cyclopropyl-3-methyl-1,2,3,4-tetrahydroquinoline-6-carboxamide;

(2S,3R,4R)-1-acetyl-4-((4-cyanophenyl)amino)-2-ethyl-3-methyl-1,2,3,4-tetrahydroquinoline-6-carboxamide;

(2S,3R,4R)-1-acetyl-2-cyclopropyl-3-methyl-4-(pyrimidin-2-ylamino)-1,2,3,4-tetrahydroquinoline-6-carboxamide;

(2S,3R,4R)-1-acetyl-N-(1,1-dioxidotetrahydro-2H-thiopyran-4-yl)-2-ethyl-3-methyl-4-((4-methylpyrimidin-2-yl)amino)-1,2,3,4-tetrahydroquinoline-6-carboxamide;

(2S,3R,4R)-1-acetyl-2-cyclopropyl-3-methyl-4-((4-methylpyrimidin-2-yl)amino)-N-(oxetan-3-yl)-1,2,3,4-tetrahydroquinoline-6-carboxamide;

(2S,3R,4R)-1-acetyl-2-cyclopropyl-N-(2-methoxyethyl)-3-methyl-4-((4-methylpyrimidin-2-yl)amino)-1,2,3,4-tetrahydroquinoline-6-carboxamide;

(2S,3R,4R)-1-acetyl-2-cyclopropyl-N,3-dimethyl-4-((4-methylpyrimidin-2-yl)amino)-1,2,3,4-tetrahydroquinoline-6-carboxamide;

(2S,3R,4R)-1-acetyl-2-cyclopropyl-3-methyl-4-((4-methylpyrimidin-2-yl)amino)-N-(tetrahydro-2H-pyran-4-yl)-1,2,3,4-tetrahydroquinoline-6-carboxamide;

(2S,3R,4R)-1-acetyl-2-cyclopropyl-N-ethyl-3-methyl-4-((4-methylpyrimidin-2-yl)amino)-1,2,3,4-tetrahydroquinoline-6-carboxamide;

(2S,3R,4R)-1-acetyl-2-cyclopropyl-N-(2-hydroxyethyl)-3-methyl-4-((4-methylpyrimidin-2-yl)amino)-1,2,3,4-tetrahydroquinoline-6-carboxamide;

(2S,3R,4R)-1-acetyl-2-cyclopropyl-4-((5-fluoropyridin-2-yl)amino)-3-methyl-N-(oxetan-3-yl)-1,2,3,4-tetrahydroquinoline-6-carboxamide;

(2S,3R,4R)-1-acetyl-2-cyclopropyl-4-((5-fluoropyridin-2-yl)amino)-N-(2-methoxyethyl)-3-methyl-1,2,3,4-tetrahydroquinoline-6-carboxamide;

(2S,3R,4R)-1-acetyl-2-cyclopropyl-3-methyl-4-(pyrimidin-2-ylamino)-N-(tetrahydro-2H-pyran-4-yl)-1,2,3,4-tetrahydroquinoline-6-carboxamide;

(2S,3R,4R)-1-acetyl-2-cyclopropyl-3-methyl-N-(oxetan-3-yl)-4-(pyrimidin-2-ylamino)-1,2,3,4-tetrahydroquinoline-6-carboxamide;

(2S,3R,4R)-1-acetyl-2-cyclopropyl-N-(2-methoxyethyl)-3-methyl-4-(pyrimidin-2-ylamino)-1,2,3,4-tetrahydroquinoline-6-carboxamide;

(2S,3R,4R)-1-acetyl-2-cyclopropyl-N-(2-hydroxypropyl)-3-methyl-4-(pyrimidin-2-ylamino)-1,2,3,4-tetrahydroquinoline-6-carboxamide;

(2S,3R,4R)-1-acetyl-4-((4-cyanophenyl)amino)-2-cyclopropyl-N-(2-methoxyethyl)-3-methyl-1,2,3,4-tetrahydroquinoline-6-carboxamide;

rac-4-(((2S,3R,4R)-1-acetyl-6-(4-acetylpiperazin-1-yl)-2-ethyl-3-methyl-1,2,3,4-tetrahydroquinolin-4-yl)amino)benzonitrile;

rac-1-((2S,3R,4R)-2,3-dimethyl-4-((6-methylpyridin-2-yl)amino)-6-(1,2,3,6-tetrahydropyridin-4-yl)-3,4-dihydroquinolin-1(2H)-yl)ethanone;

1-((2S,3R,4R)-2-cyclopropyl-6-(1-(2-hydroxyethyl)-1H-pyrazol-4-yl)-3-methyl-4-((6-methylpyridin-2-yl)amino)-3,4-dihydroquinolin-1(2H)-yl)ethanone;

1-((2S,3R,4R)-2-cyclopropyl-6-(1-(2-hydroxyethyl)-1H-pyrazol-4-yl)-3-methyl-4-(pyridin-2-ylamino)-3,4-dihydroquinolin-1(2H)-yl)ethanone;

1-((2S,3R,4R)-2-ethyl-3-methyl-6-(piperazin-1-yl)-4-(pyrimidin-2-ylamino)-3,4-dihydroquinolin-1(2H)-yl)ethanone;

or a salt thereof.

In another embodiment the compound of formula (I) is: (2S,3R,4R)-1-acetyl-2-cyclopropyl-3-methyl-4-((4-methylpyrimidin-2-yl)amino)-1,2,3,4-tetrahydroquinoline-6-carboxylic acid or a salt thereof.

In a further embodiment the compound of formula (I) is: (2S,3R,4R)-1-acetyl-2-cyclopropyl-3-methyl-4-((4-methylpyrimidin-2-yl)amino)-1,2,3,4-tetrahydroquinoline-6-carboxamide or a salt thereof.

The term "$C_{1-6}$alkyl" as used herein refers to a straight or branched alkyl containing at least 1, and at most 6, carbon atoms. Examples of "$C_{1-6}$alkyl" as used herein include, but are not limited to, methyl, ethyl, n-propyl, n-butyl, isobutyl, isopropyl, t-butyl, pentyl and hexyl.

The term "$C_{1-4}$alkyl" refers to a straight or branched alkyl containing at least 1, and at most 4, carbon atoms. Examples of "$C_{1-4}$alkyl" as used herein include, but are not limited to, methyl, ethyl, n-propyl, n-butyl, isobutyl, isopropyl and t-butyl.

The term "$C_{1-4}$alkylene" means a straight or branched saturated alkyl chain containing at least one, and at most four, carbon atoms. Examples of "$C_{1-4}$alkylene" as used herein include, but are not limited to, methylene, ethylene, propylene and butylene.

The term "$C_{3-7}$cycloalkyl" as used herein refers to a saturated or unsaturated non-aromatic carbocyclic ring containing at least 3 and at most 7 carbon atoms. Examples of $C_{3-7}$cycloalkyl groups include, but are not limited to, cyclopropyl, cyclobutyl, cyclopentyl, cyclohexyl, cycloheptyl, cyclopentenyl and cyclohexenyl.

The term "$C_{1-6}$alkoxy" as used herein refers to a straight or branched alkoxy group containing at least 1, and at most 6, carbon atoms. Examples of "$C_{1-6}$alkyloxy" groups as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy.

The term "heterocyclyl" as used herein refers to a cyclic group containing 4 to 10, for example 5 to 10, ring-atoms including 1, 2, 3 or 4 hetero-atoms independently selected from nitrogen, oxygen and sulphur; wherein said cyclic group is saturated or unsaturated but is not aromatic. This definition includes bicyclic structures provided the moiety is non-aromatic. The point of attachment to the rest of the molecule may be by any suitable carbon or nitrogen atom. Examples of heterocyclyls include, but are not limited to, oxetanyl, tetrahydrofuranyl, tetrahydrothiophenyl, pyrrolidinyl, pyrrolinyl, pyrazolidinyl, pyrazolinyl, imidazolidinyl, imidazolinyl, morpholinyl, thiomorpholinyl, piperidinyl, dihydropyridinyl, tetrahydropyridinyl, pyranyl, dihydropyranyl, tetrahydropyranyl, piperazinyl, dioxanyl, dioxolanyl, 3,6-dihydro-2H-pyranyl, 1,2,3,6-tetrahydropyridinyl, 2,5-diazabicyclo[2.2.2]octan-2-yl, 8-oxa-3-azabicyclo[3.2.1]octan-3-yl, 3,8-diazabicyclo[3.2.1]octan-3-yl and tetrahydro-2H-thiopyran 1,1-dioxide.

The term "heteroaromatic" as used herein refers to an aromatic cyclic group containing 5 to 10 ring-atoms including 1, 2, 3 or 4 hetero-atoms independently selected from nitrogen, oxygen and sulphur. This definition includes bicyclic structures at least a portion of which is aromatic. The point of attachment to the rest of the molecule may be by any suitable carbon or nitrogen atom. Examples of heteroaromatic groups include, but are not limited to, furanyl, thienyl, pyrrolyl, oxazolyl, thiazolyl, imidazolyl, oxadiazolyl, thiadiazolyl, pyridinyl, triazinyl, pyridazinyl, pyrimidinyl, isothiazolyl, isoxazolyl, pyrazinyl, pyrazolyl, indolyl, isoindolyl, benzofuranyl, isobenzofuranyl, benzothiophenyl, isobenzothiophenyl, indazolyl, benzimidazolyl, benzthiazolyl, quinolinyl, naphthridinyl, quinoxalinyl, quinazolinyl, cinnolinyl, isoquinolinyl imidazopyridinyl and imidazo[1,2-a]pyridinyl.

The term "halo" as used herein refers to fluoro, chloro, bromo or iodo.

The term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The term "rac" as used herein refers to the racemic mixture of the compounds of formula (I). For example, "rac-(2S,3R,4R)" means a racemic mixture of the (2S,3R,4R) enantiomer and the (2R,3S,4S) enantiomer.

As used herein the symbols and conventions used in these processes, schemes and examples are consistent with those used in the contemporary scientific literature, for example, the *Journal of the American Chemical Society* or the *Journal of Biological Chemistry*. Unless otherwise noted, all starting materials were obtained from commercial suppliers and used without further purification.

The compounds of formula (I) contain at least 3 chiral atoms such that optical isomers, e.g. enantiomers may be formed. Accordingly, the present invention encompasses all isomers of the compounds of formula (I) whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Separation of isomers may be achieved by conventional techniques known to those skilled in the art, e.g. by fractional crystallisation, chromatography or HPLC.

It will be appreciated that, for compounds of formula (I) tautomers may be observed, for example when V is pyridinyl substituted by hydroxy. Any comment relating to the biological activity of a tautomer should be taken to include both tautomers.

It will be further appreciated that the present invention covers compounds of formula (I) as the free base and as salts thereof, for example as a pharmaceutically acceptable salt thereof. In one embodiment the invention relates to compounds of formula (I) in the form of a free base. In one embodiment the invention relates to compounds of formula (I) or a pharmaceutically acceptable salt thereof.

Because of their potential use in medicine, salts of the compounds of formula (I) are desirably pharmaceutically acceptable. Suitable pharmaceutically acceptable salts can include acid addition salts. For a review of suitable pharmaceutically acceptable salts see Berge et al., *J. Pharm. Sci.*, 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable acid addition salt can be formed by reaction of a compound of formula (I) with a suitable inorganic or organic acid (such as hydrobromic, hydrochloric, sulphuric, nitric, phosphoric, succinic, maleic, acetic, propionic, fumaric, citric, tartaric, lactic, benzoic, salicylic, aspartic, p-toluenesulphonic, benzenesulphonic, methanesulphonic, ethanesulphonic, naphthalenesulphonic such as 2-naphthalenesulphonic, or hexanoic acid), optionally in a suitable solvent such as an organic solvent, to give the salt which is usually isolated for example by crystallisation and filtration or by evaporation followed by trituration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulphonate, benzenesulphonate, methanesulphonate, ethanesulphonate, naphthalenesulphonate (e.g. 2-naphthalenesulphonate) or hexanoate salt.

Other non-pharmaceutically acceptable salts, e.g. formates, oxalates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated that many organic compounds can form complexes with solvents in which they are reacted or from which they are precipitated or crystallised. These complexes are known as "solvates". For example, a complex with water is known as a "hydrate". Solvents with high boiling points and/or capable of forming hydrogen bonds such as water, xylene, N-methyl pyrrolidinone, methanol and ethanol may be used to form solvates. Methods for identification of solvates include, but are not limited to, NMR and microanalysis. Solvates of the compounds of formula (I) are within the scope of the invention.

The invention includes within its scope all possible stoichiometric and non-stoichiometric forms of the solvates of the compounds of formula (I).

The invention encompasses all prodrugs, of the compound of formula (I) or a pharmaceutically acceptable salt thereof, which upon administration to the recipient is capable of providing (directly or indirectly) the compound of formula (I) or a pharmaceutically acceptable salt thereof, or an active metabolite or residue thereof. Such derivatives are recognisable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives.

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

It will be appreciated from the foregoing that included within the scope of the invention are solvates, isomers and polymorphic forms of the compounds of formula (I) and salts thereof.

The compounds of formula (I) or salts thereof may be made by a variety of methods, including standard chemistry.

Illustrative general synthetic methods are set out below and then specific compounds of formula (I) and pharmaceutically acceptable salts thereof, are prepared in the Examples.

Compounds of formula (I) may be prepared as described in any of the Schemes below:

Scheme 1:

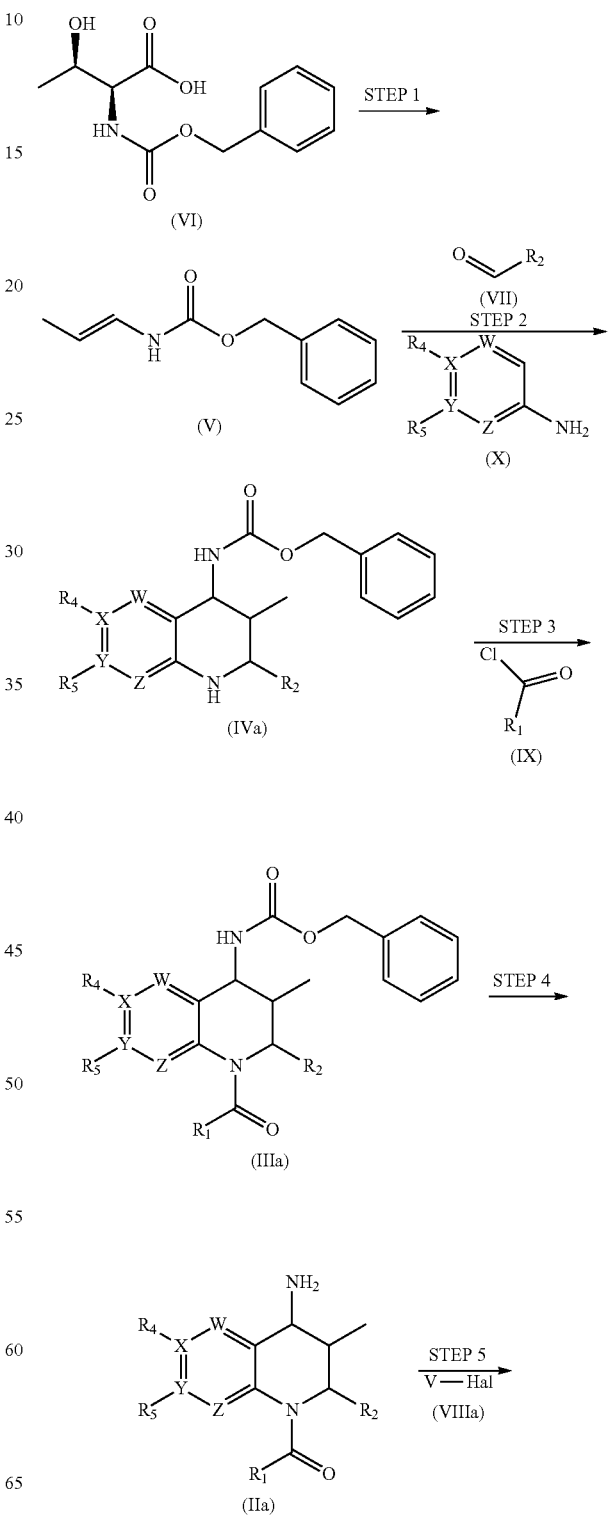

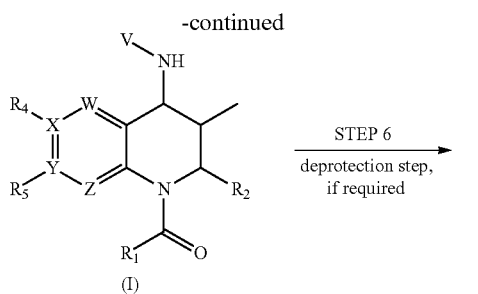

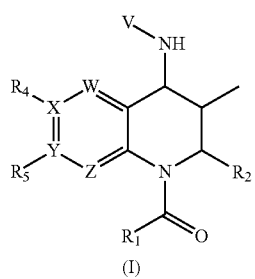

wherein $R_1$, $R_2$, $R_4$, $R_5$, V, W, X, Y and Z are as defined for a compound of formula (I); Hal is chlorine, bromine of iodine. If V or $R_4$ comprise a free amine, this will be protected by a suitable protecting group such as BOC, FMOC, Cbz or benzyl, which is removed in Step 6 of the synthesis.

In respect of steps shown in Scheme 1 the following reactions conditions may be utilised.

Step 1 may be carried out by treating with a suitable reagent such as DIAD, in the presence of a triphenylphosphine, in a suitable solvent, such as THF, at a suitable temperature, such as −78° C., for a period of for example 16 hours.

Step 2 may be carried out with a suitable acid catalyst, such as $P(OPh)_2(O)OH$, TFA or $Yb(OTf)_3$, in a suitable aprotic solvent, such as DCM, DCE, chloroform, THF or diethylether, at a suitable temperature, such as 0° C., for a period of for example 16 hours.

Step 3 may be carried out in the presence of a suitable base, such as pyridine, DIPEA or triethylamine, optionally in combination with DMAP, in a suitable aprotic solvent, such as DCM, DCE, chloroform, THF or diethylether, at a suitable temperature such as 21° C., for a period of, for example, 1 hour.

Step 4 is a hydrogenation step which may be carried out in the presence of Pd/C and $H_2$ or ammonium formate (transfer hydrogenation) in a suitable solvent, such as methanol, ethanol or EtOAc, at a suitable temperature such as 21° C., for a period of, for example, 3 hours.

Step 5 may be carried out with a suitable palladium catalyst, such as $Pd_2(dba)_3$, $PdCl_2(dppf)$, $Pd(OAc)_2$ or $Pd(PPh_3)_4$, a suitable phosphine ligand if required, such as BrettPhos, DavePhos, XantPhos, X-Phos or BINAP, a suitable base, such as $NaO^tBu$, $Cs_2CO_3$ or $K_3PO_4$, in a suitable solvent, such as toluene, THF or 1,4-dioxane, at a suitable temperature, such as 100° C., for a suitable period, such as 1 hour.

Step 6a (wherein the protecting group is BOC) may be carried out with a suitable acid, such as HCl in 1,4-dioxane or TFA in DCM, at a suitable temperature, such as 21° C., for a suitable period, for example 1 hour.

Step 6b (wherein the protecting group is FMOC) may be carried out with a piperidine solution, at a suitable temperature, such as room temperature, for a suitable period, for example 1 hour.

Step 6c (wherein the protecting group is Cbz or benzyl) may be carried out by hydrogenation in the presence of Pd/C and $H_2$ in a suitable solvent, such as methanol, ethanol or water, at a suitable temperature such as 21° C., for a period of, for example, 16 hours.

Scheme 2:

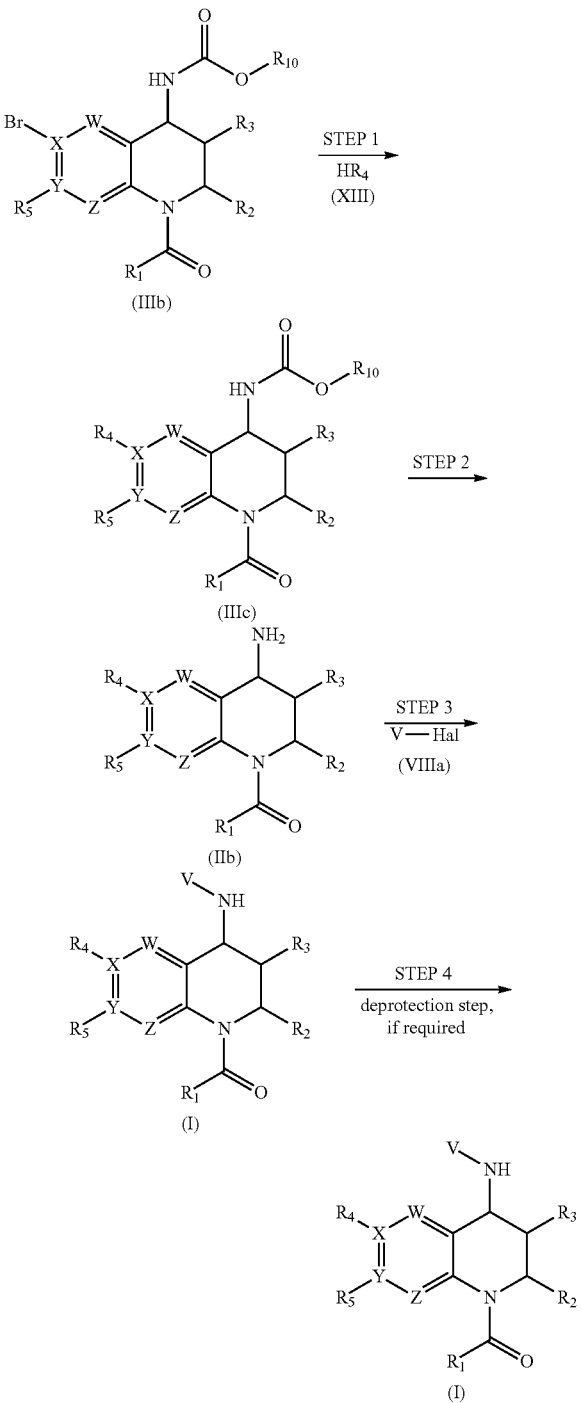

wherein $R_1$, $R_2$, $R_3$, $R_5$, V, W, X, Y and Z are as defined for a compound of formula (I). $R_{10}$ is benzyl or t-butyl. $R_4$ is —$NHR_9$, $N(C_{1-6}alkyl)$-$R_9$ or a heteroaromatic or heterocyclyl ring containing at least one nitrogen atom. $R_9$ is $C_{1-6}$alkyl, $C_{3-7}$cycloalkyl, phenyl, heterocyclyl or heteroaromatic. Hal is chlorine, bromine or iodine.

If V or $R_4$ comprise a free amine, this will be protected by a suitable protecting group such as BOC, FMOC, Cbz or benzyl, which is removed in Step 4 of the synthesis.

In respect of steps shown in Scheme 2 the following reactions conditions may be utilised.

Step 1 may be carried out with a suitable palladium catalyst, such as $Pd_2(dba)_3$, $PdCl_2(dppf)$, $Pd(OAc)_2$ or $Pd(PPh_3)_4$, a suitable phosphine ligand if required, such as BrettPhos, DavePhos, XantPhos, X-Phos or BINAP, a suitable base, such as NaO$^t$Bu, $Cs_2CO_3$ or $K_3PO_4$, in a suitable solvent, such as toluene, THF or 1,4-dioxane, at a suitable temperature, such as 100° C., for a suitable period, such as 1 hour.

Step 2 in some cases this step is not required to remove the carboxybenzyl protecting group and the compound of formula (IIIa) is converted directly into a compound of formula (IIb). Step 2 is a hydrogenation step which may be carried out in the presence of Pd/C and $H_2$ or ammonium formate (transfer hydrogenation) in a suitable solvent, such as methanol, ethanol or EtOAc, at a suitable temperature such as 21° C., for a period of, for example, 3 hours.

Step 3 may be carried out with a suitable palladium catalyst, such as $Pd_2(dba)_3$, $PdCl_2(dppf)$, $Pd(OAc)_2$ or $Pd(PPh_3)_4$, a suitable phosphine ligand if required, such as BrettPhos, DavePhos, XantPhos, X-Phos or BINAP, a suitable base, such as NaO$^t$Bu, $Cs_2CO_3$ or $K_3PO_4$, in a suitable solvent, such as toluene, THF or 1,4-dioxane, at a suitable temperature, such as 100° C., for a suitable period, such as 1 hour.

Step 4a (wherein the protecting group is BOC) may be carried out with a suitable acid, such as HCl in 1,4-dioxane or TFA in DCM, at a suitable temperature, such as 21° C., for a suitable period, for example 1 hour.

Step 4b (wherein the protecting group is FMOC) may be carried out with a piperidine solution, at a suitable temperature, such as room temperature, for a suitable period, for example 1 hour.

Step 4c (wherein the protecting group is Cbz or benzyl) may be carried out by hydrogenation in the presence of Pd/C and $H_2$ in a suitable solvent, such as methanol, ethanol or water, at a suitable temperature such as 21° C., for a period of, for example, 16 hours.

Scheme 3:

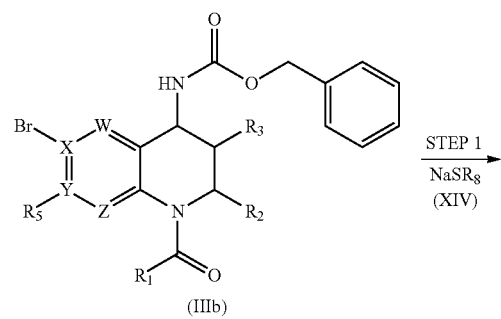

(IIIb)

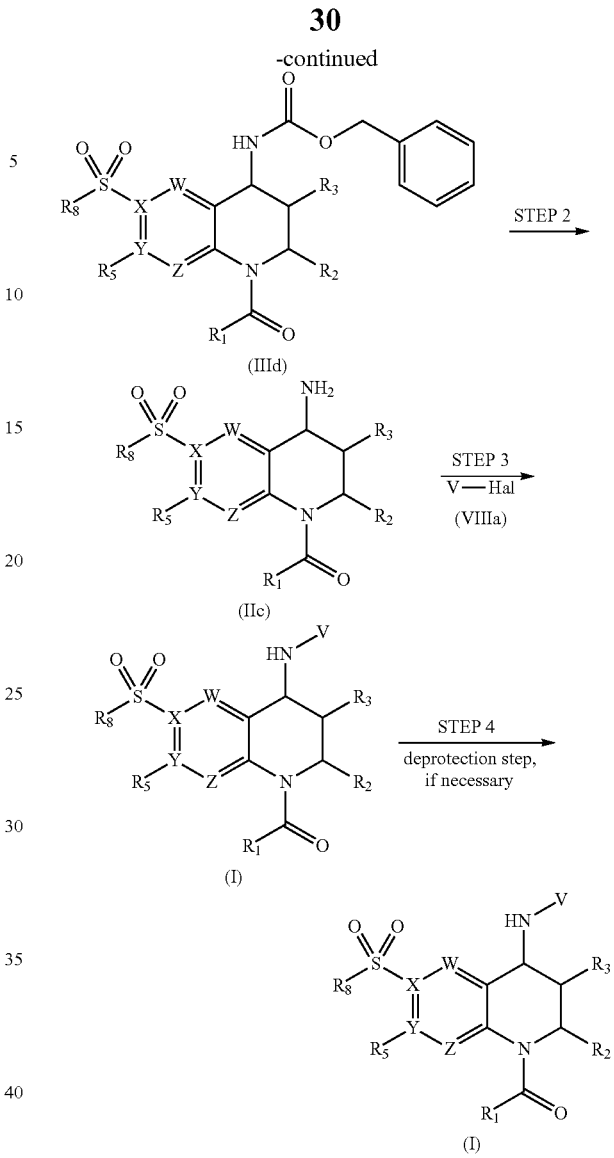

wherein $R_1$, $R_2$, $R_3$, $R_5$, V, W, X, Y and Z are as defined for a compound of formula (I). $R_8$ is $C_{1-6}$alkyl, $C_{3-7}$cycloalkyl, phenyl, heterocyclyl or heteroaromatic. Hal is chlorine, bromine or iodine. If V comprises a free amine, it will be protected by a suitable protecting group such as BOC, FMOC, Cbz or benzyl, which is removed in Step 4 of the synthesis.

In respect of steps shown in Scheme 3 the following reactions conditions may be utilised.

Step 1 may be carried out with a suitable palladium catalyst, such as $Pd_2(dba)_3$, $PdCl_2(dppf)$, $Pd(OAc)_2$ or $Pd(PPh_3)_4$, a suitable phosphine ligand, if required, such as BrettPhos, DavePhos, XantPhos, X-Phos or BINAP, a suitable base, such as NaO$^t$Bu, $Cs_2CO_3$ or $K_2CO_3$, in a suitable solvent, such as toluene, THF or 1,4-dioxane, at a suitable temperature, such as 100° C., for a suitable period, such as 1 hour, followed by oxidation with a suitable oxidising agent, such as mCPBA, $H_2O_2$, or $KMnO_4/MnO_2$, in a suitable solvent, such as toluene, THF or DCM, at a suitable temperature, such as 21° C., for a suitable period, such as 3 hours.

Step 2 is a hydrogenation step which may be carried out in the presence of Pd/C and $H_2$ or ammonium formate (transfer hydrogenation) in a suitable solvent, such as methanol, ethanol or EtOAc, at a suitable temperature such as 21° C., for a period of, for example, 3 hours.

Step 3 may be carried out with a suitable palladium catalyst, such as $Pd_2(dba)_3$, $PdCl_2(dppf)$, $Pd(OAc)_2$ or $Pd(PPh_3)_4$, a suitable phosphine ligand if required, such as BrettPhos, DavePhos, XantPhos, X-Phos and BINAP, a suitable base, such as NaO$^t$Bu, $Cs_2CO_3$ or $K_2CO_3$, in a suitable solvent, such as toluene, THF or 1,4-dioxane, at a suitable temperature, such as 100° C., for a suitable period, such as 1 hour.

Step 4a (wherein the protecting group is BOC) may be carried out with a suitable acid, such as HCl in 1,4-dioxane or TFA in DCM, at a suitable temperature, such as 21° C., for a suitable period, for example 1 hour.

Step 4b (wherein the protecting group is FMOC) may be carried out with a piperidine solution, at a suitable temperature, such as room temperature, for a suitable period, for example 1 hour.

Step 4c (wherein the protecting group is Cbz or benzyl) may be carried out by hydrogenation in the presence of Pd/C and $H_2$ in a suitable solvent, such as methanol, ethanol or water, at a suitable temperature such as 21° C., for a period of, for example, 16 hours.

Scheme 4:

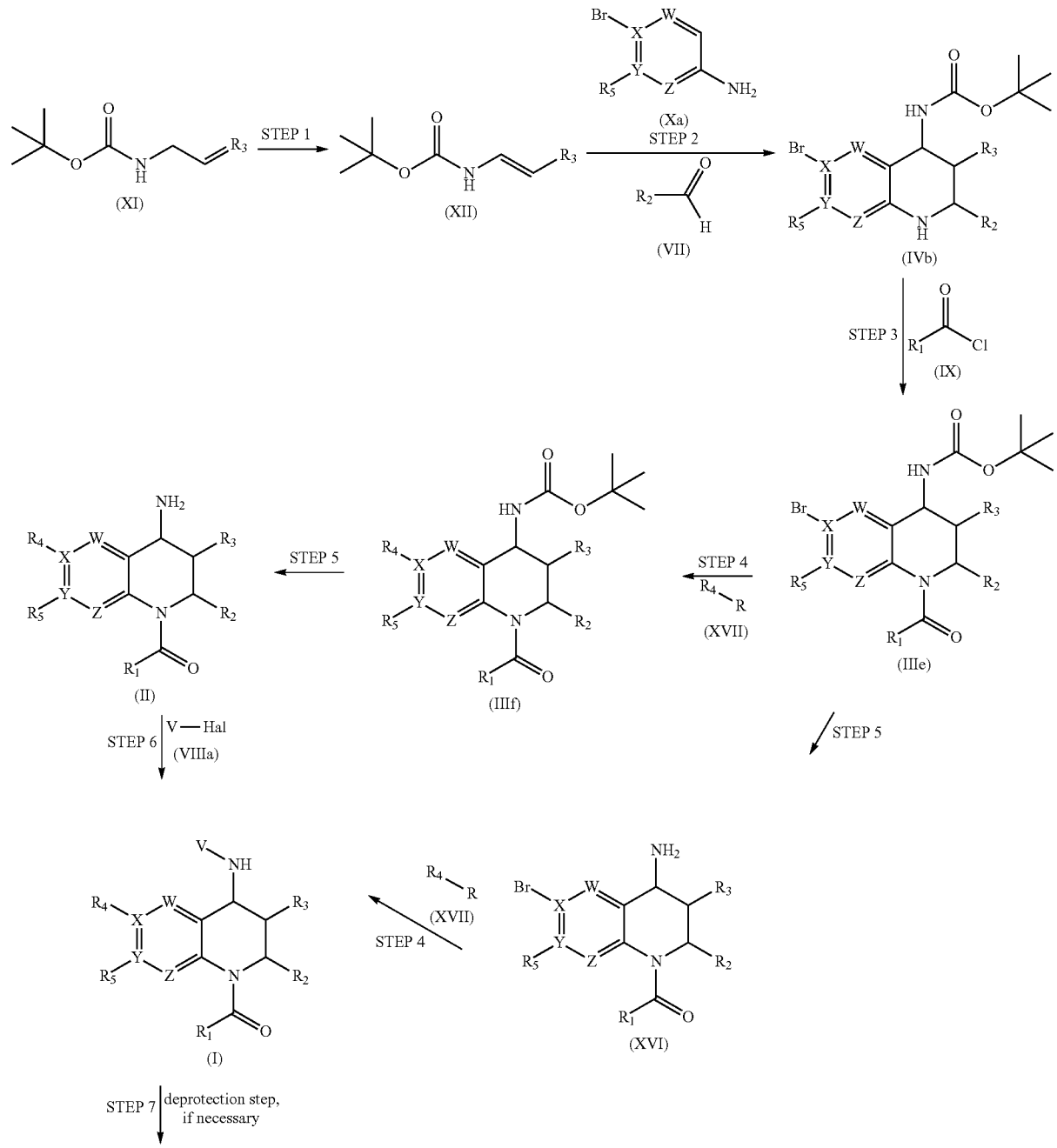

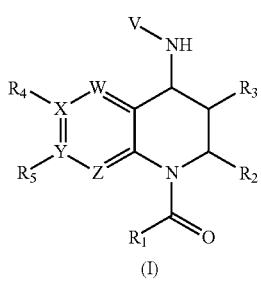

(I)

wherein $R_1$, $R_2$, $R_3$, $R_4$, $R_5$, V, W, X, Y and Z are as defined for a compound of formula (I). Hal is chlorine, bromine or iodine. If V or $R_4$ comprise a free amine, this will be protected by a suitable protecting group such as BOC, FMOC, Cbz or benzyl which is removed in Step 7 of the synthesis. R is selected from —B(OH)$_2$, —BF$_3$K and

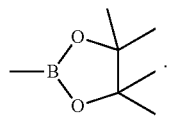

In respect of steps shown in Scheme 4 the following reactions conditions may be utilised.

Step 1 may be carried out in the presence of a suitable rhodium catalyst such as tris(triphenylphosphine)rhodium (1)carbonyl hydride, in a suitable solvent, such as THF, at a suitable temperature, such as 80° C., for a period of for example 2 hours.

Step 2 may be carried out with a suitable acid catalyst, such P(OPh)$_2$(O)OH, TFA or Yb(OTf)$_3$, in a suitable aprotic solvent, such as DCM, DCE, chloroform, THF or diethylether, at a suitable temperature, such as 0° C., for a period of for example 16 hours.

Step 3 may be carried out in the presence of a suitable base, such as pyridine, DIPEA or triethylamine, optionally in combination with DMAP, in a suitable aprotic solvent, such as DCM, DCE, chloroform, THF or diethylether, at a suitable temperature such as 21° C., for a period of, for example, 16 hours.

Step 4 may be carried out with a suitable palladium catalyst, such as Pd$_2$(dba)$_3$, PdCl$_2$(dppf), Pd(OAc)$_2$ or Pd(PPh$_3$)$_4$, a suitable phosphine ligand if required, such as BrettPhos, DavePhos, XantPhos, X-Phos or BINAP, a suitable base, such as NaO$^t$Bu, Cs$_2$CO$_3$ or K$_3$PO$_4$, in a suitable solvent, such as toluene, THF or 1,4-dioxane, at a suitable temperature, such as 100° C., for a suitable period, such as 1 hour.

Step 5 may be carried out with a suitable acid, such as HCl in 1,4-dioxane or TFA in DCM, at a suitable temperature, such as 21° C., for a suitable period, for example 1 hour.

Step 6 may be carried out with a suitable palladium catalyst, such as Pd$_2$(dba)$_3$, PdCl$_2$(dppf), Pd(OAc)$_2$ or Pd(PPh$_3$)$_4$, a suitable phosphine ligand if required, such as BrettPhos, DavePhos, XantPhos, X-Phos and BINAP, a suitable base, such as NaO$^t$Bu, Cs$_2$CO$_3$ or K$_2$CO$_3$, in a suitable solvent, such as toluene, THF or 1,4-dioxane, at a suitable temperature, such as 100° C., for a suitable period, such as 1 hour.

Step 7a (wherein the protecting group is BOC) may be carried out with a suitable acid, such as HCl in 1,4-dioxane or TFA in DCM, at a suitable temperature, such as 21° C., for a suitable period, for example 1 hour.

Step 7b (wherein the protecting group is FMOC) may be carried out with a piperidine solution, at a suitable temperature, such as room temperature, for a suitable period, for example 1 hour.

Step 7c (wherein the protecting group is Cbz or benzyl) may be carried out by hydrogenation in the presence of Pd/C and H$_2$ in a suitable solvent, such as methanol, ethanol or water, at a suitable temperature such as 21° C., for a period of, for example, 16 hours.

Scheme 5:

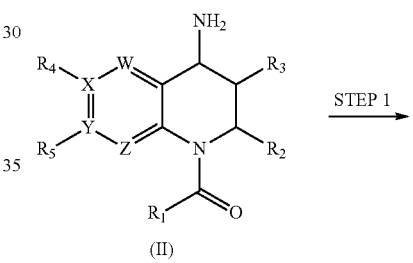

(II)

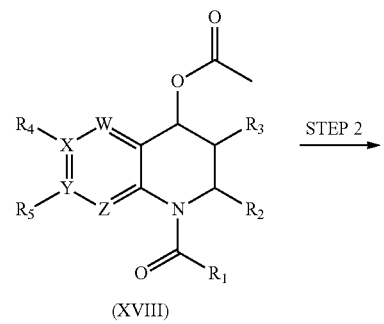

(XVIII)

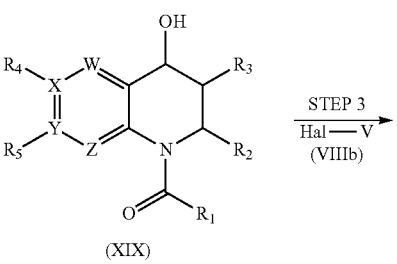

(XIX)

-continued (I)

↓ STEP 4
deprotection step,
if necessary (I)

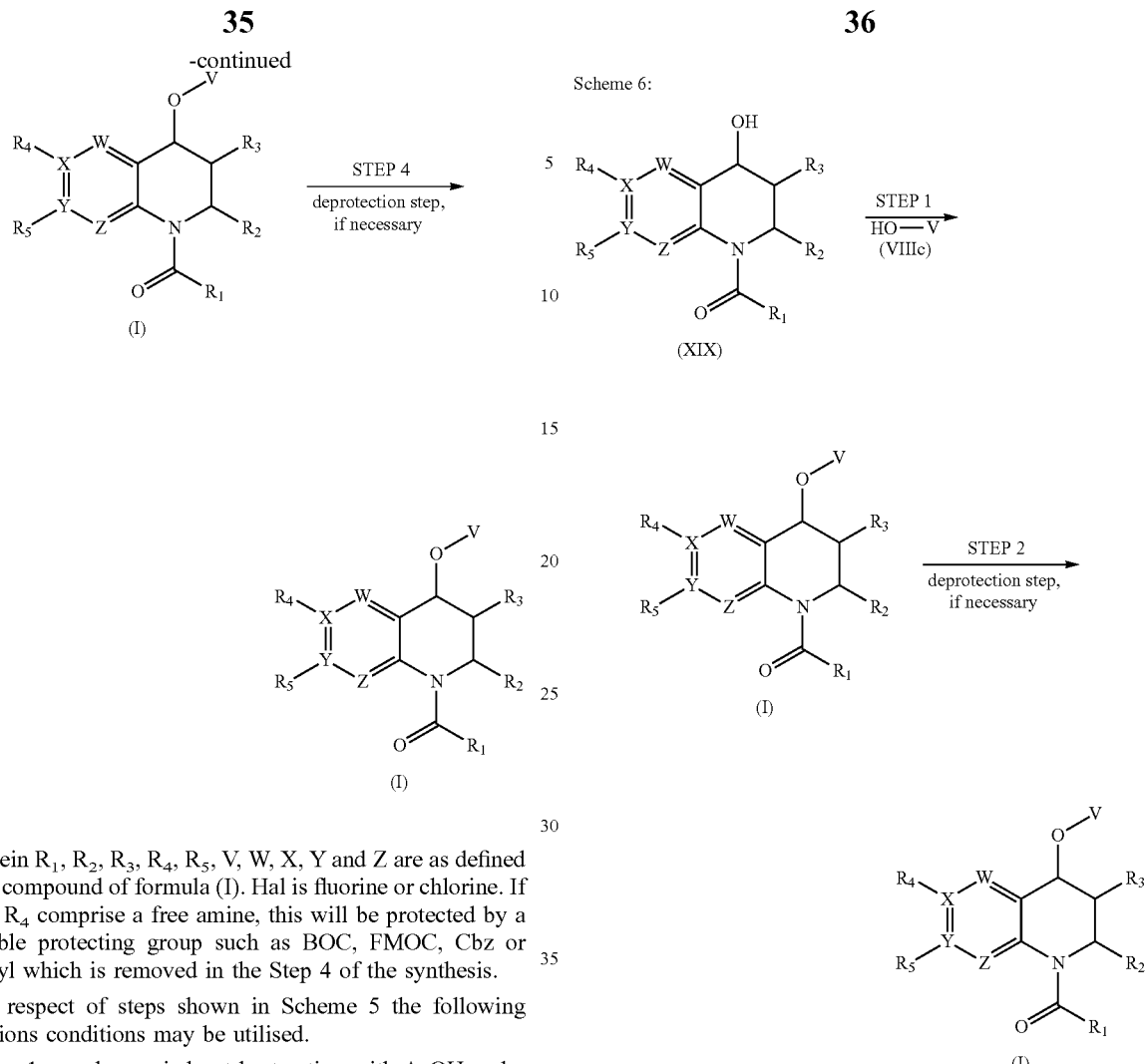

wherein $R_1$, $R_2$, $R_3$, $R_4$, $R_5$, V, W, X, Y and Z are as defined for a compound of formula (I). Hal is fluorine or chlorine. If V or $R_4$ comprise a free amine, this will be protected by a suitable protecting group such as BOC, FMOC, Cbz or benzyl which is removed in the Step 4 of the synthesis.

In respect of steps shown in Scheme 5 the following reactions conditions may be utilised.

Step 1 may be carried out by treating with AcOH and a suitable nitrite such as $NaNO_2$, in a suitable solvent, such as water, at a suitable temperature, such as 21° C., for a period of for example 1 hour.

Step 2 may be carried out with a suitable metal hydroxide such as LiOH or NaOH in an aqueous solvent such as water, methanol, ethanol or THF, at a suitable temperature, such as 21° C., for a period of for example 1 hour.

Step 3 may be carried out in the presence of a suitable strong base, such as $NaO^tBu$, NaH, BuLi or LDA, in a suitable solvent, such as DMF, THF or 1,4-dioxane, at a suitable temperature such as 70° C., for a period of, for example, 2 hours.

Step 4a (wherein the protecting group is BOC) may be carried out with a suitable acid, such as HCl in 1,4-dioxane or TFA in DCM, at a suitable temperature, such as 21° C., for a suitable period, for example 1 hour.

Step 4b (wherein the protecting group is FMOC) may be carried out with a piperidine solution, at a suitable temperature, such as room temperature, for a suitable period, for example 1 hour.

Step 4c (wherein the protecting group is Cbz or benzyl) may be carried out by hydrogenation in the presence of Pd/C and $H_2$ in a suitable solvent, such as methanol, ethanol or water, at a suitable temperature, such as 21° C., for a period of, for example, 16 hours.

wherein $R_1$, $R_2$, $R_3$, $R_4$, $R_5$, V, W, X, Y and Z are as defined for a compound of formula (I). If V or $R_4$ comprise a free amine, this will be protected by a suitable protecting group such as BOC, FMOC, Cbz or benzyl which is removed in step 2 of the synthesis.

In respect of steps shown in Scheme 6 the following reactions conditions may be utilised.

Step 1 may be carried out by treating with DIAD and $PPh_3$, in a suitable solvent, such as THF or diethylether, at a suitable temperature, such as 21° C., for a period of for example 18 hours.

Step 2a (wherein the protecting group is BOC) may be carried out with a suitable acid, such as HCl in 1,4-dioxane or TFA in DCM, at a suitable temperature, such as 21° C., for a suitable period, for example 1 hour.

Step 2b (wherein the protecting group is FMOC) may be carried out with a piperidine solution, at a suitable temperature, such as room temperature, for a suitable period, for example 1 hour.

Step 2c (wherein the protecting group is Cbz or benzyl) may be carried out by hydrogenation in the presence of Pd/C and $H_2$ in a suitable solvent, such as methanol, ethanol or water, at a suitable temperature such as 21° C., for a period of, for example, 16 hours.

Scheme 7:

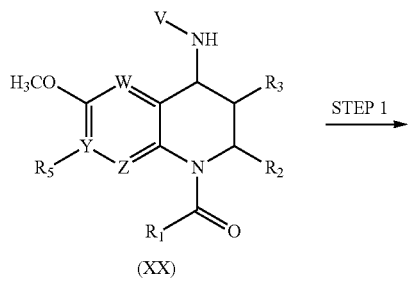

(XX)

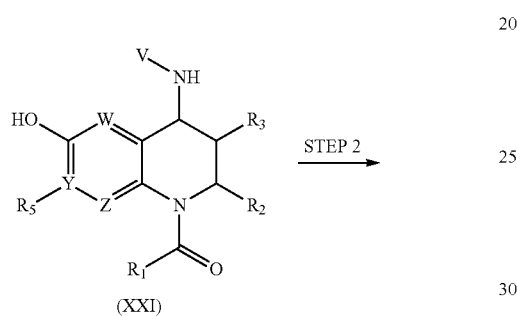

(XXI)

(XXII)

wherein $R_1$, $R_2$, $R_3$, $R_5$, V, W, Y and Z are as defined for a compound of formula (I).

In respect of steps shown in Scheme 7 the following reactions conditions may be utilised.

Step 1 may be carried out by treating with a demethylating agent such as $BBr_3$, HBr or TMSCl/NaI, in a suitable solvent, such as MeCN or DCM, at a suitable temperature, such as 0° C., for a period of for example 3 hours.

Step 2 may be carried out by treating with a triflating agent such as N,N-bis(trifluoromethylsulfonyl)aniline, Comins' reagent, or $Tf_2O$, optionally in the presence of a base, such as NaO$^t$Bu, NaOMe, or NaOEt, and optionally in the presence of DMAP, in a suitable aprotic solvent, such as DCM, THF, toluene or DMF, at a suitable temperature, such as 0° C., for a period of for example 4 hours.

Scheme 8:

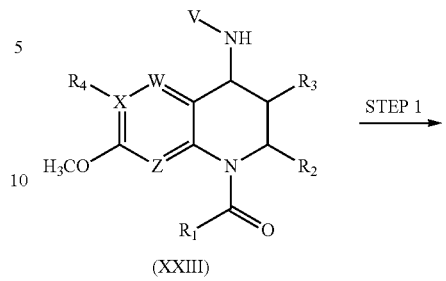

(XXIII)

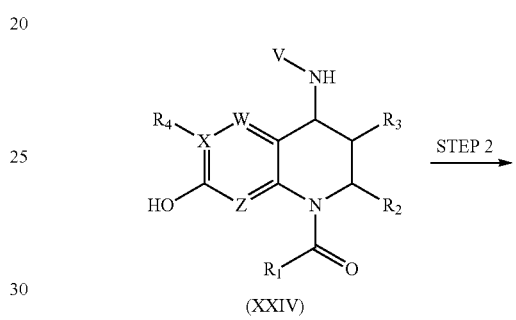

(XXIV)

(XXV)

wherein $R_1$, $R_2$, $R_3$, $R_4$, V, W, X and Z are as defined for a compound of formula (I).

In respect of steps shown in Scheme 8 the following reactions conditions may be utilised.

Step 1 may be carried out by treating with a demethylating agent such as $BBr_3$, HBr or TMSCl/NaI, in a suitable solvent, such as MeCN or DCM, at a suitable temperature, such as 0° C., for a period of for example 3 hours.

Step 2 may be carried out by treating with a triflating agent such as N,N-bis(trifluoromethylsulfonyl)aniline, Comins' reagent, or $Tf_2O$, in the presence of a base, such as NaO$^t$Bu, NaOMe, or NaOEt, ad optionally in the presence of DMAP, in a suitable aprotic solvent, such as DCM, THF, toluene or DMF, at a suitable temperature, such as 0° C., for a period of, for example, 4 hours.

Scheme 9:

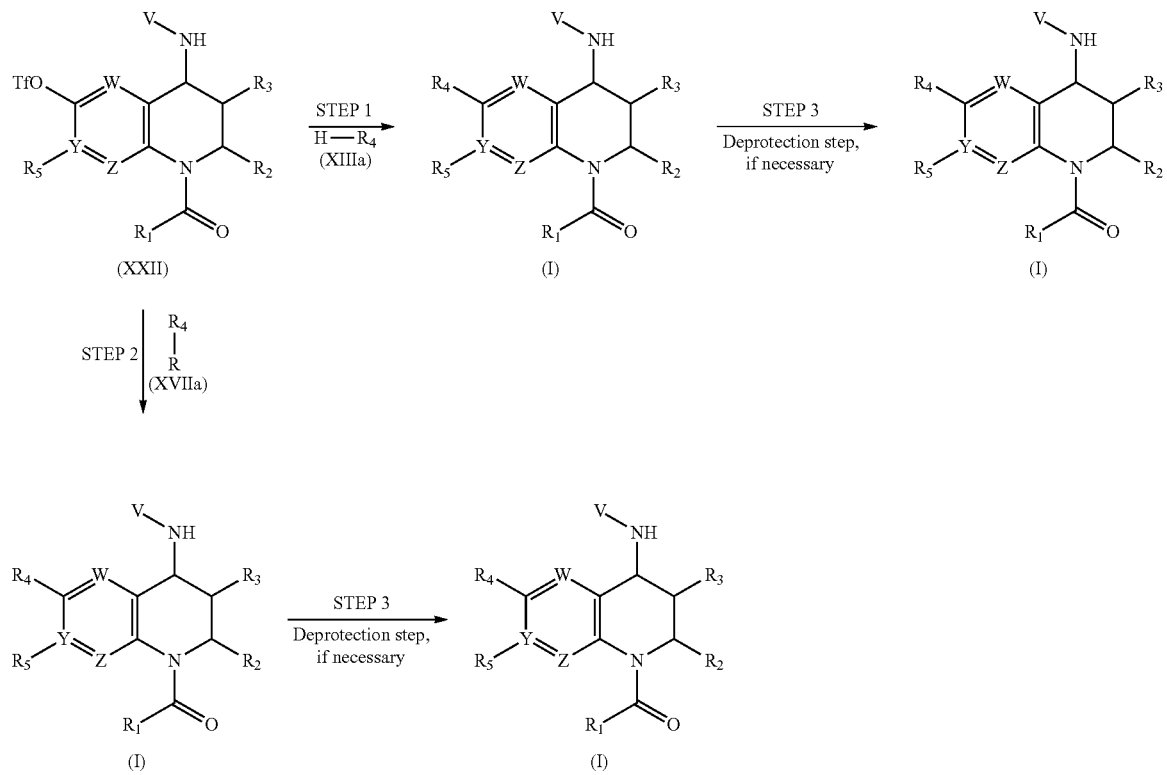

wherein $R_1$, $R_2$, $R_3$, $R_5$, V, W, X, Y and Z are as defined for a compound of formula (I). $R_4$ is —$NHR_9$, $N(C_{1-6}alkyl)$-$R_9$ or a heteroaromatic or heterocyclyl ring containing at least one nitrogen atom. $R_9$ is $C_{1-6}$ alkyl, $C_{3-7}$cycloalkyl, phenyl, heterocyclyl or heteroaromatic. If V or $R_4$ comprise a free amine, this will be protected by a suitable protecting group such as BOC, FMOC, Cbz or benzyl which is removed in the last step of the synthesis. R is selected from —$B(OH)_2$, —$BF_3K$ and

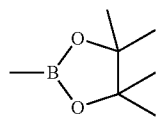

In respect of steps shown in Scheme 9 the following reactions conditions may be utilised.

Step 1 may be carried out with a suitable palladium catalyst, such as $Pd_2(dba)_3$, $PdCl_2(dppf)$, $Pd(OAc)_2$ or $Pd(PPh_3)_4$, a suitable phosphine ligand if required, such as BrettPhos, DavePhos, XantPhos, X-Phos or BINAP, a suitable base, such as $NaO^tBu$, $Cs_2CO_3$ or $K_3PO_4$, in a suitable solvent, such as toluene, THF or 1,4-dioxane, at a suitable temperature, such as 100° C., for a suitable period, such as 1 hour.

Step 2 may be carried out with a suitable palladium catalyst, such as $Pd_2(dba)_3$, $PdCl_2(dppf)$, $Pd(OAc)_2$ or $Pd(PPh_3)_4$, a suitable phosphine ligand if required, such as BrettPhos, DavePhos, XantPhos, X-Phos or BINAP, a suitable base, such as $NaO^tBu$, $Cs_2CO_3$ or $K_3PO_4$, in a suitable solvent, such as toluene, THF or 1,4-dioxane, at a suitable temperature, such as 100° C., for a suitable period, such as 1 hour.

Step 3a (wherein the protecting group is BOC) may be carried out with a suitable acid, such as HCl in 1,4-dioxane or TFA in DCM, at a suitable temperature, such as 21° C., for a suitable period, for example 1 hour.

Step 3b (wherein the protecting group is FMOC) may be carried out with a piperidine solution, at a suitable temperature, such as room temperature, for a suitable period, for example 1 hour.

Step 3c (wherein the protecting group is Cbz or benzyl) may be carried out by hydrogenation in the presence of Pd/C and $H_2$ in a suitable solvent, such as methanol, ethanol or water, at a suitable temperature such as 21° C., for a period of, for example, 16 hours.

Scheme 10:

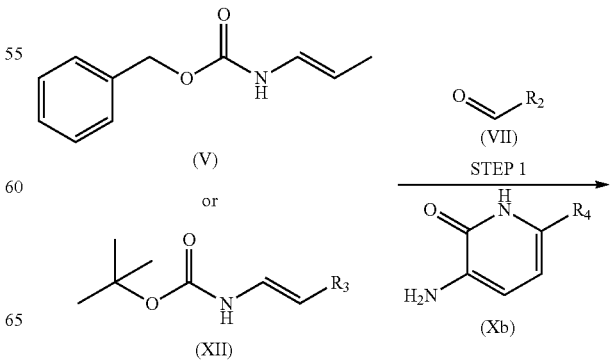

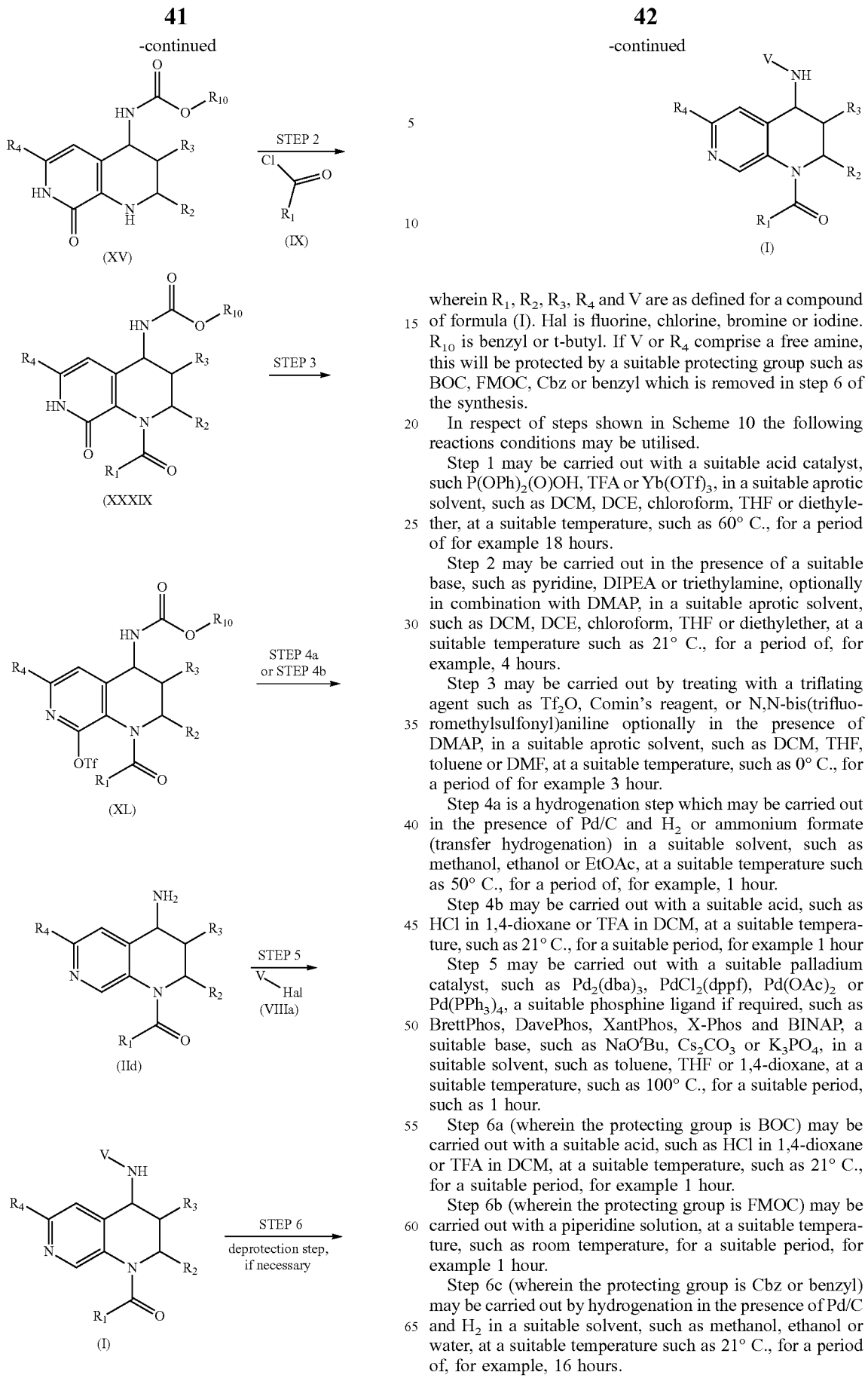

wherein $R_1$, $R_2$, $R_3$, $R_4$ and V are as defined for a compound of formula (I). Hal is fluorine, chlorine, bromine or iodine. $R_{10}$ is benzyl or t-butyl. If V or $R_4$ comprise a free amine, this will be protected by a suitable protecting group such as BOC, FMOC, Cbz or benzyl which is removed in step 6 of the synthesis.

In respect of steps shown in Scheme 10 the following reactions conditions may be utilised.

Step 1 may be carried out with a suitable acid catalyst, such $P(OPh)_2(O)OH$, TFA or $Yb(OTf)_3$, in a suitable aprotic solvent, such as DCM, DCE, chloroform, THF or diethylether, at a suitable temperature, such as 60° C., for a period of for example 18 hours.

Step 2 may be carried out in the presence of a suitable base, such as pyridine, DIPEA or triethylamine, optionally in combination with DMAP, in a suitable aprotic solvent, such as DCM, DCE, chloroform, THF or diethylether, at a suitable temperature such as 21° C., for a period of, for example, 4 hours.

Step 3 may be carried out by treating with a triflating agent such as $Tf_2O$, Comin's reagent, or N,N-bis(trifluoromethylsulfonyl)aniline optionally in the presence of DMAP, in a suitable aprotic solvent, such as DCM, THF, toluene or DMF, at a suitable temperature, such as 0° C., for a period of for example 3 hour.

Step 4a is a hydrogenation step which may be carried out in the presence of Pd/C and $H_2$ or ammonium formate (transfer hydrogenation) in a suitable solvent, such as methanol, ethanol or EtOAc, at a suitable temperature such as 50° C., for a period of, for example, 1 hour.

Step 4b may be carried out with a suitable acid, such as HCl in 1,4-dioxane or TFA in DCM, at a suitable temperature, such as 21° C., for a suitable period, for example 1 hour Step 5 may be carried out with a suitable palladium catalyst, such as $Pd_2(dba)_3$, $PdCl_2(dppf)$, $Pd(OAc)_2$ or $Pd(PPh_3)_4$, a suitable phosphine ligand if required, such as BrettPhos, DavePhos, XantPhos, X-Phos and BINAP, a suitable base, such as $NaO^tBu$, $Cs_2CO_3$ or $K_3PO_4$, in a suitable solvent, such as toluene, THF or 1,4-dioxane, at a suitable temperature, such as 100° C., for a suitable period, such as 1 hour.

Step 6a (wherein the protecting group is BOC) may be carried out with a suitable acid, such as HCl in 1,4-dioxane or TFA in DCM, at a suitable temperature, such as 21° C., for a suitable period, for example 1 hour.

Step 6b (wherein the protecting group is FMOC) may be carried out with a piperidine solution, at a suitable temperature, such as room temperature, for a suitable period, for example 1 hour.

Step 6c (wherein the protecting group is Cbz or benzyl) may be carried out by hydrogenation in the presence of Pd/C and $H_2$ in a suitable solvent, such as methanol, ethanol or water, at a suitable temperature such as 21° C., for a period of, for example, 16 hours.

Scheme 11:

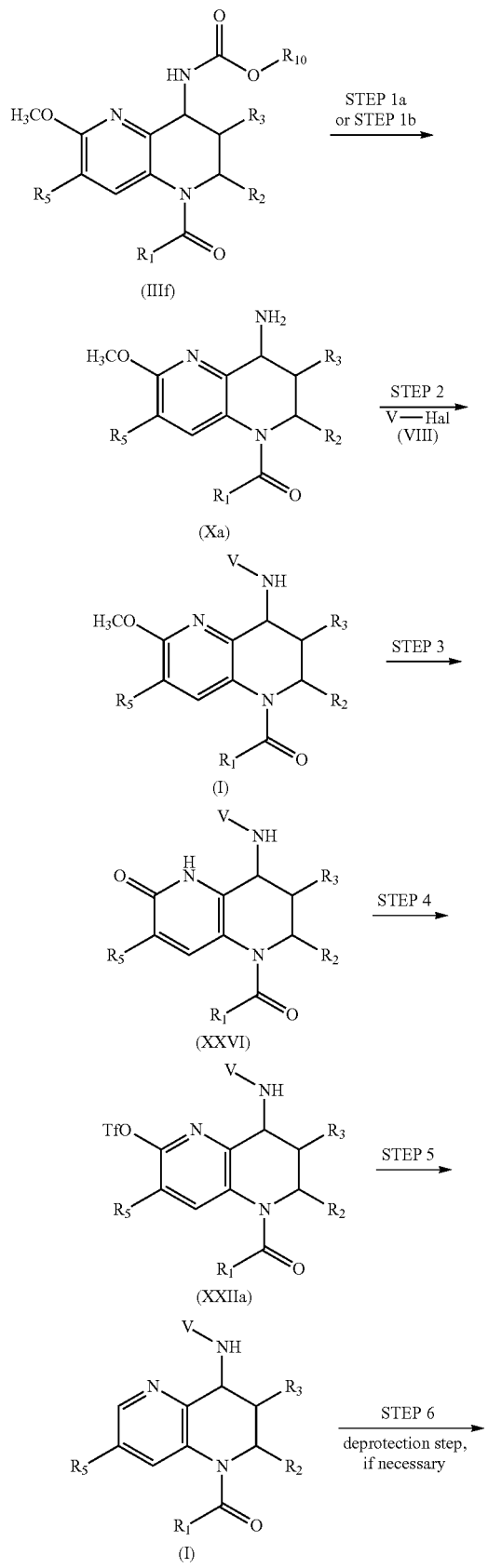
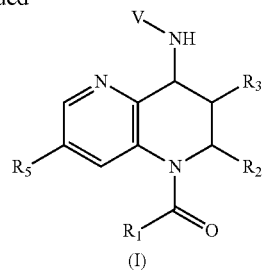

wherein $R_1$, $R_2$, $R_3$, $R_5$ and V are as defined for a compound of formula (I). $R_{10}$ is benzyl or t-butyl. Hal is fluorine, chlorine, bromine or iodine. If V comprises a free amine, this will be protected by a suitable protecting group such as BOC, FMOC, Cbz or benzyl, which is removed in the last step of the synthesis.

In respect of steps shown in Scheme 11 the following reactions conditions may be utilised.

Step 1a is a hydrogenation step which may be carried out in the presence of Pd/C and $H_2$ in a suitable solvent, such as methanol, ethanol or EtOAc, at a suitable temperature such as 21° C., for a period of, for example, 72 hours.

Step 1b may be carried out with a suitable acid, such as HCl in 1,4-dioxane or TFA in DCM, at a suitable temperature, such as 21° C., for a suitable period, for example 1 hour Step 2 may be carried out with a suitable palladium catalyst, such as $Pd_2(dba)_3$, $PdCl_2(dppf)$, $Pd(OAc)_2$ or $Pd(PPh_3)_4$, a suitable phosphine ligand if required, such as BrettPhos, DavePhos, XantPhos, X-Phos and BINAP, a suitable base, such as $NaO^tBu$, $Cs_2CO_3$ or $K_3PO_4$, in a suitable solvent, such as toluene, THF or 1,4-dioxane, at a suitable temperature, such as 100° C., for a suitable period, such as 1 hour.

Step 3 may be carried out by treating with a demethylating agent such as $BBr_3$, HBr or TMSCl/NaI, in a suitable solvent, such as MeCN or DCM, at a suitable temperature, such as 55° C., for a period of for example 3 hours.

Step 4 may be carried out by treating with a triflating agent such as Comin's reagent, N,N-bis(trifluoromethylsulfonyl)aniline, or $Tf_2O$, optionally in the presence of DMAP, in a suitable aprotic solvent, such as DCM, THF, toluene or DMF, at a suitable temperature, such as 21° C., for a period of for example 1 hour.

Step 5 may be carried out with a suitable palladium catalyst, such as $PdCl_2(dppf)$, $PdCl_2(PPh_3)_2$, or $Pd(PPh_3)_2$ a suitable base, such as triethylamine or ammonia, a suitable acid such as formic acid in a suitable solvent, such as DMF, methanol or 1,4-dioxane at a suitable temperature, such as 60° C., for a suitable period, such as 1 hour.

Step 6a (wherein the protecting group is BOC) may be carried out with a suitable acid, such as HCl in 1,4-dioxane or TFA in DCM, at a suitable temperature, such as 21° C., for a suitable period, for example 1 hour.

Step 6b (wherein the protecting group is FMOC) may be carried out with a piperidine solution, at a suitable temperature, such as room temperature, for a suitable period, for example 1 hour.

Step 6c (wherein the protecting group is Cbz or benzyl) may be carried out by hydrogenation in the presence of Pd/C and $H_2$ in a suitable solvent, such as methanol, ethanol or water, at a suitable temperature such as 21° C., for a period of, for example, 16 hours.

Scheme 12:

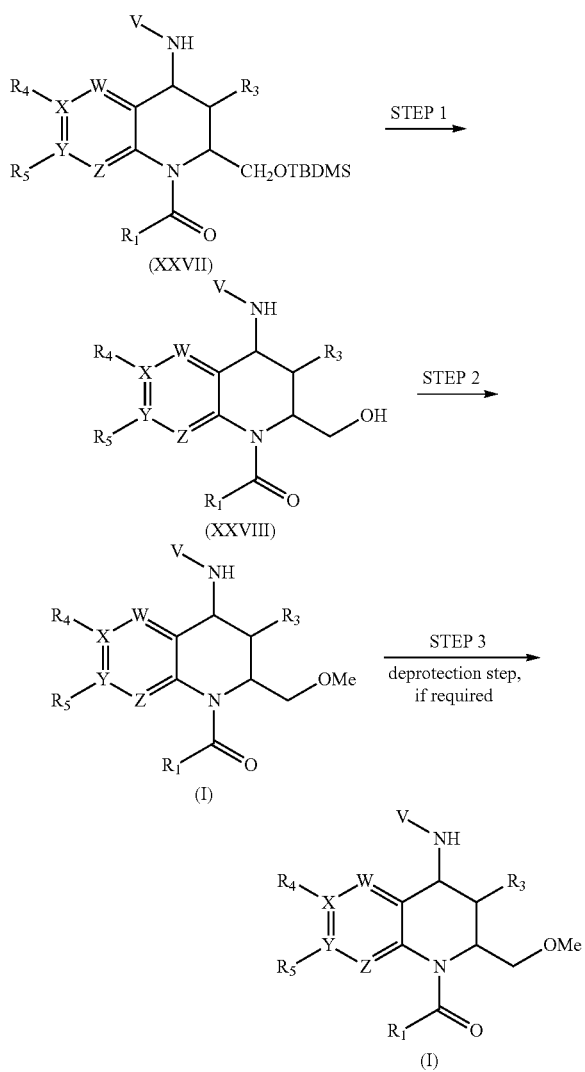

wherein $R_1$, $R_3$, $R_4$, $R_5$, V, W, X, Y and Z are as defined for a compound of formula (I). If V or $R_4$ comprise a free amine, this will be protected by a suitable protecting group such as BOC, FMOC, Cbz or benzyl, which is removed in Step 3 of the synthesis.

In respect of steps shown in Scheme 12 the following reactions conditions may be utilised.

Step 1 may be carried out by treating with a demethylating agent such as TBAF or Selectfluor, TMSCl/KF, in a suitable solvent, such as THF, MeCN, or DMF, at a suitable temperature, such as 21° C., for a period of for example 1 hour.

Step 2 may be carried out by treating with a methylating agent such as MeI, in a suitable solvent, such as THF, DMF, or toluene, in the presence of a strong base such as NaH, BuLi or LDA, at a suitable temperature, such as 0° C., for a period of for example 5 hours.

Step 3a (wherein the protecting group is BOC) may be carried out with a suitable acid, such as HCl in 1,4-dioxane or TFA in DCM, at a suitable temperature, such as 21° C., for a suitable period, for example 1 hour.

Step 3b (wherein the protecting group is FMOC) may be carried out with a piperidine solution, at a suitable temperature, such as room temperature, for a suitable period, for example 1 hour.

Step 3c (wherein the protecting group is Cbz or benzyl) may be carried out by hydrogenation in the presence of Pd/C and $H_2$ in a suitable solvent, such as methanol, ethanol or water, at a suitable temperature such as 21° C., for a period of, for example, 16 hours.

Scheme 13:

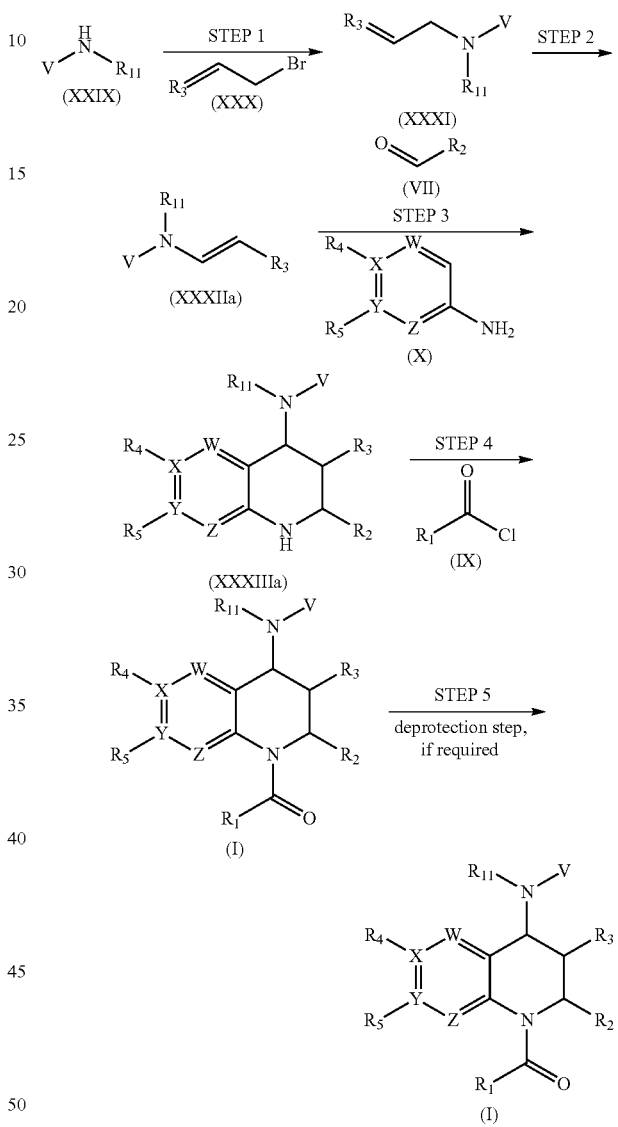

wherein $R_1$, $R_2$, $R_3$, $R_4$, $R_5$, V, W, X, Y and Z are as defined for a compound of formula (I). $R_{11}$ is $C_{1-4}$ alkyl. If V or $R_4$ comprise a free amine, this will be protected by a suitable protecting group such as BOC, FMOC, Cbz or benzyl, which is removed in Step 5 of the synthesis.

In respect of steps shown in Scheme 13 the following reactions conditions may be utilised.

Step 1 may be carried out in the presence of a base, such as KOH, NaOH, or $K_2CO_3$, in a suitable aprotic solvent, such as MeCN, DMF or THF, at a suitable temperature, such as 50° C., for a period of for example 7 hours.

Step 2 may be carried out in the presence of a rhodium catalyst, such as $(PPh_3)_3Rh(CO)H$, in a suitable aprotic solvent, such as DCM, THF or toluene, at a suitable temperature such as 60° C., for a period of, for example, 2 hours.

Step 3 may be carried out with a suitable acid catalyst, such P(OPh)$_2$(O)OH, TFA or Yb(OTf)$_3$, in a suitable aprotic solvent, such as DCM, DCE, chloroform, THF or diethylether, at a suitable temperature, such as −78° C., for a period of for example 5 hours.

Step 4 may be carried out in the presence of a suitable base, such as pyridine, DIPEA or triethylamine, optionally in combination with DMAP, in a suitable aprotic solvent, such as DCM, DCE, chloroform, THF or diethylether, at a suitable temperature such as 21° C., for a period of, for example, 1 hour.

Step 5a (wherein the protecting group is BOC) may be carried out with a suitable acid, such as HCl in 1,4-dioxane or TFA in DCM, at a suitable temperature, such as 21° C., for a suitable period, for example 1 hour.

Step 5b (wherein the protecting group is FMOC) may be carried out with a piperidine solution, at a suitable temperature, such as room temperature, for a suitable period, for example 1 hour.

Step 5c (wherein the protecting group is Cbz or benzyl) may be carried out by hydrogenation in the presence of Pd/C and H$_2$ in a suitable solvent, such as methanol, ethanol or water, at a suitable temperature such as 21° C., for a period of, for example, 16 hours.

Scheme 14:

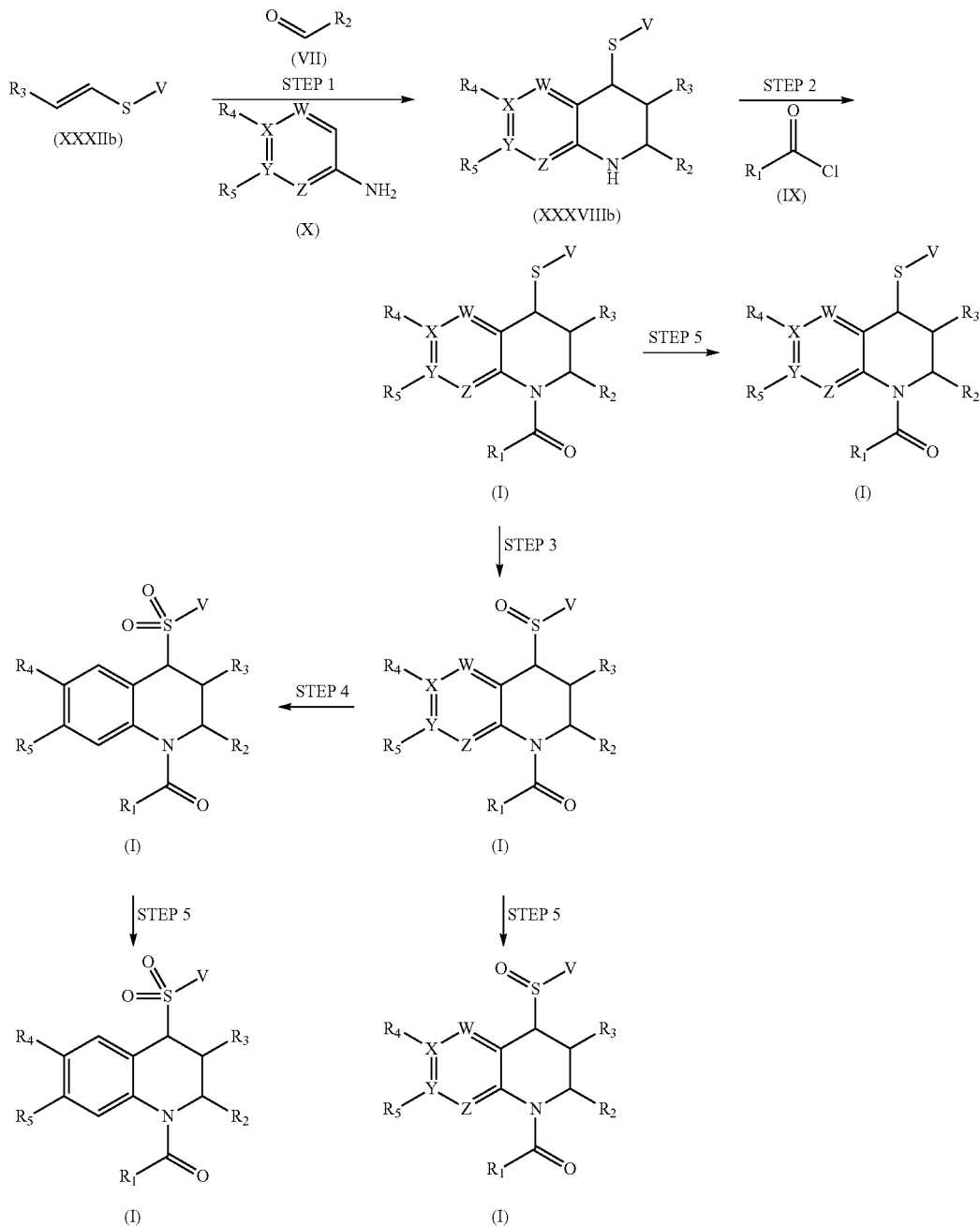

wherein $R_1$, $R_2$, $R_3$, $R_4$, $R_5$, V, W, X, Y and Z are as defined for a compound of formula (I). If V or $R_4$ comprise a free amine, this will be protected by a suitable protecting group such as BOC, FMOC, Cbz or benzyl, which is removed in Step 5 of the synthesis.

In respect of steps shown in Scheme 14 the following reactions conditions may be utilised.

Step 1 may be carried out with a suitable acid catalyst, such $P(OPh)_2(O)OH$, TFA or $Yb(OTf)_3$, in a suitable aprotic solvent, such as DCM, DCE, chloroform, THF or diethylether, at a suitable temperature, such as 0° C., for a period of for example 16 hour.

Step 2 may be carried out in the presence of a suitable base, such as pyridine, DIPEA or triethylamine, optionally in combination with DMAP, in a suitable aprotic solvent, such as DCM, DCE, chloroform, THF or diethylether, at a suitable temperature such as 21° C., for a period of, for example, 3 hours.

Step 3 may be carried out by treating with an oxidising agent such as mCPBA, $H_2O_2$, or $KMnO_4/MnO_2$, in a suitable solvent, such as DCM, toluene, or THF, at a suitable temperature, such as 21° C., for a period of for example 1 hour.

Step 5a (wherein the protecting group is BOC) may be carried out with a suitable acid, such as HCl in 1,4-dioxane or TFA in DCM, at a suitable temperature, such as 21° C., for a suitable period, for example 1 hour.

Step 5b (wherein the protecting group is FMOC) may be carried out with a piperidine solution, at a suitable temperature, such as room temperature, for a suitable period, for example 1 hour.

Step 5c (wherein the protecting group is Cbz or benzyl) may be carried out by hydrogenation in the presence of Pd/C and $H_2$ in a suitable solvent, such as methanol, ethanol or water, at a suitable temperature such as 21° C., for a period of, for example, 16 hours.

Scheme 15:

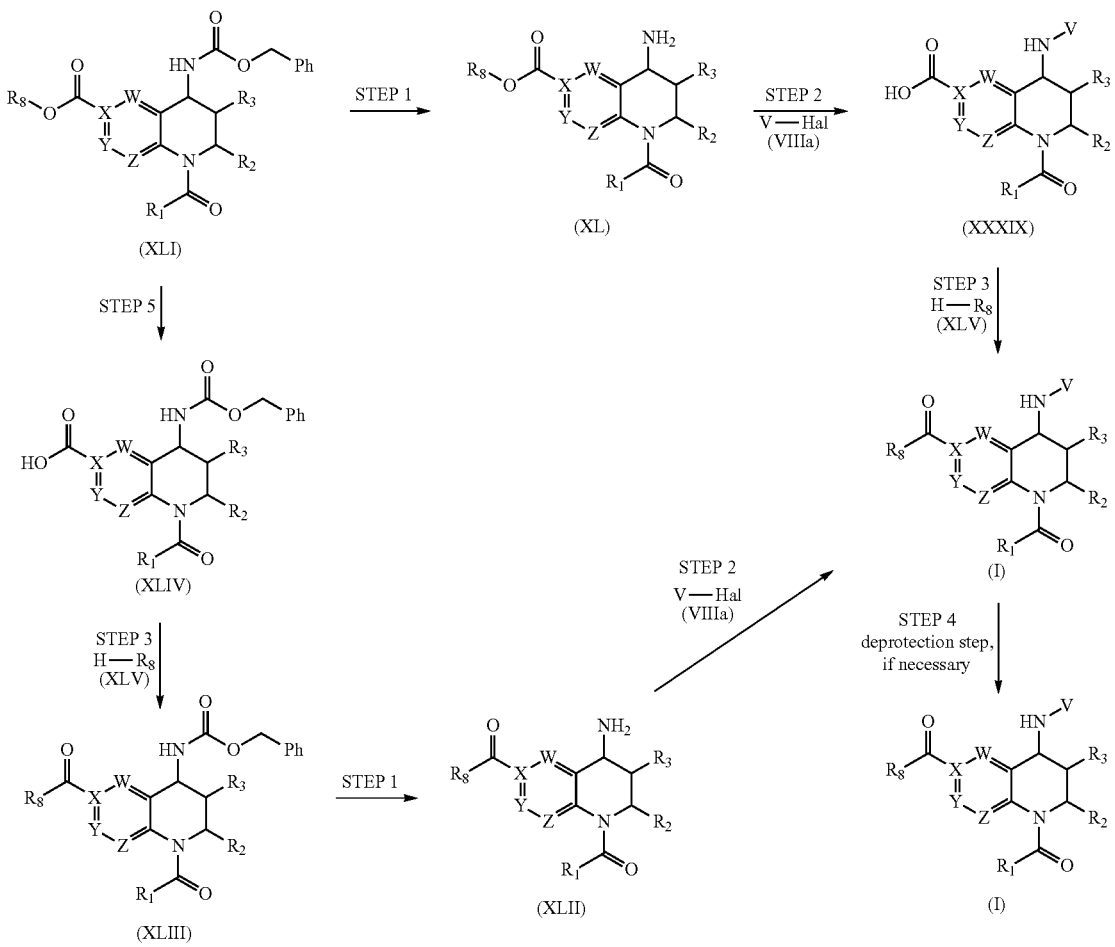

suitable solvent, such as DCM, toluene, or THF, at a suitable temperature, such as 21° C., for a period of for example 1 hour.

Step 4 may be carried out by treating with an oxidising agent such as mCPBA, $H_2O_2$, or $KMnO_4/MnO_2$, in a wherein $R_1$, $R_2$, $R_3$, $R_4$, $R_5$, V, W, X, Y and Z are as defined for a compound of formula (I). Hal is chlorine, bromine or iodine. $R_8$ is an appropriate amine; If V or $R_8$ comprise a free amine, this will be protected by a suitable protecting group such as BOC, FMOC, Cbz or benzyl, which is removed Step 4 of the synthesis.

In respect of steps shown in Scheme 1 the following reactions conditions may be utilised.

Step 1 is a hydrogenation step which may be carried out in the presence of Pd/C and $H_2$ in a suitable solvent, such as methanol, ethanol or EtOAc, at a suitable temperature such as 21° C., for a period of, for example, 4 hours.

Step 2 may be carried out with a suitable palladium catalyst, such as $Pd_2(dba)_3$, $PdCl_2(dppf)$, $Pd(OAc)_2$ or $Pd(PPh_3)_4$, a suitable phosphine ligand if required, such as BrettPhos, DavePhos, XantPhos, X-Phos and BINAP, a suitable base, such as NaO$^t$Bu, $Cs_2CO_3$ or $K_3PO_4$, in a suitable solvent, such as toluene, THF or 1,4-dioxane, at a suitable temperature, such as 100° C., for a suitable period, such as 1 hour; or alternatively under heating in a suitable solvent, such as NMP, DMSO, or DMF, in the presence of a suitable base, such as DIPEA, triethylamine or pyridine, at an appropriate temperature, for example 150 OC, for a period of, for example, 30 min.

Step 3 is an amide bond forming process which may be carried out by activating the acid as an acid chloride by reaction with a suitable chlorinating agent, such as thionyl chloride, oxalyl chloride or $POCl_3$, in a suitable solvent, such as DCM, chloroform or DCE at an appropriate temperature, for example 0° C.; or by reaction with a suitable activating group, such as HATU, COMU or DCC, in an appropriate solvent, such as DMF, THF or DCM, in the presence of a suitable base, for example DIPEA, triethylamine or pyridine, at an appropriate temperature, such as 21° C., for a period of, for example, 90 min.

Step 4 may be carried out with a suitable acid, such as HCl in 1,4-dioxane or TFA in DCM, at a suitable temperature, such as 21° C., for a suitable period, for example 1 hour.

Step 5 is a hydrolysis step and may be carried out in the presence of an aqueous hydroxide, such as LiOH, NaOH or KOH, in an appropriate solvent, for example THF, DMF or ethanol, at an appropriate temperature, for example 21° C., for a period of, for example, 2.5 hours.

Scheme 16:

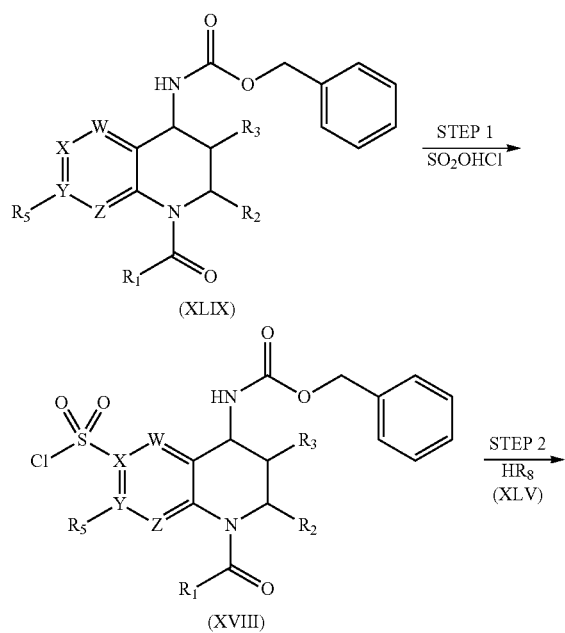

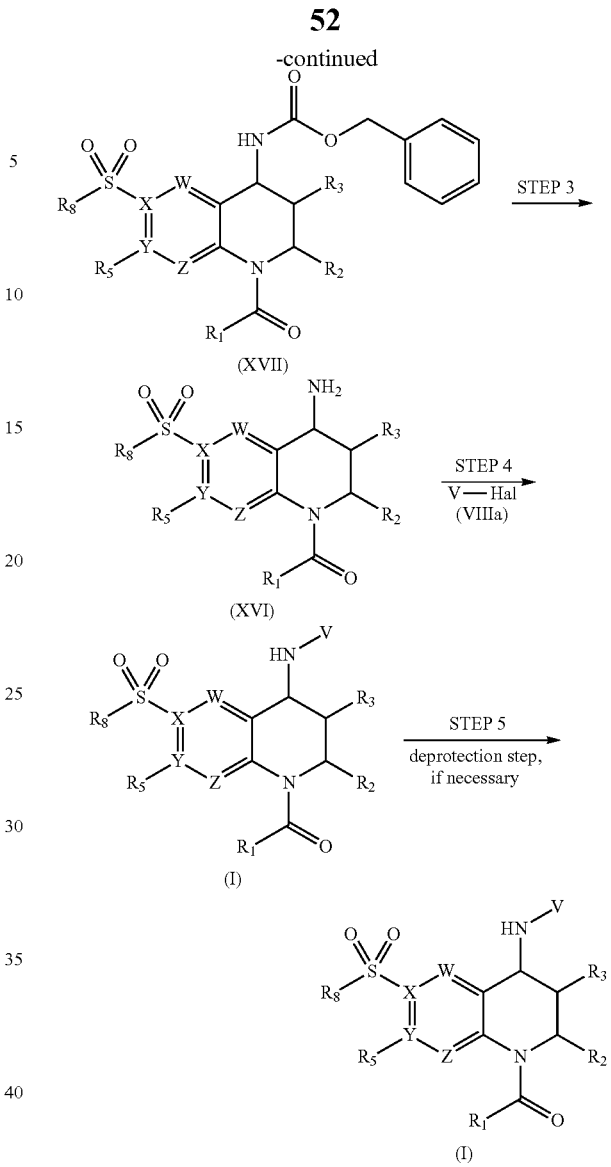

wherein $R_1$, $R_2$, $R_3$, $R_4$, $R_5$, V, W, X, Y and Z are as defined for a compound of formula (I). Hal is chlorine, bromine or iodine. $R_8$ is an appropriate amine; If V or $R_8$ comprise a free amine, this will be protected by a suitable protecting group such as BOC, FMOC, Cbz or benzyl, which is removed in Step 5 of the synthesis.

In respect of steps shown in Scheme 16 the following reactions conditions may be utilised.

Step 1 may be carried out with chlorosulfonic acid, in a suitable aprotic solvent, such as DCM, DCE or chloroform, at a suitable temperature, such as 0° C., for a period of for example 16 hours.

Step 2 may be carried out in the presence of a suitable base, such as pyridine, DIPEA or triethylamine, in a suitable aprotic solvent, such as DCM, DCE or chloroform, at a suitable temperature such as 21° C., for a period of, for example 3 hours.

Step 3 is a hydrogenation step which may be carried out in the presence of Pd/C and $H_2$ in a suitable solvent, such as methanol, ethanol or EtOAc, at a suitable temperature such as 21° C., for a period of, for example 4 hours.

Step 4 may be carried out with a suitable palladium catalyst, such as $Pd_2(dba)_3$, $PdCl_2(dppf)$, $Pd(OAc)_2$ or Pd(PPh$_3$)$_4$, a suitable phosphine ligand if required, such as BrettPhos, DavePhos, XantPhos, X-Phos and BINAP, a suitable base, such as NaO$^t$Bu, Cs$_2$CO$_3$ or K$_3$PO$_4$, in a suitable solvent, such as toluene, THF or 1,4-dioxane, at a suitable temperature, such as 100° C., for a period of, for example 1 hour.

Step 5 may be carried out with a suitable acid, such as HCl in 1,4-dioxane or TFA in DCM, at a suitable temperature, such as 21° C., for a period of, for example 1 hour.

Scheme 17:

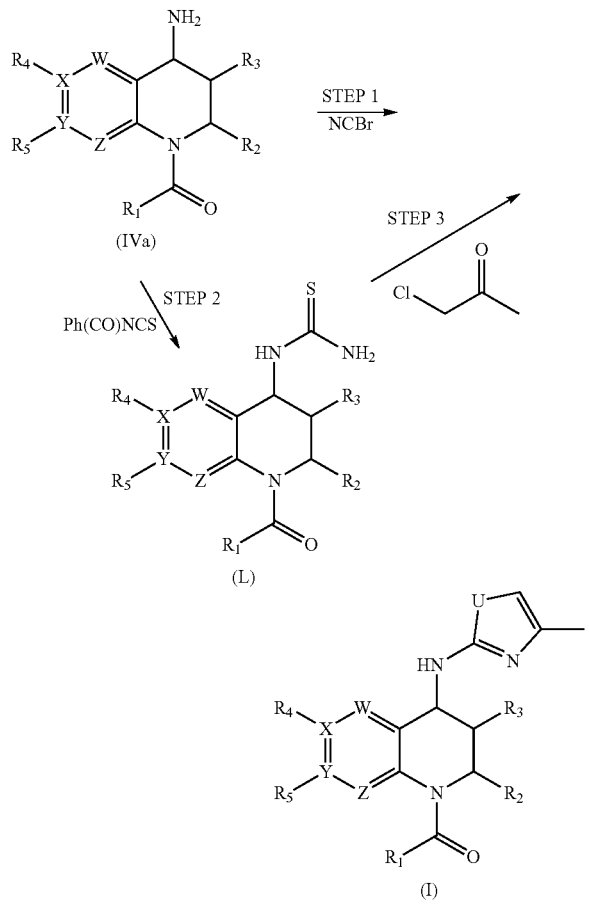

wherein R$_1$, R$_2$, R$_3$, R$_4$, R$_5$, V, W, X, Y and Z are as defined for a compound of formula (I).

In respect of steps shown in Scheme 17 the following reactions conditions may be utilised.

Step 1 may be carried out by reacting with cyanogen bromide and 1-hydroxypropan-2-one in the presence of an appropriate base, such as Na$_2$CO$_3$, K$_2$CO$_3$ or Cs$_2$CO$_3$, in a suitable solvent, such as THF, diethylether or 1,4-dioxane, at a suitable temperature, such as −20° C., for a period of, for example 20 hours.

Step 2 may be carried out by reacting with benzoyl isothiocyanate in a suitable solvent, such as DCM, chloroform or DCE at a suitable temperature, such as 21° C., for a suitable period, such as 16 hours; followed by reaction in the presence of an appropriate base, such as K$_2$CO$_3$, Na$_2$CO$_3$ or Cs$_2$CO$_3$, in a suitable solvent, such as methanol, THF and water, at a suitable temperature, such as 21° C., for a period of, for example 4 hours.

Step 3 may be carried out by reacting with 1-chloropropan-2-one in the presence of a suitable acid, such as HCl, H$_2$SO$_4$ or HBr, in a suitable solvent, such as ethanol, methanol or IPA, at a suitable temperature, such as 80° C., for a period of, for example 2 hours.

Scheme 18:

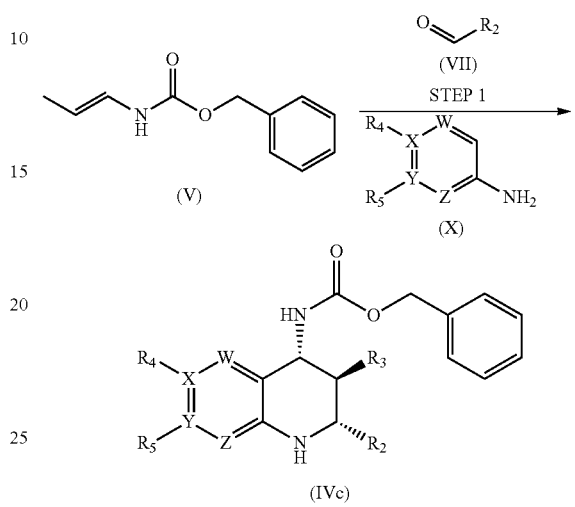

wherein R$_1$, R$_2$, R$_3$ R$_4$, R$_5$, V, W, X, Y and Z are as defined for a compound of formula (I).

In respect of steps shown in Scheme 18 the following reactions conditions may be utilised.

Step 1 may be carried out with a suitable chiral acid catalyst, such as (11bS)-2,6-bis(4-chlorophenyl)-4-hydroxy-8,9,10,11,12,13,14,15-octahydrodinaphtho[2,1-d:1',2'-f][1,3,2]dioxaphosphepine 4-oxide (for a literature reference see JACS, 2011, 133, 14804), in a suitable aprotic solvent, such as DCM, DCE, chloroform, THF or diethylether, at a suitable temperature, such as 0° C., for a period of, for example 40 hours.

Thus, in one embodiment the invention provides a process for preparing a compound of formula (I) comprising reacting a compound of formula (II)

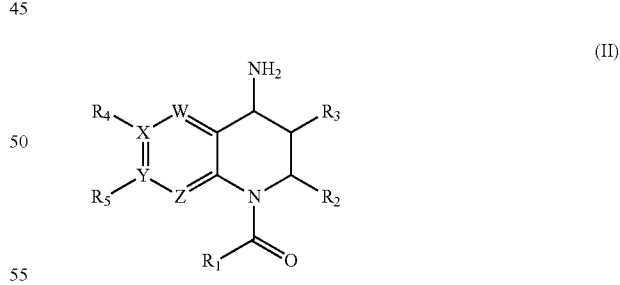

wherein R$_1$ R$_2$, R$_3$, R$_4$, R$_5$, W, X, Y and Z are as defined above, with a compound of formula (VIII)

V-Hal     (VIII)

wherein V is as defined above and Hal is fluorine, chlorine, bromine or iodine, in the presence of a catalyst, a phosphine ligand and a base; optionally followed by a deprotection step if required. In one embodiment the catalyst is Pd$_2$(dba)$_3$. In one embodiment the base is sodium tert-butoxide. In one embodiment the phosphine ligand is DavePhoss or BrettPhos.

In another embodiment the invention provides a process for preparing a compound of formula (I) comprising reacting a compound of formula (XXIV)

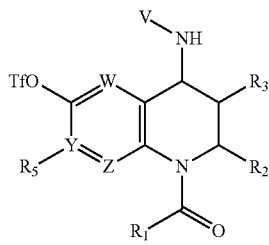

(XXIV)

wherein $R_1$, $R_2$, $R_3$, $R_5$, V, W, Y and Z are as defined above, with a compound of formula (XXXIV)

H—$R_4$ (XXXIV)

wherein $R_4$ is —$NHR_9$, $N(C_{1-6}alkyl)$-$R_9$ or a heteroaromatic or heterocyclyl ring containing at least one nitrogen atom; and $R_9$ is $C_{1-6}$alkyl, $C_{3-7}$cycloalkyl, phenyl, heterocyclyl or heteroaromatic, in the presence of a suitable catalyst and a phosphine ligand; optionally followed by a deprotection step if required. In one embodiment the catalyst is $Pd_2(dba)_3$. In one embodiment the phosphine ligand is BINAP.

In another embodiment the invention provides a process for preparing a compound of formula (I) comprising reacting a compound of formula (XXIV)

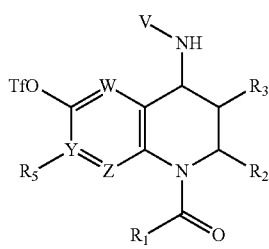

(XXIV)

wherein $R_1$ $R_2$, $R_3$, $R_5$, V, W, Y and Z are as defined above, with a compound of formula (XXXV)

R—$R_4$ (XXXV)

wherein $R_4$ is —$NHR_9$, $N(C_{1-6}alkyl)$-$R_9$ or a heteroaromatic or heterocyclyl ring containing at least one nitrogen atom; $R_9$ is $C_{1-6}$alkyl, $C_{3-7}$cycloalkyl, phenyl, heterocyclyl or heteroaromatic; and R is selected from —$B(OH)_2$, —$BF_3K$ and

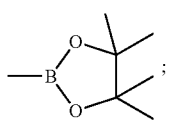

optionally followed by a deprotection step if required.

In another embodiment the invention provides a process for preparing a compound of formula (I) comprising reacting a compound of formula (XXI)

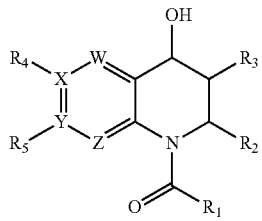

(XXI)

wherein $R_1$ $R_2$, $R_3$, $R_4$, $R_5$, W, X, Y and Z are as defined above, with a compound of formula (VIIIb)

X—V (VIIIb)

wherein V is as defined above and X is fluorine or hydroxide; optionally followed by a deprotection step if required.

In another embodiment the invention provides a process for preparing a compound of formula (II) comprising hydrogenation of a compound of formula (III)

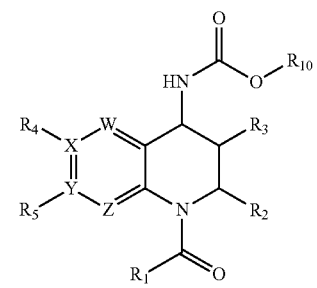

(III)

wherein $R_1$, $R_2$, $R_3$, $R_4$, $R_5$, $R_{10}$, W, X, Y and Z are as defined above.

In another embodiment the invention provides a process for preparing a compound of formula (XXI) wherein $R_{10}$ is t-butyl, comprising reacting a compound of formula (XX)

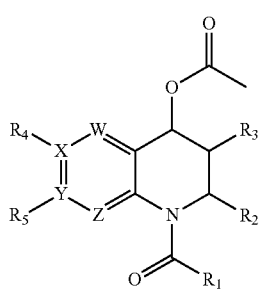

(XX)

wherein $R_1$ $R_2$, $R_3$, $R_4$, $R_5$, W, X, Y and Z are as defined above, with a base, for example potassium hydroxide.

In another embodiment the invention provides a process for preparing a compound of formula (III) wherein $R_3$ is methyl and $R_{10}$ is benzyl, comprising reacting a compound of formula (IV)

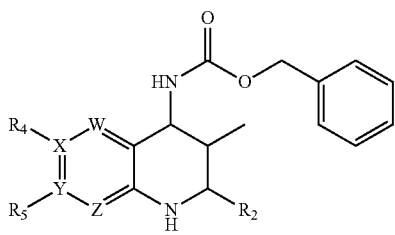

wherein $R_2$, $R_4$, $R_5$, W, X, Y and Z are as defined above, with a compound of formula (IX)

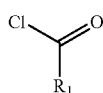

wherein $R_1$ is as defined above, in the presence of a suitable base such as pyridine or DIPEA. In one embodiment the reaction is carried out in the presence of a suitable base and DMAP.

In another embodiment the invention provides a process for preparing a compound of formula (IV) wherein $R_3$ is methyl, comprising reacting a compound of formula (V)

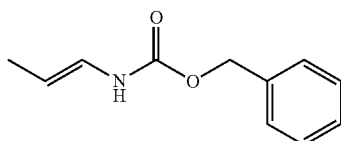

with a compound of formula (VII)

wherein $R_2$ is as defined above; and a compound of formula (VIII)

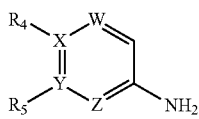

wherein $R_4$, $R_5$, W, X, Y and Z are as defined above, in the presence of a suitable acid catalyst for example, $P(OPh)_2(O)OH$.

In another embodiment the invention provides a process for preparing a compound of formula (V) wherein $R_3$ is methyl, comprising oxidation of a compound of formula (VI)

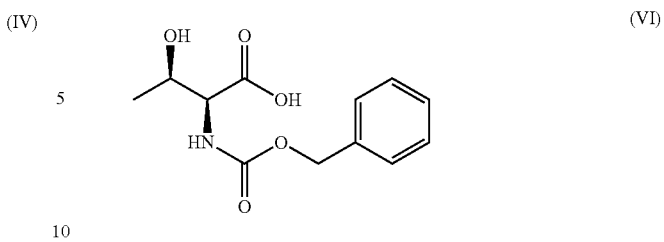

in the presence of a phosphine ligand. In one embodiment the oxidising agent is DIAD and the phosphine ligand is $PPh_3$.

In another embodiment the invention provides a process for preparing a compound of formula (XX) comprising reacting a compound of formula (X)

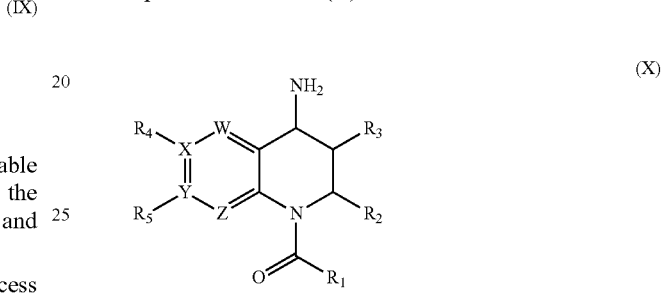

wherein $R_1$ $R_2$, $R_3$, $R_4$, $R_5$, W, X, Y and Z are as defined above, with acetic acid and sodium nitrite.

Compounds of formulae (VI), (VII), (VIII), (VIIIa), (VIIIb), (VIIIc), (IX), (X), (Xa), (Xb), (XI), (XIII), (XIIIa), (XIV), (XVII), (XVIIa), (XXIX), (XXX), (XXXIIIa), (XXXIIb) and (XLV) are commercially available or can be readily synthesised by known methods.

It will be appreciated by those skilled in the art that it may be advantageous to protect one or more functional groups of the compounds described above. Examples of protecting groups and the means for their removal can be found in T. W. Greene 'Protective Groups in Organic Synthesis' (4th edition, J. Wiley and Sons, 2006). Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—$COCF_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds described above form a yet further aspect of the invention.

The compounds of formula (I) and salts thereof are bromodomain inhibitors, and thus are believed to have potential utility in the treatment of diseases or conditions for which a bromodomain inhibitor is indicated.

The present invention thus provides a compound of formula (I) or a pharmaceutically acceptable salt thereof for use in therapy. The compound of formula (I) or a pharmaceutically salt thereof can be used in the treatment of diseases or conditions for which a bromodomain inhibitor is indicated.

The present invention thus provides a compound of formula (I) or a pharmaceutically acceptable salt thereof for use in the treatment of any diseases or conditions for which a bromodomain inhibitor is indicated. In one embodiment there is provided a compound of formula (I) or a pharmaceutically acceptable salt thereof for use in the treatment of acute or chronic auto-immune and/or inflammatory conditions. In another embodiment there is provided a compound of formula (I) or a pharmaceutically acceptable salt thereof for use in the treatment of diseases or conditions which involve inflammatory responses to infections with bacteria, viruses, fungi, parasites or their toxins. In another embodiment there is provided a compound of formula (I) or a pharmaceutically acceptable salt thereof for use in the treatment of viral infections. In a further embodiment there is provided a compound of formula (I) or a pharmaceutically acceptable salt thereof for use in the treatment of cancer.

Also provided is the use of a compound of formula (I) or a pharmaceutically acceptable salt thereof in the manufacture of a medicament for the treatment of diseases or conditions for which a bromodomain inhibitor is indicated. In one embodiment there is provided the use of a compound of formula (I) or a pharmaceutically acceptable salt thereof in the manufacture of a medicament for the treatment of acute or chronic auto-immune and/or inflammatory conditions. In another embodiment there is provided the use a compound of formula (I) or a pharmaceutically acceptable salt thereof in the manufacture of a medicament for in the treatment of diseases or conditions which involve inflammatory responses to infections with bacteria, viruses, fungi, parasites or their toxins. In another embodiment there is provided the use a compound of formula (I) or a pharmaceutically acceptable salt thereof in the manufacture of a medicament for in the treatment of viral infections. In another embodiment there is provided the use a compound of formula (I) or a pharmaceutically acceptable salt thereof in the manufacture of a medicament for in the treatment of cancer.

Also provided is a method of treating diseases or conditions for which a bromodomain inhibitor is indicated in a subject in need thereof which comprises administering a therapeutically effective amount of compound of formula (I) or a pharmaceutically acceptable salt thereof. In one embodiment there is provided a method of treating acute or chronic auto-immune and/or inflammatory conditions in a subject in need thereof which comprises administering a therapeutically effective amount of a compound of formula (I) or a pharmaceutically acceptable salt thereof. In another embodiment there is provided a method of treating diseases or conditions which involve inflammatory responses to infections with bacteria, viruses, fungi, parasites or their toxins in a subject in need thereof which comprises administering a therapeutically effective amount of a compound of formula (I) or a pharmaceutically acceptable salt thereof. In another embodiment there is provided a method of treating viral infections in a subject in need thereof which comprises administering a therapeutically effective amount of a compound of formula (I) or a pharmaceutically acceptable salt thereof. In further embodiment there is provided a method of treating cancer in a subject in need thereof which comprises administering a therapeutically effective amount of a compound of formula (I) or a pharmaceutically acceptable salt thereof.

Suitably the subject in need thereof is a mammal, particularly a human.

As used herein, the term "effective amount" means that amount of a drug or pharmaceutical agent that will elicit the biological or medical response of a tissue, system, or subject (e.g. a human) that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of acute or chronic autoimmune and/or inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, hypercholesterolemia, atherosclerosis, Alzheimer's disease, depression, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (keratoconjunctivitis Sicca), vernal keratoconjunctivitis, atopic keratoconjunctivitis, uveitis (such as anterior uveitis, pan uveitis, posterior uveitis, uveitis-associated macular edema), scleritis, diabetic retinopathy, diabetic macula edema, age-related macular dystrophy, hepatitis, pancreatitis, primary biliary cirrhosis, sclerosing cholangitis, Addison's disease, hypophysitis, thyroiditis, type I diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement and acute rejection of transplanted organs.

In one embodiment the acute or chronic autoimmune and/or inflammatory condition is a disorder of lipid metabolism via the regulation of APO-A1 such as hypercholesterolemia, atherosclerosis and Alzheimer's disease.

In another embodiment the acute or chronic autoimmune and/or inflammatory condition is a respiratory disorder such as asthma or chronic obstructive airways disease.

In another embodiment the acute or chronic autoimmune and/or inflammatory condition is a systemic inflammatory disorder such as rheumatoid arthritis, osteoarthritis, acute gout, psoriasis, systemic lupus erythematosus, multiple sclerosis or inflammatory bowel disease (Crohn's disease and Ulcerative colitis).

In another embodiment the acute or chronic autoimmune and/or inflammatory condition is multiple sclerosis.

In a further embodiment the acute or chronic autoimmune and/or inflammatory condition is Type I diabetes.

Bromodomain inhibitors may be useful in the treatment of diseases or conditions which involve inflammatory responses to infections with bacteria, viruses, fungi, parasites or their toxins, such as sepsis, acute sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus. In one embodiment the disease or condition which involves an inflammatory response to an infection with bacteria, a virus, fungi, a parasite or their toxins is acute sepsis.

Bromodomain inhibitors may be useful in the treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of fibrotic conditions such as idiopathic pulmonary fibrosis, renal fibrosis, post-operative stricture, keloid scar formation, scleroderma (including morphea) and cardiac fibrosis.

Bromodomain inhibitors may be useful in the treatment of viral infections such as herpes simplex infections and reactivations, cold sores, herpes zoster infections and reactivations, chickenpox, shingles, human papilloma virus (HPV), human immunodeficiency virus (HIV), cervical neoplasia, adenovirus infections, including acute respiratory disease, poxvirus infections such as cowpox and smallpox and African swine fever virus. In one embodiment the viral infection is a HPV infection of skin or cervical epithelia. In another embodiment the viral infection is a latent HIV infection.

Bromodomain inhibitors may be useful in the treatment of cancer, including hematological (such as leukaemia, lymphoma and multiple myeloma), epithelial including lung, breast and colon carcinomas, midline carcinomas, mesenchymal, hepatic, renal and neurological tumours.

Bromodomain inhibitors may be useful in the treatment of one or more cancers selected from brain cancer (gliomas), glioblastomas, Bannayan-Zonana syndrome, Cowden disease, Lhermitte-Duclos disease, breast cancer, inflammatory breast cancer, colorectal cancer, Wilm's tumor, Ewing's sarcoma, rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukaemia, erythroleukemia, malignant lymphoma, Hodgkins lymphoma, non-Hodgkins lymphoma, lymphoblastic T-cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), NUT-midline carcinoma and testicular cancer.

In one embodiment the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is breast cancer. In another embodiment the cancer is colorectal cancer.

In one embodiment the disease or condition for which a bromodomain inhibitor is indicated is selected from diseases associated with systemic inflammatory response syndrome, such as sepsis, burns, pancreatitis, major trauma, haemorrhage and ischaemia. In this embodiment the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac or gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns.

As used herein the reference to the "treatment" of a particular disease or condition includes the prevention or prophylaxis of such a disease or condition.

The term "diseases or conditions for which a bromodomain inhibitor is indicated", is intended to include each of or all of the above diseases or conditions.

The invention further provides for a method for inhibiting a bromodomain which comprises contacting the bromodomain with a compound of formula (I) or a pharmaceutically acceptable salt thereof.

While it is possible that for use in therapy, a compound of formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or a pharmaceutically acceptable salt and one or more pharmaceutically acceptable carriers, diluents or excipients. The compounds of formula (I) and pharmaceutically acceptable salts are as described above.

The carrier(s), diluent(s) or excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable carriers, diluents or excipients. The pharmaceutical composition can be used in the treatment of any of the conditions described herein.

Since the compounds of formula (I) are intended for use in pharmaceutical compositions it will be readily understood that they are each preferably provided in substantially pure form, for example, at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Compositions for oral administration may be designed to provide a modified release profile so as to sustain or otherwise control the release of the therapeutically active agent.

Where appropriate, dosage unit compositions for oral administration can be microencapsulated. The composition may be prepared to prolong or sustain the release as for example by coating or embedding particulate material in polymers, wax or the like.

The compounds of formula (I) and pharmaceutically acceptable salts thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of the compound of formula (I), or a pharmaceutically acceptable salt thereof, by weight of the composition.

For treatments of the eye or other external tissues, for example mouth and skin, the compositions are preferably applied as a topical ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent. Compositions to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) *Adv. Drug Deliv. Rev.* 3; 57:1595-639, herein incorporated by reference for purposes of its teachings of examples of polymers for use in ocular drug delivery.

Dosage forms for nasal or inhaled administration may conveniently be formulated as aerosols, solutions, suspensions, gels or dry powders.

For compositions suitable and/or adapted for inhaled administration, it is preferred that the compound of formula (I) or a pharmaceutically acceptable salt thereof, is in a particle-size-reduced form e.g. obtained by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metal salt of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354.

A therapeutically effective amount of a compound of formula (I) or a pharmaceutically acceptable salt thereof, will depend upon a number of factors including, for example, the age and weight of the subject, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, more preferably 0.5 to 1000 mg, of a compound of formula (I) or a pharmaceutically acceptable salt thereof, calculated as the free base. Each dosage unit for nasal or inhaled administration preferably contains from 0.001 to 50 mg, more preferably 0.01 to 5 mg, of a compound of the formula (I) or a pharmaceutically acceptable salt thereof, calculated as the free base.

The pharmaceutically acceptable compounds of formula (I) and pharmaceutically acceptable salts thereof, can be administered in a daily dose (for an adult patient) of, for example, an oral or parenteral dose of 0.01 mg to 3000 mg per day, 0.5 to 1000 mg per day or 100 mg to 2500 mg per day, or a nasal or inhaled dose of 0.001 to 50 mg per day or 0.01 to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof may be employed alone or in combination with other therapeutic agents. Combination therapies according to the present invention thus comprise the administration of at least one compound of formula (I) or a pharmaceutically acceptable salt thereof, and the use of at least one other therapeutically active agent. Preferably, combination therapies according to the present invention comprise the administration of at least one compound of formula (I) or a pharmaceutically acceptable salt thereof, and at least one other therapeutically active agent. The compound(s) of formula (I) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of formula (I) and pharmaceutically acceptable salts thereof, and the other therapeutically active agent(s) and the relative timings of administration will be selected in order to achieve the desired combined therapeutic effect. Thus in a further aspect, there is provided a combination comprising a compound of formula (I) or a pharmaceutically acceptable salt thereof, together with one or more other therapeutically active agents.

Thus in one aspect, the compound of formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example selected from antibiotics, anti-virals, glucocorticosteroids, muscarinic antagonists beta-2 agonists and Vitamin D3 analogues. In a further embodiment a compound of formula (I) or a pharmaceutically acceptable salt thereof may be used in combination with a further therapeutic agent which is suitable for the treatment of cancer. Examples of such further therapeutic agents are described in Cancer Principles and Practice of Oncology by V. T. Devita and S. Hellman (editors), $6^{th}$ edition (2001), Lippincott Williams & Wilkins Publishers. A person of ordinary skill in the art would be able to discern which combinations of agents would be useful based on the particular characteristics of the drugs and the cancer involved. Further therapeutic agents to be used in combination with the compound of formula (I) or a pharmaceutically acceptable salt thereof include, but are not limited to, anti-microtubule agents (such as diterpenoids and vinca alkaloids); platinum coordination complexes; alkylating agents (such as nitrogen mustards, oxazaphosphorines, alkylsulphonates, nitrosoureas, and triazenes); antibiotic agents (such as anthracyclins, actinomycins and bleomycins); topoisomerase II inhibitors (such as epipodophyllotoxins); antimetabolites (such as purine and pyrimidine analogues and anti-folate compounds); topoisomerase I inhibitors (such as camptothecins; hormones and hormonal analogues); signal transduction pathway inhibitors (such as tyropsine receptor inhibitors); non-receptor tyrosine kinase angiogenesis inhibitors; immunotherapeutic agents; proapoptotic agents; epigenetic or transcriptional modulators (such as histone deacetylase inhibitors) and cell cycle signaling inhibitors.

It will be appreciated that when the compound of formula (I) or a pharmaceutically acceptable salt thereof, is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The compounds of formula (I) and pharmaceutically acceptable salts thereof, may be prepared by the methods described below or by similar methods. Thus the following Intermediates and Examples serve to illustrate the preparation of the compounds of formula (I) and pharmaceutically acceptable salts thereof, and are not to be considered as limiting the scope of the invention in any way.

General Experimental Details

All temperatures referred to are in ° C.

The names of the following compounds have been obtained using the compound naming programme "ACD Name Pro 6.02" or ChemDraw Ultra 12.0.

Abbreviations 1,2-DCE 1,2-dichloroethane
AcOH acetic acid
BINAP 2,2'-bis(diphenylphosphino)-1,1'-binaphthyl
BBr$_3$ boron tribromide
BOC tert-butyloxycarbonyl
BrettPhos 2-(dicyclohexylphosphino)-3,6-dimethoxy-2'-4'-6'-tri-i-propyl-1,1'-biphenyl
BuLi butyllithium
CaCO$_3$ calcium carbonate
Comin's reagent N-(5-chloropyridin-2-yl)-1,1,1-trifluoro-N-((trifluoromethyl)sulfonyl) methanesulfonamide
Cs$_2$CO$_3$ cesium carbonate
CHCl$_3$ chloroform
CV column volume
DavePhos 2-dicyclohexylphosphino-2'-(dimethylamino)biphenyl
D6-DMSO deuterated dimethylsulfoxide
DCM dichloromethane
DIAD diisopropyl azodicarboxylate
DIPEA diisopropylethylamine
DMAP 4-dimethylaminopyridine
DMF dimethylformamide
DMSO dimethylsulfoxide
DPPA diphenylphosphoryl azide
Et$_3$N triethylamine
EtOAc ethyl acetate
FMOC fluorenylmethyloxycarbonyl
h hour(s)
HATU O-(7-azabenzotriazol-1-yl)-N,N,N',N'-tetramethyluronium hexafluorophosphate
HCl hydrochloric acid
HCO$_2$H formic acid
IPA isopropyl alcohol
i-PrOAc isopropylacetate
i-Pr$_2$O diisopropyl ether
K$_2$CO$_3$ potassium carbonate
KOH potassium hydroxide
LCMS liquid chromatography-mass spectrometry
LiOH lithium hydroxide
M molar (concentration)
mCPBA meta-chloroperoxybenzoic acid
MDAP mass directed autoprep
MeCN acetonitrile
MeI methyl iodide
MeOH methanol
min minute(s)
N normal (concentration)
N$_2$ nitrogen
Na$_2$CO$_3$ sodium carbonate
NaI sodium iodide
NaH sodium hydride
NaNO$_2$ sodium nitrite
Na(OAc)$_3$BH sodium triacetoxy borohydride
NaO$^t$Bu sodium tert-butoxide
Na$_2$SO$_4$ sodium sulphate
NBS N-bromosuccinimide
NEt$_3$ triethylamine
NMP N-methyl-2-pyrrolidone
OTf trifluoromethanesulfonate
PEPPSI pyridine-enhanced precatalyst preparation stabilization and initiation
Pd/C palladium on carbon
PdCl$_2$(PPh)$_3$ bis(triphenylphosphine)palladium(II) dichloride
PdCl$_2$(dppf) [1,1'-bis(diphenylphosphino)ferrocene]palladium(II) dichloride
Pd$_2$(dba)$_3$ tris(dibenzylideneacetone)dipalladium (0)
Pd(PPh$_3$)$_4$ tetrakis(triphenylphosphine)palladium(0)
P(OPh)$_2$(O)OH diphenyl hydrogen phosphate
PPh$_3$ triphenylphosphine
Rh cat. rhodium catalyst
Rt retention time
rt room temperature
SPE solid phase extraction
TBAF tetra-n-butylammonium fluoride
TBME tert-butyl methyl ether
Tf$_2$O trifluoromethanesulfonic anhydride
TFA trifluoroacetic acid
TPPTS 3,3',3"-phosphinidynetris(benzenesulfonic acid) trisodium salt
TMSCl trimethylsilyl chloride
THF tetrahydrofuran
UPLC ultra performance liquid chromatography
XantPhos 1,1'-(9,9-dimethyl-9H-xanthene-4,5-diyl)bis[1,1-diphenylphosphine
X-Phos 2-dicyclohexylphosphino-2',4',6'-triisopropylbiphenyl
Yb(OTf)$_3$ ytterbium triflate LCMS Methodology Formic Method LC Conditions The UPLC analysis was conducted on an Acquity UPLC BEH C18 column (50 mm×2.1 mm, i.d. 1.7 µm packing diameter) at 40° C.

The solvents employed were:
A=0.1% v/v solution of formic acid in water
B=0.1% v/v solution of formic acid in acetonitrile
The gradient employed was:

| Time (min) | Flow rate (mL/min) | % A | % B |
| --- | --- | --- | --- |
| 0 | 1 | 97 | 3 |
| 1.5 | 1 | 0 | 100 |
| 1.9 | 1 | 0 | 100 |
| 2.0 | 1 | 97 | 3 |

The UV detection was a summed signal from wavelength of 210 nm to 350 nm.

MS Conditions

MS: Waters ZQ
Ionisation mode: Alternate-scan positive and negative electrospray
Scan range: 100 to 1000 AMU
Scan time: 0.27 sec
Inter scan delay: 0.10 sec HpH Method LC Conditions The UPLC analysis was conducted on an Acquity UPLC BEH C18 column (50 mm×2.1 mm, i.d. 1.7 µm packing diameter) at 40° C.

The solvents employed were:

A=10 mM ammonium hydrogen carbonate in water adjusted to pH10 with ammonia solution B=acetonitrile The gradient employed was:

| Time (min) | Flow rate (ml/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 0 | 100 |

The UV detection was a summed signal from wavelength of 210 nm to 350 nm.

MS Conditions

MS: Waters ZQ

Ionisation mode: Alternate-scan positive and negative electrospray

Scan range: 100 to 1000 AMU

Scan time: 0.27 sec

Inter scan delay: 0.10 sec

NMR

Spectra were run on a 400 mHz NMR machine at either 302 K or for VT spectra at 392-393 K.

Intermediate 1: (E)-benzyl prop-1-en-1-ylcarbamate

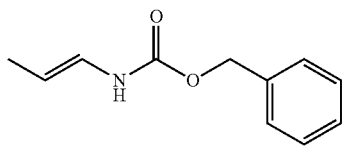

Diisopropyl azodicarboxylate (4.05 mL, 20.85 mmol) was added drop-wise over 5 min to a solution of triphenylphosphine (5.47 g, 20.85 mmol) in THF (125 mL) at −78 OC. The mixture was stirred for 15 min and then (2S,3R)-2-(((benzyloxy)carbonyl)amino)-3-hydroxybutanoic acid (4.8 g, 18.95 mmol) in THF (50 mL) was added drop-wise over 10 min still at −78° C. The solution was stirred for 1 h at −78° C. and allowed to warm to rt and stirred overnight. The solvent was then evaporated in vacuo and the residue was loaded onto a 100 g silica cartridge and purified by column chromatography using a gradient 0-30% of ethyl acetate in cyclohexane. Desired fractions were combined and evaporated in vacuo to afford the product as a white solid (3.06 g).

LCMS (2 min Formic): Rt=0.99 min, [MH]$^+$ not observed.

Intermediate 2: rac-benzyl ((2S,3S,4R)-6-bromo-2,3-dimethyl-1,2,3,4-tetrahydroquinolin-4-yl)carbamate

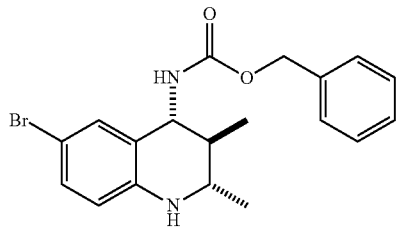 [SMILES: C[C@H]1[C@H](C)Nc2ccc(Br)cc2[C@@H]1NC(=O)OCc1ccccc1]

Under a nitrogen atmosphere, to a solution of acetaldehyde (0.027 mL, 0.475 mmol) in dry DCM (3 mL) was added 4-bromoaniline (82 mg, 0.475 mmol). The reaction was stirred at rt for 1 h and then cooled to 0° C. Solutions of diphenyl hydrogen phosphate (12 mg, 0.048 mmol) in dry DCM (1.5 mL) and (E)-benzyl prop-1-en-1-ylcarbamate (for a preparation see Intermediate 1, 100 mg, 0.523 mmol) in dry DCM (1.5 mL) were added. The reaction was stirred at 0° C. for 2 h and allowed to stand at rt overnight. The solvent was then evaporated in vacuo. The residue was loaded onto a 25 g silica cartridge and purified by column chromatography using a gradient 0-30% of ethyl acetate in cyclohexane. Desired fractions were combined and evaporated in vacuo to afford the product as a white solid (129 mg). LCMS (2 min Formic): Rt=1.23 min, [MH]$^+$=389, 391.

Intermediate 3: rac-benzyl ((2S,3R,4R)-1-acetyl-6-bromo-2,3-dimethyl-1,2,3,4-tetrahydroquinolin-4-yl)carbamate

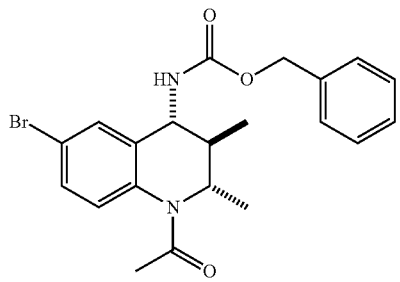 [SMILES: CC(=O)N1c2ccc(Br)cc2[C@H](NC(=O)OCc2ccccc2)[C@@H](C)[C@@H]1C]

rac-Benzyl ((2S,3S,4R)-6-bromo-2,3-dimethyl-1,2,3,4-tetrahydroquinolin-4-yl)carbamate (for a preparation see Intermediate 2, 284 mg, 0.728 mmol) was taken up in dry dichloromethane (DCM) (5 mL) under nitrogen at rt. Pyridine (0.177 mL, 2.185 mmol) then acetyl chloride (0.078 mL, 1.092 mmol) were added and the reaction was stirred for 2 h. The reaction was partitioned between ethyl acetate (40 mL) and saturated sodium bicarbonate (20 mL). The organic layer was extracted and washed with water (30 mL) and brine (30 mL) and then dried through a hydrophobic frit and concentrated in vacuo. The crude product was taken up in the minimum of DCM and applied to a 100 g silica cartridge and eluted with a gradient 0-100% of ethyl acetate in cyclohexane. Desired fractions were combined and evaporated in vacuo to afford the product as a white solid (286 mg).

LCMS (2 min Formic): Rt=1.13 min, [MH]$^+$=431, 433.

Intermediate 4: rac-benzyl ((2S,3S,4R)-2,3-dimethyl-1,2,3,4-tetrahydroquinolin-4-yl)carbamate

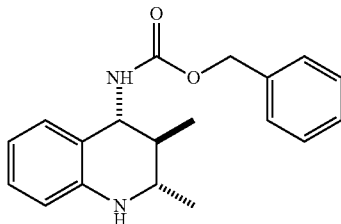

Under a nitrogen atmosphere, to a solution of acetaldehyde (1.35 mL, 24.0 mmol) in dry DCM (130 mL) was added aniline (2.19 mL, 24 mmol). The reaction was stirred at rt for 1 h and then cooled to 0° C. Solutions of diphenyl hydrogen phosphate (0.60 g, 2.40 mmol) in dry DCM (60 mL) and (E)-benzyl prop-1-en-1-ylcarbamate (for a preparation see Intermediate 1, 5.05 g, 26.4 mmol) in dry DCM (60 mL) were added. The reaction was stirred at 0° C. for 3 h and at rt for 1 h. Acetaldehyde (1.347 mL, 24.0 mmol) was then added and the reaction mixture was stirred at rt overnight. Acetaldehyde (1 mL) was then added and the reaction mixture was stirred at rt for 1 h. Acetaldehyde (1 mL) was then added and the reaction mixture was stirred at rt for 1 h. The solvent was then evaporated in vacuo, the residue was loaded onto two 100 g silica cartridges and purified by column chromatography using a gradient 0-30% of ethyl acetate in cyclohexane. Desired fractions from both purifications were combined and evaporated in vacuo to afford the product as a white solid (3.65 g).

LCMS (2 min Formic): Rt=1.08 min, [MH]$^+$=311.

Intermediate 5: rac-benzyl ((2S,3R,4R)-1-acetyl-2,3-dimethyl-1,2,3,4-tetrahydroquinolin-4-yl)carbamate

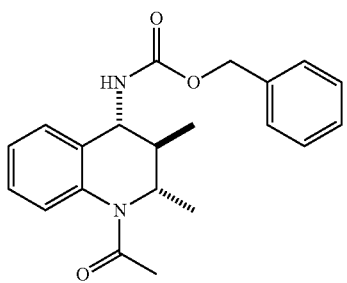 [SMILES: CC(=O)N1c2ccccc2[C@H](NC(=O)OCc2ccccc2)[C@@H](C)[C@@H]1C]

A solution of rac-benzyl ((2S,3S,4R)-2,3-dimethyl-1,2,3,4-tetrahydroquinolin-4-yl)carbamate (for a preparation see Intermediate 4, 3.22 g, 10.37 mmol) in anhydrous dichloromethane (DCM) (75 mL) was treated with pyridine (2.51 mL, 31.1 mmol) and acetyl chloride (1.11 mL, 15.56 mmol). The solution was stirred at rt under nitrogen for 1 h. The reaction mixture was transferred to a separating funnel then washed with 2M aq. HCl (50 mL) followed by sat. aqueous sodium bicarbonate (50 mL) and water (50 mL). The organic layer was dried through a hydrophobic frit and the solvent was removed by rotary evaporation to give the product as a beige solid (3.61 g, 10.24 mmol, 99% yield).

LCMS (2 min Formic): Rt=1.01 min, [MH]$^+$=353.

Intermediate 6: rac-1-((2S,3R,4R)-4-amino-2,3-dimethyl-3,4-dihydroquinolin-1(2H)-yl)ethanone

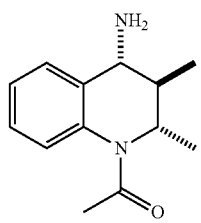

rac-benzyl ((2S,3R,4R)-1-acetyl-2,3-dimethyl-1,2,3,4-tetrahydroquinolin-4-yl)carbamate (for a preparation see Intermediate 5, 3.55 g, 10.07 mmol) was dissolved in methanol (100 mL) and was then passed through a 10% Pd/C cartridge on a H-cube (rt, full $H_2$ mode) to give a colourless filtrate. This filtrate was concentrated in vacuo to afford the product as a colourless oil which crystallised over time to become a beige solid (2.27 g). LCMS (2 min Formic): Rt=0.38 min, [MH]$^+$=219.

Intermediate 7: rac-tert-butyl 4-(3-(((2S,3R,4R)-1-acetyl-2,3-dimethyl-1,2,3,4-tetrahydroquinolin-4-yl)amino)phenyl)piperazine-1-carboxylate

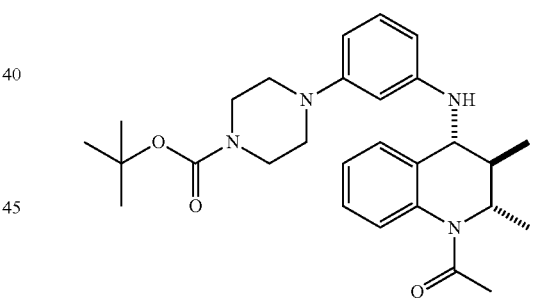

To a test tube were added rac-1-((2S,3R,4R)-4-amino-2,3-dimethyl-3,4-dihydroquinolin-1(2H)-yl)ethanone (for a preparation see Intermediate 6, 100 mg, 0.458 mmol), tert-butyl 4-(3-bromophenyl)piperazine-1-carboxylate (0.127 mL, 0.550 mmol), tris(dibenzylideneacetone)dipalladium(0) (20.97 mg, 0.023 mmol), DavePhos (18.03 mg, 0.046 mmol), sodium tert-butoxide (66.0 mg, 0.687 mmol) and 1,4-dioxane (4 mL). The reaction mixture was then heated and stirred at 100° C. in a greenhouse reactor for 1 h. After cooling to rt, the reaction mixture was filtered through a pad of celite (rinsed with EtOAc). The filtrate was then evaporated in vacuo. The residue was purified by MDAP (Formic). The desired fractions were combined and evaporated in vacuo to afford the product as a white solid (183.6 mg).

LCMS (2 min formic): Rt=1.23 min, [MH]$^+$=479.

Intermediate 8: rac-benzyl ((2S,3R,4R)-6-bromo-2-ethyl-3-methyl-1,2,3,4-tetrahydroquinolin-4-yl)carbamate

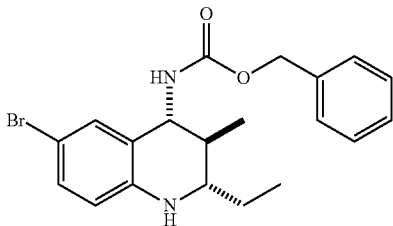 [SMILES: CC[C@@H]1Nc2ccc(Br)cc2[C@H](NC(=O)OCc2ccccc2)[C@H]1C]

Under an atmosphere of nitrogen, to a solution of 4-bromoaniline (5 g, 29.1 mmol) in dry dichloromethane (DCM) (80 mL) was added propionaldehyde (2.31 mL, 32.0 mmol). The mixture was stirred at rt for 1.5 h then cooled to 0° C. To the solution was added diphenyl hydrogen phosphate (0.727 g, 2.91 mmol) in dry dichloromethane (DCM) (30 mL) followed by (E)-benzyl prop-1-en-1-ylcarbamate (for a preparation see Intermediate 1, 6.1 g, 31.9 mmol) in dry dichloromethane (DCM) (30 mL). The solution was stirred at 0° C. for 1 h then allowed to warm to rt with stirring over the weekend. The reaction mixture was washed with sat. aq. NaHCO$_3$ (100 mL) and the aqueous layer was extracted with DCM (100 mL). The combined organics were dried through a hydrophobic frit and the solvent was removed by rotary evaporation to leave the crude. Purification was undertaken by flash column chromatography. The crude material was loaded onto a 340 g silica column and eluted using a graduating solvent system of 0-30% ethyl acetate in cyclohexane. Combination and evaporation of the desired fractions gave the product as an off-white solid (10 g).

LCMS (2 min Formic): Rt=1.29 min, [MH]$^+$=403, 405.

Intermediate 9: rac-benzyl ((2S,3R,4R)-1-acetyl-6-bromo-2-ethyl-3-methyl-1,2,3,4-tetrahydroquinolin-4-yl)carbamate

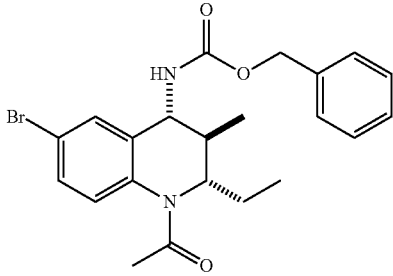 [SMILES: CC[C@H]1[C@H](C)[C@@H](NC(=O)OCc2ccccc2)c2cc(Br)ccc2N1C(C)=O]

To a solution of rac-benzyl ((2S,3S,4R)-6-bromo-2-ethyl-3-methyl-1,2,3,4-tetrahydroquinolin-4-yl)carbamate (for a preparation see Intermediate 8, 1.21 g, 3.0 mmol) in anhydrous dichloromethane (DCM) (30 mL) was added pyridine (0.726 mL, 9.0 mmol) followed by acetyl chloride (0.321 mL, 4.50 mmol). The reaction mixture was stirred at rt under nitrogen for 1 h. Saturated sodium bicarbonate (50 mL) was added and the reaction mixture partitioned. The aqueous layer was extracted with DCM (2×50 mL). The organic layers were combined, dried and evaporated in vacuo. The solid was dissolved in DCM and loaded onto a 100 g silica cartridge and purified using a gradient of 0-50% ethyl acetate in cyclohexane. The required fractions were combined and evaporated in vacuo and dried in the vacuum oven to give the required product as a pale yellow/white solid (1.15 g, 2.59 mmol, 86%). LCMS (2 min Formic): Rt=1.17 min, [MH]$^+$=445, 447.

Intermediate 10: rac-1-((2S,3R,4R)-4-amino-2-ethyl-3-methyl-3,4-dihydroquinolin-1(2H)-yl)ethanone Hydrobromide

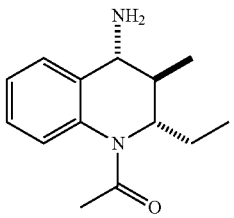 [SMILES: CC[C@H]1[C@H](C)[C@@H](N)c2ccccc2N1C(C)=O]

rac-Benzyl ((2S,3R,4R)-1-acetyl-6-bromo-2-ethyl-3-methyl-1,2,3,4-tetrahydroquinolin-4-yl)carbamate (for a preparation see Intermediate 9, 550 mg, 1.235 mmol) was taken up in ethanol (10 mL) and treated with 10% Pd/C (50 mg, 0.235 mmol) and allowed to stir under an atmosphere of hydrogen for 4 h. The catalyst was removed by filtering through celite and washing with more EtOH, the filtrate was concentrated and dried to give the product as a buff solid (369 mg).

LCMS (2 min Formic): Rt=0.47 min, [MH]$^+$=216 (loss of NH$_2^-$).

Intermediate 11 rac-1-((2S,3R,4R)-2-ethyl-3-methyl-4-((6-methylpyridin-2-yl)amino)-3,4-dihydroquinolin-1(2H)-yl)ethanone

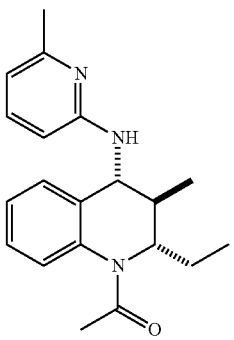 [SMILES: CC[C@H]1[C@H](C)[C@@H](Nc2cccc(C)n2)c2ccccc2N1C(C)=O]

The 2-bromo-6-methylpyridine (0.36 mL, 3.10 mmol), rac-1-((2S,3R,4R)-4-amino-2-ethyl-3-methyl-3,4-dihydroquinolin-1(2H)-yl)ethanone hydrobromide (for a preparation see Intermediate 10, 360 mg, 1.55 mmol), DavePhos (45.2 mg, 0.115 mmol), Pd$_2$(dba)$_3$ (63.1 mg, 0.069 mmol), sodium tert-butoxide (155 mg, 1.609 mmol) and 1,4-dioxane (10 mL) were placed in a round bottomed flask and allowed to stir at 100° C. for 4 h. The reaction was allowed to stir at 100° C. for a further 18 h and then was treated with more Pd$_2$(dba)$_3$ (63.1 mg, 0.069 mmol) and DavePhos (45.2 mg, 0.115 mmol) and allowed to stir at 100° C. for 24 h. The reaction was partitioned between water and EtOAc. The organic layer was washed with brine, dried using a hydrophobic frit and concentrated to a brown solid. This solid was purified using a 25 g silica column eluting with a gradient 0-50% EtOAc:cyclohexane. One major peak was eluted but with a shoulder, the non-shoulder fractions were combined and concentrated to give the product as a light brown solid (167 mg). LCMS (2 min Formic): Rt=0.66 min, [MH]$^+$=324.

Intermediate 12: rac-benzyl ((2S,3S,4R)-6-bromo-2-cyclopropyl-3-methyl-1,2,3,4-tetrahydroquinolin-4-yl)carbamate

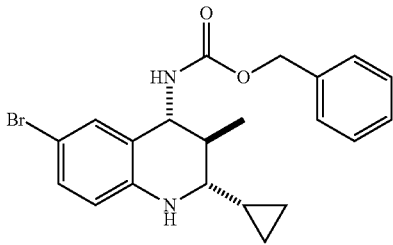

Under an atmosphere of nitrogen, to a solution of 4-bromoaniline (4.03 g, 23.43 mmol) in dry dichloromethane (DCM) (60 mL) was added cyclopropanecarbaldehyde (1.75 mL, 23.42 mmol). The mixture was stirred at rt for 1.5 h then cooled to 0° C. To the solution was added diphenyl hydrogen phosphate (0.586 g, 2.343 mmol) in dry dichloromethane (DCM) (30 mL) followed by (E)-benzyl prop-1-en-1-ylcarbamate (for a preparation see Intermediate 1, 4.9 g, 25.6 mmol) in dry dichloromethane (DCM) (30 mL). The solution was stirred at 0° C. for 1 h then allowed to warm to rt with stirring over the weekend. The reaction mixture was washed with 2M aq. NaOH (60 mL) followed by water (60 mL). The organic layer was dried through a hydrophobic frit and the solvent was removed by rotary evaporation. The residue was loaded in CHCl$_3$ (25 mL) and purified on a 330 g silica cartridge using a gradient of 0-40% EtOAc in cyclohexane. The appropriate fractions were combined and the solvent was removed by rotary evaporation to give the product as an off-white solid (8.17 g, 19.67 mmol, 84%). LCMS (2 min Formic): Rt=1.30 min, [MH]$^+$=415, 417.

Intermediate 13: rac-benzyl ((2S,3R,4R)-1-acetyl-6-bromo-2-cyclopropyl-3-methyl-1,2,3,4-tetrahydroquinolin-4-yl)carbamate

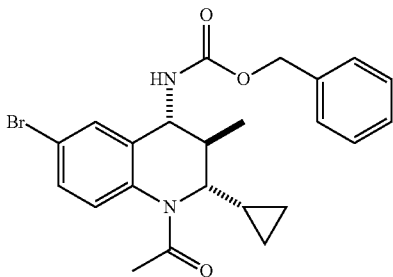

rac-Benzyl ((2S,3S,4R)-6-bromo-2-cyclopropyl-3-methyl-1,2,3,4-tetrahydroquinolin-4-yl)carbamate (for a preparation see Intermediate 12, 8.17 g, 19.67 mmol) and pyridine (4.77 mL, 59.0 mmol) in anhydrous dichloromethane (DCM) (120 mL) was treated with acetyl chloride (2.1 mL, 29.5 mmol). The mixture was stirred at rt under an atmosphere of nitrogen for 1.5 h. The reaction mixture was transferred to a separating funnel then washed with 2M aq. HCl (50 mL) followed by sat. aq. NaHCO$_3$ (50 mL) and water (50 mL). The organic layer was dried through a hydrophobic frit and the solvent was removed by rotary evaporation to give the product as an off-white solid (9.03 g, 19.74 mmol, 100%). LCMS (2 min Formic): Rt=1.18 min, [MH]$^+$=457, 459.

Intermediate 14: rac-1-((2S,3R,4R)-4-amino-2-cyclopropyl-3-methyl-3,4-dihydroquinolin-1(2H)-yl)ethanone

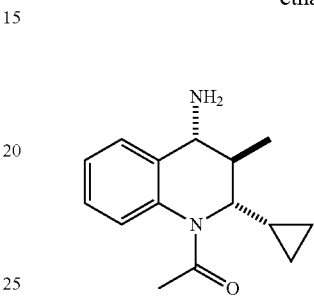

rac-Benzyl ((2S,3R,4R)-1-acetyl-6-bromo-2-cyclopropyl-3-methyl-1,2,3,4-tetrahydroquinolin-4-yl)carbamate (for a preparation see Intermediate 13, 2.51 g, 5.49 mmol), 10% Pd/C (400 mg, 3.76 mmol) and ammonium formate (3.46 g, 54.9 mmol) were all added to a flask under nitrogen. To this was added ethanol (50 mL) and ethyl acetate (15 mL), forming a suspension of both the starting material and the catalyst. The suspension was stirred at reflux for ~1 h. The reaction mixture was washed through a 10 g celite cartridge with ethanol, followed by ethyl acetate, and the mixture collected. The filtered solvent was evaporated in vacuo to afford a white powdery solid (1.79 g). The solid was dissolved in methanol loaded onto a 50 g SCX-2 SPE cartridge, washed with 4 CVs MeOH, and the product eluted with 4 CVs of 2M methanolic ammonia. The appropriate fractions were collected and evaporated in vacuo to afford a clear, pale yellow oil. The oil was held under high vacuum overnight, to afford a white crystalline solid (1.2003 g, 4.91 mmol, 90%).

LCMS (2 min Formic): Rt=0.51 min, [MH]$^+$=245.

Intermediate 15: Cyclobutanecarbaldehyde

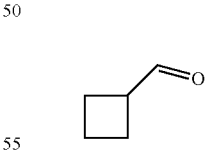

To a solution of cyclobutylmethanol (1.0 g, 11.61 mmol) in anhydrous DCM (10 mL) was added a solution of 24% KBr in water (0.63 mL, 11.61 mmol). To this mixture was added a solution of sat. NaHCO$_3$ (aq) (1.5 mL, 11.61 mmol) and the mixture cooled to 0° C. To this was added TEMPO (18 mg, 0.115 mmol) and the mixture stirred for 20 min. Slowly ~5% sodium hypochlorite solution (1.9 mL, 30.8 mmol) was charged to the mixture and stirred for 30 min. Then a solution of 8.25% KH$_2$PO$_4$ in water (4.0 mL, 11.61 mmol) was added and the mixture stirred for an additional 30 min while warming to rt. The layers were allowed to separate and the organic layer dried through a hydrophobic frit and then over MgSO$_4$. The organic layer was split into 2x~5 mL portions. One portion was carefully evaporated under vacuum in an ice/water bath to remove most of the solvent. The resulting yellow gum (~0.5 g) which contained the starting alcohol is the major component with 10% desired aldehyde present. The second separated 5 mL DCM solution was added to the gum to give a solution containing the product. LCMS no peak/mass ion observed.

Intermediate 16: rac-benzyl ((2S,3S,4R)-2-cyclobutyl-3-methyl-1,2,3,4-tetrahydroquinolin-4-yl)carbamate

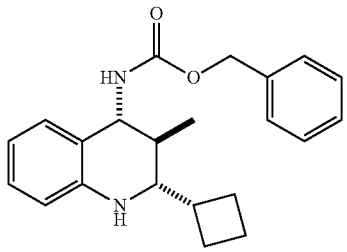

To a solution of cyclobutanecarbaldehyde (for a preparation see Intermediate 15, 100 mg, 1.19 mmol) in anhydrous DCM (5 mL)* under nitrogen was added aniline (100 µL, 1.095 mmol). The mixture was stirred at rt for 1.5 h then cooled to 0° C. To the solution was added diphenyl hydrogen phosphate (27 mg, 0.110 mmol) in anhydrous DCM (2.0 mL) followed by (E)-benzyl prop-1-en-1-ylcarbamate (209 mg, 1.095 mmol) in anhydrous DCM (1.0 mL). The mixture was stirred at 0° C. under nitrogen for 1 h, then allowed to warm to rt over 20 h. The reaction mixture was washed with sat. NaHCO$_3$ (aq) (10 mL) followed by water (10 mL). The organic layer was dried through a hydrophobic frit and the solvent removed under vacuum. The gum was loaded in CHCl$_3$ (5 mL) and purified by column chromatography on a 100 g silica cartridge using a gradient of 0-40% EtOAc in cyclohexane. The appropriate fractions were combined and the solvent removed by rotary evaporation to give the product as a white solid (264 mg, 0.753 mmol, 69%).
*crude mixture of cyclobutanecarbaldehyde (~10%) and cyclobutylmethanol in DCM (5 mL). The mass of cyclobutanecarbaldehyde in the grid was estimated from NMR of N24241-62-100 contained in the crude mixture.
LCMS (2 min Formic): Rt=1.28 min, [MH]$^+$=351.

Intermediate 17: rac-benzyl ((2S,3R,4R)-1-acetyl-2-cyclobutyl-3-methyl-1,2,3,4-tetrahydroquinolin-4-yl)carbamate

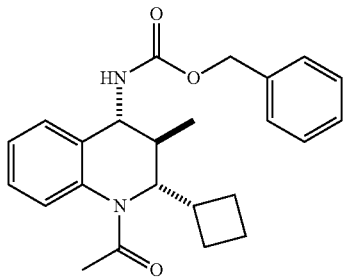

To a stirred solution of rac-benzyl ((2S,3S,4R)-2-cyclobutyl-3-methyl-1,2,3,4-tetrahydroquinolin-4-yl)carbamate (for a preparation see Intermediate 16, 259 mg, 0.739 mmol) in DCM (3 mL) and pyridine (0.179 mL, 2.217 mmol) under nitrogen at 0° C. was added acetyl chloride (0.079 mL, 1.11 mmol). The mixture was stirred for 15 min at 0° C. then allowed to warm to rt over 2 h. The reaction mixture was diluted with DCM (5 mL) and washed sequentially with 0.5M aqueous HCl solution (10 mL), saturated aqueous NaHCO$_3$ solution (10 mL) and water (10 mL). The organic layer was separated and dried through a hydrophobic frit. The solvent was removed under reduced pressure and the solid loaded in CHCl$_3$ (3 mL) and purified by column chromatography on a 50 g silica cartridge using a gradient of 0-10% MeOH in DCM. The appropriate fractions were combined and the solvent removed by rotary evaporation to give the product as a white solid (253 mg, 0.645 mmol, 87%). LCMS (2 min Formic): Rt=1.15 min, [MH]$^+$=393.

Intermediate 18: rac-1-((2S,3R,4R)-4-amino-2-cyclobutyl-3-methyl-3,4-dihydroquinolin-1(2H)-yl)ethanone

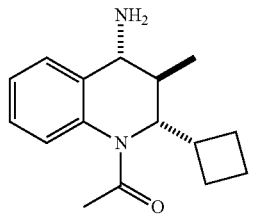 [SMILES: CC(=O)N1c2ccccc2[C@H](N)[C@@H](C)[C@@H]1C1CCC1]

A solution of rac-benzyl ((2S,3R,4R)-1-acetyl-2-cyclobutyl-3-methyl-1,2,3,4-tetrahydroquinolin-4-yl)carbamate (for a preparation see Intermediate 17, 248 mg, 0.632 mmol) in methanol (12 mL) was hydrogenated using the H-cube (rt, full H$_2$ mode, 1 mL/min flow rate) and a 10% Pd/C CatCart 30 as the catalyst. The eluent was evaporated under vacuum to give the product as a colourless oil (159 mg, 0.615 mmol, 97%). LCMS (2 min Formic): Rt=0.55 min, [M]$^+$=228 (loss of NH$_2^-$).

Intermediate 19: rac-benzyl ((2S,3S,4R)-2-isopropyl-3-methyl-1,2,3,4-tetrahydroquinolin-4-yl)carbamate

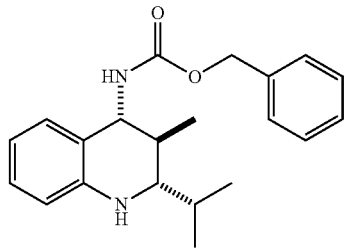 [SMILES: CC(C)[C@@H]1Nc2ccccc2[C@H](NC(=O)OCc2ccccc2)[C@H]1C]

To a solution of isobutyraldehyde (0.147 mL, 1.611 mmol) in anhydrous DCM (3.0 mL) under nitrogen was added aniline (0.147 mL, 1.611 mmol). The mixture was stirred at rt for 30 min then cooled to −45° C. (acetonitrile/dry-ice bath). To the solution was added diphenyl hydrogen phosphate (40 mg, 0.160 mmol) in anhydrous DCM (0.5 mL) followed by (E)-benzyl prop-1-en-1-ylcarbamate (for a preparation see Intermediate 1, 308 mg, 1.61 mmol) in anhydrous DCM (0.5 mL). The mixture was stirred at −45° C. under nitrogen for 1 h, then allowed to warm to rt over 20 h. The suspension was filtered. The solid was dried in a vacuum oven to give the product as an off-white solid (286 mg, 0.845 mmol, 53%).

LCMS (2 min Formic): Rt=1.27 min, [MH]$^+$=339.

Intermediate 20: rac-benzyl ((2S,3R,4R)-1-acetyl-2-isopropyl-3-methyl-1,2,3,4-tetrahydroquinolin-4-yl)carbamate

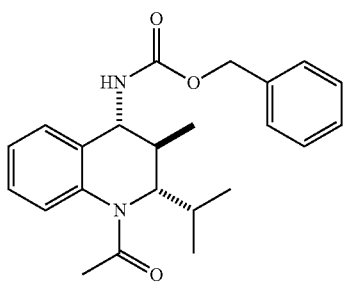 [SMILES: CC(=O)N1c2ccccc2[C@H](NC(=O)OCc2ccccc2)[C@@H](C)[C@@H]1C(C)C]

To a stirred solution of rac-benzyl ((2S,3S,4R)-2-isopropyl-3-methyl-1,2,3,4-tetrahydroquinolin-4-yl)carbamate (for a preparation see Intermediate 19, 274 mg, 0.81 mmol) in DCM (3.0 mL) and pyridine (0.20 mL, 2.473 mmol) was added acetyl chloride (0.09 mL, 1.261 mmol) and the mixture stirred for 45 min. The reaction mixture was diluted with DCM (2 mL) and washed sequentially with 0.5M aqueous HCl solution (5 mL), saturated aqueous NaHCO$_3$ solution (5 mL) and water (5 mL). The organic layer was separated and dried through a hydrophobic frit. The solvent was removed under reduced pressure and the residue loaded in DCM (3 mL) and purified by column chromatography on a 25 g silica cartridge using a gradient of 0-15% MeOH in DCM. The appropriate fractions were combined and the solvent removed by rotary evaporation. The gum was purified by MDAP (Formic). The appropriate fractions were combined and the solvent removed by rotary evaporation to give the product as a white crystals (120 mg, 0.413 mmol, 47%).

LCMS (2 min Formic): Rt=1.12 min, [MH]$^+$=381.

Intermediate 21: rac-1-((2S,3R,4R)-4-amino-2-isopropyl-3-methyl-3,4-dihydroquinolin-1(2H)-yl)ethanone

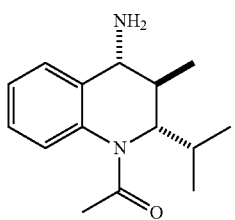

A solution of rac-benzyl ((2S,3R,4R)-1-acetyl-2-isopropyl-3-methyl-1,2,3,4-tetrahydroquinolin-4-yl)carbamate (for a preparation see Intermediate 20, 195 mg, 0.513 mmol) in methanol (10 mL) was hydrogenated using the H-cube (rt, full H$_2$ mode, 1 mL/min flow rate) and a 10% Pd/C CatCart 30 as the catalyst. The eluent was evaporated in vacuo to give the product as a yellow oil (125 mg, 0.507 mmol, 99%).

LCMS (2 min Formic): Rt=0.50 min, [MH]$^+$=247.

Intermediate 22: rac-benzyl ((2S,3S,4R)-3-methyl-2-(2,2,2-trifluoroethyl)-1,2,3,4-tetrahydroquinolin-4-yl)carbamate

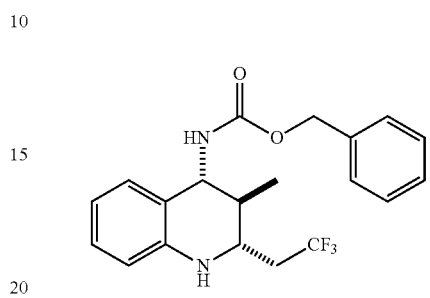

To a solution of 3,3,3-trifluoropropanal (360 mg, 3.21 mmol) in anhydrous DCM (5.0 mL) under nitrogen was added aniline (0.29 mL, 3.22 mmol). The mixture was stirred at rt for 1.5 h then cooled to 0° C. To the solution was added diphenyl hydrogen phosphate (81 mg, 0.322 mmol) in anhydrous DCM (2.0 mL) followed by (E)-benzyl prop-1-en-1-ylcarbamate (for a preparation see Intermediate 1, 615 mg, 3.22 mmol) in anhydrous DCM (1.0 mL). The mixture was stirred at 0° C. under nitrogen for 1 h, then allowed to warm to rt over 20 h. The reaction mixture was diluted with DCM (12 mL) and washed with sat. NaHCO$_3$ (aq) (20 mL) followed by water (20 mL). The organic layer was dried through a hydrophobic frit and the solvent removed under vacuum. The resulting gum was loaded in CHCl$_3$ (5 mL) on to 100 g silica cartridge and purified by column chromatography using a gradient of 0-30% EtOAc in cyclohexane. Desired fractions were combined and the solvent removed by rotary evaporation to give the product (400 mg). LCMS (2 min Formic): Rt=1.22 min, [MH]$^+$=379.

Intermediate 23: rac-benzyl ((2S,3R,4R)-1-acetyl-3-methyl-2-(2,2,2-trifluoroethyl)-1,2,3,4-tetrahydroquinolin-4-yl)carbamate

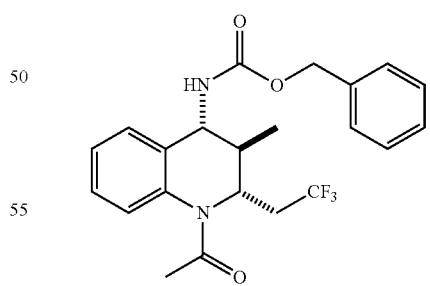

To a stirred solution of rac-benzyl ((2S,3S,4R)-3-methyl-2-(2,2,2-trifluoroethyl)-1,2,3,4-tetrahydroquinolin-4-yl)carbamate (for a preparation see Intermediate 22, 330 mg, 0.872 mmol) in DCM (3 mL) and pyridine (0.21 mL, 2.62 mmol) under nitrogen at 0° C. was added acetyl chloride (0.093 mL, 1.308 mmol). The mixture was stirred for 15 min at 0° C. then allowed to warm to rt over 2 h. The reaction mixture was diluted with DCM (7 mL) washed sequentially with 0.5M aqueous HCl solution (15 mL), saturated aqueous NaHCO$_3$ solution (15 mL) and water (15 mL). The organic layer was separated and dried through a hydrophobic frit. The solvent was removed under reduced pressure and the solid purified by MDAP (Formic). The appropriate fractions were combined and the solvent removed by rotary evaporation to give the product as an off-white solid (143 mg, 0.340 mmol, 39%).

LCMS (2 min Formic): Rt=1.10 min, [MH]$^+$=421.

Intermediate 24: rac-1-((2S,3R,4R)-4-amino-3-methyl-2-(2,2,2-trifluoroethyl)-3,4-dihydroquinolin-1(2H)-yl)ethanone

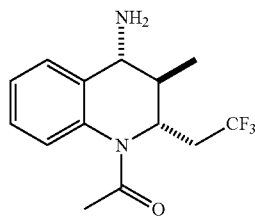 [SMILES: CC(=O)N1c2ccccc2[C@H](N)[C@@H](C)[C@@H]1CC(F)(F)F]

A solution of rac-benzyl ((2S,3R,4R)-1-acetyl-3-methyl-2-(2,2,2-trifluoroethyl)-1,2,3,4-tetrahydroquinolin-4-yl)carbamate (for a preparation see Intermediate 23, 135 mg, 0.321 mmol) in methanol (6 mL) was hydrogenated using the H-cube (rt, full H$_2$ mode, 1 mL/min flow rate) and a 10% Pd/C CatCart 30 as the catalyst. The eluent was evaporated under vacuum to give the product as a colourless oil (92 mg, 0.321 mmol, 100%).

LCMS (2 min Formic): Rt=0.79 min, [MH]$^+$=270 (loss of NH2$^-$).

Intermediate 25: rac-benzyl ((2R,3R,4R)-2-(((tert-butyldimethylsilyl)oxy)methyl)-3-methyl-1,2,3,4-tetrahydroquinolin-4-yl)carbamate

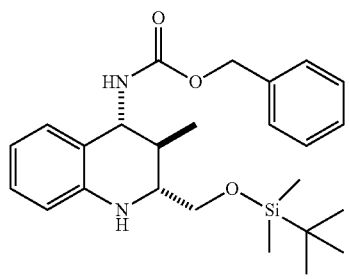 [SMILES: C[C@H]1[C@H](CO[Si](C)(C)C(C)(C)C)Nc2ccccc2[C@@H]1NC(=O)OCc1ccccc1]

To a solution of 2-((tert-butyldimethylsilyl)oxy)acetaldehyde (382 mg, 2.191 mmol) in anhydrous DCM (3 mL) was added aniline (0.2 mL, 2.191 mmol). The mixture was stirred under nitrogen at rt for 30 min then cooled to 0° C. To the solution was added diphenyl hydrogen phosphate (60 mg, 0.240 mmol) in anhydrous DCM (0.5 mL) followed by (E)-benzyl prop-1-en-1-ylcarbamate (for a preparation see Intermediate 1, 419 mg, 2.191 mmol) in anhydrous DCM (0.5 mL). The mixture was stirred at 0° C. under nitrogen for 1 h, then allowed to warm to rt over 21 h. The reaction mixture was diluted with DCM (6 mL), washed with a saturated aqueous solution of NaHCO$_3$ (10 mL) followed by water (10 mL). The organic layer was dried through a hydrophobic frit and evaporated in vacuo. The residue in DCM (5 mL) was applied to a 100 g silica cartridge and purified using a gradient of 0-100% DCM in cyclohexane. The appropriate fractions were combined and the solvent removed by rotary evaporation to give the product as a white solid (571 mg, 1.30 mmol, 59%).

LCMS (2 min Formic): Rt=1.53 min, [MH]$^+$=441.

Intermediate 26: rac-benzyl ((2R,3R,4R)-1-acetyl-2-(((tert-butyldimethylsilyl)oxy)methyl)-3-methyl-1,2,3,4-tetrahydroquinolin-4-yl)carbamate

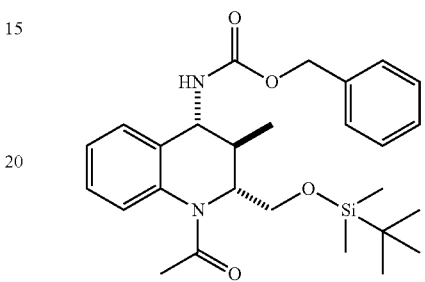

To a stirred solution of rac-benzyl ((2R,3R,4R)-2-(((tert-butyldimethylsilyl)oxy)methyl)-3-methyl-1,2,3,4-tetrahydroquinolin-4-yl)carbamate (for a preparation see Intermediate 25, 565 mg, 1.28 mmol) in DCM (8 mL) and pyridine (0.311 mL, 3.85 mmol) under nitrogen at 0° C. was added acetyl chloride (0.137 mL, 1.923 mmol). The mixture was stirred for 15 min at 0° C. then allowed to warm to rt over 2 h. The reaction mixture was diluted with DCM (7 mL) washed sequentially with 0.5M aqueous HCl solution (15 mL), saturated aqueous NaHCO$_3$ solution (15 mL) and water (15 mL). The organic layer was separated and dried through a hydrophobic frit. The solvent was removed under reduced pressure and the residue loaded in CHCl$_3$ (7 mL) and purified on a 100 g silica cartridge using a gradient of 0-75% EtOAc in cyclohexane. The appropriate fractions were combined and the solvent removed by rotary evaporation to give the product as a white solid (457 mg, 0.947 mmol, 74%).

LCMS (2 min Formic): Rt=1.40 min, [MH]$^+$=483.

Intermediate 27: rac-1-((2R,3R,4R)-4-amino-2-(((tert-butyldimethylsilyl)oxy)methyl)-3-methyl-3,4-dihydroquinolin-1(2H)-yl)ethanone

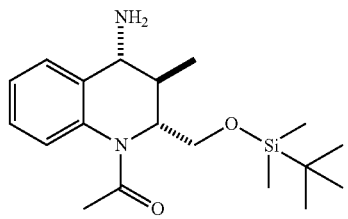 [SMILES: CC(=O)N1c2ccccc2[C@H](N)[C@@H](C)[C@@H]1CO[Si](C)(C)C(C)(C)C]

A solution of rac-benzyl ((2R,3R,4R)-1-acetyl-2-(((tert-butyldimethylsilyl)oxy)methyl)-3-methyl-1,2,3,4-tetrahydroquinolin-4-yl)carbamate (for a preparation se Intermediate 26, 450 mg, 0.932 mmol) in methanol (19 mL) was hydrogenated using the H-cube (rt, full H$_2$ mode, 1 mL/min flow rate) and a 10% Pd/C CatCart 30 as the catalyst. The eluent was evaporated under vacuum to give the product as a colourless oil (320 mg, 0.918 mmol, 98%).

LCMS (2 min Formic): Rt=1.23 min, [MH]$^+$=332 (loss of NH$_2^-$).

Intermediate 28: rac-1-((2R,3R,4R)-2-(((tert-butyldimethylsilyl)oxy)methyl)-3-methyl-4-(phenylamino)-3,4-dihydroquinolin-1(2H)-yl)ethanone

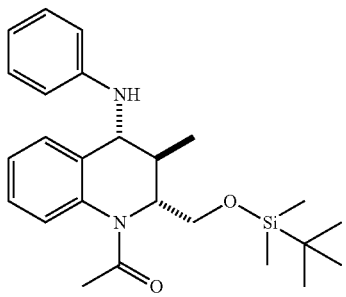 [SMILES: CC(=O)N1c2ccccc2[C@H](Nc2ccccc2)[C@@H](C)[C@@H]1CO[Si](C)(C)C(C)(C)C]

A 0.5-2 mL microwave vessel was charged with a magnetic stirrer bar, sodium tert-butoxide (130 mg, 1.356 mmol), Pd$_2$(dba)$_3$ (41.4 mg, 0.045 mmol), DavePhos (36 mg, 0.090 mmol), rac-1-((2R,3R,4R)-4-amino-2-(((tert-butyldimethylsilyl)oxy)methyl)-3-methyl-3,4-dihydroquinolin-1(2H)-yl)ethanone (for a preparation see Intermediate 27, 315 mg, 0.904 mmol), bromobenzene (0.095 mL, 0.904 mmol) and anhydrous 1,4-dioxane (4.5 mL). The vessel was sealed and nitrogen was bubbled through the reaction mixture for 5 min. The reaction was heated in a microwave reactor at 120° C. for 30 min. The reaction mixture was filtered through celite and washed with EtOAc (10 mL) and the filtrate evaporated under vacuum. The residue was loaded in CHCl$_3$ (5 mL) and purified on a 100 g silica cartridge using a gradient of 0-75% EtOAc in cyclohexane. The appropriate fractions were combined and the solvent removed by rotary evaporation to give the product as a colourless gum (165 mg, 0.389 mmol, 43%).

LCMS (2 min Formic): Rt=1.48 min, [MH]$^+$=425.

Intermediate 29: rac-1-((2R,3R,4R)-2-(hydroxymethyl)-3-methyl-4-(phenylamino)-3,4-dihydroquinolin-1(2H)-yl)ethanone

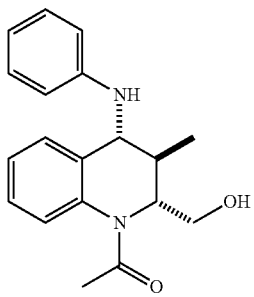 [SMILES: CC(=O)N1c2ccccc2[C@H](Nc2ccccc2)[C@@H](C)[C@@H]1CO]

To a solution of rac-1-((2R,3R,4R)-2-(((tert-butyldimethylsilyl)oxy)methyl)-3-methyl-4-(phenylamino)-3,4-dihydroquinolin-1(2H)-yl)ethanone (for a preparation see Intermediate 28, 151 mg, 0.356 mmol) in anhydrous THF (3 mL) was added TBAF (1M solution in THF) (0.373 mL, 0.373 mmol) and the mixture stirred in a sealed vessel at rt for 1 h. The reaction mixture was quenched with water (5 mL) and extracted with EtOAc (2×5 mL). The organic extracts were combined, dried through a hydrophobic frit and the solvent removed under vacuum. The residue was loaded in CHCl$_3$ (3 mL) and purified on a 100 g silica cartridge using a gradient of 0-15% MeOH in DCM. All collected fractions were combined and the solvent removed by rotary evaporation to give ~150 mg of a yellow gum. This was dissolved in 1:1 DMSO:MeOH (2 mL) and purified by MDAP (HpH) (2×1 mL runs). The appropriate fractions from both runs were combined and the solvent removed by rotary evaporation to give the product as an off-white solid (75 mg, 0.242 mmol, 68%).

LCMS (2 min Formic): Rt=0.94 min, [MH]$^+$=311.

Intermediate 30: rac-benzyl ((2S,3R,4R)-6-bromo-2-cyclopropyl-3-methyl-1-propionyl-1,2,3,4-tetrahydroquinolin-4-yl)carbamate

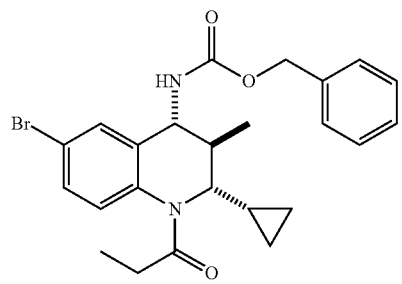 [SMILES: CCC(=O)N1c2ccc(Br)cc2[C@H](NC(=O)OCc2ccccc2)[C@@H](C)[C@@H]1C1CC1]

To a stirred solution of rac-benzyl ((2S,3S,4R)-6-bromo-2-cyclopropyl-3-methyl-1,2,3,4-tetrahydroquinolin-4-yl)carbamate (for a preparation see Intermediate 12, 411 mg, 0.99 mmol) in anhydrous dichloromethane (DCM) (6 mL) under nitrogen was added pyridine (0.24 mL, 2.97 mmol) followed by propionyl chloride (0.125 mL, 1.486 mmol). The reaction mixture was stirred at rt under nitrogen for 17 h. The reaction mixture was applied directly to a 25 g silica cartridge and was purified by flash column chromatography eluting with a gradient of 0-40% ethyl acetate in cyclohexane. The required fractions were combined and evaporated in vacuo to give the desired product as a white crunchy foam (401 mg, 0.85 mmol, 86%). LCMS (2 min Formic): Rt=1.26 min, [MH]$^+$=471, 473.

Intermediate 31: rac-1-((2S,3R,4R)-4-amino-2-cyclopropyl-3-methyl-3,4-dihydroquinolin-1(2H)-yl)propan-1-one

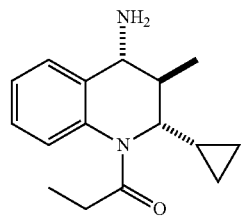 [SMILES: CCC(=O)N1c2ccccc2[C@H](N)[C@@H](C)[C@@H]1C1CC1]

rac-Benzyl ((2S,3R,4R)-2-cyclopropyl-3-methyl-1-propionyl-1,2,3,4-tetrahydroquinolin-4-yl)carbamate (90 mg, 0.229 mmol) was dissolved in ethanol (5 mL). Ammonium formate (145 mg, 2.293 mmol) and 10% Pd/C (20 mg, 0.188 mmol) were added and reaction mixture heated at reflux. The reaction mixture was cooled to rt and filtered through a celite cartridge. The reaction mixture was concentrated in vacuo and loaded onto a 2 g SCX cartridge (pre-conditioned with MeOH). This was eluted with MeOH (35 mL) followed by 2M $NH_3$ in MeOH (35 mL). Ammonia fractions were combined and concentrated to give the product (58 mg, 0.224 mmol, 98%) as a pale yellow oil.

LCMS (2 min Formic): Rt=0.57 min, $[M]^+$=242 (loss of $NH_2^-$).

Intermediate 32: N-allyl-N-methylaniline

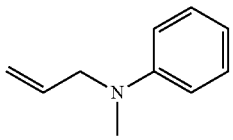

To a suspension of N-methylaniline (1.01 ml, 9.33 mmol) and potassium hydroxide (1.05 g, 18.66 mmol) in acetonitrile (34.7 mL) stirred under nitrogen at rt was added 3-bromoprop-1-ene (1.62 mL, 18.66 mmol). The reaction mixture was stirred at 50° C. for 7 h. The reaction mixture was quenched with water, partitioned between ethyl acetate (25 mL) and water (50 mL). The aqueous layer was washed with ethyl acetate (50 mL) and the combined organics dried over magnesium sulphate and evaporated in vacuo to give the crude product as a yellow oil. The crude product was added to a silica gel column and was eluted with 0-3% EtOAc/cyclohexane. Pure fractions were evaporated to afford N-allyl-N-methylaniline (80 mg, 0.53 mmol, 5.7%) as a colourless oil. Impure fractions were evaporated to afford as second batch of N-allyl-N-methylaniline (730 mg, 4.46 mmol, 48%) as a yellow oil (90% pure). LCMS (2 min HpH): Rt=1.22 min, $[MH]^+$=148.

Intermediate 33: (E)-N-methyl-N-(prop-1-en-1-yl)aniline

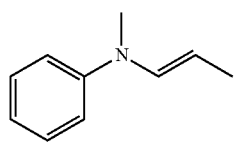

A solution of N-allyl-N-methylaniline (for a preparation see Intermediate 32, 300 mg, 2.04 mmol) and tris(triphenylphosphine)rhodium(I) carbonyl hydride (46.8 mg, 0.05 mmol) in dry tetrahydrofuran (THF) (1.56 mL) was stirred at 60° C. in a sealed vessel under an atmosphere of nitrogen for 2 h. The reaction was incomplete so further tris(triphenylphosphine)rhodium(I) carbonyl hydride (46.8 mg, 0.05 mmol) was added and the reaction stirred at 60° C. for 3 h. The reaction was cooled to rt and triethylamine (0.01 mL, 0.07 mmol) added. Pentane (5 mL) was added and the mixture was cooled to −70° C. Rhodium and phosphine impurities precipitated and the mixture was filtered. The solvent was removed under vacuum to afford a yellow oil (280 mg, 1.62 mmol, 79%). This was used immediately without purification. LCMS (2 min HpH): Rt=1.31 min, $[MH]^+$=not observed.

Intermediate 34: rac-(2S,3S,4R)-2-cyclopropyl-N,3-dimethyl-N-phenyl-1,2,3,4-tetrahydroquinolin-4-amine

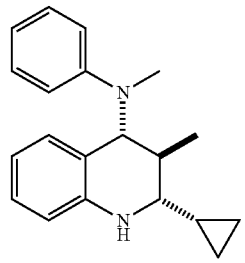 [SMILES: C[C@H]1[C@H](C2CC2)Nc2ccccc2[C@@H]1N(C)c1ccccc1]

Under an atmosphere of nitrogen, to a solution of aniline (147 μl, 1.62 mmol) and 3 Å molecular sieves in dry dichloromethane (DCM) (5 mL) in a heat-dried flask was added cyclopropanecarbaldehyde (133 μl, 1.78 mmol). The mixture was stirred at rt for 2 h then cooled to −78° C. To the solution was added diphenyl hydrogen phosphate (40.4 mg, 0.162 mmol) in dry dichloromethane (DCM) (1.5 mL) followed by (E)-N-methyl-N-(prop-1-en-1-yl)aniline (for a preparation see Intermediate 33, 280 mg, 1.617 mmol) in dry dichloromethane (DCM) (1.5 mL). The solution was stirred at −78° C. for 3 h then warmed to rt and stirred 2 h. The reaction mixture was filtered and diluted with DCM (5 mL) and $NaHCO_3$ (10 mL). The aqueous layers were washed with DCM (2×20 mL), the combined organics dried through a hydrophobic frit and the solvent removed by rotary evaporation. Crude material was purified on a 100 g silica cartridge using a gradient of 0-20% EtOAc in cyclohexane. Fractions were evaporated to dryness and the residue triturated with MeOH to afford the required product (115 mg, 0.39 mmol, 24%) as a white solid.

LCMS (2 min Formic): Rt=1.49 min, $[M]^+$=186 (loss of $PhNMe^-$).

Intermediate 35: rac-benzyl ((2S,3S,4R)-6-methoxy-2,3-dimethyl-1,2,3,4-tetrahydroquinolin-4-yl)carbamate

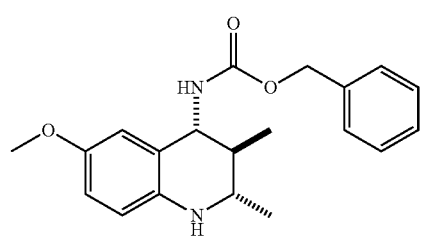 [SMILES: COc1ccc2c(c1)[C@H](NC(=O)OCc1ccccc1)[C@@H](C)[C@H](C)N2]

To a solution of acetaldehyde (1.4 mL, 24.95 mmol) in dichloromethane (DCM) (100 mL) was added 4-methoxyaniline (3.00 g, 24.36 mmol). The reaction mixture was stirred at rt under nitrogen for 30 minutes before diphenyl hydrogen phosphate (0.61 g, 2.438 mmol) was added and the mixture cooled to 0° C. (ice bath). A solution of (E)-benzyl prop-1-en-1-ylcarbamate (for a preparation see Intermediate 1, 5.15 g, 26.9 mmol) in dichloromethane (DCM) (30 mL) was added to the mixture. The reaction mixture was stirred at 0° C. under nitrogen for 1 h before being allowed to warm to rt and stirred for a further 18 h. The mixture was heated at reflux for 4 h. The mixture was cooled to 0° C. again (ice bath) and acetaldehyde (14.0 mL, 249 mmol) was added. After stirring at 0° C. for 1 h the cooling bath was removed and the reaction was allowed to warm to rt and stirred for a further 24 h after which it was left to stand for 12.5 days. The volatiles were evaporated in vacuo and the residue was re-dissolved in dichloromethane (ca. 20 mL) and was loaded onto a 100 g silica SPE cartridge. The cartridge was eluted with a gradient of 0-50% ethyl acetate in cyclohexane and the required fractions were combined and evaporated in vacuo to give the desired product which was further purified on a 50 g silica SPE cartridge eluting with a gradient of 0-10% ethyl acetate in dichloromethane. The required fractions were combined and evaporated in vacuo to give the desired product as a brown solid (903 mg, 2.65 mmol, 11%).

LCMS (2 min Formic): Rt=0.85 min, [MH]$^+$=341.

Intermediate 36: rac-benzyl ((2S,3R,4R)-1-acetyl-6-methoxy-2,3-dimethyl-1,2,3,4-tetrahydroquinolin-4-yl)carbamate

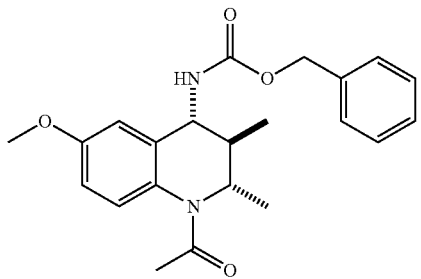 [SMILES: COc1ccc2c(c1)[C@H](NC(=O)OCc1ccccc1)[C@@H](C)[C@H](C)N2C(C)=O]

To a stirred solution of rac-benzyl ((2S,3S,4R)-6-methoxy-2,3-dimethyl-1,2,3,4-tetrahydroquinolin-4-yl)carbamate (for a preparation see Intermediate 35, 0.903 g, 2.65 mmol) in anhydrous dichloromethane (DCM) (20 mL) under nitrogen was added pyridine (0.64 mL, 7.96 mmol) followed by acetyl chloride (0.28 mL, 3.98 mmol). The reaction mixture was stirred under nitrogen at rt for 2.5 h. The reaction mixture had saturated aqueous sodium bicarbonate solution (50 mL) added and the phases were separated. The aqueous phase was extracted with further dichloromethane (2×50 mL). The organic phases were combined, dried by passing through a hydrophobic frit and the solvent evaporated in vacuo to give a dark purple oil. The residue was dissolved in dichloromethane (~8 mL) and was purified by flash column chromatography (50 g silica cartridge) eluting with a gradient of 0-60% ethyl acetate in cyclohexane. The required fractions were combined and the solvent evaporated in vacuo to give the desired product as a light brown gum (911.9 mg, 2.384 mmol, 90%).

LCMS (2 min Formic): Rt=1.01 min, [MH]$^+$=383.

Intermediate 37: rac-1-((2S,3R,4R)-4-amino-6-methoxy-2,3-dimethyl-3,4-dihydroquinolin-1(2H)-yl)ethanone

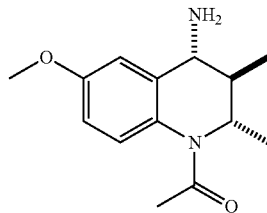

A stirred mixture of rac-benzyl ((2S,3R,4R)-1-acetyl-6-methoxy-2,3-dimethyl-1,2,3,4-tetrahydroquinolin-4-yl)carbamate (for a preparation see Intermediate 36, 907 mg, 2.372 mmol) and 10 wt. % (dry basis) palladium on activated carbon (wet, Degussa type E101 NE/W) (196 mg, 1.841 mmol) in ethanol (25 mL) was hydrogenated with vigorous stirring under an atmosphere of hydrogen at rt and pressure for 3.25 h. The mixture was filtered under nitrogen through a pad of celite filter aid and the filter cake washed with ethanol (3×5 mL). The combined filtrate was evaporated in vacuo to give the desired product as a pale brown gum (521 mg, 2.1 mmol, 89%).

LCMS (2 min Formic): Rt=0.44 min, [MH]$^+$=249.

Intermediate 38: rac-benzyl ((2S,3S,4R)-2-ethyl-6-fluoro-3-methyl-1,2,3,4-tetrahydroquinolin-4-yl)carbamate

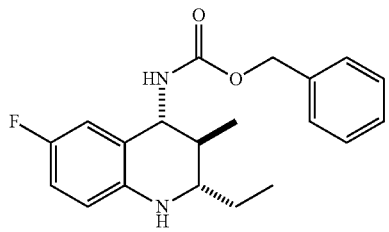 [SMILES: CC[C@@H]1Nc2ccc(F)cc2[C@H](NC(=O)OCc2ccccc2)[C@H]1C]

To a solution of propionaldehyde (0.304 mL, 4.18 mmol) in anhydrous dichloromethane (DCM) (10 mL), was added 4-fluoroaniline (0.40 mL, 4.18 mmol) and the reaction stirred at rt for 1 h. Diphenyl hydrogen phosphate (105 mg, 0.418 mmol) in anhydrous dichloromethane (DCM) (5 mL) was added and then (E)-benzyl prop-1-en-1-ylcarbamate (for a preparation see Intermediate 1, 800 mg, 4.18 mmol) in anhydrous dichloromethane (DCM) (5 mL). The reaction was left to stir for 18 h at rt. The mixture was diluted with DCM (15 mL) and washed with NaHCO$_3$ (35 mL) and then water (35 mL) and the organic and aqueous layers were separated. The organic layer was dried through a hydrophobic frit and concentrated in vacuo to give 1.503 g of crude brown solid. This was purified by chromatography on silica gel (50 g) eluting with ethyl acetate/cyclohexane (0-40%). The fractions containing only product were combined and concentrated in vacuo to give the product (627 mg, 1.83 mmol, 44%) as an off-white solid. LCMS (2 min Formic): Rt=1.20 min, [MH]$^+$=343.

Intermediate 39: rac-benzyl ((2S,3R,4R)-1-acetyl-2-ethyl-6-fluoro-3-methyl-1,2,3,4-tetrahydroquinolin-4-yl)carbamate

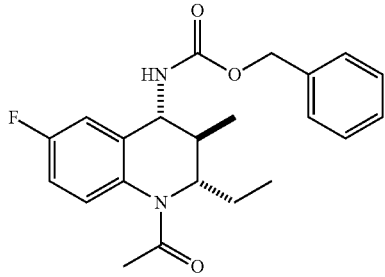 [SMILES: CC[C@H]1[C@H](C)[C@@H](NC(=O)OCc2ccccc2)c2cc(F)ccc2N1C(C)=O]

To a reaction vessel containing rac-benzyl ((2S,3S,4R)-2-ethyl-6-fluoro-3-methyl-1,2,3,4-tetrahydroquinolin-4-yl)carbamate (for a preparation see Intermediate 38, 0.54 mL, 1.831 mmol) and DIPEA (0.96 mL, 5.49 mmol) in dichloromethane (DCM) (20 mL), acetyl chloride (0.16 mL, 2.197 mmol) was added and the reaction left to stir for 16 h. A further portion of acetyl chloride (0.16 mL, 2.197 mmol) was added and the reaction left to stir for 1 h. A further portion of acetyl chloride (0.05 mL, 0.703 mmol) was added and the reaction was left to stir for 1 h. The mixture was concentrated in vacuo to give 1.85 g of crude brown solid. This was purified by chromatography on silica gel (25 g) eluting with 0-40% ethyl acetate/cyclohexane. The fractions containing product were combined and concentrated in vacuo to give the product (611 mg, 1.59 mmol, 87%) as a yellow solid.

LCMS (2 min Formic): Rt=1.08 min, [MH]$^+$=385.

Intermediate 40: rac-1-((2S,3R,4R)-4-amino-2-ethyl-6-fluoro-3-methyl-3,4-dihydroquinolin-1(2H)-yl)ethanone

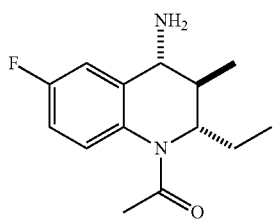 [SMILES: CC[C@H]1[C@H](C)[C@@H](N)c2cc(F)ccc2N1C(C)=O]

To a solution of rac-benzyl ((2S,3R,4R)-1-acetyl-2-ethyl-6-fluoro-3-methyl-1,2,3,4-tetrahydroquinolin-4-yl)carbamate (for a preparation see Intermediate 39, 611 mg, 1.59 mmol) in ethanol (40 mL), 10% Pd/C (85 mg, 0.795 mmol) was added and the reaction was left to stir under a hydrogen atmosphere for 2 h. The reaction mixture was filtered through celite and the celite washed with ethyl acetate (3×20 mL). The combined filtrates were concentrated in vacuo to give the product (442 mg) as a yellow solid.

LCMS (2 min Formic): Rt=0.47 min, [MH]$^+$=251.

Intermediate 41: rac-benzyl ((2S,3S,4R)-2-cyclopropyl-7-fluoro-3-methyl-1,2,3,4-tetrahydroquinolin-4-yl)carbamate

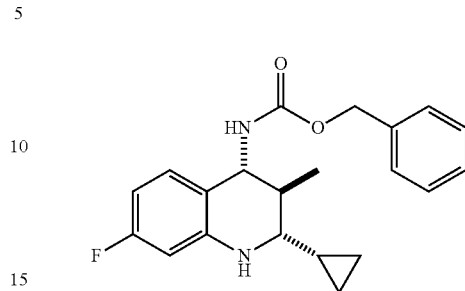

To a solution of 3-fluoroaniline (0.91 mL, 9.00 mmol) in dry dichloromethane (DCM) (11 mL) was added cyclopropanecarbaldehyde (0.67 mL, 9.00 mmol). The mixture was stirred at rt under nitrogen for 60 mins then cooled to 0° C. (ice bath). To the mixture was added first diphenyl hydrogen phosphate (22.8 g, 91 mmol) in dry dichloromethane (DCM) (13 mL) followed by (E)-benzyl prop-1-en-1-ylcarbamate (for a preparation see Intermediate 1, 187.3 g, 979 mmol) in dry dichloromethane (DCM) (13 mL). Stirring was continued at 0° C. and the reaction was allowed to warm to rtrt overnight. The reaction mixture was washed with 2M aqueous sodium hydroxide solution (30 mL) followed by water (30 mL). The organic layer was dried by passing it through a hydrophobic frit and the solvent was evaporated in vacuo. The residue was re-dissolved in dichloromethane (~10 mL) and was purified by flash column chromatography being applied to a 100 g silica cartridge and eluted with a gradient of 0-40% ethyl acetate in cyclohexane. The required fractions were combined and evaporated in vacuo to give the desired product (191 mg, 0.54 mmol, 6%).

LCMS (2 min Formic): Rt=1.29 min, [MH]$^+$=355.

Intermediate 42: rac-benzyl ((2S,3R,4R)-1-acetyl-2-cyclopropyl-7-fluoro-3-methyl-1,2,3,4-tetrahydroquinolin-4-yl)carbamate

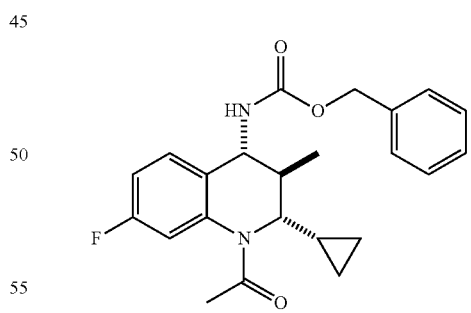

To a stirred solution of rac-benzyl ((2S,3S,4R)-2-cyclopropyl-7-fluoro-3-methyl-1,2,3,4-tetrahydroquinolin-4-yl)carbamate (for a preparation see Intermediate 41, 190 mg, 0.536 mmol) in anhydrous dichloromethane (DCM) (15 mL) under nitrogen was added pyridine (130 µl, 1.61 mmol) followed by acetyl chloride (57 µl, 0.80 mmol). The reaction mixture was stirred under nitrogen at rtrt for 90 min. The reaction mixture had saturated aqueous sodium bicarbonate solution (30 mL) added and the phases were separated. The aqueous phase was extracted with further dichloromethane (3×15 mL). The organic phases were combined, dried by passing through a cartridge fitted with a hydrophobic frit and the solvent evaporated in vacuo to give a pale brown residue. The residue was dissolved in dichloromethane (~8 mL) and was purified by flash column chromatography (50 g silica cartridge) eluting with a gradient of 0-60% ethyl acetate in cyclohexane. The required fractions were combined and the solvent evaporated in vacuo to give the desired product as a pale yellow solid (201 mg, 0.51 mmol, 95%). LCMS (2 min Formic): Rt=1.13 min, [MH]$^+$=397.

Intermediate 43: rac-1-((2S,3R,4R)-4-amino-2-cyclopropyl-7-fluoro-3-methyl-3,4-dihydroquinolin-1(2H)-yl)ethanone

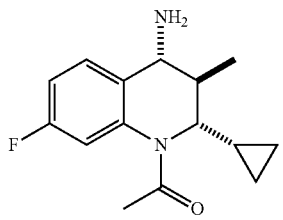 [SMILES: CC(=O)N1c2cc(F)ccc2[C@H](N)[C@@H](C)[C@@H]1C1CC1]

A stirred mixture of rac-benzyl ((2S,3R,4R)-1-acetyl-2-cyclopropyl-7-fluoro-3-methyl-1,2,3,4-tetrahydroquinolin-4-yl)carbamate (for a preparation see Intermediate 42, 201 mg, 0.51 mmol) and 10 wt. % (dry basis) palladium on activated carbon (wet, Degussa type E101 NE/W) (48.6 mg, 0.457 mmol) in ethanol (10 mL) was hydrogenated with vigorous stirring under one atmosphere of hydrogen at rtrt for 4.33 h. The reaction mixture was filtered over celite, and the filtrate was evaporated in vacuo to give the desired product as a gum (146 mg).

LCMS (2 min Formic): Rt=0.53 min, [M]$^+$=246 (loss of NH$_2^-$).

Intermediate 44: rac-benzyl ((2S,3S,4R)-2-cyclopropyl-7-methoxy-3-methyl-1,2,3,4-tetrahydroquinolin-4-yl)carbamate

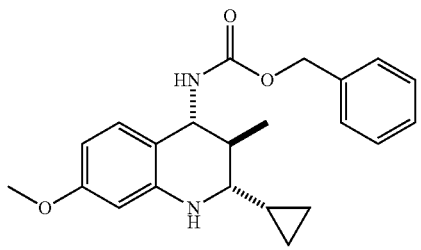 [SMILES: COc1ccc2c(c1)N[C@@H](C1CC1)[C@H](C)[C@H]2NC(=O)OCc1ccccc1]

To a solution of 3-methoxyaniline (0.91 mL, 8.12 mmol) in dry dichloromethane (DCM) (11 mL) was added cyclopropanecarbaldehyde (0.61 mL, 8.12 mmol). The mixture was stirred at rt under nitrogen for 60 min then cooled to 0° C. (ice bath). To the mixture was added first diphenyl hydrogen phosphate (0.202 g, 0.808 mmol) in dry dichloromethane (DCM) (13 mL) followed by (E)-benzyl prop-1-en-1-ylcarbamate (for a preparation see Intermediate 1, 1.7 g, 8.87 mmol) in dry dichloromethane (DCM) (13 mL). Stirring was continued at 0° C. and allowed to warm to rt overnight. The reaction mixture was washed with 2M aqueous sodium hydroxide solution (30 mL) followed by water (30 mL). The organic layer was dried by passing it through a cartridge fitted with a hydrophobic frit and the solvent was evaporated in vacuo. The residue was re-dissolved in dichloromethane (~10 mL) and was purified by flash column chromatography being applied to a 100 g silica cartridge and eluted with a gradient of 0-40% ethyl acetate in cyclohexane. The required fractions were combined and evaporated in vacuo to give the desired product a white foam solid (2.254 g, 6.15 mmol, 76%). LCMS (2 min Formic): Rt=1.19 min, [MH]$^+$=367.

Intermediate 45: rac-benzyl ((2S,3R,4R)-1-acetyl-2-cyclopropyl-7-methoxy-3-methyl-1,2,3,4-tetrahydroquinolin-4-yl)carbamate

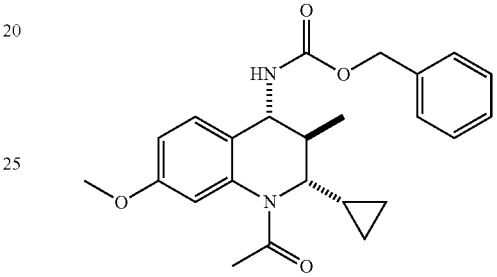

To a stirred solution of rac-benzyl ((2S,3S,4R)-2-cyclopropyl-7-methoxy-3-methyl-1,2,3,4-tetrahydroquinolin-4-yl)carbamate (for a preparation see Intermediate 41, 2.25 g, 6.15 mmol) in anhydrous dichloromethane (DCM) (42 mL) under nitrogen was added pyridine (1.49 mL, 18.45 mmol) followed by acetyl chloride (0.66 mL, 9.23 mmol). The reaction mixture was stirred at rtrt under nitrogen for 2.25 h. The reaction mixture had saturated aqueous sodium bicarbonate solution (100 mL) added and the phases were separated. The aqueous phase was extracted with further dichloromethane (3×50 mL). The organic phases were combined, dried by passing through a hydrophobic frit and the solvent evaporated in vacuo to give a dark purple oil. The residue was dissolved in dichloromethane (~8 mL) and was purified by flash column chromatography (100 g silica cartridge) eluting with a gradient of 0-60% ethyl acetate in cyclohexane. The required fractions were combined and the solvent evaporated in vacuo to give the desired product as a white solid (2.07 g, 5.08 mmol, 83%). LCMS (2 min Formic): Rt=1.10 min, [MH]$^+$=409.

Intermediate 46: rac-1-((2S,3R,4R)-4-amino-2-cyclopropyl-7-methoxy-3-methyl-3,4-dihydroquinolin-1(2H)-yl)ethanone

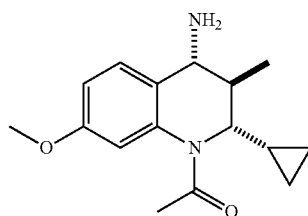

A stirred mixture of rac-benzyl ((2S,3R,4R)-1-acetyl-2-cyclopropyl-7-methoxy-3-methyl-1,2,3,4-tetrahydroquinolin-4-yl)carbamate (for a preparation see Intermediate 45, 2.07 g, 5.08 mmol) and 10 wt. % (dry basis) palladium on activated carbon (wet, Degussa type E101 NE/W) (508 mg, 4.77 mmol) in ethanol (65 mL) was hydrogenated with vigorous stirring under one atmosphere of hydrogen at rt for 2.25 h. The reaction mixture was filtered over celite, and the filtrate was transferred into a vial and evaporated down under a stream of nitrogen to give the desired product as a gum. The residue was dissolved in dichloromethane (~8 mL) and was purified by flash column chromatography (50 g silica cartridge) eluting with a gradient of 0-60% ethyl acetate in cyclohexane. The required fractions were combined and the solvent evaporated in vacuo to give the desired product as a pale yellow solid (0.87 g, 3.19 mmol, 63%).

LCMS (2 min Formic): Rt=0.47 min, [M]$^+$=258 (loss of NH$_2^-$).

Intermediate 47: rac-benzyl ((2S,3S,4R)-6-cyano-2-cyclopropyl-3-methyl-1,2,3,4-tetrahydroquinolin-4-yl)carbamate

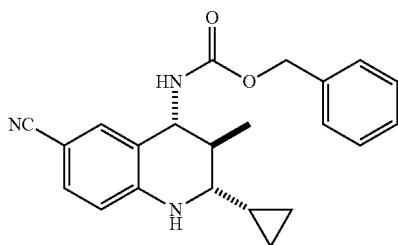

The 4-aminobenzonitrile (434 mg, 3.67 mmol) was taken up in DCM (8 mL) and was treated with cyclopropanecarbaldehyde (0.288 mL, 3.86 mmol) and allowed to stir at rt for 1 h. The reaction was then cooled to 0° C. and was treated with a solution of (E)-benzyl prop-1-en-1-ylcarbamate (for a preparation see Intermediate 1, 773 mg, 4.04 mmol) in DCM (2 mL) followed by diphenyl phosphate (92 mg, 0.367 mmol), the reaction was allowed to warm to rt and then to stir at rt for 1 h. The reaction was concentrated and then suspended in hot IPA. After cooling to rt a white precipitate resulted which was removed by filtration and dried to give the product (674 mg) as a white solid. This was used as was in the subsequent reaction.

LCMS (2 min Formic): Rt=1.15 min, [MH]$^+$=362.

Intermediate 48: rac-benzyl ((2S,3R,4R)-1-acetyl-6-cyano-2-cyclopropyl-3-methyl-1,2,3,4-tetrahydroquinolin-4-yl)carbamate

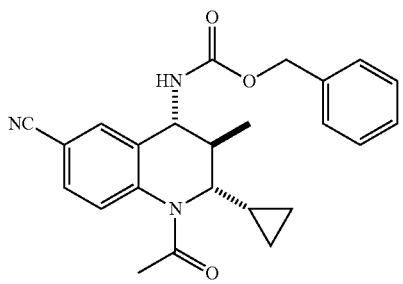 [SMILES: CC(=O)N1c2ccc(C#N)cc2[C@H](NC(=O)OCc2ccccc2)[C@@H](C)[C@@H]1C1CC1]

rac-Benzyl ((2S,3S,4R)-6-cyano-2-cyclopropyl-3-methyl-1,2,3,4-tetrahydroquinolin-4-yl)carbamate (for a preparation see Intermediate 47, 674 mg, 1.865 mmol) was taken up in dichloromethane (DCM) (30 mL) and treated with DIPEA (0.65 mL, 3.73 mmol) and acetyl chloride (0.4 mL, 5.59 mmol) and allowed to stir at rt for 3 days. The reaction was concentrated and purified using a column chromatography (10 g silica) 0-50% EtOAc:cyclohexane. The appropriate fractions were summed and concentrated to give the product (524 mg) as a white solid.

LCMS (2 min Formic): Rt=1.05 min, [MH]$^+$=404.

Intermediate 49: rac-(2S,3R,4R)-1-acetyl-4-amino-2-cyclopropyl-3-methyl-1,2,3,4-tetrahydroquinoline-6-carbonitrile

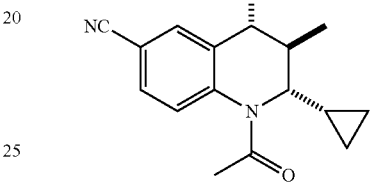

rac-Benzyl ((2S,3R,4R)-1-acetyl-6-cyano-2-cyclopropyl-3-methyl-1,2,3,4-tetrahydroquinolin-4-yl)carbamate (for a preparation see Intermediate 48, 524 mg, 1.30 mmol) was suspended in ethanol (10 mL) and was hydrogenated using the H-cube (25° C., 1 bar, 1 mL/min flow rate) and a 10% Pd/C CatCart 30 as the catalyst. The reaction mixture was concentrated and dried to give the product as a colourless gum (315 mg). LCMS (2 min Formic): Rt=0.49 min, [MH]$^+$=270.

Intermediate 50: rac-benzyl ((2S,3R,4R)-1-acetyl-2-cyclopropyl-3-methyl-6-(methylsulfonyl)-1,2,3,4-tetrahydroquinolin-4-yl)carbamate

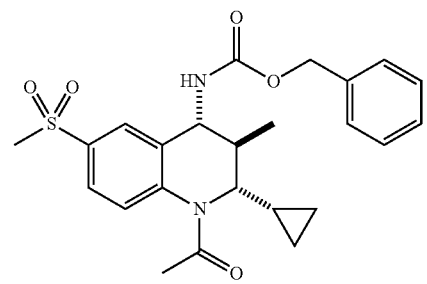 [SMILES: CC(=O)N1c2ccc(S(C)(=O)=O)cc2[C@H](NC(=O)OCc2ccccc2)[C@@H](C)[C@@H]1C1CC1]

A mixture of Pd$_2$(dba)$_3$ (30 mg, 0.033 mmol), XantPhos (40 mg, 0.069 mmol), rac-benzyl ((2S,3R,4R)-1-acetyl-6-bromo-2-cyclopropyl-3-methyl-1,2,3,4-tetrahydroquinolin-4-yl)carbamate (for a preparation see Intermediate 13, 300 mg, 0.656 mmol) and sodium methanethiolate (92 mg, 1.312 mmol) in a 2-5 mL microwave vessel was diluted with anhydrous 1,4-dioxane (2.0 mL). The vessel was sealed and heated in a microwave reactor at 140° C. for 45 min. The reaction mixture was diluted with 2M Na$_2$S$_2$O$_3$ (aq) (3.0 mL) and 2M NaHCO$_3$ (aq) (0.5 mL). The mixture was extracted with EtOAc (2×2 mL), the organic extracts were combined and dried through a hydrophobic frit. The solvent was removed under a stream of nitrogen and the residue diluted with chloroform (4 mL). The solution was cooled to 0° C., treated with 3-chlorobenzoperoxoic acid (340 mg, 1.968 mmol) and stirred in a stoppered vessel for 10 min. The mixture was allowed to warm to rt over 3 h. The reaction mixture was washed with 10% w/v Na$_2$CO$_3$ (aq) (2×5 mL) followed by water (5 mL). The organic layer was dried through a hydrophobic frit and the solvent evaporated under a stream of nitrogen to give the product (80 mg).

LCMS (2 min Formic): Rt=0.98 min, [MH]$^+$=457.

Intermediate 51: rac-1-((2S,3R,4R)-4-amino-2-cyclopropyl-3-methyl-6-(methylsulfonyl)-3,4-dihydroquinolin-1(2H)-yl)ethanone

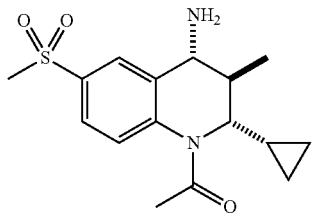 [SMILES: CC(=O)N1c2ccc(S(C)(=O)=O)cc2[C@H](N)[C@@H](C)[C@@H]1C1CC1]

rac-Benzyl ((2S,3R,4R)-1-acetyl-2-cyclopropyl-3-methyl-6-(methylsulfonyl)-1,2,3,4-tetrahydroquinolin-4-yl)carbamate (for a preparation see Intermediate 50, 80 mg, 0.175 mmol) in methanol (3.5 mL) was hydrogenated using the H-cube (rt, full H$_2$ mode, 1 mL/min flow rate) and 10% Pd/C as catalyst. The solvent was evaporated in vacuo to give the product (51 mg, 0.159 mmol, 91% yield). LCMS (2 min Formic): Rt=0.47 min, [M]$^+$=306 (loss of NH$_2^-$).

Intermediate 52: rac-benzyl ((2S,3R,4R)-1-acetyl-2-cyclopropyl-6-(isopropylsulfonyl)-3-methyl-1,2,3,4-tetrahydroquinolin-4-yl)carbamate

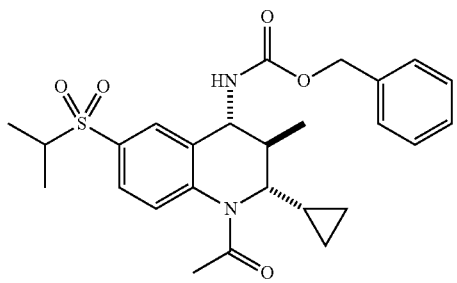 [SMILES: CC(=O)N1c2ccc(S(=O)(=O)C(C)C)cc2[C@H](NC(=O)OCc2ccccc2)[C@@H](C)[C@@H]1C1CC1]

A mixture of Pd$_2$(dba)$_3$ (30 mg, 0.033 mmol), XantPhos (40 mg, 0.069 mmol) and rac-benzyl ((2S,3R,4R)-1-acetyl-6-bromo-2-cyclopropyl-3-methyl-1,2,3,4-tetrahydroquinolin-4-yl)carbamate (for a preparation see Intermediate 13, 300 mg, 0.656 mmol) in a 0.5-2 mL microwave vessel was diluted with anhydrous 1,4-dioxane (2 mL) and treated with DIPEA (0.230 mL, 1.317 mmol) followed by propane-2-thiol (0.120 mL, 1.292 mmol). The vessel was sealed and heated in a microwave reactor at 140° C. for 45 min. The reaction mixture was diluted with 2M Na$_2$S$_2$O$_3$ (aq) (3 mL) and 2M NaHCO$_3$ (aq) (0.5 mL). The mixture was extracted with EtOAc (2×2 mL), the organic extracts were combined and dried through a hydrophobic frit. The solvent was removed under a stream of nitrogen and the residue diluted with chloroform (2 mL). The solution was treated with 3-chlorobenzoperoxoic acid (170 mg, 0.985 mmol) and left to stand in a stoppered vessel at rt for 1.5 h. Further 3-chlorobenzoperoxoic acid (215 mg, 1.246 mmol) was added and the reaction was left to stand at rt for 16 h during which time the mixture solidified. The reaction mixture was diluted with CHCl$_3$ (3 mL) and washed with 10% w/v Na$_2$CO$_3$ (aq) (2×5 mL) followed by water (5 mL). The organic layer was dried through a hydrophobic frit and the solvent evaporated under a stream of nitrogen. The residue was loaded in DCM (5 mL) and purified on a 50 g silica cartridge using a gradient of 0-100% EtOAc in cyclohexane. The appropriate fractions were combined and the solvent removed by rotary evaporation to give the product as a light yellow gum (293 mg, 0.605 mmol, 92%).

LCMS (2 min Formic): Rt=1.06 min, [MH]$^+$=484.

Intermediate 53: rac-1-((2S,3R,4R)-4-amino-2-cyclopropyl-6-(isopropylsulfonyl)-3-methyl-3,4-dihydroquinolin-1(2H)-yl)ethanone

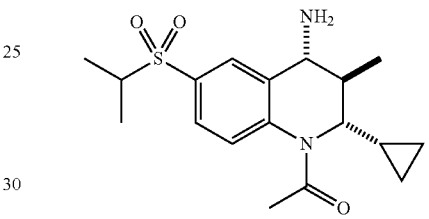

A solution of rac-benzyl ((2S,3R,4R)-1-acetyl-2-cyclopropyl-6-(isopropylsulfonyl)-3-methyl-1,2,3,4-tetrahydroquinolin-4-yl)carbamate (for a preparation see Intermediate 52, 288 mg, 0.594 mmol) in methanol (12 mL) was hydrogenated using the H-cube (rt, full H$_2$ mode, 1 mL/min flow rate) and a 10% Pd/C CatCart 30 as the catalyst. The eluent was concentrated in vacuo to ~12 mL and passed through the H-Cube using the same conditions for a second time. The eluent was concentrated in vacuo to ~12 mL and passed through the H-Cube using the same conditions but with a fresh CatCart. The eluent was evaporated in vacuo to give the product as a light yellow gum (169 mg, 0.482 mmol, 81%). LCMS (2 min HpH): Rt=0.80 min, [M]$^+$=334 (loss of NH$_2^-$).

Intermediate 54: rac-tert-butyl 4-((2S,3R,4R)-1-acetyl-4-amino-2,3-dimethyl-1,2,3,4-tetrahydroquinolin-6-yl)piperazine-1-carboxylate

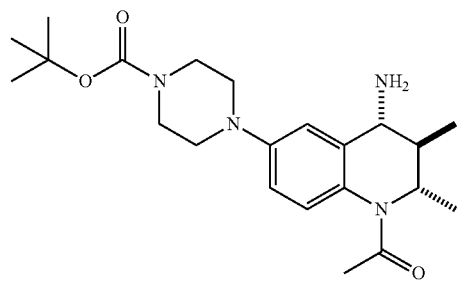 [SMILES: CC(=O)N1c2ccc(N3CCN(C(=O)OC(C)(C)C)CC3)cc2[C@H](N)[C@@H](C)[C@@H]1C]

To a solution of tert-butyl piperazine-1-carboxylate (73.8 mg, 0.396 mmol) in 1,4-dioxane (3 mL) were added rac-benzyl ((2S,3R,4R)-1-acetyl-6-bromo-2-cyclopropyl-3-methyl-1,2,3,4-tetrahydroquinolin-4-yl)carbamate (for a preparation see Intermediate 3, 142.4 mg, 0.330 mmol), DavePhos (12.99 mg, 0.033 mmol), Pd$_2$(dba)$_3$ (15.12 mg, 0.017 mmol) and sodium tert-butoxide (47.6 mg, 0.495 mmol). The reaction was irradiated in a microwave at 110° C. for 30 min. The reaction mixture was filtered through a pad of celite (rinsed with EtOAc). The filtrate was then evaporated in vacuo and purified by chromatography on silica gel eluting with 0-100% of ethyl acetate in cyclohexane. Then the column was flushed with 10% of methanol in DCM to give crude product which was further purified by chromatography on silica gel eluting with 0-10% of methanol in DCM to the product (55 mg, 41%) as a yellow solid.

LCMS (2 min Formic): Rt=0.66 min, [M]$^+$=386 (loss of NH$_2^-$).

Intermediate 55: rac-tert-butyl 4-((2S,3R,4R)-1-acetyl-2,3-dimethyl-4-(phenylamino)-1,2,3,4-tetrahydroquinolin-6-yl)piperazine-1-carboxylate

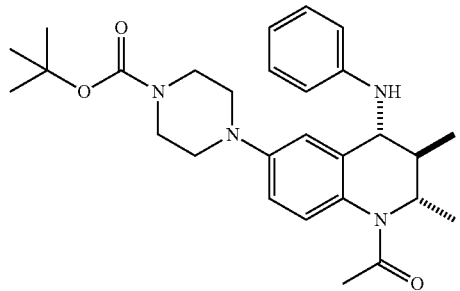 [SMILES: CC(=O)N1c2ccc(N3CCN(C(=O)OC(C)(C)C)CC3)cc2[C@H](Nc2ccccc2)[C@@H](C)[C@@H]1C]

Under nitrogen atmosphere, to a solution of bromobenzene (0.020 mL, 0.191 mmol) in 1,4-dioxane (3 mL) were added rac-tert-butyl 4-((2S,3R,4R)-1-acetyl-4-amino-2,3-dimethyl-1,2,3,4-tetrahydroquinolin-6-yl)piperazine-1-carboxylate (for a preparation see Intermediate 54, 64 mg, 0.159 mmol), DavePhos (6.26 mg, 0.016 mmol), Pd$_2$(dba)$_3$ (7.28 mg, 7.95 µmol) and sodium tert-butoxide (22.92 mg, 0.238 mmol). The reaction was irradiated at 110° C. for 1 h. The reaction was treated with further Pd$_2$(dba)$_3$ (7.28 mg, 7.95 µmol), DavePhos (6.26 mg, 0.016 mmol) and sodium tert-butoxide (22.92 mg, 0.238 mmol) and irradiated at 110° C. for 30 min. After cooling to rt, the reaction mixture was filtered through a pad of celite (rinsed with EtOAc). The filtrate was then evaporated in vacuo and purified by MDAP (Formic) to give the product (24 mg, 32%) as a yellow solid. LCMS (2 min Formic): Rt=1.26 min, [MH]$^+$=479.

Intermediate 56: rac1-((2S,3R,4R)-4-amino-2,3-dimethyl-6-morpholino-3,4-dihydroquinolin-1(2H)-yl)ethanone

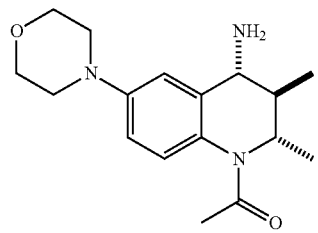

To a solution of morpholine (0.034 mL, 0.389 mmol) in 1,4-dioxane (3 mL) were added rac-benzyl ((2S,3R,4R)-1-acetyl-6-bromo-2-cyclopropyl-3-methyl-1,2,3,4-tetrahydroquinolin-4-yl)carbamate (for a preparation see Intermediate 3, 139.7 mg, 0.324 mmol), DavePhos (12.75 mg, 0.032 mmol), Pd$_2$(dba)$_3$ (14.83 mg, 0.016 mmol) and sodium tert-butoxide (46.7 mg, 0.486 mmol). The reaction was irradiated at 110° C. for 30 min. The reaction mixture was filtered through a pad of celite (rinsed with EtOAc). The filtrate was then evaporated and purified by column chromatography on silica gel eluting with 0-10% of methanol in DCM to give the product (33 mg, 33%) as a white solid.

LCMS (2 min Formic): Rt=0.44 min, [MH]$^+$=304.

Intermediate 57: tert-butyl 4-((rac-2S,3R,4R)-1-acetyl-4-amino-2,3-dimethyl-1,2,3,4-tetrahydroquinolin-6-yl)-2-methylpiperazine-1-carboxylate

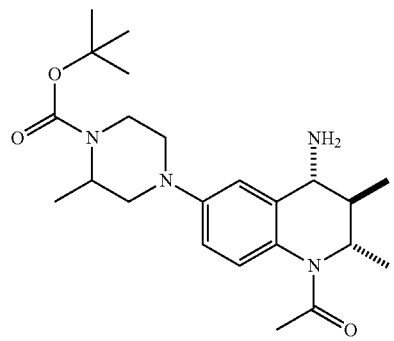 [SMILES: CC(=O)N1c2ccc(N3CCN(C(=O)OC(C)(C)C)C(C)C3)cc2[C@H](N)[C@@H](C)[C@@H]1C]

To a greenhouse test tube was added rac-benzyl ((2S,3R,4R)-1-acetyl-6-bromo-2-cyclopropyl-3-methyl-1,2,3,4-tetrahydroquinolin-4-yl)carbamate (for a preparation see Intermediate 3, 101 mg, 0.234 mmol), sodium tert-butoxide (65 mg, 0.676 mmol), DavePhos (18.1 mg, 0.046 mmol), Pd$_2$(dba)$_3$ (21.9 mg, 0.024 mmol) and 1,4-dioxane (2 mL). tert-Butyl 2-methylpiperazine-1-carboxylate (0.070 mL, 0.351 mmol) was then added and the reaction mixture stirred at 100° C. for 20 h 45 min. The reaction mixture was allowed to cool to rt and then filtered through a pad of celite and rinsed with ethyl acetate. The filtrate was concentrated and purified by MDAP (Formic) to give the product (14.1 mg, 0.034 mmol, 14.46%) as a pale yellow gum. This was a racemic mixture of diastereoisomers. LCMS (2 min Formic): Rt=0.77 min, [MH]$^+$=417.

Intermediate 58: tert-butyl 4-((rac-2S,3R,4R)-1-acetyl-2,3-dimethyl-4-(phenylamino)-1,2,3,4-tetrahydroquinolin-6-yl)-2-methylpiperazine-1-carboxylate

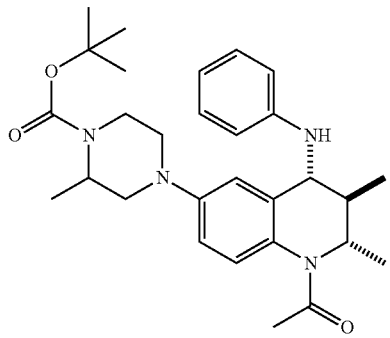 [SMILES: CC(=O)N1c2ccc(N3CCN(C(=O)OC(C)(C)C)C(C)C3)cc2[C@H](Nc2ccccc2)[C@@H](C)[C@@H]1C]

To a greenhouse test tube was added tert-butyl 4-((rac-2S,3R,4R)-1-acetyl-4-amino-2,3-dimethyl-1,2,3,4-tetrahydroquinolin-6-yl)-2-methylpiperazine-1-carboxylate (for a preparation see Intermediate 57, 14.1 mg, 0.034 mmol), bromobenzene (5 µL, 0.047 mmol), Pd$_2$(dba)$_3$ (2.2 mg, 2.402 µmol), DavePhos (1.6 mg, 4.07 µmol), sodium tert-butoxide (5.1 mg, 0.053 mmol) and 1,4-dioxane (0.5 mL). The reaction mixture was stirred at 100° C. under nitrogen for 16 h. The reaction mixture was allowed to cool to rt then loaded onto a 2.5 g celite cartridge, eluted with ethyl acetate then evaporated under a stream of nitrogen. To the residue was added 1,4-dioxane (0.5 mL), DavePhos (1.8 mg, 4.57 µmol), Pd$_2$(dba)$_3$ (2.1 mg, 2.293 µmol), sodium tert-butoxide (5.7 mg, 0.059 mmol) and bromobenzene (5 µL, 0.047 mmol). The reaction mixture was stirred at 100° C. under nitrogen for a further 4 h. The reaction mixture was allowed to cool to rt then loaded onto a 2.5 g celite cartridge, eluted with ethyl acetate then concentrated and purified by MDAP (Formic) to give the product (7.4 mg, 0.015 mmol, 44.4%) as a yellow gum. This was a racemic mixture of diastereoisomers. LCMS (2 min Formic): Rt=1.32 min, [MH]$^+$=493.

Intermediate 59: rac-tert-butyl (1-((2S,3R,4R)-1-acetyl-4-(((benzyloxy)carbonyl)amino)-2,3-dimethyl-1,2,3,4-tetrahydroquinolin-6-yl)piperidin-4-yl)carbamate

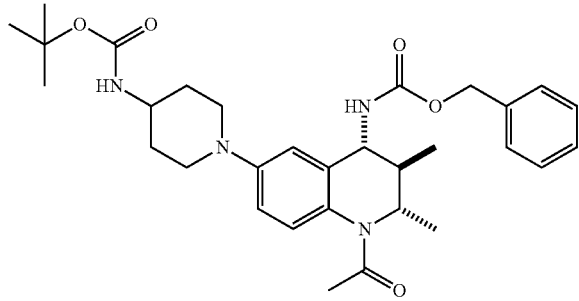 [SMILES: CC(=O)N1c2ccc(N3CCC(NC(=O)OC(C)(C)C)CC3)cc2[C@H](NC(=O)OCc2ccccc2)[C@@H](C)[C@@H]1C]

To a solution of rac-benzyl ((2S,3R,4R)-1-acetyl-6-bromo-2,3-dimethyl-1,2,3,4-tetrahydroquinolin-4-yl)carbamate (for a preparation see Intermediate 3, 148.7 mg, 0.345 mmol) in 1,4-dioxane (3 mL) were added tert-butyl piperidin-4-ylcarbamate (83 mg, 0.414 mmol), Pd$_2$(dba)$_3$ (15.78 mg, 0.017 mmol), DavePhos (13.57 mg, 0.034 mmol) and sodium tert-butoxide (49.7 mg, 0.517 mmol). The reaction was irradiated in a microwave at 110° C. for 30 min. After cooling to rt, the reaction mixture was filtered through a pad of celite (rinsed with EtOAc). The filtrate was then evaporated in vacuo and purified by column chromatography on silica gel eluting with 0-100% of ethyl acetate in cyclohexane to give the product (29.2 mg, 15%) as a yellow solid.
LCMS (2 min Formic): Rt=1.09 min, [MH]$^+$=551.

Intermediate 60: rac-tert-butyl (1-((2S,3R,4R)-1-acetyl-4-amino-2,3-dimethyl-1,2,3,4-tetrahydroquinolin-6-yl)piperidin-4-yl)carbamate

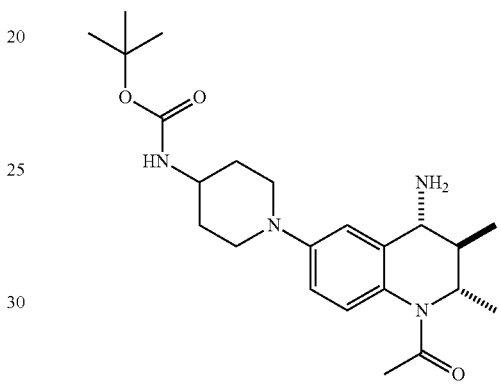

rac-tert-Butyl (1-((2S,3R,4R)-1-acetyl-4-(((benzyloxy)carbonyl)amino)-2,3-dimethyl-1,2,3,4-tetrahydroquinolin-6-yl)piperidin-4-yl)carbamate (for a preparation see Intermediate 59, 29.2 mg, 0.053 mmol) was dissolved in methanol (2 mL) and was then passed through a 10% Pd/C cartridge on a H-cube (rt, full H$_2$ mode) to give a colourless filtrate. This filtrate was concentrated in vacuo to give the product (15 mg) as a colourless solid.
LCMS (2 min Formic): Rt=0.70 min, [M]$^+$=400 (loss of NH$_2^-$).

Intermediate 61: rac-tert-butyl (1-((2S,3R,4R)-1-acetyl-2,3-dimethyl-4-(phenylamino)-1,2,3,4-tetrahydroquinolin-6-yl)piperidin-4-yl)carbamate

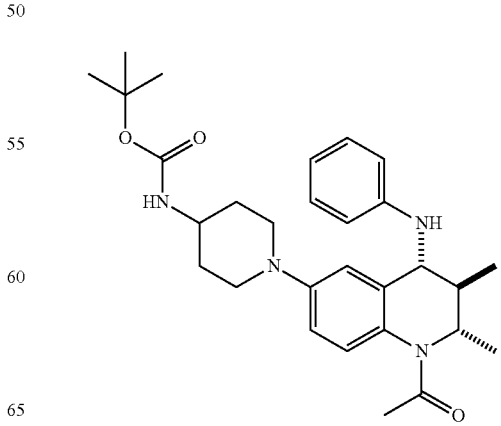

Under nitrogen atmosphere, to a solution of bromobenzene (4.63 µL, 0.043 mmol) in 1,4-dioxane (1 mL) were added rac-tert-butyl (1-((2S,3R,4R)-1-acetyl-4-amino-2,3-dimethyl-1,2,3,4-tetrahydroquinolin-6-yl)piperidin-4-yl)carbamate (for a preparation see Intermediate 60, 15.1 mg, 0.036 mmol), DavePhos (1.427 mg, 3.62 µmol), Pd$_2$(dba)$_3$ (1.660 mg, 1.812 µmol) and sodium tert-butoxide (5.23 mg, 0.054 mmol). The reaction mixture was degassed with nitrogen for 10 min and irradiated in a microwave at 110° C. for 30 min. The reaction was treated with further bromobenzene (4.63 µL, 0.043 mmol), Pd$_2$(dba)$_3$ (1.660 mg, 1.812 µmol), DavePhos (1.427 mg, 3.62 µmol) and sodium tert-butoxide (5.23 mg, 0.054 mmol) and irradiated in a microwave at 110° C. for 30 min. After cooling to rt, the reaction mixture was filtered through a pad of celite (rinsed with EtOAc). The filtrate was then evaporated in vacuo and the residue purified by chromatography on silica gel eluting with 0-100% of ethyl acetate in cyclohexane to give the product (6.8 mg, 38%) as a colourless solid. LCMS (2 min Formic): Rt=1.14 min, [MH]$^+$=493.

Intermediate 62: rac-tert-butyl 4-(((2S,3R,4R)-1-acetyl-4-(((benzyloxy)carbonyl)amino)-2,3-dimethyl-1,2,3,4-tetrahydroquinolin-6-yl)amino)piperidine-1-carboxylate Intermediate 63: rac-tert-butyl 4-(((2S,3R,4R)-1-acetyl-4-amino-2,3-dimethyl-1,2,3,4-tetrahydroquinolin-6-yl)amino)piperidine-1-carboxylate

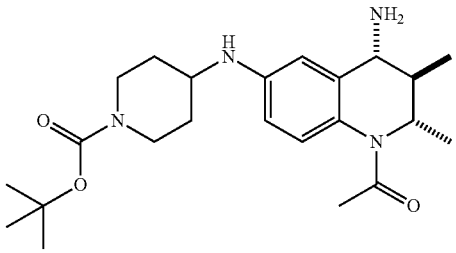 [SMILES: CC(=O)N1c2ccc(NC3CCN(C(=O)OC(C)(C)C)CC3)cc2[C@H](N)[C@@H](C)[C@@H]1C]

rac-tert-butyl 4-(((2S,3R,4R)-1-acetyl-4-(((benzyloxy)carbonyl)amino)-2,3-dimethyl-1,2,3,4-tetrahydroquinolin-6-yl)amino)piperidine-1-carboxylate (for a preparation see Intermediate 62, 19 mg, 0.035 mmol) was dissolved in methanol (2 mL) and was then passed through a 10% Pd/C cartridge on a H-cube (rt, full H$_2$ mode) to give a colourless filtrate. This filtrate was concentrated in vacuo to give the product (12 mg, 86%) as a colourless solid.

LCMS (2 min Formic): Rt=0.74 min, [M]$^+$=400 (loss of NH$_2^-$).

Intermediate 64: rac-tert-butyl 4-(((2S,3R,4R)-1-acetyl-2,3-dimethyl-4-(phenylamino)-1,2,3,4-tetrahydroquinolin-6-yl)amino)piperidine-1-carboxylate

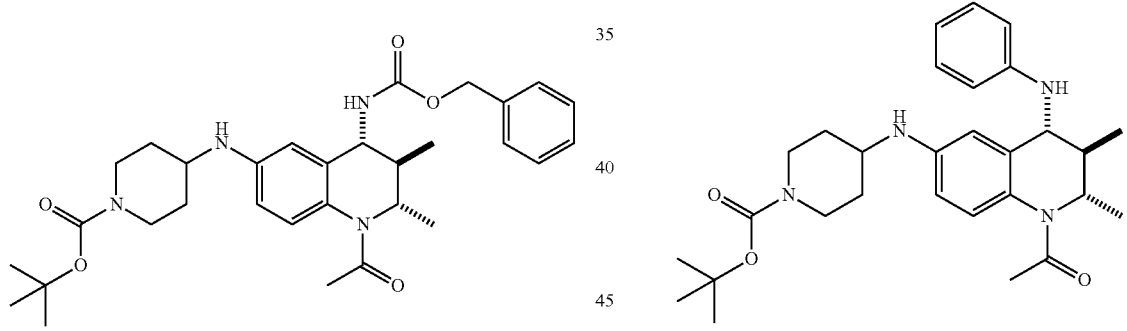

To a solution of tert-butyl 4-aminopiperidine-1-carboxylate (84 mg, 0.417 mmol) in 1,4-dioxane (3 mL) were added rac-benzyl ((2S,3R,4R)-1-acetyl-6-bromo-2,3-dimethyl-1,2,3,4-tetrahydroquinolin-4-yl)carbamate (150 mg, 0.348 mmol), DavePhos (13.69 mg, 0.035 mmol), Pd$_2$(dba)$_3$ (15.92 mg, 0.017 mmol) and sodium tert-butoxide (50.1 mg, 0.522 mmol). The reaction was irradiated in a microwave at 110° C. for 30 min. After cooling to rt, the reaction mixture was filtered through a pad of celite (rinsed with EtOAc). The filtrate was then evaporated in vacuo and purified by chromatography on silica gel eluting with 0-100% of ethyl acetate in cyclohexane to give the product (19 mg, 10%) as a yellow solid.

LCMS (2 min Formic): Rt=1.16 min, [MH]$^+$=495

Under nitrogen atmosphere, to a solution of bromobenzene (3.77 µL, 0.035 mmol) in 1,4-dioxane (1 mL) were added rac-tert-butyl 4-(((2S,3R,4R)-1-acetyl-4-amino-2,3-dimethyl-1,2,3,4-tetrahydroquinolin-6-yl)amino)piperidine-1-carboxylate (for a preparation see Intermediate 63, 12.3 mg, 0.030 mmol), DavePhos (1.162 mg, 2.95 µmol), Pd$_2$(dba)$_3$ (1.352 mg, 1.476 µmol) and sodium tert-butoxide (4.26 mg, 0.044 mmol). The reaction mixture was degassed with nitrogen for 10 min and irradiated in a microwave at 110° C. for 30 min. The reaction was treated with further bromobenzene (3.77 µL, 0.035 mmol), Pd$_2$(dba)$_3$ (1.352 mg, 1.476 µmol), DavePhos (1.162 mg, 2.95 µmol) and sodium tert-butoxide (4.26 mg, 0.044 mmol) and irradiated in a microwave at 110° C. for 30 min. After cooling to rt, the reaction mixture was filtered through a pad of celite (rinsed with EtOAc). The filtrate was then evaporated in vacuo and purified by chromatography on silica gel eluting with 0-100% of ethyl acetate in cyclohexane to give the product (11 mg, 74%) as a yellow solid. LCMS (2 min Formic): Rt=1.13 min, [MH]$^+$=493.

Intermediate 65: 1-((rac-2S,3R,4R)-4-amino-2,3-dimethyl-6-(2-methylmorpholino)-3,4-dihydroquinolin-1(2H)-yl)ethanone

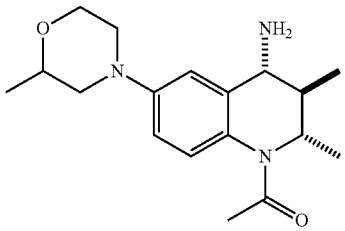

To a tube was added 2-methylmorpholine (23.0 mg, 0.227 mmol), rac-benzyl ((2S,3R,4R)-1-acetyl-6-bromo-2,3-dimethyl-1,2,3,4-tetrahydroquinolin-4-yl)carbamate (for a preparation see Intermediate 3, 62.6 mg, 0.145 mmol), sodium tert-butoxide (42.6 mg, 0.443 mmol), DavePhos (12.0 mg, 0.030 mmol, Pd$_2$(dba)$_3$ (13.0 mg, 0.014 mmol) and 1,4-dioxane (2 mL). The reaction mixture was stirred at 100° C. under nitrogen for 19 h. The reaction mixture was allowed to cool to rt then loaded onto a 2.5 g celite cartridge, eluted with ethyl acetate then evaporated under a stream of nitrogen. The residue was purified MDAP (Formic) to give the product (5.9 mg, 0.019 mmol, 12.81%) as a pale yellow gum. This was a racemic mixture of diastereoisomers.

LCMS (2 min Formic): Rt=0.52 min, [MH]$^+$=318.

Intermediate 66: tert-butyl 5-((rac-2S,3R,4R)-1-acetyl-4-amino-2,3-dimethyl-1,2,3,4-tetrahydroquinolin-6-yl)-2,5-diazabicyclo[2.2.2]octane-2-carboxylate

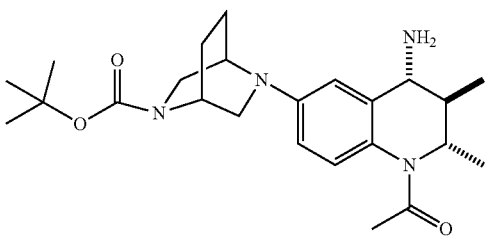 [SMILES: CC(=O)N1c2ccc(N3CC4CCC3CN4C(=O)OC(C)(C)C)cc2[C@H](N)[C@@H](C)[C@@H]1C]

A mixture of rac-benzyl ((2S,3R,4R)-1-acetyl-6-bromo-2,3-dimethyl-1,2,3,4-tetrahydroquinolin-4-yl)carbamate (for a preparation see Intermediate 3, 73.5 mg, 0.170 mmol), tert-butyl 2,5-diazabicyclo[2.2.2]octane-2-carboxylate (43.8 mg, 0.206 mmol), sodium-tert-butoxide (49.4 mg, 0.514 mmol), DavePhos (13.6 mg, 0.035 mmol) and Pd$_2$(dba)$_3$ (15.5 mg, 0.017 mmol) had 1,4-dioxane (2 mL) added and were heated with stirring under nitrogen at 100° C. The reaction mixture was allowed to cool to rt and filtered through a celite cartridge which was flushed with ethyl acetate, the filtrate was concentrated and purified by MDAP (Formic) to give the product (12.9 mg, 0.030 mmol, 17.66%) as a cream solid. This was a racemic mixture of diastereoisomers.

LCMS (2 min Formic): Rt=0.77 min, [MH]$^+$=429.

Intermediate 67: tert-butyl 5-((rac-2S,3R,4R)-1-acetyl-2,3-dimethyl-4-(phenylamino)-1,2,3,4-tetrahydroquinolin-6-yl)-2,5-diazabicyclo[2.2.2]octane-2-carboxylate

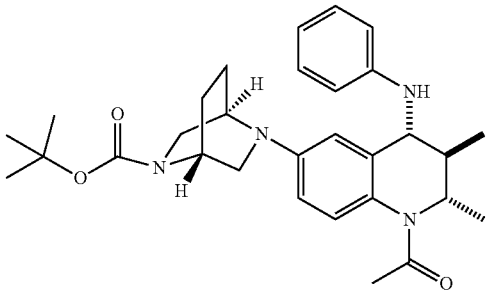 [SMILES: CC(=O)N1c2ccc(N3C[C@H]4CC[C@@H]3CN4C(=O)OC(C)(C)C)cc2[C@H](Nc2ccccc2)[C@@H](C)[C@@H]1C]

To a solution of tert-butyl 5-((rac-2S,3R,4R)-1-acetyl-4-amino-2,3-dimethyl-1,2,3,4-tetrahydroquinolin-6-yl)-2,5-diazabicyclo[2.2.2]octane-2-carboxylate (for a preparation see Intermediate 66, 12.9 mg, 0.030 mmol) in 1,4-dioxane (0.5 mL) was added bromobenzene (5 µL, 0.047 mmol), Pd$_2$(dba)$_3$ (1.4 mg, 1.529 µmol), DavePhos (1.2 mg, 3.05 µmol) and sodium tert-butoxide (4.2 mg, 0.044 mmol). The reaction mixture was stirred at 100° C. for 18 h. The reaction mixture was allowed to cool to rt then loaded onto a 2.5 g celite cartridge, eluted with ethyl acetate then evaporated under a stream of nitrogen. To the residue was added 1,4-dioxane (0.5 mL), bromobenzene (10 µL, 0.094 mmol), Pd$_2$(dba)$_3$ (2.1 mg, 2.293 µmol), DavePhos (2.3 mg, 5.84 µmol) and sodium tert-butoxide (4.6 mg, 0.048 mmol). The reaction mixture was stirred at 100° C. for a further 21 h. The reaction mixture was allowed to cool to rt then loaded onto a 2.5 g celite cartridge, eluted with ethyl acetate then evaporated under a stream of nitrogen. To the residue was added 1,4-dioxane (0.5 mL), bromobenzene (10 µL, 0.094 mmol), Pd$_2$(dba)$_3$ (2.0 mg, 2.184 µmol), DavePhos (2.2 mg, 5.59 µmol) and sodium tert-butoxide (4.4 mg, 0.046 mmol). The reaction mixture was stirred at 100° C. for a further 6 h. The reaction mixture was allowed to cool to rt then loaded onto a 2.5 g celite cartridge, eluted with ethyl acetate then evaporated under a stream of nitrogen. The residue was purified by MDAP (Formic) to give the product (4.7 mg, 9.31 µmol, 30.9%). This was a racemic mixture of diastereoisomers. LCMS (2 min Formic): Rt=1.30 min, [MH]$^+$=505.

Intermediate 68: rac-1-((2S,3R,4R)-4-amino-6-(-8-oxa-3-azabicyclo[3.2.1]octan-3-yl)-2,3-dimethyl-3,4-dihydroquinolin-1(2H)-yl)ethanone

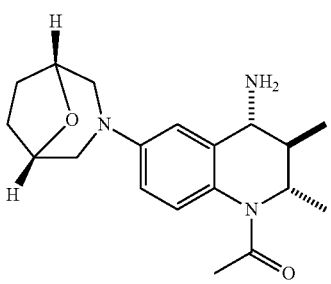 [SMILES: CC(=O)N1c2ccc(N3C[C@H]4CC[C@@H](C3)O4)cc2[C@H](N)[C@@H](C)[C@@H]1C]

A mixture of rac-benzyl ((2S,3R,4R)-1-acetyl-6-bromo-2,3-dimethyl-1,2,3,4-tetrahydroquinolin-4-yl)carbamate (for a preparation see Intermediate 3, 75.3 mg, 0.175 mmol), (1R,5S)-8-oxa-3-azabicyclo[3.2.1]octane, hydrochloride (32.3 mg, 0.216 mmol), sodium-tert-butoxide (68.4 mg, 0.712 mmol), DavePhos (14.6 mg, 0.037 mmol) and Pd$_2$(dba)$_3$ (17.1 mg, 0.019 mmol) had 1,4-dioxane (2 mL) added and were heated with stirring under nitrogen at 100° C. for 23 h. The reaction mixture was allowed to cool to rt and filtered through a celite cartridge which was flushed with ethyl acetate. The combined filtrates were concentrated and purified by MDAP (Formic) to give the product (5.6 mg, 0.017 mmol, 9.74%) as a pale yellow gum.

LCMS (2 min Formic): Rt=0.54 min, [MH]$^+$=330.

Intermediate 69: 1-((rac-2S,3R,4R)-4-amino-2,3-dimethyl-6-(3-methylpyrrolidin-1-yl)-3,4-dihydroquinolin-1(2H)-yl)ethanone

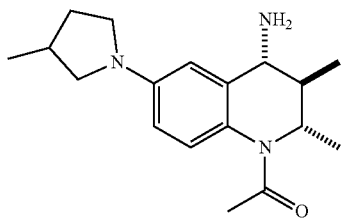

To a greenhouse test tube was added rac-benzyl ((2S,3R,4R)-1-acetyl-6-bromo-2,3-dimethyl-1,2,3,4-tetrahydroquinolin-4-yl)carbamate (for a preparation see Intermediate 3, 102.7 mg, 0.238 mmol), sodium tert-butoxide (86.1 mg, 0.896 mmol), DavePhos (18.1 mg, 0.046 mmol), Pd$_2$(dba)$_3$ (21.7 mg, 0.024 mmol) and 1,4-dioxane (2 mL). 3-methylpyrrolidine hydrochloride (42.3 mg, 0.348 mmol) was then added and the reaction mixture stirred at 100° C. under nitrogen for 20 h 45 min. The reaction mixture was allowed to cool to rt and then filtered through a pad of celite and rinsed with ethyl acetate. The filtrate was concentrated and purified by MDAP (Formic) to give the product (25.7 mg, 0.085 mmol, 35.8%) as a yellow gum. This was a racemic mixture of diastereoisomers.

LCMS (2 min Formic): Rt=0.68 min, [MH]$^+$=302.

Intermediate 70: 1-((rac-2S,3R,4R)-4-amino-2,3-dimethyl-6-(2-methylpyrrolidin-1-yl)-3,4-dihydroquinolin-1(2H)-yl)ethanone

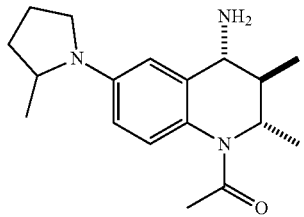 [SMILES: CC(=O)N1c2ccc(N3CCCC3C)cc2[C@H](N)[C@@H](C)[C@@H]1C]

To a greenhouse test tube was added rac-benzyl ((2S,3R,4R)-1-acetyl-6-bromo-2,3-dimethyl-1,2,3,4-tetrahydroquinolin-4-yl)carbamate (for a preparation see Intermediate 3, 103.2 mg, 0.239 mmol), sodium tert-butoxide (66.1 mg, 0.688 mmol), DavePhos (19.1 mg, 0.049 mmol), Pd$_2$(dba)$_3$ (21.2 mg, 0.023 mmol) and 1,4-dioxane (2 mL). 2-Methylpyrrolidine (0.037 mL, 0.359 mmol) was then added and the reaction mixture stirred at 100° C. under nitrogen for 20 h 45 min. The reaction mixture was allowed to cool to rt and then filtered through a pad of celite and rinsed with ethyl acetate. The filtrate was concentrated and purified by MDAP (Formic) to give the product (17.5 mg, 0.058 mmol, 24.26%) as a yellow gum. This was a racemic mixture of diastereoisomers.

LCMS (2 min Formic): Rt=0.63 min, [MH]$^+$=302.

Intermediate 71: rac-tert-butyl 3-((2S,3R,4R)-1-acetyl-4-amino-2,3-dimethyl-1,2,3,4-tetrahydroquinolin-6-yl)-3,8-diazabicyclo[3.2.1]octane-8-carboxylate

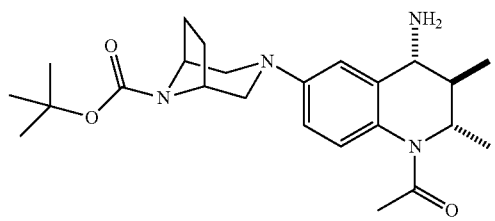 [SMILES: CC(=O)N1c2ccc(N3CC4CCC(C3)N4C(=O)OC(C)(C)C)cc2[C@H](N)[C@@H](C)[C@@H]1C]

A mixture of rac-benzyl ((2S,3R,4R)-1-acetyl-6-bromo-2,3-dimethyl-1,2,3,4-tetrahydroquinolin-4-yl)carbamate (for a preparation see Intermediate 3, (74.8 mg, 0.173 mmol), tert-butyl 3,8-diazabicyclo[3.2.1]octane-8-carboxylate (43.1 mg, 0.203 mmol), sodium-tert-butoxide (50.8 mg, 0.529 mmol), DavePhos (14.0 mg, 0.036 mmol) and Pd$_2$(dba)$_3$ (16.3 mg, 0.018 mmol) had 1,4-dioxane (2 mL) added and were heated with stirring under nitrogen at 100° C. for 23 h. The reaction mixture was allowed to cool to rt and filtered through a celite cartridge which was flushed with ethyl acetate. The filtrate was concentrated and purified by MDAP (Formic) to give the product (5.5 mg, 0.013 mmol, 7.40%) as a yellow gum. LCMS (2 min Formic): Rt=0.80 min, [MH]$^+$=429.

Intermediate 72: rac-tert-butyl 3-((2S,3R,4R)-1-acetyl-2,3-dimethyl-4-(phenylamino)-1,2,3,4-tetrahydroquinolin-6-yl)-3,8-diazabicyclo[3.2.1]octane-8-carboxylate

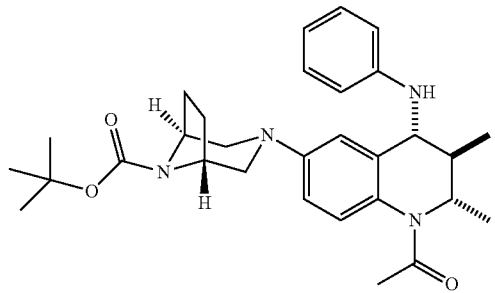 [SMILES: CC(=O)N1c2ccc(N3C[C@H]4CC[C@@H](C3)N4C(=O)OC(C)(C)C)cc2[C@H](Nc2ccccc2)[C@@H](C)[C@@H]1C]

To a solution of rac-tert-butyl 3-((2S,3R,4R)-1-acetyl-4-amino-2,3-dimethyl-1,2,3,4-tetrahydroquinolin-6-yl)-3,8-diazabicyclo[3.2.1]octane-8-carboxylate (for a preparation see Intermediate 71, 5.5 mg, 0.013 mmol) in 1,4-dioxane (0.5 mL) was added bromobenzene (5 μL, 0.047 mmol), Pd$_2$(dba)$_3$ (1.4 mg, 1.529 µmol), DavePhos (1.2 mg, 3.05 µmol) and sodium tert-butoxide (3.1 mg, 0.032 mmol). The reaction mixture was stirred at 100° C. for 18 h. The reaction mixture was allowed to cool to rt then loaded onto a 2.5 g celite cartridge, eluted with ethyl acetate then evaporated under a stream of nitrogen. To the residue was added 1,4-dioxane (0.5 mL), bromobenzene (10 µL, 0.094 mmol), Pd$_2$(dba)$_3$ (2.1 mg, 2.293 µmol), DavePhos (1.8 mg, 4.57 µmol) and sodium tert-butoxide (3.1 mg, 0.032 mmol). The reaction mixture was heated at 100° C. for a further 21 h. The reaction mixture was allowed to cool to rt then loaded onto a 2.5 g celite cartridge, eluted with ethyl acetate then evaporated under a stream of nitrogen. The residue was purified by MDAP (Formic) to give the product (3.3 mg, 6.54 µmol, 51.0%).

LCMS (2 min Formic): Rt=1.33 min, [MH]$^+$=505.

Intermediate 73: rac-1-((2S,3R,4R)-4-amino-2-ethyl-3-methyl-6-morpholino-3,4-dihydroquinolin-1(2H)-yl)ethanone

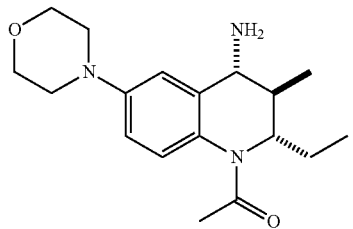 [SMILES: CC[C@H]1[C@H](C)[C@@H](N)c2cc(N3CCOCC3)ccc2N1C(C)=O]

To a solution of rac-benzyl ((2S,3R,4R)-1-acetyl-6-bromo-2-ethyl-3-methyl-1,2,3,4-tetrahydroquinolin-4-yl)carbamate (for a preparation see Intermediate 9, 499 mg, 1.120 mmol) in 1,4-dioxane (15 mL) was added sodium tert-butoxide (324.7 mg, 3.38 mmol), DavePhos (88.1 mg, 0.224 mmol), Pd$_2$(dba)$_3$ (102.1 mg, 0.111 mmol) and morpholine (0.146 mL, 1.687 mmol). The reaction mixture was stirred under nitrogen at 100° C. for 2 h. The reaction mixture was allowed to cool to rt and then filtered through a pad of celite and washed with ethyl acetate and methanol. The filtrate was evaporated in vacuo and the residue purified by column chromatography on silica gel eluting with 0-5% methanol:DCM to give a yellow gum which was further purified by MDAP (HpH) to give the product (130 mg, 0.410 mmol, 36.6%) as a yellow gum.

LCMS (2 min Formic): Rt=0.50 min, [MH]$^+$=318.

Intermediate 74: (E)-tert-butyl prop-1-en-1-ylcarbamate

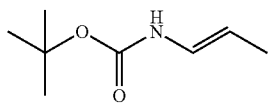

The tert-butyl allylcarbamate (4.3 g, 27.4 mmol) was placed in a microwaveable vial along with tris(triphenylphosphine)rhodium(I)carbonyl hydride (0.628 g, 0.684 mmol) and tetrahydrofuran (THF) (15 mL). nitrogen was bubbled through and the vial sealed and irradiated in a biotage microwave at 80° C. for 2 h. The reaction was treated with triethylamine (0.191 mL, 1.368 mmol) and cooled to −70° C., the reaction was filtered at this temperature and then concentrated in vacuo to give a brown oil. This oil was purified by chromatography on silica gel eluting with 0-5% EtOAc:cyclohexane to give the product (2.875 g, 67%) as a yellow solid (2.875 g).

LCMS (2 min Formic): Rt=0.95 min, [MH]$^+$ not observed.

Intermediate 75: rac-tert-butyl ((2S,3S,4R)-6-bromo-2-cyclopropyl-3-methyl-1,2,3,4-tetrahydroquinolin-4-yl)carbamate

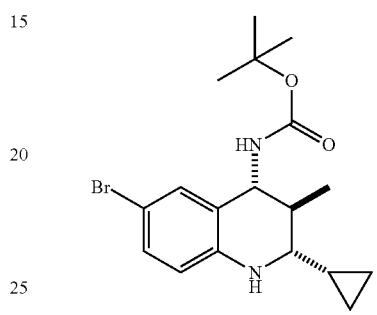

The 4-bromoaniline (750 mg, 4.36 mmol) was taken up in DCM (8 mL) and was treated with cyclopropanecarbaldehyde (321 mg, 4.58 mmol) and allowed to stir at rt for 1 h. The reaction was then cooled to 0° C. and was treated with a solution of (E)-tert-butyl prop-1-en-1-ylcarbamate (for a preparation see Intermediate 74, 754 mg, 4.80 mmol) in DCM (2 mL) followed by diphenyl phosphate (109 mg, 0.436 mmol), the reaction was allowed to warm to rt and stir at rt for 3 days. The reaction was concentrated and purified by chromatography on silica gel eluting with 0-50% EtOAc; cyclohexane to give the product (487 mg, 29%) as an off white solid.

LCMS (2 min Formic): Rt=1.32 min, [MH]$^+$=381, 383.

Intermediate 76: rac-tert-butyl ((2S,3R,4R)-1-acetyl-6-bromo-2-cyclopropyl-3-methyl-1,2,3,4-tetrahydroquinolin-4-yl)carbamate

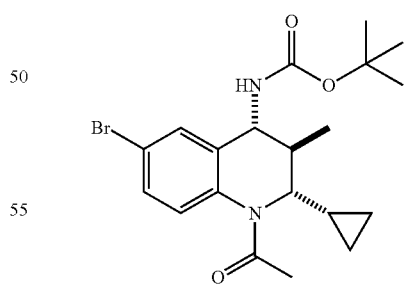

The rac-tert-butyl ((2S,3S,4R)-6-bromo-2-cyclopropyl-3-methyl-1,2,3,4-tetrahydroquinolin-4-yl)carbamate (for a preparation see Intermediate 75, 567 mg, 1.487 mmol) was taken up in dichloromethane (DCM) (10 mL) and treated with DIPEA (0.519 mL, 2.97 mmol) and acetyl chloride (0.211 mL, 2.97 mmol) and allowed to stir at rt for 3 days. Further acetyl chloride (0.211 mL, 2.97 mmol) was added and the reaction was allowed to stir at rt for 2 h. The reaction was concentrated to a gum and purified by chromatography on silica gel eluting with 0-25% EtOAc:cyclohexane to give the product (589 mg, 93%) as a white solid. LCMS (2 min Formic): Rt=1.20 min, [MH]⁺=423, 425.

Intermediate 77: rac-tert-butyl ((2S,3R,4R)-1-acetyl-2-cyclopropyl-6-(3,6-dihydro-2H-pyran-4-yl)-3-methyl-1,2,3,4-tetrahydroquinolin-4-yl)carbamate

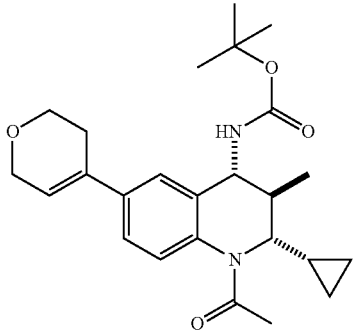 [SMILES: CC(=O)N1c2ccc(C3=CCOCC3)cc2[C@H](NC(=O)OC(C)(C)C)[C@@H](C)[C@@H]1C1CC1]

The 2-(3,6-dihydro-2H-pyran-4-yl)-4,4,5,5-tetramethyl-1,3,2-dioxaborolane (59.5 mg, 0.283 mmol), rac-tert-butyl ((2S,3S,4R)-6-bromo-2-cyclopropyl-3-methyl-1,2,3,4-tetrahydroquinolin-4-yl)carbamate (for a preparation see Intermediate 76, 80 mg, 0.189 mmol) and cesium carbonate (185 mg, 0.567 mmol) were suspended in 1,4-dioxane (10 mL): water (1 mL) and treated with tetrakis(triphenylphosphine)palladium(0) (21.84 mg, 0.019 mmol). The reaction was allowed to stir at 80° C. under reflux conditions for 5 h. The reaction was allowed to cool to rt and was partitioned between EtOAc and water, the organic layer was washed with brine, dried using a hydrophobic frit and concentrated to a gum. This gum was purified by chromatography on silica gel eluting with 0-50% EtOAc:cyclohexane to give the product (42 mg, 52%) as a colourless gum.
LCMS (2 min Formic): Rt=1.10 min, [MH]⁺=427.

Intermediate 78: rac-1-((2S,3R,4R)-4-amino-2-cyclopropyl-6-(3,6-dihydro-2H-pyran-4-yl)-3-methyl-3,4-dihydroquinolin-1(2H)-yl)ethanone

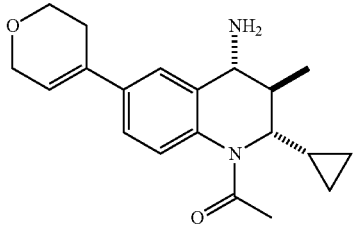 [SMILES: CC(=O)N1c2ccc(C3=CCOCC3)cc2[C@H](N)[C@@H](C)[C@@H]1C1CC1]

The rac-tert-butyl ((2S,3R,4R)-1-acetyl-2-cyclopropyl-6-(3,6-dihydro-2H-pyran-4-yl)-3-methyl-1,2,3,4-tetrahydroquinolin-4-yl)carbamate (for a preparation see Intermediate 77, 98 mg, 0.230 mmol) was taken up in dichloromethane (DCM) (5 mL), treated with TFA (0.177 mL, 2.298 mmol) and allowed to stir at rt for 18 h. The reaction was concentrated and passed through a NH₂ SPE (1 g) eluting with MeOH. The MeOH fraction was concentrated and dried to give the product (56 mg, 75%) as a colourless gum. LCMS (2 min Formic): Rt=0.59 min, [MH]⁺=327.

Intermediate 79: tert-butyl 4-((rac-2S,3R,4R)-1-acetyl-4-amino-2-cyclopropyl-3-methyl-1,2,3,4-tetrahydroquinolin-6-yl)-2-methylpiperazine-1-carboxylate

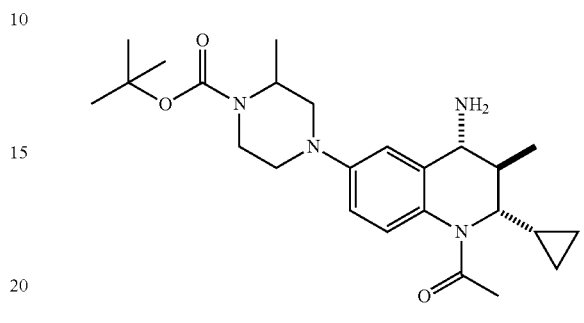

To a microwave vial tert-butyl 2-methylpiperazine-1-carboxylate (0.158 mL, 0.787 mmol), rac-benzyl ((2S,3R,4R)-1-acetyl-6-bromo-2-cyclopropyl-3-methyl-1,2,3,4-tetrahydroquinolin-4-yl)carbamate (for a preparation see Intermediate 13, 300 mg, 0.656 mmol), sodium tert-butoxide (126 mg, 1.312 mmol), Pd₂(dba)₃ (30.0 mg, 0.033 mmol), and DavePhos (25.8 mg, 0.066 mmol) were added in 1,4-dioxane (4 mL). The vessel was sealed and heated to 100° C. for 30 min in a microwave. The reaction mixture was diluted with ethyl acetate (15 mL) and filtered through celite. The celite was washed with ethyl acetate and the combined filtrates were concentrated in vacuo to a red/brown oil. This oil was purified by chromatography on silica gel eluting with 0-40% ethyl acetate/cyclohexane. Then with 0-8% 2M ammonia in methanol:dichloromethane to give the product (92 mg, 0.208 mmol, 31.7%). This was a racemic mixture of diastereoisomers.
LCMS (2 min Formic): Rt=0.84 min, [MH]⁺=443.

Intermediate 80: tert-butyl 4-((rac-2S,3R,4R)-1-acetyl-2-cyclopropyl-3-methyl-4-((6-methylpyridin-2-yl)amino)-1,2,3,4-tetrahydroquinolin-6-yl)-2-methylpiperazine-1-carboxylate

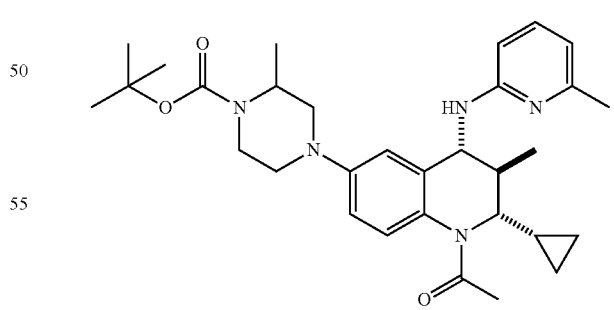

To a reaction vessel tert-butyl 4-((rac-2S,3R,4R)-1-acetyl-4-amino-2-cyclopropyl-3-methyl-1,2,3,4-tetrahydroquinolin-6-yl)-2-methylpiperazine-1-carboxylate (for a preparation see Intermediate 79,119 mg, 0.269 mmol), 2-bromo-6-methylpyridine (0.061 mL, 0.538 mmol), sodium tert-butoxide (64.6 mg, 0.672 mmol), Pd₂(dba)₃ (24.62 mg, 0.027 mmol) and DavePhos (15.87 mg, 0.040 mmol) were added in 1,4-dioxane (5 mL). The reaction mixture was stirred and heated to 100° C. under nitrogen for 16 h. The reaction was treated with further Pd$_2$(dba)$_3$ (25 mg, 0.027 mmol), sodium tert-butoxide (65 mg, 0.676 mmol), DavePhos (20 mg, 0.051 mmol), and 2-bromo-6-methylpyridine (0.06 mL, 0.527 mmol) and the reaction was left to stir for 3.5 h at 100° C. Further sodium tert-butoxide (63 mg, 0.656 mmol) was added and the reaction left to stir for 1.5 h at 100° C. Further sodium tert-butoxide (25.8 mg, 0.269 mmol) and 2-bromo-6-methylpyridine (0.08 mL, 0.703 mmol) were added and the reaction left to stir for 24 h at 100° C. The cooled reaction was filtered through celite, concentrated and by chromatography on silica gel eluting with 0-75% ethyl acetate/cyclohexane to give crude product. This was purified by chromatography on silica gel eluting with 0-60% ethyl acetate/cyclohexane to give the product (34 mg, 23.69%) as a yellow gum. This was a racemic mixture of diastereoisomers. LCMS (2 min Formic): Rt=1.05 min, [MH]$^+$=534.

Intermediate 81: rac-tert-butyl 4-((2S,3R,4R)-1-acetyl-4-amino-2-cyclopropyl-3-methyl-1,2,3,4-tetrahydroquinolin-6-yl)-5,6-dihydropyridine-1(2H)-carboxylate

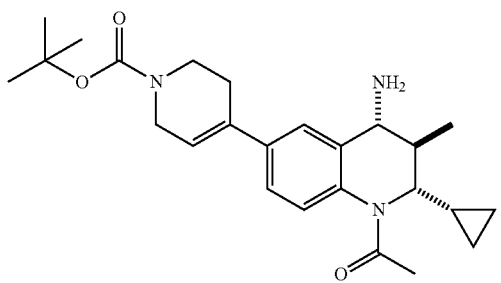 [SMILES: CC(=O)N1c2ccc(C3=CCN(C(=O)OC(C)(C)C)CC3)cc2[C@H](N)[C@@H](C)[C@@H]1C1CC1]

The tert-butyl 4-(4,4,5,5-tetramethyl-1,3,2-dioxaborolan-2-yl)-5,6-dihydropyridine-1(2H)-carboxylate (287 mg, 0.928 mmol), rac-1-((2R,3R,4R)-4-amino-6-bromo-2-cyclopropyl-3-methyl-3,4-dihydroquinolin-1(2H)-yl)ethanone (for a preparation see Intermediate 126, 200 mg, 0.619 mmol) and cesium carbonate (605 mg, 1.856 mmol) were suspended in 1,4-dioxane (10 mL):water (1 mL) and treated with tetrakis(triphenylphosphine)palladium(0) (71.5 mg, 0.062 mmol). The reaction was allowed to stir at 80° C. for 16 h. The reaction was partitioned between water and EtOAc, the aqueous layer was extracted with EtOAc and the combined organics were washed with brine, dried using a hydrophobic frit and concentrated to a orange oil. This oil was purified by chromatography on silica gel eluting with 0-100% EtOAc:cyclohexane, and then 0-10% MeOH:DCM to give the product (128 mg, 49%) as a yellow oil. LCMS (2 min Formic): Rt=0.82 min, [MH]$^+$=426.

Intermediate 82: rac-tert-butyl 4-((2S,3R,4R)-1-acetyl-2-cyclopropyl-3-methyl-4-((6-methylpyridin-2-yl)amino)-1,2,3,4-tetrahydroquinolin-6-yl)-5,6-dihydropyridine-1(2H)-carboxylate

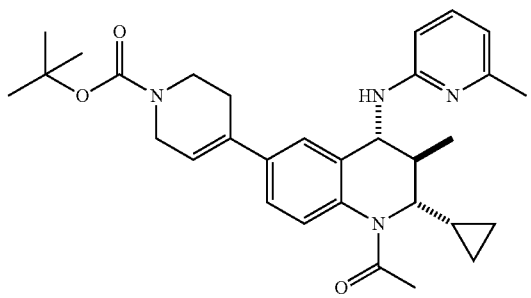 [SMILES: CC(=O)N1c2ccc(C3=CCN(C(=O)OC(C)(C)C)CC3)cc2[C@H](Nc2cccc(C)n2)[C@@H](C)[C@@H]1C1CC1]

The 2-chloro-6-methylpyridine (77 mg, 0.602 mmol), rac-tert-butyl 4-((2S,3R,4R)-1-acetyl-4-amino-2-cyclopropyl-3-methyl-1,2,3,4-tetrahydroquinolin-6-yl)-5,6-dihydropyridine-1(2H)-carboxylate (for a preparation see Intermediate 81, 128 mg, 0.301 mmol), DavePhos (11.84 mg, 0.030 mmol), Pd$_2$(dba)$_3$ (41.3 mg, 0.045 mmol), sodium tert-butoxide (87 mg, 0.902 mmol) and 1,4-dioxane (10 mL) were placed in a round bottomed flask and allowed to stir at 100° C. for 16 h. The reaction was partitioned between water and EtOAc, the aqueous layer was extracted with further EtOAc and the combined organics washed with brine, dried using a hydrophobic frit and concentrated to a brown gum. This gum was purified by chromatography on silica gel eluting with 0-50% EtOAc:cyclohexane to the product (104 mg, 67%) as a yellow solid. LCMS (2 min Formic): Rt=0.99 min, [MH]$^+$=517.

Intermediate 83: rac-1-((2S,3R,4R)-4-amino-2-cyclopropyl-3-methyl-6-morpholino-3,4-dihydroquinolin-1(2H)-yl)ethanone

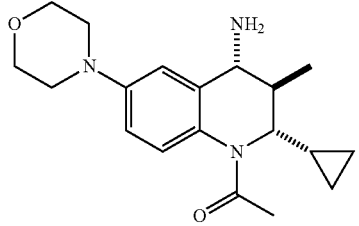 [SMILES: CC(=O)N1c2ccc(N3CCOCC3)cc2[C@H](N)[C@@H](C)[C@@H]1C1CC1]

To a microwave vial morpholine (0.229 mL, 2.62 mmol), rac-benzyl ((2S,3R,4R)-1-acetyl-6-bromo-2-cyclopropyl-3-methyl-1,2,3,4-tetrahydroquinolin-4-yl)carbamate (for a preparation see Intermediate 13, 1 g, 2.186 mmol), Pd$_2$(dba)$_3$ (0.100 g, 0.109 mmol), sodium tert-butoxide (0.420 g, 4.37 mmol) and DavePhos (0.1 g, 0.254 mmol) were added in 1,4-dioxane (18 mL). The vessel was sealed and heated to 100° C. in a microwave reactor for 30 min. The mixture was filtered through celite and the filtrate was concentrated in vacuo and purified by chromatography on silica gel eluting with 0-5% 2M methanolic ammonia:dichloromethane to give the product (244 mg, 0.741 mmol, 33.9%) as a brown gum. LCMS (2 min Formic): Rt=0.54 min, [MH]$^+$=330.

Intermediate 84: rac-tert-butyl 4-((2S,3R,4R)-1-acetyl-4-amino-2-cyclopropyl-3-methyl-1,2,3,4-tetrahydroquinolin-6-yl)piperazine-1-carboxylate

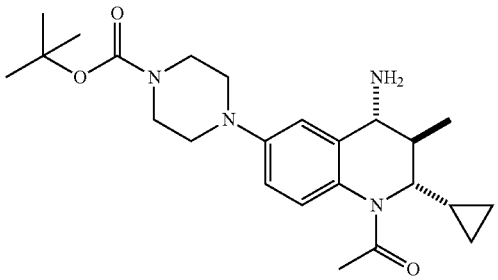 [SMILES: CC(=O)N1c2ccc(N3CCN(C(=O)OC(C)(C)C)CC3)cc2[C@H](N)[C@@H](C)[C@@H]1C1CC1]

In a microwave vessel rac-benzyl ((2S,3R,4R)-1-acetyl-6-bromo-2-cyclopropyl-3-methyl-1,2,3,4-tetrahydroquinolin-4-yl)carbamate (for a preparation see intermediate 13, 300 mg, 0.656 mmol), tert-butyl piperazine-1-carboxylate (147 mg, 0.787 mmol) sodium tert-butoxide (126 mg, 1.312 mmol), Pd$_2$(dba)$_3$ (30.0 mg, 0.033 mmol) and DavePhos (25.8 mg, 0.066 mmol) were dissolved in 1,4-dioxane. The reaction was irradiated in a microwave at 100° C. for 2 h. The reaction mixture was allowed to cool and was then filtered through celite washing through with extra 1,4-dioxane. The filtrate was concentrated in vacuo to leave the crude which was purified by chromatography on silica gel eluting with 0-5% 2M methanolic ammonia:dichloromethane to give the product (110 mg, 39%) as a yellow oil. LCMS (2 min Formic): Rt=0.77 min, [MH]$^+$=412.

Intermediate 85: rac-tert-butyl 4-((2S,3R,4R)-1-acetyl-2-cyclopropyl-3-methyl-4-(phenylamino)-1,2,3,4-tetrahydroquinolin-6-yl)piperazine-1-carboxylate

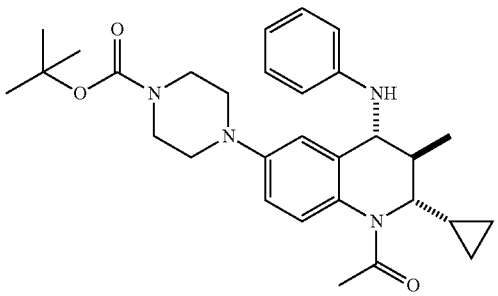 [SMILES: CC(=O)N1c2ccc(N3CCN(C(=O)OC(C)(C)C)CC3)cc2[C@H](Nc2ccccc2)[C@@H](C)[C@@H]1C1CC1]

In a 2.0-5.0 ml microwave vessel rac-tert-butyl 4-((2S,3R,4R)-1-acetyl-4-amino-2-cyclopropyl-3-methyl-1,2,3,4-tetrahydroquinolin-6-yl)piperazine-1-carboxylate (for a preparation see Intermediate 84, 110 mg, 0.257 mmol), bromobenzene (0.032 mL, 0.308 mmol) sodium tert-butoxide (49.3 mg, 0.513 mmol), Pd$_2$(dba)$_3$ (11.75 mg, 0.013 mmol) and DavePhos (10.10 mg, 0.026 mmol) were dissolved in 1,4-dioxane. The reaction was irradiated in a microwave at 100° C. for 2 h. The reaction mixture was allowed to cool and was then filtered through celite washing through with extra 1,4-dioxane. The filtrate was concentrated in vacuo to leave the crude which was purified using chromatography on silica gel eluting with 0-5% 2M methanolic ammonia in dichloromethane to give the product (43 mg, 33%) as a yellow oil. LCMS (2 min Formic): Rt=1.32 min, [MH]$^+$=505.

Intermediate 86: rac-benzyl ((2S,3S,4R)-2-cyclopropyl-3-methyl-6-((tetrahydro-2H-pyran-4-yl)oxy)-1,2,3,4-tetrahydroquinolin-4-yl)carbamate

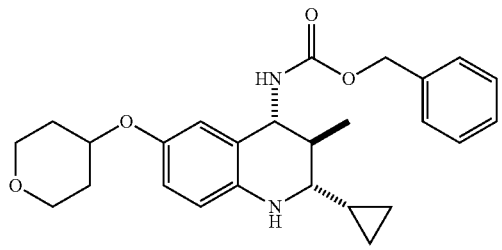 [SMILES: C[C@@H]1[C@@H](NC(=O)OCc2ccccc2)c2cc(OC3CCOCC3)ccc2N[C@H]1C1CC1]

The 4-bromoaniline (750 mg, 4.36 mmol) was taken up in DCM (8 mL) and was treated with cyclopropanecarbaldehyde (0.071 mL, 0.951 mmol) and allowed to stir at rt for 1 h. The reaction was then cooled to 0° C. and was treated with a solution of (E)-benzyl prop-1-en-1-ylcarbamate (for a preparation see Intermediate 1, 190 mg, 0.996 mmol) in DCM (2 mL) followed by diphenyl phosphate (109 mg, 0.436 mmol), the reaction was allowed to warm to rt and to stir at rt for 16 h. The reaction was concentrated to a orange solid and was purified by chromatography on silica gel eluting with 0-50% EtOAc:cyclohexane to give the product (198 mg, 50%) as a buff gum.

LCMS (2 min Formic): Rt=1.06 min, [MH]$^+$=437.

Intermediate 87: rac-benzyl ((2S,3R,4R)-1-acetyl-2-cyclopropyl-3-methyl-6-((tetrahydro-2H-pyran-4-yl)oxy)-1,2,3,4-tetrahydroquinolin-4-yl)carbamate

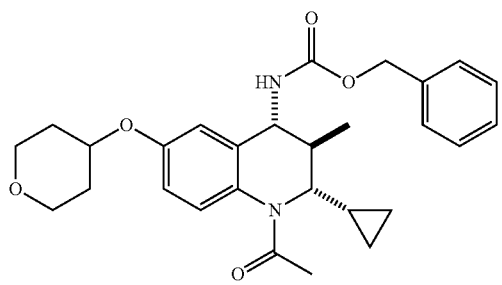 [SMILES: CC(=O)N1c2ccc(OC3CCOCC3)cc2[C@H](NC(=O)OCc2ccccc2)[C@@H](C)[C@@H]1C1CC1]

The rac-benzyl ((2S,3S,4R)-2-cyclopropyl-3-methyl-6-((tetrahydro-2H-pyran-4-yl)oxy)-1,2,3,4-tetrahydroquinolin-4-yl)carbamate (for a preparation see Intermediate 86, 198 mg, 0.454 mmol) was taken up in dichloromethane (DCM) (10 mL) and treated with DIPEA (0.158 mL, 0.907 mmol) and acetyl chloride (0.097 mL, 1.361 mmol) and allowed to stir at rt for 3 days. The reaction was concentrated and purified by chromatography on silica gel eluting with 0-50% EtOAc:cyclohexane to give the product (148 mg, 68%) as a pale yellow gum.

LCMS (2 min Formic): Rt=1.80 min, [MH]$^+$=479.

Intermediate 88: rac-1-((2S,3R,4R)-4-amino-2-cyclopropyl-3-methyl-6-((tetrahydro-2H-pyran-4-yl)oxy)-3,4-dihydroquinolin-1(2H)-yl)ethanone

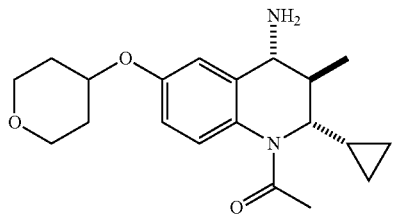 [SMILES: CC(=O)N1c2ccc(OC3CCOCC3)cc2[C@H](N)[C@@H](C)[C@@H]1C1CC1]

The rac-benzyl ((2S,3R,4R)-1-acetyl-2-cyclopropyl-3-methyl-6-((tetrahydro-2H-pyran-4-yl)oxy)-1,2,3,4-tetrahydroquinolin-4-yl)carbamate (for a preparation see Intermediate 87, 148 mg, 0.339 mmol) was taken up in ethanol (5 mL) and the reaction was hydrogenated using the H-cube (settings: 25° C., 1 bar, 1 mL/min flow rate) and 10% Pd/C CatCart 30 as the catalyst. The reaction was concentrated and dried to give the product (78 mg, 67%) as a colourless gum.

LCMS (2 min Formic): Rt=0.58 min, [MH]$^+$=345.

Intermediate 89: rac-benzyl ((2S,3R,4R)-1-acetyl-2-cyclopropyl-6-(1-ethyl-1H-pyrazol-4-yl)-3-methyl-1,2,3,4-tetrahydroquinolin-4-yl)carbamate

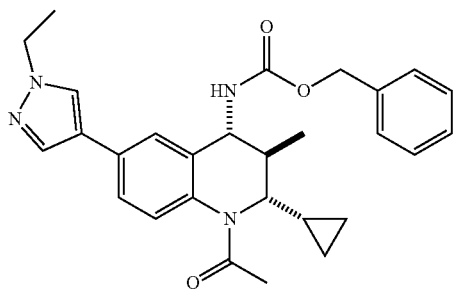 [SMILES: CCn1cc(-c2ccc3c(c2)[C@H](NC(=O)OCc2ccccc2)[C@@H](C)[C@H](C2CC2)N3C(C)=O)cn1]

A mixture of (1-ethyl-1H-pyrazol-4-yl)boronic acid (54.7 mg, 0.391 mmol), rac-benzyl ((2S,3R,4R)-1-acetyl-6-bromo-2-cyclopropyl-3-methyl-1,2,3,4-tetrahydroquinolin-4-yl)carbamate (for a preparation see intermediate 13, 149 mg, 0.326 mmol), Pd$_2$(dba)$_3$ (14.92 mg, 0.016 mmol), potassium phosphate (144 mg, 0.678 mmol), and XPhos (15.4 mg, 0.032 mmol) in 1-butanol (2 mL) was heated with stirring in a sealed vial in a microwave reactor for 30 min at 130° C. The mixture was filtered with a celite cartridge and washed with ethyl acetate. the solution was evaporated under a stream of nitrogen. The yellow/brown gum residue was purified by MDAP (HpH) to give the product (58.1 mg, 0.123 mmol, 37.7%) as a pale grey glass.

LCMS (2 min Formic): Rt=1.11 min, [MH]$^+$=473.

Intermediate 90: rac-1-((2S,3R,4R)-4-amino-2-cyclopropyl-6-(1-ethyl-1H-pyrazol-4-yl)-3-methyl-3,4-dihydroquinolin-1(2H)-yl)ethanone

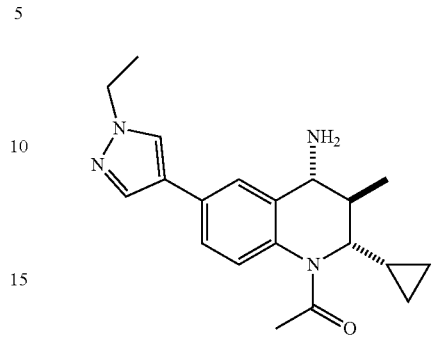

A stirred mixture of rac-benzyl ((2S,3R,4R)-1-acetyl-2-cyclopropyl-6-(1-ethyl-1H-pyrazol-4-yl)-3-methyl-1,2,3,4-tetrahydroquinolin-4-yl)carbamate (for a preparation see Intermediate 89, 58 mg, 0.123 mmol) and palladium, 10 wt. % (dry basis) on activated carbon, wet, Degussa type E101 NE/W (12.2 mg, 0.115 mmol) in ethanol (5 mL) was hydrogenated with vigorous stirring under one atmosphere of hydrogen at rt for 2.5 h. The reaction mixture was filtered over celite, concentrated and dried to give the product (39 mg, 94%).

LCMS (2 min Formic): Rt=0.60 min, [M]$^+$=322 (loss of NH$_2^-$).

Intermediate 91: rac-benzyl ((2S,3R,4R)-1-acetyl-2-cyclopropyl-3-methyl-6-(1-methyl-1H-pyrazol-4-yl)-1,2,3,4-tetrahydroquinolin-4-yl)carbamate

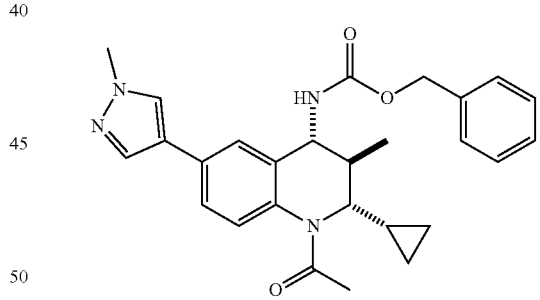

A mixture of (1-methyl-1H-pyrazol-4-yl)boronic acid (49.1 mg, 0.390 mmol), rac-benzyl ((2S,3R,4R)-1-acetyl-6-bromo-2-cyclopropyl-3-methyl-1,2,3,4-tetrahydroquinolin-4-yl)carbamate (for a preparation see intermediate 13, 148.6 mg, 0.325 mmol), Pd$_2$(dba)$_3$ (15.8 mg, 0.017 mmol), potassium phosphate (67 mg, 0.316 mmol), and X-Phos (156.4 mg, 0.328 mmol) in 1-butanol (2 mL) was heated with stirring in a sealed vial in a microwave reactor for 1 h at 100° C. The mixture was filtered through a celite cartridge and washed with ethyl acetate. The filtrate was concentrated and purified by MDAP (HpH) to give the product (58 mg, 0.126 mmol, 38.9%).

LCMS (2 min Formic): Rt=1.05 min, [MH]$^+$=459.

Intermediate 92: rac-1-((2S,3R,4R)-4-amino-2-cyclopropyl-3-methyl-6-(1-methyl-1H-pyrazol-4-yl)-3,4-dihydroquinolin-1(2H)-yl)ethanone

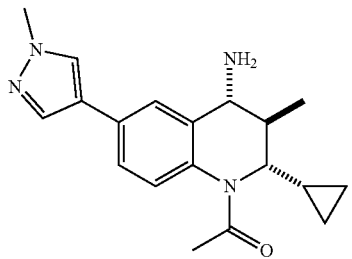 [SMILES: CC(=O)N1c2ccc(-c3cnn(C)c3)cc2[C@H](N)[C@@H](C)[C@@H]1C1CC1]

A stirred mixture of rac-benzyl ((2S,3R,4R)-1-acetyl-2-cyclopropyl-3-methyl-6-(1-methyl-1H-pyrazol-4-yl)-1,2,3,4-tetrahydroquinolin-4-yl)carbamate (for a preparation see Intermediate 91, 58 mg, 0.126 mmol) and palladium, 10 wt. % (dry basis) on activated carbon, wet, Degussa type E101 NE/W (12.4 mg, 0.117 mmol) in ethanol (5 mL) was hydrogenated with vigorous stirring under one atmosphere of hydrogen at rt for 3 h. The reaction mixture was filtered over celite, the filtrate was concentrated to give the product (39 mg, 97%) as a grey gum.

LCMS (2 min Formic): Rt=0.56 min, [MH]⁺=308 (loss of NH₂⁻).

Intermediate 93: rac-4-((2S,3R,4R)-1-acetyl-4-(((benzyloxy)carbonyl)amino)-2-cyclopropyl-3-methyl-1,2,3,4-tetrahydroquinolin-6-yl)benzoic Acid

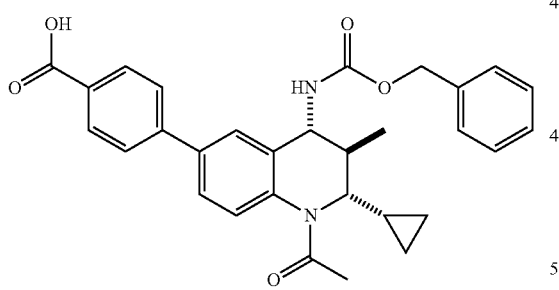

A mixture of rac-benzyl ((2S,3R,4R)-1-acetyl-6-bromo-2-cyclopropyl-3-methyl-1,2,3,4-tetrahydroquinolin-4-yl)carbamate (for a preparation see intermediate 13, 159.8 mg, 0.349 mmol), 4-boronobenzoic acid (98.4 mg, 0.593 mmol), potassium phosphate (154.3 mg, 0.727 mmol), X-Phos (16.0 mg, 0.034 mmol) and Pd₂(dba)₃ (15.6 mg, 0.017 mmol) in 1-butanol (2 mL) was irradiated in a microwave at 100° C. for 30 min and then at 120° C. for 30 min. The mixture was allowed to cool to rt and was filtered through a 2.5 g celite cartridge, washing with ethyl acetate. The combined filtrate was concentrated and purified by MDAP (Formic) to give the product (55.8 mg, 0.112 mmol, 32.0%) as a white solid. LCMS (2 min Formic): Rt=1.05 min, [MH]⁺=499.

Intermediate 94: rac-4-((2S,3R,4R)-1-acetyl-4-amino-2-cyclopropyl-3-methyl-1,2,3,4-tetrahydroquinolin-6-yl)benzoic Acid

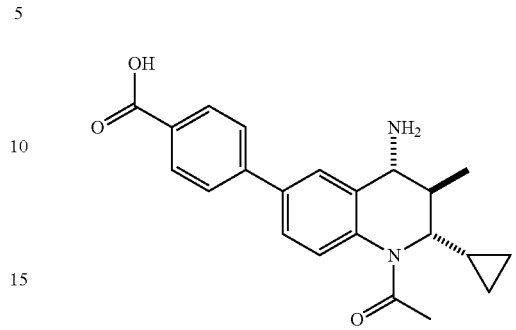

A stirred mixture of rac-4-((2S,3R,4R)-1-acetyl-4-(((benzyloxy)carbonyl)amino)-2-cyclopropyl-3-methyl-1,2,3,4-tetrahydroquinolin-6-yl)benzoic acid (for a preparation see Intermediate 93, 55.8 mg, 0.112 mmol) and palladium, 10 wt. % (dry basis) on activated carbon, wet, Degussa type E101 NE/W (17.1 mg, 0.161 mmol) in ethanol (5 mL) was hydrogenated with vigorous stirring under one atmosphere of hydrogen at rt for 3.5 h. The mixture was filtered under nitrogen through a 2.5 g celite cartridge and the filter cake washed with ethanol. The combined filtrate was evaporated in vacuo and dried to give the desired product (28.4 mg, 0.078 mmol, 69.6%) as a cream solid.

LCMS (2 min Formic): Rt=0.63 min, [M]⁺=348 (loss of NH₂⁻).

Intermediate 95: rac-benzyl ((2S,3S,4R)-2,3-dimethyl-1,2,3,4-tetrahydro-1,5-naphthyridin-4-yl)carbamate

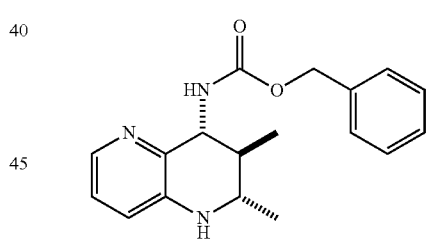

Under nitrogen atmosphere, to a solution of acetaldehyde (0.056 mL, 0.99 mmol) in chloroform (5 mL) was added pyridin-3-amine (93 mg, 0.990 mmol). The reaction was stirred at rt for 30 min and then cooled to 0° C. Solutions of diphenyl hydrogen phosphate (24.77 mg, 0.099 mmol) in chloroform (2.5 mL) and (E)-benzyl prop-1-en-1-ylcarbamate (for a preparation see Intermediate 1, 207 mg, 1.082 mmol) in chloroform (2.5 mL) were added. The reaction mixture was stirred at 0° C. for 2 h then it was heated at 60° C. and stirred for 3 h. Acetaldehyde (0.056 mL, 0.99 mmol) and pyridin-3-amine (93 mg, 0.990 mmol) were then added and the reaction mixture was stirred at 60° C. over the weekend. Acetaldehyde (0.056 mL, 0.99 mmol) was then added and the reaction mixture was stirred at 60° C. for 4 h. The reaction mixture was evaporated under vacuum and the residue was loaded onto a 25 g silica cartridge and purified by column chromatography using a gradient 0-100% of ethyl acetate in cyclohexane. Desired fractions were com-

Intermediate 96: rac-benzyl ((2S,3R,4R)-1-acetyl-2,3-dimethyl-1,2,3,4-tetrahydro-1,5-naphthyridin-4-yl)carbamate

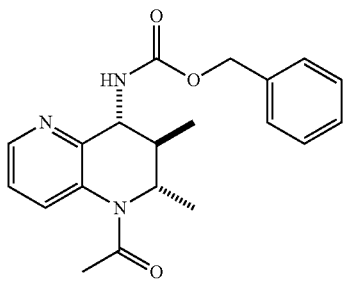 [SMILES: CC(=O)N1c2cccnc2[C@H](NC(=O)OCc2ccccc2)[C@@H](C)[C@@H]1C]

rac-Benzyl ((2S,3R,4R)-2,3-dimethyl-1,2,3,4-tetrahydro-1,5-naphthyridin-4-yl)carbamate (for a preparation see Intermediate 95, 149.7 mg, 0.481 mmol) was taken up in dry DCM (5 mL) under nitrogen at rt. Pyridine (0.117 mL, 1.442 mmol) then acetyl chloride (0.051 mL, 0.721 mmol) was added and the reaction mixture was stirred for 2 h at rt. Acetyl chloride (1.5 eq) was added and the reaction mixture was stirred at rt for 1 h. The reaction mixture was partitioned between ethyl acetate (30 mL) and saturated sodium bicarbonate (15 mL). The organic layer was extracted and washed with water (20 mL) and brine (20 mL) and then dried over a hydrophobic frit, filtered and concentrated under vacuum. The crude product was taken up in the minimum of DCM and applied to a 25 g silica cartridge and eluted with a gradient 0-100% of ethyl acetate in cyclohexane. Desired fractions were combined and evaporated in vacuo to afford the product as a colourless solid (141.5 mg). LCMS (2 min Formic): Rt=0.90 min, [MH]$^+$=354.

Intermediate 97: rac-1-((2S,3R,4R)-4-amino-2,3-dimethyl-3,4-dihydro-1,5-naphthyridin-1(2H)-yl)ethanone

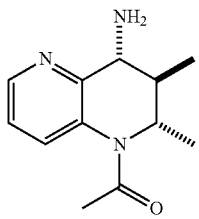 [SMILES: CC(=O)N1c2cccnc2[C@H](N)[C@@H](C)[C@@H]1C]

rac-Benzyl ((2S,3R,4R)-1-acetyl-2,3-dimethyl-1,2,3,4-tetrahydro-1,5-naphthyridin-4-yl)carbamate (for a preparation see Intermediate 96, 141.5 mg, 0.400 mmol) was dissolved in MeOH (7 mL) and was then passed through a 10% Pd/C cartridge on a H-cube (rt, full H$_2$ mode) to give a colourless filtrate. This filtrate was concentrated in vacuo to afford the product as a white solid (79 mg).

LCMS (2 min Formic): Rt=0.34 min, [MH]$^+$=220.

Intermediate 98: rac-benzyl ((2S,3S,4R)-2-cyclopropyl-6-methoxy-3-methyl-1,2,3,4-tetrahydro-1,5-naphthyridin-4-yl)carbamate

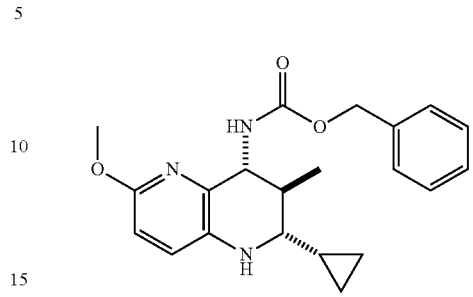

To a solution of cyclopropanecarbaldehyde (1.2 mL, 16.06 mmol) in anhydrous DCM (20 mL) was added 6-methoxypyridin-3-amine (1.59 g, 12.81 mmol). The suspension was stirred at rt under nitrogen for 1 h then cooled to 0° C. To the solution was added diphenyl hydrogen phosphate (0.42 g, 1.679 mmol) in anhydrous DCM (5 mL) followed by (E)-benzyl prop-1-en-1-ylcarbamate (for a preparation see Intermediate 1, 2.48 g, 12.97 mmol) in anhydrous DCM (5 mL). The reaction mixture was stirred at 0° C. for 1 h then allowed to warm to rt over 16 h. The reaction mixture was washed with sat. aq. NaHCO$_3$ (25 mL) followed by water (25 mL). The organic layer was dried through a hydrophobic frit and the solvent was removed by rotary evaporation to give the product as a pink solid (3.89 g, 10.59 mmol, 83%). LCMS (2 min Formic): Rt=1.11 min, [MH]$^+$=368.

Intermediate 99: rac-benzyl ((2S,3R,4R)-1-acetyl-2-cyclopropyl-6-methoxy-3-methyl-1,2,3,4-tetrahydro-1,5-naphthyridin-4-yl)carbamate

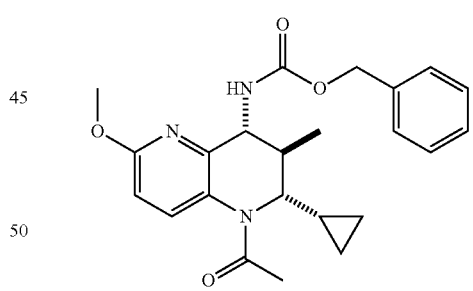

To a stirred solution of rac-benzyl ((2S,3S,4R)-2-cyclopropyl-6-methoxy-3-methyl-1,2,3,4-tetrahydro-1,5-naphthyridin-4-yl)carbamate (for a preparation see Intermediate 98, 3.88 g, 10.56 mmol) in DCM (40 mL) and pyridine (2.56 ml, 31.7 mmol) under nitrogen at 0° C. was added acetyl chloride (1.130 ml, 15.84 mmol). The mixture was stirred at 0° C. for 10 min then allowed to warm to rt over 1 h. The reaction mixture was diluted with DCM (40 mL) then washed with 0.5M HCl (50 mL) and saturated NaHCO$_3$ (50 mL) and water (50 mL). The organic layer was dried through a hydrophobic frit and concentrated under vacuum to give the product (4.5882 g).

LCMS (2 min Formic): Rt=1.12 min, [MH]$^+$=410.

Intermediate 100: rac-1-((2S,3R,4R)-4-Amino-2-cyclopropyl-6-methoxy-3-methyl-3,4-dihydro-1,5-naphthyridin-1(2H)-yl)ethanone

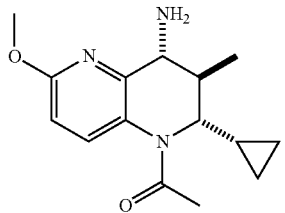

10% Pd/C (11.20 mmol) was added to a solution of rac-benzyl ((2S,3R,4R)-1-acetyl-2-cyclopropyl-6-methoxy-3-methyl-1,2,3,4-tetrahydro-1,5-naphthyridin-4-yl)carbamate (for a preparation see Intermediate 99, 4.5882 g, 11.20 mmol) in ethyl acetate (100 mL). The reaction was left to stir under an H$_2$ atmosphere for 72 h then filtered through celite, washed with ethyl acetate and concentrated in vacuo to give the product (2.8506 g, 10.35 mmol, 92%).

LCMS (2 min Formic): Rt=0.47 min, [MH]$^+$=276.

Intermediate 101: rac-1-((2S,3R,4R)-2-cyclopropyl-6-methoxy-3-methyl-4-(phenylamino)-3,4-dihydro-1,5-naphthyridin-1(2H)-yl)ethanone

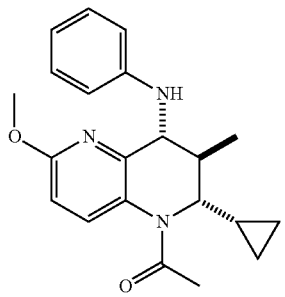

A mixture of rac-1-((2S,3R,4R)-4-amino-2-cyclopropyl-6-methoxy-3-methyl-3,4-dihydro-1,5-naphthyridin-1(2H)-yl)ethanone (for a preparation see Intermediate 100, 1.3421 g, 4.87 mmol), bromobenzene (0.521 ml, 4.95 mmol), sodium tert-butoxide (0.703 g, 7.31 mmol), Pd$_2$(dba)$_3$ (0.223 g, 0.244 mmol) and DavePhos (0.194 g, 0.492 mmol) in anhydrous 1,4-dioxane (12 mL) was stirred and heated under nitrogen to 100° C. for 1 h. The mixture was filtered through celite and washed with ethyl acetate. The filtrate was then concentrated in vacuo to give a brown gum. The crude was dissolved in DCM, loaded onto a 100 g silica cartridge and purified over a gradient of 0-75% cyclohexane/ethyl acetate. The appropriate fractions were combined and concentrated in vacuo to give the product (1.2842 g, 3.65 mmol, 75%) as a yellow gum.

LCMS (2 min Formic): Rt=1.21 min, [MH]$^+$=352.

Intermediate 102: rac-(6S,7R,8R)-5-acetyl-6-cyclopropyl-7-methyl-8-(phenylamino)-5,6,7,8-tetrahydro-1,5-naphthyridin-2-yl trifluoromethanesulfonate

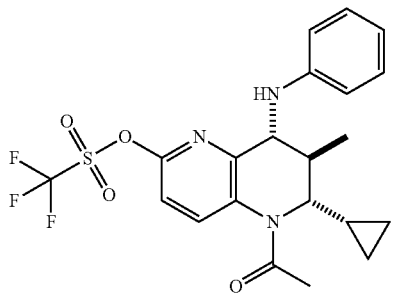 [SMILES: CC(=O)N1c2ccc(OS(=O)(=O)C(F)(F)F)nc2[C@H](Nc2ccccc2)[C@@H](C)[C@@H]1C1CC1]

A mixture of rac-(6S,7R,8R)-5-acetyl-6-cyclopropyl-7-methyl-8-(phenylamino)-5,6,7,8-tetrahydro-1,5-naphthyridin-2(1H)-one (for a preparation see Example 101, 1086 mg, 3.22 mmol), 2-(N,N-bis(trifluoromethylsulfonyl)amino)-5-chloropyridine (1517 mg, 3.86 mmol), NEt$_3$ (0.897 mL, 6.44 mmol) and DMAP (39.3 mg, 0.322 mmol) was stirred at rt in a closed vessel for 72 h. The reaction mixture was diluted with DCM (25 mL) and washed with 0.5 M HCl (50 mL) and water (50 mL) then dried through a hydrophobic frit. The solvent was evaporated in vacuo to leave a brown solid (1.4607 g). The crude was dissolved in DCM and purified on 100 g silica cartridge with a gradient of 0-2.6% DCM/MeOH over 10 CVs. The appropriate fractions were combined and concentrated in vacuo to give the product (1.078 g, 2.296 mmol, 71%) as a yellow gum.

LCMS (2 min Formic): Rt=1.31 min, [MH]$^+$=470.

Intermediate 103: tert-butyl 4-((rac-6S,7R,8R)-5-acetyl-6-cyclopropyl-7-methyl-8-(phenylamino)-5,6,7,8-tetrahydro-1,5-naphthyridin-2-yl)-2-methylpiperazine-1-carboxylate

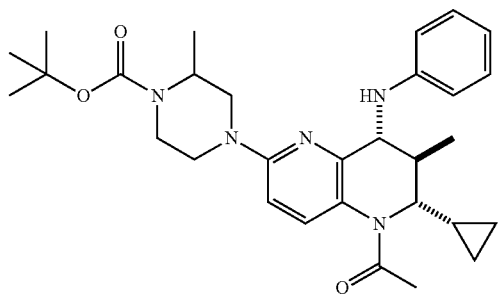 [SMILES: CC(=O)N1c2ccc(N3CCN(C(=O)OC(C)(C)C)C(C)C3)nc2[C@H](Nc2ccccc2)[C@@H](C)[C@@H]1C1CC1]

A mixture of tert-butyl 2-methylpiperazine-1-carboxylate (0.077 mL, 0.383 mmol), rac-(6S,7R,8R)-5-acetyl-6-cyclopropyl-7-methyl-8-(phenylamino)-5,6,7,8-tetrahydro-1,5-naphthyridin-2-yl trifluoromethanesulfonate (for a preparation see Intermediate 102, 90 mg, 0.192 mmol) and cesium carbonate (187 mg, 0.575 mmol) in 1,4-dioxane (7 mL) had nitrogen bubbled through it for 10 min. BINAP (23.87 mg, 0.038 mmol) and Pd$_2$(dba)$_3$ (17.55 mg, 0.019 mmol) were added and the reaction mixture was stirred at 90° C. under nitrogen for 3 h. The reaction mixture was allowed to cool to rt then filtered through celite, rinsed with ethyl acetate and concentrated under a stream of nitrogen. The sample was dissolved in 1:1 MeOH:DMSO (2×1 mL) and purified by MDAP (HpH). The appropriate fractions were combined and concentrated in vacuo. The sample was dissolved in DMSO:MeOH (1:1, 1 mL) and purified by MDAP (Formic). The appropriate fractions were combined and concentrated in vacuo to give the product (11 mg, 0.021 mmol, 11.04%) as a yellow gum. This was a racemic mixture of diastereoisomers. LCMS (2 min Formic): Rt=1.40 min, [MH]⁺=520.

Intermediate 104: rac-tert-butyl 4-((6S,7R,8R)-5-acetyl-6-cyclopropyl-7-methyl-8-(phenylamino)-5,6,7,8-tetrahydro-1,5-naphthyridin-2-yl)piperazine-1-carboxylate

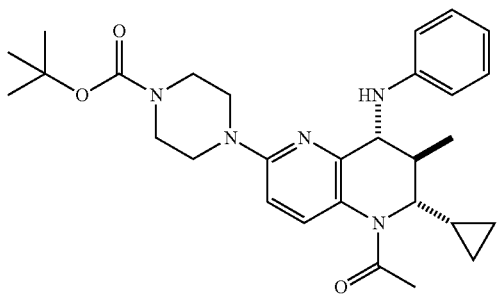 [SMILES: CC(=O)N1c2ccc(N3CCN(C(=O)OC(C)(C)C)CC3)nc2[C@H](Nc2ccccc2)[C@@H](C)[C@@H]1C1CC1]

A mixture of rac-(6S,7R,8R)-5-acetyl-6-cyclopropyl-7-methyl-8-(phenylamino)-5,6,7,8-tetrahydro-1,5-naphthyridin-2-yl trifluoromethanesulfonate (for a preparation see Intermediate 102, 30 mg, 0.064 mmol), Cs₂CO₃ (62.5 mg, 0.192 mmol) and 1-Boc-piperazine (23.80 mg, 0.128 mmol) in toluene (5 mL) had nitrogen bubbled through it for 10 min. To this solution was added BINAP (7.96 mg, 0.013 mmol) and Pd₂(dba)₃ (5.85 mg, 6.39 µmol) and the mixture was stirred at 90° C. for 3 h under nitrogen. The reaction mixture was allowed to cool then filtered through celite, rinsed with ethyl acetate and concentrated under a stream of nitrogen. The sample was dissolved in 1:1 MeOH:DMSO 1 mL and purified by MDAP (Formic). The appropriate fractions were combined and concentrated in vacuo. The sample was dissolved in a minimal amount of MeOH and applied to a 1 g NH₂ column which had been pre-equilibrated with MeOH (5 mL). The column was flushed with MeOH (5 mL) and the appropriate fraction was concentrated in vacuo to give the product (17 mg, 0.034 mmol, 52.6%) as a brown/yellow gum. LCMS (2 min HpH): Rt=1.42 min, [MH]⁺=506.

Intermediate 105: rac-tert-butyl (1-((6S,7R,8R)-5-acetyl-6-cyclopropyl-7-methyl-8-(phenylamino)-5,6,7,8-tetrahydro-1,5-naphthyridin-2-yl)piperidin-4-yl)carbamate

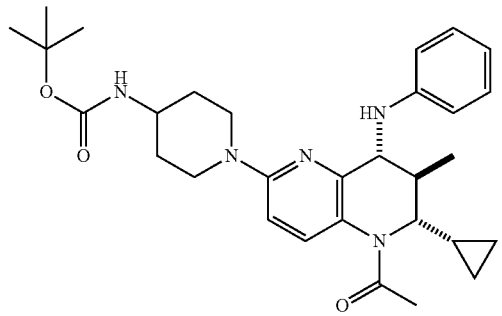 [SMILES: CC(=O)N1c2ccc(N3CCC(NC(=O)OC(C)(C)C)CC3)nc2[C@H](Nc2ccccc2)[C@@H](C)[C@@H]1C1CC1]

A solution of tert-butyl piperidin-4-ylcarbamate (66.5 mg, 0.332 mmol), rac-(6S,7R,8R)-5-acetyl-6-cyclopropyl-7-methyl-8-(phenylamino)-5,6,7,8-tetrahydro-1,5-naphthyridin-2-yl trifluoromethanesulfonate (for a preparation see Intermediate 102, 78 mg, 0.166 mmol) and cesium carbonate (162 mg, 0.498 mmol) in toluene (7 mL) had nitrogen bubbled through it for 10 min. Pd₂(dba)₃ (15.21 mg, 0.017 mmol) and BINAP (20.69 mg, 0.033 mmol) were then added to the mixture which was stirred at 90° C. for 3 h under nitrogen. The reaction mixture was filtered through celite, rinsed with ethyl acetate and concentrated under a stream of nitrogen to give a brown gum. The sample was dissolved in 1:1 MeOH:DMSO (2×1 mL) and purified by MDAP (Formic). The appropriate fractions were combined and concentrated in vacuo. The sample was dissolved in DMSO:MeOH (1:1, 1 mL) and purified by 2×MDAP (Formic). The appropriate fractions were combined and concentrated in vacuo to give the product (12 mg, 0.023 mmol, 14%).

LCMS (2 min Formic): Rt=1.18 min, [MH]⁺=520.

Intermediate 106: rac-benzyl ((2S,3S,4R)-6-bromo-2-cyclopropyl-3-methyl-1,2,3,4-tetrahydro-1,5-naphthyridin-4-yl)carbamate

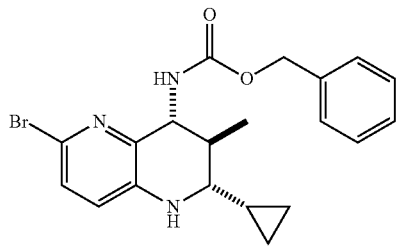 [SMILES: C[C@@H]1[C@@H](NC(=O)OCc2ccccc2)c2nc(Br)ccc2N[C@H]1C1CC1]

To a solution of cyclopropanecarbaldehyde (1.296 mL, 17.34 mmol) in anhydrous DCM (17.5 mL) was added 6-bromopyridin-3-amine (3 g, 17.34 mmol) and stirred at rt in a closed vessel for 1 h. A solution of diphenyl hydrogen phosphate (0.429 g, 1.717 mmol) in anhydrous DCM (8.75 mL) was added, followed by a solution of (E)-benzyl prop-1-en-1-ylcarbamate (for a preparation see Intermediate 1, 3.32 g, 17.34 mmol) in anhydrous DCM (8.75 ml). The mixture was stirred at rt in a closed vessel for 18 h. The reaction mixture was diluted with DCM (30 mL) then washed with sat. NaHCO₃ (aq) (30 mL) then water (30 mL). The organic layer was dried over a hydrophobic frit and the solvent was evaporated under vacuum. The sample was loaded in DCM and purified on silica (330 g) using 0-10% (MeOH/NH₃)/DCM over 12 CVs. The fractions containing product were combined and concentrated in vacuo to give the product (1.9804 g, 4.76 mmol, 27%).

LCMS (2 min Formic): Rt=1.21 min, [MH]⁺=416, 418.

Intermediate 107: rac-benzyl ((2S,3R,4R)-1-acetyl-6-bromo-2-cyclopropyl-3-methyl-1,2,3,4-tetrahydro-1,5-naphthyridin-4-yl)carbamate

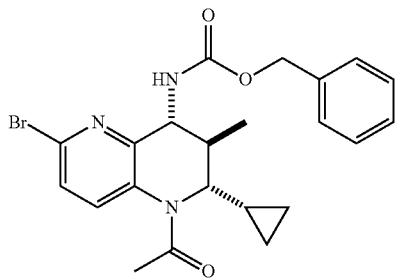 [SMILES: CC(=O)N1c2ccc(Br)nc2[C@H](NC(=O)OCc2ccccc2)[C@@H](C)[C@@H]1C1CC1]

To a cooled, stirred solution of rac-benzyl ((2S,3S,4R)-6-bromo-2-cyclopropyl-3-methyl-1,2,3,4-tetrahydro-1,5-naphthyridin-4-yl)carbamate (for a preparation see Intermediate 106, 1.9804 g, 4.76 mmol) in DCM (25 mL) and pyridine (0.577 mL, 7.14 mmol) was added acetyl chloride (0.424 mL, 5.95 mmol). The reaction mixture was stirred at rt for 1 h under nitrogen. Further pyridine (0.577 mL, 7.14 mmol) and acetyl chloride (0.424 mL, 5.95 mmol) were added and the reaction mixture was left to stir for an hour under nitrogen. Acetyl chloride (4 mL) and DMAP (0.581 g, 4.76 mmol) were added and the reaction mixture was left to stir for 22 h at rt under nitrogen. The sample was loaded in DCM and purified on silica (330 g) using 0-75% ethyl acetate/cyclohexane over 12 CVs. The fractions were combined and concentrated in vacuo to give the product (596 mg, 27%).

LCMS (2 min Formic): Rt=1.15 min, [MH]⁺=458, 460.

Intermediate 108: rac-benzyl ((2S,3R,4R)-1-acetyl-2-cyclopropyl-3-methyl-6-morpholino-1,2,3,4-tetrahydro-1,5-naphthyridin-4-yl)carbamate

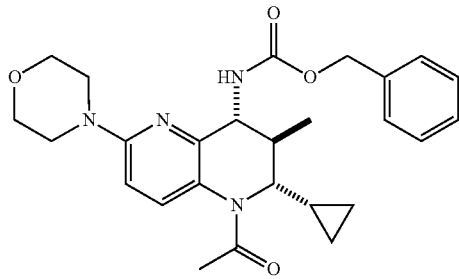 [SMILES: CC(=O)N1c2ccc(N3CCOCC3)nc2[C@H](NC(=O)OCc2ccccc2)[C@@H](C)[C@@H]1C1CC1]

A mixture of rac-benzyl ((2S,3R,4R)-1-acetyl-6-bromo-2-cyclopropyl-3-methyl-1,2,3,4-tetrahydro-1,5-naphthyridin-4-yl)carbamate (for a preparation see Intermediate 107, 596 mg, 1.300 mmol), morpholine (0.136 ml, 1.560 mmol), Pd₂dba₃ (59.5 mg, 0.065 mmol), sodium tert-butoxide (250 mg, 2.60 mmol) and DavePhos (51.2 mg, 0.130 mmol) in 1,4-dioxane (12 mL) was stirred at 100° C. for 1 h. The reaction mixture was filtered through celite and the filtrate was concentrated in vacuo. The crude was taken up in DCM and purified on a 100 g silica cartridge over a gradient of 0-7.5% DCM/MeOH over 12 CVs. The appropriate fractions were combined and evaporated in vacuo to give a yellow gum. The sample was dissolved in 1:1 MeOH: DMSO (3×1 mL) and purified by MDAP (Formic). The appropriate fractions were combined and the solvent was evaporated in vacuo to give the product (98.4 mg). LCMS (2 min Formic): Rt=1.08 min, [MH]⁺=465.

Intermediate 109: rac-1-((2S,3R,4R)-4-amino-2-cyclopropyl-3-methyl-6-morpholino-3,4-dihydro-1,5-naphthyridin-1(2H)-yl)ethanone

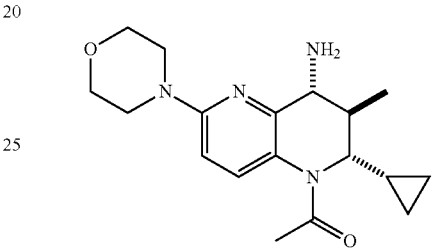

rac-Benzyl ((2S,3R,4R)-1-acetyl-2-cyclopropyl-3-methyl-6-morpholino-1,2,3,4-tetrahydro-1,5-naphthyridin-4-yl)carbamate (for a preparation see Intermediate 108, 96.4 mg, 0.208 mmol) in MeOH (4 mL) was hydrogenated using the H-cube (settings: rt, full H₂ mode, 1 mL/min flow rate) and 10% Pd/C as a catalyst. The solvent was evaporated in vacuo to give the product (62.3 mg, 0.189 mmol, 91%) as a clear gum. LCMS (2 min High pH): Rt=0.76 min, [MH]⁺=331.

Intermediate 110: rac-(6S,7R,8R)-5-acetyl-6-cyclopropyl-7-methyl-8-((6-methylpyridin-2-yl)amino)-5,6,7,8-tetrahydro-1,5-naphthyridin-2-yl trifluoromethanesulfonate

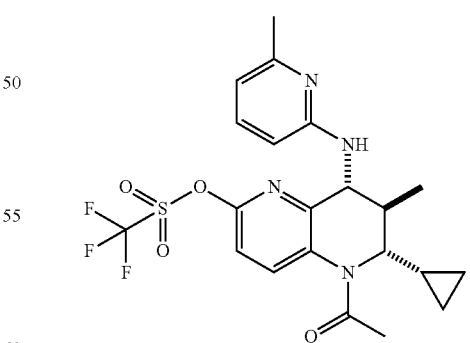

A solution of rac-1-((2S,3R,4R)-2-cyclopropyl-6-hydroxy-3-methyl-4-((6-methylpyridin-2-yl)amino)-3,4-dihydro-1,5-naphthyridin-1(2H)-yl)ethanone (for a preparation see Example 112, 400 mg, 1.135 mmol), NEt₃ (0.316 mL, 2.270 mmol), DMAP (13.87 mg, 0.113 mmol) and 2-(N,N-bis(trifluoromethylsulfonyl)amino)-5-chloropyridine (535 mg, 1.362 mmol) in DCM (10 mL) was stirred at rt in a closed vessel for 1 h. The reaction mixture was diluted with DCM (10 mL) then washed with 0.5 M HCl (20 mL) and water (20 mL). The DCM layer was dried through a hydrophobic frit then concentrated in vacuo. The crude was dissolved in DCM and applied to a 100 g silica cartridge and purified over a gradient of 0-20% DCM/MeOH over 10 CVs. The fractions containing product were combined and concentrated in vacuo. The sample was dissolved in 1:1 MeOH:DMSO (2×3 mL) and purified by MDAP (HpH). The appropriate fractions were combined and concentrated in vacuo to give the product (440 mg, 0.908 mmol, 80%).

LCMS (2 min Formic): Rt=0.78 min, [MH]$^+$=485.

Intermediate 111: rac-benzyl ((2S,3S,4R)-2,3-dimethyl-8-oxo-1,2,3,4,7,8-hexahydro-1,7-naphthyridin-4-yl)carbamate

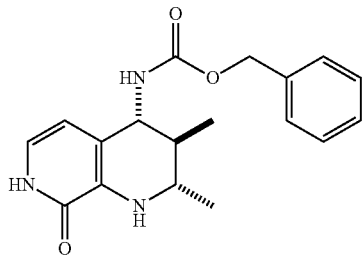 [SMILES: C[C@H]1[C@H](C)Nc2c(cc[nH]c2=O)[C@@H]1NC(=O)OCc1ccccc1]

Under nitrogen atmosphere, to a solution of acetaldehyde (0.134 mL, 2.38 mmol) in chloroform (10 mL) was added 3-aminopyridin-2(1H)-one (262 mg, 2.380 mmol). The reaction was stirred at rt for 1 h and then cooled to 0° C. Solutions of diphenyl hydrogen phosphate (59.5 mg, 0.238 mmol) in chloroform (7.5 mL) and (E)-benzyl prop-1-en-1-ylcarbamate (for a preparation see Intermediate 1, 501 mg, 2.62 mmol) in chloroform (7.5 mL) were added. The reaction was stirred at 0° C. for 2 h. Acetaldehyde (0.134 mL, 2.38 mmol) was then added and the reaction mixture was stirred at 60° C. for 1 h. Acetaldehyde (0.134 mL, 2.38 mmol) was then added and the reaction mixture was stirred at 60° C. overnight. The solvent was then evaporated in vacuo, the residue was loaded onto a 100 g silica cartridge and purified by column chromatography using a gradient 0-20% of 2 M ammonia/MeOH in DCM. Desired fractions were combined and evaporated in vacuo to afford the product as a white solid (224 mg). LCMS (2 min Formic): Rt=0.86 min, [MH]$^+$=328.

Intermediate 112: rac-benzyl ((2S,3R,4R)-1-acetyl-2,3-dimethyl-8-oxo-1,2,3,4,7,8-hexahydro-1,7-naphthyridin-4-yl)carbamate

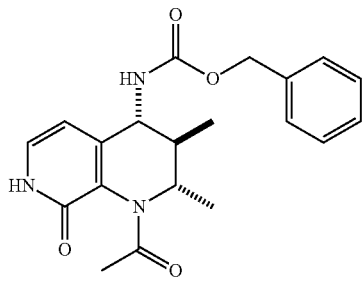 [SMILES: CC(=O)N1c2c(cc[nH]c2=O)[C@H](NC(=O)OCc2ccccc2)[C@@H](C)[C@@H]1C]

rac-Benzyl ((2S,3S,4R)-2,3-dimethyl-8-oxo-1,2,3,4,7,8-hexahydro-1,7-naphthyridin-4-yl)carbamate (for a preparation see Intermediate 111, 196 mg, 0.599 mmol) was taken up in dry DCM (7 mL) under nitrogen at rt. Pyridine (0.145 mL, 1.796 mmol) then acetyl chloride (0.064 mL, 0.898 mmol) were added and the reaction mixture was stirred for 3 h at rt. Acetyl chloride (0.5 eq) was added and the reaction mixture was stirred at rt for 1 h. The reaction mixture was partitioned between ethyl acetate (40 mL) and saturated sodium bicarbonate (20 mL). The organic layer was extracted and washed with water (30 mL) and brine (30 mL) and then dried over a hydrophobic frit, filtered and concentrated under vacuum to afford a green residue. The residue was then dissolved in water, with a small amount of MeOH to help the dissolution. Potassium carbonate (83 mg, 0.599 mmol) was then added and the solution was stirred at rt for 1 h. The aqueous layer was then extracted two times with ethyl acetate, the combined organic layers were dried over a hydrophobic frit and evaporated in vacuo to afford a green residue. The crude product was taken up in the minimum of DCM and applied to a 25 g silica cartridge and eluted with a gradient 0-10% of MeOH in DCM. Desired fractions were combined and evaporated in vacuo to afford the product as a colourless solid (128.2 mg). LCMS (2 min Formic): Rt=0.74 min, [MH]$^+$=370.

Intermediate 113: rac-(2S,3R,4R)-1-Acetyl-4-(((benzyloxy)carbonyl)amino)-2,3-dimethyl-1,2,3,4-tetrahydro-1,7-naphthyridin-8-yl trifluoromethanesulfonate

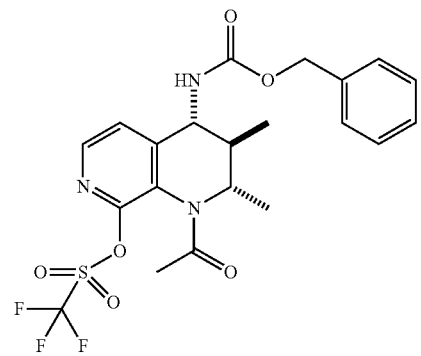 [SMILES: CC(=O)N1c2c(ccnc2OS(=O)(=O)C(F)(F)F)[C@H](NC(=O)OCc2ccccc2)[C@@H](C)[C@@H]1C]

To a solution of rac-benzyl ((2S,3R,4R)-1-acetyl-2,3-dimethyl-8-oxo-1,2,3,4,7,8-hexahydro-1,7-naphthyridin-4-yl)carbamate (for a preparation see Intermediate 112, 128.2 mg, 0.347 mmol) in pyridine (4 mL) at 0° C. was rapidly added trifluoromethanesulfonic anhydride (0.076 mL, 0.451 mmol). The solution was stirred at 0° C. for 2 h. Trifluoromethanesulfonic anhydride (0.030 mL) was added and the reaction mixture was stirred at 0° C. for 1 h. The solution was then poured into a separation funnel containing water (25 mL). The mixture was extracted with DCM (3×20 mL), the combined organic layers were dried over a hydrophobic frit and concentrated under vacuum to afford an orange oil. This oil was loaded onto a 25 g silica cartridge and purified by column chromatography using a gradient 0-50% of ethyl acetate in cyclohexane. Desired fractions were combined and evaporated in vacuo to afford the product as an orange solid (154.3 mg).

LCMS (2 min Formic): Rt=1.16 min, [MH]$^+$=502.

Intermediate 114: rac-1-((2S,3R,4R)-4-Amino-2,3-dimethyl-3,4-dihydro-1,7-naphthyridin-1(2H)-yl)ethanone

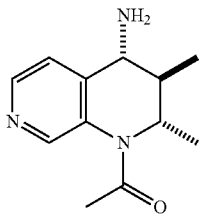 [SMILES: CC(=O)N1c2cnccc2[C@H](N)[C@@H](C)[C@@H]1C]

rac-(2S,3R,4R)-1-Acetyl-4-(((benzyloxy)carbonyl)amino)-2,3-dimethyl-1,2,3,4-tetrahydro-1,7-naphthyridin-8-yl trifluoromethanesulfonate (for a preparation see Intermediate 113, 154.3 mg, 0.308 mmol) was dissolved in MeOH (6 mL) and was then passed through a 10% Pd/C cartridge on a H-cube (50° C., full $H_2$ mode) to give a colourless filtrate. This filtrate was concentrated in vacuo to afford the product as a colourless solid (108.5 mg).

LCMS (2 min High pH): Rt=0.49 min, $[MH]^+$=220.

Intermediate 115: rac-benzyl ((2S,3S,4R)-2-cyclopropyl-3-methyl-8-oxo-1,2,3,4,7,8-hexahydro-1,7-naphthyridin-4-yl)carbamate

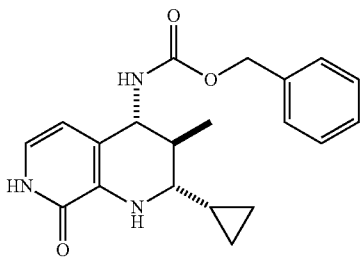 [SMILES: C[C@@H]1[C@@H](NC(=O)OCc2ccccc2)c2cc[nH]c(=O)c2N[C@H]1C1CC1]

Under nitrogen atmosphere, to a solution of cyclopropanecarbaldehyde (0.221 mL, 2.48 mmol) in dry DCM (12 mL) was added 3-aminopyridin-2(1H)-one (282 mg, 2.480 mmol). The reaction was stirred at rt for 1 h and then cooled to 0° C. Solutions of diphenyl hydrogen phosphate (62.0 mg, 0.248 mmol) in dry DCM (6 mL) and (E)-benzyl prop-1-en-1-ylcarbamate (for a preparation see Intermediate 1, 520 mg, 2.72 mmol) in dry DCM (6 mL) were added. The reaction was stirred at 0° C. for 2 h and stirred overnight at rt. Cyclopropanecarbaldehyde (0.221 mL, 2.48 mmol) was added and the reaction mixture was stirred at rt for 1 h. The reaction mixture was heated at 40° C. and stirred overnight. Cyclopropanecarbaldehyde (0.221 mL, 2.48 mmol) was then added and the reaction mixture was stirred at 40° C. for 3 h. Cyclopropanecarbaldehyde (0.221 mL, 2.48 mmol) and 3-aminopyridin-2(1H)-one (282 mg, 2.480 mmol) were then added and the reaction mixture was stirred at 40° C. for 1.5 h. Cyclopropanecarbaldehyde (0.221 mL, 2.48 mmol) was then added and the reaction mixture was stirred at 40° C. for 2.5 h. Cyclopropanecarbaldehyde (0.221 mL, 2.48 mmol) was then added and the reaction mixture was allowed to stand at rt overnight. The solvent was evaporated in vacuo, the residue was loaded onto a 100 g silica cartridge and purified by column chromatography using a gradient 0-10% of (2M ammonia in MeOH) in DCM. Desired fractions were combined and evaporated in vacuo to afford the product as a white/green solid (238.4 mg).

LCMS (2 min Formic): Rt=0.94 min, $[MH]^+$=354.

Intermediate 116: rac-benzyl ((2S,3R,4R)-1-acetyl-2-cyclopropyl-3-methyl-8-oxo-1,2,3,4,7,8-hexahydro-1,7-naphthyridin-4-yl)carbamate

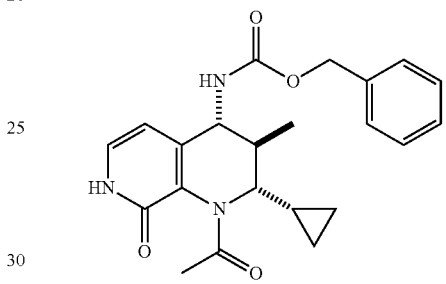

rac-Benzyl ((2S,3S,4R)-2-cyclopropyl-3-methyl-8-oxo-1,2,3,4,7,8-hexahydro-1,7-naphthyridin-4-yl)carbamate (for a preparation see Intermediate 115, 238.4 mg, 0.675 mmol) was taken up in dry DCM (7 mL) under nitrogen at rt. Pyridine (0.177 mL, 2.188 mmol) then acetyl chloride (0.058 mL, 0.809 mmol) were added and the reaction mixture was stirred for 2 h at rt. Acetyl chloride (0.5 eq) was added and the reaction mixture was stirred at rt for 1.5 h. Acetyl chloride (0.5 eq) was added and the reaction mixture was stirred at rt for 40 min. Acetyl chloride (0.5 eq) was added and the reaction mixture was stirred at rt for 1 h. The reaction mixture was partitioned between ethyl acetate (40 mL) and saturated sodium bicarbonate (20 mL). The organic layer was extracted and washed with water (30 mL) and brine (30 mL) and then dried over a hydrophobic frit and concentrated under vacuum. The residue was then dissolved in water (20 mL), with a small amount of MeOH to help the dissolution. Potassium carbonate (93 mg, 0.675 mmol) was then added and the solution was stirred at rt for 3 h. The aqueous layer was then extracted with ethyl acetate (3×30 mL), the combined organic layers were dried over a hydrophobic frit and evaporated in vacuo. The crude product was taken up in the minimum amount of DCM and applied to a 25 g silica cartridge and eluted with a gradient 0-10% of MeOH in DCM. Desired fractions were combined and evaporated in vacuo to afford the product as a colourless solid (140 mg). LCMS (2 min Formic): Rt=0.80 min, $[MH]^+$=396.

Intermediate 117: rac-(2S,3R,4R)-1-acetyl-4-(((benzyloxy)carbonyl)amino)-2-cyclopropyl-3-methyl-1,2,3,4-tetrahydro-1,7-naphthyridin-8-yl trifluoromethanesulfonate

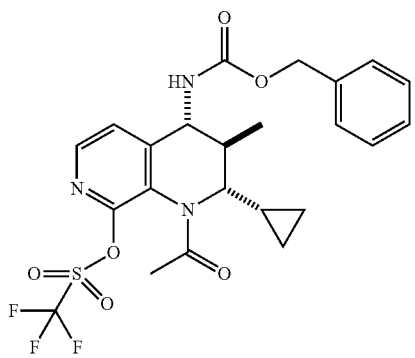 [SMILES: CC(=O)N1c2c(ccnc2OS(=O)(=O)C(F)(F)F)[C@H](NC(=O)OCc2ccccc2)[C@@H](C)[C@@H]1C1CC1]

To a solution of rac-benzyl ((2S,3R,4R)-1-acetyl-2-cyclopropyl-3-methyl-8-oxo-1,2,3,4,7,8-hexahydro-1,7-naphthyridin-4-yl)carbamate (for a preparation see Intermediate 116, 140 mg, 0.354 mmol) in pyridine (4 mL) at 0° C. was rapidly added trifluoromethanesulfonic anhydride (0.078 mL, 0.460 mmol). The solution was stirred at 0° C. for 75 min. Trifluoromethanesulfonic anhydride (0.078 mL, 0.460 mmol) was added and the reaction mixture was stirred at 0° C. for 2 h. The solution was then poured into a separation funnel containing water (25 mL). The mixture was extracted with DCM (3×20 mL), the combined organic layers were dried over a hydrophobic frit and concentrated under vacuum to afford an orange oil. This oil was loaded onto a 25 g silica cartridge and purified by column chromatography using a gradient 0-50% of ethyl acetate in cyclohexane. Desired fractions were combined and evaporated in vacuo to afford the product as a colourless solid (185.7 mg).

LCMS (2 min Formic): Rt=1.22 min, [MH]$^+$=528.

Intermediate 118: rac-1-((2S,3R,4R)-4-amino-2-cyclopropyl-3-methyl-3,4-dihydro-1,7-naphthyridin-1(2H)-yl)ethanone rac-(2S,3R,4R)-1-Acetyl-4-(((benzyloxy)carbonyl)amino)-2-cyclopropyl-3-methyl-1,2,3,4-tetrahydro-1,7-naphthyridin-8-yl trifluoromethanesulfonate (for a preparation see Intermediate 117, 151.7 mg, 0.288 mmol) was dissolved in MeOH (6 mL) and was then passed through a 10% Pd/C cartridge on an H-cube (50° C., full H$_2$ mode) to give a colourless filtrate. This filtrate was concentrated in vacuo to afford the product as a colourless solid (100.7 mg).

LCMS (2 min HpH): Rt=0.59 min, [MH]$^+$ not observed.

Intermediate 119: rac-benzyl ((2S,3S,4R)-3-methyl-8-oxo-2-propyl-1,2,3,4,7,8-hexahydro-1,7-naphthyridin-4-yl)carbamate

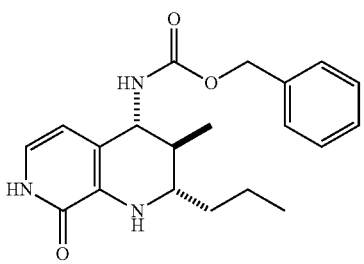 [SMILES: CCC[C@@H]1Nc2c(cc[nH]c2=O)[C@H](NC(=O)OCc2ccccc2)[C@H]1C]

Under an atmosphere of nitrogen, butyraldehyde (0.39 mL, 4.33 mmol) was added to a suspension of 3-aminopyridin-2(1H)-one (400 mg, 3.63 mmol) in anhydrous DCM (10 mL). The mixture was stirred at rt for 1.5 h then cooled to 0° C. To the solution was added diphenyl hydrogen phosphate (90 mg, 0.360 mmol) in anhydrous DCM (5 mL) followed by (E)-benzyl prop-1-en-1-ylcarbamate (for a preparation see Intermediate 1, 770 mg, 4.03 mmol) in anhydrous DCM (5 mL). The mixture was stirred at 0° C. for 1 h then allowed to warm to rt with stirring over 21 h. The reaction mixture was washed with 2 M aq. NaOH (10 mL) and the aqueous layer was extracted with DCM (10 mL). The combined organic layers were washed with water (15 mL) and then dried through a hydrophobic frit. The solvent was removed by rotary evaporation to give an off white residue. The residue was loaded in CHCl$_3$ and purified on a 100 g silica cartridge using a gradient of 0-15% MeOH in DCM over 14 CVs. The appropriate fractions were combined and the solvent was removed by rotary evaporation to give the product as a white solid (691 mg, 1.944 mmol, 53.5%).

LCMS (2 min Formic): Rt=1.00 min, [MH]$^+$=356.

Intermediate 120: rac-benzyl ((2S,3R,4R)-1-acetyl-3-methyl-8-oxo-2-propyl-1,2,3,4,7,8-hexahydro-1,7-naphthyridin-4-yl)carbamate

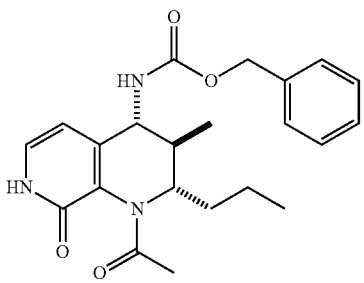 [SMILES: CCC[C@H]1[C@H](C)[C@@H](NC(=O)OCc2ccccc2)c2cc[nH]c(=O)c2N1C(C)=O]

A solution of rac-benzyl ((2S,3S,4R)-3-methyl-8-oxo-2-propyl-1,2,3,4,7,8-hexahydro-1,7-naphthyridin-4-yl)carbamate (for a preparation see Intermediate 119, 691 mg, 1.944 mmol) and pyridine (0.47 mL, 5.81 mmol) in anhydrous chloroform (10 mL) was treated with acetyl chloride (0.16 mL, 2.250 mmol). The mixture was stirred at rt under an atmosphere of nitrogen. Acetyl chloride (0.5 eq., 80 µL)

was added to the reaction mixture after 16 h and after 18 h. The reaction mixture was left to stir over the weekend. After 3 days DMAP (0.1 eq) was added to the reaction mixture, followed by acetyl chloride (0.5 eq., 80 μL). After 30 h, the reaction mixture was warmed to 60° C. overnight. The temperature was increased to 70° C. After 16 h, acetyl chloride (3 eq. 0.48 mL) was added. The reaction mixture was allowed to cool to rt and further pyridine (3 eq. 0.47 mL, 5.81 mmol) and acetyl chloride (2 eq. 0.32 mL) were added. After 2 h, further acetyl chloride (2 eq. 0.32 mL) was added. After 5 h, DMAP (0.1 eq, 25 mg) was added to the mixture. After 6.5 h, the reaction mixture was diluted with DCM (5 mL) then washed with 2 M aq. HCl (10 mL) followed by sat. aq. NaHCO$_3$ (10 mL) then water (10 mL). The organic layer was dried through a hydrophobic frit and the residue (672 mg) was loaded in CHCl$_3$ and purified on a 100 g silica cartridge using a gradient of 0-15% MeOH in DCM over 12 CVs. The appropriate fractions were combined and the solvent was removed by rotary evaporation to give the product as a colourless oil which solidified (142 mg, 0.357 mmol, 18%). LCMS (2 min Formic): Rt=0.84 min, [MH]$^+$=398.

Intermediate 121: rac-(2S,3R,4R)-1-acetyl-4-(((benzyloxy)carbonyl)amino)-3-methyl-2-propyl-1,2,3,4-tetrahydro-1,7-naphthyridin-8-yl trifluoromethanesulfonate

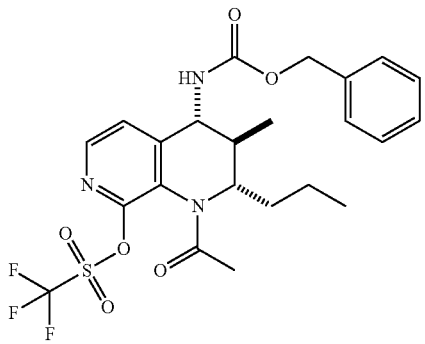 [SMILES: CCC[C@H]1[C@H](C)[C@@H](NC(=O)OCc2ccccc2)c2ccnc(OS(=O)(=O)C(F)(F)F)c2N1C(C)=O]

To a solution of rac-benzyl ((2S,3R,4R)-1-acetyl-3-methyl-8-oxo-2-propyl-1,2,3,4,7,8-hexahydro-1,7-naphthyridin-4-yl)carbamate (for a preparation see Intermediate 120, 140 mg, 0.352 mmol) in pyridine (4 mL) was added triflic anhydride (89 μL, 0.527 mmol). The solution was stirred at 0° C. for 5 h under an atmosphere of nitrogen. (A further 1 eq. of triflic anhydride (89 μL, 0.527 mmol) was added after 1 h and 4 h). The reaction mixture was quenched by the addition of water (5 mL) and stirred for 15 min at rt. The mixture was extracted with DCM (3×10 mL) and the combined organic layers were dried through a hydrophobic frit. The solvent was removed by rotary evaporation to give a light brown residue which was loaded in DCM and purified on a 25 g silica cartridge using a gradient of 0-50% EtOAc in cyclohexane over 14 CVs. The appropriate fractions were combined and the solvent was removed by rotary evaporation to give the product as a yellow oil (159 mg, 0.300 mmol, 85% yield).

LCMS (2 min Formic): Rt=1.24 min, [MH]$^+$=530.

Intermediate 122: rac-1-((2S,3R,4R)-4-Amino-3-methyl-2-propyl-3,4-dihydro-1,7-naphthyridin-1(2H)-yl)ethanone

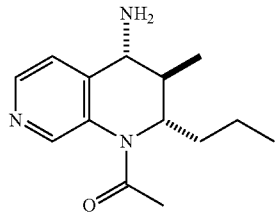 [SMILES: CCC[C@H]1[C@H](C)[C@@H](N)c2ccncc2N1C(C)=O]

A solution of rac-(2S,3R,4R)-1-acetyl-4-(((benzyloxy)carbonyl)amino)-3-methyl-2-propyl-1,2,3,4-tetrahydro-1,7-naphthyridin-8-yl trifluoromethanesulfonate (for a preparation see Intermediate 121, 156 mg, 0.295 mmol) in MeOH (5 mL) was hydrogenated using the H-cube (settings: 50° C., full H$_2$ mode, 1 mL/min flow rate) and 10% Pd/C CatCart 30 as the catalyst (4 passes through the H-cube in total). The eluent was then evaporated in vacuo. The colourless residue was suspended in DCM and the solvent was removed by rotary evaporation to give the product as a white solid (54 mg, 0.218 mmol, 74%). LCMS (2 min Formic): Rt=0.40 min, [MH]$^+$=248.

Intermediate 123: rac-(2S,3S)-1-acetyl-2-cyclopropyl-3-methyl-1,2,3,4-tetrahydroquinolin-4-yl Acetate

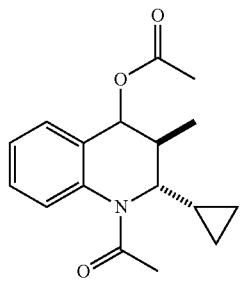 [SMILES: CC(=O)OC1c2ccccc2N(C(C)=O)[C@@H](C2CC2)[C@@H]1C]

To a flask containing rac-1-((2S,3R,4R)-4-amino-2-cyclopropyl-3-methyl-3,4-dihydroquinolin-1(2H)-yl)ethanone (for a preparation see Intermediate 14, 894 mg, 3.66 mmol) in acetic acid (10 mL, 175 mmol) was added a solution of sodium nitrite (808 mg, 11.71 mmol) in water (3 mL) drop-wise, with a cold water bath to aid cooling. There was an immediate green-yellow colour change. The reaction was stirred for 1 h. The reaction mixture was diluted with EtOAc (20 mL) and water (20 mL). The layers were separated and the aqueous layer further extracted with EtOAc (2×20 mL). The combined organics were dried and concentrated in vacuo to yield a yellow oil (1.05 g, 3.65 mmol, 100%) which also contained 25% free hydroxyl. This product mixture was not purified and used crude in the subsequent deprotection. This was a racemic mixture of diastereoisomers.

LCMS (2 min Formic): Rt=1.02 min, [MH]$^+$=288.

Intermediates 124a & 124b: rac-1-((2S,3S,4R)-2-cyclopropyl-4-hydroxy-3-methyl-3,4-dihydroquinolin-1(2H)-yl)ethanone (120a) & rac-1-((2S,3S,4S)-2-cyclopropyl-4-hydroxy-3-methyl-3,4-dihydroquinolin-1(2H)-yl)ethanone (120b)

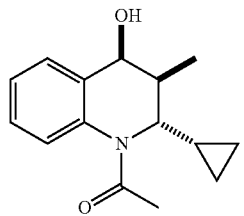

124a

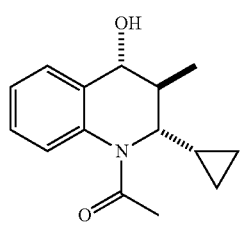

124b

To a flask containing rac-(2S,3S)-1-acetyl-2-cyclopropyl-3-methyl-1,2,3,4-tetrahydroquinolin-4-yl acetate (for a preparation see Intermediate 123, 1.05 g, 3.65 mmol) in ethanol (14 mL) was added potassium hydroxide (0.267 g, 4.75 mmol) at rt. The reaction was stirred for 1 h. The reaction mixture was partitioned between water (20 mL) and DCM (20 mL). The layers were separated and the aqueous phase washed with further DCM. The combined organic suspension was dried (Na$_2$SO$_4$) and concentrated in vacuo to afford the crude product as a yellow oil. This was dissolved in DCM and purified by flash chromatography on a silica cartridge (10 g). It was eluted with 0-60% EtOAc/cyclohexane. The appropriate fractions were concentrated in vacuo to yield rac-1-((2S,3S,4R)-2-cyclopropyl-4-hydroxy-3-methyl-3,4-dihydroquinolin-1(2H)-yl)ethanone (434 mg, 1.769 mmol, 48%) as a yellow oil which crystallised on standing.

LCMS (2 min Formic): Rt=0.79 min, [MH]$^+$=246.

A second eluting set of fractions were also collected and concentrated in vacuo to afford rac-1-((2S,3S,4S)-2-cyclopropyl-4-hydroxy-3-methyl-3,4-dihydroquinolin-1(2H)-yl)ethanone as a pale yellow oil which crystallised on standing (70 mg, 0.285 mmol, 8%).

LCMS (2 min Formic): Rt=0.82 min, [MH]$^+$=246.

Intermediate 125: rac-1-((2S,3R,4R)-4-amino-2-cyclopropyl-3-methyl-3,4-dihydroquinolin-1(2H)-yl)ethanone Hydrobromide

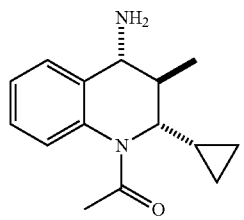 [SMILES: CC(=O)N1c2ccccc2[C@H](N)[C@@H](C)[C@@H]1C1CC1]

A stirred mixture of rac-benzyl ((2S,3R,4R)-1-acetyl-6-bromo-2-cyclopropyl-3-methyl-1,2,3,4-tetrahydroquinolin-4-yl)carbamate (for a preparation see Intermediate 13, 3.996 g, 8.74 mmol) and Palladium, 10 wt. % (dry basis) on activated carbon, wet, Degussa type E101 NE/W (0.828 g, 7.78 mmol) in ethanol (100 mL) and ethyl acetate (70 mL) was hydrogenated with vigorous stirring under one atmosphere of hydrogen at rt for 3 h. The mixture was filtered under nitrogen through a pad of celite filter aid and the filter cake washed with ethanol (3×50 mL). The combined filtrate was evaporated in vacuo and dried to give the desired product (2.488 g, 7.65 mmol, 88%).

LCMS (2 min Formic): Rt=0.49 min, [M]$^+$=228 (loss of NH$_2^-$).

Intermediate 126: rac-1-((2S,3R,4R)-4-amino-6-bromo-2-cyclopropyl-3-methyl-3,4-dihydroquinolin-1(2H)-yl)ethanone

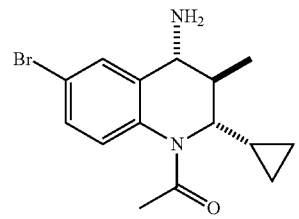 [SMILES: CC(=O)N1c2ccc(Br)cc2[C@H](N)[C@@H](C)[C@@H]1C1CC1]

The tert-butyl ((2S,3R,4R)-1-acetyl-6-bromo-2-cyclopropyl-3-methyl-1,2,3,4-tetrahydroquinolin-4-yl)carbamate (for a preparation see Intermediate 76 500 mg, 1.181 mmol) was taken up in dichloromethane (DCM) (20 mL) and treated with trifluoroacetic acid (0.455 mL, 5.91 mmol) and allowed to stir at rt for 18 h. The reaction was treated with further TFA (0.182 mL, 2.362 mmol) and allowed to stir at rt for 90 mins. The reaction was concentrated and eluted through a NH$_2$ SPE (10 g) with MeOH, the MeOH fraction was concentrated and dried to give the product as a white solid (352 mg).

LCMS (2 min Formic): Rt=0.59 min, [M]$^+$=306, 308 (loss of NH$_2^-$).

Intermediate 127: rac-tert-butyl 3-(((2S,3R,4R)-1-acetyl-2-cyclopropyl-3-methyl-1,2,3,4-tetrahydroquinolin-4-yl)amino)benzylcarbamate

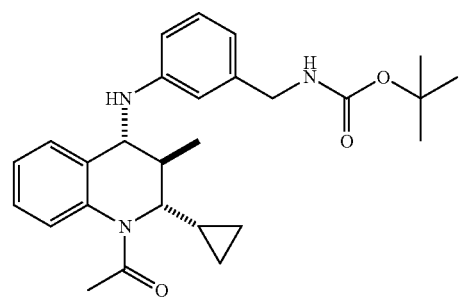 [SMILES: CC(=O)N1c2ccccc2[C@H](Nc2cccc(CNC(=O)OC(C)(C)C)c2)[C@@H](C)[C@@H]1C1CC1]

In a test tube rac-1-((2S,3R,4R)-4-amino-2-cyclopropyl-3-methyl-3,4-dihydroquinolin-1(2H)-yl)ethanone (for a preparation see Intermediate 14,141 mg, 0.491 mmol) sodium tert-butoxide (79 mg, 0.819 mmol), Pd$_2$(dba)$_3$ (18.74 mg, 0.020 mmol) and DavePhos (16.11 mg, 0.041 mmol) were dissolved in 1,4-dioxane (4 mL). The tube was placed in a greenhouse reactor and heated at 100° C. for 2 h. The reaction was incomplete so further tert-butyl 3-bromobenzylcarbamate (141 mg, 0.491 mmol), sodium tert-butoxide (79 mg, 0.819 mmol), Pd$_2$(dba)$_3$ (18.74 mg, 0.020 mmol) and DavePhos (16.11 mg, 0.041 mmol) were added and the reaction was heated at 100° C. for another 1 h. The reaction mixture was cooled and filtered through celite. The filtrate was concentrated in vacuo to leave the crude. Purification was undertaken by flash column chromatography. The crude material was loaded onto a 25 g silica column and eluted using a graduating solvent system of 0-30% ethyl acetate in cyclohexane. Combination and evaporation of the desired fractions gave the product as yellow oil (165 mg). This was only ~75% pure but was taken on as was to the subsequent reaction.

LCMS (2 min Formic): Rt=1.21 min, [MH]$^+$=450.

Intermediate 128: rac-methyl 4-(((2S,3R,4R)-1-acetyl-2-cyclopropyl-3-methyl-1,2,3,4-tetrahydroquinolin-4-yl)amino)benzoate

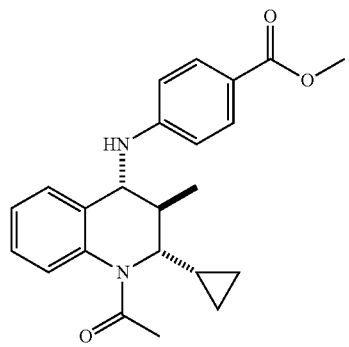 [SMILES: COC(=O)c1ccc(N[C@H]2c3ccccc3N(C(C)=O)[C@@H](C3CC3)[C@@H]2C)cc1]

Pd$_2$(dba)$_3$ (107 mg, 0.117 mmol), DavePhos (92 mg, 0.233 mmol) and sodium tert-butoxide (168 mg, 1.750 mmol) were all placed in a 2-5 mL microwave vial. To this was added methyl 4-bromobenzoate (251 mg, 1.166 mmol), followed by a fine suspension of rac-1-((2S,3R,4R)-4-amino-2-cyclopropyl-3-methyl-3,4-dihydroquinolin-1(2H)-yl)ethanone (for a preparation see Intermediate 14, 142.5 mg, 0.583 mmol) in 1,4-dioxane (5 mL). The mixture was heated at 120° C. for 40 min in a microwave heater. The reaction vessel was resealed and heated in a microwave heater for a further 20 min at 140° C. The mixture was filtered through a 2.5 g celite cartridge, washed through with ethyl acetate and concentrated in vacuo to afford a yellow crystalline solid. The crude material was taken up in dichloromethane, loaded onto a 10 g silica flash column, and eluted in 0%-35% ethyl acetate in cyclohexane. The appropriate fractions were collected and evaporated in vacuo to afford a yellow crystalline solid (51.2 mg).

LCMS (2 min formic): Rt=1.12 min, [M]$^+$=228 (loss of NHC$_6$H4CO$_2$Me$^-$).

Intermediate 129: (E)-tert-butyl but-2-en-1-ylcarbamate

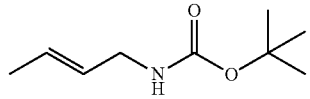

(E)-but-2-en-1-amine (300 mg, 4.22 mmol) was dissolved in dichloromethane (DCM) (7 mL) and cooled to 0° C., triethylamine (0.882 mL, 6.33 mmol), followed by Boc-anhydride (1.077 mL, 4.64 mmol) was added and the reaction stirred overnight and allowed to slowly warm to rt as the ice melted. NH$_4$Cl solution (20 mL) was added and the layers were separated. The aqueous phase was further extracted with DCM (2×20 mL) and the combined organics were dried (Na$_2$SO$_4$) and concentrated in vacuo to provide the crude product as a colourless oil. This was taken up in DCM and added to a 25 g SNAP silica cartridge. This was purified by flash chromatography, eluting with 0→100% EtOAc/cyclohexane. The appropriate fractions were collected and concentrated in vacuo to afford the desired product as a colourless oil (706 mg, 4.12 mmol, 98%).

LCMS (2 min formic): Rt=0.97 min, [MH]$^+$ not seen.

Intermediate 130: tert-butyl but-1-en-1-ylcarbamate

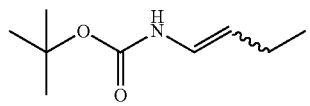

The (E)-tert-butyl but-2-en-1-ylcarbamate (for a preparation see Intermediate 129, 300 mg, 1.752 mmol) was placed in a microwaveable vial along with tris(triphenylphosphine) rhodium(I)carbonyl hydride (40.2 mg, 0.044 mmol) and tetrahydrofuran (THF) (15 mL), N$_2$ was bubbled through and the vial sealed and irradiated in a microwave at 80° C. for 2 h. The reaction was treated with triethylamine (0.012 mL, 0.088 mmol) and cooled to −70° C., the reaction was filtered at this temp and then concentrated in vacuo to give a brown oil. This oil was purified using a 25 g silica column, eluting with: 0-20% EtOAc:cyclohexane. Two closely eluting peaks (by TLC visualised with ninhydrin) were collected together and concentrated in vacuo to afford a colourless oil (160 mg, 0.934 mmol, 53.3%).

LCMS no peak/mass ion observed.

Intermediate 131: rac-tert-butyl ((2S,3S,4R)-2,3-diethyl-1,2,3,4-tetrahydroquinolin-4-yl)carbamate

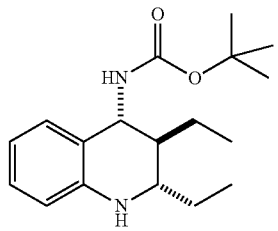 [SMILES: CC[C@H]1[C@H](CC)Nc2ccccc2[C@@H]1NC(=O)OC(C)(C)C]

To a solution of aniline (0.085 mL, 0.934 mmol) in anhydrous dichloromethane (DCM) (3 mL) was added propionaldehyde (0.074 mL, 1.028 mmol). The mixture was stirred at rt under nitrogen for ~2 h then cooled to 0° C. (ice bath). To the mixture was added first diphenyl hydrogen phosphate (23.38 mg, 0.093 mmol), followed by tert-butyl but-1-en-1-ylcarbamate (for a preparation see Intermediate 130, 160 mg, 0.934 mmol) in dichloromethane (DCM) (0.6 mL). Stirring was continued at 0° C. and allowed to warm to rt for 2 h. The reaction was allowed to stir overnight and the reaction was stopped by the addition of aqueous NaHCO₃ solution (10 mL). The layers were separated and the aqueous layer was further extracted with DCM (2×20 mL). The combined organics were dried (Na₂SO₄) and concentrated in vacuo. The crude product was taken up in DCM and added to a 25 g silica cartridge. This was purified by flash chromatography eluting with 0→10% EtOAc/cyclohexane. The appropriate fractions were collected and concentrated in vacuo to afford the desired product as a colourless oil (66.8 mg, 0.219 mmol, 23.48%). LCMS (2 min Formic): Rt=1.26 min, [MH]⁺=305.

Intermediate 132: rac-tert-butyl ((2S,3R,4R)-1-acetyl-2,3-diethyl-1,2,3,4-tetrahydroquinolin-4-yl)carbamate

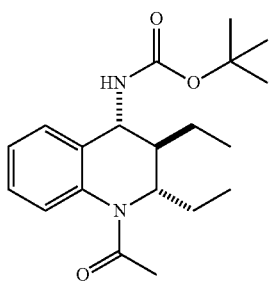 [SMILES: CC[C@@H]1[C@@H](NC(=O)OC(C)(C)C)c2ccccc2N(C(C)=O)[C@H]1CC]

The rac-tert-butyl ((2S,3S,4R)-2,3-diethyl-1,2,3,4-tetrahydroquinolin-4-yl)carbamate (for a preparation see Intermediate 131, 67 mg, 0.220 mmol) was taken up in dichloromethane (DCM) (2 mL) and treated with DIPEA (0.081 mL, 0.462 mmol) and acetyl chloride (0.031 mL, 0.440 mmol) and allowed to stir at rt for 2 h. The reaction was concentrated to a gum and purified using a 10 g silica column, eluting with 0-35% EtOAc:cyclohexane, one major peak was eluted, the appropriate fractions were collected and concentrated in vacuo to afford the product as a colourless oil (76 mg, 0.219 mmol, 100%). LCMS (2 min Formic): Rt=1.11 min, [MH]⁺=347.

Intermediate 133: rac-1-((2S,3R,4R)-4-amino-2,3-diethyl-3,4-dihydroquinolin-1(2H)-yl)ethanone

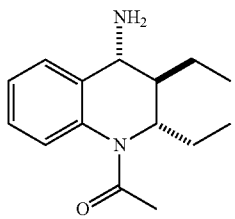 [SMILES: CC[C@@H]1[C@@H](N)c2ccccc2N(C(C)=O)[C@H]1CC]

The rac-tert-butyl ((2S,3R,4R)-1-acetyl-2,3-diethyl-1,2,3,4-tetrahydroquinolin-4-yl)carbamate (for a preparation see Intermediate 132, 76 mg, 0.219 mmol) was taken up in dichloromethane (DCM) (1 mL), treated with TFA (250 μL, 3.24 mmol) and allowed to stir at rt for 2 h, The reaction was concentrated, taken up in MeOH and added to an SCX cartridge (2.5 g). MeOH (3 CVs) was eluted and the product then eluted in 2M NH₃ in MeOH (3 CV). These fractions were concentrated to afford the desired product as a colourless oil 44 mg, 0.179 mmol, 81%).

LCMS (2 min Formic): Rt=0.51 min, [MH]⁺=230 (loss of NH₂⁻).

Intermediate 134: tert-butyl (2-hydroxyethyl)(methyl)carbamate

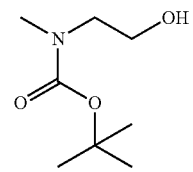

2-(Methylamino)ethanol (5.32 ml, 66.6 mmol) was dissolved in dry dichloromethane (DCM) (30 ml). Boc₂O (17.00 ml, 73.2 mmol) was added portion-wise and reaction mixture stirred under N₂ at rt. The reaction mixture was left stirring at rt for a further 2 days. The reaction mixture was diluted with water, the organic layer separated and the aq. layer further extracted with DCM. The combined organic layers were dried (Na₂SO₄) and concentrated to give the product (13.29 g, 76 mmol, 114%) as a colourless oil. LCMS (2 min Formic): Rt=0.66 min, [MH]⁺=176.

Intermediate 135: tert-butyl methyl(2-(4-(4,4,5,5-tetramethyl-1,3,2-dioxaborolan-2-yl)-1H-pyrazol-1-yl)ethyl)carbamate

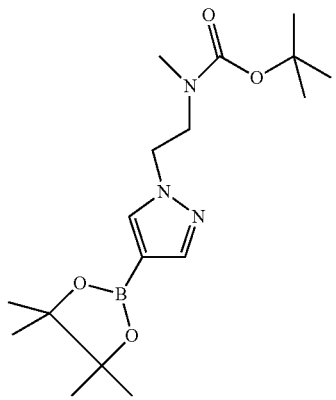 [SMILES: CN(CCn1cc(B2OC(C)(C)C(C)(C)O2)cn1)C(=O)OC(C)(C)C]

4-(4,4,5,5-tetramethyl-1,3,2-dioxaborolan-2-yl)-1H-pyrazole (3.964 g, 20.43 mmol), DIAD (4.42 mL, 22.47 mmol), triphenylphosphine (5.89 g, 22.47 mmol) and tert-butyl (2-hydroxyethyl)(methyl)carbamate (for a preparation see Intermediate 134, 3.58 g, 20.43 mmol) were dissolved in THF at 0° C. under nitrogen for 48 h. The reaction mixture was concentrated and the orange oil triturated with diethyl ether. The precipitated solid was removed by filtration and washed with more diethyl ether. The filtrate was concentrated to give 12.45 g of crude thick orange oil. This was purified by chromatography on silica (220 g cartridge, eluting with 0-100% ethyl acetate/cyclohexane over 13 CVs, collecting all fractions). Product fractions were combined to give the product (4.29 g, 12.21 mmol, 59.8%) as a yellow oil.

LCMS (2 min Formic): Rt=1.07 min, [MH]$^+$=352.

Intermediate 136: rac-tert-butyl (2-(4-((2S,3R,4R)-1-acetyl-4-(((benzyloxy)carbonyl)amino)-2-cyclopropyl-3-methyl-1,2,3,4-tetrahydroquinolin-6-yl)-1H-pyrazol-1-yl)ethyl)(methyl)carbamate

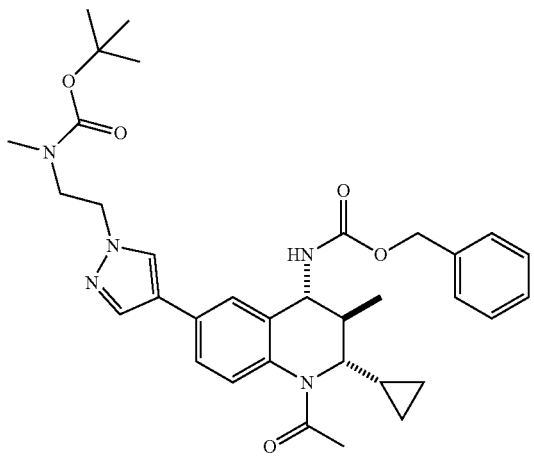 [SMILES: CC(=O)N1c2ccc(-c3cnn(CCN(C)C(=O)OC(C)(C)C)c3)cc2[C@H](NC(=O)OCc2ccccc2)[C@@H](C)[C@@H]1C1CC1]

rac-Benzyl ((2S,3R,4R)-1-acetyl-6-bromo-2-cyclopropyl-3-methyl-1,2,3,4-tetrahydroquinolin-4-yl)carbamate (for a preparation see Intermediate 13, 542 mg, 1.185 mmol), tert-butyl methyl(2-(4-(4,4,5,5-tetramethyl-1,3,2-dioxaborolan-2-yl)-1H-pyrazol-1-yl)ethyl)carbamate (for a preparation see Intermediate 135, 500 mg, 1.422 mmol), PdCl$_2$(dppf) (130 mg, 0.178 mmol) and potassium carbonate (491 mg, 3.56 mmol) in 1,4-dioxane (3 mL) and water (1 mL) was sealed in a microwave vial and heated in a microwave at 120° C. for 30 min. The reaction mixture was heated at 120° C. for a further 20 min. The reaction mixture was concentrated in vacuo and partitioned between DCM and water. The organic layer was separated and aqueous layer further extracted with DCM. The combined organic layers were dried (Na$_2$SO$_4$) and concentrated to give 1.23 g of crude brown residue. This was purified by chromatography on silica (50 g cartridge, eluting with 0-100% ethyl acetate/cyclohexane over 660 mL) to give the product (408 mg, 0.678 mmol, 57.2%) as a yellow oil.

LCMS (2 min Formic): Rt=1.16 min, [MH]$^+$=602.

Intermediate 137: rac-tert-butyl (2-(4-((2S,3R,4R)-1-acetyl-4-amino-2-cyclopropyl-3-methyl-1,2,3,4-tetrahydroquinolin-6-yl)-1H-pyrazol-1-yl)ethyl)(methyl)carbamate

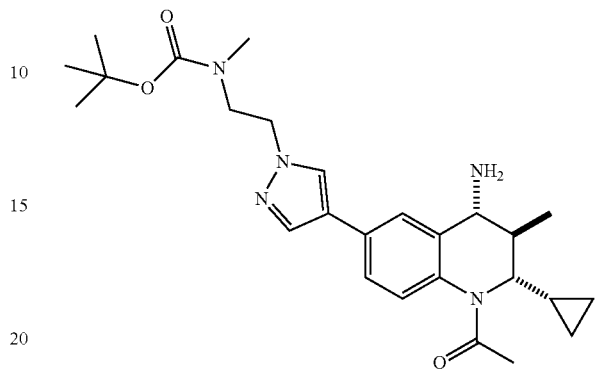

rac-tert-Butyl (2-(4-((2R,3S,4S)-1-acetyl-4-(((benzyloxy)carbonyl)amino)-2-cyclopropyl-3-methyl-1,2,3,4-tetrahydroquinolin-6-yl)-1H-pyrazol-1-yl)ethyl)(methyl)carbamate (for a preparation see Intermediate 136, 364 mg, 0.605 mmol) was suspended in ethanol (4 mL). Ethyl acetate (15 mL) was added although reaction mixture remained largely a suspension and ammonium formate (381 mg, 6.05 mmol) and 10% Pd/C (50 mg, 0.470 mmol) were added and the reaction mixture heated at reflux for 1 h 40 min. The reaction mixture was cooled to rt and filtered through a celite cartridge (2.5 g). The reaction mixture was concentrated and loaded onto a 5 g SCX cartridge equilibrated with MeOH. This was eluted with MeOH (50 mL) followed by 2M NH$_3$ in MeOH (50 mL). Ammonia fractions were combined and concentrated to give the product (209 mg, 0.447 mmol, 73.9%) as a brown oil. LCMS (2 min Formic): Rt=0.75 min, [MH]$^+$=568.

Intermediate 138: rac-tert-butyl (2-(4-((2S,3R,4R)-1-acetyl-4-((4-cyanophenyl)amino)-2-cyclopropyl-3-methyl-1,2,3,4-tetrahydroquinolin-6-yl)-1H-pyrazol-1-yl)ethyl)(methyl)carbamate

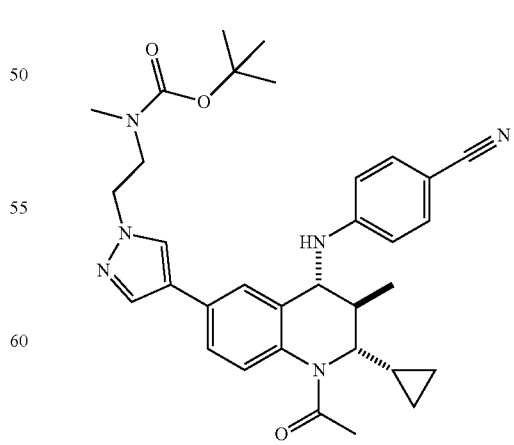

4-bromobenzonitrile (37.7 mg, 0.207 mmol), DavePhos (16.29 mg, 0.041 mmol), Pd$_2$(dba)$_3$ (18.96 mg, 0.021 mmol)

and sodium tert-butoxide (29.8 mg, 0.311 mmol) were added to a 0.5 mL-2 mL microwave vial. To this was added rac-tert-butyl (2-(4-((2S,3R,4R)-1-acetyl-4-amino-2-cyclopropyl-3-methyl-1,2,3,4-tetrahydroquinolin-6-yl)-1H-pyrazol-1-yl)ethyl)(methyl)carbamate (for a preparation see Intermediate 137, 48.4 mg, 0.104 mmol) in 1,4-dioxane (5 mL). The vessel was sealed and heated in a microwave heater to 120° C. for 40 min. The vessel was resealed and heated to 120° C. for a further 30 min. A further 0.2 eq of Pd$_2$(dba)$_3$ and 0.4 eq of DavePhos were added, the vessel resealed and the mixture heated at 120° C. for 30 min. The reaction mixture was filtered through a 2.5 g celite cartridge, washed through with ethyl acetate and concentrated in vacuo to afford a dark orange glass. The crude material was taken up in dichloromethane, loaded onto a 25 g silica flash column, and eluted in 0%-30% ethyl acetate in cyclohexane. The column was re-eluted with 5 CVs of 10% 2M NH$_3$ in dichloromethane. The eluent was collected and evaporated in vacuo. The samples were dissolved in 1:1 MeOH:DMSO 1 mL and purified by MDAP (Formic). The solvent was evaporated in vacuo to give the required product (11.6 mg).

LCMS (2 min Formic): Rt=1.12 min, [MH]$^+$=569.

Intermediate 139: rac-benzyl ((2S,3R,4R)-1-acetyl-2-cyclopropyl-6-(1-(2-methoxyethyl)-1H-pyrazol-4-yl)-3-methyl-1,2,3,4-tetrahydroquinolin-4-yl)carbamate

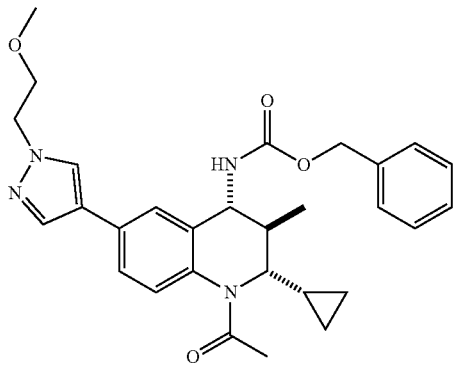 [SMILES: COCCn1cc(-c2ccc3c(c2)[C@H](NC(=O)OCc2ccccc2)[C@@H](C)[C@H](C2CC2)N3C(C)=O)cn1]

rac-Benzyl ((2S,3R,4R)-1-acetyl-6-bromo-2-cyclopropyl-3-methyl-1,2,3,4-tetrahydroquinolin-4-yl)carbamate (for a preparation see Intermediate 13, 500 mg, 1.093 mmol) was taken up in 1,4-dioxane (30 mL):water (10 mL) and treated with 1-(2-methoxyethyl)-4-(4,4,5,5-tetramethyl-1,3,2-dioxaborolan-2-yl)-1H-pyrazole (0.367 mL, 2.186 mmol), PdCl$_2$(dppf) (64.0 mg, 0.087 mmol) and potassium carbonate (332 mg, 2.405 mmol). The resulting orange solution was allowed to stir at 85° C. under N$_2$ for 2 h, The reaction was concentrated to remove dioxane and was partitioned between water and DCM, the aqueous layer was extracted with EtOAc, and the combined organics were washed with brine, dried using a hydrophobic frit and concentrated to a brown oil. This oil was purified using a 25 g silica column, elute 0-50% EtOAc:cyclohexane. Nothing eluted so the column was run again with 50-100% EtOAc:cyclohexane, one major peak was eluted, the appropriate fractions were summed and concentrated to give the product (335 mg) as a white solid.

LCMS (2 min formic): Rt=1.03 min, [MH]$^+$=503.

Intermediate 140: rac-1-((2S,3R,4R)-4-amino-2-cyclopropyl-6-(1-(2-methoxyethyl)-1H-pyrazol-4-yl)-3-methyl-3,4-dihydroquinolin-1(2H)-yl)ethanone

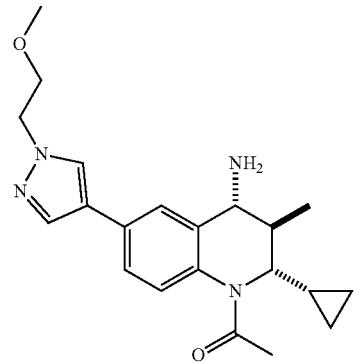 [SMILES: COCCn1cc(-c2ccc3c(c2)[C@H](N)[C@@H](C)[C@H](C2CC2)N3C(C)=O)cn1]

rac-Benzyl ((2S,3R,4R)-1-acetyl-2-cyclopropyl-6-(1-(2-methoxyethyl)-1H-pyrazol-4-yl)-3-methyl-1,2,3,4-tetrahydroquinolin-4-yl)carbamate (for a preparation see Intermediate 139, 335 mg, 0.667 mmol) was taken up in ethanol (10 mL) and the reaction was hydrogenated using the H-cube (settings: 25° C., 1 bar, 1 mL/min flow rate) and 10% Pd/C CatCart 30 as the catalyst, running through the H-Cube three times. The reaction was concentrated and dried to give the product (207 mg) as a colourless gum. LCMS (2 min formic): Rt=0.60 min, [M]$^+$=352 (loss of NH$_2^-$).

Intermediate 141: rac-benzyl ((2S,3S,4R)-6-fluoro-2,3-dimethyl-1,2,3,4-tetrahydroquinolin-4-yl)carbamate

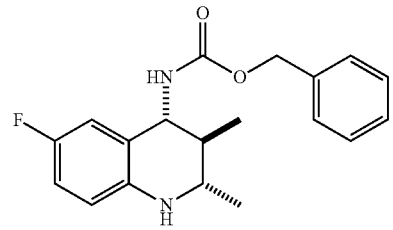 [SMILES: C[C@H]1[C@H](C)Nc2ccc(F)cc2[C@@H]1NC(=O)OCc1ccccc1]

A solution of 4-fluoroaniline (1.004 mL, 10.46 mmol) and acetaldehyde (0.588 mL, 10.46 mmol) in DCM (10 mL) was stirred under nitrogen at rt for 1 h. Diphenyl hydrogen phosphate (0.262 g, 1.046 mmol) and (E)-benzyl prop-1-en-1-ylcarbamate (for a preparation see Intermediate 1, 2 g, 10.46 mmol) were added and the reaction mixture was stirred under nitrogen at rt for 16 h. The reaction was diluted with DCM (10 mL), washed with water (2×20 mL) and dried through a hydrophobic frit. The crude material in DCM was applied to a 100 g silica snap cartridge and purified over a gradient of 0-40% cyclohexane/ethyl acetate over 12 CVs. The appropriate fractions were combined and concentrated in vacuo to give the title compound (1.4 g, 4.26 mmol, 41%).

LCMS (2 min Formic): Rt=1.09 min, [MH]$^+$=329.

Intermediate 142: rac-benzyl ((2S,3R,4R)-1-acetyl-6-fluoro-2,3-dimethyl-1,2,3,4-tetrahydroquinolin-4-yl)carbamate

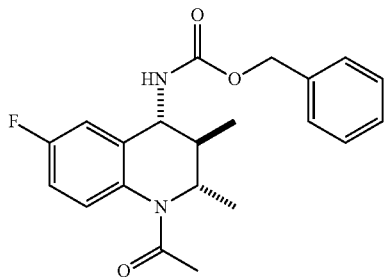 [SMILES: CC(=O)N1c2ccc(F)cc2[C@H](NC(=O)OCc2ccccc2)[C@@H](C)[C@@H]1C]

To a solution of rac-benzyl ((2S,3S,4R)-6-fluoro-2,3-dimethyl-1,2,3,4-tetrahydroquinolin-4-yl)carbamate (for a preparation see Intermediate 141, 1.4 g, 4.26 mmol) and pyridine (1.034 ml, 12.79 mmol) in DCM (20 mL) stirred under nitrogen at 0° C. was added acetyl chloride (0.455 ml, 6.40 mmol). The reaction mixture was stirred at 0° C. for 10 min then allowed to warm to rt and stirred for 1 h. The reaction mixture was washed with water (2×20 mL) and the organic layer was dried through a hydrophobic frit. The solvent was evaporated in vacuo to give the title compound (1.5 g, 4.05 mmol, 95%). LCMS (2 min Formic): Rt=1.04 min, [MH]$^+$=371.

Intermediate 143: rac-1-((2S,3R,4R)-4-amino-6-fluoro-2,3-dimethyl-3,4-dihydroquinolin-1(2H)-yl)ethanone

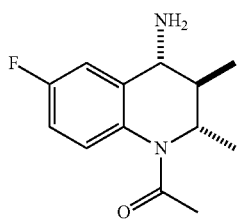 [SMILES: CC(=O)N1c2ccc(F)cc2[C@H](N)[C@@H](C)[C@@H]1C]

rac-Benzyl ((2S,3R,4R)-1-acetyl-6-fluoro-2,3-dimethyl-1,2,3,4-tetrahydroquinolin-4-yl)carbamate (for a preparation see Intermediate 142, 1.5 g, 4.05 mmol) in ethanol (40 mL) was hydrogenated using the H-cube (settings: rt, full H$_2$ mode, 1 mL/min flow rate) and 10% Pd/C as a catalyst. The solvent was evaporated in vacuo to give the title compound (950 mg, 4.02 mmol, 99%).
LCMS (2 min Formic): Rt=0.41 min, [MH]$^+$=237.

Intermediate 144: rac-benzyl ((2S,3R,4R)-1-acetyl-2-cyclopropyl-6-fluoro-3-methyl-1,2,3,4-tetrahydroquinolin-4-yl)carbamate

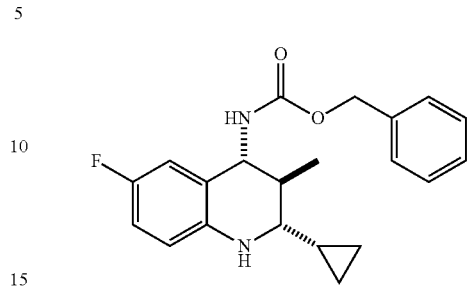

To a solution of cyclopropanecarbaldehyde (0.222 mL, 2.97 mmol) in dichloromethane (DCM) (6 mL) was added 4-fluoroaniline (0.256 mL, 2.70 mmol). The reaction mixture was stirred at rt under nitrogen for 30 min before a solution of diphenyl hydrogen phosphate (67.5 mg, 0.270 mmol) in dichloromethane (DCM) (2 mL) was added and the mixture cooled to 0° C. (ice bath). A solution of (E)-benzyl prop-1-en-1-ylcarbamate (for a preparation see Intermediate 1, 516 mg, 2.70 mmol) in dichloromethane (DCM) (2 mL) was added to the mixture. The reaction mixture was stirred at 0° C. under nitrogen and was allowed to warm to rt during the subsequent 17 h. The mixture was loaded directly onto a 50 g silica gel cartridge which was eluted with a gradient of 0-30% ethyl acetate in cyclohexane. The required fractions were combined and the solvent evaporated in vacuo to give the desired product (610 mg, 1.721 mmol, 63.7%).
LCMS (2 min Formic): Rt=1.20 min, [MH]$^+$=355.

Intermediate 145: rac-benzyl ((2S,3R,4R)-1-acetyl-2-cyclopropyl-6-fluoro-3-methyl-1,2,3,4-tetrahydroquinolin-4-yl)carbamate

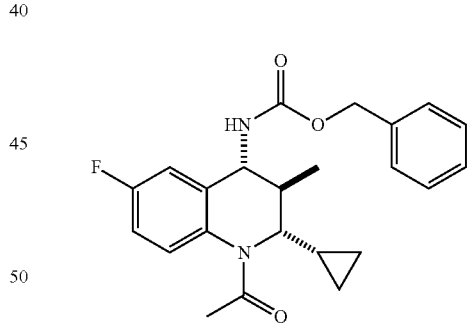

A solution of rac-benzyl ((2S,3S,4R)-2-cyclopropyl-6-fluoro-3-methyl-1,2,3,4-tetrahydroquinolin-4-yl)carbamate (for a preparation see Intermediate 145, 1.173 g, 3.31 mmol) and pyridine (0.803 mL, 9.93 mmol) in Anydrous Dichloromethane (DCM) (20 mL) was treated with acetyl chloride (0.282 mL, 3.97 mmol). The mixture was stirred at rt under an atmosphere of nitrogen overnight. The reaction mixture was transferred to a separating funnel, diluted with DCM (30 mL) and washed with 1M aq. HCl (50 mL) followed by sat. aq. NaHCO$_3$ (50 mL) and brine (50 mL). The organic layer was dried through a hydrophobic frit and the solvent was removed by rotary evaporation to give the product as a solid (1.29 g). This was pure enough to use in subsequent steps.
LCMS (2 min Formic): Rt=1.11 min, [MH]$^+$=397.

Intermediate 146: rac-1-((2S,3R,4R)-4-amino-2-cyclopropyl-6-fluoro-3-methyl-3,4-dihydroquinolin-1(2H)-yl)ethanone

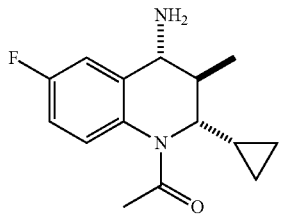 [SMILES: CC(=O)N1c2ccc(F)cc2[C@H](N)[C@@H](C)[C@@H]1C1CC1]

A solution of rac-benzyl ((2S,3R,4R)-1-acetyl-2-cyclopropyl-6-fluoro-3-methyl-1,2,3,4-tetrahydroquinolin-4-yl)carbamate (for a preparation see intermediate 146, 1.29 g, 3.25 mmol) in ethanol (30 mL) was passed through a Thales H-cube flow hydrogenator with a fitted with a 10% Pd/C CatCart at a rate of 1 mL/min in full $H_2$ mode. After 1 pass the reaction was incomplete so the solution was passed through the reactor a second time. The solvent was removed under reduced pressure to leave the product as a pale yellow solid (955 mg).

LCMS (2 min Formic): Rt=0.50 min, $[M]^+$=246 (loss of $NH_2^-$).

Intermediate 147: rac-tert-butyl ((2S,3S,4R)-6-bromo-2,3-dimethyl-1,2,3,4-tetrahydroquinolin-4-yl)carbamate

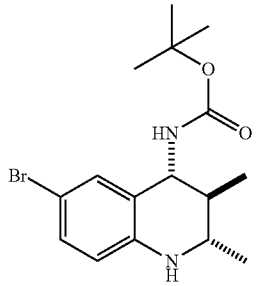 [SMILES: C[C@H]1[C@H](C)Nc2ccc(Br)cc2[C@@H]1NC(=O)OC(C)(C)C]

Under nitrogen, 4-bromoaniline (2 g, 11.63 mmol) and acetaldehyde (0.975 mL, 17.44 mmol) were dissolved in DCM (40 mL) and stirred at rt for 1 h. The reaction was then cooled to 0° C. and diphenyl hydrogen phosphate (0.291 g, 1.163 mmol) in DCM (5 mL) and (E)-tert-butyl prop-1-en-1-ylcarbamate (for a preparation see Intermediate 74, 2.193 g, 13.95 mmol) in DCM (5 mL) were sequentially added. The reaction was stirred and allowed to warm to rt overnight. The solvent was removed under reduced pressure to leave the crude. The crude material was loaded onto a 100 g silica column and eluted using a graduating solvent system of 0-20% EtOAc/cyclohexane. Combination and evaporation of the desired fractions gave the product as a yellow solid (1.32 g). Slightly less pure fractions were also combined and evaporated to give a second batch as a yellow solid (322 mg). LCMS (2 min Formic): Rt=1.23 min, $[MH]^+$=355, 357.

Intermediate 148: rac-tert-butyl ((2S,3R,4R)-1-acetyl-6-bromo-2,3-dimethyl-1,2,3,4-tetrahydroquinolin-4-yl)carbamate

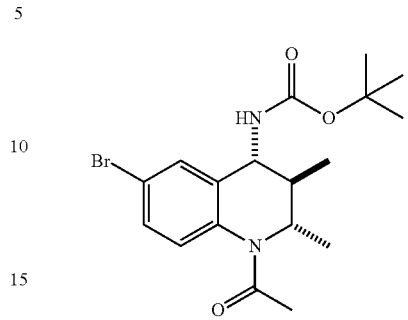

rac-tert-Butyl ((2S,3S,4R)-6-bromo-2,3-dimethyl-1,2,3,4-tetrahydroquinolin-4-yl)carbamate (for a preparation see Intermediate 148, 1.642 g, 4.62 mmol) was taken up in dichloromethane (DCM) (40 mL) and treated with DIPEA (1.695 mL, 9.71 mmol) and acetyl chloride (0.657 mL, 9.24 mmol) and allowed to stir at rt for 2 h. The reaction was concentrated to a gum, taken up in DCM and added to a silica cartridge (100 g) and purified using flash chromatography, eluting with 0-40% EtOAc/cyclohexane, one major peak was eluted, the appropriate fractions were collected and concentrated in vacuo to afford the desired product as a yellow solid (1.05 g, 2.64 mmol, 57.2%).

LCMS (2 min Formic): Rt=1.13 min, $[MH]^+$=397.

Intermediate 149: rac-tert-butyl ((2S,3R,4R)-1-acetyl-6-(3,6-dihydro-2H-pyran-4-yl)-2,3-dimethyl-1,2,3,4-tetrahydroquinolin-4-yl)carbamate

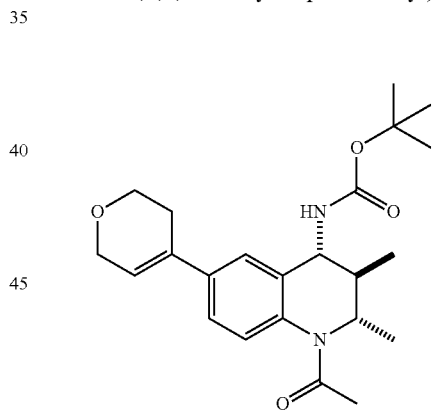

2-(3,6-dihydro-2H-pyran-4-yl)-4,4,5,5-tetramethyl-1,3,2-dioxaborolane (317 mg, 1.510 mmol), rac-tert-butyl ((2S,3R,4R)-1-acetyl-6-bromo-2,3-dimethyl-1,2,3,4-tetrahydroquinolin-4-yl)carbamate (for a preparation see Intermediate 149, 400 mg, 1.01 mmol) and cesium carbonate (984 mg, 3.02 mmol) were suspended in 1,4-dioxane (20 mL) and water (2 mL). The reaction mixture was treated with $Pd(PPh_3)_4$ (116 mg, 0.101 mmol) then stirred at 80° C. for 3 h. The reaction mixture was partitioned between water and EtOAc, the aqueous layer further extracted with EtOAc and the combined organic layer were washed with brine, dried over $Na_2SO_4$ then concentrated in vacuo to a dark oil. The dark oil was purified by silica chromatography, eluting with a 0 to 80% EtOAc/cyclohexane solvent gradient to give the desired product as a yellow foam (416 mg).

LCMS (2 min Formic): Rt=1.02 min, $[MH]^+$=401.

Intermediate 150: rac-1-((2S,3R,4R)-4-amino-6-(3,6-dihydro-2H-pyran-4-yl)-2,3-dimethyl-3,4-dihydroquinolin-1(2H)-yl)ethanone

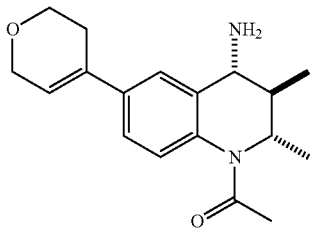 [SMILES: CC(=O)N1c2ccc(C3=CCOCC3)cc2[C@H](N)[C@@H](C)[C@@H]1C]

A solution of rac-tert-butyl ((2S,3R,4R)-1-acetyl-6-(3,6-dihydro-2H-pyran-4-yl)-2,3-dimethyl-1,2,3,4-tetrahydroquinolin-4-yl)carbamate (for a preparation see Intermediate 150, 416 mg, 1.039 mmol) in DCM (10 mL) was treated with TFA (5 mL, 64.9 mmol) and the mixture allowed to stand overnight then concentrated under reduced pressure. The resulting brown residue was dissolved in methanol then passed through a 10 g amino-propyl SPE column which was washed through with further methanol. The combined methanol washes was concentrated under reduced pressure to give the desired product as a pale yellow gum (303 mg, 97%).

LCMS (2 min Formic): Rt=0.55 min, [M]$^+$=284 (loss of NH$_2^-$).

Intermediate 151: rac-benzyl ((2S,3R,4R)-1-acetyl-6-(3,6-dihydro-2H-pyran-4-yl)-2,3-dimethyl-1,2,3,4-tetrahydroquinolin-4-yl)carbamate

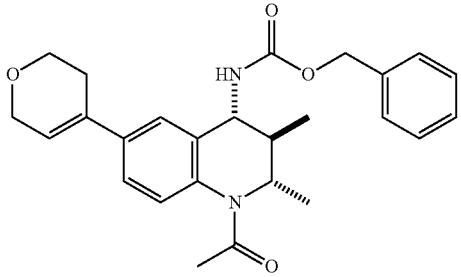 [SMILES: CC(=O)N1c2ccc(C3=CCOCC3)cc2[C@H](NC(=O)OCc2ccccc2)[C@@H](C)[C@@H]1C]

rac-Benzyl ((2S,3R,4R)-1-acetyl-6-bromo-2,3-dimethyl-1,2,3,4-tetrahydroquinolin-4-yl)carbamate (for a preparation see Intermediate 3, 0.55 g, 1.275 mmol), 2-(3,6-dihydro-2H-pyran-4-yl)-4,4,5,5-tetramethyl-1,3,2-dioxaborolane (0.402 g, 1.913 mmol) and cesium carbonate (1.246 g, 3.83 mmol) were stirred in 1,4-Dioxane (15 mL) and Water (1.5 mL) and treated with palladium tetrakis (0.147 g, 0.128 mmol). The reaction was heated under reflux. The reaction was allowed to cool to rt and was partitioned between EtOAc (50 mL) and water (50 mL), the organic layer was washed with brine (50 mL), dried using a hydrophobic frit and concentrated to give the crude product. Purification was undertaken by flash column chromatography. The crude material was loaded onto a 50 g silica column and eluted using a graduating solvent system of 0-50% ethyl acetate in cyclohexane. The desired fractions were combined and concentrated in vacuo to leave the product as a pale yellow solid (450 mg). LCMS (2 min HpH): Rt=1.04 min, [MH]$^+$=435.

Intermediate 152: rac-1-((2S,3R,4R)-4-amino-2,3-dimethyl-6-(tetrahydro-2H-pyran-4-yl)-3,4-dihydroquinolin-1(2H)-yl)ethanone

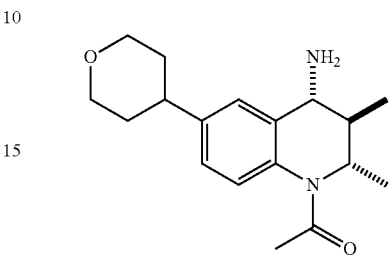

A solution of rac-benzyl ((2S,3R,4R)-1-acetyl-6-(3,6-dihydro-2H-pyran-4-yl)-2,3-dimethyl-1,2,3,4-tetrahydroquinolin-4-yl)carbamate (for a preparation see Intermediate 152, 450 mg, 1.036 mmol) in ethanol (10 mL) was passed through a Thales H-cube flow hydrogenator fitted with a 10% Pd/C CatCart at a rate of 1 mL/min in full H$_2$ mode. The reaction mixture was passed through the reactor twice. Then the solvent was removed under reduced pressure to leave the product as a white solid (225 mg). LCMS (2 min Formic): Rt=0.52 min, [M]$^+$=286 (loss of NH$_2^-$).

Intermediate 153: rac-benzyl ((2S,3R,4R)-1-acetyl-6-(3,6-dihydro-2H-pyran-4-yl)-2-ethyl-3-methyl-1,2,3,4-tetrahydroquinolin-4-yl)carbamate

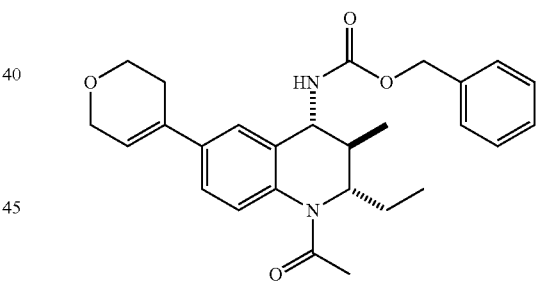

2-(3,6-Dihydro-2H-pyran-4-yl)-4,4,5,5-tetramethyl-1,3,2-dioxaborolane (163 mg, 0.778 mmol), rac-benzyl ((2S,3R,4R)-1-acetyl-6-bromo-2-ethyl-3-methyl-1,2,3,4-tetrahydroquinolin-4-yl)carbamate (for a preparation see Intermediate 9, 231 mg, 0.519 mmol), cesium carbonate (507 mg, 1.556 mmol) were suspended in 1,4-dioxane (10 mL) and water (1 mL) and were treated with Pd(PPh$_3$)$_4$(30.0 mg, 0.026 mmol). The reaction was allowed to stir at 80° C. under N$_2$ for 16 h. The reaction solution was partitioned between ethyl acetate (35 mL) and water (35 mL) and the layers separated, the aqueous layer was washed with ethyl acetate (35 mL) and the organic layers combined. The combined organics were washed with brine (30 mL) and passed through a hydrophobic frit before being concentrated in vacuo to give 388 mg of crude yellow oil. This was purified by chromatography on silica (25 g, eluting with 0-55% ethyl acetate/cyclohexane). The fractions containing product were combined and concentrated in vacuo to give the product (172

Intermediate 154: rac-1-((2S,3R,4R)-4-amino-2-ethyl-3-methyl-6-(tetrahydro-2H-pyran-4-yl)-3,4-dihydroquinolin-1(2H)-yl)ethanone

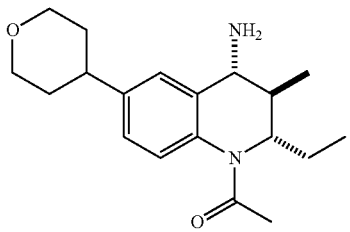 [SMILES: CC[C@H]1[C@H](C)[C@@H](N)c2cc(C3CCOCC3)ccc2N1C(C)=O]

rac-Benzyl ((2S,3R,4R)-1-acetyl-6-(3,6-dihydro-2H-pyran-4-yl)-2-ethyl-3-methyl-1,2,3,4-tetrahydroquinolin-4-yl)carbamate (for a preparation see Intermediate 154, 170 mg, 0.379 mmol) was taken up in ethanol (10 mL). The solution was hydrogenated using the H-cube (settings: rt, 1 bar, 1 mL/min flow rate) and 10% Pd/C CatCart as the catalyst. The solution was left to cycle through the H-cube on the same settings for 40 min. After a further 1.5 h the reaction mixture was concentrated in vacuo to give 143 mg of crude product as a yellow solid. The sample was loaded in methanol and purified by SPE on sulphonic acid (SCX) 2 g using a sequential solvents methanol, 2M ammonia/methanol. The appropriate fractions were combined and evaporated in vacuo to give 113 mg of an off white solid. This was purified by chromatography on silica (10 g, eluting with 0-5% methanolic ammonia/DCM). The fractions containing product were combined and concentrated in vacuo to give the product (114 mg, 0.360 mmol, 95%) as a white solid.

LCMS (2 min Formic): Rt=0.58 min, [MH]$^+$=300 (loss of NH$_2^-$).

Intermediate 155: rac-tert-butyl 4-((2S,3R,4R)-1-acetyl-4-(((benzyloxy)carbonyl)amino)-2,3-dimethyl-1,2,3,4-tetrahydroquinolin-6-yl)-5,6-dihydropyridine-1(2H)-carboxylate

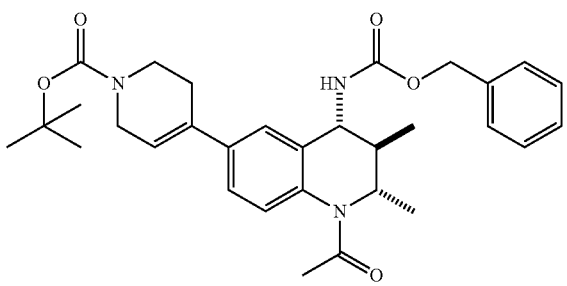 [SMILES: CC(=O)N1c2ccc(C3=CCN(C(=O)OC(C)(C)C)CC3)cc2[C@H](NC(=O)OCc2ccccc2)[C@@H](C)[C@@H]1C]

A solution of rac-benzyl ((2S,3R,4R)-1-acetyl-6-bromo-2,3-dimethyl-1,2,3,4-tetrahydroquinolin-4-yl)carbamate (for a preparation see intermediate 3, 1 g, 2.318 mmol), tert-butyl 4-(4,4,5,5-tetramethyl-1,3,2-dioxaborolan-2-yl)-5,6-dihydropyridine-1(2H)-carboxylate (1.075 g, 3.48 mmol), cesium carbonate (2.266 g, 6.96 mmol) and Pd(PPh$_3$)$_4$ (0.268 g, 0.232 mmol) in 1,4-dioxane (30 mL) and water (3 mL) was stirred under nitrogen at 100° C. for 1 h.

The reaction mixture was concentrated in vacuo and redissolved in DCM (20 mL) which was washed with water (2×20 mL). The organic layer was dried through a hydrophobic frit and applied to a 100 g silica column and purified over a gradient of 0-40% ethyl acetate/cyclohexane over 12 CVs. The appropriate fractions were combined and concentrated in vacuo to give the title compound (1.12 g, 2.10 mmol, 91%).

LCMS (2 min Formic): Rt=1.24 min, [MH]$^+$=534.

Intermediate 156: rac-tert-butyl 4-((2S,3R,4R)-1-acetyl-4-amino-2,3-dimethyl-1,2,3,4-tetrahydroquinolin-6-yl)piperidine-1-carboxylate

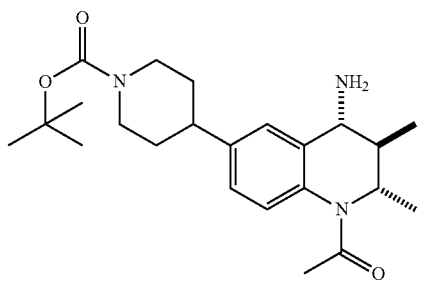 [SMILES: CC(=O)N1c2ccc(C3CCN(C(=O)OC(C)(C)C)CC3)cc2[C@H](N)[C@@H](C)[C@@H]1C]

rac-tert-Butyl 4-((2S,3R,4R)-1-acetyl-4-(((benzyloxy)carbonyl)amino)-2,3-dimethyl-1,2,3,4-tetrahydroquinolin-6-yl)-5,6-dihydropyridine-1(2H)-carboxylate (for a preparation see Intermediate 156, 1.1245 g, 2.107 mmol) in ethanol (40 mL) was hydrogenated using the H-cube (settings: rt, full H$_2$ mode, 1 mL/min flow rate) and 10% Pd/C as a catalyst. The reaction mixture was concentrated in vacuo and dissolved in ethanol (10 mL) and 10% Pd/C (1.1245 g, 10.57 mmol) was added. The reaction was left to stir under an H$_2$ atmosphere for 16 h then filtered through celite, washed with ethyl acetate and concentrated in vacuo to give the title compound (700 mg, 1.743 mmol, 83%).

LCMS (2 min Formic): Rt=0.79 min, [MH]$^+$=402.

Intermediate 157: rac-tert-butyl 4-((2S,3R,4R)-1-acetyl-2,3-dimethyl-4-((5-methylpyrazin-2-yl)amino)-1,2,3,4-tetrahydroquinolin-6-yl)piperidine-1-carboxylate

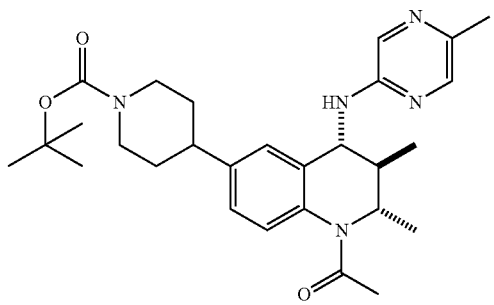 [SMILES: CC(=O)N1c2ccc(C3CCN(C(=O)OC(C)(C)C)CC3)cc2[C@H](Nc2cnc(C)cn2)[C@@H](C)[C@@H]1C]

A solution of rac-tert-butyl 4-((2S,3R,4R)-1-acetyl-4-amino-2,3-dimethyl-1,2,3,4-tetrahydroquinolin-6-yl)piperidine-1-carboxylate (for a preparation see Intermediate 157, 60 mg, 0.149 mmol), DavePhos (5.88 mg, 0.015 mmol), 2-bromo-5-methylpyrazine (25.9 mg, 0.149 mmol), Pd$_2$ (dba)₃ (6.84 mg, 7.47 µmol) and sodium tert-butoxide (28.7 mg, 0.299 mmol) in 1,4-Dioxane (3 mL) was stirred under nitrogen at 90° C. for 5 h. The reaction mixture was allowed to cool to room temp, filtered through celite and rinsed with ethyl acetate. The solvent was evaporated in vacuo and dissolved in 1:1 MeOH:DMSO (2×1 mL) and purified by MDAP (Formic). The appropriate fractions were combined and concentrated in vacuo to give the title compound (23 mg, 0.047 mmol, 31%).

LCMS (2 min Formic): Rt=1.10 min, [MH]⁺=494.

Intermediate 158: rac-tert-butyl 4-((2S,3R,4R)-1-acetyl-4-((5-fluoropyridin-2-yl)amino)-2,3-dimethyl-1,2,3,4-tetrahydroquinolin-6-yl)piperidine-1-carboxylate

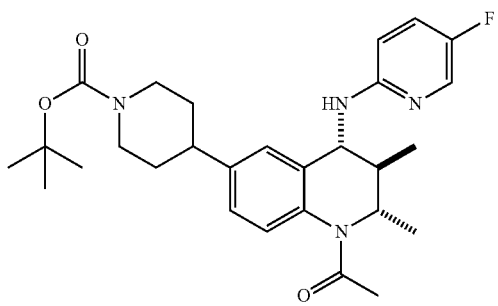 [SMILES: CC(=O)N1c2ccc(C3CCN(C(=O)OC(C)(C)C)CC3)cc2[C@H](Nc2ccc(F)cn2)[C@@H](C)[C@@H]1C]

A solution of rac-tert-butyl 4-((2S,3R,4R)-1-acetyl-4-amino-2,3-dimethyl-1,2,3,4-tetrahydroquinolin-6-yl)piperidine-1-carboxylate (for a preparation see Intermediate 157, 100 mg, 0.249 mmol), DavePhos (9.80 mg, 0.025 mmol), 2-bromo-5-fluoropyridine (43.8 mg, 0.249 mmol), Pd₂(dba)₃ (11.40 mg, 0.012 mmol) and sodium tert-butoxide (47.9 mg, 0.498 mmol) in 1,4-dioxane (3 mL) was stirred under nitrogen at 90° C. for 5 h. The reaction mixture was allowed to cool to rt, filtered through celite and rinsed with ethyl acetate. The solvent was evaporated in vacuo and the samples were dissolved in 1:1 MeOH:DMSO (1 mL) and purified by MDAP (HpH). The appropriate fractions were combined and concentrated in vacuo to give the title compound (67 mg, 0.135 mmol, 54.2%).

LCMS (2 min Formic): Rt=1.16 min, [MH]⁺=497.

Intermediate 159: rac-tert-butyl 4-((2S,3R,4R)-1-acetyl-2,3-dimethyl-4-(((6-methylpyridin-2-yl)amino)-1,2,3,4-tetrahydroquinolin-6-yl)piperidine-1-carboxylate

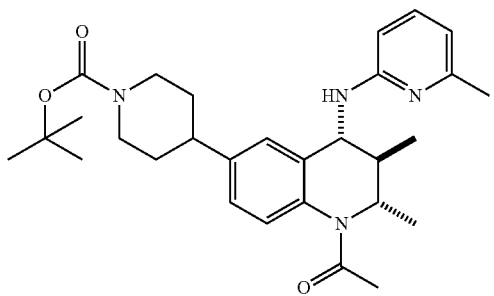 [SMILES: CC(=O)N1c2ccc(C3CCN(C(=O)OC(C)(C)C)CC3)cc2[C@H](Nc2cccc(C)n2)[C@@H](C)[C@@H]1C]

A solution of rac-tert-butyl 4-((2S,3R,4R)-1-acetyl-4-amino-2,3-dimethyl-1,2,3,4-tetrahydroquinolin-6-yl)piperidine-1-carboxylate (for a preparation see Intermediate 157, 100 mg, 0.249 mmol), DavePhos (9.80 mg, 0.025 mmol), 2-bromo-6-methylpyridine (42.8 mg, 0.249 mmol), Pd₂(dba)₃ (11.40 mg, 0.012 mmol) and sodium tert-butoxide (47.9 mg, 0.498 mmol) in 1,4-dioxane (3 mL) was stirred under nitrogen at 90° C. for 5 h. The reaction mixture was allowed to cool to rt, filtered through celite and rinsed with ethyl acetate. The solvent was evaporated in vacuo and dissolved in 1:1 MeOH:DMSO (2×1 mL) and purified by MDAP (Formic). The appropriate fractions were combined and concentrated in vacuo to give the title compound (55 mg, 0.112 mmol, 45%).

LCMS (2 min Formic): Rt=0.95 min, [MH]⁺=493.

Intermediate 160: rac-tert-butyl 4-((2S,3R,4R)-1-acetyl-4-((4-cyanophenyl)amino)-2,3-dimethyl-1,2,3,4-tetrahydroquinolin-6-yl)piperidine-1-carboxylate

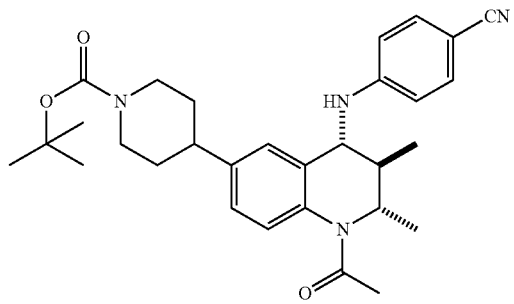 [SMILES: CC(=O)N1c2ccc(C3CCN(C(=O)OC(C)(C)C)CC3)cc2[C@H](Nc2ccc(C#N)cc2)[C@@H](C)[C@@H]1C]

A solution of rac-tert-butyl 4-((2S,3R,4R)-1-acetyl-4-amino-2,3-dimethyl-1,2,3,4-tetrahydroquinolin-6-yl)piperidine-1-carboxylate (for a preparation see Intermediate 157, 50 mg, 0.125 mmol), DavePhos (4.90 mg, 0.012 mmol), 4-bromobenzonitrile (27.2 mg, 0.149 mmol), Pd₂(dba)₃ (5.70 mg, 6.23 µmol) and sodium tert-butoxide (23.93 mg, 0.249 mmol) in 1,4-dioxane (3 mL) was stirred under nitrogen at 90° C. for 5 h. The reaction mixture was allowed to cool to rt, filtered through celite and rinsed with ethyl acetate. The solvent was evaporated in vacuo then dissolved in 1:1 MeOH:DMSO (2×1 mL) and purified by MDAP (Formic). The appropriate fractions were combined and concentrated in vacuo to give the product (20 mg, 0.040 mmol, 32.0%). LCMS (2 min Formic): Rt=1.21 min, [MH]⁺=503.

Intermediate 161: rac-tert-butyl 4-((2S,3R,4R)-1-acetyl-4-((5-cyanopyridin-2-yl)amino)-2,3-dimethyl-1,2,3,4-tetrahydroquinolin-6-yl)piperidine-1-carboxylate

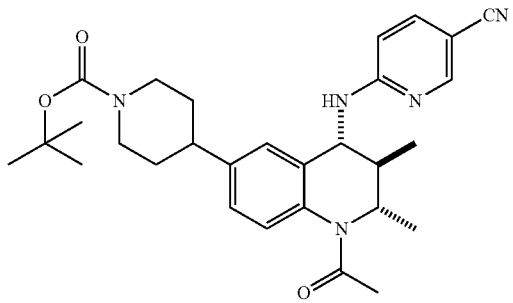 [SMILES: CC(=O)N1c2ccc(C3CCN(C(=O)OC(C)(C)C)CC3)cc2[C@H](Nc2ccc(C#N)cn2)[C@@H](C)[C@@H]1C]

A solution of rac-tert-butyl 4-((2S,3R,4R)-1-acetyl-4-amino-2,3-dimethyl-1,2,3,4-tetrahydroquinolin-6-yl)piperidine-1-carboxylate (for a preparation see Intermediate 157, 65 mg, 0.162 mmol), 6-fluoronicotinonitrile (39.5 mg, 0.324 mmol), and DIPEA (0.057 mL, 0.324 mmol) in N-methyl-2-pyrrolidone (NMP) (1.5 mL) was heated in a microwave at 200° C. for 30 min. The reaction mixture was purified directly by MDAP (Formic). The appropriate fractions were combined and concentrated in vacuo to give the product (21 mg, 0.042 mmol, 25.8% yield).
LCMS (2 min Formic): Rt=1.15 min, [MH]$^+$=504.

Intermediate 162: rac-tert-butyl 4-((2S,3R,4R)-1-acetyl-2,3-dimethyl-4-((4-(methylcarbamoyl)phenyl)amino)-1,2,3,4-tetrahydroquinolin-6-yl)piperidine-1-carboxylate

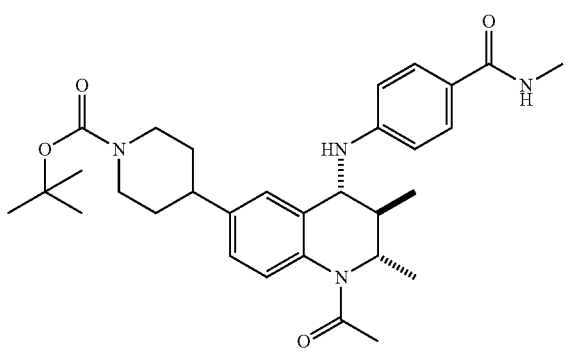 [SMILES: CNC(=O)c1ccc(N[C@H]2c3cc(C4CCN(C(=O)OC(C)(C)C)CC4)ccc3N(C(C)=O)[C@@H](C)[C@@H]2C)cc1]

A solution of rac-tert-butyl 4-((2S,3R,4R)-1-acetyl-4-amino-2,3-dimethyl-1,2,3,4-tetrahydroquinolin-6-yl)piperidine-1-carboxylate (for a preparation see Intermediate 157, 55 mg, 0.137 mmol), DavePhos (5.39 mg, 0.014 mmol), 4-bromo-N-methylbenzamide (35.2 mg, 0.164 mmol), Pd$_2$(dba)$_3$ (6.27 mg, 6.85 µmol) and sodium tert-butoxide (26.3 mg, 0.274 mmol) in 1,4-dioxane (2 mL) was stirred under nitrogen at 90° C. for 5 h. The reaction mixture was allowed to cool to rt, filtered through celite and rinsed with ethyl acetate. The solvent was evaporated in vacuo and the sample was dissolved in 1:1 MeOH:DMSO (2×1 mL) and purified by MDAP (Formic). The appropriate fractions were combined and concentrated in vacuo to give the product (15 mg, 0.028 mmol, 20.48%).
LCMS (2 min Formic): Rt=1.06 min, [MH]$^+$=535.

Intermediate 163: rac-tert-butyl 4-((2S,3R,4R)-1-acetyl-2-cyclopropyl-4-((6-methoxypyridin-2-yl)amino)-3-methyl-1,2,3,4-tetrahydroquinolin-6-yl)-5,6-dihydropyridine-1(2H)-carboxylate

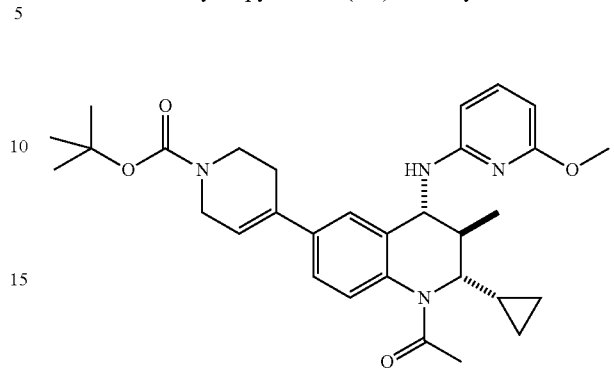

To a dried flask under nitrogen was added tert-butyl 4-((2S,3R,4R)-1-acetyl-4-amino-2-cyclopropyl-3-methyl-1,2,3,4-tetrahydroquinolin-6-yl)-5,6-dihydropyridine-1(2H)-carboxylate (for a preparation see Intermediate 81, 250 mg, 0.587 mmol), 2-bromo-6-methoxypyridine (0.087 mL, 0.705 mmol), DavePhos (88 mg, 0.223 mmol), Pd$_2$(dba)$_3$ (102 mg, 0.112 mmol) and sodium tert-butoxide (169 mg, 1.762 mmol). To this was added 1,4-dioxane (5 mL) and the solution was degassed with nitrogen for ~5 min. The mixture was then heated for 2 h at 90° C. under nitrogen. The mixture was allowed to cool to rt, filtered through a 2.5 g celite cartridge, washed through with ethyl acetate and concentrated in vacuo to afford a dark orange oil. The crude product was taken up in DCM and purified on a 25 g silica cartridge by flash chromatography eluting with 0-50% EtOAc/cyclohexane. The appropriate fractions were collected and concentrated in vacuo to afford the desired product as an off-white foam (202 mg, 0.379 mmol, 64.6%). LCMS (2 min Formic): Rt=1.33 min, [MH]$^+$=533.

Intermediate 164: rac-tert-butyl 4-((2S,3R,4R)-1-acetyl-4-((4-cyanophenyl)amino)-2-cyclopropyl-3-methyl-1,2,3,4-tetrahydroquinolin-6-yl)-5,6-dihydropyridine-1(2H)-carboxylate

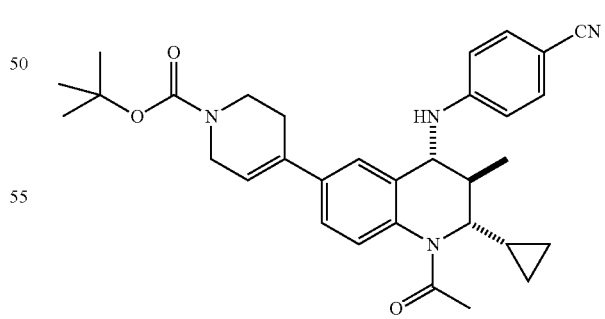

To a dried flask under nitrogen was added rac-tert-butyl 4-((2S,3R,4R)-1-acetyl-4-amino-2-cyclopropyl-3-methyl-1,2,3,4-tetrahydroquinolin-6-yl)-5,6-dihydropyridine-1(2H)-carboxylate (for a preparation see Intermediate 81, 200 mg, 0.470 mmol), 4-bromobenzonitrile (103 mg, 0.564 mmol), DavePhos (74.0 mg, 0.188 mmol), Pd$_2$(dba)$_3$ (86 mg, 0.094 mmol) and sodium tert-butoxide (135 mg, 1.410 mmol). To this was added 1,4-dioxane (4 mL), and the solution was degassed with nitrogen for ~5 min. The mixture was then heated for 2 h at 90° C. under nitrogen. Heating was continued overnight. The reaction mixture was allowed to cool to rt, filtered through a 2.5 g celite cartridge, washed through with ethyl acetate and concentrated in vacuo to afford a dark brown oil. The crude product was taken up in DCM and purified on a 25 g silica cartridge by flash chromatography eluting with 0-50% EtOAc/cyclohexane. The appropriate fractions (which contained some minor impurities) were collected and concentrated in vacuo to afford the desired product as an off-white foam (93.2 mg, 0.177 mmol, 37.7%). LCMS (2 min Formic): Rt=1.27 min, [MH]⁺=527.

Intermediate 165: rac-tert-butyl 4-((2S,3R,4R)-1-acetyl-2-cyclopropyl-3-methyl-4-((4-(methylcarbamyl))phenyl)amino)-1,2,3,4-tetrahydroquinolin-6-yl)-5,6-dihydropyridine-1(2H)-carboxylate

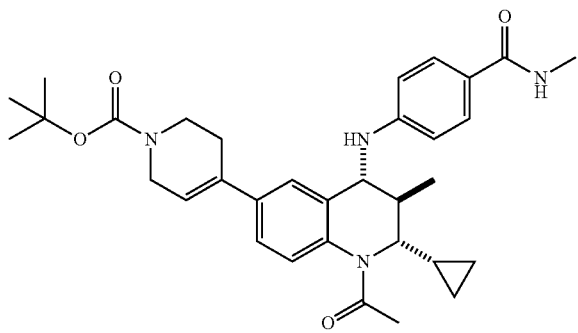 [SMILES: CNC(=O)c1ccc(N[C@H]2c3cc(C4=CCN(C(=O)OC(C)(C)C)CC4)ccc3N(C(C)=O)[C@@H](C3CC3)[C@@H]2C)cc1]

In a test tube rac-tert-butyl 4-((2S,3R,4R)-1-acetyl-4-amino-2-cyclopropyl-3-methyl-1,2,3,4-tetrahydroquinolin-6-yl)-5,6-dihydropyridine-1(2H)-carboxylate (for a preparation see Intermediate 81, 200 mg, 0.470 mmol), 4-bromo-N-methylbenzamide (121 mg, 0.564 mmol), sodium tert-butoxide (90 mg, 0.940 mmol), Pd₂(dba)₃ (21.52 mg, 0.023 mmol) and DavePhos (18.50 mg, 0.047 mmol) were dissolved in 1,4-dioxane (4 mL). The solution was stirred and heated at 100° C. for 2 h. The reaction mixture was allowed to cool and was then filtered through celite washing through with extra dioxane. The filtrate was concentrated in vacuo to leave the crude. Purification was undertaken by flash column chromatography. The crude material was loaded onto a 25 g silica column and eluted using a graduating solvent system of 0-5% 2M methanolic ammonia in dichloromethane. Combination and evaporation of the desired fractions gave the product as a yellow foam (110 mg). Less pure fractions were also pooled and concentrated to give product. This was purified using MDAP (Formic). Evaporation of the desired fractions gave the product as a white solid (10 mg).

LCMS (2 min Formic): Rt=1.13 min, [MH]⁺=559.

Intermediate 166: rac-tert-butyl 4-((2S,3R,4R)-1-acetyl-2-cyclopropyl-3-methyl-4-((4-methylpyrimidin-2-yl)amino)-1,2,3,4-tetrahydroquinolin-6-yl)-5,6-dihydropyridine-1(2H)-carboxylate

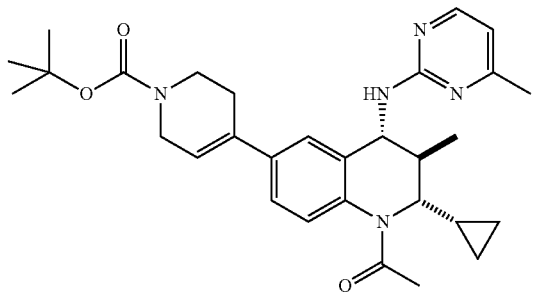 [SMILES: CC(=O)N1c2ccc(C3=CCN(C(=O)OC(C)(C)C)CC3)cc2[C@H](Nc2nccc(C)n2)[C@@H](C)[C@@H]1C1CC1]

In a test tube rac-tert-butyl 4-((2S,3R,4R)-1-acetyl-4-amino-2-cyclopropyl-3-methyl-1,2,3,4-tetrahydroquinolin-6-yl)-5,6-dihydropyridine-1(2H)-carboxylate (for a preparation see Intermediate 81, 200 mg, 0.470 mmol), 2-bromo-4-methylpyrimidine (98 mg, 0.564 mmol), sodium tert-butoxide (90 mg, 0.940 mmol), Pd₂(dba)₃ (21.52 mg, 0.023 mmol) and DavePhos (18.50 mg, 0.047 mmol) were dissolved in 1,4-dioxane (4 mL). The solution was stirred and heated at 100° C. for 2 h. The reaction mixture was allowed to cool and was then filtered through celite washing through with extra dioxane. The filtrate was concentrated in vacuo to leave the crude. Purification was undertaken by flash column chromatography. The crude material was loaded onto a 25 g silica column and eluted using a graduating solvent system of 0-5% 2M methanolic ammonia in dichloromethane. Combination and evaporation of the desired fractions gave the product as a yellow oil (10 mg).

LCMS (2 min Formic): Rt=1.18 min, [MH]⁺=518.

Intermediate 167: rac-tert-butyl 4-((2S,3R,4R)-1-acetyl-4-((4-cyanophenyl)amino)-2-cyclopropyl-3-methyl-1,2,3,4-tetrahydroquinolin-6-yl)-5,6-dihydropyridine-1(2H)-carboxylate

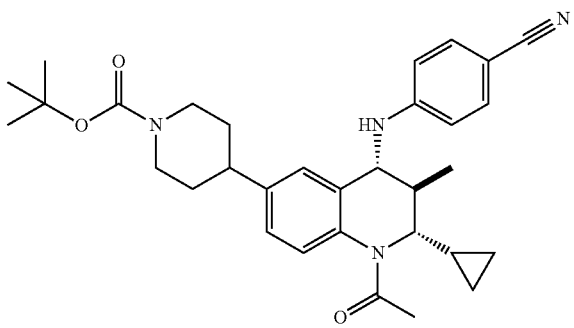 [SMILES: CC(=O)N1c2ccc(C3CCN(C(=O)OC(C)(C)C)CC3)cc2[C@H](Nc2ccc(C#N)cc2)[C@@H](C)[C@@H]1C1CC1]

rac-tert-Butyl 4-((2S,3R,4R)-1-acetyl-4-((4-cyanophenyl)amino)-2-cyclopropyl-3-methyl-1,2,3,4-tetrahydroquinolin-6-yl)-5,6-dihydropyridine-1(2H)-carboxylate (for a preparation see Intermediate 164, 78 mg, 0.15 mmol) was taken up in ethanol (10 mL) and the reaction was hydrogenated using the H-cube (settings: 25° C., 1 bar, 1 mL/min flow rate) and 10% Pd/C CatCart 30 as the catalyst. The sample was allowed to cycle through the H-cube for 30 min.

The reaction was concentrated in vacuo to give the crude product which was used in the following step without further purification.

LCMS (2 min Formic): Rt=1.26 min, [MH]⁺=529.

Intermediate 168: rac-tert-butyl 4-((2S,3R,4R)-1-acetyl-2-cyclopropyl-3-methyl-4-((4-(methylcarbamoyl)phenyl)amino)-1,2,3,4-tetrahydroquinolin-6-yl)piperidine-1-carboxylate

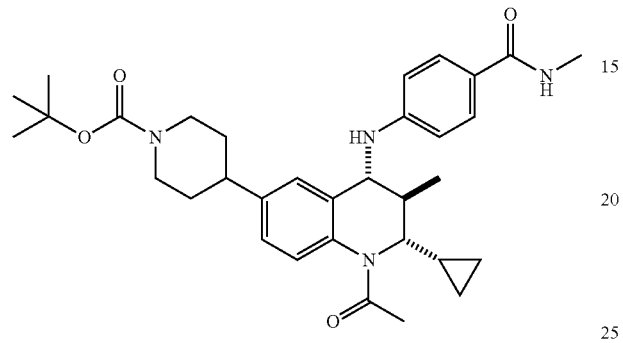

tert-Butyl 4-((2S,3R,4R)-1-acetyl-2-cyclopropyl-3-methyl-4-((4-(methylcarbamoyl)phenyl)amino)-1,2,3,4-tetrahydroquinolin-6-yl)-5,6-dihydropyridine-1(2H)-carboxylate (for a preparation see Intermediate 165, 78 mg, 0.140 mmol) was taken up in ethanol (10 mL) and the reaction was hydrogenated using the H-cube (settings: 25° C., 1 bar, 1 mL/min flow rate) and 10% Pd/C CatCart 30 as the catalyst. The sample was allowed to cycle through the H-cube for 30 min and the reaction mixture was concentrated in vacuo. The crude residue was dissolved in a 1:1 DMSO/MeOH mixture and was purified via MDAP (Formic). The appropriate fractions were combined and concentrated in vacuo to give the product a viscous colourless oil (35 mg).

LCMS (2 min Formic): Rt=1.12 min, [MH]⁺=561.

Intermediate 169: rac-benzyl ((2S,3S,4R)-2,3-dimethyl-6-morpholino-1,2,3,4-tetrahydroquinolin-4-yl)carbamate

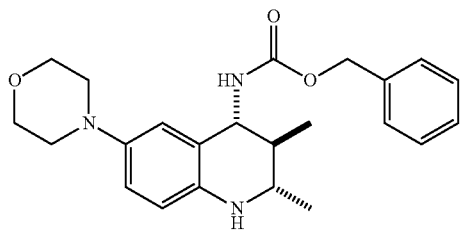 [SMILES: C[C@H]1[C@H](C)Nc2ccc(N3CCOCC3)cc2[C@@H]1NC(=O)OCc1ccccc1]

A stirred solution of (E)-benzyl prop-1-en-1-ylcarbamate (for a preparation see Intermediate 1, 1.18 g, 6.17 mmol), 4-morpholinoaniline (1.00 g, 5.61 mmol) and acetaldehyde (0.472 mL, 8.42 mmol) in DCM (45 ml) under nitrogen was cooled using an ice/water bath for 15 min then a solution of diphenyl hydrogen phosphate (0.140 g, 0.561 mmol) in DCM (5 ml) was added dropwise to the reaction mixture. The reaction mixture was allowed to warm to rt overnight then washed with sat. NaHCO₃ (aq., 100 mL) and the aqueous layer was extracted with DCM (100 mL). The combined organic layer was concentrated under reduced pressure then purified by silica column, eluting with a gradient of 0 to 50% EtOAc in cyclohexane, followed by 50% EtOAc in cyclohexane to give the desired product as a white solid (1.14 g). LCMS (2 min Formic): Rt=0.81 min, [MH]⁺=396.

Intermediate 170: rac-benzyl ((2S,3R,4R)-1-acetyl-2,3-dimethyl-6-morpholino-1,2,3,4-tetrahydroquinolin-4-yl)carbamate

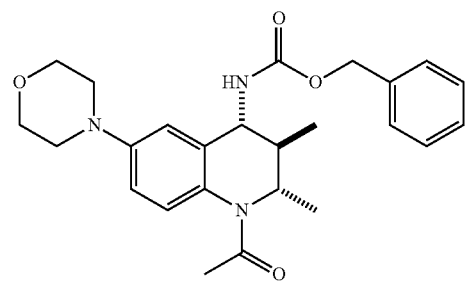 [SMILES: CC(=O)N1c2ccc(N3CCOCC3)cc2[C@H](NC(=O)OCc2ccccc2)[C@@H](C)[C@@H]1C]

A solution of rac-benzyl ((2S,3S,4R)-2,3-dimethyl-6-morpholino-1,2,3,4-tetrahydroquinolin-4-yl)carbamate (for a preparation see Intermediate 169, 1.1 g, 2.78 mmol) and pyridine (0.675 mL, 8.34 mmol) in anhydrous DCM (15 mL) was treated with acetyl chloride (0.475 mL, 6.68 mmol). The mixture was stirred at rt for 16 h then washed with 1M HCl (aq., 20 mL) followed by saturated NaHCO₃ (aq., 20 mL) and brine (20 mL). The organic layers were concentrated under reduced pressure to give the desired product as a pale brown solid (1.1 g, 90%).

LCMS (2 min Formic): Rt=0.95 min, [MH]⁺=438.

Intermediate 171: rac-1-((2S,3R,4R)-2-cyclopropyl-4-((6-methoxypyridin-2-yl)amino)-3-methyl-6-morpholino-3,4-dihydroquinolin-1(2H)-yl)ethanone

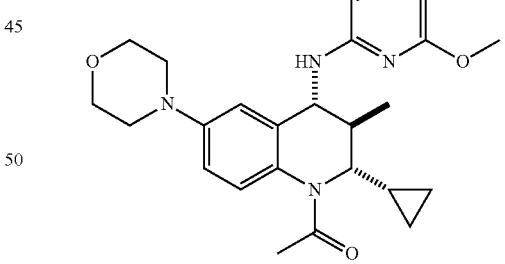

A solution of rac-1-((2S,3R,4R)-4-amino-2-cyclopropyl-3-methyl-6-morpholino-3,4-dihydroquinolin-1(2H)-yl)ethanone (for a preparation see Intermediate 83, 70 mg, 0.212 mmol), DavePhos (8.36 mg, 0.021 mmol), Pd₂(dba)₃ (9.73 mg, 10.62 µmol), sodium tert-butoxide (0.027 mL, 0.425 mmol) and 2-bromo-6-methoxy-pyridine (47.9 mg, 0.255 mmol) in 1,4-dioxane (3 mL) was stirred under nitrogen at 90° C. for 8 h. The reaction mixture was allowed to cool to rt, filtered through celite and rinsed with ethyl acetate. The solvent was evaporated in vacuo to give the title compound (120 mg, 0.275 mmol, 92% pure) as a brown gum. LCMS (2 min Formic): Rt=1.03 min, [MH]⁺=437.

Intermediate 172: rac-tert-butyl 4-((2S,3R,4R)-1-acetyl-4-amino-2-ethyl-3-methyl-1,2,3,4-tetrahydroquinolin-6-yl)piperazine-1-carboxylate

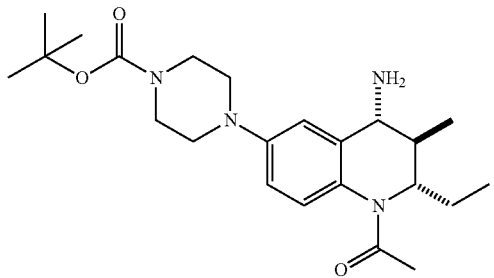 [SMILES: CC[C@H]1[C@H](C)[C@@H](N)c2cc(N3CCN(C(=O)OC(C)(C)C)CC3)ccc2N1C(C)=O]

To a flask containing rac-benzyl ((2S,3R,4R)-1-acetyl-6-bromo-2-ethyl-3-methyl-1,2,3,4-tetrahydroquinolin-4-yl) carbamate (for a preparation see Intermediate 9, 850 mg, 1.909 mmol) was added toluene (25 mL) and the flask evacuated and back filled with $N_2$ (×2). To this was added tert-butyl piperazine-1-carboxylate (0.711 mL, 3.82 mmol) and sodium tert-butoxide (367 mg, 3.82 mmol) and the resultant suspension then had $N_2$ bubbled through it for ~5 min. DavePhos (75 mg, 0.191 mmol) and $Pd_2(dba)_3$ (175 mg, 0.191 mmol) were then added and $N_2$ was bubbled through the reaction mixture for a further ~5 min. The reaction was then heated to 110° C. for 1.5 h. The reaction mixture was then diluted with EtOAc (40 mL) and filtered through celite (10 g). The celite was washed with further EtOAc (2×40 mL) and the combined organics concentrated in vacuo. The crude product was taken up in DCM and added to a silica cartridge (100 g). This was purified by flash chromatography, eluting with 0-50% (20% (2M $NH_3$ in MeOH)/DCM)/DCM. The appropriate fractions were collected and concentrated in vacuo to afford the desired product as a brown foam (371 mg, 0.891 mmol, 46.7%).

LCMS (2 min Formic): Rt=0.78 min, $[M]^+$=400 (loss of $NH_2^-$).

Intermediate 173: rac-tert-butyl 4-((2S,3R,4R)-1-acetyl-2-ethyl-3-methyl-4-((5-methylpyrazin-2-yl)amino)-1,2,3,4-tetrahydroquinolin-6-yl)piperazine-1-carboxylate

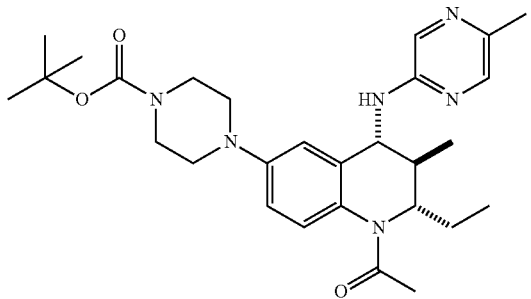 [SMILES: CC[C@H]1[C@H](C)[C@@H](Nc2cnc(C)cn2)c2cc(N3CCN(C(=O)OC(C)(C)C)CC3)ccc2N1C(C)=O]

A 0.5-2 mL microwave vial was evacuated and back filled with $N_2$. rac-tert-Butyl 4-((2S,3R,4R)-1-acetyl-4-amino-2-ethyl-3-methyl-1,2,3,4-tetrahydroquinolin-6-yl)piperazine-1-carboxylate (for a preparation see Intermediate 172, 46 mg, 0.110 mmol) in 1,4-dioxane (1.5 mL) was then added. To this was added 2-chloro-5-methylpyrazine (28.4 mg, 0.221 mmol), sodium tert-butoxide (21.23 mg, 0.221 mmol) and DavePhos (8.69 mg, 0.022 mmol) and the resultant suspension then had $N_2$ bubbled through it for ~5 min. $Pd_2(dba)_3$ (20.22 mg, 0.022 mmol) was added and $N_2$ was bubbled through the reaction mixture for a further ~5 min. The reaction was then heated to 100° C. for 30 min in a microwave. The reaction was then reheated to 100° C. in a microwave for 30 min. The reaction mixture was diluted with EtOAc and filtered though celite (2.5 g). The celite was washed with further EtOAc (2×10 mL) and the resultant solution concentrated in vacuo. This was taken up in MeOH/DMSO (1:1, 0.9 mL) and purified by MDAP (Formic). The appropriate fraction was collected and concentrated in vacuo to afford an orange glass (21.6 mg, 0.042 mmol, 38.5%).

LCMS (2 min Formic): Rt=1.07 min, $[MH]^+$=509.

Intermediate 174: rac-tert-butyl 4-((2S,3R,4R)-1-acetyl-4-((4-cyanophenyl)amino)-2-ethyl-3-methyl-1,2,3,4-tetrahydroquinolin-6-yl)piperazine-1-carboxylate

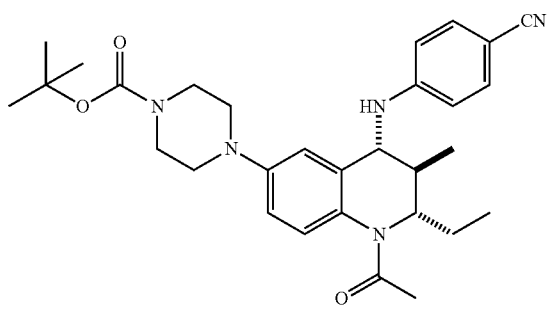 [SMILES: CC[C@H]1[C@H](C)[C@@H](Nc2ccc(C#N)cc2)c2cc(N3CCN(C(=O)OC(C)(C)C)CC3)ccc2N1C(C)=O]

A 0.5-2 mL microwave vial was evacuated and back filled with $N_2$. rac-tert-Butyl 4-((2S,3R,4R)-1-acetyl-4-amino-2-ethyl-3-methyl-1,2,3,4-tetrahydroquinolin-6-yl)piperazine-1-carboxylate (for a preparation see Intermediate 172, 46 mg, 0.110 mmol) in 1,4-dioxane (1.5 mL) was then added. To this was added 4-bromobenzonitrile (40.2 mg, 0.221 mmol), sodium tert-butoxide (21.23 mg, 0.221 mmol) and DavePhos (8.69 mg, 0.022 mmol) and the resultant suspension then had $N_2$ bubbled through it for ~5 min. $Pd_2(dba)_3$ (20.22 mg, 0.022 mmol) was added and $N_2$ was bubbled through the reaction mixture for a further ~5 min. The reaction was then heated to 100° C. for 30 min in a microwave. The reaction mixture was diluted with EtOAc and filtered though celite (2.5 g). The celite was washed with further EtOAc (2×10 mL) and the resultant solution concentrated in vacuo. This was taken up in MeOH/DMSO (1:1, 0.9 mL) and purified by MDAP (Formic). The appropriate fraction was collected and concentrated in vacuo to afford an orange glass (24 mg, 0.046 mmol, 42.0%). LCMS (2 min Formic): Rt=1.19 min, $[MH]^+$=518.

Intermediate 175: rac-tert-butyl 4-((2S,3R,4R)-1-acetyl-2-ethyl-3-methyl-4-((4-(methylcarbamyl))phenyl)amino)-1,2,3,4-tetrahydroquinolin-6-yl)piperazine-1-carboxylate

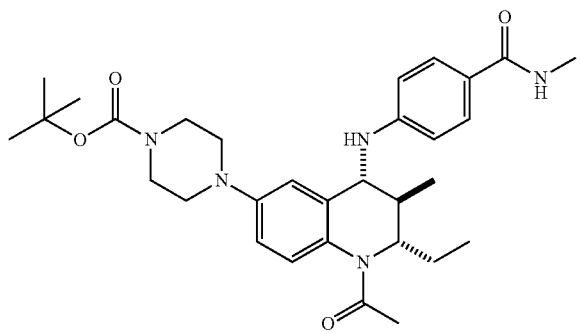 [SMILES: CC[C@H]1[C@H](C)[C@@H](Nc2ccc(C(=O)NC)cc2)c2cc(N3CCN(C(=O)OC(C)(C)C)CC3)ccc2N1C(C)=O]

A 0.5-2 mL microwave vial was evacuated and back filled with N₂. rac-tert-Butyl 4-((2S,3R,4R)-1-acetyl-4-amino-2-ethyl-3-methyl-1,2,3,4-tetrahydroquinolin-6-yl)piperazine-1-carboxylate (for a preparation see Intermediate 172, 46 mg, 0.110 mmol) in 1,4-dioxane (1.5 mL) was then added. To this was added 4-bromo-N-methylbenzamide (0.047 mL, 0.221 mmol), sodium tert-butoxide (21.23 mg, 0.221 mmol) and DavePhos (8.69 mg, 0.022 mmol) and the resultant suspension then had N₂ bubbled through it for ~5 min. Pd₂(dba)₃ (20.22 mg, 0.022 mmol) was added and N₂ was bubbled through the reaction mixture for a further ~5 min. The reaction was then heated to 100° C. for 30 min in a microwave. The reaction was then reheated to 100° C. in a microwave for 30 min. The reaction mixture was diluted with EtOAc and filtered though celite (2.5 g). The celite was washed with further EtOAc (2×10 mL) and the resultant solution concentrated in vacuo. This was taken up in MeOH/DMSO (1:1, 0.9 mL) and purified by MDAP (Formic). The appropriate fraction was collected and concentrated in vacuo to afford an orange glass (13 mg, 0.024 mmol, 21.42%).

LCMS (2 min Formic): Rt=1.04 min, [MH]⁺=550.

Intermediate 176: rac-tert-butyl 4-((2S,3R,4R)-1-acetyl-4-((5-cyanopyrazin-2-yl)amino)-2-ethyl-3-methyl-1,2,3,4-tetrahydroquinolin-6-yl)piperazine-1-carboxylate

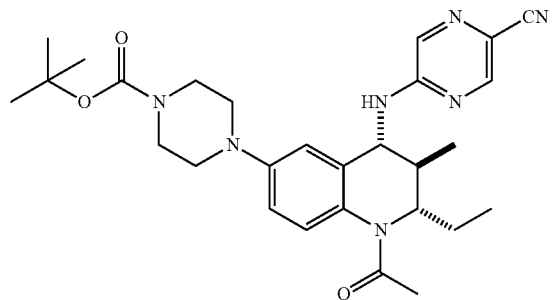 [SMILES: CC[C@H]1[C@H](C)[C@@H](Nc2cnc(C#N)cn2)c2cc(N3CCN(C(=O)OC(C)(C)C)CC3)ccc2N1C(C)=O]

A 0.5-2 mL microwave vial was evacuated and back filled with N₂. rac-tert-Butyl 4-((2S,3R,4R)-1-acetyl-4-amino-2-ethyl-3-methyl-1,2,3,4-tetrahydroquinolin-6-yl)piperazine-1-carboxylate (for a preparation see Intermediate 172, 37 mg, 0.089 mmol) in N-methyl-2-pyrrolidone (NMP) (1 mL) was then added. To this was added 5-chloropyrazine-2-carbonitrile (24.79 mg, 0.178 mmol), and DIPEA (0.047 mL, 0.266 mmol) and the resultant solution then heated to 150° C. for 30 min in a microwave. The reaction mixture was filtered through a cotton wool plug directly into two LCMS vials and was then purified by 2×MDAP (Formic). The appropriate fractions were collected and concentrated in vacuo to afford the desired product as a brown gum (26.6 mg, 0.051 mmol, 57.6%).

LCMS (2 min Formic): Rt=1.11 min, [MH]⁺=520.

Intermediate 177: rac-tert-butyl 4-((2S,3R,4R)-1-acetyl-4-((5-cyanopyridin-2-yl)amino)-2-ethyl-3-methyl-1,2,3,4-tetrahydroquinolin-6-yl)piperazine-1-carboxylate

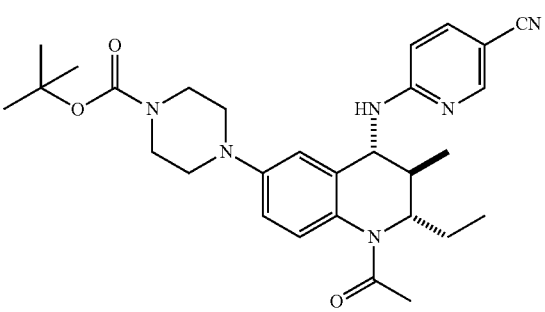 [SMILES: CC[C@H]1[C@H](C)[C@@H](Nc2ccc(C#N)cn2)c2cc(N3CCN(C(=O)OC(C)(C)C)CC3)ccc2N1C(C)=O]

A 0.5-2 mL microwave vial was evacuated and back filled with N₂. rac-tert-Butyl 4-((2S,3R,4R)-1-acetyl-4-amino-2-ethyl-3-methyl-1,2,3,4-tetrahydroquinolin-6-yl)piperazine-1-carboxylate (for a preparation see Intermediate 172, 37 mg, 0.089 mmol) in N-methyl-2-pyrrolidone (NMP) (1 mL) was then added. To this was added 6-fluoronicotinonitrile (21.69 mg, 0.178 mmol), and DIPEA (0.047 mL, 0.266 mmol) and the resultant solution then heated to 150° C. for 30 min in a microwave. The reaction was then reheated to 150° C. for 30 min. The reaction mixture was filtered through a cotton wool plug directly into two LCMS vials and was then purified by 2×MDAP (Formic). The appropriate fractions were collected and concentrated in vacuo to afford the desired product as a brown gum (16.6 mg, 0.032 mmol, 36.0%). LCMS (2 min Formic): Rt=1.12 min, [MH]⁺=519.

Intermediate 178: (S)-tert-butyl 4-((rac-2S,3R,4R)-1-acetyl-4-(((benzyloxy)carbonyl)amino)-2-cyclopropyl-3-methyl-1,2,3,4-tetrahydroquinolin-6-yl)-2-methylpiperazine-1-carboxylate

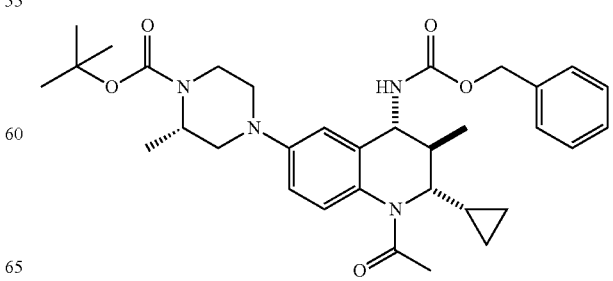

To a dried flask was added (S)-tert-butyl 2-methylpiperazine-1-carboxylate (52.3 mg, 0.261 mmol), rac-benzyl ((2S, 3R,4R)-1-acetyl-6-bromo-2-cyclopropyl-3-methyl-1,2,3,4-tetrahydroquinolin-4-yl)carbamate (for a preparation see Intermediate 13, 99.5 mg, 0.218 mmol), sodium tert-butoxide (41.8 mg, 0.435 mmol), Pd$_2$(dba)$_3$ (9.96 mg, 10.88 µmol) and DavePhos (8.56 mg, 0.022 mmol) under nitrogen. To this was added 1,4-dioxane (2 mL), and the solution was stirred and degassed with nitrogen for ~15 min. The mixture was heated to 90° C. overnight. The mixture was allowed to cool to rt, filtered through a 2.5 g celite cartridge, washed through with ethyl acetate and concentrated in vacuo. The residue was taken up in dichloromethane, loaded onto a 25 g silica flash column, and eluted in 10%-50% ethyl acetate in cyclohexane. The appropriate fractions were collected and concentrated in vacuo to afford a yellow oil (48.4 mg, 0.084 mmol, 38.6%). This was a mixture of diastereoisomers. LCMS (2 min formic): Rt=1.29 min, [MH]$^+$=577.

Intermediate 179: (S)-tert-butyl 4-((rac-2S,3R,4R)-1-acetyl-4-amino-2-cyclopropyl-3-methyl-1,2,3,4-tetrahydroquinolin-6-yl)-2-methylpiperazine-1-carboxylate

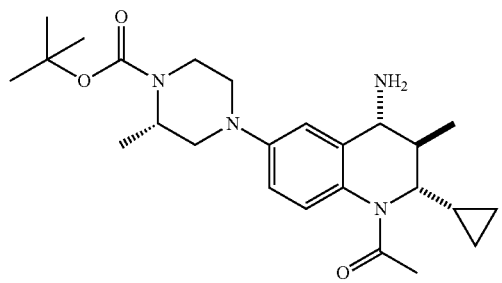 [SMILES: CC(=O)N1c2ccc(N3CCN(C(=O)OC(C)(C)C)[C@@H](C)C3)cc2[C@H](N)[C@@H](C)[C@@H]1C1CC1]

To a carousel flask, evacuated and back-filled with nitrogen, was added 10% Pd/C (35.7 mg, 0.034 mmol). To this was added a solution of (S)-tert-butyl 4-((rac-2S,3R,4R)-1-acetyl-4-(((benzyloxy)carbonyl)amino)-2-cyclopropyl-3-methyl-1,2,3,4-tetrahydroquinolin-6-yl)-2-methylpiperazine-1-carboxylate (for a preparation see Intermediate 178, 48.4 mg, 0.084 mmol) in ethanol (3 mL). The flask was allowed to stir under a hydrogen atmosphere for 4 h. The reaction mixture was filtered through a 2.5 g celite cartridge with ethanol, and the eluent collected. The eluted solution was evaporated in vacuo to afford a pale grey, transparent oil (37.7 mg, 0.085 mmol). This was a mixture of diastereoisomers. LCMS (2 min formic): Rt=0.87 min, [MH]$^+$=443.

Intermediate 180: (S)-tert-butyl 4-((rac-2S,3R,4R)-1-acetyl-4-((4-cyanophenyl)amino)-2-cyclopropyl-3-methyl-1,2,3,4-tetrahydroquinolin-6-yl)-2-methylpiperazine-1-carboxylate

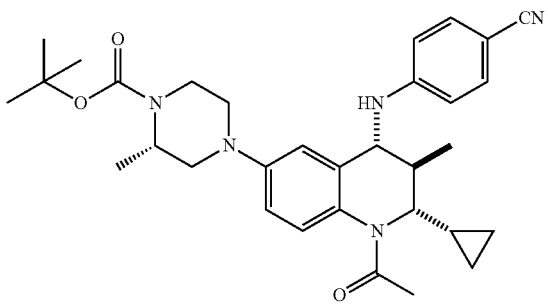 [SMILES: CC(=O)N1c2ccc(N3CCN(C(=O)OC(C)(C)C)[C@@H](C)C3)cc2[C@H](Nc2ccc(C#N)cc2)[C@@H](C)[C@@H]1C1CC1]

To a flask containing (S)-tert-butyl 4-((rac-2S,3R,4R)-1-acetyl-4-amino-2-cyclopropyl-3-methyl-1,2,3,4-tetrahydroquinolin-6-yl)-2-methylpiperazine-1-carboxylate (for a preparation see Intermediate 179, 37.7 mg, 0.085 mmol) in 1,4-dioxane (2 mL) under nitrogen was added sodium tert-butoxide (24.56 mg, 0.256 mmol), 4-bromobenzonitrile (18.60 mg, 0.102 mmol), Pd$_2$(dba)$_3$ (15.60 mg, 0.017 mmol) and DavePhos (13.41 mg, 0.034 mmol). The mixture was degassed with nitrogen for ~15 min, and then heated to 90° C. with stirring under nitrogen for ~2 h, followed by heating at 45° C. for ~64 h. The mixture was filtered over a 2.5 g celite cartridge, washed through with ethyl acetate and concentrated in vacuo. The residue was taken up in dichloromethane, loaded onto a 10 g silica flash column and eluted by silica gel chromatography in 0%-25% ethyl acetate in cyclohexane. The appropriate fractions were collected and concentrated in vacuo to afford a sticky yellow oil (25.4 mg, 0.021 mmol, 24.68%). This was a mixture of diastereoisomers.

LCMS (2 min formic): Rt=1.26 min, [MH]$^+$=544.

Intermediate 181: (R)-tert-butyl 4-((rac-2S,3R,4R)-1-acetyl-4-(((benzyloxy)carbonyl)amino)-2-cyclopropyl-3-methyl-1,2,3,4-tetrahydroquinolin-6-yl)-2-methylpiperazine-1-carboxylate

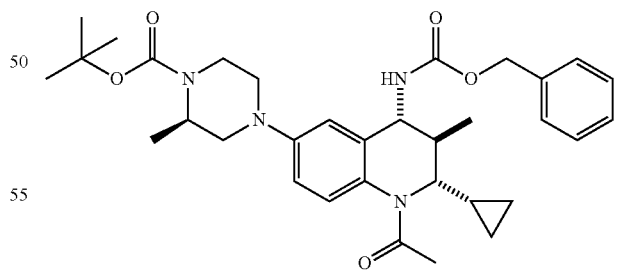

To a dried flask was added (R)-tert-butyl 2-methylpiperazine-1-carboxylate (51.6 mg, 0.258 mmol), rac-benzyl ((2S, 3R,4R)-1-acetyl-6-bromo-2-cyclopropyl-3-methyl-1,2,3,4-tetrahydroquinolin-4-yl)carbamate (for a preparation see Intermediate 13, 98.2 mg, 0.215 mmol), sodium tert-butoxide (41.3 mg, 0.429 mmol), Pd$_2$(dba)$_3$ (9.83 mg, 10.74 µmol) and DavePhos (8.45 mg, 0.021 mmol) under nitrogen. To this was added 1,4-dioxane (2 mL), and the solution was stirred and degassed with nitrogen for ~15 min. The mixture was heated to 90° C. for 2 h. The mixture was filtered through a 2.5 g celite cartridge, washed through with ethyl acetate and concentrated in vacuo. The residue was taken up in dichloromethane, loaded onto a 25 g silica flash column, and eluted by silica gel chromatography in 5%-40% ethyl acetate in cyclohexane. The appropriate fractions were collected and concentrated in vacuo to afford a yellow oil (22.9 mg, 0.040 mmol, 18.49%). This was a mixture of diastereoisomers. LCMS (2 min formic): Rt=1.29 min, [MH]$^+$=577.

Intermediate 182: (R)-tert-butyl 4-((rac-2S,3R,4R)-1-acetyl-4-amino-2-cyclopropyl-3-methyl-1,2,3,4-tetrahydroquinolin-6-yl)-2-methylpiperazine-1-carboxylate

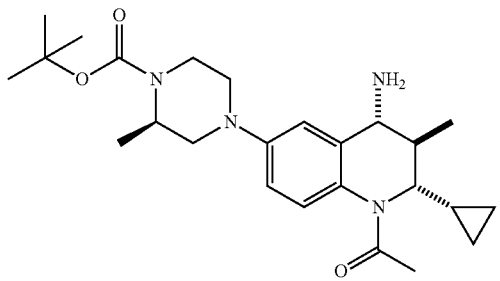 [SMILES: CC(=O)N1c2ccc(N3CCN(C(=O)OC(C)(C)C)[C@H](C)C3)cc2[C@H](N)[C@@H](C)[C@@H]1C1CC1]

To a carousel flask, evacuated and back-filled with nitrogen, was added 10% Pd/C (16.90 mg, 0.016 mmol). To this was added a solution of (R)-tert-butyl 4-((rac-2S,3R,4R)-1-acetyl-4-(((benzyloxy)carbonyl)amino)-2-cyclopropyl-3-methyl-1,2,3,4-tetrahydroquinolin-6-yl)-2-methylpiperazine-1-carboxylate (for a preparation see Intermediate 181, 22.9 mg, 0.040 mmol) in ethanol (1.2 mL). The flask was allowed to stir under a hydrogen atmosphere for 4 h. The reaction mixture was filtered through a 2.5 g celite cartridge with ethanol, and the eluent collected. The eluted solution was evaporated in vacuo to afford a pale grey, transparent oil (17.9 mg, 0.040 mmol). This was a mixture of diastereoisomers. LCMS (2 min Formic): Rt=0.84 min, [M]$^+$=426 (loss of NH$_2^-$).

Intermediate 183: (R)-tert-butyl 4-((rac-2S,3R,4R)-1-acetyl-4-((4-cyanophenyl)amino)-2-cyclopropyl-3-methyl-1,2,3,4-tetrahydroquinolin-6-yl)-2-methylpiperazine-1-carboxylate

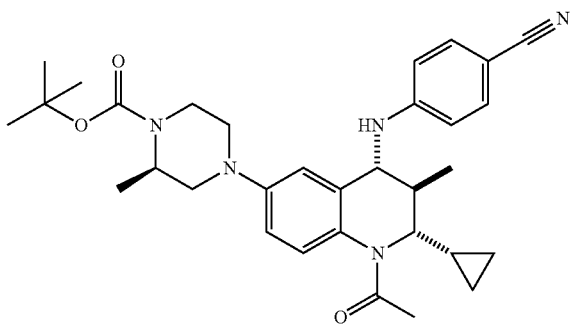 [SMILES: CC(=O)N1c2ccc(N3CCN(C(=O)OC(C)(C)C)[C@H](C)C3)cc2[C@H](Nc2ccc(C#N)cc2)[C@@H](C)[C@@H]1C1CC1]

To a flask containing (R)-tert-butyl 4-((rac-2S,3R,4R)-1-acetyl-4-amino-2-cyclopropyl-3-methyl-1,2,3,4-tetrahydroquinolin-6-yl)-2-methylpiperazine-1-carboxylate (for a preparation see Intermediate 182, 17.9 mg, 0.040 mmol) in 1,4-dioxane (2 mL) under nitrogen was added 4-bromobenzonitrile (8.83 mg, 0.049 mmol), DavePhos (6.37 mg, 0.016 mmol), Pd$_2$(dba)$_3$ (7.41 mg, 8.09 µmol) and sodium tert-butoxide (11.66 mg, 0.121 mmol). The mixture was degassed with nitrogen for ~15 min, and then heated to 90° C. with stirring under nitrogen for ~2 h, and then heated to 90° C. with stirring under nitrogen for ~2 h, followed by heating at 45° C. for ~64 h. The mixture was filtered over a 2.5 g celite cartridge, washed through with ethyl acetate and concentrated in vacuo. The residue was taken up in dichloromethane, loaded onto a 10 g silica flash column, and eluted by silica gel chromatography with 0%-35% ethyl acetate in cyclohexane. The appropriate fractions were collected and concentrated in vacuo to afford the product (9.1 mg, 0.017 mmol, 41.4%). This was a mixture of diastereoisomers.

LCMS (2 min Formic): Rt=1.26 min, [MH]$^+$=544.

Intermediate 184: (S)-tert-butyl 4-((rac-2S,3R,4R)-1-acetyl-2-cyclopropyl-3-methyl-4-((5-methylpyrazin-2-yl)amino)-1,2,3,4-tetrahydroquinolin-6-yl)-2-methylpiperazine-1-carboxylate

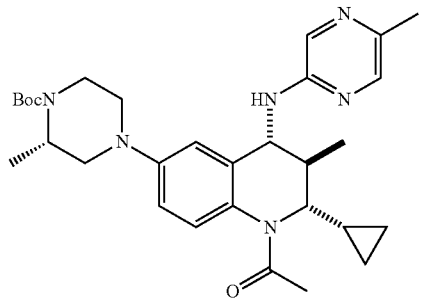

To a microwave vial was added (S)-tert-butyl 4-((rac-2S,3R,4R)-1-acetyl-4-amino-2-cyclopropyl-3-methyl-1,2,3,4-tetrahydroquinolin-6-yl)-2-methylpiperazine-1-carboxylate (for a preparation see Intermediate 179, 37.7 mg, 0.085 mmol) in 1,4-dioxane (2.5 mL). To this was added 2-chloro-5-methylpyrazine (21.90 mg, 0.170 mmol), Pd$_2$(dba)$_3$ (15.60 mg, 0.017 mmol), sodium tert-butoxide (24.56 mg, 0.256 mmol) and DavePhos (13.41 mg, 0.034 mmol). The vessel was sealed and heated on a microwave heater at 120° C. for 40 min. The reaction mixture was filtered over a 2.5 g celite cartridge, washed through with ethyl acetate and concentrated in vacuo. The residue was dissolved in MeOH:DMSO (1:1, 1 mL) and purified by MDAP (Formic). The solvent was evaporated in vacuo to give the required product (5.7 mg, 12.5%). LCMS No data.

Intermediate 185: (S)-tert-butyl 4-((rac-2S,3R,4R)-1-acetyl-2-cyclopropyl-3-methyl-4-((4-(methylcarbamyl)phenyl)amino)-1,2,3,4-tetrahydroquinolin-6-yl)-2-methylpiperazine-1-carboxylate

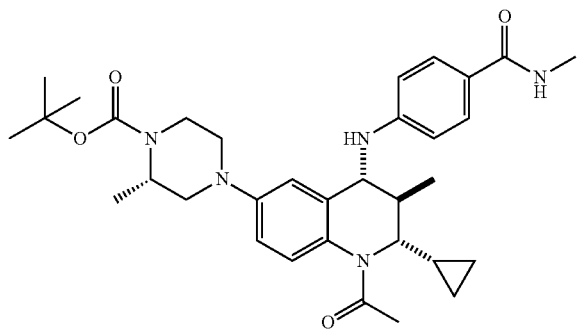 [SMILES: CNC(=O)c1ccc(N[C@H]2c3cc(N4CCN(C(=O)OC(C)(C)C)[C@@H](C)C4)ccc3N(C(C)=O)[C@@H](C3CC3)[C@@H]2C)cc1]

To a dried flask under nitrogen was added (S)-tert-butyl 4-((rac-2S,3R,4R)-1-acetyl-4-amino-2-cyclopropyl-3-methyl-1,2,3,4-tetrahydroquinolin-6-yl)-2-methylpiperazine-1-carboxylate (for a preparation see Intermediate 179, 40 mg, 0.090 mmol), DavePhos (14.23 mg, 0.036 mmol), 4-bromo-N-methylbenzamide (23.22 mg, 0.108 mmol), sodium tert-butoxide (26.1 mg, 0.271 mmol) and Pd$_2$(dba)$_3$ (16.55 mg, 0.018 mmol). The solids were dissolved in 1,4-dioxane (2 mL), and the mixture bubbled through with nitrogen. The mixture was then heated at 90° C. for ~2 h. Further portions of Pd$_2$(dba)$_3$ (0.2 eq.) and DavePhos (0.4 eq.) were added, and the mixture continued to stir at 90° C. The reaction mixture was cooled to rt, filtered over a 2.5 g celite cartridge, washed through with ethyl acetate and concentrated in vacuo. The sample was dissolved in MeOH:DMSO (1:1, 1 mL) and purified by MDAP (Formic). The solvent was evaporated in vacuo to give the required product (5.6 mg, 11%). This was a mixture of diastereoisomers.

LCMS (2 min Formic): Rt=1.12 min, [MH]$^+$=576.

Intermediate 186: (S)-tert-butyl 4-((rac-2S,3R,4R)-1-acetyl-4-((5-cyanopyridin-2-yl)amino)-2-cyclopropyl-3-methyl-1,2,3,4-tetrahydroquinolin-6-yl)-2-methylpiperazine-1-carboxylate

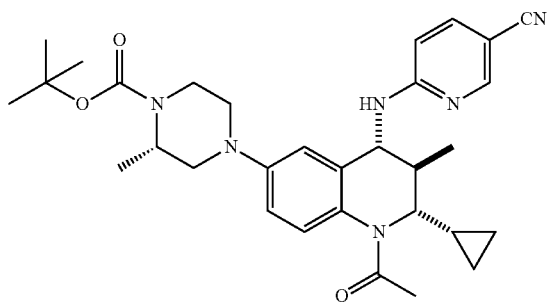

To a microwave vessel was added (S)-tert-butyl 4-((rac-2S,3R,4R)-1-acetyl-4-amino-2-cyclopropyl-3-methyl-1,2,3,4-tetrahydroquinolin-6-yl)-2-methylpiperazine-1-carboxylate (for a preparation see Intermediate 179, 40 mg, 0.090 mmol) and 6-chloronicotinonitrile (25.04 mg, 0.181 mmol) in N-methyl-2-pyrrolidone (NMP) (1 mL). To this was added DIPEA (0.047 mL, 0.271 mmol). The vessel was sealed and heated on a microwave heater to 150° C. for 30 min. Further portions of 6-chloronicotinonitrile (2 eq.) and DIPEA (3 eq.) were added, the vessel was resealed and heated to 150° C. for 30 min. The vessel was resealed and heated to 200° C. for 30 min. The reaction mixture was transferred to an LCMS vial, and purified by MDAP (Formic). The solvent was evaporated in vacuo to give the required product (7.0 mg, 12.8%). This was a mixture of diastereoisomers.

LCMS (2 min Formic): Rt=1.20 min, [MH]$^+$=545.

Intermediate 187: rac-benzyl ((2S,3S,4R)-2,3-dimethyl-6-(methylcarbamoyl)-1,2,3,4-tetrahydroquinolin-4-yl)carbamate

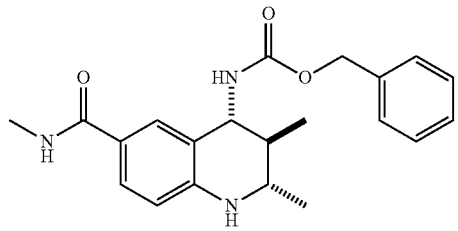 [SMILES: CNC(=O)c1ccc2c(c1)[C@H](NC(=O)OCc1ccccc1)[C@@H](C)[C@H](C)N2]

To a solution of acetaldehyde (0.292 mL, 5.23 mmol) in anhydrous DCM (10 mL) was added 4-amino-N-methylbenzamide (0.785 g, 5.23 mmol) and the reaction stirred at rt for 1 h. Diphenyl hydrogen phosphate (0.131 g, 0.523 mmol) in anhydrous DCM (5 mL) was added followed by (E)-benzyl prop-1-en-1-ylcarbamate (for a preparation see Intermediate 1, 1 g, 5.23 mmol) in anhydrous DCM (5 mL). The mixture was then left to stir for 1.5 h. The mixture was partitioned between 100 mL DCM and 25 mL sat. NaHCO$_3$. The organic and aqueous layers were combined and evaporated to dryness under reduced pressure. The residue was treated with 30 mL MeOH and filtered. The filtrate was applied to a 100 g silica gel column which was then dried in a vacuum oven at 40° C. The dry column was then eluted with 0-8% MeOH in DCM to afford the crude desired product, as a white solid (1.15 g), which was used in the next step without further purification.

LCMS (2 min Formic): Rt=0.92 min, [MH]$^+$=368.

Intermediate 188: rac-benzyl ((2S,3S,4R)-1-acetyl-2,3-dimethyl-6-(methylcarbamoyl)-1,2,3,4-tetrahydroquinolin-4-yl)carbamate

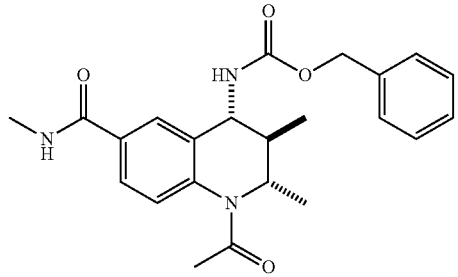 [SMILES: CNC(=O)c1ccc2c(c1)[C@H](NC(=O)OCc1ccccc1)[C@@H](C)[C@H](C)N2C(C)=O]

To a solution of rac-benzyl ((2S,3S,4R)-2,3-dimethyl-6-(methylcarbamoyl)-1,2,3,4-tetrahydroquinolin-4-yl)carbamate (for a preparation see Intermediate 187, 1.15 g, 3.13 mmol), in DCM (35 mL) was added DIPEA (1.64 mL, 9.39 mmol) and acetyl chloride (0.245 mL, 3.44 mmol) and the mixture allowed to stir at rt for 1 h. A further portion of acetyl chloride (0.668 mL, 9.39 mmol) was added and the mixture stirred for a further 2 h. The mixture was concentrated in vacuo to give a brown oily residue. This was purified by chromatography on silica gel (50 g column, eluting with 0-10% MeOH in DCM) to afford the desired product (688 mg) as a pale yellow solid.

LCMS (2 min Formic): Rt=0.83 min, [MH]$^+$=410.

Intermediate 189: rac-(2S,3R,4R)-1-acetyl-4-amino-N,2,3-trimethyl-1,2,3,4-tetrahydroquinoline-6-carboxamide

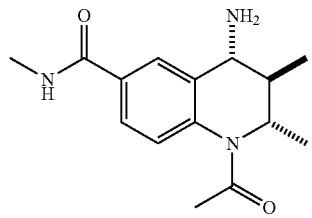

A solution of rac-benzyl ((2S,3R,4R)-1-acetyl-2,3-dimethyl-6-(methylcarbamoyl)-1,2,3,4-tetrahydroquinolin-4-yl)carbamate (for a preparation, see Intermediate 188, 688 mg, 1.68 mmol) in ethanol (30 mL) was passed through a 10% Pd/C cartridge on a H-cube (rt, full H$_2$ mode) at a flow rate of 1 mL/min. The collected solution was passed through the 10% Pd/C cartridge on the H-cube a second time (rt, full H$_2$ mode) at a flow rate of 1 mL/min. The H-cube was flushed with a further 10 mL EtOH, the collected solutions combined and the solvent removed by evaporation to afford the desired product as a yellow solid (429 mg). LCMS (2 min Formic): Rt=0.38 min, [MH]$^+$=276.

Intermediate 190: rac-benzyl ((2S,3S,4R)-2-ethyl-3-methyl-6-(methylcarbamoyl)-1,2,3,4-tetrahydroquinolin-4-yl)carbamate

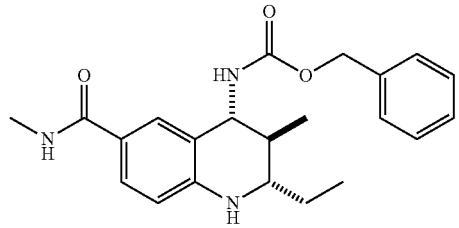 [SMILES: CC[C@@H]1Nc2ccc(C(=O)NC)cc2[C@H](NC(=O)OCc2ccccc2)[C@H]1C]

To a solution of propionaldehyde (0.105 mL, 1.464 mmol) in anhydrous DCM (10 mL), was added 4-amino-N-methylbenzamide (220 mg, 1.464 mmol) and the reaction mixture stirred at rt for 1 h. Diphenyl hydrogen phosphate (36.6 mg, 0.146 mmol) in anhydrous DCM (5 mL) was then added followed by (E)-benzyl prop-1-en-1-ylcarbamate (for a preparation see Intermediate 1, 280 mg, 1.464 mmol) in anhydrous DCM (5 mL). The reaction mixture was then left to stir for 2 h. The reaction mixture was diluted with DCM (10 mL) and washed with NaHCO$_3$ (40 mL) and then water (40 mL) and the organic and aqueous layers separated. The organic layer was passed through a hydrophobic frit and then concentrated in vacuo to give a yellow oil which was purified by chromatography on silica gel (25 g column, eluting with 0-10% MeOH in DCM) to afford the desired product as a pale yellow solid (403 mg). LCMS (2 min Formic): Rt=1.00 min, [MH]$^+$=382.

Intermediate 191: rac-benzyl ((2S,3R,4R)-1-acetyl-2-ethyl-3-methyl-6-(methylcarbamoyl)-1,2,3,4-tetrahydroquinolin-4-yl)carbamate

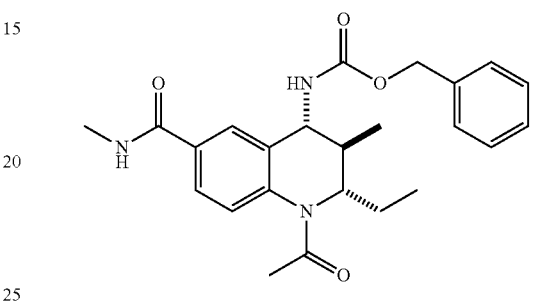

To a solution of rac-benzyl ((2S,3S,4R)-2-ethyl-3-methyl-6-(methylcarbamoyl)-1,2,3,4-tetrahydroquinolin-4-yl)carbamate (for a preparation see Intermediate 190, 403 mg, 1.056 mmol) in DCM (15 mL) was added DIPEA (0.738 mL, 4.23 mmol) and acetyl chloride (0.225 mL, 3.17 mmol) and the solution allowed to stir at rt for 1 h. The solution was concentrated in vacuo to give a brown oily residue which was purified by chromatography on silica gel (25 g column, eluting with 0-10% MeOH in DCM) followed by further purification by chromatography on silica gel (25 g column, eluting with 80-100% EtOAC in cyclohexane) to afford the desired product as a pale yellow solid (317 mg).

LCMS (2 min Formic): Rt=0.88 min, [MH]$^+$=424.

Intermediate 192: rac-(2S,3R,4R)-1-acetyl-4-amino-2-ethyl-N,3-dimethyl-1,2,3,4-tetrahydroquinoline-6-carboxamide

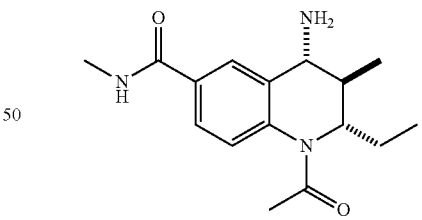

A solution of rac-benzyl ((2S,3R,4R)-1-acetyl-2-ethyl-3-methyl-6-(methylcarbamoyl)-1,2,3,4-tetrahydroquinolin-4-yl)carbamate (for a preparation, see Intermediate 191, 317 mg, 0.749 mmol) in ethanol (30 mL) was passed through a 10% Pd/C cartridge on a H-cube (rt, full H$_2$ mode) at a flow rate of 1 mL/min. The collected solution was passed through the 10% Pd/C cartridge on the H-cube a second time (rt, full H$_2$ mode) at a flow rate of 1 mL/min. The H-cube was flushed with a further 10 mL ethanol, the collected solutions were combined and the solvent removed by evaporation to afford the desired product as a yellow solid (194 mg). LCMS (2 min Formic): Rt=0.43 min, [MH]$^+$=290.

Intermediate 193: rac-(2S,3S,4R)-ethyl 4-(((benzyloxy)carbonyl)amino)-2-cyclopropyl-3-methyl-1,2,3,4-tetrahydroquinoline-6-carboxylate

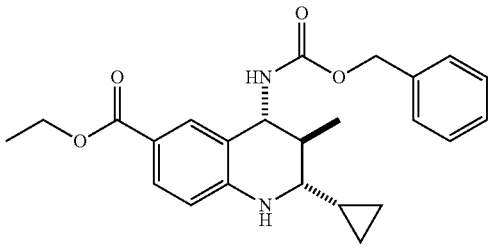 [SMILES: CCOC(=O)c1ccc2c(c1)[C@H](NC(=O)OCc1ccccc1)[C@@H](C)[C@H](C1CC1)N2]

To a solution of cyclopropanecarbaldehyde (0.313 mL, 4.18 mmol) in anhydrous dichloromethane (DCM) (10 mL), was added ethyl 4-aminobenzoate (691 mg, 4.18 mmol) and the reaction stirred at rt for 1 h. Diphenyl hydrogen phosphate (105 mg, 0.418 mmol) in anhydrous dichloromethane (DCM) (5 mL) was added and then (E)-benzyl prop-1-en-1-ylcarbamate (for a preparation see Intermediate 1, 800 mg, 4.18 mmol) in anhydrous dichloromethane (DCM) (5 mL). The reaction was then left to stir for 18 h. The reaction mixture was diluted with DCM (10 ml) and washed with NaHCO$_3$ (40 ml) and then water (40 mL) and the organic and aqueous layers separated. The organic layer was passed through a hydrophobic frit and then concentrated in vacuo to give 1.726 g of crude product as an orange oil. This was purified by chromatography on silica (25 g, eluting with ethyl acetate/cyclohexane 0-40%). Fractions containing product were combined and concentrated in vacuo to give 1.5 g of product with some impurities present. This was purified by chromatography on silica (50 g, eluting with ethyl acetate/cyclohexane 0-30%). The fractions containing product were combined and concentrated in vacuo to give 1.391 g of product as a white solid.

LCMS (2 min Formic): Rt=1.23 min, [MH]$^+$=409.

Intermediate 194: rac-(2S,3R,4R)-ethyl 1-acetyl-4-(((benzyloxy)carbonyl)amino)-2-cyclopropyl-3-methyl-1,2,3,4-tetrahydroquinoline-6-carboxylate

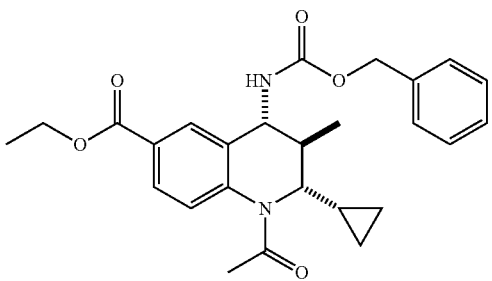 [SMILES: CCOC(=O)c1ccc2c(c1)[C@H](NC(=O)OCc1ccccc1)[C@@H](C)[C@H](C1CC1)N2C(C)=O]

To a reaction vessel rac-(2S,3S,4R)-ethyl 4-(((benzyloxy)carbonyl)amino)-2-cyclopropyl-3-methyl-1,2,3,4-tetrahydroquinoline-6-carboxylate (for a preparation see Intermediate 193, 1.391 g, 3.41 mmol), DIPEA (1.784 mL, 10.22 mmol) and acetyl chloride (0.242 mL, 3.41 mmol) were added in dichloromethane (DCM) (35 mL). This was left to stir at rt for 45 min. A further portion of acetyl chloride (0.242 mL, 3.41 mmol) was added and the reaction left to stir for 30 min. Acetyl chloride (0.121 mL, 1.703 mmol) was added and the reaction left to stir for 16 h. Acetyl chloride (0.121 mL, 1.703 mmol) was added and the reaction left to stir for 2 h. Acetyl chloride (0.242 mL, 3.41 mmol) was added and the reaction left to stir for 1 h. The mixture was concentrated in vacuo to give 3.1 g of crude brown solid. This was purified by chromatography on silica (50 g, eluting with ethyl acetate/cyclohexane 0-35%). The fractions containing mainly pure product were combined and concentrated in vacuo to give 1.433 g of product (1.368 g, 3.04 mmol, 89%) as a yellow solid.

LCMS (2 min Formic): Rt=1.16 min, [MH]$^+$=451.

Intermediate 195: rac-(2S,3R,4R)-ethyl 1-acetyl-4-amino-2-cyclopropyl-3-methyl-1,2,3,4-tetrahydroquinoline-6-carboxylate

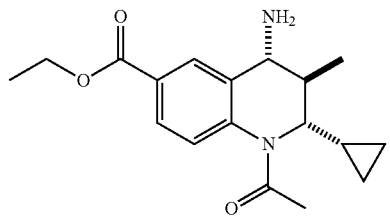 [SMILES: CCOC(=O)c1ccc2c(c1)[C@H](N)[C@@H](C)[C@H](C1CC1)N2C(C)=O]

To solution of rac-(2S,3R,4R)-ethyl 1-acetyl-4-(((benzyloxy)carbonyl)amino)-2-cyclopropyl-3-methyl-1,2,3,4-tetrahydroquinoline-6-carboxylate (for a preparation see Intermediate 194, 1.1 g, 2.442 mmol) in ethanol (50 mL), 10% Pd/C (0.130 g, 1.221 mmol) was added and the reaction was left to stir under a hydrogen atmosphere for 16 h. The mixture was filtered through celite and the celite washed with ethyl acetate (3×20 mL). The combined filtrates were concentrated in vacuo to give 798 mg of crude product. This was combined with another crude sample which was synthesised as follows:

To solution of rac-(2S,3R,4R)-ethyl 1-acetyl-4-(((benzyloxy)carbonyl)amino)-2-cyclopropyl-3-methyl-1,2,3,4-tetrahydroquinoline-6-carboxylate (for a preparation see Intermediate 192, 254 mg, 0.564 mmol) in ethanol (40 mL), 10% Pd/C (0.1 g, 0.940 mmol) was added and the reaction was left to stir under a hydrogen atmosphere for 3 h. The reaction mixture was filtered through celite and the celite washed with ethyl acetate (3×20 mL). The combined filtrates were concentrated in vacuo to give 206 mg of crude product as an off white solid.

The combined samples were purified by chromatography on silica (25 g, eluting with 0-50% ethyl acetate/cyclohexane, followed by 0-10% DCM/ammonia in methanol (2M)). The fractions containing product were combined and concentrated in vacuo to give 950 mg the product as a yellow oil. The sample was loaded in methanol and purified by SPE on sulfonic acid (SCX) 50 g using a sequential solvents methanol, 2M ammonia/methanol. The appropriate fractions were combined and concentrated in vacuo to give 747 mg of the product (747 mg, 2.361 mmol).

LCMS (2 min formic): Rt=0.62 min, [M]$^+$=317 (loss of NH$_2^-$).

Intermediate 196: rac-(2S,3R,4R)-1-acetyl-2-cyclopropyl-3-methyl-4-((6-methylpyridin-2-yl)amino)-1,2,3,4-tetrahydroquinoline-6-carbonyl chloride

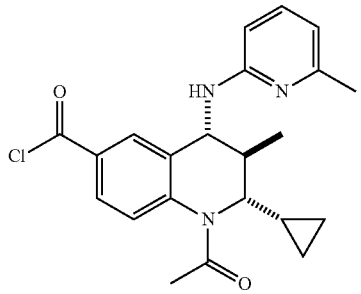 [SMILES: CC(=O)N1c2ccc(C(=O)Cl)cc2[C@H](Nc2cccc(C)n2)[C@@H](C)[C@@H]1C1CC1]

To a reaction vessel rac-(2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 131, 91 mg, 0.240 mmol) was added in dichloromethane (DCM) (5 mL) under nitrogen. Thionyl chloride (1 mL, 13.70 mmol) was added and the reaction left to stir at rt for 30 min. The reaction mixture was left to stir for 20 min and then concentrated in vacuo, to give 170 mg of product. This was redissolved in toluene (5 mL) and the solvent evaporated (×2) to give 113 mg of product (113 mg, 84% pure). This was used directly in the subsequent reaction.

LCMS (2 min Formic): Rt=0.73 min, [MH]+=394 (OMe adduct).

Intermediate 197: rac-(2S,3R,4R)-1-acetyl-4-(((benzyloxy)carbonyl)amino)-2-cyclopropyl-3-methyl-1,2,3,4-tetrahydroquinoline-6-carboxylic Acid

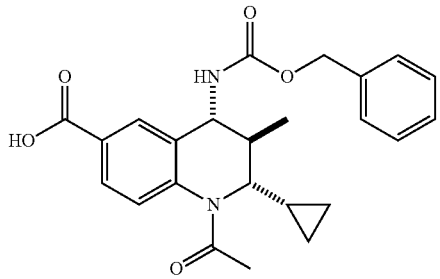 [SMILES: CC(=O)N1c2ccc(C(=O)O)cc2[C@H](NC(=O)OCc2ccccc2)[C@@H](C)[C@@H]1C1CC1]

A sample of rac-(2S,3R,4R)-ethyl 1-acetyl-4-(((benzyloxy)carbonyl)amino)-2-cyclopropyl-3-methyl-1,2,3,4-tetrahydroquinoline-6-carboxylate (for a preparation see Intermediate 194, 4.4907 g, 4.68 mmol) was dissolved in ethanol (10 mL). To this was added lithium hydroxide (0.224 g, 9.37 mmol) slowly, and the reaction was stirred at rt for ~1 h. After stirring overnight a further 0.5 eq lithium hydroxide was added (116 mg) and the mixture continued to be stirred for ~1.5 h. The reaction mixture was neutralised with 2M hydrochloric acid, and extracted with ethyl acetate. The aqueous layer was washed a further 2 times with ethyl acetate, and the combined organic layers were concentrated in vacuo to afford a yellow gum. This solid was dissolved in methanol and loaded onto a 50 g aminopropyl NH$_2$ SPE cartridge which had been pre-equilibrated with methanol. The column was eluted with 3 CVs of methanol, and then the product was eluted off with 3 CVs of 2M acetic acid in methanol. The appropriate fractions were collected and concentrated in vacuo to afford a pale yellow oil (2.6099 g, 3.71 mmol, 79%). LCMS (2 min Formic): Rt=0.94 min, [MH]+=423.

Intermediate 198: rac-benzyl ((2S,3R,4R)-1-acetyl-6-(chlorocarbonyl)-2-cyclopropyl-3-methyl-1,2,3,4-tetrahydroquinolin-4-yl)carbamate

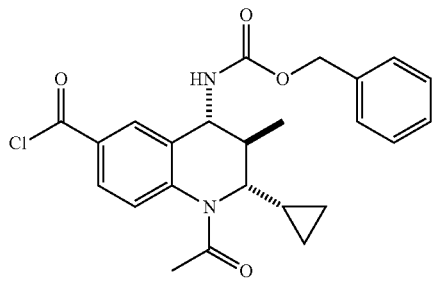 [SMILES: CC(=O)N1c2ccc(C(=O)Cl)cc2[C@H](NC(=O)OCc2ccccc2)[C@@H](C)[C@@H]1C1CC1]

To a reaction vessel rac-(2S,3R,4R)-1-acetyl-4-(((benzyloxy)carbonyl)amino)-2-cyclopropyl-3-methyl-1,2,3,4-tetrahydroquinoline-6-carboxylic acid (for a preparation see Intermediate 197, 2.604 g, 6.16 mmol) was added in dichloromethane (DCM) (30 mL) under nitrogen. Thionyl chloride (2 mL, 27.4 mmol) was added and the reaction left to stir at rt for 30 min. The reaction mixture was left to stir for a further 20 min and thionyl chloride (0.5 mL, 6.85 mmol) was added. The reaction solution was concentrated in vacuo to give 2.801 g of product as a yellow solid. This was redissolved in DCM (30 mL) and the solvent evaporated (×2) to give 2.75 g of product. This was used directly in the next experiment. LCMS (2 min Formic): Rt=1.09 min, [MH]+=437 (OMe adduct).

Intermediate 199: rac-(2S,3R,4R)-1-acetyl-4-amino-2-cyclopropyl-N,3-dimethyl-1,2,3,4-tetrahydroquinoline-6-carboxamide

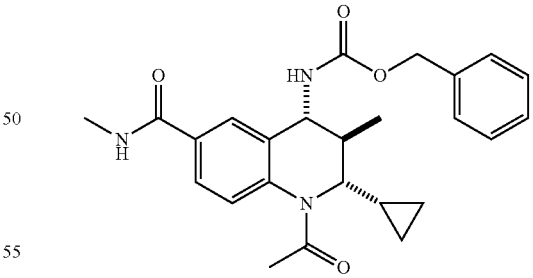

To a reaction vessel containing rac-benzyl ((2S,3R,4R)-1-acetyl-6-(chlorocarbonyl)-2-cyclopropyl-3-methyl-1,2,3,4-tetrahydroquinolin-4-yl)carbamate (for a preparation see Intermediate 198, 2.8 g, 6.35 mmol). Methylamine 2M in THF (20 mL, 40.0 mmol) and DIPEA (12 mL, 68.7 mmol) were added and the reaction left to stir for 15 min at rt under N$_2$. The solution was concentrated in vacuo to give 3.072 g of crude product as a yellow solid. This was purified by chromatography on silica (100 g, eluting with 0-100% ethyl acetate/DCM over 15 CVs). The fractions containing mostly product were combined and concentrated in vacuo to give product (540 mg). The fractions containing product and a substantial impurity were combined and concentrated in vacuo to give impure product. This was purified by chromatography on silica (100 g, eluting with 0-5% methanol/ DCM). The fractions containing product were combined and concentrated in vacuo to give the product as a white solid (1.408 g, 3.23 mmol, 50.9%).

LCMS (2 min Formic): Rt=0.91 min, [MH]⁺=436.

Intermediate 200: rac-(2S,3R,4R)-1-acetyl-4-amino-2-cyclopropyl-N,3-dimethyl-1,2,3,4-tetrahydroquinoline-6-carboxamide

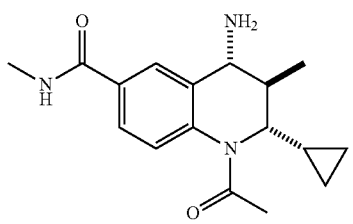 [SMILES: CNC(=O)c1ccc2c(c1)[C@H](N)[C@@H](C)[C@H](C1CC1)N2C(C)=O]

To solution of rac-benzyl ((2S,3R,4R)-1-acetyl-2-cyclopropyl-3-methyl-6-(methylcarbamoyl)-1,2,3,4-tetrahydroquinolin-4-yl)carbamate (for a preparation see Intermediate 199, 1.408 g, 3.23 mmol) in ethanol (50 mL), 10% Pd/C (0.172 g) was added and the reaction was left to stir under a hydrogen atmosphere for 16 h. The mixture was filtered through celite and the celite washed with ethyl acetate (3×20 mL). The combined filtrates were concentrated in vacuo to give 1.204 g of crude product. This was purified by chromatography on silica (25 g, eluting with 0-7% 2 M ammonia in methanol/DCM). The fractions were combined and concentrated in vacuo to give the product as a white solid (847 mg, 2.81 mmol, 87%). LCMS (2 min Formic): Rt=0.45 min, [M]⁺=285 (loss of NH₂⁻).

Intermediate 201: rac-(2S,3S,4R)-ethyl 4-(((benzyloxy)carbonyl)amino)-2,3-dimethyl-1,2,3,4-tetrahydroquinoline-6-carboxylate

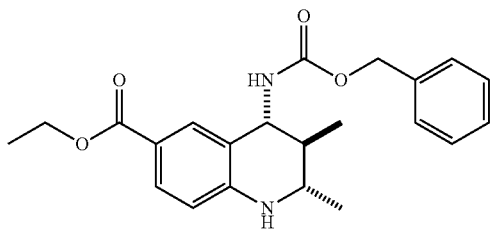 [SMILES: CCOC(=O)c1ccc2c(c1)[C@H](NC(=O)OCc1ccccc1)[C@@H](C)[C@H](C)N2]

To a solution of ethyl 4-aminobenzoate (2.04 g, 12.35 mmol) in anhydrous DCM (24 mL) was added acetaldehyde (0.7 mL, 12.39 mmol) and the mixture stirred under nitrogen at rt for 1 h. The reaction mixture was cooled to 0° C. and to this diphenyl hydrogen phosphate (0.309 g, 1.235 mmol) in anhydrous DCM (12 mL) was added followed by (E)-benzyl prop-1-en-1-ylcarbamate (for a preparation see Intermediate 1, 2.36 g, 12.34 mmol) in anhydrous DCM (12 mL). The mixture was stirred at 0° C. for 1 h then allowed to warm to rt over 2 h. The reaction mixture was washed with sat. NaHCO₃ (aq) solution (50 mL) and the aqueous layer was extracted with DCM (30 mL). The combined organic washings were washed with water (60 mL), dried through a hydrophobic frit and concentrated in vacuo. The gum was dissolved in DCM (10 mL) which was loaded onto a 100 g silica cartridge and purified using a gradient of 0-60% EtOAc in cyclohexane over 10 CVs. The appropriate fractions were combined and the solvent removed by rotary evaporation to give 4.2 g solid. The solid was dissolved in hot EtOAc (10 mL) and allowed to cool to rt. The resulting precipitate was filtered, washed with EtOAc (10 mL) and dried in a vacuum oven to give the title compound as a white amorphous solid (1.46 g, 56% purity).

LCMS (2 min HpH): Rt=1.20 min, [MH]⁺=383.

Intermediate 202: rac-(2S,3R,4R)-ethyl 1-acetyl-4-(((benzyloxy)carbonyl)amino)-2,3-dimethyl-1,2,3,4-tetrahydroquinoline-6-carboxylate

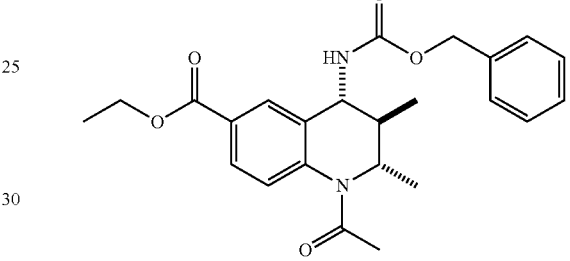

A solution of rac-(2S,3S,4R)-ethyl 4-(((benzyloxy)carbonyl)amino)-2,3-dimethyl-1,2,3,4-tetrahydroquinoline-6-carboxylate (for a preparation see Intermediate 201, 1.46 g, 3.82 mmol) in acetic anhydride (10 mL, 106 mmol) was stirred under nitrogen at 140° C. for 1 h. The reaction mixture was allowed to cool to rt and diluted with EtOAc (20 mL). The organic layer was stirred vigorously with 1 M NaOH (aq) (20 mL), separated and the process repeated. The organic layer was washed with water (20 mL), dried through a hydrophobic frit and the solvent evaporated under vacuum. The oil was dissolved in DCM (8 mL), applied to a 100 g silica cartridge and purified using a gradient of 0-80% EtOAc in cyclohexane over 8 CVs. The appropriate fractions were combined and the solvent removed by rotary evaporation to give the title compound as an off-white foam (1.39 g, 75% purity). LCMS (2 min Formic): Rt=1.11 min, [MH]⁺=425.

Intermediate 203: rac-(2S,3R,4R)-ethyl 1-acetyl-4-amino-2,3-dimethyl-1,2,3,4-tetrahydroquinoline-6-carboxylate

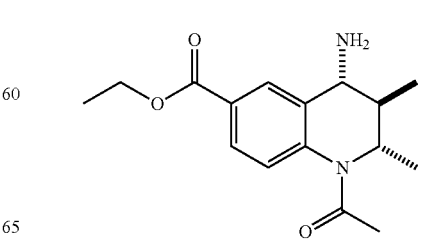

A solution of rac-(2S,3R,4R)-ethyl 1-acetyl-4-(((benzyloxy)carbonyl)amino)-2,3-dimethyl-1,2,3,4-tetrahydroquinoline-6-carboxylate (for a preparation see Intermediate 202, 1.39 g, 3.27 mmol) in ethanol (15 mL) was added to 10 wt. % palladium on carbon (140 mg, 1.316 mmol) and the mixture stirred under an atmosphere of hydrogen at rt for 16 h. The reaction mixture was filtered through celite and the cake washed with EtOH (80 mL). The filtrate was evaporated in vacuo and the gum dissolved in MeOH (5 mL). The solution was applied to a MeOH-preconditioned 25 g SCX-2 cartridge. The cartridge was washed with MeOH (40 mL) followed by 2M ammonia in MeOH solution (40 mL). The basic wash was evaporated under vacuum and dried in a vacuum oven to give the title compound as a yellow oil (943 mg, 3.25 mmol, 99%, 87% purity).

LCMS (2 min HpH): Rt=0.82 min, [M]$^+$=274 (loss of NH$_2^-$).

Intermediate 204: rac-(2S,3S,4R)-ethyl 4-(((benzyloxy)carbonyl)amino)-2-ethyl-3-methyl-1,2,3,4-tetrahydroquinoline-6-carboxylate

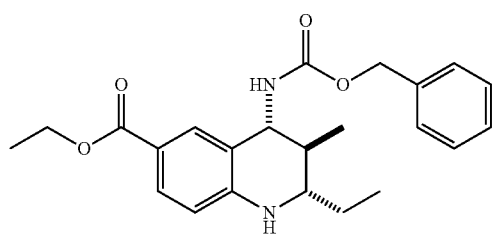 [SMILES: CCOC(=O)c1ccc2c(c1)[C@H](NC(=O)OCc1ccccc1)[C@@H](C)[C@H](CC)N2]

To a solution of ethyl 4-aminobenzoate (2.02 g, 12.23 mmol) in anhydrous DCM (24 mL) was added propionaldehyde (0.91 mL, 12.22 mmol) and the mixture stirred under nitrogen at r.t. for 1 h. The reaction mixture was cooled to 0° C. and to this diphenyl hydrogen phosphate (0.306 g, 1.223 mmol) in anhydrous DCM (12 mL) was added followed by (E)-benzyl prop-1-en-1-ylcarbamate (for a preparation see Intermediate 1, 2.34 g, 12.24 mmol) in anhydrous DCM (12 mL). The mixture was stirred at 0° C. for 1 h then allowed to warm to rt over 2 h. The reaction mixture was washed with sat. NaHCO$_3$ (aq) solution (50 mL) and the aqueous layer extracted with DCM (30 mL). The organics were combined, washed with water (60 mL), dried through a hydrophobic frit and concentrated in vacuo. The solid was dissolved in hot EtOAc (10 mL) and the solution allowed to cool to rt. The resulting precipitate was isolated by vacuum filtration and dried in a vacuum oven to give the title compound as a white amorphous solid (2.22 g, 5.60 mmol, 46%).

LCMS (2 min HpH): Rt=1.26 min, [MH]$^+$=397.

Intermediate 205: rac-(2S,3S,4R)-ethyl 1-acetyl-4-(((benzyloxy)carbonyl)amino)-2-ethyl-3-methyl-1,2,3,4-tetrahydroquinoline-6-carboxylate

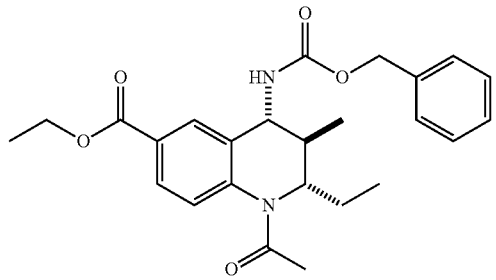 [SMILES: CCOC(=O)c1ccc2c(c1)[C@H](NC(=O)OCc1ccccc1)[C@@H](C)[C@H](CC)N2C(C)=O]

A solution of rac-(2S,3S,4R)-ethyl 4-(((benzyloxy)carbonyl)amino)-2-ethyl-3-methyl-1,2,3,4-tetrahydroquinoline-6-carboxylate (for a preparation see Intermediate 204, 2.10 g, 5.30 mmol) in acetic anhydride (15 mL, 159 mmol) was stirred under nitrogen at 140° C. for 2.5 h. The reaction mixture was allowed to cool to rt and diluted with EtOAc (30 mL). The organic layer was stirred vigorously with 1 M NaOH (aq) (30 mL), separated and the process repeated. The organic layer was washed with water (30 mL), dried through a hydrophobic frit and the solvent evaporated under vacuum. The oil was dissolved in DCM (8 mL), applied to a 100 g silica cartridge and purified using a gradient of 0-100% EtOAc in cyclohexane over 10 CVs. The appropriate fractions were combined and the solvent removed by rotary evaporation to give the title compound as an off-white foam (2.33 g, 5.31 mmol, 100%). LCMS (2 min HpH): Rt=1.18 min, [MH]$^+$=439.

Intermediate 206: rac-(2S,3R,4R)-ethyl 1-acetyl-4-amino-2-ethyl-3-methyl-1,2,3,4-tetrahydroquinoline-6-carboxylate

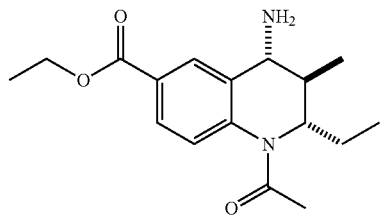 [SMILES: CCOC(=O)c1ccc2c(c1)[C@H](N)[C@@H](C)[C@H](CC)N2C(C)=O]

To a solution of rac-(2S,3R,4R)-ethyl 1-acetyl-4-(((benzyloxy)carbonyl)amino)-2-ethyl-3-methyl-1,2,3,4-tetrahydroquinoline-6-carboxylate (for a preparation see Intermediate 205, 2.33 g, 5.31 mmol) in ethanol (25 mL) was added to 10 wt. % palladium on carbon (233 mg, 2.189 mmol) and the mixture stirred under an atmosphere of hydrogen at rt for 24 h. The reaction mixture was filtered through celite and the cake washed with EtOH (80 mL). The filtrate was evaporated in vacuo and the gum dissolved in MeOH (5 mL). The solution was applied to a MeOH-preconditioned 50 g SCX-2 cartridge. The cartridge was washed with MeOH (80 mL) followed by 2M ammonia in MeOH solution (80 mL). The basic wash was evaporated under vacuum and dried in a vacuum oven to give the title compound as a yellow oil (1.62 g, 5.32 mmol, 100%).

LCMS (2 min HpH): Rt=0.89 min, [M]⁺=288 (loss of NH₂⁻).

Intermediate 207: rac-1-((2S,3R,4R)-1-acetyl-2-cyclopropyl-3-methyl-1,2,3,4-tetrahydroquinolin-4-yl)thiourea

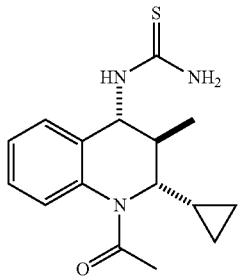 [SMILES: CC(=O)N1c2ccccc2[C@H](NC(N)=S)[C@@H](C)[C@@H]1C1CC1]

rac-1-((2S,3R,4RS)-4-amino-2-cyclopropyl-3-methyl-3,4-dihydroquinolin-1(2H)-yl)ethanone (For a preparation see Intermediate 14, 75 mg, 0.307 mmol) and benzoyl isothiocyanate (0.041 mL, 0.307 mmol) in DCM (0.5 mL) were stirred at rt overnight. The solvent was evaporated and the residue redissolved in methanol (0.5 mL), THF (0.5 mL) and water (0.5 mL). Potassium carbonate (212 mg, 1.535 mmol) was added and the reaction stirred at rt for 4 h. The solvent was evaporated, the residue partitioned between water (10 mL) and EtOAc (20 mL) and the aqueous layer extracted with EtOAc (2×20 mL). Combined organics were washed with brine, dried (MgSO₄) and evaporated to dryness. This was purified by silica chromatography (0-7% 2M NH₃ in MeOH/DCM) to afford the product (70 mg) as a clear oil. LCMS (2 min HpH): Rt=0.75 min, [MH]⁺=304.

Intermediate 208: benzyl ((2S,3S,4R)-6-bromo-2,3-dimethyl-1,2,3,4-tetrahydroquinolin-4-yl)carbamate

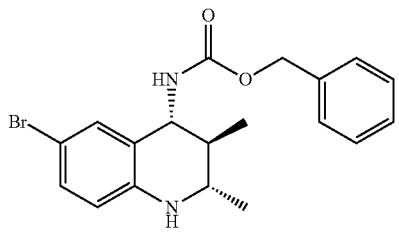 [SMILES: C[C@H]1[C@H](C)Nc2ccc(Br)cc2[C@@H]1NC(=O)OCc1ccccc1]

A solution of 4-bromoaniline (3 g, 17.44 mmol) and acetaldehyde (1.468 mL, 26.2 mmol) in dry DCM (110 mL) was stirred under nitrogen at rt for 1 h and then cooled to 0° C. Solutions of (11 bS)-2,6-bis(4-chlorophenyl)-4-hydroxy-8,9,10,11,12,13,14,15-octahydrodinaphtho[2,1-d:1',2'-f][1,3,2]dioxaphosphepine 4-oxide (for a preparation see JACS, 2011, 133, 14804, 0.101 g, 0.174 mmol) in dry DCM (20 mL) followed by (E)-benzyl prop-1-en-1-ylcarbamate (for a preparation see Intermediate 1, 3.67 g, 19.18 mmol) in dry DCM (20 mL) were added. The reaction was stirred at 0° C. overnight. The reaction mixture was warmed to rt, washed with sat. aq. NaHCO₃ (100 mL) and the aqueous layer was extracted with DCM (100 mL). The combined organics were dried through a hydrophobic frit and the solvent was removed by rotary evaporation to leave the crude product. The crude material was loaded onto a 100 g silica column and eluted using a graduating solvent system of 0-30% EtOAc/cyclohexane. Combination and evaporation of the desired fractions gave the product. This was dissolved in a minimum of hot EtOAc (~10 mL) and diluted with cyclohexane (70 mL). The solution was allowed to cool and placed in the fridge overnight. The resulting white crystals were filtered washing with cool 10% EtOAc/cyclohexane before being dried in the vacuum oven to give the product as a white crystalline solid (2.1 g). Analysis by chiral HPLC was undertaken using a 250×4.6 mm Chiralpak IC column eluting with 10% ethanol in heptanes (plus 0.1% isopropylamine) at a flow rate of 1 mL/min. Peak 1/minor enantiomer (3.1%) eluted at 6.4 min, and Peak 2/major enantiomer (96.9% by UV) eluted at 8.1 min. This indicated the product had a ee of 94%.
LCMS (2 min Formic): Rt=1.22 min, [MH]⁺=389, 391.

Intermediate 209: benzyl ((2S,3R,4R)-1-acetyl-6-bromo-2,3-dimethyl-1,2,3,4-tetrahydroquinolin-4-yl)carbamate

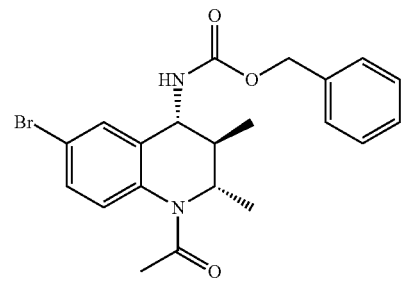 [SMILES: CC(=O)N1c2ccc(Br)cc2[C@H](NC(=O)OCc2ccccc2)[C@@H](C)[C@@H]1C]

A solution of benzyl ((2S,3S,4R)-6-bromo-2,3-dimethyl-1,2,3,4-tetrahydroquinolin-4-yl)carbamate (for a preparation see Intermediate 208, 2.0 g, 5.14 mmol) and pyridine (1.25 mL, 15.4 mmol) in DCM (37 mL) was treated with acetyl chloride (0.88 mL, 12.3 mmol) and the reaction mixture stirred at rt for 3 h. The reaction mixture was washed with HCl (1M, 40 mL), followed by saturated NaHCO₃ (aq., 40 mL) and the organic layer isolated then concentrated under reduced pressure to give the desired product as a white solid (2.22 g). LCMS (2 min Formic): Rt=1.12 min, [MH]⁺=431, 433.

Intermediate 210: benzyl ((2S,3S,4R)-2,3-dimethyl-6-morpholino-1,2,3,4-tetrahydroquinolin-4-yl)carbamate

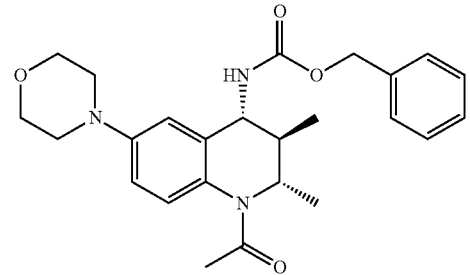 [SMILES: CC(=O)N1c2ccc(N3CCOCC3)cc2[C@H](NC(=O)OCc2ccccc2)[C@@H](C)[C@@H]1C]

A solution of DavePhos (0.091 g, 0.232 mmol), morpholine (0.404 mL, 4.64 mmol), rac-benzyl ((2S,3R,4R)-1-acetyl-6-bromo-2,3-dimethyl-1,2,3,4-tetrahydroquinolin-4-yl)carbamate (for a preparation see Intermediate 209, 1.00 g, 2.32 mmol) and Pd$_2$(dba)$_3$ (0.212 g, 0.232 mmol) in toluene (30 mL) was treated with sodium tert-butoxide (0.446 g, 4.64 mmol) and the reaction mixture heated at 110° C. for 1 hr then concentrated under reduced pressure. Material was suspended in EtOAc then filtered through a pad of celite, which was washed with EtOAc then combined EtOAc washes concentrated under reduced pressure. Crude material was purified by silica column chromatography, eluting with a gradient 0 to 100% of EtOAc in cyclohexane to give the desired product as clear, colourless gum (360 mg). LCMS (2 min Formic): Rt=0.96 min, [MH]$^+$=438.

Intermediate 211: rac-1-((2S,3R,4R)-4-amino-2,3-dimethyl-6-morpholino-3,4-dihydroquinolin-1(2H)-yl)ethanone

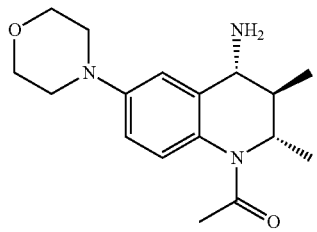 [SMILES: CC(=O)N1c2ccc(N3CCOCC3)cc2[C@H](N)[C@@H](C)[C@@H]1C]

A solution of rac-benzyl ((2S,3R,4R)-1-acetyl-2,3-dimethyl-6-morpholino-1,2,3,4-tetrahydroquinolin-4-yl)carbamate (for a preparation see Intermediate 170, 1.1 g, 90% pure) and benzyl ((2S,3R,4R)-1-acetyl-2,3-dimethyl-6-morpholino-1,2,3,4-tetrahydroquinolin-4-yl)carbamate (for a preparation see Intermediate 210, 0.36 g, 94% ee) in ethanol (70 mL) was passed through a 10% Pd/C cartridge on an H-cube (rt, full H$_2$ mode) then recycled through the machine for a total of 6 hr. The resulting filtrate was concentrated under reduced pressure to give desired product as a pale yellow amorphous solid (1.0 g, 72% purity, ~25% ee). LCMS (2 min Formic): Rt=0.46 min, [MH]$^+$=304.

Intermediates 212: tert-butyl 4-((2S,3R,4R)-1-acetyl-4-(((benzyloxy)carbonyl)amino)-2,3-dimethyl-1,2,3,4-tetrahydroquinolin-6-yl)piperazine-1-carboxylate

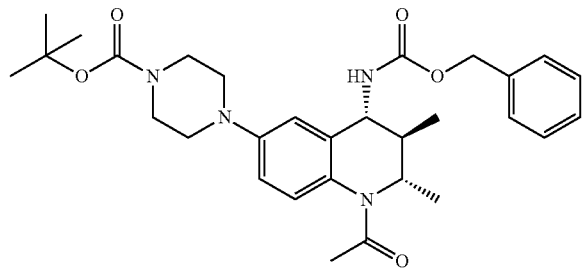 [SMILES: CC(=O)N1c2ccc(N3CCN(C(=O)OC(C)(C)C)CC3)cc2[C@H](NC(=O)OCc2ccccc2)[C@@H](C)[C@@H]1C]

A solution of DavePhos (9 mg, 0.023 mmol), tert-butyl piperazine-1-carboxylate (0.086 mL, 0.464 mmol), benzyl ((2S,3R,4R)-1-acetyl-6-bromo-2,3-dimethyl-1,2,3,4-tetrahydroquinolin-4-yl)carbamate (for a preparation see Intermediate 209, 100 mg, 0.232 mmol, Pd$_2$(dba)$_3$ (21 mg, 0.023 mmol) and sodium tert-butoxide (45 mg, 0.468 mmol) in toluene (2 mL) was heated at 110° C. under nitrogen for 1 h. Separately a solution of DavePhos (0.091 g, 0.23 mmol), tert-butyl piperazine-1-carboxylate (0.86 mL, 4.64 mmol), benzyl ((2S,3R,4R)-1-acetyl-6-bromo-2,3-dimethyl-1,2,3,4-tetrahydroquinolin-4-yl)carbamate (1 g, 2.318 mmol) and Pd$_2$(dba)$_3$ (0.212 g, 0.232 mmol) in toluene (30 mL) was treated with sodium tert-butoxide (0.446 g, 4.64 mmol) and the reaction mixture heated at 110° C. for 1 h then concentrated under reduced pressure. Material was suspended in EtOAc, combined with the previous smaller batch of material, and combined batches filtered through a 10 g pad of celite which was washed with further EtOAc. Combined EtOAc washes were concentrated under reduced pressure and crude material was purified by silica column chromatography, eluting with a 0 to 100% gradient to give the product (360 mg). LCMS (2 min Formic): Rt=1.18 min, [MH]$^+$=537.

Intermediate 213: tert-butyl 4-((2S,3R,4R)-1-acetyl-4-amino-2,3-dimethyl-1,2,3,4-tetrahydroquinolin-6-yl)piperazine-1-carboxylate

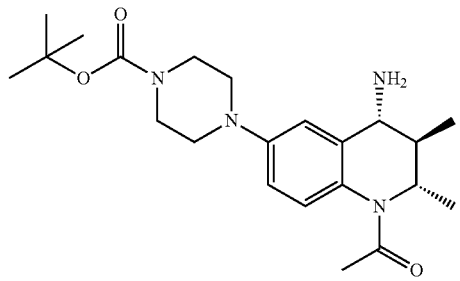 [SMILES: CC(=O)N1c2ccc(N3CCN(C(=O)OC(C)(C)C)CC3)cc2[C@H](N)[C@@H](C)[C@@H]1C]

A solution of tert-butyl 4-((2S,3R,4R)-1-acetyl-4-(((benzyloxy)carbonyl)amino)-2,3-dimethyl-1,2,3,4-tetrahydroquinolin-6-yl)piperazine-1-carboxylate (for a preparation see Intermediate 212, 360 mg, 0.671 mmol) in ethanol (14 mL) was passed through a 10% Pd/C cartridge on an H-cube (RT, full H$_2$ mode) then recycled through the machine for a total of 8 h. The resulting filtrate was combined with the previous batch of tert-butyl 4-((2S,3R,4R)-1-acetyl-4-amino-2,3-dimethyl-1,2,3,4-tetrahydroquinolin-6-yl)piperazine-1-carboxylate (400 mg), concentrated under reduced pressure to give desired product as a grey/brownish amorphous solid (550 mg, 80% purity).

LCMS (2 min Formic): Rt=0.71 min, [MH]$^+$=403.

Intermediate 214: tert-butyl 4-((2S,3R,4R)-1-acetyl-4-((4-cyanophenyl)amino)-2,3-dimethyl-1,2,3,4-tetrahydroquinolin-6-yl)piperazine-1-carboxylate

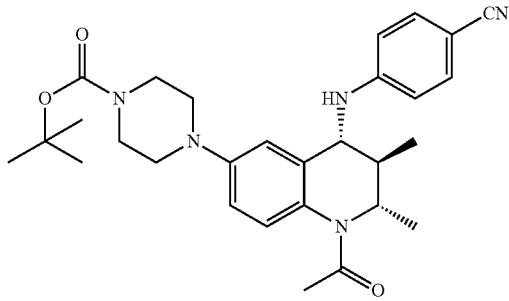 [SMILES: CC(=O)N1c2ccc(N3CCN(C(=O)OC(C)(C)C)CC3)cc2[C@H](Nc2ccc(C#N)cc2)[C@@H](C)[C@@H]1C]

A microwave vial was charged with tert-butyl 4-((2S,3R,4R)-1-acetyl-4-amino-2,3-dimethyl-1,2,3,4-tetrahydroquinolin-6-yl)piperazine-1-carboxylate (for a preparation see Intermediate 213, 69 mg, 0.151 mmol) in 1,4-dioxane (2 mL) followed by 4-bromobenzonitrile (51 mg, 0.280 mmol), then sodium tert-butoxide (27 mg, 0.281 mmol), DavePhos (12 mg, 0.030 mmol), and Pd$_2$(dba)$_3$ (26 mg, 0.028 mmol). The reaction mixture was heated to 100° C. for 45 min using a microwave reactor, then diluted with EtOAc and filtered through a pad of celite. The celite pad was washed with EtOAc (10 mL) and the filtrate concentrated under reduced pressure. The residue was purified by MDAP (Formic). The desired fractions were combined and evaporated in vacuo to afford the desired product as a white solid (22 mg). LCMS (2 min Formic): Rt=1.15 min, [MH]$^+$=504.

Intermediate 215: tert-butyl 4-((2S,3R,4R)-1-acetyl-2,3-dimethyl-4-((4-methylpyrimidin-2-yl)amino)-1,2,3,4-tetrahydroquinolin-6-yl)piperazine-1-carboxylate

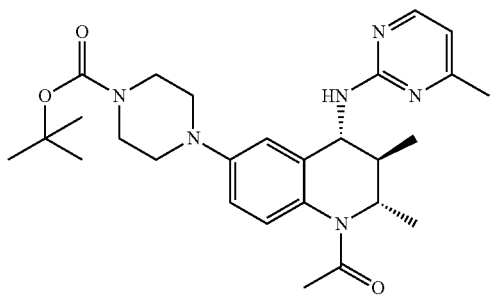 [SMILES: CC(=O)N1c2ccc(N3CCN(C(=O)OC(C)(C)C)CC3)cc2[C@H](Nc2nccc(C)n2)[C@@H](C)[C@@H]1C]

A microwave vial was charged with tert-butyl 4-((2S,3R,4R)-1-acetyl-4-amino-2,3-dimethyl-1,2,3,4-tetrahydroquinolin-6-yl)piperazine-1-carboxylate (for a preparation see Intermediate 213, 69 mg, 0.151 mmol) in 1,4-dioxane (2 mL) followed by 2-bromo-4-methylpyrimidine (49 mg, 0.283 mmol), then sodium tert-butoxide (27 mg, 0.281 mmol), DavePhos (12 mg, 0.030 mmol), and Pd$_2$(dba)$_3$ (26 mg, 0.028 mmol). The reaction mixture was heated to 100° C. for 45 min using a microwave reactor, then diluted with EtOAc and filtered through a pad of celite. The celite pad was washed with EtOAc (10 mL) and the filtrate concentrated under reduced pressure. The residue was purified by MDAP (Formic). The desired fractions were combined and evaporated in vacuo to afford the desired product as a pale brown gum (14 mg). LCMS (2 min Formic): Rt=1.01 min, [MH]$^+$=495.

Intermediate 216: tert-butyl 4-((2S,3R,4R)-1-acetyl-2,3-dimethyl-4-((4-(methylcarbamyl))phenyl)amino)-1,2,3,4-tetrahydroquinolin-6-yl)piperazine-1-carboxylate

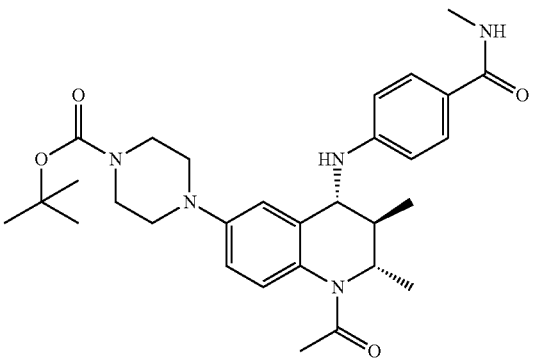 [SMILES: CNC(=O)c1ccc(N[C@H]2c3cc(N4CCN(C(=O)OC(C)(C)C)CC4)ccc3N(C(C)=O)[C@@H](C)[C@@H]2C)cc1]

A microwave vial was charged with tert-butyl 4-((2S,3R,4R)-1-acetyl-4-amino-2,3-dimethyl-1,2,3,4-tetrahydroquinolin-6-yl)piperazine-1-carboxylate (for a preparation see Intermediate 213, 69 mg, 0.151 mmol) in 1,4-dioxane (2 mL) followed by 4-bromo-N-methylbenzamide (61 mg, 0.285 mmol), then sodium tert-butoxide (27 mg, 0.281 mmol), DavePhos (12 mg, 0.030 mmol), and Pd$_2$(dba)$_3$ (26 mg, 0.028 mmol). The reaction mixture was heated to 100° C. for 45 min using a microwave reactor, then diluted with EtOAc and filtered through a pad of celite. The celite pad was washed with EtOAc (10 mL) and the filtrate concentrated under reduced pressure. The residue was purified by MDAP (Formic). The desired fractions were combined and evaporated in vacuo to afford the desired product as a pale brown gum (13 mg). LCMS (2 min Formic): Rt=0.99 min, [MH]$^+$=536.

Intermediate 217: tert-butyl 4-((2S,3R,4R)-1-acetyl-2,3-dimethyl-4-((5-methylpyrazin-2-yl)amino)-1,2,3,4-tetrahydroquinolin-6-yl)piperazine-1-carboxylate

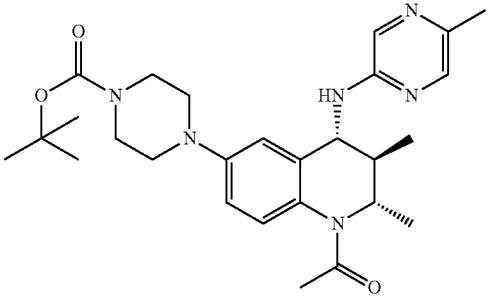 [SMILES: CC(=O)N1c2ccc(N3CCN(C(=O)OC(C)(C)C)CC3)cc2[C@H](Nc2cnc(C)cn2)[C@@H](C)[C@@H]1C]

A microwave vial was charged with tert-butyl 4-((2S,3R,4R)-1-acetyl-4-amino-2,3-dimethyl-1,2,3,4-tetrahydroquinolin-6-yl)piperazine-1-carboxylate (for a preparation see Intermediate 213, 69 mg, 0.151 mmol) in 1,4-dioxane (2 mL) followed by 2-chloro-5-methylpyrazine (37 mg, 0.288 mmol), then sodium tert-butoxide (27 mg, 0.281 mmol), DavePhos (12 mg, 0.030 mmol), and Pd$_2$(dba)$_3$ (26 mg, 0.028 mmol). The reaction mixture was heated to 100° C. for 45 min using a microwave reactor, then diluted with EtOAc and filtered through a pad of celite. The celite pad was washed with EtOAc (10 mL) and the filtrate concentrated under reduced pressure. The residue was purified by MDAP (Formic). The desired fractions were combined and evaporated in vacuo to afford the desired product as a pale brown gum (10 mg). LCMS (2 min Formic): Rt=1.02 min, [MH]$^+$=495.

Intermediate 218: benzyl ((2S,3S,4R)-6-bromo-2-cyclopropyl-3-methyl-1,2,3,4-tetrahydroquinolin-4-yl)carbamate

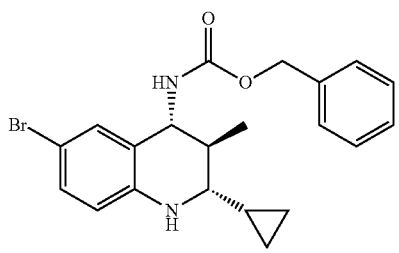 [SMILES: C[C@@H]1[C@@H](NC(=O)OCc2ccccc2)c2cc(Br)ccc2N[C@H]1C1CC1]

A solution of 4-bromoaniline (3 g, 17.44 mmol) and cyclopropanecarbaldehyde (1.303 mL, 17.44 mmol) in dry DCM (60 mL) was stirred under nitrogen at rt in a 250 mL Lara large scale reactor vessel for 90 min and then cooled to 0° C. Solutions of (11bS)-2,6-bis(4-chlorophenyl)-4-hydroxy-8,9,10,11,12,13,14,15-octahydrodinaphtho[2,1-d:1',2'-f][1,3,2]dioxaphosphepine 4-oxide (for a preparation see JACS, 2011, 133, 14804, 0.101 g, 0.174 mmol) in dry DCM (20 mL) followed by (E)-benzyl prop-1-en-1-ylcarbamate (for a preparation see Intermediate 1, 3.67 g, 19.18 mmol) in dry DCM (20 mL) were added. The reaction was stirred at 0° C. for 40 h. The reaction mixture was warmed to rt, washed with sat. aq. NaHCO$_3$ (150 mL) and the aqueous layer was extracted with DCM (2×100 mL). The combined organics were dried through a hydrophobic frit and the solvent was removed by rotary evaporation to leave the crude product. The crude product was recrystalised (dissolved in ~50 mL refluxing EtOAc, 50 mL cyclohexane added and cooled, the resulting crystals were then washed with cold cyclohexane) to afford the product (4.89 g, 11.77 mmol, 67.5%) as white needles. Analysis by chiral HPLC was undertaken using a 250×4.6 mm Chiralpak IC column eluting with 10% ethanol in heptane at a flow rate of 1 mL/min. Peak 1/minor enantiomer (<0.5% by UV) eluted at 6.5 min, and Peak 2/major enantiomer (>99.5% by UV) eluted at 11.5 min. This indicated the product had an ee of 99%. LCMS (2 min HpH): Rt=1.32 min, [MH]$^+$=415, 417.

Intermediate 219: benzyl ((2S,3R,4R)-1-acetyl-6-bromo-2-cyclopropyl-3-methyl-1,2,3,4-tetrahydroquinolin-4-yl)carbamate

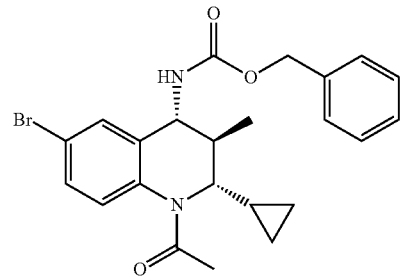 [SMILES: CC(=O)N1c2ccc(Br)cc2[C@H](NC(=O)OCc2ccccc2)[C@@H](C)[C@@H]1C1CC1]

A solution of benzyl ((2S,3S,4R)-6-bromo-2-cyclopropyl-3-methyl-1,2,3,4-tetrahydroquinolin-4-yl)carbamate (for a preparation see Intermediate 218, 4.8 g, 11.56 mmol) and pyridine (2.80 mL, 34.7 mmol) in anhydrous dichloromethane (DCM) (75 mL) was treated with acetyl chloride (0.986 mL, 13.87 mmol). The mixture was stirred at rt under an atmosphere of nitrogen overnight. The reaction was incomplete so further acetyl chloride (0.986 mL, 13.87 mmol) was added. The reaction mixture was transferred to a separating funnel and washed with 1M aq. HCl (75 mL) followed by sat. aq. NaHCO$_3$ (75 mL) and brine (75 mL). The organic layer was dried through a hydrophobic frit and the solvent was removed by rotary evaporation to give the crude product as a white solid (5.2 g). This was pure enough to use in subsequent steps.
LCMS (2 min Formic): Rt=1.19 min, [MH]$^+$=457, 459.

Intermediate 220: (S)-tert-butyl 4-((2S,3R,4R)-1-acetyl-4-amino-2-cyclopropyl-3-methyl-1,2,3,4-tetrahydroquinolin-6-yl)-2-methylpiperazine-1-carboxylate

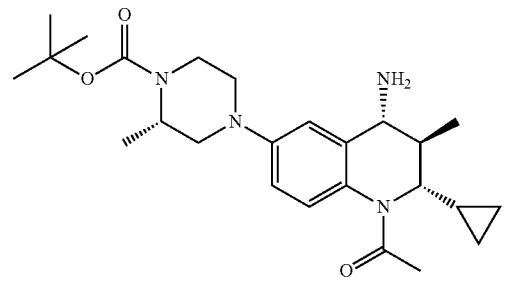 [SMILES: CC(=O)N1c2ccc(N3CCN(C(=O)OC(C)(C)C)[C@@H](C)C3)cc2[C@H](N)[C@@H](C)[C@@H]1C1CC1]

To a dried flask under nitrogen was added (S)-tert-butyl 2-methylpiperazine-1-carboxylate (0.531 g, 2.65 mmol), benzyl ((2S,3R,4R)-1-acetyl-6-bromo-2-cyclopropyl-3-methyl-1,2,3,4-tetrahydroquinolin-4-yl)carbamate (for a preparation see Intermediate 219, 1.01 g, 2.208 mmol), sodium tert-butoxide (0.424 g, 4.42 mmol), Pd$_2$(dba)$_3$ (115 mg, 0.126 mmol) and DavePhos (0.149 g, 0.378 mmol). The solids were all dissolved in 1,4-dioxane (10 mL), and the mixture was degassed with nitrogen for ~15 min. The mixture was then heated at 90° C. for 16 h. The reaction mixture was allowed to cool, washed through a 10 g celite cartridge with ethyl acetate and concentrated in vacuo to afford an orange oil. The residue was dissolved in methanol Intermediate 221: (S)-tert-butyl 4-((2S,3R,4R)-1-acetyl-2-cyclopropyl-4-((5-fluoropyridin-2-yl)amino)-3-methyl-1,2,3,4-tetrahydroquinolin-6-yl)-2-methylpiperazine-1-carboxylate

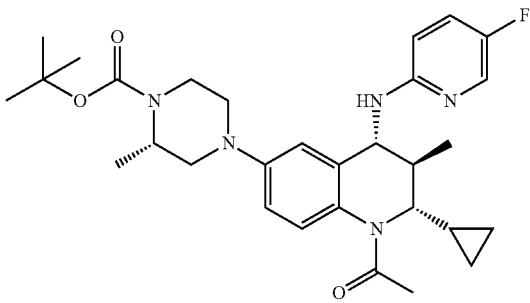 [SMILES: CC(=O)N1c2ccc(N3CCN(C(=O)OC(C)(C)C)[C@@H](C)C3)cc2[C@H](Nc2ccc(F)cn2)[C@@H](C)[C@@H]1C1CC1]

To a dried flask under nitrogen was added DavePhos (40.0 mg, 0.102 mmol), (S)-tert-butyl 4-((2S,3R,4R)-1-acetyl-4-amino-2-cyclopropyl-3-methyl-1,2,3,4-tetrahydroquinolin-6-yl)-2-methylpiperazine-1-carboxylate (for a preparation see Intermediate 220, 75 mg, 0.169 mmol), 2-bromo-5-fluoropyridine (35.8 mg, 0.203 mmol), Pd$_2$(dba)$_3$ (31.0 mg, 0.034 mmol) and sodium tert-butoxide (48.9 mg, 0.508 mmol). The reactants were dissolved in 1,4-dioxane (3 mL), and the solution was heated under nitrogen at 90° C. for 90 min. The mixture continued to be stirred at 45° C. overnight. A further portion of 2-bromo-5-fluoropyridine (1.2 eq) was added, and the mixture was stirred at 45° C. for ~1 h. A further portion of Pd$_2$(dba)$_3$ (0.2 eq) and DavePhos (0.6 eq) were added, and the mixture stirred at 90° C. for ~1 h. A further portion of 2-bromo-5-fluoropyridine (1.0 eq) was added and the mixture continued to stir at 90° C. for ~30 min. The reaction mixture was then filtered through a 2.5 g celite cartridge, washed through with ethyl acetate, and concentrated in vacuo. The residue was taken up in dichloromethane and loaded onto a 25 g silica flash column, and eluted by silica gel chromatography using 10-30% ethyl acetate in cyclohexane. The appropriate fractions were combined and concentrated in vacuo to afford the desired product (33.6 mg, 0.062 mmol, 36.9%). LCMS (2 min Formic): Rt=1.23 min, [MH]$^+$=538.

Intermediate 222: (S)-tert-butyl 4-((2S,3R,4R)-1-acetyl-2-cyclopropyl-4-(((6-methoxypyridin-2-yl)amino)-3-methyl-1,2,3,4-tetrahydroquinolin-6-yl)-2-methylpiperazine-1-carboxylate

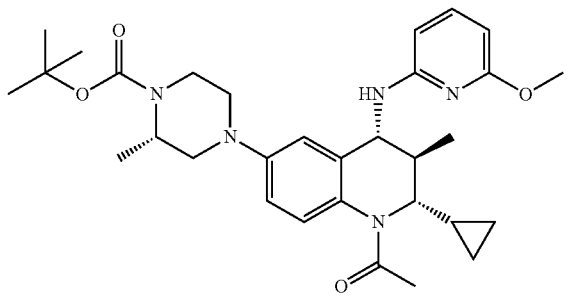 [SMILES: COc1cccc(N[C@H]2c3cc(N4CCN(C(=O)OC(C)(C)C)[C@@H](C)C4)ccc3N(C(C)=O)[C@@H](C3CC3)[C@@H]2C)n1]

To a dried flask under nitrogen was added DavePhos (40.0 mg, 0.102 mmol), (S)-tert-butyl 4-((2S,3R,4R)-1-acetyl-4-amino-2-cyclopropyl-3-methyl-1,2,3,4-tetrahydroquinolin-6-yl)-2-methylpiperazine-1-carboxylate (for a preparation see Intermediate 220, 75 mg, 0.169 mmol), 2-bromo-6-methoxypyridine (0.025 mL, 0.203 mmol), Pd$_2$(dba)$_3$ (31.0 mg, 0.034 mmol) and sodium tert-butoxide (48.9 mg, 0.508 mmol). The reactants were dissolved in 1,4-dioxane (3 mL), and the solution was heated under nitrogen at 90° C. for 90 min. The reaction mixture was allowed to cool, filtered over a 2.5 g celite cartridge, and washed through with ethyl acetate. The solution was concentrated in vacuo to afford a dark brown oil. This crude residue was dissolved in dichloromethane, loaded onto a 10 g silica flash cartridge and eluted by silica gel chromatography in 0-30% ethyl acetate in cyclohexane. The appropriate fractions were collected and concentrated in vacuo to afford a yellow oil (62.8 mg, 0.114 mmol, 67.4%).

LCMS (2 min Formic): Rt=1.32 min, [MH]$^+$=550.

Intermediate 223: (2S,3S,4R)-ethyl 4-(((benzyloxy)carbonyl)amino)-2-cyclopropyl-3-methyl-1,2,3,4-tetrahydroquinoline-6-carboxylate

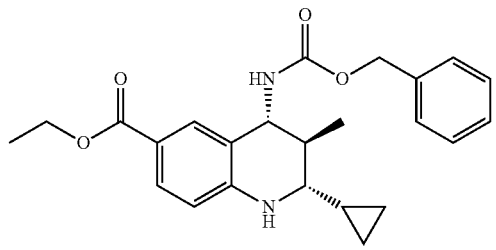 [SMILES: CCOC(=O)c1ccc2c(c1)[C@H](NC(=O)OCc1ccccc1)[C@@H](C)[C@H](C1CC1)N2]

To a solution of cyclopropanecarbaldehyde (1.357 mL, 18.16 mmol) in anhydrous dichloromethane (DCM) (35.6 ml), was added ethyl 4-aminobenzoate (3 g, 18.16 mmol) and the reaction stirred at RT for 1 hr. The reaction was cooled to 0° C. (11 bS)-2,6-bis(4-chlorophenyl)-4-hydroxy-8,9,10,11,12,13,14,15-octahydrodinaphtho[2,1-d:1',2'-f][1,3,2]dioxaphosphepine 4-oxide (for a preparation see JACS, 2011, 133, 14804, 0.105 g, 0.182 mmol) in anhydrous dichloromethane (DCM) (17.82 mL) was added and then (E)-benzyl prop-1-en-1-ylcarbamate (for a preparation see Intermediate 1, 3.47 g, 18.16 mmol) in anhydrous dichloromethane (DCM) (17.82 ml). The reaction was then left to stir at 0° C. for 18 h under $N_2$. The reaction mixture was washed with sat. $NaHCO_3$ solution (60 mL) and the aqueous layer extracted with DCM (3×60 mL). The combined organics were dried through a hydrophobic frit and concentrated in vacuo. The crude product was recrystalised from EtOAc/cyclohexane to afford the product (5.13 g) as white crystals. Analysis by chiral HPLC was undertaken using a 250×4.6 mm Chiralpak IC column eluting with 30% ethanol in heptane at a flow rate of 1 mL/min. Peak 1/minor enantiomer (<0.5%) eluted at 5.9 min, and Peak 2/major enantiomer (>99.5% by UV) eluted at 11.8 min. This indicated the product had an ee of >99%. LCMS (2 min HpH): Rt=1.27 min, $[MH]^+$=409.

Intermediate 224: (2S,3S,4R)-ethyl 1-acetyl-4-(((benzyloxy)carbonyl)amino)-2-cyclopropyl-3-methyl-1,2,3,4-tetrahydroquinoline-6-carboxylate

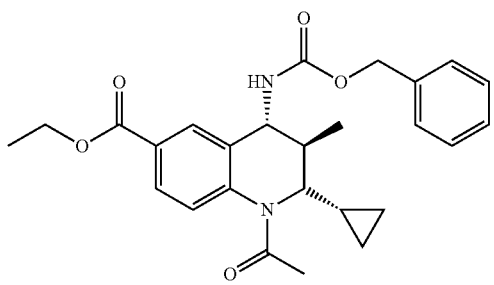

A solution of (2S,3S,4R)-ethyl 4-(((benzyloxy)carbonyl)amino)-2-cyclopropyl-3-methyl-1,2,3,4-tetrahydroquinoline-6-carboxylate (for a preparation see Intermediate 223, 5.08 g, 12.44 mmol) and pyridine (3.02 ml, 37.3 mmol) in dichloromethane (DCM) (100 ml) was treated with acetyl chloride (1.061 ml, 14.92 mmol). The mixture was stirred under $N_2$ at rt for 18 h. Incomplete conversion so 300 µL acetyl chloride added and the reaction stirred for 2 h. The reaction mixture washed with 1M aq. HCl (50 mL) followed by sat. aq. $NaHCO_3$ (50 mL) and water (50 mL). The organic layer was dried through a hydrophobic frit and the solvent was removed in vacuo to give the product (5.55 g) as a yellow solid. LCMS (2 min HpH): Rt=1.19 min, $[MH]^+$=451.

Intermediate 225: ((2S,3R,4R)-ethyl 1-acetyl-4-amino-2-cyclopropyl-3-methyl-1,2,3,4-tetrahydroquinoline-6-carboxylate

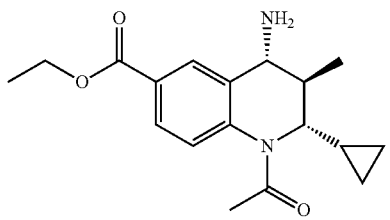 [SMILES: CCOC(=O)c1ccc2c(c1)[C@H](N)[C@@H](C)[C@H](C1CC1)N2C(C)=O]

A solution of (2S,3R,4R)-ethyl 1-acetyl-4-(((benzyloxy)carbonyl)amino)-2-cyclopropyl-3-methyl-1,2,3,4-tetrahydroquinoline-6-carboxylate (For a preparation see Intermediate 224, 5.52 g, 12.25 mmol) in ethanol (245 mL) was passed through a Thales H-cube Flow Hydrogenator with a 10% Pd/C CatCart in full $H_2$ mode at a rate of 1 mL/min. The solvent was evaporated to afford the product (3.945 g, 11.85 mmol, 97%) as a yellow oil. LCMS (2 min HpH): Rt=0.91 min, $[MH]^+$=300.

Intermediate 226: (2S,3R,4R)-1-acetyl-2-cyclopropyl-3-methyl-4-((6-methylpyridin-2-yl)amino)-1,2,3,4-tetrahydroquinoline-6-carboxylic Acid

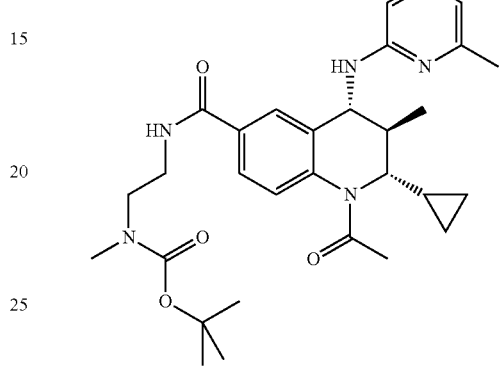

To a solution of (2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 247, 100 mg, 0.264 mmol) and HATU (120 mg, 0.316 mmol) in N,N-dimethylformamide (DMF) (3 mL) was added tert-butyl (2-aminoethyl)(methyl)carbamate (0.057 mL, 0.316 mmol) and DIPEA (0.184 mL, 1.054 mmol). The reaction mixture was stirred at rt for 1 h. The reaction mixture was partitioned between ether (25 mL) and water (50 mL) and the aqueous extracted with ether (3×25 mL). The combined organics were washed with brine (10 mL), dried over magnesium sulphate and evaporated in vacuo to afford the product (132 mg). LCMS (2 min HpH): Rt=1.11 min, $[MH]^+$=536.

Intermediate 227: (2S,3R,4R)-ethyl 1-acetyl-2-cyclopropyl-3-methyl-4-((4-methylpyrimidin-2-yl)amino)-1,2,3,4-tetrahydroquinoline-6-carboxylate

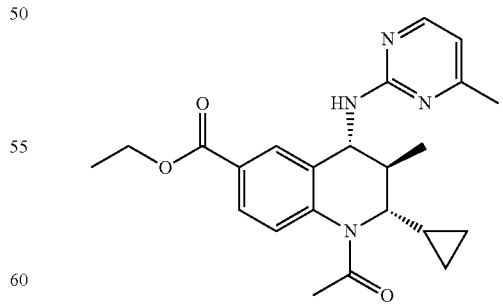

A solution of 2-chloro-4-methylpyrimidine (12.96 g, 101 mmol), potassium fluoride (7.99 g, 137 mmol), (2S,3R,4R)-ethyl 1-acetyl-4-amino-2-cyclopropyl-3-methyl-1,2,3,4-tetrahydroquinoline-6-carboxylate (for a preparation see Intermediate 225, 29 g, 92 mmol), 18-crown-6 (12.11 g, 45.8 mmol) and DIPEA (27.2 mL, 156 mmol) in dimethyl sulfoxide (DMSO) (145 mL) was added to a flask and heated to 140° C. for 22 h. The reaction was allowed to cool and then was partitioned between water (300 mL) and ethyl acetate (300 mL). The layers were separated and the aqueous layer further extracted with ethyl acetate (2×300 mL). The combined organics were washed with brine (4×300 mL), dried (MgSO$_4$), filtered and concentrated in vacuo. Purification was undertaken by flash column chromatography. The crude material was loaded onto a 340 g silica column and eluted using a graduating solvent system of 0-100% ethyl acetate in cyclohexane. The desired fractions were combined and concentrated to leave the product as a pale yellow foam (29 g).

LCMS (2 min Formic): Rt=0.99 min, [MH]$^+$=409.

Intermediate 228: 2-bromo-6-(((tert-butyldimethyl-silyl)oxy)methyl)pyridine

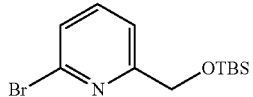

To a solution of (6-bromopyridin-2-yl)methanol (250 mg, 1.330 mmol) and imidazole (362 mg, 5.32 mmol) in anhydrous DMF (1.2 mL) was added TBDMSCl (240 mg, 1.596 mmol) and the mixture stirred in a stoppered vessel at rt for 45 min. The mixture was diluted with water (10 mL) and extracted with ether (2×10 mL). The organic extracts were combined and washed with 10% LiCl (aq) (2×10 mL). The organic layer was dried through a hydrophobic frit and concentrated under reduced pressure. The residue was loaded in cyclohexane (4 mL) and purified on a silica cartridge (50 g) using a gradient of 0-100% DCM in cyclohexane over 10 CV. The appropriate fractions were combined and the solvent evaporated in vacuo to give the title compound as a colourless mobile oil (349 mg, 1.16 mmol, 87%).

LCMS (2 min Formic): Rt=1.48 min, [MH]$^+$=302/304.

Intermediate 229: benzyl ((2S,3S,4R)-6-cyano-2-cyclopropyl-3-methyl-1,2,3,4-tetrahydroquinolin-4-yl)carbamate

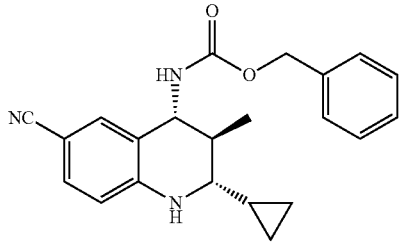 [SMILES: C[C@@H]1[C@@H](NC(=O)OCc2ccccc2)c2cc(C#N)ccc2N[C@H]1C1CC1]

To a stirred solution of 4-aminobenzonitrile (5 g, 42.3 mmol) in anhydrous dichloromethane (150 mL), cyclopropanecarbaldehyde (4.74 mL, 63.5 mmol) was added. The reaction mixture was stirred under nitrogen for 30 min. The reaction mixture was then cooled in an ice bath, (11bS)-2,6-bis(4-chlorophenyl)-4-hydroxy-8,9,10,11,12,13,14,15-octahydrodinaphtho[2,1-d:1',2'-f][1,3,2]dioxaphosphepine 4-oxide (0.489 g, 0.846 mmol) and (E)-benzyl prop-1-en-1-ylcarbamate (for a preparation see Intermediate 1, 8.90 g, 46.6 mmol) were added. The reaction mixture was stirred under nitrogen for 1 h. The reaction suspension was filtered and the cream solid obtained was dried in a vacuum oven to provide the title compound (10.24 g, 60%). Analysis by chiral HPLC was undertaken using a 250×4.6 mm Chiralpak IA column eluting with 40% ethanol in heptane at a flow rate of 1 mL/min. Peak 1/major enantiomer (>99.5%) eluted at 4.7 min, and Peak 2/minor enantiomer (<0.5% by UV) eluted at 10.0 min. This indicated the product had an ee of >99%.

LCMS (2 min Formic): Rt=1.16 min, [MH]$^+$=362.

Intermediate 230: benzyl ((2S,3R,4R)-1-acetyl-6-cyano-2-cyclopropyl-3-methyl-1,2,3,4-tetrahydroquinolin-4-yl)carbamate

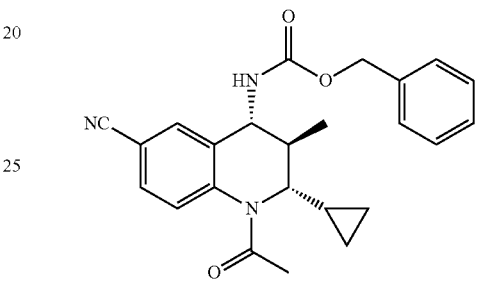

To a stirred suspension of benzyl ((2S,3S,4R)-6-cyano-2-cyclopropyl-3-methyl-1,2,3,4-tetrahydroquinolin-4-yl)carbamate (for a preparation see Intermediate 229, 10.24 g, 28.3 mmol) in anhydrous dichloromethane (200 mL), pyridine (6.87 mL, 85 mmol) was added. The reaction suspension was stirred under nitrogen and cooled in an ice bath. To the reaction suspension, acetyl chloride (2.417 mL, 34.0 mmol) was added. The reaction suspension was stirred overnight. To the reaction mixture, pyridine (2.291 mL, 28.3 mmol) was added. The reaction mixture was cooled in an ice bath and acetyl chloride (2.417 mL, 34.0 mmol) was added. The reaction suspension was stirred under nitrogen for 3.5 h The reaction mixture was left without stirring under nitrogen overnight. The reaction mixture was washed with 2M HCl (once), water (once) and sodium hydrogen carbonate (once). The organic layer was dried, concentrated in vacuo, dissolved in DCM, loaded onto a SNAP (340 g) Biotage silica cartridge and eluted with cyclohexane/ethyl acetate (12%-50%). The correct fractions were concentrated in vacuo to give the title compound as a white foam (8.7 g, 69%).

LCMS (2 min Formic): Rt=1.06 min, [MH]$^+$=404.

Intermediate 231: (2S,3R,4R)-1-acetyl-4-amino-2-cyclopropyl-3-methyl-1,2,3,4-tetrahydroquinoline-6-carbonitrile

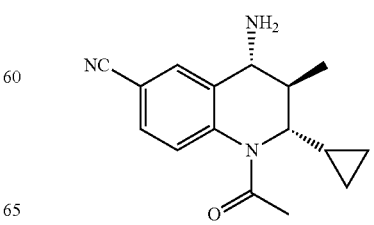

Benzyl ((2S,3R,4R)-1-acetyl-6-cyano-2-cyclopropyl-3-methyl-1,2,3,4-tetrahydroquinolin-4-yl)carbamate (for a preparation see Intermediate 230, 13.96 g, 34.6 mmol) was taken up in 1M TBAF in THF (173 mL, 173 mmol) and allowed to stir at 65° C. under $N_2$ for 2.5 h. The reaction was concentrated and then partitioned between sat aq. $NaHCO_3$ (100 mL) and DCM (100 mL). The aqueous layer was extracted with further DCM (100 mL) and the combined organics were washed with water (100 mL) and then passed through a hydrophobic frit and concentrated in vacuo. The crude material was dissolved in minimal MeOH and split into 3 equal volumes. Each volume was applied to a SCX cartridge (70 g) which had been pre-conditioned with MeOH (70 mL). The cartridges were washed with MeOH (100 mL) and 2M $NH_3$ in MeOH (100 mL). The ammonia washes of the first two runs were combined and concentrated in vacuo to give batch 1 of the title compound (5.1 g, 55%). The ammonia wash of the third run appeared to be impure so it was concentrated in vacuo and the SCX process was repeated to give batch 2 of the title compound (1.6 g, 17%). LCMS (2 min Formic): Rt=0.47 min, [M–$NH_2$]$^+$=253.

Intermediate 232: (2S,3R,4R)-1-acetyl-4-((6-(((tert-butyldimethylsilyl)oxy)methyl)pyridin-2-yl)amino)-2-cyclopropyl-3-methyl-1,2,3,4-tetrahydroquinoline-6-carbonitrile

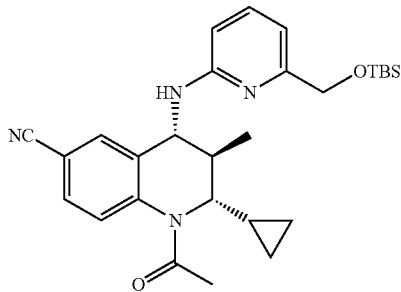

A mixture of (2S,3R,4R)-1-acetyl-4-amino-2-cyclopropyl-3-methyl-1,2,3,4-tetrahydroquinoline-6-carbonitrile (for a preparation see Intermediate 231, 150 mg, 0.557 mmol), sodium tert-butoxide (107 mg, 1.114 mmol), Pd(QPhos)$_2$ (24 mg, 0.016 mmol) and 2-bromo-6-(((tert-butyldimethylsilyl)oxy)methyl)pyridine (for a preparation see Intermediate 228, 253 mg, 0.835 mmol) in anhydrous toluene (1 mL) was evacuated and purged with nitrogen (×3) and stirred under nitrogen at 50° C. for 2 h. The reaction mixture was filtered through a 2.5 g Celite cartridge and the cartridge then washed with EtOAc (25 mL). The filtrate was evaporated in vacuo and the gum dissolved in DCM (1 mL). The solution was loaded onto a silica cartridge (50 g) and purified using a gradient of 0-100% EtOAc in cyclohexane over 10 CV. The appropriate fractions were combined and the solvent removed by rotary evaporation to give the title compound as an off-white foam (186 mg, 0.379 mmol, 68%).

LCMS (2 min Formic): Rt=1.24 min, [MH]$^+$=491.

Intermediate 233: tert-butyl 4-((6-bromopyridin-2-yl)methyl)piperazine-1-carboxylate

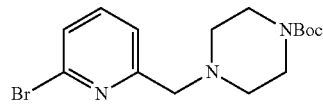 [SMILES: CC(C)(C)OC(=O)N1CCN(Cc2cccc(Br)n2)CC1]

To a solution of tert-butyl piperazine-1-carboxylate (225 mg, 1.210 mmol) and 6-bromopicolinaldehyde (150 mg, 0.806 mmol) in dichloromethane (5 mL) left stirring for 45 min, was added sodium triacetoxyborohydride (256 mg, 1.210 mmol). The mixture was stirred at rt for 17 h. Further tert-butyl piperazine-1-carboxylate (150 mg, 0.806 mmol) was added to the mixture and the reaction left stirring at rt for 1 h. Then sodium triacetoxyborohydride (171 mg, 0.806 mmol) was added and reaction mixture left stirring at rt for 1 h. As the reaction didn't show further progression, some acetic acid (4.62 µL, 0.081 mmol) was added and the reaction left stirring for 1 h. The mixture was concentrated in vacuo to afford a white gum (661 mg). The resulting crude product was quenched with sat. $NaHCO_3$. The aqueous phase was extracted with DCM (×3). The organic layers were combined, filtered through a hydrophobic frit and the volatiles removed under reduced pressure to afford a yellow gum (399.8 mg). The crude product was purified by silica chromatography using a Biotage Isolera. The product was loaded onto a silica SNAP cartridge (50 g) and eluted with 5-25% EtOAc in cyclohexane over 20 CV. The relevant fractions were combined and the volatiles were removed under reduce pressure to afford the title compound as a colourless gum (139.4 mg).

LCMS (2 min Formic): Rt=0.66 min, [MH]$^+$=356/358.

Intermediate 234: tert-butyl 4-((6-(((2S,3R,4R)-1-acetyl-6-cyano-2-cyclopropyl-3-methyl-1,2,3,4-tetrahydroquinolin-4-yl)amino)pyridin-2-yl)methyl)piperazine-1-carboxylate

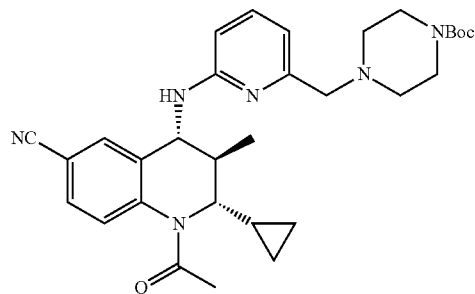 [SMILES: CC(=O)N1c2ccc(C#N)cc2[C@H](Nc2cccc(CN3CCN(C(=O)OC(C)(C)C)CC3)n2)[C@@H](C)[C@@H]1C1CC1]

In a 50 mL RB Flask were added (2S,3R,4R)-1-acetyl-4-amino-2-cyclopropyl-3-methyl-1,2,3,4-tetrahydroquinoline-6-carbonitrile (for a preparation see Intermediate 231, 50.5 mg, 0.187 mmol), tert-butyl 4-((6-bromopyridin-2-yl)methyl)piperazine-1-carboxylate (for a preparation see Intermediate 233, 62.2 mg, 0.175 mmol), Pd$_2$dba$_3$ (24.1 mg, 0.026 mmol), sodium tert-butoxide (39.3 mg, 0.409 mmol) and QPhos ligand (17 mg, 0.024 mmol) in toluene (3 mL). The reaction mixture was stirred at 50° C., under nitrogen, overnight. Further Pd$_2$dba$_3$ (17.17 mg, 0.019 mmol), sodium tert-butoxide (9.01 mg, 0.094 mmol) and QPhos ligand (13.36 mg, 0.019 mmol) were added and reaction mixture was left stirring under the same conditions for 2 h. The reaction mixture was allowed to cool to rt and allowed to stand overnight. The reaction mixture was filtered through a celite cartridge and partitioned between water and EtOAc. The aqueous phase was extracted with EtOAc (×3). The organic layers were combined and washed with brine, dried over Na$_2$SO$_4$, filtered through a hydrophobic frit and the volatiles removed under reduce pressure to afford the crude product as an orange gum (161.3 mg). The resulting crude product was purified by silica chromatography using a Biotage Isolera. The product was loaded on a silica SNAP cartridge (25 g) and eluted with 1-5% 2M NH$_3$ in MeOH in DCM over 20 CV. The relevant fractions were combined and the volatiles were removed under reduced pressure to afford the title compound as a yellow gum (88.8 mg). LCMS (2 min Formic): Rt=0.88 min, [MH]$^+$=546.

Intermediate 235:
4-((6-bromopyridin-2-yl)methyl)morpholine

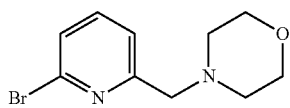

A solution of 6-bromopicolinaldehyde (2.9368 g, 15.79 mmol) and morpholine (1.376 mL, 15.79 mmol) in 2-methyltetrahydrofuran (2-MeTHF) (30 mL) under nitrogen was charged with sodium triacetoxyborohydride (5.3635 g, 25.3 mmol) and allowed to stir for 2 h at 20° C. The reaction mixture was then diluted with ethyl acetate (10 mL) and saturated aqueous sodium bicarbonate (20 mL). The organic layer was isolated and dried by passing through a hydrophobic frit, and then concentrated in vacuo to give the crude product. The crude product was applied to a silica column (100 g) which was eluted with Hex/EtOAc (0-100%, 80 min run). The appropriate fractions were combined and concentrated in vacuo to give a clear oil, which still contained impurities by NMR. In a separate vessel, a solution of 6-bromopicolinaldehyde (2.9967 g, 16.11 mmol) and morpholine (1.400 mL, 16.07 mmol) in 2-methyltetrahydrofuran (2-MeTHF) (50 mL) under nitrogen was charged with sodium triacetoxyborohydride (4.6139 g, 21.77 mmol) and allowed to stir for 14 h at 20° C. The reaction mixture was then diluted with ethyl acetate (10 mL) and saturated aqueous sodium bicarbonate (20 mL). The organic layer was isolated and dried by passing through a hydrophobic frit, then concentrated in vacuo to give the crude product. The crude product was purified on a silica column (100 g), eluting with Hex/EtOAc (0-100%, 60 min run). The appropriate fractions were combined and concentrated in vacuo to give a oils from clear oil. The two clear both reactions were combined and passed through an aminopropyl SPE cartridge which was eluted with 70 mL of MeOH. This solution was concentrated in vacuo and left to dry under high vacuum for 30 min, to give the title compound as a clear oil (3.9456 g). LCMS (2 min Formic): Rt=0.33 min, [MH]$^+$=257/259.

Intermediate 236:
1-(6-bromopyridin-2-yl)-N,N-dimethylmethanamine

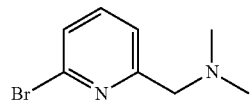

A solution of dimethylamine hydrochloride (477 mg, 5.85 mmol) and 6-bromopicolinaldehyde (439 mg, 2.360 mmol) in dichloromethane (10 mL) was left stirring for 2 h over activated molecular sieves. Sodium triacetoxyborohydride (750 mg, 3.54 mmol) was then added and the mixture stirred at rt for ~18 h. The mixture was concentrated in vacuo to afford a white/yellow gum (1.0647 g). The resulting crude product was quenched with sat. NaHCO$_3$. The aqueous phase was extracted with DCM (×3). The organic layers were combined, filtered through a hydrophobic frit and the volatiles removed under reduced pressure to afford the title compound as a yellow gum (328 mg) which was used crude in the subsequent reaction. LCMS (2 min Formic): Rt=0.34 min, [MH]$^+$=215/217.

Intermediate 237:
2-chloro-5-methoxy-4-methylpyrimidine

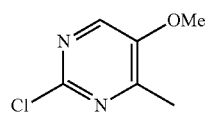

To a solution of 2,4-dichloro-5-methoxypyrimidine (1 g, 5.59 mmol) in tetrahydrofuran (32.2 mL)/N-methyl-2-pyrrolidone (2.424 mL) was added ferric acetylacetonate (0.197 g, 0.559 mmol) and the mixture was cooled to 0° C. under nitrogen. Then methylmagnesium bromide (2.62 mL, 8.38 mmol, 3.2 M in MeTHF) was added dropwise. The mixture was stirred for 30 min under nitrogen at 0° C. The reaction was quenched with saturated aqueous NH$_4$Cl solution (10 mL) and the mixture allowed to warm to rt. Diethyl ether was added, the layers were separated and the aqueous layer was further extracted with diethyl ether (4×15 mL). The combined organic extracts were dried over a hydrophobic frit and concentrated in vacuo to give an orange oil. The crude product was loaded in dichloromethane (3 mL) and purified on a silica cartridge (25 g) using a gradient of 0-30% cyclohexane/AcOEt over 10 CV. The appropriate fractions were combined and the solvent evaporated in vacuo to give the product as a white solid (475 mg, 3.00 mmol, 54%).
LCMS (2 min Formic): Rt=0.64 min, [MH]$^+$=159.

Intermediate 238:
((3-bromobenzyl)oxy)(tert-butyl)dimethylsilane

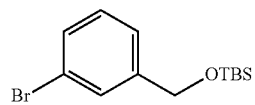 [SMILES: CC(C)(C)[Si](C)(C)OCc1cccc(Br)c1]

To a solution of (3-bromophenyl)methanol (0.321 mL, 2.67 mmol) and imidazole (728 mg, 10.69 mmol) in anhydrous N,N-dimethylformamide (5 mL), was added TBDMSCl (484 mg, 3.21 mmol) and the reaction stirred at room temperature for 1 h. The reaction was diluted with water (50 mL) and extracted with ether (2×50 mL). The organic extracts were then combined and washed with LiCl (2×20 mL). The extracts were dried over a hydrophobic frit and concentrated in vacuo to give the product ((3-bromobenzyl)oxy)(tert-butyl)dimethylsilane (236.9 mg, 0.786 mmol, 29%).

LCMS (2 min Formic): Rt=0.63 min, No [MH]$^+$ observed.

Intermediate 239: (2S,3R,4R)-1-acetyl-4-((3-(((tert-butyldimethylsilyl)oxy)methyl)phenyl)amino)-2-cyclopropyl-3-methyl-1,2,3,4-tetrahydroquinoline-6-carbonitrile

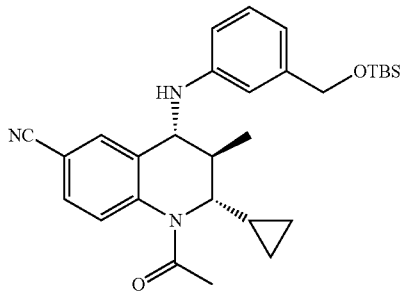

To a solution of (2S,3R,4R)-1-acetyl-4-amino-2-cyclopropyl-3-methyl-1,2,3,4-tetrahydroquinoline-6-carbonitrile (for a preparation see Intermediate 231, 100 mg, 0.371 mmol), ((3-bromobenzyl)oxy)(tert-butyl)dimethylsilane (for a preparation see Intermediate 238, 179 mg, 0.594 mmol), DavePhos (29.2 mg, 0.074 mmol) and Pd$_2$dba$_3$ (34.0 mg, 0.037 mmol) in 1,4-dioxane (3 mL) was added sodium tert-butoxide (107 mg, 1.114 mmol) and the reaction mixture degassed. The reaction was then irradiated to 120° C. for 30 min. The reaction mixture was filtered through a 2.5 g Celite column and washed with EtOAc. The filtrate was then concentrated. The sample was loaded in dichloromethane onto a silica (10 g) cartridge and purified by flash chromatography eluting with 0-40% ethyl acetate-cyclohexane over 15 CV. The appropriate fractions were combined and concentrated to give (2S,3R,4R)-1-acetyl-4-((3-(((tert-butyldimethylsilyl)oxy)methyl)phenyl)amino)-2-cyclopropyl-3-methyl-1,2,3,4-tetrahydroquinoline-6-carbonitrile (66.1 mg, 0.135 mmol, 36%) as an off-white solid. LCMS (2 min Formic): Rt=1.51 min, [MH]$^+$=490.

Intermediate 240: 2-bromo-6-(methoxymethyl)pyridine

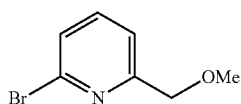

(6-Bromopyridin-2-yl)methanol (400 mg, 2.127 mmol) was taken up in N,N-dimethylformamide (5 mL) and allowed to stir at 0° C. for 5 min. Sodium hydride (128 mg, 3.19 mmol, 60% suspension in mineral oil) was then added, some effervescence occurred and the reaction was allowed to stir at 0° C. for 10 min. Methyl iodide (0.266 mL, 4.25 mmol) was then added and the reaction was allowed to warm to rt with stirring over 1 h. The reaction was diluted with water and extracted with EtOAc (×2). The combined organics were washed with 10% LiCl(aq), dried using a hydrophobic frit and concentrated to a yellow oil. This oil was purified using a silica column (25 g) and flash chromatography, eluting with 0-100% EtOAc:cyclohexane. One major peak was eluted and the appropriate fraction was concentrated and dried to give the product (335 mg, 1.658 mmol, 78%) as a colourless oil. LCMS (2 min Formic): Rt=0.78 min, [MH]$^+$=202/204.

Intermediate 241: 1-bromo-2-(methoxymethyl)benzene

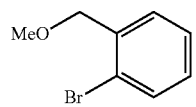

A solution of (2-bromophenyl)methanol (1 g, 5.35 mmol) in N,N-dimethylformamide (7.5 mL) was cooled to 0° C. and NaH (0.321 g, 8.02 mmol, 60% suspension in mineral oil) added portionwise over 10 min. MeI (1.672 mL, 26.7 mmol) was then added and the reaction mixture stirred for 3 h. The reaction mixture was quenched with ammonium chloride (40 mL) and extracted with EtOAc (2×75 mL). The organic layers were combined and washed with 10% LiCl (40 mL). The extracts were dried over a hydrophobic frit and concentrated in vacuo to give the product (1.0386 g, 5.17 mmol, 97%) as an orange liquid. LCMS (2 min Formic): Rt=1.10 min, [MNa]$^+$=224.

Intermediate 242: methyl 2-(((2S,3R,4R)-1-acetyl-6-cyano-2-cyclopropyl-3-methyl-1,2,3,4-tetrahydroquinolin-4-yl)amino)nicotinate

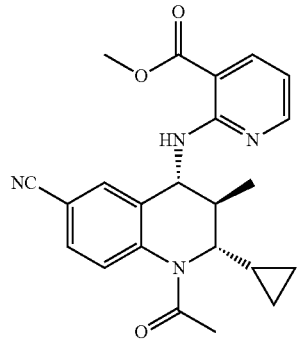 [SMILES: COC(=O)c1cccnc1N[C@H]1c2cc(C#N)ccc2N(C(C)=O)[C@@H](C2CC2)[C@@H]1C]

A solution of (2S,3R,4R)-1-acetyl-4-amino-2-cyclopropyl-3-methyl-1,2,3,4-tetrahydroquinoline-6-carbonitrile (for a preparation see Intermediate 231, 200 mg, 0.743 mmol), methyl 2-fluoronicotinate (0.192 mL, 1.485 mmol) and Et$_3$N (0.207 mL, 1.485 mmol) in N-methyl-2-pyrrolidone (4 mL) was stirred in a closed vessel in a microwave at 200° C. for 75 min. The solution was purified directly by MDAP (HpH).

Intermediate 243: 6-(((2S,3S,4R)-6-cyano-2-cyclopropyl-3-methyl-1,2,3,4-tetrahydroquinolin-4-yl)amino)picolinic Acid

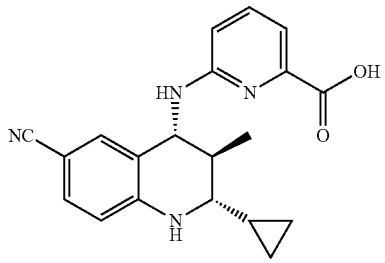 [SMILES: C[C@@H]1[C@@H](Nc2cccc(C(=O)O)n2)c2cc(C#N)ccc2N[C@H]1C1CC1]

To a reaction vessel, (2S,3R,4R)-1-acetyl-4-amino-2-cyclopropyl-3-methyl-1,2,3,4-tetrahydroquinoline-6-carbonitrile (for a preparation see Intermediate 231, 1.29 g, 4.79 mmol), and sodium tert-butoxide (1.841 g, 19.16 mmol) were added in toluene (20 mL). The solution was degassed with $N_2$ and treated with $Pd_2(dba)_3$ (0.439 g, 0.479 mmol), Q-Phos (0.341 g, 0.479 mmol) and ethyl 6-bromopicolinate (1.137 mL, 7.18 mmol). The solution was stirred and heated to 60° C. for 16 h under $N_2$. LCMS showed that the reaction had proceeded to form the deacetylated acid. The reaction mixture was filtered through celite and diluted with water/NaOH(aq) (50:50, 250 mL). This was extracted with DCM (2×200 mL) and the layers separated. The aqueous layer was acidified with 2 M HCl(aq) (150 mL), and extracted with 10% methanol in DCM (3×100 mL). The layers were separated and the organics combined and dried through a hydrophobic frit before being concentrated in vacuo to give the crude product (2.116 g) as an orange/white solid. This was taken up in methanol and purified by SPE on an —$NH_2$ column (20 g), using sequential solvents (methanol, then 2 M HCl in dioxane). The fractions containing product were combined and concentrated in vacuo to give two batches of the product: Batch 1: an orange/brown solid (331 mg). Batch 2: containing product with a substantial impurity (1.5 g) as a red solid. Batch 2 was taken up in methanol purified by SPE on an —$NH_2$ column (70 g), using sequential solvents (methanol, then 2 M acetic acid in methanol). The fractions containing product were combined and concentrated in vacuo to give the desired product as an orange/brown solid (1.218 g).

LCMS (2 min Formic): Rt=0.73 min, $[MH]^+$=349.

Intermediate 244: 6-(((2S,3R,4R)-1-acetyl-6-cyano-2-cyclopropyl-3-methyl-1,2,3,4-tetrahydroquinolin-4-yl)amino)picolinic Acid

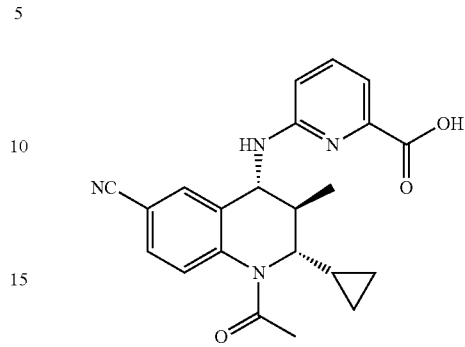

To a reaction vial, 6-(((2S,3S,4R)-6-cyano-2-cyclopropyl-3-methyl-1,2,3,4-tetrahydroquinolin-4-yl)amino)picolinic acid (for a preparation see Intermediate 243, 1.161 g, 3.33 mmol) was added in dichloromethane (50 mL). The reaction was cooled to 0° C. Acetyl chloride (0.948 mL, 13.33 mmol) was added and the reaction left to stir for 2 h at rt under $N_2$. Acetyl chloride (0.948 mL, 13.33 mmol) was added and the reaction left to stir at rt for 2 h. Further acetyl chloride (1.185 mL, 16.66 mmol) was added and the reaction left to stir at rt for 2 h. Further acetyl chloride (0.5 mL, 7.03 mmol) was added and the reaction left to stir at 39° C. for 2 h. The reaction was then left to stir at 40° C. for 16 h. The reaction mixture was concentrated in vacuo then retaken up in DCM:toluene (1:3, 150 mL) and concentrated in vacuo (×4) to give the desired product (930 mg) as a brown/white solid. The product was used crude in the next reaction. LCMS (2 min Formic): Rt=0.69 min, $[MH]^+$=391.

Intermediate 245: tert-butyl (2-((6-bromopyridin-2-yl)oxy)ethyl)carbamate

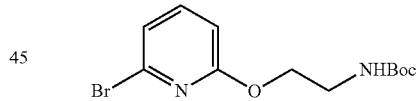

A solution of tert-butyl (2-hydroxyethyl)carbamate (0.327 mL, 2.111 mmol) in anhydrous THF (10 mL) under nitrogen was cooled in an ice-water bath and 60% sodium hydride in mineral oil (211 mg, 5.28 mmol) added. The mixture was stirred for 5 min, the ice-bath removed and allowed to warm to rt over 30 min, before a solution of 2,6-dibromopyridine (500 mg, 2.111 mmol, commercially available from, for example, Sigma-Aldrich) in anhydrous THF (5 mL) was added. The mixture was stirred under nitrogen at rt for 24 h. The reaction mixture was diluted with water (10 mL) and extracted with EtOAc (3×10 mL). The organic extracts were combined and dried through a hydrophobic frit. The residue was loaded in DCM (4 mL) and purified on a silica cartridge (50 g) using a gradient of 0-50% EtOAc in cyclohexane over 10 CV. The appropriate fractions were combined, the solvent removed in vacuo and the oil dried in a vacuum oven to give the title compound as a white crystalline solid (120 mg, 0.378 mmol, 18%).

LCMS (2 min Formic): Rt=1.12 min, $[MH]^+$=317/319.

Intermediate 246: (2S,3R,4R)-1-acetyl-2-cyclopropyl-3-methyl-4-((2-nitrophenyl)amino)-1,2,3,4-tetrahydroquinoline-6-carbonitrile

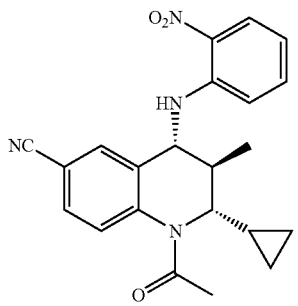 [SMILES: CC(=O)N1c2ccc(C#N)cc2[C@H](Nc2ccccc2[N+](=O)[O-])[C@@H](C)[C@@H]1C1CC1]

A solution of 1-fluoro-2-nitrobenzene (0.078 mL, 0.743 mmol), (2S,3R,4R)-1-acetyl-4-amino-2-cyclopropyl-3-methyl-1,2,3,4-tetrahydroquinoline-6-carbonitrile (for a preparation see Intermediate 231, 200 mg, 0.743 mmol) and DIPEA (0.220 mL, 1.262 mmol) in dimethyl sulfoxide (1 mL) was added to a flask and heated to 160° C. in a microwave for 4 h. The reaction mixture was partitioned between water (20 mL) and Et$_2$O (20 mL). The layers were separated and the aqueous layer further extracted with Et$_2$O (2×20 mL). The combined organics were back extracted with water (2×20 mL), dried (Na$_2$SO$_4$) and concentrated in vacuo. The crude product was taken up in DCM and added to a silica cartridge (25 g) which was purified by flash chromatography, eluting with 0-60% EtOAc/cyclohexane. The appropriate fractions were collected and concentrated in vacuo to afford the desired product as a yellow oil (216 mg, 0.553 mmol, 75%).

LCMS (2 min HpH): Rt=1.19 min, [M−H]$^-$=389.

Intermediate 247: 2-(3-bromophenoxy)ethanol

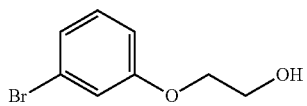 [SMILES: OCCOc1cccc(Br)c1]

To a mixture of 3-bromophenol (2.0 g, 11.56 mmol) and cesium carbonate (4.71 g, 14.45 mmol) in anhydrous DMF (5 mL) was added 2-bromoethanol (1.632 mL, 23.12 mmol) and the reaction stirred under nitrogen at 50° C. for 20 h. Further 2-bromoethanol (1.632 mL, 23.12 mmol) was added and the reaction stirred under nitrogen at 50° C. for 8 h. The reaction mixture was allowed to cool to rt and filtered. The filtrate was diluted with EtOAc (20 mL) and washed sequentially with 10% aqueous Na$_2$CO$_3$ (20 mL) and water (20 mL). The organic layer was dried through a hydrophobic frit and the solvent removed in vacuo. The oil was loaded in DCM (8 mL) and purified on a silica cartridge (100 g) using a gradient of 0-100% EtOAc in cyclohexane over 10 CV. The appropriate fractions were combined and the solvent removed by rotary evaporation to give the title compound as a colourless oil (1.10 g, 5.07 mmol, 44%). LCMS (2 min Formic): Rt=0.83 min, no [MH]$^+$ observed.

Intermediate 248: (2-(3-bromophenoxy)ethoxy)(tert-butyl)dimethylsilane

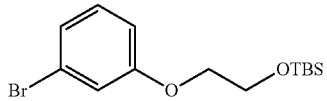 [SMILES: CC(C)(C)[Si](C)(C)OCCOc1cccc(Br)c1]

To a solution of 2-(3-bromophenoxy)ethanol (for a preparation see Intermediate 247, 1.10 g, 5.07 mmol) and imidazole (0.690 g, 10.14 mmol) in DCM (8 mL) was added TBDMSCl (0.917 g, 6.08 mmol) and the mixture stirred in a stoppered vessel at room temperature for 2 h. The reaction mixture was filtered and the filtrate washed with water (10 mL). The organic layer was dried through a hydrophobic frit and the solvent removed in vacuo. The oil was loaded in DCM (4 mL) and purified on a silica cartridge (50 g) using a gradient of 0-25% EtOAc in cyclohexane over 10 CV. The appropriate fractions were combined and the solvent evaporated in vacuo to give the title compound as a colourless oil (1.37 g, 4.13 mmol, 82%).

LCMS (2 min Formic): Rt=1.60 min, no [MH]$^+$ observed.

Intermediate 249: (2S,3R,4R)-1-acetyl-4-((3-(2-((tert-butyldimethylsilyl)oxy)ethoxy)phenyl)amino)-2-cyclopropyl-3-methyl-1,2,3,4-tetrahydroquinoline-6-carbonitrile

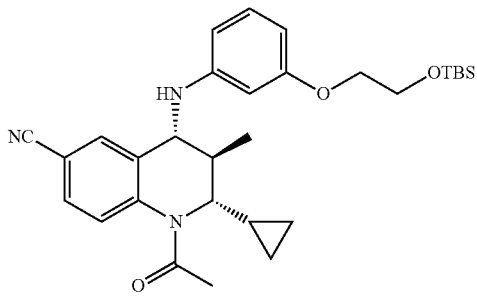 [SMILES: CC(=O)N1c2ccc(C#N)cc2[C@H](Nc2cccc(OCCO[Si](C)(C)C(C)(C)C)c2)[C@@H](C)[C@@H]1C1CC1]

The title compound was prepared in a similar manner to Intermediate 232 from (2S,3R,4R)-1-acetyl-4-amino-2-cyclopropyl-3-methyl-1,2,3,4-tetrahydroquinoline-6-carbonitrile (for a preparation see Intermediate 231,197 mg, 0.731 mmol) and (2-(3-bromophenoxy)ethoxy)(tert-butyl)dimethylsilane (for a preparation see Intermediate 248, 363 mg, 1.097 mmol) to give the title compound as a light pink gum (235 mg, 0.452 mmol, 62%). LCMS (2 min Formic): Rt=1.48 min, [MH]$^+$=520.

Intermediate 250: tert-butyl (2-(3-bromophenoxy)ethyl)carbamate

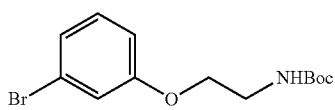 [SMILES: CC(C)(C)OC(=O)NCCOc1cccc(Br)c1]

To a mixture of 3-bromophenol (1.0 g, 5.78 mmol), potassium carbonate (2.4 g, 17.37 mmol) and potassium iodide (1.0 g, 6.02 mmol) in anhydrous DMF (8 mL) was added tert-butyl (2-bromoethyl)carbamate (2.6 g, 11.60 mmol) and the reaction mixture stirred under nitrogen for 16 h at 60° C. The reaction was filtered through celite, the filtrate diluted with EtOAc (20 mL) and washed sequentially with NaOH (10 mL, 0.5 M) and water (2×10 mL). The organic layer was dried through a hydrophobic frit and the filtrate concentrated under reduced pressure. The resulting oil was loaded in DCM (5 mL) and purified on a silica cartridge (50 g) using a gradient of 0-50% EtOAc in cyclohexane over 10 CV. The appropriate fractions were combined and the solvent removed by rotary evaporation to give the title compound as a colourless oil (1.69 g, 5.34 mmol, 92%).

LCMS (2 min Formic): Rt=1.20 min, [MH]$^+$=316/318.

Intermediate 251: tert-butyl (2-(3-(((2S,3R,4R)-1-acetyl-6-cyano-2-cyclopropyl-3-methyl-1,2,3,4-tetrahydroquinolin-4-yl)amino)phenoxy)ethyl)carbamate

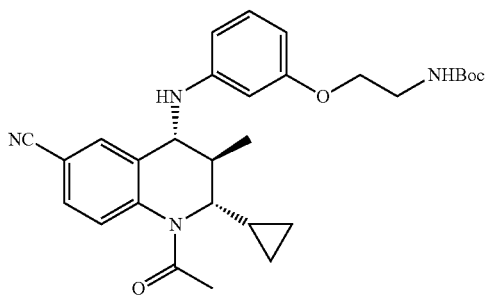 [SMILES: CC(=O)N1c2ccc(C#N)cc2[C@H](Nc2cccc(OCCNC(=O)OC(C)(C)C)c2)[C@@H](C)[C@@H]1C1CC1]

The title compound was prepared in a similar manner to Intermediate 232 from (2S,3R,4R)-1-acetyl-4-amino-2-cyclopropyl-3-methyl-1,2,3,4-tetrahydroquinoline-6-carbonitrile (for a preparation see Intermediate 231, 197 mg, 0.731 mmol) and tert-butyl (2-(3-bromophenoxy)ethyl)carbamate (for a preparation see Intermediate 250, 347 mg, 1.097 mmol) to give the title compound as a light pink gum (123 mg, 0.244 mmol, 33%). LCMS (2 min Formic): Rt=1.19 min, [MH]$^+$=505.

Intermediate 252: (2-chloropyrimidin-4-yl)methanol

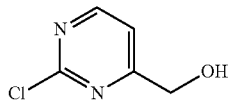

Methyl 2-chloropyrimidine-4-carboxylate (300 mg, 1.738 mmol) was taken up in dichloromethane (5 mL) and allowed to stir at 0° C. for 5 min. Diisobutylaluminium hydride (3.48 mL, 3.48 mmol, 1 M in THF) was then added dropwise and the reaction allowed to warm to rt with stirring over 16 h. The reaction was treated with 10% citric acid (aq.) and was allowed to stir at rt for 30 min. The reaction was then extracted with EtOAc (×2), the combined organics were washed with brine, dried using a hydrophobic frit and concentrated to a yellow solid product (138 mg, 0.955 mmol, 55%). This was used crude (~33% purity) in the next reaction. LCMS (2 min Formic): Rt=0.39 min, [MH]$^+$=145.

Intermediate 253: 4-(((tert-butyldimethylsilyl)oxy)methyl)-2-chloropyrimidine

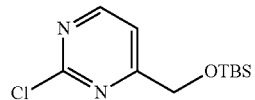 [SMILES: CC(C)(C)[Si](C)(C)OCc1ccnc(Cl)n1]

(2-Chloropyrimidin-4-yl)methanol (for a preparation see Intermediate 252, 135 mg, 0.934 mmol) and imidazole (127 mg, 1.868 mmol) were taken up in N,N-dimethylformamide (5 mL) and treated with TBDMSCl (141 mg, 0.934 mmol) and allowed to stir at rt for 2 h. The reaction was diluted with water and was extracted with DCM (×2), the combined organics were washed with 10% LiCl(aq), dried using a hydrophobic frit and concentrated to a yellow oil. This oil was purified using flash silica chromatography using a silica column (10 g) and eluting with: 0-50% DCM:cyclohexane. One broad peak was eluted and the appropriate fractions were summed and concentrated to give the product (63 mg, 0.243 mmol, 26%) as a colourless oil. LCMS (2 min Formic): Rt=1.38 min, [MH]$^+$=259.

Intermediate 254: (2S,3R,4R)-1-acetyl-4-((4-(((tert-butyldimethylsilyl)oxy)methyl)pyrimidin-2-yl)amino)-2-cyclopropyl-3-methyl-1,2,3,4-tetrahydroquinoline-6-carbonitrile

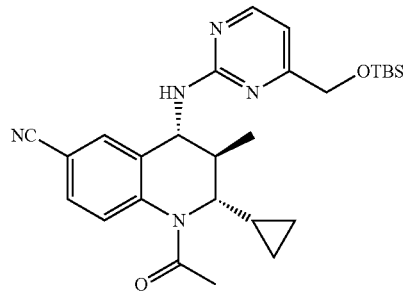

The title compound was prepared in a similar manner to intermediate 239 from (2S,3R,4R)-1-acetyl-4-amino-2-cyclopropyl-3-methyl-1,2,3,4-tetrahydroquinoline-6-carbonitrile (for a preparation see Intermediate 231, 50 mg, 0.186 mmol) and 4-(((tert-butyldimethylsilyl)oxy)methyl)-2-chloropyrimidine (for a preparation see Intermediate 253, 57.7 mg, 0.223 mmol) to give the product (30 mg, 0.061 mmol, 33%) as a yellow oil. LCMS (2 min Formic): Rt=1.42 min, [MH]$^+$=492.

Intermediate 255: ethyl 6-bromo-3-chloropicolinate

6-Bromo-3-chloropicolinic acid (560 mg, 2.368 mmol) was taken up in ethanol (5 mL) and was treated with sulfuric acid (0.126 mL, 2.368 mmol) and allowed to stir at 80° C. for 16 h. The reaction was allowed to cool to rt and was eluted through a NH$_2$ (5 g) SPE cartridge, washing with MeOH, the eluent was concentrated and dried to give the product (600 mg, 2.268 mmol, 96%) as a colourless oil. LCMS (2 min Formic): Rt=1.02 min, [MH]$^+$=264/266.

Intermediate 256: (6-bromo-3-chloropyridin-2-yl)methanol

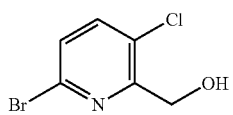

Ethyl 6-bromo-3-chloropicolinate (for a preparation see Intermediate 255, 690 mg, 2.61 mmol) was taken up in dichloromethane (5 mL) and allowed to stir at 0° C. for 5 min. Diisobutylaluminium hydride (5.22 mL, 5.22 mmol, 1 M in THF) was then added dropwise and the reaction allowed to warm to rt with stirring over 16 h. The reaction was treated with further diisobutylaluminium hydride (185 mg, 1.304 mmol, 1 M in THF) and allowed to stir at rt for 4 h and then to stand at rt for 4 days. The reaction was treated with 10% citric acid (aq) and was allowed to stir at rt for 30 min. The reaction was extracted with EtOAc (×2), the combined organics were washed with brine, dried using a hydrophobic frit and concentrated to a green oil. This oil was purified by flash chromatography using a Si column (10 g) eluting with: 0-50% EtOAc:cyclohexane. One major peak was eluted, the appropriate fractions were summed and concentrated to give the product (376 mg, 1.690 mmol, 65%) as a yellow oil. LCMS (2 min Formic): Rt=0.68 min, [MH]$^+$=222/224.

Intermediate 257: 6-bromo-2-(((tert-butyldimethylsilyl)oxy)methyl)-3-chloropyridine

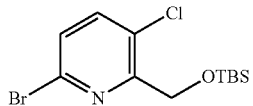

(6-Bromo-3-chloropyridin-2-yl)methanol (for a preparation see Intermediate 256, 376 mg, 1.690 mmol) and imidazole (230 mg, 3.38 mmol) were taken up in N,N-dimethylformamide (20 mL) and treated with TBDMSCl (280 mg, 1.859 mmol) and allowed to stir at rt for 16 h. The reaction was diluted with water and was extracted with DCM (×2) the combined organics were washed with 10% LiCl (aq), dried using a hydrophobic frit and concentrated to a colourless oil. This oil was purified by flash chromatography (10 g), eluting with 0-25% DCM:cyclohexane. The appropriate fractions were summed and concentrated to give the product (435 mg, 1.292 mmol, 76%) as a colourless oil. LCMS (2 min Formic): Rt=1.58 min, [MH]$^+$=336/338.

Intermediate 258: (2S,3R,4R)-1-acetyl-4-((6-(((tert-butyldimethylsilyl)oxy)methyl)-5-chloropyridin-2-yl)amino)-2-cyclopropyl-3-methyl-1,2,3,4-tetrahydroquinoline-6-carbonitrile

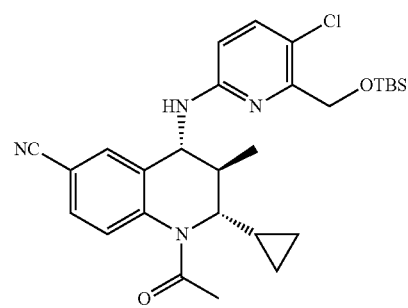 [SMILES: CC(=O)N1c2ccc(C#N)cc2[C@H](Nc2ccc(Cl)c(CO[Si](C)(C)C(C)(C)C)n2)[C@@H](C)[C@@H]1C1CC1]

To a solution of (2S,3R,4R)-1-acetyl-4-amino-2-cyclopropyl-3-methyl-1,2,3,4-tetrahydroquinoline-6-carbonitrile (for a preparation see Intermediate 231, 70 mg, 0.260 mmol) and 6-bromo-2-(((tert-butyldimethylsilyl)oxy)methyl)-3-chloropyridine (for a preparation see Intermediate 257, 140 mg, 0.416 mmol) in 1,4-dioxane (2.5 mL), was added Pd$_2$(dba)$_3$ (23.80 mg, 0.026 mmol), sodium tert-butoxide (74.9 mg, 0.780 mmol) and DavePhos (20.46 mg, 0.052 mmol). The reaction mixture was degassed and irradiated in a microwave to 120° C. for 30 min. The reaction was filtered though a 2.5 g Celite column and washed with EtOAc. The sample was concentrated and then loaded in dichloromethane and purified by flash chromatography on SP4 silica (Si, 25 g) using a 10-65% ethyl acetate-cyclohexane over 15 CV. The appropriate fractions were combined and concentrated to give the product (59.7 mg, 0.114 mmol, 44%) as an off-white solid.

LCMS (2 min Formic): Rt=1.54 min, [MH]$^+$=525.

Intermediate 259: (2S,3S,4R)-ethyl 4-(((benzyloxy)carbonyl)amino)-2-ethyl-3-methyl-1,2,3,4-tetrahydroquinoline-6-carboxylate

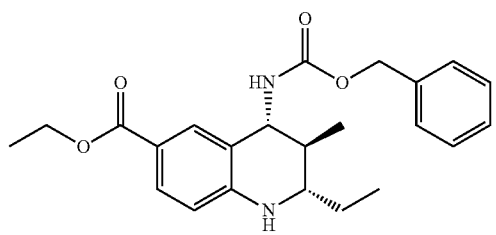 [SMILES: CCOC(=O)c1ccc2c(c1)[C@H](NC(=O)OCc1ccccc1)[C@@H](C)[C@H](CC)N2]

Ethyl 4-aminobenzoate (5.2 g, 31.5 mmol) was taken up in dichloromethane (DCM) (300 mL) under nitrogen. Propionaldehyde (3.41 ml, 47.2 mmol) was added and the reaction stirred at room temperature for 90 min. The reaction was cooled in an ice-bath and (E)-benzyl prop-1-en-1-ylcarbamate (for a preparation see Intermediate 1, 6.62 g, 34.6 mmol) in DCM (100 mL) added followed by (S)-2,6-bis(4-chlorophenyl)-4-hydroxy-8,9,10,11,12,13,14,15-octahydrodinaphtho[2,1-d:1',2'-f][1,3,2]dioxaphosphepine 4-oxide (for a preparation see JACS, 2011, 133, 14804, 0.545 g, 0.944 mmol, 0.182 g, 0.315 mmol) in one portion. The reaction was left to stir in the ice-bath. After 90 min the reaction was diluted with DCM (200 mL) and washed with sat. NaHCO₃ (500 mL). The combined organics were dried with Na₂SO₄, filtered and concentrated in vacuo to give the product (12.8 g). This was taken up in the minimum of hot EtOAc and then cyclohexane added until precipitation began. Quickly a large amount of solid formed. The mixture was reheated until a clear solution formed (additional EtOAc added) then left to cool to rt, then placed in an ice-bath. The resulting precipitate was collected by filtration, washed with cyclohexane (~100 mL) and dried in the vacuum oven to give the product (10.503 g, 25.2 mmol, 80%) as a white solid. Analysis by chiral HPLC was undertaken using a 250×4.6 mm Chiralpak IC column eluting with 25% ethanol in heptane at a flow rate of 1 mL/min. Peak 1/minor enantiomer (<0.5%) eluted at 6.3 min, and Peak 2/major enantiomer>99.5% by UV) eluted at 9.2 min. This indicated the product had an ee of >99%. LCMS (2 min HpH): Rt=1.22 min, [MH]⁺=397.

Intermediate 260: (2S,3R,4R)-ethyl 1-acetyl-4-(((benzyloxy)carbonyl)amino)-2-ethyl-3-methyl-1,2,3,4-tetrahydroquinoline-6-carboxylate

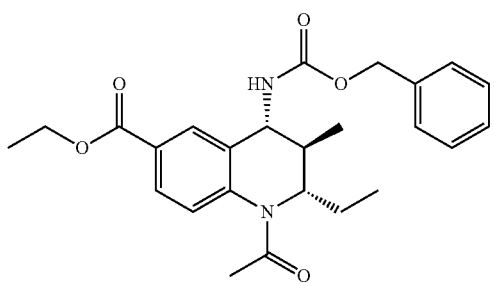 [SMILES: CCOC(=O)c1ccc2c(c1)[C@H](NC(=O)OCc1ccccc1)[C@@H](C)[C@H](CC)N2C(C)=O]

A solution of (2S,3S,4R)-ethyl 4-(((benzyloxy)carbonyl)amino)-2-ethyl-3-methyl-1,2,3,4-tetrahydroquinoline-6-carboxylate (for a preparation see Intermediate 259, 9.2 g, 23.20 mmol) and pyridine (5.63 ml, 69.6 mmol) in anhydrous dichloromethane (DCM) (800 mL) was cooled in an ice bath under nitrogen, then treated with acetyl chloride (1.980 ml, 27.8 mmol) added drop-wise over 10 min. The mixture was stirred at 0° C. for 1 h, then allowed to warm to rt and stirred for a further 3 h. The reaction mixture was transferred to a separating funnel and washed with 1M HCl (500 mL), water (500 mL) and saturated sodium bicarbonate solution (500 mL), dried and evaporated in vacuo to give the product (10.2 g, 23.26 mmol, 100%) as a colourless solid.
LCMS (2 min HpH): Rt=1.17 min, [M−NH₂]⁺=439.

Intermediate 261: (2S,3R,4R)-ethyl 1-acetyl-4-amino-2-ethyl-3-methyl-1,2,3,4-tetrahydroquinoline-6-carboxylate

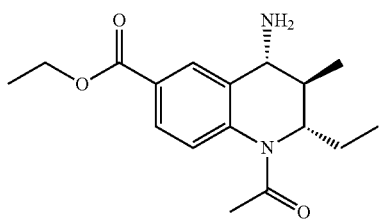 [SMILES: CCOC(=O)c1ccc2c(c1)[C@H](N)[C@@H](C)[C@H](CC)N2C(C)=O]

A conical flask was charged with (2S,3R,4R)-ethyl 1-acetyl-4-(((benzyloxy)carbonyl)amino)-2-ethyl-3-methyl-1,2,3,4-tetrahydroquinoline-6-carboxylate (for a preparation see Intermediate 260, 10 g, 22.80 mmol), ethanol (100 mL) and palladium on carbon (0.243 g, 2.280 mmol). The reaction mixture was stirred under an atmosphere of hydrogen for ~5 h. The reaction mixture was filtered through celite and eluted with ethanol (2×50 mL). The filtrate was concentrated in vacuo to give a yellow oil (6.918 g, 22.73 mmol, 100%).
LCMS (2 min Formic): Rt=0.57 min, [M−NH₂]⁺=288.

Intermediate 262: (2S,3R,4R)-ethyl 1-acetyl-4-((4-cyano-3-methylphenyl)amino)-2-cyclopropyl-3-methyl-1,2,3,4-tetrahydroquinoline-6-carboxylate

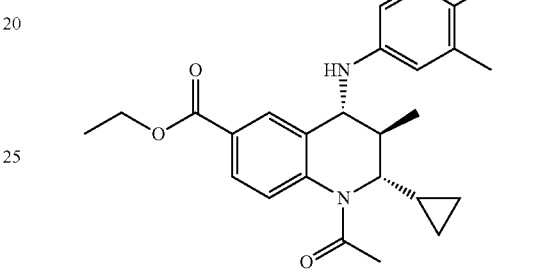

(2S,3R,4R)-ethyl 1-acetyl-4-amino-2-cyclopropyl-3-methyl-1,2,3,4-tetrahydroquinoline-6-carboxylate (for a preparation see Intermediate 225, 162 mg, 0.512 mmol), 4-bromo-2-methylbenzonitrile (181 mg, 0.922 mmol), Pd₂(dba)₃ (47 mg, 0.051 mmol), Q-Phos (38 mg, 0.053 mmol) and Cs₂CO₃ (334 mg, 1.024 mmol) were combined in dry toluene (3 mL). The reaction mixture was de-gassed and then heated at 80° C. under nitrogen for 3 h. The reaction stopped and cooled to rt and partitioned between ethyl acetate and water. The organic layer was separated and aqueous layer further extracted with ethyl acetate. The combined organic layers were dried (Na₂SO₄) and conc. to give ~403 mg of crude orange residue. This was purified by chromatography on SiO₂ (25 g) eluting with 0-50% ethyl acetate/cyclohexane over 330 mL to give the product (208 mg, 0.482 mmol, 94%) as an orange oil.
LCMS (2 min Formic): Rt=1.16 min, [MH]⁺=432.

Intermediate 263: (2S,3R,4R)-ethyl 1-acetyl-2-ethyl-3-methyl-4-((4-methylpyrimidin-2-yl)amino)-1,2,3,4-tetrahydroquinoline-6-carboxylate

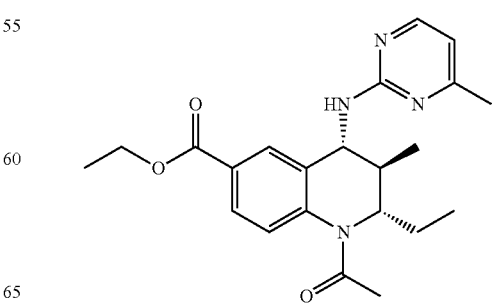

A solution of 2-chloro-4-methylpyrimidine (950 mg, 7.39 mmol) and potassium fluoride (644 mg, 11.09 mmol) and 18-crown-6 (977 mg, 3.70 mmol) in dimethyl sulfoxide (DMSO) (14 mL) was heated in a microwave at 160° C. for 60 min. Heating was continued for a further 30 min at 160° C. (2S,3R,4R)-ethyl 1-acetyl-4-amino-2-ethyl-3-methyl-1, 2,3,4-tetrahydroquinoline-6-carboxylate (for a preparation see Intermediate 261, 750 mg, 2.464 mmol) in dimethyl sulfoxide (DMSO) (3 mL) and DIPEA (2.152 mL, 12.32 mmol) were added and the vial sealed and heated to 160° C. for 3.5 h. The reaction mixture was diluted with Et$_2$O (100 mL), water (100 mL) was added and the layers separated. The aqueous layer was further extracted with Et$_2$O (2×60 mL) and the combined organics then back extracted with water (2×60 mL). The organic layer was dried (Na$_2$SO$_4$) and concentrated in vacuo to afford the crude product as an orange-brown oil. The crude product was taken up in DCM and added to a silica cartridge (100 g). This was purified by flash chromatography, eluting with 25%-100% EtOAc/cyclohexane. The appropriate fractions were collected and concentrated in vacuo to afford the desired product as a yellow foam (504 mg, 1.271 mmol, 52%).

LCMS (2 min Formic): Rt=0.95 min, [MH]$^+$=397.

Intermediate 264: (2S,3R,4R)-1-acetyl-2-cyclopropyl-4-((5-fluoropyridin-2-yl)amino)-3-methyl-1,2,3,4-tetrahydroquinoline-6-carbonitrile

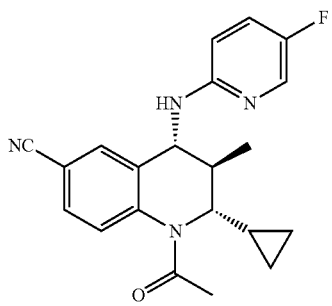 [SMILES: CC(=O)N1c2ccc(C#N)cc2[C@H](Nc2ccc(F)cn2)[C@@H](C)[C@@H]1C1CC1]

A round bottom flask was charged with (2S,3R,4R)-1-acetyl-4-amino-2-cyclopropyl-3-methyl-1,2,3,4-tetrahydroquinoline-6-carbonitrile (for a preparation see Intermediate 231, 150 mg, 0.557 mmol), 2-bromo-5-fluoropyridine (147 mg, 0.835 mmol), sodium tert-butoxide (123 mg, 1.281 mmol), toluene (4 mL) and Pd(QPhos)$_2$ (85 mg, 0.056 mmol). The reaction mixture was degassed and stirred at 50° C. for 3 h, the reaction mixture was concentrated in vacuo and purified by silica gel column chromatography eluting with a gradient cyclohexane/ethyl acetate (9%-35%) to give title compound as a red gum (188 mg, 83%). LCMS (2 min Formic): Rt=0.98 min, [MH]$^+$=365.

Intermediate 265: (2S,3S,4R)-ethyl 4-(((benzyloxy) carbonyl)amino)-2,3-dimethyl-1,2,3,4-tetrahydroquinoline-6-carboxylate

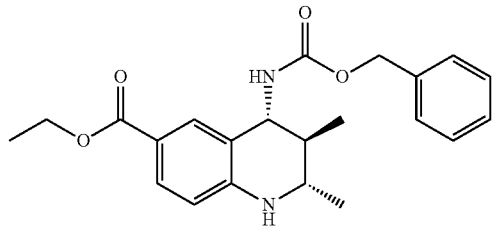 [SMILES: CCOC(=O)c1ccc2c(c1)[C@H](NC(=O)OCc1ccccc1)[C@@H](C)[C@H](C)N2]

Ethyl 4-aminobenzoate (15.6 g, 94 mmol) and acetaldehyde (8.00 ml, 142 mmol) were taken up in DCM (300 mL) and allowed to stir at rt for 1 hr. The reaction was then cooled to 0° C. and was treated with (E)-benzyl prop-1-en-1-ylcarbamate (for a preparation see Intermediate 1, 19.86 g, 104 mmol) and 2,6-bis(4-chlorophenyl)-4-hydroxy-8,9,10, 11,12,13,14,15-octahydrodinaphtho[2,1-d:1',2'-f][1,3,2]dioxaphosphepine 4-oxide (for a preparation see JACS, 2011, 133, 14804, 0.545 g, 0.944 mmol), the reaction was allowed to stir at 0° C. for 3 h. The mixture was diluted with DCM (300 mL), washed with a saturated sodium bicarbonate solution (600 mL), giving a dense emulsion, from which the organic layer was separated after half an hour of waiting. The remaining aqueous emulsion was extracted with DCM (200 mL), then diluted with saturated brine (300 mL) and extracted again with DCM (200 mL). This mixture was allowed to stand overnight, giving a nice clear organic layer and aggregation of the emulsion into clumps of white solid in the aqueous layer. The combined organics were dried and evaporated in vacuo to give a colourless solid. The crude product was recrystalised from EtOAc (300 mL)/cyclohexane to afford the title compound (23.3 g, 60.9 mmol, 65%) as a colourless solid. LCMS (2 min HpH): Rt=1.20 min, [MH]$^+$=383.

Intermediate 266: (2S,3R,4R)-ethyl 1-acetyl-4-(((benzyloxy)carbonyl)amino)-2,3-dimethyl-1,2,3,4-tetrahydroquinoline-6-carboxylate

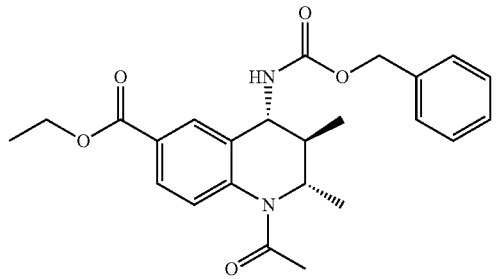

A solution of (2S,3S,4R)-ethyl 4-(((benzyloxy)carbonyl) amino)-2,3-dimethyl-1,2,3,4-tetrahydroquinoline-6-carboxylate (for a preparation see Intermediate 265, 29.5 g, 77 mmol) and pyridine (18.72 mL, 231 mmol) in anhydrous DCM (800 mL) was cooled in an ice bath under nitrogen, then treated with acetyl chloride (6.58 mL, 93 mmol) added dropwise over 10 min. The mixture was stirred at 0° C. for 1 h, then allowed to warm to room temperature and stirred for a further 3 h. The reaction mixture was transferred to a separating funnel and washed with 1M HCl (500 mL), water (500 mL) and saturated sodium bicarbonate solution (500 mL), dried and evaporated in vacuo to give the desired product (33.5 g).

LCMS (2 min HpH): Rt=1.13 min, [MH]⁺=425.

Intermediate 267: (2S,3R,4R)-ethyl 1-acetyl-4-amino-2,3-dimethyl-1,2,3,4-tetrahydroquinoline-6-carboxylate

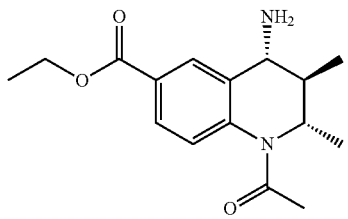 [SMILES: CCOC(=O)c1ccc2c(c1)[C@H](N)[C@@H](C)[C@H](C)N2C(C)=O]

A conical flask was charged with (2S,3R,4R)-ethyl 1-acetyl-4-(((benzyloxy)carbonyl)amino)-2,3-dimethyl-1,2,3,4-tetrahydroquinoline-6-carboxylate (for a preparation see Intermediate 266, 9.98 g, 23.51 mmol), ethanol (100 mL) and palladium on carbon (0.250 g, 2.351 mmol). The reaction mixture was stirred under an atmosphere of hydrogen for ~5 h. The reaction mixture was filtered through celite and eluted with ethanol (2×50 mL). The filtrate was concentrated in vacuo to give the desired product (6.85 g, 23.59 mmol, 100%) as a yellow oil.

LCMS (2 min Formic): Rt=0.51 min, [M−NH₂]⁺=274.

Intermediate 268: (2S,3R,4R)-1-acetyl-4-((5-fluoropyridin-2-yl)amino)-2,3-dimethyl-1,2,3,4-tetrahydroquinoline-6-carboxylic Acid

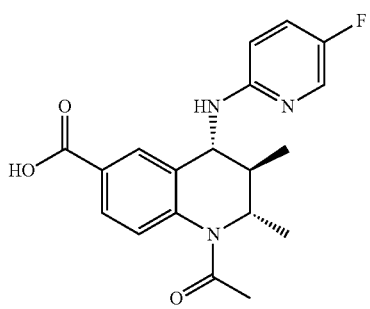 [SMILES: CC(=O)N1c2ccc(C(=O)O)cc2[C@H](Nc2ccc(F)cn2)[C@@H](C)[C@@H]1C]

(2S,3R,4R)-Ethyl 1-acetyl-4-amino-2,3-dimethyl-1,2,3,4-tetrahydroquinoline-6-carboxylate (for a preparation see Intermediate 267, 718 mg, 2.473 mmol), 2-bromo-5-fluoropyridine (653 mg, 3.71 mmol), Pd₂(dba)₃ (226 mg, 0.247 mmol), DavePhos (195 mg, 0.495 mmol) and sodium tert-butoxide (713 mg, 7.42 mmol) were combined in dry 1,4-dioxane (20 mL) and reaction mixture was stirred under N₂ at 90° C. The reaction mixture was allowed to stir at 90° C. for 3.5 h. LiOH (118 mg, 4.95 mmol) was added to the reaction mixture in water (4 mL) and reaction mixture continued to heat at 90° C. The reaction mixture was cooled to rt and diluted with ethyl acetate (20 mL) and filtered through celite (10 g). The filtrate was concentrated in vacuo to give a crude brown solid. This solid was purified by MDAP (TFA) to give the product as a yellow.

LCMS (2 min TFA): Rt=0.58 min, [MH]⁺=358.

Intermediate 269: 2-((tert-butyldimethylsilyl)oxy)-4-chlorobenzonitrile

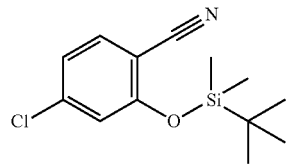 [SMILES: CC(C)(C)[Si](C)(C)Oc1cc(Cl)ccc1C#N]

4-bromo-2-hydroxybenzonitrile (500 mg, 2.53 mmol) and imidazole (344 mg, 5.05 mmol) were taken up in N,N-dimethylformamide (DMF) (20 mL) and treated with TBDMSCl (419 mg, 2.78 mmol) and allowed to stir at rt for 16 h. The reaction was diluted with water and was extracted with DCM (×2) the combined organics were washed with 10% LiCl (aq), dried using a hydrophobic frit and concentrated to a colourless oil. This oil was purified using silica gel column chromatography eluting with a gradient of 0-25% DCM:cyclohexane to give the product (248 mg, 0.794 mmol, 32%) as a colourless oil. LCMS (2 min Formic): Rt=1.52 min, [MH]⁺=No mass-ion seen.

Intermediate 270: (2S,3R,4R)-ethyl 1-acetyl-2-cyclopropyl-3-methyl-4-(pyridin-2-ylamino)-1,2,3,4-tetrahydroquinoline-6-carboxylate

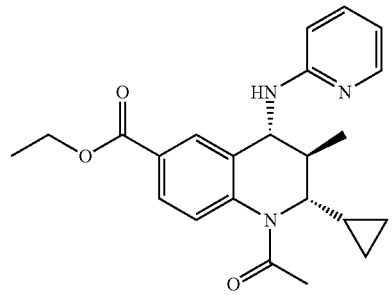 [SMILES: CCOC(=O)c1ccc2c(c1)[C@H](Nc1ccccn1)[C@@H](C)[C@H](C1CC1)N2C(C)=O]

In a RB flask were added (2S,3R,4R)-ethyl 1-acetyl-4-amino-2-cyclopropyl-3-methyl-1,2,3,4-tetrahydroquinoline-6-carboxylate (for a preparation see Intermediate 225, 157.4 mg, 0.497 mmol), 2-bromopyridine (0.071 mL, 0.746 mmol), sodium tert-butoxide (107.5 mg, 1.119 mmol) and Pd(QPhos)₂ (76.6 mg, 0.050 mmol) in toluene (10 mL). The reaction mixture was stirred under nitrogen at 50° C. for 5.5 h. Pd(QPhos)₂ (38.0 mg, 0.025 mmol) was added and reaction was left stirring at 50° C. for 20 h. Pd(QPhos)₂ (38.0 mg, 0.025 mmol) was added and reaction was left stirring at 50° C. for 16 h. The reaction mixture was partitioned between water and EtOAc. The aqueous phase was extracted with EtOAc. The organic layers were combined and washed with brine, dried over Na₂SO₄, filtered through a hydrophobic cartridge and the volatiles were removed under reduce pressure to afford a red gum. This gum was purified by silica gel column chromatography eluting with a gradient of 0-3% 2M NH₃ in MeOH to give title compound as a red gum (206 mg, 0.420 mmol, 84%). LCMS (2 min Formic): Rt=0.73 min, [MH]⁺=394.

Intermediate 271: (2S,3R,4R)-1-acetyl-2-cyclopropyl-3-methyl-4-(pyridin-2-ylamino)-1,2,3,4-tetrahydroquinoline-6-carboxylic Acid

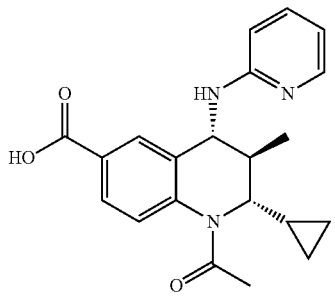 [SMILES: CC(=O)N1c2ccc(C(=O)O)cc2[C@H](Nc2ccccn2)[C@@H](C)[C@@H]1C1CC1]

(2S,3R,4R)-Ethyl 1-acetyl-2-cyclopropyl-3-methyl-4-(pyridin-2-ylamino)-1,2,3,4-tetrahydroquinoline-6-carboxylate (for a preparation see Intermediate 270, 206.7 mg, 0.525 mmol) and lithium hydroxide monohydrate (110 mg, 2.63 mmol) were dissolved in tetrahydrofuran (THF) (3 mL) and water (3.00 mL). The reaction was stirred at rt for 16 h. The reaction mixture was diluted with water and washed with EtOAc. The aqueous layer was then acidified with 1M HCl (pH=1) and extracted with EtOAc. The organic layers were combined, dried through hydrophobic cartridge and the volatiles were removed under reduce pressure to afford the title compound as a red gum (22 mg, 0.061 mmol, 12%). LCMS (2 min Formic): Rt=0.60 min, [MH]$^+$=366.

Intermediate 272: rac-(2S,3R,4R)-ethyl 1-acetyl-2-cyclopropyl-3-methyl-4-(pyrimidin-2-ylamino)-1,2,3,4-tetrahydroquinoline-6-carboxylate

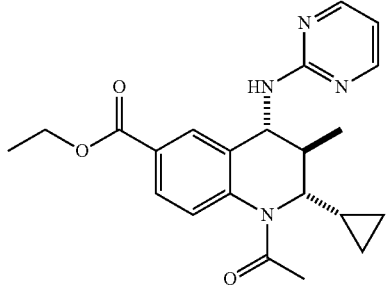 [SMILES: CCOC(=O)c1ccc2c(c1)[C@H](Nc1ncccn1)[C@@H](C)[C@H](C1CC1)N2C(C)=O]

A solution of rac-(2S,3R,4R)-ethyl 1-acetyl-4-amino-2-cyclopropyl-3-methyl-1,2,3,4-tetrahydroquinoline-6-carboxylate (for a preparation see Intermediate 225, 200 mg, 0.632 mmol), 2-fluoropyrimidine (124 mg, 1.264 mmol) and DIPEA (0.442 mL, 2.53 mmol) in N-methyl-2-pyrrolidone (NMP) (3 mL) was stirred in a closed vessel under microwave irradiation at 180° C. for 1.5 h. The solution was diluted with water and washed with DCM. The combined organic layers were concentrated in vacuo. The crude was purified by MDAP (HpH) to give the product (142 mg, 0.360 mmol, 57%).

LCMS (2 min Formic): Rt=0.96 min, [MH]$^+$=395.

Intermediate 273: rac-(2S,3R,4R)-1-acetyl-2-cyclopropyl-3-methyl-4-(pyrimidin-2-ylamino)-1,2,3,4-tetrahydroquinoline-6-carboxylic Acid

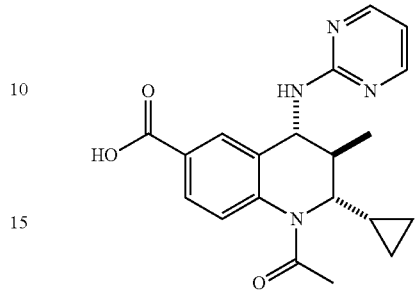

A solution of rac-(2S,3R,4R)-ethyl 1-acetyl-2-cyclopropyl-3-methyl-4-(pyrimidin-2-ylamino)-1,2,3,4-tetrahydroquinoline-6-carboxylate (for a preparation see Intermediate 264, 140 mg, 0.355 mmol) and LiOH (25.5 mg, 1.065 mmol) in tetrahydrofuran (THF) (1 mL) and water (1.000 mL) was stirred in a closed vessel at rt for 72 h. The solution was diluted with 0.5M HCl (3 mL) and washed with DCM (3×5 mL). The organic layer was dried through a hydrophobic frit to give the product (110 mg, 0.300 mmol, 85%). LCMS (2 min Formic): Rt=0.73 min, [MH]$^+$=367.

Intermediate 274: (2S,3R,4R)-1-acetyl-4-(((benzyloxy)carbonyl)amino)-2-cyclopropyl-3-methyl-1,2,3,4-tetrahydroquinoline-6-carboxylic Acid

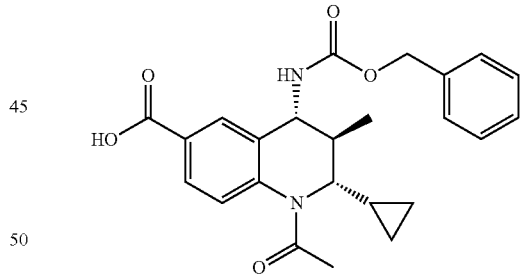

The (2S,3R,4R)-ethyl 1-acetyl-4-(((benzyloxy)carbonyl)amino)-2-cyclopropyl-3-methyl-1,2,3,4-tetrahydroquinoline-6-carboxylate (for a preparation see Intermediate 224, 3 g, 6.66 mmol) and lithium hydroxide (0.797 g, 33.3 mmol) were taken up in tetrahydrofuran (THF) (20 mL):water (20 mL) and allowed to stir at rt for 2 days. The reaction was concentrated to remove the THF and was acidified to pH2 with 2N HCl. A white precipitate formed which was removed by filtration and dried to give the product (2.765 g, 6.54 mmol, 98%) as a white solid.

LCMS (2 min Formic): Rt=0.94 min, [MH]$^+$=423.

Intermediate 275: benzyl ((2S,3R,4R)-1-acetyl-6-carbamoyl-2-cyclopropyl-3-methyl-1,2,3,4-tetrahydroquinolin-4-yl)carbamate

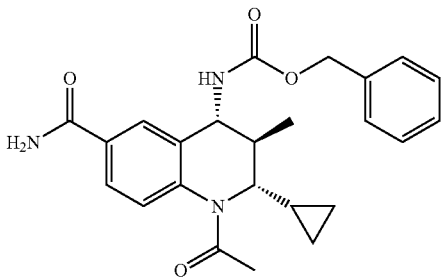 [SMILES: CC(=O)N1c2ccc(C(N)=O)cc2[C@H](NC(=O)OCc2ccccc2)[C@@H](C)[C@@H]1C1CC1]

The (2S,3R,4R)-1-acetyl-4-(((benzyloxy)carbonyl)amino)-2-cyclopropyl-3-methyl-1,2,3,4-tetrahydroquinoline-6-carboxylic acid (for a preparation see Intermediate 274, 2.76 g, 6.53 mmol) was taken up in dichloromethane (DCM) (50 mL) and was treated with thionyl chloride (2.384 mL, 32.7 mmol) and allowed to stir at rt for 2 h. The reaction was concentrated and azeotroped with toluene (×2) to give a orange gum, this gum was taken up in acetonitrile (40 mL) and was treated with DIPEA (3.42 mL, 19.60 mmol) followed by 0.88 ammonia (0.126 mL, 6.53 mmol) and was allowed to stir at rt for 30 min. The reaction was concentrated and purified by silica gel column chromatography eluting with 0-100% EtOAc:cyclohexane to give the product (2.012 g, 4.77 mmol, 73%) as a pale yellow solid.
LCMS (2 min Formic): Rt=0.87 min, [MH]+=422.

Intermediate 276: (2S,3R,4R)-1-acetyl-4-amino-2-cyclopropyl-3-methyl-1,2,3,4-tetrahydroquinoline-6-carboxamide

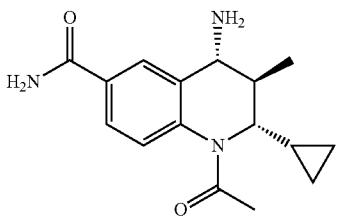 [SMILES: CC(=O)N1c2ccc(C(N)=O)cc2[C@H](N)[C@@H](C)[C@@H]1C1CC1]

A solution of benzyl ((2S,3R,4R)-1-acetyl-6-carbamoyl-2-cyclopropyl-3-methyl-1,2,3,4-tetrahydroquinolin-4-yl)carbamate (for a preparation see Intermediate 275, 2.02 g, 4.79 mmol) in ethanol (100 mL) was passed through a Thales H-cube flow hydrogenator with a 10% Pd/C CatCart in full H$_2$ mode at a rate of 1 mL/min. The solvent was evaporated to afford the product (1.2 g, 4.18 mmol, 87%) as a white foam/oil. LCMS (2 min Formic): Rt=0.60 min, [M–NH$_2$]+=271.

Intermediate 277: 2-chloro-4,5-dimethylpyrimidine

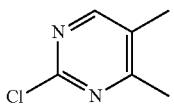

To a solution of 2,4-dichloro-5-methylpyrimidine (0.769 ml, 6.13 mmol) in tetrahydrofuran (THF) (34.6 ml)/N-methyl-2-pyrrolidone (NMP) (2.61 ml) was added ferric acetylacetonate (0.217 g, 0.613 mmol) and the mixture was cooled to 0° C. under nitrogen. Then methylmagnesium bromide (3.2 M in MeTHF) (2.88 ml, 9.20 mmol) was added drop-wise. The mixture was stirred for 30 min under nitrogen at 0° C. The reaction was then quenched with saturated aqueous NH$_4$Cl solution (10 mL). Diethyl ether was added (10 mL) and the layers were separated. The aqueous layer was further extracted with diethyl ether. The combined organic extracts were dried over a hydrophobic frit and concentrated in vacuo to give an orange oil. This oil was purified by silica gel column chromatography eluting with cyclohexane/EtOAc 0-30% to give the product (575 mg, 4.03 mmol, 66%) as a clear liquid. LCMS (2 min Formic): Rt=0.64 min, [MH]+=143.

Intermediate 278: 2-chloro-4-(3,6-dihydro-2H-pyran-4-yl)pyrimidine

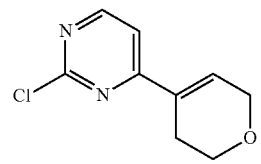 [SMILES: Clc1nccc(C2=CCOCC2)n1]

A round bottom flask was charged with palladium acetate (111 mg, 0.493 mmol), 2-(dicyclohexylphosphino)biphenyl (173 mg, 0.493 mmol), 2-(3,6-dihydro-2H-pyran-4-yl)-4,4,5,5-tetramethyl-1,3,2-dioxaborolane (1036 mg, 4.93 mmol), 2,4-dichloropyrimidine (735 mg, 4.93 mmol), potassium fluoride (860 mg, 14.80 mmol) and tetrahydrofuran (THF) (15 mL). The solution was stirred at 70° C. under a nitrogen atmosphere for 24 h. A saturated solution of NaHCO$_3$ (10 mL) was added to the mixture which was then extracted with diethyl ether (2×15 mL) The organic phase was dried through a hydrophobic frit and evaporated in vacuo. The sample purified by column chromatography on silica gel eluting with a 10-50% ethyl acetate-cyclohexane gradient to give the title compound (212.7 mg, 22%) as a yellow solid.
LCMS (2 min Formic): Rt=0.72 min, [MH]+=197.

Intermediate 279: (2S,3S,4R)-2-cyclopropyl-3-methyl-4-((1-methyl-2-oxo-1,2-dihydropyridin-3-yl)amino)-1,2,3,4-tetrahydroquinoline-6-carbonitrile

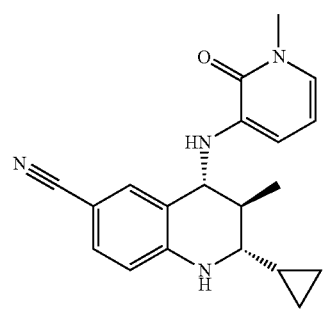 [SMILES: C[C@@H]1[C@@H](Nc2cccn(C)c2=O)c2cc(C#N)ccc2N[C@H]1C1CC1]

A round bottom flask was charged with (2S,3R,4R)-1-acetyl-4-amino-2-cyclopropyl-3-methyl-1,2,3,4-tetrahydroquinoline-6-carbonitrile (for a preparation see Intermediate 231, 200 mg, 0.743 mmol), 3-bromo-1-methylpyridin-2 (1H)-one (209 mg, 1.114 mmol), sodium tert-butoxide (164 mg, 1.708 mmol), Pd$_2$(dba)$_3$ (68.0 mg, 0.074 mmol), QPhos (52.8 mg, 0.074 mmol) and toluene (4 mL). The reaction mixture was degassed and stirred under nitrogen for 4 h 20 min. To the reaction mixture Pd$_2$(dba)$_3$ (68.0 mg, 0.074 mmol), sodium tert-butoxide (164 mg, 1.708 mmol) and QPhos (52.8 mg, 0.074 mmol) were added. The reaction mixture was stirred at 50° C. under nitrogen for 2 h 30 min. The reaction mixture was concentrated in vacuo and washed with water. The organic layer was dried, concentrated in vacuo and purified by silica gel column chromatography eluting with cyclohexane/ethyl acetate (12%-50%) to give title compound (124 mg, 90%) as a cream solid.

LCMS (2 min Formic): Rt=1.00 min, [MH]$^+$=335.

Intermediate 280: (2S,3S,4R)-2-cyclopropyl-3-methyl-4-((1-methyl-2-oxo-1,2-dihydropyridin-3-yl)amino)-1,2,3,4-tetrahydroquinoline-6-carboxamide

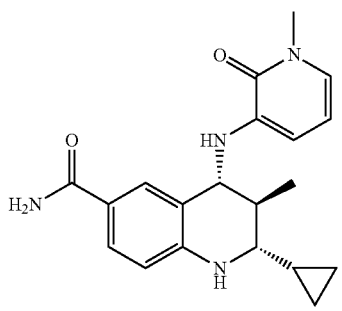 [SMILES: C[C@@H]1[C@@H](Nc2cccn(C)c2=O)c2cc(C(N)=O)ccc2N[C@H]1C1CC1]

To (2S,3S,4R)-2-cyclopropyl-3-methyl-4-((1-methyl-2-oxo-1,2-dihydropyridin-3-yl)amino)-1,2,3,4-tetrahydroquinoline-6-carbonitrile (for a preparation see Intermediate 279, 124 mg, 0.371 mmol) in a round bottom flask hydrogen peroxide (0.319 mL, 3.71 mmol), potassium carbonate (102 mg, 0.742 mmol) and dimethyl sulfoxide (DMSO) (4 mL) were added. The reaction mixture was stirred at rt for 5 h. To the reaction mixture hydrogen peroxide (0.319 mL, 3.71 mmol) was added. The reaction mixture was stirred overnight at rt, the reaction mixture was diluted with DCM and washed with water. The organic layer was dried, concentrated in vacuo and purified by silica gel column chromatography eluting with DCM/methanol (1.9%-7.6%) to give title compound as a green solid (15 mg, 77%). LCMS (2 min Formic): Rt=0.82 min, [MH]$^+$=353.

Intermediate 281: methyl 2-(((2S,3R,4R)-1-acetyl-6-cyano-2-cyclopropyl-3-methyl-1,2,3,4-tetrahydroquinolin-4-yl)amino)nicotinate

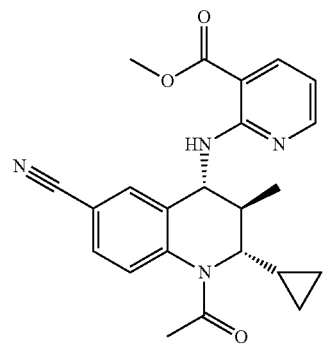 [SMILES: COC(=O)c1cccnc1N[C@H]1c2cc(C#N)ccc2N(C(C)=O)[C@@H](C2CC2)[C@@H]1C]

A solution of (2S,3R,4R)-1-acetyl-4-amino-2-cyclopropyl-3-methyl-1,2,3,4-tetrahydroquinoline-6-carbonitrile (for a preparation see Intermediate 231, 2 g, 7.43 mmol), methyl 2-fluoronicotinate (1.850 ml, 14.85 mmol) and NEt$_3$ (2.070 ml, 14.85 mmol) in dimethyl sulfoxide (DMSO) (9.41 ml) was stirred in a closed vessel under microwave irradiation at 160° C. for 1 h. The solution was diluted with 0.5M NaOH aqueous solution (30 mL) and washed with DCM (3×30 mL). The organic layers were combined, dried through a hydrophobic frit and concentrated in vacuo to give crude. This crude was purified by silica gel column chromatography eluting with a gradient 0-70% ethyl acetate in DCM to give the product (950 mg, 2.349 mmol, 32%). LCMS (2 min Formic): Rt=1.15 min, [MH]$^+$=405.

Intermediate 282: (2S,3R,4R)-1-acetyl-2-cyclopropyl-4-((3-(hydroxymethyl)pyridin-2-yl)amino)-3-methyl-1,2,3,4-tetrahydroquinoline-6-carbonitrile

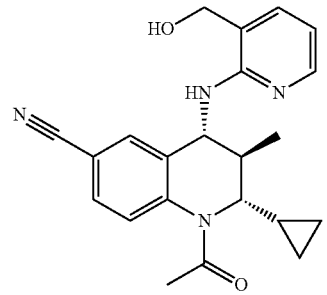 [SMILES: CC(=O)N1c2ccc(C#N)cc2[C@H](Nc2ncccc2CO)[C@@H](C)[C@@H]1C1CC1]

A solution of methyl 2-(((2S,3R,4R)-1-acetyl-6-cyano-2-cyclopropyl-3-methyl-1,2,3,4-tetrahydroquinolin-4-yl)amino)nicotinate (for a preparation see Intermediate 281, 400 mg, 0.989 mmol), calcium chloride (220 mg, 1.978 mmol) and NaBH$_4$ (748 mg, 19.78 mmol) in tetrahydrofuran (THF) (5 mL) and ethanol (2.5 mL) was stirred under nitrogen at 65° C. for 1 h. The reaction mixture was concentrated in vacuo and washed between ethyl acetate and water. The organic layer was further washed with water and concentrated in vacuo to give crude product. The crude was purified by MDAP (HpH) to give the product (89 mg, 0.236 mmol, 24%).

LCMS (2 min Formic): Rt=0.61 min, [MH]$^+$=377.

Intermediate 283: 3-(((tert-butyldimethylsilyl)oxy)methyl)-2-chloro-6-methylpyridine

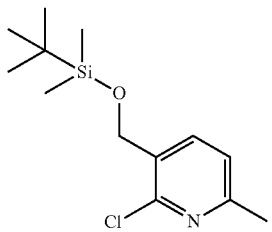 [SMILES: Cc1ccc(CO[Si](C)(C)C(C)(C)C)c(Cl)n1]

The (2-chloro-6-methylpyridin-3-yl)methanol (500 mg, 3.17 mmol) was taken up in N,N-dimethylformamide (DMF) (5 mL) and treated with imidazole (432 mg, 6.35 mmol) and TBDMSCl (478 mg, 3.17 mmol) and allowed to stir at rt for 16 h. The reaction was treated with further TBDMSCl (239 mg, 1.586 mmol) and allowed to stir at rt for 5 h. The reaction was diluted with water and extracted with DCM (×2) the combined organics were washed with 10% LiCl (aq), dried using a hydrophobic frit and concentrated to a gum. This gum was purified using a column chromatography, elute: 0-50% DCM:cyclohexane, one broad peak was eluted, the appropriate fractions were summed and concentrated to give the product (754 mg, 2.77 mmol, 87%) as a colourless oil.

LCMS (2 min Formic): Rt=1.53 min, [MH]⁺=272.

Intermediate 284: (2S,3R,4R)-1-acetyl-4-((3-(((tert-butyldimethylsilyl)oxy)methyl)-6-methylpyridin-2-yl)amino)-2-cyclopropyl-3-methyl-1,2,3,4-tetrahydroquinoline-6-carbonitrile

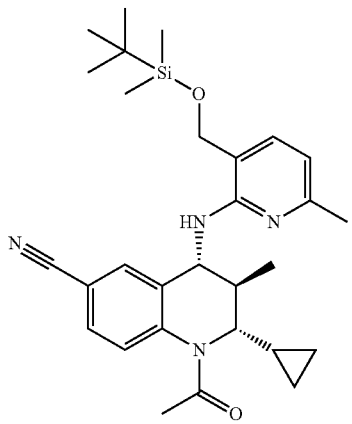 [SMILES: CC(=O)N1c2ccc(C#N)cc2[C@H](Nc2nc(C)ccc2CO[Si](C)(C)C(C)(C)C)[C@@H](C)[C@@H]1C1CC1]

The (2S,3R,4R)-1-acetyl-4-amino-2-cyclopropyl-3-methyl-1,2,3,4-tetrahydroquinoline-6-carbonitrile (for a preparation see Intermediate 231, 100 mg, 0.371 mmol), 3-(((tert-butyldimethylsilyl)oxy)methyl)-2-chloro-6-methylpyridine (for a preparation see Intermediate 283, 121 mg, 0.446 mmol), sodium tert-butoxide (107 mg, 1.114 mmol), Pd₂(dba)₃ (34.0 mg, 0.037 mmol), DavePhos (29.2 mg, 0.074 mmol) and 1,4-dioxane (2 mL) were placed in a microwaveable vial and irradiated in a microwave at 120° C. for 30 min. The reaction was filtered through celite, washing with EtOAc, the eluent was concentrated to a brown gum. This gum was purified using a column chromatography, elute: 0-50% EtOAc:cyclohexane, one major peak was eluted and the appropriate fractions were summed and concentrated to give the product (33 mg, 0.065 mmol, 18%) as a yellow gum. LCMS (2 min Formic): Rt=1.31 min, [MH]⁺=505.

Intermediate 285: (2S,3R,4R)-1-acetyl-2-cyclopropyl-4-((3-(hydroxymethyl)-6-methylpyridin-2-yl)amino)-3-methyl-1,2,3,4-tetrahydroquinoline-6-carbonitrile

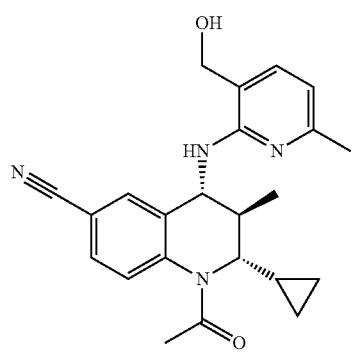 [SMILES: CC(=O)N1c2ccc(C#N)cc2[C@H](Nc2nc(C)ccc2CO)[C@@H](C)[C@@H]1C1CC1]

The (2S,3R,4R)-1-acetyl-4-((3-(((tert-butyldimethylsilyl)oxy)methyl)-6-methylpyridin-2-yl)amino)-2-cyclopropyl-3-methyl-1,2,3,4-tetrahydroquinoline-6-carbonitrile (for a preparation see Intermediate 284, 53 mg, 0.105 mmol) was taken up in 1M TBAF/THF (1 ml, 1.00 mmol) and allowed to stir at rt for 1 h. The reaction was concentrated and purified using a column chromatography, elute: 0-10% 2M NH₃/MeOH:DCM, one major peak was eluted, the appropriate fractions were summed and concentrated to give the product (75 mg, 0.192 mmol) as brown solid. This was not pure but carried through as was to the next step. LCMS (2 min Formic): Rt=0.67 min, [MH]⁺=391.

Intermediate 286: benzyl ((2S,3R,4R)-6-cyano-2-cyclopropyl-1-isobutyryl-3-methyl-1,2,3,4-tetrahydroquinolin-4-yl)carbamate

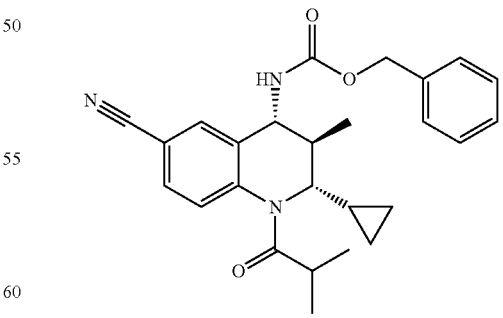

To a suspension of benzyl ((2S,3S,4R)-6-cyano-2-cyclopropyl-3-methyl-1,2,3,4-tetrahydroquinolin-4-yl)carbamate (for a preparation see Intermediate 229, 200 mg, 0.553 mmol) and DIPEA (0.145 mL, 0.830 mmol) in dichloromethane (DCM) (5 mL), was added isobutyryl chloride (0.087 mL, 0.830 mmol) and the reaction allowed to stir under nitrogen for 1 h. A further portion of isobutyryl chloride (0.087 mL, 0.830 mmol) in dichloromethane (DCM) (5 mL) was added and the reaction allowed to stir for 16 h. Further isobutyryl chloride (0.580 mL, 5.53 mmol) and acetonitrile (5.00 mL) were added and the reaction heated to 50° C. for 1 h. The reaction was allowed to cool to rt and partitioned between NaHCO₃ and DCM. The organic layer was removed and the aqueous layer re-extracted with DCM. The organic extracts were combined and washed with water, dried over a hydrophobic frit and concentrated in vacuo. The sample was purified by silica gel column chromatography eluting with a 5-25% ethyl acetate-cyclohexane gradient to give the product (92.1 mg, 0.213 mmol, 39%) as a pale yellow oil. LCMS (2 min Formic): Rt=1.19 min, [MH]⁺=432.

Intermediate 287: (2S,3R,4R)-4-amino-2-cyclopropyl-1-isobutyryl-3-methyl-1,2,3,4-tetrahydroquinoline-6-carbonitrile

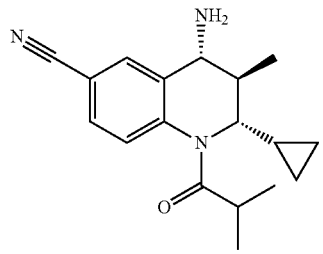 [SMILES: CC(C)C(=O)N1c2ccc(C#N)cc2[C@H](N)[C@@H](C)[C@@H]1C1CC1]

To a solution of benzyl ((2S,3R,4R)-6-cyano-2-cyclopropyl-1-isobutyryl-3-methyl-1,2,3,4-tetrahydroquinolin-4-yl)carbamate (for a preparation see Intermediate 286, 92 mg, 0.213 mmol) in tetrahydrofuran (THF) (1.36 mL), was added TBAF (1M in THF) (0.640 mL, 0.640 mmol) and the reaction allowed to stir under nitrogen at 60° C. for 26 h. The reaction mixture was concentrated and then partitioned between 1M HCl and DCM and the aqueous layer was re-extracted with DCM. The aqueous layer was basified with NaHCO₃ and extracted with DCM twice. These two organic layers were combined and concentrated. The residue was purified by silica gel column chromatography eluting with a 20-100% ethyl acetate-cyclohexane gradient to give the product (38.9 mg, 0.131 mmol, 61%) as a an off-white solid. LCMS (2 min Formic): Rt=0.65 min, [MH]⁺=298.

Intermediate 288: (2S,3R,4R)-2-cyclopropyl-1-isobutyryl-3-methyl-4-((4-methylpyrimidin-2-yl)amino)-1,2,3,4-tetrahydroquinoline-6-carbonitrile

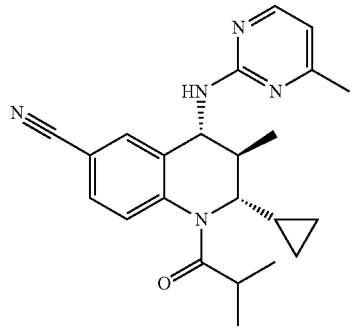 [SMILES: Cc1ccnc(N[C@H]2c3cc(C#N)ccc3N(C(=O)C(C)C)[C@@H](C3CC3)[C@@H]2C)n1]

To a solution of (2S,3R,4R)-4-amino-2-cyclopropyl-1-isobutyryl-3-methyl-1,2,3,4-tetrahydroquinoline-6-carbonitrile (for a preparation see Intermediate 287, 38.7 mg, 0.130 mmol) in dimethyl sulfoxide (DMSO) (3 mL), was added 18-crown-6 (17.20 mg, 0.065 mmol), potassium fluoride (11.34 mg, 0.195 mmol) and DIPEA (0.039 mL, 0.221 mmol) and the reaction irradiated to 140° C. for 6 h. A further portion of 2-chloro-4-methylpyrimidine (18.40 mg, 0.143 mmol), 18-crown-6 (17.20 mg, 0.065 mmol), potassium fluoride (11.34 mg, 0.195 mmol) and DIPEA (0.039 mL, 0.221 mmol) were added and the reaction irradiated to 160° C. for 4 h. The reaction mixture was diluted with water and extracted twice with EtOAc. The organic extracts were combined, washed with brine, dried over a hydrophobic frit and concentrated in vacuo. The residue was purified using silica gel column chromatography eluting with a gradient of 0-20% Methanol-DCM. The residue was further purified by MDAP (Formic) to give the product (5 mg, 0.013 mmol, 10%) as an off-white solid.

LCMS (2 min Formic): Rt=1.06 min, [MH]⁺=390.

Intermediate 289: (2S,3R,4R)-ethyl 1-acetyl-4-((5-cyanothiophen-2-yl)amino)-2-cyclopropyl-3-methyl-1,2,3,4-tetrahydroquinoline-6-carboxylate

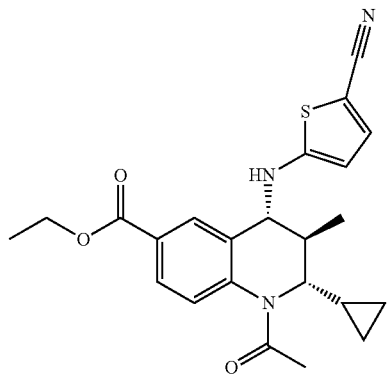 [SMILES: CCOC(=O)c1ccc2c(c1)[C@H](Nc1ccc(C#N)s1)[C@@H](C)[C@H](C1CC1)N2C(C)=O]

A mixture of (2S,3R,4R)-ethyl 1-acetyl-4-amino-2-cyclopropyl-3-methyl-1,2,3,4-tetrahydroquinoline-6-carboxylate (for a preparation see Intermediate 225, 303 mg, 0.957 mmol), 5-bromothiophene-2-carbonitrile (150 mg, 0.798 mmol), cesium carbonate (520 mg, 1.595 mmol), Pd-PEPPSI-IPent (43.4 mg, 0.064 mmol) in 1,2-dimethoxyethane (DME) (10 mL) was put in a microwave vessel. The vessel was sealed and heated in microwave at 120° C. for 3 h. The mixture was dissolved in ethyl acetate (10 mL) and washed through a celite cartridge (10 g). The washing was evaporated and purified by MDAP (Formic) to give the title compound (31.9 mg, 9%) as a yellow solid.

LCMS (2 min HpH): Rt=1.16 min, [MH]⁺=424.

Intermediate 290: (2S,3R,4R)-1-acetyl-4-((5-cyano-thiophen-2-yl)amino)-2-cyclopropyl-3-methyl-1,2,3,4-tetrahydroquinoline-6-carboxylic Acid

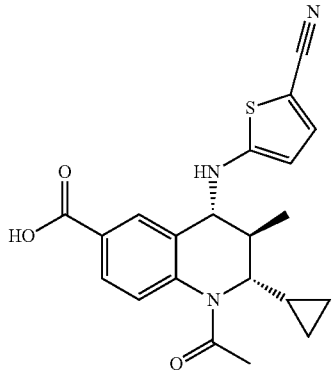 [SMILES: CC(=O)N1c2ccc(C(=O)O)cc2[C@H](Nc2ccc(C#N)s2)[C@@H](C)[C@@H]1C1CC1]

A solution of lithium hydroxide (9.02 mg, 0.377 mmol) in water (1.0 mL) was added to a solution of (2S,3R,4R)-ethyl 1-acetyl-4-((5-cyanothiophen-2-yl)amino)-2-cyclopropyl-3-methyl-1,2,3,4-tetrahydroquinoline-6-carboxylate (for a preparation see Intermediate 289, 31.9 mg, 0.075 mmol) in tetrahydrofuran (THF) (1 mL) and the mixture was stirred at RT in a sealed round-bottom flask for 5 h. HCl (0.5M) (0.753 mL, 0.377 mmol) was added to the reaction mixture followed by water (5 mL). The mixture was extracted with 10% MeOH/DCM (3×5 mL), the organic phase was dried through a hydrophobic frit and evaporated in vacuo to give title compound (21.1 mg, 71%) as a green oil.

LCMS (2 min HpH): Rt=0.68 min, [MH]$^+$=396.

Intermediate 291: (2S,3R,4R)-1-acetyl-4-(((benzyloxy)carbonyl)amino)-2,3-dimethyl-1,2,3,4-tetrahydroquinoline-6-carboxylic Acid

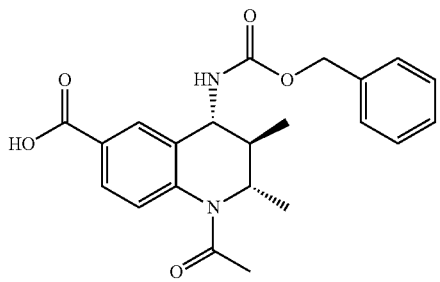 [SMILES: CC(=O)N1c2ccc(C(=O)O)cc2[C@H](NC(=O)OCc2ccccc2)[C@@H](C)[C@@H]1C]

The (2S,3R,4R)-ethyl 1-acetyl-4-(((benzyloxy)carbonyl)amino)-2,3-dimethyl-1,2,3,4-tetrahydroquinoline-6-carboxylate (for a preparation see Intermediate 266, 2 g, 4.71 mmol) and lithium hydroxide (0.564 g, 23.56 mmol) were taken up in THF (20 mL):water (20 mL) and allowed to stir at rt for 16 h. The reaction was acidified to pH2 with 2N HCl, a white precipitate formed which was removed by filtration and dried to give the desired product (1.851 g, 4.67 mmol, 99%) as a white solid. LCMS (2 min Formic): Rt=0.87 min, [MH]$^+$=397.

Intermediate 292: (2S,3R,4R)-1-acetyl-4-(((benzyloxy)carbonyl)amino)-2-ethyl-3-methyl-1,2,3,4-tetrahydroquinoline-6-carboxylic Acid

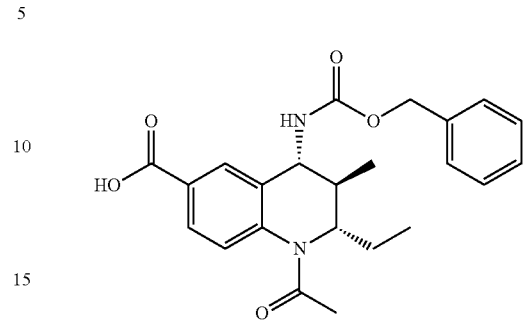

(2S,3R,4R)-Ethyl 1-acetyl-4-(((benzyloxy)carbonyl) amino)-2-ethyl-3-methyl-1,2,3,4-tetrahydroquinoline-6-carboxylate (for a preparation see Intermediate 260, 2 g, 4.56 mmol) and lithium hydroxide (0.546 g, 22.80 mmol) was taken up in THF (20 mL):Water (20 mL) and allowed to stir at rt for 16 h. The reaction was acidified to pH2 with 2N HCl and was extracted into EtOAc. The organic phase was dried using a hydrophobic frit and concentrated to give the desired product (1.89 g, 4.6 mmol) as a white solid. LCMS (2 min Formic): Rt=0.92 min, [MH]$^+$=411.

Intermediate 293: 2-((tert-butyldimethylsilyl)oxy)ethanamine

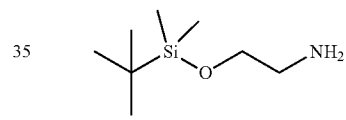

To a stirred solution of ethanolamine (1.980 mL, 32.7 mmol), DMAP (0.040 g, 0.327 mmol) and triethylamine (6.85 mL, 49.1 mmol) in DCM (50 mL) was added TBDMSCl (5.68 g, 37.7 mmol). The reaction was allowed to stir at rt for 16 h. The reaction was quenched with NH$_4$Cl$_{(aq)}$ and extracted with DCM, the organic phase was washed with water, dried using a hydrophobic frit and concentrated and dried to give the product (3.607 g, 20.57 mmol, 63%) as a yellow oil.

LCMS (2 min Formic): Not observed.

Intermediate 294: benzyl ((2S,3R,4R)-1-acetyl-6-((2-((tert-butyldimethylsilyl)oxy)ethyl)carbamoyl)-2-ethyl-3-methyl-1,2,34-tetrahydroquinolin-4-yl) carbamate

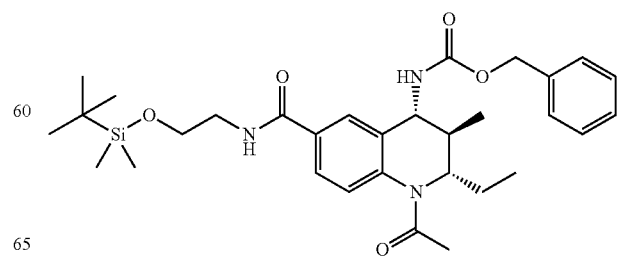

The (2S,3R,4R)-1-acetyl-4-(((benzyloxy)carbonyl)amino)-2-ethyl-3-methyl-1,2,3,4-tetrahydroquinoline-6-carboxylic acid (for a preparation see Intermediate 292, 1.89 g, 4.60 mmol) was taken up in DCM (50 mL) and was treated with thionyl chloride (1.680 mL, 23.02 mmol) and allowed to stir at rt for 2 h. The reaction was concentrated and azeotroped with toluene (×2) to give a orange gum, this gum was taken up in acetonitrile (40 mL) and was treated with DIPEA (2.413 mL, 13.81 mmol) followed by 2-((tert-butyldimethylsilyl)oxy)ethanamine (1.050 g, 5.99 mmol) and was allowed to stir at rt for 1 h. The reaction was concentrated and purified using a 25 g Si column eluting with 0-50% EtOAc:cyclohexane, the appropriate fractions were summed and concentrated to give the desired product (2.383 g, 4.20 mmol, 91%) as a yellow solid.

LCMS (2 min Formic): Rt=1.30 min, [MH]⁺=568.

The following intermediates were prepared in a similar manner to Intermediate 294 using thionyl chloride to couple Intermediate 274 (2-cPr) or 291 (2-Me) with Intermediate 293.

| Int No. | Name | Structure | Mass (mg) | Yield (%) | [MH]⁺ | Rt (mins) (LCMS method) |
|---|---|---|---|---|---|---|
| 295 | benzyl ((2S,3R,4R)-1-acetyl-6-((2-((tert-butyldimethylsilyl)oxy)ethyl)carbamoyl)-2-cyclopropyl-3-methyl-1,2,3,4-tetrahydroquinolin-4-yl)carbamate | 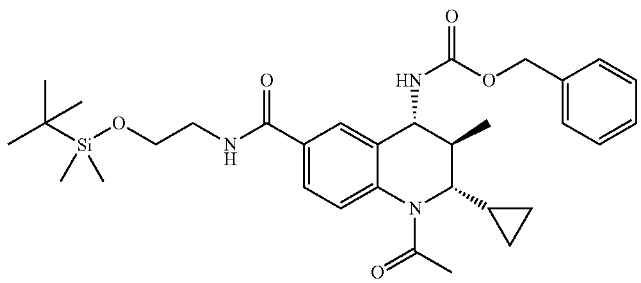 [SMILES: CC(=O)N1c2ccc(C(=O)NCCO[Si](C)(C)C(C)(C)C)cc2[C@H](NC(=O)OCc2ccccc2)[C@@H](C)[C@@H]1C1CC1] | 944 | 79 | 580 | 1.32 (2 min Formic) |
| 296 | benzyl ((2S,3R,4R)-1-acetyl-6-((2-((tert-butyldimethylsilyl)oxy)ethyl)carbamoyl)-2,3-dimethyl-1,2,3,4-tetrahydroquinolin-4-yl)carbamate | 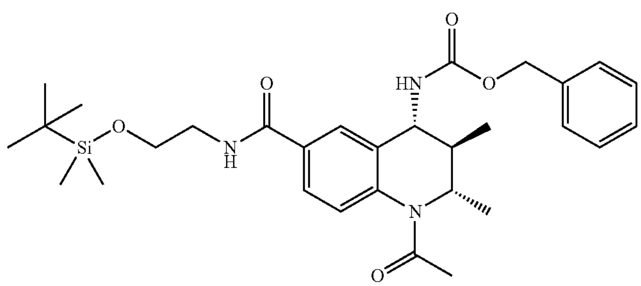 [SMILES: CC(=O)N1c2ccc(C(=O)NCCO[Si](C)(C)C(C)(C)C)cc2[C@H](NC(=O)OCc2ccccc2)[C@@H](C)[C@@H]1C] | 2057 | 80 | 554 | 1.27 (2 min Formic) |

Intermediate 297: (2S,3R,4R)-1-acetyl-4-amino-N-(2-((tert-butyldimethylsilyl)oxy)ethyl)-2-ethyl-3-methyl-1,2,3,4-tetrahydroquinoline-6-carboxamide

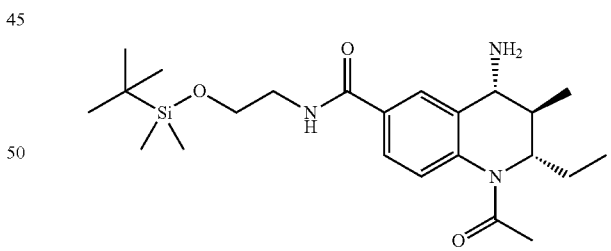

Benzyl ((2S,3R,4R)-1-acetyl-6-((2-((tert-butyldimethylsilyl)oxy)ethyl)carbamoyl)-2-ethyl-3-methyl-1,2,3,4-tetrahydroquinolin-4-yl)carbamate (for a preparation see Intermediate 294, 2.383 g, 4.20 mmol) was taken up in ethanol (30 mL) and was treated with 10% Pd/C (200 mg, 1.879 mmol) and allowed to stir at rt under a atmosphere of hydrogen for 16 h, The reaction was filtered through celite, concentrated and dried to give the desired product (1.350 g, 3.11 mmol, 96%) as an off-white solid.

LCMS (2 min Formic): Rt=0.90 min, [MH]⁺=434.

The following intermediates were prepared in a similar manner to Intermediate 297 using 10% Pd/C—H₂ to deprotect Intermediate 295 (2-cPr) or 296 (2-Me).

| Int No. | Name | Structure | Mass (mg) | Yield (%) | [MH]+ | Rt (mins) (LCMS method) |
|---|---|---|---|---|---|---|
| 298 | (2S,3R,4R)-1-acetyl-4-amino-N-(2-((tert-butyldimethylsilyl)oxy)ethyl)-2-cyclopropyl-3-methyl-1,2,3,4-tetrahydroquinoline-6-carboxamide | 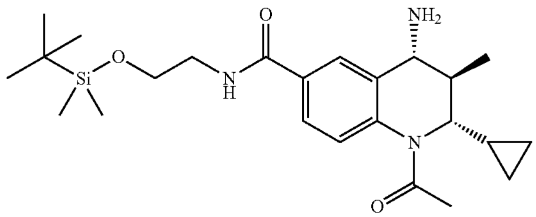 [SMILES: CC(=O)N1c2ccc(C(=O)NCCO[Si](C)(C)C(C)(C)C)cc2[C@H](N)[C@@H](C)[C@@H]1C1CC1] | 685 | 94 | 446 | 0.89 (2 min Formic) |
| 299 | (2S,3R,4R)-1-acetyl-4-amino-N-(2-((tert-butyldimethylsilyl)oxy)ethyl)-2,3-dimethyl-1,2,3,4-tetrahydroquinoline-6-carboxamide | 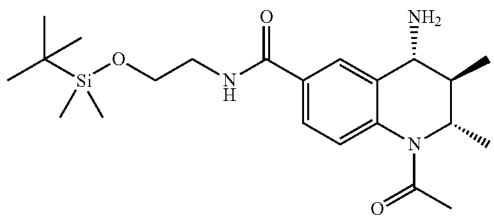 [SMILES: CC(=O)N1c2ccc(C(=O)NCCO[Si](C)(C)C(C)(C)C)cc2[C@H](N)[C@@H](C)[C@@H]1C] | 1126 | 95 | 420 | 0.86 (2 min Formic) |

Intermediate 300: (2S,3R,4R)-1-acetyl-N-(2-((tert-butyldimethylsilyl)oxy)ethyl)-2-ethyl-4-((5-fluoro-4-methylpyrimidin-2-yl)amino)-3-methyl-1,2,3,4-tetrahydroquinoline-6-carboxamide

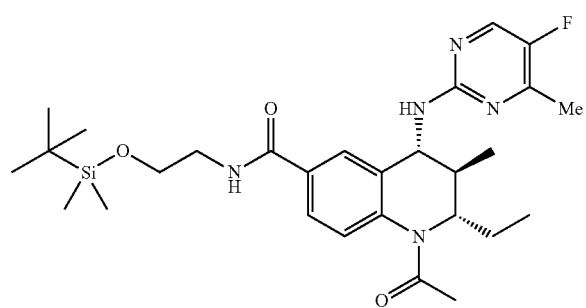

To a reaction vessel (2S,3R,4R)-1-acetyl-4-amino-N-(2-((tert-butyldimethylsilyl)oxy)ethyl)-2-ethyl-3-methyl-1,2,3,4-tetrahydroquinoline-6-carboxamide (for a preparation see Intermediate 297, 100 mg, 0.231 mmol), sodium tert-butoxide (89 mg, 0.922 mmol), Pd₂(dba)₃ (31.7 mg, 0.035 mmol), DavePhos (27.2 mg, 0.069 mmol) and 2-chloro-5-fluoro-4-methylpyrimidine (50.7 mg, 0.346 mmol) were added in 1,4-dioxane (6 mL). The solution was degassed with N₂ and left to stir at 100° C. under N₂ for 2 h. Pd₂(dba)₃ (32 mg, 0.035 mmol) and DavePhos (28 mg, 0.071 mmol) were added and the reaction left to stir at 100° C. under N₂ for 1 h. 2-Chloro-5-fluoro-4-methylpyrimidine (50.7 mg, 0.346 mmol), Pd₂(dba)₃ (32 mg, 0.035 mmol) and DavePhos (28 mg, 0.071 mmol) were added and the reaction left to stir at 100° C. under N₂ for 1 h. The reaction was left to stir at 100° C. for a further 16 h. The reaction was left to cool to rt and filtered through celite. The celite was washed with ethyl acetate (20 mL) and the combined filtrates washed with sat. aq. brine solution (2×30 mL). The layers were separated, the organic phase was dried through a hydrophobic frit and concentrated in vacuo to give 340 mg of crude product as a brown gum. This was purified by chromatography on SiO₂ (25 g, eluting with 0-100% ethyl acetate/cyclohexane). The fractions containing product were combined and concentrated in vacuo to give 37 mg of product as an orange solid.

LCMS (2 min Formic): Rt=1.27 min, [MH]+=544.

The following intermediates were prepared in a similar manner to Intermediate 300 using Pd₂(dba)₃, DavePhos and NaOtBu to couple the appropriate aryl halide with Intermediate 297 (2-Et), 298 (2-cPr) or 299 (2-Me).

| Int No. | Name | Structure | Mass (mg) | Yield (%) | [MH]+ | Rt (mins) (LCMS method) |
|---|---|---|---|---|---|---|
| 301 | (2S,3R,4R)-1-acetyl-N-(2-((tert-butyldimethylsilyl)oxy)ethyl)-2-cyclopropyl-4-((5-fluoro-4-methylpyrimidin-2-yl)amino)-3-methyl-1,2,3,4-tetrahydroquinoline-6-carboxamide | 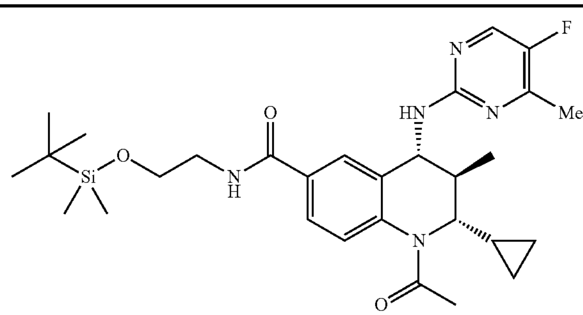 | 25 | 20 | 556 | 1.29 (2 min Formic) |

| Int No. | Name | Structure | Mass (mg) | Yield (%) | [MH]+ | Rt (mins) (LCMS method) |
|---|---|---|---|---|---|---|
| 302 | (2S,3R,4R)-1-acetyl-N-(2-((tert-butyldimethylsilyl)oxy)ethyl)-4-((5-fluoro-4-methylpyrimidin-2-yl)amino)-2,3-dimethyl-1,2,3,4-tetrahydroquinoline-6-carboxamide | 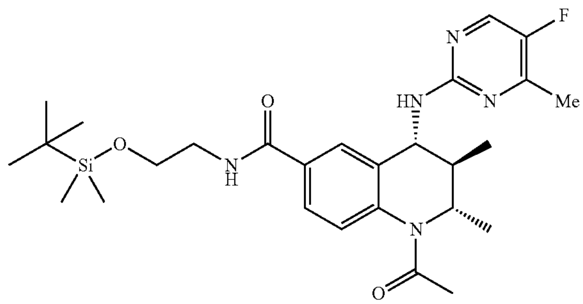 [SMILES: CC(=O)N1c2ccc(C(=O)NCCO[Si](C)(C)C(C)(C)C)cc2[C@H](Nc2ncc(F)c(C)n2)[C@@H](C)[C@@H]1C] | 20 | 16 | 530 | 1.23 (2 min Formic) |
| 303 | (2S,3R,4R)-1-acetyl-N-(2-((tert-butyldimethylsilyl)oxy)ethyl)-2-ethyl-4-((5-fluoro-6-methylpyridin-2-yl)amino)-3-methyl-1,2,3,4-tetrahydroquinoline-6-carboxamide | 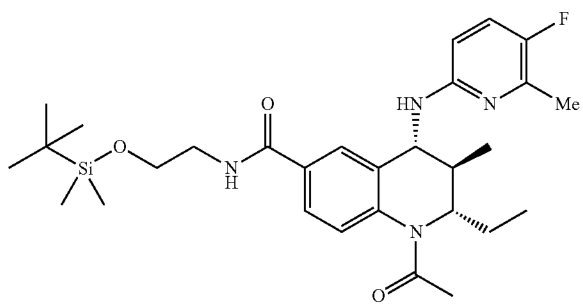 [SMILES: CC[C@H]1[C@H](C)[C@@H](Nc2ccc(F)c(C)n2)c2cc(C(=O)NCCO[Si](C)(C)C(C)(C)C)ccc2N1C(C)=O] | 131 | 84 | 543 | 1.23 (2 min Formic) |
| 304 | (2S,3R,4R)-1-acetyl-N-(2-((tert-butyldimethylsilyl)oxy)ethyl)-2-cyclopropyl-4-((5-fluoro-6-methylpyridin-2-yl)amino)-3-methyl-1,2,3,4-tetrahydroquinoline-6-carboxamide | 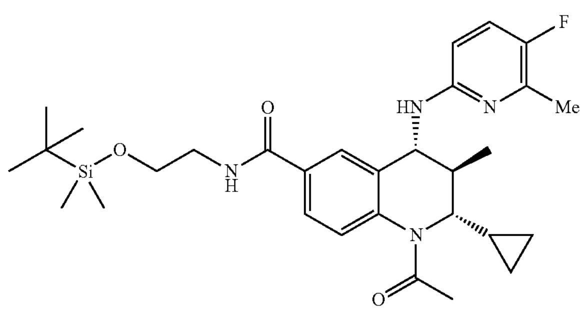 [SMILES: CC(=O)N1c2ccc(C(=O)NCCO[Si](C)(C)C(C)(C)C)cc2[C@H](Nc2ccc(F)c(C)n2)[C@@H](C)[C@@H]1C1CC1] | 25 | 40 | 555 | 1.27 (2 min Formic) |
| 305 | (2S,3R,4R)-1-acetyl-N-(2-((tert-butyldimethylsilyl)oxy)ethyl)-4-((5-fluoro-6-methylpyridin-2-yl)amino)-2,3-dimethyl-1,2,3,4-tetrahydroquinoline-6-carboxamide | 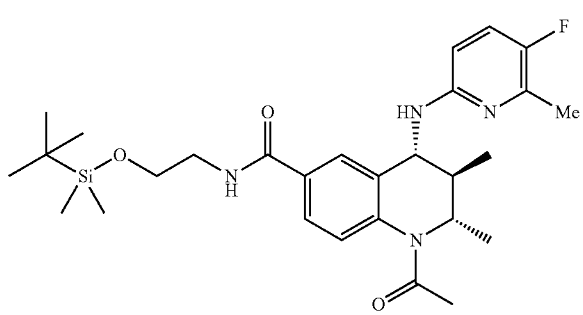 [SMILES: CC(=O)N1c2ccc(C(=O)NCCO[Si](C)(C)C(C)(C)C)cc2[C@H](Nc2ccc(F)c(C)n2)[C@@H](C)[C@@H]1C] | 36 | 29 | 529 | 1.18 (2 min Formic) |

| Int No. | Name | Structure | Mass (mg) | Yield (%) | [MH]+ | Rt (mins) (LCMS method) |
|---|---|---|---|---|---|---|
| 306 | (2S,3R,4R)-1-acetyl-N-(2-((tert-butyldimethylsilyl)oxy)ethyl)-2-ethyl-3-methyl-4-((4-methylpyridin-2-yl)amino)-1,2,3,4-tetrahydroquinoline-6-carboxamide | 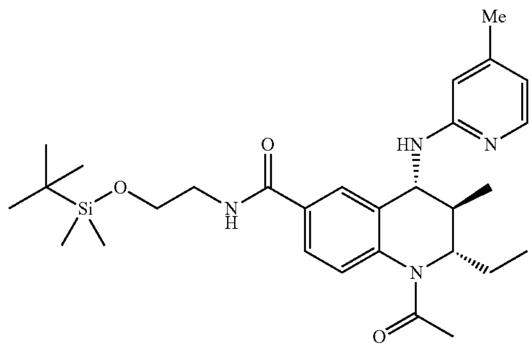 [SMILES: CC[C@H]1[C@H](C)[C@@H](Nc2cc(C)ccn2)c2cc(C(=O)NCCO[Si](C)(C)C(C)(C)C)ccc2N1C(C)=O] | 66 | 55 | 525 | 1.00 (2 min Formic) |
| 307 | (2S,3R,4R)-1-acetyl-N-(2-((tert-butyldimethylsilyl)oxy)ethyl)-2-cyclopropyl-3-methyl-4-((4-methylpyridin-2-yl)amino)-1,2,3,4-tetrahydroquinoline-6-carboxamide | 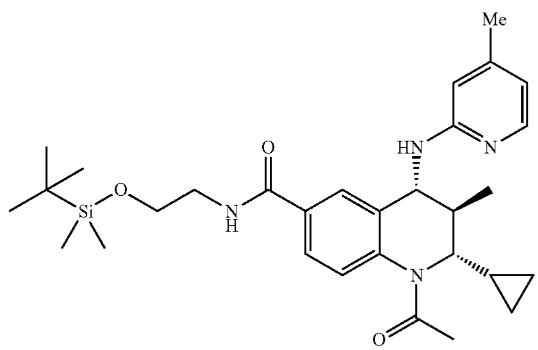 [SMILES: CC(=O)N1c2ccc(C(=O)NCCO[Si](C)(C)C(C)(C)C)cc2[C@H](Nc2cc(C)ccn2)[C@@H](C)[C@@H]1C1CC1] | 39 | 32 | 537 | 1.00 (2 min Formic) |
| 308 | (2S,3R,4R)-1-acetyl-N-(2-((tert-butyldimethylsilyl)oxy)ethyl)-2,3-dimethyl-4-((4-methylpyridin-2-yl)amino)-1,2,3,4-tetrahydroquinoline-6-carboxamide | 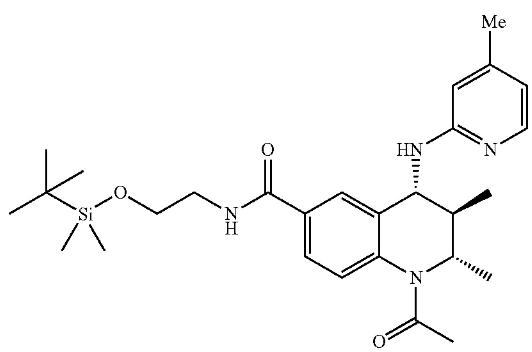 [SMILES: CC(=O)N1c2ccc(C(=O)NCCO[Si](C)(C)C(C)(C)C)cc2[C@H](Nc2cc(C)ccn2)[C@@H](C)[C@@H]1C] | 66 | 54 | 511 | 0.97 (2 min Formic) |
| 309 | (2S,3R,4R)-1-acetyl-N-(2-((tert-butyldimethylsilyl)oxy)ethyl)-4-((4-cyano-2-fluorophenyl)amino)-2-cyclopropyl-3-methyl-1,2,3,4-tetrahydroquinoline-6-carboxamide | 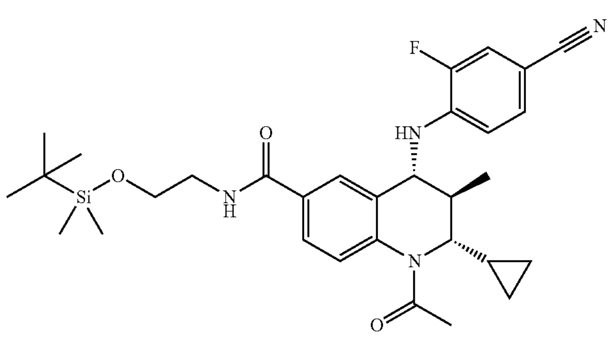 [SMILES: CC(=O)N1c2ccc(C(=O)NCCO[Si](C)(C)C(C)(C)C)cc2[C@H](Nc2ccc(C#N)cc2F)[C@@H](C)[C@@H]1C1CC1] | 36 | 14 | 565 | 1.32 (2 min Formic) |

Intermediate 310: (2S,3R,4R)-1-acetyl-2-cyclopropyl-N-(rac-2-hydroxypropyl)-3-methyl-4-((6-methylpyridin-2-yl)amino)-1,2,3,4-tetrahydroquinoline-6-carboxamide

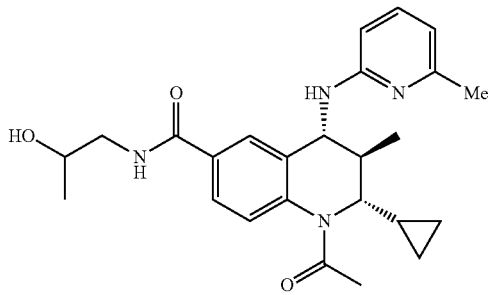 [SMILES: CC(=O)N1c2ccc(C(=O)NCC(C)O)cc2[C@H](Nc2cccc(C)n2)[C@@H](C)[C@@H]1C1CC1]

To a solution of (2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 247, 70 mg, 0.184 mmol) and HATU (84 mg, 0.221 mmol) in DMF (2 mL) was added 1-aminopropan-2-ol (0.017 mL, 0.221 mmol) and DIPEA (0.129 mL, 0.738 mmol). The reaction mixture was stirred at rt for 1 h. The reaction mixture was partitioned between ether 25 mL and water 50 mL and the aqueous extracted with ether (3×25 mL). The combined organics were washed with saturated brine (10 mL), dried over magnesium sulphate and evaporated in vacuo to afford the desired product (50 mg, 0.103 mmol, 56%) as a yellow oil. LCMS (2 min HpH): Rt=0.87 min, [MH]$^+$=437.

Intermediate 311: benzyl ((2S,3S,4R)-6-(ethylcarbamoyl)-2,3-dimethyl-1,2,3,4-tetrahydroquinolin-4-yl)carbamate

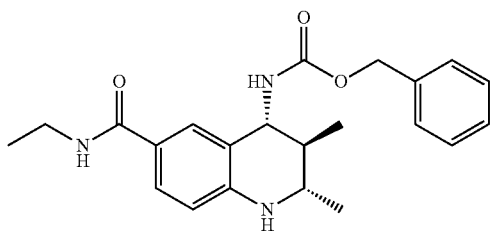 [SMILES: CCNC(=O)c1ccc2c(c1)[C@H](NC(=O)OCc1ccccc1)[C@@H](C)[C@H](C)N2]

4-Amino-N-ethylbenzamide (550 mg, 3.35 mmol) and acetaldehyde (0.284 mL, 5.02 mmol) were taken up in dichloromethane (DCM) (50 mL) and allowed to stir at rt for 1 h. The reaction was then cooled to 0° C. and was treated with (E)-benzyl prop-1-en-1-ylcarbamate (for a preparation see Intermediate 1, 705 mg, 3.68 mmol) and 2,6-bis(4-chlorophenyl)-4-hydroxy-8,9,10,11,12,13,14,15-octahydrodinaphtho[2,1-d:1',2'-f][1,3,2]dioxaphosphepine 4-oxide (for a preparation see JACS, 2011, 133, 14804, 19.34 mg, 0.033 mmol) the reaction was allowed to stir at 0° C. for 16 h, a precipitate resulted. The precipitate was removed by filtration and dried to give the product (981 mg, 2.57 mmol, 77%) as a white solid. Analysis by chiral HPLC was undertaken using a 250×4.6 mm Chiralcel OD-H column eluting with 15% ethanol in heptane at a flow rate of 1 mL/min. Peak 1/major enantiomer (96% by UV) eluted at 10.2 min, and Peak 2/minor enantiomer (4% by UV) eluted at 13.4 min. This indicated the product had an ee of 92%. LCMS (2 min Formic): Rt=0.98 min, [MH]$^+$=382.

Intermediate 312: benzyl ((2S,3R,4R)-1-acetyl-6-(ethylcarbamoyl)-2,3-dimethyl-1,2,3,4-tetrahydroquinolin-4-yl)carbamate

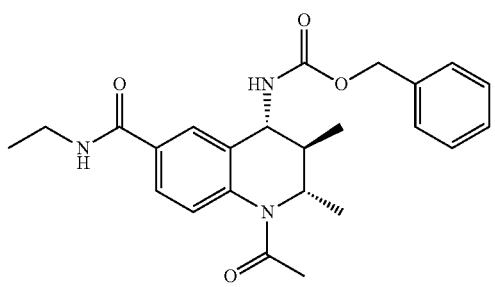 [SMILES: CCNC(=O)c1ccc2c(c1)[C@H](NC(=O)OCc1ccccc1)[C@@H](C)[C@H](C)N2C(C)=O]

Benzyl ((2S,3S,4R)-6-(ethylcarbamoyl)-2,3-dimethyl-1,2,3,4-tetrahydroquinolin-4-yl)carbamate (for a preparation see Intermediate 311, 500 mg, 1.311 mmol) was treated with acetic anhydride (5 ml, 53.0 mmol) and allowed to stir at 140° C. for 1 h, The reaction was diluted with EtOAc and was washed with 1N NaOH (aq) and was dried using a hydrophobic frit to give a yellow solid. This solid was purified using a 25 g Si column eluting with 0-100% EtOAc:cyclohexane, the appropriate fractions were summed, concentrated and dried to give the product (395 mg, 0.933 mmol, 71%) as a buff solid.

LCMS (2 min Formic): Rt=0.89 min, [MH]$^+$=424.

Intermediate 313: (2S,3R,4R)-1-acetyl-4-amino-N-ethyl-2,3-dimethyl-1,2,3,4-tetrahydroquinoline-6-carboxamide

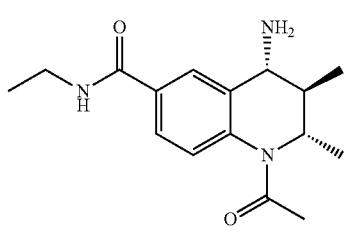 [SMILES: CCNC(=O)c1ccc2c(c1)[C@H](N)[C@@H](C)[C@H](C)N2C(C)=O]

Benzyl ((2S,3R,4R)-1-acetyl-6-(ethylcarbamoyl)-2,3-dimethyl-1,2,3,4-tetrahydroquinolin-4-yl)carbamate (for a preparation see Intermediate 312, 395 mg, 0.933 mmol) was taken up in Ethanol (10 mL) and the reaction was hydrogenated using the H-cube (settings: 25° C., 1 bar, 1 ml/min flow rate) and 10% Pd/C CatCart 30 as the catalyst. The reaction was concentrated and dried to give the product (255 mg, 0.881 mmol, 94%) as a white solid.

LCMS (2 min Formic): Rt=0.43 min, [MH]$^+$=290.

Intermediate 314: (2S,3R,4R)-ethyl 1-acetyl-2-cyclopropyl-3-methyl-4-((2-methylpyrimidin-4-yl)amino)-1,2,3,4-tetrahydroquinoline-6-carboxylate

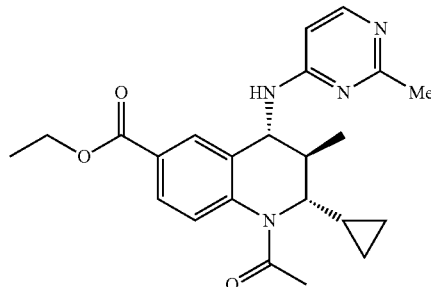

A solution of (2S,3R,4R)-ethyl 1-acetyl-4-amino-2-cyclopropyl-3-methyl-1,2,3,4-tetrahydroquinoline-6-carboxylate (for a preparation see Intermediate 225, 300 mg, 0.948 mmol), 4-chloro-2-methylpyrimidine (244 mg, 1.896 mmol) and DIPEA (0.331 mL, 1.896 mmol) in N-methyl-2-pyrrolidone (NMP) (10 mL) was heated in a microwave in a sealed vessel at 200° C. for 3.5 h. The solution was diluted with ethyl acetate (30 mL) and washed with water (2×20 mL). The organic layer was washed through a hydrophobic frit and concentrated in vacuo. It appeared that NMP was still present so the solution was diluted with ethyl acetate (20 mL) and washed again with water (2×20 mL). The solvent was evaporated in vacuo to give 350 mg crude as an orange gum. The crude was dissolved in DCM and loaded to a 50 g silica flash cartridge and purified over a gradient of 0-50% ethyl acetate in cyclohexane over 12 CVs. The appropriate fractions were combined and concentrated in vacuo to give the product (150 mg, 0.367 mmol, 39%).

LCMS (2 min Formic): Rt=0.73 min, [MH]$^+$=409.

Intermediate 315: (2S,3R,4R)-1-acetyl-2-cyclopropyl-3-methyl-4-((2-methylpyrimidin-4-yl)amino)-1,2,3,4-tetrahydroquinoline-6-carboxylic Acid

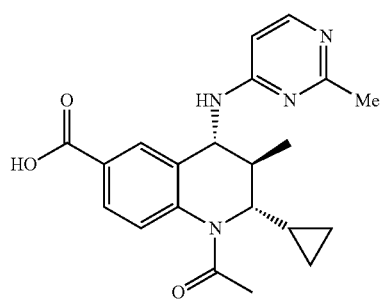 [SMILES: CC(=O)N1c2ccc(C(=O)O)cc2[C@H](Nc2ccnc(C)n2)[C@@H](C)[C@@H]1C1CC1]

A solution of (2S,3R,4R)-ethyl 1-acetyl-2-cyclopropyl-3-methyl-4-((2-methylpyrimidin-4-yl)amino)-1,2,3,4-tetrahydroquinoline-6-carboxylate (for a preparation see Intermediate 314, 60 mg, 0.147 mmol) and LiOH (10.55 mg, 0.441 mmol) in tetrahydrofuran (THF) (1 mL) and Water (1.0 mL) was stirred in a closed vessel at room temp for 16 h. The reaction mixture was concentrated in vacuo, diluted with DCM and washed with water. The aqueous layer was acidified to pH 1 and washed with DCM. The product remained in the aqueous layer. The layers were combined and concentrated in vacuo. The crude was then dissolved in 1:1 MeOH:DMSO (1 mL) and purified by MDAP (Formic). The appropriate fractions were combined and concentrated in vacuo to give the product (37 mg, 0.097 mmol, 66%).

LCMS (2 min Formic): Rt=0.58 min, [MH]$^+$=381.

Intermediate 316: (2S,3R,4R)-1-acetyl-N-(2-((tert-butyldimethylsilyl)oxy)ethyl)-2-ethyl-3-methyl-4-((2-methylpyrimidin-4-yl)amino)-1,2,3,4-tetrahydroquinoline-6-carboxamide

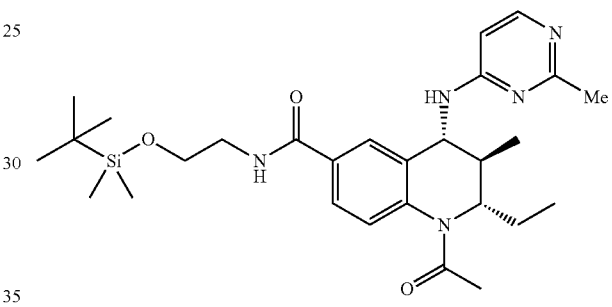

To a microwave vial (2S,3R,4R)-1-acetyl-4-amino-N-(2-((tert-butyldimethylsilyl)oxy)ethyl)-2-ethyl-3-methyl-1,2,3,4-tetrahydroquinoline-6-carboxamide (for a preparation see Intermediate 297, 100 mg, 0.231 mmol), 4-chloro-2-methylpyrimidine (59.3 mg, 0.461 mmol), and DIPEA (0.121 mL, 0.692 mmol) were added and the reaction heated to 200° C. in a microwave for 30 min. The reaction vessel was sealed and heated to 200° C. in a microwave for a further 1 h. The reaction vessel was sealed and heated to 200° C. in a microwave for a further 1 h. The reaction vessel was sealed and heated to 200° C. in a microwave for a further 1 h. The reaction was partitioned between water (10 mL) and diethyl ether (15 mL). The layers were separated and the aqueous layer was extracted with diethyl ether (15 mL) a further two times. The reaction mixture was concentrated in vacuo to give the crude product as an orange oil. This was purified by chromatography on SiO$_2$ (10 g, eluting with 0-40% ethyl acetate/cyclohexane) the product was found to have stayed on the column so it was eluted again with 40-100% ethyl acetate cyclohexane. The product was found to have stayed on the column, it was eluted again with 0-20% methanol DCM. The fractions containing product were combined and concentrated in vacuo to give the product (35 mg, 0.067 mmol, 29%) as an orange solid. LCMS (2 min Formic): Rt=0.96 min, [MH]$^+$=526.

Intermediate 317: (2S,3R,4R)-ethyl 1-acetyl-2-ethyl-3-methyl-4-((4-methylpyrimidin-2-yl)amino)-1,2,3,4-tetrahydroquinoline-6-carboxylate

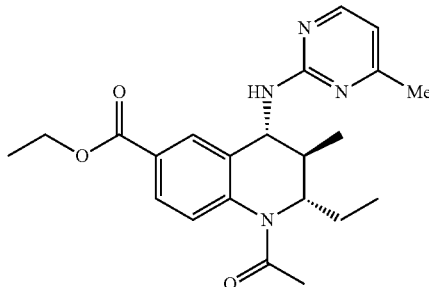

A solution of 2-chloro-4-methylpyrimidine (950 mg, 7.39 mmol), potassium fluoride (644 mg, 11.09 mmol) and 18-crown-6 (977 mg, 3.70 mmol) in DMSO (15 mL) was heated in a microwave at 180° C. for 90 min. (2S,3R,4R)-ethyl 1-acetyl-4-amino-2-ethyl-3-methyl-1,2,3,4-tetrahydroquinoline-6-carboxylate (for a preparation see Intermediate 261, 750 mg, 2.464 mmol) in DMSO (4 mL) and DIPEA (2.152 mL, 12.32 mmol) were added and the vial sealed and heated to 160° C. for 2 h. The reaction was then heated to 160° C. for an additional 1.5 h. The reaction mixture was diluted with Et$_2$O (100 mL), water (100 mL) was added and the layers separated. The aqueous layer was further extracted with Et$_2$O (2×60 mL) and the combined organics then back extracted with water (2×60 mL). The organic layer was dried (Na$_2$SO$_4$) and concentrated in vacuo to afford the crude product as an orange-brown oil. The crude product was taken up in DCM and added to a silica cartridge (100 g). This was purified by flash SP4 chromatography, eluting with 30-100% EtOAc/cyclohexane. The appropriate fractions were collected and concentrated in vacuo to afford the desired product as a yellow foam (439 mg, 1.107 mmol, 45%). LCMS (2 min Formic): Rt=0.94 min, [MH]$^+$=397.

Intermediate 318: (2S,3R,4R)-1-acetyl-2-ethyl-3-methyl-4-((4-methylpyrimidin-2-yl)amino)-1,2,3,4-tetrahydroquinoline-6-carboxylic Acid

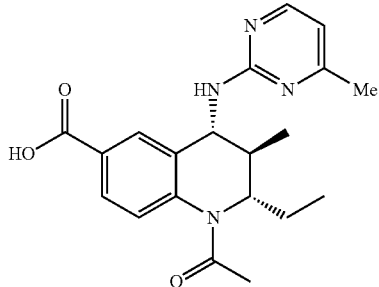 [SMILES: CC[C@H]1[C@H](C)[C@@H](Nc2nccc(C)n2)c2cc(C(=O)O)ccc2N1C(C)=O]

(2S,3R,4R)-Ethyl 1-acetyl-2-ethyl-3-methyl-4-((4-methylpyrimidin-2-yl)amino)-1,2,3,4-tetrahydroquinoline-6-carboxylate (for a preparation see Intermediate 317, 439 mg, 1.107 mmol) was taken up in THF (5 mL) and water (5.00 mL). lithium hydroxide (66.3 mg, 2.77 mmol) was added and the reaction stirred for ~1 h at rt. Stirring was continued for a further 1 h. 2M HCl(aq) (1.384 mL, 2.77 mmol) was added followed by 10% MeOH/DCM (40 mL) and water (30 mL). The biphasic mixture was stirred for 5 min and the layers then separated. The aqueous layer was further extracted with 10% MeOH/DCM (2×30 mL). After three washes the aqueous layer was analysed and found to contain a trace of product, therefore the aqueous was further extracted with 10% MeOH/DCM (20 mL) and DCM (2×20 mL). The combined organics were collected, dried (Na$_2$SO$_4$) and concentrated in vacuo to afford the desired product as a yellow solid (375.2 mg, 1.018 mmol, 92%).

LCMS (2 min Formic): Rt=0.70 min, [MH]$^+$=369.

Intermediate 319: (2S,3R,4R)-ethyl 1-cetyl-2,3-dimethyl-4-((4-methylpyrimidin-2-yl)amino)-1,2,3,4-tetrahydroquinoline-6-carboxylate

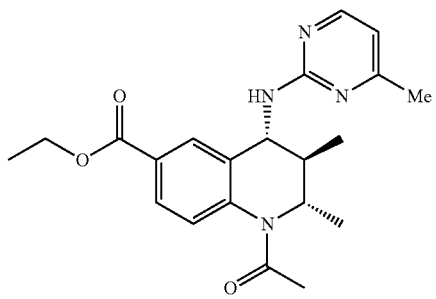 [SMILES: CCOC(=O)c1ccc2c(c1)[C@H](Nc1nccc(C)n1)[C@@H](C)[C@H](C)N2C(C)=O]

Two identical reactions set up in series to run one after the other on the same scale, each vial set up as follows: 2-chloro-4-methylpyrimidine (996 mg, 7.75 mmol), potassium fluoride (675 mg, 11.62 mmol) and 18-crown-6 (1024 mg, 3.87 mmol) were added to a 10-20 mL microwave vial. (2S,3R,4R)-ethyl 1-acetyl-4-amino-2,3-dimethyl-1,2,3,4-tetrahydroquinoline-6-carboxylate (for a preparation see Intermediate 261, 730 mg, 2.51 mmol) in dimethyl sulfoxide (DMSO) (17 mL) and DIPEA (2.255 mL, 12.91 mmol) were added and the vial sealed and heated to 160° C. for 4 h. The vials were combined and the reaction mixture was diluted with Et$_2$O (100 mL), water (100 mL) was added and the layers separated. The aqueous layer was further extracted with Et$_2$O (2×100 mL) and the combined organics then back extracted with water (2×60 mL). The organic layer was dried (Na$_2$SO$_4$) and concentrated in vacuo to afford the crude product as an orange-oil. The crude product was taken up in DCM and added to a silica cartridge (100 g). This was purified by flash chromatography, eluting with 25%-100% EtOAc/cyclohexane. The product was recolumned by flash chromatography, eluting with 25%-100% EtOAc/cyclohexane. The appropriate fractions were collected and concentrated in vacuo to afford the desired product as an orange foam (861 mg, 2.251 mmol, 45%). LCMS (2 min Formic): Rt=0.88 min, [MH]$^+$=383.

Intermediate 320: (2S,3R,4R)-1-acetyl-2,3-dimethyl-4-((4-methylpyrimidin-2-yl)amino)-1,2,3,4-tetrahydroquinoline-6-carboxylic Acid

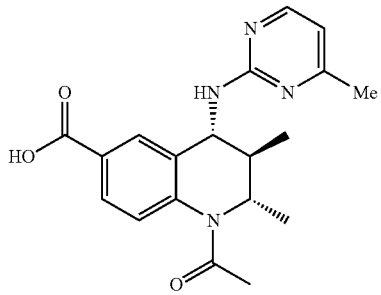 [SMILES: CC(=O)N1c2ccc(C(=O)O)cc2[C@H](Nc2nccc(C)n2)[C@@H](C)[C@@H]1C]

(2S,3R,4R)-Ethyl 1-acetyl-2,3-dimethyl-4-((4-methylpyrimidin-2-yl)amino)-1,2,3,4-tetrahydroquinoline-6-carboxylate (for a preparation see Intermediate 319, 861 mg, 2.251 mmol) was taken up in THF (9.7 mL) and Water (9.70 mL). lithium hydroxide (135 mg, 5.63 mmol) was added and the reaction stirred for ~1 h at RT. Stirring was continued for a further 1 h. 2M HCl$_{(aq)}$ (2.81 mL, 5.63 mmol) was added followed by 10% MeOH/DCM (40 mL) and water (30 mL). The biphasic mixture was stirred for 5 min and the layers then separated. The aqueous layer was further extracted with 10% MeOH/DCM (3×30 mL) and DCM (30 mL). The combined organics were collected, dried (Na$_2$SO$_4$) and concentrated in vacuo to afford the desired product as a yellow solid (824 mg, 2.093 mmol, 93%).

LCMS (2 min Formic): Rt=0.64 min, [MH]$^+$=355.

Intermediate 321: (2S,3R,4R)-1-acetyl-4-((5-fluoropyridin-2-yl)amino)-2,3-dimethyl-1,2,3,4-tetrahydroquinoline-6-carboxylic acid TFA Salt

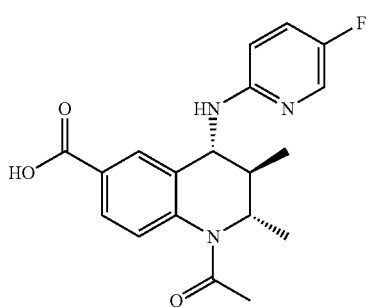 [SMILES: CC(=O)N1c2ccc(C(=O)O)cc2[C@H](Nc2ccc(F)cn2)[C@@H](C)[C@@H]1C]

(2S,3R,4R)-ethyl 1-acetyl-4-amino-2,3-dimethyl-1,2,3,4-tetrahydroquinoline-6-carboxylate (718 mg, 2.473 mmol), 2-bromo-5-fluoropyridine (653 mg, 3.71 mmol), Pd$_2$(dba)$_3$ (226 mg, 0.247 mmol), DavePhos (195 mg, 0.495 mmol) and sodium tert-butoxide (713 mg, 7.42 mmol) were combined in dry 1,4-dioxane (20 mL) and reaction mixture was stirred under N$_2$ at 90° C. for 3.5 h. LiOH (118 mg, 4.95 mmol) was added to the reaction mixture in water (4 mL) and reaction mixture continued to heat at 90° C. for a further 2 h. Reaction mixture was cooled to rt and diluted with ethyl acetate (20 mL) and filtered through celite (10 g). The filtrate was conc. in vacuo to give ~980 mg crude brown solid. This was purified by 4× large scale MDAP (TFA). The fractions containing desired product concentrated in vacuo to give the product (119 mg, 0.252 mmol, 10%) as a yellow solid.

LCMS (2 min TFA): Rt=0.58 min, [MH]$^+$=358.

Intermediate 322: (2S,3R,4R)-ethyl 1-acetyl-2,3-dimethyl-4-(pyrimidin-2-ylamino)-1,2,3,4-tetrahydroquinoline-6-carboxylate

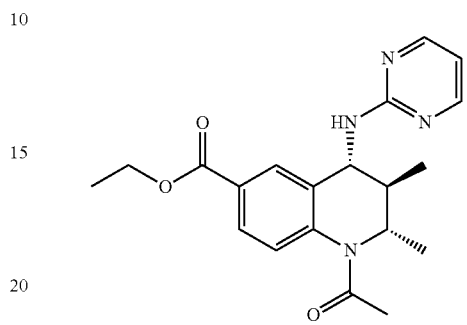

A solution of (2S,3R,4R)-ethyl 1-acetyl-4-amino-2,3-dimethyl-1,2,3,4-tetrahydroquinoline-6-carboxylate (for a preparation see Intermediate 267, 500 mg, 1.722 mmol), 2-fluoropyrimidine (203 mg, 2.066 mmol) and DIPEA (0.602 mL, 3.44 mmol) in anhydrous dimethyl sulfoxide (DMSO) (2.5 mL) was heated at 140° C. for 16 h. The reaction mixture was diluted with EtOAc (50 mL) and washed with water (2×50 mL) and brine (2×50 mL) before being dried through a hydrophobic frit. The filtrate was evaporated to leave the crude product. Purification was undertaken by flash column chromatography. The crude material was loaded onto a 50 g silica column and eluted using a graduating solvent system of 0-100% ethyl acetate in cyclohexane. Combination and evaporation of the desired fractions gave the product as a yellow oil (620 mg, 1.683 mmol, 98%).

LCMS (2 min Formic): Rt=0.87 min, [MH]$^+$=369.

Intermediate 323: (2S,3R,4R)-1-acetyl-2,3-dimethyl-4-(pyrimidin-2-ylamino)-1,2,3,4-tetrahydroquinoline-6-carboxylic Acid

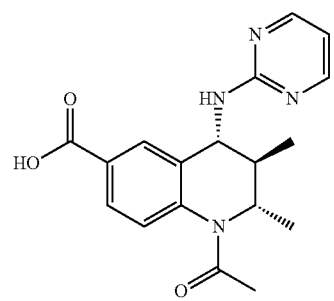 [SMILES: CC(=O)N1c2ccc(C(=O)O)cc2[C@H](Nc2ncccn2)[C@@H](C)[C@@H]1C]

(2S,3R,4R)-Ethyl 1-acetyl-2,3-dimethyl-4-(pyrimidin-2-ylamino)-1,2,3,4-tetrahydroquinoline-6-carboxylate (for a preparation see Intermediate 322, 620 mg, 1.683 mmol) was taken up in tetrahydrofuran (THF) (4 mL) and water (4.00 mL). Lithium hydroxide (101 mg, 4.21 mmol) was added and the reaction stirred for at rt overnight. 2M HCl(aq) (2 mL, 4.00 mmol) was added followed by 10% MeOH/DCM (30 mL) and water (30 mL). The biphasic mixture was stirred for 5 min and the layers then separated. The aqueous layer was further extracted with 10% MeOH/DCM (2×200 mL) and the combined organics were dried through a hydrophobic frit and concentrated to leave the product as a pale yellow foam (160 mg, 0.47 mmol, 28%). The aqueous layer was concentrated and the residue was dissolved in MeOH (~10 mL), dried (MgSO4), filtered and concentrated to leave further product as a yellow solid (300 mg, 0.88 mmol, 52%).

LCMS (2 min Formic): Rt=0.63 min, [MH]⁺=341.

Intermediate 324: (2S,3R,4R)-ethyl 1-acetyl-4-((4-cyanophenyl)amino)-2-cyclopropyl-3-methyl-1,2,3,4-tetrahydroquinoline-6-carboxylate

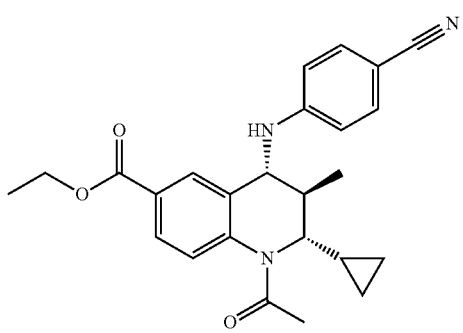 [SMILES: CCOC(=O)c1ccc2c(c1)[C@H](Nc1ccc(C#N)cc1)[C@@H](C)[C@H](C1CC1)N2C(C)=O]

(2S,3R,4R)-Ethyl 1-acetyl-4-amino-2-cyclopropyl-3-methyl-1,2,3,4-tetrahydroquinoline-6-carboxylate (for a preparation see Intermediate 225, 800 mg, 2.53 mmol), 4-bromobenzonitrile (828 mg, 4.55 mmol), Pd₂(dba)₃ (232 mg, 0.253 mmol), Pd(Q-Phos) (180 mg, 0.253 mmol) and Cs₂CO₃ (1.6 g, 4.91 mmol) were combined in dry toluene (12 mL). The reaction mixture was de-gassed and then heated at 80° C. under N₂. After 4 h further portions of Pd₂(dba)₃ (232 mg, 0.253 mmol), Pd (Q-Phos) (180 mg, 0.253 mmol) and Cs₂CO₃ (1.6 g, 4.91 mmol) were added and the reaction mixture and heating was continued at 80° C. under N₂. The reaction mixture left to heat at 80° C. overnight under N₂. The reaction mixture cooled to rt and partitioned between ethyl acetate and water. The organic layer was separated and aqueous layer further extracted with ethyl acetate. The combined organic layers were dried (Na₂SO₄) and concentrated to give ~2.3 g of crude orange residue. This was purified by chromatography on SiO₂ (100 g cartridge, eluting with 0-50% ethyl acetate/cyclohexane over 1320 mL) to give 615 mg of dark orange foamy solid product.

LCMS (2 min Formic): Rt=1.12 min, [M–H]⁻=416.

Intermediate 325: (2S,3R,4R)-1-acetyl-4-((4-cyanophenyl)amino)-2-cyclopropyl-3-methyl-1,2,3,4-tetrahydroquinoline-6-carboxylic Acid

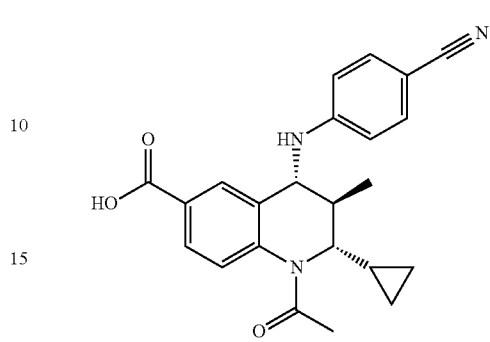

(2S,3R,4R)-Ethyl 1-acetyl-4-((4-cyanophenyl)amino)-2-cyclopropyl-3-methyl-1,2,3,4-tetrahydroquinoline-6-carboxylate (for a preparation see Intermediate 324, 599 mg, 1.435 mmol) was dissolved in 1,4-dioxane (4 mL). Water (4.0 mL) was added followed by LiOH (68.7 mg, 2.87 mmol) and reaction the mixture was stirred at rt. After 3.5 h the dioxane was removed in vacuo and acetic acid (0.164 mL, 2.87 mmol) was added. The reaction mixture was partitioned between DCM and water. The organic layer was separated and the aqueous layer extracted with DCM (3×30 mL). The combined organic layers were dried (Na₂SO₄) and concentrated to give the product (536 mg, 1.376 mmol, 96%) as a red solid. LCMS (2 min Formic): Rt=0.92 min, [M–NHAr]⁺=272.

Intermediate 326: tert-butyl (2-((2S,3R,4R)-1-acetyl-4-((4-cyanophenyl)amino)-2-cyclopropyl-3-methyl-1,2,3,4-tetrahydroquinoline-6-carboxamido)ethyl)carbamate

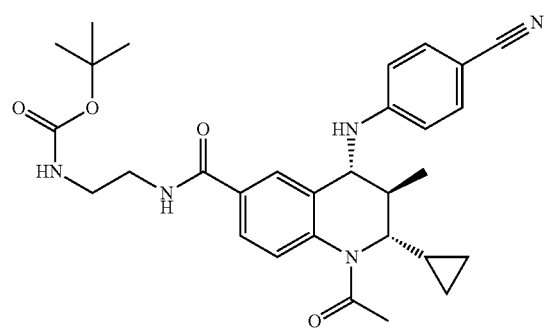 [SMILES: CC(=O)N1c2ccc(C(=O)NCCNC(=O)OC(C)(C)C)cc2[C@H](Nc2ccc(C#N)cc2)[C@@H](C)[C@@H]1C1CC1]

(2S,3R,4R)-1-Acetyl-4-((4-cyanophenyl)amino)-2-cyclopropyl-3-methyl-1,2,3,4-tetrahydroquinoline-6-carboxylic acid (for a preparation see Intermediate 325, 100 mg, 0.257 mmol) was dissolved in N,N-dimethylformamide (DMF) (2 mL) and HATU (146 mg, 0.385 mmol) was added followed by tert-butyl (2-aminoethyl)carbamate (0.051 mL, 0.325 mmol) and DIPEA (0.135 mL, 0.770 mmol). The reaction mixture stirred under N₂ at rt for 4 h. Reaction mixture was conc. to give 396 mg of crude orange oil. This was purified by chromatography on SiO₂ (25 g cartridge, eluting with 0-6% MeOH/DCM over 330 mL) to give the product (136 mg, 0.256 mmol, 100%) as an orange oil.

LCMS (2 min Formic): Rt=1.02 min, [MH]⁺=532.

Intermediate 327: benzyl ((2S,3S,4R)-6-fluoro-2,3-dimethyl-1,2,3,4-tetrahydroquinolin-4-yl)carbamate

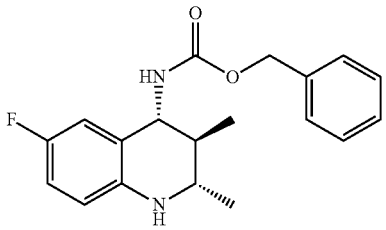 [SMILES: C[C@H]1[C@H](C)Nc2ccc(F)cc2[C@@H]1NC(=O)OCc1ccccc1]

4-Fluoroaniline (3 g, 27.0 mmol) and acetaldehyde (2.287 mL, 40.5 mmol) were taken up in DCM (120 mL) and allowed to stir at rt for 1 h. The reaction was then cooled to 0° C. and was treated with (E)-benzyl prop-1-en-1-ylcarbamate (for a preparation see Intermediate 1, 5.68 g, 29.7 mmol) and 2,6-bis(4-chlorophenyl)-4-hydroxy-8,9,10,11,12,13,14,15-octahydrodinaphtho[2,1-d:1',2'-f][1,3,2]dioxaphosphepine 4-oxide (for a preparation see JACS, 2011, 133, 14804, 0.156 g, 0.270 mmol). The reaction was allowed to stir at 0° C. for 3 h, then the solution was decanted into a separating funnel. The mixture was washed with saturated sodium bicarbonate solution (200 mL), giving a dense emulsion, from which the organic layer was separated after half an hour of waiting, and the aqueous extracted with DCM (2×50 mL). The organic phase was dried over sodium sulphate and evaporated in vacuo, giving a colourless solid. This was dissolved in hot EtOAc (30 mL), then cyclohexane (around 50 mL) was added, giving a suspension. This was heated to reflux, giving a clear, colourless solution, which was then allowed to stand and cooled to room temperature, then cooled further in an ice bath and the resulting suspension filtered to give the desired product as a colourless solid (3.85 g, 11.72 mmol, 43%). Analysis by chiral HPLC was undertaken using a 250×4.6 mm Chiralpak IC column eluting with 5% ethanol in heptane (containing 0.1% isopropylamine) at a flow rate of 1 mL/min. Peak 1/minor enantiomer (2.7% by UV) eluted at 10.3 min, and Peak 2/major enantiomer (97.3% by UV) eluted at 11.4 min. This indicated the product had an ee of >94%. LCMS (2 min HpH): Rt=1.17 min, [MH]+=329.

Intermediate 328: benzyl ((2S,3R,4R)-1-acetyl-6-fluoro-2,3-dimethyl-1,2,3,4-tetrahydroquinolin-4-yl)carbamate

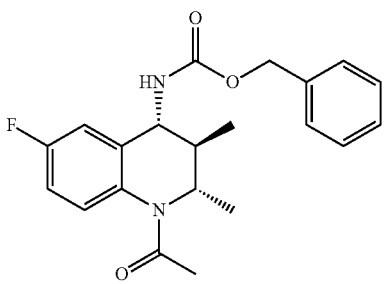 [SMILES: CC(=O)N1c2ccc(F)cc2[C@H](NC(=O)OCc2ccccc2)[C@@H](C)[C@@H]1C]

Benzyl ((2S,3S,4R)-6-fluoro-2,3-dimethyl-1,2,3,4-tetrahydroquinolin-4-yl)carbamate (For a preparation see Intermediate 327, 3.8 g, 11.57 mmol) was dissolved in DCM (50 mL) and pyridine (2.81 mL, 34.7 mmol) was added. The solution was cooled in an ice bath and acetyl chloride (0.987 mL, 13.89 mmol) was added dropwise over 5 min, then the mixture stirred for 1 hr at 0° C. The reaction mixture was washed with 1M HCl (50 mL), water (50 mL) and sodium bicarbonate solution (50 mL), dried and evaporated in vacuo to give the desired product as a pink solid (4.1 g, 11.07 mmol, 96%).

LCMS (2 min HpH): Rt=1.08 min, [MH]+=371.

Intermediate 329: 1-((2S,3R,4R)-4-amino-6-fluoro-2,3-dimethyl-3,4-dihydroquinolin-1(2H)-yl)ethanone

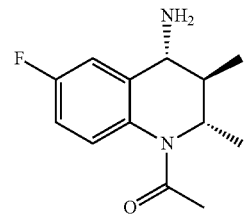 [SMILES: CC(=O)N1c2ccc(F)cc2[C@H](N)[C@@H](C)[C@@H]1C]

To a solution of benzyl ((2S,3R,4R)-1-acetyl-6-fluoro-2,3-dimethyl-1,2,3,4-tetrahydroquinolin-4-yl)carbamate (For a preparation see Intermediate 328, 4.02 g, 10.85 mmol) in EtOH (50 mL) was added to 10 wt. % palladium on carbon (402 mg, 3.78 mmol) and the mixture stirred under an atmosphere of hydrogen at r.t. for 16 hr. The reaction mixture was filtered through celite and the cake washed with EtOH (80 mL). The filtrate was evaporated in vacuo and dried in a vacuum oven to give the desired product as a yellow oil (2.36 g, 9.99 mmol, 92%).

LCMS (2 min Formic): Rt=0.41 min, [MH]+=237 and [M−NH$_2$]+=220 observed.

Intermediate 330: benzyl ((2S,3S,4R)-2-cyclopropyl-6-fluoro-3-methyl-1,2,3,4-tetrahydroquinolin-4-yl)carbamate

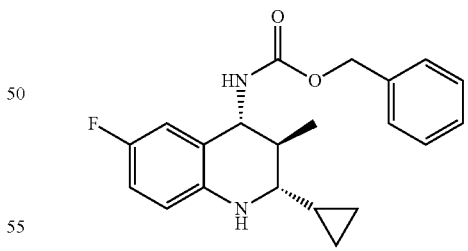

The 4-fluoroaniline (7 g, 63.0 mmol) and cyclopropanecarbaldehyde (7.05 mL, 94 mmol) were taken up in DCM (200 mL) and allowed to stir at rt for 1 h. The reaction was then cooled to 0° C. and was treated with (E)-benzyl prop-1-en-1-ylcarbamate (for a preparation see Intermediate 1, 13.25 g, 69.3 mmol) and 2,6-bis(4-chlorophenyl)-4-hydroxy-8,9,10,11,12,13,14,15-octahydrodinaphtho[2,1-d:1',2'-f][1,3,2]dioxaphosphepine 4-oxide (for a preparation see JACS, 2011, 133, 14804, 0.364 g, 0.630 mmol). The reaction was allowed to stir at 0° C. for 20 h. The reaction was washed with NaHCO$_{3(aq)}$, the aqueous phase was washed with EtOAc and the combined organics were dried using a hydrophobic frit and concentrated to give a yellow/orange solid. This solid was recrystallised twice from EtOAc: cyclohexane to give the desired product as a white solid (6.123 g, 17.28 mmol, 27%). Analysis by chiral HPLC was undertaken using a 250×4.6 mm Chiralcel OJ column eluting with 25% ethanol in heptane at a flow rate of 1 mL/min. Peak 1/minor enantiomer (5.5% by UV) eluted at 11.9 min, and Peak 2/major enantiomer (94.5% by UV) eluted at 14.8 min. This indicated the product had an ee of 89%. LCMS (2 min Formic): Rt=1.19 min, [MH]$^+$=355.

Intermediate 331: benzyl ((2S,3R,4R)-1-acetyl-2-cyclopropyl-6-fluoro-3-methyl-1,2,3,4-tetrahydroquinolin-4-yl)carbamate

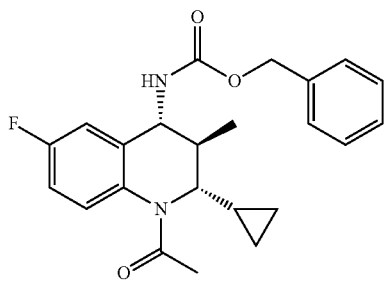 [SMILES: CC(=O)N1c2ccc(F)cc2[C@H](NC(=O)OCc2ccccc2)[C@@H](C)[C@@H]1C1CC1]

The benzyl ((2S,3S,4R)-2-cyclopropyl-6-fluoro-3-methyl-1,2,3,4-tetrahydroquinolin-4-yl)carbamate (for a preparation see intermediate 330, 6.12 g, 17.27 mmol) was taken up in DCM (200 mL) and treated with DIPEA (6.03 mL, 34.5 mmol) and acetyl chloride (2.456 mL, 34.5 mmol), the resulting yellow solution was allowed to stir at rt for 16 hr. The reaction was washed with NaHCO$_{3\ (aq)}$ and NH$_4$Cl $_{(aq)}$ dried using a hydrophobic frit and concentrated and dried to give a pale yellow solid. This solid was suspended in Et$_2$O, sonicated and the resulting cream suspension was removed by filtration and dried to give the desired product (5.865 g, 14.79 mmol, 86%) as a white solid.

LCMS (2 min Formic): Rt=1.11 min, [MH]$^+$=397.

Intermediate 332: 1-((2S,3R,4R)-4-amino-2-cyclopropyl-6-fluoro-3-methyl-3,4-dihydroquinolin-1(2H)-yl)ethanone

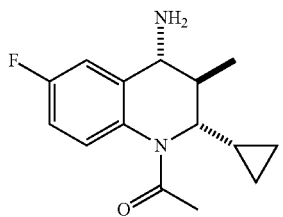 [SMILES: CC(=O)N1c2ccc(F)cc2[C@H](N)[C@@H](C)[C@@H]1C1CC1]

A solution of benzyl ((2S,3R,4R)-1-acetyl-2-cyclopropyl-6-fluoro-3-methyl-1,2,3,4-tetrahydroquinolin-4-yl)carbamate (for a preparation see Intermediate 331, 5 g, 12.61 mmol) and 10% Pd/C (0.9 g, 8.46 mmol) in ethyl acetate (100 mL) was stirred under an atmosphere of hydrogen at room temp for 16 hr. The reaction mixture was filtered through celite, rinsed with ethyl acetate and concentrated in vacuo to give the desired product (2.8 g, 10.67 mmol, 85% yield).

LCMS (2 min Formic): Rt=0.51 min, [MH]$^+$=263 (weakly) and [(M−NH4)+]=246 observed.

Intermediate 333: 1-((2S,3R,4R)-6-fluoro-4-((2-methoxypyrimidin-4-yl)amino)-2,3-dimethyl-3,4-dihydroquinolin-1(2H)-yl)ethanone

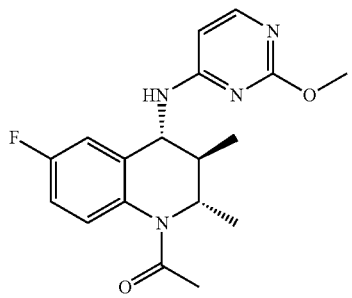 [SMILES: COc1nccc(N[C@H]2c3cc(F)ccc3N(C(C)=O)[C@@H](C)[C@@H]2C)n1]

In a test tube 1-((2S,3R,4R)-4-amino-6-fluoro-2,3-dimethyl-3,4-dihydroquinolin-1(2H)-yl)ethanone (for a preparation see Intermediate 329, 20 mg, 0.085 mmol), 4-bromo-2-methoxypyrimidine (19.20 mg, 0.102 mmol), sodium tert-butoxide (16.27 mg, 0.169 mmol), Pd$_2$(dba)$_3$ (3.88 mg, 4.23 µmol) and DavePhos (3.33 mg, 8.46 µmol) were dissolved in 1,4-dioxane (1 mL). Using a greenhouse apparatus the solution was stirred and heated at 100° C. overnight. The reaction mixture was allowed to cool and was then filtered through celite washing through with extra 1,4-dioxane. The filtrate was concentrated in vacuo to leave the crude product. Purification was undertaken using MDAP (Formic). Evaporation of the desired fractions gave the desired product as a white solid (10 mg, 0.029 mmol, 34%). LCMS (2 min Formic): Rt=0.60 min, [MH]$^+$=345.

Intermediate 334: 1-((2S,3R,4R)-2-cyclopropyl-6-fluoro-4-((2-methoxypyrimidin-4-yl)amino)-3-methyl-3,4-dihydroquinolin-1(2H)-yl)ethanone

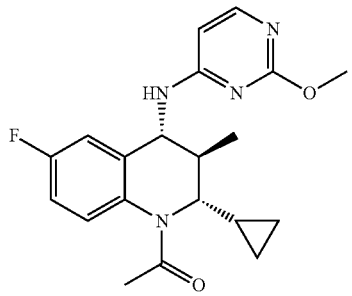 [SMILES: COc1nccc(N[C@H]2c3cc(F)ccc3N(C(C)=O)[C@@H](C3CC3)[C@@H]2C)n1]

A solution of 1-((2S,3R,4R)-4-amino-2-cyclopropyl-6-fluoro-3-methyl-3,4-dihydroquinolin-1(2H)-yl)ethanone (for a preparation see Intermediate 332, 75 mg, 0.286 mmol), 4-bromo-2-methoxypyrimidine (64.8 mg, 0.343 mmol), DavePhos (11.25 mg, 0.029 mmol), Pd$_2$(dba)$_3$ (13.09 mg, 0.014 mmol) and sodium tert-butoxide (27.5 mg, 0.286 mmol) was stirred under nitrogen for 8 hr. The reaction mixture was allowed to cool to room temp, filtered through Celite and rinsed with ethyl acetate. The solvent was evaporated in vacuo and a further portion of 4-bromo-2-methoxypyrimidine (64.8 mg, 0.343 mmol), DavePhos (11.25 mg, 0.029 mmol), Pd$_2$(dba)$_3$ (13.09 mg, 0.014 mmol) and sodium tert-butoxide (27.5 mg, 0.286 mmol) were added. 1,4-Dioxane (2 mL) was added and the solution was once again stirred under nitrogen at 90° C. for 72 hr. The reaction mixture was allowed to cool to room temp, filtered through celite and rinsed with ethyl acetate. Once the solvent had been removed in vacuo, the sample was dissolved in 1:1 MeOH:DMSO 1 mL and purified by MDAP (HpH) to give the desired product (26 mg, 0.070 mmol, 25%).

LCMS (2 min Formic): Rt=0.70 min, [MH]$^+$=371.

Intermediate 335: 1-((2S,3R,4R)-2-cyclopropyl-6-fluoro-4-((2-methoxypyridin-3-yl)amino)-3-methyl-3,4-dihydroquinolin-1(2H)-yl)ethanone

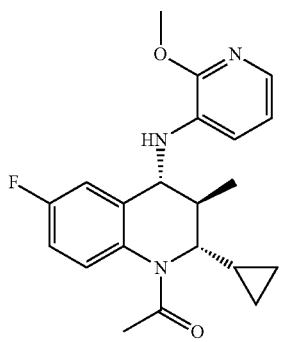 [SMILES: COc1ncccc1N[C@H]1c2cc(F)ccc2N(C(C)=O)[C@@H](C2CC2)[C@@H]1C]

A solution of 1-((2S,3R,4R)-4-amino-2-cyclopropyl-6-fluoro-3-methyl-3,4-dihydroquinolin-1(2H)-yl)ethanone (for a preparation see Intermediate 332, 75 mg, 0.286 mmol), 3-bromo-2-methoxypyridine (0.041 mL, 0.343 mmol), DavePhos (11.25 mg, 0.029 mmol), Pd$_2$(dba)$_3$ (13.09 mg, 0.014 mmol) and sodium tert-butoxide (27.5 mg, 0.286 mmol) was stirred under nitrogen at 90° C. for 8 hr. The reaction mixture was allowed to cool to room temp, filtered through celite and rinsed with ethyl acetate. The solvent was evaporated in vacuo and a further portion of 3-bromo-2-methoxypyridine (0.041 mL, 0.343 mmol), DavePhos (11.25 mg, 0.029 mmol), Pd$_2$(dba)$_3$ (13.09 mg, 0.014 mmol) and sodium tert-butoxide (27.5 mg, 0.286 mmol) was added. 1,4-Dioxane (2 mL) was added and the solution was once again stirred under nitrogen at 90° C. for 72 hr. The reaction mixture was allowed to cool to room temp, filtered through celite and rinsed with ethyl acetate. Once the solvent had been removed in vacuo, the sample was dissolved in DCM, loaded onto a 25 g silica cartridge and purified over a gradient of 0-100% ethyl acetate in cyclohexane over 12 CVs. The appropriate fractions were combined and concentrated in vacuo to afford the desired product (49 mg, 0.133 mmol, 46%). LCMS (2 min Formic): Rt=1.14 min, [MH]$^+$=370.

Intermediate 336: 1-((2S,3R,4R)-2-cyclopropyl-6-fluoro-4-((3-methoxypyridin-2-yl)amino)-3-methyl-3,4-dihydroquinolin-1(2H)-yl)ethanone

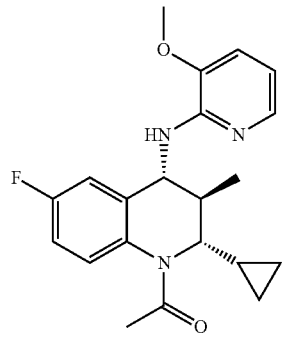 [SMILES: COc1cccnc1N[C@H]1c2cc(F)ccc2N(C(C)=O)[C@@H](C2CC2)[C@@H]1C]

A solution of 1-((2S,3R,4R)-4-amino-2-cyclopropyl-6-fluoro-3-methyl-3,4-dihydroquinolin-1(2H)-yl)ethanone (for a preparation see Intermediate 332, 75 mg, 0.286 mmol), 2-bromo-3-methoxypyridine (64.5 mg, 0.343 mmol), DavePhos (11.25 mg, 0.029 mmol), Pd$_2$(dba)$_3$ (13.09 mg, 0.014 mmol) and sodium tert-butoxide (27.5 mg, 0.286 mmol) in 1,4-dioxane (1 mL) was stirred under nitrogen at 90° C. for 8 hr. The reaction mixture was allowed to cool to rt, filtered through celite and rinsed with ethyl acetate. The solvent was evaporated in vacuo and a further portion of 2-bromo-3-methoxypyridine (64.5 mg, 0.343 mmol), DavePhos (11.25 mg, 0.029 mmol), Pd$_2$(dba)$_3$ (13.09 mg, 0.014 mmol) and sodium tert-butoxide (27.5 mg, 0.286 mmol) 1,4-dioxane (1 mL) were added. The solution was once again stirred under nitrogen at 90° C. for 72 hr. The reaction mixture was allowed to cool to room temp, filtered through Celite and rinsed with ethyl acetate. Once the solvent had been removed in vacuo, the sample was dissolved in DCM, loaded onto a 25 g silica cartridge and purified over a gradient of 0-100% ethyl acetate in cyclohexane over 12 CVs. The appropriate fractions were combined and concentrated in vacuo to give the desired product (87 mg, 0.235 mmol, 82%). LCMS (2 min Formic): Rt=0.74 min, [MH]$^+$=370.

Intermediate 337: 6-(((2S,3R,4R)-1-acetyl-2-cyclopropyl-6-fluoro-3-methyl-1,2,3,4-tetrahydroquinolin-4-yl)amino)nicotinonitrile

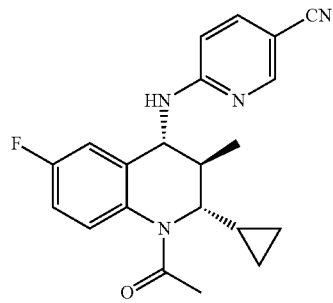 [SMILES: CC(=O)N1c2ccc(F)cc2[C@H](Nc2ccc(C#N)cn2)[C@@H](C)[C@@H]1C1CC1]

A solution of 1-((2S,3R,4R)-4-amino-2-cyclopropyl-6-fluoro-3-methyl-3,4-dihydroquinolin-1(2H)-yl)ethanone (for a preparation see Intermediate 332, 150 mg, 0.572 mmol), 6-fluoronicotinonitrile (140 mg, 1.144 mmol) and triethylamine (0.159 mL, 1.144 mmol) in N,N-dimethylformamide (DMF) (3 mL) was stirred in a µwave at 150° C. for 2.5 h. The reaction mixture was purified directly (3 injections of 1 ml DMF) by MDAP (Formic). The appropriate fractions were combined and concentrated in vacuo to give the product (96 mg, 0.263 mmol, 46%).

LCMS (2 min Formic): Rt=1.00 min, [MH]⁺=364.

Intermediate 338: 6-(((2S,3R,4R)-1-acetyl-2-cyclopropyl-6-fluoro-3-methyl-1,2,3,4-tetrahydroquinolin-4-yl)amino)picolinonitrile

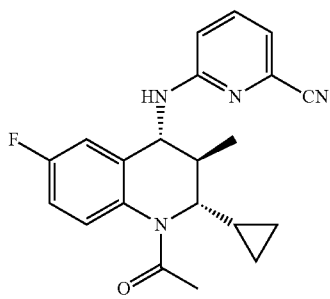 [SMILES: CC(=O)N1c2ccc(F)cc2[C@H](Nc2cccc(C#N)n2)[C@@H](C)[C@@H]1C1CC1]

In a flask were added 1-((2S,3R,4R)-4-amino-2-cyclopropyl-6-fluoro-3-methyl-3,4-dihydroquinolin-1(2H)-yl)ethanone (for a preparation see Intermediate 332, 150 mg, 0.572 mmol), 6-bromopicolinonitrile (157 mg, 0.858 mmol), sodium tert-butoxide (110 mg, 1.144 mmol) and Pd(QPhos)₂ (87 mg, 0.057 mmol) in toluene (4 mL). Reaction mixture was stirred under nitrogen at 50° C. for 3 h. A further portion of Pd(QPhos)₂ (43.7 mg, 0.029 mmol) was added and reaction mixture left stirring at 50° C. in the stirrer plate overnight. Reaction mixture was concentrated in vacuo to afford 561.9 mg of red gum crude. Resulting crude was purified by silica gel chromatography, 25 g column, 0-3% 2M NH₃ in MeOH in DCM gradient over 15 column volumes. Relevant fractions were combined and volatiles were removed under reduced pressure to afford 177 mg of red gum. This compound was repurified by silica gel chromatography, (25 g column, 15-75% EtOAc in cyclohexane over 20 CVs). Relevant fractions were combined and volatiles were removed under reduced pressure to afford the desired product as a pale red gum which was used directly in the next step without further purification. 143 mg, 0.392 mmol, 69%)

LCMS (2 min Formic): Rt=1.05 min, [MH]⁺=365.

Intermediate 339: 2-(((2S,3R,4R)-1-acetyl-6-fluoro-2,3-dimethyl-1,2,3,4-tetrahydroquinolin-4-yl)amino)-6-methylnicotinonitrile

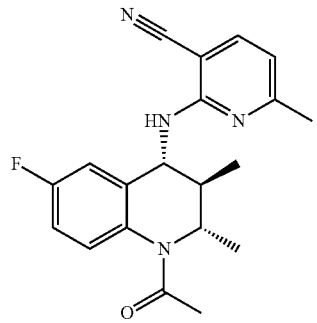 [SMILES: CC(=O)N1c2ccc(F)cc2[C@H](Nc2nc(C)ccc2C#N)[C@@H](C)[C@@H]1C]

A mixture of 1-((2S,3R,4R)-4-amino-6-fluoro-2,3-dimethyl-3,4-dihydroquinolin-1(2H)-yl)ethanone (for a preparation see Intermediate 329, 150 mg, 0.635 mmol), sodium tert-butoxide (122 mg, 1.270 mmol), Pd(QPhos)₂ (24 mg, 0.016 mmol) and 2-chloro-6-methylnicotinonitrile (145 mg, 0.952 mmol) in anhydrous toluene (2 mL) was evacuated and purged with nitrogen (×3) and stirred under nitrogen at 50° C. for 17 h. The reaction mixture was filtered through a 2.5 g celite cartridge and the cartridge then washed with EtOAc (25 mL). The filtrate was evaporated in vacuo and the gum dissolved in DCM (1 mL). The solution was purified by silica gel column chromatography (25 g column, 0-100% EtOAc in DCM over 10 CVs). The appropriate fractions were combined and the solvent removed by rotary evaporation to give the desired product as an off-white solid (20 mg, 0.057 mmol, 9%).

LCMS (2 min Formic): Rt=1.06 min, [MH]⁺=353.

Intermediate 340: methyl 4-(((2S,3R,4R)-1-acetyl-2-cyclopropyl-6-fluoro-3-methyl-1,2,3,4-tetrahydroquinolin-4-yl)amino)benzoate

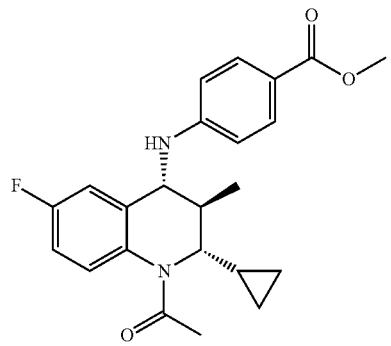 [SMILES: COC(=O)c1ccc(N[C@H]2c3cc(F)ccc3N(C(C)=O)[C@@H](C3CC3)[C@@H]2C)cc1]

In a 100 mL RB flask were added 1-((2S,3R,4R)-4-amino-2-cyclopropyl-6-fluoro-3-methyl-3,4-dihydroquinolin-1 (2H)-yl)ethanone (For a preparation see Intermediate 332, 1006.2 mg, 3.84 mmol), methyl 4-bromobenzoate (1262 mg, 5.87 mmol), cesium carbonate (2496 mg, 7.66 mmol), and Pd(QPhos)₂ (584 mg, 0.382 mmol) in cyclopentylmethylether (10 mL). The reaction mixture was degassed with nitrogen for 20 min and stirred at 80° C. for 3.5 h. A further portion of Pd(QPhos)₂ (293 mg, 0.192 mmol) was added and mixture left stirring at same 80° C. overnight. Reaction mixture was partitioned between water and EtOAc. Aqueous phase was extracted with EtOAc (×3). Organic layers were combined and washed with brine, dried over $Na_2SO_4$, filtered through hydrophobic cartridge and volatiles removed under reduce pressure to afford 2.7 g of dark red gum. The crude product was purified by silica gel chromatography, (100 g column, 0-4% 2M $NH_3$ in MeOH in DCM gradient over 15 CVs). Relevant fractions were combined and volatiles were removed under reduce pressure to afford the desired product as a red powder (1.82 g, 3.07 mmol, 80%).

LCMS (2 min Formic): Rt=1.12 min, $[MH]^+$=397.

Intermediate 341: 4-(((2S,3R,4R)-1-acetyl-2-cyclopropyl-6-fluoro-3-methyl-1,2,3,4-tetrahydroquinolin-4-yl)amino)benzoic Acid

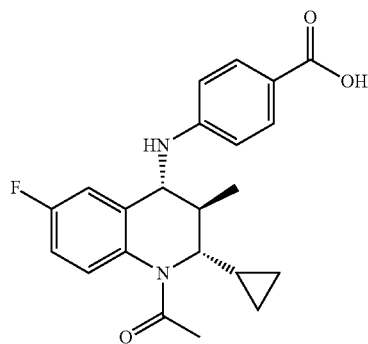

Methyl 4-(((2S,3R,4R)-1-acetyl-2-cyclopropyl-6-fluoro-3-methyl-1,2,3,4-tetrahydroquinolin-4-yl)amino)benzoate (for a preparation see Intermediate 341, 1822 mg, 4.60 mmol) and lithium hydroxide monohydrate (964 mg, 22.98 mmol) were dissolved in THF (10 mL) and water (10 mL). The reaction was stirred at rt for 15 h. A further portion of lithium hydroxide monohydrate (964 mg, 22.98 mmol) was added and reaction mixture left stirring at rt for 3 h. Sodium hydroxide (919 mg, 22.98 mmol) was added and reaction mixture was stirred at rt overnight. The reaction mixture was heated at 50° C. for 30 min. Lithium hydroxide monohydrate (964 mg, 22.98 mmol) and sodium hydroxide (919 mg, 22.98 mmol) were added. The reaction mixture was left stirring at 60° C. for 4.5 days. The reaction mixture was cooled down to rt. Mixture was diluted with water and washed with EtOAc. The aqueous layer was then acidified with 1M HCl (to pH=4) and filtered to obtain the desired product as a brown solid (1.3632 g, 3.588 mmol, 78%).

LCMS (2 min Formic): Rt=0.96 min, $[MH]^+$=383.

Intermediate 342: tert-butyl 4-((6-(((2S,3R,4R)-1-acetyl-2-cyclopropyl-6-fluoro-3-methyl-1,2,3,4-tetrahydroquinolin-4-yl)amino)pyridin-2-yl)methyl)piperazine-1-carboxylate In a 50 mL RB flask were added 1-((2S,3R,4R)-4-amino-2-cyclopropyl-6-fluoro-3-methyl-3,4-dihydroquinolin-1(2H)-yl)ethanone (for a preparation see Intermediate 332, 48.9 mg, 0.186 mmol), tert-butyl 4-((6-bromopyridin-2-yl)methyl)piperazine-1-carboxylate (for a preparation see Intermediate 233, 64.4 mg, 0.181 mmol), $Pd_2(dba)_3$ (21.7 mg, 0.024 mmol), sodium tert-butoxide (38.2 mg, 0.397 mmol) and QPhos (16.7 mg, 0.023 mmol) in toluene (3 mL). Reaction mixture was stirred at 50° C. under nitrogen overnight. A further portion of $Pd_2(dba)_3$ (17.07 mg, 0.019 mmol), sodium tert-butoxide (8.96 mg, 0.093 mmol) and QPhos (13.29 mg, 0.019 mmol) were added and reaction mixture was left stirring under same conditions for 2 h. Reaction mixture was allowed to cool down at rt and left to stand overnight. The reaction mixture was filtered through celite cartridge and partitioned between water and EtOAc. Aqueous phase was extracted with EtOAc (×3). Organic layers were combined and washed with brine, dried over $Na_2SO_4$, filtered through hydrophobic cartridge and volatiles removed under reduce pressure to afford 155.1 mg of orange gum. This resulting crude product was purified by silica gel chromatography (25 g column, 1-5% 2M $NH_3$ in MeOH in DCM in gradient over 20 CVs). Relevant fractions were combined and volatiles were removed under reduce pressure to afford the desired product as a yellow gum (87.4 mg, 0.157 mmol, 87%). LCMS (2 min Formic): Rt=0.92 min, $[MH]^+$=538.

Intermediate 343: (S)-tert-butyl 4-((rac-2S,3R,4R)-1-acetyl-2-cyclopropyl-3-methyl-4-((4-methylpyrimidin-2-yl)amino)-1,2,3,4-tetrahydroquinolin-6-yl)-2-methylpiperazine-1-carboxylate

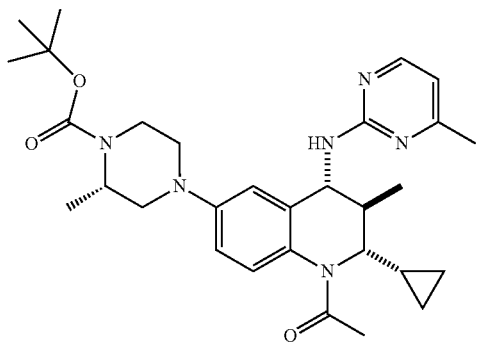 [SMILES: CC(=O)N1c2ccc(N3CCN(C(=O)OC(C)(C)C)[C@@H](C)C3)cc2[C@H](Nc2nccc(C)n2)[C@@H](C)[C@@H]1C1CC1]

To a microwave vial was added (S)-tert-butyl 4-((rac-2S,3R,4R)-1-acetyl-4-amino-2-cyclopropyl-3-methyl-1,2,3,4-tetrahydroquinolin-6-yl)-2-methylpiperazine-1-carboxylate (for a preparation see Intermediate 179, 50 mg, 0.113 mmol) in 1,4-dioxane (2.5 mL). To this was added 2-bromo-4-methylpyrimidine (39.1 mg, 0.226 mmol), $Pd_2(dba)_3$ (20.69 mg, 0.023 mmol), sodium tert-butoxide (32.6 mg, 0.339 mmol) and DavePhos (26.7 mg, 0.068 mmol). The vessel was sealed and heated in a microwave reactor at 120° C. for 40 min. A further 2 eq 2-bromo-4-methylpyrimidine (39.1 mg, 0.226 mmol) was added, the vessel resealed and the reaction heated to 120° C. for 30 minutes. The reaction mixture was filtered over a 2.5 g celite cartridge, washed through with ethyl acetate and concentrated in vacuo. The residue was dissolved in 1:1 MeOH:DMSO 1 mL and purified by MDAP (Formic). The solvent was evaporated in vacuo to give the required product (18 mg).

LCMS (2 min Formic): Rt=1.17 min, [MH]⁺=535.

Intermediate 344: 1-((2S,3R,4R)-4-amino-6-bromo-2-cyclopropyl-3-methyl-3,4-dihydroquinolin-1(2H)-yl)ethanone

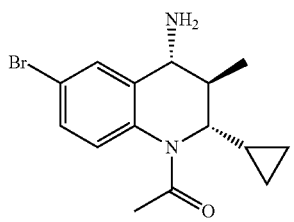 [SMILES: CC(=O)N1c2ccc(Br)cc2[C@H](N)[C@@H](C)[C@@H]1C1CC1]

A sample of benzyl ((2S,3R,4R)-1-acetyl-6-bromo-2-cyclopropyl-3-methyl-1,2,3,4-tetrahydroquinolin-4-yl)carbamate (for a preparation see Intermediate 219, 2.5 g, 5.47 mmol) and potassium hydroxide (3.07 g, 54.7 mmol) were added to a flask, and to this was added water (50 mL) and ethanol (50 mL), forming a suspension. The reaction vessel was heated to 80° C. for 16 h. After this time a yellow solution had formed. A further portion of KOH (307 mg, 5.47 mmol) was added and the reaction heated to 80° C. for a further 4 h and then to 90° C. with stirring for a further 1.5 h. The reaction was allowed to cool to rt and water (150 mL) and DCM (150 mL) were added. The layers were separated and the aqueous layer further extracted with DCM (2×50 mL). The combined organics were dried ($Na_2SO_4$) and concentrated in vacuo to afford the crude product as a yellow oil. The crude product was taken up in DCM and added to a SNAP silica cartridge (100 g). This was purified by flash chromatography, eluting with 0%→20% (20% (2M $NH_3$ in MeOH)/DCM)/DCM. The appropriate fractions were collected and concentrated in vacuo to afford the desired product as a white crystalline solid (1.27 g, 3.93 mmol, 72%).

LCMS (2 min Formic): Rt=0.57 min, [M−NH₂]⁺=323, 325.

Intermediate 345: 1-((2S,3R,4R)-4-amino-2-cyclopropyl-6-(3,6-dihydro-2H-pyran-4-yl)-3-methyl-3,4-dihydroquinolin-1(2H)-yl)ethanone

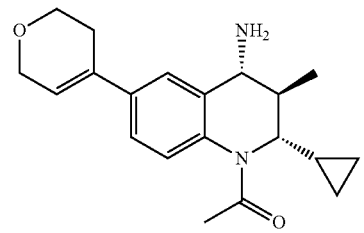 [SMILES: CC(=O)N1c2ccc(C3=CCOCC3)cc2[C@H](N)[C@@H](C)[C@@H]1C1CC1]

The 2-(3,6-dihydro-2H-pyran-4-yl)-4,4,5,5-tetramethyl-1,3,2-dioxaborolane (390 mg, 1.856 mmol), 1-((2S,3R,4R)-4-amino-6-bromo-2-cyclopropyl-3-methyl-3,4-dihydroquinolin-1(2H)-yl)ethanone (for a preparation see Intermediate 344, 400 mg, 1.238 mmol) and caesium carbonate (1210 mg, 3.71 mmol) were suspended in 1,4-dioxane (15 mL):water (1.5 mL) and treated with $Pd(PPh_3)_4$ (143 mg, 0.124 mmol). The reaction was allowed to stir at 80° C. for 16 h. The reaction was partitioned between water and EtOAc, the aqueous layer was extracted with EtOAc and the combined organics were washed with brine, dried ($Na_2SO_4$) and concentrated in vacuo to a dark oil. This oil was purified using a by flash chromatography using a SNAP (100 g) Si column, eluting with 0-25% (20% 2M $NH_3$ in MeOH in DCM)/DCM. The appropriate fractions were summed and concentrated to give impure product. Therefore the column was re-eluted with 25%→50% (20% 2M $NH_3$ in MeOH in DCM)/DCM. The appropriate fraction was collected and concentrated in vacuo to afford the desired product as a yellow oil (213 mg, 0.653 mmol, 53%).

LCMS (2 min Formic): Rt=0.60 min, [M−NH₂]⁺=310.

Intermediate 346: benzyl ((2S,3R,4R)-1-acetyl-6-(2-((tert-butyldimethylsilyl)oxy)ethoxy)-2-cyclopropyl-3-methyl-1,2,3,4-tetrahydroquinolin-4-yl)carbamate

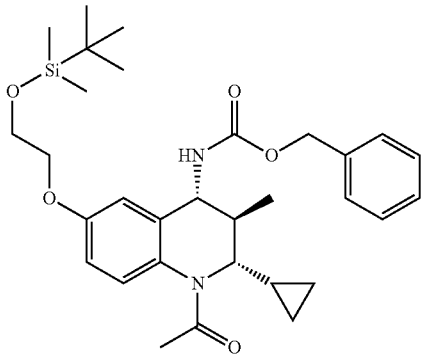 [SMILES: CC(=O)N1c2ccc(OCCO[Si](C)(C)C(C)(C)C)cc2[C@H](NC(=O)OCc2ccccc2)[C@@H](C)[C@@H]1C1CC1]

To a reaction vessel, 2-((tert-butyldimethylsilyl)oxy)ethanol (0.433 mL, 2.186 mmol), benzyl ((2S,3R,4R)-1-acetyl-6-bromo-2-cyclopropyl-3-methyl-1,2,3,4-tetrahydroquinolin-4-yl)carbamate (for a preparation see Intermediate 219, 500 mg, 1.093 mmol), 5-(di(adamantan-1-yl)phosphino)-1',3',5'-triphenyl-1'H-1,4'-bipyrazole (145 mg, 0.219 mmol), Pd(OAc)$_2$ (49.1 mg, 0.219 mmol) and Cs$_2$CO$_3$ (712 mg, 2.186 mmol) were added in toluene (10 mL) and the reaction left to stir for 2 h at 90° C. The reaction mixture was allowed to cool to rt and then filtered through celite. The filtrate was washed with water (2×35 mL) and the layers separated. The organic layer was dried through a hydrophobic frit and concentrated in vacuo to give 774 mg of crude product as a pale yellow solid. This was purified by chromatography on SiO$_2$ (50 g) eluting with 0-30% ethyl acetate/cyclohexane. The fractions containing product were combined and concentrated in vacuo to give 335 mg of impure product as an off-white solid. The sample was dissolved in 1:1 MeOH:DMSO 6 mL and purified by 2×MDAP (HpH). The solvent was evaporated in vacuo to give 190 mg of the product (190 mg, 0.344 mmol, 31%) as an off-white solid. LCMS (2 min Formic): Rt=1.48 min, [MH]$^+$=553.

Intermediate 347: 1-((2S,3R,4R)-4-amino-6-(2-((tert-butyldimethylsilyl)oxy)ethoxy)-2-cyclopropyl-3-methyl-3,4-dihydroquinolin-1(2H)-yl)ethanone

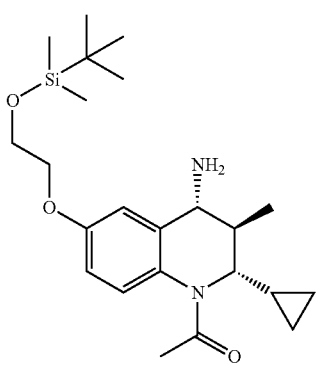 [SMILES: CC(=O)N1c2ccc(OCCO[Si](C)(C)C(C)(C)C)cc2[C@H](N)[C@@H](C)[C@@H]1C1CC1]

Benzyl ((2S,3R,4R)-1-acetyl-6-(2-((tert-butyldimethylsilyl)oxy)ethoxy)-2-cyclopropyl-3-methyl-1,2,3,4-tetrahydroquinolin-4-yl)carbamate (for a preparation see Intermediate 346, 190 mg, 0.344 mmol) was taken up in ethanol (10 mL). The solution was hydrogenated using the H-cube (settings: rt, 1 bar, 1 mL/min flow rate) and 10% Pd/C CatCart as the catalyst. The solution was left to cycle through the H-cube for a further 1 h. The reaction mixture was concentrated in vacuo to give the desired product (130 mg, 0.311 mmol, 90%) as a white solid.

LCMS (2 min Formic): Rt=1.01 min, [M−NH$_2$]$^+$=402.

Intermediate 348: 1-((2S,3R,4R)-6-(2-((tert-butyldimethylsilyl)oxy)ethoxy)-2-cyclopropyl-3-methyl-4-((4-methylpyrimidin-2-yl)amino)-3,4-dihydroquinolin-1(2H)-yl)ethanone

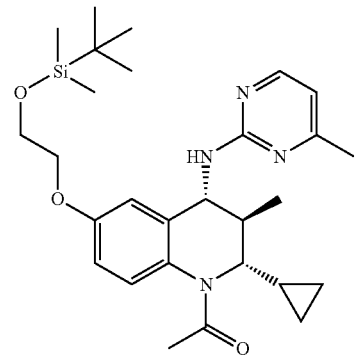 [SMILES: CC(=O)N1c2ccc(OCCO[Si](C)(C)C(C)(C)C)cc2[C@H](Nc2nccc(C)n2)[C@@H](C)[C@@H]1C1CC1]

To a reaction vessel 1-((2S,3R,4R)-4-amino-6-(2-((tert-butyldimethylsilyl)oxy)ethoxy)-2-cyclopropyl-3-methyl-3,4-dihydroquinolin-1(2H)-yl)ethanone (for a preparation see Intermediate 347, 125 mg, 0.299 mmol), 2-bromo-4-methylpyrimidine (77 mg, 0.448 mmol) and sodium tert-butoxide (143 mg, 1.493 mmol) were added in 1,4-dioxane (10 mL). This solution was treated with Pd$_2$(dba)$_3$ (41.0 mg, 0.045 mmol) and DavePhos (24 mg, 0.061 mmol) and left to stir at 100° C. for 3 h. The reaction mixture was filtered through celite and washed with water (2×25 mL). The layers were separated and the organic phase dried through a hydrophobic frit. The organic phase was then concentrated in vacuo to give 178 mg of crude product as an orange gum. This was purified by chromatography on SiO$_2$ 10 g column, eluting with 0-100% ethyl acetate/cyclohexane. The fractions containing product were combined and concentrated in vacuo to give 43 mg of the product as an orange solid.

LCMS (2 min Formic): Rt=1.37 min, [MH]$^+$=511.

Intermediate 349: benzyl ((2R,3R,4R)-1-acetyl-2-cyclopropyl-6-(1-(2-methoxyethyl)-1H-pyrazol-4-yl)-3-methyl-1,2,3,4-tetrahydroquinolin-4-yl)carbamate

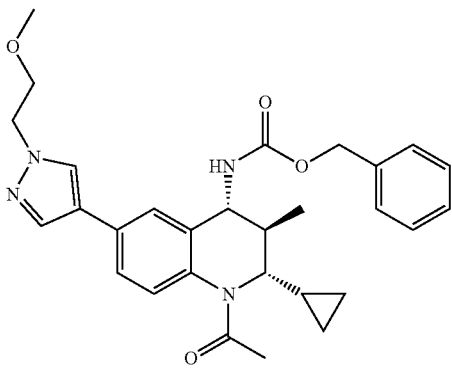 [SMILES: COCCn1cc(-c2ccc3c(c2)[C@H](NC(=O)OCc2ccccc2)[C@@H](C)[C@H](C2CC2)N3C(C)=O)cn1]

The 1-(2-methoxyethyl)-4-(4,4,5,5-tetramethyl-1,3,2-dioxaborolan-2-yl)-1H-pyrazole (551 mg, 2.186 mmol), benzyl ((2R,3R,4R)-1-acetyl-6-bromo-2-cyclopropyl-3-methyl-1,2,3,4-tetrahydroquinolin-4-yl)carbamate (for a preparation see Intermediate 219, 500 mg, 1.093 mmol), $PdCl_2(dppf)$ (64.0 mg, 0.087 mmol) and potassium carbonate (332 mg, 2.405 mmol) were taken up in water (10 mL):1,4-dioxane (30 mL) and allowed to stir at 85° C. for 2 h. The reaction was treated with further $PdCl_2(dppf)$ (80 mg, 0.109 mmol) and allowed to stir at 85° C. under nitrogen for 1 h. The reaction was allowed to cool to rt and was concentrated to remove the 1,4-dioxane and was partitioned between water and EtOAc, the aqueous layer was extracted with further EtOAc, the combined organics were washed with brine, dried using a hydrophobic frit and concentrated to an orange gum. This gum was purified using a 25 g Si column, elute 0-100% EtOAc:cyclohexane. The appropriate fractions were summed and concentrated to give the product (433 mg, 0.862 mmol, 79%) as an orange solid. LCMS (2 min Formic): Rt=1.03 min, $[M-NH_2]^+$=503.

Intermediate 350: 1-((2S,3R,4R)-4-amino-2-cyclopropyl-6-(1-(2-methoxyethyl)-1H-pyrazol-4-yl)-3-methyl-3,4-dihydroquinolin-1(2H)-yl)ethanone

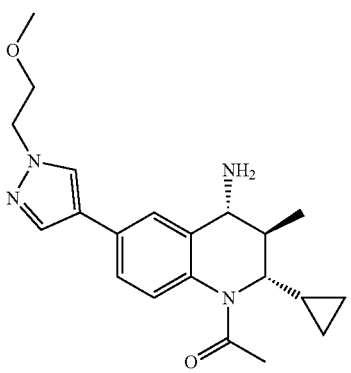 [SMILES: COCCn1cc(-c2ccc3c(c2)[C@H](N)[C@@H](C)[C@H](C2CC2)N3C(C)=O)cn1]

The benzyl ((2S,3R,4R)-1-acetyl-2-cyclopropyl-6-(1-(2-methoxyethyl)-1H-pyrazol-4-yl)-3-methyl-1,2,3,4-tetrahydroquinolin-4-yl)carbamate (for a preparation see Intermediate 349, 433 mg, 0.862 mmol) was taken up in ethanol (10 mL). The reaction was hydrogenated using the H-cube (settings: 25° C., 1 bar, 1 mL/min flow rate) and 10% Pd/C CatCart 30 as the catalyst. The solution was allowed to cycle through the machine for 4 h. The reaction was concentrated to give the product (408 mg) as a yellow oil which contained some solvent and minor impurities but was used as was in the subsequent step. LCMS (2 min Formic): Rt=0.58 min, $[M-NH_2]^+$=369.

Intermediate 351: 2-(4-(4,4,5,5-tetramethyl-1,3,2-dioxaborolan-2-yl)-1H-pyrazol-1-yl)ethanol

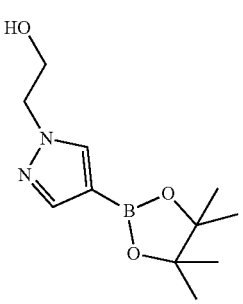 [SMILES: CC1(C)OB(c2cnn(CCO)c2)OC1(C)C]

A solution of 1,3-dioxolan-2-one (1.902 mL, 28.5 mmol), 4-(4,4,5,5-tetramethyl-1,3,2-dioxaborolan-2-yl)-1H-pyrazole (5.0239 g, 25.9 mmol) and sodium hydroxide (0.0998 g, 2.495 mmol) in N,N-dimethylformamide (DMF) (20 mL) was heated to 140° C. overnight. The mixture was cooled down to rt and then activated charcoal (200 mg) was added and this was stirred for 4 h before filtering through celite cartridge (10 g). The mixture was washed with EtOAc (50 mL) and EtOH (50 mL and the combined filtrate was concentrated in vacuo to afford 7.53 g of brown oil. This was used crude in further reactions. LCMS: Not recorded.

Intermediate 352: 1-((2S,3R,4R)-4-amino-2-cyclopropyl-6-(1-(2-hydroxyethyl)-1H-pyrazol-4-yl)-3-methyl-3,4-dihydroquinolin-1(2H)-yl)ethanone

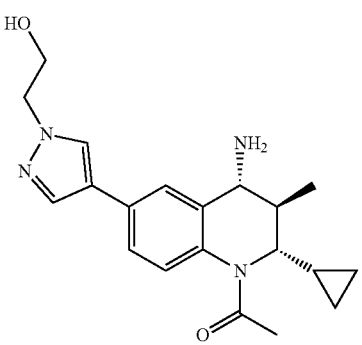 [SMILES: CC(=O)N1c2ccc(-c3cnn(CCO)c3)cc2[C@H](N)[C@@H](C)[C@@H]1C1CC1]

1-((2S,3R,4R)-4-amino-6-bromo-2-cyclopropyl-3-methyl-3,4-dihydroquinolin-1(2H)-yl)ethanone (for a preparation see Intermediate 344, 860 mg, 2.66 mmol), 2-(4-(4,4,5,5-tetramethyl-1,3,2-dioxaborolan-2-yl)-1H-pyrazol-1-yl)ethanol (for a preparation see Intermediate 351, 950 mg, 3.99 mmol), potassium carbonate (1103 mg, 7.98 mmol) and $Pd(PPh_3)_2Cl_2$ (374 mg, 0.532 mmol) were combined in a mixture of 1,4-dioxane (12 mL) and water (4 mL)

and heated in the microwave reactor at 120° C. for 1 h. The reaction mixture was diluted with ethyl acetate and water and combined with the reaction mixture from the same reaction carried out on 200 mg of starting THQ. The organic layer was separated, dried and evaporated in vacuo to give ~2.3 g of crude orange oil. This was dissolved in the minimum amount of MeOH (~5 mL) and loaded onto a 50 g SCX cartridge (pre-conditioned with MeOH). This was then eluted with MeOH (200 mL) followed by 2M NH$_3$ in MeOH (300 mL). Ammonia fractions containing desired product by TLC were combined and concentrated in vacuo to give 1.29 g of yellow oil. This was further purified by chromatography on SiO$_2$ (100 g cartridge, eluting with 0-20% methanol/DCM over 1300 mL) to give the product (645 mg, 1.820 mmol, 68%) as a pale yellow foamy solid. LCMS (2 min Formic): Rt=0.51 min, [M−NH$_2$]$^+$=338.

Intermediate 353: 1-(2-((tert-butyldimethylsilyl)oxy)ethyl)-4-(4,4,5,5-tetramethyl-1,3,2-dioxaborolan-2-yl)-1H-pyrazole

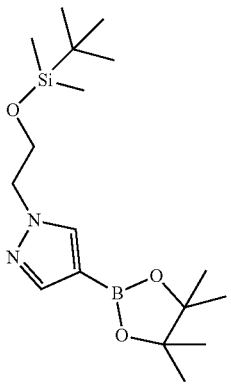 [SMILES: CC1(C)OB(c2cnn(CCO[Si](C)(C)C(C)(C)C)c2)OC1(C)C]

To a solution of 2-(4-(4,4,5,5-tetramethyl-1,3,2-dioxaborolan-2-yl)-1H-pyrazol-1-yl)ethanol (for a preparation see Intermediate 351, 1.057 g, 4.44 mmol) in N,N-dimethylformamide (DMF) (5 mL) was added imidazole (3 g, 44.1 mmol) and TBDMSCl (3.35 g, 22.20 mmol) and reaction mixture stirred at rt. After 2 h a catalytic amount of DMAP was added and reaction mixture was continued to stir at rt overnight. The reaction mixture diluted with water and diethyl ether. The organic layer was separated and the aqueous layer extracted with further portions of diethyl ether (2×50 mL). The combined organic layers were dried (Na$_2$SO$_4$) and concentrated to give 2.82 g of crude pale yellow oil. This was further purified by chromatography on SiO$_2$ (100 g cartridge, eluting with 0-100% ethyl acetate/cyclohexane over 1320 mL, collecting all fractions and visualising with KMnO4) to give the product (712 mg, 2.021 mmol, 46%) as a colourless oil LCMS: (2 min Formic): Rt=1.40 min, [MH]$^+$=353.

Intermediate 354: 1-((2S,3R,4R)-4-amino-6-(1-(2-((tert-butyldimethylsilyl)oxy)ethyl)-1H-pyrazol-4-yl)-2-cyclopropyl-3-methyl-3,4-dihydroquinolin-1(2H)-yl)ethanone

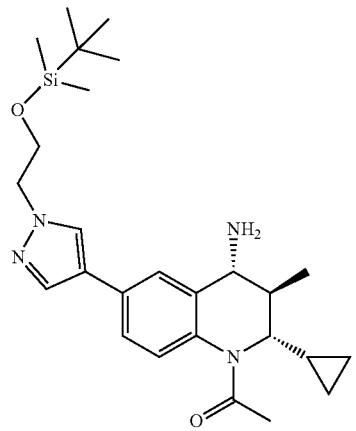 [SMILES: CC(=O)N1c2ccc(-c3cnn(CCO[Si](C)(C)C(C)(C)C)c3)cc2[C@H](N)[C@@H](C)[C@@H]1C1CC1]

1-((2S,3R,4R)-4-amino-6-bromo-2-cyclopropyl-3-methyl-3,4-dihydroquinolin-1(2H)-yl)ethanone (for a preparation see Intermediate 344, 200 mg, 0.619 mmol), 1-(2-((tert-butyldimethylsilyl)oxy)ethyl)-4-(4,4,5,5-tetramethyl-1,3,2-dioxaborolan-2-yl)-1H-pyrazole (for a preparation see Intermediate 353, 436 mg, 1.238 mmol), potassium carbonate (257 mg, 1.856 mmol) and Pd(PPh$_3$)$_2$Cl$_2$ (87 mg, 0.124 mmol) were combined in a mixture of 1,4-dioxane (3 mL) and water (1.0 mL) and heated in the microwave reactor at 120° C. for 1 h. The reaction mixture was diluted with EtOAc (50 mL) and water (50 mL) and the organic layer was separated, dried and evaporated in vacuo to give the crude. Purification was undertaken by flash column chromatography. The crude material was loaded onto a 25 g silica column and eluted using a graduating solvent system of 0-10% 2M methanolic ammonia in dichloromethane. Combination and evaporation of the desired fractions gave the product as a yellow oil (190 mg). LCMS (2 min Formic): Rt=0.89 min, [M−NH$_2$]$^+$=452.

Intermediate 355: 1-((2S,3R,4R)-6-(1-(2-((tert-butyldimethylsilyl)oxy)ethyl)-1H-pyrazol-4-yl)-2-cyclopropyl-3-methyl-4-(pyridin-2-ylamino)-3,4-dihydroquinolin-1(2H)-yl)ethanone

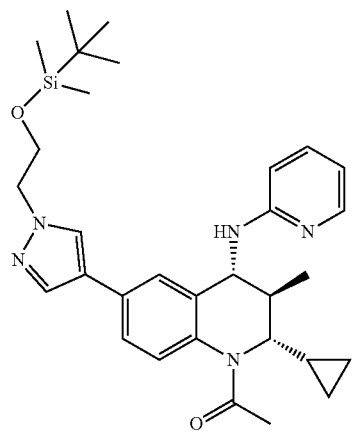 [SMILES: CC(=O)N1c2ccc(-c3cnn(CCO[Si](C)(C)C(C)(C)C)c3)cc2[C@H](Nc2ccccn2)[C@@H](C)[C@@H]1C1CC1]

1-((2S,3R,4R)-4-Amino-6-(1-(2-((tert-butyldimethylsilyl)oxy)ethyl)-1H-pyrazol-4-yl)-2-cyclopropyl-3-methyl-3,4-dihydroquinolin-1(2H)-yl)ethanone (for a preparation see Intermediate 354, 190 mg, 0.405 mmol), 2-bromopyridine (0.058 mL, 0.608 mmol), sodium tert-butoxide (78 mg, 0.811 mmol), Pd$_2$(dba)$_3$ (18.56 mg, 0.020 mmol) and Q-Phos (28.9 mg, 0.041 mmol) were combined in anhydrous toluene (2 mL). The reaction was heated at 50° C. overnight. The reaction was incomplete so further 2-bromopyridine (0.058 mL, 0.608 mmol), sodium tert-butoxide (78 mg, 0.811 mmol), Pd$_2$(dba)$_3$ (18.56 mg, 0.020 mmol) and Q-Phos (28.9 mg, 0.041 mmol) were added and heating was continued for 5 h. The reaction mixture was partitioned between EtOAc (50 mL) and water (50 mL). The organic layer was separated and passed through a hydrophobic frit. The filtrate was concentrated in vacuo to leave the crude. Purification was undertaken by flash column chromatography. The crude material was loaded onto a 25 g silica column and eluted using a graduating solvent system of 0-75% EtOAc in cyclohexane. Combination and evaporation of the desired fractions gave the product as a red oil (70 mg). LCMS (2 min Formic): Rt=0.99 min, [MH]$^+$=546.

Intermediate 356: 1-((2S,3R,4R)-4-amino-6-bromo-2,3-dimethyl-3,4-dihydroquinolin-1(2H)-yl)ethanone

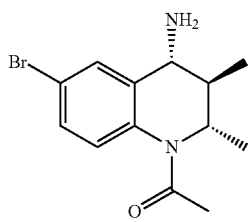 [SMILES: CC(=O)N1c2ccc(Br)cc2[C@H](N)[C@@H](C)[C@@H]1C]

A sample of benzyl ((2S,3R,4R)-1-acetyl-6-bromo-2,3-dimethyl-1,2,3,4-tetrahydroquinolin-4-yl)carbamate (for a preparation see Intermediate 209, 3.0268 g, 7.02 mmol) was dissolved in ethanol (64 mL), and to this was added water (64 mL), forming a suspension. To the suspension was added potassium hydroxide (3.985 g, 71.0 mmol). The mixture was stirred at 80° C. for 4 h. The reaction temperature was raised to 90° C. and allowed to stir overnight. The reaction mixture was allowed to cool, diluted with water and washed with dichloromethane (75 mL). The layers were separated, and the aqueous layer was washed two further times with dichloromethane (2×75 mL). The organic layers were passed over a hydrophobic frit, combined and concentrated in vacuo to afford a yellow oil. This oil was dissolved in methanol and loaded onto a 50 g SCX-2 SPE cartridge which had been pre-equilibrated with methanol. The column was flushed through with 4 CVs of methanol, and then 4 CVs of 2M ammonia in methanol. The appropriate fractions were combined and concentrated in vacuo to afford a colourless oil (1.17 g, 3.94 mmol, 56%).
LCMS (2 min Formic): Rt=0.83 min, [MH]$^+$=297, 299.

Intermediate 357: tert-butyl 4-((2S,3R,4R)-1-acetyl-4-amino-2,3-dimethyl-1,2,3,4-tetrahydroquinolin-6-yl)-5,6-dihydropyridine-1(2H)-carboxylate

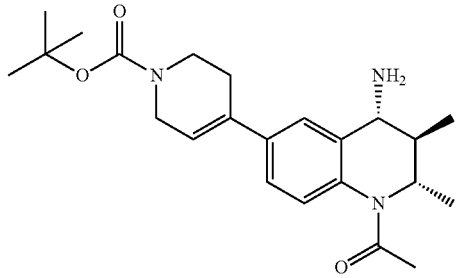 [SMILES: CC(=O)N1c2ccc(C3=CCN(C(=O)OC(C)(C)C)CC3)cc2[C@H](N)[C@@H](C)[C@@H]1C]

A sample of 1-((2S,3R,4R)-4-amino-6-bromo-2,3-dimethyl-3,4-dihydroquinolin-1(2H)-yl)ethanone (1.17 g, 3.94 mmol) was dissolved in a mixture of 1,4-dioxane (40 mL) and water (4.00 mL) under nitrogen. To this stirring solution was added tert-butyl 4-(4,4,5,5-tetramethyl-1,3,2-dioxaborolan-2-yl)-5,6-dihydropyridine-1(2H)-carboxylate (for a preparation see Intermediate 356, 1.357 g, 4.39 mmol), caesium carbonate (1.283 g, 3.94 mmol) and palladium tetrakis (0.455 g, 0.394 mmol). The mixture was stirred at 80° C. under nitrogen for ~3.5 hours. A further sample of caesium carbonate (2.57 g, 7.87 mmol) was added, and the mixture left to cool to rt over a 4 day period. A further sample of palladium tetrakis (0.455 g, 0.394 mmol) was added, and the reaction mixture was again stirred at 80° C. overnight. The reaction mixture was allowed to cool to rt, and concentrated in vacuo. The residue was separated between ethyl acetate and water, and the aqueous layer was washed twice more with ethyl acetate. The organic layers were combined, passed through a hydrophobic frit and concentrated in vacuo to form an orange oil. The oil was dissolved in dichloromethane and loaded onto a 100 g silica flash column, and eluted by silica gel flash chromatography using 0%-10% methanol in dichloromethane. The appropriate fractions were collected and concentrated in vacuo to afford the product (502.7 mg, 1.258 mmol, 32%).
LCMS (2 min Formic): Rt=0.81 min, [MH]$^+$=383.

Intermediate 358: tert-butyl 4-((2S,3R,4R)-1-acetyl-2,3-dimethyl-4-((4-methylpyrimidin-2-yl)amino)-1,2,3,4-tetrahydroquinolin-6-yl)-5,6-dihydropyridine-1(2H)-carboxylate

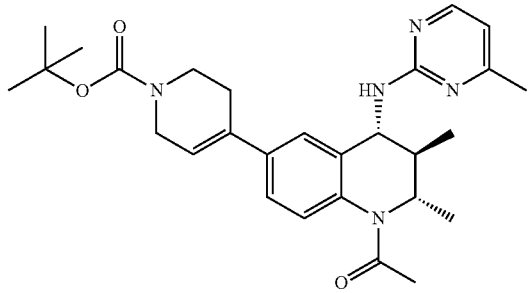 [SMILES: CC(=O)N1c2ccc(C3=CCN(C(=O)OC(C)(C)C)CC3)cc2[C@H](Nc2nccc(C)n2)[C@@H](C)[C@@H]1C]

To a 10 mL-20 mL microwave vial was added 2-chloro-4-methylpyrimidine (421 mg, 3.27 mmol), potassium fluoride (285 mg, 4.91 mmol) and 18-crown-6 (432 mg, 1.636 mmol), followed by a solution of tert-butyl 4-((2S,3R,4R)-1-acetyl-4-amino-2,3-dimethyl-1,2,3,4-tetrahydroquinolin-6-yl)-5,6-dihydropyridine-1(2H)-carboxylate (for a preparation see Intermediate 357, 435.7 mg, 1.091 mmol) in dimethyl sulfoxide (DMSO) (12 mL). The reaction vessel was sealed and heated to 160° C. for ~40 minutes. Some DIPEA (0.952 mL, 5.45 mmol) was added, and the vessel was resealed and heated at 160° C. for 4 h. The reaction mixture was diluted with diethyl ether, washed with water and the layers separated. The aqueous layer was extracted twice more with diethyl ether. The organic layers were combined and back-washed a further 2 times with water. The organic layer was dried over sodium sulfate, filtered and concentrated in vacuo. The residue was taken up in dichloromethane and loaded onto a 100 g silica flash column, and purified by silica gel flash chromatography, eluting in 55%-75% ethyl acetate in cyclohexane. The appropriate fractions were collected and concentrated in vacuo to afford a yellow oil (27%).

LCMS (2 min Formic): Rt=1.10 min, [MH]⁺=492.

Intermediate 359: 1-((2S,3R,4R)-2,3-dimethyl-4-((4-methylpyrimidin-2-yl)amino)-6-(1,2,3,6-tetrahydropyridin-4-yl)-3,4-dihydroquinolin-1(2H)-yl)ethanone

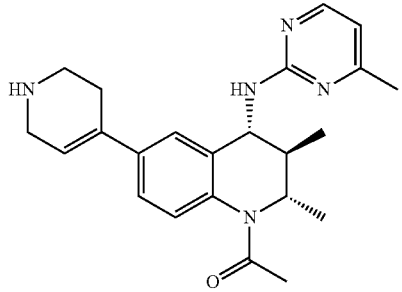 [SMILES: CC(=O)N1c2ccc(C3=CCNCC3)cc2[C@H](Nc2nccc(C)n2)[C@@H](C)[C@@H]1C]

A sample of tert-butyl 4-((2S,3R,4R)-1-acetyl-2,3-dimethyl-4-((4-methylpyrimidin-2-yl)amino)-1,2,3,4-tetrahydroquinolin-6-yl)-5,6-dihydropyridine-1(2H)-carboxylate (for a preparation see Intermediate 358, 60.4 mg, 0.123 mmol) was placed in a flask under nitrogen and dissolved in dichloromethane (DCM) (2 mL). The solution was stirred, and to this was added trifluoroacetic acid (0.5 mL, 6.49 mmol). The mixture was allowed to stir at rt for 1 h. The reaction mixture was diluted with dichloromethane and concentrated in vacuo. The residue was dissolved in methanol and loaded onto a 2 g SCX-2 SPE column, which had been pre-equilibrated with methanol. The column was flushed with 4 CVs of methanol, and then the product eluted using 3 CVs of 2M NH₃ in methanol. The appropriate fractions were collected and concentrated in vacuo to afford a yellow glass (44.5 mg, 0.097 mmol, 79%). LCMS (2 min Formic): Rt=0.57 min, [MH]⁺=392.

Intermediate 360:
rac-4-((tetrahydrofuran-3-yl)oxy)aniline

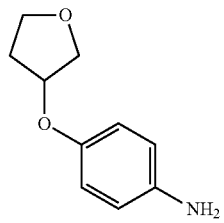

The N-oxo-N-(4-((tetrahydrofuran-3-yl)oxy)phenyl)hydroxylammonium (1.063 g, 5.06 mmol) was taken up in acetic acid (15 mL) and allowed to stir at 0° C., zinc (3.31 g, 50.6 mmol) was added portion-wise and the reaction allowed to warm to rt over 2 h. The reaction was concentrated and eluted through a NH₂ SPE (5 g) using MeOH, the MeOH was concentrated in vacuo to give 1.163 g of desired product (1.163 g, 4.69 mmol, 93%) as a brown solid.

LCMS (2 min Formic): Rt=0.35 min, [MH]⁺=180.

Intermediate 361: benzyl ((2S,3S,4R)-2,3-dimethyl-rac-6-((tetrahydrofuran-3-yl)oxy)-1,2,3,4-tetrahydroquinolin-4-yl)carbamate

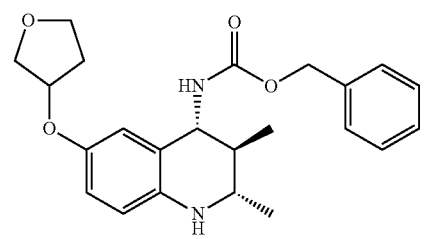 [SMILES: C[C@H]1[C@H](C)Nc2ccc(OC3CCOC3)cc2[C@@H]1NC(=O)OCc1ccccc1]

To a solution of acetaldehyde (0.524 mL, 11.16 mmol) in anhydrous dichloromethane (DCM) (20 mL), was added rac-4-((tetrahydrofuran-3-yl)oxy)aniline (for a preparation see Intermediate 360, 400 mg, 2.232 mmol) and the reaction stirred at rt for 1 h. The reaction was cooled to 0° C. and (S)-2,6-bis(4-chlorophenyl)-4-hydroxy-8,9,10,11,12,13,14,15-octahydrodinaphtho[2,1-d:1',2'-f][1,3,2]dioxaphosphepine 4-oxide (for a preparation see for a preparation see JACS, 2011, 133, 14804, 129 mg, 0.223 mmol) was added and then (E)-benzyl prop-1-en-1-ylcarbamate (for a preparation see Intermediate 1, 750 mg, 3.92 mmol) (500 mg added here). The reaction was then left to stir for 3 h under nitrogen and allowed to warm to rt. Acetaldehyde (0.252 mL, 4.46 mmol) and (E)-benzyl prop-1-en-1-ylcarbamate (750 mg, 3.92 mmol) (250 mg) were added and the reaction left to stir at rt for 72 h. The solution was diluted with DCM (5 mL) and washed with aq. NaHCO₃ solution (30 mL). The layers were separated and the aqueous phase extracted with DCM (3×25 mL). The organics were combined, dried through a hydrophobic frit, and concentrated in vacuo to give 451 mg the desired product (451 mg, 1.138 mmol, 51%) as a yellow/brown solid. Analysis by chiral HPLC was undertaken using a 250×4.6 mm Chiralpak ID column eluting with 20% isopropanol in heptane at a flow rate of 1 mL/min. Peak(s) 1/major isomers (96% by UV) eluted at 26.5 & 39.8 min, and Peak(s) 2/minor isomers (4% by UV)

eluted at 67.8 &73.4 min. This indicated the product had an ee of 92% (about positions 2, 3 & 4). LCMS (2 min Formic): Rt=0.87 min, [M−NH$_2$]$^+$=397.

Intermediate 362: benzyl ((2S,3R,4R)-1-acetyl-2,3-dimethyl-rac-6-((tetrahydrofuran-3-yl)oxy)-1,2,3,4-tetrahydroquinolin-4-yl)carbamate

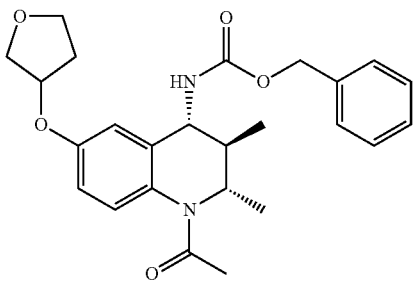 [SMILES: CC(=O)N1c2ccc(OC3CCOC3)cc2[C@H](NC(=O)OCc2ccccc2)[C@@H](C)[C@@H]1C]

To a reaction mixture benzyl ((2S,3S,4R)-2,3-dimethyl-rac-6-((tetrahydrofuran-3-yl)oxy)-1,2,3,4-tetrahydroquinolin-4-yl)carbamate (for a preparation see Intermediate 361, 450 mg, 1.135 mmol) and DIPEA (0.595 mL, 3.40 mmol) were added in dichloromethane (DCM) (20 mL). Acetyl chloride (0.161 mL, 2.270 mmol) was added and the reaction left to stir for 2 h at rt under nitrogen. The reaction mixture was concentrated in vacuo to give 1.003 g if crude product as a brown solid. This was purified by chromatography on SiO$_2$ (50 g), eluting with 0-100% ethyl acetate/cyclohexane. The fractions containing product were combined and concentrated in vacuo to give 439 mg of the desired product (439 mg, 1.001 mmol, 88%) as a pale yellow gum.

LCMS (2 min Formic): Rt=0.98 min, [MH$^+$]=439.

Intermediate 363: 1-((2S,3R,4R)-4-amino-2,3-dimethyl-rac-6-((tetrahydrofuran-3-yl)oxy)-3,4-dihydroquinolin-1(2H)-yl)ethanone

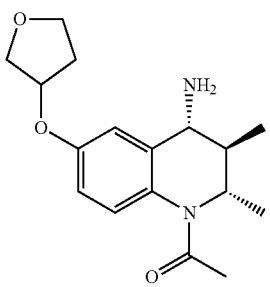 [SMILES: CC(=O)N1c2ccc(OC3CCOC3)cc2[C@H](N)[C@@H](C)[C@@H]1C]

Benzyl ((2S,3R,4R)-1-acetyl-2,3-dimethyl-rac-6-((tetrahydrofuran-3-yl)oxy)-1,2,3,4-tetrahydroquinolin-4-yl)carbamate (for a preparation see Intermediate 362, 439 mg, 1.001 mmol) was taken up in ethanol (10 mL). The solution was hydrogenated using the H-cube (settings: rt, 1 bar, 1 mL/min flow rate) and 10% Pd/C CatCart as the catalyst. The reaction mixture was concentrated in vacuo to give 300 mg of the desired product (300 mg, 0.986 mmol, 98%) as a yellow oil. LCMS (2 min Formic): Rt=0.48 min, [M−NH$_2$]$^+$=288.

Intermediate 364: benzyl ((2S,3S,4R)-2-cyclopropyl-3-methyl-rac-6-((tetrahydrofuran-3-yl)oxy)-1,2,3,4-tetrahydroquinolin-4-yl)carbamate

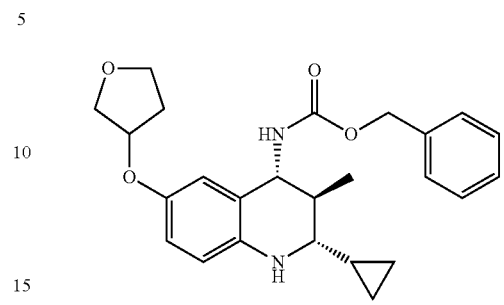

To a solution of cyclopropanecarbaldehyde (0.334 mL, 4.46 mmol) in anhydrous dichloromethane (DCM) (30 mL), was added 4-((tetrahydrofuran-3-yl)oxy)aniline (for a preparation see Intermediate 360, 400 mg, 2.232 mmol) and the reaction stirred at rt for 1 h. The reaction was cooled to 0° C. and (S)-2,6-bis(4-chlorophenyl)-4-hydroxy-8,9,10,11,12,13,14,15-octahydrodinaphtho[2,1-d:1′,2′-f][1,3,2]dioxaphosphepine 4-oxide (for a preparation see JACS, 2011, 133, 14804, 12.89 mg, 0.022 mmol) was added and then (E)-benzyl prop-1-en-1-ylcarbamate (for a preparation see Intermediate 1, 469 mg, 2.455 mmol). The reaction was then left to stir for 16 h under nitrogen and allowed to warm to rt. The solution was washed with sat. NaHCO$_3$ solution (2×20 mL) and the layers separated. The organic phase was dried through a hydrophobic frit and concentrated in vacuo to give 1.280 g of crude product as a brown gum. This was purified by chromatography on SiO$_2$ (50 g) eluting with 0-40% ethyl acetate/cyclohexane. The fractions containing product were combined and concentrated in vacuo to give 665 mg of the desired product (665 mg, 1.574 mmol, 71%) as a white solid. Analysis by chiral HPLC was undertaken using a 250×4.6 mm Chiralpak IC column eluting with 10% ethanol in heptane at a flow rate of 1 mL/min. Peak(s) 1/minor isomers (5% by UV) eluted at 18.7 & 20.2 min, and Peak(s) 2/major isomers (95% by UV) eluted at 46.8 & 58.1 min. This indicated the product had an ee of 90% (about positions 2, 3 & 4).

LCMS (2 min Formic): Rt=1.02 min, [MH$^+$]=423.

Intermediate 365: benzyl ((2S,3R,4R)-1-acetyl-2-cyclopropyl-3-methyl-rac-6-((tetrahydrofuran-3-yl)oxy)-1,2,3,4-tetrahydroquinolin-4-yl)carbamate

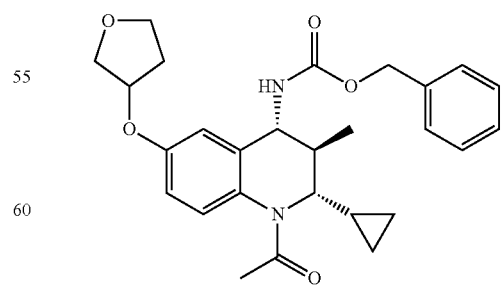

To a reaction mixture benzyl ((2S,3S,4R)-2-cyclopropyl-3-methyl-rac-6-((tetrahydrofuran-3-yl)oxy)-1,2,3,4-tetrahydroquinolin-4-yl)carbamate (for a preparation see Intermediate 364, 655 mg, 1.550 mmol) and DIPEA (0.812 mL, 4.65 mmol) were added in dichloromethane (DCM) (20 mL). Acetyl chloride (0.198 mL, 2.79 mmol) was added and the reaction left to stir for 45 mins at rt under nitrogen. Acetyl chloride (0.05 mL, 0.703 mmol) was added and the reaction left to stir for 1 h under nitrogen at rt. The reaction solution was concentrated in vacuo to give 1.421 g of crude product as an orange/brown gum. This was purified by chromatography on SiO$_2$ (50 g) eluting with 0-75% ethyl acetate/cyclohexane. The fractions containing product were combined and concentrated in vacuo to give 674 mg of the desired product (674 mg, 1.451 mmol, 94%) as a yellow gum.

LCMS (2 min Formic): Rt=1.05 min, [MH$^+$]=465.

Intermediate 366: 1-((2S,3R,4R)-4-amino-2-cyclopropyl-3-methyl-rac-6-((tetrahydrofuran-3-yl)oxy)-3,4-dihydroquinolin-1(2H)-yl)ethanone

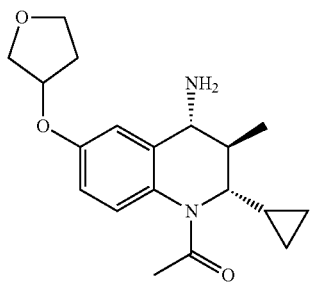 [SMILES: CC(=O)N1c2ccc(OC3CCOC3)cc2[C@H](N)[C@@H](C)[C@@H]1C1CC1]

Benzyl ((2S,3R,4R)-1-acetyl-2-cyclopropyl-3-methyl-rac-6-((tetrahydrofuran-3-yl)oxy)-1,2,3,4-tetrahydroquinolin-4-yl)carbamate (for a preparation se Intermediate 365, 664 mg, 1.429 mmol) was taken up in tetrahydrofuran (THF) (10 mL), TBAF 1M in THF (2.86 mL, 2.86 mmol) was added and the solution was stirred under reflux for 16 h. Further TBAF 1M in THF (1.429 mL, 1.429 mmol) was added and the reaction left to stir under N$_2$ and reflux for 1 h. Further TBAF 1M in THF (1.429 mL, 1.429 mmol) was added and the reaction was left to stir under N$_2$ and reflux for 45 min. Further TBAF 1M in THF (2.86 mL, 2.86 mmol) was added and the reaction was left to stir under N$_2$ and reflux for 45 min. Further TBAF 1M in THF (1.429 mL, 1.429 mmol) was added and the reaction was left to stir for 40 min under N$_2$ and reflux. The solution was partitioned between DCM and aq. NaHCO$_3$. The organic layer was separated and the aqueous layer extracted with DCM (2×20 mL). The combined organic fractions were dried through a hydrophobic frit and concentrated in vacuo to give a brown oil. The sample was loaded in methanol and purified by SPE on sulphonic acid (SCX) 20 g using sequential solvents methanol, 2M ammonia/methanol. The appropriate fractions were combined concentrated in vacuo to give 1.486 g of crude product as a brown oil. This was purified by chromatography on SiO$_2$ (100 g, eluting with 0-7% 2M ammonia in methanol/DCM). The fractions containing product were combined and concentrated in vacuo to the product (277 mg, 0.838 mmol, 59%) as a colourless gum. LCMS (2 min Formic): Rt=0.56 min, [M–NH$_2$]$^+$=314.

Intermediate 367: tert-butyl 4-((2S,3R,4R)-1-acetyl-2,3-dimethyl-4-(pyrimidin-2-ylamino)-1,2,3,4-tetrahydroquinolin-6-yl)piperazine-1-carboxylate

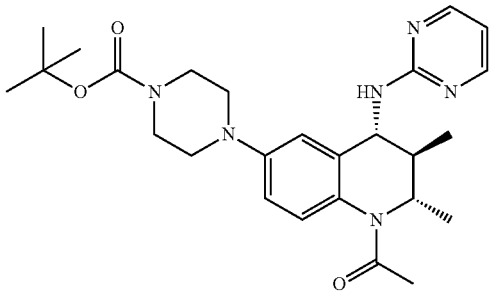 [SMILES: CC(=O)N1c2ccc(N3CCN(C(=O)OC(C)(C)C)CC3)cc2[C@H](Nc2ncccn2)[C@@H](C)[C@@H]1C]

A solution of 2-fluoropyrimidine (110 mg, 1.118 mmol), tert-butyl 4-((2S,3R,4R)-1-acetyl-4-amino-2,3-dimethyl-1,2,3,4-tetrahydroquinolin-6-yl)piperazine-1-carboxylate (for a preparation see Intermediate 213, 150 mg, 0.373 mmol) and DIPEA (0.260 mL, 1.491 mmol) in dimethyl sulfoxide (DMSO) (2.6 mL) was added to a microwave vial and the vial sealed and heated to 160° C. for 4 h. The reaction mixture was filtered, washed with a small amount of 1:1 DMSO/MeOH directly into a vial and was purified by MDAP (HpH). The appropriate fractions were collected and concentrated in vacuo to afford the desired product as a beige oil (119 mg, 0.248 mmol, 66%)

LCMS (2 min Formic): Rt=1.00 min, [MH]$^+$=481.

Intermediate 368: tert-butyl 4-((2S,3R,4R)-1-acetyl-4-((4-(methoxycarbonyl)phenyl)amino)-2,3-dimethyl-1,2,3,4-tetrahydroquinolin-6-yl)piperazine-1-carboxylate

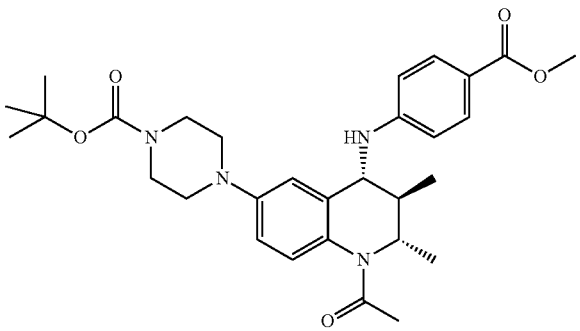 [SMILES: COC(=O)c1ccc(N[C@H]2c3cc(N4CCN(C(=O)OC(C)(C)C)CC4)ccc3N(C(C)=O)[C@@H](C)[C@@H]2C)cc1]

To a 25 mL flask were added tert-butyl 4-((2S,3R,4R)-1-acetyl-4-amino-2,3-dimethyl-1,2,3,4-tetrahydroquinolin-6-yl)piperazine-1-carboxylate (for a preparation see Intermediate 213, 300 mg, 0.745 mmol), methyl 4-bromobenzoate (226 mg, 1.051 mmol), cesium carbonate (456 mg, 1.400 mmol), and Pd(QPhos)$_2$ (107 mg, 0.070 mmol) in CPME (1.8 mL). The reaction mixture was degassed with nitrogen for 15 min and stirred at 80° C. for 16 h. The reaction mixture was partitioned between EtOAc (20 mL) and water (20 mL). The layers were separated and the aqueous layer was further extracted with EtOAc (2×20 mL). The combined organics were dried (MgSO$_4$) and concentrated in vacuo to afford the crude product as a red oil. This was taken up in DCM and added to a silica cartridge (50 g). This was eluted by flash chromatography, eluting with a gradient of 0-60% EtOAc/cyclohexane. The appropriate fractions were collected and concentrated in vacuo to afford the desired product as a red oil (308 mg, 0.574 mmol, 77%).

LCMS (2 min Formic): Rt=1.18 min, [MH]⁺=537.

Intermediate 369: 4-(((2S,3R,4R)-1-acetyl-6-(4-(tert-butoxycarbonyl)piperazin-1-yl)-2,3-dimethyl-1,2,3,4-tetrahydroquinolin-4-yl)amino)benzoic Acid

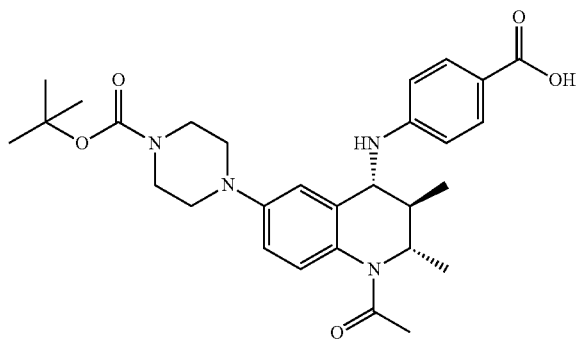 [SMILES: CC(=O)N1c2ccc(N3CCN(C(=O)OC(C)(C)C)CC3)cc2[C@H](Nc2ccc(C(=O)O)cc2)[C@@H](C)[C@@H]1C]

tert-Butyl 4-((2S,3R,4R)-1-acetyl-4-((4-(methoxycarbonyl)phenyl)amino)-2,3-dimethyl-1,2,3,4-tetrahydroquinolin-6-yl)piperazine-1-carboxylate (for a preparation see Intermediate 368, 300 mg, 0.559 mmol) and lithium hydroxide (66.9 mg, 2.80 mmol) were dissolved in tetrahydrofuran (THF) (2.5 mL) and water (2.5 mL). The reaction was stirred at rt for 2 h and then allowed to stand for ~16 h at rt. Lithium hydroxide (69.6 mg, 2.91 mmol) was added and the reaction was stirred vigorously at rt for 4 h. Sodium hydroxide (179 mg, 4.47 mmol) was added and the reaction left to stir at 55° C. for 4.5 h. The solution was allowed to cool to rt and the solvent was evaporated in vacuo. The resulting solid was taken up in water (40 mL) and acidified to a pH 3 at which point a white/purple solid crashed out. This was filtered off and dried in vacuo to give 164 mg of the crude product as a brown solid. The filtrate was extracted with DCM (2×15 mL) and the layers separated. The organic phase was dried through a hydrophobic frit and concentrated in vacuo to give 221 mg of the crude product as a yellow solid. The two crude batches were combined and purified by chromatography on SiO₂ (25 g, eluting with 0-100% ethyl acetate/cyclohexane). The fractions containing product were combined and concentrated in vacuo to give 164 mg of product as a white solid. The column was eluted again with 20% methanol/DCM, the fractions containing product were combined and concentrated in vacuo to give 75 mg of product as an off-white solid.

LCMS (2 min Formic): Rt=1.02 min, [MH]⁺=523.

Intermediate 370: tert-butyl 4-((2S,3R,4R)-1-acetyl-4-((4-carbamoylphenyl)amino)-2,3-dimethyl-1,2,3,4-tetrahydroquinolin-6-yl)piperazine-1-carboxylate

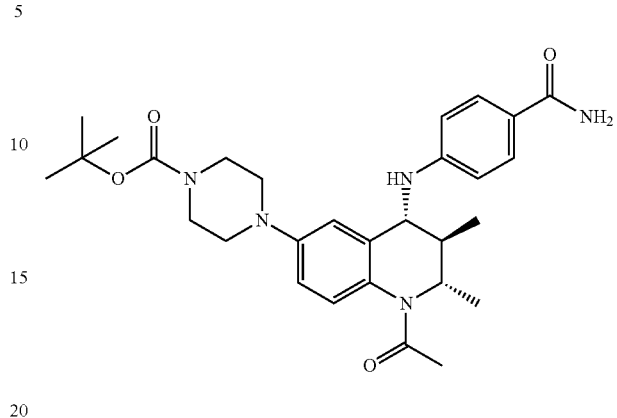

To a solution of 4-(((2S,3R,4R)-1-acetyl-6-(4-(tert-butoxycarbonyl)piperazin-1-yl)-2,3-dimethyl-1,2,3,4-tetrahydroquinolin-4-yl)amino)benzoic acid (for a preparation see Intermediate 369, 50 mg, 0.096 mmol) and HATU (43.7 mg, 0.115 mmol) in N,N-dimethylformamide (DMF) (0.8 mL), DIPEA (0.067 mL, 0.383 mmol) was added and the solution left to stir for 1 minute then ammonium chloride (6.14 mg, 0.115 mmol) was added and the reaction left to stir at rt for 30 minutes. The solution was diluted to 1 mL with methanol and purified by MDAP (Formic). The solvent was evaporated in vacuo to give 52 mg of the desired product as a white solid.

LCMS (2 min Formic): Rt=0.98 min, [MH]⁺=522.

Intermediate 371: 1-((2S,3R,4R)-6-bromo-2-cyclopropyl-3-methyl-4-(pyrimidin-2-ylamino)-3,4-dihydroquinolin-1(2H)-yl)ethanone

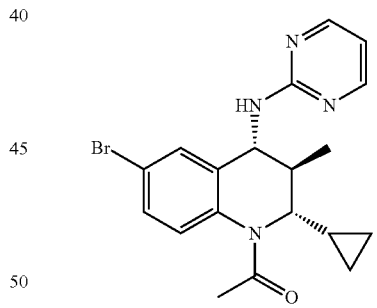

A solution of 1-((2S,3R,4R)-4-amino-6-bromo-2-cyclopropyl-3-methyl-3,4-dihydroquinolin-1(2H)-yl)ethanone (for a preparation see Intermediate 344, 300 mg, 0.928 mmol), 2-fluoropyrimidine (182 mg, 1.856 mmol) and DIPEA (0.324 mL, 1.856 mmol) in N-methyl-2-pyrrolidone (NMP) (4.5 mL) was stirred in the microwave in a closed vessel at 200° C. for 1 h. The reaction mixture was diluted with ethyl acetate (10 mL) and washed with water (3×7 mL). The organic layer was concentrated in vacuo. The crude was dissolved in DCM, loaded onto a 50 g silica cartridge and purified over a gradient of 0-100% ethyl acetate in cyclohexane over 12 CVs. The appropriate fractions were combined and concentrated in vacuo to give the product (220 mg, 0.548 mmol, 59%).

LCMS (2 min Formic): Rt=1.00 min, [MH]⁺=401, 403.

Intermediate 372: benzyl ((2S,3S,4R)-6-bromo-2-ethyl-3-methyl-1,2,3,4-tetrahydroquinolin-4-yl)carbamate

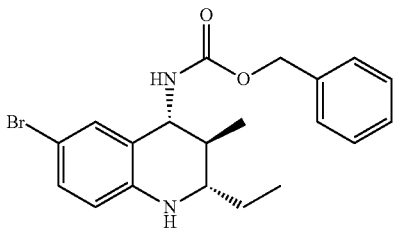 [SMILES: CC[C@@H]1Nc2ccc(Br)cc2[C@H](NC(=O)OCc2ccccc2)[C@H]1C]

A solution of 4-bromoaniline (5 g, 29.1 mmol) and propionaldehyde (3.15 mL, 43.6 mmol) in anhydrous dichloromethane (DCM) (150 mL) was stirred under nitrogen at rt for 1 h and then cooled to 0° C. (ice bath). (11 bS)-2,6-bis(4-chlorophenyl)-4-hydroxy-8,9,10,11,12,13,14,15-octahydrodinaphtho[2,1-d:1',2'-f][1,3,2]dioxaphosphepine 4-oxide (for a preparation see JACS, 2011, 133, 14804, 0.336 g, 0.581 mmol) was added followed by (E)-benzyl prop-1-en-1-ylcarbamate (for a preparation see Intermediate 1, 5.93 g, 31.0 mmol) in anhydrous DCM (5 mL). The reaction mixture was stirred at 0° C. (ice bath) and allowed to reach rt overnight (17 h). The reaction mixture was combined with the mixture from another reaction (starting with 1.6 g aniline) then washed with sat. aq. NaHCO$_3$ (140 mL) and the aqueous layer was extracted with DCM (100 mL). The combined organics were dried through a hydrophobic frit and the solvent removed by rotary evaporation. The crude was loaded in DCM (10 mL) and purified by silica gel chromatography, (340 g) 0-10% EtOAc in cyclohexane gradient over 20 CV. The appropriate fractions were combined and the solvent removed by rotary evaporation. The resulting white solid (12.6 g) was recrystalised in an EtOAc-cyclohexane (1-3) mixture and the recrystallised material was isolated by vacuum filtration to give (after 2 hours in vacuum oven) the product (10.8 g, 26.8 mmol, 92%) as a fine white crystals. Analysis by chiral HPLC was undertaken using a 250×4.6 mm Chiralcel OJ column eluting with 25% ethanol in heptane at a flow rate of 1 mL/min. Peak 1/minor enantiomers (<0.5% by UV) eluted at 9.6 min, and Peak 2/major enantiomers (>99.5% by UV) eluted at 13.2 min. This indicated the product had an ee of >99%. LCMS (2 min Formic): Rt=1.28 min, [MH]$^+$=403, 405.

Intermediate 373: benzyl ((2S,3R,4R)-1-acetyl-6-bromo-2-ethyl-3-methyl-1,2,3,4-tetrahydroquinolin-4-yl)carbamate

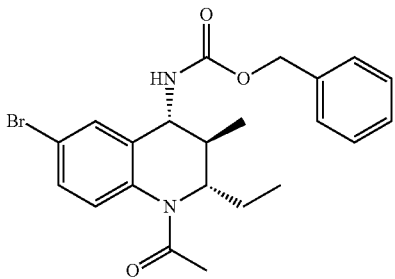 [SMILES: CC[C@H]1[C@H](C)[C@@H](NC(=O)OCc2ccccc2)c2cc(Br)ccc2N1C(C)=O]

To a stirred solution of benzyl ((2S,3S,4R)-6-bromo-2-ethyl-3-methyl-1,2,3,4-tetrahydroquinolin-4-yl)carbamate (for a preparation see Intermediate 372, 10.5 g, 26.0 mmol) and pyridine (6.0 ml, 74.2 mmol) in anhydrous dichloromethane (DCM) (252 mL) at 0° C. (ice bath) was added acetyl chloride (2.2 mL, 30.9 mmol) in anhydrous DCM (18 ml) drop-wise and the resulting mixture was stirred for 1 h, then allowed to reach rt. The reaction mixture was transferred to a separating funnel and washed with 1M HCl (250 mL), water (250 mL) and saturated sodium bicarbonate solution (250 mL), dried (phase separator) and evaporated in vacuo to give the product (11 g, 24.70 mmol, 95%) as light white powder. LCMS (2 min Formic): Rt=1.17 min, [MH]$^+$= 445, 447.

Intermediate 374: 1-((2S,3R,4R)-4-amino-6-bromo-2-ethyl-3-methyl-3,4-dihydroquinolin-1(2H)-yl)ethanone

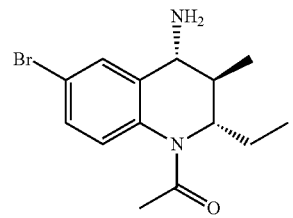 [SMILES: CC[C@H]1[C@H](C)[C@@H](N)c2cc(Br)ccc2N1C(C)=O]

A sample of benzyl ((2S,3R,4R)-1-acetyl-6-bromo-2-ethyl-3-methyl-1,2,3,4-tetrahydroquinolin-4-yl)carbamate (for a preparation see Intermediate 373, 2.57 g, 5.77 mmol) and potassium hydroxide (3.22 g, 57.4 mmol) were added to a flask, and to this was added water (40 mL) and ethanol (40 mL), forming a suspension. The reaction vessel was heated to 80° C. The reaction mixture was cooled to rt water (50 mL) and DCM (100 mL) were added. The organic layer was separated and aqueous layer was further extracted with DCM (2×50 mL). The pH of aqueous layer (~11) was adjusted to pH9 with 2M HCl and re-extracted with DCM (2×100 mL). Organic layers at pH9 containing clean product were combined, dried (Na$_2$SO$_4$) and concentrated to give the product (539 mg, 1.732 mmol, 30%) as a white solid. The first organic extractions at pH11 were combined, dried (Na$_2$SO$_4$) and concentrated to give 1.63 g of crude yellow oil. This was purified by chromatography on SiO$_2$ (100 g), eluting with 0-20% 2M NH$_3$ in MeOH/DCM over 1320 mL). All fractions were mixed so fractions combined to give 1.53 g of crude yellow oil. This was re-purified by chromatography on SiO$_2$ (50 g) eluting with 0-100% ethyl acetate/cyclohexane over 460 mL). Fractions containing desired product were concentrated to give the product (494 mg, 1.587 mmol, 28%) as a white solid.

LCMS (2 min Formic): Rt=0.57 min, [MH]$^+$=311, 313.

Intermediate 375: 1-((2S,3R,4R)-6-bromo-2-ethyl-3-methyl-4-(pyrimidin-2-ylamino)-3,4-dihydroquinolin-1(2H)-yl)ethanone

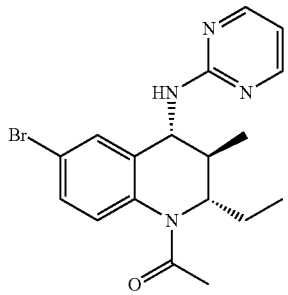 [SMILES: CC[C@H]1[C@H](C)[C@@H](Nc2ncccn2)c2cc(Br)ccc2N1C(C)=O]

A solution of 1-((2S,3R,4R)-4-amino-6-bromo-2-ethyl-3-methyl-3,4-dihydroquinolin-1(2H)-yl)ethanone (for a preparation see Intermediate 374, 530 mg, 1.703 mmol), 2-fluoropyrimidine (357 mg, 3.64 mmol) and DIPEA (1.190 mL, 6.81 mmol) in dimethyl sulfoxide (DMSO) (5 mL) was heated in a 5 mL microwave vial for 4 h at 160° C. The reaction mixture partitioned between ethyl acetate and sat. LiCl solution. The organic layer was separated, washed with water, dried ($Na_2SO_4$) and concentrated to give 1.05 g crude yellow oil. This was purified by chromatography on $SiO_2$ (25 g) eluting with 0-100% ethyl acetate/cyclohexane over 330 mL to give the product (571 mg, 1.467 mmol, 86%) as a pale yellow solid. LCMS (2 min Formic): Rt=0.97 min, $[MH]^+$=389, 391.

Intermediate 376: tert-butyl 4-((2S,3R,4R)-1-acetyl-2-ethyl-3-methyl-4-(pyrimidin-2-ylamino)-1,2,3,4-tetrahydroquinolin-6-yl)piperazine-1-carboxylate

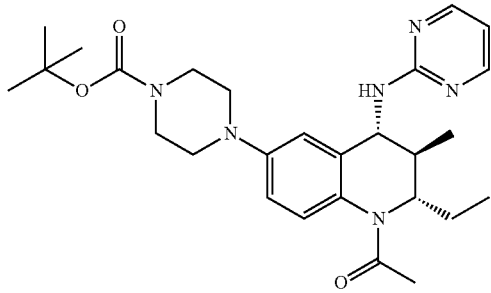 [SMILES: CC[C@H]1[C@H](C)[C@@H](Nc2ncccn2)c2cc(N3CCN(C(=O)OC(C)(C)C)CC3)ccc2N1C(C)=O]

1-((2S,3R,4R)-6-Bromo-2-ethyl-3-methyl-4-(pyrimidin-2-ylamino)-3,4-dihydroquinolin-1(2H)-yl)ethanone (for a preparation see Intermediate 375, 77 mg, 0.198 mmol), tert-butyl piperazine-1-carboxylate (60 mg, 0.322 mmol), $Pd_2(dba)_3$ (30 mg, 0.033 mmol), DavePhos (30 mg, 0.076 mmol) and sodium tert-butoxide (57.0 mg, 0.593 mmol) were combined in dry 1,4-dioxane (2 mL) in a 5 mL microwave vial. The reaction mixture was degassed for 15 mins and heated at 120° C. for 30 mins in the microwave. The reaction mixture was cooled to rt and filtered through celite (2.5 g cartridge) washing with ethyl acetate. This was concentrated to give 210 mg of crude orange oil. This was purified by chromatography on $SiO_2$ (10 g), eluting with 0-100% ethyl acetate/cyclohexane over 120 mLs to give the product (55 mg, 0.111 mmol, 56%) as a yellow oil. LCMS (2 min Formic): Rt=1.05 min, $[MH]^+$=495.

Intermediate 377: tert-butyl 4-((2S,3R,4R)-1-acetyl-2-ethyl-3-methyl-4-(pyrimidin-2-ylamino)-1,2,3,4-tetrahydroquinolin-6-yl)-5,6-dihydropyridine-1(2H)-carboxylate

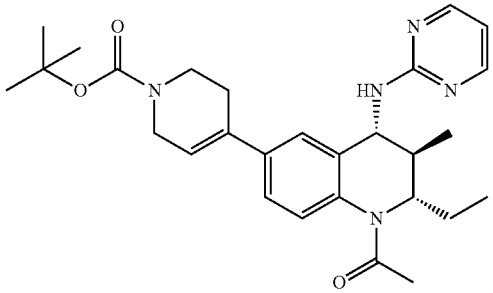 [SMILES: CC[C@H]1[C@H](C)[C@@H](Nc2ncccn2)c2cc(C3=CCN(C(=O)OC(C)(C)C)CC3)ccc2N1C(C)=O]

1-((2S,3R,4R)-6-bromo-2-ethyl-3-methyl-4-(pyrimidin-2-ylamino)-3,4-dihydroquinolin-1(2H)-yl)ethanone (for a preparation see Intermediate 375, 346 mg, 0.889 mmol), tert-butyl 4-(4,4,5,5-tetramethyl-1,3,2-dioxaborolan-2-yl)-5,6-dihydropyridine-1(2H)-carboxylate (412 mg, 1.333 mmol), potassium carbonate (369 mg, 2.67 mmol) and $PdCl_2P(Ph_3)_2$(64 mg, 0.091 mmol) were combined in a mixture of 1,4-dioxane (3 ml) and water (1 ml) and heated in the microwave reactor at 120° C. for 40 min. The reaction mixture was diluted with ethyl acetate and water. The organic layer was separated, washed with water, dried ($Na_2SO_4$) and concentrated to give ~927 mg of crude brown residue. This was purified by chromatography on $SiO_2$ (50 g) eluting with 0-100% ethyl acetate/cyclohexane over 660 mL to give the product (352 mg, 0.716 mmol, 81%) as a pale yellow oil. LCMS (2 min Formic): Rt=1.13 min, $[MH]^+$=492.

Intermediate 378: tert-butyl 4-((2S,3R,4R)-1-acetyl-2-cyclopropyl-3-methyl-4-(pyrimidin-2-ylamino)-1,2,3,4-tetrahydroquinolin-6-yl)-5,6-dihydropyridine-1(2H)-carboxylate

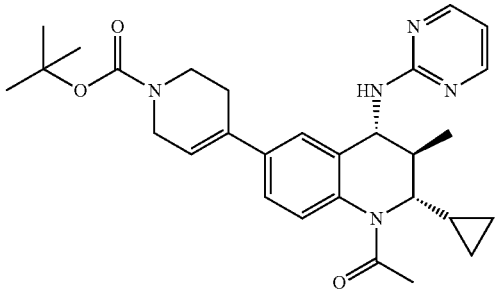 [SMILES: CC(=O)N1c2ccc(C3=CCN(C(=O)OC(C)(C)C)CC3)cc2[C@H](Nc2ncccn2)[C@@H](C)[C@@H]1C1CC1]

To a flask under nitrogen was added a sample of 1-((2S,3R,4R)-6-bromo-2-cyclopropyl-3-methyl-4-(pyrimidin-2-ylamino)-3,4-dihydroquinolin-1(2H)-yl)ethanone (for a preparation see Intermediate 371, 250 mg, 0.623 mmol). The sample was dissolved in 1,4-dioxane (10 mL) and water (1.0 mL), and then to this solution was added, with stirring, caesium carbonate (609 mg, 1.869 mmol), tert-butyl 4-(4,4,5,5-tetramethyl-1,3,2-dioxaborolan-2-yl)-5,6-dihydropyridine-1(2H)-carboxylate (289 mg, 0.934 mmol) and palladium tetrakis (72.0 mg, 0.062 mmol). The mixture was heated, with stirring, at 80° C. under nitrogen for ~1 h. The reaction mixture was allowed to stir at 80° C. for a total of 4 h. The reaction mixture was allowed to cool to rt, and diluted with ethyl acetate and water. The layers were separated, and the aqueous layer was extracted with further ethyl acetate. The organic layers were combined and twice washed with brine. The organic layer was then dried over sodium sulphate, filtered and concentrated in vacuo to afford a dark brown oil. This oil was taken up in dichloromethane, loaded onto a 50 g silica flash column, and purified by flash silica gel chromatography—the product eluting in 60%-80% ethyl acetate in cyclohexane. The appropriate fractions were collected and concentrated in vacuo to afford the purified product, (295.2 mg, 0.498 mmol, 80%). LCMS (2 min Formic): Rt=1.16 min, [MH]$^+$=504.

Intermediate 379: tert-butyl 4-((2S,3R,4R)-1-acetyl-2-cyclopropyl-3-methyl-4-(pyrimidin-2-ylamino)-1,2,3,4-tetrahydroquinolin-6-yl)-3-oxopiperazine-1-carboxylate

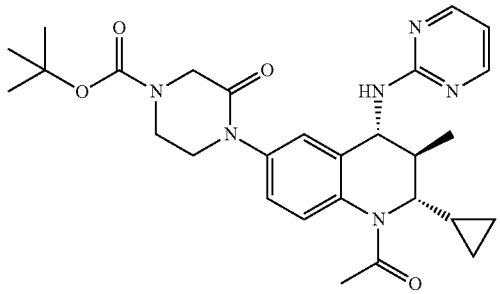 [SMILES: CC(=O)N1c2ccc(N3CCN(C(=O)OC(C)(C)C)CC3=O)cc2[C@H](Nc2ncccn2)[C@@H](C)[C@@H]1C1CC1]

A solution of 1-((2S,3R,4R)-6-bromo-2-cyclopropyl-3-methyl-4-(pyrimidin-2-ylamino)-3,4-dihydroquinolin-1(2H)-yl)ethanone (for a preparation see Intermediate 371, 100 mg, 0.249 mmol), tert-butyl 3-oxopiperazine-1-carboxylate (49.9 mg, 0.249 mmol), (1R,2R)—N1,N2-dimethylcyclohexane-1,2-diamine (3.85 µL, 0.025 mmol), copper (I) iodide (4.75 mg, 0.025 mmol) and K$_2$CO$_3$ (68.9 mg, 0.498 mmol) in 1,4-dioxane (4 mL) was stirred under nitrogen at 100° C. for 16 h. The reaction mixture was allowed to cool to rt, filtered through celite and rinsed with ethyl acetate. The solution was concentrated in vacuo and the crude was dissolved in 1:1 MeOH:DMSO (2×1 mL) and purified by MDAP (HpH). The appropriate fractions were combined and concentrated in vacuo to give the product (40 mg, 0.077 mmol, 31%). LCMS (2 min Formic): Rt=0.92 min, [MH]$^+$=521.

Intermediate 380: tert-butyl 4-((2S,3R,4R)-1-acetyl-2-cyclopropyl-3-methyl-4-(pyrimidin-2-ylamino)-1,2,3,4-tetrahydroquinolin-6-yl)piperazine-1-carboxylate

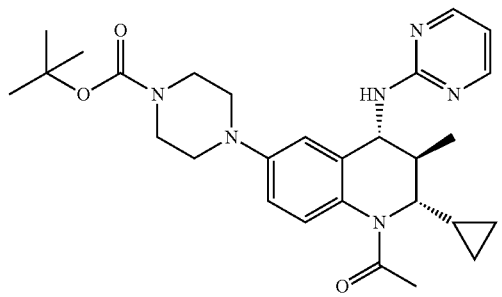 [SMILES: CC(=O)N1c2ccc(N3CCN(C(=O)OC(C)(C)C)CC3)cc2[C@H](Nc2ncccn2)[C@@H](C)[C@@H]1C1CC1]

To a 2 mL-5 mL microwave vial was added samples of Pd$_2$(dba)$_3$ (22.82 mg, 0.025 mmol), DavePhos (29.4 mg, 0.075 mmol), tert-butyl piperazine-1-carboxylate (46.4 mg, 0.249 mmol) and sodium tert-butoxide (35.9 mg, 0.374 mmol). To this was then added a sample of 1-((2S,3R,4R)-6-bromo-2-cyclopropyl-3-methyl-4-(pyrimidin-2-ylamino)-3,4-dihydroquinolin-1(2H)-yl)ethanone (for a preparation see Intermediate 371, 50 mg, 0.125 mmol), which had been dissolved in 1,4-dioxane (2 mL). The vessel was sealed, and the solution was degassed with nitrogen for ~15 min. The vial was then loaded into a microwave reactor, and heated at 120° C. for 30 min. The reaction mixture was diluted with ethyl acetate, filtered through a 2.5 g celite cartridge and concentrated in vacuo. The residue was taken up in dichloromethane, loaded onto a 10 g silica flash column, and purified by flash silica gel chromatography—the product eluting in 45%-100% ethyl acetate/cyclohexane. The appropriate fractions were combined and concentrated in vacuo to afford a yellow glass (16.1 mg, 0.022 mmol, 18%). LCMS (2 min Formic): Rt=1.10 min, [MH]$^+$=507.

Intermediate 381: benzyl ((2S,3R,4R)-1-acetyl-6-(1-benzyl-1H-pyrazol-4-yl)-2-cyclopropyl-3-methyl-1,2,3,4-tetrahydroquinolin-4-yl)carbamate

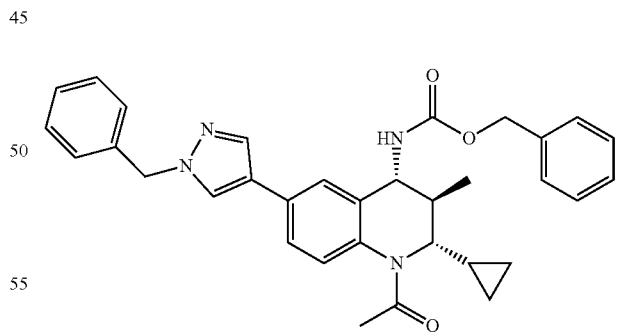

To a reaction vessel benzyl ((2S,3R,4R)-1-acetyl-6-bromo-2-cyclopropyl-3-methyl-1,2,3,4-tetrahydroquinolin-4-yl)carbamate (for a preparation see Intermediate 219, 2.036 g, 4.45 mmol), 1-benzyl-4-(4,4,5,5-tetramethyl-1,3,2-dioxaborolan-2-yl)-1H-pyrazole (1.15 g, 4.05 mmol) and caesium carbonate (3.96 g, 12.14 mmol) were added in 1,4-dioxane (60 mL)/water (6 mL). The solution was degassed with nitrogen and treated with palladium tetrakis (0.468 g, 0.405 mmol) before being degassed again with nitrogen and then it was left to stir at 80° C. for 16 h under nitrogen. The reaction solution was partitioned between water (80 mL) and ethyl acetate (80 mL) and the layers separated. The aqueous phase was extracted with ethyl acetate (100 mL) and combined organics washed with brine soln. (80 mL) before being concentrated in vacuo to give 3.413 g of the crude product as a yellow foam. This was purified by chromatography on $SiO_2$ (100 g) eluting with 0-65% ethyl acetate/cyclohexane. The fractions containing product were combined and concentrated in vacuo to give 1.643 g of the desired product as a white solid.

LCMS (2 min Formic): Rt=1.17 min, $[M-NH_2]^+=535$.

Intermediate 382: 1-((2S,3R,4R)-4-amino-6-(1-benzyl-1H-pyrazol-4-yl)-2-cyclopropyl-3-methyl-3,4-dihydroquinolin-1(2H)-yl)ethanone

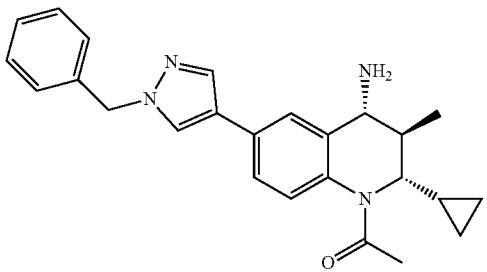 [SMILES: CC(=O)N1c2ccc(-c3cnn(Cc4ccccc4)c3)cc2[C@H](N)[C@@H](C)[C@@H]1C1CC1]

Benzyl ((2S,3R,4R)-1-acetyl-6-(1-benzyl-1H-pyrazol-4-yl)-2-cyclopropyl-3-methyl-1,2,3,4-tetrahydroquinolin-4-yl)carbamate (for a preparation see Intermediate 381, 1.643 g, 3.07 mmol) was taken up in tetrahydrofuran (THF) (25 mL), TBAF 1M in THF (9.4 mL, 9.40 mmol) was added and the solution was stirred under reflux for 5 h. TBAF 1M in THF (3.07 mL, 3.07 mmol) was added and the reaction left to stir under reflux for 72 h. The reaction solution was partitioned between sat. aq. $NaHCO_3$ solution (80 mL) and DCM (80 mL), the aqueous phase was extracted with a further 80 mL of DCM and the organics combined and dried through a hydrophobic frit before being concentrated in vacuo to give the crude product as an orange/brown mixture. This was purified by chromatography on $SiO_2$ (50 g) eluting with 0-4% 2 M ammonia in methanol/DCM. The fractions containing product were combined and concentrated in vacuo to give 1.241 g of the desired product.

LCMS (2 min Formic): Rt=0.74 min, $[M-NH_2]^+=384$.

Intermediate 383: 1-((2S,3R,4R)-6-(1-benzyl-1H-pyrazol-4-yl)-2-cyclopropyl-3-methyl-4-((4-methylpyrimidin-2-yl)amino)-3,4-dihydroquinolin-1(2H)-yl)ethanone

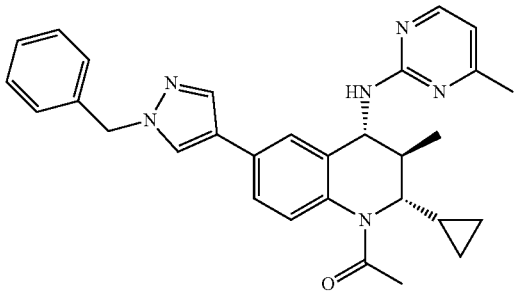 [SMILES: CC(=O)N1c2ccc(-c3cnn(Cc4ccccc4)c3)cc2[C@H](Nc2nccc(C)n2)[C@@H](C)[C@@H]1C1CC1]

To a 2-5 ml microwave vial was added 2-chloro-4-methylpyrimidine (69.3 mg, 0.539 mmol), potassium fluoride (39.2 mg, 0.674 mmol) and 18-crown-6 (59.4 mg, 0.225 mmol), followed by a solution of 1-((2S,3R,4R)-4-amino-6-(1-benzyl-1H-pyrazol-4-yl)-2-cyclopropyl-3-methyl-3,4-dihydroquinolin-1(2H)-yl)ethanone (for a preparation see Intermediate 382, 180 mg, 0.449 mmol) and DIPEA (0.133 mL, 0.764 mmol) in dimethyl sulfoxide (DMSO) (5 mL). The reaction vessel was sealed and heated to 160° C. for 4 h. Potassium fluoride (39.2 mg, 0.674 mmol), 18-crown-6 (59.4 mg, 0.225 mmol) and 2-chloro-4-methylpyrimidine (46.2 mg, 0.360 mmol) were added and the reaction heated under microwave radiation to 160° C. for 2 h. The reaction solution was partitioned between diethyl ether (40 mL) and and water (40 mL). The layers were separated and the aqueous layer was extracted with diethyl ether (2×40 mL). The organic layer was dried through a hydrophobic frit and concentrated in vacuo to give the crude product as an orange oil. This was purified by chromatography on $SiO_2$ (25 g) eluting with 0-100% ethyl acetate/cyclohexane. The fractions containing product were combined and concentrated in vacuo to give 133 mg of the desired product as a pale yellow solid. LCMS (2 min Formic): Rt=1.05 min, $[MH]^+=493$.

Intermediate 384: benzyl ((2S,3S,4R)-2-cyclopropyl-6-methoxy-3-methyl-1,2,3,4-tetrahydroquinolin-4-yl)carbamate

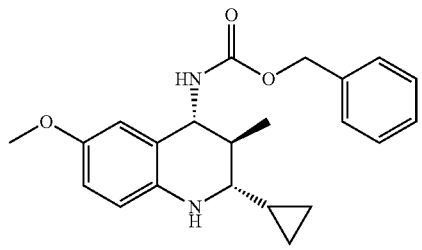 [SMILES: COc1ccc2c(c1)[C@H](NC(=O)OCc1ccccc1)[C@@H](C)[C@H](C1CC1)N2]

4-Methoxyaniline (200 mg, 1.624 mmol) was taken up in DCM (7 mL) under nitrogen and cyclopropanecarbaldehyde (0.182 mL, 2.436 mmol) added. The reaction was stirred at rt for 2 h with molecular sieves (25 g). The reaction was cooled in an ice-bath for 10 min then (E)-benzyl prop-1-en-1-ylcarbamate (for a preparation see Intermediate 1, 342 mg, 1.786 mmol) in DCM (3 mL) was added. (11 bS)-2,6-bis (4-chlorophenyl)-4-hydroxy-8,9,10,11,12,13,14,15-octahydrodinaphtho[2,1-d:1',2'-f][1,3,2]dioxaphosphepine 4-oxide (for a preparation see JACS, 2011, 133, 14804, 9.38 mg, 0.016 mmol) was then added in one portion and the reaction left to stir for 16 h. The reaction mixture was filtered and washed with DCM (10 mL), then washed with sat. $NaHCO_3$ (10 mL). The organic phase was filtered through a hydrophobic frit and evaporated in vacuo giving a white solid. The sample was loaded in dichloromethane (1 mL) and purified on silica gel (25 g) cartridge using a 0-50% ethyl acetate-cyclohexane over 10 CV. The appropriate fractions were combined and evaporated in vacuo to give the required product (287.6 mg) as a white solid. Analysis by chiral HPLC was undertaken using a 250×4.6 mm Chiralcel OJ column eluting with 25% ethanol in heptane at a flow rate of 1 mL/min. Peak 1/minor enantiomer (3% by UV) eluted at 9.6 min, and Peak 2/major enantiomer (97% by UV) eluted at 15.9 min. This indicated the product had an ee of >94%.
LCMS (2 min HpH): Rt=1.21 min, [MH]⁺=367.

Intermediate 385: benzyl ((2S,3R,4R)-1-acetyl-2-cyclopropyl-6-methoxy-3-methyl-1,2,3,4-tetrahydroquinolin-4-yl)carbamate

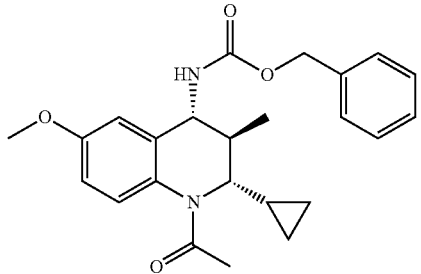 [SMILES: COc1ccc2c(c1)[C@H](NC(=O)OCc1ccccc1)[C@@H](C)[C@H](C1CC1)N2C(C)=O]

A round bottom flask containing benzyl ((2S,3S,4R)-2-cyclopropyl-6-methoxy-3-methyl-1,2,3,4-tetrahydroquinolin-4-yl)carbamate (for a preparation see Intermediate 384, 279.5 mg, 0.763 mmol) was suspended in 2-methyltetrahydrofuran (2-MeTHF) (2 mL) under nitrogen. Acetyl chloride (0.163 mL, 2.288 mmol) was added to the mixture which was stirred at rt under nitrogen for 5 h. DIPEA (0.400 mL, 2.288 mmol) was then added and the reaction mixture stirred under nitrogen for 1 h. The reaction mixture was dissolved in ethyl acetate (5 mL) and a saturated solution of NaHCO₃ (10 mL) was then added. The phases were separated; the aqueous phase was extracted with ethyl acetate (5 mL). The organic phases were combined and further washed with NH₄Cl sat. (10 mL). The organic phase was filtered through a hydrophobic frit and evaporated in vacuo giving the product (216 mg, 0.529 mmol, 69%) as a white solid. LCMS (2 min Formic): Rt=1.12 min, [MH]⁺=409.

Intermediate 386: 1-((2S,3R,4R)-4-amino-2-cyclopropyl-6-methoxy-3-methyl-3,4-dihydroquinolin-1(2H)-yl)ethanone

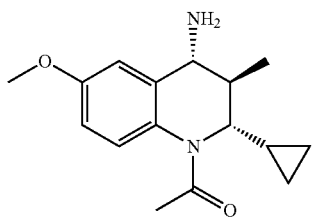 [SMILES: COc1ccc2c(c1)[C@H](N)[C@@H](C)[C@H](C1CC1)N2C(C)=O]

A solution of benzyl ((2S,3R,4R)-1-acetyl-2-cyclopropyl-6-methoxy-3-methyl-1,2,3,4-tetrahydroquinolin-4-yl)carbamate (for a preparation see Intermediate 385, 216 mg, 0.529 mmol) in ethanol (5 mL) was added to 10 wt. % palladium on carbon (dry basis on activated carbon, wet, Degussa type E101 NE/W) (700 mg, 6.58 mmol) and the mixture stirred under an atmosphere of hydrogen at rt for 16 h. The reaction mixture was filtered through a EtOH-preconditioned 2 g celite cartridge, and the cartridge washed with EtOH (10 mL). The filtrate was evaporated in vacuo and dried in a vacuum oven to give the product (122 mg, 0.445 mmol, 84%) as a yellow solid.
LCMS (2 min Formic): Rt=0.53 min, [M−NH₂]⁺=258.

Intermediate 387: 1-((2S,3R,4R)-4-amino-2-cyclopropyl-3-methyl-3,4-dihydroquinolin-1(2H)-yl)ethanone

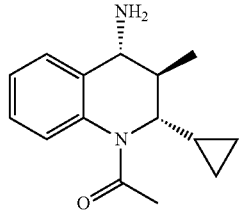 [SMILES: CC(=O)N1c2ccccc2[C@H](N)[C@@H](C)[C@@H]1C1CC1]

Benzyl ((2S,3R,4R)-1-acetyl-6-bromo-2-cyclopropyl-3-methyl-1,2,3,4-tetrahydroquinolin-4-yl)carbamate (for a preparation see Intermediate 344, 2 g, 4.37 mmol) was dissolved in ethanol (25 mL) and 10% Pd/C 50% wet (0.2 g, 1.879 mmol) was added. The reaction mixture was hydrogenated for 25 h. The reaction mixture was filtered through celite (10 g) and washed with further ethanol (50 mL). The fractions were concentrated in vacuo to give a yellow solid (589 mg).
LCMS (2 min Formic): Rt=0.49 min, [MH]⁺=245.

Intermediate 388: 1-((2S,3R,4R)-2-cyclopropyl-3-methyl-4-(pyrimidin-2-ylamino)-6-(4,4,5,5-tetramethyl-1,3,2-dioxaborolan-2-yl)-3,4-dihydroquinolin-1(2H)-yl)ethanone

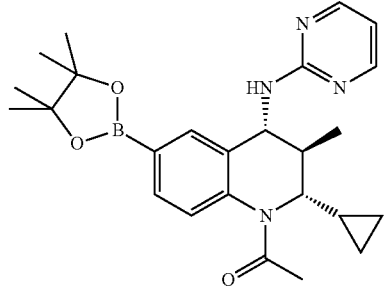 [SMILES: CC(=O)N1c2ccc(B3OC(C)(C)C(C)(C)O3)cc2[C@H](Nc2ncccn2)[C@@H](C)[C@@H]1C1CC1]

1-((2S,3R,4R)-6-bromo-2-cyclopropyl-3-methyl-4-(pyrimidin-2-ylamino)-3,4-dihydroquinolin-1(2H)-yl)ethanone (for a preparation see Intermediate 371, 2.5474 g, 6.35 mmol) was dissolved in dry dimethyl sulfoxide (DMSO) (20 mL). bis(pinacolato)diboron (3.22 g, 12.70 mmol), PdCl₂(dppf) (0.464 g, 0.635 mmol) and potassium acetate (1.246 g, 12.70 mmol) were added and reaction mixture de-gassed under N₂. Reaction mixture was then heated at 80° C. and stirred under N₂ for 16 h. The reaction mixture was cooled to rt and partitioned between ethyl acetate and water. The bi-phasic mixture was passed through a celite cartridge. The organic and aqueous layers were separated and the aqueous layer was extracted with more ethyl acetate (2×50 mL). The organic fractions were combined, dried by passing through a hydrophobic frit and concentrated to give 7.1 g of crude brown residue. This was purified by chromatography (100 g cartridge, eluting with 10-70% ethyl acetate/cyclohexane over 10 CVs). Appropriate fractions were combined and the solvent removed in vacuo to give the product (2.98 g) as a brown glassy foam.
LCMS (2 min Formic): Rt=1.13 min, [MH]⁺=449.

Intermediate 389: rac-(2S,3S,4R)-methyl 2-cyclopropyl-4-(phenylamino)-1,2,3,4-tetrahydroquinoline-3-carboxylate

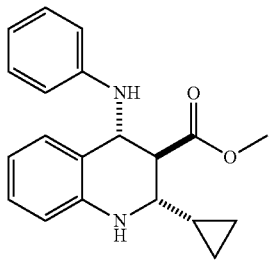 [SMILES: COC(=O)[C@@H]1[C@@H](Nc2ccccc2)c2ccccc2N[C@H]1C1CC1]

A solution of aniline (1138 µL, 11.24 mmol) and methyl propiolate (500 µL, 5.62 mmol) in ethanol (12 mL) was stirred at rt overnight. Cyclopropanecarbaldehyde (420 µL, 5.62 mmol), and 4-methylbenzenesulfonic acid hydrate (267 mg, 1.405 mmol) were added and the reaction stirred at rt for a further 6 h. A precipitate formed immediately. The reaction was allowed to stir overnight. The reaction mixture was cooled to 0° C. and the precipitate was filtered off and washed with cold ethanol to afford the product as a white solid (945 mg, 2.93 mmol, 52%).

LCMS (2 min Formic): Rt=1.21 min, [M−NHPh]⁺=230.

Intermediate 390: rac-((2S,3S,4R)-2-cyclopropyl-4-(phenylamino)-1,2,3,4-tetrahydroquinolin-3-yl)methanol

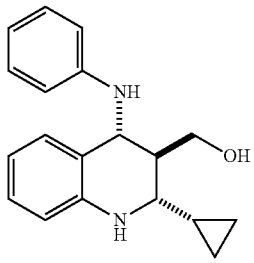 [SMILES: OC[C@@H]1[C@@H](Nc2ccccc2)c2ccccc2N[C@H]1C1CC1]

rac-(2S,3S,4R)-methyl 2-cyclopropyl-4-(phenylamino)-1,2,3,4-tetrahydroquinoline-3-carboxylate (for a preparation see Intermediate 389, 736 mg, 2.283 mmol) was dissolved in dichloromethane (DCM) (20 mL) and cooled in a dry ice/acetone bath under nitrogen. 25% w/v DIBAL-H in toluene (2662 mg, 4.68 mmol) was added drop-wise and the resulting solution stirred for 3 h. Further 25% w/v DIBAL-H in toluene (2662 mg, 4.68 mmol) was added in one portion and the resulting solution stirred for 2 h. The reaction mixture was warmed to rt and TBME (20 mL) added. Water (0.4 mL), followed by 15% aq. NaOH (0.4 mL) and a subsequent portion of water (0.94 mL) were added and the reaction mixture stirred vigorously at 20° C. for 15 min. Copious MgSO₄ was added, the suspension stirred for 30 min and allowed to stand overnight. The resulting suspension was filtered and the filtered solid washed with DCM. The filtrate was evaporated to a pale yellow solid and redissolved in the minimum amount of DCM. The solution was loaded on to a 25 g SNAP silica column and eluted with cyclohexane:EtOAc (5→25%). The product containing fractions were evaporated to a pale brown gum, redissolved in TBME and cyclohexane and evaporated in vacuo to a white solid (591 mg). LCMS (2 min HpH): Rt=1.12 min, [M−H]⁺=293.

Intermediate 391: rac-(2S,3S,4R)-methyl 4-(((benzyloxy)carbonyl)amino)-2-cyclopropyl-7-methoxy-3-methyl-1,2,3,4-tetrahydroquinoline-6-carboxylate

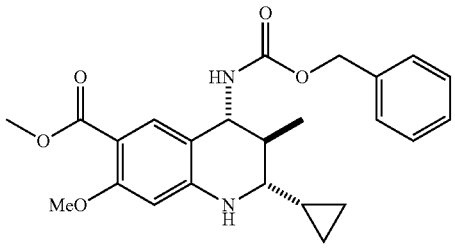 [SMILES: COC(=O)c1cc2c(cc1OC)N[C@@H](C1CC1)[C@H](C)[C@H]2NC(=O)OCc1ccccc1]

To a dry flask was added 3 Å molecular sieves (1 g), the flask was evacuated and heated under vacuum to activate the molecular sieves. The flask was backfilled with nitrogen and allowed to cool. A solution of methyl 4-amino-2-methoxybenzoate (1 g, 5.52 mmol) in dry DCM (37 mL), followed by cyclopropanecarbaldehyde (0.619 mL, 8.28 mmol) were added to the reaction vessel under nitrogen and the resultant suspension stirred at rt for 1 h and then cooled to 0° C. Solutions of diphenyl hydrogen phosphate (0.069 g, 0.276 mmol) followed by (E)-benzyl prop-1-en-1-ylcarbamate (for a preparation see Intermediate 1, 1.548 g, 6.07 mmol) in dry DCM (2×7.5 mL) were added. The reaction was stirred at 0° C. for 3 h and then allowed to warm to rt overnight. The reaction mixture was filtered, the residue was washed with MeOH (2×50 mL) and EtOAc (25 mL) into a separate flask to the initial filtrate. The DCM filtrate was concentrated in vacuo to give the product as a yellow solid (2.44 g, 2.87 mmol, 52%—only ~50% pure). The MeOH/EtOAc washings were also concentrated in vacuo to leave the product as a white solid (239 mg, 0.563 mmol, 10%). The solid residue was also collected and provided further product as a beige solid (1.44 g, 3.39 mmol, 62%).

LCMS (2 min Formic): Rt=1.13 min, [MH]⁺=425.

Intermediate 392: rac-(2S,3R,4R)-methyl 1-acetyl-4-(((benzyloxy)carbonyl)amino)-2-cyclopropyl-7-methoxy-3-methyl-1,2,3,4-tetrahydroquinoline-6-carboxylate

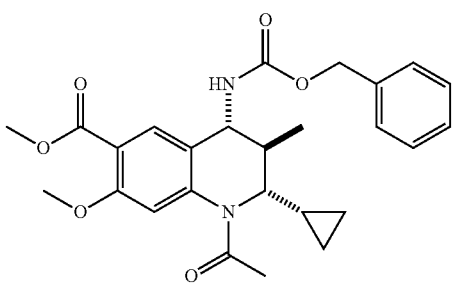 [SMILES: COC(=O)c1cc2c(cc1OC)N(C(C)=O)[C@@H](C1CC1)[C@H](C)[C@H]2NC(=O)OCc1ccccc1]

rac-(2S,3S,4R)-Methyl 4-(((benzyloxy)carbonyl)amino)-2-cyclopropyl-7-methoxy-3-methyl-1,2,3,4-tetrahydroquinoline-6-carboxylate (for a preparation see Intermediate 391, 2.44 g, 2.87 mmol) was taken up in dichloromethane (DCM) (25 mL) and treated with DIPEA (2.008 mL, 11.50 mmol) and acetyl chloride (1.022 mL, 14.37 mmol) and allowed to stir at rt for 1 h. Water (30 mL) was added and further DCM (20 mL) and the layers separated. The aqueous layer was further extracted with DCM (2×40 mL) and the organics combined. This was dried (Na$_2$SO$_4$) and concentrated in vacuo to afford the crude product as a yellow oil. This was taken up in DCM and added to a 100 g silica cartridge and purified by flash chromatography, eluting with 20%→100% EtOAc/cyclohexane. The appropriate fractions were collected and concentrated in vacuo to afford the desired product as a white foam (1.27 g, 2.72 mmol, 95%). LCMS (2 min Formic): Rt=1.05 min, [MH]$^+$=467.

Intermediate 393: rac-(2S,3R,4R)-methyl 1-acetyl-4-amino-2-cyclopropyl-7-methoxy-3-methyl-1,2,3,4-tetrahydroquinoline-6-carboxylate

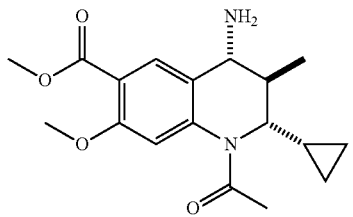 [SMILES: COC(=O)c1cc2c(cc1OC)N(C(C)=O)[C@@H](C1CC1)[C@H](C)[C@H]2N]

A conical flask was charged with rac-(2S,3R,4R)-methyl 1-acetyl-4-(((benzyloxy)carbonyl)amino)-2-cyclopropyl-7-methoxy-3-methyl-1,2,3,4-tetrahydroquinoline-6-carboxylate (for a preparation see Intermediate 392, 1.27 g, 2.72 mmol), ethanol (53 mL) and 10% palladium on carbon (0.116 g, 1.089 mmol). The reaction mixture was stirred under an atmosphere of hydrogen for ~24 h. The reaction mixture was filtered through celite and eluted with ethanol (2×20 mL). The filtrate was concentrated in vacuo to give a yellow oil. This was taken up in DCM and added to a 100 g silica column, this was purified by flash chromatography, eluting with 0%→20% (20% (2M NH$_3$ in MeOH)/DCM)/DCM. The appropriate fractions were combined and concentrated in vacuo to afford the desired product as a yellow solid (628 mg, 1.889 mmol, 69%). LCMS (2 min Formic): Rt=0.50 min, [M−NH$_2$]$^+$=316.

Intermediate 394: rac-(2S,3R,4R)-1-acetyl-2-cyclopropyl-7-methoxy-3-methyl-4-((4-methylpyrimidin-2-yl)amino)-1,2,3,4-tetrahydroquinoline-6-carboxylic Acid

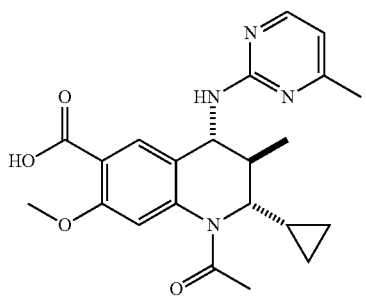 [SMILES: COc1cc2c(cc1C(=O)O)[C@H](Nc1nccc(C)n1)[C@@H](C)[C@H](C1CC1)N2C(C)=O]

rac-(2S,3R,4R)-Methyl 1-acetyl-2-cyclopropyl-7-methoxy-3-methyl-4-((4-methylpyrimidin-2-yl)amino)-1,2,3,4-tetrahydroquinoline-6-carboxylate (for a preparation see Intermediate 393, 85 mg, 0.200 mmol) was taken up in tetrahydrofuran (THF) (870 μL) and water (870 μL). Lithium hydroxide (11.99 mg, 0.501 mmol) was added and the reaction stirred for 16 h at rt. 2M HCl (aq) (250 μL, 0.501 mmol) was added followed by 10% MeOH/DCM (20 mL) and water (20 mL). The biphasic mixture was stirred for 5 min and the layers then separated. The aqueous layer was further extracted with 10% MeOH/DCM (2×20 mL). The combined organics were collected, dried (Na$_2$SO$_4$) and concentrated in vacuo to afford the desired product as a yellow solid (82 mg, 0.200 mmol, 100%). LCMS (2 min Formic): Rt=0.70 min, [MH]$^+$=411.

Intermediate 395: (2S,3S,4R)-methyl 4-(((benzyloxy)carbonyl)amino)-2-cyclopropyl-5-fluoro-3-methyl-1,2,3,4-tetrahydroquinoline-6-carboxylate & (2S,3S,4R)-methyl 4-(((benzyloxy)carbonyl)amino)-2-cyclopropyl-7-fluoro-3-methyl-1,2,3,4-tetrahydroquinoline-6-carboxylate (~1:1)

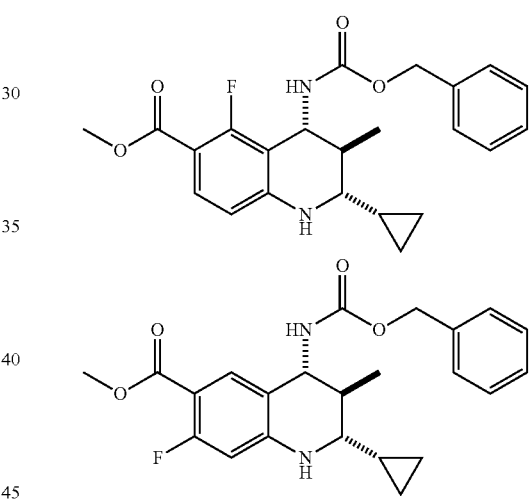

A solution of methyl 4-amino-2-fluorobenzoate (1 g, 5.91 mmol) and cyclopropanecarbaldehyde (0.663 mL, 8.87 mmol) in dry DCM (37 mL) was stirred in a reaction vessel under nitrogen at room temperature for 1 hour and then cooled to 0° C. Solutions of (11 bS)-2,6-bis(4-chlorophenyl)-4-hydroxy-8,9,10,11,12,13,14,15-octahydrodinaphtho[2,1-d:1',2'-f][1,3,2]dioxaphosphepine 4-oxide (for a preparation see for a preparation see JACS, 2011, 133, 14804, 0.034 g, 0.059 mmol) followed by (E)-benzyl prop-1-en-1-ylcarbamate (for a preparation see Intermediate 1, 1.244 g, 6.50 mmol) in dry DCM (2×7.5 mL) were added. The reaction was stirred at 0° C. for 3 h and then allowed to warm to rt overnight. The reaction mixture was filtered and the filtrate was concentrated in vacuo to afford the crude product as a beige solid (1.059 g, 1.284 mmol, 43.4% yield). The residue was also collected to give further product as a white solid (1.456 g, 1.765 mmol, 60%).

LCMS (2 min Formic): Rt=1.18 min, [MH]$^+$=413.

Intermediate 396: (2S,3R,4R)-methyl 1-acetyl-4-(((benzyloxy)carbonyl)amino)-2-cyclopropyl-7-fluoro-3-methyl-1,2,3,4-tetrahydroquinoline-6-carboxylate

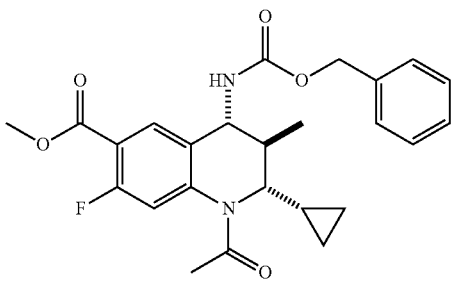 [SMILES: COC(=O)c1cc2c(cc1F)N(C(C)=O)[C@@H](C1CC1)[C@H](C)[C@H]2NC(=O)OCc1ccccc1]

(2S,3S,4R)-methyl 4-(((benzyloxy)carbonyl)amino)-2-cyclopropyl-5-fluoro-3-methyl-1,2,3,4-tetrahydroquinoline-6-carboxylate compound & (2S,3S,4R)-methyl 4-(((benzyloxy)carbonyl)amino)-2-cyclopropyl-7-fluoro-3-methyl-1,2,3,4-tetrahydroquinoline-6-carboxylate (~1:1) (for a preparation see Intermediate 395, 403 mg, 0.489 mmol) was taken up in dichloromethane (DCM) (10 mL) and treated with acetyl chloride (0.139 mL, 1.954 mmol) and allowed to stir at rt for 58 h. Further acetyl chloride (0.139 mL, 1.954 mmol) was added and the reaction allowed to stir for ~3 h. The reaction was diluted with DCM (20 mL) and 2M HCl(aq) (20 mL) and the layers separated. The aqueous layer was washed with further DCM (2×20 mL) and the combined organics were then washed with NaHCO$_3$ (aq) solution (20 mL), dried (Na$_2$SO$_4$) and concentrated in vacuo. As the product still contained a significant impurity, the crude was further purified by MDAP (HpH) to give the product (116 mg, 0.255 mmol, 26%). LCMS (2 min Formic): Rt=1.10 min, [MH]$^+$=455.

Intermediate 397: (2S,3R,4R)-methyl 1-acetyl-4-amino-2-cyclopropyl-7-fluoro-3-methyl-1,2,3,4-tetrahydroquinoline-6-carboxylate

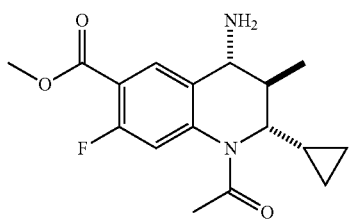 [SMILES: COC(=O)c1cc2c(cc1F)N(C(C)=O)[C@@H](C1CC1)[C@H](C)[C@H]2N]

A conical flask was charged with (2S,3R,4R)-methyl 1-acetyl-4-(((benzyloxy)carbonyl)amino)-2-cyclopropyl-7-fluoro-3-methyl-1,2,3,4-tetrahydroquinoline-6-carboxylate (for a preparation see Intermediate 396, 235 mg, 0.517 mmol), ethanol (10 mL) and 10% palladium on carbon (22.01 mg, 0.207 mmol). The reaction mixture was stirred under an atmosphere of hydrogen for ~16 h. The reaction mixture was filtered through celite and eluted with ethanol (2×20 mL). The filtrate was concentrated in vacuo to give a yellow oil MDAP (HpH) to afford the product (40 mg, 0.125 mmol, 24%) as a colourless gum. LCMS (2 min Formic): Rt=0.57 min, [M−NH$_2$]$^+$=304.

Intermediate 398: (2S,3R,4R)-methyl 1-acetyl-2-cyclopropyl-7-fluoro-3-methyl-4-((4-methylpyrimidin-2-yl)amino)-1,2,3,4-tetrahydroquinoline-6-carboxylate

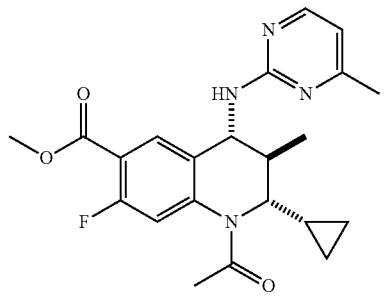

A solution of 2-chloro-4-methylpyrimidine (48.2 mg, 0.375 mmol), potassium fluoride (32.6 mg, 0.562 mmol), (2S,3R,4R)-methyl 1-acetyl-4-amino-2-cyclopropyl-7-fluoro-3-methyl-1,2,3,4-tetrahydroquinoline-6-carboxylate (for a preparation see Intermediate 397, 40 mg, 0.125 mmol), 18-crown-6 (49.5 mg, 0.187 mmol) and DIPEA (0.109 mL, 0.624 mmol) in Dimethyl Sulfoxide (DMSO) (0.7 mL) was added to a microwave vial and the vial sealed and heated to 160° C. for 2 h. The reaction mixture was partitioned between water and Et$_2$O. The layers were separated and the aqueous layer further extracted with Et$_2$O. The combined organics were back extracted with water, dried (Na$_2$SO$_4$) and concentrated in vacuo. The crude product was purified by Silica gel column chromatography eluting with a gradient of 25 to 100% EtOAc/cyclohexane to give the product (21.9 mg, 0.053 mmol, 43%) as a yellow solid. LCMS (2 min Formic): Rt=0.92 min, [MH]$^+$=413.

Intermediate 399: (2S,3R,4R)-1-acetyl-2-cyclopropyl-7-fluoro-3-methyl-4-((4-methylpyrimidin-2-yl)amino)-1,2,3,4-tetrahydroquinoline-6-carboxylic Acid

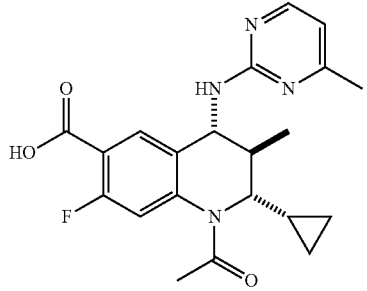 [SMILES: CC(=O)N1c2cc(F)c(C(=O)O)cc2[C@H](Nc2nccc(C)n2)[C@@H](C)[C@@H]1C1CC1]

(2S,3R,4R)-Methyl 1-acetyl-2-cyclopropyl-7-fluoro-3-methyl-4-((4-methylpyrimidin-2-yl)amino)-1,2,3,4-tetrahydroquinoline-6-carboxylate (for a preparation see Intermediate 398, 21.9 mg, 0.053 mmol) was taken up in tetrahydrofuran (THF) (1 mL) and water (1000 μL). lithium hydroxide (6.36 mg, 0.265 mmol) was added and the reaction stirred for ~1 h at rt. 2M HCl(aq) (150 μL, 0.300 mmol) was added, followed by 10% MeOH/DCM and water. The layers were separated and the aqueous layer was further extracted with 10% MeOH/DCM and DCM. The combined organics were dried (Na$_2$SO$_4$) and concentrated in vacuo to afford the crude product as a yellow oil (19.7 mg, 0.049 mmol, 93%).

LCMS (2 min Formic): Rt=0.75 min, [MH]$^+$=399

Intermediate 400: rac-benzyl ((2S,3S,4R)-6-bromo-2-cyclopropyl-8-methoxy-3-methyl-1,2,3,4-tetrahydro-1,7-naphthyridin-4-yl)carbamate

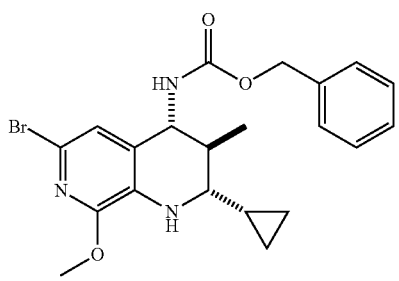 [SMILES: COc1nc(Br)cc2c1N[C@@H](C1CC1)[C@H](C)[C@H]2NC(=O)OCc1ccccc1]

To a solution of 6-bromo-2-methoxypyridin-3-amine (3.10 g, 15.27 mmol) in 2-Me THF (30 mL) was added cyclopropanecarbaldehyde (2.30 mL, 30.8 mmol). The mixture was stirred in a stoppered vessel at rt for 1 h. To the solution was added ytterbium(III) triflate (9.50 g, 15.32 mmol) followed by (E)-benzyl prop-1-en-1-ylcarbamate (for a preparation see Intermediate 1, 3.10 g, 16.21 mmol) and the mixture stirred at rt for 4 h. The reaction mixture was evaporated under vacuum and the foam/gum was partially dissolved in DCM (100 mL) and washed with water (3×100 mL). The organic layer was dried through a hydrophobic frit and the solvent removed by rotary evaporation to give the product as a light brown solid (6.80 g, 15.24 mmol, 100%, 76% pure).

LCMS (2 min HpH): Rt=1.37 min, [MH]$^+$=446, 448.

Intermediate 401: rac-benzyl ((2S,3R,4R)-1-acetyl-6-bromo-2-cyclopropyl-8-methoxy-3-methyl-1,2,3,4-tetrahydro-1,7-naphthyridin-4-yl)carbamate

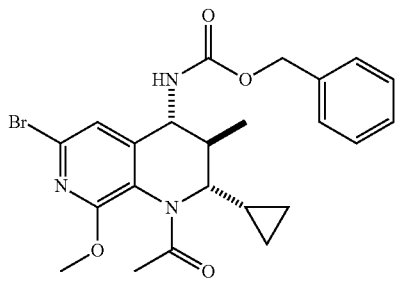 [SMILES: COc1nc(Br)cc2c1N(C(C)=O)[C@@H](C1CC1)[C@H](C)[C@H]2NC(=O)OCc1ccccc1]

A solution of rac-benzyl ((2S,3S,4R)-6-bromo-2-cyclopropyl-8-methoxy-3-methyl-1,2,3,4-tetrahydro-1,7-naphthyridin-4-yl)carbamate (for a preparation see Intermediate 400, 6.80 g, 15.24 mmol) in acetic anhydride (50 ml, 530 mmol) was stirred at 100° C. for 20 h. The reaction mixture was allowed to cool to rt and diluted with EtOAc (50 mL). The organic layer was stirred vigorously with 1 M NaOH (aq) (50 mL), separated and the processed repeated twice. The organic layer was washed with water (50 mL), dried through a hydrophobic frit and the solvent evaporated under vacuum. The residue was dissolved in DCM (20 mL), applied to a 340 g silica cartridge and purified using a gradient of 0-100% EtOAc in cyclohexane over 8 CVs. The appropriate fractions were combined and the solvent removed by rotary evaporation to give the product as a light brown foam (4.77 g, 9.77 mmol, 64%). LCMS (2 min Formic): Rt=1.19 min, [MH]$^+$=488, 490.

Intermediate 402: rac-benzyl ((2S,3R,4R)-1-acetyl-2-cyclopropyl-8-methoxy-3-methyl-6-morpholino-1,2,3,4-tetrahydro-1,7-naphthyridin-4-yl)carbamate

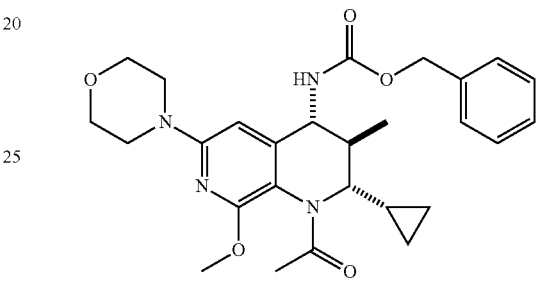

To a mixture of sodium tert-butoxide (0.550 g, 5.72 mmol), Pd$_2$(dba)$_3$ (0.200 g, 0.218 mmol), Dave Phos (0.160 g, 0.407 mmol), rac-benzyl ((2S,3R,4R)-1-acetyl-6-bromo-2-cyclopropyl-8-methoxy-3-methyl-1,2,3,4-tetrahydro-1,7-naphthyridin-4-yl)carbamate (for a preparation see Intermediate 401, 2.15 g, 4.40 mmol) in anhydrous 1,4-dioxane (25 mL) was added morpholine (0.42 mL, 4.82 mmol) and the mixture stirred at 100° C. under nitrogen for 3 h. The reaction mixture was filtered through celite and the cake washed with EtOAc (50 mL). The filtrate was evaporated under vacuum and the residue dissolved in DCM (5 mL). The solution was loaded onto a silica cartridge and purified using a gradient of 0-60% EtOAc in DCM over 10 CVs. The appropriate fractions were combined and the solvent removed by rotary evaporation to give the product as a light brown foam (1.09 g, 2.204 mmol, 50%). LCMS (2 min Formic): Rt=1.10 min, [MH]$^+$=495.

Intermediate 403: rac-1-((2S,3R,4R)-4-amino-2-cyclopropyl-8-methoxy-3-methyl-6-morpholino-3,4-dihydro-1,7-naphthyridin-1(2H)-yl)ethanone

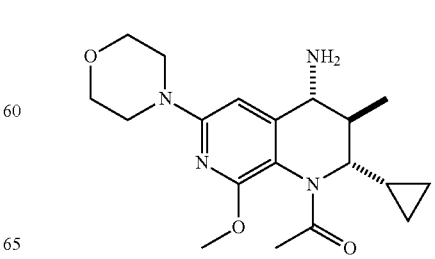

A solution of rac-benzyl ((2S,3R,4R)-1-acetyl-2-cyclopropyl-8-methoxy-3-methyl-6-morpholino-1,2,3,4-tetrahydro-1,7-naphthyridin-4-yl)carbamate (for a preparation see Intermediate 402, 1.05 g, 2.123 mmol) in ethanol (15 mL) was added to 10 wt. % palladium on carbon (dry basis) on activated carbon (wet, Degussa type E101 NE/W) (110 mg, 1.034 mmol) and the mixture stirred under an atmosphere of hydrogen at rt for 16 h. The reaction mixture was filtered through celite and the cake washed with EtOH (80 mL). The filtrate was evaporated in vacuo and the residue dried in a high-vacuum oven to give the product as a yellow solid (746 mg, 2.070 mmol, 97%).

LCMS (2 min HpH): Rt=0.86 min, [MH]$^+$=361.

Intermediate 404: rac-1-((2S,3R,4R)-2-cyclopropyl-8-methoxy-3-methyl-4-((6-methylpyridin-2-yl)amino)-6-morpholino-3,4-dihydro-1,7-naphthyridin-1(2H)-yl)ethanone

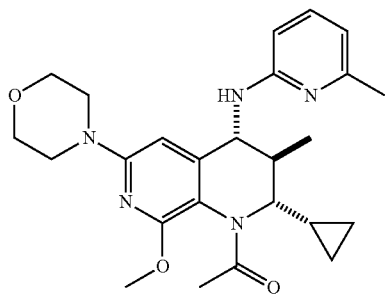 [SMILES: COc1nc(N2CCOCC2)cc2c1N(C(C)=O)[C@@H](C1CC1)[C@H](C)[C@H]2Nc1cccc(C)n1]

A mixture of sodium tert-butoxide (144 mg, 1.494 mmol), Pd$_2$(dba)$_3$ (45.6 mg, 0.050 mmol), Dave Phos (39.2 mg, 0.100 mmol) and rac-1-((2S,3R,4R)-4-amino-2-cyclopropyl-8-methoxy-3-methyl-6-morpholino-3,4-dihydro-1,7-naphthyridin-1(2H)-yl)ethanone (for a preparation see Intermediate 403, 359 mg, 0.996 mmol). The mixture was diluted with anhydrous 1,4-dioxane (5 mL) and treated with 2-bromo-6-methylpyridine (0.136 mL, 1.195 mmol). The vessel was evacuated, purged with nitrogen and stirred under nitrogen at 100° C. for 4 h. The reaction mixture was filtered through celite and the cake washed with EtOAc (40 mL). The filtrate was evaporated under vacuum and the residue dissolved in MeOH (5 mL). The solution was applied to a 20 g SCX-2 cartridge and the cartridge washed with MeOH (120 mL) followed by 2 M NH$_3$ in MeOH (120 mL). The basic wash was evaporated in vacuo, the residue loaded in DCM (4 mL) and purified on a 100 g silica cartridge using a gradient of 0-100% EtOAc (+1% NEt$_3$) in DCM (+1% NEt$_3$) over 10 CVs. The appropriate fractions were combined and the solvent removed by rotary evaporation to give the product (445 mg) as an orange gum. The compound not completely pure but was used as was in further chemistry.

LCMS (2 min Formic): Rt=0.71 min, [MH]$^+$=452.

Intermediate 405: rac-1-((2S,3R,4R)-2-cyclopropyl-8-hydroxy-3-methyl-4-((6-methylpyridin-2-yl)amino)-6-morpholino-3,4-dihydro-1,7-naphthyridin-1(2H)-yl)ethanone

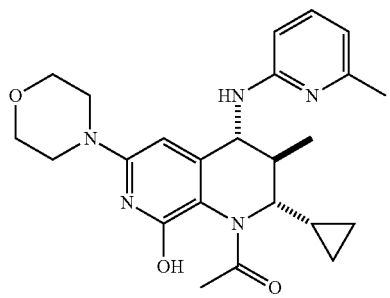 [SMILES: CC(=O)N1c2c(cc(N3CCOCC3)nc2O)[C@H](Nc2cccc(C)n2)[C@@H](C)[C@@H]1C1CC1]

A mixture of rac-1-((2S,3R,4R)-2-cyclopropyl-8-methoxy-3-methyl-4-((6-methylpyridin-2-yl)amino)-6-morpholino-3,4-dihydro-1,7-naphthyridin-1(2H)-yl)ethanone (for a preparation see Intermediate 404, 358 mg, 0.793 mmol) and sodium iodide (713 mg, 4.76 mmol) was diluted with acetonitrile (1 mL) and TMSCl (0.608 mL, 4.76 mmol) was added. The mixture was stirred under nitrogen at 55° C. for 3 h. The reaction solution was allowed to cool rt and evaporated under vacuum. The residue was suspended in EtOAc (25 mL) and washed sequentially with saturated aqueous NaHCO$_3$ (2×25 mL) and water (25 mL). The organic layer was dried through a hydrophobic frit and the solvent removed under vacuum. The residue was loaded in DCM (5 mL) and purified on a 100 g silica cartridge using a gradient of 0-15% MeOH in DCM over 10 CVs. The appropriate fractions were combined and the solvent removed by rotary evaporation to give the product as a dark green glass (84 mg, 0.192 mmol, 24%). LCMS (2 min Formic): Rt=0.48 min, [MH]$^+$=438.

Intermediate 406: rac-(2S,3R,4R)-1-acetyl-2-cyclopropyl-3-methyl-4-((6-methylpyridin-2-yl)amino)-6-morpholino-1,2,3,4-tetrahydro-1,7-naphthyridin-8-yl trifluoromethanesulfonate

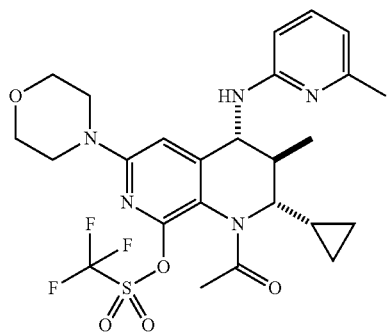 [SMILES: CC(=O)N1c2c(cc(N3CCOCC3)nc2OS(=O)(=O)C(F)(F)F)[C@H](Nc2cccc(C)n2)[C@@H](C)[C@@H]1C1CC1]

A solution of rac-1-((2S,3R,4R)-2-cyclopropyl-8-hydroxy-3-methyl-4-((6-methylpyridin-2-yl)amino)-6-morpholino-3,4-dihydro-1,7-naphthyridin-1(2H)-yl)ethanone (for a preparation see Intermediate 405, 84 mg, 0.192 mmol) in DCM (1 mL) was treated with triethylamine (0.054 mL, 0.384 mmol), DMAP (2 mg, 0.016 mmol) and N-(5-chloropyridin-2-yl)-1,1,1-trifluoro-N-((trifluoromethyl)sulfonyl)methanesulfonamide (94 mg, 0.240 mmol). The mixture was stirred at rt in a stoppered vessel for 64 h. The reaction mixture was diluted with DCM (4 mL) and washed with water (3×5 mL). The organic layer was dried through a hydrophobic frit and concentrated in vacuo. The brown gum was loaded in DCM (2 mL) and purified on a 25 g silica cartridge using a gradient of 0-15% 2M $NH_3$/MeOH in DCM over 10 CVs. The appropriate fractions were combined and the solvent removed by rotary evaporation. The gum was purified by MDAP (HpH). The appropriate fractions were combined and the solvent removed by rotary evaporation to give the product as a purple foam (52 mg, 0.091 mmol, 48%). LCMS (2 min HpH): Rt=1.27 min, $[MH]^+$=570.

Intermediate 407: rac-1-((2S,3R,4R)-2-cyclopropyl-3-methyl-4-((6-methylpyridin-2-yl)amino)-6-morpholino-3,4-dihydro-1,7-naphthyridin-1(2H)-yl)ethanone

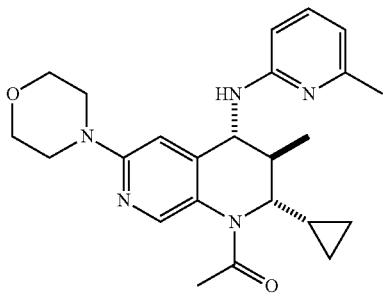 [SMILES: CC(=O)N1c2cnc(N3CCOCC3)cc2[C@H](Nc2cccc(C)n2)[C@@H](C)[C@@H]1C1CC1]

A mixture of rac-(2S,3R,4R)-1-acetyl-2-cyclopropyl-3-methyl-4-((6-methylpyridin-2-yl)amino)-6-morpholino-1,2,3,4-tetrahydro-1,7-naphthyridin-8-yl trifluoromethanesulfonate (for a preparation see Intermediate 406, 50 mg, 0.088 mmol) and Pd(dppf)Cl$_2$ (10 mg, 0.012 mmol) in anhydrous DMF (1 mL) was treated with triethylamine (50 μL, 0.359 mmol) and formic acid (10 μL, 0.261 mmol) and the mixture stirred under nitrogen at 60° C. for 1 h. Further Pd(dppf)Cl$_2$ (10 mg, 0.012 mmol) was added and the mixture stirred under nitrogen at 60° C. for 15 h. Further formic acid (20 μL, 0.522 mmol) was added and the mixture stirred under nitrogen at 100° C. for 5 h. Further formic acid (20 μL, 0.522 mmol) and Pd(dppf)Cl$_2$ (10 mg, 0.012 mmol) was added and the mixture stirred under nitrogen at 100° C. for 15 h. The reaction mixture was allowed to cool to rt and applied directly to a MeOH-preconditioned 2 g SCX-2 cartridge. The cartridge was washed with MeOH (10 mL) followed by 2 M NH$_3$ in MeOH solution (10 mL). The basic wash was concentrated under vacuum and the residue purified by MDAP (HpH). The appropriate fractions were combined and concentrated in vacuo to give the product as an off-white solid (22 mg, 0.052 mmol, 60%).

LCMS (2 min HpH): Rt=1.00 min, $[MH]^+$=422.

Intermediate 408: rac-(2S,3R,4R)-ethyl 1-acetyl-4-(((benzyloxy)carbonyl)amino)-2-cyclopropyl-8-methoxy-3-methyl-1,2,3,4-tetrahydro-1,7-naphthyridine-6-carboxylate

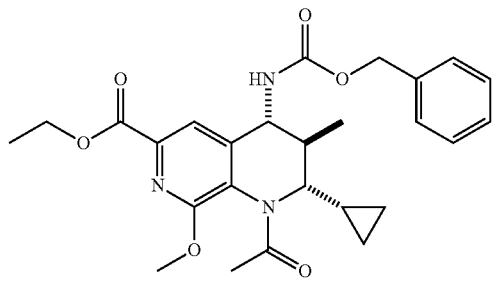 [SMILES: CCOC(=O)c1cc2c(c(OC)n1)N(C(C)=O)[C@@H](C1CC1)[C@H](C)[C@H]2NC(=O)OCc1ccccc1]

A solution of benzyl rac-((2S,3R,4R)-1-acetyl-6-bromo-2-cyclopropyl-8-methoxy-3-methyl-1,2,3,4-tetrahydro-1,7-naphthyridin-4-yl)carbamate (for a preparation see Intermediate 401, 4.96 g, 10.16 mmol), Et$_3$N (14.16 mL, 102 mmol) and Pd(PPh$_3$)$_4$ (2.93 g, 2.54 mmol) in 1,4-dioxane (50 mL) and ethanol (50 mL) was made up in a 3 necked round bottom flask under nitrogen and the flask was purged with carbon monoxide for 1 h at 80° C. The reaction mixture was stirred under an atmosphere of carbon monoxide (balloon filled with carbon monoxide) at 80° C. After 6.5 h the balloon was refilled and reaction mixture was stirred at 80° C. for 17 h. Carbon monoxide was bubbled through the solution for 1 h at 80° C. The reaction mixture was allowed to cool to rt. The reaction mixture was concentrated under reduced pressure, the residue was partitioned between DCM (100 mL) and water (100 mL). The organic layer was dried through hydrophobic frit and concentrated under reduced pressure. The residue (9.8 g) was loaded on 2×100 g silica cartridges, purified by column chromatography, eluting with 10-40% EtOAc in cyclohexane (20 CV). The appropriate fractions were combined and concentrated under reduced pressure to give 2 batches of desired product (1.94 g, 4.03 mmol, 40%) as a colourless oil; (2.06 g, 4.28 mmol, 42%) as a brown solid. LCMS (2 min HpH): Rt=1.14 min, $[MH]^+$=482.

Intermediate 409: rac-(2S,3R,4R)-ethyl 1-acetyl-4-(((benzyloxy)carbonyl)amino)-2-cyclopropyl-8-hydroxy-3-methyl-1,2,3,4-tetrahydro-1,7-naphthyridine-6-carboxylate

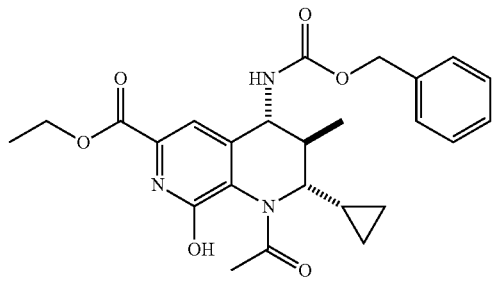 [SMILES: CCOC(=O)c1cc2c(c(O)n1)N(C(C)=O)[C@@H](C1CC1)[C@H](C)[C@H]2NC(=O)OCc1ccccc1]

TMSCl (0.256 mL, 2.014 mmol) and sodium iodide (0.302 g, 2.014 mmol) were added to a solution of rac-(2S,3R,4R)-ethyl 1-acetyl-4-(((benzyloxy)carbonyl)amino)-2- cyclopropyl-8-methoxy-3-methyl-1,2,3,4-tetrahydro-1,7-naphthyridine-6-carboxylate (for a preparation see Intermediate 408, 1.94 g, 4.03 mmol) in acetonitrile (50 mL). After stirring at rt for 6 h the reaction mixture was concentrated under reduced pressure. The residue was taken up in EtOAc (100 mL), quenched with a saturated solution of sodium bicarbonate (100 mL). The organic layer was separated and the aqueous layer was extracted with EtOAc (100 mL). The combined organic layer was dried through hydrophobic frit and concentrated under reduced pressure. The residue (2.05 g) was loaded on a 100 g silica cartridge, purified by column chromatography, eluting with 0-10% MeOH in DCM (20 CV). The appropriate fractions were combined and concentrated under reduced pressure to give the required product (1.6 g) as a colourless oil. LCMS (2 min HpH): Rt=0.93 min, [MH]$^+$=468.

Intermediate 410: rac-(2S,3R,4R)-ethyl 1-acetyl-4-(((benzyloxy)carbonyl)amino)-2-cyclopropyl-3-methyl-8-(((trifluoromethyl)sulfonyl)oxy)-1,2,3,4-tetrahydro-1,7-naphthyridine-6-carboxylate

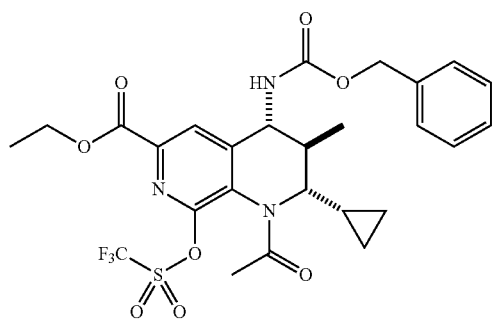 [SMILES: CCOC(=O)c1cc2c(c(OS(=O)(=O)C(F)(F)F)n1)N(C(C)=O)[C@@H](C1CC1)[C@H](C)[C@H]2NC(=O)OCc1ccccc1]

A solution of rac-(2S,3R,4R)-ethyl 1-acetyl-4-(((benzyloxy)carbonyl)amino)-2-cyclopropyl-8-hydroxy-3-methyl-1,2,3,4-tetrahydro-1,7-naphthyridine-6-carboxylate (for a preparation see Intermediate 409, 1.6 g, 3.42 mmol) in DCM (50 mL) was cooled with an ice bath. Triethylamine (0.954 mL, 6.84 mmol), DMAP (0.084 g, 0.684 mmol) and N-(5-chloropyridin-2-yl)-1,1,1-trifluoro-N-((trifluoromethyl)sulfonyl)methanesulfonamide (1.680 g, 4.28 mmol) were added. The mixture was stirred at rt under nitrogen for 18 h. Triethylamine (0.954 mL, 6.84 mmol), DMAP (0.084 g, 0.684 mmol) and N-(5-chloropyridin-2-yl)-1,1,1-trifluoro-N-((trifluoromethyl)sulfonyl)methanesulfonamide (1.680 g, 4.28 mmol) were added. After stirring for 1 h. the reaction mixture was diluted with DCM (50 mL) and washed with water (2×100 mL). The organic layer was dried through a hydrophobic frit and concentrated in vacuo. The residue was loaded in DCM on a 100 g silica cartridge and eluted using a gradient of 10-60% EtOAc in cyclohexane (15 CV). The appropriate fractions were combined and concentrated under reduced pressure to give the required product (1.69 g) as a yellow oil.

LCMS (2 min HpH): Rt=1.30 min, [MH]$^+$=600.

Intermediate 411: rac-(2S,3R,4R)-ethyl 1-acetyl-4-amino-2-cyclopropyl-3-methyl-1,2,3,4-tetrahydro-1,7-naphthyridine-6-carboxylate

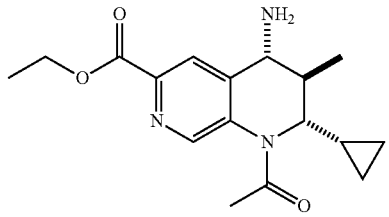 [SMILES: CCOC(=O)c1cc2c(cn1)N(C(C)=O)[C@@H](C1CC1)[C@H](C)[C@H]2N]

A solution of rac-(2S,3R,4R)-ethyl 1-acetyl-4-(((benzyloxy)carbonyl)amino)-2-cyclopropyl-3-methyl-8-(((trifluoromethyl)sulfonyl)oxy)-1,2,3,4-tetrahydro-1,7-naphthyridine-6-carboxylate (for a preparation see Intermediate 410, 600 mg, 1.001 mmol) and Pd/C (368 mg, 3.46 mmol) in ethanol (30 mL) was hydrogenated at rt. After 20 h of stirring at rt, the reaction mixture was filtered through celite and concentrated under reduced pressure. The residue (474 mg) was loaded on a 50 g silica column in MeOH/DCM 1:3 which was then dried in the vacuum oven for 20 min. The purification was carried out by column chromatography, eluting with 0-5% methanolic ammonia (2M) in DCM (15 CV). The appropriate fractions were combined and concentrated under reduced pressure to give the required product (153 mg) as a yellow oil. LCMS (2 min HpH): Rt=0.70 min, [MH]$^+$=318.

Intermediate 412: rac-(2S,3R,4R)-ethyl 1-acetyl-2-cyclopropyl-3-methyl-4-(pyrimidin-2-ylamino)-1,2,3,4-tetrahydro-1,7-naphthyridine-6-carboxylate

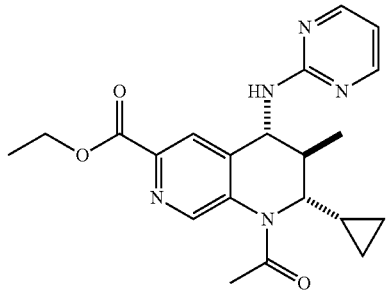 [SMILES: CCOC(=O)c1cc2c(cn1)N(C(C)=O)[C@@H](C1CC1)[C@H](C)[C@H]2Nc1ncccn1]

DIPEA (0.080 mL, 0.457 mmol) and 2-fluoropyrimidine (49.3 mg, 0.503 mmol) were added to a solution of rac-(2S,3R,4R)-ethyl 1-acetyl-4-amino-2-cyclopropyl-3-methyl-1,2,3,4-tetrahydro-1,7-naphthyridine-6-carboxylate (for a preparation see Intermediate 411, 145 mg, 0.457 mmol) in dimethyl sulfoxide (DMSO) (0.2 mL) in a microwave vessel. The vessel was sealed and heated at 120° C. for 19 h. The reaction mixture was partitioned between EtOAc (40 mL) and water (40 mL). The organic layer was further washed with water (40 mL) and brine (2×40 mL). The organic layer was dried through a hydrophobic frit and concentrated under reduced pressure. The residue (164 mg) was loaded on a 25 g silica column, purified by column chromatography, eluting with a gradient of 0-8% MeOH in DCM (15 CV). The appropriate fractions were combined and evaporated in vacuo to give the required product (124 mg) as a yellow oil. LCMS (2 min HpH): Rt=0.84 min, [MH]⁺=396.

Intermediate 413: rac-(2S,3R,4R)-1-acetyl-2-cyclopropyl-3-methyl-4-(pyrimidin-2-ylamino)-1,2,3,4-tetrahydro-1,7-naphthyridine-6-carboxylic Acid

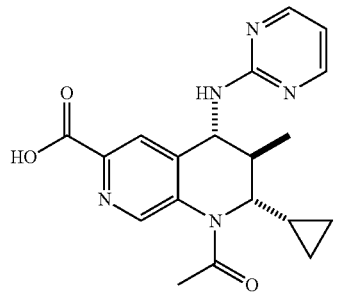 [SMILES: CC(=O)N1c2cnc(C(=O)O)cc2[C@H](Nc2ncccn2)[C@@H](C)[C@@H]1C1CC1]

Lithium hydroxide.H₂O (26 mg, 0.620 mmol) was added to a solution of rac-(2S,3R,4R)-ethyl 1-acetyl-2-cyclopropyl-3-methyl-4-(pyrimidin-2-ylamino)-1,2,3,4-tetrahydro-1,7-naphthyridine-6-carboxylate (for a preparation see Intermediate 412, 120 mg, 0.303 mmol) in a mixture of tetrahydrofuran (THF) (3 mL) and water (1 mL). After stirring at rt for 5 h the reaction mixture was concentrated under reduced pressure. The residue was taken up in water (20 mL), cooled with an ice bath and acidified with aqueous HCl (0.310 mL, 0.620 mmol). The aqueous solution was extracted with EtOAc (2×20 mL) and 20% MeOH in DCM (2×50 mL). The organic layers were combined, dried through hydrophobic frit and concentrated under reduced pressure to give the required product (97 mg) as a yellow solid. LCMS (2 min Formic): Rt=0.61 min, [MH]⁺=368.

Intermediate 414: rac-benzyl ((2S,3S,4R)-2-cyclopropyl-5-methoxy-3-methyl-1,2,3,4-tetrahydro-1,6-naphthyridin-4-yl)carbamate & benzyl ((2S,3S,4R)-2-cyclopropyl-7-methoxy-3-methyl-1,2,3,4-tetrahydro-1,6-naphthyridin-4-yl)carbamate (~1:1)

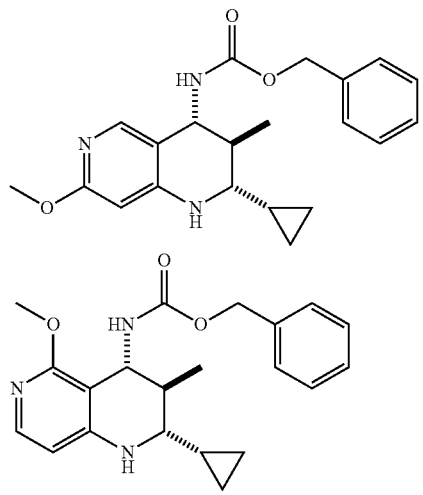

The 2-methoxypyridin-4-amine (1 g, 8.06 mmol) was taken up in tetrahydrofuran (THF) (10 mL) and was treated with cyclopropanecarbaldehyde (0.721 mL, 9.67 mmol) and allowed to stir at rt for 1 h. (E)-benzyl prop-1-en-1-ylcarbamate (for a preparation see Intermediate 1, 1.694 g, 8.86 mmol) and ytterbium(III) trifluoromethanesulfonate (2.498 g, 4.03 mmol) were added and the reaction allowed to stir at 65° C. for ~24 h. The reaction was allowed to cool and was concentrated and partitioned between water and EtOAc, the organic layer was washed with NaHCO₃ (aq), dried using a hydrophobic frit and concentrated to a gum. This gum was purified using a 100 g column elute 0-50% EtOAc:cyclohexane the appropriate fractions were summed and concentrated to give what was believed to be a mixture of the title compounds (1.855 g, 2.52 mmol, 31%) as a white solid.

LCMS (2 min Formic): Rt=0.81, 0.83 min, [MH]⁺=368.

Intermediate 415: rac-benzyl ((2S,3R,4R)-1-acetyl-2-cyclopropyl-5-methoxy-3-methyl-1,2,3,4-tetrahydro-1,6-naphthyridin-4-yl)carbamate & benzyl ((2S,3R,4R)-1-acetyl-2-cyclopropyl-7-methoxy-3-methyl-1,2,3,4-tetrahydro-1,6-naphthyridin-4-yl)carbamate (~1:1)

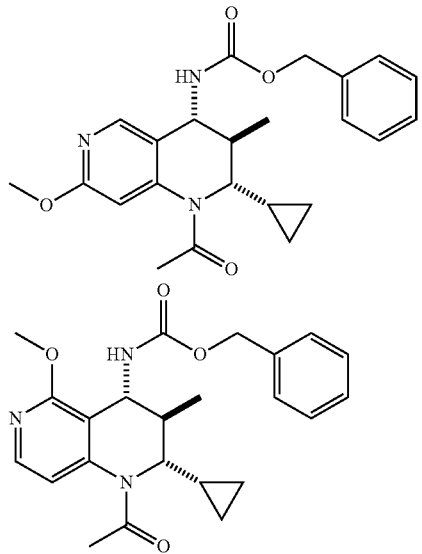

The rac-benzyl ((2S,3S,4R)-2-cyclopropyl-5-methoxy-3-methyl-1,2,3,4-tetrahydro-1,6-naphthyridin-4-yl)carbamate & benzyl ((2S,3S,4R)-2-cyclopropyl-7-methoxy-3-methyl-1,2,3,4-tetrahydro-1,6-naphthyridin-4-yl)carbamate (~1:1) (for a preparation see Intermediate 414, 1.855 g, 2.52 mmol) was taken up in acetic anhydride (20 ml, 212 mmol) and allowed to stir at 50° C. for 16 h. The reaction was allowed to stir at 100° C. for 3 h. The reaction was allowed to stir at 120° C. for 6 h. The reaction was allowed to stir at 80° C. overnight and then at 110° C. for 5 h. The reaction was allowed to cool to rt and was concentrated and purified using a 50 g silica column elute 0-50% EtOAc:cyclohexane. The appropriate fractions were summed and concentrated to give what was believed to be a mixture of the title compounds (1.512 g, 1.846 mmol, 73%) as a yellow solid.

LCMS (2 min Formic): Rt=1.06 min, [MH]⁺=410.

Intermediate 416: rac-1-((2S,3R,4R)-4-amino-2-cyclopropyl-5-methoxy-3-methyl-3,4-dihydro-1,6-naphthyridin-1(2H)-yl)ethanone & 1-((2S,3R,4R)-4-amino-2-cyclopropyl-7-methoxy-3-methyl-3,4-dihydro-1,6-naphthyridin-1(2H)-yl)ethanone (~1:1)

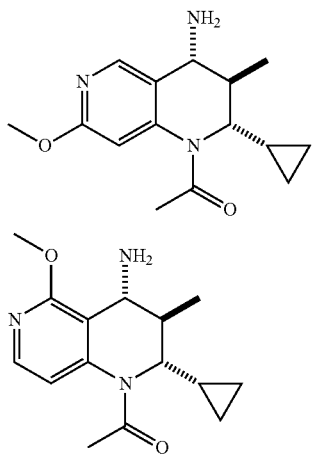

The rac-benzyl ((2S,3R,4R)-1-acetyl-2-cyclopropyl-5-methoxy-3-methyl-1,2,3,4-tetrahydro-1,6-naphthyridin-4-yl)carbamate & benzyl ((2S,3R,4R)-1-acetyl-2-cyclopropyl-7-methoxy-3-methyl-1,2,3,4-tetrahydro-1,6-naphthyridin-4-yl)carbamate (~1:1) (for a preparation see Intermediate 415, 1.5 g, 1.832 mmol) was taken up in ethanol (20 mL) and treated with 10% Pd/C (150 mg, 1.410 mmol) and allowed to stir under a atmosphere of hydrogen for 3 h. The reaction was filtered through celite to remove catalyst and was concentrated to a yellow gum. This gum was purified using a 50 g silica column elute 0-10% 2M NH$_3$/MeOH:DCM, the appropriate fractions were summed and concentrated to give what was believed to be a mixture of the title compounds (685 mg, 1.244 mmol, 68%) as a yellow gum. LCMS (2 min Formic): Rt=0.47 & 0.57 min, [MH]$^+$=276.

Intermediate 417: rac-1-((2S,3R,4R)-2-cyclopropyl-5-methoxy-3-methyl-4-((4-methylpyrimidin-2-yl)amino)-3,4-dihydro-1,6-naphthyridin-1(2H)-yl)ethanone & 1-((2S,3R,4R)-2-cyclopropyl-7-methoxy-3-methyl-4-((4-methylpyrimidin-2-yl)amino)-3,4-dihydro-1,6-naphthyridin-1(2H)-yl)ethanone (~1:1)

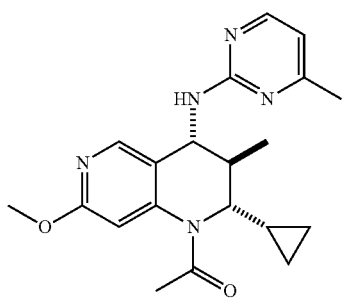

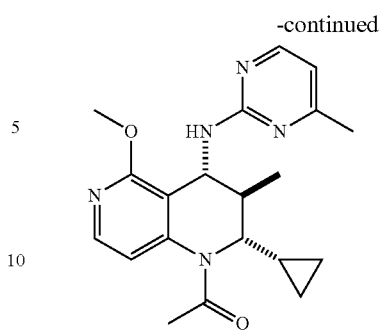

The rac-1-((2S,3R,4R)-4-amino-2-cyclopropyl-5-methoxy-3-methyl-3,4-dihydro-1,6-naphthyridin-1(2H)-yl)ethanone & 1-((2S,3R,4R)-4-amino-2-cyclopropyl-7-methoxy-3-methyl-3,4-dihydro-1,6-naphthyridin-1(2H)-yl)ethanone (~1:1) (for a preparation see Intermediate 416, 675 mg, 1.226 mmol), 2-chloro-4-methylpyrimidine (189 mg, 1.471 mmol), 18-crown-6 (162 mg, 0.613 mmol), potassium fluoride (107 mg, 1.839 mmol), DIPEA (0.364 mL, 2.084 mmol) and dimethyl sulfoxide (DMSO) (20 mL) were all placed in a microwaveable vial and irradiated at 160° C. for 4 h. The reaction was treated with further 2-chloro-4-methylpyrimidine (60 mg, 0.467 mmol) and irradiated in microwave at 160° C. for 1 h. The reaction was diluted with water and extracted with EtOAc (x2) the combined organics were washed with 10% LiCl(aq) and dried using a hydrophobic frit and concentrated to a gum. This gum was purified using a 25 g silica column, elute 0-100% EtOAc:cyclohexane, the appropriate fractions were summed, concentrated and dried to give what was believed to be a mixture of the title compounds (420 mg, 0.572 mmol, 47%) as a buff solid.

LCMS (2 min Formic): Rt=0.77 & 0.80 min, [MH]$^+$=368.

Intermediate 418: rac-1-((2S,3R,4R)-2-cyclopropyl-5-hydroxy-3-methyl-4-((4-methylpyrimidin-2-yl)amino)-3,4-dihydro-1,6-naphthyridin-1(2H)-yl)ethanone & 1-((2S,3R,4R)-2-cyclopropyl-7-hydroxy-3-methyl-4-((4-methylpyrimidin-2-yl)amino)-3,4-dihydro-1,6-naphthyridin-1(2H)-yl)ethanone (~1:1)

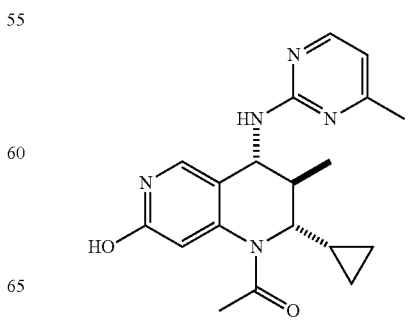

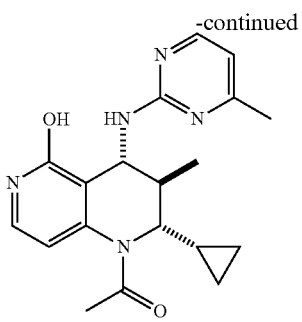

The rac-1-((2S,3R,4R)-2-cyclopropyl-5-methoxy-3-methyl-4-((4-methylpyrimidin-2-yl)amino)-3,4-dihydro-1,6-naphthyridin-1(2H)-yl)ethanone & 1-((2S,3R,4R)-2-cyclopropyl-7-methoxy-3-methyl-4-((4-methylpyrimidin-2-yl)amino)-3,4-dihydro-1,6-naphthyridin-1(2H)-yl)ethanone (1:1) (for a preparation see Intermediate 417, 420 mg, 0.572 mmol) was suspended in acetonitrile (5 mL) and was treated with sodium iodide (514 mg, 3.43 mmol) followed by TMSCl (0.438 mL, 3.43 mmol), the resulting suspension was allowed to stir at 55° C. for 2 h. The reaction was concentrated and partitioned between water and EtOAc, the organic layer was separated and the aqueous phase extracted with further EtOAc, the combined organics were washed with NaHCO₃ (aq), dried using a hydrophobic frit and concentrated to a yellow solid. This solid was purified using a 25 g silica column elute: 0-15% MeOH:DCM. The appropriate fractions were summed and concentrated to give what was believed to be a mixture of the title compounds (213 mg, 0.301 mmol, 53%) as an orange glass.

LCMS (2 min Formic): Rt=0.58 & 0.59 min, [MH]⁺=354.

Intermediate 419: rac-(2S,3R,4R)-1-acetyl-2-cyclopropyl-3-methyl-4-((4-methylpyrimidin-2-yl)amino)-1,2,3,4-tetrahydro-1,6-naphthyridin-5-yl trifluoromethanesulfonate & (2S,3R,4R)-1-acetyl-2-cyclopropyl-3-methyl-4-((4-methylpyrimidin-2-yl)amino)-1,2,3,4-tetrahydro-1,6-naphthyridin-7-yl trifluoromethanesulfonate (~1:1)

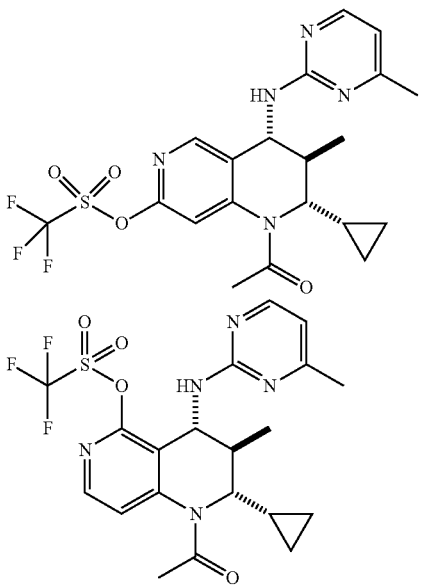

The rac-1-((2S,3R,4R)-2-cyclopropyl-5-hydroxy-3-methyl-4-((4-methylpyrimidin-2-yl)amino)-3,4-dihydro-1,6-naphthyridin-1(2H)-yl)ethanone & 1-((2S,3R,4R)-2-cyclopropyl-7-hydroxy-3-methyl-4-((4-methylpyrimidin-2-yl)amino)-3,4-dihydro-1,6-naphthyridin-1(2H)-yl)ethanone (~1:1) (for a preparation see Intermediate 418, 210 mg, 0.297 mmol) was taken up in dichloromethane (DCM) (5 mL) and was treated with triethylamine (0.083 mL, 0.594 mmol), DMAP (3.63 mg, 0.030 mmol) and N-(5-chloropyridin-2-yl)-1,1,1-trifluoro-N-((trifluoromethyl)sulfonyl)methanesulfonamide (152 mg, 0.386 mmol) and allowed to stir at rt under nitrogen for 20 h. The reaction was treated with further N-(5-chloropyridin-2-yl)-1,1,1-trifluoro-N-((trifluoromethyl)sulfonyl)methanesulfonamide (58.3 mg, 0.149 mmol) and allowed to stir at rt for 24 h. The reaction was treated with further N-(5-chloropyridin-2-yl)-1,1,1-trifluoro-N-((trifluoromethyl)sulfonyl)methanesulfonamide (58.3 mg, 0.149 mmol) and triethylamine (0.041 mL, 0.297 mmol) and allowed to stir at rt for 3 h. The reaction was diluted with DCM and washed with water, the organic phase was dried through a hydrophobic frit and concentrated to a gum. This gum was purified using a 25 g silica column elute: 0-100% EtOAc:cyclohexane, the appropriate fractions were summed and concentrated to give 271 mg of a yellow solid, This was further purified using a MDAP (HpH). The appropriate fractions were summed and concentrated and dried to give what was believed to be a mixture of the title compounds (133 mg, 0.137 mmol, 46%) yellow solid. LCMS (2 min Formic): Rt=1.11 & 1.13 min, [MH]⁺=486.

Intermediate 420: rac-benzyl ((2S,3R,4R)-2-cyclopropyl-3-methyl-1,2,3,4-tetrahydroquinolin-4-yl)carbamate

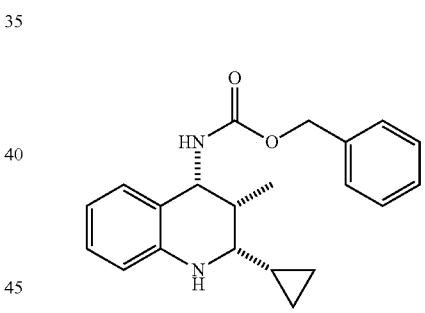

Cyclopropanecarboxaldehyde (0.080 ml, 1.074 mmol) was added to a stirred solution of aniline (0.098 ml, 1.074 mmol) in toluene (8 mL) under N₂, over 3 A molecular sieves (1.0 g) at rt for 3 h and cooled in a cyclohexane:dry ice bath. The reaction mixture was allowed to warm to room temperature overnight and cooled in an acetone:dry ice bath. (Z)-benzyl prop-1-en-1-ylcarbamate (for a preparation see JACS, 2013, 135, 16010, 0.246 g, 1.289 mmol) dissolved in toluene (1 mL) was added, followed by BF₃.OEt₂ (0.136 ml, 1.074 mmol) and the cold bath removed. The reaction mixture was stirred for 1 h. The reaction mixture was partitioned between DCM and water. The organic layer was removed, the aqueous portion extracted with DCM, the organic portions combined, dried over MgSO₄ and evaporated in vacuo to a brown oil. The residue was dissolved in DCM (10 mL) and cyclohexane (10 mL) added. The resulting suspension was loaded on to a 25 g silica column and eluted with cyclohexane:DCM (25-100%). The first eluting fractions contained impure desired product. The following fractions contained the rac-(2S,3S,4R) isomer (47 mg). The final eluting product was impure rac-(2S,3R,4S) isomer (45 mg). The impure desired material was purified by MDAP (TFA). Evaporation of the desired fraction gave the product as a pale green solid (150 mg). LCMS (2 min TFA): Rt=1.03 min, [MH]⁺=337.

Intermediate 421: rac-benzyl ((2S,3S,4R)-1-acetyl-2-cyclopropyl-3-methyl-1,2,3,4-tetrahydroquinolin-4-yl)carbamate

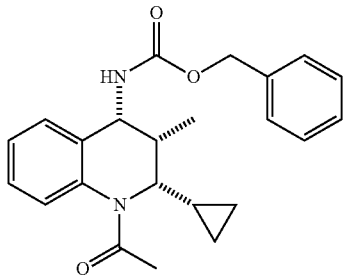 [SMILES: CC(=O)N1c2ccccc2[C@H](NC(=O)OCc2ccccc2)[C@H](C)[C@@H]1C1CC1]

Acetyl chloride (0.063 mL, 0.892 mmol) was added to a stirred solution of pyridine (0.108 mL, 1.338 mmol) and rac-benzyl ((2S,3R,4R)-2-cyclopropyl-3-methyl-1,2,3,4-tetrahydroquinolin-4-yl)carbamate (for a preparation see Intermediate 420, 150 mg, 0.446 mmol) in dichloromethane (DCM) (5 mL) under N₂. The resulting solution was stirred for 2.5 h. The reaction mixture was partitioned between EtOAc and aq. sat. NaHCO₃. The aqueous layer was removed, the organic layer washed (1× aq. sat. NaHCO₃, 1× brine), dried over MgSO₄ and evaporated in vacuo to a green gum. The residue was dissolved in DCM, loaded on to a 10 g silica column and eluted with cyclohexane:EtOAc (5-33%). The product containing fractions were evaporated in vacuo to a colourless gum (95 mg).

LCMS (2 min TFA): Rt=1.11 min, [MH]⁺=379.

Intermediate 422: rac-1-((2S,3S,4R)-4-amino-2-cyclopropyl-3-methyl-3,4-dihydroquinolin-1(2H)-yl)ethanone

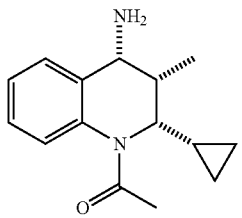 [SMILES: CC(=O)N1c2ccccc2[C@H](N)[C@H](C)[C@@H]1C1CC1]

A suspension of rac-benzyl ((2S,3S,4R)-1-acetyl-2-cyclopropyl-3-methyl-1,2,3,4-tetrahydroquinolin-4-yl)carbamate (for a preparation see Intermediate 421, 95 mg, 0.251 mmol) and 10% Pd/C (26.7 mg, 0.025 mmol) was stirred in ethanol (6 mL) under hydrogen for 5 h. The resulting suspension was filtered through celite and evaporated in vacuo to a colourless oil (58 mg).

LCMS (2 min TFA): Rt=0.56 min, [M–NH₂]⁺=228.

Example 1: rac-1-((2S,3R,4R)-2,3-dimethyl-4-(phenylamino)-3,4-dihydroquinolin-1(2H)-yl)ethanone

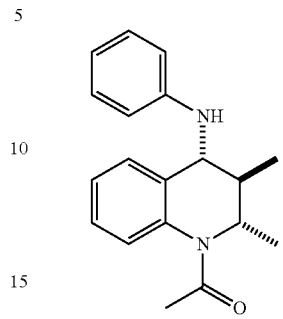

Under nitrogen atmosphere, to a solution of bromobenzene (0.04 mL, 0.380 mmol) in 1,4-dioxane (3 mL) were added rac-1-((2S,3R,4R)-4-amino-2,3-dimethyl-3,4-dihydroquinolin-1(2H)-yl)ethanone (for a preparation see Intermediate 6, 69 mg, 0.317 mmol), DavePhos (12 mg, 0.032 mmol), tris(dibenzylideneacetone)dipalladium(0) (14 mg, 0.016 mmol) and sodium tert-butoxide (46 mg, 0.475 mmol). The reaction was degassed with nitrogen for 10 min. Using a microwave reactor the solution was stirred and irradiated with microwaves so as to maintain a temperature of 110° C. for 30 min. The solution was transferred into another 2-5 mL microwave vial via syringe, bromobenzene (0.04 mL, 0.380 mmol), tris(dibenzylideneacetone)dipalladium(0) (14 mg, 0.016 mmol), DavePhos (12 mg, 0.032 mmol) and sodium tert-butoxide (46 mg, 0.475 mmol) were added, the reaction mixture was degassed with nitrogen for 10 min, then stirred and irradiated with microwaves so as to maintain a temperature of 110° C. for 30 min. After cooling to rt, the reaction mixture was filtered through a pad of celite (rinsed with EtOAc). The filtrate was then evaporated in vacuo. The residue was loaded onto a 25 g silica cartridge and purified by column chromatography using a gradient of 0-40% ethyl acetate in cyclohexane. Desired fractions were combined and evaporated in vacuo to afford the product as a yellow solid (26 mg).

LCMS (2 min Formic): Rt=1.11 min, [MH]⁺=295.

Example 2: rac-1-((2S,3R,4R)-2,3-dimethyl-4-((6-methylpyridin-2-yl)amino)-3,4-dihydroquinolin-1(2H)-yl)ethanone

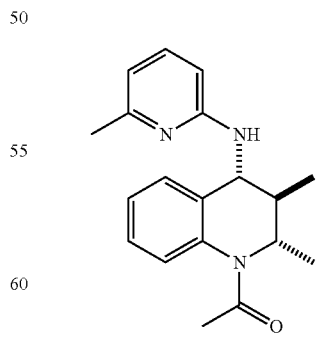

To a test tube were added rac-1-((2S,3R,4R)-4-amino-2,3-dimethyl-3,4-dihydroquinolin-1(2H)-yl)ethanone (for a preparation see Intermediate 6, 44 mg, 0.20 mmol), 2-chloro-6-methylpyridine (0.02 mL, 0.24 mmol), tris Example 3: rac-1-((2S,3R,4R)-4-((6-methoxypyridin-2-yl)amino)-2,3-dimethyl-3,4-dihydroquinolin-1(2H)-yl)ethanone (dibenzylideneacetone)dipalladium(0) (9 mg, 9.99 μmol), sodium tert-butoxide (29 mg, 0.30 mmol), DavePhos (8 mg, 0.02 mmol) and 1,4-dioxane (2.5 mL). The reaction mixture was then heated and stirred at 100° C. in a greenhouse reactor for 3 h. After cooling to rt, the reaction mixture was filtered through a pad of celite (rinsed with EtOAc). The filtrate was then evaporated in vacuo. The residue was purified by MDAP (Formic) chromatography. Desired fractions were combined and evaporated under vacuum to afford a colourless solid. This solid was not pure enough so it was purified again by MDAP (Formic) chromatography. Desired fractions were combined and evaporated under vacuum to afford the product as a colourless solid (38 mg).

LCMS (2 min Formic): Rt=0.59 min, [MH]⁺=310.

Example 3: rac-1-((2S,3R,4R)-4-((6-methoxypyridin-2-yl)amino)-2,3-dimethyl-3,4-dihydroquinolin-1(2H)-yl)ethanone

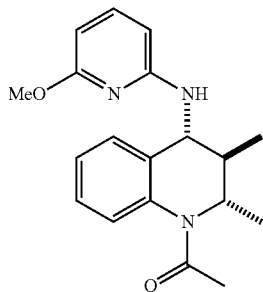 [SMILES: COc1cccc(N[C@H]2c3ccccc3N(C(C)=O)[C@@H](C)[C@@H]2C)n1]

To a greenhouse test tube was added rac-1-((2S,3R,4R)-4-amino-2,3-dimethyl-3,4-dihydroquinolin-1(2H)-yl)ethanone (for a preparation see Intermediate 6, 52.0 mg, 0.238 mmol), Pd₂(dba)₃ (21.8 mg, 0.024 mmol), DavePhos (5.6 mg, 0.014 mmol), sodium tert-butoxide (67.4 mg, 0.701 mmol), 1,4-dioxane (2 mL) and 2-bromo-6-methoxypyridine (0.028 mL, 0.228 mmol). The reaction mixture was stirred at 100° C. under nitrogen for 16 h. The reaction mixture was allowed to cool to rt, then filtered through a celite cartridge, washing with ethyl acetate. The filtrate was evaporated under a stream of nitrogen and the residue dissolved in methanol (1 mL). The dissolved material was purified by MDAP (Formic). The required fractions were evaporated under a stream of nitrogen to give the required product as a beige solid (22.8 mg, 0.070 mmol, 29.4%).

LCMS (2 min formic): Rt=0.99 min, MH⁺=326.

Example 4: rac-1-((2S,3R,4R)-4-(imidazol[,2-a]pyridin-8-ylamino)-2,3-dimethyl-3,4-dihydroquinolin-1(2H)-yl)ethanone

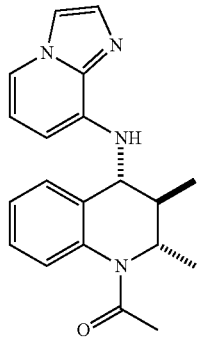 [SMILES: CC(=O)N1c2ccccc2[C@H](Nc2cccn3ccnc23)[C@@H](C)[C@@H]1C]

To a 0.5-2 mL microwave vial was added rac-1-(2S,3R,4R)-4-amino-2,3-dimethyl-3,4-dihydroquinolin-1(2H)-yl)ethanone (for a preparation see Intermediate 6, 40 mg, 0.183 mmol), DavePhos (7 mg, 0.018 mmol), Pd₂(dba)₃ (17 mg, 0.019 mmol), sodium tert-butoxide (26.4 mg, 0.275 mmol) and 8-bromoimidazo[1,2-a]pyridine (46 mg, 0.233 mmol). The mixture was suspended in anhydrous 1,4-dioxane (1 mL). The reaction vessel was sealed and the vial was evacuated then backfilled with nitrogen twice. The reaction mixture was heated in a microwave at 110° C. for 30 min. The reaction mixture was filtered through a layer of celite, washing through with EtOAc. The solvent was removed by rotary evaporation and the residue was dissolved in anhydrous 1,4-dioxane (1 mL) then transferred to a 0.5-2 mL microwave vial containing a mixture of DavePhos (7 mg, 0.018 mmol), Pd₂(dba)₃ (17 mg, 0.019 mmol), sodium tert-butoxide (26.4 mg, 0.275 mmol) and 8-bromoimidazo[1,2-a]pyridine (46 mg, 0.233 mmol). The reaction vessel was sealed and the solution was bubbled with nitrogen for 10 min. The reaction mixture was heated in a microwave at 110° C. for 30 min. The reaction mixture was filtered through a celite cartridge, washing through with EtOAc. The solvent was removed by rotary evaporation and the residue was purified by MDAP (Formic). The appropriate fractions were combined and the solvent was removed by rotary evaporation to give the desired product as a light brown solid (5 mg, 0.015 mmol, 8.16%).

LCMS (2 min Formic): Rt=0.62 min, [MH]⁺=335.

Example 5: rac-1-((2S,3R,4R)-4-((3-methoxyphenyl)amino)-2,3-dimethyl-3,4-dihydroquinolin-1(2H)-yl)ethanone

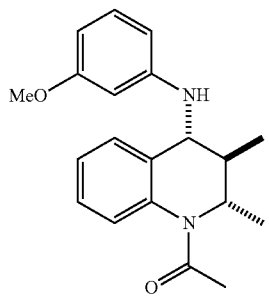 [SMILES: COc1cccc(N[C@H]2c3ccccc3N(C(C)=O)[C@@H](C)[C@@H]2C)c1]

To a test tube was added rac-1-((2S,3R,4R)-4-amino-2,3-dimethyl-3,4-dihydroquinolin-1(2H)-yl)ethanone (for a preparation see Intermediate 6, 35 mg, 0.160 mmol), DavePhos (7 mg, 0.018 mmol), Pd$_2$(dba)$_3$ (17 mg, 0.019 mmol) and sodium tert-butoxide (25 mg, 0.260 mmol). The mixture was suspended in anhydrous 1,4-dioxane (2 mL) and to the suspension was added 1-bromo-3-methoxybenzene (24 μL, 0.190 mmol). The reaction mixture was heated in a greenhouse reactor at 100° C. for 2 h under an atmosphere of nitrogen. The reaction mixture was allowed to cool, then was filtered through a celite cartridge, washing through with EtOAc. The solvent was removed by rotary evaporation and the residue was dissolved in DMSO:MeOH (1:1) and purified by MDAP (Formic). The appropriate fractions were combined and the solvent was removed by rotary evaporation to give the desired product as a light yellow foam (30 mg, 0.092 mmol, 57.7%).

LCMS (2 min Formic): Rt=1.08 min, [MH]$^+$=325.

Example 6: rac-1-((2S,3R,4R)-2,3-dimethyl-4-((3-morpholinophenyl)amino)-3,4-dihydroquinolin-1(2H)-yl)ethanone

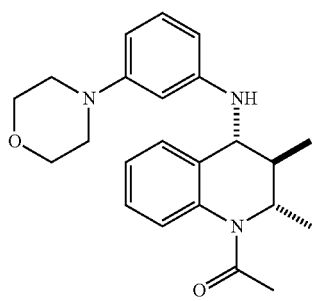 [SMILES: CC(=O)N1c2ccccc2[C@H](Nc2cccc(N3CCOCC3)c2)[C@@H](C)[C@@H]1C]

To a test tube were added rac-1-((2S,3R,4R)-4-amino-2,3-dimethyl-3,4-dihydroquinolin-1(2H)-yl)ethanone (for a preparation see Intermediate 6, 51 mg, 0.234 mmol), 4-(3-bromophenyl)morpholine (67.9 mg, 0.280 mmol), Pd$_2$(dba)$_3$ (10.70 mg, 0.012 mmol), sodium tert-butoxide (33.7 mg, 0.350 mmol), BrettPhos (12.54 mg, 0.023 mmol) and 1,4-dioxane (2.5 mL). The reaction mixture was then heated and stirred at 100° C. in a greenhouse reactor for 1 h. After cooling to rt, the reaction mixture was filtered through a pad of celite (rinsed with EtOAc). The filtrate was then evaporated in vacuo. The residue was purified by MDAP (Formic). The desired fractions were combined and evaporated in vacuo to afford the desired product as a brown solid (42.5 mg).

LCMS (2 min Formic): Rt=0.97 min, [MH]$^+$=380.5

Example 7: rac-1-((2S,3R,4R)-2,3-dimethyl-4-(quinolin-5-ylamino)-3,4-dihydroquinolin-1(2H)-yl)ethanone, Formic Acid Salt

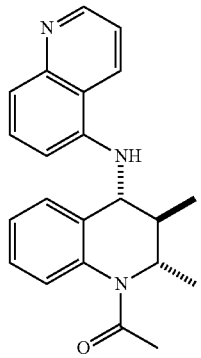 [SMILES: CC(=O)N1c2ccccc2[C@H](Nc2cccc3ncccc23)[C@@H](C)[C@@H]1C]

To a 0.5-2 mL microwave vial was added rac-1-((2S,3R,4R)-4-amino-2,3-dimethyl-3,4-dihydroquinolin-1(2H)-yl)ethanone (for a preparation see Intermediate 6, 40 mg, 0.183 mmol), DavePhos (7 mg, 0.018 mmol), Pd$_2$(dba)$_3$ (17 mg, 0.019 mmol), sodium tert-butoxide (26 mg, 0.271 mmol) and 5-bromoquinoline (46 mg, 0.221 mmol). The mixture was suspended in anhydrous 1,4-dioxane (1 mL). The reaction vessel was sealed and the solution was bubbled with nitrogen for 10 min. The reaction mixture was heated in microwave at 110° C. for 30 min. After cooling, the reaction mixture was filtered through a celite cartridge, washing through with EtOAc. The solvent was removed by rotary evaporation, leaving a residue which was subsequently dissolved in DMSO:MeOH (1:1), then purified by MDAP (Formic). The appropriate fractions were combined and the solvent was removed by rotary evaporation. A 10% impurity remained and so the residue (32 mg) was dissolved in DMSO:MeOH (1:1) then re-purified by MDAP (Formic). The appropriate fractions were combined and the solvent was removed by rotary evaporation to give the desired product as an orange solid (23 mg, 0.059 mmol, 32.1%). LCMS (2 min Formic): Rt=0.66 min, [MH]$^+$=346.

Example 8: rac-1-((2S,3R,4R)-2,3-dimethyl-4-((3-(piperazin-1-yl)phenyl)amino)-3,4-dihydroquinolin-1(2H)-yl)ethanone, Formic Acid Salt

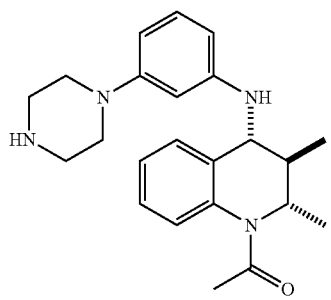 [SMILES: CC(=O)N1c2ccccc2[C@H](Nc2cccc(N3CCNCC3)c2)[C@@H](C)[C@@H]1C]

To rac-tert-butyl 4-(3-(((2S,3R,4R)-1-acetyl-2,3-dimethyl-1,2,3,4-tetrahydroquinolin-4-yl)amino)phenyl)piperazine-1-carboxylate (for a preparation see Intermediate 7, 183.6 mg, 0.384 mmol) in methanol (4 mL) was added HCl (0.959 mL, 3.84 mmol, 4M in 1,4-dioxane). The reaction mixture was stirred at rt for 4 h. The solution was then evaporated in vacuo and the residue was purified by MDAP (Formic). The desired fractions were combined and evaporated in vacuo to afford the desired product as a yellow solid (127.2 mg).

LCMS (2 min Formic): Rt=0.72 min, [MH]⁺=379.

Example 9: rac-1-((2S,3R,4R)-4-((4-chloro-2-methoxyphenyl)amino)-2,3-dimethyl-3,4-dihydroquinolin-1(2H)-yl)ethanone

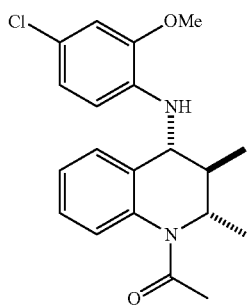 [SMILES: COc1cc(Cl)ccc1N[C@H]1c2ccccc2N(C(C)=O)[C@@H](C)[C@@H]1C]

To a greenhouse test tube was added rac-1-((2S,3R,4R)-4-amino-2,3-dimethyl-3,4-dihydroquinolin-1(2H)-yl)ethanone (for a preparation see Intermediate 6, 39.0 mg, 0.179 mmol), 1-bromo-4-chloro-2-methoxybenzene (47.5 mg, 0.214 mmol), Pd₂(dba)₃ (17.4 mg, 0.019 mmol, DavePhos (7.4 mg, 0.019 mmol), sodium tert-butoxide (26.1 mg, 0.272 mmol) and 1,4-dioxane (2 mL). The reaction mixture was heated under nitrogen at 100° C. using a greenhouse reactor for 1 h 30 min. The reaction mixture was allowed to cool to rt and filtered through a celite cartridge, washing with ethyl acetate. The filtrate was evaporated in vacuo and the residue dissolved in a mixture of methanol:DMSO (2 mL, 1:1) and purified by MDAP (Formic). The required fractions were combined and evaporated in vacuo. Not all of the sample was injected into the MDAP, hence the residues were combined, diluted in methanol (1 mL) and purified by MDAP (Formic). The required fraction was added to the previous fractions and evaporated in vacuo to give the required product as a yellow solid (30.9 mg, 0.086 mmol, 48.2% yield). This was impure so the product was dissolved in DCM (1 mL) and purified on a 5 g silica cartridge eluting with 20% ethyl acetate in cyclohexane. The required fractions were combined and evaporated under a stream of nitrogen to give the required product as a yellow solid (20 mg, 0.056 mmol, 31.2%).

LCMS (2 min Formic): Rt=1.26 min, [MH]⁺=359.

Example 10: rac-1-((2S,3R,4R)-1-acetyl-2,3-dimethyl-1,2,3,4-tetrahydroquinolin-4-yl)amino)pyridin-2(1H)-one

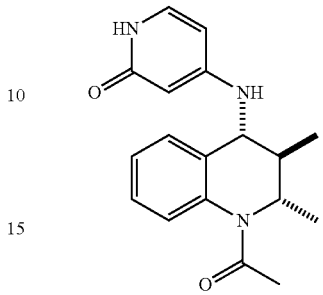

To a greenhouse test tube was added rac-1-((2S,3R,4R)-4-amino-2,3-dimethyl-3,4-dihydroquinolin-1(2H)-yl)ethanone (for a preparation see Intermediate 6, 41.2 mg, 0.189 mmol), 4-bromopyridin-2(1H)-one (37.4 mg, 0.215 mmol), Pd₂(dba)₃ (17.5 mg, 0.019 mmol), DavePhos (7.5 mg, 0.019 mmol), sodium tert-butoxide (27.2 mg, 0.283 mmol) and 1,4-dioxane (2 mL). The reaction mixture was stirred at 100° C. under nitrogen for 17 h. The reaction mixture was allowed to cool to rt and filtered through a celite cartridge, washing with ethyl acetate. The filtrate was evaporated in vacuo and the residue dissolved in methanol (1 mL). The dissolved material was purified by MDAP (HpH). The required fractions were combined and evaporated in vacuo to give a yellow solid. The product was impure and was therefore dissolved in methanol and re-purified by MDAP (Formic). The required fraction was evaporated under a stream of nitrogen to give the required product as a yellow gum (8.6 mg, 0.028 mmol, 14.63%). LCMS (2 min Formic): Rt=0.64 min, [MH]⁺=312.

Example 11: rac-1-((2S,3R,4R)-2,3-dimethyl-4-(pyridin-2-ylamino)-3,4-dihydroquinolin-1(2H)-yl)ethanone

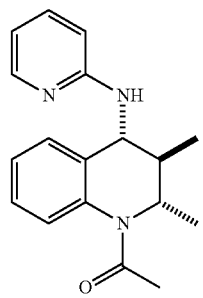 [SMILES: CC(=O)N1c2ccccc2[C@H](Nc2ccccn2)[C@@H](C)[C@@H]1C]

To a test tube were added rac-1-((2S,3R,4R)-4-amino-2,3-dimethyl-3,4-dihydroquinolin-1(2H)-yl)ethanone (for a preparation see Intermediate 6, 47.3 mg, 0.217 mmol), 2-chloropyridine (0.025 mL, 0.260 mmol), Pd₂(dba)₃ (9.92 mg, 10.83 μmol), sodium tert-butoxide (31.2 mg, 0.325 mmol), DavePhos (8.53 mg, 0.022 mmol) and 1,4-dioxane (2.5 mL). The reaction mixture was then heated and stirred at 100° C. in a greenhouse reactor for 3 h. After cooling to rt, the reaction mixture was filtered through a pad of celite (rinsed with EtOAc). The filtrate was then evaporated in vacuo. The residue was purified by MDAP (Formic). The desired fractions were combined and evaporated in vacuo to afford the desired product as a colourless solid (47.9 mg).

LCMS (2 min formic): Rt=0.54 min, [MH]$^+$=296.

Example 12: rac-1-((2S,3R,4R)-2,3-dimethyl-4-(thiophen-3-ylamino)-3,4-dihydroquinolin-1(2H)-yl)ethanone

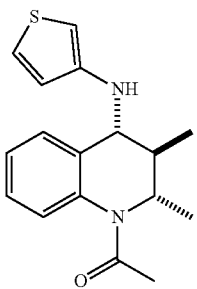 [SMILES: CC(=O)N1c2ccccc2[C@H](Nc2ccsc2)[C@@H](C)[C@@H]1C]

To a microwave vial was added rac-1-((2S,3R,4R)-4-amino-2,3-dimethyl-3,4-dihydroquinolin-1(2H)-yl)ethanone (for a preparation see Intermediate 6, 50 mg, 0.229 mmol), 3-bromothiophene (0.021 mL, 0.229 mmol), copper powder (1.6 mg, 0.025 mmol), cesium acetate (88.6 mg, 0.462 mmol) and dimethyl sulfoxide (DMSO) (0.5 mL). The reaction vessel was sealed and the mixture was heated in an oil bath at 90° C. for 68 h. The reaction mixture was diluted to 2 mL with methanol and purified by MDAP (Formic) (2×1 mL injection). The required fractions were combined and evaporated under a stream of nitrogen to give a brown gum (5.3 mg). The product was shown to contain some impurities by LCMS and was therefore dissolved in DCM (1 mL) and loaded onto a 2 g silica cartridge and eluted with 50% ethyl acetate in cyclohexane. The appropriate fraction was evaporated under a stream of nitrogen to give the desired product as a yellow gum (1.8 mg, 5.99 µmol, 2.62%).

LCMS (2 min Formic): Rt=1.07 min, [MH]$^+$=301.0

Example 13: rac-1-((2S,3R,4R)-4-((4-chlorophenyl)amino)-2,3-dimethyl-3,4-dihydroquinolin-1(2H)-yl)ethanone

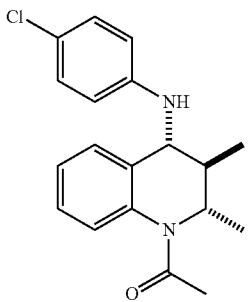 [SMILES: CC(=O)N1c2ccccc2[C@H](Nc2ccc(Cl)cc2)[C@@H](C)[C@@H]1C]

To a greenhouse test tube was added rac-1-((2S,3R,4R)-4-amino-2,3-dimethyl-3,4-dihydroquinolin-1(2H)-yl)ethanone (for a preparation see Intermediate 6, 39.2 mg, 0.180 mmol), 1-bromo-4-chlorobenzene (41.2 mg, 0.215 mmol), Pd$_2$(dba)$_3$ (17.6 mg, 0.019 mmol), DavePhos (7.4 mg, 0.019 mmol), sodium tert-butoxide (26.3 mg, 0.274 mmol) followed by 1,4-dioxane (2 mL). The reaction mixture was heated under nitrogen at 100° C. using a greenhouse reactor for 1.5 h. The reaction mixture was allowed to cool overnight, then was filtered through a celite cartridge, washing with ethyl acetate. The filtrate was evaporated in vacuo and the residue dissolved in a mixture of methanol:DMSO (1 mL, 1:1) and purified by MDAP (HpH). The required fractions were combined and evaporated in vacuo to give the required product as a light brown solid (28.6 mg, 0.087 mmol, 48.4%).

LCMS (2 min Formic): Rt=1.19 min, [M]$^+$=202 (loss of PhNH$_2^-$).

Example 14: rac-1-((2S,3R,4R)-2,3-dimethyl-4-((3-methylpyridin-2-yl)amino)-3,4-dihydroquinolin-1(2H)-yl)ethanone

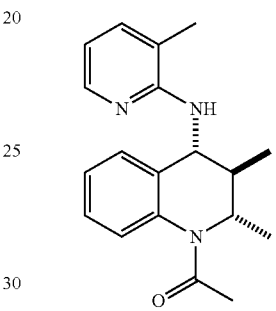

To a test tube were added rac-1-((2S,3R,4R)-4-amino-2,3-dimethyl-3,4-dihydroquinolin-1(2H)-yl)ethanone (for a preparation see Intermediate 6, 47.3 mg, 0.217 mmol), 2-chloro-3-methylpyridine (0.029 mL, 0.260 mmol), Pd$_2$(dba)$_3$ (9.92 mg, 10.83 µmol), sodium tert-butoxide (31.2 mg, 0.325 mmol), DavePhos (8.53 mg, 0.022 mmol) and 1,4-dioxane (2.5 mL). The reaction mixture was then heated and stirred at 100° C. in a greenhouse reactor for 3 h. After cooling to rt, the reaction mixture was filtered through a pad of celite (rinsed with EtOAc). The filtrate was then evaporated in vacuo. The residue was purified by MDAP (Formic). The desired fractions were combined and evaporated in vacuo to afford the desired product as a white solid (37.7 mg).

LCMS (2 min Formic): Rt=0.58 min, [MH]$^+$=310.

Example 15: rac-1-((2S,3R,4R)-4-((4-methoxyphenyl)amino)-2,3-dimethyl-3,4-dihydroquinolin-1(2H)-yl)ethanone

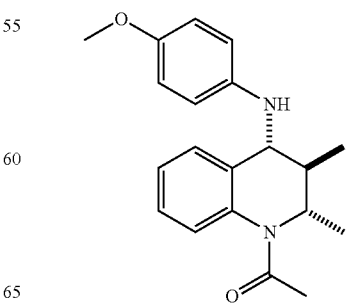

To a test tube was added rac-1-((2S,3R,4R)-4-amino-2,3-dimethyl-3,4-dihydroquinolin-1(2H)-yl)ethanone (for a preparation see Intermediate 6, 35 mg, 0.160 mmol), Davephos, (7 mg, 0.018 mmol), Pd$_2$(dba)$_3$ (17 mg, 0.019 mmol) and sodium tert-butoxide (25 mg, 0.260 mmol). The mixture was suspended in anhydrous 1,4-dioxane (2 mL) and to the suspension was added 4-bromoanisole (0.024 mL, 0.192 mmol). The reaction mixture was heated in a greenhouse reactor at 100° C. overnight (16 h) under an atmosphere of nitrogen. The reaction mixture was filtered through a celite cartridge, washing through with EtOAc. The solvent was removed by rotary evaporation and the residue was dissolved in a mixture DMSO:MeOH (1:1) then purified by MDAP (Formic). The appropriate fractions were combined and the solvent was removed by rotary evaporation to give the desired product as a brown solid (17 mg, 0.052 mmol, 32.7%).

LCMS (2 min Formic): Rt=1.07 min, [MH]$^+$=325.

Example 16: rac-1-((2S,3R,4R)-2,3-dimethyl-4-(m-tolylamino)-3,4-dihydroquinolin-1(2H)-yl)ethanone

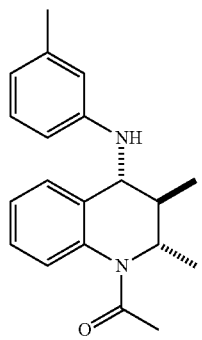 [SMILES: CC(=O)N1c2ccccc2[C@H](Nc2cccc(C)c2)[C@@H](C)[C@@H]1C]

To a greenhouse test tube was added rac-1-((2S,3R,4R)-4-amino-2,3-dimethyl-3,4-dihydroquinolin-1(2H)-yl)ethanone (for a preparation see Intermediate 6, 38.8 mg, 0.178 mmol), 1-bromo-3-methylbenzene (40.1 mg, 0.234 mmol), Pd$_2$(dba)$_3$ (16.6 mg, 0.018 mmol), DavePhos (7.4 mg, 0.019 mmol), sodium tert-butoxide (27.2 mg, 0.283 mmol) followed by 1,4-dioxane (2 mL). The reaction mixture was heated under nitrogen at 100° C. using a greenhouse reactor for 1 h 30 min. The reaction mixture was allowed to cool overnight and then filtered through a celite cartridge, washing with ethyl acetate. The filtrate was evaporated in vacuo and the residue dissolved in a mixture of methanol:DMSO (1 mL, 1:1) and purified by MDAP (HpH). The required fractions were combined and evaporated in vacuo to give the required product, as a light brown solid (33.5 mg, 0.109 mmol, 61.1%).

LCMS (2 min Formic): Rt=1.17 min, [MH]$^+$=309.

Example 17: rac-1-((2S,3R,4R)-2,3-dimethyl-4-((5-methylpyridin-3-yl)amino)-3,4-dihydroquinolin-1(2H)-yl)ethanone

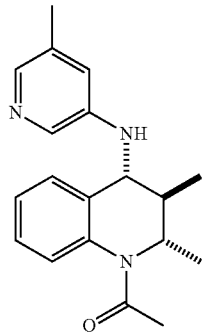 [SMILES: CC(=O)N1c2ccccc2[C@H](Nc2cncc(C)c2)[C@@H](C)[C@@H]1C]

To a test tube were added rac-1-((2S,3R,4R)-4-amino-2,3-dimethyl-3,4-dihydroquinolin-1(2H)-yl)ethanone (for a preparation see Intermediate 6, 53 mg, 0.243 mmol), 3-bromo-5-methylpyridine (0.034 mL, 0.291 mmol), Pd$_2$(dba)$_3$ (11.12 mg, 0.012 mmol), sodium tert-butoxide (35.0 mg, 0.364 mmol), DavePhos (9.56 mg, 0.024 mmol) and 1,4-dioxane (2.5 mL). The reaction mixture was then heated and stirred at 100° C. in a greenhouse reactor for 2 h. After cooling to rt, the reaction mixture was filtered through a pad of celite (rinsed with EtOAc). The filtrate was then evaporated in vacuo. The residue was purified by MDAP (Formic). The desired fractions were combined and evaporated in vacuo to afford the desired product as a beige solid (49.8 mg).

LCMS (2 min formic): Rt=0.60 min, [MH]$^+$=310.3

Example 18: rac-1-((2S,3R,4R)-2,3-dimethyl-4-(pyrimidin-2-ylamino)-3,4-dihydroquinolin-1(2H)-yl)ethanone

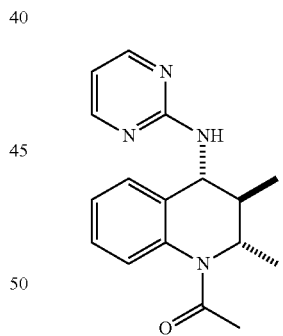

To a test tube were added rac-1-((2S,3R,4R)-4-amino-2,3-dimethyl-3,4-dihydroquinolin-1(2H)-yl)ethanone (for a preparation see Intermediate 6, 40.5 mg, 0.186 mmol), 2-chloropyrimidine (26.0 mg, 0.223 mmol), Pd$_2$(dba)$_3$ (8.49 mg, 9.28 µmol), sodium tert-butoxide (26.7 mg, 0.278 mmol), DavePhos (7.30 mg, 0.019 mmol) and 1,4-dioxane (2.5 mL). The reaction mixture was then heated and stirred at 100° C. in a greenhouse reactor overnight. After cooling to rt, the reaction mixture was filtered through a pad of celite (rinsed with EtOAc). The filtrate was then evaporated in vacuo. The residue was purified by MDAP (Formic). The desired fractions were combined and evaporated in vacuo to afford the desired product as a brown solid (3 mg).

LCMS (2 min Formic): Rt=0.74 min, [MH]$^+$=297.

Example 19: rac-1-((2S,3R,4R)-2,3-dimethyl-4-((4-methylpyridin-2-yl)amino)-3,4-dihydroquinolin-1(2H)-yl)ethanone

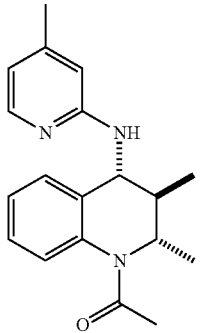 [SMILES: CC(=O)N1c2ccccc2[C@H](Nc2cc(C)ccn2)[C@@H](C)[C@@H]1C]

To a test tube were added rac-1-((2S,3R,4R)-4-amino-2,3-dimethyl-3,4-dihydroquinolin-1(2H)-yl)ethanone (for a preparation see Intermediate 6, 41.8 mg, 0.191 mmol), 2-bromo-4-methylpyridine (0.026 mL, 0.230 mmol), Pd$_2$(dba)$_3$ (8.77 mg, 9.57 µmol), sodium tert-butoxide (27.6 mg, 0.287 mmol), DavePhos (7.54 mg, 0.019 mmol) and 1,4-dioxane (2.5 mL). The reaction mixture was then heated and stirred at 100° C. in a greenhouse reactor for 3 h. After cooling to rt, the reaction mixture was filtered through a pad of celite (rinsed with EtOAc). The filtrate was then evaporated in vacuo. The residue was purified by MDAP (Formic). Pure fractions were evaporated in vacuo to afford the product as a colourless solid (18.4 mg). LCMS (2 min Formic): Rt=0.61 min, [MH]$^+$=310.

Example 20: rac-1-((2S,3R,4R)-2,3-dimethyl-4-(p-tolylamino)-3,4-dihydroquinolin-1(2H)-yl)ethanone

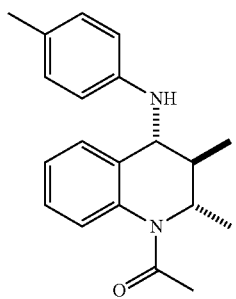

To a greenhouse test tube was added rac-1-((2S,3R,4R)-4-amino-2,3-dimethyl-3,4-dihydroquinolin-1(2H)-yl)ethanone (for a preparation see Intermediate 6, 38.0 mg, 0.174 mmol), 1-bromo-4-methylbenzene (42.2 mg, 0.247 mmol), Pd$_2$(dba)$_3$ (16.8 mg, 0.018 mmol), DavePhos (7.3 mg, 0.019 mmol), sodium tert-butoxide (26.1 mg, 0.272 mmol) followed by 1,4-dioxane (2 mL). The reaction mixture was heated under nitrogen at 100° C. using a greenhouse reactor for 1 h 30 min. The reaction mixture was allowed to cool overnight and then filtered though a celite cartridge, washing with ethyl acetate. The filtrate was evaporated in vacuo and the residue dissolved in a mixture of methanol:DMSO (1 mL, 1:1) and purified by MDAP (HpH). The required fractions were combined and evaporated in vacuo to give the required product as a light brown solid (29.3 mg, 0.095 mmol, 54.6%).
LCMS (2 min Formic): Rt=1.19 min, [MH]$^+$=309.

Example 21: rac-1-((2S,3R,4R)-2,3-dimethyl-4-((5-methylpyridin-2-yl)amino)-3,4-dihydroquinolin-1(2H)-yl)ethanone

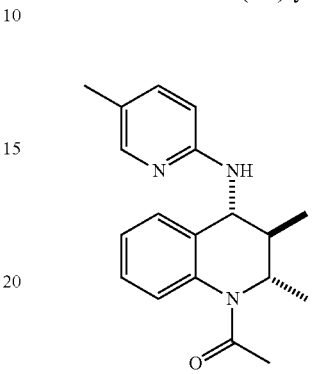

To a test tube were added rac-1-((2S,3R,4R)-4-amino-2,3-dimethyl-3,4-dihydroquinolin-1(2H)-yl)ethanone (for a preparation see Intermediate 6, 40.4 mg, 0.185 mmol), 2-chloro-5-methylpyridine (0.026 mL, 0.222 mmol), Pd$_2$(dba)$_3$ (8.47 mg, 9.25 µmol), sodium tert-butoxide (26.7 mg, 0.278 mmol), DavePhos (7.28 mg, 0.019 mmol) and 1,4-dioxane (2.5 mL). The reaction mixture was then heated and stirred at 100° C. in a greenhouse reactor for 5 h. After cooling to rt, the reaction mixture was filtered through a pad of celite (rinsed with EtOAc). The filtrate was then evaporated in vacuo. The residue was purified by MDAP (Formic). The desired fractions were combined and evaporated in vacuo to afford the product as a pink solid (37.5 mg).
LCMS (2 min Formic): Rt=0.60 min, [MH]$^+$=310.

Example 22: rac-1-((2S,3R,4R)-4-((5-chloropyridin-3-yl)amino)-2,3-dimethyl-3,4-dihydroquinolin-1(2H)-yl)ethanone

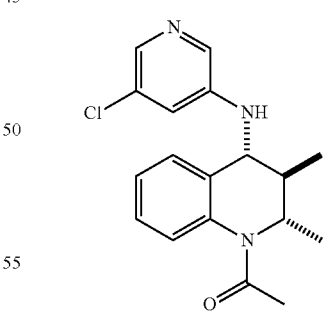

To a greenhouse test tube was added rac-1-((2S,3R,4R)-4-amino-2,3-dimethyl-3,4-dihydroquinolin-1(2H)-yl)ethanone (for a preparation see Intermediate 6, 39.9 mg, 0.183 mmol), 3-bromo-5-chloropyridine (43.2 mg, 0.224 mmol), Pd$_2$(dba)$_3$ (16.8 mg, 0.018 mmol), DavePhos (7.6 mg, 0.019 mmol), sodium tert-butoxide (26.6 mg, 0.277 mmol) and 1,4-dioxane (2 mL). The reaction mixture was stirred at 100° C. under nitrogen for 17 h. The reaction mixture was allowed to cool to rt and filtered through a celite cartridge, washing with ethyl acetate. The filtrate was evaporated in vacuo and the residue dissolved in methanol (1 mL). The dissolved material was purified by MDAP (HpH). The required fractions were combined and evaporated in vacuo to give a yellow solid. The product was impure hence was dissolved in methanol and re-purified by MDAP (Formic). The required fractions were combined and evaporated under a stream of nitrogen to give the required product as a beige solid (21.3 mg, 0.065 mmol, 35.3%). LCMS (2 min Formic): Rt=0.87 min, [MH]+=330.

Example 23: rac-1-((2S,3R,4R)-2,3-dimethyl-4-((2-methylpyridin-4-yl)amino)-3,4-dihydroquinolin-1(2H)-yl)ethanone

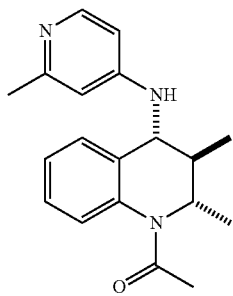

To a greenhouse test tube was added rac-1-((2S,3R,4R)-4-amino-2,3-dimethyl-3,4-dihydroquinolin-1(2H)-yl)ethanone (for a preparation see Intermediate 6, 51.0 mg, 0.234 mmol), Pd$_2$(dba)$_3$ (21.5 mg, 0.023 mmol), DavePhos (5.2 mg, 0.013 mmol), sodium tert-butoxide (67.2 mg, 0.699 mmol), 1,4-dioxane (2 mL) and 4-bromo-2-methylpyridine (0.033 mL, 0.280 mmol). The reaction mixture was stirred at 100° C. under nitrogen for 16 hours. The reaction mixture was allowed to cool to rt then filtered through a celite cartridge, washing with ethyl acetate. The filtrate was evaporated under a stream of nitrogen and the residue dissolved in methanol (1 mL). The dissolved material was purified by MDAP (Formic). The required fractions were combined and evaporated in vacuo to give the required product, as a white solid (61.0 mg, 0.197 mmol, 84%).

LCMS (2 min Formic): Rt=0.59 min, MH+=310.

Example 24: rac-1-((2S,3R,4R)-2,3-dimethyl-4-((5-methylpyrazin-2-yl)amino)-3,4-dihydroquinolin-1(2H)-yl)ethanone

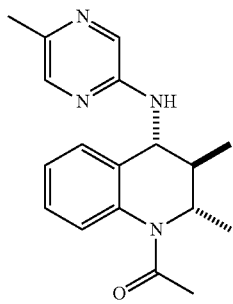

To a test tube were added rac-1-((2S,3R,4R)-4-amino-2,3-dimethyl-3,4-dihydroquinolin-1(2H)-yl)ethanone (for a preparation see Intermediate 6, 55 mg, 0.252 mmol), 2-bromo-5-methylpyrazine (52.3 mg, 0.302 mmol), Pd$_2$(dba)$_3$ (11.54 mg, 0.013 mmol), DavePhos (9.92 mg, 0.025 mmol) and 1,4-dioxane (2.5 mL). The reaction mixture was then heated and stirred at 100° C. in a greenhouse reactor for 1 h 30 min. After cooling to rt, the reaction mixture was filtered through a pad of celite (rinsed with EtOAc). The filtrate was then evaporated in vacuo. The residue was purified by MDAP (Formic). Desired fractions were combined and evaporated in vacuo to afford the product as a yellow solid (54.1 mg). LCMS (2 min Formic): Rt=0.79 min, [MH]+=311.

Examples 25a & 25b: 1-((2S,3R,4R)-2-ethyl-3-methyl-4-((6-methylpyridin-2-yl)amino)-3,4-dihydroquinolin-1(2H)-yl)ethanone (N26052-57-A2) & 1-((2R,3S,4S)-2-ethyl-3-methyl-4-((6-methylpyridin-2-yl)amino)-3,4-dihydroquinolin-1(2H)-yl)ethanone

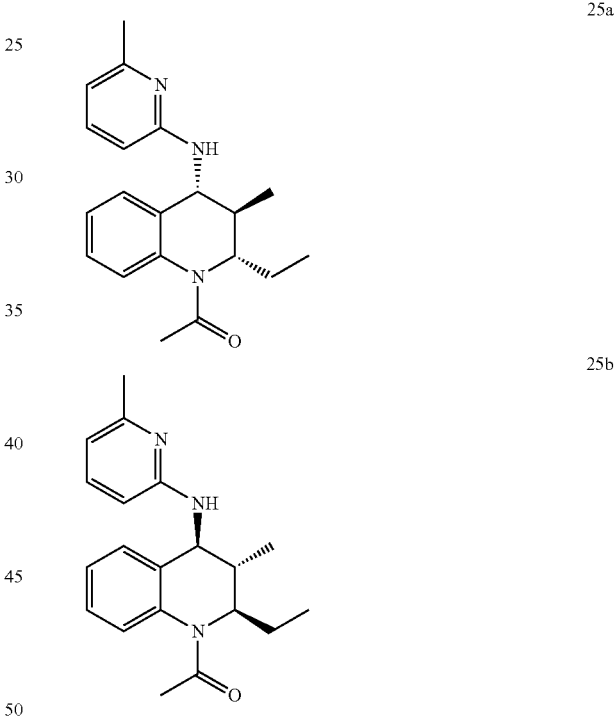

rac-1-((2S,3R,4R)-2-ethyl-3-methyl-4-((6-methylpyridin-2-yl)amino)-3,4-dihydroquinolin-1(2H)-yl)ethanone (for a preparation see Intermediate 11, 167 mg) was submitted for chiral separation into its enantiomers (A and B) using a 250×30 mm Chiralpak IC column eluting with 10% ethanol in heptane at a flow rate of 42.5 mL/min. Peak 1/Enantiomer A fractions were collected between 8 and 9.5 min. Peak 2/Enantiomer B fractions were collected between 10.5 and 11.5 min. Fraction solutions were combined then evaporated to dryness to give Enantiomer A (61 mg) and Enantiomer B (66 mg) as white solids.

The absolute configurations were determined by comparative vibrational circular dichroism (VCD), utilizing a reference VCD spectrum to make the assignments (Appl. Spectrosc. 65 (7), 699 (2011)). Conc—equimolar solutions (0.2-M) in DCM; Cell—sealed transmission/BaF$_2$ windows/

100 um pathlength; Spectrometer—ChirallR-2X™ FT-VCD spectrometer (BioTools, Inc.); Scan Parameters—2200-800 cm$^{-1}$ at 4 cm$^{-1}$ resolution.

Enantiomer A, Example 25b

Analytical Chiral HPLC using a 250×4.6 mm Chiralpak IC column eluting with 10% ethanol in heptane at 1 mL/min)—Rt=9.5 min, >99% ee by UV. Assigned with (2R,3S,4S) absolute configuration by VCD with a confidence limit of >99% (based on confidence limit estimated for reference).

Enantiomer B, Example 25a

Analytical Chiral HPLC using a 250×4.6 mm Chiralpak IC column eluting with 10% ethanol in heptane at 1 mL/min)—Rt=10.3 min, >95% ee by UV. Assigned with (2S,3R,4R) absolute configuration by VCD with a confidence limit of >99% (based on confidence limit estimated for reference).

Example 26: rac-1-((2S,3R,4R)-2-cyclopropyl-3-methyl-4-(phenylamino)-3,4-dihydroquinolin-1(2H)-yl)ethanone

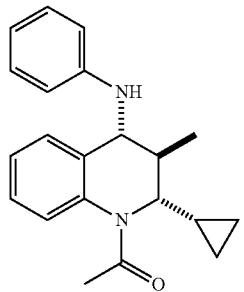 [SMILES: CC(=O)N1c2ccccc2[C@H](Nc2ccccc2)[C@@H](C)[C@@H]1C1CC1]

A mixture of rac-1-((2S,3R,4R)-4-amino-2-cyclopropyl-3-methyl-3,4-dihydroquinolin-1(2H)-yl)ethanone, hydrobromide (for a preparation see Intermediate 125, 408 mg, 1.25 mmol), bromobenzene (0.26 mL, 2.51 mmol), DavePhos (49.6 mg, 0.126 mmol), tris(dibenzylideneacetone)dipalladium (0) (Pd$_2$(dba)$_3$) (173 mg, 0.189 mmol) and sodium tert-butoxide (318 mg, 3.31 mmol) in 1,4-dioxane (8.5 mL) was heated under nitrogen at 100° C. for 30 min and cooled slowly to rt and stirred for 19 h. The mixture was filtered through a 10 g celite cartridge, washing with ethyl acetate (3×20 mL). The combined filtrate was evaporated in vacuo and the residue was loaded in dichloromethane (~10 mL) onto a 25 g silica cartridge and was purified by flash column chromatography eluting with a gradient of 0-50% ethyl acetate in dichloromethane. The required fractions were combined and evaporated in vacuo to give a brown gummy residue which was re-dissolved in methanol (3 mL) and was purified by MDAP (Formic) (3×1 mL injection). The required fractions were combined and evaporated in vacuo to give the desired product (255 mg, 0.80 mmol, 64%). LCMS (2 min Formic): Rt=1.18 min, [MH]$^+$=321.

Examples 27a & 27b: 1-((2S,3R,4R)-2-cyclopropyl-3-methyl-4-(phenylamino)-3,4-dihydroquinolin-1(2H)-yl)ethanone & 1-((2R,3S,4S)-2-cyclopropyl-3-methyl-4-(phenylamino)-3,4-dihydroquinolin-1(2H)-yl)ethanone

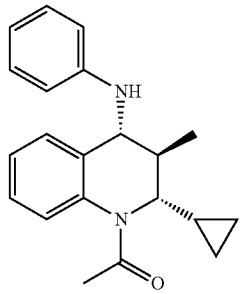

27a

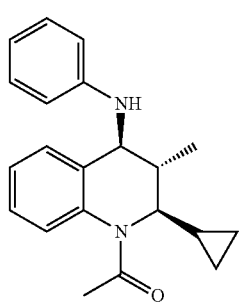

27b rac-1-((2S,3R,4R)-2-Cyclopropyl-3-methyl-4-(phenylamino)-3,4-dihydroquinolin-1(2H)-yl)ethanone (for a preparation see Example 26, ~200 mg) was submitted for chiral separation into its enantiomers (A and B) using a 250×30 mm Chiralpak AD-H column eluting with 10% ethanol in heptane at a flow rate of 20 mL/min. Peak 1/Enantiomer A fractions were collected between 11 and 13 min. Peak 2/Enantiomer B fractions were collected between 16 and 20 min. Fraction solutions were combined then evaporated to dryness to give Enantiomer A (85 mg) and Enantiomer B (63 mg) as white solids. The absolute configurations were determined by ab initio vibrational circular dichroism (VCD), a form of differential vibrational spectroscopy that combines experimental and computational VCD data to determine absolute stereochemistry (Appl. Spectrosc. 65 (7), 699 (2011)). Conc—equimolar solutions (0.2-M) in DCM; Cell—sealed transmission/BaF$_2$ windows/100 um pathlength; Spectrometer—ChirallR-2X™ FT-VCD spectrometer (BioTools, Inc.); Scan Parameters—2200-800 cm$^{-1}$ at 4 cm$^{-1}$ resolution. Computation: Conformational Search—stochastic with MMFF94x; Model Chemistry (vibrational properties)—B3LYP/dgdzvp with PCM solvent modelling; Spectral Synthesis—Boltzmann statistics; Quantitative Analysis—CompareVOA™ (BioTools, Inc.).

Enantiomer A, Example 27a

Analytical Chiral HPLC using a 250×4.6 mm Chiralpak AD-H column eluting with 10% ethanol in heptane at 1 mL/min)—Rt=6.0 min.>95% ee by UV. Assigned with (2S,3R,4R) absolute configuration by VCD with a confidence limit of >99% (based on confidence limit estimated for reference).

Enantiomer B, Example 27b

Analytical Chiral HPLC using a 250×4.6 mm Chiralpak AD-H column eluting with 10% ethanol in heptane at 1 mL/min)—Rt=8.6 min, >99% ee by UV. Assigned with (2R,3S,4S) absolute configuration by VCD with a confidence limit of >99% (based on confidence limit estimated for reference).

Example 28: rac-1-((2S,3R,4R)-2-cyclopropyl-3-methyl-4-((6-methylpyridin-2-yl)amino)-3,4-dihydroquinolin-1(2H)-yl)ethanone

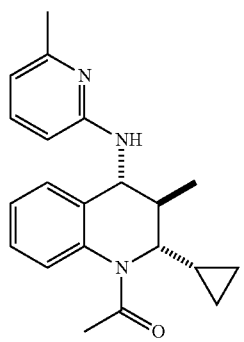 [SMILES: CC(=O)N1c2ccccc2[C@H](Nc2cccc(C)n2)[C@@H](C)[C@@H]1C1CC1]

A mixture of rac-1-((2S,3R,4R)-4-amino-2-cyclopropyl-3-methyl-3,4-dihydroquinolin-1(2H)-yl)ethanone, hydrobromide (for a preparation see Intermediate 125, 407.5 mg, 1.253 mmol), 2-bromo-6-methylpyridine (0.286 mL, 2.51 mmol), DavePhos (49.6 mg, 0.126 mmol), tris(dibenzylideneacetone)dipalladium(0) (Pd$_2$(dba)$_3$) (177.0 mg, 0.193 mmol) and sodium tert-butoxide (313.5 mg, 3.26 mmol) in 1,4-dioxane (8.5 mL) was heated under nitrogen at 100° C. for 2 h. The mixture was allowed to cool to rt and was filtered through a 10 g celite cartridge, washing with ethyl acetate (3×20 mL). The combined filtrate was evaporated in vacuo and the residue was loaded in dichloromethane (~10 mL) onto a 25 g silica cartridge and was purified by flash column chromatography eluting with a gradient of 0-50% ethyl acetate in dichloromethane. The required fractions were combined and evaporated in vacuo to give a orange gummy residue which was re-dissolved in methanol (3 mL) and was purified by MDAP (HpH) (3×1 mL injection). The required fractions were combined and evaporated in vacuo to give the desired product as a white crunchy foam (186.0 mg, 0.554 mmol, 44%). LCMS (2 min HpH): Rt=1.12 min, [MH]$^+$=336.

Examples 29a & 29b: 1-((2S,3R,4R)-2-cyclopropyl-3-methyl-4-((6-methylpyridin-2-yl)amino)-3,4-dihydroquinolin-1(2H)-yl)ethanone & 1-((2R,3S,4S)-2-cyclopropyl-3-methyl-4-((6-methylpyridin-2-yl)amino)-3,4-dihydroquinolin-1(2H)-yl)ethanone

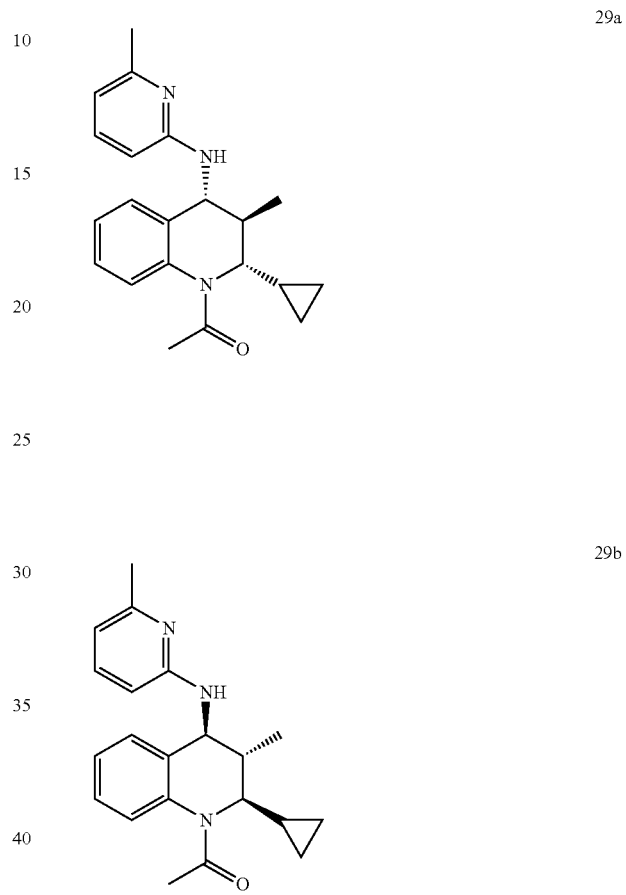

rac-1-((2S,3R,4R)-2-cyclopropyl-3-methyl-4-((6-methylpyridin-2-yl)amino)-3,4-dihydroquinolin-1(2H)-yl)ethanone (for a preparation see Example 28, ~170 mg) was submitted for chiral separation into its enantiomers (A and B) using a 250×30 mm Chiralcel OD-H column eluting with 10% ethanol in heptane at a flow rate of 20 mL/min. Peak 1/Enantiomer A fractions were collected between 17 and 19 min. Peak 2/Enantiomer B fractions were collected between 21.5 and 25 min. Fraction solutions were combined then evaporated to dryness to give Enantiomer A (78 mg) and Enantiomer B (86 mg) as white solids.

Enantiomer A, Example 29b

Analytical Chiral HPLC using a 250×4.6 mm Chiralcel OD-H column eluting with 5% ethanol in heptane at 1 mL/min)—Rt=7.0 min.>99% ee by UV.

Enantiomer B, Example 29a

Analytical Chiral HPLC using a 250×4.6 mm Chiralcel OD-H column eluting with 5% ethanol in heptane at 1 mL/min)—Rt=8.6 min, >95% ee by UV.

Example 30: rac-4-(((2S,3R,4R)-1-Acetyl-2-cyclopropyl-3-methyl-1,2,3,4-tetrahydroquinolin-4-yl)amino)benzonitrile

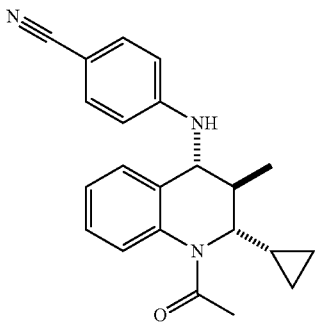 [SMILES: CC(=O)N1c2ccccc2[C@H](Nc2ccc(C#N)cc2)[C@@H](C)[C@@H]1C1CC1]

Pd$_2$(dba)$_3$ (72.7 mg, 0.079 mmol), DavePhos (62.5 mg, 0.159 mmol) and sodium tert-butoxide (114 mg, 1.191 mmol) were all placed in a 2-5 mL microwave vial. To this was added 4-bromobenzonitrile (148.2 mg, 0.814 mmol), followed by rac-1-((2S,3R,4R)-4-amino-2-cyclopropyl-3-methyl-3,4-dihydroquinolin-1(2-H)-yl)ethanone (for a preparation see Intermediate 14, 97 mg, 0.397 mmol) in 1,4-dioxane (4 mL). The mixture was heated at 120° C. for 40 min in a microwave. The mixture was filtered through a 2.5 g celite cartridge and concentrated in vacuo to afford a dark brown oil. This was taken up in ethyl acetate and purified on a silica cartridge (25 g) by flash column chromatography, eluting with 10%-50% ethyl acetate in cyclohexane. The appropriate fractions were combined and concentrated in vacuo in two batches, to afford the desired product as a yellow glass (38.9 mg) and a reduced purity batch of the desired product, also as a yellow glass (30 mg).
LCMS (2 min Formic): Rt=1.06 min, [M−H]$^-$=344.

Example 31: rac-1-((2S,3R,4R)-2-Cyclopropyl-3-methyl-4-(o-tolylamino)-3,4-dihydroquinolin-1(2H)-yl)ethanone

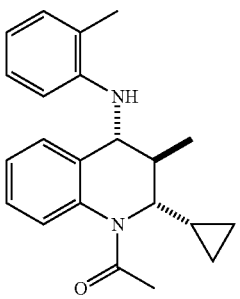 [SMILES: CC(=O)N1c2ccccc2[C@H](Nc2ccccc2C)[C@@H](C)[C@@H]1C1CC1]

Pd$_2$(dba)$_3$ (67.7 mg, 0.074 mmol), DavePhos (58.2 mg, 0.148 mmol) and sodium tert-butoxide (107 mg, 1.109 mmol) were all placed in a 2 mL microwave vial. To this was added 1-bromo-2-methylbenzene (0.089 mL, 0.739 mmol), followed by rac-1-((2S,3R,4R)-4-amino-2-cyclopropyl-3-methyl-3,4-dihydroquinolin-1(2H)-yl)ethanone (for a preparation see Intermediate 14, 90.3 mg, 0.370 mmol) in 1,4-dioxane (4 mL). The mixture was heated at 120° C. for 40 min in a microwave reactor. The reaction mixture was passed through a 2.5 g celite cartridge with ethyl acetate, and concentrated in vacuo. The mixture was taken up in ethyl acetate and purified on a silica cartridge (25 g) by flash column chromatography, eluting with 5-30% ethyl acetate in cyclohexane. The appropriate fractions were combined and concentrated in vacuo to afford an orange-brown crystalline solid (54.3 mg).
LCMS (2 min Formic): Rt=1.25 min, [MH]$^+$=335.

Example 32: rac-1-((2S,3R,4R)-2-Cyclopropyl-4-((4-fluorophenyl)amino)-3-methyl-3,4-dihydroquinolin-1(2H)-yl)ethanone

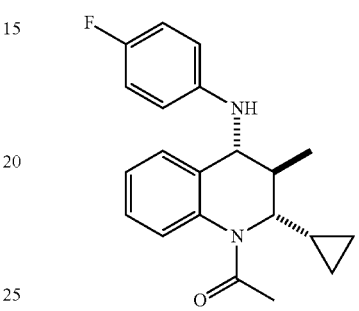

Pd$_2$(dba)$_3$ (42.6 mg, 0.046 mmol), DavePhos (36.6 mg, 0.093 mmol) and sodium tert-butoxide (67.0 mg, 0.697 mmol) were all placed in a 2 mL microwave vial. To this was added 1-bromo-4-fluorobenzene (0.051 mL, 0.465 mmol), followed by rac-1-((2S,3R,4R)-4-amino-2-cyclopropyl-3-methyl-3,4-dihydroquinolin-1(2H)-yl)ethanone (for a preparation see Intermediate 14, 56.8 mg, 0.232 mmol) in 1,4-dioxane (2 mL). The mixture was heated at 120° C. for 40 min in a microwave heater. The reaction mixture was passed through a 2.5 g celite cartridge and washed through with ethyl acetate. The solution was then concentrated in vacuo, taken up in ethyl acetate and purified on a silica cartridge (25 g) by flash column chromatography, eluting with 0%-30% ethyl acetate in cyclohexane. The appropriate fractions were combined and concentrated in vacuo to afford a yellow oil (40 mg). LCMS (2 min Formic): Rt=1.18 min, [M]+=228 (loss of NHC$_6$H$_4$F$^-$).

Example 33: rac-3-(((2S,3R,4R)-1-Acetyl-2-cyclopropyl-3-methyl-1,2,3,4-tetrahydroquinolin-4-yl)amino)benzonitrile

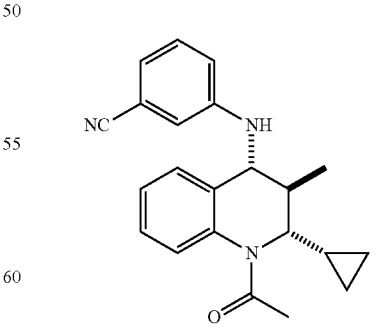

Pd$_2$(dba)$_3$ (34.9 mg, 0.038 mmol), DavePhos (30.0 mg, 0.076 mmol) and sodium tert-butoxide (55.0 mg, 0.572 mmol) were all placed in a 2 mL microwave vial. To this was added 3-bromobenzonitrile (69.4 mg, 0.381 mmol), followed by rac-1-((2S,3R,4R)-4-amino-2-cyclopropyl-3-methyl-3,4-dihydroquinolin-1(2H)-yl)ethanone (for a preparation see Intermediate 14, 46.6 mg, 0.191 mmol) in 1,4-dioxane (2 mL). The mixture was then heated at 120° C. for 40 min in a microwave heater. The reaction mixture was passed through a 2.5 g celite cartridge with ethyl acetate, and concentrated in vacuo. The crude product was taken up in dichloromethane and purified on a silica cartridge (10 g) by flash column chromatography, eluting with 5-45% ethyl acetate in cyclohexane. The appropriate fractions were collected and evaporated in vacuo to afford a yellow solid (21.5 mg).

LCMS (2 min Formic): Rt=1.12 min, [M]$^+$=228 (loss of NHC$_6$H4CN$^-$).

Example 34: rac-1-((2S,3R,4R)-2-cyclopropyl-4-((3-cyclopropylphenyl)amino)-3-methyl-3,4-dihydroquinolin-1(2H)-yl)ethanone

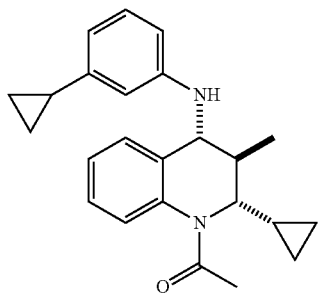 [SMILES: CC(=O)N1c2ccccc2[C@H](Nc2cccc(C3CC3)c2)[C@@H](C)[C@@H]1C1CC1]

A mixture of rac-1-((2S,3R,4R)-4-amino-2-cyclopropyl-3-methyl-3,4-dihydroquinolin-1(2H)-yl)ethanone, hydrobromide (for a preparation see Intermediate 125, 50.3 mg, 0.155 mmol), 1-bromo-3-cyclopropylbenzene (0.041 mL, 0.309 mmol), DavePhos (6.9 mg, 0.018 mmol), Pd$_2$(dba)$_3$ (23.3 mg, 0.025 mmol) and sodium tert-butoxide (38.1 mg, 0.396 mmol) in 1,4-dioxane (1 mL) was heated under nitrogen at 100° C. for 100 min. The mixture was allowed to cool to rt and was filtered through a 2.5 g celite cartridge, washing with ethyl acetate (3×5 mL). The combined filtrate was evaporated under a stream of nitrogen and the residue was re-dissolved in methanol/DMSO (1 mL, 9:1) and was purified by MDAP (Formic). The required fraction was evaporated under a stream of nitrogen to give the desired product as an orange/brown gum (29.7 mg, 0.082 mmol, 53.3%).

LCMS (2 min Formic): Rt=1.29 min, [MH]$^+$=361.

Example 35: rac-1-((2S,3R,4R)-2-Cyclopropyl-4-((3-fluorophenyl)amino)-3-methyl-3,4-dihydroquinolin-1(2H)-yl)ethanone

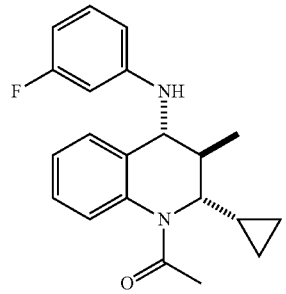 [SMILES: CC(=O)N1c2ccccc2[C@H](Nc2cccc(F)c2)[C@@H](C)[C@@H]1C1CC1]

Pd$_2$(dba)$_3$ (35.7 mg, 0.039 mmol), DavePhos (30.7 mg, 0.078 mmol) and sodium tert-butoxide (56.2 mg, 0.584 mmol) were all placed in a 2 mL microwave vial. To this was added 1-bromo-3-fluorobenzene (0.043 mL, 0.390 mmol), followed by rac-1-((2S,3R,4R)-4-amino-2-cyclopropyl-3-methyl-3,4-dihydroquinolin-1(2-H)-yl)ethanone (for a preparation see Intermediate 14, 47.6 mg, 0.195 mmol) in 1,4-dioxane (2 mL). The mixture was then heated at 120° C. for 40 min in a microwave heater. The reaction mixture was filtered through a 2.5 g celite cartridge, washed through with ethyl acetate and concentrated in vacuo. The crude material was taken up in dichloromethane and purified on a silica cartridge (10 g) by flash column chromatography, eluting with 5%-40% ethyl acetate in cyclohexane. The appropriate fractions were collected and evaporated in vacuo to afford a yellow glass. The sample was dissolved in MeOH:DMSO (1 mL, 1:1) and purified by MDAP (Formic). The solvent was evaporated in vacuo to give the required product (7.7 mg).

LCMS (2 min Formic): Rt=1.20 min, [M]$^+$=228 (loss of NHC$_6$H4F)=228.

Example 36: rac-1-((2S,3R,4R)-2-cyclopropyl-4-((6-methoxypyridin-2-yl)amino)-3-methyl-3,4-dihydroquinolin-1(2H)-yl)ethanone

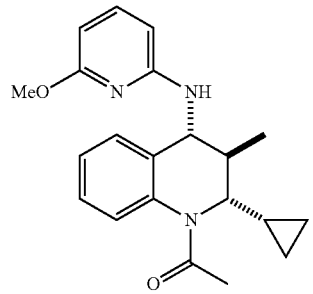 [SMILES: COc1cccc(N[C@H]2c3ccccc3N(C(C)=O)[C@@H](C3CC3)[C@@H]2C)n1]

Pd$_2$(dba)$_3$ (37.1 mg, 0.041 mmol), DavePhos (31.9 mg, 0.081 mmol) and sodium tert-butoxide (58.4 mg, 0.608 mmol) were all placed in a 2 mL microwave vial. To this was added 2-bromo-6-methoxypyridine (0.050 mL, 0.405 mmol), followed by rac-1-((2S,3R,4R)-4-amino-2-cyclopropyl-3-methyl-3,4-dihydroquinolin-1(2H)-yl)ethanone (for a preparation see Intermediate 14, 49.5 mg, 0.203 mmol) in 1,4-dioxane (2 mL). The mixture was degassed with nitrogen for ~15 min, and then heated at 120° C. for 40 min in a microwave heater. The reaction mixture was passed through a 2.5 g celite cartridge with further 1,4-dioxane. The mixture was concentrated in vacuo and the crude material dissolved in dichloromethane. This crude material was purified on a silica cartridge (10 g) by flash column chromatography, eluting with 0%-50% ethyl acetate in cyclohexane. The appropriate fractions were combined and concentrated in vacuo to afford a yellow glass (46.9 mg).

LCMS (2 min Formic): Rt=1.10 min, [MH]⁺=352.

Example 37: rac-2-(((2S,3R,4R)-1-Acetyl-2-cyclopropyl-3-methyl-1,2,3,4-tetrahydroquinolin-4-yl)amino)benzonitrile

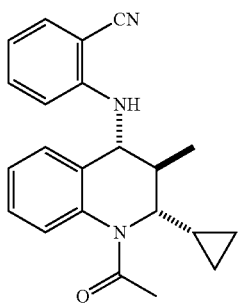 [SMILES: CC(=O)N1c2ccccc2[C@H](Nc2ccccc2C#N)[C@@H](C)[C@@H]1C1CC1]

Pd₂(dba)₃ (35.0 mg, 0.038 mmol), DavePhos (30.1 mg, 0.076 mmol) and sodium tert-butoxide (55.1 mg, 0.573 mmol) were all placed in a 2 mL microwave vial. To this was added 2-bromobenzonitrile (69.6 mg, 0.382 mmol), followed by rac-1-(2S,3R,4R)-4-amino-2-cyclopropyl-3-methyl-3,4-dihydroquinolin-1(2H)-yl)ethanone (for a preparation see Intermediate 14, 46.7 mg, 0.191 mmol) in 1,4-dioxane (2 mL). The mixture was then heated at 120° C. for 40 min in a microwave heater. The vessel was resealed and heated to 120° C. for 40 min in a microwave heater. The reaction mixture was filtered through a 2.5 g celite cartridge with ethyl acetate, collected and concentrated in vacuo. The crude product was taken up in dichloromethane and purified on a silica cartridge (10 g) by flash column chromatography, eluting with 5%-45% ethyl acetate in cyclohexane. The appropriate fractions were collected and concentrated in vacuo to afford a yellow crystalline solid (8.6 mg). The sample was dissolved in MeOH:DMSO (1 mL, 1:1) and purified by MDAP (Formic). The solvent was evaporated in vacuo to give the required product (5.0 mg).

LCMS (2 min Formic): Rt=1.16 min, [M]+=228 (loss of NHC₆H4CN⁻).

Example 38: rac-1-(((2S,3R,4R)-2-cyclopropyl-3-methyl-4-((4-methylpyrimidin-2-yl)amino)-3,4-dihydroquinolin-1(2H)-yl)ethanone

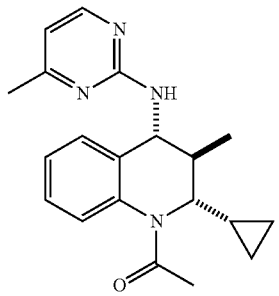 [SMILES: CC(=O)N1c2ccccc2[C@H](Nc2nccc(C)n2)[C@@H](C)[C@@H]1C1CC1]

Pd₂(dba)₃ (34.0 mg, 0.037 mmol), DavePhos (29.3 mg, 0.074 mmol) and sodium tert-butoxide (53.6 mg, 0.557 mmol) were all placed in a 2 mL microwave vial. To this was added 2-bromo-4-methylpyrimidine (73.9 mg, 0.427 mmol), followed by rac-1-((2S,3R,4R)-4-amino-2-cyclopropyl-3-methyl-3,4-dihydroquinolin-1(2H)-yl)ethanone (for a preparation see Intermediate 14, 45.4 mg, 0.186 mmol) in 1,4-dioxane (2 mL). The mixture was heated at 120° C. for 40 min in a microwave heater. A further portion of 2-bromo-4-methylpyrimidine (42.5 mg) was added, the vessel resealed and the reaction heated in a microwave heater for 20 min at 130° C. The mixture was passed through a 2.5 g celite cartridge and washed through with ethyl acetate. The collected solution was evaporated in vacuo to afford a dark brown oil. The crude product was taken up in dichloromethane and purified on a silica cartridge (10 g) by flash column chromatography, eluting with 40%-80% ethyl acetate in cyclohexane. The appropriate fractions were collected and concentrated in vacuo to afford a yellow solid (16 mg).

LCMS (2 min Formic): Rt=0.85 min, [MH]⁺=337.

Example 39: rac-1-(((2S,3R,4R)-2-cyclopropyl-4-((3-methoxypyridin-2-yl)amino)-3-methyl-3,4-dihydroquinolin-1(2H)-yl)ethanone

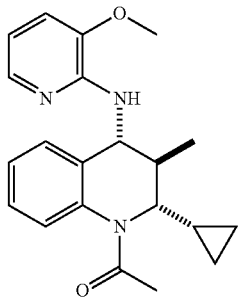 [SMILES: COc1cccnc1N[C@H]1c2ccccc2N(C(C)=O)[C@@H](C2CC2)[C@@H]1C]

Pd₂(dba)₃ (75 mg, 0.082 mmol), DavePhos (64.6 mg, 0.164 mmol) and sodium tert-butoxide (118 mg, 1.230 mmol) were all placed in a 2 mL microwave vial. To this was added 2-bromo-3-methoxypyridine (159.3 mg, 0.847 mmol), followed by rac-1-((2S,3R,4R)-4-amino-2-cyclopropyl-3-methyl-3,4-dihydroquinolin-1(2H)-yl)ethanone (for a preparation see Intermediate 14, 100.2 mg, 0.410 mmol) in 1,4-dioxane (4 mL). The mixture was heated at 120° C. for 40 min in a microwave heater. The mixture was passed through a 2.5 g celite cartridge with further 1,4-dioxane, and the concentrated in vacuo to afford a dark brown oil. This crude material was dissolved in dichloromethane and purified on a silica cartridge (10 g) by flash column chromatography, eluting with 10%-50% ethyl acetate in cyclohexane. The desired fractions were combined and concentrated in vacuo to afford the desired product as a yellow glass (126.1 mg).

LCMS (2 min Formic): Rt=0.70 min, M[H]$^+$=352.

Example 40: rac-1-(((2S,3R,4R)-2-cyclopropyl-4-((6-fluoropyridin-2-yl)amino)-3-methyl-3,4-dihydroquinolin-1(2H)-yl)ethanone

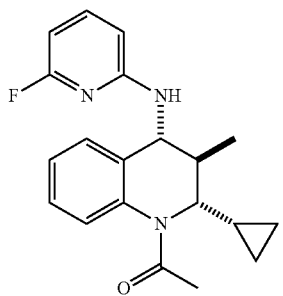

rac-1-((2S,3R,4R)-4-Amino-2-cyclopropyl-3-methyl-3,4-dihydroquinolin-1(2H)-yl)ethanone (for a preparation see Intermediate 14, 45 mg, 0.184 mmol), 2-bromo-6-fluoropyridine (64.8 mg, 0.368 mmol), DavePhos (29.0 mg, 0.074 mmol), Pd$_2$(dba)$_3$ (33.7 mg, 0.037 mmol) and sodium tert-butoxide (53.1 mg, 0.553 mmol) were combined in dry 1,4-dioxane (2 mL) in a 2 mL microwave vial. The reaction mixture was degassed for 15 min and then heated at 120° C. for 40 min in the microwave. The reaction mixture was filtered through celite and concentrated to give a crude orange oil (178 mg). This was purified on a silica cartridge (10 g) by flash column chromatography, eluting with 0-100% ethyl acetate/cyclohexane to give the desired product as an orange oil (36 mg).

LCMS (2 min Formic): Rt=1.09 min, [MH]$^+$=340.

Example 41: rac-1-((2S,3R,4R)-2-cyclopropyl-4-((5-fluoropyridin-2-yl)amino)-3-methyl-3,4-dihydroquinolin-1(2H)-yl)ethanone

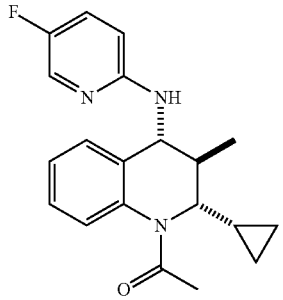

rac-1-((2S,3R,4R)-4-amino-2-cyclopropyl-3-methyl-3,4-dihydroquinolin-1(2H)-yl)ethanone (for a preparation see Intermediate 14, 48 mg, 0.196 mmol), 2-bromo-5-fluoropyridine (69.1 mg, 0.393 mmol), DavePhos (30.9 mg, 0.079 mmol), Pd$_2$(dba)$_3$ (36.0 mg, 0.039 mmol) and sodium tert-butoxide (56.6 mg, 0.589 mmol) were combined in dry 1,4-dioxane (2 mL) in a 2 mL microwave vial. The reaction mixture was degassed for 15 min and then heated at 120° C. for 40 min in the microwave. Further portions of 2-bromo-5-fluoropyridine (69.1 mg, 0.393 mmol), DavePhos (30.9 mg, 0.079 mmol), Pd$_2$(dba)$_3$ (36.0 mg, 0.039 mmol) and sodium tert-butoxide (56.6 mg, 0.589 mmol) were added and reaction mixture heated for a further 40 min at 120° C. The reaction mixture was filtered through celite and concentrated to give a crude brown oil (314 mg). This was purified on a Biotage SNAP silica cartridge (10 g) by flash column chromatography, eluting with 0-100% ethyl acetate/cyclohexane to give the product as an orange oil (49 mg). This was further purified by dissolving the crude sample in MeOH:DMSO (0.9 mL, 1:1) and purifying by MDAP (Formic). The fractions containing product were partitioned between DCM and sat. NaHCO$_3$ (aq solution). The organic layer was separated, dried (Na$_2$SO$_4$) and concentrated to give the product (22 mg, 0.065 mmol, 33.0%) as a pale yellow solid.

LCMS (2 min Formic): Rt=0.94 min, [MH]$^+$=340.

Example 42: rac-1-((2S,3R,4R)-2-cyclopropyl-4-((6-isopropoxypyridin-2-yl)amino)-3-methyl-3,4-dihydroquinolin-1(2H)-yl)ethanone

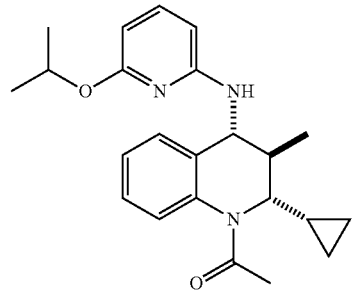 [SMILES: CC(=O)N1c2ccccc2[C@H](Nc2cccc(OC(C)C)n2)[C@@H](C)[C@@H]1C1CC1]

Pd$_2$(dba)$_3$ (39.7 mg, 0.043 mmol), DavePhos (34.1 mg, 0.087 mmol) and sodium tert-butoxide (62.4 mg, 0.650 mmol) were all placed in a 2 mL microwave vial. To this was added 2-bromo-6-isopropoxypyridine (94 mg, 0.433 mmol), followed by rac-1-((2S,3R,4R)-4-amino-2-cyclopropyl-3-methyl-3,4-dihydroquinolin-1(2H)-yl)ethanone (for a preparation see Intermediate 14, 52.9 mg, 0.217 mmol) in 1,4-dioxane (2 mL). The mixture was degassed with nitrogen for ~45 min, and then heated at 120° C. for 40 min in a microwave heater. The reaction mixture was filtered through a 2.5 g celite cartridge with 1,4-dioxane, and the collected solution concentrated in vacuo. The crude material was dissolved in dichloromethane and purified on a silica cartridge (10 g) by flash column chromatography, eluting with 0%-50% ethyl acetate in cyclohexane. The appropriate fractions were collected and evaporated in vacuo to afford the desired product as a pale yellow glass (60.1 mg).

LCMS (2 min Formic): Rt=1.23 min, [MH]$^+$=380.

Example 43: rac-1-(((2S,3R,4R)-2-cyclopropyl-4-((4-cyclopropylphenyl)amino)-3-methyl-3,4-dihydroquinolin-1(2H)-yl)ethanone

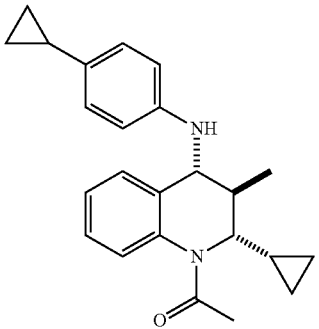 [SMILES: CC(=O)N1c2ccccc2[C@H](Nc2ccc(C3CC3)cc2)[C@@H](C)[C@@H]1C1CC1]

A mixture of rac-1-((2S,3R,4R)-4-amino-2-cyclopropyl-3-methyl-3,4-dihydroquinolin-1(2H)-yl)ethanone, hydrobromide (for a preparation see Intermediate 125, 50.5 mg, 0.155 mmol), 1-bromo-4-cyclopropylbenzene (0.042 mL, 0.311 mmol), DavePhos (6.2 mg, 0.016 mmol), $Pd_2(dba)_3$ (24.2 mg, 0.026 mmol) and sodium tert-butoxide (38.9 mg, 0.405 mmol) in 1,4-dioxane (1 mL) was heated under nitrogen at 100° C. for 100 min. The mixture was allowed to cool to rt and was filtered through a 2.5 g celite cartridge, washing with ethyl acetate (3×5 mL). The combined filtrate was evaporated under a stream of nitrogen and the residue was re-dissolved in methanol/DMSO (1 mL, 9:1) and was purified by MDAP (Formic). The required fraction was evaporated under a stream of nitrogen to give the desired product as an orange/brown gum (21.8 mg, 0.060 mmol, 38.9%)

LCMS (2 min Formic): Rt=1.31 min, $[MH]^+$=361.

Example 44: rac-4-(((2S,3R,4R)-1-Acetyl-2-cyclopropyl-3-methyl-1,2,3,4-tetrahydroquinolin-4-yl)amino)-N-methylbenzamide

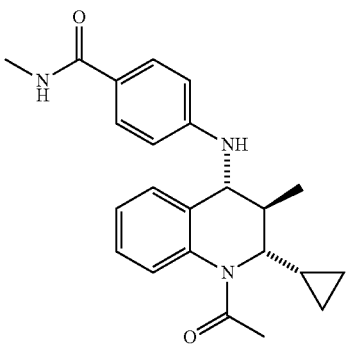 [SMILES: CNC(=O)c1ccc(N[C@H]2c3ccccc3N(C(C)=O)[C@@H](C3CC3)[C@@H]2C)cc1]

$Pd_2(dba)_3$ (27.5 mg, 0.030 mmol), DavePhos (23.65 mg, 0.060 mmol) and sodium tert-butoxide (43.3 mg, 0.451 mmol) were all placed in a 2-5 mL microwave vial. To this was added 4-bromo-N-methylbenzamide (64.3 mg, 0.300 mmol), followed by a fine suspension of rac-1-((2S,3R,4R)-4-amino-2-cyclopropyl-3-methyl-3,4-dihydroquinolin-1(2H)-yl)ethanone (for a preparation see Intermediate 14, 36.7 mg, 0.150 mmol) in 1,4-dioxane (2 mL). The mixture was heated at 120° C. for 40 min in a microwave heater. The mixture was filtered through a 2.5 g celite cartridge, washed through with ethyl acetate and concentrated in vacuo to afford a viscous orange liquid. This crude material was taken up in dichloromethane and purified on a silica cartridge (10 g) by flash column chromatography, eluting with 25%-100% ethyl acetate in cyclohexane. The appropriate fractions were collected and evaporated in vacuo to afford a yellow glass. The sample was dissolved in MeOH:DMSO (1 mL, 1:1) and purified by MDAP (Formic). The solvent was evaporated in vacuo to give the required product (5.8 mg). LCMS (2 min formic): Rt=0.89 min, $[MH]^+$=378.

Example 45: rac-6-(((2S,3R,4R)-1-Acetyl-2-cyclopropyl-3-methyl-1,2,3,4-tetrahydroquinolin-4-yl)amino)nicotinonitrile

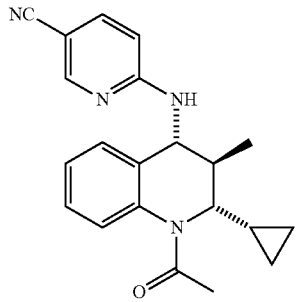 [SMILES: CC(=O)N1c2ccccc2[C@H](Nc2ccc(C#N)cn2)[C@@H](C)[C@@H]1C1CC1]

rac-1-((2S,3R,4R)-4-amino-2-cyclopropyl-3-methyl-3,4-dihydroquinolin-1(2H)-yl)ethanone (for a preparation see Intermediate 14, 41 mg, 0.168 mmol) was dissolved in dimethyl sulfoxide (DMSO) (0.9 mL). 6-Chloronicotinonitrile (46.5 mg, 0.336 mmol) and DIPEA (0.088 mL, 0.503 mmol) were added and reaction mixture was heated in a microwave vial at 200° C. for 2 h. The crude reaction mixture was dissolved in MeOH:DMSO (0.9 mL, 1:1) and purified by MDAP (Formic). The fractions containing product were partitioned between DCM and sat. $NaHCO_3$ (aq solution). The organic layer was separated, dried ($Na_2SO_4$) and concentrated to give the product (15 mg, 0.043 mmol, 25.8%) as a yellow solid. LCMS (2 min Formic): Rt=0.98 min, $[MH]^+$=347.

Example 46: rac-methyl 4-(((2S,3R,4R)-1-Acetyl-2-cyclopropyl-3-methyl-1,2,3,4-tetrahydroquinolin-4-yl)amino)benzoate

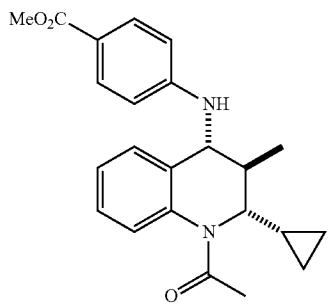 [SMILES: COC(=O)c1ccc(N[C@H]2c3ccccc3N(C(C)=O)[C@@H](C3CC3)[C@@H]2C)cc1]

$Pd_2(dba)_3$ (107 mg, 0.117 mmol), DavePhos (92 mg, 0.233 mmol) and sodium tert-butoxide (168 mg, 1.750 mmol) were all placed in a 2-5 mL microwave vial. To this was added methyl 4-bromobenzoate (251 mg, 1.166 mmol), followed by a fine suspension of rac-1-((2S,3R,4R)-4-amino-2-cyclopropyl-3-methyl-3,4-dihydroquinolin-1(2H)-yl)ethanone (for a preparation see Intermediate 14, 142.5 mg, 0.583 mmol) in 1,4-dioxane (5 mL). The mixture was heated at 120° C. for 40 min in a microwave heater. The reaction vessel was resealed and heated in a microwave heater for a further 20 min at 140° C. The mixture was filtered through a 2.5 g celite cartridge, washed through with ethyl acetate and concentrated in vacuo to afford a yellow crystalline solid. The crude material was taken up in dichloromethane and purified on a silica cartridge (10 g) by flash column chromatography, eluting with 0%-35% ethyl acetate in cyclohexane. The appropriate fractions were collected and evaporated in vacuo to afford a yellow crystalline solid (51.2 mg).

LCMS (2 min Formic): Rt=1.12 min, [M]+=228 (loss of NHC$_6$H$_4$CO$_2$CH$_3$$^-$).

Example 47: rac-1-((2S,3R,4R)-2-cyclopropyl-4-((6-hydroxypyridin-2-yl)amino)-3-methyl-3,4-dihydroquinolin-1(2H)-yl)ethanone

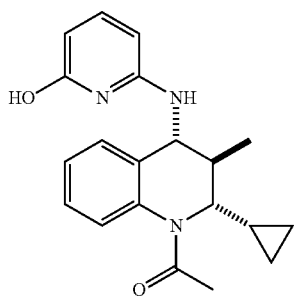

A stirring solution of sodium iodide (104 mg, 0.693 mmol) and rac-1-((2S,3R,4R)-2-cyclopropyl-4-((6-methoxypyridin-2-yl)amino)-3-methyl-3,4-dihydroquinolin-1(2H)-yl)ethanone (for a preparation see Example 36, 48.7 mg, 0.139 mmol) in acetonitrile (1.2 mL) was treated with TMSCl, (0.176 mL, 0.139 mmol, 10% v/v in acetonitrile). The mixture was heated to reflux for ~16 h. A further 1.0 eq of 10% v/v TMSCl in acetonitrile solution was added, and the reaction mixture continued to stir at reflux for a further 2 h. The mixture was allowed to cool, and then quenched with methanol (10 mL). The mixture was allowed to stir at rt for ~90 min. The mixture was then concentrated in vacuo, dissolved in ethyl acetate and separated with water. The organic layer was washed with water (3×50 mL) and then saturated aqueous sodium chloride solution. The organic layer was dried over magnesium sulphate and concentrated in vacuo. The crude residue was taken up in dichloromethane and purified on a silica cartridge (10 g) by flash column chromatography, eluting with 0-5% methanol in dichloromethane. The appropriate fractions were combined and concentrated in vacuo to afford a white crystalline solid (18.5 mg). LCMS (2 min Formic): Rt=0.76 min, [MH]$^+$=338.

Example 48: rac-1-((2S,3R,4R)-2-cyclopropyl-3-methyl-4-((6-methylpyrazin-2-yl)amino)-3,4-dihydroquinolin-1(2H)-yl)ethanone

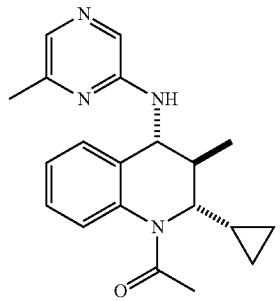 [SMILES: CC(=O)N1c2ccccc2[C@H](Nc2cncc(C)n2)[C@@H](C)[C@@H]1C1CC1]

Pd$_2$(dba)$_3$ (38.4 mg, 0.042 mmol), DavePhos (33.0 mg, 0.084 mmol) and sodium tert-butoxide (60.4 mg, 0.629 mmol) were all placed in a 2 mL microwave vial. To this was added 2-bromo-6-methylpyrazine (81 mg, 0.469 mmol), followed by rac-1-((2S,3R,4R)-4-amino-2-cyclopropyl-3-methyl-3,4-dihydroquinolin-1(2H)-yl)ethanone (for a preparation see Intermediate 14, 51.2 mg, 0.210 mmol) in 1,4-dioxane (2 mL). The mixture was heated at 120° C. for 40 min in a microwave heater. The reaction mixture was passed through a 2.5 g celite cartridge and washed through with 3 CVs of ethyl acetate. The solution was evaporated in vacuo to afford a deep orange oil. The crude product was taken up in dichloromethane and purified on a silica cartridge (25 g) by flash column chromatography, eluting with 30%-70% ethyl acetate in cyclohexane. The appropriate fractions were collected and concentrated in vacuo to afford a yellow solid (40.6 mg).

LCMS (2 min Formic): Rt=0.91 min, [MH]$^+$=337.

Example 49: rac-1-((2S,3R,4R)-2-cyclopropyl-4-((3-hydroxypyridin-2-yl)amino)-3-methyl-3,4-dihydroquinolin-1(2H)-yl)ethanone

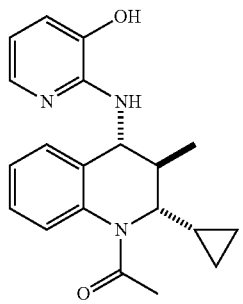 [SMILES: CC(=O)N1c2ccccc2[C@H](Nc2ncccc2O)[C@@H](C)[C@@H]1C1CC1]

To a stirring solution of rac-1-((2S,3R,4R)-2-cyclopropyl-4-((3-methoxypyridin-2-yl)amino)-3-methyl-3,4-dihydroquinolin-1(2H)-yl)ethanone (for a preparation see Example 39, 47 mg, 0.134 mmol) in dichloromethane (DCM) (1 mL), cooled to 0° C. under nitrogen, was added boron tribromide (0.655 mL, 0.655 mmol, 1M in DCM). The mixture was stirred at 0° C. for 2 h. The mixture was allowed to warm to rt over 40 min and stirred for a further 55 min at rt. The reaction was quenched with methanol (~6 mL) at 0° C. and concentrated in vacuo to afford a brown liquid. The concentrated mixture was taken up in methanol and purified on a silica cartridge (10 g) by flash column chromatography, eluting with 0-10% methanol in dichloromethane. The fractions containing product were collected and concentrated in vacuo. The sample was dissolved in MeOH:DMSO (1 mL, 1:1) and purified by MDAP (Formic). The solvent was evaporated in vacuo to give the required product (2.9 mg). LCMS (2 min Formic): Rt=0.65 min, [MH]⁺=338.

Example 50: rac-6-(((2S,3R,4R)-1-acetyl-2-cyclopropyl-3-methyl-1,2,3,4-tetrahydroquinolin-4-yl)amino)picolinonitrile

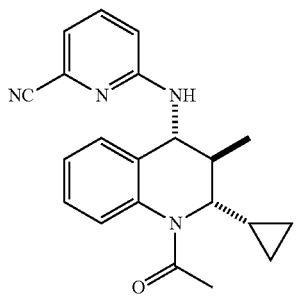

rac-1-((2S,3R,4R)-4-amino-2-cyclopropyl-3-methyl-3,4-dihydroquinolin-1(2H)-yl)ethanone (for a preparation see Intermediate 14, 48 mg, 0.196 mmol) was dissolved in dimethyl sulfoxide (DMSO) (0.9 mL). 6-chloropicolinonitrile (54.4 mg, 0.393 mmol) and DIPEA (0.103 mL, 0.589 mmol) were added and reaction was heated in a microwave vial at 200° C. for 2 h. The crude reaction mixture was dissolved in MeOH:DMSO (0.9 mL, 1:1) and purified by MDAP (Formic). The fractions containing product were partitioned between DCM and sat. NaHCO₃ (aq solution). The organic layer was separated, dried (Na₂SO₄) and concentrated to give the product (5.5 mg, 0.016 mmol, 8.08%) as a pale yellow oil. LCMS (2 min Formic): Rt=1.04 min, [MH]⁺=347.

Example 51: rac-1-((2S,3R,4R)-2-cyclobutyl-3-methyl-4-(phenylamino)-3,4-dihydroquinolin-1(2H)-yl)ethanone

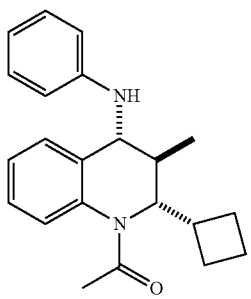 [SMILES: CC(=O)N1c2ccccc2[C@H](Nc2ccccc2)[C@@H](C)[C@@H]1C1CCC1]

A 0.5-2 mL microwave vessel was charged with a magnetic stirrer bar, sodium tert-butoxide (45 mg, 0.468 mmol), Pd₂(dba)₃ (14 mg, 0.015 mmol), DavePhos (12 mg, 0.030 mmol), rac-1-((2S,3R,4R)-4-amino-2-cyclobutyl-3-methyl-3,4-dihydroquinolin-1(2H)-yl)ethanone (for a preparation see Intermediate 18, 80 mg, 0.31 mmol), bromobenzene (0.035 mL, 0.332 mmol) and anhydrous 1,4-dioxane (1.0 mL). The vessel was sealed and nitrogen was bubbled through the reaction mixture for 5 min. The reaction was heated in a using a microwave reactor at 120° C. for 30 min. The reaction mixture was filtered through celite and washed with EtOAc (8 mL). The filtrate was evaporated under vacuum and the residue purified by MDAP (Formic). The appropriate fractions were combined and the solvent evaporated in vacuo to give the product as an off-white solid (32 mg, 0.096 mmol, 31%).
LCMS (2 min Formic): Rt=1.24 min, [MH]⁺=335.

Example 52: rac-1-((2S,3R,4R)-2-isopropyl-3-methyl-4-(phenylamino)-3,4-dihydroquinolin-1(2H)-yl)ethanone

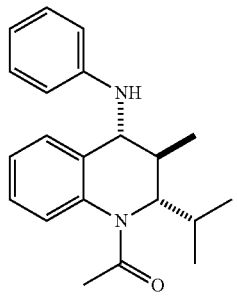 [SMILES: CC(=O)N1c2ccccc2[C@H](Nc2ccccc2)[C@@H](C)[C@@H]1C(C)C]

A 0.5-2 mL microwave vessel was charged with a magnetic stirrer bar, sodium tert-butoxide (70 mg, 0.728 mmol), Pd₂(dba)₃ (23 mg, 0.025 mmol), DavePhos (19 mg, 0.048 mmol), rac-1-((2S,3R,4R)-4-amino-2-isopropyl-3-methyl-3,4-dihydroquinolin-1(2H)-yl)ethanone (for a preparation see Intermediate 21, 120 mg, 0.487 mmol), bromobenzene (0.051 mL, 0.487 mmol) and anhydrous 1,4-dioxane (4 mL). The vessel was sealed and nitrogen was bubbled through the reaction mixture for 5 min. The reaction was heated in a microwave reactor at 110° C. for 30 min. The reaction mixture was filtered through celite and washed with EtOAc (10 mL). The filtrate was evaporated under vacuum and the residue purified by MDAP (Formic). The appropriate fractions were combined and the solvent was removed by rotary evaporation to give the product as an off-white solid (80 mg, 0.248 mmol, 51%).
LCMS (2 min Formic): Rt=1.21 min, [MH]⁺=323.

Example 53: rac-1-((2S,3R,4R)-3-methyl-4-(phenylamino)-2-(2,2,2-trifluoroethyl)-3,4-dihydroquinolin-1(2H)-yl)ethanone

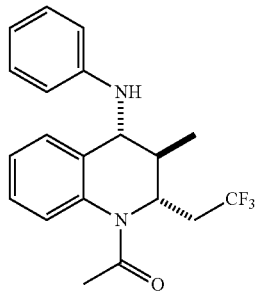 [SMILES: CC(=O)N1c2ccccc2[C@H](Nc2ccccc2)[C@@H](C)[C@@H]1CC(F)(F)F]

A 0.5-2 mL microwave vessel was charged with a magnetic stirrer bar, sodium tert-butoxide (45 mg, 0.468 mmol), Pd$_2$(dba)$_3$ (14 mg, 0.015 mmol), DavePhos (12 mg, 0.030 mmol), rac-1-((2S,3R,4R)-4-amino-3-methyl-2-(2,2,2-trifluoroethyl)-3,4-dihydroquinolin-1(2H)-yl)ethanone (90 mg, 0.314 mmol), bromobenzene (for a preparation see Intermediate 24, 0.035 mL, 0.332 mmol) and anhydrous 1,4-dioxane (1.25 mL). The vessel was sealed and nitrogen was bubbled through the reaction mixture for 5 min. The reaction was heated in a microwave reactor at 120° C. for 30 min. The reaction mixture was filtered through celite and washed with EtOAc (8 mL). The filtrate was evaporated under vacuum and the residue purified by MDAP (Formic). The desired product was sent to the waste and so the waste was evaporated under vacuum. The residue was purified by MDAP (Formic). The appropriate fractions were combined and the solvent evaporated in vacuo to give the product as a light brown foam (53 mg, 0.146 mmol, 47%). LCMS (2 min Formic): Rt=1.18 min, [MH]$^+$=363.

Example 54: rac-1-((2R,3R,4R)-2-(methoxymethyl)-3-methyl-4-(phenylamino)-3,4-dihydroquinolin-1(2H)-yl)ethanone

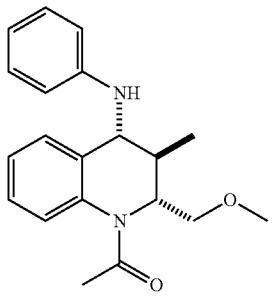 [SMILES: COC[C@H]1[C@H](C)[C@@H](Nc2ccccc2)c2ccccc2N1C(C)=O]

To a solution of rac-1-((2R,3R,4R)-2-(hydroxymethyl)-3-methyl-4-(phenylamino)-3,4-dihydroquinolin-1(2H)-yl)ethanone (for a preparation see Intermediate 29, 36 mg, 0.116 mmol) in anhydrous THF (1 mL) was added sodium hydride (60% in mineral oil) (6 mg, 0.150 mmol) and the mixture stirred under nitrogen at 0° C. for 15 min. Methyl iodide (7.5 µl, 0.120 mmol) was added and the mixture stirred at rt for 5 h. The reaction mixture was quenched by the addition of water (3 mL) and the mixture extracted with EtOAc (3 mL). The organic extract was washed with water (3 mL) and dried through a hydrophobic frit. The solvent was removed under vacuum and the residue was purified by MDAP (Formic). The appropriate fractions were combined and the solvent removed by rotary evaporation to give the product as a colourless gum (11 mg, 0.034 mmol, 29%).

LCMS (2 min Formic): Rt=1.07 min, [MH]$^+$=325.

Example 55: rac-1-((2S,3R,4R)-2-cyclopropyl-3-methyl-4-(phenylamino)-3,4-dihydroquinolin-1(2H)-yl)propan-1-one

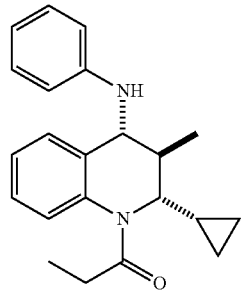 [SMILES: CCC(=O)N1c2ccccc2[C@H](Nc2ccccc2)[C@@H](C)[C@@H]1C1CC1]

A mixture of rac-1-((2S,3R,4R)-4-amino-2-cyclopropyl-3-methyl-3,4-dihydroquinolin-1(2H)-yl)propan-1-one hydrobromide (for a preparation see Intermediate 31, 80 mg, 0.236 mmol), bromobenzene (0.05 mL, 0.471 mmol), DavePhos (10 mg, 0.025 mmol), Pd$_2$(dba)$_3$ (33 mg, 0.036 mmol) and sodium tert-butoxide (60 mg, 0.62 mmol) in 1,4-dioxane (2 mL) was heated under nitrogen at 100° C. for 90 min. The mixture was allowed to cool to rt and was filtered through a 2.5 g celite cartridge, washing with ethyl acetate (3×5 mL). The combined filtrate was evaporated under a stream of nitrogen and the residue was re-dissolved in 9:1 methanol/DMSO (1 mL) and was purified by MDAP (Formic) (1 mL injection). As all of the sample was not injected, a further purification using the remaining crude solution was undertaken (1 mL injection; formic). The required fractions were combined and evaporated in vacuo to give the desired product as a pale yellow crunchy foam (65 mg, 0.196 mmol, 83%). LCMS (2 min Formic): Rt=1.26 min, [MH]$^+$=335.

Example 56: rac-1-((2S,3R,4R)-2-cyclopropyl-3-methyl-4-((6-methylpyridin-2-yl)amino)-3,4-dihydroquinolin-1(2H)-yl)propan-1-one

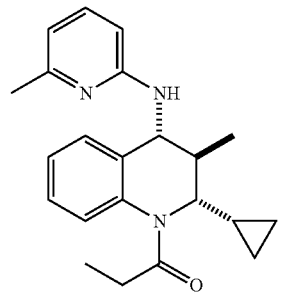 [SMILES: CCC(=O)N1c2ccccc2[C@H](Nc2cccc(C)n2)[C@@H](C)[C@@H]1C1CC1]

rac-1-((2S,3R,4R)-4-amino-2-cyclopropyl-3-methyl-3,4-dihydroquinolin-1(2H)-yl)propan-1-one (for a preparation see Intermediate 31, 58 mg, 0.224 mmol), 2-bromo-6-methylpyridine (77 mg, 0.45 mmol), DavePhos (35 mg, 0.09 mmol), Pd$_2$(dba)$_3$ (41 mg, 0.045 mmol) and sodium tert-butoxide (65 mg, 0.673 mmol) were combined in dry 1,4-dioxane (2 mL) in a 2 mL microwave vial. The reaction mixture was degassed for 15 min and then heated at 120° C. for 40 min in the microwave. The reaction mixture was filtered through celite and concentrated to give 180 mg of crude brown oil. This was purified by chromatography on silica gel (10 g) eluting with 0-50% ethyl acetate/cyclohexane over 120 mL to give the product (60 mg, 0.172 mmol, 76%) as a yellow oil.

LCMS (2 min HpH): Rt=0.77 min, [MH]$^+$=350.

Example 57: rac-1-((2S,3S,4R)-2-cyclopropyl-3-methyl-4-(methyl(phenyl)amino)-3,4-dihydroquinolin-1(2H)-yl)ethanone

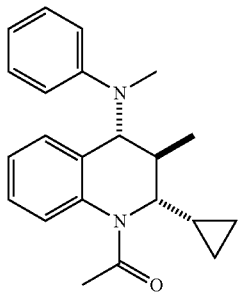 [SMILES: CC(=O)N1c2ccccc2[C@H](N(C)c2ccccc2)[C@@H](C)[C@@H]1C1CC1]

To a solution of rac-(2S,3S,4R)-2-cyclopropyl-N,3-dimethyl-N-phenyl-1,2,3,4-tetrahydroquinolin-4-amine (for a preparation see Intermediate 34, 70 mg, 0.239 mmol) and pyridine (0.077 mL, 0.96 mmol) in dichloromethane (DCM) (1.04 mL) stirred under nitrogen was added acetyl chloride (0.026 mL, 0.36 mmol) drop-wise. The reaction mixture was stirred at rt for 30 min. The reaction mixture was partitioned between dichloromethane (10 mL) and saturated sodium bicarbonate solution (10 mL). The aqueous layer was extracted with DCM (10 mL) and the combined organics dried through a phase separator and evaporated to dryness. The crude product was added to a 25 g silica gel column and was eluted with 10-30% EtOAc/cyclohexane. Collected fractions were evaporated to afford the product (50 mg, 0.147 mmol, 61%). A second batch of less pure material (90%) was also collected (10 mg). LCMS (2 min Formic): Rt=1.36 min, [MH]$^+$=335.

Example 58: rac-1-((2S,3R,4R)-6-methoxy-2,3-dimethyl-4-(phenylamino)-3,4-dihydroquinolin-1(2H)-yl)ethanone

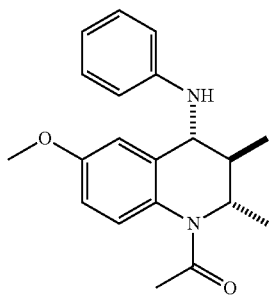

A mixture of rac-1-((2S,3R,4R)-4-amino-6-methoxy-2,3-dimethyl-3,4-dihydroquinolin-1(2H)-yl)ethanone (for a preparation see Intermediate 37, 521 mg, 2.10 mmol), bromobenzene (0.287 mL, 2.73 mmol), DavePhos (82 mg, 0.209 mmol), Pd$_2$(dba)$_3$ (188.7 mg, 0.206 mmol) and sodium tert-butoxide (334 mg, 3.48 mmol) in 1,4-dioxane (20 mL) was heated under nitrogen at 100° C. for 1.5 h. After leaving to stand at rt for 17 h, further bromobenzene (0.144 mL, 1.367 mmol) was added and the stirred mixture was heated for a further 3 hours at 100° C. After cooling further tris(dibenzylideneacetone)dipalladium (0) (Pd$_2$(dba)$_3$) (90 mg, 0.099 mmol) was added and heating at 100° C. was continued for a further 3.5 h. The reaction mixture was filtered through a 10 g celite cartridge, which was subsequently eluted with ethyl acetate (3×20 mL). The combined filtrate was evaporated in vacuo and the residue was loaded in dichloromethane (~10 mL) onto a 50 g silica cartridge and was purified by flash column chromatography eluting with a gradient of 0-50% ethyl acetate in dichloromethane. The required fractions were combined and evaporated in vacuo to give the desired product as an orange crunchy foam (268 mg, 0.825 mmol, 39%).

LCMS (2 min Formic): Rt=1.09 min, [MH]$^+$=325.

Example 59: rac-1-((2S,3R,4R)-6-hydroxy-2,3-dimethyl-4-(phenylamino)-3,4-dihydroquinolin-1(2H)-yl)ethanone

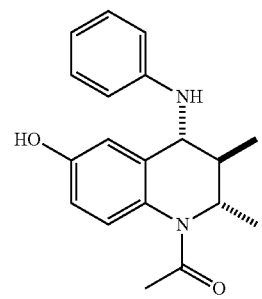 [SMILES: CC(=O)N1c2ccc(O)cc2[C@H](Nc2ccccc2)[C@@H](C)[C@@H]1C]

To a stirred solution of rac-1-((2S,3R,4R)-6-methoxy-2,3-dimethyl-4-(phenylamino)-3,4-dihydroquinolin-1(2H)-yl) ethanone (for a preparation see Example 58, 265 mg, 0.816 mmol) in dichloromethane (DCM) (10 mL) cooled to 0° C. (ice bath) under nitrogen was added boron tribromide (1M solution in dichloromethane) (4.0 mL, 4.00 mmol). After 90 min the cooling bath was removed and the mixture allowed to warm to rt. After stirring at rt for 1 h 2M hydrochloric acid (5 mL) was added carefully to the mixture and stirring was continued for 5 min. The phases were separated and water (5 mL) was added to the aqueous phase which was extracted with ethyl acetate (2×15 mL). The combined organic phases (dichloromethane and ethyl acetate) were dried (MgSO$_4$), filtered and evaporated to give a residue which was loaded in 10:1 dichloromethane/methanol (~10 mL) onto a 25 g silica cartridge and was purified by flash column chromatography eluting with a gradient of 0-80% ethyl acetate in dichloromethane. The required fractions were combined and evaporated in vacuo to give the desired product as a yellow crystalline solid (122 mg, 0.393 mmol, 48%).

LCMS (2 min Formic): Rt=0.91 min, [MH]$^+$=311.

Example 60: rac-(2S,3R,4R)-1-acetyl-2,3-dimethyl-4-(phenylamino)-1,2,3,4-tetrahydroquinolin-6-yl trifluoromethanesulfonate

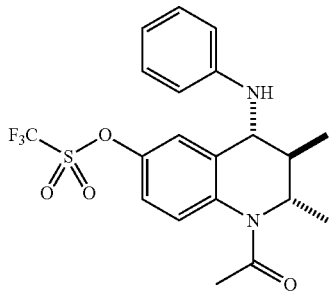 [SMILES: CC(=O)N1c2ccc(OS(=O)(=O)C(F)(F)F)cc2[C@H](Nc2ccccc2)[C@@H](C)[C@@H]1C]

To a stirred solution of rac-1-((2S,3R,4R)-6-hydroxy-2,3-dimethyl-4-(phenylamino)-3,4-dihydroquinolin-1(2H)-yl)ethanone (for a preparation see Example 59, 119 mg, 0.382 mmol) in dry tetrahydrofuran (THF) (3 mL) cooled to 0° C. (ice bath) and stirred under nitrogen was added sodium tert-butoxide (43 mg, 0.45 mmol). After 5 minutes 1,1,1-trifluoro-N-phenyl-N-((trifluoromethyl)sulfonyl)methanesulfonamide (152 mg, 0.424 mmol) was added and stirring continued. After 3 h further 1,1,1-trifluoro-N-phenyl-N-((trifluoromethyl)sulfonyl)methanesulfonamide (41 mg, 0.115 mmol) was added to the mixture and stirring continued for a further 15 min. After a total of 4 h stirring at 0° C. the mixture was allowed to warm to rt and was partitioned between saturated aqueous sodium bicarbonate solution (5 mL) and ethyl acetate (5 mL). The phases were separated and the aqueous phase extracted with further ethyl acetate (3×5 mL). The combined organic phases were filtered through a cartridge fitted with a hydrophobic frit and evaporated under a stream of nitrogen. The residue was loaded in dichloromethane (~2 mL) onto a 10 g silica cartridge and was purified by flash column chromatography eluting with a gradient of 0-60% ethyl acetate in dichloromethane. The required fractions were combined and evaporated in vacuo to give the desired product as a yellow solid (133 mg, 0.301 mmol, 79%).

LCMS (2 min Formic): Rt=1.25 min, $[MH]^+$=443.

Example 61: rac-1-((2S,3R,4R)-2-ethyl-6-fluoro-3-methyl-4-((6-methylpyridin-2-yl)amino)-3,4-dihydroquinolin-1(2H)-yl)ethanone

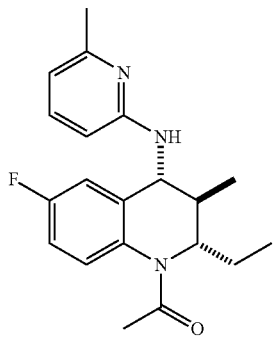 [SMILES: CC[C@H]1[C@H](C)[C@@H](Nc2cccc(C)n2)c2cc(F)ccc2N1C(C)=O]

To a reaction vessel, rac-1-((2S,3R,4R)-4-amino-2-ethyl-6-fluoro-3-methyl-3,4-dihydroquinolin-1(2H)-yl)ethanone (for a preparation see Intermediate 40, 50 mg, 0.20 mmol), DavePhos (12 mg, 0.03 mmol), $Pd_2(dba)_3$ (27 mg, 0.03 mmol) and sodium tert-butoxide (65 mg, 0.676 mmol) were added in 1,4-dioxane (5 mL). 2-Bromo-6-methylpyridine (0.034 mL, 0.30 mmol) was added and the reaction left to stir at 100° C. under nitrogen for 3 h. The mixture was filtered through celite and the celite washed with ethyl acetate (2×10 mL). The combined filtrates were washed with water (2×25 mL) and the layers separated. The organic layer was passed through a hydrophobic frit and concentrated in vacuo to give an orange solid. This was purified by chromatography on silica gel (10 g) eluting with 0-75% ethyl acetate/cyclohexane. The fractions containing only product were combined and concentrated in vacuo to give the product (22 mg, 0.064 mmol, 32%) as a yellow solid. LCMS (2 min Formic): Rt=0.69 min, $[MH]^+$=342.

Example 62: rac-4-(((2S,3R,4R)-1-acetyl-2-ethyl-6-fluoro-3-methyl-1,2,3,4-tetrahydroquinolin-4-yl)amino)benzonitrile

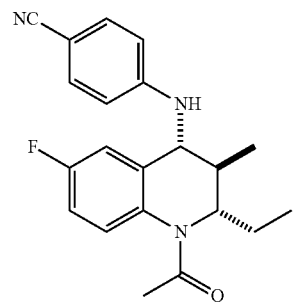 [SMILES: CC[C@H]1[C@H](C)[C@@H](Nc2ccc(C#N)cc2)c2cc(F)ccc2N1C(C)=O]

To a reaction vessel rac-1-((2S,3R,4R)-4-amino-2-ethyl-6-fluoro-3-methyl-3,4-dihydroquinolin-1(21)-yl)ethanone (for a preparation see Intermediate 40, 171 mg, 0.68 mmol), DavePhos (54 mg, 0.137 mmol), sodium tert-butoxide (250 mg, 2.60 mmol) and $Pd_2(dba)_3$ (100 mg, 0.109 mmol) were added in 1,4-dioxane (5 mL). 4-Bromobenzonitrile (187 mg, 1.03 mmol) was added and the vessel heated to 100° C. for 3 h whilst stirring. The reaction mixture was filtered through celite and the celite washed with ethyl acetate (2×15 mL). The combined filtrates were washed with water (2×30 mL) and separated. The organic layer was passed through a hydrophobic frit and concentrated in vacuo to give 450 mg of a brown gum. This was purified by chromatography on silica gel (25 g) eluting with 0-35% ethyl acetate/cyclohexane. No product was isolated so the column was run again with 0-10% DCM/methanol and the fractions containing pure product were combined and concentrated in vacuo to give 64 mg of product as a yellow solid. The fractions containing impure product were combined and concentrated in vacuo to give 161 mg of impure brown gum. The impure product was purified by chromatography on silica gel (10 g) eluting with cyclohexane/ethyl acetate (0-50%). The fractions containing product were combined and concentrated in vacuo to give a yellow solid. This was combined with the earlier material to give the product (74 mg) as a yellow solid.

LCMS (2 min Formic): Rt=1.10 min, $[MH]^+$=352.

Example 63: rac-1-((2S,3R,4R)-2-cyclopropyl-7-fluoro-3-methyl-4-((6-methylpyridin-2-yl)amino)-3,4-dihydroquinolin-1(2H)-yl)ethanone

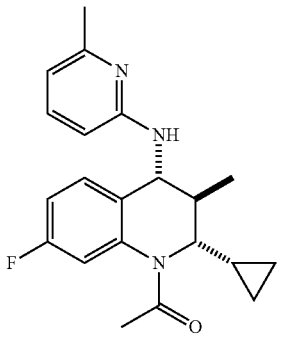 [SMILES: CC(=O)N1c2cc(F)ccc2[C@H](Nc2cccc(C)n2)[C@@H](C)[C@@H]1C1CC1]

A mixture of 2-bromo-6-methylpyridine (0.13 mL, 1.115 mmol), rac-1-((2S,3R,4R)-4-amino-2-cyclopropyl-7-fluoro-3-methyl-3,4-dihydroquinolin-1(2H)-yl)ethanone (for a preparation see Intermediate 43, 146 mg, 0.56 mmol), DavePhos (22 mg, 0.056 mmol), Pd$_2$(dba)$_3$ (74 mg, 0.081 mmol), sodium tert-butoxide (90 mg, 0.93 mmol)) in 1,4-dioxane (10 mL) was heated to 100° C. for 2 h under nitrogen. The reaction mixture was filtered through a celite cartridge, washed with ethyl acetate and the solvent was evaporated under a stream of nitrogen to give a dark red gum residue. The residue was re-dissolved in methanol (3 mL) and purified by MDAP (HpH). The third injection was made up of the remaining sample of the first two MDAP runs, the appropriate fractions were combined and evaporated under a stream of nitrogen to give the product (45 mg). This sample was re-dissolved in methanol (1 mL) and again purified MDAP (HpH). The appropriate fractions were combined and evaporated under a stream of nitrogen to give the final product (38 mg).

LCMS (2 min Formic): Rt=1.17 min, [MH]$^+$=354.

Example 64: rac-1-((2S,3R,4R)-2-cyclopropyl-7-methoxy-3-methyl-4-((6-methylpyridin-2-yl)amino)-3,4-dihydroquinolin-1(2H)-yl)ethanone formic acid salt

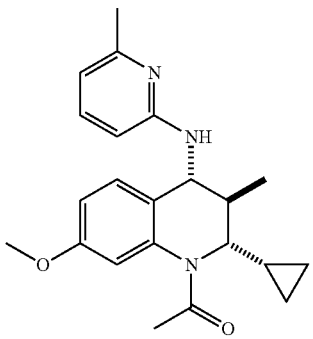 [SMILES: COc1ccc2c(c1)N(C(C)=O)[C@@H](C1CC1)[C@H](C)[C@H]2Nc1cccc(C)n1]

A mixture of 2-bromo-6-methylpyridine (0.17 mL, 1.46 mmol), DavePhos (29 mg, 0.073 mmol), Pd$_2$(dba)$_3$ (101 mg, 0.11 mmol), and sodium tert-butoxide (111 mg, 1.16 mmol) was added to rac-1-((2S,3R,4R)-4-amino-2-cyclopropyl-7-methoxy-3-methyl-3,4-dihydroquinolin-1(2H)-yl)ethanone (for a preparation see Intermediate 46, 200 mg, 0.73 mmol) in 1,4-dioxane (10 mL) and heated to 100° C. for 2 h under nitrogen. The reaction mixture was filtered through a celite cartridge, washed with ethyl acetate and the solvent was evaporated under a stream of nitrogen to give a dark red gum residue. The residue was re-dissolved in methanol (3 mL) and purified by MDAP (Formic). The appropriate fractions were collected and evaporated under a stream of nitrogen to give the desired product (146 mg). LCMS (2 min Formic): Rt=0.68 min, [MH]$^+$=366.

Example 65: rac-1-((2S,3R,4R)-2-cyclopropyl-7-hydroxy-3-methyl-4-((6-methylpyridin-2-yl)amino)-3,4-dihydroquinolin-1(2H)-yl)ethanone

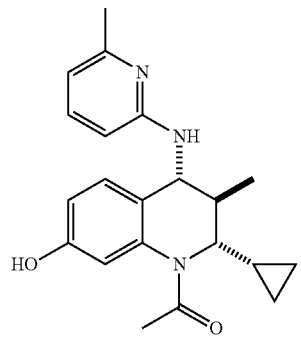 [SMILES: CC(=O)N1c2cc(O)ccc2[C@H](Nc2cccc(C)n2)[C@@H](C)[C@@H]1C1CC1]

To a stirred solution of rac-1-((2S,3R,4R)-2-cyclopropyl-7-methoxy-3-methyl-4-((6-methyl pyridin-2-yl)amino)-3,4-dihydroquinolin-1(2H)-yl)ethanone, formic acid salt (for a preparation see Example 64, 100 mg, 0.243 mmol) in dichloromethane (DCM) (3 mL) cooled to 0° C. under nitrogen was added boron tribromide (0.115 mL, 1.215 mmol) and the reaction was stirred for 90 min. The reaction mixture was removed from the ice bath and gradually warmed to 20° C. where stirring continued for 60 min. Hydrochloric acid (2M, 1 mL) was carefully added and stirring continued for 5 min. The phases were separated and water (1 mL) was added to the aqueous phase which was extracted with ethyl acetate (2×3 mL). The organic phases were combined and passed through a hydrophobic frit and solvent evaporated under a stream of nitrogen. The yellow residue was re-dissolved in methanol (1 mL) and purified by MDAP (HpH) and appropriate fractions were combined and collected. The solvent was evaporated under a stream of nitrogen. Due to a high percent of impurity, purification was repeated twice by MDAP (Formic) repeating the procedure above to give the product as a colourless glass (3 mg, 8.54 µmol, 4%). LCMS (2 min Formic): Rt=0.59 min, [MH]$^+$=352.

Example 66: rac-(2S,3R,4R)-1-acetyl-2-cyclopropyl-3-methyl-4-((6-methylpyridin-2-yl)amino)-1,2,3,4-tetrahydroquinoline-6-carbonitrile

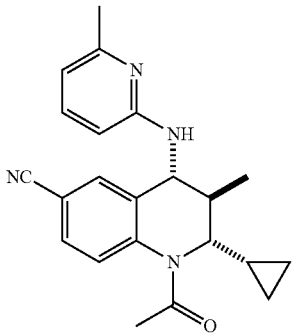 [SMILES: CC(=O)N1c2ccc(C#N)cc2[C@H](Nc2cccc(C)n2)[C@@H](C)[C@@H]1C1CC1]

The 2-bromo-6-methylpyridine (0.043 mL, 0.371 mmol), rac-(2S,3R,4R)-1-acetyl-4-amino-2-cyclopropyl-3-methyl-1,2,3,4-tetrahydroquinoline-6-carbonitrile (for preparation see Intermediate 49, 50 mg, 0.186 mmol), DavePhos (7 mg, 0.02 mmol), Pd$_2$(dba)$_3$ (26 mg, 0.028 mmol), sodium tert-butoxide (54 mg, 0.557 mmol) and 1,4-dioxane (8 mL) were placed in a round bottomed flask and allowed to stir at 100° C. for 16 h. The reaction was treated with further DavePhos (7 mg, 0.019 mmol), sodium tert-butoxide (54 mg, 0.557 mmol) and Pd$_2$dba$_3$ (26 mg, 0.028 mmol), the reaction was allowed to stir at 100° C. for 3 h. The reaction was allowed to cool to rt and was partitioned between water and EtOAc, the organic phase was washed with brine, dried using a hydrophobic frit and concentrated to a gum. This gum was purified using a column chromatography (10 g silica) eluting with 0-50% EtOAc:cyclohexane. The fractions relating to product were summed and concentrated to give the product (16 mg) as an orange solid.

LCMS (2 min Formic): Rt=0.69 min, [MH]$^+$=361.

Example 67: rac-1-((2S,3R,4R)-2-cyclopropyl-3-methyl-4-((6-methylpyridin-2-yl)amino)-6-(methylsulfonyl)-3,4-dihydroquinolin-1(2H)-yl)ethanone

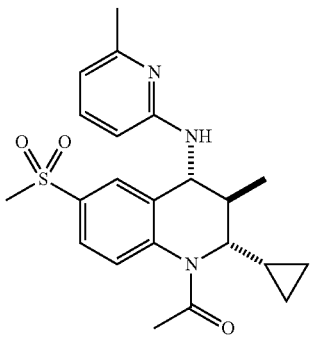 [SMILES: CC(=O)N1c2ccc(S(C)(=O)=O)cc2[C@H](Nc2cccc(C)n2)[C@@H](C)[C@@H]1C1CC1]

rac-1-((2S,3R,4R)-4-Amino-2-cyclopropyl-3-methyl-6-(methylsulfonyl)-3,4-dihydroquinolin-1(2H)-yl)ethanone (for a preparation see Intermediate 51, 40 mg, 0.124 mmol), DavePhos (5.9 mg, 0.015 mmol), 2-bromo-6-methylpyridine (0.017 mL, 0.149 mmol), Pd$_2$(dba)$_3$ (6.8 mg, 7.44 µmol) and sodium tert-butoxide (26 mg, 0.273 mmol) in 1,4-dioxane (2 mL) was stirred under nitrogen at 90° C. for 16 h. The reaction mixture was filtered through celite, rinsed with ethyl acetate then concentrated in vacuo to recover starting material. All reactants were added again and the reaction mixture was left to stir under nitrogen at 90° C. for 4 h. The reaction mixture was allowed to cool to rt then was filtered through celite and washed with ethyl acetate. The solvent was evaporated to give 150 mg crude as an orange gum. The sample was dissolved in 1:1 MeOH:DMSO (2×1 mL) and purified by MDAP (Formic). The appropriate fractions were combined and concentrated in vacuo. The product was dissolved in methanol then applied to a 5 g NH$_2$ cartridge which had been pre-equilibrated with methanol (5 mL). The column was flushed with methanol (5 mL) and the fraction was concentrated under a stream of nitrogen. The product was dissolved in 1:1 MeOH:DMSO (1 mL) and purified by MDAP (HpH). The appropriate fractions were combined and concentrated in vacuo to give the product (8 mg, 0.019 mmol, 16%). LCMS (2 min Formic): Rt=0.60 min, [MH]$^+$=414.

Example 68: rac-1-((2S,3R,4R)-2-cyclopropyl-6-(isopropylsulfonyl)-3-methyl-4-((6-methylpyridin-2-yl)amino)-3,4-dihydroquinolin-1(2H)-yl)ethanone

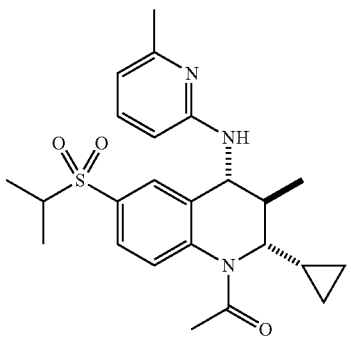 [SMILES: CC(=O)N1c2ccc(S(=O)(=O)C(C)C)cc2[C@H](Nc2cccc(C)n2)[C@@H](C)[C@@H]1C1CC1]

A mixture of sodium tert-butoxide (50 mg, 0.520 mmol), Pd$_2$(dba)$_3$ (12 mg, 0.013 mmol), DavePhos (11 mg, 0.028 mmol) and rac-1-((2S,3R,4R)-4-amino-2-cyclopropyl-6-(isopropylsulfonyl)-3-methyl-3,4-dihydroquinolin-1(2H)-yl)ethanone (for a preparation see Intermediate 53, 83 mg, 0.237 mmol) in anhydrous 1,4-dioxane (2 mL) was treated with 2-bromo-6-methylpyridine (0.032 mL, 0.284 mmol) and stirred at 100° C. under nitrogen for 16 h. The reaction mixture was allowed to cool to rt and filtered through cotton wool. The filtrate was applied to a MeOH pre-conditioned 2 g SCX-2 cartridge which was then washed with MeOH (10 mL) followed by 2M ammonia/MeOH (10 mL). The basic wash was evaporated under vacuum and the residue purified by MDAP (HpH). The appropriate fractions were combined and the solvent removed by rotary evaporation to give the product as an off-white powder (18 mg, 0.041 mmol, 17%). LCMS (2 min Formic): Rt=0.70 min, [MH]$^+$=442.

Example 69: rac-1-((2S,3R,4R)-2,3-dimethyl-4-(phenylamino)-6-(piperazin-1-yl)-3,4-dihydroquinolin-1(2H)-yl)ethanone

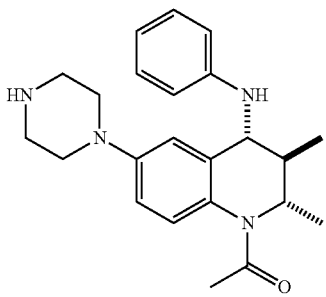 [SMILES: CC(=O)N1c2ccc(N3CCNCC3)cc2[C@H](Nc2ccccc2)[C@@H](C)[C@@H]1C]

To rac-tert-butyl 4-((2S,3R,4R)-1-acetyl-2,3-dimethyl-4-(phenylamino)-1,2,3,4-tetrahydroquinolin-6-yl)piperazine-1-carboxylate (for a preparation see Intermediate 55, 24.3 mg, 0.051 mmol) in methanol (0.5 mL) was added HCl in dioxane (0.127 mL, 0.508 mmol). The reaction mixture was stirred at rt for 3 h. The reaction mixture was then evaporated in vacuo and was purified by MDAP (Formic) to give the product (13 mg, 67%) as a black solid.

LCMS (2 min Formic): Rt=0.67 min, [MH]$^+$=379.

Example 70: rac-1-((2S,3R,4R)-2,3-dimethyl-6-morpholino-4-(phenylamino)-3,4-dihydroquinolin-1(2H)-yl)ethanone

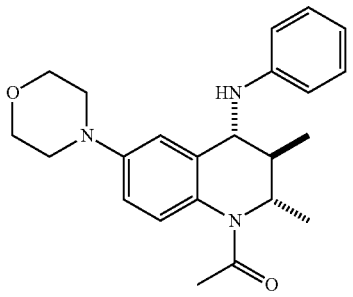 [SMILES: CC(=O)N1c2ccc(N3CCOCC3)cc2[C@H](Nc2ccccc2)[C@@H](C)[C@@H]1C]

Under nitrogen atmosphere, to a solution of bromobenzene (0.063 mL, 0.593 mmol) in 1,4-dioxane (8 mL) were added rac-1-((2S,3R,4R)-4-amino-2,3-dimethyl-6-morpholino-3,4-dihydroquinolin-1(2H)-yl)ethanone (for a preparation see Intermediate 56, 150 mg, 0.494 mmol), DavePhos (19.46 mg, 0.049 mmol), Pd$_2$(dba)$_3$ (22.64 mg, 0.025 mmol) and sodium tert-butoxide (71.3 mg, 0.742 mmol). The reaction was irradiated in a microwave at 110° C. for 30 minutes. The reaction was treated with further tris Pd$_2$(dba)$_3$ (22.64 mg, 0.025 mmol), DavePhos (19.46 mg, 0.049 mmol), sodium tert-butoxide (71.3 mg, 0.742 mmol) and bromobenzene (0.063 mL, 0.593 mmol) and the reaction irradiated at 110° C. for 30 minutes. This was repeated one more time, however at the end of the 30 min, the vial was found broken in the microwave reactor. A maximum of the reaction mixture was retrieved using methanol, the resulting solution was evaporated in vacuo and the residue was transferred into a 2-5 mL microwave vial. Pd$_2$(dba)$_3$ (22.64 mg, 0.025 mmol), DavePhos (19.46 mg, 0.049 mmol), sodium tert-butoxide (71.3 mg, 0.742 mmol) and bromobenzene (0.063 mL, 0.593 mmol) were added and the reaction irradiated in a microwave at 110° C. for 30 min. This was repeated two more times as the starting material was still present. At the end of the last reaction the vial was found broken again in the reactor. Like before, the reaction mixture was retrieved with methanol and the resulting solution was evaporated in vacuo. The residue was purified by column chromatography on silica gel eluting with 0-60% of ethyl acetate in cyclohexane to give crude product which was further purified using a MDAP (Formic) to give the product (29 mg, 15%) as a orange solid. LCMS (2 min Formic): Rt=1.03 min, [MH]$^+$=380.

Example 71a & 71b: 1-((2S,3R,4R)-2,3-dimethyl-6-morpholino-4-(phenylamino)-3,4-dihydroquinolin-1(2H)-yl)ethanone (71a) & 1-((2R,3S,4S)-2,3-dimethyl-6-morpholino-4-(phenylamino)-3,4-dihydroquinolin-1(2H)-yl)ethanone (71b)

71a

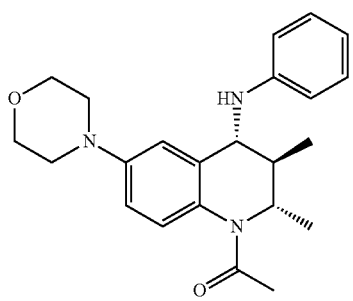

71b

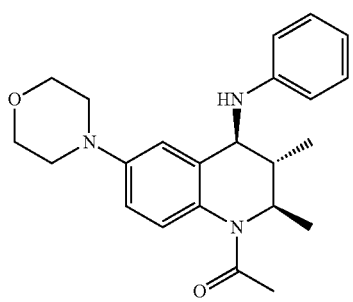

1-((2S,3R,4R)-2,3-dimethyl-6-morpholino-4-(phenylamino)-3,4-dihydroquinolin-1(2H)-yl)ethanone (for a preparation see Example 70, 29 mg) was submitted for chiral separation into its enantiomers (A and B) using a 250×30 mm Chiralpak AD-H column eluting with 10% ethanol in heptane at a flow rate of 45 mL/min. Peaks 1 and 2 were collected separately and then evaporated to dryness to give Enantiomer A (12 mg) and Enantiomer B (12 mg) as white solids.

Enantiomer A, Example 71b

Analytical Chiral HPLC using a 250×4.6 mm Chiralpak AD-H column eluting with 10% ethanol in heptane at 1 mL/min)—Rt=9.5 min.>99% ee by UV.

Enantiomer B, Example 71a

Analytical Chiral HPLC using a 250×4.6 mm Chiralpak AD-H column eluting with 10% ethanol in heptane at 1 mL/min)—Rt=13.0 min, >99% ee by UV.

Example 72: 1-((rac-2S,3R,4R)-2,3-dimethyl-6-(3-methylpiperazin-1-yl)-4-(phenylamino)-3,4-dihydroquinolin-1(2H)-yl)ethanone, formate salt

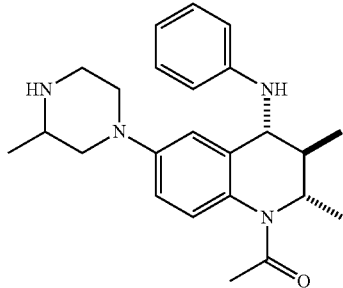

To a solution of tert-butyl 4-((rac-2S,3R,4R)-1-acetyl-2,3-dimethyl-4-(phenylamino)-1,2,3,4-tetrahydroquinolin-6-yl)-2-methylpiperazine-1-carboxylate (for a preparation see Intermediate 58, 7.4 mg, 0.015 mmol) in methanol (0.5 mL) was added HCl (4M in 1,4-dioxane) (150 μL, 0.600 mmol). The reaction mixture was stirred at rt for 23 h. The solvent was evaporated in vacuo and the residue purified MDAP (Formic) to the product (4.1 mg, 8.81 μmol, 58.6%). This was a racemic mixture of diastereoisomers. LCMS (2 min Formic): Rt=0.69 min, [MH]⁺=393.

Example 73: rac-1-((2S,3R,4R)-2,3-dimethyl-6-morpholino-4-(pyridin-3-ylamino)-3,4-dihydroquinolin-1(2H)-yl)ethanone

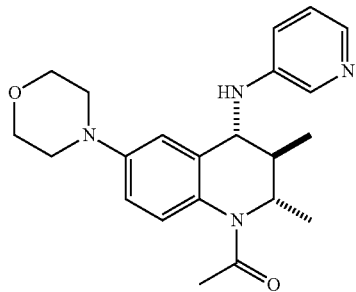 [SMILES: CC(=O)N1c2ccc(N3CCOCC3)cc2[C@H](Nc2cccnc2)[C@@H](C)[C@@H]1C]

Under a nitrogen atmosphere, to a solution of 3-bromopyridine (0.016 mL, 0.164 mmol) in 1,4-Dioxane (3 mL) were added rac-1-((2S,3R,4R)-4-amino-2,3-dimethyl-6-morpholino-3,4-dihydroquinolin-1(2H)-yl)ethanone (for a preparation see Intermediate 56, 41.4 mg, 0.136 mmol), DavePhos (5.37 mg, 0.014 mmol), Pd$_2$(dba)$_3$ (6.25 mg, 6.82 μmol) and sodium tert-butoxide (19.67 mg, 0.205 mmol). The reaction was irradiated in a microwave at 110° C. for 30 min. The reaction was treated with further 3-bromopyridine (0.016 mL, 0.164 mmol), Pd$_2$(dba)$_3$ (6.25 mg, 6.82 μmol), DavePhos (5.37 mg, 0.014 mmol) and sodium tert-butoxide (19.67 mg, 0.205 mmol) and irradiated in a microwave at 110° C. for 30 min. This process was repeated one more time. After cooling to rt, the reaction mixture was filtered through a pad of celite (rinsed with EtOAc). The filtrate was then evaporated in vacuo and purified by column chromatography on silica gel eluting with 0-10% of methanol in DCM to give crude product which was further purified by MDAP (Formic) to give the product (10 mg, 20%) as a yellow solid.
LCMS (2 min Formic): Rt=0.56 min, [MH]⁺=381

Example 74: rac-1-((2S,3R,4R)-6-(4-aminopiperidin-1-yl)-2,3-dimethyl-4-(phenylamino)-3,4-dihydroquinolin-1(2H)-yl)ethanone, hydrochloride

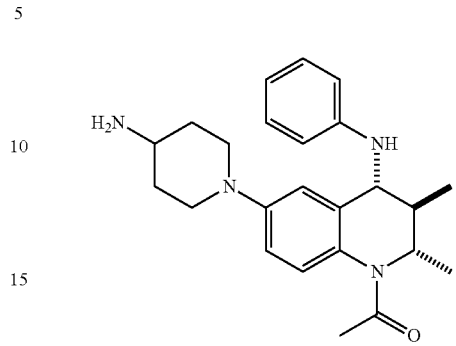

To rac-tert-butyl (1-((2S,3R,4R)-1-acetyl-2,3-dimethyl-4-(phenylamino)-1,2,3,4-tetrahydroquinolin-6-yl)piperidin-4-yl)carbamate (for a preparation see Intermediate 61, 12.5 mg, 0.025 mmol) in methanol (0.2 mL) was added 4M HCl in 1,4-dioxane (0.063 mL, 0.254 mmol). The reaction mixture was stirred at rt for 4 h. The solution was then evaporated in vacuo and the residue was purified by chromatography on silica gel eluting with 0-20% of methanol in DCM to give the product (7 mg, 62%) as a yellow solid. LCMS (2 min Formic): Rt=0.71 min, [MH]⁺=393.

Example 75: rac-1-((2S,3R,4R)-2,3-dimethyl-4-((6-methylpyridin-2-yl)amino)-6-morpholino-3,4-dihydroquinolin-1(2H)-yl)ethanone

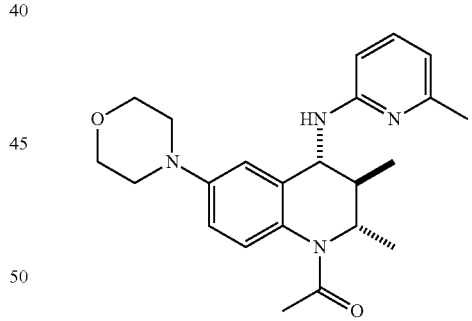

To a test tube were added rac-1-((2S,3R,4R)-4-amino-2,3-dimethyl-6-morpholino-3,4-dihydroquinolin-1(2H)-yl)ethanone (For a preparation see Intermediate 56, 53.2 mg, 0.175 mmol), 2-chloro-6-methylpyridine (0.021 mL, 0.269 mmol), Pd$_2$(dba)$_3$ (9.95 mg, 10.87 μmol), sodium tert-butoxide (31.4 mg, 0.327 mmol), DavePhos (8.54 mg, 0.022 mmol) and 1,4-Dioxane (2.5 mL). The reaction mixture was then heated and stirred at 100° C. for 4 h. After cooling to rt, the reaction mixture was filtered through a pad of celite (rinsed with EtOAc). The filtrate was then evaporated in vacuo and purified by MDAP (Formic) to give the product (29 mg, 42%) as a yellow solid.
LCMS (2 min Formic): Rt=0.59 min, [MH]⁺=395.

Example 76: rac-1-((2S,3R,4R)-2,3-dimethyl-4-(phenylamino)-6-(piperidin-4-ylamino)-3,4-dihydroquinolin-1(2H)-yl)ethanone

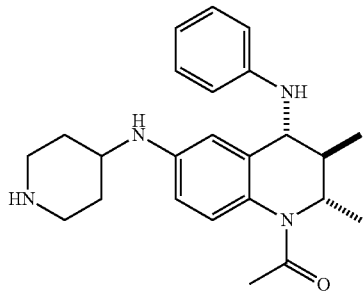 [SMILES: CC(=O)N1c2ccc(NC3CCNCC3)cc2[C@H](Nc2ccccc2)[C@@H](C)[C@@H]1C]

To rac-tert-butyl 4-(((2S,3R,4R)-1-acetyl-2,3-dimethyl-4-(phenylamino)-1,2,3,4-tetrahydroquinolin-6-yl)amino)piperidine-1-carboxylate (for a preparation see Intermediate 64, 10.8 mg, 0.022 mmol) in methanol (0.2 mL) was added 4M HCl in 1,4-dioxane (0.055 mL, 0.219 mmol). The reaction mixture was stirred at rt for 6 h. The solution was then evaporated in vacuo and the residue purified by chromatography on silica gel eluting with 0-20% (2M ammonia in methanol) in DCM to give the product: (1.7 mg, 20%) as a yellow solid.

LCMS (2 min Formic): Rt=0.68 min, [MH]$^+$=300 (loss of NHPh$^-$).

Example 77: 1-((rac-2S,3R,4R)-2,3-dimethyl-6-(2-methylmorpholino)-4-(phenylamino)-3,4-dihydroquinolin-1(2H)-yl)ethanone

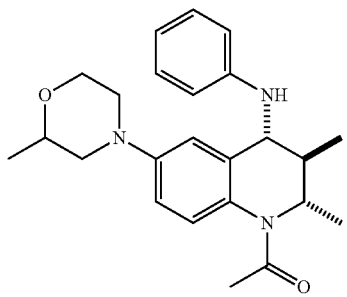

To a solution of 1-((rac-2S,3R,4R)-4-amino-2,3-dimethyl-6-(2-methylmorpholino)-3,4-dihydroquinolin-1(2H)-yl)ethanone (for a preparation see Intermediate 65, 5.9 mg, 0.019 mmol) in 1,4-dioxane (0.5 mL) was added bromobenzene (5 µL, 0.047 mmol), Pd$_2$(dba)$_3$ (1.1 mg, 1.201 µmol), DavePhos (0.9 mg, 2.287 µmol) and sodium tert-butoxide (3.2 mg, 0.033 mmol). The reaction mixture was heated at 100° C. for 18 h. The reaction mixture was allowed to cool to rt then loaded onto a 2.5 g celite cartridge, eluted with ethyl acetate then concentrated. To the residue was added 1,4-dioxane (0.5 mL), sodium tert-butoxide (3.4 mg, 0.035 mmol), DavePhos (2 mg, 5.08 µmol), Pd$_2$(dba)$_3$ (2 mg, 2.184 µmol) and bromobenzene (10 µL, 0.094 mmol). The reaction mixture was heated at 100° C. for a further 21 h. The reaction mixture was allowed to cool to rt then loaded onto a 2.5 g celite cartridge, eluted with ethyl acetate the filtrate was concentrated and purified by MDAP (Formic) to give the product (6.4 mg, 0.016 mmol, 87%). This was a racemic mixture of diastereoisomers.

LCMS (2 min Formic): Rt=1.10 min, [MH]$^+$=394.

Example 78: 1-((rac-2S,3R,4R)-6-((1R,4R)-2,5-diazabicyclo[2.2.2]octan-2-yl)-2,3-dimethyl-4-(phenylamino)-3,4-dihydroquinolin-1(2H)-yl)ethanone, 2 Hydrochloride

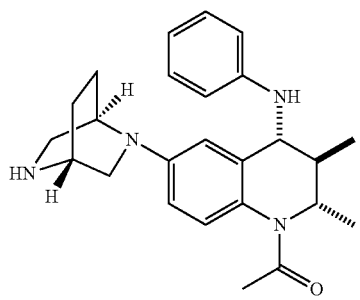 [SMILES: CC(=O)N1c2ccc(N3C[C@H]4CC[C@@H]3CN4)cc2[C@H](Nc2ccccc2)[C@@H](C)[C@@H]1C]

To a solution of tert-butyl 5-((rac-2S,3R,4R)-1-acetyl-2,3-dimethyl-4-(phenylamino)-1,2,3,4-tetrahydroquinolin-6-yl)-2,5-diazabicyclo[2.2.2]octane-2-carboxylate (for a preparation see Intermediate 67, 4.7 mg, 9.31 µmol) in methanol (0.2 mL) was added HCl (4M in 1,4-dioxane) (0.093 mL, 0.373 mmol). The reaction mixture was stirred at rt under nitrogen for 70.5 h. The solvent was evaporated under a stream of nitrogen to give the product (4.5 mg, 8.48 µmol, 91%). This was a racemic mixture of diastereoisomers. LCMS (2 min Formic): Rt=0.73 min, [MH]$^+$=405.

Example 79: rac-1-((2S,3R,4R)-6-(8-oxa-3-azabicyclo[3.2.1]octan-3-yl)-2,3-dimethyl-4-(phenylamino)-3,4-dihydroquinolin-1(2H)-yl)ethanone

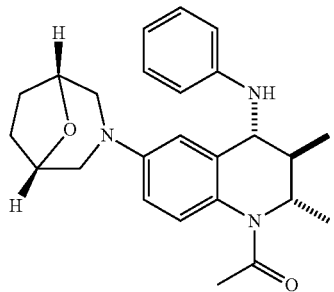 [SMILES: CC(=O)N1c2ccc(N3C[C@H]4CC[C@@H](C3)O4)cc2[C@H](Nc2ccccc2)[C@@H](C)[C@@H]1C]

To a solution of rac-1-((2S,3R,4R)-4-amino-6-((1R,5S)-8-oxa-3-azabicyclo[3.2.1]octan-3-yl)-2,3-dimethyl-3,4-dihydroquinolin-1(2H)-yl)ethanone (for a preparation see Intermediate 68, 5.6 mg, 0.017 mmol) in 1,4-dioxane (0.5 mL) was added bromobenzene (5 µL, 0.047 mmol), Pd$_2$(dba)$_3$ (2.1 mg, 2.293 µmol), DavePhos (2.1 mg, 5.34 µmol) and sodium tert-butoxide (3.6 mg, 0.037 mmol). The reaction mixture was stirred at 100° C. for 18 h. The reaction mixture was allowed to cool to rt then loaded onto a 2.5 g celite cartridge, eluted with ethyl acetate then evaporated under a stream of nitrogen. To the residue was added 1,4-dioxane (0.5 mL), bromobenzene (10 µL, 0.094 mmol), Pd$_2$(dba)$_3$ (2.1 mg, 2.293 µmol), DavePhos (2.1 mg, 5.34 µmol) and sodium tert-butoxide (3.4 mg, 0.035 mmol). The reaction mixture was stirred at 100° C. for a further 21 h. The reaction mixture was allowed to cool to rt then loaded onto a 2.5 g celite cartridge, eluted with ethyl acetate then evaporated under a stream of nitrogen. To the residue was added 1,4-dioxane (0.5 mL), bromobenzene (10 µL, 0.094 mmol), Pd$_2$(dba)$_3$ (1.9 mg, 2.075 µmol), DavePhos (2.2 mg, 5.59 µmol) and sodium tert-butoxide (3.7 mg, 0.039 mmol). The reaction mixture was stirred for a further 6 h. The reaction mixture was allowed to cool to rt then loaded onto a 2.5 g celite cartridge, eluted with ethyl acetate then evaporated under a stream of nitrogen. The residue was purified by MDAP (Formic) to give the product (2.3 mg, 5.67 µmol, 33.4%). LCMS (2 min Formic): Rt=1.12 min, [MH]$^+$=406.

Example 80: 1-((rac-2S,3R,4R)-2,3-dimethyl-6-(3-methylpyrrolidin-1-yl)-4-(phenylamino)-3,4-dihydroquinolin-1(2H)-yl)ethanone

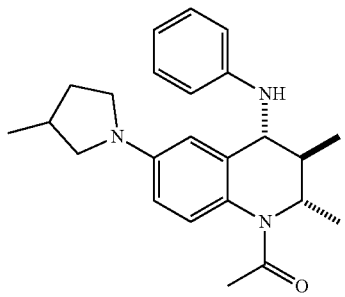

To a test tube was added 1-((rac-2S,3R,4R)-4-amino-2,3-dimethyl-6-(3-methylpyrrolidin-1-yl)-3,4-dihydroquinolin-1(2H)-yl)ethanone (for a preparation see Intermediate 69, 25.7 mg, 0.085 mmol), bromobenzene (11 µL, 0.103 mmol), Pd$_2$(dba)$_3$ (4.6 mg, 5.02 µmol), DavePhos (3.8 mg, 9.66 µmol), sodium tert-butoxide (11.1 mg, 0.116 mmol) and 1,4-dioxane (1 mL). The reaction mixture was stirred at 100° C. under nitrogen for 16 h. The reaction mixture was allowed to cool to rt then loaded onto a 2.5 g celite cartridge, eluted with ethyl acetate then evaporated under a stream of nitrogen. To the residue was added 1,4-dioxane (1 mL), DavePhos (3.8 mg, 9.66 µmol), Pd$_2$(dba)$_3$ (4.1 mg, 4.48 µmol), sodium tert-butoxide (11.8 mg, 0.123 mmol) and bromobenzene (11 µL, 0.103 mmol). The reaction mixture was stirred at 100° C. under nitrogen for a further 4 h. The reaction mixture was allowed to cool to rt then loaded onto a 2.5 g celite cartridge, eluted with ethyl acetate then evaporated under a stream of nitrogen. The residue was purified by MDAP (Formic) to give 1 the product (18.9 mg, 0.050 mmol, 58.7%) as a yellow/orange gum. This was a racemic mixture of diastereoisomers. LCMS (2 min Formic): Rt=1.32 min, [MH]$^+$=378.

Example 81: 1-((rac-2S,3R,4R)-2,3-dimethyl-6-(2-methylpyrrolidin-1-yl)-4-(phenylamino)-3,4-dihydroquinolin-1(2H)-yl)ethanone

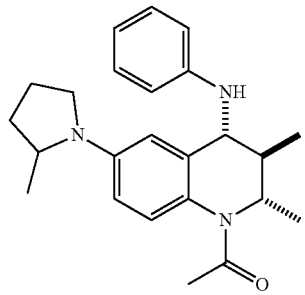 [SMILES: CC(=O)N1c2ccc(N3CCCC3C)cc2[C@H](Nc2ccccc2)[C@@H](C)[C@@H]1C]

To a greenhouse test tube was added 1-((rac-2S,3R,4R)-4-amino-2,3-dimethyl-6-(2-methylpyrrolidin-1-yl)-3,4-dihydroquinolin-1(2H)-yl)ethanone (for a preparation see Intermediate 70, 7.5 mg, 0.058 mmol), bromobenzene (7.5 µL, 0.070 mmol), Pd$_2$(dba)$_3$ (3.1 mg, 3.39 µmol), DavePhos (2.7 mg, 6.86 µmol), sodium tert-butoxide (8.1 mg, 0.084 mmol) and 1,4-dioxane (1 mL). The reaction mixture was stirred at 100° C. under nitrogen for 16 h. The reaction mixture was allowed to cool to rt then loaded onto a 2.5 g celite cartridge, eluted with ethyl acetate then evaporated under a stream of nitrogen. To the residue was added 1,4-dioxane (1 mL), DavePhos (2.7 mg, 6.86 µmol), Pd$_2$(dba)$_3$ (3.1 mg, 3.39 µmol), sodium tert-butoxide (8.4 mg, 0.087 mmol) and bromobenzene (7.5 µL, 0.070 mmol). The reaction mixture was stirred at 100° C. under nitrogen for a further 4 h. The reaction mixture was allowed to cool to rt then loaded onto a 2.5 g celite cartridge, eluted with ethyl acetate then evaporated under a stream of nitrogen. The residue was purified by MDAP (Formic) to give the product (11.0 mg, 0.029 mmol, 50.2%) as a yellow gum. This was a racemic mixture of diastereoisomers. LCMS (2 min Formic): Rt=1.23 min, [MH]$^+$=378.

Example 82: rac-1-((2S,3R,4R)-6-(-3,8-diazabicyclo[3.2.1]octan-3-yl)-2,3-dimethyl-4-(phenylamino)-3,4-dihydroquinolin-1(2H)-yl)ethanone, 2 Hydrochloride

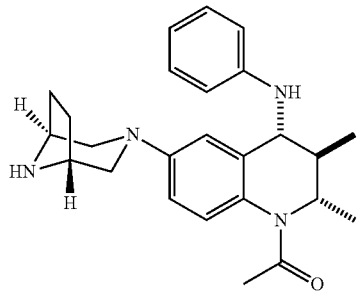 [SMILES: CC(=O)N1c2ccc(N3C[C@H]4CC[C@@H](C3)N4)cc2[C@H](Nc2ccccc2)[C@@H](C)[C@@H]1C]

To a solution of rac-(1R,5S)-tert-butyl 3-((2S,3R,4R)-1-acetyl-2,3-dimethyl-4-(phenylamino)-1,2,3,4-tetrahydroquinolin-6-yl)-3,8-diazabicyclo[3.2.1]octane-8-carboxylate (for a preparation see Intermediate 72, 3.3 mg, 6.54 µmol) in methanol (0.2 mL) was added HCl (4M in 1,4-dioxane) (0.065 mL, 0.262 mmol). The reaction mixture was stirred at rt under nitrogen for 70.5 h. The solvent was evaporated under a stream of nitrogen to give the product (2.6 mg, 4.90 µmol, 74.9%).

LCMS (2 min Formic): Rt=0.75 min, [MH]⁺=405.

Example 83: rac-6-(((2S,3R,4R)-1-acetyl-2,3-dimethyl-6-morpholino-1,2,3,4-tetrahydroquinolin-4-yl)amino)nicotinonitrile

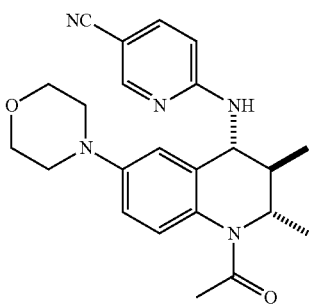 [SMILES: CC(=O)N1c2ccc(N3CCOCC3)cc2[C@H](Nc2ccc(C#N)cn2)[C@@H](C)[C@@H]1C]

To a solution of rac-1-((2S,3R,4R)-4-amino-2,3-dimethyl-6-morpholino-3,4-dihydroquinolin-1(2H)-yl)ethanone (for a preparation see Intermediate 56, 16.2 mg, 0.053 mmol) in N-methyl-2-pyrrolidone (NMP) (0.5 ml) were added 6-chloronicotinonitrile (14.80 mg, 0.107 mmol) and DIPEA (0.028 ml, 0.160 mmol). Using a microwave reactor the solution was stirred and irradiated with microwaves so as to maintain a temperature of 200° C. for 2 h. The reaction mixture was then concentrated in vacuo and the residue was purified by MDAP (Formic) chromatography. Desired fractions were combined and evaporated in vacuo to afford the product as a beige solid (1.7 mg).

LCMS (2 min Formic): Rt=0.83 min, [MH]⁺=406.

Example 84: rac-1-((2S,3R,4R)-2-ethyl-3-methyl-6-morpholino-4-(phenylamino)-3,4-dihydroquinolin-1(2H)-yl)ethanone

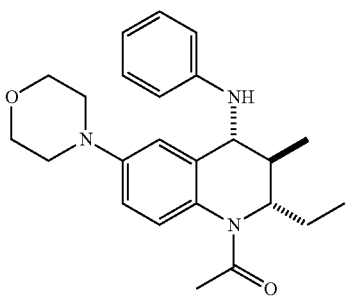 [SMILES: CC[C@H]1[C@H](C)[C@@H](Nc2ccccc2)c2cc(N3CCOCC3)ccc2N1C(C)=O]

To a 10 mL round bottomed flask was added Pd₂(dba)₃ (6.5 mg, 7.10 µmol), DavePhos (5.6 mg, 0.014 mmol), sodium tert-butoxide (20.2 mg, 0.210 mmol), rac-1-((2S,3R,4R)-4-amino-2-ethyl-3-methyl-6-morpholino-3,4-dihydroquinolin-1(2H)-yl)ethanone (for a preparation see Intermediate 73, 46.2 mg, 0.146 mmol) and 1,4-dioxane (2 mL). Bromobenzene (18 µL, 0.169 mmol) was then added and the reaction mixture heated at 100° C. under nitrogen for 45 min. Further bromobenzene (18 µL, 0.169 mmol) was added and stirring continued for a further 16 h at 100° C. The reaction mixture was allowed to cool, then further Pd₂(dba)₃ (6.9 mg, 7.54 µmol) and DavePhos (5.9 mg, 0.015 mmol) were added and stirring continued for a further 3 h. Further bromobenzene (19 µl, 0.179 mmol) was added and stirring continued for a further 19 h. The reaction mixture was allowed to cool to rt. The reaction mixture was filtered through a celite cartridge and washed with ethyl acetate. The residue was by MDAP (Formic) to give the product (13.2 mg, 0.034 mmol, 23.05%) as a yellow solid.

LCMS (2 min Formic): Rt=1.09 min, [MH]⁺=394.

Example 85: rac-1-((2S,3R,4R)-2-cyclopropyl-6-(3,6-dihydro-2H-pyran-4-yl)-3-methyl-4-(((6-methylpyridin-2-yl)amino)-3,4-dihydroquinolin-1(2H)-yl)ethanone, Formic Acid Salt

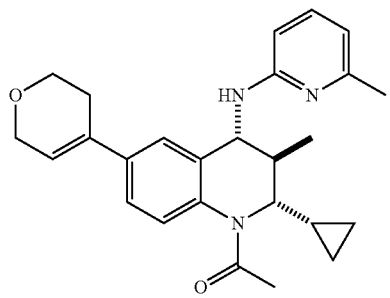 [SMILES: CC(=O)N1c2ccc(C3=CCOCC3)cc2[C@H](Nc2cccc(C)n2)[C@@H](C)[C@@H]1C1CC1]

The 2-chloro-6-methylpyridine (61.0 mg, 0.478 mmol), rac-1-((2S,3R,4R)-4-amino-2-cyclopropyl-6-(3,6-dihydro-2H-pyran-4-yl)-3-methyl-3,4-dihydroquinolin-1(2H)-yl)ethanone (for a preparation see Intermediate 78, 78 mg, 0.239 mmol), DavePhos (9.40 mg, 0.024 mmol), Pd₂(dba)₃ (32.8 mg, 0.036 mmol), sodium tert-butoxide (68.9 mg, 0.717 mmol) and 1,4-dioxane (10 mL) were placed in a round bottomed flask and allowed to stir at 100° C. for 18 h. The reaction was partitioned between water and EtOAc, the aqueous layer was extracted with further EtOAc and the combined organics washed with brine, dried using a hydrophobic frit and concentrated to a yellow gum. This gum was purified by chromatography on silica gel eluting with 0-50% EtOAc:cyclohexane to give the product (76 mg, 68%) as a yellow solid LCMS (2 min Formic): Rt=0.75 min, [MH]⁺=418

Example 86: 1-((rac-2S,3R,4R)-2-cyclopropyl-3-methyl-6-(3-methylpiperazin-1-yl)-4-((6-methylpyridin-2-yl)amino)-3,4-dihydroquinolin-1(2H)-yl)ethanone

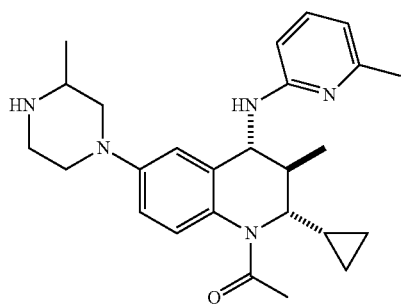 [SMILES: CC(=O)N1c2ccc(N3CCNC(C)C3)cc2[C@H](Nc2cccc(C)n2)[C@@H](C)[C@@H]1C1CC1]

To a reaction vessel tert-butyl 4-((rac-2S,3R,4R)-1-acetyl-2-cyclopropyl-3-methyl-4-((6-methylpyridin-2-yl)amino)-1,2,3,4-tetrahydroquinolin-6-yl)-2-methylpiperazine-1-carboxylate (for a preparation see Intermediate 80, 34 mg, 0.064 mmol) and TFA (0.2 mL, 2.60 mmol) were added in dichloromethane (DCM) (5 mL). The reaction was left to stir at rt for 17.5 h. The reaction mixture was concentrated and purified by SPE on aminopropyl (NH$_2$) 2 g eluting with methanol to give crude product which was purified by chromatography on silica gel eluting with 0-4% 2M ammonia in methanol/dichloromethane to give the product (10 mg, 36%). This was a racemic mixture of diastereoisomers. LCMS (2 min Formic): Rt=0.57 min, [MH]$^+$=434.

Example 87: rac-1-((2S,3R,4R)-2-cyclopropyl-3-methyl-4-((6-methylpyridin-2-yl)amino)-6-(1,2,3,6-tetrahydropyridin-4-yl)-3,4-dihydroquinolin-1(2H)-yl)ethanone

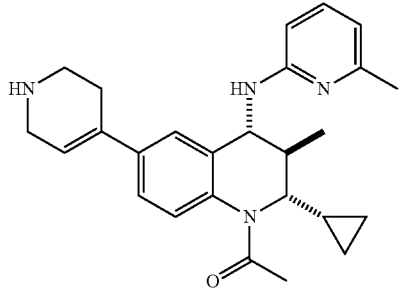 [SMILES: CC(=O)N1c2ccc(C3=CCNCC3)cc2[C@H](Nc2cccc(C)n2)[C@@H](C)[C@@H]1C1CC1]

The rac-tert-butyl 4-((2S,3R,4R)-1-acetyl-2-cyclopropyl-3-methyl-4-((6-methylpyridin-2-yl)amino)-1,2,3,4-tetrahydroquinolin-6-yl)-5,6-dihydropyridine-1(2H)-carboxylate (for a preparation see Intermediate 82, 104 mg, 0.201 mmol) was taken up in dichloromethane (DCM) (10 mL) and treated with TFA (0.078 mL, 1.006 mmol) the resulting solution was allowed to stir at rt for 16 h. The reaction was concentrated and eluted through a SCX SPE (2 g) elute MeOH and 2M NH$_3$/MeOH, the ammonia fraction was concentrated and dried to give a brown gum a portion of which was further purified using a MDAP (Formic) to give the product (3 mg, 4%) as a white solid.
LCMS (2 min Formic): Rt=0.52 min, [MH]$^+$=417.

Example 88: rac-1-((2S,3R,4R)-2-cyclopropyl-3-methyl-4-((6-methylpyridin-2-yl)amino)-6-(piperidin-4-yl)-3,4-dihydroquinolin-1(2H)-yl)ethanone

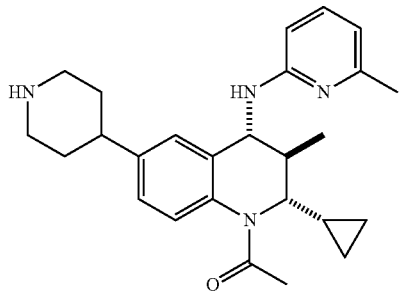 [SMILES: CC(=O)N1c2ccc(C3CCNCC3)cc2[C@H](Nc2cccc(C)n2)[C@@H](C)[C@@H]1C1CC1]

The rac-1-((2S,3R,4R)-2-cyclopropyl-3-methyl-4-((6-methylpyridin-2-yl)amino)-6-(1,2,3,6-tetrahydropyridin-4-yl)-3,4-dihydroquinolin-1(2H)-yl)ethanone (for a preparation see Example 87, 50 mg, 0.120 mmol) was taken up in ethanol (10 mL) treated with 10% Pd/C (128 mg, 0.120 mmol) and allowed to stir at rt under a atmosphere of hydrogen for 4 h. The catalyst was removed by filtering through celite washing with EtOH. The filtrate was concentrated and purified using a MDAP (HpH) to give the product (9 mg, 18%) as a white solid. LCMS (2 min Formic): Rt=0.99 min, [MH]$^+$=419.

Example 89: rac-1-((2S,3R,4R)-2-cyclopropyl-3-methyl-4-((6-methylpyridin-2-yl)amino)-6-morpholino-3,4-dihydroquinolin-1(2H)-yl)ethanone

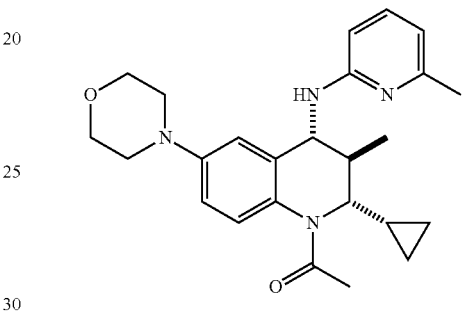

To a reaction vessel DavePhos (16 mg, 0.041 mmol), Pd$_2$(dba)$_3$ (51 mg, 0.056 mmol), sodium tert-butoxide (93 mg, 0.968 mmol), 2-bromo-6-methylpyridine (0.104 mL, 0.692 mmol) and rac-1-((2S,3R,4R)-4-amino-2-cyclopropyl-3-methyl-6-morpholino-3,4-dihydroquinolin-1(2H)-yl)ethanone (for a preparation see Intermediate 83, 114 mg, 0.346 mmol) were added in 1,4-dioxane (5 mL) and the reaction was left to stir at 100° C. The reaction mixture was filtered through celite and washed with ethyl acetate. The combined filtrates were concentrated in vacuo and purified by chromatography on silica gel eluting with 20-80% ethyl acetate:dichloromethane to give the product (28 mg, 0.067 mmol, 19.24%) as a beige solid. LCMS (2 min Formic): Rt=0.68 min, [MH]$^+$=421.

Example 90: rac-1-((2S,3R,4R)-2-cyclopropyl-3-methyl-6-morpholino-4-(phenylamino)-3,4-dihydroquinolin-1(2H)-yl)ethanone

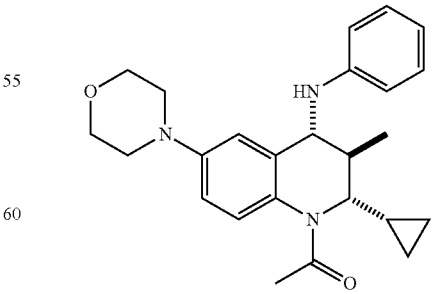

In a test tube rac-1-((2S,3R,4R)-4-amino-2-cyclopropyl-3-methyl-6-morpholino-3,4-dihydroquinolin-1(2H)-yl)ethanone (for a preparation see Intermediate 83, 90 mg, 0.273 mmol), bromobenzene (0.035 mL, 0.328 mmol), sodium tert-butoxide (52.5 mg, 0.546 mmol), Pd$_2$(dba)$_3$ (12.51 mg, 0.014 mmol) and DavePhos (10.75 mg, 0.027 mmol) were dissolved in 1,4-dioxane (3 mL). The tube was placed in a Greenhouse Reactor and heated at 100° C. for 2 h. The reaction mixture was filtered through a plug of celite and washed through with extra 1,4-dioxane. The filtrate was evaporated to leave the crude which was purified by column chromatography using silica gel eluting with 0-50% ethyl acetate:cyclohexane to give the product (60 mg, 54%) as an off-white solid.

LCMS (2 min Formic): Rt=1.11 min, [MH]$^+$=406.

Example 91a & 91b: 1-((2S,3R,4R)-2-cyclopropyl-3-methyl-6-morpholino-4-(phenylamino)-3,4-dihydroquinolin-1(2H)-yl)ethanone (91a) & 1-((2R,3S,4S)-2-cyclopropyl-3-methyl-6-morpholino-4-(phenylamino)-3,4-dihydroquinolin-1(2H)-yl)ethanone (91b)

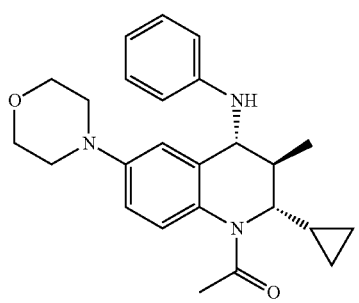

91a

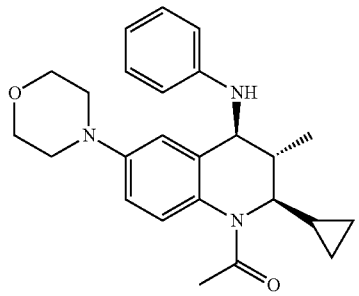

91b rac-1-((2S,3R,4R)-2-cyclopropyl-3-methyl-6-morpholino-4-(phenylamino)-3,4-dihydroquinolin-1(2H)-yl) ethanone (for a preparation see Example 90, 60 mg) was submitted for chiral separation into its enantiomers (A and B) using a 250×20 mm Chiralpak IC column eluting with 10% ethanol in 90% heptane (plus 0.2% isopropylamine) at a flow rate of 20 mL/min. Peak 1/Enantiomer A fractions were collected between 15 and 17 min. Peak 2/Enantiomer B fractions were collected between 18.5 and 21 min. Fraction solutions were combined then evaporated to dryness to give Enantiomer A (24 mg) and Enantiomer B (23 mg) as white solids.

Enantiomer A, Example 91b

Analytical Chiral HPLC using a 250×4.6 mm Chiralpak IC column eluting with 10% ethanol in heptanes (plus 0.2% isopropylamine) at 1 mU/min—Rt=15.5 min.>99% ee by UV.

Enantiomer B, Example 91a

Analytical Chiral HPLC using a 250×4.6 mm Chiralpak IC column eluting with 10% ethanol in heptane (plus 0.2% isopropylamine) at 1 mU/min—Rt=18.2 min, >99% ee by UV.

Example 92: rac-1-((2S,3R,4R)-2-cyclopropyl-6-(3,6-dihydro-2H-pyran-4-yl)-3-methyl-4-(pyridin-2-ylamino)-3,4-dihydroquinolin-1(2H)-yl)ethanone

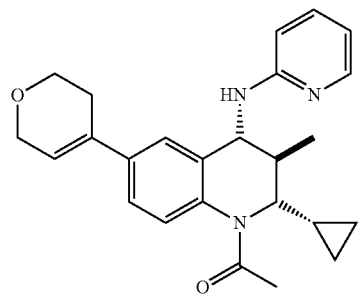

The 2-bromopyridine (78 mg, 0.496 mmol), rac-1-((2S,3R,4R)-4-amino-2-cyclopropyl-6-(3,6-dihydro-2H-pyran-4-yl)-3-methyl-3,4-dihydroquinolin-1(2H)-yl)ethanone (for a preparation see Intermediate 78, 81 mg, 0.248 mmol), DavePhos (9.77 mg, 0.025 mmol), Pd$_2$(dba)$_3$ (34.1 mg, 0.037 mmol), sodium tert-butoxide (71.5 mg, 0.744 mmol) and 1,4-dioxane (10 mL) were placed in a round bottomed flask and allowed to stir at 100° C. for 3 days. The reaction was partitioned between water and EtOAc, the organic layer was washed with brine, dried using a hydrophobic frit and concentrated to a gum. This gum was purified by chromatography on silica gel eluting with 0-50% EtOAc:Cyclohexane to give the product (32 mg, 32%) as an orange solid. LCMS (2 min Formic): Rt=0.72 min, [MH]$^+$=404.

Example 93: rac-1-((2S,3R,4R)-2-cyclopropyl-3-methyl-4-((6-methylpyridin-2-yl)amino)-6-(tetrahydro-2H-pyran-4-yl)-3,4-dihydroquinolin-1(2H)-yl) ethanone

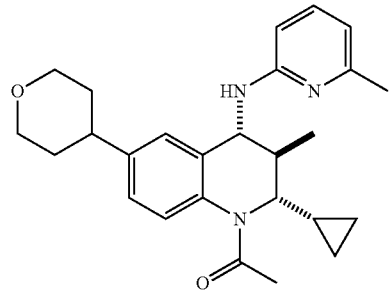 [SMILES: CC(=O)N1c2ccc(C3CCOCC3)cc2[C@H](Nc2cccc(C)n2)[C@@H](C)[C@@H]1C1CC1]

The rac-1-((2S,3R,4R)-2-cyclopropyl-6-(3,6-dihydro-2H-pyran-4-yl)-3-methyl-4-((6-methylpyridin-2-yl)amino)-3,4-dihydroquinolin-1(2H)-yl)ethanone, Formic acid salt (for a preparation see example 85, 56 mg, 0.134 mmol) was taken up in ethanol (10 mL) and the reaction was hydrogenated using the H-cube (settings: 25° C., 1 bar, 1 mL/min flow rate) and 10% Pd/C CatCart 30 as the catalyst. The sample was allowed to cycle through the H-cube for 90 min. The reaction was concentrated, dried and purified using MDAP (Formic) to give the product (12 mg, 21%) as a white solid.

LCMS (2 min Formic): Rt=0.74 min, [MH]+=420.

Example 94: rac-1-((2S,3R,4R)-2-cyclopropyl-3-methyl-4-(phenylamino)-6-(piperazin-1-yl)-3,4-dihydroquinolin-1(2H)-yl)ethanone, hydrochloride

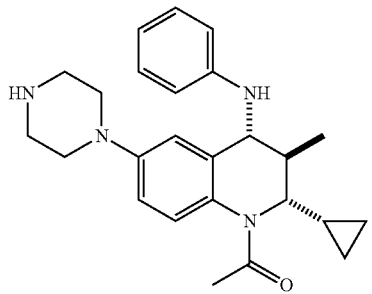 [SMILES: CC(=O)N1c2ccc(N3CCNCC3)cc2[C@H](Nc2ccccc2)[C@@H](C)[C@@H]1C1CC1]

rac-tert-Butyl 4-((2S,3R,4R)-1-acetyl-2-cyclopropyl-3-methyl-4-(phenylamino)-1,2,3,4-tetrahydroquinolin-6-yl)piperazine-1-carboxylate (for a preparation see Intermediate 85, 43 mg, 0.085 mmol) was dissolved in methanol (1 mL) and treated with 4M hydrochloric acid (0.021 mL, 0.085 mmol) in 1,4-dioxane. The reaction was stirred for 1 h and then the solvent and excess HCl were removed under reduced pressure to leave the crude product which was purified by MDAP (Formic) to give product but this was contaminated with the N-formyl by-product. This was dissolved in MeOH (0.5 mL) and treated with base $K_2CO_3$ (100 mg). The solution was stirred overnight and then this was dissolved in DCM (0.5 mL) and treated with 1M HCl in $Et_2O$ (0.1 mL). The resulting solid was titrated and the solvent was carefully pipetted off. The resulting solid was dried to give the product (25 mg, 66%) as a tan solid.

LCMS (2 min Formic): Rt=0.75 min, [MH]+=405.

Example 95: rac-1-((2S,3R,4R)-2-cyclopropyl-3-methyl-4-((6-methylpyridin-2-yl)amino)-6-((tetrahydro-2H-pyran-4-yl)oxy)-3,4-dihydroquinolin-1(2H)-yl)ethanone

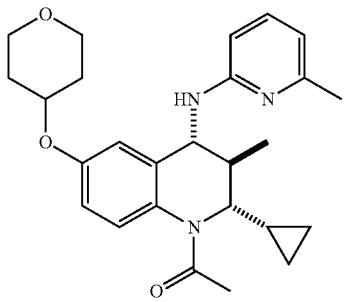 [SMILES: CC(=O)N1c2ccc(OC3CCOCC3)cc2[C@H](Nc2cccc(C)n2)[C@@H](C)[C@@H]1C1CC1]

The 2-bromo-6-methylpyridine (0.052 mL, 0.453 mmol), rac-1-((2S,3R,4R)-4-amino-2-cyclopropyl-3-methyl-6-((tetrahydro-2H-pyran-4-yl)oxy)-3,4-dihydroquinolin-1(2H)-yl)ethanone ((for a preparation see Intermediate 88, 78 mg, 0.226 mmol), DavePhos (8.91 mg, 0.023 mmol), Pd$_2$(dba)$_3$ (31.1 mg, 0.034 mmol), sodium tert-butoxide (65.3 mg, 0.679 mmol) and 1,4-dioxane (10 mL) were placed in a round bottomed flask and allowed to stir at 100° C. for 16 h. The reaction was partitioned between water and EtOAc, the aqueous layer was extracted with further EtOAc, the combined organics were washed with brine, dried using a hydrophobic frit and concentrated to a gum. This gum was purified by chromatography on silica gel eluting with 5-60% EtOAc:Cyclohexane to give the product (51 mg, 52%) as a orange solid. LCMS (2 min Formic): Rt=0.73 min, [MH]+= 436.

Example 96: rac-1-((2S,3R,4R)-2-cyclopropyl-3-methyl-6-morpholino-4-(pyridin-2-ylamino)-3,4-dihydroquinolin-1(2H)-yl)ethanone

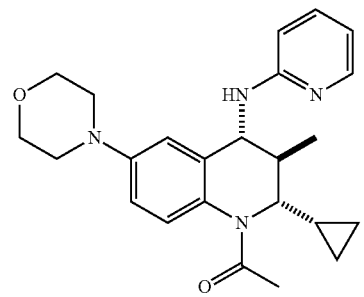 [SMILES: CC(=O)N1c2ccc(N3CCOCC3)cc2[C@H](Nc2ccccn2)[C@@H](C)[C@@H]1C1CC1]

To a reaction vessel DavePhos (15 mg, 0.038 mmol), Pd$_2$(dba)$_3$ (53 mg, 0.058 mmol), sodium tert-butoxide (100 mg, 1.041 mmol), 2-bromopyridine (0.091 mL, 0.692 mmol) and rac-1-((2S,3R,4R)-4-amino-2-cyclopropyl-3-methyl-6-morpholino-3,4-dihydroquinolin-1(2H)-yl)ethanone (for a preparation see Intermediate 83, 114 mg, 0.346 mmol) were added in 1,4-dioxane (5 mL) and the reaction was left to stir at 100° C. The reaction mixture was filtered through celite and washed with ethyl acetate. The combined filtrates were concentrated in vacuo to a crude brown gum. This was purified by chromatography silica gel eluting with 20-80% ethyl acetate in dichloromethane to give the product (12 mg, 8%) as a beige solid. LCMS (2 min Formic): Rt=0.65 min, [MH]+=407.

Example 97: rac-1-((2S,3R,4R)-2-cyclopropyl-6-(1-ethyl-1H-pyrazol-4-yl)-3-methyl-4-(phenylamino)-3,4-dihydroquinolin-(2H)-yl)ethanone

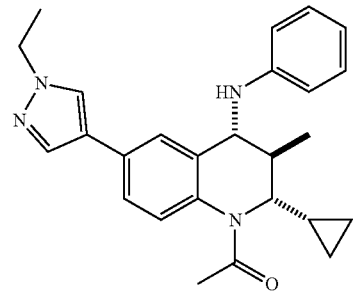 [SMILES: CCn1cc(-c2ccc3c(c2)[C@H](Nc2ccccc2)[C@@H](C)[C@H](C2CC2)N3C(C)=O)cn1]

A mixture of bromobenzene (0.020 mL, 0.190 mmol), DavePhos (4.4 mg, 0.011 mmol), Pd$_2$(dba)$_3$ (12.4 mg, 0.014 mmol) and sodium tert-butoxide (18.4 mg, 0.191 mmol) was added to rac-1-((2S,3R,4R)-4-amino-2-cyclopropyl-6-(1-ethyl-1H-pyrazol-4-yl)-3-methyl-3,4-dihydroquinolin-1(2H)-yl)ethanone (for a preparation see Intermediate 90, 39.1 mg, 0.116 mmol) in 1,4-dioxane (2 mL) and heated to 100° C. for 15.5 h under nitrogen. The reaction mixture was filtered using a celite cartridge, washed with ethyl acetate and the solvent was evaporated. The residue was purified by MDAP (Formic) to give the product (17 mg, 48%) as a pale brown gum.

LCMS (2 min Formic): Rt=1.13 min, [MH]$^+$=415.

Example 98: rac-1-((2S,3R,4R)-2-cyclopropyl-3-methyl-6-(1-methyl-H-pyrazol-4-yl)-4-(phenylamino)-3,4-dihydroquinolin-1(2H)-yl)ethanone

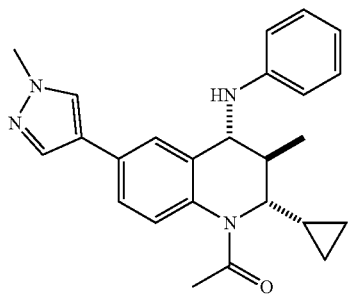 [SMILES: CC(=O)N1c2ccc(-c3cnn(C)c3)cc2[C@H](Nc2ccccc2)[C@@H](C)[C@@H]1C1CC1]

A mixture of rac-1-((2S,3R,4R)-4-amino-2-cyclopropyl-3-methyl-6-(1-methyl-1H-pyrazol-4-yl)-3,4-dihydroquinolin-1(2H)-yl)ethanone (for a preparation see Intermediate 92, 39.8 mg, 0.123 mmol), bromobenzene (0.021 ml, 0.199 mmol), Pd$_2$(dba)$_3$ (12.8 mg, 0.014 mmol), DavePhos (4.5 mg, 0.011 mmol), and sodium tert-butoxide (20 mg, 0.208 mmol) in 1,4-dioxane (2 mL) and heated to 100° C. for 15.5 h under nitrogen. The reaction mixture was filtered using a celite cartridge, washed with ethyl acetate and then solvent was evaporated and purified by MDAP (Formic) to give the product (8 mg, 15%) as a pale brown gum.

LCMS (2 min Formic): Rt=1.07 min, [MH]$^+$=308.

Example 99: rac-4-((2S,3R,4R)-1-acetyl-2-cyclopropyl-3-methyl-4-(phenylamino)-1,2,3,4-tetrahydroquinolin-6-yl)benzoic Acid

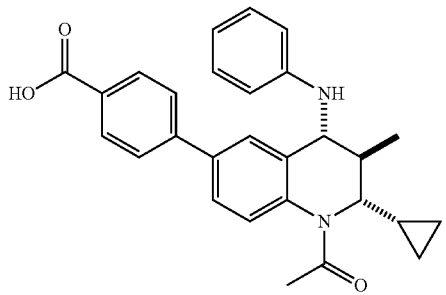 [SMILES: CC(=O)N1c2ccc(-c3ccc(C(=O)O)cc3)cc2[C@H](Nc2ccccc2)[C@@H](C)[C@@H]1C1CC1]

A mixture of rac-4-((2S,3R,4R)-1-acetyl-4-amino-2-cyclopropyl-3-methyl-1,2,3,4-tetrahydroquinolin-6-yl)benzoic acid (for a preparation see Intermediate 94, 28.4 mg, 0.078 mmol), bromobenzene (0.016 mL, 0.156 mmol), DavePhos (3.6 mg, 9.15 μmol), Pd$_2$(dba)$_3$ (11.7 mg, 0.013 mmol) and sodium tert-butoxide (13.2 mg, 0.137 mmol) in 1,4-dioxane (1 mL) was heated under nitrogen at 100° C. 1.75 h, further sodium tert-butoxide (9.6 mg, 0.100 mmol) was added and heating continued for a further 1.5 h. After leaving to cool and stand at rt for 15.75 h, further bromobenzene (0.032 mL, 0.304 mmol) was added and heating at 100° C. continued for a further 4.5 h. The mixture was allowed to cool to rt and was filtered through a 2.5 g celite cartridge, washing with ethyl acetate and methanol. The combined filtrates were evaporated under a stream of nitrogen. The residue was redissolved in 1,4-dioxane (1 mL) and had fresh reagents added as follows; bromobenzene (0.025 mL, 0.234 mmol), DavePhos (4.0 mg, 10.16 μmol), Pd$_2$(dba)$_3$ (11.2 mg, 0.012 mmol), sodium tert-butoxide (20.2 mg, 0.210 mmol) and 1,4-dioxane (1 mL). The mixture was again heated at 100° C. under nitrogen for 2.75 h before further DavePhos (16.7 mg, 0.042 mmol) and Pd$_2$(dba)$_3$ (55.9 mg, 0.061 mmol) were added and heating at 100° C. continued for a further 45 min. After cooling, the mixture was partitioned between saturated aqueous sodium bicarbonate solution (4 mL) and dichloromethane (5 mL). The phases were separated and the aqueous phase further extracted with dichloromethane (2×5 mL). The combined organics were concentrated and purified by MDAP (Formic) to give the product (4.4 mg, 9.99 μmol, 12.82%) as a cream solid.

LCMS (2 min Formic): Rt=1.12 min, [M−H]$^-$=439.

Example 100: rac-1-((2S,3R,4R)-2,3-dimethyl-4-(phenylamino)-3,4-dihydro-1,5-naphthyridin-1(2H)-yl)ethanone

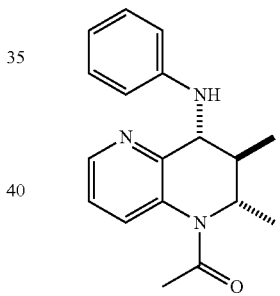

Under nitrogen atmosphere, to a solution of bromobenzene (0.058 mL, 0.540 mmol) in 1,4-dioxane (3 mL) were added rac-1-((2S,3R,4R)-4-amino-2,3-dimethyl-3,4-dihydro-1,5-naphthyridin-1(2H)-yl)ethanone (for a preparation see Intermediate 97, 79 mg, 0.360 mmol), BrettPhos (19.34 mg, 0.036 mmol), Pd$_2$(dba)$_3$ (16.50 mg, 0.018 mmol) and sodium tert-butoxide (51.9 mg, 0.540 mmol). Using a microwave reactor the solution was stirred and irradiated with microwaves so as to maintain a temperature of 110° C. for 30 min. The solution was transferred into another 2-5 mL microwave vial using a syringe. Bromobenzene (0.058 mL, 0.540 mmol), Pd$_2$(dba)$_3$ (16.50 mg, 0.018 mmol), BrettPhos (19.34 mg, 0.036 mmol) and sodium tert-butoxide (51.9 mg, 0.540 mmol) were added, the reaction mixture was stirred and irradiated with microwaves so as to maintain a temperature of 110° C. for 30 min. The reaction mixture was filtered through a pad of celite (rinsed with EtOAc). The filtrate was then evaporated in vacuo. The residue was loaded onto a 25 g SNAP cartridge and purified by column chromatography using a gradient 0-10% of MeOH in DCM. Desired fractions were combined and evaporated in vacuo to afford a yellow solid. This residue was purified by MDAP (Formic) chromatography. Desired fractions were combined and evaporated in vacuo to afford a yellow solid. This solid was dissolved in DCM and loaded onto a 10 g SNAP cartridge and purified by column chromatography using a gradient 0-100% of ethyl acetate in cyclohexane. Desired fractions were combined and evaporated in vacuo to afford a white solid. This solid was purified by MDAP (Formic) chromatography. Desired fractions were combined and evaporated in vacuo to afford the product as a beige solid (7 mg). LCMS (2 min Formic): Rt=0.80 min, [MH]$^+$=296.

Example 101: rac-(6S,7R,8R)-5-acetyl-6-cyclopropyl-7-methyl-8-(phenylamino)-5,6,7,8-tetrahydro-1,5-naphthyridin-2(1H)-one

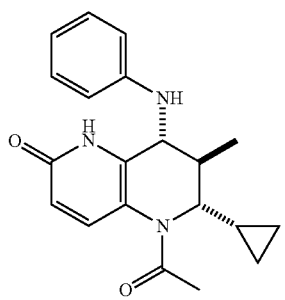 [SMILES: CC(=O)N1c2ccc(=O)[nH]c2[C@H](Nc2ccccc2)[C@@H](C)[C@@H]1C1CC1]

A mixture of rac-1-((2S,3R,4R)-2-cyclopropyl-6-methoxy-3-methyl-4-(phenylamino)-3,4-dihydro-1,5-naphthyridin-1(2H)-yl)ethanone (for a preparation see Intermediate 101, 458 mg, 1.303 mmol) and sodium iodide (1172 mg, 7.82 mmol) was diluted with acetonitrile (8 mL) and TMSCl (0.999 mL, 7.82 mmol) added. The mixture was stirred under nitrogen at 55° C. for 3 h. The reaction solution was allowed to cool to rt and evaporated under vacuum. The residue was partitioned between water (10 mL) and EtOAc (10 mL). The organic layer was separated and extracted with EtOAc (2×10 mL). The organic extracts were combined, dried through a hydrophobic frit and the solvent removed under vacuum. The residue was loaded in CHCl$_3$ (8 mL) and purified on a 100 g silica cartridge using a gradient of 0-10% MeOH in DCM over 12 CVs. The appropriate fractions were combined and the solvent removed by rotary evaporation to give the product (312 mg, 0.925 mmol, 71%) as a dark brown gum which was used as an intermediate for synthesis of further examples. 30 mg of the intermediate was purified by MDAP (Formic). The appropriate fractions were combined and the solvent evaporated under a stream of nitrogen to give the product as a light brown solid (13 mg, 0.039 mmol). LCMS (2 min Formic): Rt=0.82 min, [MH]$^+$=338.

Example 102a & 102b: 1-((2S,3R,4R)-2-cyclopropyl-3-methyl-4-(phenylamino)-3,4-dihydro-1,5-naphthyridin-1(2H)-yl)ethanone (102a) & 1-((2S, 3R,4R)-2-cyclopropyl-3-methyl-4-(phenylamino)-3,4-dihydro-1,5-naphthyridin-1(2H)-yl)ethanone (102b)

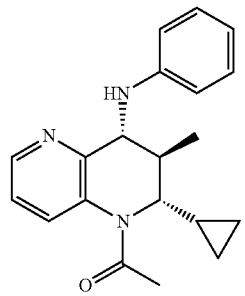

102a

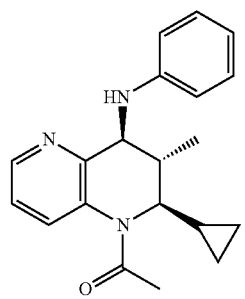

102b

A mixture of rac-(6S,7R,8R)-5-acetyl-6-cyclopropyl-7-methyl-8-(phenylamino)-5,6,7,8-tetrahydro-1,5-naphthyridin-2-yl trifluoromethanesulfonate (for a preparation see Intermediate 102, 300 mg, 0.639 mmol), triethylamine (0.534 mL, 3.83 mmol). Pd(dppf)Cl$_2$ (354 mg, 0.432 mmol) and formic acid (0.123 mL, 3.20 mmol) in DMF (10 mL) was stirred under nitrogen at 60° C. for 1 h. The solution was applied directly to a 20 g Flash SCX SPE column which had been pre-equilibrated with MeOH (30 mL). The column was flushed with MeOH (30 mL) then with MeOH/NH$_3$ (2M, 30 mL). All fractions were combined and concentrated in vacuo and the SCX method was repeated. The MeOH/NH$_3$ fractions were combined and evaporated. The samples were dissolved in 1:1 MeOH:DMSO (3×1 mL) and purified by MDAP (HpH). The appropriate fractions were concentrated in vacuo to leave the racemic product (92 mg). LCMS (2 min Formic): Rt=0.95 min, [MH]$^+$=322. rac-1-((2S,3R,4R)-2-Cyclopropyl-3-methyl-4-(phenylamino)-3,4-dihydro-1,5-naphthyridin-1(2H)-yl)ethanone, 92 mg) was submitted for chiral separation into its enantiomers (A and B) using a 250×30 mm Chiralpak IA column eluting with 25% ethanol in heptane at a flow rate of 30 mL/min. Peak 1/Enantiomer A fractions were collected between 5.5 and 6.5 min. Peak 2/Enantiomer B fractions were collected between 10 and 14 min. Fraction solutions were combined then evaporated to dryness to give Enantiomer A (40 mg) and Enantiomer B (40 mg) as white solids.

Enantiomer A, Example 102a

Analytical Chiral HPLC using a 250×4.6 mm Chiralpak IC column eluting with 25% ethanol in heptane at 1 mL/min—Rt=4.8 min.>99% ee by UV.

Enantiomer B, Example 102b

Analytical Chiral HPLC using a 250×4.6 mm Chiralpak IC column eluting with 25% ethanol in heptane at 1 mL/min—Rt=7.2 min, >99% ee by UV.

Example 103: rac-4-((6S,7R,8R)-5-Acetyl-6-cyclopropyl-7-methyl-8-(phenylamino)-5,6,7,8-tetrahydro-1,5-naphthyridin-2-yl)-N-methylbenzamide

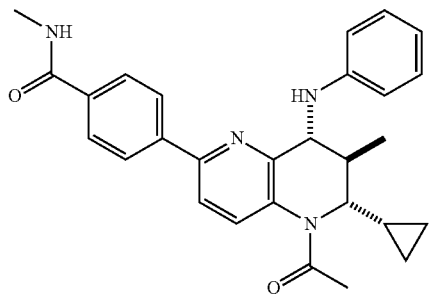 [SMILES: CNC(=O)c1ccc(-c2ccc3c(n2)[C@H](Nc2ccccc2)[C@@H](C)[C@H](C2CC2)N3C(C)=O)cc1]

A mixture of rac-(6S,7R,8R)-5-acetyl-6-cyclopropyl-7-methyl-8-(phenylamino)-5,6,7,8-tetrahydro-1,5-naphthyridin-2-yl trifluoromethanesulfonate (for a preparation see Intermediate 102, 75 mg, 0.160 mmol), N-methyl-4-(4,4,5,5-tetramethyl-1,3,2-dioxaborolan-2-yl)benzamide (50.1 mg, 0.192 mmol), PdCl$_2$(dppf) (17.53 mg, 0.024 mmol) and potassium carbonate (66.2 mg, 0.479 mmol) in 1,4-dioxane (1.4 mL) and water (0.350 mL) was stirred under nitrogen at 100° C. for 1 h. The reaction mixture was concentrated in vacuo and diluted with DCM, then washed with water (3×10 mL) and dried with a hydrophobic frit. The solution was applied to a 5 g Flash SCX SPE column which had been pre-equilibrated with MeOH (20 mL). The column was flushed with MeOH (20 mL) then with MeOH/NH$_3$ (2M, 20 mL). The MeOH/NH$_3$ fraction was collected and the solvent was evaporated to give a crude brown gum (72 mg). The sample was dissolved in 1:1 MeOH:DMSO (1 mL) and purified by MDAP (HpH). The appropriate fractions were combined and concentrated in vacuo to give the product (15 mg, 0.033 mmol, 21%) as a yellow gum. LCMS (2 min Formic): Rt=1.07 min, [MH]$^+$=455.

Example 104: rac-5-((6S,7R,8R)-5-Acetyl-6-cyclopropyl-7-methyl-8-(phenylamino)-5,6,7,8-tetrahydro-1,5-naphthyridin-2-yl)-N-methylpicolinamide

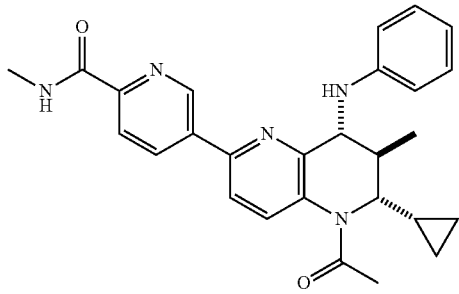 [SMILES: CNC(=O)c1ccc(-c2ccc3c(n2)[C@H](Nc2ccccc2)[C@@H](C)[C@H](C2CC2)N3C(C)=O)cn1]

A mixture of rac-(6S,7R,8R)-5-acetyl-6-cyclopropyl-7-methyl-8-(phenylamino)-5,6,7,8-tetrahydro-1,5-naphthyridin-2-yl trifluoromethanesulfonate (for a preparation see Intermediate 102, 75 mg, 0.160 mmol), potassium carbonate (66.2 mg, 0.479 mmol), PdCl$_2$(dppf) (17.53 mg, 0.024 mmol) and N-methyl-5-(4,4,5,5-tetramethyl-1,3,2-dioxaborolan-2-yl)picolinamide (50.2 mg, 0.192 mmol) in 1,4-dioxane (1.400 mL) and water (0.35 mL) was stirred under nitrogen at 100° C. for 4 h. The reaction mixture was concentrated in vacuo then dissolved in DCM. This solution was washed with water (3×10 mL), dried through a hydrophobic frit and concentrated in vacuo to give a dark red gum. The samples were dissolved in 1:1 MeOH:DMSO (2×1 mL) and purified by MDAP (HpH). The solvent was evaporated in vacuo. The sample was dissolved in MeOH (2 mL) and was applied to a 2 g Flash SCX SPE column which had been pre-equilibrated with MeOH (10 mL). The column was flushed with MeOH (10 mL) then with MeOH/NH$_3$ (2 M, 10 mL). The MeOH/NH$_3$ fraction was collected and the solvent was evaporated to give the product (14 mg, 0.031 mmol, 19%) as a yellow gum. LCMS (2 min Formic): Rt=1.09 min, [MH]$^+$=456.

Example 105: rac-1-((2S,3R,4R)-2-cyclopropyl-6-(6-methoxypyridin-3-yl)-3-methyl-4-(phenylamino)-3,4-dihydro-1,5-naphthyridin-1(2H)-yl)ethanone

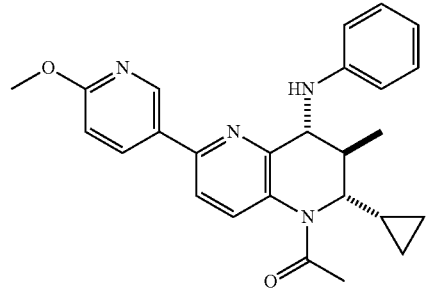 [SMILES: COc1ccc(-c2ccc3c(n2)[C@H](Nc2ccccc2)[C@@H](C)[C@H](C2CC2)N3C(C)=O)cn1]

A mixture of rac-(6S,7R,8R)-5-acetyl-6-cyclopropyl-7-methyl-8-(phenylamino)-5,6,7,8-tetrahydro-1,5-naphthyridin-2-yl trifluoromethanesulfonate (for a preparation see Intermediate 102, 75 mg, 0.160 mmol), 2-methoxy-5-(4,4,5,5-tetramethyl-1,3,2-dioxaborolan-2-yl)pyridine (45.1 mg, 0.192 mmol), PdCl$_2$(dppf) (17.53 mg, 0.024 mmol) and potassium carbonate (66.2 mg, 0.479 mmol) in 1,4-dioxane (1.4 mL) and water (0.35 mL) was stirred under nitrogen at 100° C. for 1 h. The reaction mixture was allowed to cool then concentrated in vacuo. The sample was diluted with DCM (7 mL), washed with water (3×10 mL) and dried through a hydrophobic frit. The solution was applied to a 5 g Flash SCX SPE column which had been pre-equilibrated with MeOH. The column was flushed with MeOH then with MeOH/NH$_3$ (2 M). The MeOH/NH$_3$ fraction was collected and the solvent was evaporated to give a brown gum. The sample was dissolved in 1:1 MeOH:DMSO (1 mL) and purified by MDAP (HpH). The solvent was evaporated in vacuo to give the product (25.1 mg, 0.059 mmol, 37%) as a clear gum.

LCMS (2 min Formic): Rt=1.27 min, [MH]$^+$=429.

Example 106: rac-1-((2S,3R,4R)-2-cyclopropyl-6-(1-ethyl-1H-pyrazol-4-yl)-3-methyl-4-(phenylamino)-3,4-dihydro-1,5-naphthyridin-1(2H)-yl)ethanone

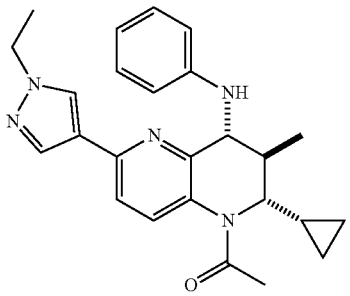 [SMILES: CCn1cc(-c2ccc3c(n2)[C@H](Nc2ccccc2)[C@@H](C)[C@H](C2CC2)N3C(C)=O)cn1]

A solution of rac-(6S,7R,8R)-5-acetyl-6-cyclopropyl-7-methyl-8-(phenylamino)-5,6,7,8-tetrahydro-1,5-naphthyridin-2-yl trifluoromethanesulfonate (for a preparation see Intermediate 102, 55 mg, 0.117 mmol), 1-ethyl-4-(4,4,5,5-tetramethyl-1,3,2-dioxaborolan-2-yl)-1H-pyrazole (31 mg, 0.140 mmol), PdCl$_2$(dppf) (13 mg, 0.018 mmol) and potassium carbonate (49 mg, 0.355 mmol) in water (0.250 mL) and 1,4-dioxane (1 mL) was heated for 1 h at 100° C. The mixture was concentrated in vacuo and separated between DCM (10 mL) and water (10 mL). The aqueous phase was extracted with DCM (2×10 mL) and the combined organic phases were washed with water (2×10 mL), dried through a hydrophobic frit and concentrated in vacuo. The sample was dissolved in DMSO:MeOH (1:1, 1 ml) and purified by 2×MDAP (Formic). The appropriate fractions were combined and concentrated in vacuo to give the product (5.6 mg, 12%).

LCMS (2 min Formic): Rt=1.14 min, [MH]$^+$=416

Example 107: 1-((rac-2S,3R,4R)-2-cyclopropyl-3-methyl-6-(3-methylpiperazin-1-yl)-4-(phenylamino)-3,4-dihydro-1,5-naphthyridin-1(2H)-yl)ethanone

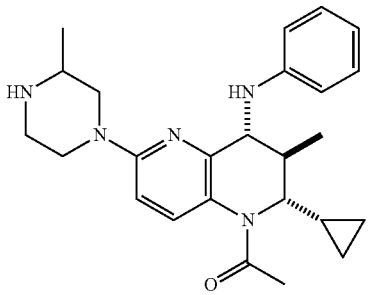 [SMILES: CC(=O)N1c2ccc(N3CCNC(C)C3)nc2[C@H](Nc2ccccc2)[C@@H](C)[C@@H]1C1CC1]

To a solution of tert-butyl 4-((rac-6S,7R,8R)-5-acetyl-6-cyclopropyl-7-methyl-8-(phenylamino)-5,6,7,8-tetrahydro-1,5-naphthyridin-2-yl)-2-methylpiperazine-1-carboxylate (for a preparation see Intermediate 103, 11 mg, 0.021 mmol) in 1,4-dioxane (0.1 mL) was added 4 M HCl in 1,4-dioxane (0.212 mL, 0.847 mmol). The reaction mixture was stirred at rt in a closed vessel for 1 h. The reaction mixture was concentrated under a stream of nitrogen then dissolved in MeOH (1 mL). The solution was applied directly to a 2 g Flash SCX SPE column which had been pre-equilibrated with MeOH. The column was flushed with MeOH (6 mL) then with MeOH/NH$_3$ (2M, 6 mL). The MeOH/NH$_3$ fraction was concentrated under a stream of nitrogen to give the product (7.1 mg, 0.017 mmol, 80%) as a yellow gum. This was a racemic mixture of diastereoisomers.

LCMS (2 min Formic): Rt=0.78 min, [MH]$^+$=420.

Example 108: rac-1-((2S,3R,4R)-2-cyclopropyl-3-methyl-4-(phenylamino)-6-(piperazin-1-yl)-3,4-dihydro-1,5-naphthyridin-1(2H)-yl)ethanone

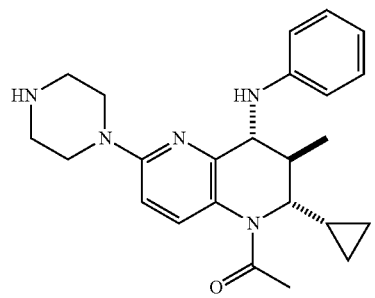 [SMILES: CC(=O)N1c2ccc(N3CCNCC3)nc2[C@H](Nc2ccccc2)[C@@H](C)[C@@H]1C1CC1]

A solution of rac-tert-butyl 4-((6S,7R,8R)-5-acetyl-6-cyclopropyl-7-methyl-8-(phenylamino)-5,6,7,8-tetrahydro-1,5-naphthyridin-2-yl)piperazine-1-carboxylate (for a preparation see Intermediate 104, 12 mg, 0.024 mmol) and 4M HCl in 1,4-dioxane (250 µl, 1.000 mmol) in 1,4-dioxane (0.1 mL) was stirred in a closed vessel at rt for 1 h. The sample was concentrated under a stream of nitrogen then dissolved in 1:1 MeOH:DMSO (1 mL) and purified by MDAP (HpH). The solvent was evaporated in vacuo to give the product (5.4 mg, 0.013 mmol, 56%) as a clear gum.

LCMS (2 min Formic): Rt=0.70 min, [MH]$^+$=406.

Example 109: rac-1-((2S,3R,4R)-6-(4-aminopiperidin-1-yl)-2-cyclopropyl-3-methyl-4-(phenylamino)-3,4-dihydro-1,5-naphthyridin-1(2H)-yl)ethanone

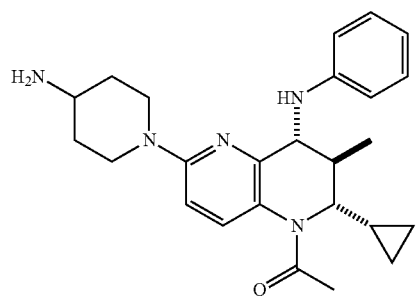 [SMILES: CC(=O)N1c2ccc(N3CCC(N)CC3)nc2[C@H](Nc2ccccc2)[C@@H](C)[C@@H]1C1CC1]

A mixture of rac-tert-butyl (1-((6S,7R,8R)-5-acetyl-6-cyclopropyl-7-methyl-8-(phenylamino)-5,6,7,8-tetrahydro-1,5-naphthyridin-2-yl)piperidin-4-yl)carbamate (for a preparation see Intermediate 105, 8 mg, 0.015 mmol) and 4M HCl in 1,4-dioxane (0.2 mL, 0.800 mmol) in 1,4-dioxane (0.1 mL) was stirred at rt in a closed vessel for 1 h. The reaction mixture was concentrated under a stream of nitrogen then dissolved in MeOH (1 mL). The solution was applied directly to a 2 g Flash SCX SPE column which had been pre-equilibrated with MeOH. The column was flushed with MeOH (6 mL) then with MeOH/NH$_3$ (2 M, 6 mL). The MeOH/NH₃ fraction was concentrated under a stream of nitrogen to give the product (2.1 mg, 5.01 µmol, 33%).
LCMS (2 min Formic): Rt=0.66 min, [MH]⁺=420.

Example 110: rac-1-((2S,3R,4R)-2-cyclopropyl-3-methyl-6-morpholino-4-(phenylamino)-3,4-dihydro-1,5-naphthyridin-1(2H)-yl)ethanone

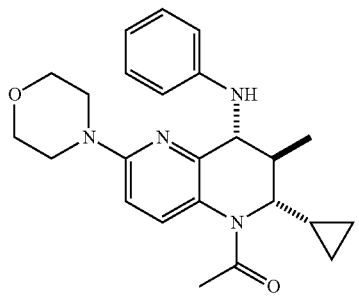 [SMILES: CC(=O)N1c2ccc(N3CCOCC3)nc2[C@H](Nc2ccccc2)[C@@H](C)[C@@H]1C1CC1]

A mixture of rac-1-((2S,3R,4R)-4-amino-2-cyclopropyl-3-methyl-6-morpholino-3,4-dihydro-1,5-naphthyridin-1(2H)-yl)ethanone (for a preparation see Intermediate 109, 63.4 mg, 0.192 mmol), Pd₂(dba)₃ (8.79 mg, 9.59 µmol), sodium tert-butoxide (27.7 mg, 0.288 mmol), DavePhos (7.55 mg, 0.019 mmol) and bromobenzene (0.021 mL, 0.195 mmol) in 1,4-dioxane (2.5 mL) was heated to 100° C. for 20 h. The reaction mixture was filtered through celite, washed with ethyl acetate then concentrated in vacuo. The sample was dissolved in DMSO:MeOH (1:1, 2×1 mL) and purified by 2× MDAP (HpH). The appropriate fractions were combined and concentrated in vacuo. The sample was purified on a Zorbax SB phenyl column (150 mm×21.2 mm, 7.0 µm) at 20 mL/min flow rate. Gradient elution was carried out at ambient temperature, with the mobile phases as (A) water containing 0.1% (v/v) TFA and (B) acetonitrile. The UV detection was a summed signal from wavelength of 210 nm to 400 nm. The appropriate fractions were dried under a stream of nitrogen and combined to give the product (19.3 mg, 25%).
LCMS (2 min Formic): Rt=1.15 min, [MH]⁺=407.

Example 111: rac-1-((2S,3R,4R)-2-cyclopropyl-6-methoxy-3-methyl-4-((6-methylpyridin-2-yl)amino)-3,4-dihydro-1,5-naphthyridin-1(2H)-yl)ethanone

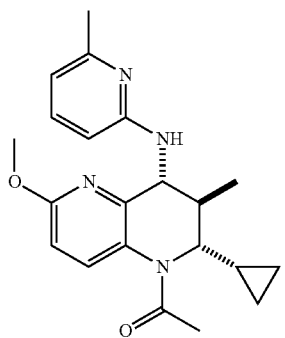 [SMILES: COc1ccc2c(n1)[C@H](Nc1cccc(C)n1)[C@@H](C)[C@H](C1CC1)N2C(C)=O]

A mixture of rac-1-((2S,3R,4R)-4-amino-2-cyclopropyl-6-methoxy-3-methyl-3,4-dihydro-1,5-naphthyridin-1(2H)-yl)ethanone (for a preparation see Intermediate 100, 500 mg, 1.816 mmol), 2-bromo-6-methylpyridine (0.248 ml, 2.179 mmol), DavePhos (71.5 mg, 0.182 mmol), Pd₂(dba)₃ (83 mg, 0.091 mmol) and sodium tert-butoxide (262 mg, 2.72 mmol) in 1,4-dioxane (6 mL) was heated at 100° C. under nitrogen for 1 h. The reaction mixture was allowed to cool to rt, filtered through celite and rinsed with ethyl acetate. The solvent was then evaporated in vacuo. The crude material was dissolved in DCM, loaded onto a 100 g silica cartridge and purified over a gradient of 0-75% cyclohexane/(1% NEt₃/ethyl acetate) over 10 CVs. The appropriate fractions were concentrated in vacuo to give the product (445 mg, 1.214 mmol, 66.9%).
LCMS (2 min Formic): Rt=0.66 min, [MH]⁺=367.

Example 112: rac-1-((2S,3R,4R)-2-cyclopropyl-6-hydroxy-3-methyl-4-((6-methylpyridin-2-yl)amino)-3,4-dihydro-1,5-naphthyridin-1(2H)-yl)ethanone

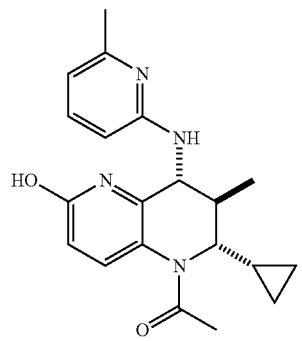 [SMILES: CC(=O)N1c2ccc(O)nc2[C@H](Nc2cccc(C)n2)[C@@H](C)[C@@H]1C1CC1]

A mixture of rac-1-((2S,3R,4R)-2-cyclopropyl-6-methoxy-3-methyl-4-((6-methylpyridin-2-yl)amino)-3,4-dihydro-1,5-naphthyridin-1(2H)-yl)ethanone (for a preparation see Example 111, 455 mg, 1.242 mmol), sodium iodide (1117 mg, 7.45 mmol) and TMSCl (0.952 mL, 7.45 mmol) in acetonitrile (10 mL) was stirred under nitrogen at 45° C. for 3 h. The reaction mixture was allowed to cool to rt and was concentrated in vacuo. The sample was then dissolved in MeOH and applied directly to a 20 g Flash SCX SPE column which had been pre-equilibrated with MeOH (20 mL). The column was flushed with MeOH (20 mL) then with MeOH/NH₃ (2M, 20 mL). The MeOH/NH₃ fraction was concentrated under a stream of nitrogen to give the product (400 mg, 1.135 mmol, 91%).
LCMS (2 min Formic): Rt=0.51 min, [MH]⁺=353.

Example 113: rac-1-((2S,3R,4R)-2-cyclopropyl-3-methyl-4-((6-methylpyridin-2-yl)amino)-3,4-dihydro-1,5-naphthyridin-1(2H)-yl)ethanone

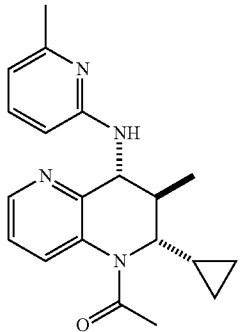 [SMILES: CC(=O)N1c2cccnc2[C@H](Nc2cccc(C)n2)[C@@H](C)[C@@H]1C1CC1]

A mixture of rac-(6S,7R,8R)-5-acetyl-6-cyclopropyl-7-methyl-8-((6-methylpyridin-2-yl)amino)-5,6,7,8-tetrahydro-1,5-naphthyridin-2-yl trifluoromethanesulfonate (188.5 mg, 0.389 mmol), Pd(dppf)Cl$_2$ (216 mg, 0.264 mmol), formic acid (0.075 ml, 1.945 mmol) and triethylamine (0.325 ml, 2.334 mmol) in DMF (7 mL) was stirred at 60° C. under nitrogen for 3 h. The reaction mixture was allowed to cool to rt and applied directly to a 20 g Flash SCX SPE column which had been pre-equilibrated with MeOH (20 mL). The column was flushed with MeOH then with MeOH/NH$_3$ (2M, 20 mL). The MeOH/NH$_3$ (20 mL) fractions were combined and concentrated under vacuum. The sample was dissolved in 1:1 MeOH:DMSO (2×1 mL) and purified by MDAP (HpH). The appropriate fractions were combined and concentrated in vacuo to give the product (86.3 mg, 0.257 mmol, 65.9%).

LCMS (2 min Formic): Rt=0.57 min, [MH]$^+$=337.

Examples 114a and 114b: 1-((2S,3R,4R)-2-cyclopropyl-3-methyl-4-((6-methylpyridin-2-yl)amino)-3,4-dihydro-1,5-naphthyridin-1(2H)-yl)ethanone (114a) & 1-((2R,3S,4S)-2-cyclopropyl-3-methyl-4-((6-methylpyridin-2-yl)amino)-3,4-dihydro-1,5-naphthyridin-1(2H)-yl)ethanone (114b)

114a

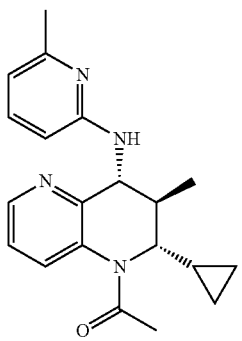

-continued

114b

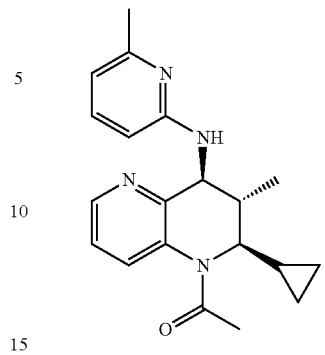

rac-1-((2S,3R,4R)-2-Cyclopropyl-3-methyl-4-((6-methylpyridin-2-yl)amino)-3,4-dihydro-1,5-naphthyridin-1(2H)-yl)ethanone (for a preparation see Example 113, 86 mg) was submitted for chiral separation into its enantiomers (A and B) using a 250×30 mm Chiralpak IA column eluting with 10% ethanol in heptanes (plus 0.2% isopropylamine) at a flow rate of 35 mL/min. Peak 1/Enantiomer A fractions were collected between 7.5 and 8.5 min. Peak 2/Enantiomer B fractions were collected between 11.5 and 14 min. Fraction solutions were combined then evaporated to dryness to give Enantiomer A (35 mg) and Enantiomer B (43 mg) as white solids.

Enantiomer A, Example 114a

Analytical Chiral HPLC using a 250×4.6 mm Chiralpak IA column eluting with 10% ethanol in heptane (plus 0.2% isopropanol) at 1 mL/min—Rt 7.0=min.>99% ee by UV.

Enantiomer B, Example 114b

Analytical Chiral HPLC using a 250×4.6 mm Chiralpak IA column eluting with 10% ethanol in heptanes (plus 0.2% isopropanol) at 1 mL/min—Rt=9.5 min, >99% ee by UV.

Example 115: rac-1-((2S,3R,4R)-2,3-dimethyl-4-(phenylamino)-3,4-dihydro-1,7-naphthyridin-1(2H)-yl)ethanone Formate

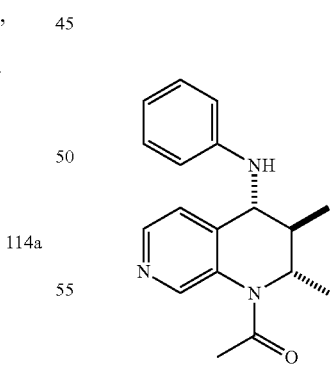

Under a nitrogen atmosphere, to a solution of bromobenzene (0.047 mL, 0.445 mmol) in 1,4-dioxane (3 mL) were added rac-1-((2S,3R,4R)-4-amino-2,3-dimethyl-3,4-dihydro-1,7-naphthyridin-1(2H)-yl)ethanone (for a preparation see Intermediate 114, 108.5 mg, 0.297 mmol), BrettPhos (15.94 mg, 0.030 mmol), Pd$_2$(dba)$_3$ (13.59 mg, 0.015 mmol) and sodium tert-butoxide (42.8 mg, 0.445 mmol). Using a microwave reactor the solution was stirred and irradiated with microwaves so as to maintain a temperature of 110° C. for 30 min. The solution was transferred into another 2-5 mL microwave vial using a syringe, bromobenzene (0.047 mL, 0.445 mmol), Pd₂(dba)₃ (13.59 mg, 0.015 mmol), BrettPhos (15.94 mg, 0.030 mmol) and sodium tert-butoxide (42.8 mg, 0.445 mmol) were added, the reaction mixture was stirred and irradiated with microwaves so as to maintain a temperature of 110° C. for 30 min. The reaction mixture was filtered through a pad of celite (rinsed with EtOAc). The filtrate was then evaporated in vacuo. The residue was loaded onto a 25 g SNAP cartridge and purified by column chromatography using a gradient 0-100% of ethyl acetate in cyclohexane over 10 CVs, followed by 100% of ethyl acetate over 10 CVs. Desired fractions were combined and evaporated in vacuo to afford a yellow residue. This residue was purified by MDAP (Formic). Desired fractions were combined and evaporated in vacuo to afford the product as a brown solid (4.2 mg). LCMS (2 min Formic): Rt=0.74 min, [MH]⁺=296

Example 116: rac-1-((2S,3R,4R)-2-cyclopropyl-3-methyl-4-(phenylamino)-3,4-dihydro-1,7-naphthyridin-1(2H)-yl)ethanone

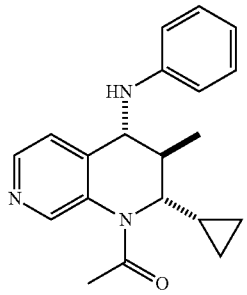 [SMILES: CC(=O)N1c2cnccc2[C@H](Nc2ccccc2)[C@@H](C)[C@@H]1C1CC1]

To a test tube were added rac-1-((2S,3R,4R)-4-amino-2-cyclopropyl-3-methyl-3,4-dihydro-1,7-naphthyridin-1(2H)-yl)ethanone (for a preparation see Intermediate 118, 46.3 mg, 0.189 mmol), bromobenzene (0.030 mL, 0.226 mmol), Pd₂(dba)₃ (8.64 mg, 9.44 µmol), sodium tert-butoxide (27.2 mg, 0.283 mmol), DavePhos (7.43 mg, 0.019 mmol) and 1,4-dioxane (2.5 mL). The reaction mixture was then heated and stirred at 100° C. for 4 h. After cooling to rt, the reaction mixture was filtered through a pad of celite (rinsed with EtOAc). The filtrate was then evaporated in vacuo. The residue was purified by MDAP (HpH). Desired fractions were combined and evaporated under vacuum to afford a white solid. The solid was dissolved in DCM, loaded onto a 10 g SNAP cartridge and purified by column chromatography using a gradient 0-100% of ethyl acetate in cyclohexane. Desired fractions were combined and evaporated under vacuum to afford the product as a colourless solid (1.7 mg).

LCMS (2 min Formic): Rt=0.85 min, [MH]⁺=322.

Example 117: rac-1-((2S,3R,4R)-2-cyclopropyl-3-methyl-4-((6-methylpyridin-2-yl)amino)-3,4-dihydro-1,7-naphthyridin-1(2H)-yl)ethanone

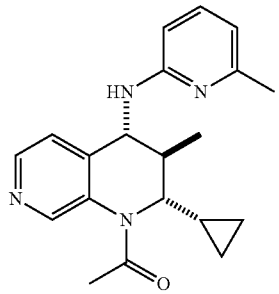 [SMILES: CC(=O)N1c2cnccc2[C@H](Nc2cccc(C)n2)[C@@H](C)[C@@H]1C1CC1]

To a test tube were added rac-1-((2S,3R,4R)-4-amino-2-cyclopropyl-3-methyl-3,4-dihydro-1,7-naphthyridin-1(2H)-yl)ethanone (for a preparation see Intermediate 118, 56.4 mg, 0.230 mmol), 2-chloro-6-methylpyridine (0.022 mL, 0.276 mmol), Pd₂(dba)₃ (10.53 mg, 0.011 mmol), sodium tert-butoxide (33.1 mg, 0.345 mmol), DavePhos (9.05 mg, 0.023 mmol) and 1,4-dioxane (2.5 mL). The reaction mixture was then heated and stirred at 100° C. for 4 h. After cooling to rt, the reaction mixture was filtered through a pad of celite (rinsed with EtOAc). The filtrate was then evaporated in vacuo. The residue was purified by MDAP (HpH). Desired fractions were combined and evaporated under vacuum to afford the product as a white solid (5.9 mg).

LCMS (2 min Formic): Rt=0.50 min, [MH]⁺=337

Example 118: rac-1-((2S,3R,4R)-3-methyl-4-(phenylamino)-2-propyl-3,4-dihydro-1,7-naphthyridin-1(2H)-yl)ethanone

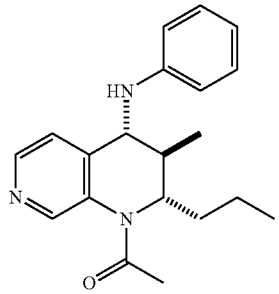 [SMILES: CCC[C@H]1[C@H](C)[C@@H](Nc2ccccc2)c2ccncc2N1C(C)=O]

To a 0.5-2 mL vial containing a suspension of rac-1-((2S,3R,4R)-4-Amino-3-methyl-2-propyl-3,4-dihydro-1,7-naphthyridin-1(2H)-yl)ethanone (for a preparation see Intermediate 122, 50 mg, 0.202 mmol), DavePhos (9 mg, 0.023 mmol), Pd₂dba₃ (10 mg, 10.92 µmol) and sodium tert-butoxide (20 mg, 0.208 mmol) in anhydrous 1,4-dioxane (1.5 mL) was added bromobenzene (26 µl, 0.247 mmol). The vial was sealed and the solution was bubbled with nitrogen for 10 min. The reaction mixture was heated in a microwave using settings as to maintain a temperature of 110° C. for 45 min. After cooling, the reaction mixture was filtered through a layer of celite, washing through with EtOAc. The solvent was removed by rotary evaporation leaving a yellow residue which was purified by MDAP (HpH). The appropriate fractions were combined and the solvent was removed by rotary evaporation to give the product as a colourless oil which solidified (4.8 mg, 0.015 mmol, 7%).

LCMS (2 min Formic): Rt=0.89 min, [MH]⁺=324.

Example 119: rac-1-((2S,3S,4R)-2-cyclopropyl-3-methyl-4-phenoxy-3,4-dihydroquinolin-1(2H)-yl) ethanone

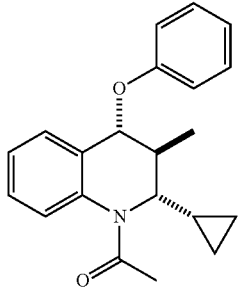 [SMILES: CC(=O)N1c2ccccc2[C@H](Oc2ccccc2)[C@@H](C)[C@@H]1C1CC1]

To a flask containing rac-1-((2S,3S,4S)-2-cyclopropyl-4-hydroxy-3-methyl-3,4-dihydroquinolin-1(2H)-yl)ethanone (for a preparation see Intermediate 124a, 35 mg, 0.143 mmol) in tetrahydrofuran (THF) (1 mL) was added phenol (13.70 mg, 0.146 mmol) and triphenylphosphine (37.4 mg, 0.143 mmol) at rt. DIAD (0.03 mL, 0.143 mmol) was added and the reaction was stirred for 10 min at rt. Further phenol (13.7 mg, 0.146 mmol) was added and the reaction stirred for a further 1.5 h and then allowed to stand overnight. Further phenol (13.7 mg, 0.146 mmol) was added, followed by triphenylphosphine (23 mg) and DIAD (14 uL). The reaction was allowed to stir for 1.5 h. The reaction mixture was partitioned between water (20 mL) and EtOAc (20 mL). The layers were separated and the aqueous phase washed with further EtOAc. The combined organics were dried ($Na_2SO_4$) and concentrated in vacuo to afford the crude product as a yellow oil. This was dissolved in DCM and purified by flash chromatography on a silica cartridge (10 g). It was eluted with 0-60% EtOAc/cyclohexane. The appropriate fractions were concentrated in vacuo to yield the desired product as a pale yellow oil. This was taken up in DMSO/MeOH (1:1) and further purified by MDAP (HpH). The appropriate fractions were concentrated in vacuo to afford the desired product as a colourless oil (7 mg, 0.023 mmol, 16%).

LCMS (2 min Formic): Rt=1.29 min, MH+=322.

Example 120: rac-1-((2S,3S,4R)-2-cyclopropyl-3-methyl-4-((6-methylpyridin-2-yl)oxy)-3,4-dihydroquinolin-1(2H)-yl)ethanone

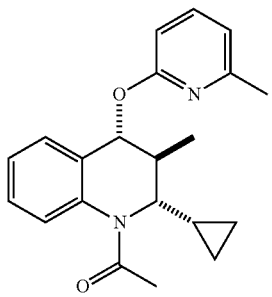 [SMILES: CC(=O)N1c2ccccc2[C@H](Oc2cccc(C)n2)[C@@H](C)[C@@H]1C1CC1]

rac-1-((2S,3S,4R)-2-cyclopropyl-4-hydroxy-3-methyl-3,4-dihydroquinolin-1(2H)-yl)ethanone (for a preparation see Intermediate 124b, 50 mg, 0.204 mmol) was dissolved in N,N-dimethylformamide (DMF) (1 mL) at rt. Sodium hydride (20 mg, 0.51 mmol) was then added in 1 portion and the reaction stirred at rt for 10 min. 2-Fluoro-6-methylpyridine (68 mg, 0.611 mmol) was added drop-wise and the reaction mixture heated at 70° C. for ~2 h. The reaction was quenched by the addition of $H_2O$ (10 mL). The organics were extracted into $Et_2O$ (20 mL) and the aqueous layer further extracted with $Et_2O$ (2×20 mL). The combined organics were then washed with further $H_2O$ (2×20 mL), dried ($Na_2SO_4$) and concentrated in vacuo to afford the crude product as a colourless oil. This was taken up in DCM and added to a 10 g silica cartridge. This was purified by flash chromatography, eluting with 0-50% EtOAc/cyclohexane. The appropriate fractions were concentrated in vacuo to afford the desired product as a white solid (18 mg, 0.054 mmol, 27%).

LCMS (2 min Formic): Rt=1.34 min, [MH]⁺=336.

Example 121: rac-1-((2S,3R,4R)-2,3-dimethyl-4-(pyridin-2-ylamino)-3,4-dihydroquinolin-1(2H)-yl) ethanone

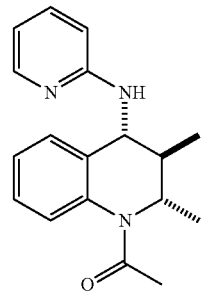 [SMILES: CC(=O)N1c2ccccc2[C@H](Nc2ccccn2)[C@@H](C)[C@@H]1C]

To a test tube were added rac-1-((2S,3R,4R)-4-amino-2,3-dimethyl-3,4-dihydroquinolin-1(2H)-yl)ethanone (for a preparation see Intermediate 6, 47.3 mg, 0.217 mmol), 2-bromopyridine (0.025 mL, 0.260 mmol), $Pd_2(dba)_3$ (9.92 mg, 10.83 µmol), sodium tert-butoxide (31.2 mg, 0.325 mmol), DavePhos (8.53 mg, 0.022 mmol) and 1,4-dioxane (2.5 mL). The reaction mixture was then heated and stirred at 100° C. in a greenhouse reactor for 3 h. After cooling to rt, the reaction mixture was filtered through a pad of celite (rinsed with EtOAc). The filtrate was then evaporated in vacuo. The residue was purified by MDAP (Formic). The desired fractions were combined and evaporated in vacuo to afford the desired product as a colourless solid (47.9 mg).

LCMS (2 min formic): Rt=0.54 min, [MH]⁺=296.

Example 122: rac-1-((2S,3R,4R)-2-ethyl-3-methyl-4-((6-methylpyridin-2-yl)amino)-3,4-dihydroquinolin-1(2H)-yl)ethanone

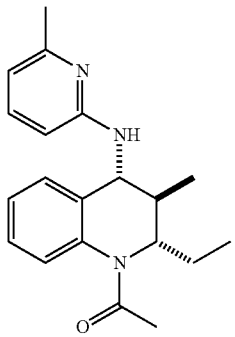 [SMILES: CC[C@H]1[C@H](C)[C@@H](Nc2cccc(C)n2)c2ccccc2N1C(C)=O]

The 2-bromo-6-methylpyridine (0.355 mL, 3.10 mmol), rac-1-((2S,3R,4R)-4-amino-2-ethyl-3-methyl-3,4-dihydroquinolin-1(2H)-yl)ethanone (for a preparation see Intermediate 10, 360 mg, 1.550 mmol), Dave Phos (60.9 mg, 0.155 mmol), Pd$_2$(dba)$_3$ (85 mg, 0.093 mmol), sodium tert-butoxide (208 mg, 2.169 mmol) and 1,4-dioxane (10 mL) were placed in a round bottomed flask and allowed to stir at 100° C. for 4 h. The reaction was allowed to stir at 100° C. for a further 18 h, and then treated with more Pd$_2$(dba)$_3$ (85 mg, 0.093 mmol) and DavePhos (60.9 mg, 0.155 mmol) and allowed to stir at 100° C. for 24 h. The reaction was partitioned between water and EtOAc, the organic layer was washed with brine, dried using a hydrophobic frit and concentrated to a brown solid. This solid was purified using a 25 g silica column, elute: 0-50% EtOAc:cyclohexane. Clean fractions were combined and concentrated to leave the product as a light brown solid (167 mg).

LCMS (2 min Formic): Rt=0.66 min, [MH]$^+$=324.

Example 123: rac-1-((2S,3R,4R)-2-cyclopropyl-3-methyl-4-((4-methyloxazol-2-yl)amino)-3,4-dihydroquinolin-1(2H)-yl)ethanone

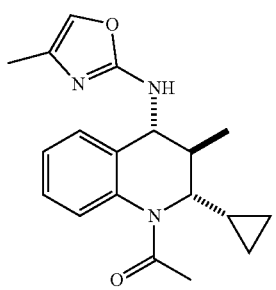 [SMILES: CC(=O)N1c2ccccc2[C@H](Nc2nc(C)co2)[C@@H](C)[C@@H]1C1CC1]

To a solution of cyanogen bromide (21.68 mg, 0.205 mmol) and sodium carbonate (43.4 mg, 0.409 mmol) in THF (2 mL) at −20° C. was added rac-1-((2S,3R,4R)-4-amino-2-cyclopropyl-3-methyl-3,4-dihydroquinolin-1(2H)-yl)ethanone (For a preparation see Intermediate, 50 mg, 0.205 mmol). The mixture was stirred at −20° C. for 2 hr then allowed to warm to rt, further cyanogen bromide (21.68 mg, 0.205 mmol) added and stirred for 18 hr. The reaction mixture was filtered. To the filtrate was added water (2 mL), 1-hydroxypropan-2-one (0.028 mL, 0.41 mmol) and 1M NaOH (0.2 mL) and the reaction heated to 120° C. for 3 h in a microwave reactor. The reaction mixture was diluted with water and extracted with diethyl ether (2×30 mL). The combined organics were washed with brine, dried (MgSO$_4$) and evaporated to give crude product. The samples were purified by MDAP (HpH) to afford the product (7 mg) as a clear oil. LCMS (2 min HpH): Rt=0.94 min, [MH]$^+$=326.

Example 124: rac-1-((2S,3R,4R)-4-((3-(aminomethyl)phenyl)amino)-2-cyclopropyl-3-methyl-3,4-dihydroquinolin-1(2H)-yl)ethanone, hydrochloride

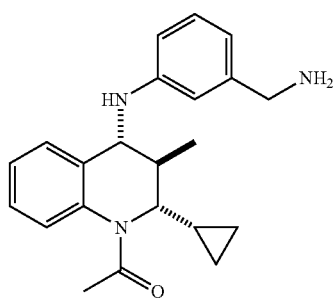 [SMILES: CC(=O)N1c2ccccc2[C@H](Nc2cccc(CN)c2)[C@@H](C)[C@@H]1C1CC1]

rac-tert-Butyl 3-(((2S,3R,4R)-1-acetyl-2-cyclopropyl-3-methyl-1,2,3,4-tetrahydroquinolin-4-yl)amino)benzylcarbamate (for a preparation see Intermediate 127, 165 mg, 0.367 mmol) was dissolved in methanol (1 mL) and treated with 4M hydrochloric acid (3 mL, 12.00 mmol) in 1,4-dioxane. The reaction was stirred at rt for 3 h. The solvent and excess HCl were removed under reduced pressure. The residue was loaded on to a 5 g SCX cartridge and washed with DCM and then MeOH. The product was eluted with 2M NH$_3$ in MeOH and this basic filtrate was concentrated to leave the crude. Purification was undertaken using MDAP (Formic). Evaporation of the collected fractions gave the product. This was dissolved in DCM (0.5 mL) and treated with 1M HCl in Et$_2$O (0.1 mL). The resulting solid was triturated and the solvent was carefully pipetted off. The resulting solid was dried in the vac oven to leave the product HCl salt as a tan solid (28 mg).

LCMS (2 min Formic): Rt=0.73 min, [MH]$^+$=350.

Example 125: rac-4-(((2S,3R,4R)-1-acetyl-2-cyclopropyl-3-methyl-1,2,3,4-tetrahydroquinolin-4-yl)amino)-N,N-dimethylbenzamide

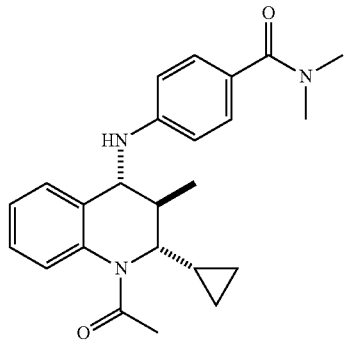 [SMILES: CC(=O)N1c2ccccc2[C@H](Nc2ccc(C(=O)N(C)C)cc2)[C@@H](C)[C@@H]1C1CC1]

Pd$_2$(dba)$_3$ (37.6 mg, 0.041 mmol), DavePhos (32.3 mg, 0.082 mmol), sodium tert-butoxide (59.2 mg, 0.616 mmol) and 4-bromo-N,N-dimethylbenzamide (94 mg, 0.411 mmol) were all added to a 0.5-2.0 mL microwave vial. To this was added rac-1-((2S,3R,4R)-4-amino-2-cyclopropyl-3-methyl-3,4-dihydroquinolin-1(2H)-yl)ethanone (for a preparation see Intermediate 14, 50.2 mg, 0.205 mmol) in 1,4-dioxane (2 mL). The vessel was sealed and, following stirring of the reaction mixture, was heated in a microwave heater at 120° C. for 40 min. The reaction mixture was filtered through a 2.5 g celite cartridge, washed through with ethyl acetate, and concentrated in vacuo to give a dark yellow oil. The crude residue was taken up in dichloromethane and loaded onto a 25 g silica flash column, and eluted in 60-100% ethyl acetate in cyclohexane. The appropriate fractions were collected and concentrated in vacuo to afford a pale yellow crystalline powder (59.1 mg, 66.1%).

LCMS (2 min Formic): Rt=0.96 min, [MH]$^+$=392.

Example 126: rac-1-((2S,3R,4R)-4-((5-chloropyridin-2-yl)amino)-2-cyclopropyl-3-methyl-3,4-dihydroquinolin-1(2H)-yl)ethanone

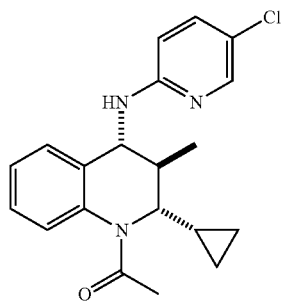 [SMILES: CC(=O)N1c2ccccc2[C@H](Nc2ccc(Cl)cn2)[C@@H](C)[C@@H]1C1CC1]

rac-1-((2S,3R,4R)-4-Amino-2-cyclopropyl-3-methyl-3,4-dihydroquinolin-1(2H)-yl)ethanone (for a preparation see Intermediate 14, 205 mg, 0.839 mmol) was added to a reaction vessel in anhydrous 1,4-dioxane (5 mL). 2-bromo-5-chloropyridine (242 mg, 1.259 mmol), DavePhos (66.0 mg, 0.168 mmol), sodium tert-butoxide (242 mg, 2.52 mmol) and Pd$_2$(dba)$_3$ (115 mg, 0.126 mmol) were added and the reaction left to stir at 100° C. for 1 h under N$_2$. The reaction mixture was filtered through celite and the celite washed with ethyl acetate (3×10 mL). The combined filtrates were washed with water (2×40 mL) and the layers separated. The organic phase was dried through a hydrophobic frit and concentrated in vacuo to give 665 mg of crude orange/brown solid. This was purified by chromatography on silica (25 g, eluting with 0-2.5% methanolic ammonia/DCM). The fractions containing product were combined and concentrated in vacuo to give 256 mg of product as an orange solid. This was still of insufficient purity so was purified by chromatography on silica (10 g, eluting with 0-25% ethyl acetate/cyclohexane). The fractions containing mainly product were combined and concentrated in vacuo to give 160 mg of product (160 mg, 0.450 mmol, 53.6%) as an orange solid. The fractions containing product with a substantial impurity were combined and concentrated in vacuo to give 139 mg of impure product (139 mg, 0.391 mmol, 46.6%) as an orange solid. LCMS (2 min Formic): Rt=1.06 min, [MH]$^+$=356.

Example 127: rac-4-(((2S,3R,4R)-1-acetyl-2-cyclopropyl-3-methyl-1,2,3,4-tetrahydroquinolin-4-yl)amino)benzoic Acid

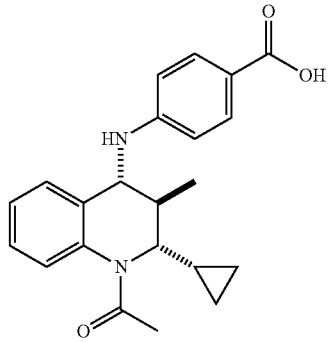 [SMILES: CC(=O)N1c2ccccc2[C@H](Nc2ccc(C(=O)O)cc2)[C@@H](C)[C@@H]1C1CC1]

A sample of rac-methyl 4-(((2S,3R,4R)-1-acetyl-2-cyclopropyl-3-methyl-1,2,3,4-tetrahydroquinolin-4-yl)amino)benzoate (for a preparation see Intermediate 128, 66 mg, 0.174 mmol) was dissolved in acetonitrile (1 mL), and to this was added sodium hydroxide (2M) (0.5 mL, 1.0 mmol). The mixture was stirred at 60° C. for 90 min. The mixture continued to stir at 60° C. for 2 h 30 min. The mixture continued to stir at 60° C. for a further 68 h. The mixture continued to stir at 60° C. and 0.25 mL sodium hydroxide (2M) was added, and the mixture continued to stir at 60° C. The reaction did not proceed further. A further 0.75 mL sodium hydroxide (2M) and 0.25 mL acetonitrile was added, and the mixture stirred at 80° C. for 2 h. The mixture was allowed to cool to rt, neutralised with 2M hydrochloric acid, and extracted into ethyl acetate. The aqueous layer was washed a further 2 times with ethyl acetate, the organic layers combined and concentrated in vacuo to afford a dark yellow oil. The residue was taken up in 1:1 MeOH:DMSO 1 mL and purified by MDAP (Formic). The solvent was evaporated in vacuo to give the required product (10.6 mg).

LCMS (2 min Formic): Rt=0.94 min, [M-H]$^-$=363.

Example 128: rac-6-(((2S,3R,4R)-1-acetyl-2-cyclopropyl-3-methyl-1,2,3,4-tetrahydroquinolin-4-yl)amino)-2-methylnicotinonitrile

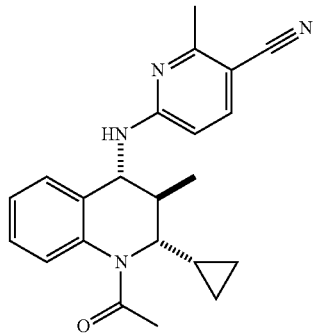 [SMILES: CC(=O)N1c2ccccc2[C@H](Nc2ccc(C#N)c(C)n2)[C@@H](C)[C@@H]1C1CC1]

To a dried flask under nitrogen was added rac-1-((2S,3R,4R)-4-amino-2-cyclopropyl-3-methyl-3,4-dihydroquinolin-1(2H)-yl)ethanone (for a preparation see Intermediate 14 50 mg, 0.205 mmol), 6-bromo-2-methylnicotinonitrile (48.4 mg, 0.246 mmol), DavePhos (32.2 mg, 0.082 mmol), Pd$_2$ (dba)₃ (37.5 mg, 0.041 mmol) and sodium tert-butoxide (59.0 mg, 0.614 mmol). To this was added 1,4-dioxane (4 mL), and the solution was degassed with nitrogen for ~15 min. The mixture was then heated for 2 h at 90° C. under nitrogen. A further 33.0 mg of 6-bromo-2-methylnicotinonitrile was added, and the mixture continued to stir at 90° C. for a further 2 h under nitrogen. The mixture was allowed to cool to rt, filtered through a 2.5 g celite cartridge, washed through with ethyl acetate and concentrated in vacuo to afford a dark orange oil. The residue was taken up in dichloromethane, loaded onto a 25 g silica flash column and eluted by silica gel chromatography with 5%-40% ethyl acetate in cyclohexane. The appropriate fractions were collected and concentrated in vacuo to afford a yellow oil (26.1 mg, 0.072 mmol, 35.4%).

LCMS (2 min Formic): Rt=1.05 min, [MH]⁺=361.

Example 129: rac-2-(((2S,3R,4R)-1-acetyl-2-cyclopropyl-3-methyl-1,2,3,4-tetrahydroquinolin-4-yl)amino)pyrimidine-5-carbonitrile

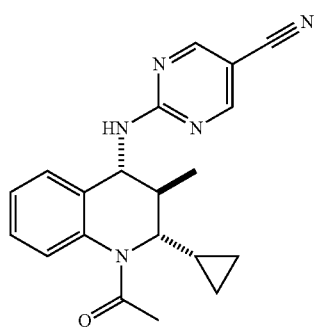 [SMILES: CC(=O)N1c2ccccc2[C@H](Nc2ncc(C#N)cn2)[C@@H](C)[C@@H]1C1CC1]

rac-1-((2S,3R,4R)-4-Amino-2-cyclopropyl-3-methyl-3,4-dihydroquinolin-1(2H)-yl)ethanone (for a preparation see Intermediate 14, 48 mg, 0.196 mmol) was dissolved in dimethyl sulfoxide (DMSO) (1.5 mL) and transferred to a 0.5-2.0 mL microwave vessel. To this was added 2-chloropyrimidine-5-carbonitrile (54.8 mg, 0.393 mmol) and DIPEA (0.103 mL, 0.589 mmol). The vessel was sealed and the reaction heated on a microwave heater to 200° C. for 1 h. The reaction mixture was dissolved in 1:1 MeOH:DMSO (1 mL) and purified by MDAP (HpH). The solvent was evaporated in vacuo to give the required product (19.8 mg). LCMS (2 min Formic): Rt=0.93 min, [MH]⁺=348.

Example 130: rac-1-((2S,3R,4R)-2,3-diethyl-4-((6-methylpyridin-2-yl)amino)-3,4-dihydroquinolin-1(2H)-yl)ethanone

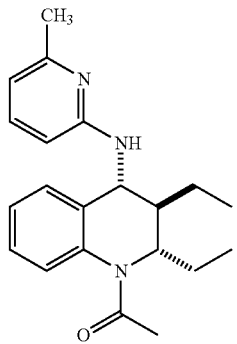 [SMILES: CC[C@@H]1[C@@H](Nc2cccc(C)n2)c2ccccc2N(C(C)=O)[C@H]1CC]

To a microwave vial containing a solution of rac-1-((2S,3R,4R)-4-amino-2,3-diethyl-3,4-dihydroquinolin-1(2H)-yl)ethanone (for a preparation see Intermediate 133, 42 mg, 0.170 mmol) was added 2-bromo-6-methylpyridine (0.039 mL, 0.341 mmol) and sodium tert-butoxide (49.2 mg, 0.511 mmol) and the vial evacuated and back filled with N₂ (×2). To this was added DavePhos (26.8 mg, 0.068 mmol) and Pd₂(dba)₃ (31.2 mg, 0.034 mmol) and the reaction mixture then heated at 120° C. for 40 min in a microwave heater. The reaction mixture was passed through a 2.5 g celite cartridge and washed with EtOAc (30 mL). The filtrate was concentrated in vacuo and the crude material dissolved in dichloromethane. This crude material was loaded onto a 10 g silica flash column, and purified by flash chromatography, eluting with 0%-40% ethyl acetate in cyclohexane. The appropriate fractions were combined and concentrated in vacuo to afford the product as a yellow oil (57 mg, 0.169 mmol, 99%). A 7.4 mg sample was retained in case further purification was unsuccessful. The remainder was taken up in 0.9 mL DMSO/MeOH (1:1) and purified by MDAP (HpH). The appropriate fractions were collected and concentrated in vacuo to afford the desired product as a colourless oil (31 mg, 0.092 mmol, 53.9%).

LCMS (2 min Formic): Rt=0.72 min, [MH]⁺=338.

Example 131: rac-(2S,3R,4R)-1-acetyl-2-cyclopropyl-3-methyl-4-((6-methylpyridin-2-yl)amino)-1,2,3,4-tetrahydroquinoline-6-carboxylic Acid

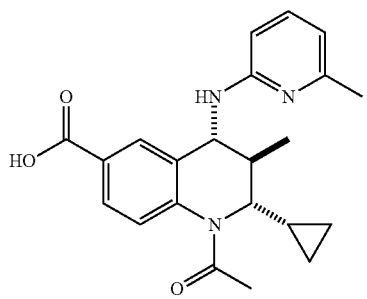 [SMILES: CC(=O)N1c2ccc(C(=O)O)cc2[C@H](Nc2cccc(C)n2)[C@@H](C)[C@@H]1C1CC1]

To a reaction vessel sodium tert-butoxide (838 mg, 8.72 mmol), Pd₂(dba)₃ (300 mg, 0.327 mmol), DavePhos (172 mg, 0.436 mmol), and rac-(2S,3R,4R)-ethyl 1-acetyl-4- amino-2-cyclopropyl-3-methyl-1,2,3,4-tetrahydroquinoline-6-carboxylate (for a preparation see Intermediate 195, 690 mg, 2.181 mmol) were added in 1,4-dioxane (25 mL). 2-Bromo-6-methylpyridine (0.372 mL, 3.27 mmol) was added and the reaction left to stir for 2.5 h under nitrogen at 100° C. The reaction mixture was left to cool to rt and then filtered through celite and the celite washed with ethyl acetate (2×30 mL). The combined filtrates were concentrated in vacuo to give 1.109 g of crude product. This was purified by chromatography on silica (50 g, eluting with 2M ammonia in methanol/DCM 0-20%). The fractions containing product were combined and concentrated in vacuo to give 303 mg of the product as a yellow/brown solid. 30 mg of this was dissolved in 1:1 MeOH:DMSO 1 mL and purified by MDAP (Formic). The solvent was evaporated in vacuo to give 4 mg of the product.

LCMS (2 min formic): Rt=0.62 min, [MH]⁺=380.

Example 132: rac-(2S,3R,4R)-1-acetyl-2-cyclopropyl-N,N,3-trimethyl-4-((6-methylpyridin-2-yl)amino)-1,2,3,4-tetrahydroquinoline-6-carboxamide

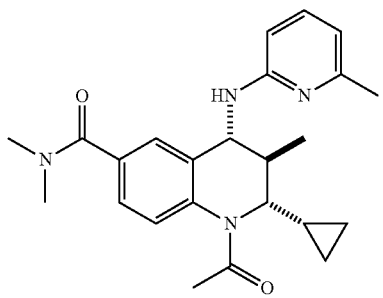

To a reaction vessel rac-(2S,3R,4R)-1-acetyl-2-cyclopropyl-3-methyl-4-((6-methylpyridin-2-yl)amino)-1,2,3,4-tetrahydroquinoline-6-carbonyl chloride (for a preparation see Intermediate 196, 117 mg, 0.294 mmol) in anhydrous acetonitrile (3 mL) was added. The vessel was put under an inert atmosphere (N₂) and the solution left to stir. Dimethylamine hydrochloride (620 mg, 7.60 mmol) was dissolved in acetonitrile (12 mL) and DIPEA (2.260 mL, 12.94 mmol) was added, this solution was added slowly to the stirring solution The reaction mixture was left to stir at rt for 1 h. The solution was concentrated in vacuo and retaken up in DCM (15 mL), this was washed with water (2×15 mL) and separated. The organic layer was dried and concentrated in vacuo to give 117 mg of an orange/brown solid. This was purified by chromatography on silica (10 g, eluting with 0-8% methanol/DCM over 15 CVs). The fractions containing mostly product were combined and concentrated in vacuo to give 23 mg of product. The fractions containing product with some impurity were combined and concentrated in vacuo to give 58 mg of less pure product. This second batch was dissolved in 1:1 MeOH:DMSO 1 mL and purified by MDAP (HpH). The solvent was evaporated in vacuo to give 27 mg product. LCMS (2 min formic): Rt=0.61 min, [MH]⁺=406.

Example 133: rac-(2S,3R,4R)-1-acetyl-2-cyclopropyl-3-methyl-4-((6-methylpyridin-2-yl)amino)-1,2,3,4-tetrahydroquinoline-6-carboxamide

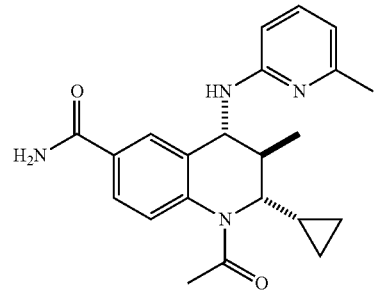 [SMILES: CC(=O)N1c2ccc(C(N)=O)cc2[C@H](Nc2cccc(C)n2)[C@@H](C)[C@@H]1C1CC1]

To a reaction vessel containing rac-(2S,3R,4R)-1-acetyl-2-cyclopropyl-3-methyl-4-((6-methylpyridin-2-yl)amino)-1,2,3,4-tetrahydroquinoline-6-carbonyl chloride (for a preparation see Intermediate 196 93 mg, 0.234 mmol). Ammonia 0.5M in 1,4-dioxane (10 mL, 5.00 mmol) and DIPEA (0.898 mL, 5.14 mmol) were added and the reaction left to stir for 15 min at rt under N₂. This was purified by chromatography on silica (25 g, eluting with 0-5% methanol/DCM). The fractions containing product were combined and concentrated in vacuo to give 13 mg of product as an off white solid. This was insufficiently pure so the column was run again eluting with methanol/DCM 0-7%. The fractions containing starting material (the acid) were combined and concentrated in vacuo to give 49 mg of recovered starting material. Product containing fractions were dissolved in 1:1 MeOH:DMSO 1 mL and purified by MDAP (Formic). The pure fractions were combined and concentrated in vacuo to give 4 mg of product (4 mg, 10.57 µmol, 4.52%) as an off white solid.

LCMS (2 min formic): Rt=0.56 min, [MH]⁺=379.

Example 134: rac-4-(((2S,3R,4R)-1-acetyl-2-cyclopropyl-3-methyl-6-(1-(2-(methylamino)ethyl)-1H-pyrazol-4-yl)-1,2,3,4-tetrahydroquinolin-4-yl)amino)benzonitrile

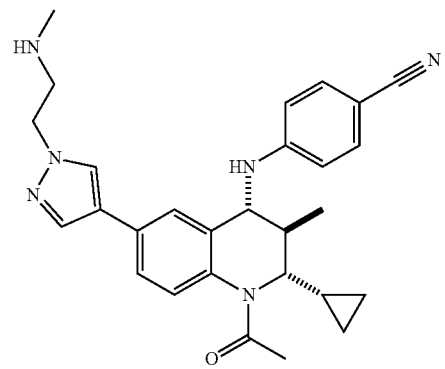 [SMILES: CNCCn1cc(-c2ccc3c(c2)[C@H](Nc2ccc(C#N)cc2)[C@@H](C)[C@H](C2CC2)N3C(C)=O)cn1]

rac-tert-Butyl (2-(4-((2S,3R,4R)-1-acetyl-4-((4-cyanophenyl)amino)-2-cyclopropyl-3-methyl-1,2,3,4-tetrahydroquinolin-6-yl)-1H-pyrazol-1-yl)ethyl)(methyl)carbamate (for a preparation see Intermediate 138, 11.6 mg, 0.020 mmol) was dissolved in dichloromethane (DCM) (1 mL) in a flask, and sealed. To this was carefully added trifluoroacetic acid (250 µL, 3.24 mmol). The mixture was allowed to stir for 2 h at rt. The reaction mixture was diluted with dichloromethane and evaporated in vacuo. The residue was taken up in methanol and loaded onto a 2 g SCX cartridge which had been pre-wet with methanol. The column was eluted with 3 CVs of methanol, followed by a further 3 CVs of 2M $NH_3$ in methanol. The methanolic ammonia fraction was concentrated in vacuo to afford a colourless glass (10.9 mg, 0.020 mmol, 100%). LCMS (2 min Formic): Rt=0.80 min, $[MH]^+$=469.

Example 135: rac-1-((2S,3R,4R)-2-cyclopropyl-6-(1-(2-methoxyethyl)-1H-pyrazol-4-yl)-3-methyl-4-((6-methylpyridin-2-yl)amino)-3,4-dihydroquinolin-1(2H)-yl)ethanone

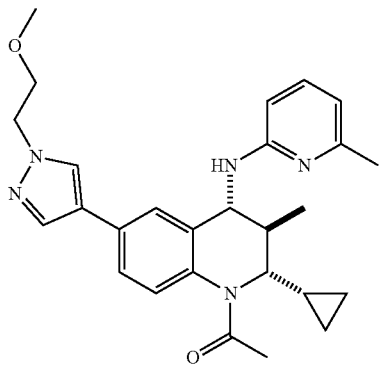 [SMILES: COCCn1cc(-c2ccc3c(c2)[C@H](Nc2cccc(C)n2)[C@@H](C)[C@H](C2CC2)N3C(C)=O)cn1]

The rac-1-((2S,3R,4R)-4-amino-2-cyclopropyl-6-(1-(2-methoxyethyl)-1H-pyrazol-4-yl)-3-methyl-3,4-dihydroquinolin-1(2H)-yl)ethanone (for a preparation see Intermediate 140, 70 mg, 0.190 mmol) was dispensed into a round bottomed flask and treated with DavePhos (7.48 mg, 0.019 mmol), $Pd_2(dba)_3$ (26.1 mg, 0.028 mmol), sodium tert-butoxide (54.8 mg, 0.570 mmol), 1,4-dioxane (12 mL) and the 2-bromo-6-methylpyridine (0.044 mL, 0.380 mmol). The reaction was allowed to stir at 100° C. for 16 h, The reaction was allowed to cool to rt and partitioned between water and DCM, the aqueous layer was extracted with more DCM and the combined organics were washed with brine, dried using a hydrophobic frit and concentrate to a gum. This was purified using a 10 g silica column elute: 0-50% EtOAc:cyclohexane. Nothing eluted so the column was run again 0-5% MeOH:DCM one major peak was eluted and the appropriate fractions were summed and concentrated to give the product but this was still impure Therefore this was further purified using a 10 g silica column elute: 0-5% MeOH:DCM. The appropriate fractions were summed and concentrated to give the product (48 mg) as a yellow solid. LCMS (2 min formic): Rt=0.70 min, $[MH]^+$=460.

Example 136a & 136b: 1-((2S,3R,4R)-2-cyclopropyl-6-(1-(2-methoxyethyl)-1H-pyrazol-4-yl)-3-methyl-4-((6-methylpyridin-2-yl)amino)-3,4-dihydroquinolin-1(2H)-yl)ethanone (136a) & 1-((2R,3S,4S)-2-cyclopropyl-6-(1-(2-methoxyethyl)-1H-pyrazol-4-yl)-3-methyl-4-((6-methylpyridin-2-yl)amino)-3,4-dihydroquinolin-1(2H)-yl)ethanone (136b)

136a

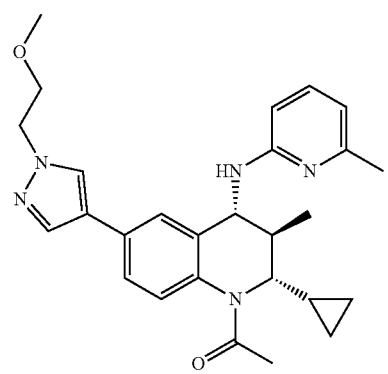

136b

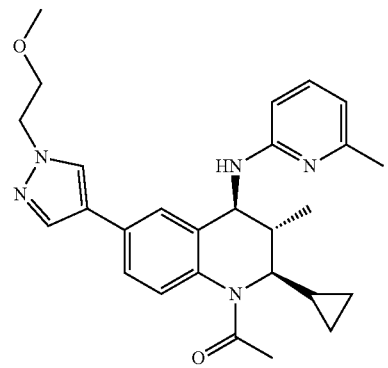

rac-1-((2S,3R,4R)-2-cyclopropyl-6-(1-(2-methoxyethyl)-1H-pyrazol-4-yl)-3-methyl-4-((6-methylpyridin-2-yl)amino)-3,4-dihydroquinolin-1(2H)-yl)ethanone (for a preparation see Example 135, ~40 mg) was submitted for chiral separation into its enantiomers (A and B) using a 250×20 mm Chiralpak IA column eluting with 10% ethanol in heptane at a flow rate of 20 mL/min. Peak 1/Enantiomer A fractions were collected between 21 and 26 min, and Peak 2/Enantiomer B fractions were collected between 32 and 39 min. Fraction solutions were combined and then evaporated to dryness to give Enantiomer A (12 mg) and Enantiomer B (14 mg) as white solids.

Enantiomer A, Example 136a

Analytical Chiral HPLC using a 250×4.6 mm Chiralpak IA column eluting with 15% ethanol in heptane at 1 mL/min—Rt=17.5 min.>99% ee by UV.

Enantiomer B, Example 136b

Analytical Chiral HPLC using a 250×4.6 mm Chiralpak IA column eluting with 15% ethanol in heptane at 1 mL/min—Rt=23.5 min, >99% ee by UV.

Example 137: rac-1-((2S,3R,4R)-2-cyclopropyl-6-(1-(2-methoxyethyl)-1H-pyrazol-4-yl)-3-methyl-4-((5-methylpyrazin-2-yl)amino)-3,4-dihydroquinolin-1(2H)-yl)ethanone

Example 138a & 138b: 1-((2S,3R,4R)-2-cyclopropyl-6-(1-(2-methoxyethyl)-1H-pyrazol-4-yl)-3-methyl-4-((5-methylpyrazin-2-yl)amino)-3,4-dihydroquinolin-1(2H)-yl)ethanone (138a) & 1-((2R,3S,4S)-2-cyclopropyl-6-(1-(2-methoxyethyl)-1H-pyrazol-4-yl)-3-methyl-4-((5-methylpyrazin-2-yl)amino)-3,4-dihydroquinolin-1(2H)-yl)ethanone (138b)

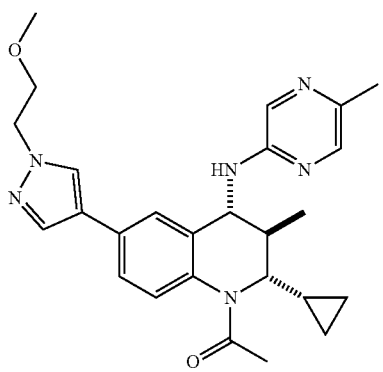 [SMILES: COCCn1cc(-c2ccc3c(c2)[C@H](Nc2cnc(C)cn2)[C@@H](C)[C@H](C2CC2)N3C(C)=O)cn1]

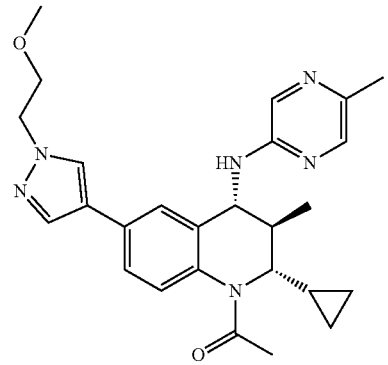

138a

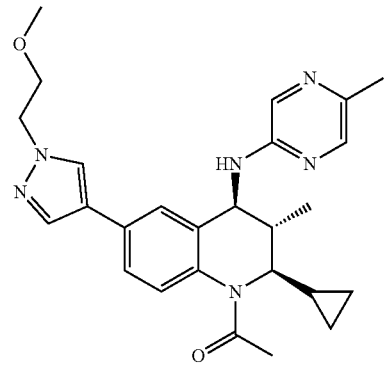

138b

The rac-1-((2S,3R,4R)-4-amino-2-cyclopropyl-6-(1-(2-methoxyethyl)-1H-pyrazol-4-yl)-3-methyl-3,4-dihydroquinolin-1(2H)-yl)ethanone (for a preparation see Intermediate 140, 70 mg, 0.190 mmol) was dispensed into a round bottomed flask and treated with DavePhos (7.48 mg, 0.019 mmol), Pd$_2$(dba)$_3$ (26.1 mg, 0.028 mmol), sodium tert-butoxide (54.8 mg, 0.570 mmol), 1,4-dioxane (12 mL) and the 2-bromo-5-methylpyrazine (65.7 mg, 0.380 mmol) the reaction was allowed to stir at 100° C. for 16 h. Further 2-bromo-5-methylpyrazine (65.7 mg, 0.380 mmol) was added and the reaction was allowed to stir at 100° C. for 2 h. The reaction was allowed to cool to rt and partitioned between water and DCM, the aqueous layer was extracted with more DCM and the combined organics were washed with brine, dried using a hydrophobic frit and concentrate to a gum. This was purified using a 10 g silica column elute: 0-50% EtOAc:cyclohexane. Nothing eluted so the column was run again 0-5% MeOH:DCM one major peak was eluted and the appropriate fractions were summed and concentrated to give the product but this was still impure. Therefore this was further purified using a 10 g silica column, elute: 0-5% 2M NH$_3$/MeOH:DCM, the appropriate fractions were summed and concentrated to give the product (36 mg) as a yellow solid.

LCMS (2 min Formic): Rt=0.86 min, [MH]$^+$=461.

rac-1-((2S,3R,4R)-2-Cyclopropyl-6-(1-(2-methoxyethyl)-1H-pyrazol-4-yl)-3-methyl-4-((5-methylpyrazin-2-yl)amino)-3,4-dihydroquinolin-1(2H)-yl)ethanone (for a preparation see Example 137, 38 mg) was submitted for chiral separation into its enantiomers (A and B) using a 250×30 mm Chiralpak AD-H column eluting with 50% ethanol in heptane at a flow rate of 30 mL/min. Peak 1/Enantiomer A fractions were collected between 9 and 12 min, and Peak 2/Enantiomer B fractions were collected between 24 and 34 min. Fraction solutions were combined and then evaporated to dryness to give Enantiomer A (13 mg) and Enantiomer B (9 mg) as white solids.

Enantiomer A, Example 138a

Analytical Chiral HPLC using a 250×4.6 mm Chiralpak AD-H column eluting with 50% ethanol in heptane at 1 mL/min—Rt=7.0 min.>99% ee by UV.

This contained ~10% impurity so was purified further by HPLC on an Atlantis T3 OBD, 150×19 mm, 5 um column using a graduating solvent system of 10-99% MeCN in 0.1% v/v formic acid/water at a flow rate of 20 mL/min. The product eluted at 13.4 min. The desired fractions were combined and concentrated to leave the product (3.9 mg).

LCMS (2 min Formic): Rt=0.86 min, [MH]$^+$=461.

Enantiomer B, Example 138b

Analytical Chiral HPLC using a 250×4.6 mm Chiralpak AD-H column eluting with 50% ethanol in heptane at 1 mL/min—Rt=16.5 min, >99% ee by UV.

Example 139: rac-4-(((2S,3R,4R)-1-acetyl-6-fluoro-2,3-dimethyl-1,2,3,4-tetrahydroquinolin-4-yl)amino)benzonitrile

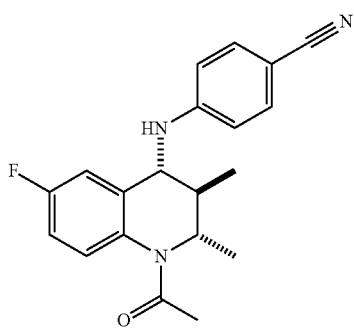 [SMILES: CC(=O)N1c2ccc(F)cc2[C@H](Nc2ccc(C#N)cc2)[C@@H](C)[C@@H]1C]

A solution of rac-1-((2S,3R,4R)-4-amino-6-fluoro-2,3-dimethyl-3,4-dihydroquinolin-1(2H)-yl)ethanone (for a preparation see Intermediate 143, 82 mg, 0.347 mmol), DavePhos (13.66 mg, 0.035 mmol), 4-bromobenzonitrile (76 mg, 0.416 mmol), Pd$_2$(dba)$_3$ (15.89 mg, 0.017 mmol) and sodium tert-butoxide (66.7 mg, 0.694 mmol) in 1,4-dioxane (3 mL) was stirred under nitrogen at 90° C. for 5 h. The reaction mixture was allowed to cool to rt, filtered through celite and rinsed with ethyl acetate. The solvent was evaporated in vacuo then dissolved in 1:1 MeOH:DMSO (2×1 mL) and purified MDAP (Formic). The appropriate fractions were combined and concentrated in vacuo to give the title compound (50 mg, 0.148 mmol, 43%). LCMS (2 min Formic): Rt=1.01 min, [MH]$^+$=338.

Example 140: rac-1-((2S,3R,4R)-6-fluoro-2,3-dimethyl-4-((5-methylpyrazin-2-yl)amino)-3,4-dihydroquinolin-1(2H)-yl)ethanone

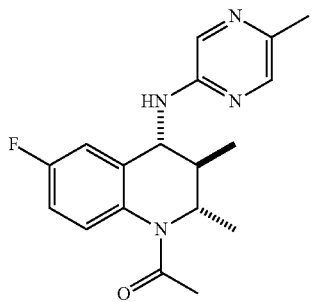 [SMILES: CC(=O)N1c2ccc(F)cc2[C@H](Nc2cnc(C)cn2)[C@@H](C)[C@@H]1C]

A solution of rac-1-((2S,3R,4R)-4-amino-6-fluoro-2,3-dimethyl-3,4-dihydroquinolin-1(2H)-yl)ethanone (for a preparation see Intermediate 143, 97 mg, 0.411 mmol), DavePhos (16.16 mg, 0.041 mmol), 2-bromo-5-methylpyrazine (71.0 mg, 0.411 mmol), Pd$_2$(dba)$_3$ (18.80 mg, 0.021 mmol) and sodium tert-butoxide (79 mg, 0.821 mmol) in 1,4-dioxane (3 mL) was stirred under nitrogen at 90° C. for 5 h. The reaction mixture was allowed to cool to rt, filtered through celite and rinsed with ethyl acetate. The solvent was evaporated in vacuo, dissolved in 1:1 MeOH:DMSO and purified by MDAP (HpH). The appropriate fractions were combined and concentrated in vacuo to give the title compound (20 mg, 0.061 mmol, 15%). LCMS (2 min Formic): Rt=0.83 min, [MH]$^+$=329.

Example 141: rac-1-((2S,3R,4R)-6-fluoro-4-((5-fluoropyridin-2-yl)amino)-2,3-dimethyl-3,4-dihydroquinolin-1(2H)-yl)ethanone

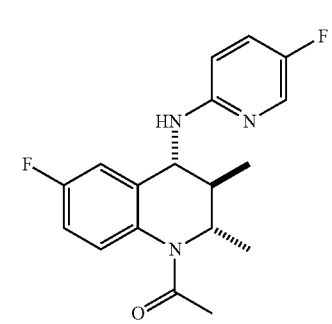

A solution of rac-1-((2S,3R,4R)-4-amino-6-fluoro-2,3-dimethyl-3,4-dihydroquinolin-1(2H)-yl)ethanone (for a preparation see Intermediate 143, 93 mg, 0.394 mmol), DavePhos (15.49 mg, 0.039 mmol), 2-bromo-5-fluoropyridine (69.3 mg, 0.394 mmol), Pd$_2$(dba)$_3$ (18.02 mg, 0.020 mmol) and sodium tert-butoxide (76 mg, 0.787 mmol) in 1,4-dioxane (3 mL) was stirred under nitrogen at 90° C. for 5 h. The reaction mixture was allowed to cool to rt, filtered through celite and rinsed with ethyl acetate. The solvent was evaporated in vacuo and the samples were dissolved in 1:1 MeOH:DMSO (1 mL) and purified by MDAP (HpH). The appropriate fractions were combined and concentrated in vacuo to give the title compound (32 mg, 0.097 mmol, 25%). LCMS (2 min Formic): Rt=0.90 min, [MH]$^+$=332.

Example 142: rac-5-(((2S,3R,4R)-1-acetyl-6-fluoro-2,3-dimethyl-1,2,3,4-tetrahydroquinolin-4-yl)amino)pyrazine-2-carbonitrile

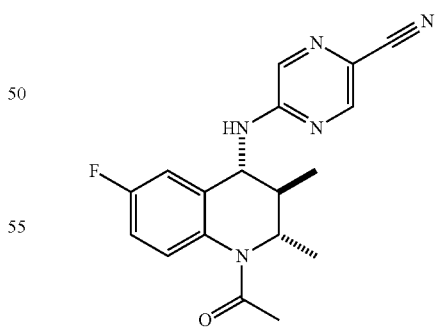

A solution of rac-1-((2S,3R,4R)-4-amino-6-fluoro-2,3-dimethyl-3,4-dihydroquinolin-1(2H)-yl)ethanone (for a preparation see Intermediate 143, 86 mg, 0.364 mmol), 5-chloropyrazine-2-carbonitrile (102 mg, 0.728 mmol) and DIPEA (0.127 mL, 0.728 mmol) in NMP (1.5 mL) was heated in a microwave at 200° C. for 1 h. The solution was applied directly and purified by MDAP (formic). The appropriate fractions were combined and concentrated in vacuo to give the title compound (30 mg, 0.088 mmol, 24%).

LCMS (2 min Formic): Rt=0.88 min, [MH]⁺=340.

Example 143: rac-6-(((2S,3R,4R)-1-acetyl-6-fluoro-2,3-dimethyl-1,2,3,4-tetrahydroquinolin-4-yl)amino)nicotinonitrile

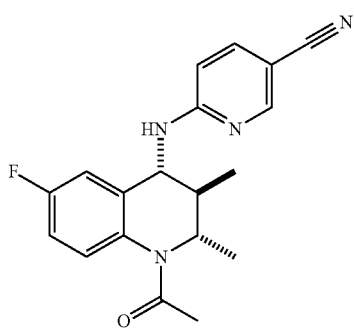 [SMILES: CC(=O)N1c2ccc(F)cc2[C@H](Nc2ccc(C#N)cn2)[C@@H](C)[C@@H]1C]

A solution of rac-1-((2S,3R,4R)-4-amino-6-fluoro-2,3-dimethyl-3,4-dihydroquinolin-1(2H)-yl)ethanone (for a preparation see Intermediate 143, 90 mg, 0.381 mmol), 6-fluoronicotinonitrile (93 mg, 0.762 mmol) and DIPEA (0.133 ml, 0.762 mmol) in NMP (1 mL) was heated in the microwave at 200° C. for 30 min. The solution was directly purified by MDAP (Formic). The appropriate fractions were combined and concentrated in vacuo to give the title compound (41 mg, 0.121 mmol, 32%).

LCMS (2 min Formic): Rt=0.91 min, [MH]⁺=339.

Example 144: rac-1-((2S,3R,4R)-6-fluoro-2,3-dimethyl-4-((4-methylpyrimidin-2-yl)amino)-3,4-dihydroquinolin-1(2H)-yl)ethanone

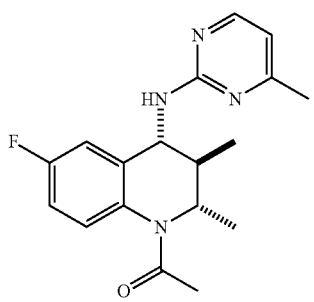 [SMILES: CC(=O)N1c2ccc(F)cc2[C@H](Nc2nccc(C)n2)[C@@H](C)[C@@H]1C]

A solution of rac-1-((2S,3R,4R)-4-amino-6-fluoro-2,3-dimethyl-3,4-dihydroquinolin-1(2H)-yl)ethanone (for a preparation see Intermediate 143, 85 mg, 0.360 mmol), 2-chloro-4-methylpyrimidine (92 mg, 0.719 mmol) and DIPEA (0.126 mL, 0.719 mmol) in NMP (1.5 mL) was heated in a microwave at 200° C. for 1 h. The solution was purified directly by MDAP (Formic). The appropriate fractions were combined and concentrated in vacuo to give the title compound (50 mg, 0.152 mmol, 42%).

LCMS (2 min Formic): Rt=0.79 min, [MH]⁺=329.

Example 145: rac-4-(((2S,3R,4R)-1-acetyl-6-fluoro-2,3-dimethyl-1,2,3,4-tetrahydroquinolin-4-yl)amino)-N-methylbenzamide

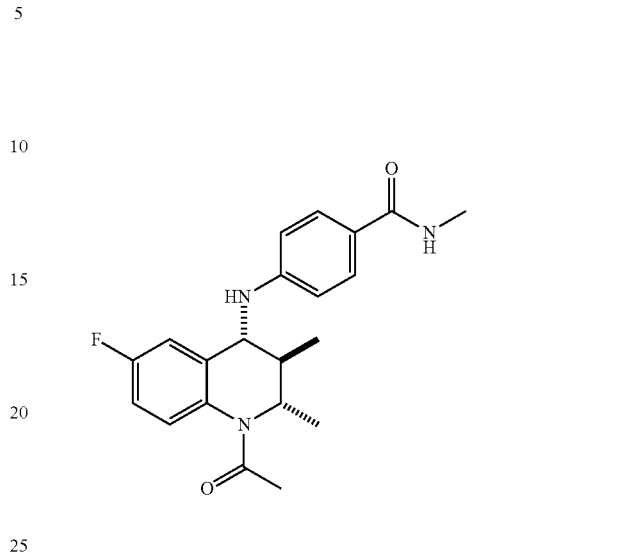

A solution of rac-1-((2S,3R,4R)-4-amino-6-fluoro-2,3-dimethyl-3,4-dihydroquinolin-1(2H)-yl)ethanone (for a preparation see Intermediate 143, 80 mg, 0.339 mmol), DavePhos (13.32 mg, 0.034 mmol), 4-bromo-N-methylbenzamide (87 mg, 0.406 mmol), sodium tert-butoxide (65.1 mg, 0.677 mmol) and Pd₂(dba)₃ (15.50 mg, 0.017 mmol) in 1,4-dioxane (3 mL) was stirred under nitrogen at 90° C. for 16 h. The reaction mixture was allowed to cool to rt, filtered through celite and rinsed with ethyl acetate. The solvent was evaporated in vacuo and the sample was dissolved in 1:1 MeOH:DMSO (1 mL) and purified by MDAP (Formic). The appropriate fractions were combined and concentrated in vacuo to give the title compound (20 mg, 0.054 mmol, 16%).

LCMS (2 min Formic): Rt=0.82 min, [MH]⁺=370.

Example 146a & 146b: 1-((2S,3R,4R)-2-ethyl-6-fluoro-3-methyl-4-((6-methylpyridin-2-yl)amino)-3,4-dihydroquinolin-1(2H)-yl)ethanone (146a) & 1-((2R,3S,4S)-2-ethyl-6-fluoro-3-methyl-4-((6-methylpyridin-2-yl)amino)-3,4-dihydroquinolin-1(2H)-yl)ethanone (146b)

146a

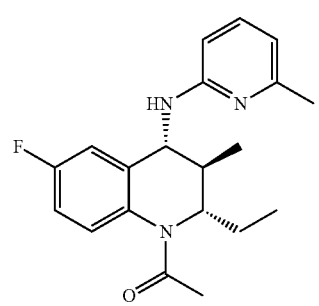

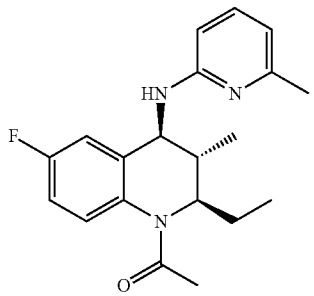

rac-1-((2S,3R,4R)-2-Ethyl-6-fluoro-3-methyl-4-((6-methylpyridin-2-yl)amino)-3,4-dihydroquinolin-1(2H)-yl)ethanone (for a preparation see Example 61, ~130 mg) was submitted for chiral separation into its enantiomers (A and B) using a 250×30 mm Chiralpak AD-H column eluting with 5% ethanol in heptane at a flow rate of 30 mL/min. Peak 1/Enantiomer A fractions were collected between 7 and 9 min, and Peak 2/Enantiomer B fractions were collected between 10.5 and 12.5 min. Fraction solutions were combined and then evaporated to dryness to give Enantiomer A (63 mg) and Enantiomer B (60 mg) as white solids.

Enantiomer A, Example 146a

Analytical Chiral HPLC using a 250×4.6 mm Chiralpak AD-H column eluting with 5% ethanol in heptane at 1 mL/min—Rt=7.0 min.>99% ee by UV.

Enantiomer B, Example 146b

Analytical Chiral HPLC using a 250×4.6 mm Chiralpak AD-H column eluting with 5% ethanol in heptane at 1 mL/min—Rt=10.3 min, >99% ee by UV.

Example 147a & 147b: 4-(((2S,3R,4R)-1-acetyl-2-ethyl-6-fluoro-3-methyl-1,2,3,4-tetrahydroquinolin-4-yl)amino)benzonitrile (147a) & 4-(((2R,3S,4S)-1-acetyl-2-ethyl-6-fluoro-3-methyl-1,2,3,4-tetrahydroquinolin-4-yl)amino)benzonitrile (147b)

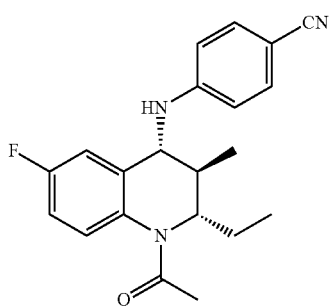

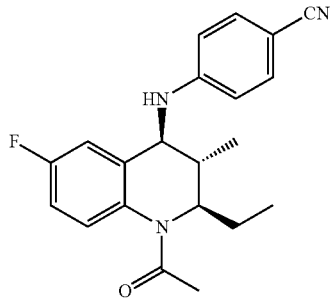

rac-4-(((2S,3R,4R)-1-Acetyl-2-ethyl-6-fluoro-3-methyl-1,2,3,4-tetrahydroquinolin-4-yl)amino)benzonitrile (for a preparation see Example 62, ~70 mg) was submitted for chiral separation into its enantiomers (A and B) using a 250×30 mm Chiralpak OD-H column eluting with 10% ethanol in heptane at a flow rate of 30 mL/min. Peak 1/Enantiomer A fractions were collected between 12 and 14 min, and Peak 2/Enantiomer B fractions were collected between 15.5 and 17.5 min. Fraction solutions were combined and then evaporated to dryness to give Enantiomer A (29 mg) and Enantiomer B (29 mg) as white solids.

Enantiomer A, Example 147b

Analytical Chiral HPLC using a 250×4.6 mm Chiralcel OD-H column eluting with 10% ethanol in heptane at 1 mL/min—Rt=10 min.>99% ee by UV.

Enantiomer B, Example 147a

Analytical Chiral HPLC using a 250×4.6 mm Chiralcel OD-H column eluting with 10% ethanol in heptane at 1 mL/min—Rt=12 min, >96% ee by UV.

Example 148: rac-1-((2S,3R,4R)-2-ethyl-6-fluoro-3-methyl-4-((4-methylpyrimidin-2-yl)amino)-3,4-dihydroquinolin-1(2H)-yl)ethanone

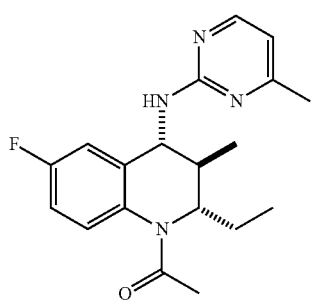 [SMILES: CC[C@H]1[C@H](C)[C@@H](Nc2nccc(C)n2)c2cc(F)ccc2N1C(C)=O]

To a reaction vessel 2-bromo-4-methylpyrimidine (159 mg, 0.919 mmol), rac-1-((2S,3R,4R)-4-amino-2-ethyl-6-fluoro-3-methyl-3,4-dihydroquinolin-1(2H)-yl)ethanone (for a preparation see Intermediate 40, 115 mg, 0.459 mmol), sodium tert-butoxide (132 mg, 1.378 mmol), in 1,4-dioxane (5 mL) were added. The solution was treated with Pd$_2$(dba)$_3$ (63.1 mg, 0.069 mmol) and DavePhos (36.2 mg, 0.092 mmol) and left to stir at 100° C. for 16 h under N$_2$. The reaction mixture was filtered through celite and the celite washed with ethyl acetate (2×20 mL). The combined filtrates were washed with water (2×35 mL+10 ml brine added to each wash) and passed through a hydrophobic frit before being concentrated in vacuo to give 615 mg of crude orange gum. This was purified by chromatography on silica (25 g, eluting with 0-100% ethyl acetate/cyclohexane). The fractions containing product were combined and concentrated in vacuo to give 41 mg of product as an orange solid. The sample was dissolved in 1:1 MeOH:DMSO 1 mL and purified by MDAP (Formic). The solvent was evaporated in vacuo to give 18 mg of product (18 mg, 0.053 mmol, 11.44%) as a white solid. LCMS (2 min formic): Rt=0.86 min, [MH]+=343.

Example 149: rac-1-((2S,3R,4R)-2-ethyl-6-fluoro-4-((5-fluoropyridin-2-yl)amino)-3-methyl-3,4-dihydroquinolin-1(2H)-yl)ethanone

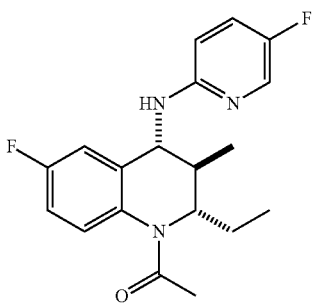 [SMILES: CC[C@H]1[C@H](C)[C@@H](Nc2ccc(F)cn2)c2cc(F)ccc2N1C(C)=O]

The rac-1-((2S,3R,4R)-4-amino-2-ethyl-6-fluoro-3-methyl-3,4-dihydroquinolin-1(2H)-yl)ethanone (for a preparation see Intermediate 40, 100 mg, 0.400 mmol), 2-bromo-5-fluoropyridine (105 mg, 0.599 mmol), Pd$_2$(dba)$_3$ (54.9 mg, 0.060 mmol), sodium tert-butoxide (115 mg, 1.199 mmol) and DavePhos (15.72 mg, 0.040 mmol) were suspended in 1,4-dioxane (10 mL) and allowed to stir at 100° C. for 4 h. The reaction was filtered through celite and concentrated to a oil, this oil was purified using a MDAP (Formic) to give a solid which was eluted through a NH$_2$ SPE (5 g) with MeOH, the eluent was concentrated and dried to give the product (58 mg, 0.168 mmol, 42.0%) as a orange solid.

LCMS (2 min Formic): Rt=0.97 min, [MH]+=346.

Example 150: rac-4-(((2S,3R,4R)-1-acetyl-2-ethyl-6-fluoro-3-methyl-1,2,3,4-tetrahydroquinolin-4-yl)amino)benzonitrile

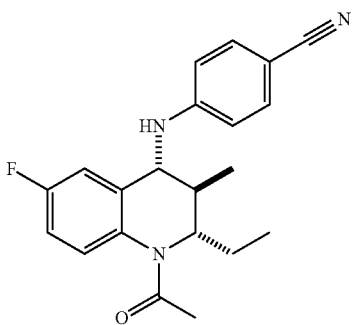 [SMILES: CC[C@H]1[C@H](C)[C@@H](Nc2ccc(C#N)cc2)c2cc(F)ccc2N1C(C)=O]

The rac-1-((2S,3R,4R)-4-amino-2-ethyl-6-fluoro-3-methyl-3,4-dihydroquinolin-1(2H)-yl)ethanone (for a preparation see Intermediate 40, 100 mg, 0.400 mmol) 4-bromobenzonitrile (109 mg, 0.599 mmol), Pd$_2$(dba)$_3$ (54.9 mg, 0.060 mmol), sodium tert-butoxide (115 mg, 1.199 mmol) and DavePhos (15.72 mg, 0.040 mmol) were suspended in 1,4-dioxane (10 mL) and allowed to stir at 100° C. for 4 h. The reaction was filtered through celite and concentrated to a oil, this oil was purified using a MDAP (HpH) to give a solid which was eluted through a NH$_2$ SPE (5 g) with MeOH, the eluent was concentrated and dried to give the product (50 mg, 0.142 mmol, 35.6%) as a yellow solid.

LCMS (2 min Formic): Rt=1.06 min, [MH]+=352.

Example 151: rac-4-(((2S,3R,4R)-1-acetyl-2-ethyl-6-fluoro-3-methyl-1,2,3,4-tetrahydroquinolin-4-yl)amino)-N-methylbenzamide

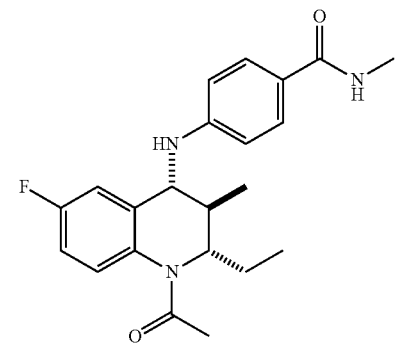 [SMILES: CC[C@H]1[C@H](C)[C@@H](Nc2ccc(C(=O)NC)cc2)c2cc(F)ccc2N1C(C)=O]

The rac-1-((2S,3R,4R)-4-amino-2-ethyl-6-fluoro-3-methyl-3,4-dihydroquinolin-1(2H)-yl)ethanone (for a preparation see Intermediate 40, 100 mg, 0.400 mmol) 4-bromo-N-methylbenzamide (128 mg, 0.599 mmol), Pd$_2$(dba)$_3$ (54.9 mg, 0.060 mmol), sodium tert-butoxide (115 mg, 1.199 mmol) and DavePhos (15.72 mg, 0.040 mmol) were suspended in 1,4-dioxane (10 mL) and allowed to stir at 100° C. for 16 h, the reaction was treated with further Pd$_2$(dba)$_3$ (54.9 mg, 0.060 mmol) and allowed to stir at 100° C. for a further 5 h. The reaction was allowed to cool to rt and was filtered through celite and concentrated to a gum. This gum was purified using a MDAP (Formic) to give a solid, this solid was eluted through a NH$_2$ SPE (5 g) with MeOH, the eluent was concentrated and dried to give the product (28 mg, 0.073 mmol, 18.28%) as an off-white solid.

LCMS (2 min Formic): Rt=0.88 min, [MH]+=384.

Example 152: rac-1-((2S,3R,4R)-2-ethyl-6-fluoro-4-((6-methoxypyridin-2-yl)amino)-3-methyl-3,4-dihydroquinolin-1(2H)-yl)ethanone

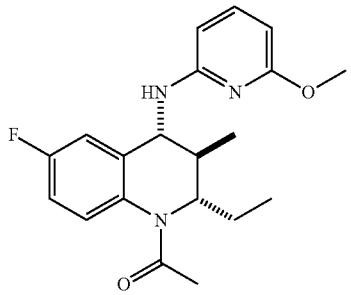 [SMILES: CC[C@H]1[C@H](C)[C@@H](Nc2cccc(OC)n2)c2cc(F)ccc2N1C(C)=O]

The rac-1-((2S,3R,4R)-4-amino-2-ethyl-6-fluoro-3-methyl-3,4-dihydroquinolin-1(2H)-yl)ethanone (for a preparation see Intermediate 40, 100 mg, 0.400 mmol) 2-bromo-6-methoxypyridine (113 mg, 0.599 mmol), Pd$_2$(dba)$_3$ (54.9 mg, 0.060 mmol), sodium tert-butoxide (115 mg, 1.199 mmol) and DavePhos (15.72 mg, 0.040 mmol) were suspended in 1,4-dioxane (10 mL) and allowed to stir at 100° C. for 16 h. The reaction was allowed to cool to rt and was filtered through celite and concentrated to a gum. This gum was purified using a MDAP (Formic) to give a solid, this solid was eluted through a NH$_2$ SPE (5 g) with MeOH, the eluent was concentrated and dried to the product (49 mg, 0.137 mmol, 34.3%) as an off-white solid. LCMS (2 min Formic): Rt=1.11 min, [MH]$^+$=358.

Example 153: rac-6-(((2S,3R,4R)-1-acetyl-2-ethyl-6-fluoro-3-methyl-1,2,3,4-tetrahydroquinolin-4-yl)amino)nicotinonitrile

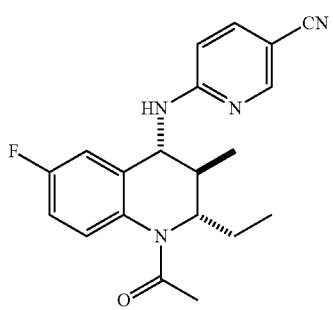 [SMILES: CC[C@H]1[C@H](C)[C@@H](Nc2ccc(C#N)cn2)c2cc(F)ccc2N1C(C)=O]

The rac-1-((2S,3R,4R)-4-amino-2-ethyl-6-fluoro-3-methyl-3,4-dihydroquinolin-1(2H)-yl)ethanone (for a preparation see Intermediate 40, 100 mg, 0.400 mmol), 6-fluoronicotinonitrile (98 mg, 0.799 mmol), DIPEA (0.140 mL, 0.799 mmol) and N-methyl-2-pyrrolidone (NMP) (2 mL) were placed in a microwaveable vial and irradiated in a microwave at 200° C. for 2.5 h. The reaction was purified directly using a MDAP (Formic) to give a solid, this solid was eluted through a NH$_2$ SPE (5 g) with MeOH, the eluent was concentrated and dried to give the product (29 mg, 0.082 mmol, 20.60%) as a off white solid. LCMS (2 min Formic): Rt=0.96 min, [MH]$^+$=353.

Example 154: rac-5-(((2S,3R,4R)-1-acetyl-2-ethyl-6-fluoro-3-methyl-1,2,3,4-tetrahydroquinolin-4-yl)amino)pyrazine-2-carbonitrile

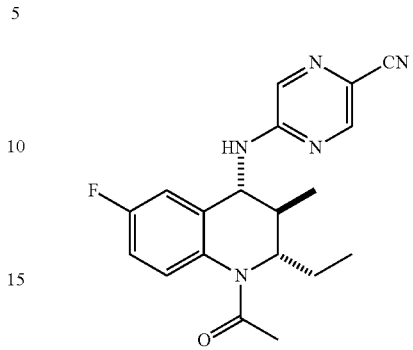

The rac-1-((2S,3R,4R)-4-amino-2-ethyl-6-fluoro-3-methyl-3,4-dihydroquinolin-1(2H)-yl)ethanone (for a preparation see Intermediate 40, 100 mg, 0.400 mmol), 5-chloropyrazine-2-carbonitrile (111 mg, 0.799 mmol), DIPEA (0.140 mL, 0.799 mmol) and N-methyl-2-pyrrolidone (NMP) (2 mL) were placed in a microwaveable vial and irradiated in a microwave at 200° C. for 2.5 h. The reactions purified directly using a MDAP (Formic) to give a solid, this solid was eluted through a NH$_2$ SPE (5 g) with MeOH, the eluent was concentrated and dried to give the product (77 mg, 0.218 mmol, 54.5%) as an orange solid.

LCMS (2 min Formic): Rt=0.93 min, [MH]$^+$=354.

Example 155: rac-1-((2S,3R,4R)-2-ethyl-6-fluoro-3-methyl-4-((5-methylpyrazin-2-yl)amino)-3,4-dihydroquinolin-1(2H)-yl)ethanone

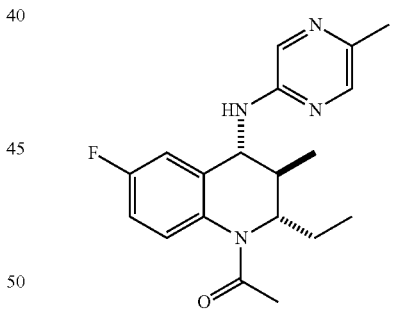

The rac-1-((2S,3R,4R)-4-amino-2-ethyl-6-fluoro-3-methyl-3,4-dihydroquinolin-1(2H)-yl)ethanone (for a preparation see Intermediate 40, 100 mg, 0.400 mmol), 2-chloro-5-methylpyrazine (77 mg, 0.599 mmol), Pd$_2$(dba)$_3$ (54.9 mg, 0.060 mmol), sodium tert-butoxide (115 mg, 1.199 mmol) and DavePhos (15.72 mg, 0.040 mmol) were suspended 1,4-dioxane (10 mL) and allowed to stir at 100° C. for 18 h. The reaction was allowed to cool to rt and were filtered through celite and concentrated to a gum. This gum was purified using a MDAP (Formic) to give a solid, this solid was eluted through a NH$_2$ SPE (5 g) with MeOH, the eluent was concentrated and dried to give the product (50 mg, 0.146 mmol, 36.6%) as an off-white solid. LCMS (2 min Formic): Rt=0.89 min, [MH]$^+$=343.

Example 156: rac-6-(((2S,3R,4R)-1-acetyl-2-cyclopropyl-6-fluoro-3-methyl-1,2,3,4-tetrahydroquinolin-4-yl)amino)nicotinonitrile

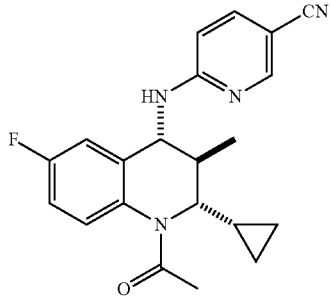 [SMILES: CC(=O)N1c2ccc(F)cc2[C@H](Nc2ccc(C#N)cn2)[C@@H](C)[C@@H]1C1CC1]

The rac-1-((2S,3R,4R)-4-amino-2-cyclopropyl-6-fluoro-3-methyl-3,4-dihydroquinolin-1(2H)-yl)ethanone (for a preparation see Intermediate 146, 100 mg, 0.381 mmol), 6-fluoronicotinonitrile (93 mg, 0.762 mmol), DIPEA (0.133 mL, 0.762 mmol) and N-methyl-2-pyrrolidone (NMP) (2 mL) were irradiated in a microwave at 200° C. for 1 h. The reaction was purified directly using a MDAP (Formic) to give a solid. This solid was eluted through a NH$_2$ SPE (5 g) with MeOH, the eluent was concentrated and dried to give the product (73 mg, 0.200 mmol, 52.5%) as an off-white solid.

LCMS (2 min Formic): Rt=1.00 min, [MH]$^+$=365.

Example 157: rac-5-(((2S,3R,4R)-1-acetyl-2-cyclopropyl-6-fluoro-3-methyl-1,2,3,4-tetrahydroquinolin-4-yl)amino)pyrazine-2-carbonitrile

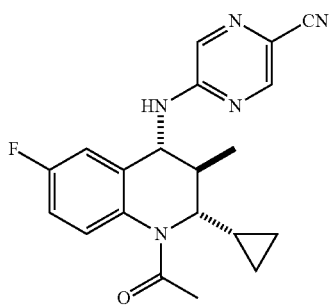 [SMILES: CC(=O)N1c2ccc(F)cc2[C@H](Nc2cnc(C#N)cn2)[C@@H](C)[C@@H]1C1CC1]

The rac-1-((2S,3R,4R)-4-amino-2-cyclopropyl-6-fluoro-3-methyl-3,4-dihydroquinolin-1(2H)-yl)ethanone (for a preparation see Intermediate 146, 100 mg, 0.381 mmol), 5-chloropyrazine-2-carbonitrile (106 mg, 0.762 mmol) DIPEA (0.133 mL, 0.762 mmol) and N-methyl-2-pyrrolidone (NMP) (2 mL) were irradiated in a microwave at 200° C. for 30 min, the reaction was purified directly using a MDAP (Formic) to give a solid. This solid was eluted through a NH$_2$ SPE (5 g) with MeOH, the eluent was concentrated and dried to give the product (72 mg, 0.197 mmol, 51.7%) as a brown solid. LCMS (2 min Formic): Rt=0.96 min, [MH]$^+$=366.

Example 158: rac-1-((2S,3R,4R)-2-cyclopropyl-6-fluoro-3-methyl-4-((4-methylpyrimidin-2-yl)amino)-3,4-dihydroquinolin-1(2H)-yl)ethanone

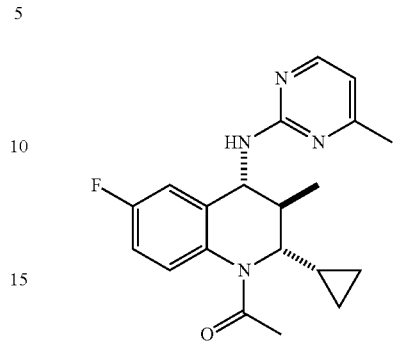

The rac-1-((2S,3R,4R)-4-amino-2-cyclopropyl-6-fluoro-3-methyl-3,4-dihydroquinolin-1(2H)-yl)ethanone (for a preparation see Intermediate 146, 100 mg, 0.381 mmol), 2-chloro-4-methylpyrimidine (98 mg, 0.762 mmol) DIPEA (0.133 mL, 0.762 mmol) and N-methyl-2-pyrrolidone (NMP) (2 mL) were irradiated in a microwave at 200° C. for 2.5 h, the reaction was purified directly using a MDAP (Formic) to give a solid. This solid was eluted through a NH$_2$ SPE (5 g) with MeOH, the eluent was concentrated and dried to the product (13 mg, 0.037 mmol, 9.62%) as a light brown solid.

LCMS (2 min Formic): Rt=0.90 min, [MH]$^+$=355.

Example 159: rac-1-((2S,3R,4R)-2-cyclopropyl-6-fluoro-3-methyl-4-((5-methylpyrazin-2-yl)amino)-3,4-dihydroquinolin-1(2H)-yl)ethanone

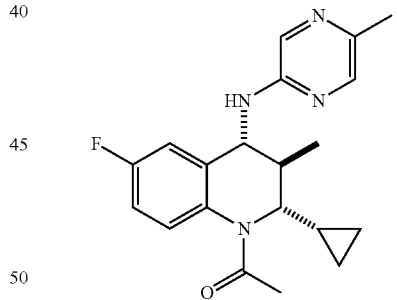

The rac-1-((2S,3R,4R)-4-amino-2-cyclopropyl-6-fluoro-3-methyl-3,4-dihydroquinolin-1(2H)-yl)ethanone (for a preparation see Intermediate 146, 100 mg, 0.381 mmol), 2-bromo-5-methylpyrazine (99 mg, 0.572 mmol), Pd$_2$(dba)$_3$ (52.4 mg, 0.057 mmol), sodium tert-butoxide (110 mg, 1.144 mmol) and DavePhos (15.00 mg, 0.038 mmol), were suspended in 1,4-dioxane (10 mL) and allowed to stir at 100° C. for 4 h. The reaction was filtered through celite and concentrated to an oil. This oil was purified using a MDAP (Formic) to give a solid which was eluted through a NH$_2$ SPE (5 g) with MeOH, the eluent was concentrated and dried to give the product (26 mg, 0.073 mmol, 19.24%) as a yellow solid. LCMS (2 min Formic): Rt=0.92 min, [MH]$^+$= 355.

Example 160: rac-1-((2S,3R,4R)-2-cyclopropyl-6-fluoro-4-((5-fluoropyridin-2-yl)amino)-3-methyl-3,4-dihydroquinolin-1(2H)-yl)ethanone

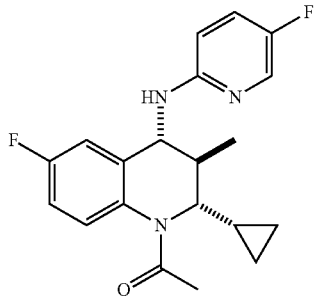 [SMILES: CC(=O)N1c2ccc(F)cc2[C@H](Nc2ccc(F)cn2)[C@@H](C)[C@@H]1C1CC1]

The rac-1-((2S,3R,4R)-4-amino-2-cyclopropyl-6-fluoro-3-methyl-3,4-dihydroquinolin-1(2H)-yl)ethanone (for a preparation see Intermediate 146, 100 mg, 0.381 mmol), 2-bromo-5-fluoropyridine (101 mg, 0.572 mmol), $Pd_2(dba)_3$ (52.4 mg, 0.057 mmol), sodium tert-butoxide (110 mg, 1.144 mmol) and DavePhos (15.00 mg, 0.038 mmol), were suspended in 1,4-dioxane (10 mL) and allowed to stir at 100° C. for 20 h. The reaction was filtered through celite and concentrated to an oil. This oil was purified using a MDAP (Formic) to give a solid which was eluted through a $NH_2$ SPE (5 g) with MeOH, the MeOH was concentrated and dried to give the product (6 mg, 0.017 mmol, 4.40%).

LCMS (2 min Formic): Rt=1.00 min, $[MH]^+$=358.

Example 161: rac-4-(((2S,3R,4R)-1-acetyl-2-cyclopropyl-6-fluoro-3-methyl-1,2,3,4-tetrahydroquinolin-4-yl)amino)benzonitrile

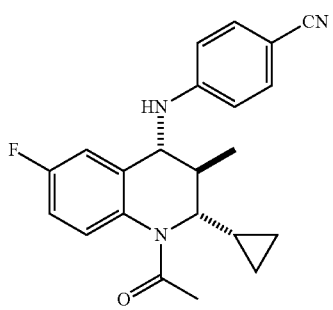 [SMILES: CC(=O)N1c2ccc(F)cc2[C@H](Nc2ccc(C#N)cc2)[C@@H](C)[C@@H]1C1CC1]

The rac-1-((2S,3R,4R)-4-amino-2-cyclopropyl-6-fluoro-3-methyl-3,4-dihydroquinolin-1(2H)-yl)ethanone (for a preparation see Intermediate 146, 100 mg, 0.381 mmol), 4-bromobenzonitrile (104 mg, 0.572 mmol), $Pd_2(dba)_3$ (52.4 mg, 0.057 mmol), sodium tert-butoxide (110 mg, 1.144 mmol) and DavePhos (15.00 mg, 0.038 mmol), were suspended in 1,4-dioxane (10 mL) and allowed to stir at 100° C. for 4 h. The reaction was filtered through celite and concentrated to a oil. This oil was purified using a MDAP (Formic) to give a solid which was eluted through a $NH_2$ SPE (5 g) with MeOH, the eluent was concentrated and dried to give the product (30 mg, 0.083 mmol, 21.65%) as a white solid.

LCMS (2 min Formic): Rt=1.09 min, $[MH]^+$=364.

Example 162: rac-1-((2S,3R,4R)-2-cyclopropyl-6-fluoro-3-methyl-4-((6-methylpyridin-2-yl)amino)-3,4-dihydroquinolin-1(2H)-yl)ethanone

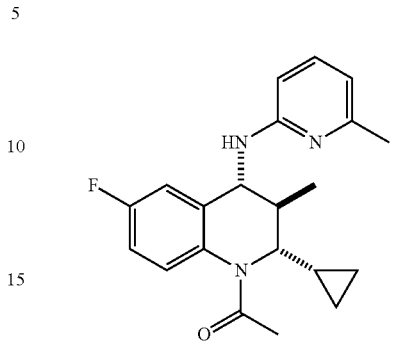

The rac-1-((2S,3R,4R)-4-amino-2-cyclopropyl-6-fluoro-3-methyl-3,4-dihydroquinolin-1(2H)-yl)ethanone (for a preparation see Intermediate 146, 100 mg, 0.381 mmol), 2-bromo-6-methylpyridine (98 mg, 0.572 mmol), $Pd_2(dba)_3$ (52.4 mg, 0.057 mmol), sodium tert-butoxide (110 mg, 1.144 mmol) and DavePhos (15.00 mg, 0.038 mmol) were suspended in 1,4-dioxane (10 mL). The reactions were allowed to stir at 100° C. for 16 h. The reaction was allowed to cool to rt and was filtered through celite and concentrated to a gum. This gum was purified using a MDAP (Formic) to give a solid which was eluted through a $NH_2$ SPE (5 g) with MeOH, the eluent was concentrated and dried to give the product (36 mg, 0.102 mmol, 26.7%).

LCMS (2 min Formic): Rt=0.73 min, $[MH]^+$=354.

Example 163: rac-4-(((2S,3R,4R)-1-acetyl-2-cyclopropyl-6-fluoro-3-methyl-1,2,3,4-tetrahydroquinolin-4-yl)amino)-N-methylbenzamide

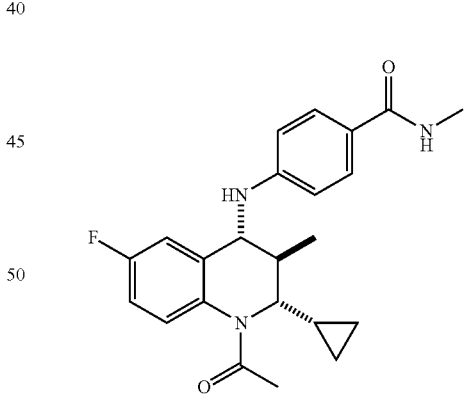

The rac-1-((2S,3R,4R)-4-amino-2-cyclopropyl-6-fluoro-3-methyl-3,4-dihydroquinolin-1(2H)-yl)ethanone (for a preparation see Intermediate 146, 100 mg, 0.381 mmol) 4-bromo-N-methylbenzamide (122 mg, 0.572 mmol), $Pd_2$(dba)$_3$ (52.4 mg, 0.057 mmol), sodium tert-butoxide (110 mg, 1.144 mmol) and DavePhos (15.00 mg, 0.038 mmol) were suspended in 1,4-dioxane (10 mL). The reaction was allowed to stir at 100° C. for 16 h. The reaction was allowed to cool to rt and was filtered through celite and concentrated to a gum. This gum was purified using a MDAP (Formic) to give a solid which was eluted through a $NH_2$ SPE (5 g) with MeOH, the eluent was concentrated and dried to give the product (9 mg, 0.023 mmol, 5.97%).

LCMS (2 min Formic): Rt=0.91 min, [MH]⁺=396.

Example 164: rac-1-((2S,3R,4R)-2-cyclopropyl-6-fluoro-4-((6-methoxypyridin-2-yl)amino)-3-methyl-3,4-dihydroquinolin-1(2H)-yl)ethanone

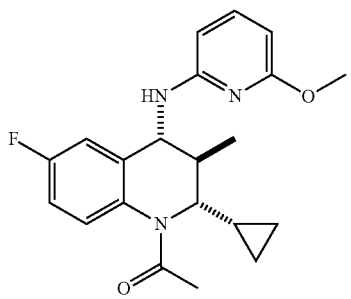 [SMILES: COc1cccc(N[C@H]2c3cc(F)ccc3N(C(C)=O)[C@@H](C3CC3)[C@@H]2C)n1]

The rac-1-((2S,3R,4R)-4-amino-2-cyclopropyl-6-fluoro-3-methyl-3,4-dihydroquinolin-1(2H)-yl)ethanone (for a preparation see Intermediate 146, 100 mg, 0.381 mmol) 2-bromo-6-methoxypyridine (108 mg, 0.572 mmol), Pd₂(dba)₃ (52.4 mg, 0.057 mmol), sodium tert-butoxide (110 mg, 1.144 mmol) and DavePhos (15.00 mg, 0.038 mmol) were suspended in 1,4-dioxane (10 mL) and allowed to stir at 100° C. for 16 h. The reaction was allowed to cool to rt and was filtered through celite and concentrated to a gum. This gum was purified using a MDAP (Formic) to give a solid which was eluted through a NH₂ SPE (5 g) with MeOH, the eluent was concentrated and dried to give the product (69 mg, 0.187 mmol, 49.0%). LCMS (2 min Formic): Rt=1.14 min, [MH]⁺=370.

Example 165: rac-1-((2S,3R,4R)-2-cyclopropyl-6-fluoro-4-((6-hydroxypyridin-2-yl)amino)-3-methyl-3,4-dihydroquinolin-1(2H)-yl)ethanone

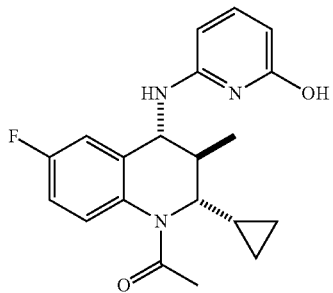 [SMILES: CC(=O)N1c2ccc(F)cc2[C@H](Nc2cccc(O)n2)[C@@H](C)[C@@H]1C1CC1]

The rac-1-((2S,3R,4R)-2-cyclopropyl-6-fluoro-4-((6-methoxypyridin-2-yl)amino)-3-methyl-3,4-dihydroquinolin-1(2H)-yl)ethanone (for a preparation see Example 164, 63 mg, 0.171 mmol) and sodium iodide (128 mg, 0.853 mmol) were suspended in acetonitrile (10 mL), TMSCl (0.044 mL, 0.341 mmol) was added portion-wise and the reaction was allowed to stir at 60° C. under reflux conditions for 16 h. The reaction was allowed to cool to rt and was concentrated to a solid, this solid was partitioned between 1M NaOH and DCM, the organic layer was washed with 10% Na₂S₂O₃ (aq) dried using a hydrophobic frit and concentrated to a brown solid. This solid was purified using a MDAP (Formic) to give a yellow solid, this solid was eluted through a NH₂ SPE (1 g) with MeOH, the eluent was concentrated and dried to give the product (8 mg, 0.023 mmol, 13.20%) as a pale red solid. LCMS (2 min Formic): Rt=0.78 min, [MH]⁺=356.

Example 166: rac-5-(((2S,3R,4R)-1-acetyl-6-(3,6-dihydro-2H-pyran-4-yl)-2,3-dimethyl-1,2,3,4-tetrahydroquinolin-4-yl)amino)pyrazine-2-carbonitrile

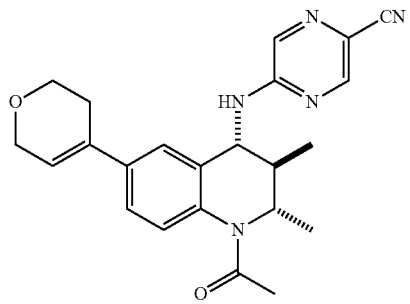 [SMILES: CC(=O)N1c2ccc(C3=CCOCC3)cc2[C@H](Nc2cnc(C#N)cn2)[C@@H](C)[C@@H]1C]

A 0.5-2 mL microwave vial was evacuated and back filled with N₂. rac-1-((2S,3R,4R)-4-amino-6-(3,6-dihydro-2H-pyran-4-yl)-2,3-dimethyl-3,4-dihydroquinolin-1(2H)-yl) ethanone (for a preparation see Intermediate 150, 23.3 mg, 0.078 mmol) in N-methyl-2-pyrrolidone (NMP) (0.7 mL) was then added. To this was added 5-chloropyrazine-2-carbonitrile (21.65 mg, 0.155 mmol), and DIPEA (0.041 mL, 0.233 mmol) and the resultant solution then heated to 150° C. for 30 min in a microwave. The reaction mixture was filtered through a cotton wool plug directly into an LCMS vial and was then purified by MDAP (Formic). The appropriate fraction was collected and concentrated in vacuo to afford the desired product as a yellow gum which was still impure. Therefore the crude product was taken up in DCM and loaded onto a silica cartridge (10 g). This was purified by flash chromatography, eluting with 0-100% EtOAc/cyclohexane. The appropriate fractions were collected and concentrated in vacuo to afford the desired product as a colourless oil (6.3 mg, 0.016 mmol, 20.13%). LCMS (2 min Formic): Rt=0.90 min, [MH]⁺=404.

Example 167: rac-1-((2S,3R,4)-6-(3,6-dihydro-2H-pyran-4-yl)-2,3-dimethyl-4-((5-methylpyrazin-2-yl)amino)-3,4-dihydroquinolin-1(2H)-yl)ethanone

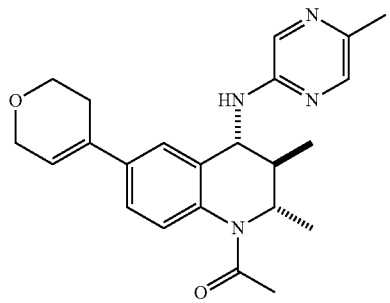 [SMILES: CC(=O)N1c2ccc(C3=CCOCC3)cc2[C@H](Nc2cnc(C)cn2)[C@@H](C)[C@@H]1C]

A 0.5-2 mL microwave vial was evacuated and back filled with N₂. 1-((2S,3R,4R)-4-Amino-6-(3,6-dihydro-2H-pyran- 4-yl)-2,3-dimethyl-3,4-dihydroquinolin-1(2H)-yl)ethanone (for a preparation see Intermediate 150, 23 mg, 0.077 mmol) in 1,4-dioxane (0.75 mL) was then added. To this was added 2-bromo-5-methylpyrazine (0.017 mL, 0.153 mmol), sodium tert-butoxide (14.72 mg, 0.153 mmol) and DavePhos (6.03 mg, 0.015 mmol) and the resultant suspension then had $N_2$ bubbled through it for ~5 min. $Pd_2(dba)_3$ (14.02 mg, 0.015 mmol) was added and $N_2$ was bubbled through the reaction mixture for a further ~5 min. The reaction was then heated to 100° C. for 30 min in a microwave. The reaction was then re-heated to 100° C. for a further 30 min. The reaction mixture was then diluted with EtOAc and filtered though celite (2.5 g). The celite was washed with further EtOAc (2×10 mL) and the resultant solution concentrated in vacuo. This was taken up in MeOH/DMSO (1:1, 0.9 mL) and purified by MDAP (Formic). The appropriate fraction was collected and concentrated in vacuo to afford a colourless gum (3.3 mg, 8.41 μmol, 10.98%).

LCMS (2 min Formic): Rt=0.85 min, $[MH]^+$=393.

Example 168: rac-1-((2S,3R,4R)-6-(3,6-dihydro-2H-pyran-4-yl)-2,3-dimethyl-4-((4-methylpyrimidin-2-yl)amino)-3,4-dihydroquinolin-1(2H)-yl)ethanone

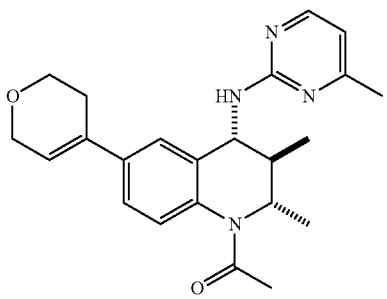 [SMILES: CC(=O)N1c2ccc(C3=CCOCC3)cc2[C@H](Nc2nccc(C)n2)[C@@H](C)[C@@H]1C]

A 0.5-2 mL microwave vial was evacuated and back filled with $N_2$. rac-1-((2S,3R,4R)-4-Amino-6-(3,6-dihydro-2H-pyran-4-yl)-2,3-dimethyl-3,4-dihydroquinolin-1(2H)-yl) ethanone (for a preparation see Intermediate 150, 100 mg, 0.333 mmol) in N-methyl-2-pyrrolidone (NMP) (1.6 mL) was then added. To this was added 2-chloro-4-methylpyrimidine (86 mg, 0.666 mmol), and DIPEA (0.174 mL, 0.999 mmol) and the resultant solution then heated to 200° C. for 30 min in a microwave. The reaction mixture was then heated to 200° C. in a microwave for a further 30 min. The reaction mixture was filtered through a cotton wool plug directly into two LCMS vials and was then purified by 2×MDAP (Formic). The appropriate fractions were collected and concentrated in vacuo to afford the desired product as a yellow oil (7.8 mg, 0.020 mmol, 5.97%).

LCMS (2 min Formic): Rt=0.82 min, $[MH]^+$=393.

Example 169: rac-6-(((2S,3R,4R)-1-acetyl-6-(3,6-dihydro-2H-pyran-4-yl)-2,3-dimethyl-1,2,3,4-tetrahydroquinolin-4-yl)amino)nicotinonitrile

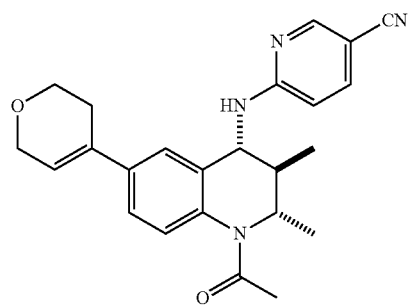 [SMILES: CC(=O)N1c2ccc(C3=CCOCC3)cc2[C@H](Nc2ccc(C#N)cn2)[C@@H](C)[C@@H]1C]

A solution of rac-1-((2S,3R,4R)-4-amino-6-(3,6-dihydro-2H-pyran-4-yl)-2,3-dimethyl-3,4-dihydroquinolin-1(2H)-yl)ethanone (for a preparation see Intermediate 150, 101 mg, 0.336 mmol) in NMP (1 mL) was treated with DIPEA (0.061 mL, 0.350 mmol) and 6-fluoronicotinonitrile (43 mg, 0.352 mmol) then heated at 150° C. for 1 h using a microwave reactor. Crude product was purified directly by MDAP (HpH) and appropriate fractions combined then concentrated under reduced pressure to give the desired product as a white foamy solid (70 mg).

LCMS (2 min Formic): Rt=0.93 min, $[MH]^+$=403.

Example 170: rac-1-((2S,3R,4R)-2,3-dimethyl-4-((6-methylpyridin-2-yl)amino)-6-(tetrahydro-2H-pyran-4-yl)-3,4-dihydroquinolin-1(2H)-yl)ethanone

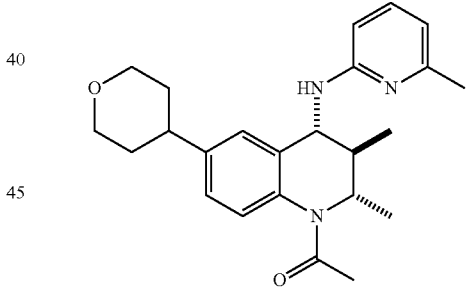

To a reaction vessel 2-bromo-6-methylpyridine (0.028 mL, 0.248 mmol), rac-1-((2S,3R,4R)-4-amino-2,3-dimethyl-6-(tetrahydro-2H-pyran-4-yl)-3,4-dihydroquinolin-1 (2H)-yl)ethanone (for preparation see Intermediate 152, 37.5 mg, 0.124 mmol), sodium tert-butoxide (35.8 mg, 0.372 mmol), in 1,4-Dioxane (5 mL) were added. The solution was treated with $Pd_2(dba)_3$ (17.03 mg, 0.019 mmol) and DavePhos (9.76 mg, 0.025 mmol) and left to stir at 100° C. for 2 h under $N_2$. The reaction mixture was allowed to cool to rt and was then filtered through celite and the celite washed with ethyl acetate. The combined filtrates were concentrated in vacuo to give a crude orange/brown gum. This gum was purified by MDAP (Formic) to give an off-white solid. This solid was eluted through a $NH_2$ SPE (5 g) with MeOH, the eluent was concentrated to give the product (18 mg, 0.046 mmol, 36.9%) as an off-white solid.

LCMS (2 min Formic): Rt=0.69 min, $[MH]^+$=394.

Example 171: rac-1-((2S,3R,4R)-2,3-dimethyl-4-((4-methylpyrimidin-2-yl)amino)-6-(tetrahydro-2H-pyran-4-yl)-3,4-dihydroquinolin-1(2H)-yl)ethanone

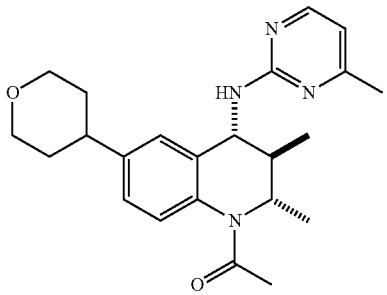 [SMILES: CC(=O)N1c2ccc(C3CCOCC3)cc2[C@H](Nc2nccc(C)n2)[C@@H](C)[C@@H]1C]

To a reaction vessel 2-bromo-4-methylpyrimidine (42.9 mg, 0.248 mmol), rac-1-((2S,3R,4R)-4-amino-2,3-dimethyl-6-(tetrahydro-2H-pyran-4-yl)-3,4-dihydroquinolin-1(2H)-yl)ethanone (for preparation see Intermediate 152, 37.5 mg, 0.124 mmol), sodium tert-butoxide (35.8 mg, 0.372 mmol), in 1,4-dioxane (5 mL) were added. The solution was treated with Pd$_2$(dba)$_3$ (17.03 mg, 0.019 mmol) and DavePhos (9.76 mg, 0.025 mmol) and left to stir at 75° C. for 72 h under N$_2$. The reaction was treated with further sodium tert-butoxide (37 mg, 0.385 mmol) DavePhos (10 mg, 0.025 mmol), Pd$_2$(dba)$_3$ (18 mg, 0.020 mmol), and 2-bromo-4-methylpyrimidine (21.4 mg, 0.124 mmol) were added and the reaction left to stir at 100° C. for 3.5 h. The reaction mixture was allowed to cool to rt and then filtered through celite and the celite washed with ethyl acetate. The combined filtrates were concentrated in vacuo to give a crude orange/brown gum. This gum was purified by MDAP (Formic) to give an off-white solid. This solid was eluted through a NH$_2$ SPE (5 g) with MeOH, the eluent was concentrated to give the product (6 mg, 0.015 mmol, 12.26%) as a yellow solid.

LCMS (2 min Formic): Rt=0.80 min, [MH]$^+$=395.

Example 172: rac-4-(((2S,3R,4R)-1-acetyl-2,3-dimethyl-6-(tetrahydro-2H-pyran-4-yl)-1,2,3,4-tetrahydroquinolin-4-yl)amino)-N-methylbenzamide

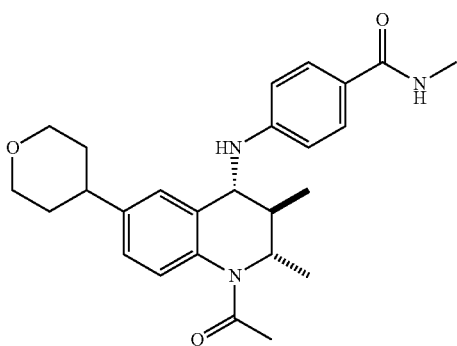 [SMILES: CNC(=O)c1ccc(N[C@H]2c3cc(C4CCOCC4)ccc3N(C(C)=O)[C@@H](C)[C@@H]2C)cc1]

To a reaction vessel 4-bromo-N-methylbenzamide (53.1 mg, 0.248 mmol), rac-1-((2S,3R,4R)-4-amino-2,3-dimethyl-6-(tetrahydro-2H-pyran-4-yl)-3,4-dihydroquinolin-1(2H)-yl)ethanone (for a preparation see Intermediate 152, 37.5 mg, 0.124 mmol), sodium tert-butoxide (35.8 mg, 0.372 mmol), in 1,4-Dioxane (5 mL) were added. The solution was treated with Pd$_2$(dba)$_3$ (17.03 mg, 0.019 mmol) and DavePhos (9.76 mg, 0.025 mmol) and left to stir at 100° C. for 2 h under N$_2$. The reaction mixture was allowed to cool to rt and then filtered through celite and the celite washed with ethyl acetate. The combined filtrates were concentrated in vacuo to a crude orange/brown gum. This gum was purified by MDAP (Formic) to give a solid. This solid was eluted through a NH$_2$ SPE (5 g) with MeOH, the eluent was concentrated to give the product (17 mg, 0.039 mmol, 31.5%) as an off-white solid. LCMS (2 min Formic): Rt=0.83 min, [MH]$^+$=436.

Example 173: rac-5-(((2S,3R,4R)-1-acetyl-2,3-dimethyl-6-(tetrahydro-2H-pyran-4-yl)-1,2,3,4-tetrahydroquinolin-4-yl)amino)pyrazine-2-carbonitrile

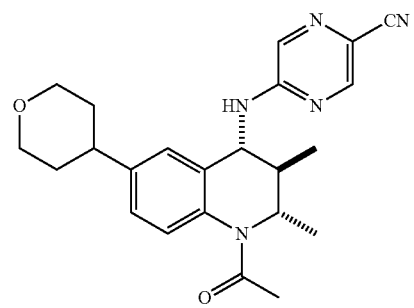 [SMILES: CC(=O)N1c2ccc(C3CCOCC3)cc2[C@H](Nc2cnc(C#N)cn2)[C@@H](C)[C@@H]1C]

To a microwave vial 5-chloropyrazine-2-carbonitrile (34.6 mg, 0.248 mmol), rac-1-((2S,3R,4R)-4-amino-2,3-dimethyl-6-(tetrahydro-2H-pyran-4-yl)-3,4-dihydroquinolin-1(2H)-yl)ethanone (for preparation see Intermediate 152, 37.5 mg, 0.124 mmol), and DIPEA (0.065 mL, 0.372 mmol) were added and the reaction irradiated in a microwave at 200° C. for 30 min. The reaction was purified directly by MDAP (Formic) to give a pale yellow solid. This solid was eluted through a NH$_2$ SPE (5 g) with MeOH, the eluent was concentrated to give the product (22 mg, 0.054 mmol, 43.8%) as an orange/red solid. LCMS (2 min Formic): Rt=0.89 min, [MH]$^+$=406.

Example 174: rac-1-((2S,3R,4R)-2,3-dimethyl-4-((5-methylpyrazin-2-yl)amino)-6-(tetrahydro-2H-pyran-4-yl)-3,4-dihydroquinolin-1(2H)-yl)ethanone

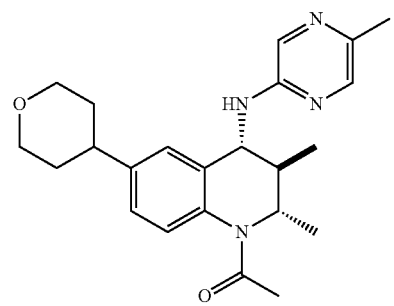 [SMILES: CC(=O)N1c2ccc(C3CCOCC3)cc2[C@H](Nc2cnc(C)cn2)[C@@H](C)[C@@H]1C]

To a reaction vessel 2-chloro-5-methylpyrazine (31.9 mg, 0.248 mmol), rac-1-((2S,3R,4R)-4-amino-2,3-dimethyl-6-(tetrahydro-2H-pyran-4-yl)-3,4-dihydroquinolin-1(2H)-yl)ethanone (for preparation see Intermediate 152, 37.5 mg, 0.124 mmol), sodium tert-butoxide (35.8 mg, 0.372 mmol), in 1,4-dioxane (5 mL) were added. The solution was treated with Pd$_2$(dba)$_3$ (17.03 mg, 0.019 mmol) and DavePhos (9.76 mg, 0.025 mmol) and left to stir at 100° C. for 72 h under N$_2$. The reaction mixture was allowed to cool to rt and then filtered through celite and the celite washed with ethyl acetate. The combined filtrates were concentrated in vacuo to give a crude orange/brown gum. This gum was purified by MDAP (Formic). This was dissolved in methanol (15 mL) and eluted through a pre-equilibrated —NH$_2$ column (5 g) and the column washed with methanol (2×15 mL). The resulting solution was evaporated to give 28 mg of the product as an off white solid.

LCMS (2 min Formic): Rt=0.82 min, [MH]$^+$=395.

Example 175: rac-(2S,3R,4R)-1-acetyl-2-cyclopropyl-N,3-dimethyl-4-((5-methylpyrazin-2-yl)amino)-1,2,3,4-tetrahydroquinoline-6-carboxamide

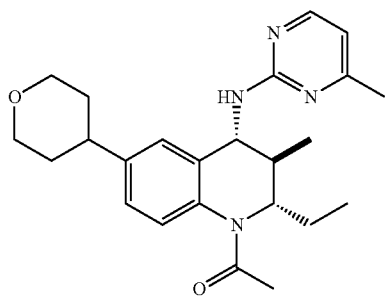 [SMILES: CC[C@H]1[C@H](C)[C@@H](Nc2nccc(C)n2)c2cc(C3CCOCC3)ccc2N1C(C)=O]

To a reaction vessel 2-bromo-4-methylpyrimidine (120 mg, 0.695 mmol), rac-1-((2S,3R,4R)-4-amino-2-ethyl-3-methyl-6-(tetrahydro-2H-pyran-4-yl)-3,4-dihydroquinolin-1(2H)-yl)ethanone (for preparation see Intermediate 154, 110 mg, 0.348 mmol), sodium tert-butoxide (100 mg, 1.043 mmol), in 1,4-dioxane (5 mL) were added. The solution was treated with Pd$_2$(dba)$_3$ (47.7 mg, 0.052 mmol) and DavePhos (27.4 mg, 0.070 mmol) and left to stir at 100° C. for 2 h under N$_2$. The reaction was treated with further sodium tert-butoxide (50 mg, 0.520 mmol), Pd$_2$(dba)$_3$ (25 mg, 0.027 mmol), 2-bromo-4-methylpyrimidine (45.7 mg, 0.264 mmol) and DavePhos (19.56 mg, 0.050 mmol) were added and the reaction was left to stir for a further 67 h at 100° C. under N$_2$. The reaction was treated with further sodium tert-butoxide (45 mg, 0.468 mmol) DavePhos (19 mg, 0.048 mmol) and Pd$_2$(dba)$_3$ (30 mg, 0.033 mmol) and the reaction left to stir at 100° C. for 4 h under N$_2$. The reaction mixture was allowed to cool to rt and was filtered through celite and the celite washed with ethyl acetate (3×15 mL). The combined filtrates were washed with brine (45 mL) the organic phase was dried through a hydrophobic frit and concentrated in vacuo to give a crude brown gum. This was purified by column chromatography on silica gel eluting with 0-100% ethyl acetate/cyclohexane to give a yellow solid. This solid was purified by MDAP (Formic) but the product was still of insufficient purity so was again purified by MDAP (HpH). The solvent was evaporated in vacuo to give the product (9 mg, 0.022 mmol, 6.34%) as a colourless gum.

LCMS (2 min Formic): Rt=0.86 min, [MH]$^+$=409.

Example 176: rac-1-((2S,3R,4R)-2-cyclopropyl-6-(3,6-dihydro-2H-pyran-4-yl)-4-((6-methoxypyridin-2-yl)amino)-3-methyl-3,4-dihydroquinolin-1(2H)-yl)ethanone

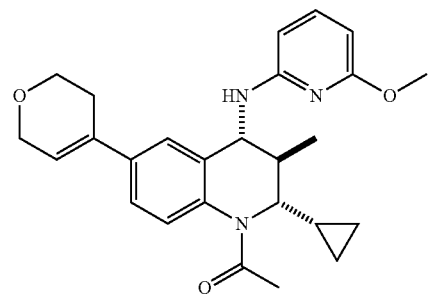 [SMILES: COc1cccc(N[C@H]2c3cc(C4=CCOCC4)ccc3N(C(C)=O)[C@@H](C3CC3)[C@@H]2C)n1]

The 2-bromo-6-methoxypyridine (0.200 mL, 1.593 mmol), rac-1-((2S,3R,4R)-4-amino-2-cyclopropyl-6-(3,6-dihydro-2H-pyran-4-yl)-3-methyl-3,4-dihydroquinolin-1(2H)-yl)ethanone (for a preparation see Intermediate 78, 260 mg, 0.796 mmol), Pd$_2$(dba)$_3$ (109 mg, 0.119 mmol), sodium tert-butoxide (230 mg, 2.389 mmol) and DavePhos (31.3 mg, 0.080 mmol) were suspended in 1,4-dioxane (10 mL) and allowed to stir at 100° C. for 16 h. The reaction was concentrated and partitioned between water and EtOAc, the organic layer was washed with brine, dried using a hydrophobic frit and concentrated to a gum. This gum was purified using a 25 g silica column, elute: 0-50% EtOAc:cyclohexane one major peak was eluted, the appropriate fractions were summed and concentrated to give the product (242 mg, 0.558 mmol, 70.1%) as a yellow solid.

LCMS (2 min Formic): Rt=1.12 min, [MH]$^+$=434.

Example 177: rac-1-((2S,3R,4R)-2-cyclopropyl-6-(3,6-dihydro-2H-pyran-4-yl)-3-methyl-4-(pyrimidin-2-ylamino)-3,4-dihydroquinolin-1(2H)-yl)ethanone, Formic Acid Salt

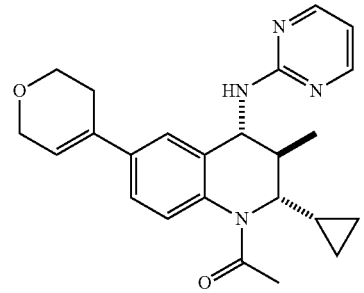 [SMILES: CC(=O)N1c2ccc(C3=CCOCC3)cc2[C@H](Nc2ncccn2)[C@@H](C)[C@@H]1C1CC1]

The rac-1-((2S,3R,4R)-4-amino-2-cyclopropyl-6-(3,6-dihydro-2H-pyran-4-yl)-3-methyl-3,4-dihydroquinolin-1(2H)-yl)ethanone (for a preparation see Intermediate 78, 117 mg, 0.358 mmol), 2-chloropyrimidine (82 mg, 0.717 mmol) and DIPEA (0.188 mL, 1.075 mmol) were taken up in N-methyl-2-pyrrolidone (NMP) (5 mL) placed in a microwaveable vial and irradiated in a microwave at 150° C. for 1 h. The reaction was irradiated for a further 1 h at 200° C. and then 2 h at 200° C. The reaction was partitioned between water and EtOAc, the organic layer was washed with 10% LiCl(aq), dried using a hydrophobic frit and concentrated to a orange oil. This oil was purified using a MDAP (Formic). The appropriate fractions were summed and concentrated to give the product (21 mg, 0.047 mmol, 13.0%) as an orange solid. LCMS (2 min formic): Rt=0.91 min, [MH]⁺=405.

Example 178: rac-4-(((2S,3R,4R)-1-acetyl-2-cyclopropyl-6-(3,6-dihydro-2H-pyran-4-yl)-3-methyl-1,2,3,4-tetrahydroquinolin-4-yl)amino)-N-methylbenzamide

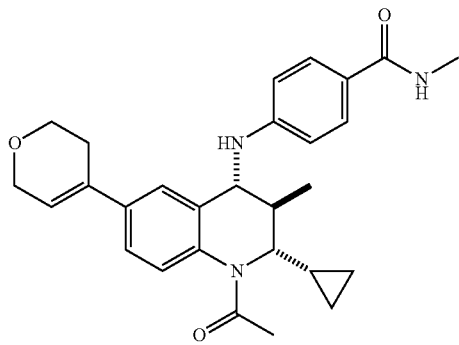 [SMILES: CNC(=O)c1ccc(N[C@H]2c3cc(C4=CCOCC4)ccc3N(C(C)=O)[C@@H](C3CC3)[C@@H]2C)cc1]

The rac-1-((2S,3R,4R)-4-amino-2-cyclopropyl-6-(3,6-dihydro-2H-pyran-4-yl)-3-methyl-3,4-dihydroquinolin-1(2H)-yl)ethanone (for a preparation see Intermediate 78, 200 mg, 0.613 mmol), Pd₂(dba)₃ (84 mg, 0.092 mmol), sodium tert-butoxide (177 mg, 1.838 mmol), DavePhos (24.11 mg, 0.061 mmol) and 4-bromo-N-methylbenzamide (262 mg, 1.225 mmol) were suspended in 1,4 dioxane (10 mL) and allowed to stir at 100° C. for 16 h. The reaction was allowed to cool to rt and was partioned between water and EtOAc, the organic phase was washed with brine, dried using a hydrophobic frit and concentrated to a gum. This gum was purified using column chromatography on silica gel eluting with 0-100% EtOAc:cyclohexane, and then 0-10% MeOH:DCM, to give a crude solid which was further purified by MDAP (Formic) to give a solid which was eluted through a NH₂ SPE (1 g) with MeOH, the eluent was concentrated and dried to give the product (45 mg, 0.098 mmol, 15.98%) as a white solid.

LCMS (2 min Formic): Rt=0.92 min, [M−H]⁻=458.

Example 179: rac-1-(((2S,3R,4R)-2-cyclopropyl-6-(3,6-dihydro-2H-pyran-4-yl)-3-methyl-4-((5-methylpyrazin-2-yl)amino)-3,4-dihydroquinolin-1(2H)-yl)ethanone

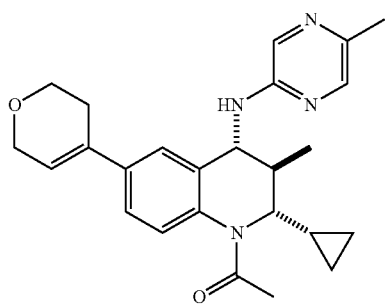 [SMILES: CC(=O)N1c2ccc(C3=CCOCC3)cc2[C@H](Nc2cnc(C)cn2)[C@@H](C)[C@@H]1C1CC1]

The 2-chloro-5-methylpyrazine (0.053 mL, 0.613 mmol), rac-1-((2S,3R,4R)-4-amino-2-cyclopropyl-6-(3,6-dihydro-2H-pyran-4-yl)-3-methyl-3,4-dihydroquinolin-1(2H)-yl) ethanone (for a preparation see Intermediate 78, 100 mg, 0.306 mmol), Pd₂(dba)₃ (42.1 mg, 0.046 mmol), sodium tert-butoxide (88 mg, 0.919 mmol) and DavePhos (12.06 mg, 0.031 mmol) were suspended in 1,4-dioxane (10 mL) and allowed to stir at 100° C. for 3 h. The reaction was allowed to cool and was partitioned between water and EtOAc, the organic layer was washed with brine, dried using a hydrophobic frit and concentrated to a gum. This gum was purified by column chromatography on silica gel eluting with 0-50% EtOAc:cyclohexane and then 0-10% MeOH:DCM, to give a crude gum. This gum was further purified using a MDAP (Formic) to give a white solid, this solid was eluted through a NH₂ SPE (2 g) with MeOH the eluent was concentrated and dried to give the product (46 mg, 0.110 mmol, 35.9%) as an off-white solid. LCMS (2 min Formic): Rt=0.93 min, [MH]⁺=419.

Example 180: rac-5-(((2S,3R,4R)-1-acetyl-2-cyclopropyl-6-(3,6-dihydro-2H-pyran-4-yl)-3-methyl-1,2,3,4-tetrahydroquinolin-4-yl)amino)pyrazine-2-carbonitrile

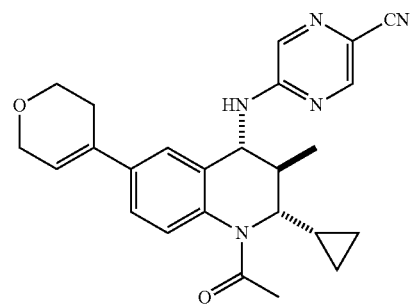 [SMILES: CC(=O)N1c2ccc(C3=CCOCC3)cc2[C@H](Nc2cnc(C#N)cn2)[C@@H](C)[C@@H]1C1CC1]

The 5-chloropyrazine-2-carbonitrile (0.034 mL, 0.368 mmol), rac-1-((2S,3R,4R)-4-amino-2-cyclopropyl-6-(3,6-dihydro-2H-pyran-4-yl)-3-methyl-3,4-dihydroquinolin-1(2H)-yl)ethanone (for a preparation see Intermediate 78, 60 mg, 0.184 mmol), DIPEA (0.096 mL, 0.551 mmol) and N-methyl-2-pyrrolidone (NMP) (2 mL) were irradiated in a microwave at 200° C. for 1 h. The reaction was purified directly using a MDAP (Formic) to give a brown solid. This solid was eluted through a NH₂ SPE (5 g) using MeOH, the eluent was concentrated and dried to give the product (34 mg, 0.079 mmol, 43.1%) as a brown solid. LCMS (2 min Formic): Rt=0.98 min, [MH]⁺=430.

Example 181: rac-6-(((2S,3R,4R)-1-acetyl-2-cyclopropyl-6-(3,6-dihydro-2H-pyran-4-yl)-3-methyl-1,2,3,4-tetrahydroquinolin-4-yl)amino)nicotinonitrile

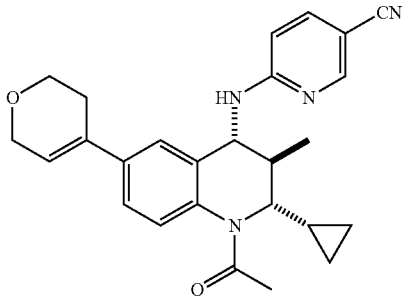 [SMILES: CC(=O)N1c2ccc(C3=CCOCC3)cc2[C@H](Nc2ccc(C#N)cn2)[C@@H](C)[C@@H]1C1CC1]

The 6-fluoronicotinonitrile (0.030 mL, 0.368 mmol), rac-1-((2S,3R,4R)-4-amino-2-cyclopropyl-6-(3,6-dihydro-2H-pyran-4-yl)-3-methyl-3,4-dihydroquinolin-1(2H)-yl)ethanone (for a preparation see Intermediate 78, 60 mg, 0.184 mmol), 6-fluoronicotinonitrile (0.030 mL, 0.368 mmol), DIPEA (0.096 mL, 0.551 mmol) and N-methyl-2-pyrrolidone (NMP) (2 mL) were irradiated in a microwave at 200° C. for 30 min. The reaction was purified directly using a MDAP (Formic) to give a brown solid. This solid was eluted through a NH$_2$ SPE (5 g) using MeOH, the eluent was concentrated and dried to give the product (43 mg, 0.100 mmol, 54.6%) as a yellow solid.

LCMS (2 min Formic): Rt=1.01 min, [MH]$^+$=429.

Example 182: rac-1-((2S,3R,4R)-2-cyclopropyl-6-(3,6-dihydro-2H-pyran-4-yl)-3-methyl-4-((4-methylpyrimidin-2-yl)amino)-3,4-dihydroquinolin-1(2H)-yl)ethanone

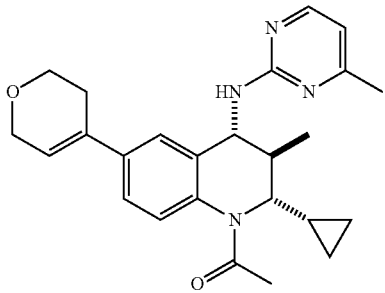 [SMILES: CC(=O)N1c2ccc(C3=CCOCC3)cc2[C@H](Nc2nccc(C)n2)[C@@H](C)[C@@H]1C1CC1]

The rac-1-((2S,3R,4R)-4-amino-2-cyclopropyl-6-(3,6-dihydro-2H-pyran-4-yl)-3-methyl-3,4-dihydroquinolin-1(2H)-yl)ethanone (for a preparation see Intermediate 78, 200 mg, 0.613 mmol), Pd$_2$(dba)$_3$ (84 mg, 0.092 mmol), sodium tert-butoxide (177 mg, 1.838 mmol), DavePhos (24.11 mg, 0.061 mmol) and 2-bromo-4-methylpyrimidine (212 mg, 1.225 mmol) were suspended in 1,4 dioxane (10 mL) and allowed to stir at 100° C. for 16 h. The reaction was treated with further Pd$_2$(dba)$_3$ (84 mg, 0.092 mmol) and was allowed to stir at 100° C. for a further 24 h. The reaction was transferred to microwave vial and was irradiated in a microwave at 140° C. for 2 h. The reaction was allowed to cool to rt and was partioned between water and EtOAc, the organic phase was washed with brine, dried using a hydrophobic frit and concentrated to a gum. This gum was purified by column chromatography on silica gel eluting with 0-10% MeOH:DCM to give a crude oil. This oil was purified using a MDAP (Formic) and the appropriate fractions were concentrated to give an oil which was eluted through a NH$_2$ SPE (1 g) with MeOH, washing with further MeOH. The eluent was concentrated to give the product (10 mg, 0.024 mmol, 3.90%) as a yellow oil.

LCMS (2 min Formic): Rt=0.90 min, [MH]$^+$=419.

Example 183: rac-1-((2S,3R,4R)-2,3-dimethyl-4-((5-methylpyrazin-2-yl)amino)-6-(piperidin-4-yl)-3,4-dihydroquinolin-1(2H)-yl)ethanone, hydrochloride

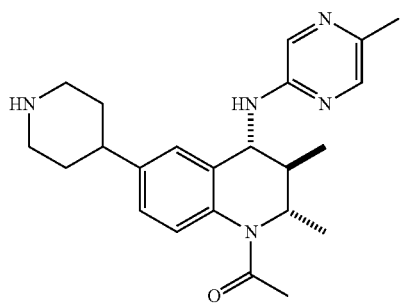 [SMILES: CC(=O)N1c2ccc(C3CCNCC3)cc2[C@H](Nc2cnc(C)cn2)[C@@H](C)[C@@H]1C]

A solution of rac-tert-butyl 4-((2S,3R,4R)-1-acetyl-2,3-dimethyl-4-((5-methylpyrazin-2-yl)amino)-1,2,3,4-tetrahydroquinolin-6-yl)piperidine-1-carboxylate (for a preparation see Intermediate 157, 23 mg, 0.047 mmol) in 1,4-dioxane (1 mL) was treated with 4M HCl in dioxane (1 mL, 4.00 mmol) and stirred in a closed vessel at rt for 1 h. The solvent was evaporated in vacuo to give the title compound (18 mg, 0.042 mmol, 90%). LCMS (2 min Formic): Rt=0.58 min, [MH]$^+$=394.

Example 184: rac-1-((2S,3R,4R)-4-((5-fluoropyridin-2-yl)amino)-2,3-dimethyl-6-(piperidin-4-yl)-3,4-dihydroquinolin-1(2H)-yl)ethanone, 2 hydrochloride

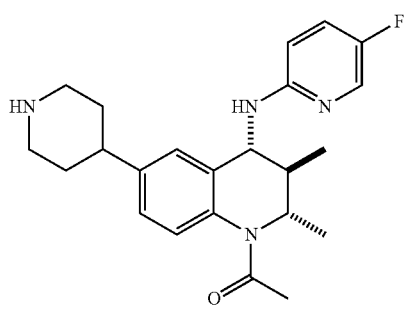 [SMILES: CC(=O)N1c2ccc(C3CCNCC3)cc2[C@H](Nc2ccc(F)cn2)[C@@H](C)[C@@H]1C]

A solution of rac-tert-butyl 4-((2S,3R,4R)-1-acetyl-4-((5-fluoropyridin-2-yl)amino)-2,3-dimethyl-1,2,3,4-tetrahydroquinolin-6-yl)piperidine-1-carboxylate (for a preparation see Intermediate 158, 67 mg, 0.135 mmol) in 1,4-dioxane (1 mL) was treated with 4M HCl in dioxane (1 mL, 4.00 mmol) and stirred in a closed vessel at rt for 1 h. The solvent was evaporated in vacuo to give the title compound (60 mg, 0.128 mmol, 95%). LCMS (2 min Formic): Rt=0.59 min, [MH]$^+$=397.

Example 185: rac-1-((2S,3R,4R)-2,3-dimethyl-4-((6-methylpyridin-2-yl)amino)-6-(piperidin-4-yl)-3,4-dihydroquinolin-1(2H)-yl)ethanone, 2 hydrochloride

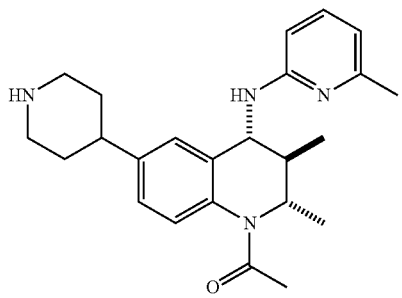 [SMILES: CC(=O)N1c2ccc(C3CCNCC3)cc2[C@H](Nc2cccc(C)n2)[C@@H](C)[C@@H]1C]

A solution of rac-tert-butyl 4-((2S,3R,4R)-1-acetyl-2,3-dimethyl-4-((6-methylpyridin-2-yl)amino)-1,2,3,4-tetrahydroquinolin-6-yl)piperidine-1-carboxylate (for a preparation see Intermediate 159, 55 mg, 0.112 mmol) in 1,4-dioxane (1 mL) was treated with 4 M HCl in 1,4-dioxane (1 mL, 4.00 mmol) and stirred in a closed vessel at rt for 1 h. The solvent was evaporated in vacuo to give the title compound (50 mg, 0.107 mmol, 96%). LCMS (2 min Formic): Rt=0.47 min, [MH]$^+$=393.

Example 186: rac-4-(((2S,3R,4R)-1-acetyl-2,3-dimethyl-6-(piperidin-4-yl)-1,2,3,4-tetrahydroquinolin-4-yl)amino)benzonitrile

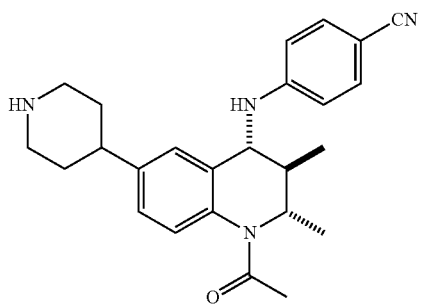 [SMILES: CC(=O)N1c2ccc(C3CCNCC3)cc2[C@H](Nc2ccc(C#N)cc2)[C@@H](C)[C@@H]1C]

A solution of tert-butyl 4-((2S,3R,4R)-1-acetyl-4-((4-cyanophenyl)amino)-2,3-dimethyl-1,2,3,4-tetrahydroquinolin-6-yl)piperidine-1-carboxylate (for a preparation see Intermediate 160, 15 mg, 0.030 mmol) and 4M HCl in dioxane (1 mL, 4.00 mmol) in 1,4-dioxane (1 mL) was stirred in a closed vessel at rt for 1 h. The solvent was concentrated in vacuo and the sample was dissolved in 1:1 MeOH:DMSO (1 mL) and purified by MDAP (HpH). The appropriate fractions were combined and concentrated in vacuo to give the product (6.2 mg, 0.015 mmol, 51.6%).

LCMS (2 min Formic): Rt=0.68 min, [MH]$^+$=403.

Example 187: rac-6-(((2S,3R,4R)-1-acetyl-2,3-dimethyl-6-(piperidin-4-yl)-1,2,3,4-tetrahydroquinolin-4-yl)amino)nicotinonitrile

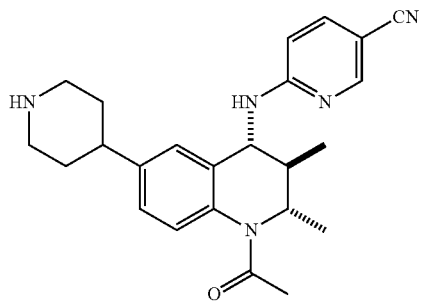 [SMILES: CC(=O)N1c2ccc(C3CCNCC3)cc2[C@H](Nc2ccc(C#N)cn2)[C@@H](C)[C@@H]1C]

A solution of rac-tert-butyl 4-((2S,3R,4R)-1-acetyl-4-((5-cyanopyridin-2-yl)amino)-2,3-dimethyl-1,2,3,4-tetrahydroquinolin-6-yl)piperidine-1-carboxylate (for a preparation see Intermediate 161, 21 mg, 0.042 mmol) and 4M HCl in dioxane (1.042 mL, 4.17 mmol) in 1,4-dioxane (1 mL) was stirred at rt for 1 h in a closed vessel. The solvent was evaporated in vacuo and the sample was dissolved in 1:1 MeOH:DMSO (1 mL) and purified by MDAP (Formic). The appropriate fractions were combined and concentrated in vacuo to give the product (6.1 mg, 0.015 mmol, 36.3%).

LCMS (2 min Formic): Rt=0.64 min, [MH]$^+$=404.

Example 188: rac-4-(((2S,3R,4R)-1-acetyl-2,3-dimethyl-6-(piperidin-4-yl)-1,2,3,4-tetrahydroquinolin-4-yl)amino)-N-methylbenzamide

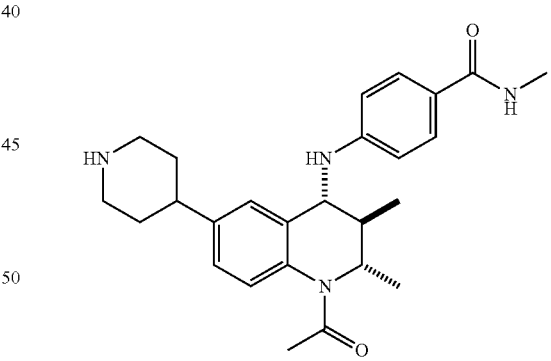

A solution of rac-tert-butyl 4-((2S,3R,4R)-1-acetyl-2,3-dimethyl-4-((4-(methylcarbamoyl)phenyl)amino)-1,2,3,4-tetrahydroquinolin-6-yl)piperidine-1-carboxylate (for a preparation see Intermediate 162, 15 mg, 0.028 mmol) and 4M HCl in dioxane (1 mL, 4.00 mmol) in 1,4-dioxane (1 mL) was stirred in a closed vessel at rt for 1 h. The solvent was evaporated in vacuo and the sample was dissolved in 1:1 MeOH:DMSO (1 mL) and purified by MDAP (HpH). The appropriate fractions were combined and concentrated in vacuo to give the product (5.3 mg, 0.012 mmol, 43.5%).

LCMS (2 min Formic): Rt=0.59 min, [MH]$^+$=435.

Example 189a & 189b: 1-((2S,3R,4R)-2-cyclopropyl-3-methyl-4-((6-methylpyridin-2-yl)amino)-6-(1,2,3,6-tetrahydropyridin-4-yl)-3,4-dihydroquinolin-1(2H)-yl)ethanone (189a) & 1-((2R,3S,4S)-2-cyclopropyl-3-methyl-4-((6-methylpyridin-2-yl)amino)-6-(1,2,3,6-tetrahydropyridin-4-yl)-3,4-dihydroquinolin-1(2H)-yl)ethanone (189b)

189a

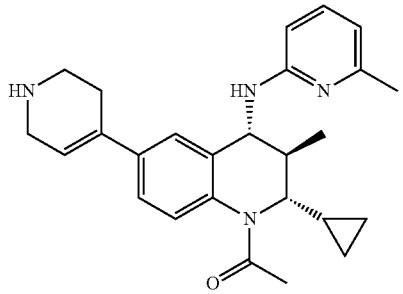

189b

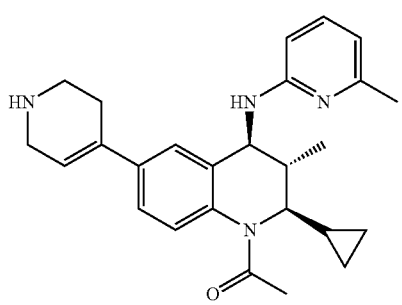

rac-1-((2S,3R,4R)-2-Cyclopropyl-3-methyl-4-((6-methylpyridin-2-yl)amino)-6-(1,2,3,6-tetrahydropyridin-4-yl)-3,4-dihydroquinolin-1(2H)-yl)ethanone (for a preparation see Example 87, 70 mg) was submitted for chiral separation into its enantiomers (A and B) using a 250×30 mm Chiralpak AD-H column eluting with 92.5:7.5 (plus 0.2% isopropylamine) at a flow rate of 42.5 mL/min. Peak 1/Enantiomer A fractions were collected between 13 and 15 min, and Peak 2/Enantiomer B fractions were collected between 22.5 and 26 min. Fraction solutions were combined and then evaporated to dryness to give Enantiomer A (30 mg) and Enantiomer B (30 mg) as white solids.

Enantiomer A, Example 189a

Analytical Chiral HPLC using a 250×4.6 mm Chiralpak AD-H column eluting with 10% ethanol in heptanes (plus 0.2% isopropylamine) at 1 mL/min—Rt=8.5 min.>99% ee by UV.

Enantiomer B, Example 189b

Analytical Chiral HPLC using a 250×4.6 mm Chiralpak AD-H column eluting with 10% ethanol in heptanes (plus 0.2% isopropylamine) at 1 mL/min—Rt=11.5 min, >99% ee by UV.

Example 190: rac-1-((2S,3R,4R)-2-cyclopropyl-4-((6-hydroxypyridin-2-yl)amino)-3-methyl-6-(1,2,3,6-tetrahydropyridin-4-yl)-3,4-dihydroquinolin-1(2H)-yl)ethanone

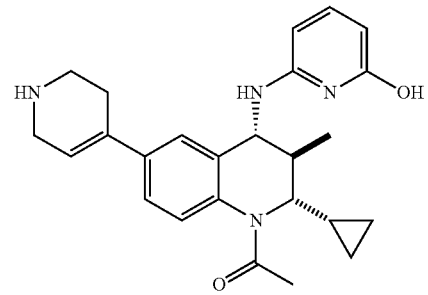 [SMILES: CC(=O)N1c2ccc(C3=CCNCC3)cc2[C@H](Nc2cccc(O)n2)[C@@H](C)[C@@H]1C1CC1]

rac-tert-Butyl 4-((2S,3R,4R)-1-acetyl-2-cyclopropyl-4-((6-methoxypyridin-2-yl)amino)-3-methyl-1,2,3,4-tetrahydroquinolin-6-yl)-5,6-dihydropyridine-1(2H)-carboxylate (for a preparation see Intermediate 163, 20 mg, 0.038 mmol), TMSCl (0.029 mL, 0.225 mmol) and sodium iodide (33.8 mg, 0.225 mmol) were stirred in acetonitrile (0.05 mL) and heated at 55° C. for 2 days. The reaction mixture was filtered though a cotton wool plug and the filtrate was concentrated. The residue was purified using MDAP (Formic). Evaporation of the desired fractions gave the product as a white solid (8 mg).

LCMS (2 min Formic): Rt=0.58 min, [MH]$^+$=419.

Example 191: rac-1-((2S,3R,4R)-2-cyclopropyl-4-((6-methoxypyridin-2-yl)amino)-3-methyl-6-(1,2,3,6-tetrahydropyridin-4-yl)-3,4-dihydroquinolin-1(2H)-yl)ethanone

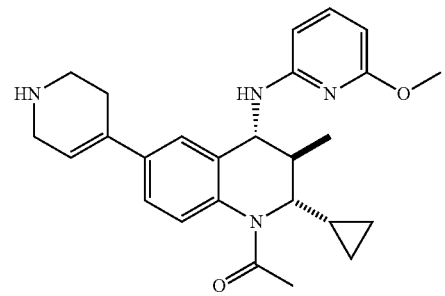 [SMILES: COc1cccc(N[C@H]2c3cc(C4=CCNCC4)ccc3N(C(C)=O)[C@@H](C3CC3)[C@@H]2C)n1]

rac-tert-Butyl 4-((2S,3R,4R)-1-acetyl-2-cyclopropyl-4-((6-methoxypyridin-2-yl)amino)-3-methyl-1,2,3,4-tetrahydroquinolin-6-yl)-5,6-dihydropyridine-1(2H)-carboxylate (for a preparation see Intermediate 163, 10 mg, 0.019 mmol) was dissolved in 4M hydrochloric acid (0.5 mL, 2.0 mmol) in 1,4-dioxane. The reaction was stirred at rt for 1 h. The solvent and excess HCl were removed under reduced pressure to leave the product HCl salt as a yellow solid. Purification was undertaken using MDAP (Formic). The collected fractions were evaporated to leave the product as a white solid (5 mg).

LCMS (2 min Formic): Rt=0.75 min, [MH]$^+$=433.

Example 192: rac-4-(((2S,3R,4R)-1-acetyl-2-cyclo-propyl-3-methyl-6-(1,2,3,6-tetrahydropyridin-4-yl)-1,2,3,4-tetrahydroquinolin-4-yl)amino)benzonitrile

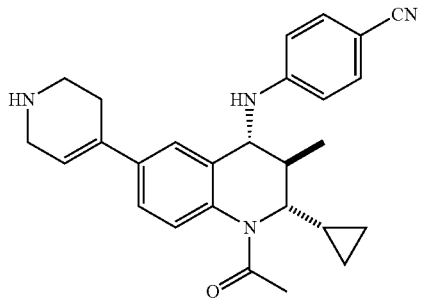 [SMILES: CC(=O)N1c2ccc(C3=CCNCC3)cc2[C@H](Nc2ccc(C#N)cc2)[C@@H](C)[C@@H]1C1CC1]

rac-tert-Butyl 4-((2S,3R,4R)-1-acetyl-4-((4-cyanophenyl)amino)-2-cyclopropyl-3-methyl-1,2,3,4-tetrahydroquinolin-6-yl)-5,6-dihydropyridine-1(2H)-carboxylate (for a preparation see Intermediate 164, 10 mg, 0.019 mmol) was dissolved in 4M hydrochloric acid (0.5 mL, 2.0 mmol) in 1,4-dioxane. The reaction was stirred at rt for 1 h. The solvent and excess HCl were removed under reduced pressure to leave the product HCl salt. Purification was undertaken using MDAP (HpH). The collected fractions were evaporated to leave the product as a white solid (5 mg).

LCMS (2 min Formic): Rt=0.76 min, [MH]$^+$=427.

Example 193: rac-4-(((2S,3R,4R)-1-acetyl-2-cyclopropyl-3-methyl-6-(1,2,3,6-tetrahydropyridin-4-yl)-1,2,3,4-tetrahydroquinolin-4-yl)amino)-N-methylbenzamide

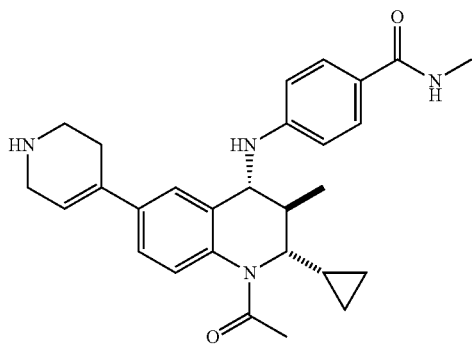 [SMILES: CNC(=O)c1ccc(N[C@H]2c3cc(C4=CCNCC4)ccc3N(C(C)=O)[C@@H](C3CC3)[C@@H]2C)cc1]

rac-tert-Butyl 4-((2S,3R,4R)-1-acetyl-2-cyclopropyl-3-methyl-4-((4-(methylcarbamoyl)phenyl)amino)-1,2,3,4-tetrahydroquinolin-6-yl)-5,6-dihydropyridine-1(2H)-carboxylate (for a preparation see Intermediate 165, 10 mg, 0.018 mmol) was dissolved in 4M hydrochloric acid (0.5 mL, 2.0 mmol) in 1,4-dioxane. The reaction was stirred at rt for 1 h. The solvent and excess HCl were removed under reduced pressure to leave the product HCl salt. Purification was undertaken using MDAP (HpH). The collected fractions were evaporated to leave the product as a white solid (7 mg).

LCMS (2 min Formic): Rt=0.65 min, [MH]$^+$=459.

Example 194: rac-1-((2S,3R,4R)-2-cyclopropyl-3-methyl-4-((4-methylpyrimidin-2-yl)amino)-6-(1,2,3,6-tetrahydropyridin-4-yl)-3,4-dihydroquinolin-1(2H)-yl)ethanone

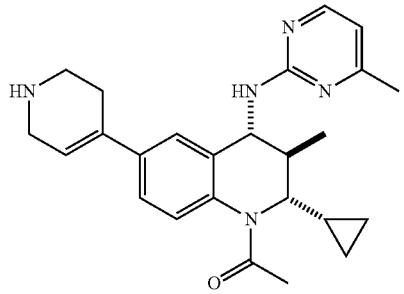 [SMILES: CC(=O)N1c2ccc(C3=CCNCC3)cc2[C@H](Nc2nccc(C)n2)[C@@H](C)[C@@H]1C1CC1]

rac-tert-Butyl 4-((2S,3R,4R)-1-acetyl-2-cyclopropyl-3-methyl-4-((4-methylpyrimidin-2-yl)amino)-1,2,3,4-tetrahydroquinolin-6-yl)-5,6-dihydropyridine-1(2H)-carboxylate (for a preparation see Intermediate 166, 10 mg, 0.019 mmol) was dissolved in 4M hydrochloric acid (0.5 mL, 2.0 mmol) in 1,4-dioxane. The reaction was stirred at rt for 1 h. The solvent and excess HCl were removed under reduced pressure to leave the crude product. Purification was undertaken using MDAP (HpH). The collected fractions were evaporated to leave the product as a white solid (8 mg).

LCMS (2 min Formic): Rt=0.62 min, [MH]$^+$=418.

Example 195: rac-4-(((2S,3R,4R)-1-acetyl-2-cyclopropyl-3-methyl-6-(piperidin-4-yl)-1,2,3,4-tetrahydroquinolin-4-yl)amino)benzonitrile, Formic Acid Salt

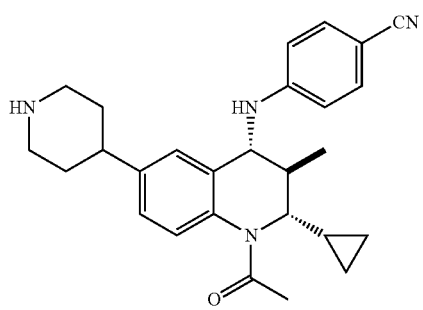

To a solution of rac-tert-butyl 4-((2S,3R,4R)-1-acetyl-4-((4-cyanophenyl)amino)-2-cyclopropyl-3-methyl-1,2,3,4-tetrahydroquinolin-6-yl)piperidine-1-carboxylate (for a preparation see Intermediate 167, 80 mg, 0.152 mmol) in 1,4-dioxane (2 mL) was added 4M HCl in 1,4-dioxane (2.00 mL). The resulting reaction mixture was stirred at rt for 1 hour, whereupon it was concentrated in vacuo. The crude residue was dissolved in a 1:1 DMSO/MeOH mixture and was purified via MDAP (Formic). The appropriate fractions were combined and concentrated in vacuo to give the product as a white solid (11 mg). LCMS (2 min Formic): Rt=0.77 min, [MH]$^+$=429.

Example 196: rac-4-(((2S,3R,4R)-1-acetyl-2-cyclopropyl-3-methyl-6-(piperidin-4-yl)-1,2,3,4-tetrahydroquinolin-4-yl)amino)-N-methylbenzamide, Formic Acid Salt

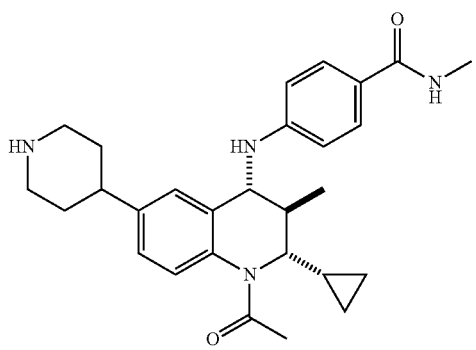 [SMILES: CNC(=O)c1ccc(N[C@H]2c3cc(C4CCNCC4)ccc3N(C(C)=O)[C@@H](C3CC3)[C@@H]2C)cc1]

To a solution of rac-tert-butyl 4-((2S,3R,4R)-1-acetyl-2-cyclopropyl-3-methyl-4-((4-(methylcarbamoyl)phenyl)amino)-1,2,3,4-tetrahydroquinolin-6-yl)piperidine-1-carboxylate (for a preparation see Intermediate 168, 29 mg, 0.052 mmol) in 1,4-dioxane (2 mL) was added 4M HCl in 1,4-dioxane (2.00 mL). The resulting reaction mixture was stirred at rt for 1 h, whereupon it was concentrated in vacuo. The crude residue was dissolved in a 1:1 DMSO/MeOH mixture and was purified via MDAP (Formic). The appropriate fractions were combined and concentrated in vacuo to give the product as an off-white solid (12 mg). LCMS (2 min Formic): Rt=0.65 min, [MH]$^+$=461.

Example 197: 4-(((2S,3R,4R)-1-acetyl-2,3-dimethyl-6-morpholino-1,2,3,4-tetrahydroquinolin-4-yl)amino)benzonitrile

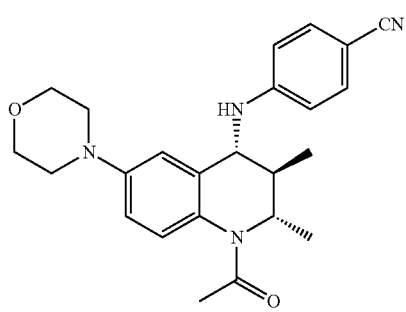 [SMILES: CC(=O)N1c2ccc(N3CCOCC3)cc2[C@H](Nc2ccc(C#N)cc2)[C@@H](C)[C@@H]1C]

A microwave vial was charged with 1-((2S,3R,4R)-4-amino-2,3-dimethyl-6-morpholino-3,4-dihydroquinolin-1(2H)-yl)ethanone (for a preparation see Intermediate 211, 125 mg, 72% purity, 0.297 mmol, ~25% ee) in 1,4-dioxane (2 mL) followed by 4-bromobenzonitrile (108 mg, 0.593 mmol), then sodium tert-butoxide (57 mg, 0.593 mmol), DavePhos (24 mg, 0.061 mmol), and Pd$_2$(dba)$_3$ (54 mg, 0.059 mmol). The reaction mixture was heated to 100° C. for 45 min using a microwave reactor, then diluted with EtOAc and filtered through a pad of celite. The celite pad was washed with EtOAc (10 mL) and the filtrate concentrated under reduced pressure. The residue was purified by MDAP (Formic). The desired fractions were combined and evaporated in vacuo and the residue dissolved in methanol then passed through an amino-propyl SPE column which was washed with further methanol. The methanol washes were combined then concentrated in vacuo to afford the desired product as a white solid (13 mg, ~25% ee).

LCMS (2 min Formic): Rt=0.93 min, [MH]$^+$=405.

Example 198: 1-((2S,3R,4R)-2,3-dimethyl-4-((4-methylpyrimidin-2-yl)amino)-6-morpholino-3,4-dihydroquinolin-1(2H)-yl)ethanone

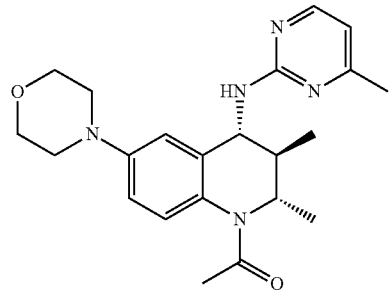 [SMILES: CC(=O)N1c2ccc(N3CCOCC3)cc2[C@H](Nc2nccc(C)n2)[C@@H](C)[C@@H]1C]

A microwave vial was charged with 1-((2S,3R,4R)-4-amino-2,3-dimethyl-6-morpholino-3,4-dihydroquinolin-1(2H)-yl)ethanone (for a preparation see Intermediate 211, 125 mg, 72% purity, 0.297 mmol, ~25% ee) in 1,4-dioxane (2 mL) followed by 2-bromo-4-methylpyrimidine (103 mg, 0.593 mmol), then sodium tert-butoxide (57 mg, 0.593 mmol), DavePhos (24 mg, 0.061 mmol), and Pd$_2$(dba)$_3$ (54 mg, 0.059 mmol). The reaction mixture was heated to 100° C. for 45 min using a microwave reactor, then diluted with EtOAc and filtered through a pad of celite. The celite pad was washed with EtOAc (10 mL) and the filtrate concentrated under reduced pressure. The residue was purified by MDAP (Formic). The desired fractions were combined and evaporated in vacuo and the residue dissolved in methanol then passed through an amino-propyl SPE column which was washed with further methanol. The methanol washes were combined then concentrated in vacuo to afford the desired product as a white solid (17 mg, ~25% ee).

LCMS (2 min Formic): Rt=0.71 min, [MH]$^+$=396.

Example 199: rac-4-(((2S,3R,4R)-1-acetyl-2,3-dimethyl-6-morpholino-1,2,3,4-tetrahydroquinolin-4-yl)amino)-N-methylbenzamide

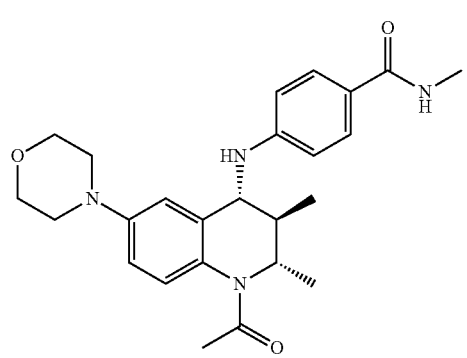 [SMILES: CNC(=O)c1ccc(N[C@H]2c3cc(N4CCOCC4)ccc3N(C(C)=O)[C@@H](C)[C@@H]2C)cc1]

A microwave vial was charged with 1-((2S,3R,4R)-4-amino-2,3-dimethyl-6-morpholino-3,4-dihydroquinolin-1

(2H)-yl)ethanone (for a preparation see Intermediate 211, 125 mg, 72% purity, 0.297 mmol, ~25% ee) in 1,4-dioxane (2 mL) followed by 4-bromo-N-methylbenzamide (127 mg, 0.593 mmol), then sodium tert-butoxide (57 mg, 0.593 mmol), DavePhos (24 mg, 0.061 mmol), and Pd₂(dba)₃ (54 mg, 0.059 mmol). The reaction mixture was heated to 100° C. for 45 min using a microwave reactor, then diluted with EtOAc and filtered through a pad of celite. The celite pad was washed with EtOAc (10 mL) and the filtrate concentrated under reduced pressure. The residue was purified by MDAP (Formic). The desired fractions were combined and evaporated in vacuo and the residue dissolved in methanol then passed through an amino-propyl SPE column which was washed with further methanol. The methanol washes were combined then concentrated in vacuo to afford the desired product as a white solid (8 mg, ~25% ee).

LCMS (2 min Formic): Rt=0.76 min, [MH]⁺=437.

Example 200: 1-((2S,3R,4R)-2,3-dimethyl-4-((5-methylpyrazin-2-yl)amino)-6-morpholino-3,4-dihydroquinolin-1(2H)-yl)ethanone

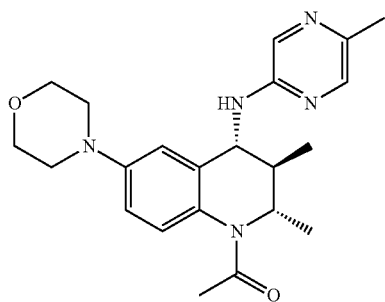 [SMILES: CC(=O)N1c2ccc(N3CCOCC3)cc2[C@H](Nc2cnc(C)cn2)[C@@H](C)[C@@H]1C]

A microwave vial was charged with 1-((2S,3R,4R)-4-amino-2,3-dimethyl-6-morpholino-3,4-dihydroquinolin-1(2H)-yl)ethanone (for a preparation see Intermediate 211, 125 mg, 72% purity, 0.297 mmol, ~25% ee) in 1,4-dioxane (2 mL) followed by 2-chloro-5-methylpyrazine (76 mg, 0.593 mmol), then sodium tert-butoxide (57 mg, 0.593 mmol), DavePhos (24 mg, 0.061 mmol), and Pd₂(dba)₃ (54 mg, 0.059 mmol). The reaction mixture was heated to 100° C. for 45 min using a microwave. reactor, then diluted with EtOAc and filtered through a pad of celite. The celite pad was washed with EtOAc (10 mL) and the filtrate concentrated under reduced pressure. The residue was purified by MDAP (Formic). The desired fractions were combined and evaporated in vacuo and the residue dissolved in methanol then passed through an amino-propyl SPE column which was washed with further methanol. The methanol washes were combined then concentrated in vacuo to afford the desired product as a white solid (9 mg, ~25% ee).

LCMS (2 min Formic): Rt=0.75 min, [MH]⁺=396.

Example 201: rac-1-((2S,3R,4R)-2-ethyl-3-methyl-4-((4-methylpyrimidin-2-yl)amino)-6-morpholino-3,4-dihydroquinolin-1(2H)-yl)ethanone

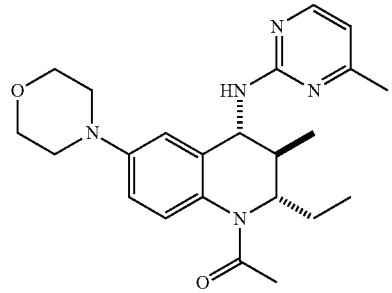 [SMILES: CC[C@H]1[C@H](C)[C@@H](Nc2nccc(C)n2)c2cc(N3CCOCC3)ccc2N1C(C)=O]

To a solution of rac-1-((2S,3R,4R)-4-amino-2-ethyl-3-methyl-6-morpholino-3,4-dihydroquinolin-1(2H)-yl)ethanone (for a preparation see Intermediate 73, 40 mg, 0.126 mmol) in N-methyl-2-pyrrolidone (1.6 mL) was added N,N-diisopropylethylamine (0.066 mL, 0.378 mmol) and 2-bromo-4-methylpyrimidine (43.6 mg, 0.252 mmol). The reaction mixture was heated under microwave conditions, using initial high absorption setting, to 200° C. for 30 min. N-Methyl-2-pyrrolidone (0.3 mL) was added and the solution was purified by MDAP (HpH). The solvent was blown down under a stream of nitrogen to give a brown gum. The sample was dissolved in DMSO (1 mL) and purified by MDAP (Formic). The solvent was blown down under a stream of nitrogen to give the required product (9 mg) as an off-white gum.

LCMS (2 min HpH): Rt=0.90 min, [MH]⁺=410.

Example 202: rac-6-(((2S,3R,4R)-1-acetyl-2-ethyl-3-methyl-6-morpholino-1,2,3,4-tetrahydroquinolin-4-yl)amino)nicotinonitrile

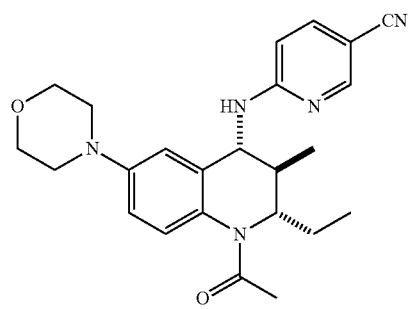 [SMILES: CC[C@H]1[C@H](C)[C@@H](Nc2ccc(C#N)cn2)c2cc(N3CCOCC3)ccc2N1C(C)=O]

To a solution of rac-1-((2S,3R,4R)-4-amino-2-ethyl-3-methyl-6-morpholino-3,4-dihydroquinolin-1(2H)-yl)ethanone (for a preparation see Intermediate 73, 40 mg, 0.126 mmol) in N-methyl-2-pyrrolidone (1.6 mL) was added N,N-diisopropylethylamine (0.066 mL, 0.378 mmol) and 6-fluoronicotinonitrile (30.8 mg, 0.252 mmol). The reaction mixture was heated under microwave conditions, using initial high absorption setting, to 200° C. for 30 min. N-Methyl-2-pyrrolidone (0.3 ml) was added and the solution purified by MDAP (HpH). The solvent was blown down under a stream of nitrogen to give a dark brown gum. The sample was loaded in methanol and purified by aminopropyl SPE (1 g) eluted using methanol. The appropriate fractions were combined and blown down under a stream of nitrogen to give the required product (23 mg) as a yellow gum.

LCMS (2 min HpH): Rt=0.94 min, [MH]⁺=420.

Example 203: rac-1-((2S,3R,4R)-2-ethyl-3-methyl-4-((5-methylpyrazin-2-yl)amino)-6-morpholino-3,4-dihydroquinolin-1(2H)-yl)ethanone

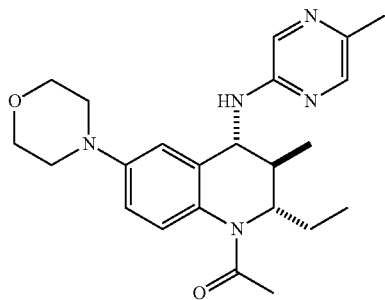 [SMILES: CC[C@H]1[C@H](C)[C@@H](Nc2cnc(C)cn2)c2cc(N3CCOCC3)ccc2N1C(C)=O]

To a solution of rac-1-((2S,3R,4R)-4-amino-2-ethyl-3-methyl-6-morpholino-3,4-dihydroquinolin-1(2H)-yl)ethanone (for a preparation see Intermediate 73, 50 mg, 0.158 mmol) in 1,4-dioxane (1.5 ml) was added tris(dibenzylideneacetone)dipalladium(0) (28.8 mg, 0.032 mmol), Davephos (12.40 mg, 0.032 mmol), sodium tert-butoxide (30.3 mg, 0.315 mmol) and 2-chloro-5-methylpyrazine (40.5 mg, 0.315 mmol). The reaction mixture was heated under microwave conditions, using initial normal absorption setting, to 120° C. for 30 min. The sample was diluted with ethyl acetate (5 mL) and loaded onto a celite cartridge (2.5 g). The cartridge was washed with further ethyl acetate (2×10 mL), and the combined fractions dried under a stream of nitrogen. The sample was dissolved in DMSO (2×1 mL) and purified by MDAP (HpH). The solvent was blown down under a stream of nitrogen to give the required product (14 mg) as a yellow gum. LCMS (2 min HpH): Rt=0.87 min, [MH]⁺=410.

Example 204: rac-1-((2S,3R,4R)-2-ethyl-3-methyl-4-((6-methylpyridin-2-yl)amino)-6-morpholino-3,4-dihydroquinolin-1(2H)-yl)ethanone

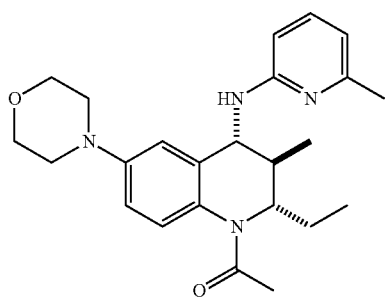 [SMILES: CC[C@H]1[C@H](C)[C@@H](Nc2cccc(C)n2)c2cc(N3CCOCC3)ccc2N1C(C)=O]

To a solution of rac-1-((2S,3R,4R)-4-amino-2-ethyl-3-methyl-6-morpholino-3,4-dihydroquinolin-1(2H)-yl)ethanone (for a preparation see Intermediate 73, 50 mg, 0.158 mmol) in 1,4-dioxane (1.5 mL) was added 2-bromo-6-methylpyridine (0.036 mL, 0.315 mmol), Pd₂(dba)₃ (28.8 mg, 0.032 mmol), DavePhos (12.40 mg, 0.032 mmol) and sodium tert-butoxide (30.3 mg, 0.315 mmol). The reaction mixture was degassed for 5 min, and then heated under microwave conditions, using initial normal absorption setting, to 120° C. for 30 min. The sample was diluted with ethyl acetate (5 mL) and loaded onto a celite cartridge (2.5 g). The cartridge was washed with further ethyl acetate (2×10 mL), and the combined fractions dried under a stream of nitrogen. The residue was dissolved in DMSO (2×1 mL) and purified by MDAP (HpH). The first of the two MDAP runs sent the product to the waste bottle. The waste was therefore evaporated under reduced pressure to give a yellow gum. This sample was dissolved in DMSO (1 mL) and re-purified by MDAP (HpH). The solvent was blown down under a stream of nitrogen to give a yellow gum (14 mg). The second of the two MDAP runs collected correctly, the solvent was blown down under a stream of nitrogen to give a yellow gum (13 mg). Both samples were combined and dissolved in DMSO (0.5 mL) and purified by MDAP (Formic). The product was sent to the waste bottle. The waste was therefore evaporated under reduced pressure to give a yellow gum. This residue was dissolved in DMSO (1 mL) and purified by MDAP (Formic). The solvent was blown down under a stream of nitrogen to give the required product (14 mg) as a colourless gum.

LCMS (2 min HpH): Rt=1.03 min, [MH]⁺=409.

Example 205: rac-4-(((2S,3R,4R)-1-acetyl-2-ethyl-3-methyl-6-morpholino-1,2,3,4-tetrahydroquinolin-4-yl)amino)benzonitrile

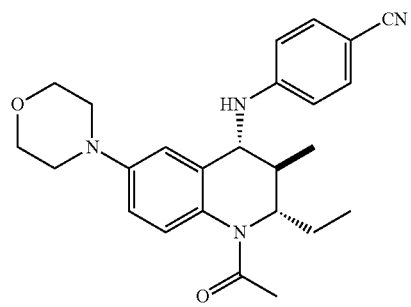 [SMILES: CC[C@H]1[C@H](C)[C@@H](Nc2ccc(C#N)cc2)c2cc(N3CCOCC3)ccc2N1C(C)=O]

To a solution of rac-1-((2S,3R,4R)-4-amino-2-ethyl-3-methyl-6-morpholino-3,4-dihydroquinolin-1(2H)-yl)ethanone (for a preparation see Intermediate 73, 50 mg, 0.158 mmol) in 1,4-dioxane (1.5 mL) was added 4-bromobenzonitrile (57.3 mg, 0.315 mmol), Pd₂(dba)₃ (28.8 mg, 0.032 mmol), DavePhos (12.40 mg, 0.032 mmol) and sodium tert-butoxide (30.3 mg, 0.315 mmol). The reaction mixture was degassed for 5 min, and then heated under microwave conditions, using initial normal absorption setting, to 120° C. for 30 min. The sample was diluted with ethyl acetate (5 mL) and loaded onto a celite cartridge (2.5 g). The cartridge was washed with further ethyl acetate (2×10 mL), and the combined fractions dried under a stream of nitrogen. The residue was dissolved in DMSO (2×1 mL) and purified by MDAP (HpH). Only one of the two runs collected correctly. The solvent from this run was blown down under a stream of nitrogen to give the required product (11 mg) as a yellow gum.

LCMS (2 min HpH): Rt=1.03 min, [MH]⁺=419.

Example 206: rac-1-((2S,3R,4R)-2-ethyl-4-((6-methoxypyridin-2-yl)amino)-3-methyl-6-morpholino-3,4-dihydroquinolin-1(2H)-yl)ethanone

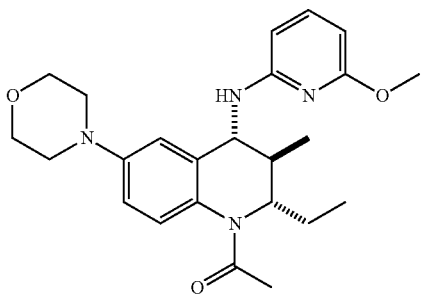 [SMILES: CC[C@H]1[C@H](C)[C@@H](Nc2cccc(OC)n2)c2cc(N3CCOCC3)ccc2N1C(C)=O]

To a solution of rac-1-((2S,3R,4R)-4-amino-2-ethyl-3-methyl-6-morpholino-3,4-dihydroquinolin-1(2H)-yl)ethanone (for a preparation see Intermediate 73, 100 mg, 0.315 mmol) in 1,4-dioxane (3 mL) was added 2-bromo-6-methoxypyridine (0.077 ml, 0.630 mmol), $Pd_2(dba)_3$ (57.7 mg, 0.063 mmol), DavePhos (24.80 mg, 0.063 mmol) and sodium tert-butoxide (60.6 mg, 0.630 mmol). The reaction mixture was degassed for 5 min, and then heated under microwave conditions, using initial normal absorption setting, to 120° C. for 30 min. The sample was diluted with ethyl acetate (10 mL) and loaded onto a celite cartridge (2.5 g). The cartridge was washed with further ethyl acetate (2×20 mL), and the combined fractions dried under a stream of nitrogen. The residue was dissolved in DMSO (3×1 mL) and purified by MDAP (HpH). The solvent was blown down under a stream of nitrogen to give the required product (83 mg) as an off-white gum.

LCMS (2 min HpH): Rt=1.08 min, $[MH]^+$=425.

Example 207: rac-1-((2S,3R,4R)-2-ethyl-4-((5-fluoropyridin-2-yl)amino)-3-methyl-6-morpholino-3,4-dihydroquinolin-1(2H)-yl)ethanone

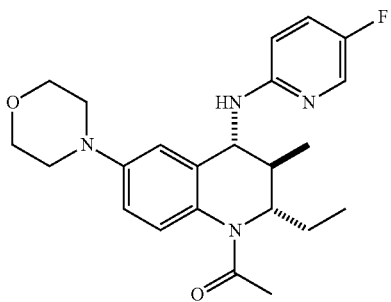 [SMILES: CC[C@H]1[C@H](C)[C@@H](Nc2ccc(F)cn2)c2cc(N3CCOCC3)ccc2N1C(C)=O]

To a solution of rac-1-((2S,3R,4i)-4-amino-2-ethyl-3-methyl-6-morpholino-3,4-dihydroquinolin-1(2H)-yl)ethanone (for a preparation see Intermediate 73, 50 mg, 0.158 mmol) in 1,4-dioxane (1.5 mL) was added 2-bromo-5-fluoropyridine (55.4 mg, 0.315 mmol), $Pd_2(dba)_3$ (28.8 mg, 0.032 mmol), DavePhos (12.40 mg, 0.032 mmol) and sodium tert-butoxide (30.3 mg, 0.315 mmol). The reaction mixture was degassed for 5 min, and then heated under microwave conditions, using initial normal absorption setting, to 120° C. for 30 min. The sample was diluted with ethyl acetate (5 mL) and loaded onto a celite cartridge (2.5 g). The cartridge was washed with further ethyl acetate (2×10 mL), and the combined fractions dried under a stream of nitrogen. The residue was dissolved in DMSO (2×1 mL) and purified by MDAP (HpH). The solvent was blown down under a stream of nitrogen to give an off-white gum (12 mg). The sample was dissolved in DMSO (0.5 mL) and purified by MDAP (Formic). The solvent was blown down under a stream of nitrogen to give the required product (11 mg) as an off-white gum. LCMS (2 min HpH): Rt=1.00 min, $[MH]^+$=413.

Example 208: rac-4-(((2S,3R,4R)-1-acetyl-2-cyclopropyl-3-methyl-6-morpholino-1,2,3,4-tetrahydroquinolin-4-yl)amino)-N-methylbenzamide

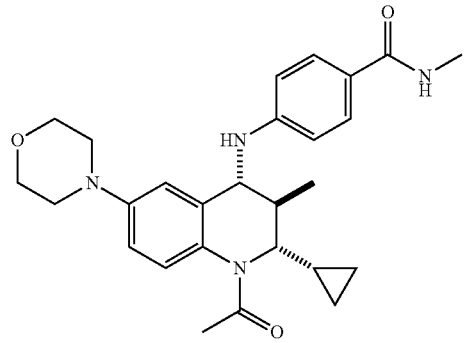 [SMILES: CNC(=O)c1ccc(N[C@H]2c3cc(N4CCOCC4)ccc3N(C(C)=O)[C@@H](C3CC3)[C@@H]2C)cc1]

A solution of rac-1-((2S,3R,4R)-4-amino-2-cyclopropyl-3-methyl-6-morpholino-3,4-dihydroquinolin-1(2H)-yl)ethanone (for a preparation see Intermediate 60 mg, 0.182 mmol), DavePhos (7.17 mg, 0.018 mmol), $Pd_2(dba)_3$ (8.34 mg, 9.11 µmol), sodium tert-butoxide (35.0 mg, 0.364 mmol) and 4-bromo-N-methylbenzamide (46.8 mg, 0.219 mmol) in 1,4-dioxane (3 mL) was stirred under nitrogen at 90° C. for 6 h. The reaction mixture was allowed to cool to rt, filtered through celite and rinsed with ethyl acetate. The solvent was evaporated in vacuo to give 120 mg crude as an orange gum. The crude was dissolved in 1:1 MeOH:DMSO (2×1 mL) and purified by MDAP (HpH). The appropriate fractions were combined and concentrated in vacuo to give the product (20 mg, 0.043 mmol, 23.74%). LCMS (2 min Formic): Rt=0.84 min, $[MH]^+$=463.

Example 209: rac-1-((2S,3R,4R)-2-cyclopropyl-3-methyl-4-((4-methylpyrimidin-2-yl)amino)-6-morpholino-3,4-dihydroquinolin-1(2H)-yl)ethanone, Formic Acid Salt

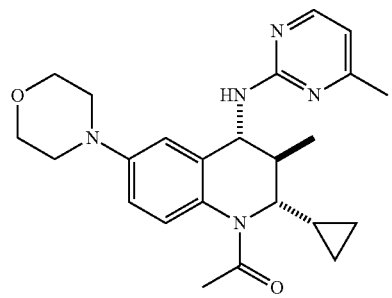 [SMILES: CC(=O)N1c2ccc(N3CCOCC3)cc2[C@H](Nc2nccc(C)n2)[C@@H](C)[C@@H]1C1CC1]

A solution of rac-1-((2S,3R,4R)-4-amino-2-cyclopropyl-3-methyl-6-morpholino-3,4-dihydroquinolin-1(2H)-yl)ethanone (for a preparation see Intermediate 83, 60 mg, 0.182 mmol), DavePhos (7.17 mg, 0.018 mmol), 2-bromo-4-methylpyrimidine (37.8 mg, 0.219 mmol), sodium tert-butoxide (35.0 mg, 0.364 mmol) and Pd$_2$(dba)$_3$ (8.34 mg, 9.11 µmol) in 1,4-dioxane (2 mL) was stirred under nitrogen at 90° C. for 72 h. All reactants were added again to the reaction. The reaction mixture was stirred under nitrogen at 90° C. for 7 h. The reaction mixture was allowed to cool to rt, filtered through celite and rinsed with ethyl acetate. The solvent was evaporated in vacuo then a solution of DavePhos (7.17 mg, 0.018 mmol), 2-bromo-4-methylpyrimidine (37.8 mg, 0.219 mmol), sodium tert-butoxide (35.0 mg, 0.364 mmol) and Pd$_2$(dba)$_3$ (8.34 mg, 9.11 µmol) in 1,4-dioxane (2 mL) was added. The reaction mixture was stirred under nitrogen at 90° C. for 16 h. The reaction mixture was allowed to cool to rt, filtered through celite and rinsed with ethyl acetate. The solvent was evaporated in vacuo then the sample was dissolved in 1:1 MeOH:DMSO (3×1 mL) and purified by MDAP (3×Formic). Only the 3$^{rd}$ run collected material. The appropriate fraction was concentrated in vacuo to give the title compound (10 mg, 0.021 mmol, 11.74%). LCMS (2 min Formic): Rt=0.81 min, [MH]$^+$=422.

Example 210: rac-1-((2S,3R,4R)-2-cyclopropyl-4-((6-hydroxypyridin-2-yl)amino)-3-methyl-6-morpholino-3,4-dihydroquinolin-1(2H)-yl)ethanone

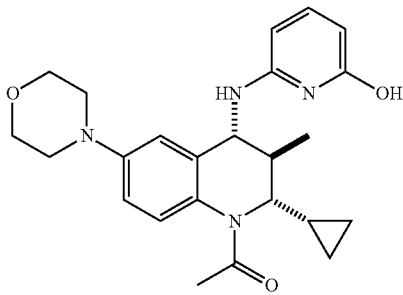 [SMILES: CC(=O)N1c2ccc(N3CCOCC3)cc2[C@H](Nc2cccc(O)n2)[C@@H](C)[C@@H]1C1CC1]

A solution of rac-1-((2S,3R,4R)-2-cyclopropyl-4-((6-methoxypyridin-2-yl)amino)-3-methyl-6-morpholino-3,4-dihydroquinolin-1(2H)-yl)ethanone (for a preparation see Intermediate 171, 120 mg, 0.275 mmol), sodium iodide (247 mg, 1.649 mmol) and TMSCl (0.211 mL, 1.649 mmol) in acetonitrile (2 mL) was stirred under nitrogen at 55° C. for 16 h. TMSCl (0.211 mL, 1.649 mmol) was added and the reaction was stirred under nitrogen at 55° C. for 4 h. The temperature was raised to 75° C. and left to stir under nitrogen for 16 h. The reaction mixture was concentrated in vacuo then dissolved in DCM (10 mL). The organic solution was washed with 0.5M NaOH (2×10 mL), filtered through a hydrophobic frit then concentrated in vacuo to give 40 mg crude. The crude was dissolved in 1:1 MeOH:DMSO (1 mL) and purified by MDAP (Formic). The appropriate fraction was concentrated in vacuo to give the title compound (8 mg, 0.019 mmol, 7%).

LCMS (2 min Formic): Rt=0.75 min, [MH]$^+$=423.

Example 211: rac-1-((2S,3R,4R)-2-cyclopropyl-3-methyl-4-((5-methylpyrazin-2-yl)amino)-6-morpholino-3,4-dihydroquinolin-1(2H)-yl)ethanone

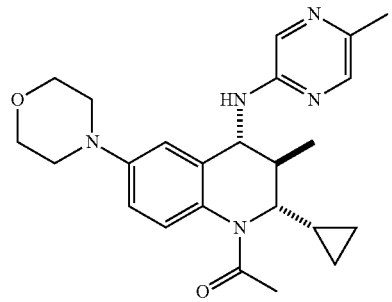 [SMILES: CC(=O)N1c2ccc(N3CCOCC3)cc2[C@H](Nc2cnc(C)cn2)[C@@H](C)[C@@H]1C1CC1]

A solution of rac-1-((2S,3R,4R)-4-amino-2-cyclopropyl-3-methyl-6-morpholino-3,4-dihydroquinolin-1(2H)-yl)ethanone (for a preparation see Intermediate 83, 100 mg, 0.304 mmol), DavePhos (11.95 mg, 0.030 mmol), 2-chloro-5-methylpyrazine (46.8 mg, 0.364 mmol), Pd$_2$(dba)$_3$ (13.90 mg, 0.015 mmol) and sodium tert-butoxide (58.3 mg, 0.607 mmol) in 1,4-dioxane (3 mL) was stirred under nitrogen at 90° C. for 20 h. The reaction mixture was allowed to cool to rt, filtered through celite and rinsed with ethyl acetate. The solvent was evaporated in vacuo then the sample was dissolved in 1:1 MeOH:DMSO (1 mL) and purified by MDAP (HpH). The appropriate fractions were combined and concentrated in vacuo to give the title compound (36 mg, 0.085 mmol, 28%).

LCMS (2 min Formic): Rt=0.84 min, [MH]$^+$=422.

Example 212: rac-6-(((2S,3R,4R)-1-acetyl-2-cyclopropyl-3-methyl-6-morpholino-1,2,3,4-tetrahydroquinolin-4-yl)amino)nicotinonitrile

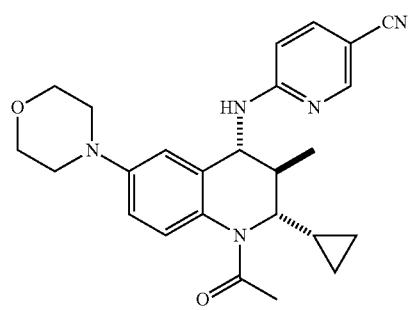 [SMILES: CC(=O)N1c2ccc(N3CCOCC3)cc2[C@H](Nc2ccc(C#N)cn2)[C@@H](C)[C@@H]1C1CC1]

A solution of rac-1-((2S,3R,4R)-4-amino-2-cyclopropyl-3-methyl-6-morpholino-3,4-dihydroquinolin-1(2H)-yl)ethanone (for a preparation see Intermediate 83, 128 mg, 0.389 mmol), DavePhos (15.29 mg, 0.039 mmol), 6-bromonicotinonitrile (85 mg, 0.466 mmol), Pd$_2$(dba)$_3$ (17.79 mg, 0.019 mmol) and sodium tert-butoxide (74.7 mg, 0.777 mmol) in 1,4-dioxane (3 mL) was stirred under nitrogen at 90° C. for 7 h. The reaction mixture was allowed to cool to rt, filtered through celite and rinsed with ethyl acetate. The solvent was evaporated in vacuo then the sample was dissolved in 1:1 MeOH:DMSO (1 mL) and purified by MDAP (HpH). The appropriate fractions were combined and concentrated in vacuo to give the title compound (61 mg, 0.141 mmol, 36%).

LCMS (2 min Formic): Rt=0.92 min, [MH]$^+$=432.

Example 213: 5-(((2S,3R,4R)-1-acetyl-2,3-dimethyl-6-(piperazin-1-yl)-1,2,3,4-tetrahydroquinolin-4-yl)amino)pyrazine-2-carbonitrile

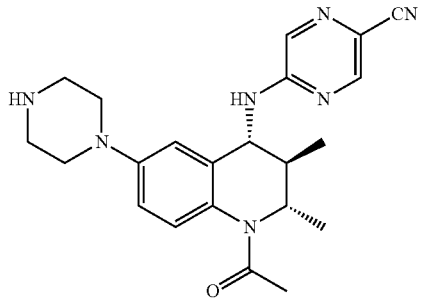 [SMILES: CC(=O)N1c2ccc(N3CCNCC3)cc2[C@H](Nc2cnc(C#N)cn2)[C@@H](C)[C@@H]1C]

A solution of tert-butyl 4-((2S,3R,4R)-1-acetyl-4-amino-2,3-dimethyl-1,2,3,4-tetrahydroquinolin-6-yl)piperazine-1-carboxylate (for a preparation see Intermediate 213, 69 mg, 0.151 mmol) in NMP (1.5 mL) was treated with 5-chloropyrazine-2-carbonitrile (22 mg, 0.158 mmol) and DIPEA (0.079 mL, 0.453 mmol) then the mixture was heated at 200° C. for 30 min using a microwave reactor. The residue was purified by MDAP (Formic). The desired fractions were combined and evaporated in vacuo to afford the desired product as a white solid (17 mg).

LCMS (2 min Formic): Rt=0.82 min, [MH]$^+$=407.

Example 214: 4-(((2S,3R,4R)-1-acetyl-2,3-dimethyl-6-(piperazin-1-yl)-1,2,3,4-tetrahydroquinolin-4-yl)amino)benzonitrile

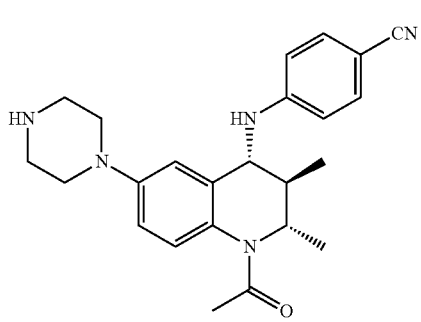 [SMILES: CC(=O)N1c2ccc(N3CCNCC3)cc2[C@H](Nc2ccc(C#N)cc2)[C@@H](C)[C@@H]1C]

tert-Butyl 4-((2S,3R,4R)-1-acetyl-4-((4-cyanophenyl)amino)-2,3-dimethyl-1,2,3,4-tetrahydroquinolin-6-yl)piperazine-1-carboxylate (for a preparation see Intermediate 214, 22 mg, 0.044 mmol) was dissolved in DCM (2 mL), then TFA added (1 mL). The reaction mixture was stirred for 2 h then concentrated under a stream of nitrogen. The resulting residue was dissolved in methanol then passed through an amino-propyl SPE column which was washed with further methanol. The methanol washes were combined then concentrated under a stream of nitrogen to give the desired product as a pale brown gum (17 mg). LCMS (2 min Formic): Rt=0.67 min, [MH]$^+$=404.

Example 215: 1-((2S,3R,4R)-2,3-dimethyl-4-((4-methylpyrimidin-2-yl)amino)-6-(piperazin-1-yl)-3,4-dihydroquinolin-1(2H)-yl)ethanone

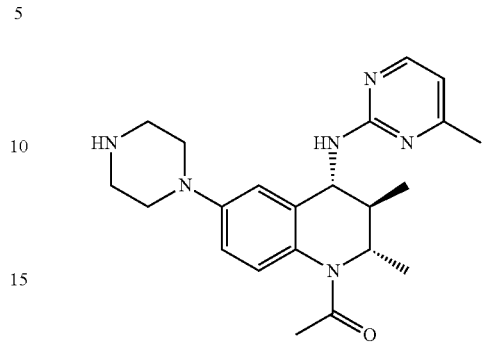

tert-Butyl 4-((2S,3R,4R)-1-acetyl-2,3-dimethyl-4-((4-methylpyrimidin-2-yl)amino)-1,2,3,4-tetrahydroquinolin-6-yl)piperazine-1-carboxylate (for a preparation see Intermediate 215, 14 mg, 0.028 mmol) was dissolved in DCM (2 mL), then TFA added (1 mL). The reaction mixture was stirred for 2 h then concentrated under a stream of nitrogen. The resulting residue was dissolved in methanol then passed through an amino-propyl SPE column which was washed with further methanol. The methanol washes were combined then concentrated under a stream of nitrogen to give the desired product as a pale brown gum (12 mg).

LCMS (2 min Formic): Rt=0.53 min, [MH]$^+$=395.

Example 216: 4-(((2S,3R,4R)-1-acetyl-2,3-dimethyl-6-(piperazin-1-yl)-1,2,3,4-tetrahydroquinolin-4-yl)amino)-N-methylbenzamide

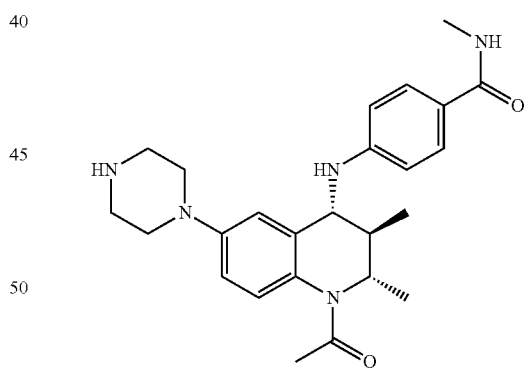

tert-Butyl 4-((2S,3R,4R)-1-acetyl-2,3-dimethyl-4-((4-(methylcarbamoyl)phenyl)amino)-1,2,3,4-tetrahydroquinolin-6-yl)piperazine-1-carboxylate (for a preparation see Intermediate 216, 13 mg, 0.024 mmol) was dissolved in DCM (2 mL), then TFA added (1 mL). The reaction mixture was stirred for 2 h then concentrated under a stream of nitrogen. The resulting residue was dissolved in methanol then passed through an amino-propyl SPE column which was washed with further methanol. The methanol washes were combined then concentrated under a stream of nitrogen to give the desired product as a pale brown gum (8 mg).

LCMS (2 min Formic): Rt=0.56 min, [MH]$^+$=436.

Example 217: 1-((2S,3R,4R)-2,3-dimethyl-4-((5-methylpyrazin-2-yl)amino)-6-(piperazin-1-yl)-3,4-dihydroquinolin-1(2H)-yl)ethanone

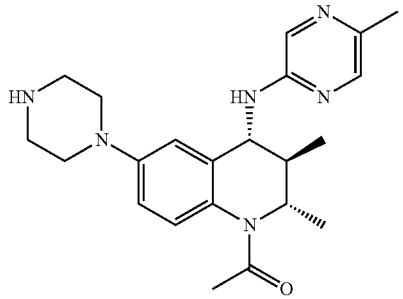 [SMILES: CC(=O)N1c2ccc(N3CCNCC3)cc2[C@H](Nc2cnc(C)cn2)[C@@H](C)[C@@H]1C]

tert-Butyl 4-((2S,3R,4R)-1-acetyl-2,3-dimethyl-4-((5-methylpyrazin-2-yl)amino)-1,2,3,4-tetrahydroquinolin-6-yl)piperazine-1-carboxylate (for a preparation see Intermediate 217, 10 mg, 0.020 mmol) was dissolved in DCM (2 mL), then TFA added (1 mL). The reaction mixture was stirred for 2 h then concentrated under a stream of nitrogen. The resulting residue was dissolved in methanol then passed through an amino-propyl SPE column which was washed with further methanol. The methanol washes were combined then concentrated under a stream of nitrogen to give the desired product as a pale brown gum (9 mg).

LCMS (2 min Formic): Rt=0.56 min, [MH]$^+$=395.

Example 218: rac-1-((2S,3R,4R)-2-ethyl-3-methyl-4-((5-methylpyrazin-2-yl)amino)-6-(piperazin-1-yl)-3,4-dihydroquinolin-1(2H)-yl)ethanone

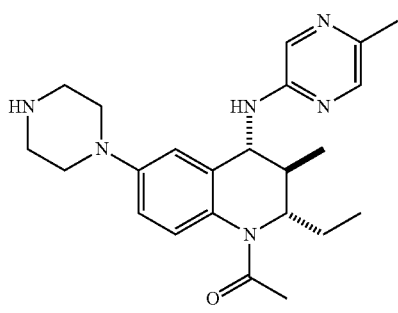 [SMILES: CC[C@H]1[C@H](C)[C@@H](Nc2cnc(C)cn2)c2cc(N3CCNCC3)ccc2N1C(C)=O]

To a flask containing rac-tert-butyl 4-((2S,3R,4R)-1-acetyl-2-ethyl-3-methyl-4-((5-methylpyrazin-2-yl)amino)-1,2,3,4-tetrahydroquinolin-6-yl)piperazine-1-carboxylate (for a preparation see Intermediate 173, 21.6 mg, 0.042 mmol) in dichloromethane (DCM) (1 mL) was added TFA (250 μL, 3.24 mmol) and the reaction was stirred for 1 h. The reaction mixture was concentrated in vacuo to afford a brown oil. This was dissolved in methanol and loaded onto an SCX cartridge (5 g). It was eluted with methanol (3 CVs) and the product was eluted as its free base with 2M ammonia in methanol. The filtrate from the ammonia fractions was concentrated in vacuo to yield a colourless gum (16.6 mg, 0.041 mmol, 96%). LCMS (2 min Formic): Rt=0.60 min, [MH]$^+$=409.

Example 219: rac-4-(((2S,3R,4R)-1-acetyl-2-ethyl-3-methyl-6-(piperazin-1-yl)-1,2,3,4-tetrahydroquinolin-4-yl)amino)benzonitrile

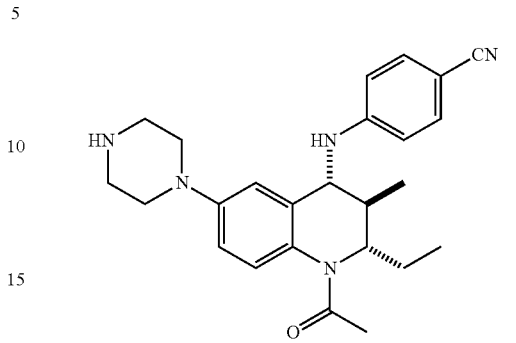

To a flask containing rac-tert-butyl 4-((2S,3R,4R)-1-acetyl-4-((4-cyanophenyl)amino)-2-ethyl-3-methyl-1,2,3,4-tetrahydroquinolin-6-yl)piperazine-1-carboxylate (for a preparation see Intermediate 174, 24 mg, 0.046 mmol) in dichloromethane (DCM) (1 mL) was added TFA (250 μL, 3.24 mmol) and the reaction was stirred for 1 h. The reaction mixture was concentrated in vacuo to afford a brown oil. This was dissolved in methanol and loaded onto an SCX cartridge (5 g). It was eluted with methanol (3 CVs) and the product eluted as its free base with 2M ammonia in methanol. The filtrate from the ammonia fractions was concentrated in vacuo to yield a colourless gum (18.9 mg, 0.045 mmol, 98%).

LCMS (2 min Formic): Rt=0.72 min, [MH]$^+$=418.

Example 220: rac-4-(((2S,3R,4R)-1-acetyl-2-ethyl-3-methyl-6-(piperazin-1-yl)-1,2,3,4-tetrahydroquinolin-4-yl)amino)-N-methylbenzamide

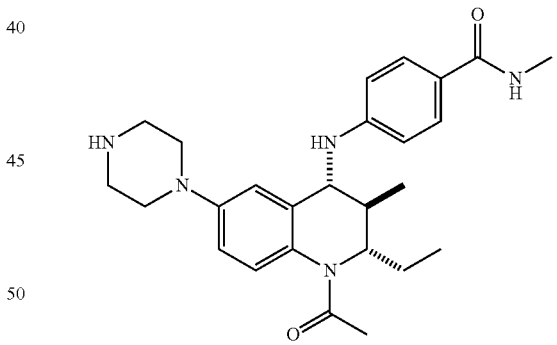

To a flask containing rac-tert-butyl 4-((2S,3R,4R)-1-acetyl-2-ethyl-3-methyl-4-((4-(methylcarbamoyl)phenyl)amino)-1,2,3,4-tetrahydroquinolin-6-yl)piperazine-1-carboxylate (for a preparation see Intermediate 175, 13 mg, 0.024 mmol) in dichloromethane (DCM) (1 mL) was added TFA (250 μL, 3.24 mmol) and the reaction was stirred for 1 h. The reaction mixture was concentrated in vacuo to afford a brown oil. This was dissolved in methanol and loaded onto an SCX cartridge (5 g). It was eluted with methanol (3 CVs) and the product was eluted as its free base with 2M ammonia in methanol. The filtrate from the ammonia fractions was concentrated in vacuo to yield a colourless gum (10.1 mg, 0.022 mmol, 95%).

LCMS (2 min Formic): Rt=0.61 min, [MH]$^+$=450.

Example 221: rac-5-(((2S,3R,4R)-1-acetyl-2-ethyl-3-methyl-6-(piperazin-1-yl)-1,2,3,4-tetrahydroquinolin-4-yl)amino)pyrazine-2-carbonitrile

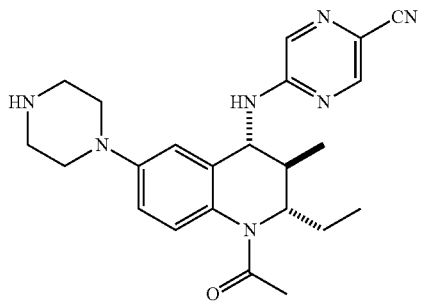 [SMILES: CC[C@H]1[C@H](C)[C@@H](Nc2cnc(C#N)cn2)c2cc(N3CCNCC3)ccc2N1C(C)=O]

To a flask containing rac-tert-butyl 4-((2S,3R,4R)-1-acetyl-4-((5-cyanopyrazin-2-yl)amino)-2-ethyl-3-methyl-1,2,3,4-tetrahydroquinolin-6-yl)piperazine-1-carboxylate (for a preparation see Intermediate 176, 26.6 mg, 0.051 mmol) in dichloromethane (DCM) (1 mL) was added TFA (250 μL, 3.24 mmol) and the reaction was stirred for 1 h. The reaction mixture was concentrated in vacuo to afford a brown oil. This was dissolved in methanol and loaded onto an SCX cartridge (5 g). It was eluted with methanol (3 CVs) and product eluted as free base with 2M ammonia in methanol. The filtrate from the ammonia fractions was concentrated in vacuo to yield a yellow gum, which was still impure. The crude product was therefore further purified. It was taken up in DCM and added to a silica cartridge (10 g). This was purified by flash chromatography eluting with 0-10% 2M NH$_3$ in MeOH/DCM. The appropriate fractions were collected and concentrated in vacuo to afford the desired product as a yellow solid (15.6 mg, 0.037 mmol, 72.6%). LCMS (2 min Formic): Rt=0.63 min, [MH]$^+$=420.

Example 222: rac-6-(((2S,3R,4R)-1-acetyl-2-ethyl-3-methyl-6-(piperazin-1-yl)-1,2,3,4-tetrahydroquinolin-4-yl)amino)nicotinonitrile

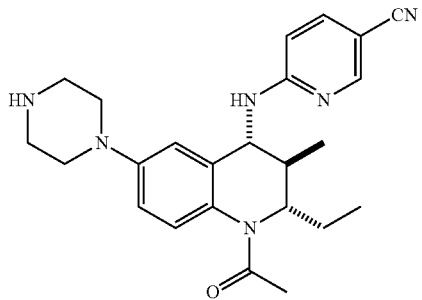 [SMILES: CC[C@H]1[C@H](C)[C@@H](Nc2ccc(C#N)cn2)c2cc(N3CCNCC3)ccc2N1C(C)=O]

To a flask containing rac-tert-butyl 4-((2S,3R,4R)-1-acetyl-4-((5-cyanopyridin-2-yl)amino)-2-ethyl-3-methyl-1,2,3,4-tetrahydroquinolin-6-yl)piperazine-1-carboxylate (for a preparation see Intermediate 177, 16.6 mg, 0.032 mmol) in dichloromethane (DCM) (1 mL) was added TFA (250 μL, 3.24 mmol) and the reaction was stirred for 1 h. The reaction mixture was concentrated in vacuo to afford a brown oil. This was dissolved in methanol and loaded onto an SCX cartridge (5 g). It was eluted with methanol (3 CVs) and the product eluted as its free base with 2M ammonia in methanol. The filtrate from the ammonia fractions was concentrated in vacuo to yield a colourless gum (13.3 mg, 0.032 mmol, 99%).
LCMS (2 min Formic): Rt=0.66 min, [MH]$^+$=419.

Example 223: 4-(((rac-2S,3R,4R)-1-acetyl-2-cyclopropyl-3-methyl-6-((S)-3-methylpiperazin-1-yl)-1,2,3,4-tetrahydroquinolin-4-yl)amino)benzonitrile

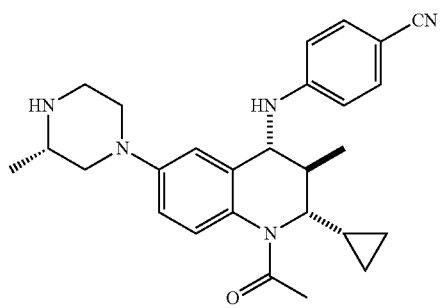 [SMILES: CC(=O)N1c2ccc(N3CCN[C@@H](C)C3)cc2[C@H](Nc2ccc(C#N)cc2)[C@@H](C)[C@@H]1C1CC1]

To a stirring solution of (S)-tert-butyl 4-((rac-2S,3R,4R)-1-acetyl-4-((4-cyanophenyl)amino)-2-cyclopropyl-3-methyl-1,2,3,4-tetrahydroquinolin-6-yl)-2-methylpiperazine-1-carboxylate (for a preparation see Intermediate 180, 22 mg, 0.018 mmol) in dichloromethane (DCM) (1 mL) was added trifluoroacetic acid (0.140 mL, 1.821 mmol). The mixture was stirred at rt for 30 min. The solution was concentrated in vacuo. The sample was dissolved in 1:1 MeOH/DMSO (1 mL) and purified by MDAP (HpH). The solvent was evaporated in vacuo to give the required product (4.2 mg). This was a mixture of diastereoisomers. LCMS (2 min formic): Rt=0.78 min, [MH]$^+$=444.

Example 224: 4-(((rac-2S,3R,4R)-1-acetyl-2-cyclopropyl-3-methyl-6-((R)-3-methylpiperazin-1-yl)-1,2,3,4-tetrahydroquinolin-4-yl)amino)benzonitrile

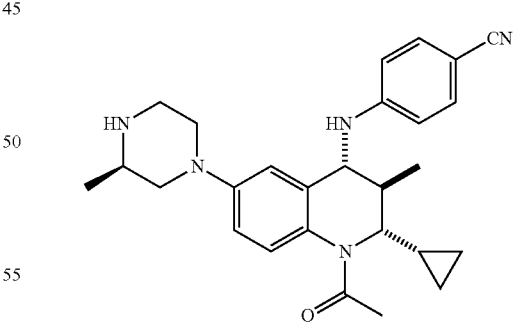

To a stirring solution of (R)-tert-butyl 4-((rac-2S,3R,4R)-1-acetyl-4-((4-cyanophenyl)amino)-2-cyclopropyl-3-methyl-1,2,3,4-tetrahydroquinolin-6-yl)-2-methylpiperazine-1-carboxylate (for a preparation see Intermediate 183, 9.1 mg, 0.017 mmol) in dichloromethane (DCM) (0.5 mL) under nitrogen was added trifluoroacetic acid (0.129 mL, 1.674 mmol). The mixture was stirred at rt for ~30 min. The reaction mixture was concentrated in vacuo. The sample was dissolved in 1:1 MeOH/DMSO (1 mL) and purified by MDAP (HpH). The solvent was evaporated in vacuo to give the required product (5.2 mg). This was a mixture of diastereoisomers.

LCMS (2 min formic): Rt=0.78 min, [MH]$^+$=444.

Example 225: 1-((2S,3R,4R)-2-cyclopropyl-4-((6-methoxypyridin-2-yl)amino)-3-methyl-6-((S)-3-methylpiperazin-1-yl)-3,4-dihydroquinolin-1(2H)-yl)ethanone

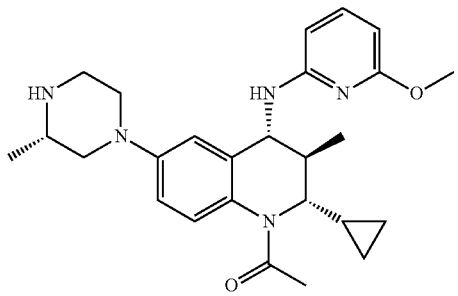

(S)-tert-Butyl 4-((2S,3R,4R)-1-acetyl-2-cyclopropyl-4-((6-methoxypyridin-2-yl)amino)-3-methyl-1,2,3,4-tetrahydroquinolin-6-yl)-2-methylpiperazine-1-carboxylate (for a preparation see Intermediate 222, 68 mg, 0.124 mmol) was dissolved, in a dried flask, in acetonitrile (0.5 mL). To this was added TMSCl (0.095 mL, 0.742 mmol) and sodium iodide (111 mg, 0.742 mmol). The mixture was heated to 55° C. under nitrogen for ~2 h. The mixture was diluted with more acetonitrile, filtered through a cotton wool plug, and concentrated in vacuo. The samples were dissolved in MeOH:DMSO (1:1, 1 mL) and purified by MDAP (HpH). The solvent was evaporated in vacuo to give the required product (21.5 mg, 38.7%). LCMS (2 min HpH): Rt=0.99 min, [MH]$^+$=450.

Example 226: 1-((2S,3R,4R)-2-cyclopropyl-4-((5-fluoropyridin-2-yl)amino)-3-methyl-6-((S)-3-methylpiperazin-1-yl)-3,4-dihydroquinolin-1(2H)-yl)ethanone

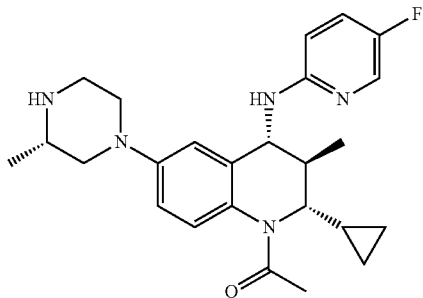 [SMILES: CC(=O)N1c2ccc(N3CCN[C@@H](C)C3)cc2[C@H](Nc2ccc(F)cn2)[C@@H](C)[C@@H]1C1CC1]

To a stirring solution of (S)-tert-butyl 4-((2S,3R,4R)-1-acetyl-2-cyclopropyl-4-((5-fluoropyridin-2-yl)amino)-3-methyl-1,2,3,4-tetrahydroquinolin-6-yl)-2-methylpiperazine-1-carboxylate (for a preparation see Intermediate 221, 33.7 mg, 0.063 mmol) in dichloromethane (DCM) (1.5 mL) was added trifluoroacetic acid (0.483 mL, 6.27 mmol). The mixture was stirred at rt for ~1 h. The mixture was diluted with dichloromethane (DCM) and evaporated in vacuo. The residue was dissolved in methanol and loaded onto a 2 g SCX SPE cartridge which had been primed with methanol. The column was eluted with 4 CVs of methanol, and the product was then eluted with 6 CVs 2M NH$_3$ in methanol. The appropriate fractions were collected and concentrated in vacuo to afford the product (9.1 mg). This sample was dissolved in MeOH:DMSO (1:1, 1 mL) and purified by MDAP (HpH). The solvent was evaporated in vacuo to give the required product (3.7 mg, 13.5%).

LCMS (2 min Formic): Rt=0.68 min, [MH]$^+$=438.

Example 227: 1-((rac-2S,3R,4R)-2-cyclopropyl-3-methyl-6-((S)-3-methylpiperazin-1-yl)-4-((5-methyl-pyrazin-2-yl)amino)-3,4-dihydroquinolin-1(2H)-yl)ethanone

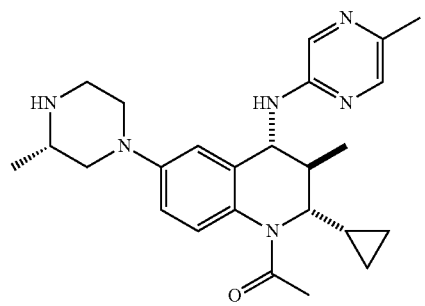

To a stirring solution of (S)-tert-butyl 4-((rac-2S,3R,4R)-1-acetyl-2-cyclopropyl-3-methyl-4-((5-methylpyrazin-2-yl)amino)-1,2,3,4-tetrahydroquinolin-6-yl)-2-methylpiperazine-1-carboxylate (for a preparation see Intermediate 184, 5.7 mg, 10.66 μmol) in dichloromethane (DCM) (1 mL) under nitrogen was added trifluoroacetic acid (0.25 mL, 3.24 mmol). The mixture was stirred at rt for 45 min. The reaction was allowed to stir for a further 15 min at rt. A further 100 μL of trifluoroacetic acid was added, and the mixture was allowed to stir at rt for a further 20 min. The reaction mixture was concentrated in vacuo and the residue was dissolved in methanol. This solution was loaded onto a 1 g SCX SPE cartridge, which had been pre-equilibrated with methanol. The column was eluted with 3 CVs of methanol, and then the sample was eluted with 3 CVs of 2M NH$_3$ in methanol. The appropriate fraction was concentrated in vacuo to give the product (2.4 mg, 5.52 μmol, 51.8%). This was a mixture of diastereoisomers. LCMS (2 min Formic): Rt=0.65 min, [MH]$^+$=436.

Example 228: 4-(((rac-2S,3R,4R)-1-acetyl-2-cyclopropyl-3-methyl-6-((S)-3-methylpiperazin-1-yl)-1,2,3,4-tetrahydroquinolin-4-yl)amino)-N-methylbenzamide

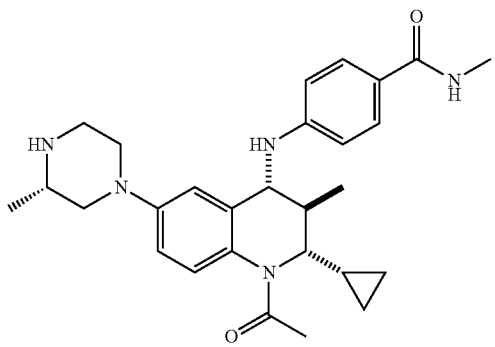

To a stirring solution of (S)-tert-butyl 4-((rac-2S,3R,4R)-1-acetyl-2-cyclopropyl-3-methyl-4-((4-(methylcarbamoyl)phenyl)amino)-1,2,3,4-tetrahydroquinolin-6-yl)-2-methylpiperazine-1-carboxylate (for a preparation see Intermediate 185, 5.6 mg, 9.73 µmol) in dichloromethane (DCM) (1 mL) under nitrogen was added trifluoroacetic acid (0.25 mL, 3.24 mmol). The mixture was stirred at rt for 45 min. The reaction mixture was allowed to stir for a further 15 min. The reaction mixture was concentrated in vacuo and the residue then dissolved in methanol and loaded onto a 1 g SCX SPE cartridge, which had been pre-equilibrated with methanol. The column was eluted with methanol, and then 2M NH$_3$ in methanol. The appropriate fraction was collected and concentrated in vacuo to afford the product (4.4 mg, 9.25 µmol, 95%). This was a mixture of diastereoisomers.

LCMS (2 min Formic): Rt=0.66 min, [MH]$^+$=476.

Example 229: 6-(((rac-2S,3R,4R)-1-acetyl-2-cyclopropyl-3-methyl-6-((S)-3-methylpiperazin-1-yl)-1,2,3,4-tetrahydroquinolin-4-yl)amino)nicotinonitrile

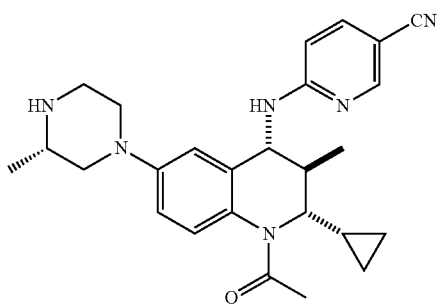 [SMILES: CC(=O)N1c2ccc(N3CCN[C@@H](C)C3)cc2[C@H](Nc2ccc(C#N)cn2)[C@@H](C)[C@@H]1C1CC1]

To a stirring solution of (S)-tert-butyl 4-((rac-2S,3R,4R)-1-acetyl-4-((5-cyanopyridin-2-yl)amino)-2-cyclopropyl-3-methyl-1,2,3,4-tetrahydroquinolin-6-yl)-2-methylpiperazine-1-carboxylate (for a preparation see Intermediate 186, 7.0 mg, 0.013 mmol) in dichloromethane (DCM) (1. mL) under nitrogen was added trifluoroacetic acid (0.25 mL, 3.24 mmol). The mixture was stirred at rt for 45 min. The reaction mixture was concentrated in vacuo. The residue was dissolved in methanol and loaded onto a 1 g SCX SPE cartridge which had been pre-equilibrated with methanol. The column was eluted with methanol into one fraction, and then the product was eluted with 2M NH$_3$ in methanol into a separate fraction. The appropriate fraction was concentrated in vacuo to afford the product (2.3 mg, 5.17 µmol, 40.3%). This was a mixture of diastereoisomers.

LCMS (2 min Formic): Rt=0.71 min, [MH]$^+$=445.

Example 230: rac-(2S,3R,4R)-1-acetyl-4-((5-cyanopyridin-2-yl)amino)-N,2,3-trimethyl-1,2,3,4-tetrahydroquinoline-6-carboxamide

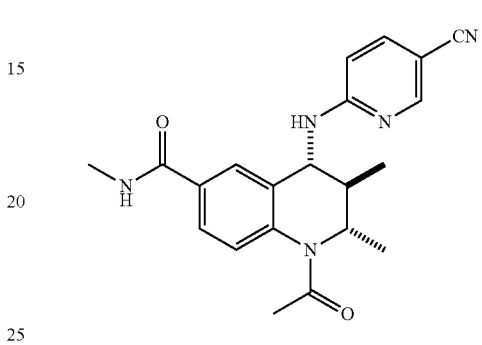

A solution of 6-chloronicotinonitrile (25.4 mg, 0.183 mmol), DavePhos (6.00 mg, 0.015 mmol), Pd$_2$(dba)$_3$ (7 mg, 7.64 µmol), sodium tert-butoxide (29.3 mg, 0.305 mmol) and rac-(2S,3R,4R)-1-acetyl-4-amino-N,2,3-trimethyl-1,2,3,4-tetrahydroquinoline-6-carboxamide (for a preparation see Intermediate 189, 42 mg, 0.153 mmol) in 1,4-dioxane (3 mL) was stirred under nitrogen at 90° C. for 64 h. A further portion of Pd$_2$(dba)$_3$ (7 mg, 7.64 µmol) was added and the mixture stirred at 90° C. for a further 3 h. The reaction mixture was allowed to cool to rt, diluted with 5 mL MeOH, filtered through a cotton wool plug and evaporated to dryness under reduced pressure. The residue was purified by MDAP (Formic) to afford the desired product as a pale yellow solid (3.6 mg).

LCMS (2 min Formic): Rt=0.71 min, [MH]$^+$=378.

Example 231: rac-(2S,3R,4R)-1-acetyl-N,2,3-trimethyl-4-((6-methylpyridin-2-yl)amino)-1,2,3,4-tetrahydroquinoline-6-carboxamide

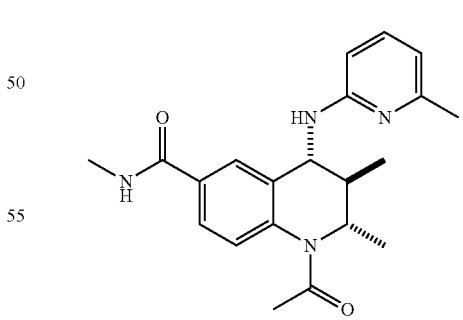

A solution of 2-bromo-6-methylpyridine (31.5 mg, 0.183 mmol), DavePhos (6.00 mg, 0.015 mmol), Pd$_2$(dba)$_3$ (7 mg, 7.64 µmol), sodium tert-butoxide (29.3 mg, 0.305 mmol) and rac-(2S,3R,4R)-1-acetyl-4-amino-N,2,3-trimethyl-1,2,3,4-tetrahydroquinoline-6-carboxamide (for a preparation see Intermediate 189, 42 mg, 0.153 mmol) in 1,4-dioxane (3 mL) was stirred under nitrogen at 90° C. for 64 h. A further portion of Pd$_2$(dba)$_3$ (7 mg, 7.64 µmol) was added and the mixture stirred at 90° C. for a further 3 h. The reaction mixture was allowed to cool to rt, diluted with 5 mL MeOH, filtered through a cotton wool plug and evaporated to dryness under reduced pressure. The residue was purified by MDAP (Formic) to afford the desired product as a pale yellow solid (4.4 mg).

LCMS (2 min Formic): Rt=0.51 min, [MH]$^+$=367.

Example 232: rac-(2S,3R,4R)-1-acetyl-4-((5-cyano-pyrazin-2-yl)amino)-N,2,3-trimethyl-1,2,3,4-tetrahydroquinoline-6-carboxamide

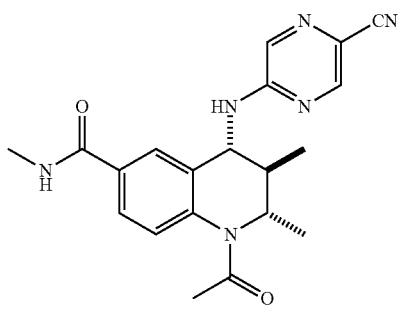 [SMILES: CNC(=O)c1ccc2c(c1)[C@H](Nc1cnc(C#N)cn1)[C@@H](C)[C@H](C)N2C(C)=O]

To a solution of rac-(2S,3R,4R)-1-acetyl-4-amino-N,2,3-trimethyl-1,2,3,4-tetrahydroquinoline-6-carboxamide (for a preparation, see Intermediate 189, 37 mg, 0.134 mmol) in NMP (1 mL) was added 5-chloropyrazine-2-carbonitrile (37.5 mg, 0.269 mmol), and DIPEA (0.070 mL, 0.403 mmol) and the resultant solution heated to 150° C. for 30 min by microwave irradiation. The reaction mixture was directly purified by MDAP (Formic) to afford the desired product as a yellow solid (11 mg). LCMS (2 min Formic): Rt=0.69 min, [M–H]$^-$=377.

Example 233: rac-(2S,3R,4R)-1-acetyl-2-ethyl-N,3-dimethyl-4-((5-methylpyrazin-2-yl)amino)-1,2,3,4-tetrahydroquinoline-6-carboxamide

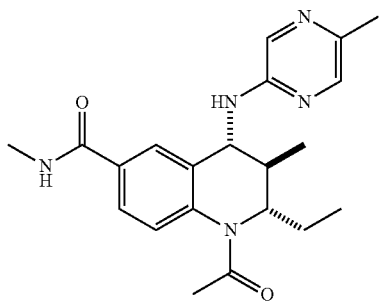

A solution of 2-bromo-5-methylpyrazine (27.3 mg, 0.158 mmol), DavePhos (5.2 mg, 0.013 mmol), Pd$_2$(dba)$_3$ (7 mg, 7.64 µmol), sodium tert-butoxide (25.2 mg, 0.263 mmol) and rac-(2S,3R,4R)-1-acetyl-4-amino-2-ethyl-N,3-dimethyl-1,2,3,4-tetrahydroquinoline-6-carboxamide (for a preparation see Intermediate 192, 38 mg, 0.131 mmol) in 1,4-dioxane (3 mL) was stirred under a nitrogen atmosphere at 90° C. for 16 h. The reaction mixture was diluted with 5 mL MeOH and filtered through a plug of cotton wool. The solvent was removed by evaporation to give a residue which was purified by MDAP (Formic) to afford the desired product as a pale brown solid (5.4 mg).

LCMS (2 min Formic): Rt=0.68 min, [MH]$^+$=382.

Example 234: rac-(2S,3R,4R)-1-acetyl-2-ethyl-N,3-dimethyl-4-((4-methylpyrimidin-2-yl)amino)-1,2,3,4-tetrahydroquinoline-6-carboxamide

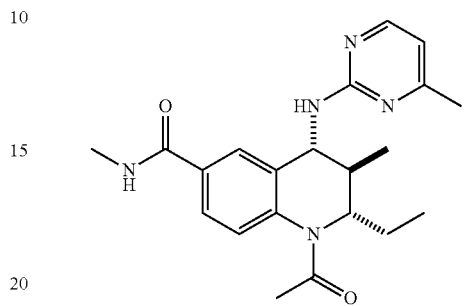

A solution of 2-bromo-4-methylpyrimidine (27.3 mg, 0.158 mmol), DavePhos (5.2 mg, 0.013 mmol), Pd$_2$(dba)$_3$ (7 mg, 7.64 µmol), sodium tert-butoxide (25.2 mg, 0.263 mmol) and rac-(2S,3R,4R)-1-acetyl-4-amino-2-ethyl-N,3-dimethyl-1,2,3,4-tetrahydroquinoline-6-carboxamide (for a preparation see Intermediate 192, 38 mg, 0.131 mmol) in 1,4-dioxane (3 mL) was stirred under a nitrogen atmosphere at 90° C. for 16 h. The reaction mixture was diluted with 5 mL MeOH and filtered through a plug of cotton wool. The solvent was removed by evaporation to give a residue which was purified by MDAP (Formic) to afford the desired product as a pale brown solid (3.0 mg).

LCMS (2 min Formic): Rt=0.64 min, [MH]$^+$=382.

Example 235: rac-(2S,3R,4R)-1-acetyl-2-ethyl-N,3-dimethyl-4-((6-methylpyridin-2-yl)amino)-1,2,3,4-tetrahydroquinoline-6-carboxamide

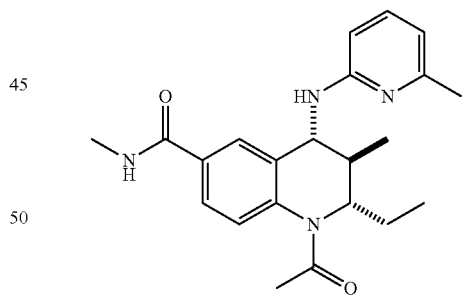

A solution of 2-bromo-6-methylpyridine (27.1 mg, 0.158 mmol), DavePhos (5.2 mg, 0.013 mmol), Pd$_2$(dba)$_3$ (7 mg, 7.64 µmol), sodium tert-butoxide (25.2 mg, 0.263 mmol) and rac-(2S,3R,4R)-1-acetyl-4-amino-2-ethyl-N,3-dimethyl-1,2,3,4-tetrahydroquinoline-6-carboxamide (for a preparation see Intermediate 192, 38 mg, 0.131 mmol) in 1,4-dioxane (3 mL) was stirred under a nitrogen atmosphere at 90° C. for 16 h. The reaction mixture was diluted with 5 mL MeOH and filtered through a plug of cotton wool. The solvent was removed by evaporation to give a residue which was purified by MDAP (Formic) to afford the desired product as a pale brown solid (7.8 mg).

LCMS (2 min Formic): Rt=0.55 min, [MH]$^+$=381.

Example 236: rac-(2S,3R,4R)-1-acetyl-4-((5-cyano-pyrazin-2-yl)amino)-2-ethyl-N,3-dimethyl-1,2,3,4-tetrahydroquinoline-6-carboxamide

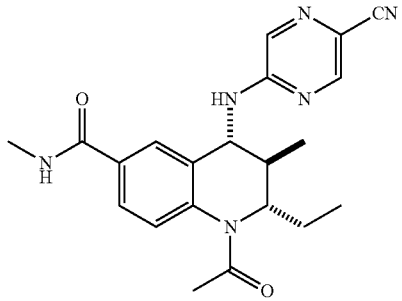 [SMILES: CC[C@H]1[C@H](C)[C@@H](Nc2cnc(C#N)cn2)c2cc(C(=O)NC)ccc2N1C(C)=O]

To a solution of rac-(2S,3R,4R)-1-acetyl-4-amino-2-ethyl-N,3-dimethyl-1,2,3,4-tetrahydroquinoline-6-carboxamide (for a preparation see Intermediate 192, 37 mg, 0.128 mmol) in NMP (1 mL) was added 5-chloropyrazine-2-carbonitrile (35.7 mg, 0.256 mmol), and DIPEA (0.067 mL, 0.384 mmol) and the resultant solution then heated to 150° C. for 30 min by microwave irradiation. The reaction mixture was directly purified by MDAP (Formic) to afford the desired product as a yellow solid (24.1 mg). LCMS (2 min Formic): Rt=0.75 min, [MH]$^+$=393.

Example 237: rac-(2S,3R,4R)-1-acetyl-4-((5-cyano-pyridin-2-yl)amino)-2-ethyl-N,3-dimethyl-1,2,3,4-tetrahydroquinoline-6-carboxamide

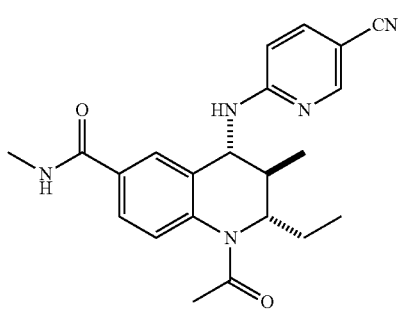 [SMILES: CC[C@H]1[C@H](C)[C@@H](Nc2ccc(C#N)cn2)c2cc(C(=O)NC)ccc2N1C(C)=O]

To a solution of rac-(2S,3R,4R)-1-acetyl-4-amino-2-ethyl-N,3-dimethyl-1,2,3,4-tetrahydroquinoline-6-carboxamide (for a preparation, see Intermediate 192, 37 mg, 0.128 mmol) in NMP (1 mL) was added 6-chloronicotinonitrile (35.4 mg, 0.256 mmol), and DIPEA (0.067 mL, 0.384 mmol) and the resultant solution then heated to 150° C. for 3 h 30 min by microwave irradiation. The reaction mixture was directly purified by MDAP (Formic) to afford the desired product as a yellow solid (4.8 mg). LCMS (2 min Formic): Rt=0.76 min, [MH]$^+$=392.

Example 238: rac-(2S,3R,4R)-1-acetyl-2-cyclopropyl-N,3-dimethyl-4-((6-methylpyridin-2-yl)amino)-1,2,3,4-tetrahydroquinoline-6-carboxamide

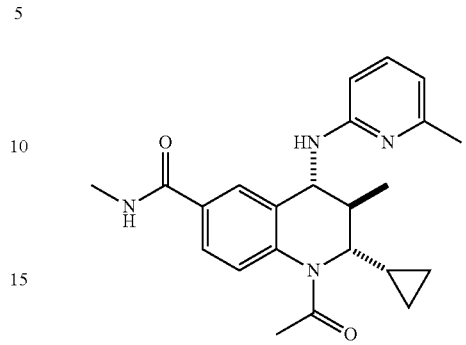

To a reaction vessel containing rac-(2S,3R,4R)-1-acetyl-2-cyclopropyl-3-methyl-4-((6-methylpyridin-2-yl)amino)-1,2,3,4-tetrahydroquinoline-6-carbonyl chloride (for a preparation see Intermediate 196, 93 mg, 0.234 mmol). Methylamine 2M in THF (5 mL, 10.00 mmol) and DIPEA (1.225 mL, 7.01 mmol) were added and the reaction left to stir for 15 min at rt under N$_2$. The solution was concentrated in vacuo and retaken up in DCM (15 mL), this was washed with water (2×15 ml) and separated. The organic layer was dried and concentrated in vacuo to give 100 mg of an orange/brown solid. This was purified by chromatography on silica (10 g, eluting with 0-8% methanol/DCM over 15 CVs). The fractions containing product were combined and concentrated in vacuo to give 78 mg of product. This was of insufficient purity so was purified by chromatography on silica (10 g, eluting with 0-100% EtOAc/DCM). The fractions containing pure product were combined and concentrated in vacuo to give 40 mg of product. The fractions containing product with some impurities present were combined and concentrated in vacuo to give 34 mg of impure product. This was dissolved in 1:1 MeOH:DMSO 1 mL and purified by MDAP (HpH). The solvent was evaporated in vacuo to give 8 mg of product (8 mg, 0.020 mmol, 8.72%) as a white solid.

LCMS (2 min formic): Rt=0.61 min, [MH]$^+$=393.

Example 239a & 239b: (2S,3R,4R)-1-acetyl-2-cyclopropyl-N,3-dimethyl-4-((6-methylpyridin-2-yl)amino)-1,2,3,4-tetrahydroquinoline-6-carboxamide (239a) & (2R,3S,4S)-1-acetyl-2-cyclopropyl-N,3-dimethyl-4-((6-methylpyridin-2-yl)amino)-1,2,3,4-tetrahydroquinoline-6-carboxamide (239b)

239a

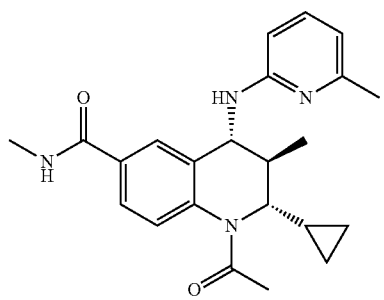

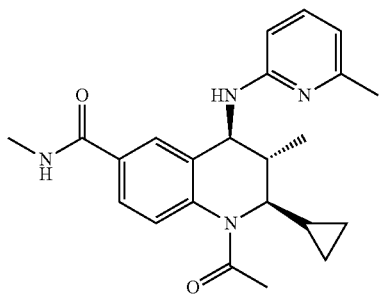

rac-(2S,3R,4R)-1-Acetyl-2-cyclopropyl-N,3-dimethyl-4-((6-methylpyridin-2-yl)amino)-1,2,3,4-tetrahydroquinoline-6-carboxamide (for a preparation see Example 238, ~32 mg) was submitted for chiral separation into its enantiomers (A and B) using a 250×20 mm Chiralpak IA column eluting with 10% ethanol in heptane at a flow rate of 20 mL/min. Peak 1/Enantiomer A fractions were collected between 8 and 9.5 min, and Peak 2/Enantiomer B fractions were collected between 11.5 and 13.5 min. Fraction solutions were combined and then evaporated to dryness to give Enantiomer A (13 mg) and Enantiomer B (14 mg) as white solids.

Enantiomer A, Example 2391a

Analytical Chiral HPLC using a 250×4.6 mm Chiralpak IA column eluting with 10% ethanol in heptane at 1 mL/min—Rt=15 min.>99% ee by UV.

Enantiomer B, Example 239b

Analytical Chiral HPLC using a 250×4.6 mm Chiralpak IA column eluting with 10% ethanol in heptane at 1 mL/min—Rt=21.5 min, >99% ee by UV.

Example 240: rac-(2S,3R,4R)-1-acetyl-2-cyclopropyl-N,3-dimethyl-4-((4-methylpyrimidin-2-yl)amino)-1,2,3,4-tetrahydroquinoline-6-carboxamide

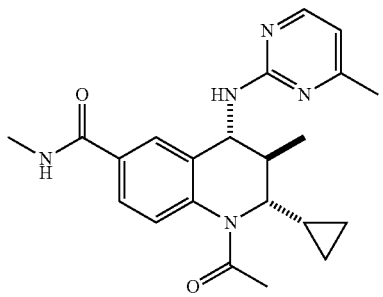

To a reaction vessel 2-bromo-4-methylpyrimidine (88 mg, 0.509 mmol), rac-(2S,3R,4R)-1-acetyl-4-amino-2-cyclopropyl-N,3-dimethyl-1,2,3,4-tetrahydroquinoline-6-carboxamide (for preparation see intermediate 200, 80 mg, 0.265 mmol), sodium tert-butoxide (77 mg, 0.796 mmol), in 1,4-Dioxane (5 mL) were added. The solution was treated with $Pd_2(dba)_3$ (36.5 mg, 0.040 mmol) and DavePhos (20.89 mg, 0.053 mmol) and left to stir at 100° C. for 16 h under $N_2$. The reaction mixture was filtered through celite and the celite washed with ethyl acetate. The combined filtrates were washed with water, the organic phase was passed through a hydrophobic frit and concentrated in vacuo to give a crude solid. This solid was purified by MDAP (Formic) to give a solid which was eluted through a $NH_2$ SPE (5 g) with MeOH, the eluent was concentrated to the product (14 mg, 0.036 mmol, 13.40%) as a white solid. LCMS (2 min Formic): Rt=0.68 min, $[MH]^+$=394.

Example 241: rac-(2S,3R,4R)-1-acetyl-4-((5-cyano-pyridin-2-yl)amino)-2-cyclopropyl-N,3-dimethyl-1,2,3,4-tetrahydroquinoline-6-carboxamide

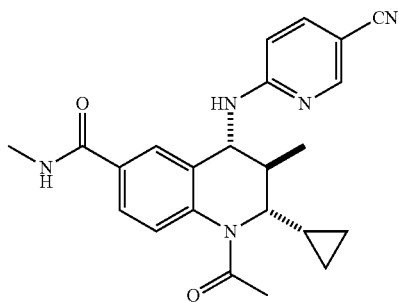

To a reaction vessel 6-fluoronicotinonitrile (64.8 mg, 0.531 mmol), rac-(2S,3R,4R)-1-acetyl-4-amino-2-cyclopropyl-N,3-dimethyl-1,2,3,4-tetrahydroquinoline-6-carboxamide (for preparation see Intermediate 200, 80 mg, 0.265 mmol) and DIPEA (0.139 mL, 0.796 mmol) were added and the reaction irradiated in a microwave at 200° C. for 30 min. The reaction was purified directly by MDAP (Formic) to give a crude solid. This solid was purified by MDAP (Formic) to give a solid which was eluted through a $NH_2$ SPE (5 g) with MeOH, the eluent was concentrated to the product (47 mg, 0.116 mmol, 43.9%) as a white solid. LCMS (2 min Formic): Rt=0.80 min, $[MH]^+$=404.

Example 242: rac-(2S,3R,4R)-1-acetyl-4-((5-cyano-pyrazin-2-yl)amino)-2-cyclopropyl-N,3-dimethyl-1,2,3,4-tetrahydroquinoline-6-carboxamide

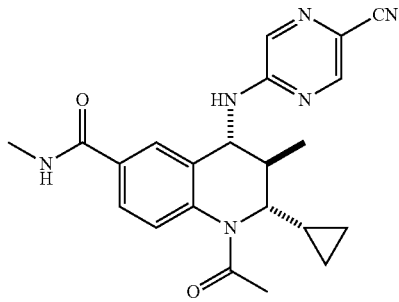

To a microwave vial 5-chloropyrazine-2-carbonitrile (74.1 mg, 0.531 mmol), rac-(2S,3R,4R)-1-acetyl-4-amino-2-cyclopropyl-N,3-dimethyl-1,2,3,4-tetrahydroquinoline-6-carboxamide (for preparation see Intermediate 200, 80 mg, 0.265 mmol), and DIPEA (0.139 mL, 0.796 mmol) were added and the reaction irradiated at 200° C. in a microwave for 30 mins. The reaction was purified directly using a MDAP (Formic) to give a beige solid. This solid was eluted through a NH$_2$ SPE (5 g) with MeOH, the eluent was concentrated to the product (63 mg, 0.156 mmol, 58.7%) as a beige solid.

LCMS (2 min Formic): Rt=0.78 min, [MH]$^+$=405.

Example 243: rac-(2S,3R,4R)-1-acetyl-4-((4-cyanophenyl)amino)-2-cyclopropyl-N,3-dimethyl-1,2,3,4-tetrahydroquinoline-6-carboxamide

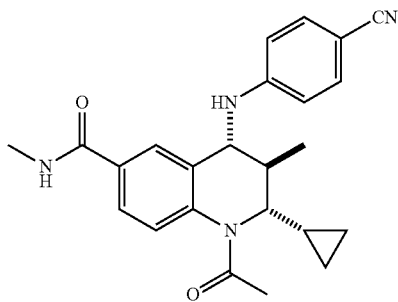 [SMILES: CNC(=O)c1ccc2c(c1)[C@H](Nc1ccc(C#N)cn1)[C@@H](C)[C@H](C1CC1)N2C(C)=O]

To a reaction vessel 4-bromobenzonitrile (88 mg, 0.483 mmol), rac-(2S,3R,4R)-1-acetyl-4-amino-2-cyclopropyl-N,3-dimethyl-1,2,3,4-tetrahydroquinoline-6-carboxamide (for preparation see Intermediate 200, 80 mg, 0.265 mmol), sodium tert-butoxide (77 mg, 0.796 mmol), in 1,4-Dioxane (5 mL) were added. The solution was treated with Pd$_2$(dba)$_3$ (36.5 mg, 0.040 mmol) and DavePhos (20.89 mg, 0.053 mmol) and left to stir at 100° C. for 3 h under N$_2$. The mixture was allowed to cool to rt and then filtered through celite and the celite washed with ethyl acetate. The combined filtrates were washed with brine, the organic phase was dried through a hydrophobic frit and concentrated to give a orange gum. This gum was purified using a MDAP (Formic) to give a white solid. This solid was eluted through a NH$_2$ SPE (5 g) with MeOH, the eluent was concentrated to give the product (5 mg, 0.012 mmol, 4.68%) as a white solid. LCMS (2 min Formic): Rt=0.87 min, [MH]$^+$=403.

Example 244: rac-(2S,3R,4R)-1-acetyl-2-cyclopropyl-4-((5-fluoropyridin-2-yl)amino)-N,3-dimethyl-1,2,3,4-tetrahydroquinoline-6-carboxamide

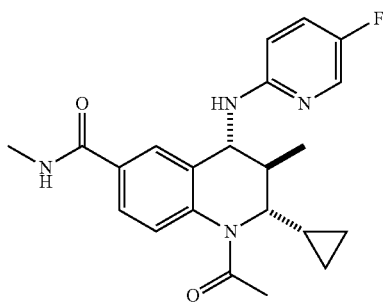 [SMILES: CNC(=O)c1ccc2c(c1)[C@H](Nc1ccc(F)cn1)[C@@H](C)[C@H](C1CC1)N2C(C)=O]

To a reaction vessel 2-bromo-5-fluoropyridine (90 mg, 0.511 mmol), rac-(2S,3R,4R)-1-acetyl-4-amino-2-cyclopropyl-N,3-dimethyl-1,2,3,4-tetrahydroquinoline-6-carboxamide (for preparation see Intermediate 200, 80 mg, 0.265 mmol), sodium tert-butoxide (77 mg, 0.796 mmol), in 1,4-dioxane (5 mL) were added. The solution was treated with Pd$_2$(dba)$_3$ (36.5 mg, 0.040 mmol) and DavePhos (20.89 mg, 0.053 mmol) and left to stir at 100° C. for 3 h under N$_2$. The reaction was treated with further 2-bromo-5-fluoropyridine (80 mg, 0.455 mmol), DavePhos (14 mg, 0.036 mmol), Pd$_2$(dba)$_3$ (18 mg, 0.020 mmol) and sodium tert-butoxide (50 mg, 0.520 mmol) and the reaction left to stir at 100° C. for 16 h under N$_2$. The reaction mixture was allowed to cool to rt and then filtered through celite and the celite washed with ethyl acetate. The combined filtrates were washed with brine solution the organic phase was dried through a hydrophobic frit and concentrated to give a crude brown gum (333 mg). This gum was purified by MDAP (Formic) to give a white solid. This solid was eluted through a NH$_2$ SPE (5 g) with MeOH, the eluent was concentrated and dried to give the product (34 mg). LCMS (2 min Formic): Rt=0.74 min, [MH]$^+$=397.

Example 245: rac-(2S,3R,4R)-1-acetyl-2-cyclopropyl-4-((6-methoxypyridin-2-yl)amino)-N,3-dimethyl-1,2,3,4-tetrahydroquinoline-6-carboxamide

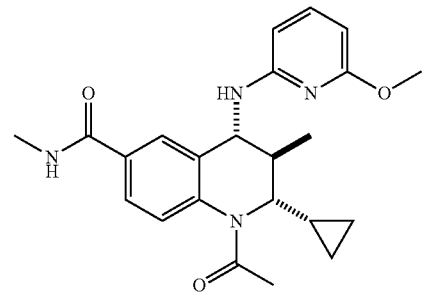

To a reaction vessel 2-bromo-6-methoxypyridine (0.06 mL, 0.488 mmol), rac-(2S,3R,4R)-1-acetyl-4-amino-2-cyclopropyl-N,3-dimethyl-1,2,3,4-tetrahydroquinoline-6-carboxamide (for preparation se Intermediate 200, 80 mg, 0.265 mmol), sodium tert-butoxide (77 mg, 0.796 mmol), in 1,4-dioxane (5 mL) were added. The solution was treated with Pd$_2$(dba)$_3$ (36.5 mg, 0.040 mmol) and DavePhos (20.89 mg, 0.053 mmol) and left to stir at 100° C. for 3 h under N$_2$. The reaction was allowed to cool to rt and then filtered through celite and the celite washed with ethyl acetate. The combined filtrates were washed with brine the organic phase was dried through a hydrophobic frit and concentrated in vacuo to give a crude brown gum. This was purified by column chromatography on silica gel, eluting with 0-100% ethyl acetate/cyclohexane to give the product as an orange gum (49 mg, 86% pure). This gum could be purified by MDAP (Formic) to give a solid. This solid was eluted through a NH$_2$ SPE (5 g) with MeOH, the eluent was concentrated to give the product (7 mg).

LCMS (2 min Formic): Rt=0.85 min, [MH]$^+$=409.

Example 246: rac-(2S,3R,4R)-1-acetyl-2-cyclopropyl-N,3-dimethyl-4-((5-methylpyrazin-2-yl)amino)-1,2,3,4-tetrahydroquinoline-6-carboxamide

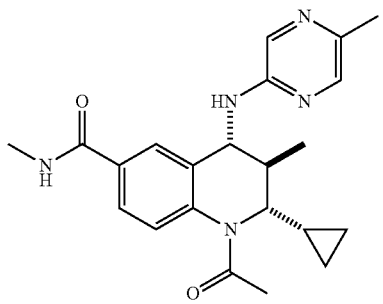

To a reaction vessel 2-chloro-5-methylpyrazine (81 mg, 0.630 mmol), rac-(2S,3R,4R)-1-acetyl-4-amino-2-cyclopropyl-N,3-dimethyl-1,2,3,4-tetrahydroquinoline-6-carboxamide (for preparation see Intermediate 200, 80 mg, 0.265 mmol), sodium tert-butoxide (77 mg, 0.796 mmol), in 1,4-dioxane (5 mL) were added. The solution was treated with Pd$_2$(dba)$_3$ (36.5 mg, 0.040 mmol) and DavePhos (20.89 mg, 0.053 mmol) and left to stir at 100° C. for 2 h under N$_2$. The reaction mixture was allowed to cool to rt and then filtered through celite and the celite washed with ethyl acetate. The combined filtrates were concentrated in vacuo to give a crude orange/brown gum. This gum was purified by MDAP (Formic) to give a solid, this solid was eluted through a NH$_2$ SPE (5 g) with MeOH, the eluent was concentrated to give the product (59 mg, 0.150 mmol, 56.5%) as a beige solid.

LCMS (2 min Formic): Rt=0.70 min, [MH]$^+$=394.

Example 247: (2S,3R,4R)-1-acetyl-2-cyclopropyl-3-methyl-4-((6-methylpyridin-2-yl)amino)-1,2,3,4-tetrahydroquinoline-6-carboxylic Acid

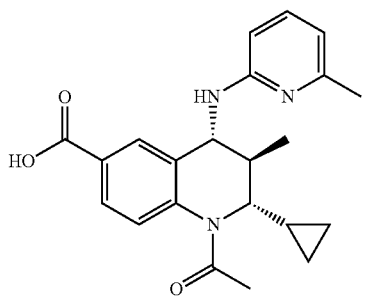 [SMILES: CC(=O)N1c2ccc(C(=O)O)cc2[C@H](Nc2cccc(C)n2)[C@@H](C)[C@@H]1C1CC1]

Sodium tert-butoxide (1.968 g, 20.48 mmol), Pd$_2$(dba)$_3$ (0.313 g, 0.341 mmol), DavePhos (0.269 g, 0.683 mmol), and (2S,3R,4R)-ethyl 1-acetyl-4-amino-2-cyclopropyl-3-methyl-1,2,3,4-tetrahydroquinoline-6-carboxylate (for a preparation see Intermediate 225, 2.16 g, 6.83 mmol) were dissolved in 1,4-dioxane (136 mL). 2-bromo-6-methylpyridine (0.932 mL, 8.19 mmol) was added and the reaction stirred for 1 h under N$_2$ at 100° C. The reaction mixture was cooled to rt, filtered through celite (washed with EtOAc) and the filtrates concentrated in vacuo. The residue was taken up in EtOAc (75 mL) and saturated sodium bicarbonate solution (100 mL), the organic layer was discarded. The aqueous layer was acidified to pH1 with 2M hydrochloric acid (250 mL) and extracted multiple times with EtOAc, DCM and chloroform. The combined organics were dried using a hydrophobic frit and evaporated in vacuo to give (the product (555 mg) as a yellow solid. The aqueous was evaporated to dryness, taken up in MeOH (50 mL), filtered and evaporated to afford crude product that was added to a silica gel column and was eluted with 10-20% 2M NH3 in methanol/DCM. Fractions containing product were evaporated to afford the product (450 mg) as a yellow oil. LCMS (2 min HpH): Rt=0.68 min, [MH]$^+$=380.

Example 248: (2S,3R,4R)-1-acetyl-2-cyclopropyl-N-ethyl-3-methyl-4-((6-methylpyridin-2-yl)amino)-1,2,3,4-tetrahydroquinoline-6-carboxamide

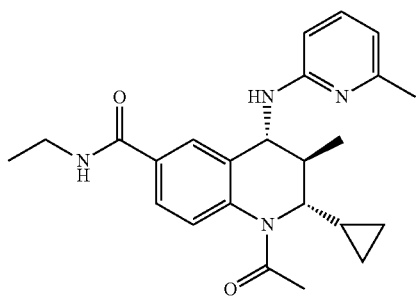 [SMILES: CCNC(=O)c1ccc2c(c1)[C@H](Nc1cccc(C)n1)[C@@H](C)[C@H](C1CC1)N2C(C)=O]

To a solution of (2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 247, 50 mg, 0.132 mmol) and HATU (90 mg, 0.198 mmol) in N,N-dimethylformamide (DMF) (1 mL) was added ethylamine (2M in THF, 80 µL, 0.158 mmol) followed by DIPEA (0.097 mL, 0.553 mmol). The reaction mixture was stirred at rt for 90 min, then purified directly by MDAP (HpH). The solvent was evaporated in vacuo to give the product (15 mg). LCMS (2 min HpH): Rt=0.96 min, [MH]$^+$= 407.

Example 249: (2S,3R,4R)-1-acetyl-2-cyclopropyl-N-propyl-3-methyl-4-((6-methylpyridin-2-yl)amino)-1,2,3,4-tetrahydroquinoline-6-carboxamide

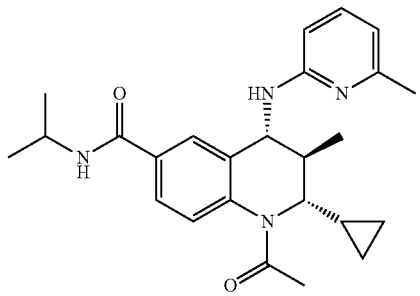 [SMILES: CC(=O)N1c2ccc(C(=O)NC(C)C)cc2[C@H](Nc2cccc(C)n2)[C@@H](C)[C@@H]1C1CC1]

To a solution of (2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 247, 50 mg, 0.132 mmol) and HATU (90 mg, 0.198 mmol) in N,N-dimethylformamide (DMF) (1 mL) was added propylamine (14 µL, 0.158 mmol) followed by DIPEA (0.097 mL, 0.553 mmol). The reaction mixture was stirred at rt for 90 min, then purified directly by MDAP (HpH). The solvent was evaporated in vacuo to give the product (29 mg). LCMS (2 min HpH): Rt=1.03 min, [MH]$^+$= 421.

Example 250: 1-((2S,3R,4R)-2-cyclopropyl-3-methyl-4-((6-methylpyridin-2-yl)amino)-6-(pyrrolidine-1-carbonyl)-3,4-dihydroquinolin-1(2H)-yl)ethanone

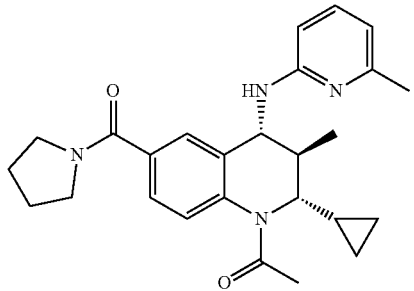 [SMILES: CC(=O)N1c2ccc(C(=O)N3CCCC3)cc2[C@H](Nc2cccc(C)n2)[C@@H](C)[C@@H]1C1CC1]

To a solution of (2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 247, 50 mg, 0.132 mmol) and HATU (90 mg, 0.198 mmol) in N,N-dimethylformamide (DMF) (1 mL) was added pyrrolidine (13 μL, 0.158 mmol) followed by DIPEA (0.097 mL, 0.553 mmol). The reaction mixture was stirred at rt for 90 min, then purified directly by MDAP (Hph). The solvent was evaporated in vacuo to give the product (14 mg). LCMS (2 min HpH): Rt=1.00 min, [MH]$^+$=433.

Example 251: 1-((2S,3R,4R)-2-cyclopropyl-3-methyl-4-((6-methylpyridin-2-yl)amino)-6-(morpholine-4-carbonyl)-3,4-dihydroquinolin-1(2H)-yl)ethanone

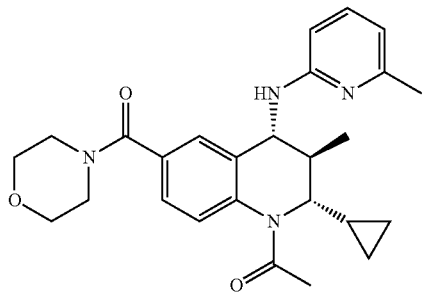 [SMILES: CC(=O)N1c2ccc(C(=O)N3CCOCC3)cc2[C@H](Nc2cccc(C)n2)[C@@H](C)[C@@H]1C1CC1]

To a solution of (2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 247, 50 mg, 0.132 mmol) and HATU (90 mg, 0.198 mmol) in N,N-dimethylformamide (DMF) (1 mL) was added pyrrolidine (13 μL, 0.158 mmol) followed by DIPEA (0.097 mL, 0.553 mmol). The reaction mixture was stirred at rt for 90 min, then purified directly by MDAP (HpH). The solvent was evaporated in vacuo to give the product (32 mg). LCMS (2 min HpH): Rt=0.92 min, [MH]$^+$=449.

Example 252: 1-((2S,3R,4R)-2-cyclopropyl-3-methyl-4-((6-methylpyridin-2-yl)amino)-6-(morpholine-4-carbonyl)-3,4-dihydroquinolin-1(2H)-yl)ethanone

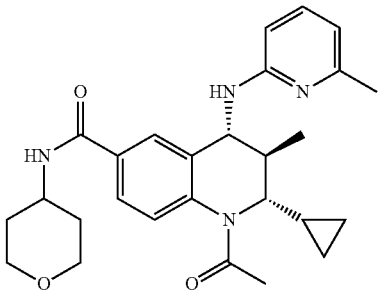 [SMILES: CC(=O)N1c2ccc(C(=O)NC3CCOCC3)cc2[C@H](Nc2cccc(C)n2)[C@@H](C)[C@@H]1C1CC1]

To a solution of (2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 247, 50 mg, 0.132 mmol) and HATU (90 mg, 0.198 mmol) in N,N-dimethylformamide (DMF) (1 mL) was added tetrahydro-2H-pyran-4-amine (16 μL, 0.158 mmol) followed by DIPEA (0.097 mL, 0.553 mmol). The reaction mixture was stirred at rt for 90 min, then purified directly by MDAP (HpH). The solvent was evaporated in vacuo to give the product (38 mg). LCMS (2 min HpH): Rt=0.94 min, [MH]$^+$=463.

Example 253: (2S,3R,4R)-1-acetyl-2-cyclopropyl-3-methyl-4-((6-methylpyridin-2-yl)amino)-N-(pyridin-3-ylmethyl)-1,2,3,4-tetrahydroquinoline-6-carboxamide

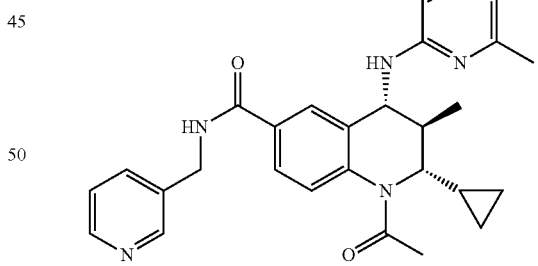

To a solution of (2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 247, 50 mg, 0.132 mmol) and HATU (90 mg, 0.198 mmol) in N,N-dimethylformamide (DMF) (1 mL) was added pyridin-3-ylmethanamine (16 μL, 0.158 mmol) followed by DIPEA (0.097 mL, 0.553 mmol). The reaction mixture was stirred at rt for 90 min, then purified directly by MDAP (HpH). The solvent was evaporated in vacuo to give the product (37 mg). LCMS (2 min HpH): Rt=0.93 min, [MH]$^+$=470.

Example 254: (2S,3R,4R)-1-acetyl-2-cyclopropyl-3-methyl-4-((6-methylpyridin-2-yl)amino)-N-(1H-pyrazol-4-yl)-1,2,3,4-tetrahydroquinoline-6-carboxamide

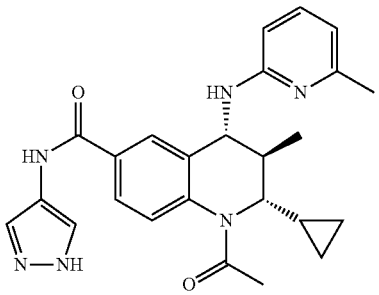 [SMILES: CC(=O)N1c2ccc(C(=O)Nc3cn[nH]c3)cc2[C@H](Nc2cccc(C)n2)[C@@H](C)[C@@H]1C1CC1]

To a solution of (2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 247, 50 mg, 0.132 mmol) and HATU (90 mg, 0.198 mmol) in N,N-dimethylformamide (DMF) (1 mL) was added 1H-pyrazol-4-amine (13 mg, 0.158 mmol) followed by DIPEA (0.097 mL, 0.553 mmol). The reaction mixture was stirred at rt for 90 min, then purified directly by MDAP (HpH). The solvent was evaporated in vacuo to give the product (8 mg). LCMS (2 min High pH): Rt=0.88 min, [MH]$^+$=445.

Example 255: (2S,3R,4R)-1-acetyl-2-cyclopropyl-3-methyl-4-((6-methylpyridin-2-yl)amino)-N-(2-morpholinoethyl)-1,2,3,4-tetrahydroquinoline-6-carboxamide

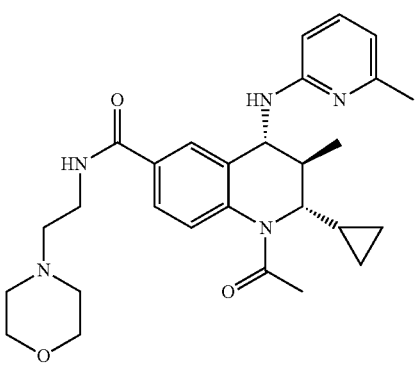 [SMILES: CC(=O)N1c2ccc(C(=O)NCCN3CCOCC3)cc2[C@H](Nc2cccc(C)n2)[C@@H](C)[C@@H]1C1CC1]

To a solution of (2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 247, 50 mg, 0.132 mmol) and HATU (90 mg, 0.198 mmol) in N,N-dimethylformamide (DMF) (1 mL) was added 2-morpholineethanamine (21 µL, 0.158 mmol) followed by DIPEA (0.097 mL, 0.553 mmol). The reaction mixture was stirred at rt for 90 min, then purified directly by MDAP (HpH). The solvent was evaporated in vacuo to give the product (48 mg). LCMS (2 min HpH): Rt=0.90 min, [MH]$^+$=492.

Example 256: (2S,3R,4R)-1-acetyl-2-cyclopropyl-N-(2-methoxyethyl)-3-methyl-4-((6-methylpyridin-2-yl)amino)-1,2,3,4-tetrahydroquinoline-6-carboxamide

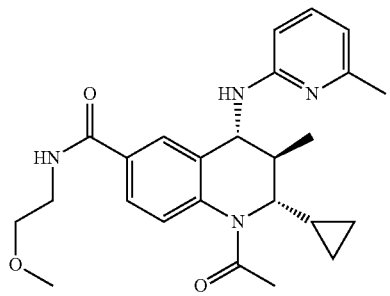 [SMILES: COCCNC(=O)c1ccc2c(c1)[C@H](Nc1cccc(C)n1)[C@@H](C)[C@H](C1CC1)N2C(C)=O]

To a solution of (2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 247, 50 mg, 0.132 mmol) and HATU (90 mg, 0.198 mmol) in N,N-dimethylformamide (DMF) (1 mL) was added 2-methoxyethanamine (14 µL, 0.158 mmol) followed by DIPEA (0.097 mL, 0.553 mmol). The reaction mixture was stirred at rt for 90 min, then purified directly by MDAP (HpH). The solvent was evaporated in vacuo to give the product (32 mg). LCMS (2 min HpH): Rt=0.94 min, [MH]$^+$=437.

Example 257: (2S,3R,4R)-1-acetyl-2-cyclopropyl-N-(2-methoxyethyl)-3-methyl-4-((6-methylpyridin-2-yl)amino)-1,2,3,4-tetrahydroquinoline-6-carboxamide

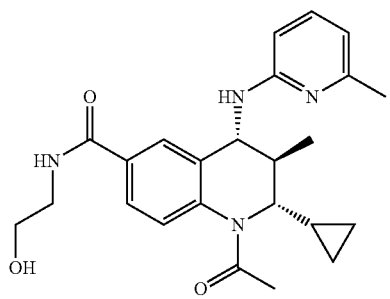 [SMILES: CC(=O)N1c2ccc(C(=O)NCCO)cc2[C@H](Nc2cccc(C)n2)[C@@H](C)[C@@H]1C1CC1]

To a solution of (2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 247, 50 mg, 0.132 mmol) and HATU (90 mg, 0.198 mmol) in N,N-dimethylformamide (DMF) (1 mL) was added 2-aminoethanol (10 µL, 0.158 mmol) followed by DIPEA (0.097 mL, 0.553 mmol). The reaction mixture was stirred at rt for 90 min, then purified directly by MDAP (HpH). The solvent was evaporated in vacuo to give the product (39 mg). LCMS (2 min HpH): Rt=0.84 min, [MH]$^+$=423.

Example 258: (2S,3R,4R)-1-acetyl-2-cyclopropyl-N-(1,1-dioxidotetrahydro-2H-thiopyran-4-yl)-3-methyl-4-((6-methylpyridin-2-yl)amino)-1,2,3,4-tetrahydroquinoline-6-carboxamide

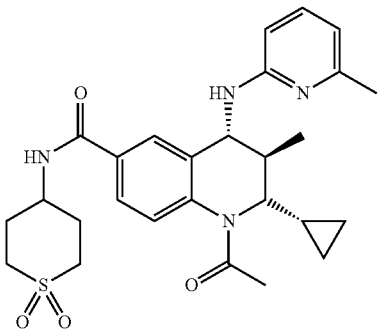

To a solution of (2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 247, 50 mg, 0.791 mmol) and HATU (90 mg, 0.198 mmol) in N,N-dimethylformamide (DMF) (1 mL) was added 4-aminotetrahydro-2H-thiopyran 1,1-dioxide hydrochloride (30 mg, 0.158 mmol) followed by DIPEA (0.097 mL, 0.553 mmol). The reaction mixture was stirred at rt for 90 min, then purified directly by MDAP (HpH) The solvent was evaporated in vacuo to give the product (45 mg).

LCMS (2 min HpH): Rt=0.91 min, [MH]$^+$=511.

Example 259: (2S,3R,4R)-1-acetyl-2-cyclopropyl-N-(1,1-dioxidotetrahydro-2H-thiopyran-4-yl)-3-methyl-4-((6-methylpyridin-2-yl)amino)-1,2,3,4-tetrahydroquinoline-6-carboxamide

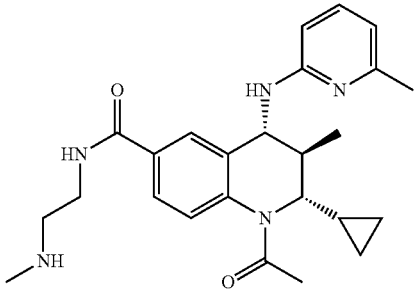

A suspension of tert-butyl (2-((2S,3R,4R)-1-acetyl-2-cyclopropyl-3-methyl-4-((6-methylpyridin-2-yl)amino)-1,2,3,4-tetrahydroquinoline-6-carboxamido)ethyl)(methyl)carbamate (for a preparation see Intermediate 226, 117 mg, 0.218 mmol) in HCl (4M in 1,4-dioxane) (5 mL, 20.00 mmol) was stirred at rt for 18 hr. The solvent and excess HCl were removed under reduced pressure and the crude was purified by MDAP (HpH). The solvent was evaporated in vacuo to give the product (17 mg).

LCMS (2 min HpH): Rt=0.85 min, [MH]$^+$=436.

Example 260: (2S,3R,4R)-1-acetyl-2-cyclopropyl-3-methyl-4-((6-methylpyridin-2-yl)amino)-N—((S)-tetrahydrofuran-3-yl)-1,2,3,4-tetrahydroquinoline-6-carboxamide

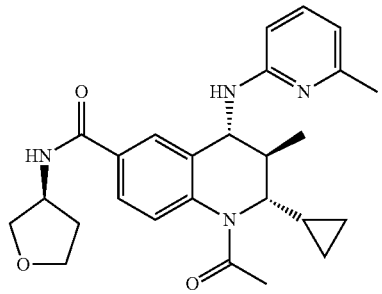 [SMILES: CC(=O)N1c2ccc(C(=O)N[C@H]3CCOC3)cc2[C@H](Nc2cccc(C)n2)[C@@H](C)[C@@H]1C1CC1]

To a solution of (2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 247, 25 mg, 0.066 mmol) and HATU (38 mg, 0.99 mmol) in N,N-dimethylformamide (DMF) (1 mL) was added (S)-tetrahydrofuran-3-amine hydrochloride (10 mg, 0.08 mmol) followed by DIPEA (0.055 mL, 0.316 mmol). The reaction mixture was stirred at rt for 90 min, then purified directly by MDAP (HpH). The solvent was evaporated in vacuo to give the product (18 mg). LCMS (2 min HpH): Rt=0.93 min, [MH]$^+$=449.

Example 261: (2S,3R,4R)-1-acetyl-2-cyclopropyl-3-methyl-4-((6-methylpyridin-2-yl)amino)-N—((R)-tetrahydrofuran-3-yl)-1,2,3,4-tetrahydroquinoline-6-carboxamide

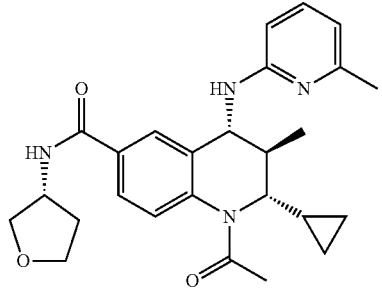 [SMILES: CC(=O)N1c2ccc(C(=O)N[C@@H]3CCOC3)cc2[C@H](Nc2cccc(C)n2)[C@@H](C)[C@@H]1C1CC1]

To a solution of (2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 247, 25 mg, 0.066 mmol) and HATU (38 mg, 0.99 mmol) in N,N-dimethylformamide (DMF) (1 mL) was added (R)-tetrahydrofuran-3-amine 4-methylbenzenesulfonate (21 mg, 0.08 mmol) followed by DIPEA (0.055 mL, 0.316 mmol). The reaction mixture was stirred at rt for 90 min, then purified directly by MDAP (HpH). The solvent was evaporated in vacuo to give the product (14 mg).

LCMS (2 min HpH): Rt=0.93 min, [MH]$^+$=449.

Example 262: (2S,3R,4R)-1-acetyl-2-cyclopropyl-3-methyl-4-((6-methylpyridin-2-yl)amino)-N-(2-(methylsulfonyl)ethyl)-1,2,3,4-tetrahydroquinoline-6-carboxamide

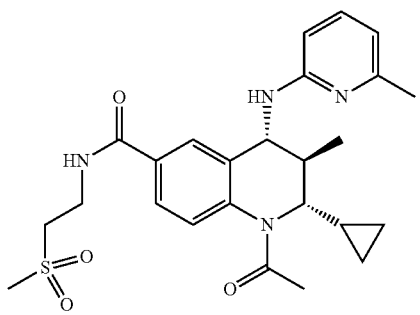

To a solution of (2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 247, 25 mg, 0.066 mmol) and HATU (38 mg, 0.99 mmol) in N,N-dimethylformamide (DMF) (1 mL) was added 2-(methylsulfonyl)ethanamine hydrochloride (13 mg, 0.08 mmol) followed by DIPEA (0.055 mL, 0.316 mmol). The reaction mixture was stirred at rt for 90 min, then purified directly by MDAP (HpH). The solvent was evaporated in vacuo to give the product (13 mg).
LCMS (2 min HpH): Rt=0.89 min, [MH]⁺=485.

Example 263: (2S,3R,4R)-1-acetyl-2-cyclopropyl-N-(2-hydroxypropyl)-3-methyl-4-((6-methylpyridin-2-yl)amino)-1,2,3,4-tetrahydroquinoline-6-carboxamide

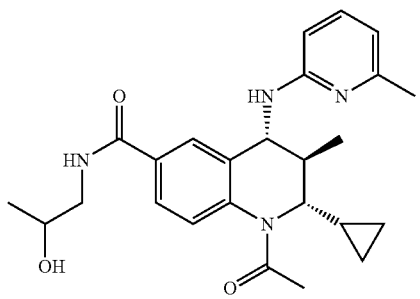 [SMILES: CC(=O)N1c2ccc(C(=O)NCC(C)O)cc2[C@H](Nc2cccc(C)n2)[C@@H](C)[C@@H]1C1CC1]

To a solution of (2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 247, 705 mg, 0.184 mmol) and HATU (84 mg, 0.221 mmol) in N,N-dimethylformamide (DMF) (2 mL) was added 1-aminopropan-2-ol (0.017 mL, 0.221 mmol) and DIPEA (0.129 mL, 0.738 mmol). The reaction mixture was stirred at rt for 60 min, then partitioned between ether (25 mL) and water (50 mL) and the aqueous extracted with ether (3×25 mL). The combined organics were washed with brine (10 mL), dried (MgSO₄) and evaporated in vacuo to afford the product (50 mg). This was a mixture of diastereoisomers.
LCMS (2 min HpH): Rt=0.87 min, [MH]⁺=437.

Example 264: rac-(2S,3R,4R)-1-acetyl-2,3-dimethyl-4-((6-methylpyridin-2-yl)amino)-1,2,3,4-tetrahydroquinoline-6-carboxylic acid, TFA Salt

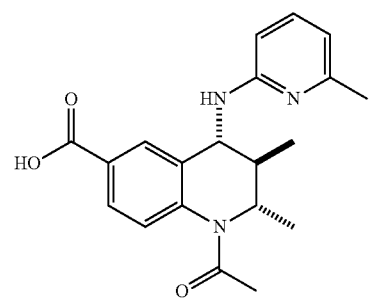 [SMILES: CC(=O)N1c2ccc(C(=O)O)cc2[C@H](Nc2cccc(C)n2)[C@@H](C)[C@@H]1C]

To a mixture of rac-(2S,3R,4R)-ethyl 1-acetyl-4-amino-2,3-dimethyl-1,2,3,4-tetrahydroquinoline-6-carboxylate (for a preparation see Intermediate 203, 934 mg, 3.22 mmol), sodium tert-butoxide (930 mg, 9.68 mmol), Pd₂(dba)₃ (150 mg, 0.164 mmol) and DavePhos (130 mg, 0.330 mmol) were added anhydrous 1,4-dioxane (15 mL) and 2-bromo-6-methylpyridine (0.40 mL, 3.52 mmol). The mixture was evacuated and purged with nitrogen 3 times and stirred under nitrogen at 100° C. for 1.5 h. The reaction mixture was allowed to cool to rt and filtered through celite. The cake was washed with EtOAc (60 mL). The solvent was concentrated in vacuo and the gum dissolved in MeOH (5 mL). The solution was applied to a MeOH-preconditioned 20 g SCX-2 cartridge which was then washed with MeOH (60 mL) followed by 2M ammonia in MeOH solution (60 mL). The basic wash was evaporated in vacuo and the brown gum purified by MDAP (TFA). The appropriate fractions were combined and the solvent removed by rotary evaporation to give the title compound as a yellow gum (496 mg, 1.061 mmol, 33%). LCMS (2 min HpH): Rt=0.62 min, [MH]⁺=354.

Examples 265-276: amide array of rac-(2S,3R,4R)-1-acetyl-2,3-dimethyl-4-((6-methylpyridin-2-yl)amino)-1,2,3,4-tetrahydroquinoline-6-carboxylic acid, TFA Salt (Example 264)

Monomers

| Ex No. | Reagent Name | Structure | MW | Reagent Mass (g) | Reagent Volume (mL) | mmol |
|---|---|---|---|---|---|---|
| 265 | 2-aminoethanol | H₂N—\—OH | 61.08 | — | 0.012 | 0.198 |
| 266 | ethanamine | \—NH₂ | 45.08 | — | 0.099 | 0.198 |

-continued

| Ex No. | Reagent Name | Structure | MW | Reagent Mass (g) | Reagent Volume (mL) | mmol |
|---|---|---|---|---|---|---|
| 267 | tert-butyl 4-aminopiperidine-1-carboxylate | 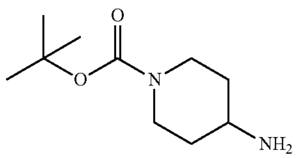 | 200.28 | 0.040 | — | 0.200 |
| 268 | tert-butyl(2-aminoethyl)(methyl)carbamate | 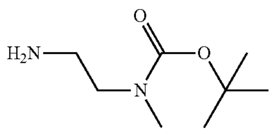 | 174.24 | — | 0.035 | 0.195 |
| 269 | 2-methoxyethanamine | 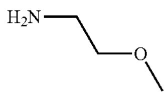 | 75.11 | — | 0.017 | 0.200 |
| 270 | 3-aminopropanenitrile | 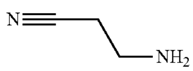 | 70.09 | 0.014 | — | 0.200 |
| 271 | 2-morpholinoethanamine | 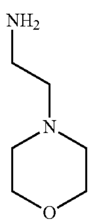 | 130.19 | — | 0.026 | 0.200 |
| 272 | propan-2-amine | 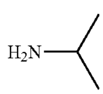 | 59.11 | — | 0.017 | 0.203 |
| 273 | tetrahydro-2H-pyran-4-amine | 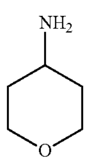 | 101.15 | — | 0.020 | 0.198 |
| 274 | 4-aminotetrahydro-2H-thiopyran 1,1-dioxide hydrochloride | 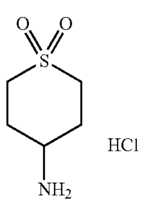 | 183.05 | 0.036 | — | 0.194 |
| 275 | morpholine | 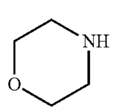 | 87.12 | — | 0.017 | 0.195 |
| 276 | tert-butyl 3-aminopyrrolidine-1-carboxylate | 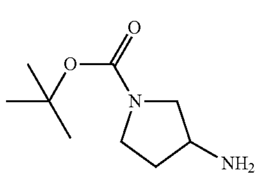 | 186.25 | — | 0.036 | 0.199 |

A mixture of rac-(2S,3R,4R)-1-acetyl-2,3-dimethyl-4-((6-methylpyridin-2-yl)amino)-1,2,3,4-tetrahydroquinoline-6-carboxylic acid, trifluoroacetic acid salt (for a preparation see Example 264, 444 mg, 0.95 mmol) and HATU (900 mg, 2.37 mmol) was suspended in anhydrous DMF (6.0 mL) and treated with DIPEA (0.420 mL, 3.24 mmol). The mixture was allowed to stand in a stoppered vessel at rt for 10 min then dispensed evenly (~0.54 mL) into each amine. (Note: Further DIPEA (0.035 mL, 0.198 mmol) was added to reaction 274). The mixtures were left to stand in stoppered vessels at rt for 15 h. The reaction mixtures were diluted with MeOH (0.25 mL) and purified on a Waters CSH C18 column (150 mm×30 mm, 5 μm packing diameter) at 40 mL/min flow rate. Gradient elution was carried out with acetonitrile in the mobile phases as (A) 10 mM ammonium bicarbonate in water solution, adjusted to pH 10 with 0.88 ammonia solution and (B) acetonitrile. The UV detection was a summed signal from wavelength of 210 nm to 400 nm. The appropriate fractions were combined and evaporated. Samples from reactions 267, 268 & 276 were dissolved in DCM (0.4 mL) and treated with TFA (0.2 mL) and the solutions left to stand in stoppered vessels at rt for 30 min. The reaction mixtures were evaporated under a stream of nitrogen and the residues dissolved in MeOH (0.4 mL). The solutions were applied to MeOH-preconditioned 0.5 g SCX-2 cartridges which were then washed with MeOH (3 mL) followed by 2M ammonia in MeOH solution (3 mL). The basic washes were evaporated under a stream of nitrogen to give final deprotected compounds.

EXAMPLES

| Ex No. | Name | Structure | Mass (mg) | Yield (%) | [MH]+ | Rt (min)* |
|---|---|---|---|---|---|---|
| 265 | rac-(2S,3R,4R)-1-acetyl-N-(2-hydroxyethyl)-2,3-dimethyl-4-((6-methylpyridin-2-yl)amino)-1,2,3,4-tetrahydroquinoline-6-carboxamide | 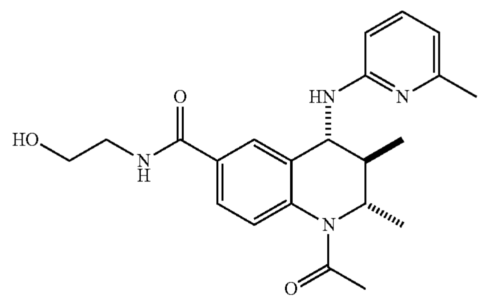 [SMILES: CC(=O)N1c2ccc(C(=O)NCCO)cc2[C@H](Nc2cccc(C)n2)[C@@H](C)[C@@H]1C] | 23 | 73 | 397 | 0.76 |
| 266 | rac-(2S,3R,4R)-1-acetyl-N-ethyl-2,3-dimethyl-4-((6-methylpyridin-2-yl)amino)-1,2,3,4-tetrahydroquinoline-6-carboxamide | 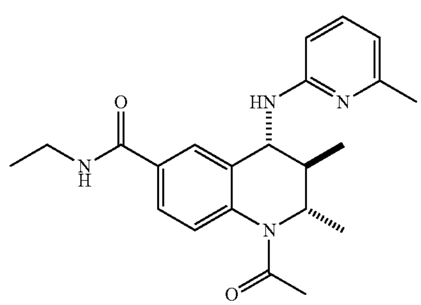 [SMILES: CCNC(=O)c1ccc2c(c1)[C@H](Nc1cccc(C)n1)[C@@H](C)[C@H](C)N2C(C)=O] | 24 | 80 | 381 | 0.88 |
| 267 | rac-(2S,3R,4R)-1-acetyl-2,3-dimethyl-4-((6-methylpyridin-2-yl)amino)-N-(piperidin-4-yl)-1,2,3,4-tetrahydroquinoline-6-carboxamide | 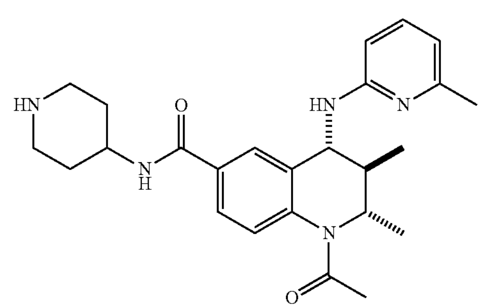 | 20 | 58 | 436 | 0.77 |

-continued

| Ex No. | Name | Structure | Mass (mg) | Yield (%) | [MH]+ | Rt (min)* |
|---|---|---|---|---|---|---|
| 268 | rac-(2S,3R,4R)-1-acetyl-2,3-dimethyl-N-(2-(methylamino)ethyl)-4-((6-methylpyridin-2-yl)amino)-1,2,3,4-tetrahydroquinoline-6-carboxamide | 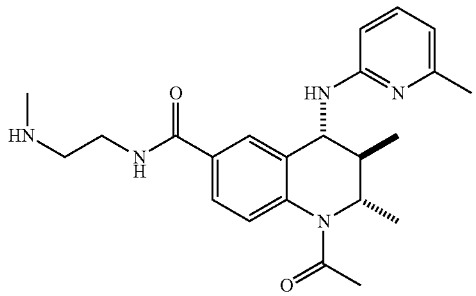 [SMILES: CNCCNC(=O)c1ccc2c(c1)[C@H](Nc1cccc(C)n1)[C@@H](C)[C@H](C)N2C(C)=O] | 21 | 65 | 410 | 0.77 |
| 269 | rac-(2S,3R,4R)-1-acetyl-N-(2-methoxyethyl)-2,3-dimethyl-4-((6-methylpyridin-2-yl)amino)-1,2,3,4-tetrahydroquinoline-6-carboxamide | 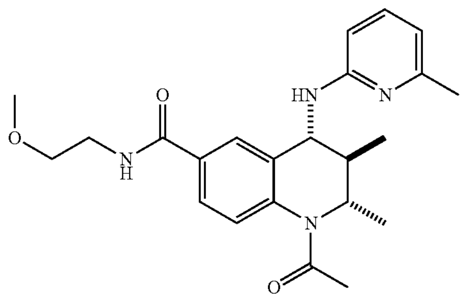 [SMILES: COCCNC(=O)c1ccc2c(c1)[C@H](Nc1cccc(C)n1)[C@@H](C)[C@H](C)N2C(C)=O] | 27 | 83 | 411 | 0.85 |
| 270 | rac-(2S,3R,4R)-1-acetyl-N-(2-cyanoethyl)-2,3-dimethyl-4-((6-methylpyridin-2-yl)amino)-1,2,3,4-tetrahydroquinoline-6-carboxamide | 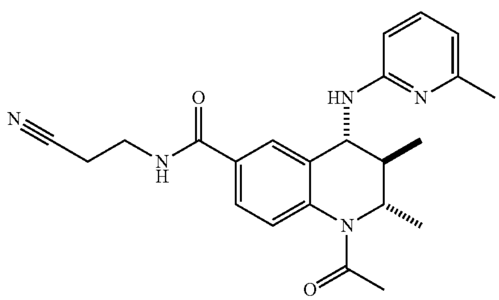 [SMILES: CC(=O)N1c2ccc(C(=O)NCCC#N)cc2[C@H](Nc2cccc(C)n2)[C@@H](C)[C@@H]1C] | 14 | 44 | 406 | 0.84 |
| 271 | rac-(2S,3R,4R)-1-acetyl-2,3-dimethyl-4-((6-methylpyridin-2-yl)amino)-N-(2-morpholinoethyl)-1,2,3,4-tetrahydroquinoline-6-carboxamide | 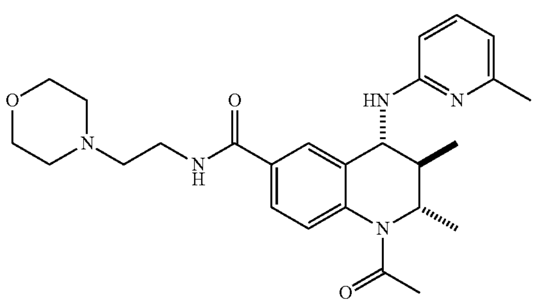 [SMILES: CC(=O)N1c2ccc(C(=O)NCCN3CCOCC3)cc2[C@H](Nc2cccc(C)n2)[C@@H](C)[C@@H]1C] | 31 | 84 | 466 | 0.83 |
| 272 | rac-(2S,3R,4R)-1-acetyl-N-isopropyl-2,3-dimethyl-4-((6-methylpyridin-2-yl)amino)-1,2,3,4-tetrahydroquinoline-6-carboxamide | 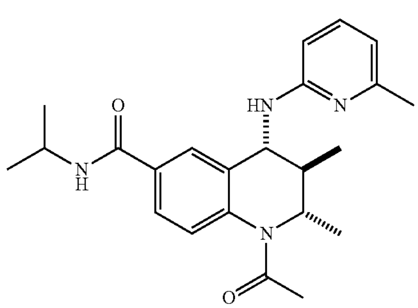 | 26 | 83 | 395 | 0.94 |

-continued

| Ex No. | Name | Structure | Mass (mg) | Yield (%) | [MH]+ | Rt (min)* |
|---|---|---|---|---|---|---|
| 273 | rac-(2S,3R,4R)-1-acetyl-2,3-dimethyl-4-((6-methylpyridin-2-yl)amino)-N-(tetrahydro-2H-pyran-4-yl)-1,2,3,4-tetrahydroquinoline-6-carboxamide | 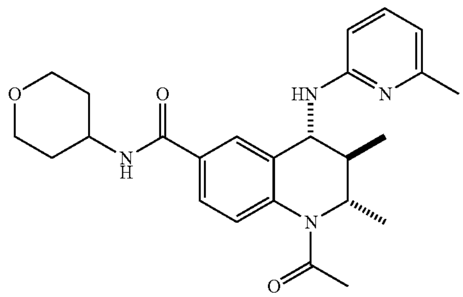 [SMILES: CC(=O)N1c2ccc(C(=O)NC3CCOCC3)cc2[C@H](Nc2cccc(C)n2)[C@@H](C)[C@@H]1C] | 29 | 84 | 437 | 0.86 |
| 274 | rac-(2S,3R,4R)-1-acetyl-N-(1,1-dioxidotetrahydro-2H-thiopyran-4-yl)-2,3-dimethyl-4-((6-methylpyridin-2-yl)amino)-1,2,3,4-tetrahydroquinoline-6-carboxamide | 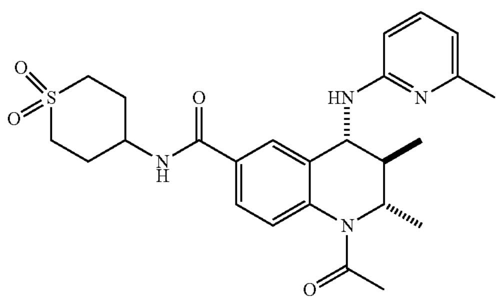 [SMILES: CC(=O)N1c2ccc(C(=O)NC3CCS(=O)(=O)CC3)cc2[C@H](Nc2cccc(C)n2)[C@@H](C)[C@@H]1C] | 29 | 76 | 485 | 0.83 |
| 275 | rac-1-((2S,3R,4R)-2,3-dimethyl-4-(6-methylpyridin-2-yl)amino)-6-(morpholine-4-carbonyl)-3,4-dihydroquinolin-1(2H)-yl)ethanone | 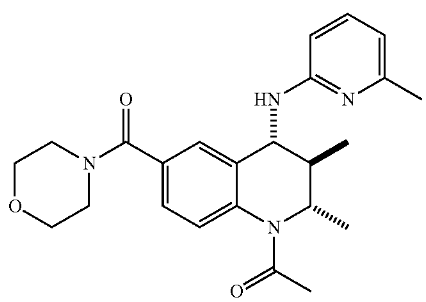 [SMILES: CC(=O)N1c2ccc(C(=O)N3CCOCC3)cc2[C@H](Nc2cccc(C)n2)[C@@H](C)[C@@H]1C] | 25 | 75 | 423 | 0.84 |
| 276 | (rac-2S,3R,4R)-1-acetyl-2,3-dimethyl-4-((6-methylpyridin-2-yl)amino)-N-(pyrrolidin-3-yl)-1,2,3,4-tetrahydroquinoline-6-carboxamide; racemic mixture of diatereoisomers. | 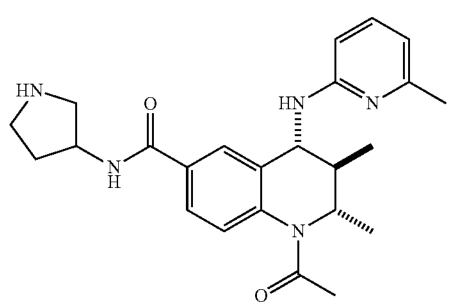 [SMILES: CC(=O)N1c2ccc(C(=O)NC3CCNC3)cc2[C@H](Nc2cccc(C)n2)[C@@H](C)[C@@H]1C] | 20 | 60 | 422 | 0.76 |

*All LCMS were conducted using 2 min HpH.

Example 277: rac-(2S,3R,4R)-1-acetyl-2-ethyl-3-methyl-4-((6-methylpyridin-2-yl)amino)-1,2,3,4-tetrahydroquinoline-6-carboxylic acid, TFA salt

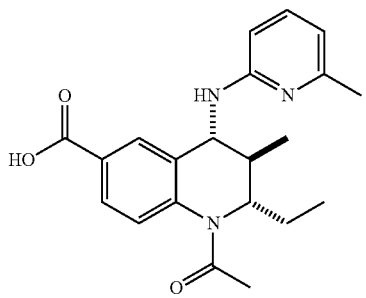 [SMILES: CC[C@H]1[C@H](C)[C@@H](Nc2cccc(C)n2)c2cc(C(=O)O)ccc2N1C(C)=O]

To a mixture of rac-(2S,3R,4R)-ethyl 1-acetyl-4-amino-2-ethyl-3-methyl-1,2,3,4-tetrahydroquinoline-6-carboxylate (for a preparation see Intermediate 206, 1.62 g, 5.32 mmol), sodium tert-butoxide (1.534 g, 15.97 mmol), Pd₂(dba)₃ (0.244 g, 0.266 mmol) and DavePhos (0.210 g, 0.534 mmol) were added anhydrous 1,4-dioxane (20 mL) and 2-bromo-6-methylpyridine (0.727 mL, 6.39 mmol). The mixture was evacuated and purged with nitrogen 3 times and stirred under nitrogen at 100° C. for 1.5 h. The reaction mixture was allowed to cool to rt and filtered through celite. The cake was washed with EtOAc (80 mL). The solvent was concentrated in vacuo and the gum dissolved in MeOH (5 mL). The solution was applied to a MeOH-preconditioned 50 g SCX-2 cartridge which was then washed with MeOH (100 mL) followed by 2M ammonia in MeOH solution (100 mL). The basic wash was evaporated in vacuo to give brown gum. The gum was purified by MDAP (TFA). The appropriate fractions were combined and the solvent removed by rotary evaporation to give the title compound as a yellow gum (1.01 g, 2.098 mmol, 39%). LCMS (2 min HpH): Rt=0.65 min, [MH]⁺=368.

Examples 278-289: amide array of rac-(2S,3R,4R)-1-acetyl-2-ethyl-3-methyl-4-((6-methylpyridin-2-yl)amino)-1,2,3,4-tetrahydroquinoline-6-carboxylic acid, TFA salt (Example 277)

Monomers

| Ex No. | Reagent Name | Structure | MW | Reagent Mass (mg) | Reagent Volume (mL) | mmol |
|---|---|---|---|---|---|---|
| 278 | 2-aminoethanol | 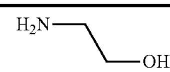 | 61.08 | — | 0.015 | 0.246 |
| 279 | ethanamine | 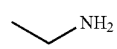 | 45.08 | — | 0.126 | 0.252 |
| 280 | tert-butyl 4-aminopiperidine-1-carboxylate | 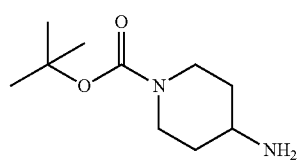 | 200.28 | 0.050 | — | 0.250 |
| 281 | tert-butyl(2-aminoethyl)(methyl)carbamate | 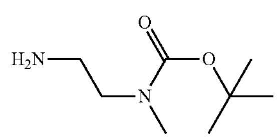 | 174.24 | — | 0.045 | 0.253 |
| 282 | 2-methoxyethanamine | 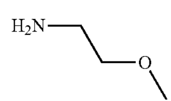 | 75.11 | — | 0.022 | 0.253 |
| 283 | 3-aminopropanenitrile | 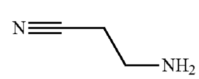 | 70.09 | 0.018 | — | 0.257 |
| 284 | 2-morpholinoethanamine | 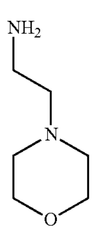 | 130.19 | — | 0.033 | 0.253 |
| 285 | propan-2-amine | 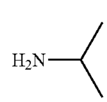 | 59.11 | — | 0.021 | 0.254 |

-continued

| Ex No. | Reagent Name | Structure | MW | Reagent Mass (mg) | Reagent Volume (mL) | mmol |
|---|---|---|---|---|---|---|
| 286 | tetrahydro-2H-pyran-4-amine | 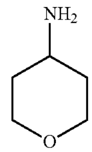 | 101.15 | — | 0.026 | 0.247 |
| 287 | 4-aminotetrahydro-2H-thiopyran 1,1-dioxide hydrochloride | 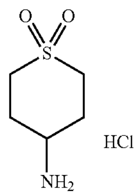 | 183.05 | 0.046 | — | 0.251 |
| 288 | morpholine | 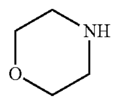 | 87.12 | — | 0.022 | 0.253 |
| 289 | tert-butyl 3-aminopyrrolidine-1-carboxylate | 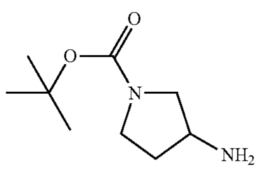 | 186.25 | — | 0.046 | 0.252 |

A mixture of rac-(2S,3R,4R)-1-acetyl-2-ethyl-3-methyl-4-((6-methylpyridin-2-yl)amino)-1,2,3,4-tetrahydroquinoline-6-carboxylic acid, TFA salt (for a preparation see Example 277, 444 mg, 0.922 mmol) and HATU (1.15 g, 3.03 mmol) was suspended in anhydrous DMF (6.0 mL) and treated with DIPEA (0.528 mL, 4.09 mmol). The mixture was allowed to stand in a stoppered vessel at rt for 10 min then dispensed evenly (~0.54 mL) into each amine. (Note: Further DIPEA (0.044 mL, 0.254 mmol) was added to reaction). The mixtures were left to stand in stoppered vessels at rt for 15 h. The reaction mixtures were diluted with MeOH (0.25 mL) and purified on a Waters CSH C18 column (150 mm×30 mm, 5 μm packing diameter) at 40 mL/min flow rate. Gradient elution was carried out with acetonitrile in the mobile phases as (A) 10 mM ammonium bicarbonate in water solution, adjusted to pH 10 with 0.88 ammonia solution and (B) acetonitrile. The UV detection was a summed signal from wavelength of 210 nm to 400 nm. The appropriate fractions were combined and evaporated. Samples from reactions 280, 281 & 289 were dissolved in DCM (0.4 mL) and treated with TFA (0.2 mL) and the solutions left to stand in stoppered vessels at r.t. for 30 min. The reaction mixtures were evaporated under a stream of nitrogen and the residues dissolved in MeOH (0.4 mL). The solutions were applied to MeOH-preconditioned 0.5 g SCX-2 cartridges which were then washed with MeOH (3 mL) followed by 2M ammonia in MeOH solution (3 mL). The basic washes were evaporated under a stream of nitrogen to give final deprotected compounds.

The following compounds of formula (I) were also prepared:

| Ex No. | Name | Structure | Mass (mg) | Yield (%) | [MH]+ | Rt (min)* |
|---|---|---|---|---|---|---|
| 278 | rac-(2S,3R,4R)-1-acetyl-2-ethyl-N-(2-hydroxyethyl)-3-methyl-4-((6-methylpyridin-2-yl)amino)-1,2,3,4-tetrahydroquinoline-6-carboxamide | 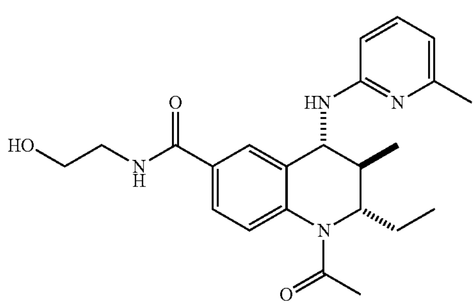 [SMILES: CC[C@H]1[C@H](C)[C@@H](Nc2cccc(C)n2)c2cc(C(=O)NCCO)ccc2N1C(C)=O] | 28 | 89 | 411 | 0.81 |

| Ex No. | Name | Structure | Mass (mg) | Yield (%) | [MH]+ | Rt (min)* |
|---|---|---|---|---|---|---|
| 279 | rac-(2S,3R,4R)-1-acetyl-N,2-diethyl-3-methyl-4-((6-methylpyridin-2-yl)amino)-1,2,3,4-tetrahydro-quinoline-6-carboxamide | 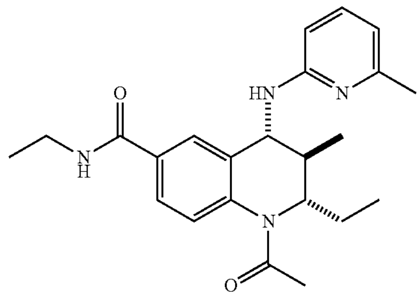 [SMILES: CCNC(=O)c1ccc2c(c1)[C@H](Nc1cccc(C)n1)[C@@H](C)[C@H](CC)N2C(C)=O] | 25 | 82 | 395 | 0.93 |
| 280 | rac-(2S,3R,4R)-1-acetyl-2-ethyl-3-methyl-4-((6-methylpyridin-2-yl)amino)-N-(piperidin-4-yl)-1,2,3,4-tetrahydro-quinoline-6-carboxamide | 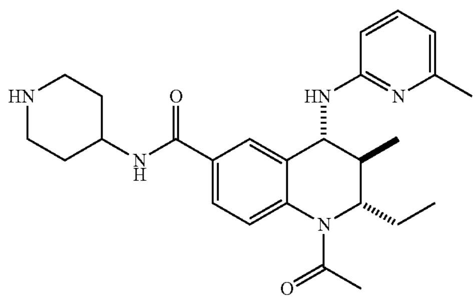 [SMILES: CC[C@H]1[C@H](C)[C@@H](Nc2cccc(C)n2)c2cc(C(=O)NC3CCNCC3)ccc2N1C(C)=O] | 25 | 72 | 450 | 0.83 |
| 281 | rac-(2S,3R,4R)-1-acetyl-2-ethyl-3-methyl-N-(2-(methylamino)ethyl)-4-((6-methylpyridin-2-yl)amino)-1,2,3,4-tetrahydro-quinoline-6-carboxamide | 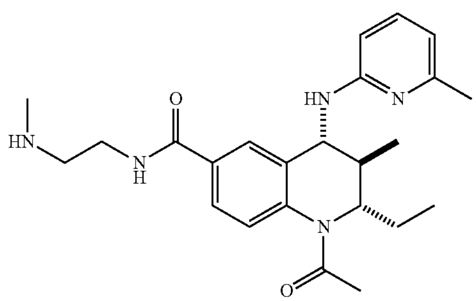 [SMILES: CC[C@H]1[C@H](C)[C@@H](Nc2cccc(C)n2)c2cc(C(=O)NCCNC)ccc2N1C(C)=O] | 24 | 73 | 424 | 0.82 |
| 282 | rac-(2S,3R,4R)-1-acetyl-2-ethyl-N-(2-methoxyethyl)-3-methyl-4-((6-methylpyridin-2-yl)amino)-1,2,3,4-tetrahydro-quinoline-6-carboxamide | 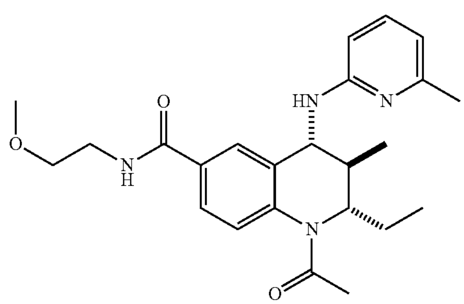 [SMILES: CC[C@H]1[C@H](C)[C@@H](Nc2cccc(C)n2)c2cc(C(=O)NCCOC)ccc2N1C(C)=O] | 23 | 70 | 425 | 0.90 |
| 283 | rac-(2S,3R,4R)-1-acetyl-N-(2-cyanoethyl)-2-ethyl-3-methyl-4-((6-methylpyridin-2-yl)amino)-1,2,3,4-tetrahydro-quinoline-6-carboxamide | 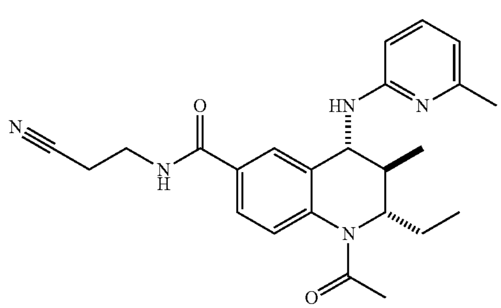 [SMILES: CC[C@H]1[C@H](C)[C@@H](Nc2cccc(C)n2)c2cc(C(=O)NCCC#N)ccc2N1C(C)=O] | 13 | 40 | 420 | 0.90 |

| Ex No. | Name | Structure | Mass (mg) | Yield (%) | [MH]+ | Rt (min)* |
|---|---|---|---|---|---|---|
| 284 | rac-(2S,3R,4R)-1-acetyl-2-ethyl-3-methyl-4-((6-methylpyridin-2-yl)amino)-N-(2-morpholinoethyl)-1,2,3,4-tetrahydroquinoline-6-carboxamide | 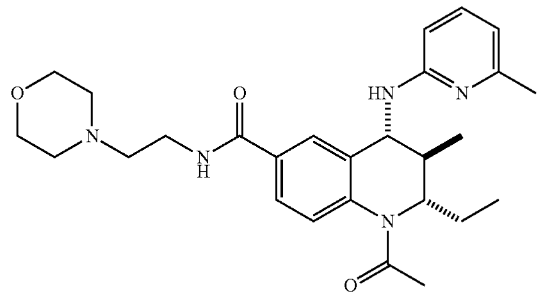 [SMILES: CC[C@H]1[C@H](C)[C@@H](Nc2cccc(C)n2)c2cc(C(=O)NCCN3CCOCC3)ccc2N1C(C)=O] | 28 | 76 | 480 | 0.87 |
| 285 | rac-(2S,3R,4R)-1-acetyl-2-ethyl-N-isopropyl-3-methyl-4-((6-methylpyridin-2-yl)amino)-1,2,3,4-tetrahydroquinoline-6-carboxamide | 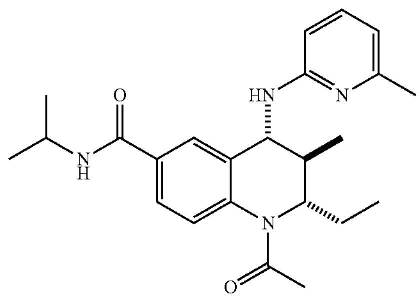 [SMILES: CC[C@H]1[C@H](C)[C@@H](Nc2cccc(C)n2)c2cc(C(=O)NC(C)C)ccc2N1C(C)=O] | 23 | 73 | 409 | 0.99 |
| 286 | rac-(2S,3R,4R)-1-acetyl-2-ethyl-3-methyl-4-((6-methylpyridin-2-yl)amino)-N-(tetrahydro-2H-pyran-4-yl)-1,2,3,4-tetrahydroquinoline-6-carboxamide | 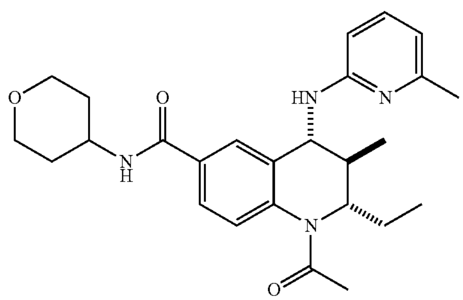 [SMILES: CC[C@H]1[C@H](C)[C@@H](Nc2cccc(C)n2)c2cc(C(=O)NC3CCOCC3)ccc2N1C(C)=O] | 28 | 81 | 451 | 0.91 |
| 287 | rac-(2S,3R,4R)-1-acetyl-N-(1,1-dioxidotetrahydro-2H-thiopyran-4-yl)-2-ethyl-3-methyl-4-((6-methylpyridin-2-yl)amino)-1,2,3,4-tetrahydroquinoline-6-carboxamide | 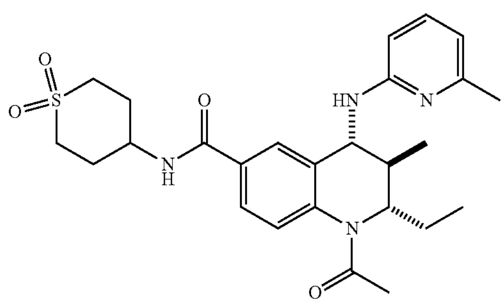 [SMILES: CC[C@H]1[C@H](C)[C@@H](Nc2cccc(C)n2)c2cc(C(=O)NC3CCS(=O)(=O)CC3)ccc2N1C(C)=O] | 30 | 78 | 499 | 0.87 |
| 288 | rac-1-((2S,3R,4R)-2-ethyl-3-methyl-4-((6-methylpyridin-2-yl)amino)-6-(morpholine-4-carbonyl)-3,4-dihydroquinolin-1(2H)-yl)ethanone | 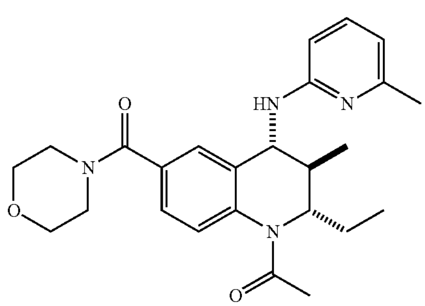 [SMILES: CC[C@H]1[C@H](C)[C@@H](Nc2cccc(C)n2)c2cc(C(=O)N3CCOCC3)ccc2N1C(C)=O] | 20 | 60 | 437 | 0.89 |

| Ex No. | Name | Structure | Mass (mg) | Yield (%) | [MH]+ | Rt (min)* |
|---|---|---|---|---|---|---|
| 289 | (rac-2S,3R,4R)-1-acetyl-2-ethyl-3-methyl-4-((6-methylpyridin-2-yl)amino)-N-(pyrrolidin-3-yl)-1,2,3,4-tetrahydroquinoline-6-carboxamide; racemic mixture of diatereoisomers | 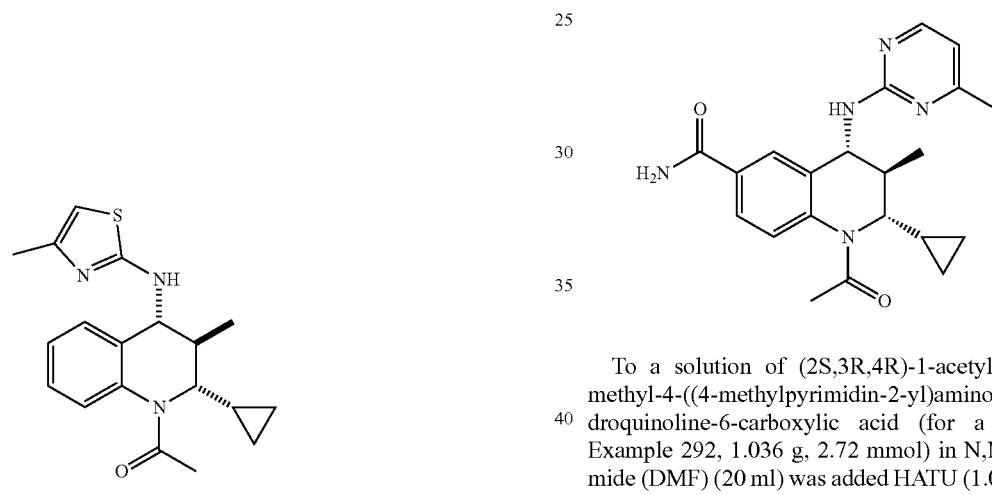 | 23 | 69 | 436 | 0.81 |

*All LCMS were conducted using 2 min HpH.

Example 290: rac-1-((2S,3R,4R)-2-cyclopropyl-3-methyl-4-((4-methylthiazol-2-yl)amino)-3,4-dihydroquinolin-1(2H)-yl)ethanone To a solution of rac-1-((2S,3R,4R)-1-acetyl-2-cyclopropyl-3-methyl-1,2,3,4-tetrahydroquinolin-4-yl)thiourea (for a preparation see Intermediate 207, 65 mg, 0.214 mmol) and conc. HCl (0.325 µL, 10.71 µmol) in ethanol (3 mL) stirred at rt was added 1-chloropropan-2-one (0.020 mL, 0.257 mmol). The reaction mixture was heated to 80° C. for 2 h, then evaporated and the residue redissolved in EtOAc (10 mL) and sat. aq. NaHCO₃ (10 mL). The aqueous layer was washed with EtOAc (10 mL) and the combined organics washed with brine, dried (MgSO₄) and evaporated. Purification by silica chromatography (40-60% EtOAc/cyclohexane) gave the product (65 mg) as a clear oil.

LCMS (2 min HpH): Rt=1.02 min, [MH]⁺=342.

Example 291: (2S,3R,4R)-1-acetyl-2-cyclopropyl-3-methyl-4-((4-methylpyrimidin-2-yl)amino)-1,2,3,4-tetrahydroquinoline-6-carboxamide To a solution of (2S,3R,4R)-1-acetyl-2-cyclopropyl-3-methyl-4-((4-methylpyrimidin-2-yl)amino)-1,2,3,4-tetrahydroquinoline-6-carboxylic acid (for a preparation see Example 292, 1.036 g, 2.72 mmol) in N,N-dimethylformamide (DMF) (20 ml) was added HATU (1.056 g, 2.78 mmol) followed by DIPEA (0.951 ml, 5.45 mmol). The resulting reaction mixture was stirred at room temperature under N₂ for 15 min. Ammonium chloride (0.291 g, 5.45 mmol) was then added and the reaction stirred for ~1 h. The reaction mixture was quenched with brine (30 mL) and ethyl acetate (30 mL) was then added. A small amount of water (10 mL) was added to re-dissolve any inorganics and the resultant biphasic mixture allowed to sit overnight. The layers were separated and the aqueous layer further extracted with ethyl acetate (2×30 mL). The combined organics were back-extracted with sat. aq. LiCl solution (3×20 mL). Product was found to have partitioned into the aqueous layer. Therefore the aqueous layer was diluted with brine (30 mL) and DCM (30 mL) was added. The layers were separated and the aqueous layer further extracted with DCM (2×30 mL). The combined DCM layers were combined with the earlier EtOAc washings and the organics dried (Na₂SO₄) and concentrated in vacuo. The crude product was taken up in DCM and added to a 100 g silica cartridge and purified by flash chromatography, eluting with 0%→40% acetone/ethyl acetate. Purer fractions were collected and concentrated in vacuo to afford the desired product as a cream foam (732 mg, 1.929 mmol, 70.8%). LCMS (2 min Formic): Rt=0.63 min, [MH]⁺=380.

Example 292: (2S,3R,4R)-1-acetyl-2-cyclopropyl-3-methyl-4-((4-methylpyrimidin-2-yl)amino)-1,2,3,4-tetrahydroquinoline-6-carboxylic Acid

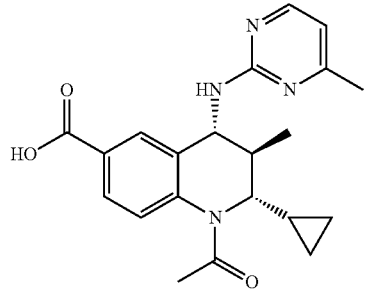 [SMILES: CC(=O)N1c2ccc(C(=O)O)cc2[C@H](Nc2nccc(C)n2)[C@@H](C)[C@@H]1C1CC1]

(2S,3R,4R)-Ethyl 1-acetyl-2-cyclopropyl-3-methyl-4-((4-methylpyrimidin-2-yl)amino)-1,2,3,4-tetrahydroquinoline-6-carboxylate (for a preparation see Intermediate 227, 29 g, 71.0 mmol) was taken up in tetrahydrofuran (THF) (175 mL) and water (175 mL). Lithium hydroxide (4.25 g, 177 mmol) was added and the reaction stirred at room temperature overnight. 2M HCl(aq) (89 mL, 177 mmol) was added followed by 10% MeOH/DCM (200 mL) and water (200 mL). The biphasic mixture was stirred for 5 min and the layers then separated. The aqueous layer was further extracted with 10% MeOH/DCM (2×200 mL) and the combined organics were dried (MgSO$_4$), filtered and concentrated to leave the product as a pale yellow foam (26.5 g).

LCMS (2 min Formic): Rt=0.73 min, [MH]$^+$=381.

The following examples were prepared in a similar manner to Intermediate 232 using Pd(QPhos)$_2$ and NaOtBu to couple the appropriate aryl halide to Intermediate 231.

| Ex No. | Name | Structure | Mass (mg) | Yield (%) | [MH]$^+$ | Rt (min) (LCMS Method) |
|---|---|---|---|---|---|---|
| 293 | (2S,3R,4R)-1-acetyl-2-cyclopropyl-4-((3-methoxypyridin-2-yl)amino)-3-methyl-1,2,3,4-tetrahydroquinoline-6-carbonitrile | 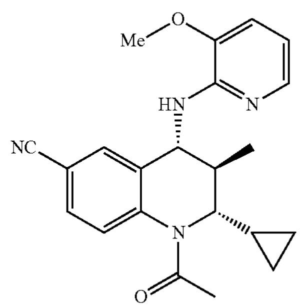 [SMILES: COc1cccnc1N[C@H]1c2cc(C#N)ccc2N(C(C)=O)[C@@H](C2CC2)[C@@H]1C] | 181 | 78 | 377 | 0.71 (2 min Formic) |
| 294 | (2S,3R,4R)-1-acetyl-2-cyclopropyl-3-methyl-4-((4-methylpyridin-2-yl)amino)-1,2,3,4-tetrahydroquinoline-6-carbonitrile | 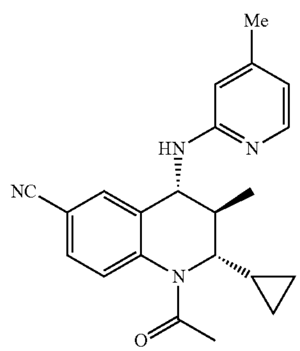 [SMILES: CC(=O)N1c2ccc(C#N)cc2[C@H](Nc2cc(C)ccn2)[C@@H](C)[C@@H]1C1CC1] | 117 | 53 | 361 | 0.68 (2 min Formic) |
| 295 | (2S,3R,4R)-1-acetyl-2-cyclopropyl-3-methyl-4-((5-methylpyridin-2-yl)amino)-1,2,3,4-tetrahydroquinoline-6-carbonitrile | 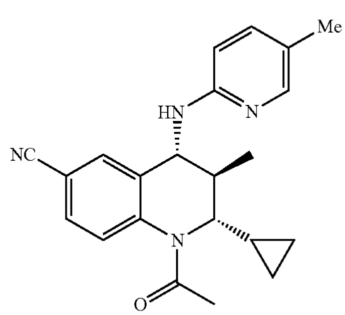 [SMILES: CC(=O)N1c2ccc(C#N)cc2[C@H](Nc2ccc(C)cn2)[C@@H](C)[C@@H]1C1CC1] | 26 | 14 | 361 | 0.66 (2 min Formic) |

| Ex No. | Name | Structure | Mass (mg) | Yield (%) | [MH]+ | Rt (min) (LCMS Method) |
|---|---|---|---|---|---|---|
| 296 | (2S,3R,4R)-1-Acetyl-2-cyclopropyl-3-methyl-4-((3-methylpyridin-2-yl)amino)-1,2,3,4-tetrahydroquinoline-6-carbonitrile | 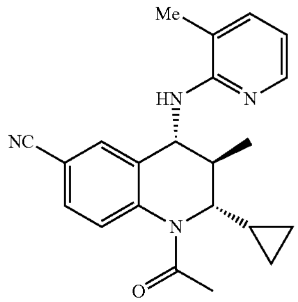 [SMILES: CC(=O)N1c2ccc(C#N)cc2[C@H](Nc2ncccc2C)[C@@H](C)[C@@H]1C1CC1] | 15 | 8 | 361 | 0.66 (2 min Formic) |

The following examples were prepared in a similar manner to Intermediate 234 using Pd$_2$(dba)$_3$, Q-Phos and NaOtBu to couple the appropriate aryl halide to Intermediate 231.

| Ex No. | Name | Structure | Mass (mg) | Yield (%) | [MH]+ | Rt (min) (LCMS Method) |
|---|---|---|---|---|---|---|
| 297 | (2S,3R,4R)-1-acetyl-2-cyclopropyl-3-methyl-4-((6-(morpholinomethyl)pyridin-2-yl)amino)-1,2,3,4-tetrahydroquinoline-6-carbonitrile | 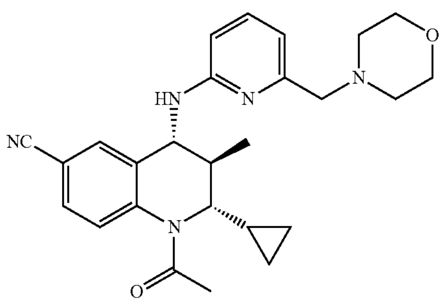 [SMILES: CC(=O)N1c2ccc(C#N)cc2[C@H](Nc2cccc(CN3CCOCC3)n2)[C@@H](C)[C@@H]1C1CC1] | 26 | 21 | 447 | 0.71 (2 min Formic) |
| 298 | (2S,3R,4R)-1-acetyl-2-cyclopropyl-4-((6-((dimethylamino)methyl)pyridin-2-yl)amino)-3-methyl-1,2,3,4-tetrahydroquinoline-6-carbonitrile | 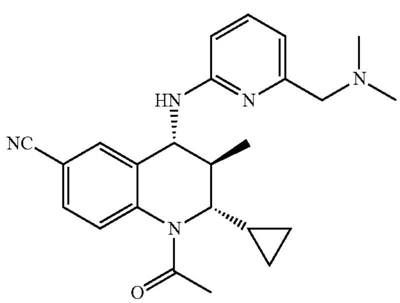 [SMILES: CC(=O)N1c2ccc(C#N)cc2[C@H](Nc2cccc(CN(C)C)n2)[C@@H](C)[C@@H]1C1CC1] | 210 | 93 | 405 | 0.71 (2 min Formic) |
| 299 | (2S,3R,4R)-1-acetyl-2-cyclopropyl-4-((5-methoxy-4-methylpyrimidin-2-yl)amino)-3-methyl-1,2,3,4-tetrahydroquinoline-6-carbonitrile | 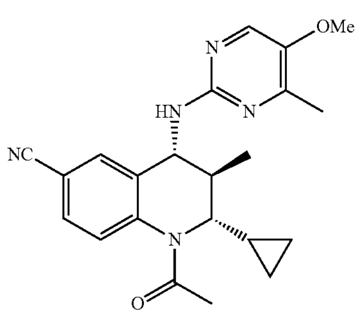 [SMILES: COc1cnc(N[C@H]2c3cc(C#N)ccc3N(C(C)=O)[C@@H](C3CC3)[C@@H]2C)nc1C] | 79 | 27 | 392 | 1.02 (2 min HpH) |

-continued

| Ex No. | Name | Structure | Mass (mg) | Yield (%) | [MH]+ | Rt (min) (LCMS Method) |
|---|---|---|---|---|---|---|
| 300 | (2S,3R,4R)-1-acetyl-4-((5-chloro-4-methylpyrimidin-2-yl)amino)-2-cyclopropyl-3-methyl-1,2,3,4-tetrahydroquinoline-6-carbonitrile | 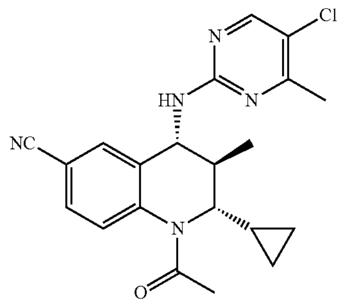 [SMILES: CC(=O)N1c2ccc(C#N)cc2[C@H](Nc2ncc(Cl)c(C)n2)[C@@H](C)[C@@H]1C1CC1] | 40 | 14 | 396 | 1.15 (2 min HpH) |
| 301 | (2S,3R,4R)-1-acetyl-2-cyclopropyl-4-((3-fluoropyridin-2-yl)amino)-3-methyl-1,2,3,4-tetrahydroquinoline-6-carbonitrile | 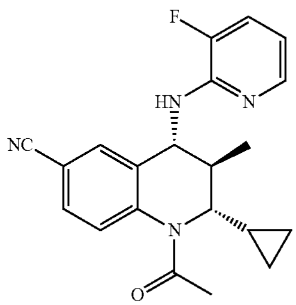 [SMILES: CC(=O)N1c2ccc(C#N)cc2[C@H](Nc2ncccc2F)[C@@H](C)[C@@H]1C1CC1] | 7 | 5 | 365 | 1.08 (2 min HpH) |

The following examples were prepared in a similar manner to Intermediate 239 using Pd$_2$(dba)$_3$, DavePhos, NaOtBu and the appropriate aryl halide in 1,4-dioxane).

| Ex No. | Name | Structure | Mass (mg) | Yield (%) | [MH]+ | Rt (min) (LCMS Method) |
|---|---|---|---|---|---|---|
| 302 | (2S,3R,4R)-1-acetyl-2-cyclopropyl-4-((4-fluorophenyl)amino)-3-methyl-1,2,3,4-tetrahydroquinoline-6-carbonitrile | 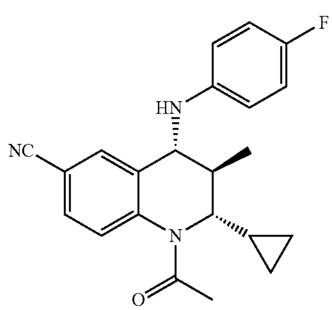 | 55 | 33 | 364 | 1.13 (2 min Formic) |
| 303 | (2S,3R,4R)-1-acetyl-4-((4-chlorophenyl)amino)-2-cyclopropyl-3-methyl-1,2,3,4-tetrahydroquinoline-6-carbonitrile | 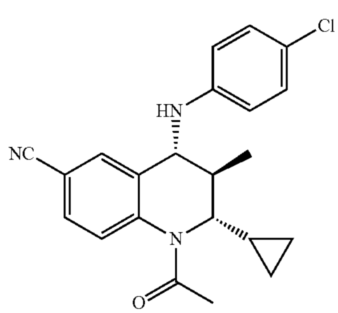 [SMILES: CC(=O)N1c2ccc(C#N)cc2[C@H](Nc2ccc(Cl)cc2)[C@@H](C)[C@@H]1C1CC1] | 13 | 18 | 380 | 1.22 (2 min Formic) |

-continued

| Ex No. | Name | Structure | Mass (mg) | Yield (%) | [MH]+ | Rt (min) (LCMS Method) |
|---|---|---|---|---|---|---|
| 304 | (2S,3R,4R)-1-acetyl-4-((3-chlorophenyl)amino)-2-cyclopropyl-3-methyl-1,2,3,4-tetrahydroquinoline-6-carbonitrile | 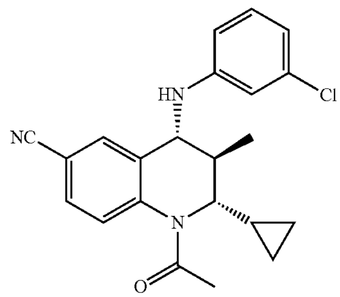 [SMILES: CC(=O)N1c2ccc(C#N)cc2[C@H](Nc2cccc(Cl)c2)[C@@H](C)[C@@H]1C1CC1] | 24 | 33 | 380 | 1.22 (2 min Formic) |
| 305 | (2S,3R,4R)-1-acetyl-2-cyclopropyl-4-((6-(methoxymethyl)pyridin-2-yl)amino)-3-methyl-1,2,3,4-tetrahydroquinoline-6-carbonitrile | 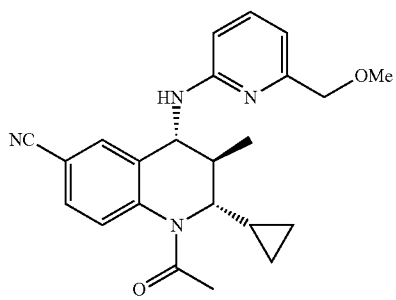 [SMILES: COCc1cccc(N[C@H]2c3cc(C#N)ccc3N(C(C)=O)[C@@H](C3CC3)[C@@H]2C)n1] | 38 | 26 | 391 | 0.75 (2 min Formic) |
| 306 | (2S,3R,4R)-1-acetyl-2-cyclopropyl-4-((2-(methoxymethyl)phenyl)amino)-3-methyl-1,2,3,4-tetrahydroquinoline-6-carbonitrile | 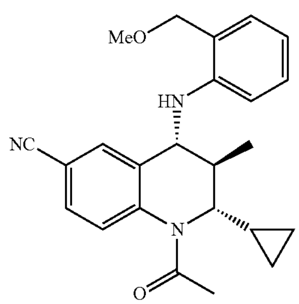 [SMILES: COCc1ccccc1N[C@H]1c2cc(C#N)ccc2N(C(C)=O)[C@@H](C2CC2)[C@@H]1C] | 67 | 46 | 390 | 1.20 (2 min Formic) |
| 307 | (2S,3R,4R)-1-acetyl-2-cyclopropyl-4-((3-fluorophenyl)amino)-3-methyl-1,2,3,4-tetrahydroquinoline-6-carbonitrile | 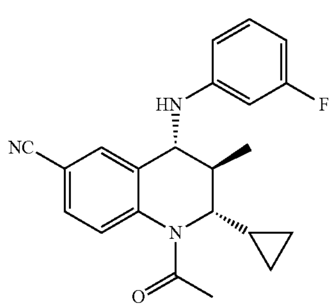 [SMILES: CC(=O)N1c2ccc(C#N)cc2[C@H](Nc2cccc(F)c2)[C@@H](C)[C@@H]1C1CC1] | 51 | 54 | 364 | 1.14 (2 min Formic) |

-continued

| Ex No. | Name | Structure | Mass (mg) | Yield (%) | [MH]⁺ | Rt (min) (LCMS Method) |
|---|---|---|---|---|---|---|
| 308 | (2S,3R,4R)-1-acetyl-2-cyclopropyl-4-((4-methoxyphenyl)amino)-3-methyl-1,2,3,4-tetrahydroquinoline-6-carbonitrile | 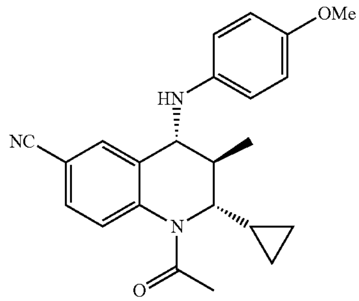 [SMILES: COc1ccc(N[C@H]2c3cc(C#N)ccc3N(C(C)=O)[C@@H](C3CC3)[C@@H]2C)cc1] | 45 | 65 | 376 | 1.11 (2 min Formic) |
| 309 | (2S,3R,4R)-1-acetyl-2-cyclopropyl-4-((3-ethoxyphenyl)amino)-3-methyl-1,2,3,4-tetrahydroquinoline-6-carbonitrile | 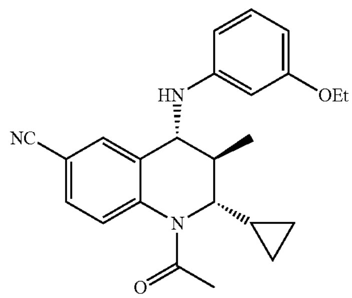 [SMILES: CCOc1cccc(N[C@H]2c3cc(C#N)ccc3N(C(C)=O)[C@@H](C3CC3)[C@@H]2C)c1] | 36 | 50 | 390 | 1.19 (2 min Formic) |

The following examples were prepared in a similar manner to Intermediate 161 using an SnAr reaction with DIPEA to couple the appropriate aryl fluoride with Intermediate 231.

| Ex No. | Name | Structure | Mass (mg) | Yield (%) | [MH]⁺ | Rt (min) (LCMS Method) |
|---|---|---|---|---|---|---|
| 310 | (2S,3R,4R)-1-acetyl-2-cyclopropyl-3-methyl-4-(pyrimidin-2-ylamino)-1,2,3,4-tetrahydroquinoline-6-carbonitrile | 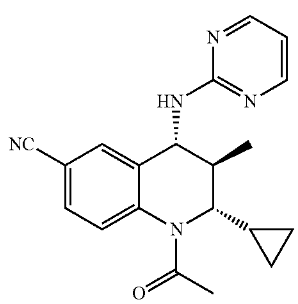 [SMILES: CC(=O)N1c2ccc(C#N)cc2[C@H](Nc2ncccn2)[C@@H](C)[C@@H]1C1CC1] | 102 | 61 | 348 | 0.84 (2 min Formic) |
| 311 | (2S,3R,4R)-1-acetyl-4-((3-cyanopyridin-2-yl)amino)-2-cyclopropyl-3-methyl-1,2,3,4-tetrahydroquinoline-6-carbonitrile | 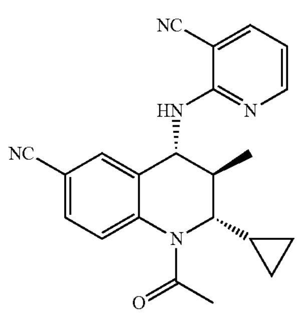 [SMILES: CC(=O)N1c2ccc(C#N)cc2[C@H](Nc2ncccc2C#N)[C@@H](C)[C@@H]1C1CC1] | 109 | 61 | 365 | 1.01 (2 min Formic) |

Example 312: (2S,3R,4R)-1-acetyl-2-cyclopropyl-4-((6-(hydroxymethyl)pyridin-2-yl)amino)-3-methyl-1,2,3,4-tetrahydroquinoline-6-carbonitrile

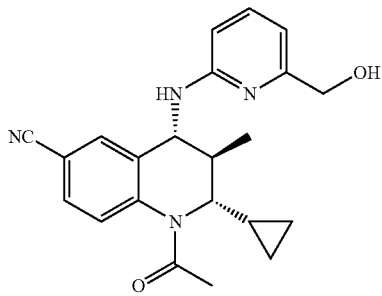 [SMILES: CC(=O)N1c2ccc(C#N)cc2[C@H](Nc2cccc(CO)n2)[C@@H](C)[C@@H]1C1CC1]

A solution of (2S,3R,4R)-1-acetyl-4-((6-(((tert-butyldimethylsilyl)oxy)methyl)pyridin-2-yl)amino)-2-cyclopropyl-3-methyl-1,2,3,4-tetrahydroquinoline-6-carbonitrile (for a preparation see Intermediate 232, 50 mg, 0.102 mmol) in anhydrous THF (0.5 mL) was treated with TBAF (0.5 mL, 0.500 mmol, 1 M solution in THF) and the mixture allowed to stand at rt for 1.5 h. The reaction mixture was evaporated in vacuo and the residue purified by MDAP (HpH). The appropriate fractions were combined and the solvent removed by rotary evaporation to give the crude product as a white solid. This was loaded in DCM (2 mL) and purified by flash chromatography on a silica cartridge (25 g) using a gradient of 0-15% MeOH in DCM over 10 CV. The appropriate fractions were combined and the solvent removed by rotary evaporation to give the title compound as a white solid (51 mg, 0.135 mmol, 98%). LCMS (2 min Formic): Rt=0.62 min, [MH]⁺=377.

Example 313: 2-(((2S,3R,4R)-1-acetyl-6-cyano-2-cyclopropyl-3-methyl-1,2,3,4-tetrahydroquinolin-4-yl)amino)nicotinic Acid

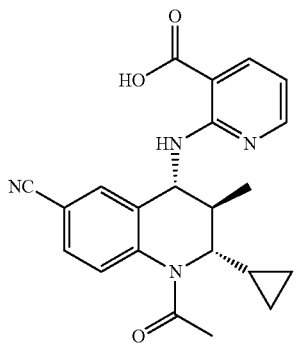

A solution of methyl 2-(((2S,3R,4R)-1-acetyl-6-cyano-2-cyclopropyl-3-methyl-1,2,3,4-tetrahydroquinolin-4-yl)amino)nicotinate (for a preparation see Intermediate 242, 65 mg, 0.161 mmol) and LiOH (11.55 mg, 0.482 mmol) in tetrahydrofuran (1 mL) and water (1 mL) was stirred in a closed vessel at rt for 16 h. The solution was diluted with HCl solution (5 mL, 0.5 M) and washed with DCM (3×5 mL). The organic layers were combined and concentrated in vacuo to give 2-(((2S,3R,4R)-1-acetyl-6-cyano-2-cyclopropyl-3-methyl-1,2,3,4-tetrahydroquinolin-4-yl)amino)nicotinic acid (59 mg, 0.151 mmol, 94% yield). LCMS (2 min HpH): Rt=0.65 min, [MH]⁺=391.

Example 314: 2-(((2S,3R,4R)-1-acetyl-6-cyano-2-cyclopropyl-3-methyl-1,2,3,4-tetrahydroquinolin-4-yl)amino)nicotinamide

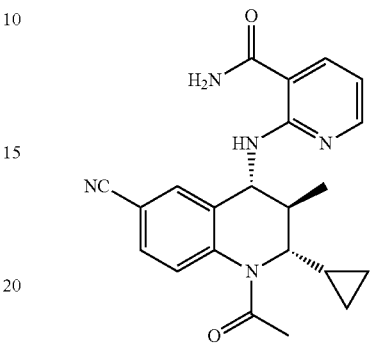

A solution of 2-(((2S,3R,4R)-1-acetyl-6-cyano-2-cyclopropyl-3-methyl-1,2,3,4-tetrahydroquinolin-4-yl)amino)nicotinic acid (for a preparation see Example 313, 50 mg, 0.128 mmol), HATU (63.3 mg, 0.166 mmol), DIPEA (0.089 mL, 0.512 mmol) and ammonium chloride (20.55 mg, 0.384 mmol) in N,N-dimethylformamide (1 mL) was stirred in a closed vessel at rt for 20 min. The solvent was evaporated under a stream of nitrogen, the residue was then dissolved in 1:1 MeOH:DMSO (1 mL) and purified by MDAP (Formic). The appropriate fractions were combined and concentrated in vacuo to give the product (29.2 mg, 0.075 mmol, 59%). LCMS (2 min HpH): Rt=0.88 min, [MH]⁺=390.

Example 315: (2S,3R,4R)-1-acetyl-2-cyclopropyl-3-methyl-4-((6-(piperazin-1-ylmethyl)pyridin-2-yl)amino)-1,2,3,4-tetrahydroquinoline-6-carbonitrile

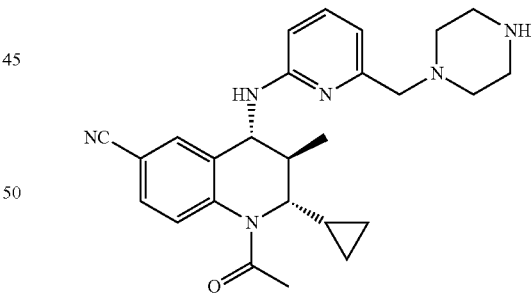

In a 50 mL RB flask, 4M HCl in 1,4-dioxane (0.335 mL, 1.338 mmol) was added to a stirred solution of tert-butyl 4-((6-(((2S,3R,4R)-1-acetyl-6-cyano-2-cyclopropyl-3-methyl-1,2,3,4-tetrahydroquinolin-4-yl)amino)pyridin-2-yl)methyl)piperazine-1-carboxylate (for a preparation see Intermediate 234, 24.3 mg, 0.045 mmol) in 1,4-dioxane (3 mL). The resulting solution was left stirring for 1 h at rt. Further 4M HCl in 1,4-dioxane (0.167 mL, 0.669 mmol) was added and reaction mixture left stirring at rt for 2 h. The volatiles were removed under reduced pressure to afford the crude product as a yellow gum (30.5 mg). The resulting crude product was dissolved in MeOH and loaded onto a 5 g SCX cartridge, this was washed with methanol (3 CV) and then flushed with MeOH/NH₃ (2 M, 3CV). The ammonia fractions were combined and the volatiles removed under reduced pressure to afford the title compound as a yellow gum (23.4 mg). An MDAP was carried out to further purify the compound. Accordingly, the sample was dissolved in MeOH (0.9 mL) and purified by MDAP (Formic). The appropriate fractions were combined and the solvent was evaporated in vacuo to give the required product (12.3 mg). LCMS (2 min Formic): Rt=0.55 min, [MH]⁺=445.

Example 316: 6-(((2S,3R,4R)-1-acetyl-6-cyano-2-cyclopropyl-3-methyl-1,2,3,4-tetrahydroquinolin-4-yl)amino)picolinamide

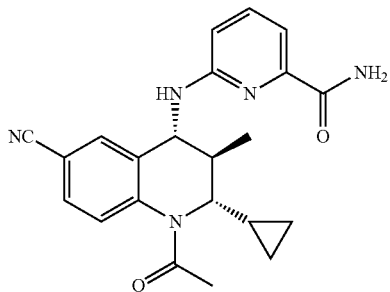 [SMILES: CC(=O)N1c2ccc(C#N)cc2[C@H](Nc2cccc(C(N)=O)n2)[C@@H](C)[C@@H]1C1CC1]

To a reaction vessel, 6-(((2S,3R,4R)-1-acetyl-6-cyano-2-cyclopropyl-3-methyl-1,2,3,4-tetrahydroquinolin-4-yl)amino)picolinic acid (for a preparation see Intermediate 244, 200 mg, 0.512 mmol) and HATU (390 mg, 1.024 mmol) were taken up in N,N-dimethylformamide (4 mL). DIPEA (0.358 mL, 2.049 mmol) was added and the reaction left to stir for 1 min at rt. Ammonium chloride (41.1 mg, 0.768 mmol) was then added and the reaction left to stir at rt for 45 min and left to stand for 16 h. The reaction solution was diluted with ethyl acetate (35 mL) and washed with 10% LiCl (aq, 2×40 mL) before being dried through a hydrophobic frit and concentrated in vacuo to give the crude product as a brown solid. This was purified by flash chromatography using a Biotage SNAP (10 g) silica cartridge, eluting with 0-3.5% methanol/DCM. The fractions containing product were combined and concentrated in vacuo to give the desired product (109 mg). This was still impure so was redissolved in 1:1 MeOH:DMSO (1 mL) and purified by MDAP (Formic). The solvent was evaporated in vacuo to give the desired product as an off white solid. This was re-taken up in methanol and eluted through a pre-equilibrated —NH₂ SPE column (2 g), the solution was then concentrated in vacuo to give the desired product (36 mg) as an off white solid.

LCMS (2 min Formic): Rt=0.85 min, [MH]⁺=390.

Example 317: (2S,3R,4R)-1-acetyl-2-cyclopropyl-4-((3-(hydroxymethyl)pyridin-2-yl)amino)-3-methyl-1,2,3,4-tetrahydroquinoline-6-carbonitrile

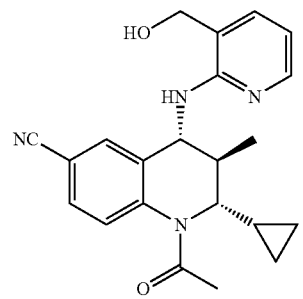 [SMILES: CC(=O)N1c2ccc(C#N)cc2[C@H](Nc2ncccc2CO)[C@@H](C)[C@@H]1C1CC1]

A solution of methyl 2-(((2S,3R,4R)-1-acetyl-6-cyano-2-cyclopropyl-3-methyl-1,2,3,4-tetrahydroquinolin-4-yl)amino)nicotinate (for a preparation see Intermediate 242, 400 mg, 0.989 mmol), calcium chloride (220 mg, 1.978 mmol) and NaBH₄ (748 mg, 19.78 mmol) in tetrahydrofuran (5 mL) and ethanol (2.5 mL) was stirred under nitrogen at 65° C. for 1 h. The reaction mixture was concentrated in vacuo and partitioned between ethyl acetate (8 mL) and water (8 mL). The organic layer was further washed with water (2×8 mL) and concentrated in vacuo to give the crude product (400 mg). The crude product was dissolved in 1:1 MeOH:DMSO (2×3 mL) and purified by MDAP (HpH). The appropriate fractions were combined and concentrated in vacuo to give the product (89 mg, 0.236 mmol, 24%). LCMS (2 min Formic): Rt=0.62 min, [MH]⁺=377.

Example 318: (2S,3R,4R)-1-acetyl-4-((6-(2-aminoethoxy)pyridin-2-yl)amino)-2-cyclopropyl-3-methyl-1,2,3,4-tetrahydroquinoline-6-carbonitrile

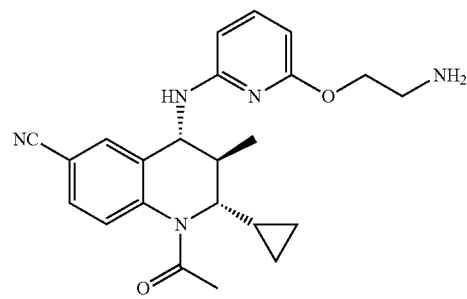 [SMILES: CC(=O)N1c2ccc(C#N)cc2[C@H](Nc2cccc(OCCN)n2)[C@@H](C)[C@@H]1C1CC1]

A mixture of (2S,3R,4R)-1-acetyl-4-amino-2-cyclopropyl-3-methyl-1,2,3,4-tetrahydroquinoline-6-carbonitrile (for a preparation see Intermediate 231, 80 mg, 0.296 mmol), sodium tert-butoxide (59.8 mg, 0.622 mmol), Pd₂(dba)₃ (27.1 mg, 0.030 mmol), QPhos (21.12 mg, 0.030 mmol) and tert-butyl (2-((6-bromopyridin-2-yl)oxy)ethyl)carbamate (for a preparation see Intermediate 245, 94 mg, 0.296 mmol) in anhydrous toluene (1 mL) was stirred under nitrogen at 70° C. for 15 h. The reaction mixture was diluted with EtOAc (5 mL) and filtered through a Celite cartridge. The cartridge was washed with EtOAc (15 mL) and the filtrate evaporated in vacuo. The residue was dissolved in MeOH (2 mL) and applied to a MeOH-preconditioned SCX-2 cartridge (2 g). The cartridge was washed with MeOH (12 mL), followed by 2 M NH₃/MeOH (12 mL). The basic wash was evaporated in vacuo and the residue dissolved in anhydrous 1,4-dioxane (0.5 mL). The solution was treated with 4 M HCl in 1,4-dioxane (0.5 mL, 16.46 mmol) and left to stand in a stoppered vessel for 1 h. The reaction mixture was evaporated in vacuo and the residue purified by MDAP (HpH). The appropriate fractions were combined and the solvent removed by rotary evaporation to give the title compound as a light brown solid (46 mg, 0.113 mmol, 38%). LCMS (2 min Formic): Rt=0.72 min, [MH]⁺=406.

Example 319: N-(2-((6-(((2S,3R,4R)-1-acetyl-6-cyano-2-cyclopropyl-3-methyl-1,2,3,4-tetrahydroquinolin-4-yl)amino)pyridin-2-yl)oxy)ethyl)acetamide

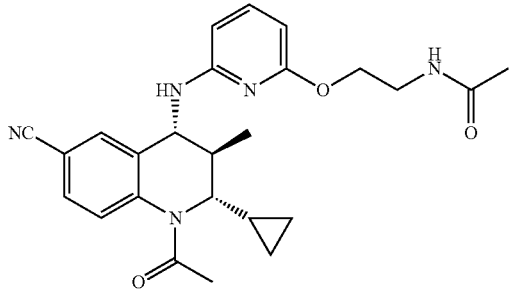 [SMILES: CC(=O)NCCOc1cccc(N[C@H]2c3cc(C#N)ccc3N(C(C)=O)[C@@H](C3CC3)[C@@H]2C)n1]

To (2S,3R,4R)-1-acetyl-4-((6-(2-aminoethoxy)pyridin-2-yl)amino)-2-cyclopropyl-3-methyl-1,2,3,4-tetrahydroquinoline-6-carbonitrile (for a preparation see Example 318, 30 mg, 0.074 mmol) and pyridine (12 µL, 0.148 mmol) in DCM (0.25 mL) was added acetyl chloride (0.023 mL, 0.327 mmol) and the mixture stirred in a stoppered vessel at rt for 1.5 h. Further acetyl chloride (4 µL) was added and the mixture stirred in a stoppered vessel at rt for 1.5 h. The reaction mixture was evaporated under a stream of nitrogen and the residue was purified by MDAP (Formic). The appropriate fractions were combined and the solvent evaporated in vacuo to give the title compound as an off-white solid (22 mg, 0.049 mmol, 66%). LCMS (2 min Formic): Rt=0.91 min, [MH]⁺=448.

Example 320: (2S,3R,4R)-1-acetyl-2-cyclopropyl-4-((3-(hydroxymethyl)phenyl)amino)-3-methyl-1,2,3,4-tetrahydroquinoline-6-carbonitrile

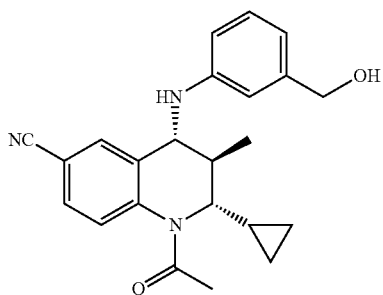 [SMILES: CC(=O)N1c2ccc(C#N)cc2[C@H](Nc2cccc(CO)c2)[C@@H](C)[C@@H]1C1CC1]

To a solution of (2S,3R,4R)-1-acetyl-4-((3-(((tert-butyldimethylsilyl)oxy)methyl)phenyl)amino)-2-cyclopropyl-3-methyl-1,2,3,4-tetrahydroquinoline-6-carbonitrile (for a preparation see Intermediate 239, 66.1 mg, 0.135 mmol) in tetrahydrofuran (1.5 mL), was added 1M TBAF in THF (0.675 mL, 0.675 mmol) and the reaction stirred under nitrogen for 1 h. The reaction was then concentrated and the sample was redissolved in 1:1 MeOH:DMSO (1 mL) and purified by MDAP (Formic). The solvent was concentrated to give the required product (25.2 mg, 0.067 mmol, 50%) as a colourless oil. LCMS (2 min Formic): Rt=0.96 min, [MH]⁺=376.

Example 321: (2S,3R,4R)-1-acetyl-4-((2-aminophenyl)amino)-2-cyclopropyl-3-methyl-1,2,3,4-tetrahydroquinoline-6-carbonitrile

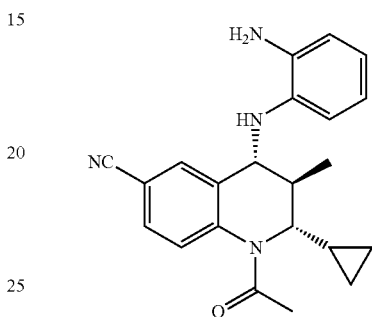

To a suspension of (2S,3R,4R)-1-acetyl-2-cyclopropyl-3-methyl-4-((2-nitrophenyl)amino)-1,2,3,4-tetrahydroquinoline-6-carbonitrile (for a preparation see Intermediate 246, 90 mg, 0.231 mmol) in isopropanol (11 mL) under a nitrogen atmosphere was added iron powder (154 mg, 2.77 mmol) and ammonium chloride (1.233 mg, 0.023 mmol). The flask was heated to 100° C. and stirred for 2 h. Further ammonium chloride (1.233 mg, 0.023 mmol) was added and the reaction heated to 115° C. for 2 h. The heat on the reaction was reduced to 105° C. and the reaction allowed to stir at this temperature for 16 h. The reaction mixture was diluted with MeOH and filtered. The residue was washed with further MeOH (2×20 mL) and the combined filtrates concentrated in vacuo, to afford a brown residue. This was taken up in DCM and added to a SNAP silica cartridge (10 g) and was purified by flash chromatography on a Biotage SP4, eluting with 0→60% EtOAc/cyclohexane. The appropriate fractions were collected and concentrated in vacuo to afford the desired product as a beige solid (69 mg, 0.191 mmol, 83%). LCMS (2 min Formic): Rt=1.04 min, [MH]⁺=361.

Example 322: (2S,3R,4R)-1-acetyl-2-cyclopropyl-4-((3-(2-hydroxyethoxy)phenyl)amino)-3-methyl-1,2,3,4-tetrahydroquinoline-6-carbonitrile

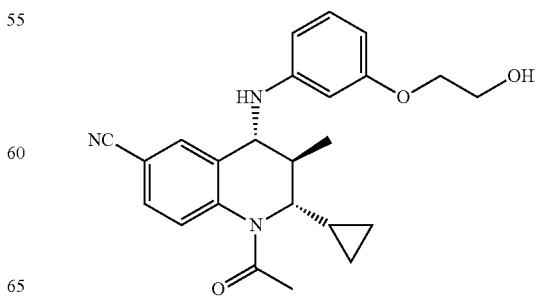

A solution of (2S,3R,4R)-1-acetyl-4-((3-(2-((tert-butyldimethylsilyl)oxy)ethoxy)phenyl)amino)-2-cyclopropyl-3-methyl-1,2,3,4-tetrahydroquinoline-6-carbonitrile (for a preparation see Intermediate 249, 231 mg, 0.444 mmol) in anhydrous THF (1 mL) was treated with TBAF (1 M solution in THF) (2.0 mL, 2.000 mmol) and the mixture allowed to stand at rt for 45 min. The reaction mixture was evaporated in vacuo and the residue purified by MDAP (HpH). The appropriate fractions were combined and the solvent removed by rotary evaporation to give the desired product which was still impure. This was loaded in DCM (1 mL) and purified on a silica cartridge (25 g) using a gradient of 0-15% MeOH in DCM over 10 CV. The appropriate fractions were combined and the solvent evaporated in vacuo to give the desired product which was still impure. This was further purified by MDAP (Formic). The appropriate fractions were combined and the solvent removed by rotary evaporation to give the title compound as a white foam (91 mg, 0.224 mmol, 51%).

LCMS (2 min Formic): Rt=0.95 min, [MH]$^+$=406.

Example 323: (2S,3R,4R)-1-acetyl-4-((3-(2-aminoethoxy)phenyl)amino)-2-cyclopropyl-3-methyl-1,2,3,4-tetrahydroquinoline-6-carbonitrile

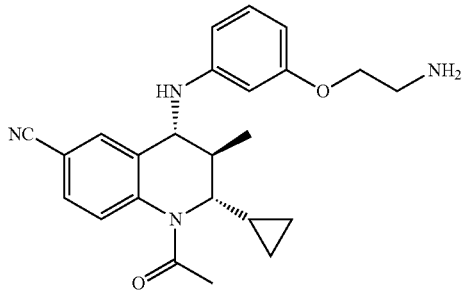 [SMILES: CC(=O)N1c2ccc(C#N)cc2[C@H](Nc2cccc(OCCN)c2)[C@@H](C)[C@@H]1C1CC1]

A solution of tert-butyl (2-(3-(((2S,3R,4R)-1-acetyl-6-cyano-2-cyclopropyl-3-methyl-1,2,3,4-tetrahydroquinolin-4-yl)amino)phenoxy)ethyl)carbamate (for a preparation see Intermediate 251, 123 mg, 0.244 mmol) in 1,4-dioxane (0.5 mL) was treated with 4 M HCl in 1,4-dioxane (1 mL, 4.00 mmol) and the mixture left to stand in a stoppered vessel for 16 h. The reaction mixture was evaporated in vacuo and the gum purified by MDAP (HpH). The appropriate fractions were combined and the solvent evaporated in vacuo to give the title compound as a light brown solid (49 mg, 0.121 mmol, 50%).

LCMS (2 min Formic): Rt=0.74 min, [MH]$^+$=405.

Example 324: (2S,3R,4R)-1-acetyl-2-cyclopropyl-4-((4-(hydroxymethyl)pyrimidin-2-yl)amino)-3-methyl-1,2,3,4-tetrahydroquinoline-6-carbonitrile

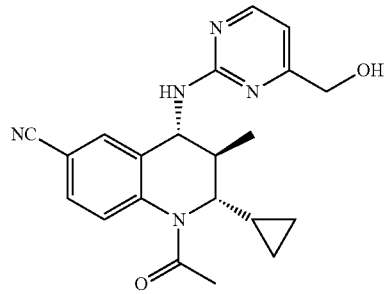 [SMILES: CC(=O)N1c2ccc(C#N)cc2[C@H](Nc2nccc(CO)n2)[C@@H](C)[C@@H]1C1CC1]

(2S,3R,4R)-1-Acetyl-4-((4-(((tert-butyldimethylsilyl)oxy)methyl)pyrimidin-2-yl)amino)-2-cyclopropyl-3-methyl-1,2,3,4-tetrahydroquinoline-6-carbonitrile (for a preparation see Intermediate 254, 30 mg, 0.061 mmol) was taken up in 1M TBAF in THF (1 mL, 1.00 mmol) and allowed to stir at rt for 1 h. The reaction was concentrated and purified using a SP4 SNAP silica (10 g) column, eluting with 0-100% EtOAc:cyclohexane—nothing UV active was collected. The column was run again, eluting with 0-10% 2M NH$_3$/MeOH:DCM—nothing UV active was collected. The waste column eluent was concentrated to an orange gum which was purified by MDAP (Formic). One fraction was collected which was concentrated and dried to give the product (2 mg, 5.30 µmol, 9%), as a colourless gum.

LCMS (2 min Formic): Rt=0.75 min, [MH]$^+$=378.

Example 325: (2S,3R,4R)-1-acetyl-2-cyclopropyl-4-((5-isopropylpyrimidin-2-yl)amino)-3-methyl-1,2,3,4-tetrahydroquinoline-6-carbonitrile

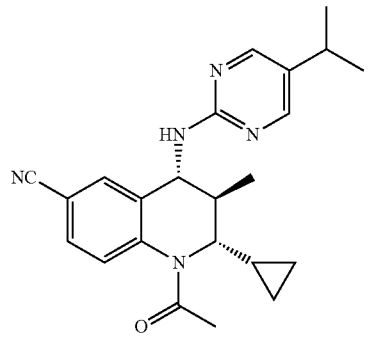 [SMILES: CC(=O)N1c2ccc(C#N)cc2[C@H](Nc2ncc(C(C)C)cn2)[C@@H](C)[C@@H]1C1CC1]

A mixture of (2S,3R,4R)-1-acetyl-4-amino-2-cyclopropyl-3-methyl-1,2,3,4-tetrahydroquinoline-6-carbonitrile (for a preparation see Intermediate 231, 80 mg, 0.297 mmol), 18-crown-6 (38 mg, 0.144 mmol), potassium fluoride (26 mg, 0.448 mmol) and 2-chloro-5-isopropylpyrimidine (52 mg, 0.332 mmol) was suspended in anhydrous DMSO (5 mL) and treated with DIPEA (0.086 mL, 0.495 mmol). The mixture was stirred under nitrogen at 140° C. for 16 h. The reaction was allowed to cool to rt and purified by formic MDAP. The appropriate fractions were evaporated under a stream of nitrogen to give the desired product as a yellow solid. LCMS (2 min Formic): Rt=1.05 min, [MH]$^+$=390.

Example 326: (2S,3R,4R)-1-acetyl-4-((5-chloro-6-(hydroxymethyl)pyridin-2-yl)amino)-2-cyclopropyl-3-methyl-1,2,3,4-tetrahydroquinoline-6-carbonitrile

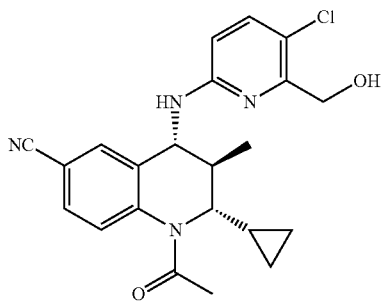 [SMILES: CC(=O)N1c2ccc(C#N)cc2[C@H](Nc2ccc(Cl)c(CO)n2)[C@@H](C)[C@@H]1C1CC1]

To a solution of (2S,3R,4R)-1-acetyl-4-((6-(((tert-butyldimethylsilyl)oxy)methyl)-5-chloropyridin-2-yl)amino)-2-cyclopropyl-3-methyl-1,2,3,4-tetrahydroquinoline-6-carbonitrile (for a preparation see Intermediate 258, 60 mg, 0.114 mmol) in tetrahydrofuran (1 mL), was added TBAF (0.571 mL, 0.571 mmol, 1M in THF) and the reaction allowed to stir under nitrogen at rt for 2 h. The reaction was concentrated and partitioned between EtOAc and water. The aqueous layer was further extracted with EtOAc and the organic layers combined, washed with water and dried over a hydrophobic frit. The sample was concentrated and loaded in dichloromethane and purified by flash chromatography on SP4 silica (10 g) using 10-50% EtOAc/dichloromethane over 10CV. The appropriate fractions were combined and concentrated to give the product (36 mg, 0.088 mmol, 77%) as a colourless oil. LCMS (2 min Formic): Rt=1.00 min, [MH]$^+$=411.

Example 327: (2S,3R,4R)-1-acetyl-2-cyclopropyl-4-((5-fluoropyridin-2-yl)amino)-3-methyl-1,2,3,4-tetrahydroquinoline-6-carboxylic Acid

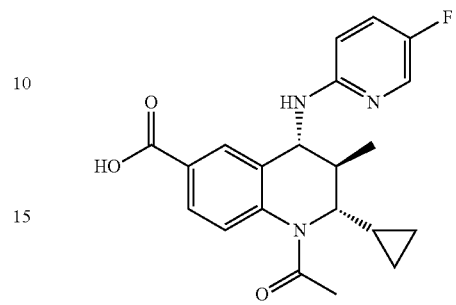

A solution of (2S,3R,4R)-ethyl 1-acetyl-4-amino-2-cyclopropyl-3-methyl-1,2,3,4-tetrahydroquinoline-6-carboxylate (for a preparation see Intermediate 225, 515 mg, 1.628 mmol), DavePhos (64.1 mg, 0.163 mmol), 2-bromo-5-fluoropyridine (344 mg, 1.953 mmol), Pd$_2$(dba)$_3$ (74.5 mg, 0.081 mmol) and sodium tert-butoxide (469 mg, 4.88 mmol) in 1,4-dioxane (30 mL) was stirred under nitrogen at 90° C. for 1 h. The reaction mixture was cooled to rt and then filtered through celite and the celite washed with ethyl acetate (50 mL). The combined filtrates were concentrated in vacuo and taken up in EtOAc (75 mL) and saturated sodium bicarbonate solution (20 mL). The product entered the aqueous layer and the organic layer was discarded. The aqueous layer was acidified to pH2 with 2M hydrochloric acid (10 mL) and evaporated in vacuo. The crude product was added to a silica gel column and was eluted with 0-20% 2M NH$_3$ in methanol/DCM. The desired fractions were combined and concentrated to give the product (45 mg, 0.117 mmol, 7%).

LCMS (2 min Formic): Rt=0.80 min, [MH]$^+$=384.

The following example was prepared in a similar manner to Example 327 using Pd$_2$(dba)$_3$, DavePhos and NaOtBu to couple the appropriate aryl halide to Intermediate 261.

| Ex No. | Name | Structure | Mass (mg) | Yield (%) | [MH]$^+$ | Rt (min) (LCMS Method) |
|---|---|---|---|---|---|---|
| 328 | (2S,3R,4R)-1-acetyl-2-ethyl-4-((5-fluoropyridin-2-yl)amino)-3-methyl-1,2,3,4-tetrahydroquinoline-6-carboxylic acid, TFA salt | 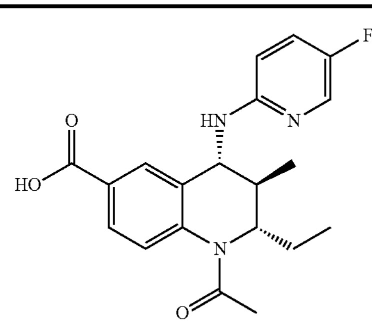 | 310 | 37 | 372 | 0.64 (2 min TFA) |

Example 329: (2S,3R,4R)-1-acetyl-4-((4-cyano-3-methylphenyl)amino)-2-cyclopropyl-3-methyl-1,2,3,4-tetrahydroquinoline-6-carboxylic Acid

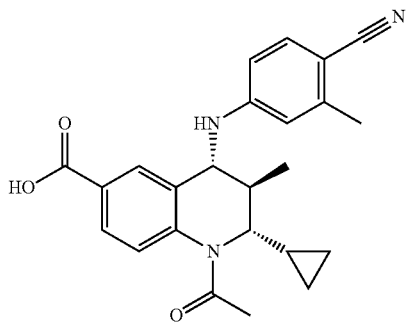 [SMILES: CC(=O)N1c2ccc(C(=O)O)cc2[C@H](Nc2ccc(C#N)c(C)c2)[C@@H](C)[C@@H]1C1CC1]

(2S,3R,4R)-ethyl 1-acetyl-4-((4-cyano-3-methylphenyl)amino)-2-cyclopropyl-3-methyl-1,2,3,4-tetrahydroquinoline-6-carboxylate (for a preparation see Intermediate 262, 200 mg, 0.463 mmol) was dissolved in 1,4-dioxane (2 mL). Water (2.0 mL) was added followed by LiOH (22.20 mg, 0.927 mmol) and reaction mixture stirred at rt for ~3 h. The dioxane was removed in vacuo and acetic acid (0.053 mL, 0.927 mmol) was added. The reaction mixture was partitioned between DCM and water. The organic layer was separated and the aqueous layer extracted with DCM (3×30 mL). The combined organic layers were dried ($Na_2SO_4$) and concentrated to give the product (153 mg, 0.379 mmol, 82%) as a pale orange solid. LCMS (2 min Formic): Rt=0.96 min, $[MH]^+$=404.

The following examples were prepared in a similar manner to Example 329 using $Pd_2(dba)_3$, QPhos and $Cs_2CO_3$ to couple the appropriate aryl halide to Intermediate 225 (2-cPr) or 263 (2-Et); followed by hydrolysis with LiOH.

| Ex No. | Name | Structure | Mass (mg) | Yield (%) | $[MH]^+$ | Rt (min) (LCMS Method) |
|---|---|---|---|---|---|---|
| 330 | (2S,3R,4R)-1-acetyl-4-((4-cyano-3-fluorophenyl)amino)-2-cyclopropyl-3-methyl-1,2,3,4-tetrahydroquinoline-6-carboxylic acid | 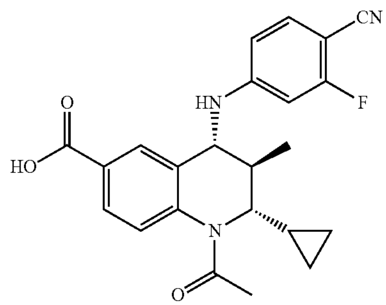 [SMILES: CC(=O)N1c2ccc(C(=O)O)cc2[C@H](Nc2ccc(C#N)c(F)c2)[C@@H](C)[C@@H]1C1CC1] | 105 | 96 | 406 ([M − H]⁻) | 0.95 (2 min Formic) |
| 331 | (2S,3R,4R)-1-acetyl-4-((4-cyanophenyl)amino)-2-ethyl-3-methyl-1,2,3,4-tetrahydroquinoline-6-carboxylic acid | 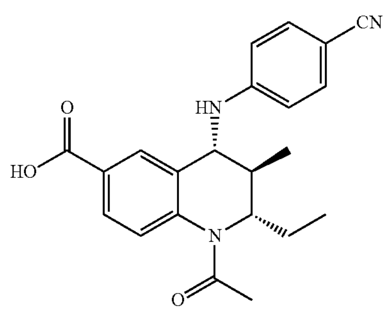 [SMILES: CC[C@H]1[C@H](C)[C@@H](Nc2ccc(C#N)cc2)c2cc(C(=O)O)ccc2N1C(C)=O] | 92 | 92 | 378 | 0.89 (2 min Formic) |
| 332 | (2S,3R,4)-1-acetyl-2-cyclopropyl-3-methyl-4-((4-(methylsulfonyl)phenyl)amino)-1,2,3,4-tetrahydroquinoline-6-carboxylic acid | 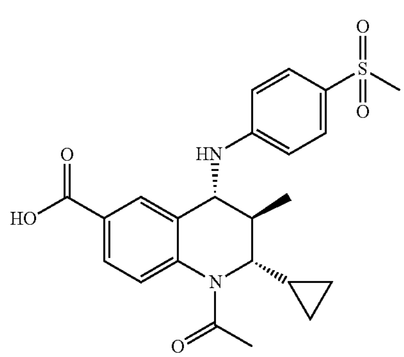 [SMILES: CC(=O)N1c2ccc(C(=O)O)cc2[C@H](Nc2ccc(S(C)(=O)=O)cc2)[C@@H](C)[C@@H]1C1CC1] | 54 | 92 | 441 | 0.63 (2 min HpH) |

| Ex No. | Name | Structure | Mass (mg) | Yield (%) | [MH]+ | Rt (min) (LCMS Method) |
|---|---|---|---|---|---|---|
| 333 | (2S,3R,4R)-1-acetyl-4-((4-chloropyridin-2-yl)amino)-2-cyclopropyl-3-methyl-1,2,3,4-tetrahydroquinoline-6-carboxylic acid | 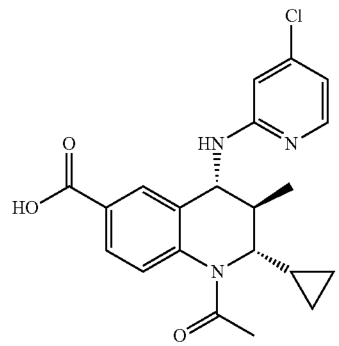 [SMILES: CC(=O)N1c2ccc(C(=O)O)cc2[C@H](Nc2cc(Cl)ccn2)[C@@H](C)[C@@H]1C1CC1] | 49 | 79 | 400 | 0.82 (2 min Formic) |
| 334 | (2S,3R,4R)-1-acetyl-4-((4-cyano-2-methoxyphenyl)amino)-2-cyclopropyl-3-methyl-1,2,3,4-tetrahydroquinoline-6-carboxylic acid | 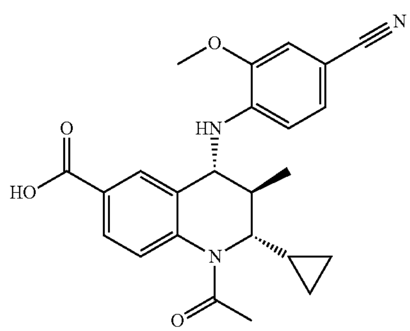 [SMILES: COc1cc(C#N)ccc1N[C@H]1c2cc(C(=O)O)ccc2N(C(C)=O)[C@@H](C2CC2)[C@@H]1C] | 43 | 100 | 420 | 0.99 (2 min Formic) |

Example 335: (2S,3R,4R)-1-acetyl-2-ethyl-3-methyl-4-((4-methylpyrimidin-2-yl)amino)-1,2,3,4-tetrahydroquinoline-6-carboxylic Acid

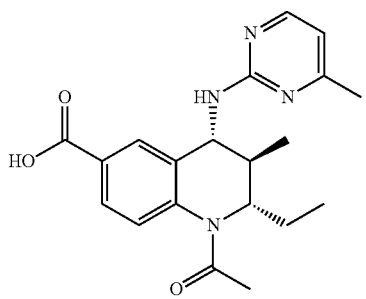 [SMILES: CC[C@H]1[C@H](C)[C@@H](Nc2nccc(C)n2)c2cc(C(=O)O)ccc2N1C(C)=O]

(2S,3R,4R)-Ethyl-1-acetyl-2-ethyl-3-methyl-4-((4-methylpyrimidin-2-yl)amino)-1,2,3,4-tetrahydroquinoline-6-carboxylate (for a preparation see Intermediate 263, 439 mg, 1.107 mmol) was taken up in tetrahydrofuran (THF) (5 mL) and water (5.00 mL). Lithium hydroxide (66.3 mg, 2.77 mmol) was added and the reaction stirred for ~2 h at rt. 2M HCl(aq) (1.384 mL, 2.77 mmol) was added followed by 10% MeOH/DCM and water. The biphasic mixture was stirred for 5 min and the layers then separated. The aqueous layer was further extracted with 10% MeOH/DCM. After four washes the combined organics were collected, dried (Na$_2$SO$_4$) and concentrated in vacuo to afford the desired product as a yellow solid (375.2 mg, 1.018 mmol, 92%).

LCMS (2 min Formic): Rt=0.70 min, [MH]+=369.

The following examples were prepared in a similar manner to Example 335 using KF, 18-crown-6 and DIPEA to couple the appropriate aryl halide with Intermediate 225; followed by hydrolysis with LiOH.

| Ex No. | Name | Structure | Mass (mg) | Yield (%) | [MH]+ | Rt (min) (LCMS Method) |
|---|---|---|---|---|---|---|
| 336 | (2S,3R,4R)-1-acetyl-2-cyclopropyl-3-methyl-4-(pyrimidin-2-ylamino)-1,2,3,4-tetrahydroquinoline-6-carboxylic acid | 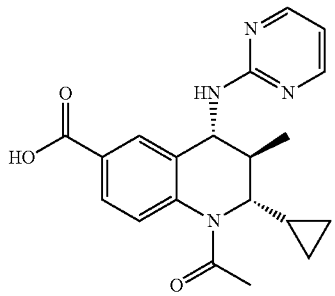 [SMILES: CC(=O)N1c2ccc(C(=O)O)cc2[C@H](Nc2ncccn2)[C@@H](C)[C@@H]1C1CC1] | 775 | 100 | 367 | 0.74 (2 min Formic) |

Example 337: (2S,3R,4R)-1-acetyl-2-cyclopropyl-4-((3-(hydroxymethyl)phenyl)amino)-3-methyl-1,2,3,4-tetrahydroquinoline-6-carboxamide

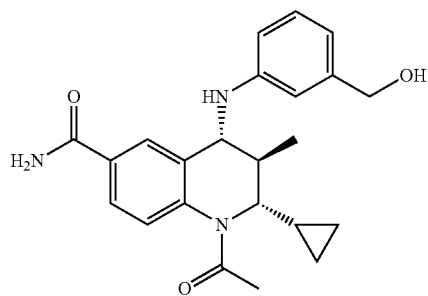 [SMILES: CC(=O)N1c2ccc(C(N)=O)cc2[C@H](Nc2cccc(CO)c2)[C@@H](C)[C@@H]1C1CC1]

To a solution of (2S,3R,4R)-1-acetyl-2-cyclopropyl-4-((3-(hydroxymethyl)phenyl)amino)-3-methyl-1,2,3,4-tetrahydroquinoline-6-carbonitrile (for a preparation see Example 320, 20.2 mg, 0.054 mmol) and potassium carbonate (14.87 mg, 0.108 mmol) in dimethyl sulfoxide (DMSO) (3 mL), was added hydrogen peroxide (0.047 mL, 0.538 mmol) and the reaction stirred under nitrogen for 1 h. The reaction was quenched with 10% sodium thiosulfate (40 mL) and extracted with DCM (2×40 mL). The organic extracts were combined and washed with water. The extracts were then dried over a hydrophobic frit and concentrated in vacuo. The sample was loaded in dichloromethane and purified by chromatography on silica 10 g using a 0-10% methanol-dichloromethane over 25 CV. The appropriate fractions were combined and concentrated to give the required product (19.8 mg, 0.050 mmol, 94%) as an off-white solid. LCMS (2 min Formic): Rt=0.76 min, [MH]+= 394.

The following Examples were prepared in a similar manner to Example 337 by hydrolysis of Examples 300, 323 & 322 using $H_2O_2$.

| Ex No. | Name | Structure | Mass (mg) | Yield (%) | [MH]+ | Rt (min) (LCMS Method) |
|---|---|---|---|---|---|---|
| 338 | (2S,3R,4R)-1-acetyl-4-((5-chloro-4-methylpyrimidin-2-yl)amino)-2-cyclopropyl-3-methyl-1,2,3,4-tetrahydroquinoline-6-carboxamide | 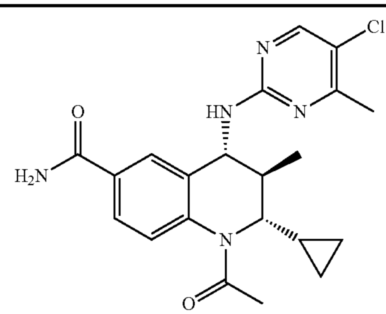 | 12 | 40 | 414 | 0.91 (2 min HpH) |
| 339 | (2S,3R,4R)-1-acetyl-4-((3-(2-aminoethoxy)phenyl)amino)-2-cyclopropyl-3-methyl-1,2,3,4-tetrahydroquinoline-6-carboxamide | 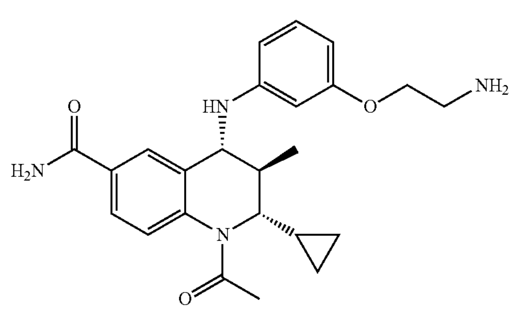 [SMILES: CC(=O)N1c2ccc(C(N)=O)cc2[C@H](Nc2cccc(OCCN)c2)[C@@H](C)[C@@H]1C1CC1] | 22 | 62 | 423 | 0.76 (2 min HpH) |

| Ex No. | Name | Structure | Mass (mg) | Yield (%) | [MH]+ | Rt (min) (LCMS Method) |
|---|---|---|---|---|---|---|
| 340 | (2S,3R,4R)-1-acetyl-2-cyclopropyl-4-((3-(2-hydroxyethoxy)phenyl)amino)-3-methyl-1,2,3,4-tetrahydroquinoline-6-carboxamide | 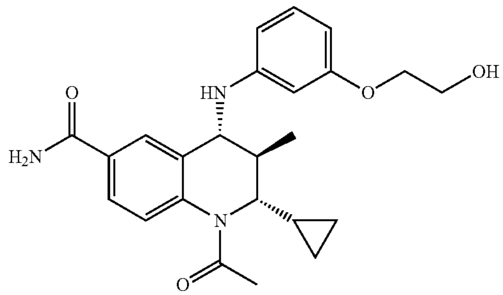 [SMILES: CC(=O)N1c2ccc(C(N)=O)cc2[C@H](Nc2cccc(OCCO)c2)[C@@H](C)[C@@H]1C1CC1] | 50 | 74 | 424 | 0.78 (2 min HpH) |

Example 341: (2S,3R,4R)-1-acetyl-2-cyclopropyl-4-((5-fluoropyridin-2-yl)amino)-3-methyl-1,2,3,4-tetrahydroquinoline-6-carboxamide

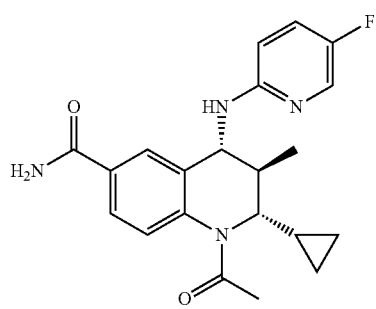 [SMILES: CC(=O)N1c2ccc(C(N)=O)cc2[C@H](Nc2ccc(F)cn2)[C@@H](C)[C@@H]1C1CC1]

To (2S,3R,4R)-1-acetyl-2-cyclopropyl-4-((5-fluoropyridin-2-yl)amino)-3-methyl-1,2,3,4-tetrahydroquinoline-6-carbonitrile (for a preparation see Intermediate 264, 188 mg, 0.516 mmol) in a round bottom flask hydrogen peroxide (0.444 mL, 5.16 mmol), potassium carbonate (143 mg, 1.032 mmol) and dimethyl sulfoxide (DMSO) (3.5 mL) were added. The reaction mixture was stirred at rt for 1 h and was quenched with sodium thiosulphate, diluted with DCM and washed with water. The organic layer was dried, concentrated in vacuo and purified by silica gel column chromatography eluting with a gradient of cyclohexane/ethyl acetate (20%-85%). The cartridge was then flushed with 90% ethyl acetate in cyclohexane to give title compound (137 mg, 63%)

LCMS (2 min Formic): Rt=0.69 min, [MH]+=383.

The following examples were prepared in a similar manner to Example 341 using Pd(QPhos)$_2$ and NaOtBu or Cs$_2$CO$_3$ to couple the appropriate aryl halide with Intermediate 231; followed by hydrolysis with H$_2$O$_2$.

| Ex No. | Name | Structure | Mass (mg) | Yield (%) | [MH]+ | Rt (min) (LCMS Method) |
|---|---|---|---|---|---|---|
| 342 | (2S,3R,4R)-1-acetyl-2-cyclopropyl-4-((3-methoxypyridin-2-yl)amino)-3-methyl-1,2,3,4-tetrahydroquinoline-6-carboxamide | 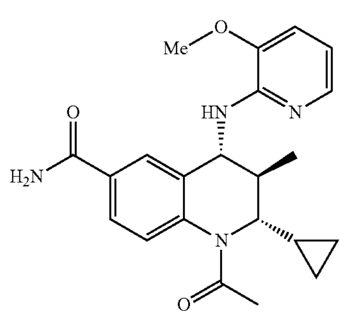 [SMILES: COc1cccnc1N[C@H]1c2cc(C(N)=O)ccc2N(C(C)=O)[C@@H](C2CC2)[C@@H]1C] | 80 | 45 | 395 | 0.56 (2 min Formic) |

-continued

| Ex No. | Name | Structure | Mass (mg) | Yield (%) | [MH]+ | Rt (min) (LCMS Method) |
|---|---|---|---|---|---|---|
| 343 | (2S,3R,4R)-1-acetyl-2-cyclopropyl-3-methyl-4-((4-methylpyridin-2-yl)amino)-1,2,3,4-tetrahydroquinoline-6-carboxamide | 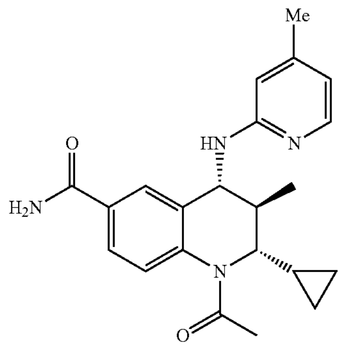 | 44 | 33 | 356 | 0.78 (2 min Formic) |
| 344 | (2S,3R,4R)-1-acetyl-2-cyclopropyl-3-methyl-4-((6-methylpyridin-3-yl)amino)-1,2,3,4-tetrahydroquinoline-6-carboxamide | 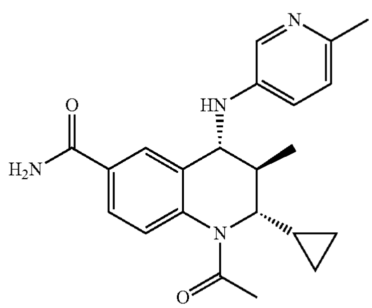 [SMILES: CC(=O)N1c2ccc(C(N)=O)cc2[C@H](Nc2ccc(C)nc2)[C@@H](C)[C@@H]1C1CC1] | 127 | 82 | 379 | 0.54 (2 min Formic) |
| 345 | (2S,3R,4R)-1-acetyl-2-cyclopropyl-3-methyl-4-((5-methylpyridin-2-yl)amino)-1,2,3,4-tetrahydroquinoline-6-carboxamide | 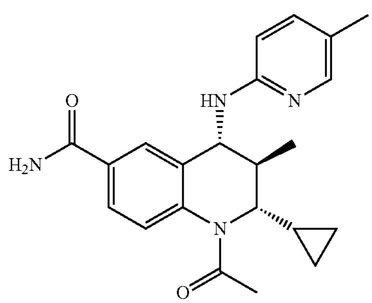 [SMILES: CC(=O)N1c2ccc(C(N)=O)cc2[C@H](Nc2ccc(C)cn2)[C@@H](C)[C@@H]1C1CC1] | 50 | 40 | 379 | 0.55 (2 min Formic) |
| 346 | (2S,3R,4R)-1-acetyl-2-cyclopropyl-3-methyl-4-((3-methylpyridin-2-yl)amino)-1,2,3,4-tetrahydroquinoline-6-carboxamide | 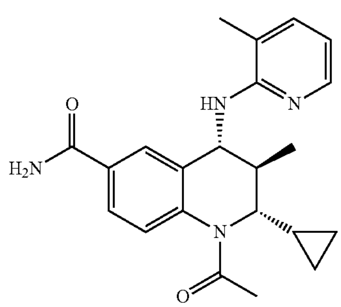 [SMILES: CC(=O)N1c2ccc(C(N)=O)cc2[C@H](Nc2ncccc2C)[C@@H](C)[C@@H]1C1CC1] | 116 | 97 | 379 | 0.54 (2 min Formic) |
| 347 | (2S,3R,4R)-1-acetyl-2-cyclopropyl-3-methyl-4-((6-(morpholinomethyl)pyridin-2-yl)amino)-1,2,3,4-tetrahydroquinoline-6-carboxamide | 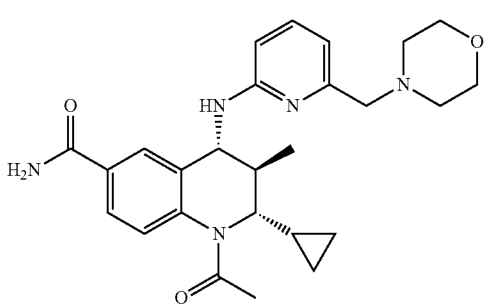 [SMILES: CC(=O)N1c2ccc(C(N)=O)cc2[C@H](Nc2cccc(CN3CCOCC3)n2)[C@@H](C)[C@@H]1C1CC1] | 18 | 91 | 464 | 0.58 (2 min Formic) |

| Ex No. | Name | Structure | Mass (mg) | Yield (%) | [MH]+ | Rt (min) (LCMS Method) |
|---|---|---|---|---|---|---|
| 348 | (2S,3R,4R)-1-acetyl-2-cyclopropyl-4-((5-methoxy-4-methylpyrimidin-2-yl)amino)-3-methyl-1,2,3,4-tetrahydroquinoline-6-carboxamide | 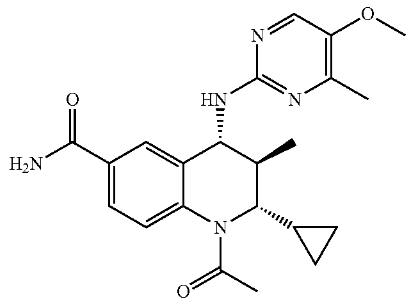 [SMILES: COc1cnc(N[C@H]2c3cc(C(N)=O)ccc3N(C(C)=O)[C@@H](C3CC3)[C@@H]2C)nc1C] | 41 | 50 | 410 | 0.81 (2 min HpH) |
| 349 | (2S,3R,4R)-1-acetyl-2-cyclopropyl-4-((5-methoxypyridin-2-yl)amino)-3-methyl-1,2,3,4-tetrahydroquinoline-6-carboxamide | 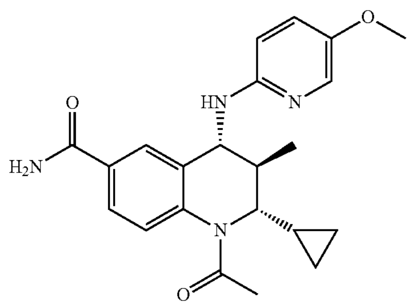 [SMILES: COc1ccc(N[C@H]2c3cc(C(N)=O)ccc3N(C(C)=O)[C@@H](C3CC3)[C@@H]2C)nc1] | 26 | 34 | 377 | 0.69 (2 min Formic) |

The following Examples (350-352) were prepared in a similar manner to Example 341 using PdQPhos)₂ and NaOtBu or Cs₂CO₃ to couple the appropriate protected aryl halide with Intermediate 231; followed by hydrolysis with H₂O₂; followed by a deprotection step as detailed below:

Example 350: (2S,3R,4R)-1-acetyl-2-cyclopropyl-4-((6-(hydroxymethyl)pyridin-2-yl)amino)-3-methyl-1,2,3,4-tetrahydroquinoline-6-carboxamide

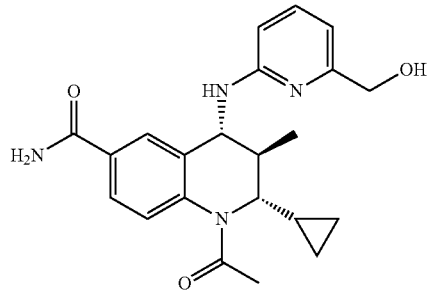

A solution of (2S,3R,4R)-1-acetyl-4-((6-(((tert-butyldimethylsilyl)oxy)methyl)pyridin-2-yl)amino)-2-cyclopropyl-3-methyl-1,2,3,4-tetrahydroquinoline-6-carboxamide (102 mg, 0.201 mmol) in anhydrous THF (0.5 mL) was treated with TBAF (1M solution in THF) (1.0 mL, 1.0 mmol) and the mixture allowed to stand at rt for 45 min. The reaction mixture was evaporated in vacuo and the residue purified by MDAP (HpH) to give crude title compound as a white solid. This solid was dissolved in MeOH and applied to a 1 g MeOH-preconditioned SCX-2 cartridge. The cartridge was washed with MeOH (6 mL) followed by 2M NH₃ in MeOH and the basic wash evaporated under a stream of nitrogen to give title compound as a white solid (39 mg, 0.099 mmol, 49%).

LCMS (2 min Formic): Rt=0.51 min, [MH]⁺=395.

Example 351: (2S,3R,4R)-1-acetyl-2-cyclopropyl-3-methyl-4-((6-(piperazin-1-ylmethyl)pyridin-2-yl)amino)-1,2,3,4-tetrahydroquinoline-6-carboxamide

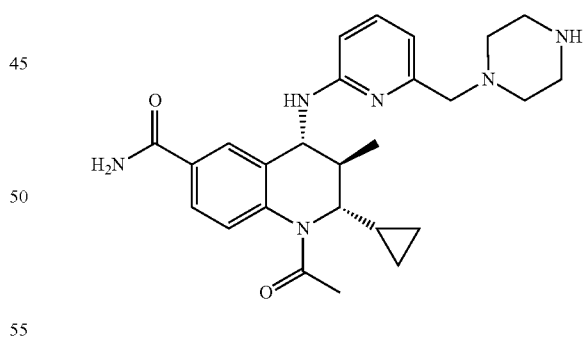

In a 50 mL RB flask, 4M HCl in 1,4-dioxane (0.533 mL, 2.133 mmol) was added to a stirred solution of tert-butyl 4-((6-(((2S,3R,4R)-1-acetyl-6-carbamoyl-2-cyclopropyl-3-methyl-1,2,3,4-tetrahydroquinolin-4-yl)amino)pyridin-2-yl)methyl)piperazine-1-carboxylate (40 mg, 0.071 mmol) in 1,4-dioxane (3 mL). The resulting solution was left stirring for 1.5 h at rt. Volatiles were removed under reduce pressure to afford a yellow gum. This gum was dissolved in MeOH and loaded on a 5 g SCX cartridge, washed with methanol (3 CV) and flushed with MeOH/NH3 (2M, 3CV). Ammonia fractions were combined and volatiles removed under reduce pressure to afford 27.8 mg of yellow gum. The compound was purified my MDAP (Formic). The compound was not collected, so the waste fraction was filtered through a SCX cartridge, and eluted with 2M $NH_3$ in MeOH solution. The appropriate fraction was evaporated in vacuo to give title compound (31.7 mg, 0.069 mmol, 96%)

LCMS (2 min Formic): Rt=0.47 min, $[MH]^+$=463.

Example 352: (2S,3R,4R)-1-acetyl-2-cyclopropyl-3-methyl-4-((3-(piperazin-1-yl)phenyl)amino)-1,2,3,4-tetrahydroquinoline-6-carboxamide

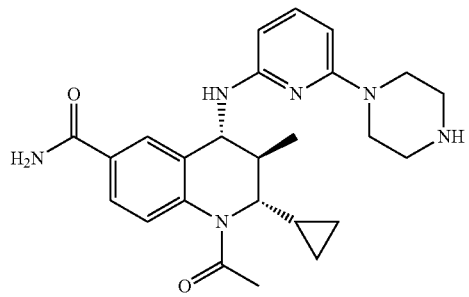 [SMILES: CC(=O)N1c2ccc(C(N)=O)cc2[C@H](Nc2cccc(N3CCNCC3)n2)[C@@H](C)[C@@H]1C1CC1]

Trifluoroacetic acid (0.5 ml, 6.49 mmol) was added to tert-butyl 4-(3-(((2S,3R,4R)-1-acetyl-6-carbamoyl-2-cyclopropyl-3-methyl-1,2,3,4-tetrahydroquinolin-4-yl)amino)phenyl)piperazine-1-carboxylate (41 mg, 0.075 mmol) and stirred at rt for 0.5 h. The solvent was evaporated in vacuo to give a colourless residue. The residue was loaded in methanol and purified by SPE on sulphonic acid (SCX) 2 g using sequential solvents of MeOH, NH3 in MeOH (2M). The appropriate fractions were combined and evaporated in vacuo to give the required product as a colourless oil (31 mg). The sample was dissolved in 1:1 MeOH:DMSO (1 mL) and purified MDAP (HpH). The solvent was evaporated in vacuo to give the required product 11.2 mg.

LCMS (2 min HpH): Rt=0.74 min, $[MH]^+$=448.

Example 353: (2S,3R,4R)-1-acetyl-2-cyclopropyl-4-((4-fluorophenyl)amino)-3-methyl-1,2,3,4-tetrahydroquinoline-6-carboxamide

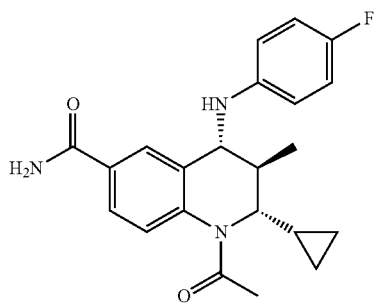 [SMILES: CC(=O)N1c2ccc(C(N)=O)cc2[C@H](Nc2ccc(F)cc2)[C@@H](C)[C@@H]1C1CC1]

To a solution of (2S,3R,4R)-1-acetyl-2-cyclopropyl-4-((4-fluorophenyl)amino)-3-methyl-1,2,3,4-tetrahydroquinoline-6-carbonitrile (for a preparation see Example 302, 54 mg, 0.149 mmol) in dimethyl sulfoxide (DMSO) (2 mL) was added hydrogen peroxide (0.130 mL, 1.486 mmol) and potassium carbonate (41.1 mg, 0.297 mmol) and reaction mixture was stirred at rt. The reaction mixture was quenched with sat. sodium thiosulfate solution and partitioned between DCM and water. The organic layer was separated and aq. layer re-extracted with DCM. Combined organic layers were dried ($Na_2SO_4$) and concentrated to give a crude yellow oil. This was purified by silica gel column chromatography on $SiO_2$ eluting with 0-100% ethyl acetate/cyclohexane to give the product (50 mg, 0.131 mmol, 88%) as a colourless oil. LCMS (2 min Formic): Rt=0.92 min, $[MH]^+$=382.

The following examples were prepared in a similar manner to Example 353 using $Pd_2(dba)_3$ DavePhos and NaOtBu to couple the appropriate aryl halide with Intermediate 231; followed by hydrolysis with $H_2O_2$.

| Ex No. | Name | Structure | Mass (mg) | Yield (%) | $[MH]^+$ | Rt (min) (LCMS Method) |
|---|---|---|---|---|---|---|
| 354 | (2S,3R,4R)-1-acetyl-2-cyclopropyl-4-((3,4-difluorophenyl)amino)-3-methyl-1,2,3,4-tetrahydroquinoline-6-carboxamide | 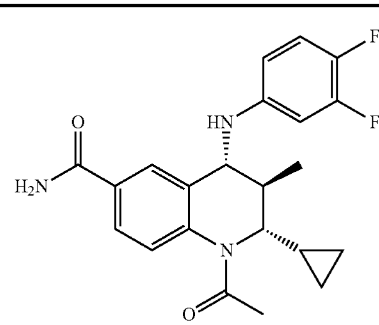 | 47 | 53 | 271 ([M − NHAr]$^+$) | 0.95 (2 min Formic) |

-continued

| Ex No. | Name | Structure | Mass (mg) | Yield (%) | [MH]+ | Rt (min) (LCMS Method) |
|---|---|---|---|---|---|---|
| 355 | (2S,3R,4R)-1-acetyl-2-cyclopropyl-4-((2,4-difluorophenyl)amino)-3-methyl-1,2,3,4-tetrahydroquinoline-6-carboxamide | 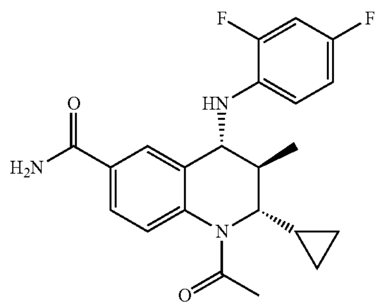 [SMILES: CC(=O)N1c2ccc(C(N)=O)cc2[C@H](Nc2ccc(F)cc2F)[C@@H](C)[C@@H]1C1CC1] | 7 | 99 | 400 | 0.96 (2 min Formic) |
| 356 | (2S,3R,4R)-1-acetyl-4-((4-chlorophenyl)amino)-2-cyclopropyl-3-methyl-1,2,3,4-tetrahydroquinoline-6-carboxamide | 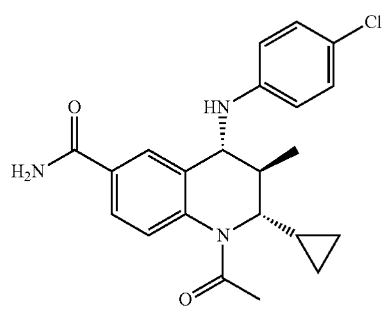 [SMILES: CC(=O)N1c2ccc(C(N)=O)cc2[C@H](Nc2ccc(Cl)cc2)[C@@H](C)[C@@H]1C1CC1] | 63 | 68 | 398 | 1.00 (2 min Formic) |
| 357 | (2S,3R,4R)-1-acetyl-4-((3-chlorophenyl)amino)-2-cyclopropyl-3-methyl-1,2,3,4-tetrahydroquinoline-6-carboxamide | 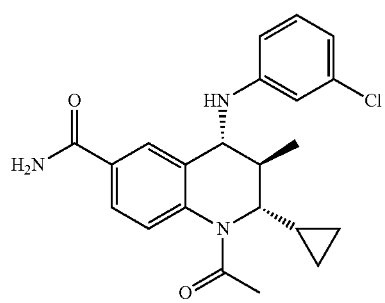 [SMILES: CC(=O)N1c2ccc(C(N)=O)cc2[C@H](Nc2cccc(Cl)c2)[C@@H](C)[C@@H]1C1CC1] | 18 | 85 | 271 ([M − NHAr]+) | 0.99 (2 min Formic) |
| 358 | (2S,3R,4R)-1-acetyl-2-cyclopropyl-4-((6-(methoxymethyl)pyridin-2-yl)amino)-3-methyl-1,2,3,4-tetrahydroquinoline-6-carboxamide | 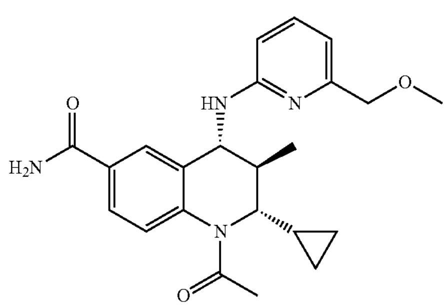 [SMILES: COCc1cccc(N[C@H]2c3cc(C(N)=O)ccc3N(C(C)=O)[C@@H](C3CC3)[C@@H]2C)n1] | 12 | 33 | 409 | 0.59 (2 min Formic) |
| 359 | (2S,3R,4R)-1-acetyl-2-cyclopropyl-4-((3-fluorophenyl)amino)-3-methyl-1,2,3,4-tetrahydroquinoline-6-carboxamide | 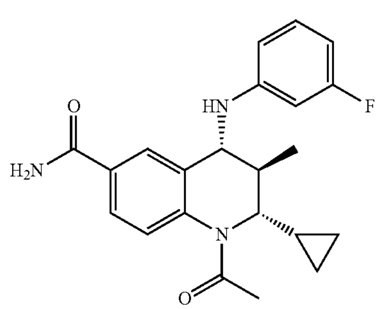 [SMILES: CC(=O)N1c2ccc(C(N)=O)cc2[C@H](Nc2cccc(F)c2)[C@@H](C)[C@@H]1C1CC1] | 38 | 85 | 382 | 0.93 (2 min Formic) |

| Ex No. | Name | Structure | Mass (mg) | Yield (%) | [MH]+ | Rt (min) (LCMS Method) |
|---|---|---|---|---|---|---|
| 360 | (2S,3R,4R)-1-acetyl-2-cyclopropyl-4-((3-methoxyphenyl)amino)-3-methyl-1,2,3,4-tetrahydroquinoline-6-carboxamide | 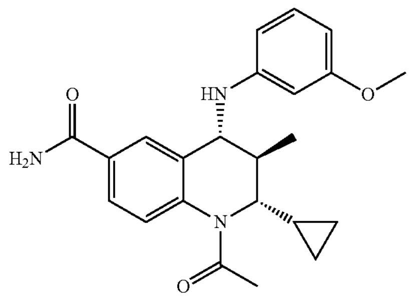 [SMILES: COc1cccc(N[C@H]2c3cc(C(N)=O)ccc3N(C(C)=O)[C@@H](C3CC3)[C@@H]2C)c1] | 73 | 56 | 394 | 0.89 (2 min Formic) |
| 361 | (2S,3R,4R)-1-acetyl-2-cyclopropyl-4-((4-methoxyphenyl)amino)-3-methyl-1,2,3,4-tetrahydroquinoline-6-carboxamide | 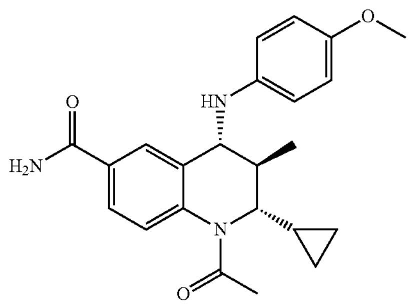 [SMILES: COc1ccc(N[C@H]2c3cc(C(N)=O)ccc3N(C(C)=O)[C@@H](C3CC3)[C@@H]2C)cc1] | 23 | 55 | 394 | 0.88 (2 min Formic) |
| 362 | (2S,3R,4R)-1-acetyl-4-((3-chloro-4-cyanophenyl)amino)-2-cyclopropyl-3-methyl-1,2,3,4-tetrahydroquinoline-6-carboxamide | 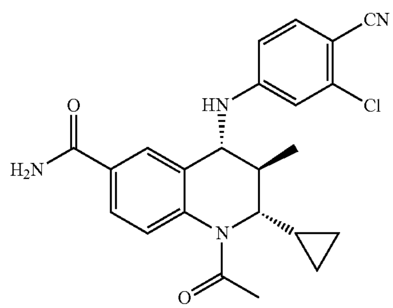 [SMILES: CC(=O)N1c2ccc(C(N)=O)cc2[C@H](Nc2ccc(C#N)c(Cl)c2)[C@@H](C)[C@@H]1C1CC1] | 7 | 31 | 423 | 0.91 (2 min Formic) |
| 363 | (2S,3R,4R)-1-acetyl-4-((4-chloro-3-methoxyphenyl)amino)-2-cyclopropyl-3-methyl-1,2,3,4-tetrahydroquinoline-6-carboxamide | 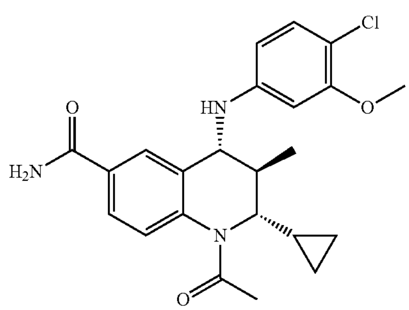 [SMILES: COc1cc(N[C@H]2c3cc(C(N)=O)ccc3N(C(C)=O)[C@@H](C3CC3)[C@@H]2C)ccc1Cl] | 35 | 15 | 428 | 0.97 (2 min Formic) |
| 364 | (2S,3R,4R)-1-acetyl-2-cyclopropyl-4-((2-methoxyphenyl)amino)-3-methyl-1,2,3,4-tetrahydroquinoline-6-carboxamide | 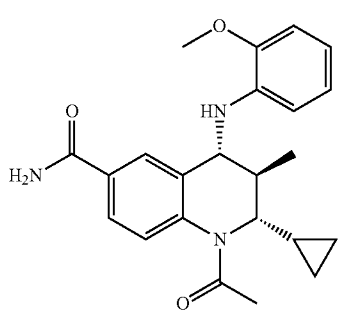 [SMILES: COc1ccccc1N[C@H]1c2cc(C(N)=O)ccc2N(C(C)=O)[C@@H](C2CC2)[C@@H]1C] | 18 | 57 | 394 | 0.95 (2 min Formic) |

-continued

| Ex No. | Name | Structure | Mass (mg) | Yield (%) | [MH]+ | Rt (min) (LCMS Method) |
|---|---|---|---|---|---|---|
| 365 | (2S,3R,4R)-1-acetyl-4-((4-chloro-2-methoxyphenyl)amino)-2-cyclopropyl-3-methyl-1,2,3,4-tetrahydroquinoline-6-carboxamide | 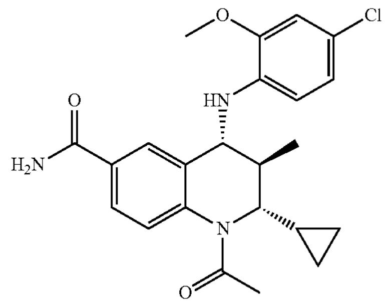 [SMILES: COc1cc(Cl)ccc1N[C@H]1c2cc(C(N)=O)ccc2N(C(C)=O)[C@@H](C2CC2)[C@@H]1C] | 22 | 90 | 428 | 1.04 (2 min Formic) |

The following examples (366-369) were prepared in a similar manner to Example 352 using $Pd_2(dba)_3$ DavePhos and NaOtBu or $Cs_2CO_3$ to couple the appropriate protected aryl halide with Intermediate 231; followed by hydrolysis with $H_2O_2$; followed by deprotection as detailed below:

Example 366: (2S,3R,4R)-1-acetyl-2-cyclopropyl-3-methyl-4-((4-(piperazin-1-yl)phenyl)amino)-1,2,3,4-tetrahydroquinoline-6-carboxamide

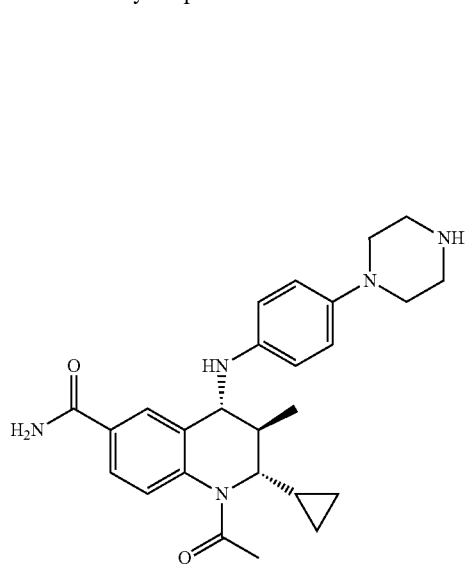

4M hydrogen chloride in dioxane (1.014 mL, 4.05 mmol) was added to tert-butyl 4-(4-(((2S,3R,4R)-1-acetyl-6-carbamoyl-2-cyclopropyl-3-methyl-1,2,3,4-tetrahydroquinolin-4-yl)amino)phenyl)piperazine-1-carboxylate (69.4 mg, 0.101 mmol) and stirred at rt for 4 h. The solvent was removed in vacuo to give an orange residue. The residue purified by MDAP (HpH) to give the title compound as a yellow solid (18 mg, 40%). LCMS (2 min Formic): Rt=0.60 min, [MH]+=448.

Example 367: (2S,3R,4R)-1-acetyl-2-cyclopropyl-4-((6-(rac-1-hydroxyethyl)pyridin-2-yl)amino)-3-methyl-1,2,3,4-tetrahydroquinoline-6-carboxamide

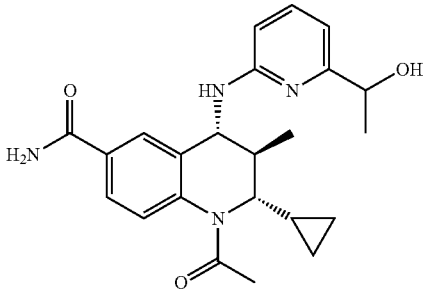

To a solution of (2S,3R,4R)-1-acetyl-4-((6-(1-((tert-butyldimethylsilyl)oxy)ethyl)pyridin-2-yl)amino)-2-cyclopropyl-3-methyl-1,2,3,4-tetrahydroquinoline-6-carboxamide (94 mg, 0.180 mmol) in tetrahydrofuran (THF) (1.5 mL) was added TBAF (1M in THF) (0.899 mL, 0.899 mmol) and the reaction allowed to stir under nitrogen for 1 h. The reaction was concentrated, partitioned between EtOAc and water and the aqueous layer further extracted with EtOAc. The organic layers were combined, dried over a hydrophobic frit and concentrated. The residue was purified by column chromatography eluting with a gradient of 10-50% methanol-dichloromethane to give the product (59.8 mg, 0.146 mmol, 81%) as a colourless oil. LCMS (2 min Formic): Rt=0.54 min, [MH]+=409.

Example 368a & 368b: (2S,3R,4R)-1-acetyl-2-cyclopropyl-4-((6-(S-1-hydroxyethyl)pyridin-2-yl)amino)-3-methyl-1,2,3,4-tetrahydroquinoline-6-carboxamide (386a) & (2S,3R,4R)-1-acetyl-2-cyclopropyl-4-((6-(R-1-hydroxyethyl)pyridin-2-yl)amino)-3-methyl-1,2,3,4-tetrahydroquinoline-6-carboxamide (386b)

386a

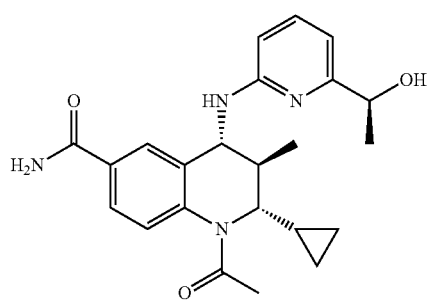 [SMILES: CC(=O)N1c2ccc(C(N)=O)cc2[C@H](Nc2cccc(C(C)O)n2)[C@@H](C)[C@@H]1C1CC1]

386b

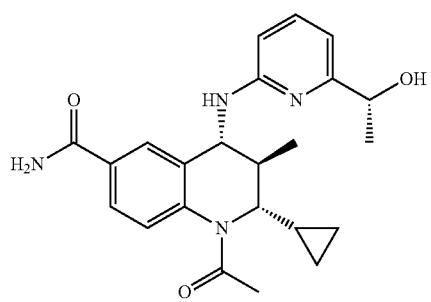

(2S,3R,4R)-1-acetyl-2-cyclopropyl-4-((6-(rac-1-hydroxyethyl)pyridin-2-yl)amino)-3-methyl-1,2,3,4-tetrahydroquinoline-6-carboxamide (for a preparation see Example 367, ~45 mg) was submitted for chiral separation into its enantiomers (A and B) using a 300×20 mm Chiralpak AD-H column eluting with 15% ethanol in 80% hexane at a flow rate of 20 mL/min. Peak 1/Enantiomer A fractions were collected between 20 and 23.5 min. Peak 2/Enantiomer B fractions were collected between 25.5 and 30 min. Fraction solutions were combined then evaporated to dryness to give Enantiomer A (22 mg) and Enantiomer B (25 mg) as white solids.

Enantiomer A

Analytical Chiral HPLC using a 250×4.6 mm Chiralpak AD-H column eluting with 15% ethanol in heptane at 1 mL/min—Rt=11 min.>99% ee by UV.

Enantiomer B

Analytical Chiral HPLC using a 250×4.6 mm Chiralpak AD-H column eluting with 15% ethanol in heptane at 1 mL/min—Rt=13 min, 94% ee by UV.

Example 369: (2S,3R,4R)-1-acetyl-2-cyclopropyl-3-methyl-4-((2-(piperazin-1-yl)phenyl)amino)-1,2,3,4-tetrahydroquinoline-6-carboxamide

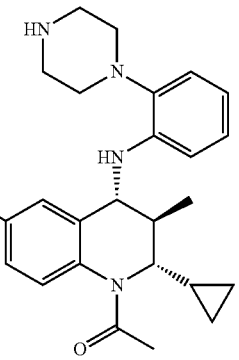

Hydrogen chloride (1.186 mL, 4.74 mmol) in 1,4-dioxane (0.5 mL) was added to tert-butyl 4-(2-(((2S,3R,4R)-1-acetyl-6-carbamoyl-2-cyclopropyl-3-methyl-1,2,3,4-tetrahydroquinolin-4-yl)amino)phenyl)piperazine-1-carboxylate (81.2 mg, 0.119 mmol) and stirred at rt for 1.5 h. The solvent was evaporated in vacuo to give a yellow residue. The residue was purified by MDAP (Formic). The sample was loaded in methanol and purified by SPE on sulphonic acid (SCX) 1 g using sequential solvents of methanol, 2M ammonia/methanol. The appropriate fractions were combined and evaporated in vacuo to give a crude yellow oil. This crude was further purified using a MDAP (HpH) to give title compound as a white solid (8 mg, 14%). LCMS (2 min Formic): Rt=0.65 min, [MH]$^+$=448.

Example 370: (2S,3R,4R)-1-acetyl-4-((5-fluoropyridin-2-yl)amino)-2,3-dimethyl-1,2,3,4-tetrahydroquinoline-6-carboxamide

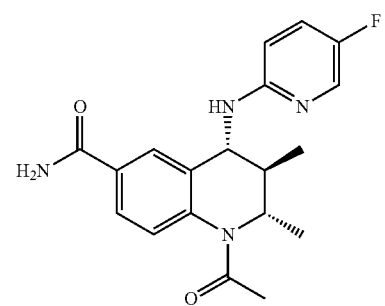 [SMILES: CC(=O)N1c2ccc(C(N)=O)cc2[C@H](Nc2ccc(F)cn2)[C@@H](C)[C@@H]1C]

To a solution of (2S,3R,4R)-1-acetyl-4-((5-fluoropyridin-2-yl)amino)-2,3-dimethyl-1,2,3,4-tetrahydroquinoline-6-carboxylic acid (for a preparation see Intermediate 268, 64 mg, 0.179 mmol) in N,N-dimethylformamide (DMF) (1 mL) was added HATU (102 mg, 0.269 mmol) followed by ammonium chloride (20 mg ml, 0.374 mmol) and DIPEA (0.125 ml, 0.716 mmol). The resulting reaction mixture was stirred at rt under $N_2$ for 16 h. The crude reaction mixture was purified directly by MDAP (TFA) the fractions containing product were extracted with DCM. The pH of the aqueous layer was adjusted to ~pH9. The aqueous layer was then extracted with ethyl acetate (100 mL). The combined organic layers were dried ($Na_2SO_4$) and concentrated to give the title compound as a white solid (23 mg, 27%). LCMS (2 min TFA): Rt=0.53 min, [MH]$^+$=357.

The following examples were prepared in a similar manner to Example 370 using $Pd_2(dba)_3$ DavePhos and NaOtBu or $Cs_2CO_3$ to couple the appropriate aryl halide with Intermediate 225 (2-cPr) or 261 (2-Et); followed by amide formation with HATU, DIPEA and $NH_4Cl$.

| Ex No. | Name | Structure | Mass (mg) | Yield (%) | [MH]$^+$ | Rt (min) (LCMS Method) |
|---|---|---|---|---|---|---|
| 371 | (2S,3R,4R)-1-acetyl-2-cyclopropyl-3-methyl-4-((6-methylpyridin-2-yl)amino)-1,2,3,4-tetrahydroquinoline-6-carboxamide | 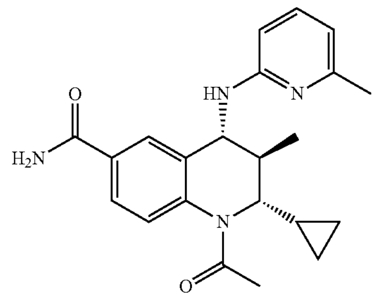 [SMILES: CC(=O)N1c2ccc(C(N)=O)cc2[C@H](Nc2cccc(C)n2)[C@@H](C)[C@@H]1C1CC1] | 26 | 43 | 379 | 0.55 (2 min HpH) |
| 372 | (2S,3R,4R)-1-acetyl-2-ethyl-4-((5-fluoropyridin-2-yl)amino)-3-methyl-1,2,3,4-tetrahydroquinoline-6-carboxamide | 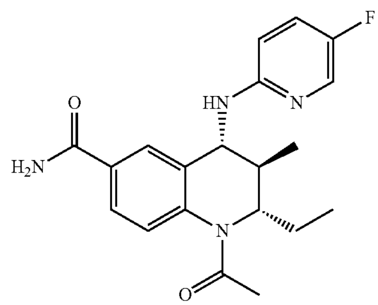 [SMILES: CC[C@H]1[C@H](C)[C@@H](Nc2ccc(F)cn2)c2cc(C(N)=O)ccc2N1C(C)=O] | 11 | 14 | 371 | 0.56 (2 min TFA) |
| 373 | (2S,3R,4R)-1-acetyl-4-((4-cyano-2-fluorophenyl)amino)-2-cyclopropyl-3-methyl-1,2,3,4-tetrahydroquinoline-6-carboxamide | 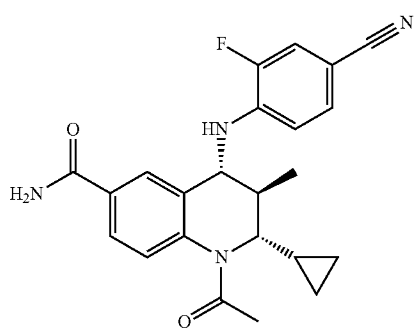 [SMILES: CC(=O)N1c2ccc(C(N)=O)cc2[C@H](Nc2ccc(C#N)cc2F)[C@@H](C)[C@@H]1C1CC1] | 11 | 16 | 407 | 0.88 (2 min Formic) |
| 374 | (2S,3R,4R)-1-acetyl-4-((4-cyano-3-methoxyphenyl)amino)-2-cyclopropyl-3-methyl-1,2,3,4-tetrahydroquinoline-6-carboxamide | 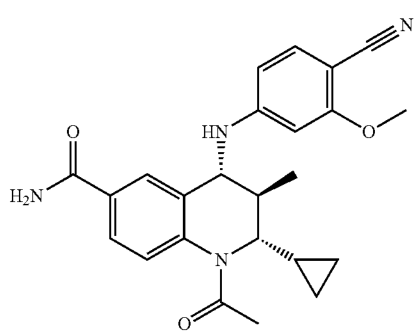 [SMILES: COc1cc(N[C@H]2c3cc(C(N)=O)ccc3N(C(C)=O)[C@@H](C3CC3)[C@@H]2C)ccc1C#N] | 20 | 34 | 419 | 0.85 (2 min Formic) |

| Ex No. | Name | Structure | Mass (mg) | Yield (%) | [MH]+ | Rt (min) (LCMS Method) |
|---|---|---|---|---|---|---|
| 375 | (2S,3R,4R)-1-acetyl-4-((4-cyano-3-hydroxyphenyl)amino)-2-cyclopropyl-3-methyl-1,2,3,4-tetrahydroquinoline-6-carboxamide | 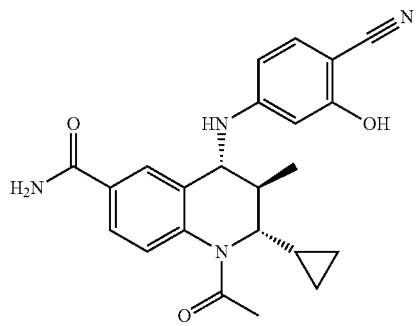 [SMILES: CC(=O)N1c2ccc(C(N)=O)cc2[C@H](Nc2ccc(C#N)c(O)c2)[C@@H](C)[C@@H]1C1CC1] | 9 | 18 | 403 | 0.76 (2 min Formic) |

Example 376: (2S,3R,4R)-1-acetyl-2-cyclopropyl-3-methyl-4-(pyridin-2-ylamino)-1,2,3,4-tetrahydroquinoline-6-carboxamide

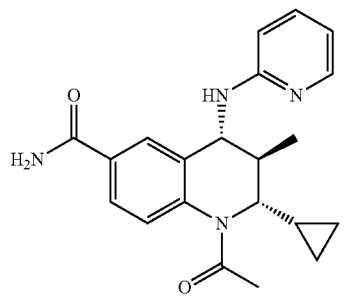 [SMILES: CC(=O)N1c2ccc(C(N)=O)cc2[C@H](Nc2ccccn2)[C@@H](C)[C@@H]1C1CC1]

To a solution of (2S,3R,4R)-1-acetyl-2-cyclopropyl-3-methyl-4-(pyridin-2-ylamino)-1,2,3,4-tetrahydroquinoline-6-carboxylic acid (for a preparation see Intermediate 271, 22 mg, 0.060 mmol) and HATU (27.5 mg, 0.072 mmol) in N,N-dimethylformamide (2 mL) was added ammonium chloride (6.44 mg, 0.120 mmol) followed by DIPEA (0.042 mL, 0.241 mmol). The reaction mixture was stirred at for 2 h. The volatiles were removed under reduced pressure and the resulting crude was purified by MDAP (Formic) to give title compound as a white powder. (11 mg, 0.030 mmol, 50%).

LCMS (2 min Formic): Rt=0.52 min, [MH]+=365.

The following examples were prepared in a similar manner to Example 376 using PdQPhos$_2$ and NaOtBu or Cs$_2$CO$_3$ to couple the appropriate aryl halide with Intermediate 225 (2-cPr), 261 (2-Et) or 267 (2-Me); followed by hydrolysis with LiOH; followed by amide formation with HATU, DIPEA and NH$_4$Cl.

| Ex No. | Name | Structure | Mass (mg) | Yield (%) | [MH]+ | Rt (min) (LCMS Method) |
|---|---|---|---|---|---|---|
| 377 | (2S,3R,4R)-1-acetyl-2-cyclopropyl-4-((5-fluoro-6-methylpyridin-2-yl)amino)-3-methyl-1,2,3,4-tetrahydroquinoline-6-carboxamide | 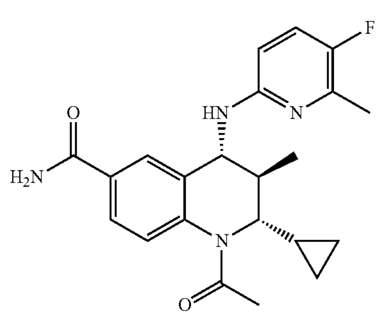 [SMILES: CC(=O)N1c2ccc(C(N)=O)cc2[C@H](Nc2ccc(F)c(C)n2)[C@@H](C)[C@@H]1C1CC1] | 105 | 77 | 397 | 0.70 (2 min Formic) |

| Ex No. | Name | Structure | Mass (mg) | Yield (%) | [MH]+ | Rt (min) (LCMS Method) |
|---|---|---|---|---|---|---|
| 378 | (2S,3R,4R)-1-acetyl-4-((4-cyanophenyl)amino)-2-cyclopropyl-3-methyl-1,2,3,4-tetrahydroquinoline-6-carboxamide | 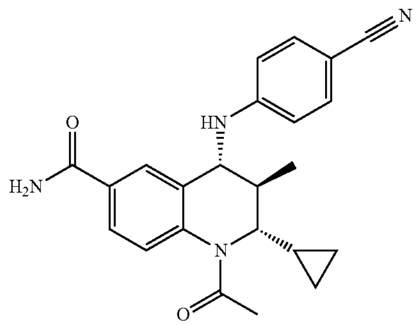 [SMILES: CC(=O)N1c2ccc(C(N)=O)cc2[C@H](Nc2ccc(C#N)cc2)[C@@H](C)[C@@H]1C1CC1] | 72 | 40 | 389 | 0.84 (2 min Formic) |
| 379 | (2S,3R,4R)-1-acetyl-4-((5-chloropyridin-2-yl)amino)-2-cyclopropyl-3-methyl-1,2,3,4-tetrahydroquinoline-6-carboxamide | 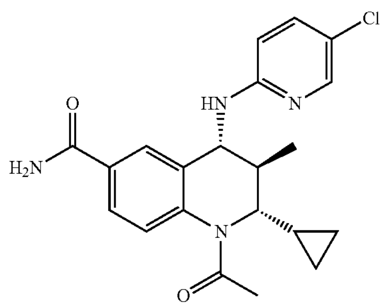 [SMILES: CC(=O)N1c2ccc(C(N)=O)cc2[C@H](Nc2ccc(Cl)cn2)[C@@H](C)[C@@H]1C1CC1] | 198 | 80 | 399 | 0.81 (2 min Formic) |
| 380 | (2S,3R,4R)-1-acetyl-2-cyclopropyl-3-methyl-4-((5-methylpyrazin-2-yl)amino)-1,2,3,4-tetrahydroquinoline-6-carboxamide | 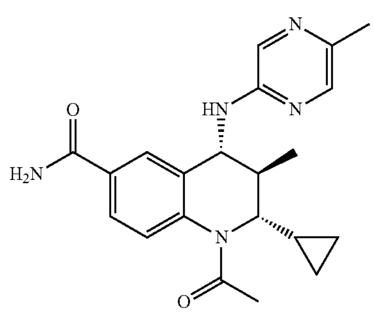 [SMILES: CC(=O)N1c2ccc(C(N)=O)cc2[C@H](Nc2cnc(C)cn2)[C@@H](C)[C@@H]1C1CC1] | 35 | 35 | 380 | 0.69 (2 min Formic) |
| 381 | (2S,3R,4R)-1-acetyl-4-((4-cyano-3-fluorophenyl)amino)-2-cyclopropyl-3-methyl-1,2,3,4-tetrahydroquinoline-6-carboxamide | 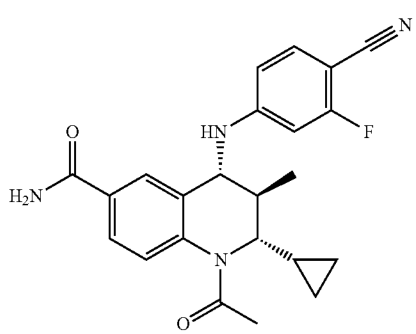 [SMILES: CC(=O)N1c2ccc(C(N)=O)cc2[C@H](Nc2ccc(C#N)c(F)c2)[C@@H](C)[C@@H]1C1CC1] | 54 | 56 | 407 | 0.88 (2 min Formic) |

-continued

| Ex No. | Name | Structure | Mass (mg) | Yield (%) | [MH]+ | Rt (min) (LCMS Method) |
|---|---|---|---|---|---|---|
| 382 | (2S,3R,4R)-1-acetyl-4-((4-cyano-3-methylphenyl)amino)-2-cyclopropyl-3-methyl-1,2,3,4-tetrahydroquinoline-6-carboxamide | 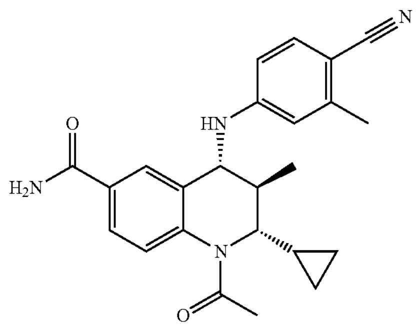 [SMILES: CC(=O)N1c2ccc(C(N)=O)cc2[C@H](Nc2ccc(C#N)c(C)c2)[C@@H](C)[C@@H]1C1CC1] | 7 | 6 | 271 [M − NHAr]+ | 0.88 (2 min Formic) |
| 383 | (2S,3R,4R)-1-acetyl-4-((4-cyanophenyl)amino)-2-ethyl-3-methyl-1,2,3,4-tetrahydroquinoline-6-carboxamide | 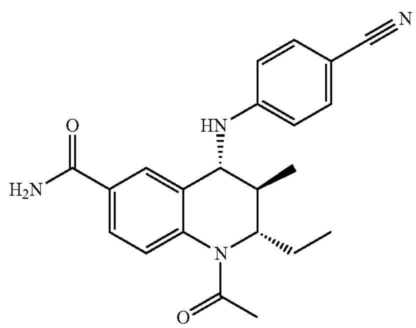 [SMILES: CC[C@H]1[C@H](C)[C@@H](Nc2ccc(C#N)cc2)c2cc(C(N)=O)ccc2N1C(C)=O] | 56 | 66 | 377 | 0.81 (2 min Formic) |
| 384 | (2S,3R,4R)-1-acetyl-4-((4-cyanophenyl)amino)-2,3-dimethyl-1,2,3,4-tetrahydroquinoline-6-carboxamide | 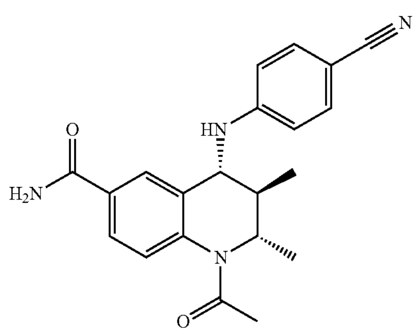 [SMILES: CC(=O)N1c2ccc(C(N)=O)cc2[C@H](Nc2ccc(C#N)cc2)[C@@H](C)[C@@H]1C] | 43 | 43 | 363 | 0.78 (2 min Formic) |
| 385 | (2S,3R,4R)-1-acetyl-4-((6-cyanopyridin-3-yl)amino)-2-cyclopropyl-3-methyl-1,2,3,4-tetrahydroquinoline-6-carboxamide | 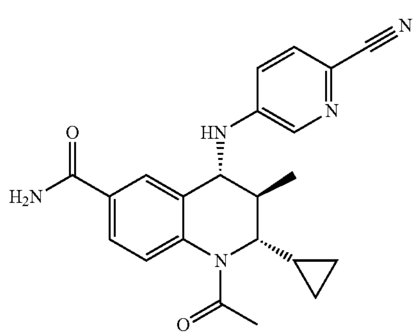 [SMILES: CC(=O)N1c2ccc(C(N)=O)cc2[C@H](Nc2ccc(C#N)nc2)[C@@H](C)[C@@H]1C1CC1] | 4 | 6 | 390 | 0.75 (2 min Formic) |

-continued

| Ex No. | Name | Structure | Mass (mg) | Yield (%) | [MH]+ | Rt (min) (LCMS Method) |
|---|---|---|---|---|---|---|
| 386 | (2S,3R,4R)-1-acetyl-2-cyclopropyl-4-((4-methoxypyrimidin-2-yl)amino)-3-methyl-1,2,3,4-tetrahydroquinoline-6-carboxamide | 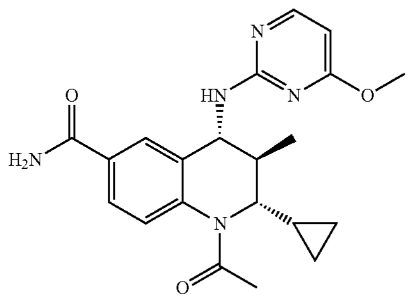 [SMILES: COc1ccnc(N[C@H]2c3cc(C(N)=O)ccc3N(C(C)=O)[C@@H](C3CC3)[C@@H]2C)n1] | 16 | 82 | 396 | 0.58 (2 min Formic) |
| 387 | (2S,3R,4R)-1-acetyl-2-cyclopropyl-4-((4-(dimethylamino)pyrimidin-2-yl)amino)-3-methyl-1,2,3,4-tetrahydroquinoline-6-carboxamide | 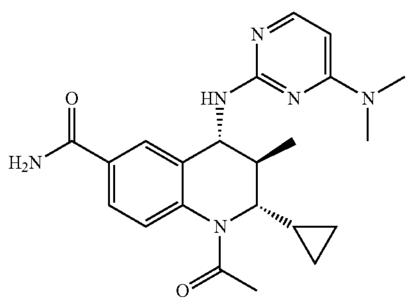 [SMILES: CC(=O)N1c2ccc(C(N)=O)cc2[C@H](Nc2nccc(N(C)C)n2)[C@@H](C)[C@@H]1C1CC1] | 33 | 36 | 409 | 0.59 (2 min Formic) |
| 388 | (2S,3R,4R)-1-acetyl-2-cyclopropyl-3-methyl-4-((4-(methylsulfonyl)phenyl)amino)-1,2,3,4-tetrahydroquinoline-6-carboxamide | 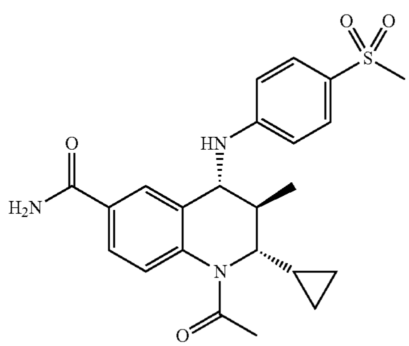 [SMILES: CC(=O)N1c2ccc(C(N)=O)cc2[C@H](Nc2ccc(S(C)(=O)=O)cc2)[C@@H](C)[C@@H]1C1CC1] | 47 | 88 | 442 | 0.75 (2 min Formic) |
| 389 | (2S,3R,4R)-1-acetyl-4-((4-chloropyridin-2-yl)amino)-2-cyclopropyl-3-methyl-1,2,3,4-tetrahydroquinoline-6-carboxamide | 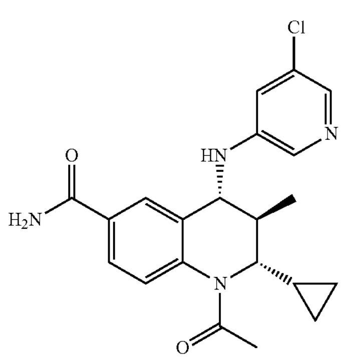 [SMILES: CC(=O)N1c2ccc(C(N)=O)cc2[C@H](Nc2cncc(Cl)c2)[C@@H](C)[C@@H]1C1CC1] | 29 | 59 | 399 | 0.72 (2 min Formic) |

| Ex No. | Name | Structure | Mass (mg) | Yield (%) | [MH]+ | Rt (min) (LCMS Method) |
|---|---|---|---|---|---|---|
| 390 | (2S,3R,4R)-1-acetyl-4-((4-cyano-2-methoxyphenyl)amino)-2-cyclopropyl-3-methyl-1,2,3,4-tetrahydroquinoline-6-carboxamide | 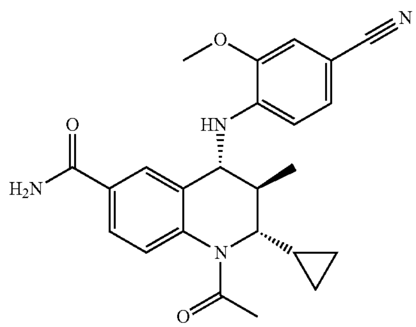 [SMILES: COc1cc(C#N)ccc1N[C@H]1c2cc(C(N)=O)ccc2N(C(C)=O)[C@@H](C2CC2)[C@@H]1C] | 29 | 67 | 419 | 0.90 (2 min Formic) |
| 391 | (2S,3R,4R)-1-acetyl-4-((5-chloro-6-cyanopyridin-3-yl)amino)-2-cyclopropyl-3-methyl-1,2,3,4-tetrahydroquinoline-6-carboxamide | 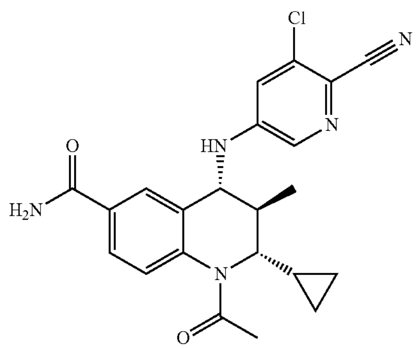 [SMILES: CC(=O)N1c2ccc(C(N)=O)cc2[C@H](Nc2cnc(C#N)c(Cl)c2)[C@@H](C)[C@@H]1C1CC1] | 24 | 75 | 422 | 0.88 (2 min Formic) |
| 392 | (2S,3R,4R)-1-acetyl-4-((2-cyano-4-methoxyphenyl)amino)-2-cyclopropyl-3-methyl-1,2,3,4-tetrahydroquinoline-6-carboxamide | 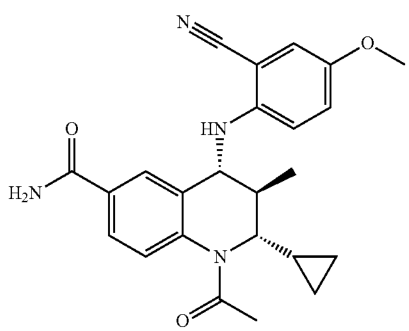 [SMILES: COc1ccc(N[C@H]2c3cc(C(N)=O)ccc3N(C(C)=O)[C@@H](C3CC3)[C@@H]2C)c(C#N)c1] | 6 | 63 | 419 | 0.91 (2 min Formic) |
| 393 | (2S,3R,4R)-1-acetyl-2-cyclopropyl-4-((6-methoxypyridin-2-yl)amino)-3-methyl-1,2,3,4-tetrahydroquinoline-6-carboxamide | 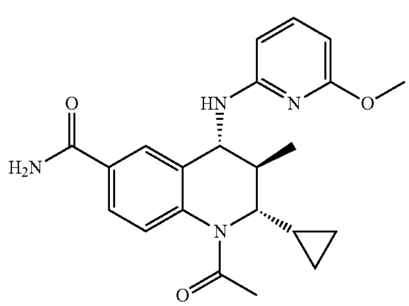 [SMILES: COc1cccc(N[C@H]2c3cc(C(N)=O)ccc3N(C(C)=O)[C@@H](C3CC3)[C@@H]2C)n1] | 57 | 85 | 423 | 1.17 (2 min Formic) |

| Ex No. | Name | Structure | Mass (mg) | Yield (%) | [MH]+ | Rt (min) (LCMS Method) |
|---|---|---|---|---|---|---|
| 394 | (2S,3R,4R)-1-acetyl-2,3-dimethyl-4-((6-methylpyridin-2-yl)amino)-1,2,3,4-tetrahydroquinoline-6-carboxamide | 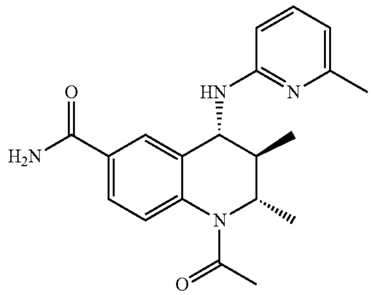 [SMILES: CC(=O)N1c2ccc(C(N)=O)cc2[C@H](Nc2cccc(C)n2)[C@@H](C)[C@@H]1C] | 2 | 10 | 353 | 0.46 (2 min Formic) |

Example 395: (2S,3R,4R)-1-acetyl-2-ethyl-3-methyl-4-((4-methylpyrimidin-2-yl)amino)-1,2,3,4-tetrahydroquinoline-6-carboxamide

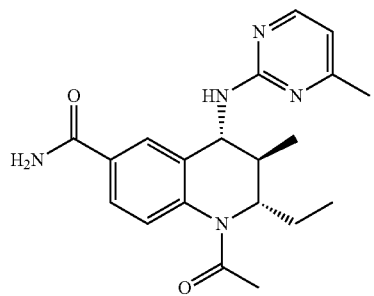 [SMILES: CC[C@H]1[C@H](C)[C@@H](Nc2nccc(C)n2)c2cc(C(N)=O)ccc2N1C(C)=O]

To a solution of (2S,3R,4R)-1-acetyl-2-ethyl-3-methyl-4-((4-methylpyrimidin-2-yl)amino)-1,2,3,4-tetrahydroquinoline-6-carboxylic acid (for a preparation see Example 335, 75 mg, 0.204 mmol) in N,N-dimethylformamide (DMF) (2 ml) was added HATU (116 mg, 0.305 mmol) followed by DIPEA (0.107 ml, 0.611 mmol). The resulting reaction mixture was stirred at rt under $N_2$ for 15 min. Ammonium chloride (10.89 mg, 0.204 mmol) was then added and the reaction stirred for ~1 h. The reaction mixture was quenched by the addition of water. $Et_2O$ was added and the layers separated. The aqueous layer was further extracted with $Et_2O$. The combined organics were then back extracted with $H_2O$. The aqueous layer was further extracted with DCM and the combined $Et_2O$/DCM organics dried (hydrophobic frit) and concentrated in vacuo to afford the crude product. The crude product was taken up in DCM and purified by silica gel column chromatography eluting with 0-40% (20% MeOH/DCM) to give the product (51.8 mg, 0.141 mmol, 69%) as a colourless gum.

LCMS (2 min Formic): Rt=0.61 min, [MH]+=368.

The following examples were prepared in a similar manner to Example 395 using KF, 18-crown-6 and DIPEA to couple the appropriate aryl halide with Intermediate 225 (2-cPr) or 267 (2-Me); followed by hydrolysis with LiOH; followed by amide formation with HATU, DIPEA and $NH_4Cl$.

| Ex No. | Name | Structure | Mass (mg) | Yield (%) | [MH]+ | Rt (min) (LCMS Method) |
|---|---|---|---|---|---|---|
| 396 | (2S,3R,4R)-1-acetyl-2,3-dimethyl-4-((4-methylpyrimidin-2-yl)amino)-1,2,3,4-tetrahydroquinoline-6-carboxamide | 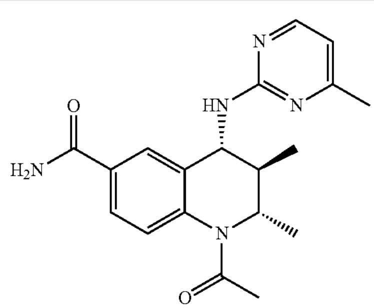 [SMILES: CC(=O)N1c2ccc(C(N)=O)cc2[C@H](Nc2nccc(C)n2)[C@@H](C)[C@@H]1C] | 40 | 80 | 354 | 0.56 (2 min Formic) |

| Ex No. | Name | Structure | Mass (mg) | Yield (%) | [MH]+ | Rt (min) (LCMS Method) |
|---|---|---|---|---|---|---|
| 397 | (2R,3S,4S)-1-acetyl-2-cyclopropyl-3-methyl-4-((4-methylpyrimidin-2-yl)amino)-1,2,3,4-tetrahydroquinoline-6-carboxamide* | 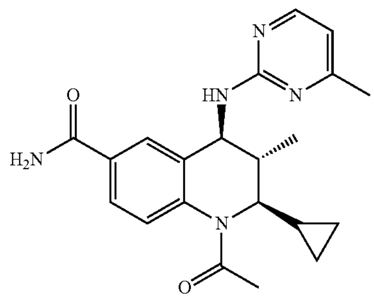 [SMILES: CC(=O)N1c2ccc(C(N)=O)cc2[C@@H](Nc2nccc(C)n2)[C@H](C)[C@H]1C1CC1] | 20 | 14 | 380 | 0.65 (2 min Formic) |

*After chiral HPLC separation of the racemate using a 250 × 30 mm Chiralcel OD-H column eluting with 15% ethanol in heptane. This (2nd eluting) isomer eluted at t = 12.5-16 min.

Example 398: rac-(2S,3R,4R)-1-acetyl-2-cyclopropyl-3-methyl-4-(pyrimidin-2-ylamino)-1,2,3,4-tetrahydroquinoline-6-carboxamide

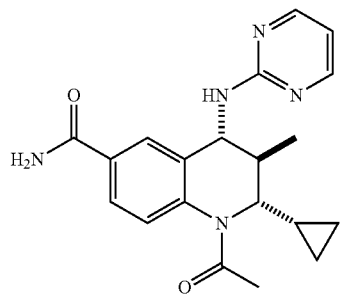 [SMILES: CC(=O)N1c2ccc(C(N)=O)cc2[C@H](Nc2ncccn2)[C@@H](C)[C@@H]1C1CC1]

A solution of (2S,3R,4R)-1-acetyl-2-cyclopropyl-3-methyl-4-(pyrimidin-2-ylamino)-1,2,3,4-tetrahydroquinoline-6-carboxylic acid (for a preparation see Intermediate 273, 110 mg, 0.300 mmol), ammonium chloride (48.2 mg, 0.901 mmol), HATU (148 mg, 0.390 mmol) and DIPEA (0.210 mL, 1.201 mmol) was stirred in a closed vessel at rt for 45 min. The solution was purified directly by MDAP (HpH) to give the product (65 mg, 0.178 mmol, 59%).

LCMS (2 min Formic): Rt=0.65 min, [MH]+=366.

The following examples were prepared in a similar manner to Example 398 using KF, 18-crown-6 and DIPEA to couple the appropriate aryl halide with Intermediate 225; followed by hydrolysis with LiOH; followed by amide formation with HATU, DIPEA and NH4Cl.

| Ex No. | Name | Structure | Mass (mg) | Yield (%) | [MH]+ | Rt (min) (LCMS Method) |
|---|---|---|---|---|---|---|
| 399 | (2S,3R,4R)-1-acetyl-2-cyclopropyl-3-methyl-4-(pyrimidin-2-ylamino)-1,2,3,4-tetrahydroquinoline-6-carboxamide | 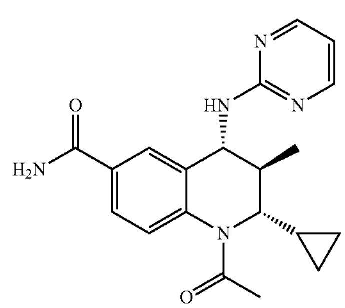 | 852 | 49 | 366 | 0.65 (2 min Formic) |

| Ex No. | Name | Structure | Mass (mg) | Yield (%) | [MH]+ | Rt (min) (LCMS Method) |
|---|---|---|---|---|---|---|
| 400 | (2S,3R,4R)-1-acetyl-4-((5-cyanopyridin-2-yl)amino)-2-cyclopropyl-3-methyl-1,2,3,4-tetrahydroquinoline-6-carboxamide | 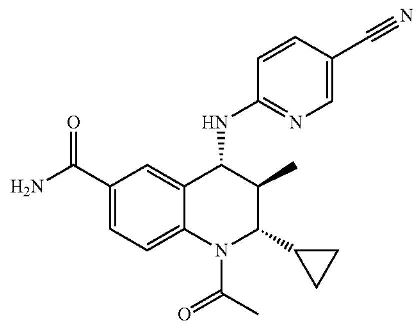 [SMILES: CC(=O)N1c2ccc(C(N)=O)cc2[C@H](Nc2ccc(C#N)cn2)[C@@H](C)[C@@H]1C1CC1] | 86 | 56 | 390 | 0.77 (2 min Formic) |

Example 401: (2S,3R,4R)-1-acetyl-2-cyclopropyl-3-methyl-4-((4-(trifluoromethyl)pyrimidin-2-yl)amino)-1,2,3,4-tetrahydroquinoline-6-carboxamide

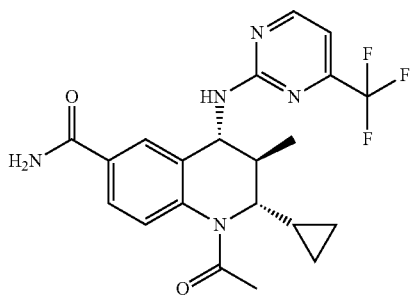 [SMILES: CC(=O)N1c2ccc(C(N)=O)cc2[C@H](Nc2nccc(C(F)(F)F)n2)[C@@H](C)[C@@H]1C1CC1]

2-chloro-4-(trifluoromethyl)pyrimidine (191 mg, 1.044 mmol), potassium fluoride (91 mg, 1.566 mmol) and 18-crown-6 (138 mg, 0.522 mmol) were added to a 2 mL microwave vial in DMSO (1 mL). (2S,3R,4R)-1-Acetyl-4-amino-2-cyclopropyl-3-methyl-1,2,3,4-tetrahydroquinoline-6-carboxamide (for a preparation see Intermediate 276, 100 mg, 0.348 mmol) and DIPEA (0.304 mL, 1.740 mmol) were added and reaction mixture was heated at 160° C. for 4 h. The reaction mixture partitioned between ethyl acetate and sat. LiCl solution. The organic layer was separated, washed with water, dried (Na$_2$SO$_4$) and concentrated to give a crude brown residue. This was purified by silica gel column chromatography eluting with 0-10% methanol/DCM to give the product (134 mg, 0.309 mmol, 89%) as a brown oil. LCMS (2 min Formic): Rt=0.85 min, [MH]+= 434.

The following examples were prepared in a similar manner to Example 401 using KF, 18-crown-6 and DIPEA to couple the appropriate aryl halide with Intermediate 276.

| Ex No. | Name | Structure | Mass (mg) | Yield (%) | [MH]+ | Rt (min) (LCMS Method) |
|---|---|---|---|---|---|---|
| 402 | (2S,3R,4R)-1-acetyl-2-cyclopropyl-4-((5-fluoropyrimidin-2-yl)amino)-3-methyl-1,2,3,4-tetrahydroquinoline-6-carboxamide | 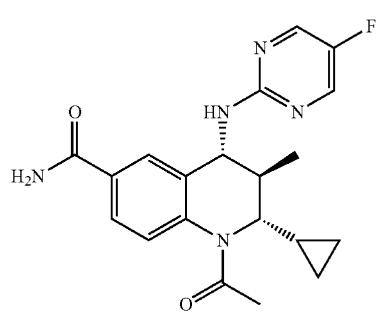 | 110 | 82 | 384 | 0.75 (2 min Formic) |

| Ex No. | Name | Structure | Mass (mg) | Yield (%) | [MH]+ | Rt (min) (LCMS Method) |
|---|---|---|---|---|---|---|
| 403 | (2S,3R,4R)-1-acetyl-4-((5-chloropyrimidin-2-yl)amino)-2-cyclopropyl-3-methyl-1,2,3,4-tetrahydroquinoline-6-carboxamide | 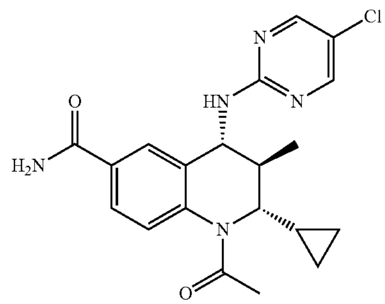 [SMILES: CC(=O)N1c2ccc(C(N)=O)cc2[C@H](Nc2ncc(Cl)cn2)[C@@H](C)[C@@H]1C1CC1] | 91 | 65 | 400 | 0.82 (2 min Formic) |
| 404 | (2S,3R,4R)-1-acetyl-4-((5-cyanopyrimidin-2-yl)amino)-2-cyclopropyl-3-methyl-1,2,3,4-tetrahydroquinoline-6-carboxamide | 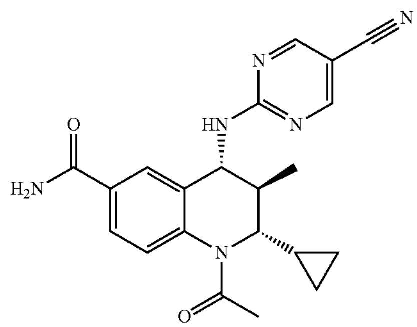 [SMILES: CC(=O)N1c2ccc(C(N)=O)cc2[C@H](Nc2ncc(C#N)cn2)[C@@H](C)[C@@H]1C1CC1] | 30 | 22 | 391 | 0.73 (2 min Formic) |
| 405 | (2S,3R,4R)-1-acetyl-2-cyclopropyl-3-methyl-4-((5-methylpyrimidin-2-yl)amino)-1,2,3,4-tetrahydroquinoline-6-carboxamide | 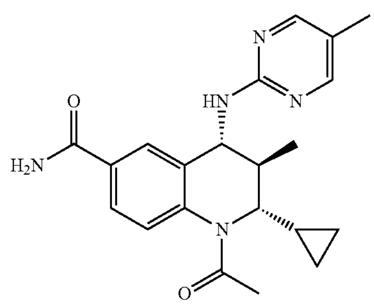 [SMILES: CC(=O)N1c2ccc(C(N)=O)cc2[C@H](Nc2ncc(C)cn2)[C@@H](C)[C@@H]1C1CC1] | 4 | 3 | 380 | 0.69 (2 min Formic) |
| 406 | (2S,3R,4R)-1-acetyl-2-cyclopropyl-4-((4,5-dimethylpyrimidin-2-yl)amino)-3-methyl-1,2,3,4-tetrahydroquinoline-6-carboxamide | 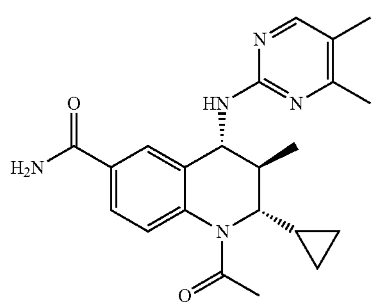 [SMILES: CC(=O)N1c2ccc(C(N)=O)cc2[C@H](Nc2ncc(C)c(C)n2)[C@@H](C)[C@@H]1C1CC1] | 37 | 13 | 394 | 0.81 (2 min HpH) |
| 407 | (2S,3R,4R)-1-acetyl-2-cyclopropyl-4-((4-ethylpyrimidin-2-yl)amino)-3-methyl-1,2,3,4-tetrahydroquinoline-6-carboxamide | 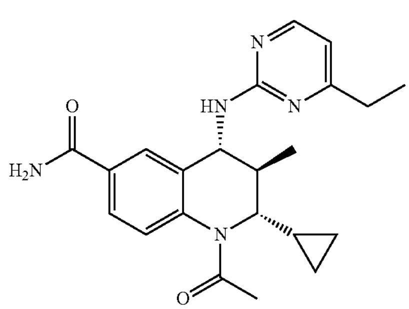 [SMILES: CCc1ccnc(N[C@H]2c3cc(C(N)=O)ccc3N(C(C)=O)[C@@H](C3CC3)[C@@H]2C)n1] | 53 | 22 | 394 | 0.72 (2 min Formic) |

| Ex No. | Name | Structure | Mass (mg) | Yield (%) | [MH]+ | Rt (min) (LCMS Method) |
|---|---|---|---|---|---|---|
| 408 | (2S,3R,4R)-1-acetyl-2-cyclopropyl-4-((4,6-dimethylpyrimidin-2-yl)amino)-3-methyl-1,2,3,4-tetrahydroquinoline-6-carboxamide | 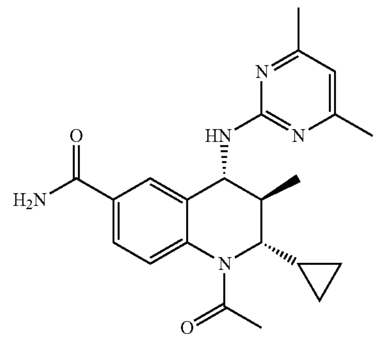 [SMILES: CC(=O)N1c2ccc(C(N)=O)cc2[C@H](Nc2nc(C)cc(C)n2)[C@@H](C)[C@@H]1C1CC1] | 87 | 31 | 394 | 0.82 (2 min HpH) |
| 409 | (2S,3R,4R)-1-acetyl-4-((5-cyano-6-methylpyridin-2-yl)amino)-2-cyclopropyl-3-methyl-1,2,3,4-tetrahydroquinoline-6-carboxamide | 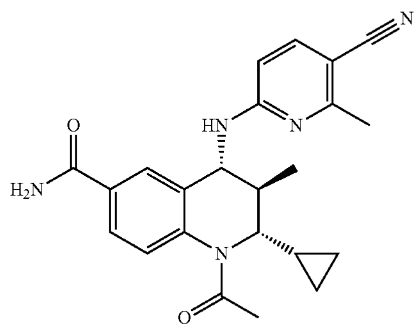 [SMILES: CC(=O)N1c2ccc(C(N)=O)cc2[C@H](Nc2ccc(C#N)c(C)n2)[C@@H](C)[C@@H]1C1CC1] | 158 | 56 | 404 | 0.83 (2 min Formic) |
| 410 | (2S,3R,4R)-1-acetyl-2-cyclopropyl-4-((5-fluoro-4-methylpyrimidin-2-yl)amino)-3-methyl-1,2,3,4-tetrahydroquinoline-6-carboxamide | 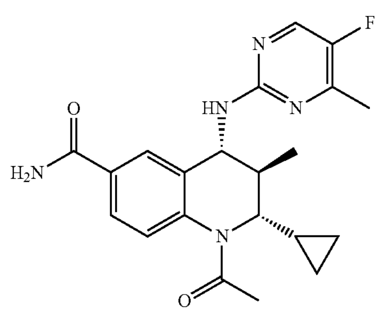 [SMILES: CC(=O)N1c2ccc(C(N)=O)cc2[C@H](Nc2ncc(F)c(C)n2)[C@@H](C)[C@@H]1C1CC1] | 100 | 48 | 398 | 0.80 (2 min Formic) |
| 411 | (2S,3R,4R)-1-acetyl-2-cyclopropyl-4-((4-isopropylpyrimidin-2-yl)amino)-3-methyl-1,2,3,4-tetrahydroquinoline-6-carboxamide | 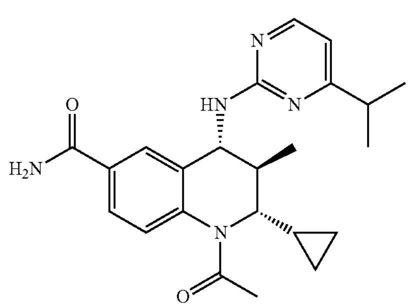 [SMILES: CC(=O)N1c2ccc(C(N)=O)cc2[C@H](Nc2nccc(C(C)C)n2)[C@@H](C)[C@@H]1C1CC1] | 67 | 32 | 408 | 0.80 (2 min Formic) |

| Ex No. | Name | Structure | Mass (mg) | Yield (%) | [MH]+ | Rt (min) (LCMS Method) |
|---|---|---|---|---|---|---|
| 412 | (2S,3R,4R)-1-acetyl-4-((5-cyano-4-methylpyrimidin-2-yl)amino)-2-cyclopropyl-3-methyl-1,2,3,4-tetrahydroquinoline-6-carboxamide | 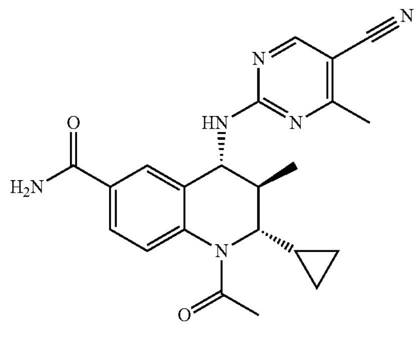 [SMILES: CC(=O)N1c2ccc(C(N)=O)cc2[C@H](Nc2ncc(C#N)c(C)n2)[C@@H](C)[C@@H]1C1CC1] | 46 | 22 | 405 | 0.77 (2 min Formic) |
| 413 | (2S,3R,4R)-1-acetyl-2-cyclopropyl-4-((4-(3,6-dihydro-2H-pyran-4-yl)pyrimidin-2-yl)amino)-3-methyl-1,2,3,4-tetrahydroquinoline-6-carboxamide | 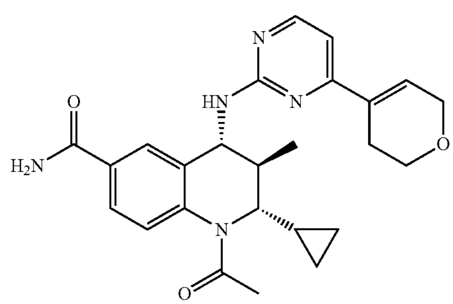 [SMILES: CC(=O)N1c2ccc(C(N)=O)cc2[C@H](Nc2nccc(C3=CCOCC3)n2)[C@@H](C)[C@@H]1C1CC1] | 15 | 6 | 448 | 0.79 (2 min Formic) |

Example 414: (2S,3R,4R)-1-acetyl-4-((3-cyanopyridin-2-yl)amino)-2-cyclopropyl-3-methyl-1,2,3,4-tetrahydroquinoline-6-carboxamide

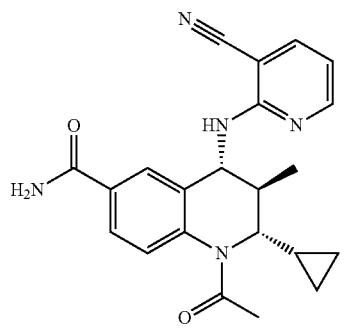 [SMILES: CC(=O)N1c2ccc(C(N)=O)cc2[C@H](Nc2ncccc2C#N)[C@@H](C)[C@@H]1C1CC1]

A solution of (2S,3R,4R)-1-acetyl-4-amino-2-cyclopropyl-3-methyl-1,2,3,4-tetrahydroquinoline-6-carboxamide (for a preparation see Intermediate 276, 60 mg, 0.209 mmol), 2-fluoronicotinonitrile (51.0 mg, 0.418 mmol) and triethylamine (0.058 mL, 0.418 mmol) in N-methyl-2-pyrrolidone (NMP) (2 mL) was stirred in a closed vessel in a microwave at 200° C. for 1 h. The reaction mixture was purified directly by MDAP (Formic) to give a partial formic salt so the material was dissolved in MeOH and applied to a 2 g NH$_2$ cartridge which had been pre-equilibrated with MeOH (2 mL). The cartridge was washed with MeOH (2 mL) and this solution was concentrated in vacuo to give the product (25 mg, 0.064 mmol, 31% yield). LCMS (2 min Formic): Rt=0.79 min, [MH]+=390.

The following example was prepared in a similar manner to Example 414 using NEt$_3$ in NMP to couple the appropriate aryl halide with Intermediate 276.

| Ex No. | Name | Structure | Mass (mg) | Yield (%) | [MH]+ | Rt (min) (LCMS Method) |
|---|---|---|---|---|---|---|
| 415 | (2S,3R,4R)-1-acetyl-4-((5-cyanopyrimidin-2-yl)amino)-2-cyclopropyl-3-methyl-1,2,3,4-tetrahydroquinoline-6-carboxamide | 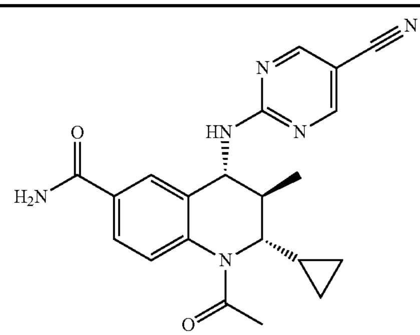 | 100 | 74 | 391 | 0.74 (2 min Formic) |

Example 416: (2S,3R,4R)-1-acetyl-2-cyclopropyl-3-methyl-4-((1-methyl-2-oxo-1,2-dihydropyridin-3-yl)amino)-1,2,3,4-tetrahydroquinoline-6-carboxamide

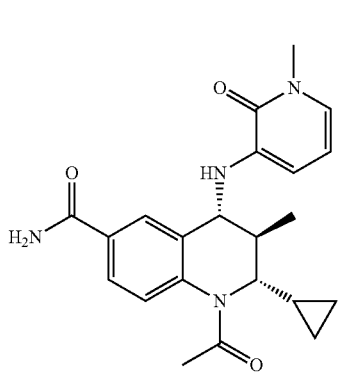 [SMILES: CC(=O)N1c2ccc(C(N)=O)cc2[C@H](Nc2cccn(C)c2=O)[C@@H](C)[C@@H]1C1CC1]

To (2S,3S,4R)-2-cyclopropyl-3-methyl-4-((1-methyl-2-oxo-1,2-dihydropyridin-3-yl)amino)-1,2,3,4-tetrahydroquinoline-6-carboxamide (for a preparation see Intermediate 280, 72 mg, 0.204 mmol) in a round bottom flask pyridine (0.049 mL, 0.613 mmol), acetyl chloride (0.029 mL, 0.409 mmol) and anhydrous dichloromethane (DCM) (4 mL) were added. The reaction mixture was stirred at rt under nitrogen for 16 h. To the reaction mixture pyridine (0.050 mL, 0.613 mmol), acetyl chloride (0.029 mL, 0.409 mmol) and chloroform (2 mL) were added. The reaction mixture was stirred at 60° C. under nitrogen for 1 h 30 min. The reaction mixture was cooled, concentrated in vacuo and purified by MDAP (Formic) to give title compound as a white solid (6 mg, 6%).

LCMS (2 min Formic): Rt=0.70 min, [MH]+=395.

Example 417: (2S,3R,4R)-1-acetyl-2-cyclopropyl-4-((3-(hydroxymethyl)pyridin-2-yl)amino)-3-methyl-1,2,3,4-tetrahydroquinoline-6-carboxamide

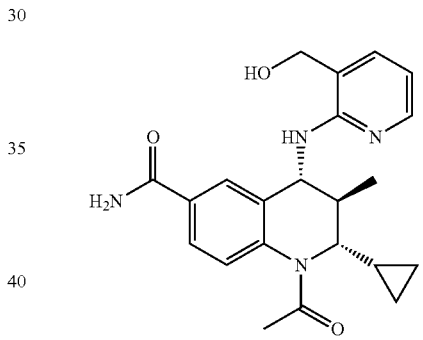

To a stirred mixture of (2S,3R,4R)-1-acetyl-2-cyclopropyl-4-((3-(hydroxymethyl)pyridin-2-yl)amino)-3-methyl-1,2,3,4-tetrahydroquinoline-6-carbonitrile (for a preparation see Intermediate 282, 83 mg, 0.220 mmol) and potassium carbonate (60.9 mg, 0.441 mmol) in DMSO (0.75 mL) was added hydrogen peroxide (35 wt % in water) (0.045 mL, 0.514 mmol). The mixture was stirred in a stoppered vessel at rt for 5 h. The reaction mixture was diluted with water and extracted with DCM. The organic extracts were combined and dried through a hydrophobic frit. The residue was purified by MDAP (HpH) to give title compound as a white solid (49 mg, 0.124 mmol, 56%).

LCMS (2 min Formic): Rt=0.51 min, [MH]+=395.

Example 418: (2S,3R,4R)-1-acetyl-4-((3-carbamoylpyridin-2-yl)amino)-2-cyclopropyl-3-methyl-1,2,3,4-tetrahydroquinoline-6-carboxamide

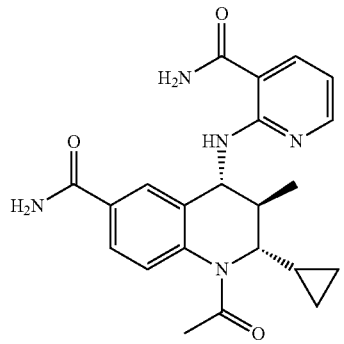 [SMILES: CC(=O)N1c2ccc(C(N)=O)cc2[C@H](Nc2ncccc2C(N)=O)[C@@H](C)[C@@H]1C1CC1]

To a stirred mixture of (2S,3R,4R)-1-acetyl-4-((3-cyanopyridin-2-yl)amino)-2-cyclopropyl-3-methyl-1,2,3,4-tetrahydroquinoline-6-carbonitrile (for a preparation see Example 311, 81 mg, 0.218 mmol) and potassium carbonate (121 mg, 0.872 mmol) in DMSO (0.75 mL) was added hydrogen peroxide (35 wt % in water) (0.057 mL, 0.654 mmol). The reaction mixture was diluted with water (2 mL) and a precipitate formed. The solid was isolated by vacuum filtration, washed with water (10 mL) and dried in a vacuum oven to give title compound as a white solid (68 mg, 0.167 mmol, 77%).

LCMS (2 min Formic): Rt=0.60 min, [MH]⁺=408.

Example 419: (2S,3R,4R)-1-acetyl-2-cyclopropyl-N-hydroxy-3-methyl-4-((4-methylpyrimidin-2-yl)amino)-1,2,3,4-tetrahydroquinoline-6-carboxamide

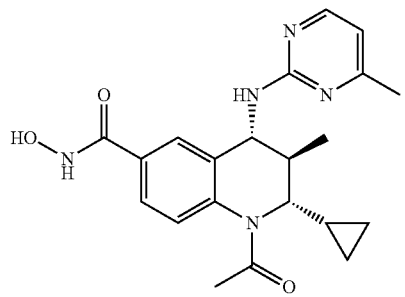 [SMILES: CC(=O)N1c2ccc(C(=O)NO)cc2[C@H](Nc2nccc(C)n2)[C@@H](C)[C@@H]1C1CC1]

A solution of (2S,3R,4R)-1-acetyl-2-cyclopropyl-3-methyl-4-((4-methylpyrimidin-2-yl)amino)-1,2,3,4-tetrahydroquinoline-6-carboxylic acid (for a preparation see Example 357, 50 mg, 0.131 mmol) HATU (60.0 mg, 0.158 mmol) and DIPEA (0.092 mL, 0.526 mmol) in N,N-dimethylformamide (DMF) (1 mL) was stirred at rt for 30 min. Hydroxylamine hydrochloride (18.27 mg, 0.263 mmol) was added and the reaction was stirred for a further 1 h. The solvent was removed under reduced pressure and the residue was purified by MDAP (HpH) to give title compound as a light brown solid (2 mg, 4%).

LCMS (2 min Formic): Rt=0.61 min, [MH]⁺=396.

Example 420: (2S,3R,4R)-1-acetyl-2-cyclopropyl-4-((3-(hydroxymethyl)-6-methylpyridin-2-yl)amino)-3-methyl-1,2,3,4-tetrahydroquinoline-6-carbonitrile

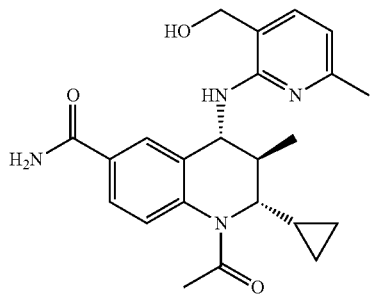 [SMILES: CC(=O)N1c2ccc(C(N)=O)cc2[C@H](Nc2nc(C)ccc2CO)[C@@H](C)[C@@H]1C1CC1]

The (2S,3R,4R)-1-acetyl-2-cyclopropyl-4-((3-(hydroxymethyl)-6-methylpyridin-2-yl)amino)-3-methyl-1,2,3,4-tetrahydroquinoline-6-carbonitrile (for a preparation see Intermediate 285, 75 mg, 0.192 mmol) was taken up in dimethyl sulfoxide (DMSO) (2 mL) and was treated with potassium carbonate (53.1 mg, 0.384 mmol) and hydrogen peroxide (0.168 mL, 1.921 mmol) and allowed to stir at rt for 1 h. Further hydrogen peroxide (0.168 mL, 1.921 mmol) was added and the reaction allowed to stir at rt for 2 h. The reaction was diluted with sodium thiosulphate (aq) and was extracted with EtOAc, the organic phase was dried using a hydrophobic frit and concentrated to a oil. This oil was purified using a MDAP (Formic) and the appropriate fractions were summed and concentrated to give the product (11 mg, 0.027 mmol, 14%) as a white solid. LCMS (2 min Formic): Rt=0.55 min, [MH]⁺=409.

The following example was prepared in a similar manner to Example 420 using NEt₃ in NMP to couple the Intermediate 228 with Intermediate 231; followed by deprotection with TBAF; followed by hydrolysis with H₂O₂.

| Ex No. | Name | Structure | Mass (mg) | Yield (%) | [MH]⁺ | Rt (min) (LCMS Method) |
|---|---|---|---|---|---|---|
| 421 | (2S,3R,4R)-1-acetyl-4-((5-chloro-6-(hydroxymethyl)pyridin-2-yl)amino)-2-cyclopropyl-3-methyl-1,2,3,4-tetrahydroquinoline-6-carboxamide | 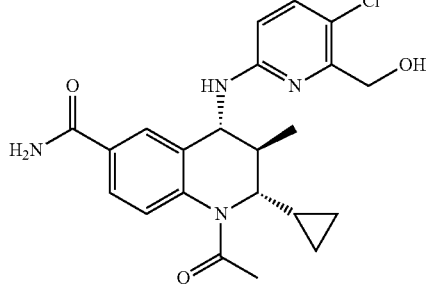 | 19 | 72 | 429 | 0.74 (2 min Formic) |

Example 422: (2S,3R,4R)-2-cyclopropyl-1-isobutyryl-3-methyl-4-((4-methylpyrimidin-2-yl)amino)-1,2,3,4-tetrahydroquinoline-6-carboxamide

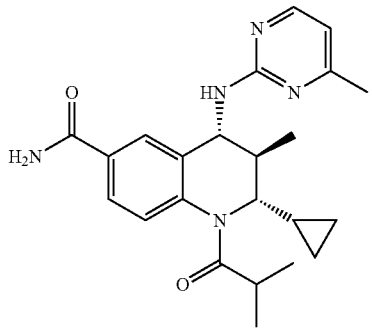 [SMILES: Cc1ccnc(N[C@H]2c3cc(C(N)=O)ccc3N(C(=O)C(C)C)[C@@H](C3CC3)[C@@H]2C)n1]

To a solution of (2S,3R,4R)-2-cyclopropyl-1-iso butyryl-3-methyl-4-((4-methylpyrimidin-2-yl)amino)-1,2,3,4-tetrahydroquinoline-6-carbonitrile (for a preparation see Intermediate 288, 5 mg, 0.013 mmol) in dimethyl sulfoxide (DMSO) (2 mL), was added hydrogen peroxide (11.24 μl, 0.128 mmol) and potassium carbonate (3.55 mg, 0.026 mmol) and the reaction allowed to stir at rt for 3 h. A further portion of hydrogen peroxide (11.24 μl, 0.128 mmol) was added and the reaction allowed to stir for 2 h. Further hydrogen peroxide (100 μl, 1.142 mmol) and potassium carbonate (35.5 mg, 0.257 mmol) were added and the reaction stirred for a further 30 min. The reaction mixture was quenched with 10% sodium thiosulfate and extracted twice with DCM. The organic extracts were combined, washed with water, dried over a hydrophobic frit and concentrated in vacuo to give the product (3 mg, 7.36 μmol, 57%) as a pale yellow oil. LCMS (2 min Formic): Rt=0.82 min, [MH]$^+$=408.

The following example was prepared in a similar manner to Example 422 using propionyl chloride to acylate Intermediate 229, followed by deprotection with TBAF; followed by the use of KF, 18-crown-6 and DIPEA to couple the appropriate aryl halide; followed by hydrolysis with $H_2O_2$.

Example 424: (2S,3R,4R)-1-acetyl-4-((4-cyano-2-hydroxyphenyl)amino)-2-cyclopropyl-3-methyl-1,2,3,4-tetrahydroquinoline-6-carboxamide

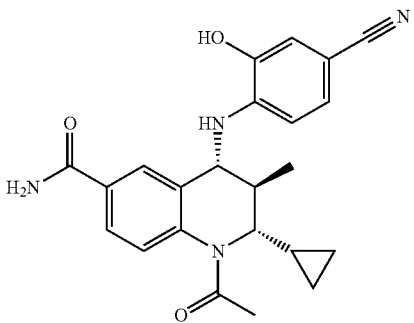 [SMILES: CC(=O)N1c2ccc(C(N)=O)cc2[C@H](Nc2ccc(C#N)cc2O)[C@@H](C)[C@@H]1C1CC1]

(2S,3R,4R)-1-Acetyl-4-((4-cyano-2-methoxyphenyl)amino)-2-cyclopropyl-3-methyl-1,2,3,4-tetrahydroquinoline-6-carboxamide (for a preparation see Example 390, 98 mg, 0.234 mmol) was suspended in dichloromethane (DCM) (2 mL) and cooled to 0° C. in an ice bath. BBr$_3$ (1M in DCM) (2.342 mL, 2.342 mmol) was added dropwise forming an orange suspension and reaction mixture stirred at r. under $N_2$ for 1 h. The reaction mixture was carefully poured onto ice-water and extracted with DCM. The organic layer was dried ($Na_2SO_4$) and concentrated to give 59 mg of crude orange oily solid. This was purified by MDAP (Formic). Fractions containing desired product were partitioned between sat. NaHCO$_3$ and DCM. The organic layer was separated, dried ($Na_2SO_4$) and concentrated to give the product (11 mg, 0.027 mmol, 12%) as a white solid. The residue from the work up, which was insoluble in DCM was dissolved in MeOH and concentrated to give 35 mg of crude orange oily solid. This was purified directly by MDAP (Formic) to give a further batch of product (13 mg, 0.032 mmol, 14%) as a slightly off-white solid. These two solids were combined to give final product (20 mg, 0.049 mmol, 21%) of an orange solid.

LCMS (2 min Formic): Rt=0.80 min, [MH]$^+$=271.

The following were similarly prepared using BBr$_3$ to demethylate Examples 363 & 365 respectively.

| Ex No. | Name | Structure | Mass (mg) | Yield (%) | [MH]$^+$ | Rt (min) (LCMS Method) |
|---|---|---|---|---|---|---|
| 423 | (2S,3R,4R)-2-cyclopropyl-3-methyl-4-((4-methylpyrimidin-2-yl)amino)-1-propionyl-1,2,3,4-tetrahydroquinoline-6-carboxamide | 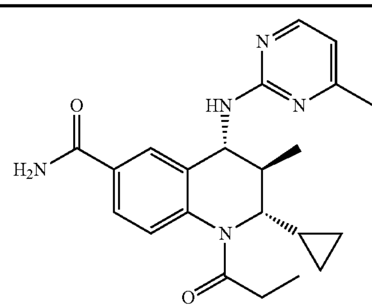 | 9 | 86 | 394 | 0.73 (2 min Formic) |

| Ex No. | Name | Structure | Mass (mg) | Yield (%) | [MH]+ | Rt (min) (LCMS Method) |
|---|---|---|---|---|---|---|
| 425 | (2S,3R,4R)-1-acetyl-4-((4-chloro-3-hydroxyphenyl)amino)-2-cyclopropyl-3-methyl-1,2,3,4-tetrahydroquinoline-6-carboxamide | 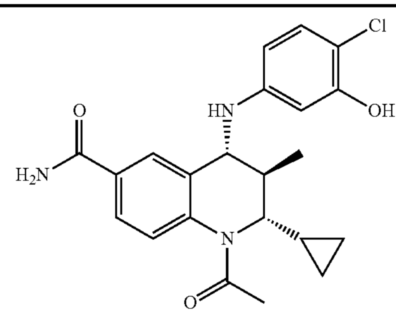 | 28 | 44 | 414 | 0.85 (2 min Formic) |
| 426 | (2S,3R,4R)-1-acetyl-4-((4-chloro-2-hydroxyphenyl)amino)-2-cyclopropyl-3-methyl-1,2,3,4-tetrahydroquinoline-6-carboxamide | 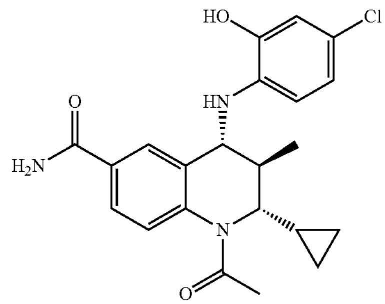 [SMILES: CC(=O)N1c2ccc(C(N)=O)cc2[C@H](Nc2ccc(Cl)cc2O)[C@@H](C)[C@@H]1C1CC1] | 11 | 8 | 414 | 0.91 (2 min Formic) |

Example 427: (2S,3R,4R)-1-acetyl-4-((5-cyanothiophen-2-yl)amino)-2-cyclopropyl-3-methyl-1,2,3,4-tetrahydroquinoline-6-carboxamide

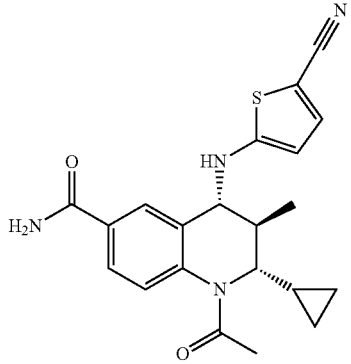 [SMILES: CC(=O)N1c2ccc(C(N)=O)cc2[C@H](Nc2ccc(C#N)s2)[C@@H](C)[C@@H]1C1CC1]

A mixture of (2S,3R,4R)-1-acetyl-4-((5-cyanothiophen-2-yl)amino)-2-cyclopropyl-3-methyl-1,2,3,4-tetrahydroquinoline-6-carboxylic acid (for a preparation see Intermediate 290, 21.1 mg, 0.053 mmol) and HATU (24.34 mg, 0.064 mmol) in anhydrous DMF (1 mL) was treated with DIPEA (0.037 mL, 0.213 mmol) and stirred in a sealed vial at rt for 15 min. Ammonium chloride (8.56 mg, 0.160 mmol) was added and the mixture stirred for 1 h at rt. The mixture was directly purified by MDAP (HpH) to give the crude product 15 mg as a green solid. The sample was further purified by MDAP (Formic) to title compound (5 mg, 24%) as a white solid. LCMS (2 min HpH): Rt=0.86 min, [MH]+=395.

Example 428: (2S,3R,4R)-1-acetyl-2-ethyl-4-((5-fluoro-4-methylpyrimidin-2-yl)amino)-N-(2-hydroxyethyl)-3-methyl-1,2,3,4-tetrahydroquinoline-6-carboxamide

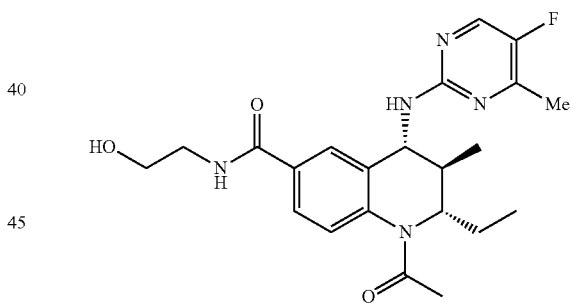

To a reaction vessel (2S,3R,4R)-1-acetyl-N-(2-((tert-butyldimethylsilyl)oxy)ethyl)-2-ethyl-4-((5-fluoro-4-methylpyrimidin-2-yl)amino)-3-methyl-1,2,3,4-tetrahydroquinoline-6-carboxamide (for a preparation see Intermediate 300, 37 mg, 0.068 mmol) in THF (3 mL) was added. The solution was cooled to 0° C. and TBAF (1 M in THF) (0.272 mL, 0.272 mmol) was added and the reaction left to stir and warm to room temperature for 60 min. The reaction solution was poured onto water (10 mL) and the aqueous phase extracted with DCM (3×10 mL). The organic extracts were combined, washed with brine (25 mL) and dried through a hydrophobic frit. The resulting solution was concentrated in vacuo to give 54 mg of crude product as an orange/brown solid. This was purified by chromatography on SiO2 (10 g, eluting with 20-13% methanol/DCM). The fractions containing product were combined and concentrated in vacuo to give 44 mg of crude product as an orange solid. This was purified by chromatography on SiO2 (Biotage SNAP 10 g, eluting with 0-7% methanol DCM). The fractions containing product were combined and concentrated in vacuo to give the desired product as an orange solid (24 mg, 0.056 mmol, 82%). LCMS (2 min Formic): Rt=0.76 min, [MH]+=430.

The following examples were prepared in a similar manner to Example 428 using TBAF to deprotect Intermediates 301-309.

| Ex. No. | Name | Structure | Mass (mg) | Yield (%) | [MH]+ | Rt (mins) (LCMS method) |
|---|---|---|---|---|---|---|
| 429 | (2S,3R,4R)-1-acetyl-2-cyclopropyl-4-((5-fluoro-4-methylpyrimidin-2-yl)amino)-N-(2-hydroxyethyl)-3-methyl-1,2,3,4-tetrahydroquinoline-6-carboxamide | 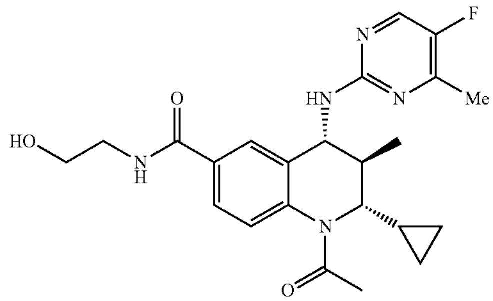 [SMILES: CC(=O)N1c2ccc(C(=O)NCCO)cc2[C@H](Nc2ncc(F)c(C)n2)[C@@H](C)[C@@H]1C1CC1] | 11 | 55 | 442 | 0.79 (2 min Formic) |
| 430 | (2S,3R,4R)-1-acetyl-4-((5-fluoro-4-methylpyrimidin-2-yl)amino)-N-(2-hydroxyethyl)-2,3-dimethyl-1,2,3,4-tetrahydroquinoline-6-carboxamide | 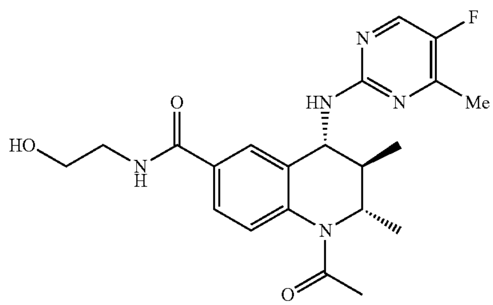 [SMILES: CC(=O)N1c2ccc(C(=O)NCCO)cc2[C@H](Nc2ncc(F)c(C)n2)[C@@H](C)[C@@H]1C] | 12 | 77 | 416 | 0.71 (2 min Formic) |
| 431 | (2S,3R,4R)-1-acetyl-2-ethyl-4-((5-fluoro-6-methylpyridin-2-yl)amino)-N-(2-hydroxyethyl)-3-methyl-1,2,3,4-tetrahydroquinoline-6-carboxamide | 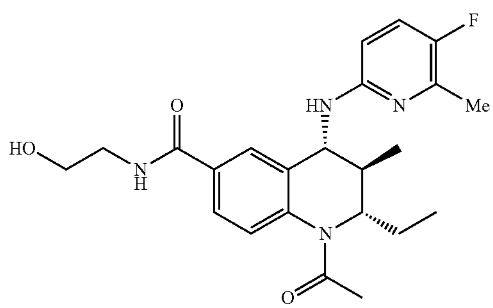 [SMILES: CC[C@H]1[C@H](C)[C@@H](Nc2ccc(F)c(C)n2)c2cc(C(=O)NCCO)ccc2N1C(C)=O] | 66 | 64 | 429 | 0.63 (2 min Formic) |
| 432 | (2S,3R,4R)-1-acetyl-2-cyclopropyl-4-((5-fluoro-6-methylpyridin-2-yl)amino)-N-(2-hydroxyethyl)-3-methyl-1,2,3,4-tetrahydroquinoline-6-carboxamide | 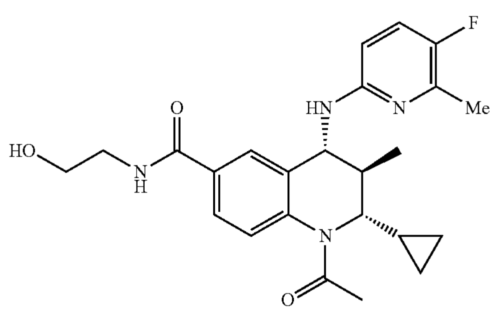 [SMILES: CC(=O)N1c2ccc(C(=O)NCCO)cc2[C@H](Nc2ccc(F)c(C)n2)[C@@H](C)[C@@H]1C1CC1] | 16 | 81 | 441 | 0.67 (2 min Formic) |

| Ex. No. Name | Structure | Mass (mg) | Yield (%) | [MH]+ | Rt (mins) (LCMS) method |
|---|---|---|---|---|---|
| 433 (2S,3R,4R)-1-acetyl-4-((5-fluoro-6-methylpyridin-2-yl)amino)-N-(2-hydroxyethyl)-2,3-dimethyl-1,2,3,4-tetrahydroquinoline-6-carboxamide | | 21 | 74 | 415 | 0.58 (2 min Formic) |
| 434 (2S,3R,4R)-1-acetyl-2-ethyl-N-(2-hydroxyethyl)-3-methyl-4-((4-methylpyridin-2-yl)amino)-1,2,3,4-tetrahydroquinoline-6-carboxamide | | 13 | 25 | 411 | 0.54 (2 min Formic) |
| 435 (2S,3R,4R)-1-acetyl-2-cyclopropyl-N-(2-hydroxyethyl)-3-methyl-4-((4-methylpyridin-2-yl)amino)-1,2,3,4-tetrahydroquinoline-6-carboxamide | | 29 | 94 | 423 | 0.57 (2 min Formic) |
| 436 (2S,3R,4R)-1-acetyl-N-(2-hydroxyethyl)-2,3-dimethyl-4-((4-methylpyridin-2-yl)amino)-1,2,3,4-tetrahydroquinoline-6-carboxamide | | 30 | 59 | 397 | 0.49 (2 min Formic) |

| Ex. No. Name | Structure | Mass (mg) | Yield (%) | [MH]+ | Rt (mins) (LCMS) method |
|---|---|---|---|---|---|
| 437 (2S,3R,4R)-1-acetyl-4-((4-cyano-2-fluorophenyl)amino)-2-cyclopropyl-N-(2-hydroxyethyl)-3-methyl-1,2,3,4-tetrahydroquinoline-6-carboxamide | | 13.5 | 47 | 451 | 0.87 (2 min Formic) |

Example 438: (2S,3R,4R)-1-acetyl-2-cyclopropyl-N-(rac-2-methoxypropyl)-3-methyl-4-((6-methylpyridin-2-yl)amino)-1,2,3,4-tetrahydroquinoline-6-carboxamide Example 439: (2S,3R,4R)-1-acetyl-N-ethyl-2,3-dimethyl-4-((6-methylpyridin-2-yl)amino)-1,2,3,4-tetrahydroquinoline-6-carboxamide

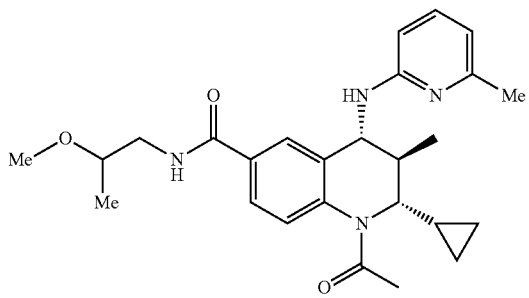 [SMILES: COC(C)CNC(=O)c1ccc2c(c1)[C@H](Nc1cccc(C)n1)[C@@H](C)[C@H](C1CC1)N2C(C)=O]
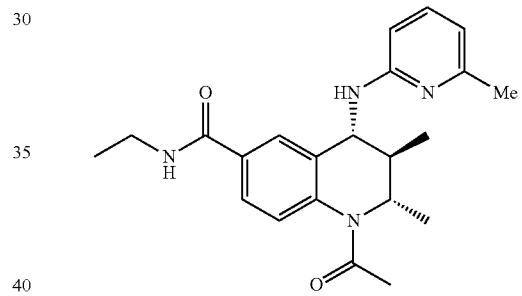

To a solution of (2S,3R,4R)-1-acetyl-2-cyclopropyl-N-(2-hydroxypropyl)-3-methyl-4-((6-methylpyridin-2-yl)amino)-1,2,3,4-tetrahydroquinoline-6-carboxamide (for a preparation see Intermediate 310, 42 mg, 0.096 mmol) in tetrahydrofuran (THF) (3 mL) was added sodium hydride (4.23 mg, 0.106 mmol). The reaction mixture was stirred at rt for 1 hr then a solution of iodomethane (6.59 µL, 0.106 mmol) in tetrahydrofuran (THF) (1.000 mL) added dropwise. The reaction was stirred at rt for 3 hr. Further sodium hydride (4.23 mg, 0.106 mmol) and iodomethane (6.59 µL, 0.106 mmol) was added. The reaction was stirred for 3 h. The reaction was quenched with water, partitioned between ethyl acetate (50 mL) and saturated sodium bicarbonate solution (10 mL) and extracted. The aqueous was extracted with ethyl acetate (3×25 mL). The combined organics were washed with saturated brine 10 mL, dried over magnesium sulphate and evaporated in vacuo. The crude product was purified by MDAP (HpH) to afford a mixture of mono- and di-methylated products. Further purification by MDAP (Formic) afforded the title compound (5 mg, 0.011 mmol, 12%) as a clear oil.

LCMS (2 min Formic): Rt=0.62 min, [MH]+=451.

(2S,3R,4R)-1-Acetyl-4-amino-N-ethyl-2,3-dimethyl-1,2,3,4-tetrahydroquinoline-6-carboxamide (for a preparation see Intermediate 313, 85 mg, 0.294 mmol) was treated with Pd$_2$(dba)$_3$ (40.3 mg, 0.044 mmol), sodium tert-butoxide (85 mg, 0.881 mmol), DavePhos (11.56 mg, 0.029 mmol) and 2-bromo-6-methylpyridine (76 mg, 0.441 mmol) and allowed to stir at 100° C. for 16 h. The reaction was treated with further Pd$_2$(dba)$_3$ (26.9 mg, 0.029 mmol) and sodium tert-butoxide (56.5 mg, 0.587 mmol) and allowed to stir at 100° C. for 4 h. The reaction was allowed to cool to rt and was filtered through celite, washing with EtOAc. The eluent was concentrated and purified by MDAP (Formic). The appropriate fractions were summed and concentrated to give a yellow gum. This was eluted through a NH$_2$ SPE (5 g) with MeOH, the eluent was concentrated and dried to give the title compound (5 mg, 0.013 mmol, 4%) as a yellow solid.

LCMS (2 min Formic): Rt=0.57 min, [MH]+=381.

The following examples were prepared in a similar manner to Example 439 using Pd$_2$(dba)$_3$, DavePhos and NaOtBu to couple the appropriate aryl halide with Intermediate 313.

| Ex. No. | Name | Structure | Mass (mg) | Yield (%) | [MH]+ | Rt (mins) (LCMS) method |
|---|---|---|---|---|---|---|
| 440 | (2S,3R,4R)-1-acetyl-N-ethyl-2,3-dimethyl-4-((5-methylpyrazin-2-yl)amino)-1,2,3,4-tetrahydroquinoline-6-carboxamide | 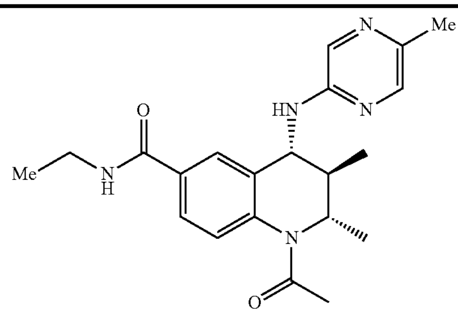 | 49 | 41 | 382 | 0.69 (2 min Formic) |

Example 441: (2S,3R,4R)-1-acetyl-2-cyclopropyl-N-(2-hydroxyethyl)-3-methyl-4-((2-methylpyrimidin-4-yl)amino)-1,2,3,4-tetrahydroquinoline-6-carboxamide Example 442: (2S,3R,4R)-1-acetyl-2-ethyl-N-(2-hydroxyethyl)-3-methyl-4-((2-methylpyrimidin-4-yl)amino)-1,2,3,4-tetrahydroquinoline-6-carboxamide

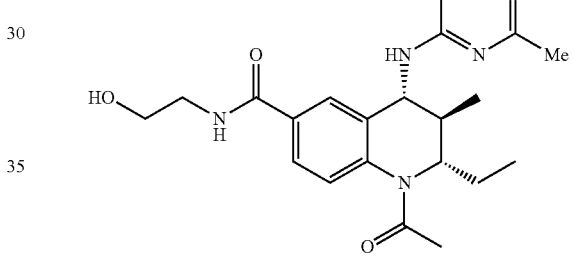

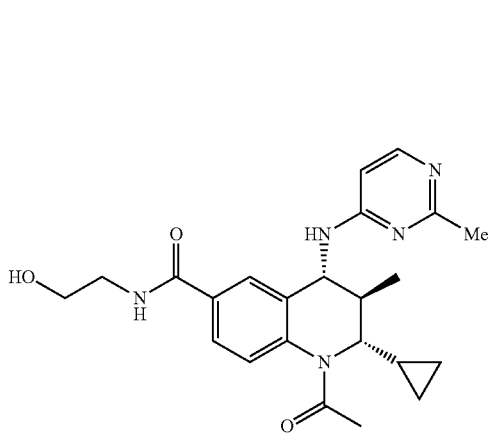 [SMILES: CC(=O)N1c2ccc(C(=O)NCCO)cc2[C@H](Nc2ccnc(C)n2)[C@@H](C)[C@@H]1C1CC1]

A solution of (2S,3R,4R)-1-acetyl-2-cyclopropyl-3-methyl-4-((2-methylpyrimidin-4-yl)amino)-1,2,3,4-tetrahydroquinoline-6-carboxylic acid (for a preparation see Intermediate 315, 35 mg, 0.092 mmol), 2-aminoethanol (6.66 μl, 0.110 mmol), DIPEA (0.064 ml, 0.368 mmol) and HATU (42.0 mg, 0.110 mmol) in N,N-dimethylformamide (DMF) (1 mL) was stirred in a closed vessel at room temp for 8 h. The reaction mixture was purified directly by MDAP (Formic). The appropriate fractions were combined and concentrated in vacuo to give the product (12 mg, 0.028 mmol, 31%).

LCMS (2 min Formic): Rt=0.53 min, [MH]+=424.

To a reaction vessel (2S,3R,4R)-1-acetyl-N-(2-((tert-butyldimethylsilyl)oxy)ethyl)-2-ethyl-3-methyl-4-((2-methylpyrimidin-4-yl)amino)-1,2,3,4-tetrahydroquinoline-6-carboxamide (for a preparation see Intermediate 316, 35 mg, 0.067 mmol) in tetrahydrofuran (THF) (3 mL) was added. The solution was cooled to 0° C. and TBAF (1 M in THF) (0.266 mL, 0.266 mmol) was added and the reaction left to stir and warm to room temperature for 60 minutes. The reaction solution was poured onto water (10 mL) and the aqueous phase extracted with DCM (3×10 mL). The organic extracts were combined, washed with brine (25 mL) and dried through a hydrophobic frit. The resulting solution was concentrated in vacuo to give the crude product as a yellow solid. This was purified by chromatography on SiO$_2$ (10 g, eluting with 0-10% methanol/DCM). The fractions containing product were combined and concentrated in vacuo to give 9 mg of desired product as a colourless gum. The sample was dissolved in 1:1 MeOH:DMSO (1 mL) and purified by MDAP (HpH). The solvent was evaporated in vacuo to give 5 mg of title compound as a white solid.

LCMS (2 min Formic): Rt=0.50 min, [MH]+=412.

Example 443: (2S,3R,4R)-1-acetyl-N-(1,1-dioxido-tetrahydro-2H-thiopyran-4-yl)-2-ethyl-3-methyl-4-((4-methylpyrimidin-2-yl)amino)-1,2,3,4-tetrahydro-quinoline-6-carboxamide

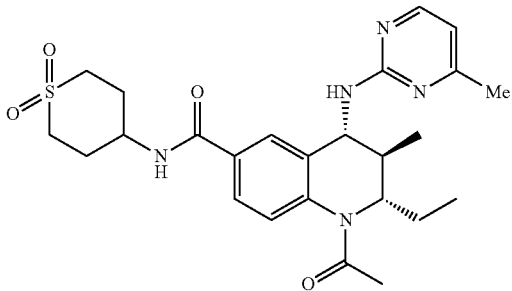 [SMILES: CC[C@H]1[C@H](C)[C@@H](Nc2nccc(C)n2)c2cc(C(=O)NC3CCS(=O)(=O)CC3)ccc2N1C(C)=O]

To a solution of (2S,3R,4R)-1-acetyl-2-ethyl-3-methyl-4-((4-methylpyrimidin-2-yl)amino)-1,2,3,4-tetrahydroquinoline-6-carboxylic acid (for a preparation see Intermediate 318, 50 mg, 0.136 mmol) and HATU (61.9 mg, 0.163 mmol) in N,N-dimethylformamide (DMF) (0.8 mL) was added 4-aminotetrahydro-2H-thiopyran 1,1-dioxide (24.30 mg, 0.163 mmol) and DIPEA (0.095 mL, 0.543 mmol). The reaction mixture was stirred at rt for 1 h. The reaction was diluted to 1 mL with methanol and purified by MDAP (HpH). The solvent was concentrated in vacuo to give the product (32 mg, 0.064 mmol, 47%) as an off-white solid. LCMS (2 min Formic): Rt=0.69 min, [MH]$^+$=500.

The following examples were prepared in a similar manner to Example 443 using HATU and DIPEA to couple the appropriate amine with Example 357 (2-cPr) or Intermediate 318 (2-Et) or 320 (2-Me).

| Ex. No. Name | Structure | Mass (mg) | Yield (%) | [MH]$^+$ | Rt (mins) (LCMS) method |
|---|---|---|---|---|---|
| 444 (2S,3R,4R)-1-acetyl-2-cyclopropyl-3-methyl-4-((4-methylpyrimidin-2-yl)amino)-N-(oxetan-3-yl)-1,2,3,4-tetrahydroquinoline-6-carboxamide | | 15 | 52 | 436 | 0.80 (2 min HpH) |
| 445 (2S,3R,4R)-1-acetyl-2-cyclopropyl-N-(2-methoxyethyl)-3-methyl-4-((4-methylpyrimidin-2-yl)amino)-1,2,3,4-tetrahydroquinoline-6-carboxamide | | 19 | 66 | 438 | 0.83 (2 min HpH) |
| 446 (2S,3R,4R)-1-acetyl-2-cyclopropyl-N,3-dimethyl-4-((4-methylpyrimidin-2-yl)amino)-1,2,3,4-tetrahydroquinoline-6-carboxamide | | 20 | 77 | 394 | 0.80 (2 min HpH) |

| Ex. No. | Name | Structure | Mass (mg) | Yield (%) | [MH]+ | Rt (mins) (LCMS method) |
|---|---|---|---|---|---|---|
| 447 | (2S,3R,4R)-1-acetyl-2-cyclopropyl-3-methyl-4-((4-methylpyrimidin-2-yl)amino)-N-(tetrahydro-2H-pyran-4-yl)-1,2,3,4-tetrahydroquinoline-6-carboxamide | 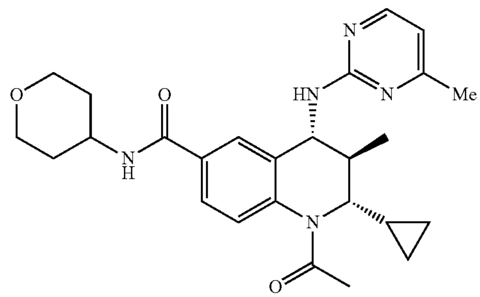 [SMILES: CC(=O)N1c2ccc(C(=O)NC3CCOCC3)cc2[C@H](Nc2nccc(C)n2)[C@@H](C)[C@@H]1C1CC1] | 22 | 72 | 464 | 0.84 (2 min HpH) |
| 448 | (2S,3R,4R)-1-acetyl-2-cyclopropyl-N-ethyl-3-methyl-4-((4-methylpyrimidin-2-yl)amino)-1,2,3,4-tetrahydroquinoline-6-carboxamide | 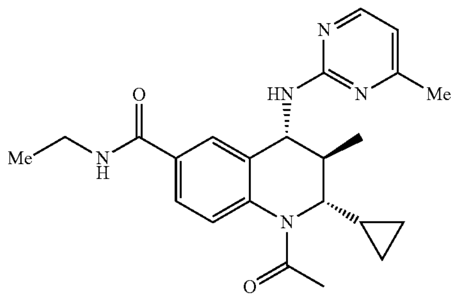 [SMILES: CCNC(=O)c1ccc2c(c1)[C@H](Nc1nccc(C)n1)[C@@H](C)[C@H](C1CC1)N2C(C)=O] | 18 | 67 | 408 | 0.86 (2 min HpH) |
| 449 | (2S,3R,4R)-1-acetyl-2-cyclopropyl-N-(2-hydroxyethyl)-3-methyl-4-((4-methylpyrimidin-2-yl)amino)-1,2,3,4-tetrahydroquinoline-6-carboxamide | 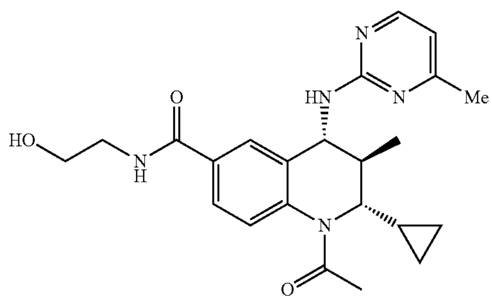 [SMILES: CC(=O)N1c2ccc(C(=O)NCCO)cc2[C@H](Nc2nccc(C)n2)[C@@H](C)[C@@H]1C1CC1] | 38 | 68 | 424 | 0.74 (2 min HpH) |
| 450 | (2S,3R,4R)-1-acetyl-2-cyclopropyl-N-(1,1-dioxidotetrahydro-2H-thiopyran-4-yl)-3-methyl-4-((4-methylpyrimidin-2-yl)amino)-1,2,3,4-tetrahydroquinoline-6-carboxamide | 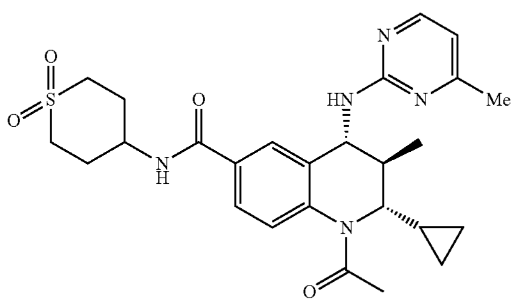 [SMILES: CC(=O)N1c2ccc(C(=O)NC3CCS(=O)(=O)CC3)cc2[C@H](Nc2nccc(C)n2)[C@@H](C)[C@@H]1C1CC1] | 28 | 42 | 512 | 0.81 (2 min HpH) |
| 451 | (2S,3R,4R)-1-acetyl-2-ethyl-N-(2-hydroxyethyl)-3-methyl-4-((4-methylpyrimidin-2-yl)amino)-1,2,3,4-tetrahydroquinoline-6-carboxamide | 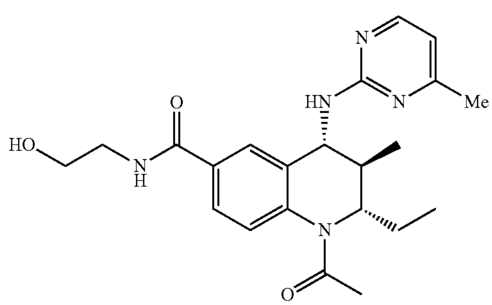 [SMILES: CC[C@H]1[C@H](C)[C@@H](Nc2nccc(C)n2)c2cc(C(=O)NCCO)ccc2N1C(C)=O] | 60 | 71 | 412 | 0.61 (2 min Formic) |

| Ex. No. | Name | Structure | Mass (mg) | Yield (%) | [MH]+ | Rt (mins) (LCMS) method) |
|---|---|---|---|---|---|---|
| 452 | (2S,3R,4R)-1-acetyl-2-ethyl-3-methyl-4-((4-methylpyrimidin-2-yl)amino)-N-(tetrahydro-2H-pyran-4-yl)-1,2,3,4-tetrahydroquinoline-6-carboxamide | 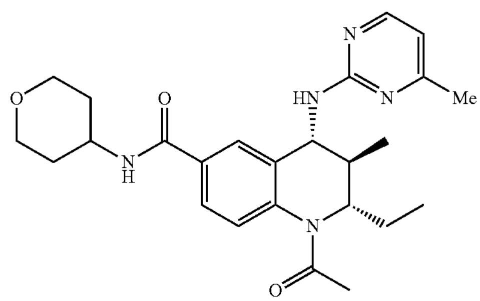 [SMILES: CC[C@H]1[C@H](C)[C@@H](Nc2nccc(C)n2)c2cc(C(=O)NC3CCOCC3)ccc2N1C(C)=O] | 27 | 44 | 452 | 0.71 (2 min Formic) |
| 453 | (2S,3R,4R)-1-acetyl-2-ethyl-N-(2-hydroxyethyl)-3-methyl-4-((4-methylpyrimidin-2-yl)amino)-1,2,3,4-tetrahydroquinoline-6-carboxamide | 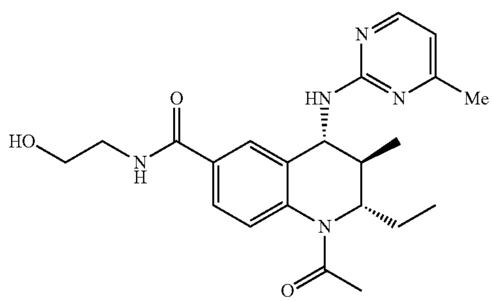 [SMILES: CC[C@H]1[C@H](C)[C@@H](Nc2nccc(C)n2)c2cc(C(=O)NCCO)ccc2N1C(C)=O] | 23 | 41 | 412 | 0.61 (2 min Formic) |
| 454 | (2S,3R,4R)-1-acetyl-2-ethyl-N-(2-methoxyethyl)-3-methyl-4-((4-methylpyrimidin-2-yl)amino)-1,2,3,4-tetrahydroquinoline-6-carboxamide | 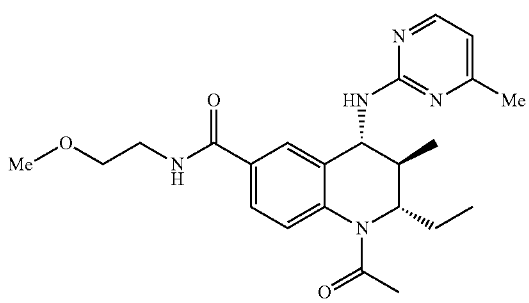 [SMILES: CC[C@H]1[C@H](C)[C@@H](Nc2nccc(C)n2)c2cc(C(=O)NCCOC)ccc2N1C(C)=O] | 21 | 36 | 426 | 0.80 (2 min HpH) |
| 455 | (2S,3R,4R)-1-acetyl-2-ethyl-3-methyl-4-((4-methylpyrimidin-2-yl)amino)-N-(oxetan-3-yl)-1,2,3,4-tetrahydroquinoline-6-carboxamide | 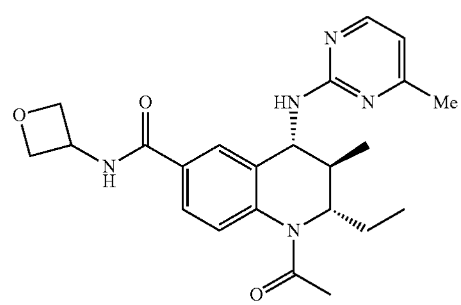 [SMILES: CC[C@H]1[C@H](C)[C@@H](Nc2nccc(C)n2)c2cc(C(=O)NC3COC3)ccc2N1C(C)=O] | 45 | 78 | 424 | 0.77 (2 min HpH) |
| 456 | (2S,3R,4R)-1-acetyl-N,2-diethyl-3-methyl-4-((4-methylpyrimidin-2-yl)amino)-1,2,3,4-tetrahydroquinoline-6-carboxamide | 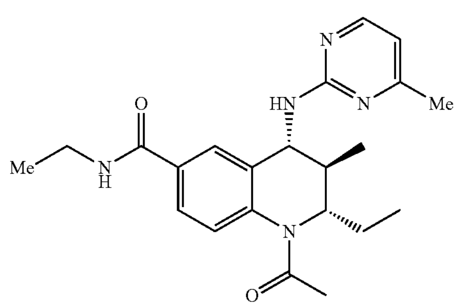 [SMILES: CCNC(=O)c1ccc2c(c1)[C@H](Nc1nccc(C)n1)[C@@H](C)[C@H](CC)N2C(C)=O] | 40 | 75 | 396 | 0.82 (2 min HpH) |

| Ex. No. Name | Structure | Mass (mg) | Yield (%) | [MH]+ | Rt (mins) (LCMS) method |
|---|---|---|---|---|---|
| 457 (2S,3R,4R)-1-acetyl-N-(2-cyanoethyl)-2-ethyl-3-methyl-4-((4-methylpyrimidin-2-yl)amino)-1,2,3,4-tetrahydroquinoline-6-carboxamide | | 47 | 82 | 421 | 0.80 (2 min HpH) |
| 458 (2S,3R,4R)-1-acetyl-N-(2-hydroxyethyl)-2,3-dimethyl-4-((4-methylpyrimidin-2-yl)amino)-1,2,3,4-tetrahydroquinoline-6-carboxamide | | 45 | 80 | 398 | 0.56 (2 min Formic) |
| 459 (2S,3R,4R)-1-acetyl-N-(1,1-dioxidotetrahydro-2H-thiopyran-4-yl)-2,3-dimethyl-4-((4-methylpyrimidin-2-yl)amino)-1,2,3,4-tetrahydroquinoline-6-carboxamide | | 32 | 47 | 486 | 0.63 (2 min Formic) |
| 460 (2S,3R,4R)-1-acetyl-N-(2-cyanoethyl)-2,3-dimethyl-4-((4-methylpyrimidin-2-yl)amino)-1,2,3,4-tetrahydroquinoline-6-carboxamide | | 43 | 75 | 407 | 0.74 (2 min HpH) |
| 461 (2S,3R,4R)-1-acetyl-2,3-dimethyl-4-((4-methylpyrimidin-2-yl)amino)-N-(tetrahydro-2H-pyran-4-yl)-1,2,3,4-tetrahydroquinoline-6-carboxamide | | 42 | 68 | 438 | 0.76 (2 min HpH) |

| Ex. No. Name | Structure | Mass (mg) | Yield (%) | [MH]+ | Rt (mins) (LCMS) method |
|---|---|---|---|---|---|
| 462 (2S,3R,4R)-1-acetyl-N-ethyl-2,3-dimethyl-4-((4-methylpyrimidin-2-yl)amino)-1,2,3,4-tetrahydroquinoline-6-carboxamide | | 37 | 69 | 382 | 0.77 (2 min HpH) |
| 463 (2S,3R,4R)-1-acetyl-N,2,3-trimethyl-4-((4-methylpyrimidin-2-yl)amino)-1,2,3,4-tetrahydroquinoline-6-carboxamide | | 38 | 73 | 368 | 0.71 (2 min HpH) |
| 464 (2S,3R,4R)-1-acetyl-N-(3-methoxypropyl)-2,3-dimethyl-4-((4-methylpyrimidin-2-yl)amino)-1,2,3,4-tetrahydroquinoline-6-carboxamide | | 48 | 80 | 426 | 0.79 (2 min HpH) |
| 465 (2S,3R,4R)-1-acetyl-2,3-dimethyl-4-((4-methylpyrimidin-2-yl)amino)-N-(oxetan-3-yl)-1,2,3,4-tetrahydroquinoline-6-carboxamide | | 45 | 78 | 410 | 0.72 (2 min HpH) |
| 466 (2S,3R,4R)-1-acetyl-N-isopropyl-2,3-dimethyl-4-((4-methylpyrimidin-2-yl)amino)-1,2,3,4-tetrahydroquinoline-6-carboxamide | | 41 | 74 | 396 | 0.84 (2 min HpH) |

| Ex. No. Name | Structure | Mass (mg) | Yield (%) | [MH]+ | Rt (mins) (LCMS) method |
|---|---|---|---|---|---|
| 467 (2S,3R,4R)-1-acetyl-N-(2-methoxyethyl)-2,3-dimethyl-4-((4-methylpyrimidin-2-yl)amino)-1,2,3,4-tetrahydroquinoline-6-carboxamide | | 40 | 69 | 412 | 0.75 (2 min HpH) |
| 468 (2S,3R,4R)-1-acetyl-2-cyclopropyl-N-ethyl-3-methyl-4-((5-methylpyrazin-2-yl)amino)-1,2,3,4-tetrahydroquinoline-6-carboxamide | | 20 | 30 | 408 | 0.77 (2 min Formic) |

Example 469: (2S,3R,4R)-1-acetyl-2-cyclopropyl-4-((5-fluoropyridin-2-yl)amino)-3-methyl-N-(tetrahydro-2H-pyran-4-yl)-1,2,3,4-tetrahydroquinoline-6-carboxamide

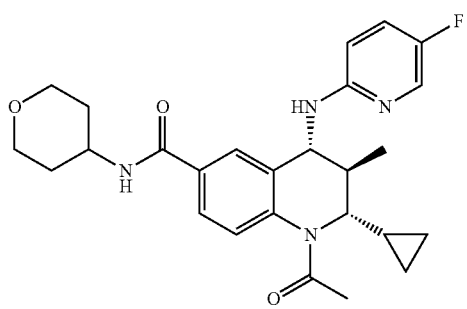 [SMILES: CC(=O)N1c2ccc(C(=O)NC3CCOCC3)cc2[C@H](Nc2ccc(F)cn2)[C@@H](C)[C@@H]1C1CC1]

To a solution of (2S,3R,4R)-1-acetyl-2-cyclopropyl-4-((5-fluoropyridin-2-yl)amino)-3-methyl-1,2,3,4-tetrahydroquinoline-6-carboxylic acid (for a preparation see Example 327, 35 mg, 0.070 mmol) and HATU (32.1 mg, 0.084 mmol) in N,N-dimethylformamide (DMF) (0.6 mL) was added tetrahydro-2H-pyran-4-amine (8.74 µL, 0.084 mmol) followed by DIPEA (0.049 mL, 0.281 mmol). The reaction mixture was stirred at rt for 1 h. The reaction mixture was purified by MDAP (HpH). The solvent was evaporated in vacuo to afford the product (17 mg, 0.036 mmol, 52%) as a white solid.

LCMS (2 min High pH): Rt=0.91 min, [MH]+=467.

The following examples were prepared in a similar manner to Example 404 using HATU and DIPEA to couple the appropriate amine with Example 327 (2-cPr) or 328 (2-Et) or Intermediate 321 (2-Me).

| Ex No. | Name | Structure | Mass (mg) | Yield (%) | [MH]+ | Rt (mins) (LCMS method) |
|---|---|---|---|---|---|---|
| 470 | (2S,3R,4R)-1-acetyl-2-cyclopropyl-4-((5-fluoropyridin-2-yl)amino)-3-methyl-N-(oxetan-3-yl)-1,2,3,4-tetrahydroquinoline-6-carboxamide | 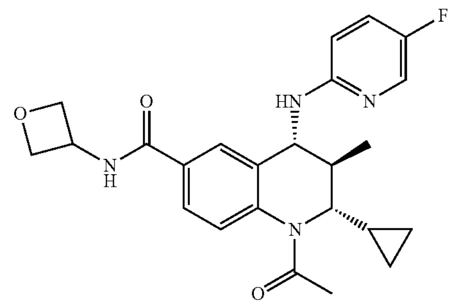 [SMILES: CC(=O)N1c2ccc(C(=O)NC3COC3)cc2[C@H](Nc2ccc(F)cn2)[C@@H](C)[C@@H]1C1CC1] | 22 | 96 | 439 | 0.87 (2 min HpH) |
| 471 | (2S,3R,4R)-1-acetyl-2-cyclopropyl-4-((5-fluoropyridin-2-yl)amino)-N-(2-methoxyethyl)-3-methyl-1,2,3,4-tetrahydroquinoline-6-carboxamide | 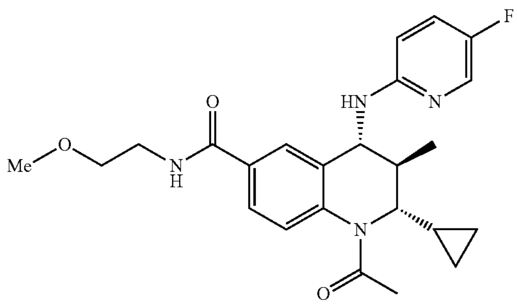 [SMILES: COCCNC(=O)c1ccc2c(c1)[C@H](Nc1ccc(F)cn1)[C@@H](C)[C@H](C1CC1)N2C(C)=O] | 15 | 83 | 441 | 0.91 (2 min HpH) |
| 472 | (2S,3R,4R)-1-acetyl-2-cyclopropyl-4-((5-fluoropyridin-2-yl)amino)-N-(2-hydroxyethyl)-3-methyl-1,2,3,4-tetrahydroquinoline-6-carboxamide | 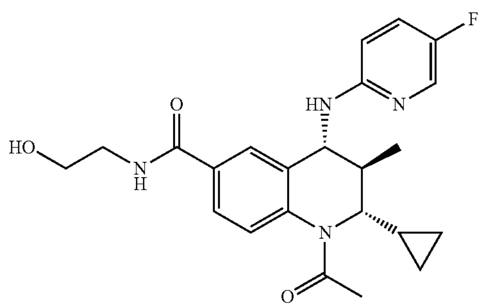 [SMILES: CC(=O)N1c2ccc(C(=O)NCCO)cc2[C@H](Nc2ccc(F)cn2)[C@@H](C)[C@@H]1C1CC1] | 8 | 36 | 425 | 0.82 (2 min HpH) |
| 473 | (2S,3R,4R)-1-acetyl-2-cyclopropyl-N-(1,1-dioxidotetrahydro-2H-thiopyran-4-yl)-4-((5-fluoropyridin-2-yl)amino)-3-methyl-1,2,3,4-tetrahydroquinoline-6-carboxamide | 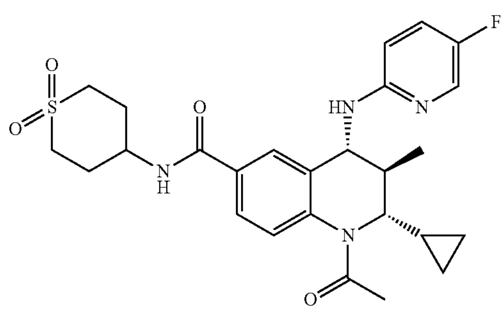 [SMILES: CC(=O)N1c2ccc(C(=O)NC3CCS(=O)(=O)CC3)cc2[C@H](Nc2ccc(F)cn2)[C@@H](C)[C@@H]1C1CC1] | 11 | 41 | 515 | 0.89 (2 min HpH) |
| 474 | (2S,3R,4R)-1-acetyl-2-cyclopropyl-N-ethyl-4-((5-fluoropyridin-2-yl)amino)-3-methyl-1,2,3,4-tetrahydroquinoline-6-carboxamide | 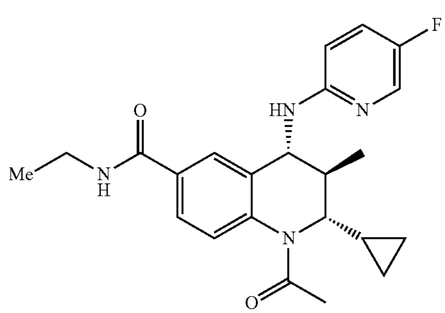 [SMILES: CCNC(=O)c1ccc2c(c1)[C@H](Nc1ccc(F)cn1)[C@@H](C)[C@H](C1CC1)N2C(C)=O] | 17 | 79 | 411 | 0.94 (2 min HpH) |

| Ex No. Name | Structure | Mass (mg) | Yield (%) | [MH]+ | Rt (mins) (LCMS method) |
|---|---|---|---|---|---|
| 475 (2S,3R,4R)-1-acetyl-2-ethyl-4-((5-fluoropyridin-2-yl)amino)-N-(2-hydroxyethyl)-3-methyl-1,2,3,4-tetrahydroquinoline-6-carboxamide | | 25 | 27 | 415 | 0.55 (2 min TFA) |
| 476 (2S,3R,4R)-1-acetyl-N,2-diethyl-4-((5-fluoropyridin-2-yl)amino)-3-methyl-1,2,3,4-tetrahydroquinoline-6-carboxamide | | 31 | 51 | 399 | 0.77 (2 min Formic) |
| 477 (2S,3R,4R)-1-acetyl-2-ethyl-4-((5-fluoropyridin-2-yl)amino)-3-methyl-N-(tetrahydro-2H-pyran-4-yl)-1,2,3,4-tetrahydroquinoline-6-carboxamide | | 57 | 82 | 455 | 0.76 (2 min Formic) |
| 478 (2S,3R,4R)-1-acetyl-2-ethyl-4-((5-fluoropyridin-2-yl)amino)-3-methyl-N-(oxetan-3-yl)-1,2,3,4-tetrahydroquinoline-6-carboxamide | | 33 | 51 | 427 | 0.70 (2 min Formic) |
| 479 (2S,3R,4R)-1-acetyl-4-((5-fluoropyridin-2-yl)amino)-N-(2-hydroxyethyl)-2,3-dimethyl-1,2,3,4-tetrahydroquinoline-6-carboxamide | | 18 | 29 | 401 | 0.53 (2 min TFA) |

579

Example 480: (2S,3R,4R)-1-acetyl-2-cyclopropyl-N-(3-methoxypropyl)-3-methyl-4-((6-methylpyridin-2-yl)amino)-1,2,3,4-tetrahydroquinoline-6-carboxamide

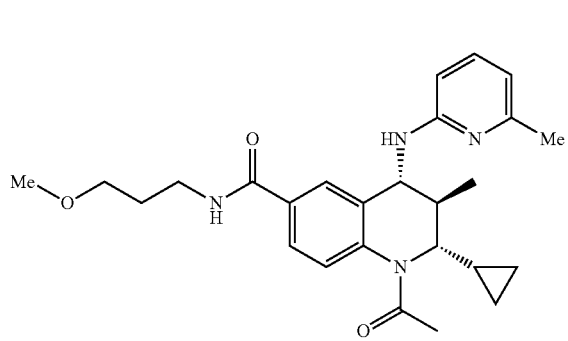 [SMILES: COCCCNC(=O)c1ccc2c(c1)[C@H](Nc1cccc(C)n1)[C@@H](C)[C@H](C1CC1)N2C(C)=O]

To a solution of (2S,3R,4R)-1-acetyl-2-cyclopropyl-3-methyl-4-((6-methylpyridin-2-yl)amino)-1,2,3,4-tetrahydroquinoline-6-carboxylic acid (for a preparation see Example 247, 25 mg, 0.066 mmol) and HATU (30.1 mg, 0.079 mmol) in N,N-dimethylformamide (DMF) (0.6 mL) was added 3-methoxypropan-1-amine (8.32 µL, 0.079 mmol) and DIPEA (46 µL, 0.263 mmol). The reaction mixture was stirred at rt for 1 h. The reaction mixture was purified directly by MDAP (HpH). The solvent was evaporated in vacuo to afford the product (17 mg, 0.038 mmol, 57%) as a white solid.

LCMS (2 min High pH): Rt=0.97 min, [MH]$^+$=451.

The following example was prepared in a similar manner to Example 415 using HATU and DIPEA to couple the appropriate amine with Example 247.

580

Example 482: (2S,3R,4R)-1-acetyl-2-cyclopropyl-N-isopropyl-3-methyl-4-(pyrimidin-2-ylamino)-1,2,3,4-tetrahydroquinoline-6-carboxamide

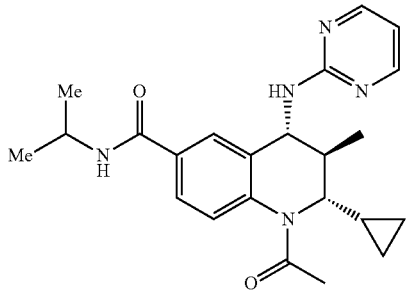 [SMILES: CC(=O)N1c2ccc(C(=O)NC(C)C)cc2[C@H](Nc2ncccn2)[C@@H](C)[C@@H]1C1CC1]

To (2S,3R,4R)-1-acetyl-2-cyclopropyl-3-methyl-4-(pyrimidin-2-ylamino)-1,2,3,4-tetrahydroquinoline-6-carboxylic acid (for a preparation see Example 336, 91 mg, 0.248 mmol), HATU (113 mg, 0.298 mmol), DIPEA (0.174 mL, 0.993 mmol) and N,N-dimethylformamide (DMF) (1.5 mL) were added. The reaction mixture was stirred at rt for 15 min. To the reaction mixture propan-2-amine (0.064 mL, 0.745 mmol) was added. The reaction mixture was stirred at rt for 2 h 45 min. The reaction mixture was partitioned between DCM and water. The organic layer was dried and concentrated in vacuo, dissolved in DCM, loaded into a 10 g SiO$_2$ cartridge and eluted with cyclohexane/ethyl acetate (18-75%). The correct fractions were concentrated in vacuo to give an orange solid containing DMF. The solid was dissolved in ethyl acetate and washed with a 10% solution

| Ex No. | Name | Structure | Mass (mg) | Yield (%) | [MH]$^+$ | Rt (mins) (LCMS method) |
|---|---|---|---|---|---|---|
| 481 | (2S,3R,4R)-1-acetyl-2-cyclopropyl-3-methyl-4-((6-methylpyridin-2-yl)amino)-N-(oxetan-3-yl)-1,2,3,4-tetrahydroquinoline-6-carboxamide | | 26 | 91 | 435 | 0.57 (2 min Formic) | of LiCl in water (twice). The organic layer was dried, concentrated in vacuo to give the title compound as a cream solid.

LCMS (2 min Formic): Rt=0.80 min, [MH]$^+$=408.

The following examples were prepared in a similar manner to Example 417 using HATU and DIPEA to couple the appropriate amine with Example 336 (2-cPr) or Intermediate 323 (2-Me).

| | | | | | | |
|---|---|---|---|---|---|---|
| 483 | (2S,3R,4R)-1-acetyl-2-cyclopropyl-N-(1,3-dihydroxypropan-2-yl)-3-methyl-4-(pyrimidin-2-ylamino)-1,2,3,4-tetrahydroquinoline-6-carboxamide | 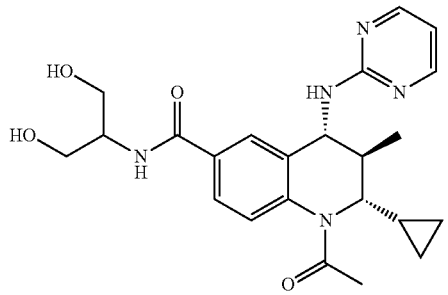 [SMILES: CC(=O)N1c2ccc(C(=O)NC(CO)CO)cc2[C@H](Nc2ncccn2)[C@@H](C)[C@@H]1C1CC1] | 29 | 24 | 440 | 0.61 (2 min Formic) |
| 484 | (2S,3R,4R)-1-acetyl-2-cyclopropyl-3-methyl-4-(pyrimidin-2-ylamino)-N-(tetrahydro-2H-pyran-4-yl)-1,2,3,4-tetrahydroquinoline-6-carboxamide | 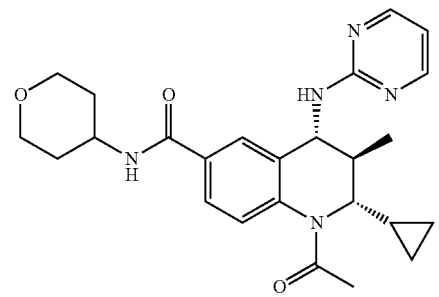 [SMILES: CC(=O)N1c2ccc(C(=O)NC3CCOCC3)cc2[C@H](Nc2ncccn2)[C@@H](C)[C@@H]1C1CC1] | 76 | 56 | 450 | 0.73 (2 min Formic) |
| 485 | 1-((2S,3R,4R)-2,3-dimethyl-4-(pyrimidin-2-ylamino)-6-(pyrrolidine-1-carbonyl)-3,4-dihydroquinolin-1(2H)-yl)ethanone | 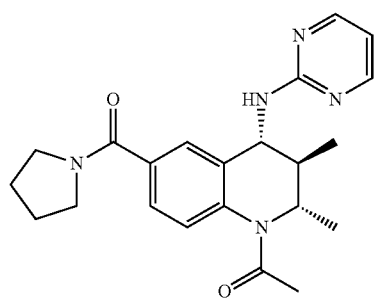 [SMILES: CC(=O)N1c2ccc(C(=O)N3CCCC3)cc2[C@H](Nc2ncccn2)[C@@H](C)[C@@H]1C] | 11 | 19 | 394 | 0.69 (2 min Formic) |
| 486 | 1-((2S,3R,4R)-2,3-dimethyl-6-(morpholine-4-carbonyl)-4-(pyrimidin-2-ylamino)-3,4-dihydroquinolin-1(2H)-yl)ethanone | 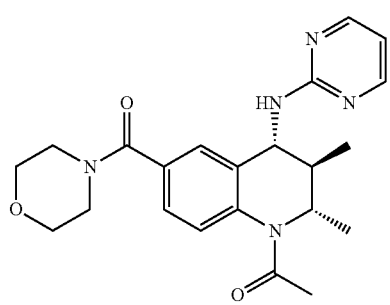 [SMILES: CC(=O)N1c2ccc(C(=O)N3CCOCC3)cc2[C@H](Nc2ncccn2)[C@@H](C)[C@@H]1C] | 19 | 32 | 410 | 0.62 (2 min Formic) |
| 487 | (2S,3R,4R)-1-acetyl-2-cyclopropyl-N-(2-hydroxy-2-methylpropyl)-3-methyl-4-(pyrimidin-2-ylamino)-1,2,3,4-tetrahydroquinoline-6-carboxamide | 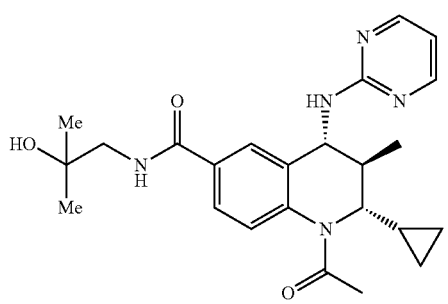 [SMILES: CC(=O)N1c2ccc(C(=O)NCC(C)(C)O)cc2[C@H](Nc2ncccn2)[C@@H](C)[C@@H]1C1CC1] | 53 | 63 | 438 | 0.70 (2 min Formic) |

| | | | | | |
|---|---|---|---|---|---|
| 488 | (2S,3R,4R)-1-acetyl-2-cyclopropyl-3-methyl-N-(oxetan-3-yl)-4-(pyrimidin-2-ylamino)-1,2,3,4-tetrahydroquinoline-6-carboxamide | 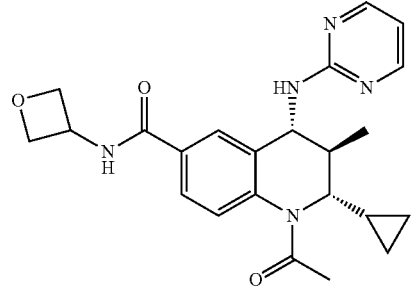 [SMILES: CC(=O)N1c2ccc(C(=O)NC3COC3)cc2[C@H](Nc2ncccn2)[C@@H](C)[C@@H]1C1CC1] | 53 66 | 422 | 0.69 (2 min Formic) |
| 489 | (2S,3R,4R)-1-acetyl-2-cyclopropyl-N-(2-methoxyethyl)-3-methyl-4-(pyrimidin-2-ylamino)-1,2,3,4-tetrahydroquinoline-6-carboxamide | 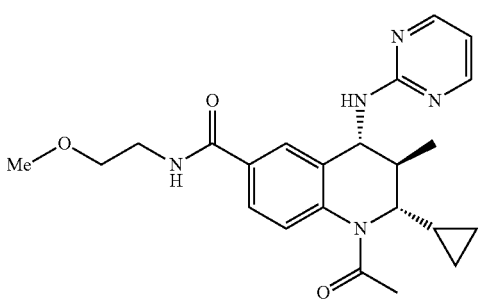 [SMILES: COCCNC(=O)c1ccc2c(c1)[C@H](Nc1ncccn1)[C@@H](C)[C@H](C1CC1)N2C(C)=O] | 52 64 | 424 | 0.71 (2 min Formic) |
| 490 | (2S,3R,4R)-1-acetyl-2-cyclopropyl-N-(2-hydroxypropyl)-3-methyl-4-(pyrimidin-2-ylamino)-1,2,3,4-tetrahydroquinoline-6-carboxamide | 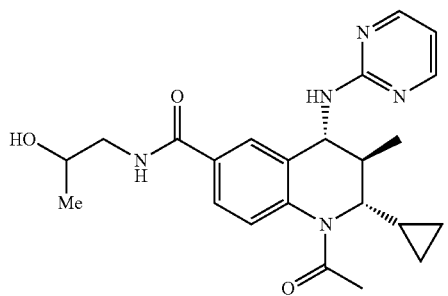 [SMILES: CC(=O)N1c2ccc(C(=O)NCC(C)O)cc2[C@H](Nc2ncccn2)[C@@H](C)[C@@H]1C1CC1] | 70 87 | 424 | 0.66 (2 min Formic) |
| 491 | (2S,3R,4R)-1-acetyl-2-cyclopropyl-N-(1-hydroxypropan-2-yl)-3-methyl-4-(pyrimidin-2-ylamino)-1,2,3,4-tetrahydroquinoline-6-carboxamide | 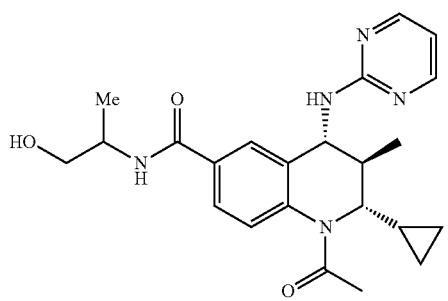 [SMILES: CC(=O)N1c2ccc(C(=O)NC(C)CO)cc2[C@H](Nc2ncccn2)[C@@H](C)[C@@H]1C1CC1] | 49 61 | 424 | 0.67 (2 min Formic) |

Example 492: (2S,3R,4R)-1-acetyl-4-((4-cyanophenyl)amino)-2-cyclopropyl-N-(2-hydroxyethyl)-3-methyl-1,2,3,4-tetrahydroquinoline-6-carboxamide

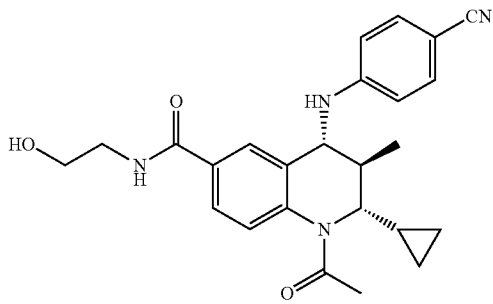 [SMILES: CC(=O)N1c2ccc(C(=O)NCCO)cc2[C@H](Nc2ccc(C#N)cc2)[C@@H](C)[C@@H]1C1CC1]

(2S,3R,4R)-1-acetyl-4-((4-cyanophenyl)amino)-2-cyclopropyl-3-methyl-1,2,3,4-tetrahydroquinoline-6-carboxylic acid (for a preparation see Intermediate 325, 60 mg, 0.154 mmol) was dissolved in N,N-dimethylformamide (DMF) (2 mL) and HATU (88 mg, 0.231 mmol) was added followed by 2-aminoethanol (12 mg, 0.196 mmol) and DIPEA (0.09 mL, 0.515 mmol). Reaction mixture stirred under N2 at r.t. for 1.5 days. Reaction mixture was concentrated to remove DMF and partitioned between ethyl acetate and sat. NaHCO$_3$ (aq.). The organic layer was separated, dried (Na$_2$SO$_4$) and conc. to give ~153 mg of crude pink oil. This was purified by chromatography on SiO$_2$ (25 g cartridge, eluting with 0-5% MeOH/DCM over 330 mL) to give the product (40 mg, 0.092 mmol, 60%) as an off-white solid. LCMS (2 min Formic): Rt=0.83 min, [MH]$^+$=433.

The following examples were prepared in a similar manner to Example 492 using HATU and DIPEA to couple the appropriate amine with Intermediate 325.

| Ex No. Name | Structure | Mass (mg) | Yield (%) | [MH]$^+$ | Rt (mins) (LCMS method) |
|---|---|---|---|---|---|
| 493 (2S,3R,4R)-1-acetyl-4-((4-cyanophenyl)amino)-2-cyclopropyl-N-(1,3-dihydroxypropan-2-yl)-3-methyl-1,2,3,4-tetrahydroquinoline-6-carboxamide | | 51 | 61 | 463 | 0.79 (2 min Formic) |
| 494 (2S,3R,4R)-1-acetyl-4-((4-cyanophenyl)amino)-2-cyclopropyl-N-(2-(dimethylamino)ethyl)-3-methyl-1,2,3,4-tetrahydroquinoline-6-carboxamide | | 31 | 38 | 460 | 0.75 (2 min Formic) |
| 495 (2S,3R,4R)-1-acetyl-4-((4-cyanophenyl)amino)-2-cyclopropyl-3-methyl-N-(2-(methylsulfonyl)ethyl)-1,2,3,4-tetrahydroquinoline-6-carboxamide | | 65 | 73 | 495 | 0.87 (2 min Formic) |

| Ex No. Name | Structure | Mass (mg) | Yield (%) | [MH]+ | Rt (mins) (LCMS method) |
|---|---|---|---|---|---|
| 496 (2S,3R,4R)-1-acetyl-4-((4-cyanophenyl)amino)-2-cyclopropyl-N,3-dimethyl-1,2,3,4-tetrahydroquinoline-6-carboxamide | | 29.5 | 68 | 403 | 0.89 (2 min Formic) |
| 497 (2S,3R,4R)-1-acetyl-4-((4-cyanophenyl)amino)-2-cyclopropyl-N-(2-hydroxypropyl)-3-methyl-1,2,3,4-tetrahydroquinoline-6-carboxamide | | 30.2 | 63 | 447 | 0.86 (2 min Formic) |
| 498 (2S,3R,4R)-1-acetyl-4-((4-cyanophenyl)amino)-2-cyclopropyl-N-(2-methoxyethyl)-3-methyl-1,2,3,4-tetrahydroquinoline-6-carboxamide | | 24 | 50 | 447 | 0.92 (2 min Formic) |

Example 499: (2S,3R,4R)-1-acetyl-N-(2-aminoethyl)-4-((4-cyanophenyl)amino)-2-cyclopropyl-3-methyl-1,2,3,4-tetrahydroquinoline-6-carboxamide

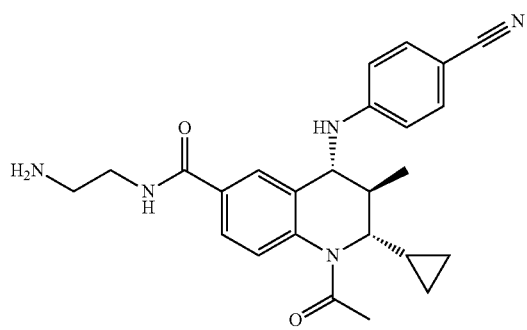 [SMILES: CC(=O)N1c2ccc(C(=O)NCCN)cc2[C@H](Nc2ccc(C#N)cc2)[C@@H](C)[C@@H]1C1CC1]

To a solution of tert-butyl (2-((2S,3R,4R)-1-acetyl-4-((4-cyanophenyl)amino)-2-cyclopropyl-3-methyl-1,2,3,4-tetrahydroquinoline-6-carboxamido)ethyl)carbamate (for a preparation see Intermediate 326, 123 mg, 0.231 mmol) in dichloromethane (DCM) (5 mL) was added TFA (1 mL, 12.98 mmol) and reaction mixture stirred at rt under $N_2$ for 2.5 h. The reaction mixture was concentrated and loaded onto a 2 g SCX cartridge (pre-conditioned with MeOH) and eluted with MeOH (30 mL) followed by 2M $NH_3$ in MeOH (30 mL). Ammonia fractions containing product were combined and concentrated to give the product (71 mg, 0.165 mmol, 71%) as an off-white solid.

LCMS (2 min Formic): Rt=0.73 min, [MH]+=432.

The following examples (500-505) were prepared in a similar manner to Example 181, using DIPEA to couple the appropriate heteroaryl fluoride to Intermediate 332 (2-cPr) or 329 (2-Me).

| Ex No. | Name | Structure | Mass (mg) | Yield (%) | [MH]+ | Rt (mins) (LCMS method) |
|---|---|---|---|---|---|---|
| 500 | 1-((2S,3R,4R)-6-fluoro-2,3-dimethyl-4-((4-methylpyrimidin-2-yl)amino)-3,4-dihydroquinolin-1(2H)-yl)ethanone | 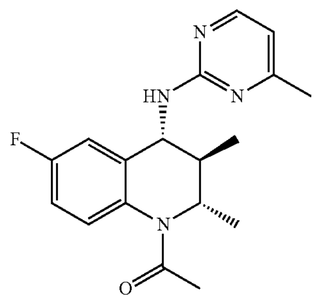 [SMILES: CC(=O)N1c2ccc(F)cc2[C@H](Nc2nccc(C)n2)[C@@H](C)[C@@H]1C] | 14 | 14 | 329 | 0.79 (2 min Formic) |
| 501 | 1-((2S,3R,4R)-6-fluoro-2,3-dimethyl-4-(pyrimidin-2-ylamino)-3,4-dihydroquinolin-1(2H)-yl)ethanone | 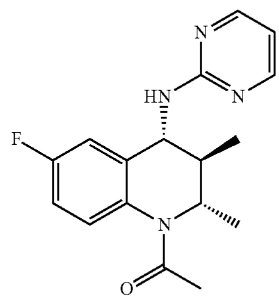 [SMILES: CC(=O)N1c2ccc(F)cc2[C@H](Nc2ncccn2)[C@@H](C)[C@@H]1C] | 9 | 10 | 315 | 0.78 (2 min Formic) |
| 502 | 2-(((2S,3R,4R)-1-acetyl-2-cyclopropyl-6-fluoro-3-methyl-1,2,3,4-tetrahydroquinolin-4-yl)amino)nicotinonitrile | 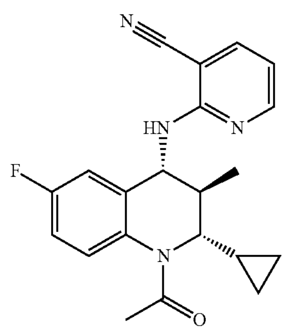 [SMILES: CC(=O)N1c2ccc(F)cc2[C@H](Nc2ncccc2C#N)[C@@H](C)[C@@H]1C1CC1] | 137 | 66 | 365 | 1.05 (2 min Formic) |
| 503 | 3-(((2S,3R,4R)-1-acetyl-2-cyclopropyl-6-fluoro-3-methyl-1,2,3,4-tetrahydroquinolin-4-yl)amino)picolinonitrile | 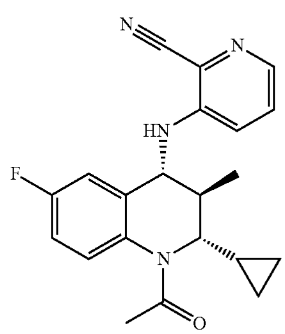 [SMILES: CC(=O)N1c2ccc(F)cc2[C@H](Nc2cccnc2C#N)[C@@H](C)[C@@H]1C1CC1] | 32 | 18 | 365 | 1.01 (2 min Formic) |
| 504 | 2-(((2S,3R,4R)-1-acetyl-6-fluoro-2,3-dimethyl-1,2,3,4-tetrahydroquinolin-4-yl)amino)nicotinonitrile | 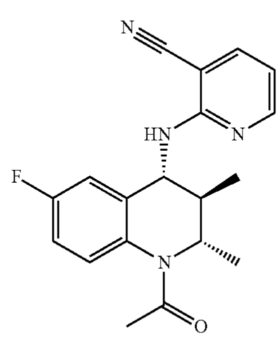 [SMILES: CC(=O)N1c2ccc(F)cc2[C@H](Nc2ncccc2C#N)[C@@H](C)[C@@H]1C] | 54 | 36 | 339 | 0.96 (2 min Formic) |

-continued

| Ex No. Name | Structure | Mass (mg) | Yield (%) | [MH]⁺ | Rt (mins) (LCMS method) |
|---|---|---|---|---|---|
| 505 2-(((2S,3R,4R)-1-acetyl-2-cyclopropyl-6-fluoro-3-methyl-1,2,3,4-tetrahydroquinolin-4-yl)amino)pyrimidine-4-carbonitrile | | 180 | 64 | 366 | 1.01 (2 min Formic) |

The following examples (506-510) were prepared in a similar manner to Example 161, using Pd₂(dba)₃, DavePhos and NaOtBu to couple the appropriate aryl or heteroaryl halide to Intermediate 329.

| Ex No. Name | Structure | Mass (mg) | Yield (%) | [MH]⁺ | Rt (mins) (LCMS method) |
|---|---|---|---|---|---|
| 506 4-(((2S,3R,4R)-1-acetyl-6-fluoro-2,3-dimethyl-1,2,3,4-tetrahydroquinolin-4-yl)amino)-N-methylbenzamide | | 81 | 40 | 370 | 0.82 (2 min Formic) |
| 507 6-(((2S,3R,4R)-1-acetyl-6-fluoro-2,3-dimethyl-1,2,3,4-tetrahydroquinolin-4-yl)amino)nicotinamide | | 1 | 3.3 | 357 | 0.61 (2 min Formic) |

| Ex No. Name | Structure | Mass (mg) | Yield (%) | [MH]+ | Rt (mins) (LCMS method) |
|---|---|---|---|---|---|
| 508 1-((2S,3R,4R)-6-fluoro-4-((3-methoxypyridin-2-yl)amino)-2,3-dimethyl-3,4-dihydroquinolin-1(2H)-yl)ethanone | | 28 | 96 | 344 | 0.65 (2 min Formic) |
| 509 1-((2S,3R,4R)-6-fluoro-4-((2-methoxypyridin-3-yl)amino)-2,3-dimethyl-3,4-dihydroquinolin-1(2H)-yl)ethanone | | 22 | 76 | 344 | 1.05 (2 min Formic) |
| 510 1-((2S,3R,4R)-6-fluoro-4-((4-methoxypyridin-2-yl)amino)-2,3-dimethyl-3,4-dihydroquinolin-1(2H)-yl)ethanone | | 62 | 85 | 344 | 0.62 (2 min Formic) |

Example 511: 1-((2S,3R,4R)-2-cyclopropyl-6-fluoro-4-((3-methoxypyrazin-2-yl)amino)-3-methyl-3,4-dihydroquinolin-1(2H)-yl)ethanone

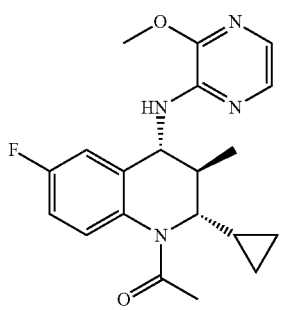 [SMILES: COc1nccnc1N[C@H]1c2cc(F)ccc2N(C(C)=O)[C@@H](C2CC2)[C@@H]1C]

To a 2-5 mL microwave vial, 1-((2S,3R,4R)-4-amino-2-cyclopropyl-6-fluoro-3-methyl-3,4-dihydroquinolin-1(2H)-yl)ethanone (for a preparation see Intermediate 332, 50 mg, 0.191 mmol) and sodium tert-butoxide (73.3 mg, 0.762 mmol) were taken up in toluene (3 mL). The solutions were degassed with $N_2$ and the solutions were treated with $Pd_2(dba)_3$ (17.45 mg, 0.019 mmol) and Q-Phos (13.58 mg, 0.019 mmol). 2-chloro-3-methoxypyrazine (41.3 mg, 0.286 mmol) was added and the reaction was heated in a microwave reactor to 60° C. for 3 h. The reaction mixture was filtered through celite and the celite washed with ethyl acetate (2×15 mL). The combined filtrates were washed with 50:50 sat. aqueous. Brine solution:water (2×30 mL) and the layers separated. The organic phase was dried through a hydrophobic frit and concentrated in vacuo to give 155 mg of the crude product as an orange/red solid. This was purified by chromatography on a 10 g silica gel column, eluting with 0-40% ethyl acetate/cyclohexane. The appropriate fractions were combined, concentrated in vacuo and dried under high vacuum to give the desired product as an orange solid (67 mg, 0.181 mmol, 95%)

LCMS (2 min Formic): Rt=1.05 min, [MH]+=371.

The following examples were prepared in a similar manner to Example 511 using $Pd_2(dba)_3$, Q-Phos and NaOtBu to couple the appropriate aryl halide to Intermediate 332.

| Ex No. | Name | Structure | Mass (mg) | Yield (%) | [MH]+ | Rt (mins) (LCMS method) |
|---|---|---|---|---|---|---|
| 512 | 1-((2S,3R,4R)-2-cyclopropyl-6-fluoro-4-((6-methoxypyridin-3-yl)amino)-3-methyl-3,4-dihydroquinolin-1(2H)-yl)ethanone | 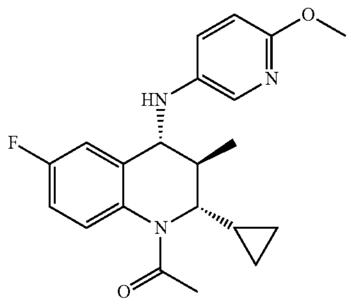 [SMILES: COc1ccc(N[C@H]2c3cc(F)ccc3N(C(C)=O)[C@@H](C3CC3)[C@@H]2C)cn1] | 4 | 1.6 | 370 | 0.99 (2 min Formic) |
| 513 | 1-((2S,3R,4R)-2-cyclopropyl-6-fluoro-3-methyl-4-((6-(morpholinomethyl)pyridin-2-yl)amino)-3,4-dihydroquinolin-1(2H)-yl)ethanone | 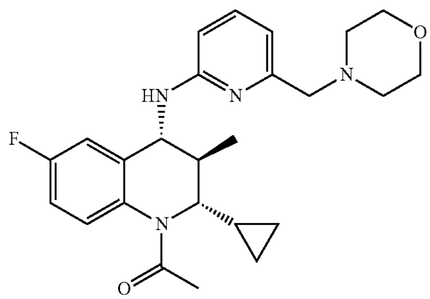 [SMILES: CC(=O)N1c2ccc(F)cc2[C@H](Nc2cccc(CN3CCOCC3)n2)[C@@H](C)[C@@H]1C1CC1] | 26 | 48 | 439 | 0.74 (2 min Formic) |
| 514 | 1-((2S,3R,4R)-2-cyclopropyl-6-fluoro-4-((2-methoxypyridin-4-yl)amino)-3-methyl-3,4-dihydroquinolin-1(2H)-yl)ethanone | 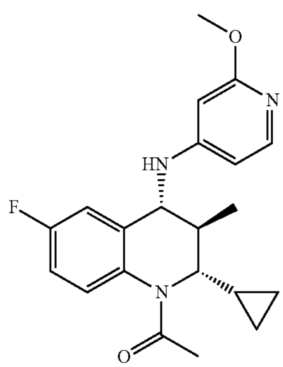 [SMILES: COc1cc(N[C@H]2c3cc(F)ccc3N(C(C)=O)[C@@H](C3CC3)[C@@H]2C)ccn1] | 15 | 5.8 | 370 | 0.69 (2 min Formic) |
| 515 | 1-((2S,3R,4R)-2-cyclopropyl-6-fluoro-4-((4-methoxypyridin-2-yl)amino)-3-methyl-3,4-dihydroquinolin-1(2H)-yl)ethanone | 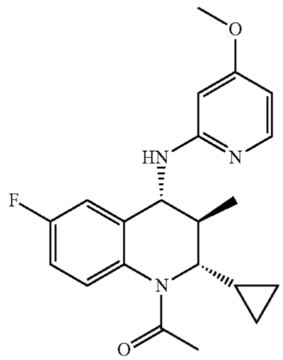 [SMILES: COc1ccnc(N[C@H]2c3cc(F)ccc3N(C(C)=O)[C@@H](C3CC3)[C@@H]2C)c1] | 8 | 3.1 | 370 | 0.70 (2 min Formic) |

| Ex No. | Name | Structure | Mass (mg) | Yield (%) | [MH]+ | Rt (mins) (LCMS method) |
|---|---|---|---|---|---|---|
| 516 | 1-((2S,3R,4R)-2-cyclopropyl-4-((6-((dimethylamino)methyl)pyridin-2-yl)amino)-6-fluoro-3-methyl-3,4-dihydroquinolin-1(2H)-yl)ethanone | 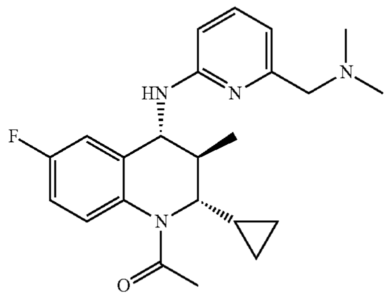 [SMILES: CC(=O)N1c2ccc(F)cc2[C@H](Nc2cccc(CN(C)C)n2)[C@@H](C)[C@@H]1C1CC1] | 104 | 63 | 397 | 0.75 (2 min Formic) |

The following examples (517-521) were prepared in a similar manner to Example 165, using NaI and TMSCl to demethylate Intermediate 333, 334, 335 or Example 509, 511.

| Ex No. | Name | Structure | Mass (mg) | Yield (%) | [MH]+ | Rt (mins) (LCMS method) |
|---|---|---|---|---|---|---|
| 517 | 1-((2S,3R,4R)-6-fluoro-4-((2-hydroxypyrimidin-4-yl)amino)-2,3-dimethyl-3,4-dihydroquinolin-1(2H)-yl)ethanone | 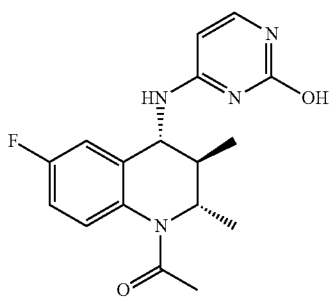 [SMILES: CC(=O)N1c2ccc(F)cc2[C@H](Nc2ccnc(O)n2)[C@@H](C)[C@@H]1C] | 5 | 52 | 331 | 0.56 (2 min Formic) |
| 518 | 1-((2S,3R,4R)-6-fluoro-4-((2-hydroxypyridin-3-yl)amino)-2,3-dimethyl-3,4-dihydroquinolin-1(2H)-yl)ethanone | 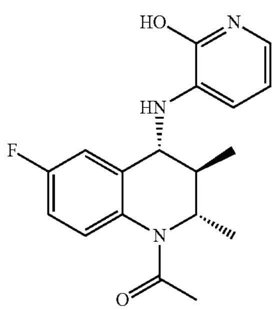 [SMILES: CC(=O)N1c2ccc(F)cc2[C@H](Nc2cccnc2O)[C@@H](C)[C@@H]1C] | 32 | 61 | 330 | 0.76 (2 min Formic) |
| 519 | 1-((2S,3R,4R)-2-cyclopropyl-6-fluoro-4-((2-hydroxypyrimidin-4-yl)amino)-3-methyl-3,4-dihydroquinolin-1(2H)-yl)ethanone | 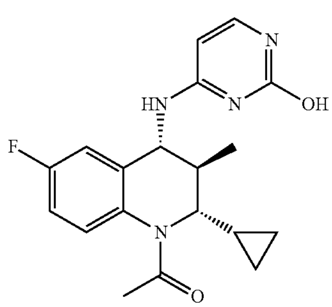 [SMILES: CC(=O)N1c2ccc(F)cc2[C@H](Nc2ccnc(O)n2)[C@@H](C)[C@@H]1C1CC1] | 1.5 | 5.5 | 357 | 0.66 (2 min Formic) |

-continued

| Ex No. | Name | Structure | Mass (mg) | Yield (%) | [MH]+ | Rt (mins) (LCMS method) |
|---|---|---|---|---|---|---|
| 520 | 1-((2S,3R,4R)-2-cyclopropyl-6-fluoro-4-((2-hydroxypyridin-3-yl)amino)-3-methyl-3,4-dihydroquinolin-1(2H)-yl)ethanone | 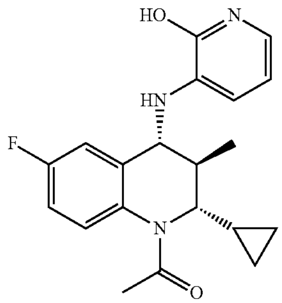 [SMILES: CC(=O)N1c2ccc(F)cc2[C@H](Nc2cccnc2O)[C@@H](C)[C@@H]1C1CC1] | 4.3 | 18 | 356 | 0.85 (2 min Formic) |
| 521 | 1-((2S,3R,4R)-2-cyclopropyl-6-fluoro-4-((3-hydroxypyrazin-2-yl)amino)-3-methyl-3,4-dihydroquinolin-1(2H)-yl)ethanone | 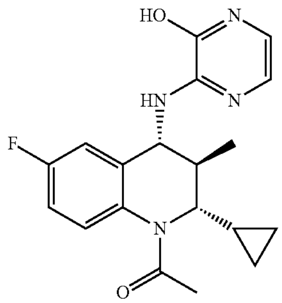 [SMILES: CC(=O)N1c2ccc(F)cc2[C@H](Nc2nccnc2O)[C@@H](C)[C@@H]1C1CC1] | 50 | 91 | 357 | 0.75 (2 min Formic) |

The following examples (522-529) were prepared in a similar manner to Example 320, using $H_2O_2$ to hydrolyse Examples 502-505, 538 or Intermediate 337-339.

| Ex No. | Name | Structure | Mass (mg) | Yield (%) | [MH]+ | Rt (mins) (LCMS method) |
|---|---|---|---|---|---|---|
| 522 | 6-(((2S,3R,4R)-1-acetyl-2-cyclopropyl-6-fluoro-3-methyl-1,2,3,4-tetrahydroquinolin-4-yl)amino)nicotinamide | 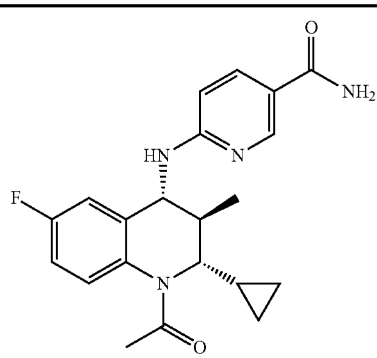 | 4.5 | 5 | 383 | 0.72 (2 min Formic) |
| 523 | 2-(((2S,3R,4R)-1-acetyl-2-cyclopropyl-6-fluoro-3-methyl-1,2,3,4-tetrahydroquinolin-4-yl)amino)nicotinamide | 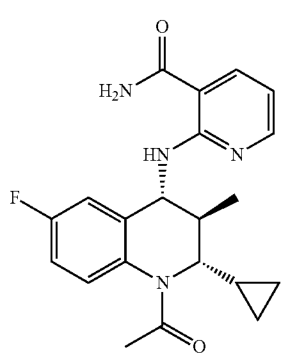 [SMILES: CC(=O)N1c2ccc(F)cc2[C@H](Nc2ncccc2C(N)=O)[C@@H](C)[C@@H]1C1CC1] | 101 | 78 | 383 | 0.82 (2 min Formic) |

-continued

| Ex No. Name | Structure | Mass (mg) | Yield (%) | [MH]+ | Rt (mins) (LCMS method) |
|---|---|---|---|---|---|
| 524 3-(((2S,3R,4R)-1-acetyl-2-cyclopropyl-6-fluoro-3-methyl-1,2,3,4-tetrahydroquinolin-4-yl)amino)picolinamide | | 12 | 41 | 383 | 1.00 (2 min Formic) |
| 525 3-(((2S,3R,4R)-1-acetyl-2-cyclopropyl-6-fluoro-3-methyl-1,2,3,4-tetrahydroquinolin-4-yl)amino)pyrazine-2-carboxamide | | 15 | 24 | 384 | 0.95 (2 mm Formic) |
| 526 6-(((2S,3R,4R)-1-acetyl-2-cyclopropyl-6-fluoro-3-methyl-1,2,3,4-tetrahydroquinolin-4-yl)amino)picolinamide | | 110 | 80 | 383 | 0.89 (2 min Formic) |
| 527 2-(((2S,3R,4R)-1-acetyl-6-fluoro-2,3-dimethyl-1,2,3,4-tetrahydroquinolin-4-yl)amino)nicotinamide | | 33 | 60 | 357 | 0.83 (2 min HpH) |

-continued

| Ex No. Name | Structure | Mass (mg) | Yield (%) | [MH]+ | Rt (mins) (LCMS method) |
|---|---|---|---|---|---|
| 528 2-(((2S,3R,4R)-1-acetyl-6-fluoro-2,3-dimethyl-1,2,3,4-tetrahydroquinolin-4-yl)amino)-6-methylnicotinamide | | 13 | 65 | 371 | 0.93 (2 min HpH) |
| 529 2-(((2S,3R,4R)-1-acetyl-2-cyclopropyl-6-fluoro-3-methyl-1,2,3,4-tetrahydroquinolin-4-yl)amino)pyrimidine-4-carboxamide | | 65 | 52 | 384 | 0.83 (2 min Formic) |

Example 530: 1-((2S,3R,4R)-2-cyclopropyl-6-fluoro-4-((3-hydroxypyridin-2-yl)amino)-3-methyl-3,4-dihydroquinolin-1(2H)-yl)ethanone

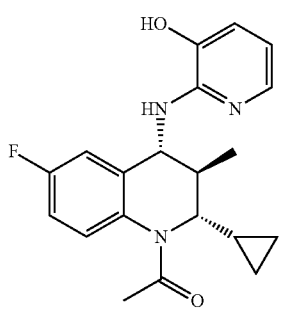

A solution of 1-((2S,3R,4R)-2-cyclopropyl-6-fluoro-4-((3-methoxypyridin-2-yl)amino)-3-methyl-3,4-dihydroquinolin-1(2H)-yl)ethanone (for a preparation see Intermediate 336, 50 mg, 0.135 mmol) and lithium iodide (362 mg, 2.71 mmol) in NMP (2 mL) was stirred under microwave radiation in a closed vessel at 200° C. for 30 min. 1 mL of the remaining solution was then purified by MDAP (High pH). The appropriate fractions were combined and concentrated in vacuo to give the desired product (4.4 mg, 0.012 mmol, 9%). LCMS (2 min Formic): Rt=0.67 min, [MH]+=356.

The following examples were prepared in a similar manner to Example 530, using LiI to demethylate Examples 512, 514 or 515.

| Ex No. | Name | Structure | Mass (mg) | Yield (%) | [MH]+ | Rt (mins) (LCMS method) |
|---|---|---|---|---|---|---|
| 531 | 1-((2S,3R,4R)-2-cyclopropyl-6-fluoro-4-((2-hydroxypyridin-4-yl)amino)-3-methyl-3,4-dihydroquinolin-1(2H)-yl)ethanone | 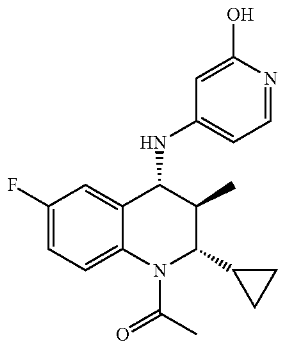 [SMILES: CC(=O)N1c2ccc(F)cc2[C@H](Nc2ccnc(O)c2)[C@@H](C)[C@@H]1C1CC1] | 11 | 15 | 356 | 0.73 (2 min Formic) |
| 532 | 1-((2S,3R,4R)-2-cyclopropyl-6-fluoro-4-((4-hydroxypyridin-2-yl)amino)-3-methyl-3,4-dihydroquinolin-1(2H)-yl)ethanone | 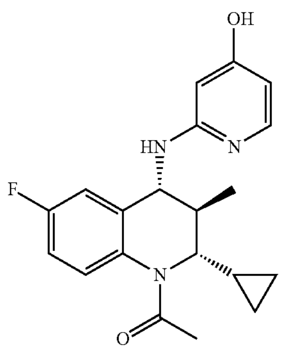 [SMILES: CC(=O)N1c2ccc(F)cc2[C@H](Nc2cc(O)ccn2)[C@@H](C)[C@@H]1C1CC1] | 15 | 21 | 356 | 0.65 (2 min Formic) |
| 533 | 1-((2S,3R,4R)-2-cyclopropyl-6-fluoro-4-((6-hydroxypyridin-3-yl)amino)-3-methyl-3,4-dihydroquinolin-1(2H)-yl)ethanone | 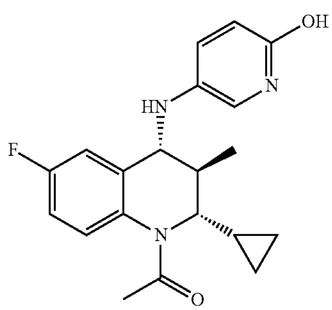 [SMILES: CC(=O)N1c2ccc(F)cc2[C@H](Nc2ccc(O)nc2)[C@@H](C)[C@@H]1C1CC1] | 4 | 8.7 | 356 | 0.77 (2 min (Formic) |

The following examples (534-537) were prepared in a similar manner to Example 249, using HATU and DIPEA to couple the appropriate amine with Intermediate 341.

| Ex No. | Name | Structure | Mass (mg) | Yield (%) | [MH]+ | Rt (mins) (LCMS method) |
|---|---|---|---|---|---|---|
| 534 | 4-(((2S,3R,4R)-1-acetyl-2-cyclopropyl-6-fluoro-3-methyl-1,2,3,4-tetrahydroquinolin-4-yl)amino)benzamide | 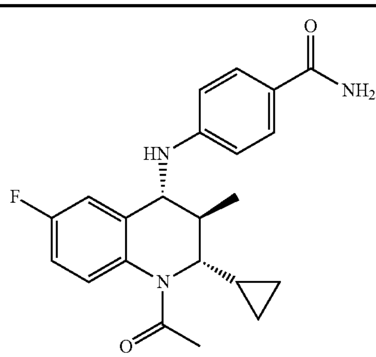 | 23 | 48 | 382 | 0.88 (2 min Formic) |

| Ex No. | Name | Structure | Mass (mg) | Yield (%) | [MH]+ | Rt (mins) (LCMS method) |
|---|---|---|---|---|---|---|
| 535 | 4-(((2S,3R,4R)-1-acetyl-2-cyclopropyl-6-fluoro-3-methyl-1,2,3,4-tetrahydroquinolin-4-yl)amino)-N-methylbenzamide | 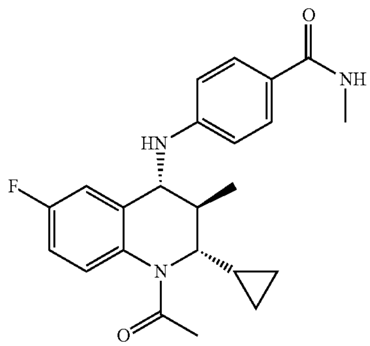 [SMILES: CNC(=O)c1ccc(N[C@H]2c3cc(F)ccc3N(C(C)=O)[C@@H](C3CC3)[C@@H]2C)cc1] | 24 | 49 | 396 | 0.92 (2 min Formic) |
| 536 | 4-(((2S,3R,4R)-1-acetyl-2-cyclopropyl-6-fluoro-3-methyl-1,2,3,4-tetrahydroquinolin-4-yl)amino)-N,N-dimethylbenzamide | 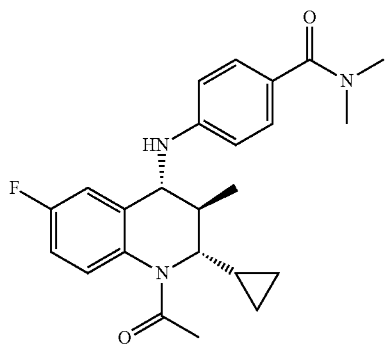 [SMILES: CC(=O)N1c2ccc(F)cc2[C@H](Nc2ccc(C(=O)N(C)C)cc2)[C@@H](C)[C@@H]1C1CC1] | 31 | 62 | 410 | 1.00 (2 mm Formic) |
| 537 | 4-(((2S,3R,4R)-1-acetyl-2-cyclopropyl-6-fluoro-3-methyl-1,2,3,4-tetrahydroquinolin-4-yl)amino)-N-isopropylbenzamide | 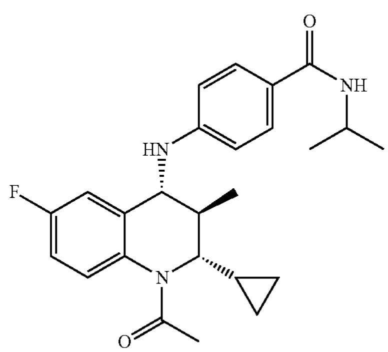 [SMILES: CC(=O)N1c2ccc(F)cc2[C@H](Nc2ccc(C(=O)NC(C)C)cc2)[C@@H](C)[C@@H]1C1CC1] | 32 | 61 | 424 | 1.03 (2 min Formic) |

Example 538: 3-(((2S,3R,4R)-1-acetyl-2-cyclopropyl-6-fluoro-3-methyl-1,2,3,4-tetrahydroquinolin-4-yl)amino)pyrazine-2-carbonitrile

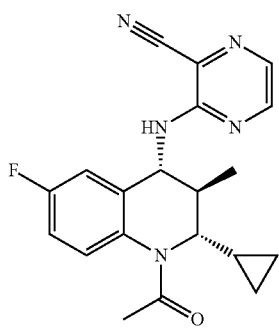 [SMILES: CC(=O)N1c2ccc(F)cc2[C@H](Nc2nccnc2C#N)[C@@H](C)[C@@H]1C1CC1]

A solution of 1-((2S,3R,4R)-4-amino-2-cyclopropyl-6-fluoro-3-methyl-3,4-dihydroquinolin-1(2H)-yl)ethanone (for a preparation see Intermediate 332, 100 mg, 0.381 mmol), 3-chloropyrazine-2-carbonitrile (106 mg, 0.762 mmol) and triethylamine (0.106 mL, 0.762 mmol) in N-methyl-2-pyrrolidone (2 mL) was stirred in a closed vessel in the microwave at 200° C. for 1.5 h. The solution was diluted with ethyl acetate (4 mL) and washed with water (3×4 mL). The organic layer was concentrated in vacuo to give 270 mg crude material. The material was dissolved in 1:1 MeOH:DMSO (3×1 mL) and purified by MDAP (Formic). The fractions from the first run were combined and concentrated in vacuo to give the desired product (22 mg, 0.060 mmol, 16%).

LCMS (2 min Formic): Rt=1.02 min, [MH]+=366.

Example 539: 1-((2S,3R,4R)-2-cyclopropyl-6-fluoro-3-methyl-4-((6-(piperazin-1-ylmethyl)pyridin-2-yl)amino)-3,4-dihydroquinolin-1(2H)-yl)ethanone

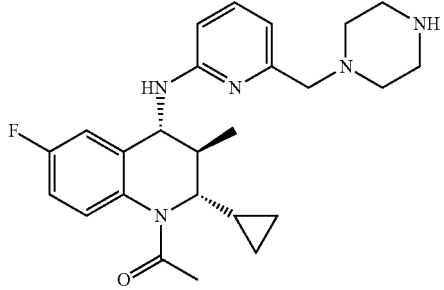 [SMILES: CC(=O)N1c2ccc(F)cc2[C@H](Nc2cccc(CN3CCNCC3)n2)[C@@H](C)[C@@H]1C1CC1]

In a 50 mL flask, 4M HCl in 1,4-dioxane (1.07 mL, 4.28 mmol) was added to a stirred solution of tert-butyl 4-((6-(((2S,3R,4R)-1-acetyl-2-cyclopropyl-6-fluoro-3-methyl-1,2,3,4-tetrahydroquinolin-4-yl)amino)pyridin-2-yl)methyl)piperazine-1-carboxylate (for a preparation see Intermediate 342, 76.7 mg, 0.143 mmol) in 1,4-dioxane (3 mL). The resulting solution was left stirring for 1 h at rt. Volatiles were removed under reduced pressure to afford 95.8 mg of yellow gum. This resulting crude gum was dissolved in MeOH and loaded on a 5 g SCX cartridge, washed with methanol (3 CV) and flushed with MeOH/NH$_3$ (2M) (3 CV). The appropriate ammonia fractions were combined and volatiles removed under reduced pressure to afford 61.9 mg of yellow gum. This gum was purified by MDAP (Formic) to give the desired product (40.7 mg, 0.093 mmol, 65%).

LCMS (2 min Formic): Rt=0.56 min, [MH]$^+$=438.

Example 540: rac-4-(((2S,3R,4R)-1-acetyl-6-(4-acetylpiperazin-1-yl)-2-ethyl-3-methyl-1,2,3,4-tetrahydroquinolin-4-yl)amino)benzonitrile

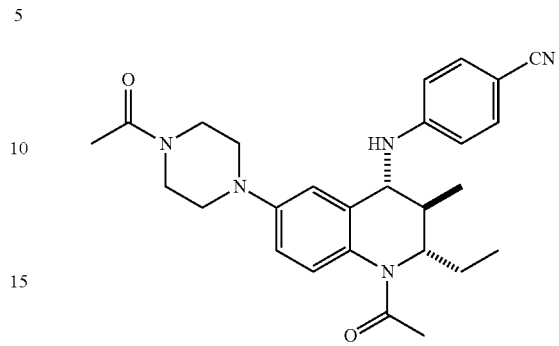

To a dried flask under nitrogen was added a solution of rac-4-(((2S,3R,4R)-1-acetyl-2-ethyl-3-methyl-6-(piperazin-1-yl)-1,2,3,4-tetrahydroquinolin-4-yl)amino)benzonitrile (for a preparation see Example 219, 10.1 mg, 0.019 mmol) in dichloromethane (DCM) (1 mL), followed by N,N-diisopropylethylamine (0.034 mL, 0.194 mmol) and acetyl chloride (6.88 μL, 0.097 mmol). The mixture was allowed to stir at rt for 45 min. The reaction mixture was diluted with dichloromethane and washed with 2M HCl solution (2×20 mL) and saturated sodium hydrogen carbonate solution (20 mL). The organic layer was passed over a hydrophobic frit and concentrated in vacuo to afford a transparent yellow solid product (7.8 mg, 0.016 mmol, 83%).

LCMS (2 min Formic): Rt=0.89 min, [MH]$^+$=460.

The following examples (541-544) were prepared in a similar manner to Intermediate 358 using KF, 18-crown-6 and DIPEA to couple the appropriate aryl halide to Intermediate 81 or 357; followed by deprotection with TFA as described for Example 87.

| Ex No. | Name | Structure | Mass (mg) | Yield (%) | [MH]$^+$ | Rt (mins) (LCMS method) |
|---|---|---|---|---|---|---|
| 541 | rac-5-(((2S,3R,4R)-1-acetyl-2,3-dimethyl-6-(1,2,3,6-tetrahydropyridin-4-yl)-1,2,3,4-tetrahydroquinolin-4-yl)amino)pyrazine-2-carbonitrile | 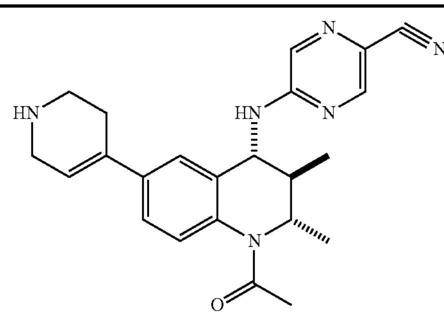 | 10 | 53 | 403 | 0.63 (2 min Formic) |
| 542 | rac-6-(((2S,3R,4R)-1-acetyl-2,3-dimethyl-6-(1,2,3,6-tetrahydropyridin-4-yl)-1,2,3,4-tetrahydroquinolin-4-yl)amino)nicotinonitrile | 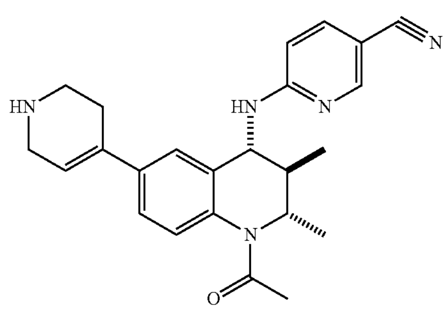 [SMILES: CC(=O)N1c2ccc(C3=CCNCC3)cc2[C@H](Nc2ccc(C#N)cn2)[C@@H](C)[C@@H]1C] | 7 | 48 | 402 | 0.64 (2 min Formic) |

-continued

| Ex No. | Name | Structure | Mass (mg) | Yield (%) | [MH]+ | Rt (mins) (LCMS method) |
|---|---|---|---|---|---|---|
| 543 | rac-6-(((2S,3R,4R)-1-acetyl-2-cyclopropyl-3-methyl-6-(1,2,3,6-tetrahydropyridin-4-yl)-1,2,3,4-tetrahydroquinolin-4-yl)amino)nicotinonitrile | 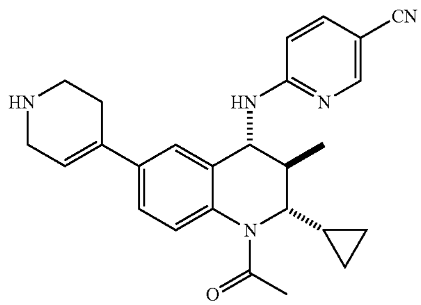 [SMILES: CC(=O)N1c2ccc(C3=CCNCC3)cc2[C@H](Nc2ccc(C#N)cn2)[C@@H](C)[C@@H]1C1CC1] | 54 | 42 | 428 | 0.71 (2 min Formic) |
| 544 | rac-5-(((2S,3R,4R)-1-acetyl-2-cyclopropyl-3-methyl-6-(1,2,3,6-tetrahydropyridin-4-yl)-1,2,3,4-tetrahydroquinolin-4-yl)amino)pyrazine-2-carbonitrile | 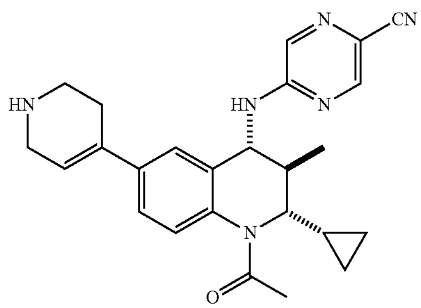 | 69 | 53 | 429 | 0.68 (2 min Formic) |

The following examples (545-550) were prepared in a similar manner to Example 81 using Pd$_2$(dba)$_3$, DavePhos and NaOtBu to couple the appropriate aryl halide with Intermediate 81 or 357; followed by deprotection with TFA as described for Example 87.

| Ex No. | Name | Structure | Mass (mg) | Yield (%) | [MH]+ | Rt (mins) (LCMS method) |
|---|---|---|---|---|---|---|
| 545 | rac-4-(((2S,3R,4R)-1-acetyl-2,3-dimethyl-6-(1,2,3,6-tetrahydropyridin-4-yl)-1,2,3,4-tetrahydroquinolin-4-yl)amino)benzonitrile | 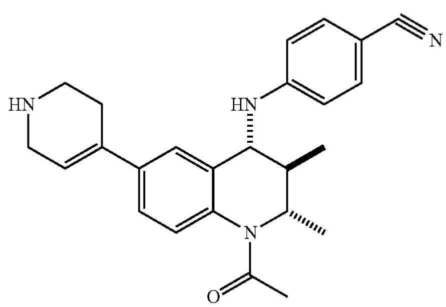 | 5 | 44 | 401 | 0.72 (2 min Formic) |
| 546 | rac-1-((2S,3R,4R)-2,3-dimethyl-4-((6-methylpyridin-2-yl)amino)-6-(1,2,3,6-tetrahydropyridin-4-yl)-3,4-dihydroquinolin-1(2H)-yl)ethanone | 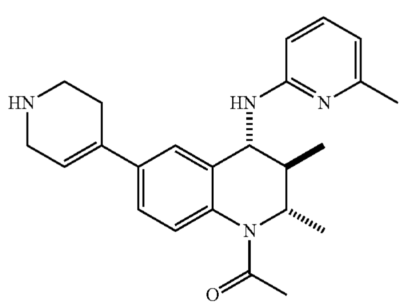 | 14 | 90 | 391 | 0.90 (2 min HpH) |

| Ex No. | Name | Structure | Mass (mg) | Yield (%) | [MH]+ | Rt (mins) (LCMS method) |
|---|---|---|---|---|---|---|
| 547 | rac-1-((2S,3R,4R)-2,3-dimethyl-4-((4-methylpyrimidin-2-yl)amino)-6-(1,2,3,6-tetrahydropyridin-4-yl)-3,4-dihydroquinolin-1(2H)-yl)ethanone | 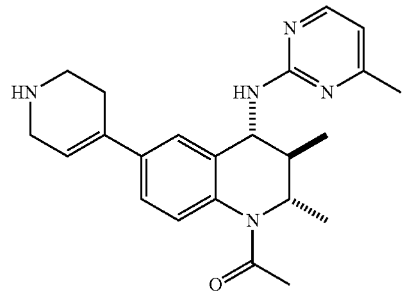 [SMILES: CC(=O)N1c2ccc(C3=CCNCC3)cc2[C@H](Nc2nccc(C)n2)[C@@H](C)[C@@H]1C] | 5 | 52 | 392 | 0.79 (2 min HpH) |
| 548 | rac-1-((2S,3R,4R)-2,3-dimethyl-4-((5-methylpyrazin-2-yl)amino)-6-(1,2,3,6-tetrahydropyridin-4-yl)-3,4-dihydroquinolin-1(2H)-yl)ethanonecarboxamide | 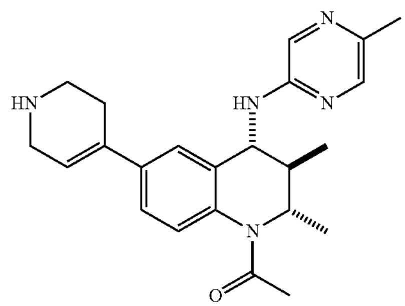 [SMILES: CC(=O)N1c2ccc(C3=CCNCC3)cc2[C@H](Nc2cnc(C)cn2)[C@@H](C)[C@@H]1C] | 6 | 48 | 392 | 0.77 (2 min HpH) |
| 549 | rac-1-((2S,3R,4R)-2-cyclopropyl-3-methyl-4-((5-methylpyrazin-2-yl)amino)-6-(1,2,3,6-tetrahydropyridin-4-yl)-3,4-dihydroquinolin-1(2H)-yl)ethanone | 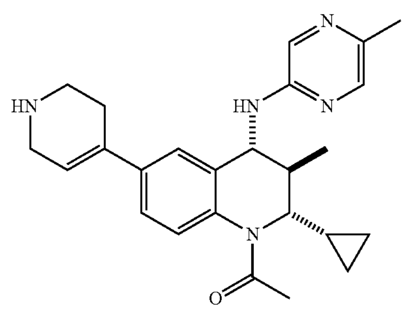 [SMILES: CC(=O)N1c2ccc(C3=CCNCC3)cc2[C@H](Nc2cnc(C)cn2)[C@@H](C)[C@@H]1C1CC1] | 50 | 40 | 418 | 0.66 (2 min Formic) |
| 550 | rac-1-((2S,3R,4R)-2-cyclopropyl-4-((5-fluoropyridin-2-yl)amino)-3-methyl-6-(1,2,3,6-tetrahydropyridin-4-yl)-3,4-dihydroquinolin-1(2H)-yl)ethanone | 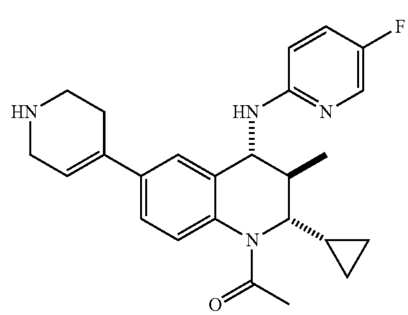 [SMILES: CC(=O)N1c2ccc(C3=CCNCC3)cc2[C@H](Nc2ccc(F)cn2)[C@@H](C)[C@@H]1C1CC1] | 59 | 46 | 421 | 0.68 (2 min Formic) |

Examples 551a & 551b: 4-(((2R,3S,4S)-1-acetyl-2-cyclopropyl-6-(3,6-dihydro-2H-pyran-4-yl)-3-methyl-1,2,3,4-tetrahydroquinolin-4-yl)amino)-N-methylbenzamide (551a) & 4-(((2S,3R,4R)-1-acetyl-2-cyclopropyl-6-(3,6-dihydro-2H-pyran-4-yl)-3-methyl-1,2,3,4-tetrahydroquinolin-4-yl)amino)-N-methylbenzamide (551 b)

551a

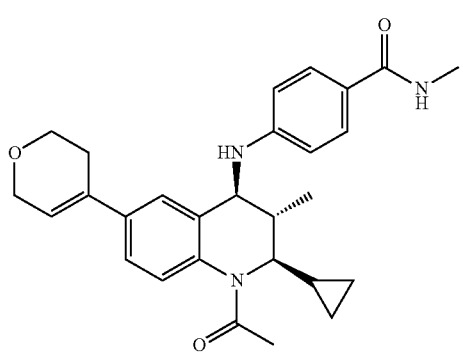

551b

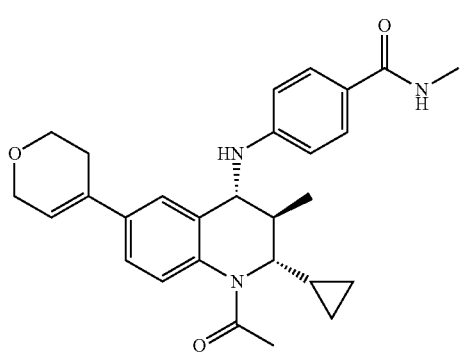

rac-4-(((2S,3R,4R)-1-Acetyl-2-cyclopropyl-6-(3,6-dihydro-2H-pyran-4-yl)-3-methyl-1,2,3,4-tetrahydroquinolin-4-yl)amino)-N-methylbenzamide (for a preparation see Example 178, 90, ~40 mg) was submitted for chiral separation into its enantiomers (A and B) using a 250×20 mm Chiralpak IC column eluting with 50% ethanol in 50% heptane at a flow rate of 17.5 mL/min. Peak 1/Enantiomer A fractions were collected between 9 and 13 min. Peak 2/Enantiomer B fractions were collected between 16 and 20 min. Fraction solutions were combined then evaporated to dryness to give Enantiomer A (19.5 mg) and Enantiomer B (22.4 mg) as white solids.

Enantiomer A, Example 551a

Analytical Chiral HPLC using a 250×4.6 mm Chiralpak IC column eluting with 50% ethanol in heptanes at 1 mL/min—Rt=8.9 min.>99% ee by UV.

Enantiomer B, Example 551 b

Analytical Chiral HPLC using a 250×4.6 mm Chiralpak IC column eluting with 10% ethanol in heptane (plus 0.2% isopropylamine) at 1 mL/min—Rt=13.0 min, >99% ee by UV.

Example 552: rac-6-(((2S,3R,4R)-1-acetyl-2,3-dimethyl-6-(tetrahydro-2H-pyran-4-yl)-1,2,3,4-tetrahydroquinolin-4-yl)amino)nicotinonitrile

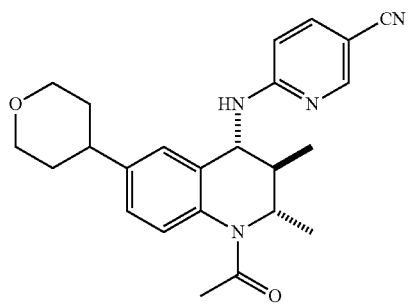 [SMILES: CC(=O)N1c2ccc(C3CCOCC3)cc2[C@H](Nc2ccc(C#N)cn2)[C@@H](C)[C@@H]1C]

To a microwave vial 6-fluoronicotinonitrile (30.3 mg, 0.248 mmol), rac-1-((2S,3R,4R)-4-amino-2,3-dimethyl-6-(tetrahydro-2H-pyran-4-yl)-3,4-dihydroquinolin-1(2H)-yl)ethanone (for a preparation see Intermediate 152, 37.5 mg, 0.124 mmol), and DIPEA (0.065 mL, 0.372 mmol) were added and the reaction heated to 200° C. in a microwave reactor for 30 minutes. The reaction mixture was diluted to 2 ml with methanol and purified in 2 batches by MDAP (Formic). The clean fractions from both runs were combined and the solvent was evaporated in vacuo to give 21 mg of product as a yellow solid. This was dissolved in methanol and run through a pre-equilibrated —NH$_2$ column (5 g) in order to form the free base. The methanol was evaporated in vacuo to give 17 mg of product.

LCMS (2 min Formic): Rt=0.91 min, [MH]$^+$=405.

Example 553: rac-1-((2S,3R,4R)-2-cyclopropyl-3-methyl-4-((5-methylpyrazin-2-yl)amino)-6-(tetrahydro-2H-pyran-4-yl)-3,4-dihydroquinolin-1(2H)-yl)ethanone

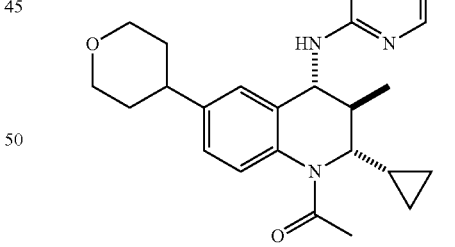

The rac-1-((2S,3R,4R)-2-cyclopropyl-6-(3,6-dihydro-2H-pyran-4-yl)-3-methyl-4-((5-methylpyrazin-2-yl)amino)-3,4-dihydroquinolin-1(2H)-yl)ethanone (for a preparation see Example 179, 46 mg, 0.110 mmol) was taken up in ethanol (5 mL) and the reaction was hydrogenated using the H-cube (settings: 25° C., 1 bar, 1 ml/min flow rate) and 10% Pd/C CatCart 30 as the catalyst. The reaction was concentrated and dried to give the product. This was further purified using a MDAP (Formic). The appropriate fraction was concentrated to give the product (5 mg, 0.012 mmol, 11%) as a white solid.

LCMS (2 min Formic): Rt=0.92 min, [MH]$^+$=421.

Example 554: 1-((rac-2S,3R,4R)-2-cyclopropyl-3-methyl-6-((S)-3-methylpiperazin-1-yl)-4-((4-methylpyrimidin-2-yl)amino)-3,4-dihydroquinolin-1(2H)-yl)ethanone

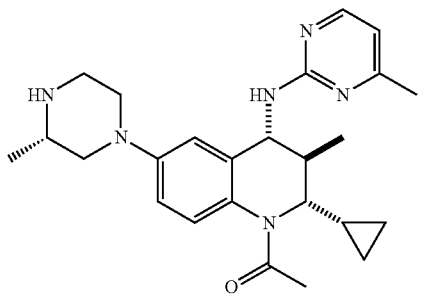

To a stirring solution of (S)-tert-butyl 4-((rac-2S,3R,4R)-1-acetyl-2-cyclopropyl-3-methyl-4-((4-methylpyrimidin-2-yl)amino)-1,2,3,4-tetrahydroquinolin-6-yl)-2-methylpiperazine-1-carboxylate (for a preparation see Intermediate 343, 18 mg, 0.034 mmol) in dichloromethane (DCM) (1 mL) under nitrogen was added trifluoroacetic acid (0.25 mL, 3.24 mmol). The mixture was stirred at rt for 1 h. The reaction mixture was concentrated in vacuo. The residue was dissolved in methanol and loaded onto a 1 g SCX SPE cartridge, which had been pre-equilibrated with methanol. The column was first eluted with methanol into one fraction, and then the product was eluted into a separate fraction with 2M NH$_3$ in methanol. The appropriate fraction was concentrated in vacuo to afford the product. The sample was dissolved in 1:1 MeOH:DMSO 1 mL and purified by MDAP (HpH). The solvent was evaporated in vacuo to give the required product (1.5 mg).

LCMS (2 min HpH): Rt=0.83 min, [MH]$^+$=435.

Example 555: 1-((2S,3R,4R)-2-cyclopropyl-6-(3,6-dihydro-2H-pyran-4-yl)-3-methyl-4-(pyrimidin-2-ylamino)-3,4-dihydroquinolin-1(2H)-yl)ethanone

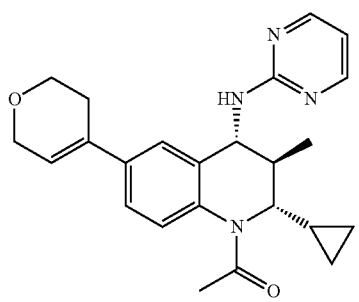 [SMILES: CC(=O)N1c2ccc(C3=CCOCC3)cc2[C@H](Nc2ncccn2)[C@@H](C)[C@@H]1C1CC1]

A 0.5-2 mL microwave vial was evacuated and back filled with nitrogen. 1-((2S,3R,4R)-4-amino-2-cyclopropyl-6-(3,6-dihydro-2H-pyran-4-yl)-3-methyl-3,4-dihydroquinolin-1(2H)-yl)ethanone (for a preparation see Intermediate 345, 95 mg, 0.291 mmol) in N-methyl-2-pyrrolidone (NMP) (1.6 mL) was then added. To this was added 2-fluoropyrimidine (57.1 mg, 0.582 mmol), and DIPEA (0.152 mL, 0.873 mmol) and the resultant solution then heated in a microwave reactor to 150° C. for 30 min, then 45 min, then 30 min and finally 30 min at 170° C. The reaction mixture was filtered through a cotton wool plug directly into two LCMS vials and was then purified by 2×MDAP (Formic). Not all of the crude sample was injected by the machine so two further MDAPs (Formic) were run. All of the appropriate fractions were collected and concentrated in vacuo to afford the desired product as an off-white crystalline solid (57 mg, 0.141 mmol, 48%).

LCMS (2 min Formic): Rt=0.91 min, [MH]$^+$=405.

Example 556: 1-((2S,3R,4R)-2-cyclopropyl-6-(2-hydroxyethoxy)-3-methyl-4-((4-methylpyrimidin-2-yl)amino)-3,4-dihydroquinolin-1(2H)-yl)ethanone

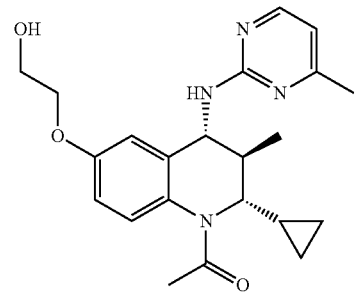 [SMILES: CC(=O)N1c2ccc(OCCO)cc2[C@H](Nc2nccc(C)n2)[C@@H](C)[C@@H]1C1CC1]

To a reaction vessel 1-((2S,3R,4R)-6-(2-((tert-butyldimethylsilyl)oxy)ethoxy)-2-cyclopropyl-3-methyl-4-((4-methylpyrimidin-2-yl)amino)-3,4-dihydroquinolin-1(2H)-yl)ethanone (for a preparation see Intermediate 348, 43 mg, 0.084 mmol) in tetrahydrofuran (THF) (9 mL) was added. The solution was cooled to 0° C. and TBAF (1 M in THF) (0.337 mL, 0.337 mmol) was added and the reaction left to stir and warm to rt for 60 minutes. The reaction solution was poured onto water (10 mL) and the aqueous phase extracted with DCM (3×10 mL). The organic extracts were combined, washed with brine (25 mL) and dried through a hydrophobic frit. The resulting solution was concentrated in vacuo to give 53 mg of crude product as an orange gum. The sample was dissolved in 1:1 DMSO:methanol (1.5 mL) and purified by MDAP (Formic). The solvent was evaporated in vacuo to give the product (12 mg, 0.030 mmol, 36%) as an off-white solid. LCMS (2 min Formic): Rt=0.74 min, [MH]$^+$=397.

Example 557: 1-((2S,3R,4R)-2-cyclopropyl-6-(1-(2-methoxyethyl)-1H-pyrazol-4-yl)-3-methyl-4-((4-methylpyrimidin-2-yl)amino)-3,4-dihydroquinolin-1(2H)-yl)ethanone

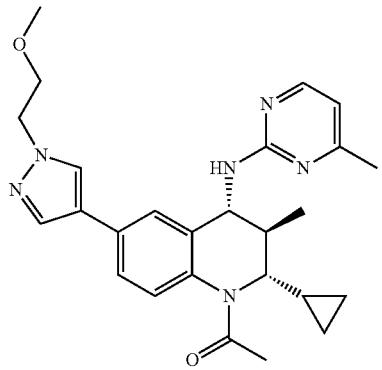 [SMILES: COCCn1cc(-c2ccc3c(c2)[C@H](Nc2nccc(C)n2)[C@@H](C)[C@H](C2CC2)N3C(C)=O)cn1]

The 2-chloro-4-methylpyrimidine (200 mg, 1.556 mmol), 18-crown-6 (586 mg, 1.556 mmol) and potassium fluoride (108 mg, 1.867 mmol) were suspended in N-methyl-2-pyrrolidone (NMP) (5 mL) and irradiated in a microwave at 200° C. for 1 h. The reaction was treated with 1-((2S,3R,4R)-4-amino-2-cyclopropyl-6-(1-(2-methoxyethyl)-1H-pyrazol-4-yl)-3-methyl-3,4-dihydroquinolin-1(2H)-yl)ethanone (for a preparation see Intermediate 350, 85 mg, 0.231 mmol) and DIPEA (0.136 mL, 0.778 mmol) and was irradiated in a microwave at 180° C. for 30 mins. The reaction was partitioned between 10% LiCl(aq) and EtOAc, the organic layer was dried using a hydrophobic frit and concentrated to a gum, this gum was purified using MDAP (Formic). The appropriate fraction was concentrated and eluted through a NH$_2$ SPE (1 g) with MeOH, the eluent was concentrated and dried to give the product (5 mg, 10.86 μmol, 1%). LCMS (2 min Formic): Rt=0.83 min, [MH]$^+$=461.

The following examples were prepared in a similar manner to Example 557 using Pd$_2$(dba)$_3$, DavePhos and NaOtBu to couple the appropriate aryl halide with Intermediate 352.

| Ex No. | Name | Structure | Mass (mg) | Yield (%) | [MH]$^+$ | Rt (mins) (LCMS method) |
|---|---|---|---|---|---|---|
| 558 | 4-(((2S,3R,4R)-1-acetyl-2-cyclopropyl-6-(1-(2-hydroxyethyl)-1H-pyrazol-4-yl)-3-methyl-1,2,3,4-tetrahydroquinolin-4-yl)amino)pyridin-2(1H)-one | 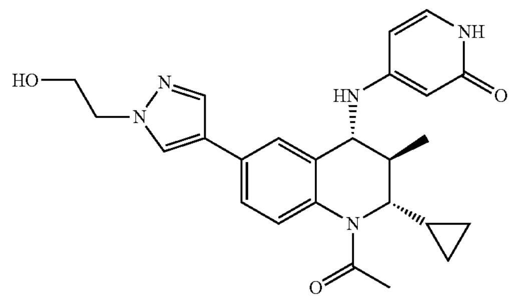 [SMILES: CC(=O)N1c2ccc(-c3cnn(CCO)c3)cc2[C@H](Nc2cc[nH]c(=O)c2)[C@@H](C)[C@@H]1C1CC1] | 4 | 6 | 448 | 0.65 (2 min HpH) |
| 559 | 1-((2S,3R,4R)-2-cyclopropyl-6-(1-(2-hydroxyethyl)-1H-pyrazol-4-yl)-3-methyl-4-(pyrimidin-2-ylamino)-3,4-dihydroquinolin-1(2H)-yl)ethanone | 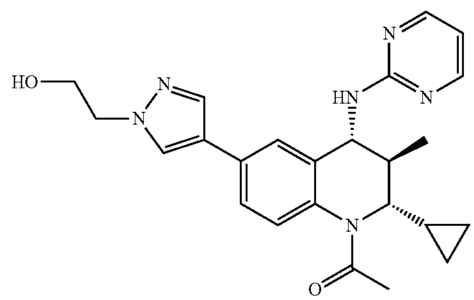 [SMILES: CC(=O)N1c2ccc(-c3cnn(CCO)c3)cc2[C@H](Nc2ncccn2)[C@@H](C)[C@@H]1C1CC1] | 55 | 64 | 433 | 0.72 (2 min Formic) |
| 560 | 1-((2S,3R,4R)-2-cyclopropyl-4-((5-fluoropyridin-2-yl)amino)-6-(1-(2-hydroxyethyl)-1H-pyrazol-4-yl)-3-methyl-3,4-dihydroquinolin-1(2H)-yl)ethanone | 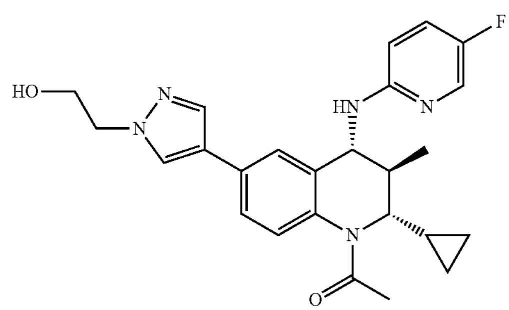 [SMILES: CC(=O)N1c2ccc(-c3cnn(CCO)c3)cc2[C@H](Nc2ccc(F)cn2)[C@@H](C)[C@@H]1C1CC1] | 5 | 8 | 450 | 0.77 (2 min Formic) |
| 561 | 1-((2S,3R,4R)-2-cyclopropyl-4-((5-fluoro-6-methylpyridin-2-yl)amino)-6-(1-(2-hydroxyethyl)-1H-pyrazol-4-yl)-3-methyl-3,4-dihydroquinolin-1(2H)-yl)ethanone | 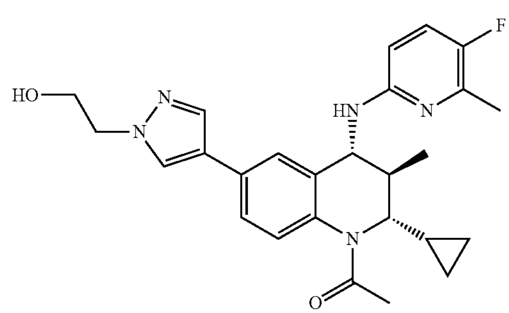 [SMILES: CC(=O)N1c2ccc(-c3cnn(CCO)c3)cc2[C@H](Nc2ccc(F)c(C)n2)[C@@H](C)[C@@H]1C1CC1] | 6 | 8 | 464 | 0.78 (2 min Formic) |

| Ex No. | Name | Structure | Mass (mg) | Yield (%) | [MH]+ | Rt (mins) (LCMS method) |
|---|---|---|---|---|---|---|
| 562 | 1-((2S,3R,4R)-2-cyclopropyl-6-(1-(2-hydroxyethyl)-1H-pyrazol-4-yl)-3-methyl-4-((4-methylpyrimidin-2-yl)amino)-3,4-dihydroquinolin-1(2H)-yl)ethanone | 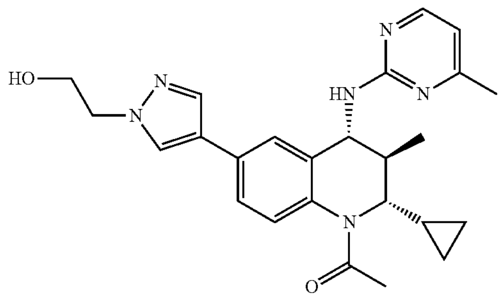 [SMILES: CC(=O)N1c2ccc(-c3cnn(CCO)c3)cc2[C@H](Nc2nccc(C)n2)[C@@H](C)[C@@H]1C1CC1] | 25 | 45 | 447 | 0.73 (2 min Formic) |
| 563 | 1-((2S,3R,4R)-2-cyclopropyl-6-(1-(2-hydroxyethyl)-1H-pyrazol-4-yl)-3-methyl-4-((6-methylpyridin-2-yl)amino)-3,4-dihydroquinolin-1(2H)-yl)ethanone | 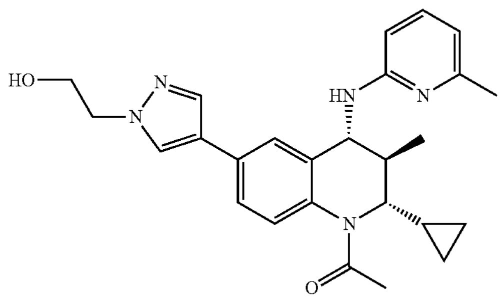 [SMILES: CC(=O)N1c2ccc(-c3cnn(CCO)c3)cc2[C@H](Nc2cccc(C)n2)[C@@H](C)[C@@H]1C1CC1] | 8 | 8 | 446 | 0.65 (2 min Formic) |

Example 564: 1-((2S,3R,4R)-2-cyclopropyl-6-(1-(2-hydroxyethyl)-1H-pyrazol-4-yl)-3-methyl-4-(pyridin-2-ylamino)-3,4-dihydroquinolin-1(2H)-yl)ethanone

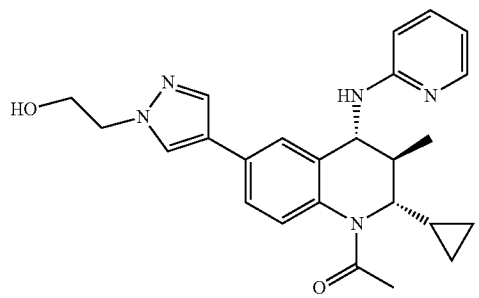 [SMILES: CC(=O)N1c2ccc(-c3cnn(CCO)c3)cc2[C@H](Nc2ccccn2)[C@@H](C)[C@@H]1C1CC1]

To a reaction vessel 1-((2S,3R,4R)-6-(1-(2-((tert-butyldimethylsilyl)oxy)ethyl)-1H-pyrazol-4-yl)-2-cyclopropyl-3-methyl-4-(pyridin-2-ylamino)-3,4-dihydroquinolin-1 (2H)-yl)ethanone (for a preparation see Intermediate 355, 70 mg, 0.128 mmol) in tetrahydrofuran (THF) (3 mL) was added. The solution was cooled to 0° C. and TBAF (1 M in THF) (0.513 mL, 0.513 mmol) was added and the reaction left to stir and warm to rt under N₂ for 1 h. The reaction mixture was diluted with water (10 mL) and DCM (10 ml). The organic layer was separated and aqueous layer was further extracted with DCM (3×10 mL). The combined organic extracts were dried (Na₂SO₄) and concentrated to give ~79 mg crude pink residue. This was purified by chromatography on SiO₂ (25 g cartridge, eluting with 0-10% methanol/DCM over 330 mL, followed by 10-20% methanol/DCM over 170 mL) to give the product (46 mg, 0.107 mmol, 83%) as a colourless oil. LCMS (2 min Formic): Rt=0.61 min, [MH]+=432.

Example 565: 1-((2S,3R,4R)-6-(1-acetyl-1,2,3,6-tetrahydropyridin-4-yl)-2,3-dimethyl-4-((4-methylpyrimidin-2-yl)amino)-3,4-dihydroquinolin-1(2H)-yl)ethanone

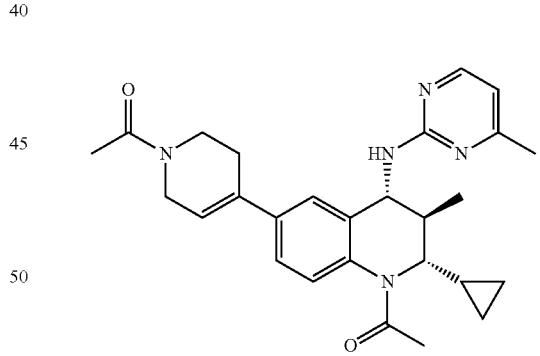

A sample of 1-((2S,3R,4R)-2,3-dimethyl-4-((4-methylpyrimidin-2-yl)amino)-6-(1,2,3,6-tetrahydropyridin-4-yl)-3,4-dihydroquinolin-1(2H)-yl)ethanone (for a preparation see Intermediate 359, 22.3 mg, 0.046 mmol) was dissolved in dichloromethane (DCM) (1 mL) and placed in a dried flask under nitrogen. To this was added N,N-diisopropylethylamine (0.080 mL, 0.456 mmol), followed by acetyl chloride (0.016 mL, 0.228 mmol). The mixture was allowed to stir for 90 min. The reaction mixture was diluted with dichloromethane, and washed with 2M aqueous HCl (2×20 mL) followed by saturated aqueous sodium hydrogen carbonate solution (2×20 mL). The organic layer was then passed through a hydrophobic frit, collected and concentrated in vacuo. The crude residue was dissolved in 1:1 MeOH:DMSO (1 mL) and purified by MDAP (Formic). The solvent was evaporated in vacuo to give the required product (4.8 mg, 9.96 μmol, 22%).

LCMS (2 min Formic): Rt=0.69 min, [MH]⁺=434.

Example 566: 1-((2S,3R,4R)-6-(1-(2-hydroxyethyl)-1,2,3,6-tetrahydropyridin-4-yl)-2,3-dimethyl-4-((4-methylpyrimidin-2-yl)amino)-3,4-dihydroquinolin-1(2H)-yl)ethanone

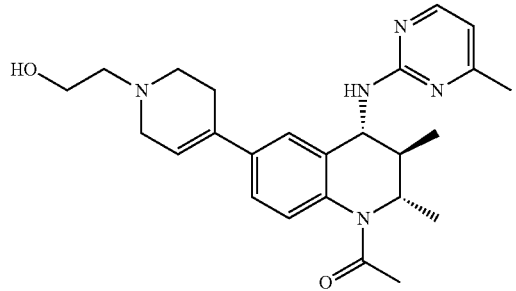 [SMILES: CC(=O)N1c2ccc(C3=CCN(CCO)CC3)cc2[C@H](Nc2nccc(C)n2)[C@@H](C)[C@@H]1C]

A dried flask under nitrogen was charged with a sample of 1-((2S,3R,4R)-2,3-dimethyl-4-((4-methylpyrimidin-2-yl)amino)-6-(1,2,3,6-tetrahydropyridin-4-yl)-3,4-dihydroquinolin-1(2H)-yl)ethanone (for a preparation see Intermediate 359, 34.2 mg, 0.087 mmol), which was then dissolved in dichloromethane (DCM) (1 mL). To this stirring solution was added 2-bromoethanol (0.015 mL, 0.218 mmol), and the mixture was left to stir at rt for 16 h. The reaction mixture was concentrated in vacuo, taken up in dichloromethane and loaded onto a 10 g silica flash column, and eluted by flash silica gel chromatography, eluting in 6%-10% 2M NH₃/MeOH in dichloromethane. The purest fractions were combined and concentrated in vacuo to afford a pale yellow glass (11.1 mg, 0.024 mmol, 28%). LCMS (2 min Formic): Rt=0.57 min, [MH]⁺=436.

Example 567: 1-((2S,3R,4R)-2,3-dimethyl-4-((4-methylpyrimidin-2-yl)amino)-rac-6-((tetrahydrofuran-3-yl)oxy)-3,4-dihydroquinolin-1(2H)-yl)ethanone

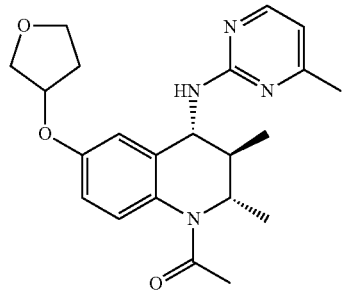 [SMILES: CC(=O)N1c2ccc(OC3CCOC3)cc2[C@H](Nc2nccc(C)n2)[C@@H](C)[C@@H]1C]

To a 10 mL-20 mL microwave vial was added 2-chloro-4-methylpyrimidine (127 mg, 0.986 mmol), potassium fluoride (86 mg, 1.478 mmol) and 18-crown-6 (130 mg, 0.493 mmol), followed by a solution of 1-((2S,3R,4R)-4-amino-2,3-dimethyl-rac-6-((tetrahydrofuran-3-yl)oxy)-3,4-dihydroquinolin-1(2H)-yl)ethanone (for a preparation see Intermediate 363, 100 mg, 0.329 mmol) and DIPEA (0.287 mL, 1.643 mmol) in dimethyl sulfoxide (DMSO) (5 mL). The reaction vessel was sealed and heated to 160° C. for 4 h. The reaction mixture was partitioned between diethyl ether (25 mL) and water (25 mL). The layers were separated and the aqueous layer was extracted with diethyl ether (2×25 mL). The organic layer was dried through a hydrophobic frit and concentrated in vacuo to give 189 mg of crude product as an orange oil. This was purified by chromatography on SiO₂ (10 g) eluting with 50-100% ethyl acetate/cyclohexane. The fractions containing product were combined and concentrated in vacuo to give 46 mg of desired product (46 mg, 0.116 mmol, 35%) as a yellow solid.

LCMS (2 min Formic): Rt=0.75 min, [MH]⁺=397.

Example 568: 1-((2S,3R,4R)-2-cyclopropyl-3-methyl-4-((4-methylpyrimidin-2-yl)amino)-rac-6-((tetrahydrofuran-3-yl)oxy)-3,4-dihydroquinolin-1(2H)-yl)ethanone

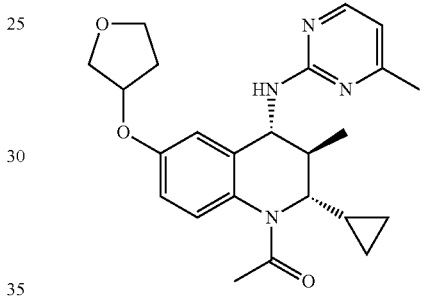

To a reaction vessel 1-((2S,3R,4R)-4-amino-2-cyclopropyl-3-methyl-rac-6-((tetrahydrofuran-3-yl)oxy)-3,4-dihydroquinolin-1(2H)-yl)ethanone (for a preparation see Intermediate 366, 184 mg, 0.557 mmol), 2-bromo-4-methylpyrimidine (193 mg, 1.114 mmol) and sodium tert-butoxide (268 mg, 2.78 mmol) were added in 1,4-dioxane (10 mL). This solution was treated with Pd₂(dba)₃ (76 mg, 0.084 mmol) and DavePhos (43.8 mg, 0.111 mmol) and left to stir at 100° C. for 3 h. Further 2-bromo-4-methylpyrimidine (150 mg, 0.867 mmol), DavePhose (43 mg, 0.109 mmol), and Pd₂(dba)₃ (78 mg, 0.085 mmol) were added and the reaction left to stir for 1 h. Pd₂(dba)₃ (670 mg, 0.732 mmol) and DavePhos (40 mg, 0.102 mmol) were added and the reaction left to stir at 100° C. for 19 h. The reaction mixture was filtered through celite and the celite washed with ethyl acetate (15 mL). The combined filtrates were washed with sat. aq. NaHCO₃ (2×25 mL) and the layers separated. The organic phase was dried through a hydrophobic frit and concentrated in vacuo to give 592 mg of crude product as a brown gum. This was purified by chromatography on SiO₂ (25 g, eluting with 0-100% ethyl acetate/cyclohexane). The fractions containing product were combined and concentrated in vacuo to give 90 mg of product as a brown gum. The sample was dissolved in 1:1 MeOH:DMSO (1 mL) and (47 mg, 0.111 mmol, 20%) as an off-white solid.

LCMS (2 min HpH): Rt=0.95 min, [MH]⁺=423.

Example 569: 1-((2S,3R,4R)-2,3-dimethyl-6-(piperazin-1-yl)-4-(pyrimidin-2-ylamino)-3,4-dihydroquinolin-1(2H)-yl)ethanone, hydrochloride

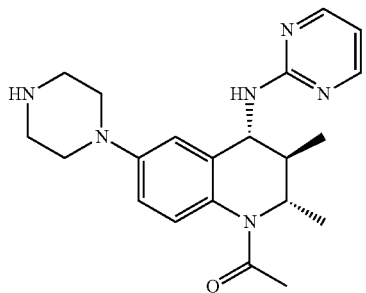 [SMILES: CC(=O)N1c2ccc(N3CCNCC3)cc2[C@H](Nc2ncccn2)[C@@H](C)[C@@H]1C]

To a flask containing tert-butyl 4-((2S,3R,4R)-1-acetyl-2,3-dimethyl-4-(pyrimidin-2-ylamino)-1,2,3,4-tetrahydroquinolin-6-yl)piperazine-1-carboxylate (for a preparation see Intermediate 367, 119 mg, 0.248 mmol) in dichloromethane (DCM) (1 mL) was added TFA (300 µL, 3.89 mmol) and the reaction was stirred for 1 h. The reaction mixture was concentrated in vacuo to afford a brown oil. This was dissolved in methanol and loaded onto an SCX cartridge (5 g). It was eluted with methanol (3 CVs) and product eluted as free base with 2M ammonia in methanol. The filtrate from the ammonia fractions was concentrated in vacuo to yield a yellow oil. This was taken up in DMSO/MeOH (1:1, 1.8 mL) and purified by MDAP (HpH) The fractions were combined together and concentrated in vacuo to afford the desired product as a pale yellow glass (75 mg, 0.197 mmol, 80%). 45 mg of the sample was used in subsequent chemistry the other 30 mg was taken up in dichloromethane (DCM) (1.0 mL) in a vial. HCl (1M in Et$_2$O) (79 µL, 0.079 mmol) was added and the sample sonicated for 2 min and allowed to stand for 15 min before the solvents were removed under a stream of nitrogen and the sample further dried in vacuo to afford the desired HCl salt (35.2 mg, 0.084 mmol, 34%). LCMS (2 min Formic): Rt=0.53 min, [MH]$^+$=381.

Example 570: 1-((2S,3R,4R)-6-(4-(2-hydroxyethyl)piperazin-1-yl)-2,3-dimethyl-4-(pyrimidin-2-ylamino)-3,4-dihydroquinolin-1(2H)-yl)ethanone

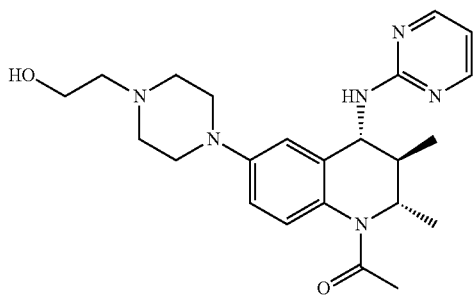 [SMILES: CC(=O)N1c2ccc(N3CCN(CCO)CC3)cc2[C@H](Nc2ncccn2)[C@@H](C)[C@@H]1C]

A dried flask under nitrogen was charged with a sample of 1-((2S,3R,4R)-2,3-dimethyl-6-(piperazin-1-yl)-4-(pyrimidin-2-ylamino)-3,4-dihydroquinolin-1(2H)-yl)ethanone (for a preparation see Example 569, 20 mg, 0.053 mmol), which was then dissolved in dichloromethane (DCM) (2 mL). To this stirring solution was added 2-bromoethanol (0.019 mL, 0.263 mmol), and the mixture was left to stir at rt for 72 h. Further 2-bromoethanol (0.019 mL, 0.263 mmol) was added and the reaction stirred for a further 5 h. Triethylamine (0.073 mL, 0.526 mmol) was added (solution turned yellow) and the reaction stirred for 24 h. The reaction mixture was loaded directly onto a 10 g silica flash column, and eluted by flash silica gel chromatography, eluting in 0%-50% (20% (2M NH$_3$/MeOH) in dichloromethane) in DCM. The appropriate fractions were collected and combined to afford the product as a white solid (42 mg). This was taken up in 1:1 MeOH/DMSO (0.9 mL) and purified by MDAP (HpH). The appropriate fraction was collected and concentrated in vacuo to afford the desired product as a colourless oil (14.7 mg, 0.035 mmol, 66%).

LCMS (2 min Formic): Rt=0.52 min, [MH]$^+$=425.

Example 571: 4-(((2S,3R,4R)-1-acetyl-2,3-dimethyl-6-(piperazin-1-yl)-1,2,3,4-tetrahydroquinolin-4-yl)amino)benzamide

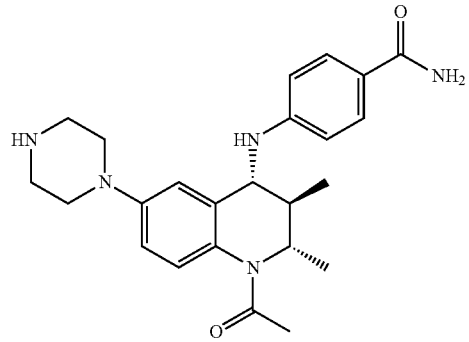 [SMILES: CC(=O)N1c2ccc(N3CCNCC3)cc2[C@H](Nc2ccc(C(N)=O)cc2)[C@@H](C)[C@@H]1C]

tert-Butyl 4-((2S,3R,4R)-1-acetyl-4-((4-carbamoylphenyl)amino)-2,3-dimethyl-1,2,3,4-tetrahydroquinolin-6-yl)piperazine-1-carboxylate (for a preparation see Intermediate 370, 52 mg, 0.100 mmol) was taken up in DCM (5 mL). Trifluoroacetic acid (0.1 mL, 1.298 mmol) was added, and the reaction left to stir for 1 h at rt. Further trifluoroacetic acid (0.1 ml, 1.298 mmol) was added and the reaction was left to stir for 16 h at rt. The reaction solution was concentrated in vacuo then retaken up in DCM (5 mL) and concentrated in vacuo to give the crude product as a colourless oil. This was retaken up in methanol and purified by sulphonic acid SPE (SCX) 5 g using a sequential solvents methanol, 2M ammonia/methanol. The appropriate fractions were combined and concentrated in vacuo to give 35 mg of the desired product as an off-white solid.

LCMS (2 min Formic): Rt=0.54 min, [MH]$^+$=422.

Example 572: 4-((2S,3R,4R)-1-acetyl-2-cyclopropyl-3-methyl-4-(pyrimidin-2-ylamino)-1,2,3,4-tetrahydroquinolin-6-yl)-1-methylpiperazin-2-one

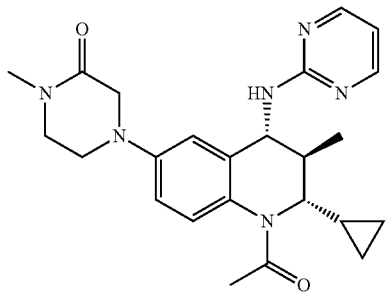 [SMILES: CC(=O)N1c2ccc(N3CCN(C)C(=O)C3)cc2[C@H](Nc2ncccn2)[C@@H](C)[C@@H]1C1CC1]

A solution of 1-((2S,3R,4R)-6-bromo-2-cyclopropyl-3-methyl-4-(pyrimidin-2-ylamino)-3,4-dihydroquinolin-1(2H)-yl)ethanone (for a preparation see Intermediate 371, 165 mg, 0.411 mmol), 1-methylpiperazin-2-one, hydrochloride (124 mg, 0.822 mmol), DavePhos (16.18 mg, 0.041 mmol), Pd$_2$(dba)$_3$ (18.83 mg, 0.021 mmol) and sodium tert-butoxide (158 mg, 1.645 mmol) in 1,4-dioxane (5 mL) was stirred under nitrogen at 90° C. for 16 h. The reaction mixture was allowed to cool to rt, filtered through celite and rinsed with ethyl acetate. The solvent was evaporated in vacuo and the remaining mixture was dissolved in 1,4-dioxane (5 mL). 1-methylpiperazin-2-one, hydrochloride (124 mg, 0.822 mmol), DavePhos (16.18 mg, 0.041 mmol), Pd$_2$(dba)$_3$ (18.83 mg, 0.021 mmol) and sodium tert-butoxide (158 mg, 1.645 mmol) were added and the reaction was heated under nitrogen at 90° C. for a further 16 h. The reaction mixture was allowed to cool to rt, filtered through celite and rinsed with ethyl acetate. The solvent was evaporated in vacuo and the crude was re-dissolved in DCM. This solution was applied to a 50 g silica cartridge and purified over a gradient of 0-50% ethyl acetate in cyclohexane over 12 CVs. The appropriate fractions were combined and concentrated in vacuo to give the product (34 mg, 0.078 mmol, 19%).

LCMS (2 min Formic): Rt=0.72 min, [MH]$^+$=435.

Example 573: 1-((2S,3R,4R)-2-ethyl-3-methyl-6-(piperazin-1-yl)-4-(pyrimidin-2-ylamino)-3,4-dihydroquinolin-1(2H)-yl)ethanone

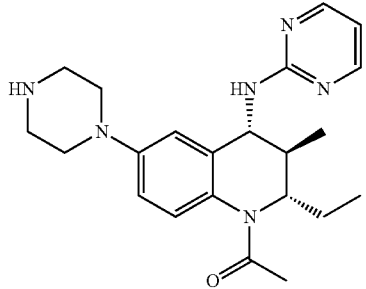 [SMILES: CC[C@H]1[C@H](C)[C@@H](Nc2ncccn2)c2cc(N3CCNCC3)ccc2N1C(C)=O]

To a solution of tert-butyl 4-((2S,3R,4R)-1-acetyl-2-ethyl-3-methyl-4-(pyrimidin-2-ylamino)-1,2,3,4-tetrahydroquinolin-6-yl)piperazine-1-carboxylate (for a preparation see Intermediate 376, 51 mg, 0.103 mmol) in dichloromethane (DCM) (4 mL) was added TFA (1 ml, 12.98 mmol) and reaction mixture was stirred under nitrogen at rt. Reaction mixture was concentrated and loaded onto a 2 g SCX cartridge (pre-conditioned with MeOH) and eluted with MeOH (30 mL) followed by 2M NH$_3$ in MeOH (30 mL). Ammonia fractions were combined and concentrated to give the product (39 mg, 0.099 mmol, 96%) as a pale yellow solid. LCMS (2 min Formic): Rt=0.56 min, [MH]$^+$=395.

Example 574: 1-((2S,3R,4R)-2-ethyl-3-methyl-4-(pyrimidin-2-ylamino)-6-(1,2,3,6-tetrahydropyridin-4-yl)-3,4-dihydroquinolin-1(2H)-yl)ethanone

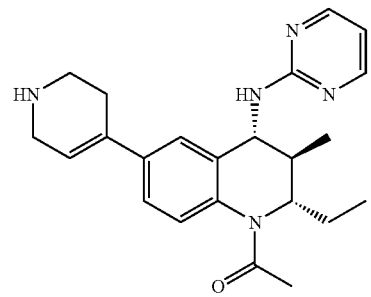 [SMILES: CC[C@H]1[C@H](C)[C@@H](Nc2ncccn2)c2cc(C3=CCNCC3)ccc2N1C(C)=O]

To a solution of tert-butyl 4-((2S,3R,4R)-1-acetyl-2-ethyl-3-methyl-4-(pyrimidin-2-ylamino)-1,2,3,4-tetrahydroquinolin-6-yl)-5,6-dihydropyridine-1(2H)-carboxylate (for a preparation see Intermediate 377, 346 mg, 0.704 mmol) in dichloromethane (DCM) (4 mL) was added TFA (1 mL, 12.98 mmol) and reaction mixture stirred at rt under nitrogen. Reaction mixture turned dark orange colour on addition of TFA. The reaction mixture was concentrated and loaded onto a 2 g SCX cartridge (pre-conditioned with MeOH) and eluted with MeOH (30 ml) followed by 2M NH$_3$ in MeOH (30 mL). Ammonia fractions containing product were combined and concentrated to give the product (219 mg, 0.559 mmol, 79%) as a pale yellow foamy solid.

LCMS (2 min Formic): Rt=0.59 min, [MH]$^+$=392.

Example 575: 1-((2S,3R,4R)-2-ethyl-6-(1-(2-hydroxyethyl)-1,2,3,6-tetrahydropyridin-4-yl)-3-methyl-4-(pyrimidin-2-ylamino)-3,4-dihydroquinolin-1(2H)-yl)ethanone

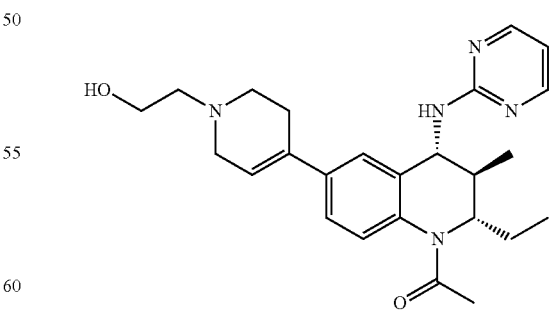

To a solution of 1-((2S,3R,4R)-2-ethyl-3-methyl-4-(pyrimidin-2-ylamino)-6-(1,2,3,6-tetrahydropyridin-4-yl)-3,4-dihydroquinolin-1(2H)-yl)ethanone (for a preparation see Example 574, 66 mg, 0.169 mmol) in dichloromethane (DCM) (2 mL) was added 2-bromoethanol (0.036 mL, 0.506 mmol) dropwise. The reaction mixture was stirred at rt for 1.5 h. The reaction mixture was concentrated to give ~150 mg of crude yellow residue. This was purified by chromatography on SiO$_2$ (10 g) eluting with 0-20% methanol/DCM over 120 mL to the product (31 mg, 0.071 mmol, 42% yield) as a pale yellow solid.

LCMS (2 min Formic): Rt=0.59 min, [MH]$^+$=436.

Example 576: 1-((2S,3R,4R)-6-(1-acetyl-1,2,3,6-tetrahydropyridin-4-yl)-2-ethyl-3-methyl-4-(pyrimidin-2-ylamino)-3,4-dihydroquinolin-1(2H)-yl)ethanone

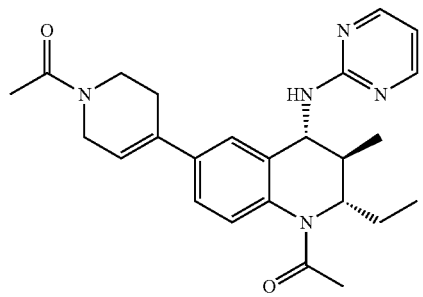 [SMILES: CC[C@H]1[C@H](C)[C@@H](Nc2ncccn2)c2cc(C3=CCN(C(C)=O)CC3)ccc2N1C(C)=O]

To a solution of 1-((2S,3R,4R)-2-ethyl-3-methyl-4-(pyrimidin-2-ylamino)-6-(1,2,3,6-tetrahydropyridin-4-yl)-3,4-dihydroquinolin-1(2H)-yl)ethanone (for a preparation see Example 574, 30 mg, 0.077 mmol) in dichloromethane (DCM) (2 mL) was added DIPEA (0.027 mL, 0.153 mmol) followed by acetyl chloride (6.54 μL, 0.092 mmol) in dichloromethane (DCM) (1 mL). The reaction mixture was stirred under nitrogen at rt. The reaction mixture was diluted with DCM and H$_2$O. 2M aq. HCl was added and the organic layer was separated. The organic layer was then washed with sat. NaHCO$_3$ solution dried (Na$_2$SO$_4$) and concentrated to give 45 mg of crude residue. This was purified by MDAP (Formic). Fractions containing product were partitioned between sat. NaHCO$_3$ solution (10 mL) and DCM (30 mL). The organic layer was separated, dried (Na$_2$SO$_4$) and concentrated to give the product (18 mg, 0.042 mmol, 54%) as a white solid.

LCMS (2 min Formic): Rt=0.78 min, [MH]$^+$=434.

Example 577: 1-((2S,3R,4R)-2-cyclopropyl-3-methyl-4-(pyrimidin-2-ylamino)-6-(1,2,3,6-tetrahydropyridin-4-yl)-3,4-dihydroquinolin-1(2H)-yl)ethanone

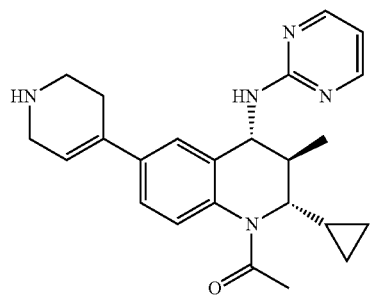 [SMILES: CC(=O)N1c2ccc(C3=CCNCC3)cc2[C@H](Nc2ncccn2)[C@@H](C)[C@@H]1C1CC1]

A flask under Nitrogen was charged with a sample of tert-butyl 4-((2S,3R,4R)-1-acetyl-2-cyclopropyl-3-methyl-4-(pyrimidin-2-ylamino)-1,2,3,4-tetrahydroquinolin-6-yl)-5,6-dihydropyridine-1(2H)-carboxylate (for a preparation see Intermediate 378, 295.2 mg, 0.586 mmol). The material was dissolved in dichloromethane (DCM) (12 mL), and to this solution was added trifluoroacetic acid (3 mL, 38.9 mmol). The mixture was left to stir at rt for 20 min. The reaction mixture was concentrated in vacuo. The residue was taken up in methanol and loaded onto a 10 g SCX-2 SPE cartridge, which had been pre-wet with methanol. The column was washed with 2 CVs of methanol, and the product was then eluted in 2 CVs of 2M methanolic ammonia. The fractions were analysed by TLC, and the appropriate fractions were collected and concentrated in vacuo to afford a transparent yellow glass (179.4 mg, 0.422 mmol, 72%).

LCMS (2 min Formic): Rt=0.62 min, [MH]$^+$=404.

Example 578: 1-((2S,3R,4R)-2-cyclopropyl-6-(1-(2-hydroxyethyl)-1,2,3,6-tetrahydropyridin-4-yl)-3-methyl-4-(pyrimidin-2-ylamino)-3,4-dihydroquinolin-1(2H)-yl)ethanone

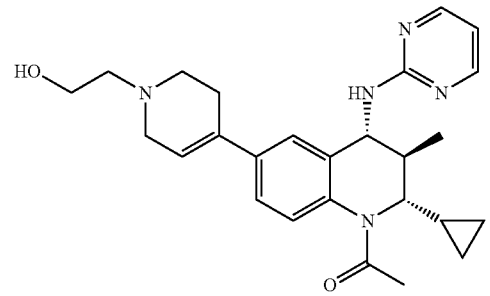 [SMILES: CC(=O)N1c2ccc(C3=CCN(CCO)CC3)cc2[C@H](Nc2ncccn2)[C@@H](C)[C@@H]1C1CC1]

To a flask under nitrogen was added a sample of 1-((2S,3R,4R)-2-cyclopropyl-3-methyl-4-(pyrimidin-2-ylamino)-6-(1,2,3,6-tetrahydropyridin-4-yl)-3,4-dihydroquinolin-1 (2H)-yl)ethanone (for a preparation see Example 577, 50 mg, 0.124 mmol), which had been dissolved in dichloromethane (DCM) (1 mL). The solution was stirred, and to it was added 2-bromoethanol (0.018 mL, 0.248 mmol). The mixture was left to stir at rt for 1 h. The reaction mixture was concentrated in vacuo. The residue was taken up in dichloromethane, loaded onto a 10 g silica column, and the mixture was purified by flash silica gel chromatography—the product eluting in 7.5%-12.5% 2M methanolic ammonia/dichloromethane. The appropriate fractions were collected and concentrated in vacuo to afford a colourless glass. Some starting material remained so the sample was dissolved in dichloromethane (DCM) (1 mL), and then to this solution was added DIPEA (0.043 mL, 0.248 mmol), followed by 2-bromoethanol (0.018 mL, 0.248 mmol). The mixture was left to stir at rt overnight. The reaction mixture was concentrated in vacuo. The residue was dissolved in 1:1 MeOH: DMSO 1 mL and purified by MDAP (HpH). The solvent was evaporated in vacuo to give the required product (14.3 mg, 0.030 mmol, 25%). LCMS (2 min Formic): Rt=0.61 min, [MH]$^+$=448.

Example 579: 1-((2S,3R,4R)-1-acetyl-2-cyclopropyl-3-methyl-4-(pyrimidin-2-ylamino)-1,2,3,4-tetrahydroquinolin-6-yl)piperazin-2-one

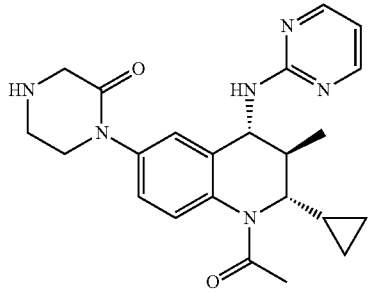 [SMILES: CC(=O)N1c2ccc(N3CCNCC3=O)cc2[C@H](Nc2ncccn2)[C@@H](C)[C@@H]1C1CC1]

A solution of tert-butyl 4-((2S,3R,4R)-1-acetyl-2-cyclopropyl-3-methyl-4-(pyrimidin-2-ylamino)-1,2,3,4-tetrahydroquinolin-6-yl)-3-oxopiperazine-1-carboxylate (for a preparation see Intermediate 379, 40 mg, 0.077 mmol) and 4M HCl in dioxane (1 ml, 4.00 mmol) in 1,4-dioxane (1 mL) was stirred in a closed vessel at rt for 20 h. The reaction mixture was concentrated under a stream of nitrogen and the material was dissolved in MeOH (2 mL). This solution was applied to a 2 g SCX cartridge which had been pre-equilibrated with MeOH (2 mL). The cartridge was washed with MeOH (4 mL) and $NH_3$ in MeOH (2M, 4 mL). The ammonia wash was concentrated in vacuo to afford the product (23 mg, 0.055 mmol, 71%). LCMS (2 min Formic): Rt=0.54 min, [MH]$^+$=421.

Example 580: 1-((2S,3R,4R)-2-cyclopropyl-3-methyl-6-(piperazin-1-yl)-4-(pyrimidin-2-ylamino)-3,4-dihydroquinolin-1(2H)-yl)ethanone

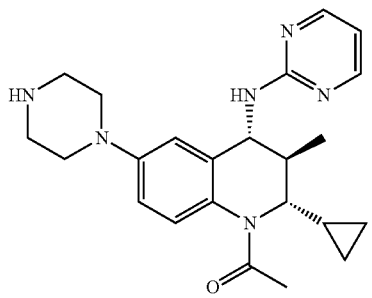 [SMILES: CC(=O)N1c2ccc(N3CCNCC3)cc2[C@H](Nc2ncccn2)[C@@H](C)[C@@H]1C1CC1]

A flask containing tert-butyl 4-((2S,3R,4R)-1-acetyl-2-cyclopropyl-3-methyl-4-(pyrimidin-2-ylamino)-1,2,3,4-tetrahydroquinolin-6-yl)piperazine-1-carboxylate (for a preparation see Intermediate 380, 16.1 mg, 0.032 mmol) was evacuated and back-filled with nitrogen. The sample was dissolved in dichloromethane (DCM) (1 mL), and then to this solution was added trifluoroacetic acid (0.25 mL, 3.24 mmol). The mixture was stirred at rt under nitrogen for 30 min. The reaction mixture was concentrated in vacuo. The residue was taken up in methanol and loaded onto a 2 g SCX-2 SPE cartridge, which had been pre-wet with methanol. The column was washed with methanol, and then the product was eluted with a 2M solution of ammonia in methanol. The appropriate fractions were collected and concentrated in vacuo. The residue was dissolved in 1:1 MeOH:DMSO 1 mL and purified by MDAP (Hph). The solvent was evaporated in vacuo to give the required product (8.1 mg).

LCMS (2 min HpH): Rt=0.73 min, [MH]$^+$=407.

Example 581: 1-((2S,3R,4R)-2-cyclopropyl-3-methyl-6-(1H-pyrazol-4-yl)-4-(pyrimidin-2-ylamino)-3,4-dihydroquinolin-1(2H)-yl)ethanone

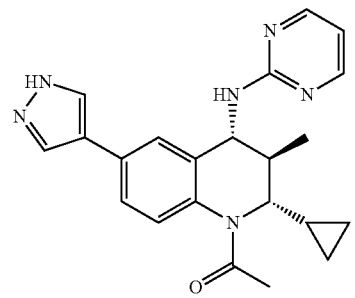 [SMILES: CC(=O)N1c2ccc(-c3cn[nH]c3)cc2[C@H](Nc2ncccn2)[C@@H](C)[C@@H]1C1CC1]

1-((2S,3R,4R)-6-bromo-2-cyclopropyl-3-methyl-4-(pyrimidin-2-ylamino)-3,4-dihydroquinolin-1(2H)-yl)ethanone (for a preparation see Intermediate 371, 106 mg, 0.264 mmol), tert-butyl 4-(4,4,5,5-tetramethyl-1,3,2-dioxaborolan-2-yl)-1H-pyrazole-1-carboxylate, potassium carbonate (110 mg, 0.792 mmol) and $PdCl_2P(Ph_3)_2$ (37 mg, 0.053 mmol) were combined in a mixture of 1,4-dioxane (3 mL) and water (1 mL) and heated in the microwave reactor at 120° C. for 40 min. The reaction mixture was diluted with ethyl acetate and water. The organic layer was separated, washed with water, dried ($Na_2SO_4$) and concentrated to give ~159 mg of crude yellow residue. This was purified by chromatography on $SiO_2$ (25 g) eluting with 0-10% methanol/DCM over 330 mL to give a mixture of products. Fractions containing desired product were combined to give 126 mg of crude yellow oil. This was re-purified by chromatography on $SiO_2$ (25 g) eluting with 0-100% ethyl acetate/cyclohexane over 330 mL then 100% ethyl acetate to elute the desired product to give the product (36 mg, 0.093 mmol, 35%) as a white solid.

LCMS (2 min Formic): Rt=0.75 min, [MH]$^+$=389.

Example 582: 1-((2S,3R,4R)-2-cyclopropyl-3-methyl-4-((4-methylpyrimidin-2-yl)amino)-6-(1H-pyrazol-4-yl)-3,4-dihydroquinolin-1(2H)-yl)ethanone

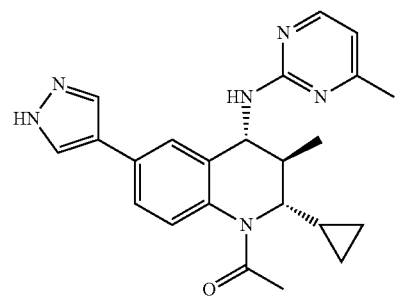 [SMILES: CC(=O)N1c2ccc(-c3cn[nH]c3)cc2[C@H](Nc2nccc(C)n2)[C@@H](C)[C@@H]1C1CC1]

The 1-((2S,3R,4R)-6-(1-benzyl-1H-pyrazol-4-yl)-2-cyclopropyl-3-methyl-4-((4-methylpyrimidin-2-yl)amino)-3, 4-dihydroquinolin-1(2H)-yl)ethanone (for a preparation see Intermediate 383, 133 mg, 0.270 mmol) was taken up in ethanol (10 mL), treated with 10% Pd/C (13 mg, 0.012 mmol) and allowed to stir under a atmosphere of hydrogen for 17 h—no reaction. The reaction was filtered through celite to remove the catalyst and the filtrate concentrated to give a colourless oil. This oil was taken up in EtOH (5 mL) and was hydrogenated using the H-cube (settings: 50° C., 20 bar, 1 mL/min flow rate) and 10% Pd/C CatCart 30 as the catalyst. The compound was cycled through the H-cube for 3 h—no reaction. The reaction was concentrated to a gum. This gum was re-dissolved in ethanol (10 mL) and treated with formic acid (1 ml, 26.1 mmol) and 10% Pd/C (13 mg, 0.012 mmol) and allowed to stir at 80° C. for 4 days. The reaction was filtered through celite to remove the catalyst and the filtrate concentrated and dried to give a yellow oil. This oil was purified using a MDAP (Formic). The appropriate fractions were summed and concentrated to give the product (13 mg, 0.032 mmol, 12%) as a white solid. LCMS (2 min Formic): Rt=0.75 min, [MH]+=403.

Example 583: 1-((2S,3R,4R)-2-cyclopropyl-6-methoxy-3-methyl-4-(pyrimidin-2-ylamino)-3,4-dihydroquinolin-1(2H)-yl)ethanone

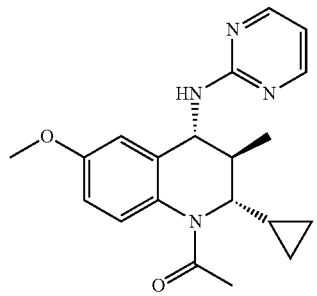 [SMILES: COc1ccc2c(c1)[C@H](Nc1ncccn1)[C@@H](C)[C@H](C1CC1)N2C(C)=O]

A mixture of 1-((2S,3R,4R)-4-amino-2-cyclopropyl-6-methoxy-3-methyl-3,4-dihydroquinolin-1(2H)-yl)ethanone (for a preparation see Intermediate 386, 122 mg, 0.445 mmol), 18-crown-6 (58.6 mg, 0.222 mmol), potassium fluoride (38.6 mg, 0.665 mmol), 2-fluoropyrimidine (48.0 mg, 0.489 mmol) and DIPEA (0.132 mL, 0.756 mmol) was suspended in anhydrous DMSO (1 mL). The mixture was stirred under nitrogen at 140° C. for 16 h. The reaction was allowed to cool to rt, diluted with water (5 mL) and extracted with EtOAc (3×5 mL). The organic layers were combined, washed with brine (5 mL) and dried over a hydrophobic frit. The solvent was evaporated in vacuo to give a brown solid. The sample was dissolved in 1:1 MeOH:DMSO 1 mL and purified by MDAP (HpH). The solvent was evaporated in vacuo to give the required product (5 mg) as a brown solid. LCMS (2 min Formic): Rt=0.86 min, [MH]+=353.

Example 584: 1-((2S,3R,4R)-2-cyclopropyl-6-hydroxy-3-methyl-4-(pyrimidin-2-ylamino)-3,4-dihydroquinolin-1(2H)-yl)ethanone

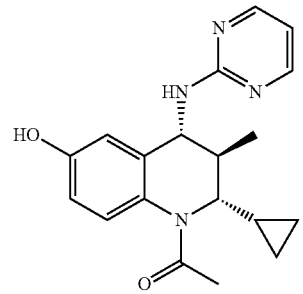

A solution of 1-((2S,3R,4R)-2-cyclopropyl-6-methoxy-3-methyl-4-(pyrimidin-2-ylamino)-3,4-dihydroquinolin-1(2H)-yl)ethanone (for a preparation see Example 583, 210.4 mg, 0.597 mmol) in dichloromethane (DCM) (5 mL) was cooled to 0° C. and put under nitrogen. Boron tribromide (1M in DCM) (0.071 mL, 0.746 mmol) was added to the mixture and the reaction left at rt for 16 h. Further boron tribromide (1M in DCM) (0.566 mL, 5.99 mmol) was added at 0° C. and the mixture left to stir at rt for 16 h. Ice and ethyl acetate (20 mL) were added and the solution was washed with water (15 mL) and sat. Na2CO3 (15 mL). The organic layer was dried through a hydrophobic frit and evaporated in vacuo to give the crude product as a brown oil. The sample was dissolved in 1:1 MeOH:DMSO 1 mL and purified by MDAP (HpH). The solvent was evaporated in vacuo to give the required product (54.3 mg) as a white solid. LCMS (2 min Formic): Rt=0.70 min, [MH]+=339.

Example 585: 1-((2S,3R,4R)-2-cyclopropyl-6-(2-hydroxyethoxy)-3-methyl-4-(pyrimidin-2-ylamino)-3,4-dihydroquinolin-1(2H)-yl)ethanone

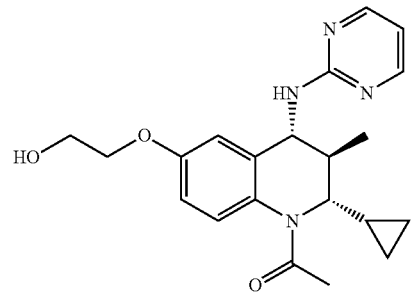 [SMILES: CC(=O)N1c2ccc(OCCO)cc2[C@H](Nc2ncccn2)[C@@H](C)[C@@H]1C1CC1]

1-((2S,3R,4R)-2-cyclopropyl-6-hydroxy-3-methyl-4-(pyrimidin-2-ylamino)-3,4-dihydroquinolin-1(2H)-yl)ethanone (for a preparation see Example 584, 20 mg, 0.059 mmol) was dissolved in N,N-dimethylformamide (DMF) (0.6 mL) and treated with 2-bromoethanol (4.54 µL, 0.064 mmol) and potassium carbonate (10 mg, 0.072 mmol). The heterogeneous mixture was stirred at 100° C. for 2.5 days. The reaction was incomplete so further 2-bromoethanol (4.54 µL, 0.064 mmol) was added and heating was continued for a further 5 h. The solvent was removed under reduced pressure. The residue was dissolved in 1:1 DMSO/MeCN and purification was undertaken using MDAP (Formic). The Example 586: 1-((2S,3R,4R)-2-cyclopropyl-3-methyl-4-(pyrimidin-2-ylamino)-3,4-dihydroquinolin-1(2H)-yl)ethanone

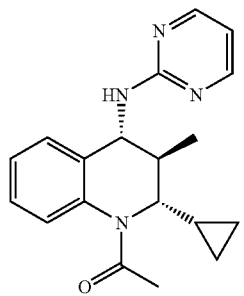 [SMILES: CC(=O)N1c2ccccc2[C@H](Nc2ncccn2)[C@@H](C)[C@@H]1C1CC1]

A solution of 1-((2S,3R,4R)-4-amino-2-cyclopropyl-3-methyl-3,4-dihydroquinolin-1(2H)-yl)ethanone (for a preparation see Intermediate 387, 100 mg, 0.409 mmol), 2-fluoropyrimidine (48.2 mg, 0.491 mmol) and DIPEA (0.143 mL, 0.819 mmol) in anhydrous dimethyl sulfoxide (DMSO) (2 mL) was heated at 140° C. for 19 h under nitrogen. The reaction mixture was diluted with EtOAc (10 mL) and washed with saturated sodium bicarbonate (2×10 mL) before being dried with anhydrous Na$_2$SO$_4$. The filtrate was evaporated in vacuo to give the crude product (141 mg) as an orange oil. The residue was loaded on a 25 g SNAP silica cartridge in DCM, purified by column chromatography, eluting with: 0-100% EtOAc in cyclohexane (10 CV). The appropriate fractions were combined and evaporated in vacuo to give the required product as a yellow oil (69 mg). The sample was dissolved in 1:1 MeOH:DMSO 1 mL and purified by MDAP (Formic). The solvent was evaporated in vacuo to give the required product (39 mg). LCMS (2 min Formic): Rt=0.85 min, [MH]$^+$=323.

Example 587: 1-((2S,3R,4R)-2-cyclopropyl-3-methyl-4-((6-methylpyridin-2-yl)amino)-3,4-dihydroquinolin-1(2H)-yl)ethanone

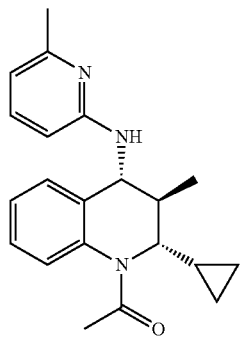 [SMILES: CC(=O)N1c2ccccc2[C@H](Nc2cccc(C)n2)[C@@H](C)[C@@H]1C1CC1]

A mixture of 1-((2S,3R,4R)-4-amino-2-cyclopropyl-3-methyl-3,4-dihydroquinolin-1(2H)-yl)ethanone (for a preparation see Intermediate 387, 0.3 g, 1.228 mmol), 2-bromo-6-methylpyridine (0.280 mL, 2.456 mmol), DavePhos (0.048 g, 0.123 mmol), Pd$_2$(dba)$_3$ (0.112 g, 0.123 mmol) and sodium tert-butoxide (0.236 g, 2.456 mmol) in 1,4-dioxane (8 mL) was heated under nitrogen at 100° C. for 2 h. The reaction was stopped after 80 mins and left over the weekend. The reaction mixture was then heated to 100° C. for 4 h. Next, further amounts of 2-bromo-6-methylpyridine (0.280 mL, 2.456 mmol), DavePhos (0.048 g, 0.123 mmol), Pd$_2$(dba)$_3$ (0.169 g, 0.184 mmol) and sodium tert-butoxide (0.307 g, 3.19 mmol) were added and the reaction was heated to 100° C., with stirring, under nitrogen for 30 h. The mixture was allowed to cool to rt and was filtered through a 10 g celite cartridge, washing with ethyl Acetate (3×20 mL). The combined filtrate (dark brown/red) was evaporated in vacuo and the residue was loaded on a 25 g silica cartridge in DCM, purified by column chromatography, eluting with: 0-50% EtOAc/DCM (10 CV). The appropriate fractions were combined and evaporated in vacuo to give the crude product as an orange residue, 140 mg. The sample was dissolved in 1:1 MeOH:DMSO (3×1 mL injections) and purified by MDAP (Formic). The appropriate fractions were combined and the solvent was evaporated in vacuo to give the required product as the formic acid salt (111 mg). The sample was loaded in methanol and purified by sulphonic acid SPE (SCX) 2 g using sequential solvents methanol, 2M ammonia/methanol. The appropriate fractions were combined and evaporated in vacuo to give the required product as the free base as a colourless oil. The oil was redissolved in MeOH and then evaporated in the blowdown unit before being dried further in the vacuum oven. The product was freeze dried to give the desired product (68 mg, 0.203 mmol, 17%). LCMS (2 min Formic): Rt=0.66 min, [MH]$^+$=336.

Example 588: 1-((2S,3R,4R)-2-cyclopropyl-6-(1H-imidazol-2-yl)-3-methyl-4-(pyrimidin-2-ylamino)-3,4-dihydroquinolin-1(2H)-yl)ethanone

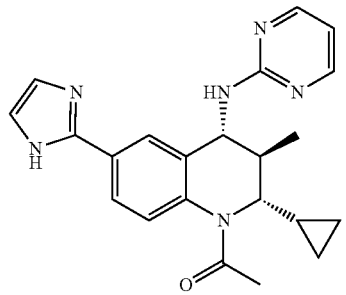 [SMILES: CC(=O)N1c2ccc(-c3ncc[nH]3)cc2[C@H](Nc2ncccn2)[C@@H](C)[C@@H]1C1CC1]

1-((2S,3R,4R)-2-cyclopropyl-3-methyl-4-(pyrimidin-2-ylamino)-6-(4,4,5,5-tetramethyl-1,3,2-dioxaborolan-2-yl)-3,4-dihydroquinolin-1(2H)-yl)ethanone (for a preparation see Intermediate 388, 51 mg, 0.114 mmol), 2-bromo-1H-imidazole (33.4 mg, 0.227 mmol), potassium carbonate (47.2 mg, 0.341 mmol) and PdCl$_2$(PPh$_3$)$_2$ (15.97 mg, 0.023 mmol) were combined in a mixture of 1,4-dioxane (2 mL) and water (0.667 mL) and heated in the microwave reactor at 120° C. for 1 h. The reaction mixture was diluted with EtOAc (25 mL) and water (25 mL). The mixture was run through a 2.5 g celite cartridge and the layers were separated. The aqueous phase was washed with EtOAc (2×25 mL). The organic extracts were dried by passing through a hydrophobic frit and the solvent evaporated in vacuo to give the crude (86 mg). Purification was undertaken by flash column chromatography. The crude material was loaded onto a 10 g silica column and eluted using a graduating solvent system of 0-15% methanol in DCM. Appropriate fractions were combined and the solvent removed in vacuo to give the product (15.5 mg) as a clear oil.

LCMS (2 min Formic): Rt=0.56 min, [MH]⁺=389.

The following examples were prepared in a similar manner to Example 588 using PdCl$_2$(PPh$_3$)$_2$ and K$_2$CO$_3$ to couple the appropriate heteroaryl halide with Intermediate 388.

DIPEA (1.052 mL, 6.02 mmol) in dichloromethane (DCM) (10 mL). The resulting solution was stirred for 1 h. The reaction mixture was evaporated in vacuo to a yellow oil. The residue was dissolved in DCM, loaded on to a 25 g silica column and eluted with cyclohexane:EtOAc (5-25%). The product containing fractions were evaporated in vacuo to a white solid (549 mg). LCMS (2 min TFA): Rt=1.12 min, [MH]⁺=379.

| Ex No. | Name | Structure | Mass (mg) | Yield (%) | [MH]⁺ | Rt (mins) (LCMS method) |
|---|---|---|---|---|---|---|
| 589 | 1-((2S,3R,4R)-2-cyclopropyl-3-methyl-6-(5-methyl-1,3,4-oxadiazol-2-yl)-4-(pyrimidin-2-ylamino)-3,4-dihydroquinolin-1(2H)-yl)ethanone | 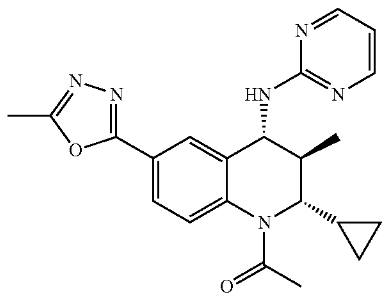 [SMILES: CC(=O)N1c2ccc(-c3nnc(C)o3)cc2[C@H](Nc2ncccn2)[C@@H](C)[C@@H]1C1CC1] | 24 | 50 | 405 | 0.78 (2 min Formic) |
| 590 | 1-((2S,3R,4R)-2-cyclopropyl-3-methyl-6-(5-methyl-1,3,4-thiadiazol-2-yl)-4-(pyrimidin-2-ylamino)-3,4-dihydroquinolin-1(2H)-yl)ethanone | 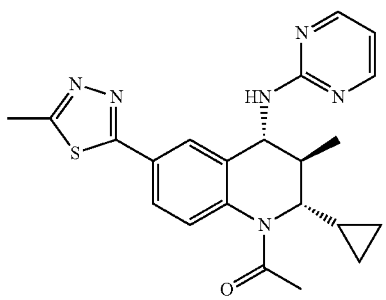 [SMILES: CC(=O)N1c2ccc(-c3nnc(C)s3)cc2[C@H](Nc2ncccn2)[C@@H](C)[C@@H]1C1CC1] | 31 | 65 | 421 | 0.82 (2 min Formic) |

Example 591: rac-((2S,3R,4R)-1-acetyl-2-cyclopropyl-4-(phenylamino)-1,2,3,4-tetrahydroquinolin-3-yl)methyl Acetate

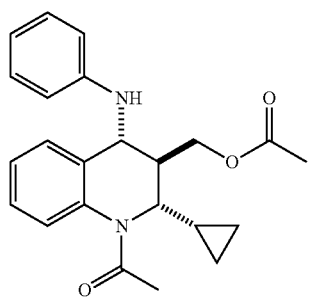 [SMILES: CC(=O)OC[C@@H]1[C@@H](Nc2ccccc2)c2ccccc2N(C(C)=O)[C@H]1C1CC1]

Acetyl chloride (0.300 mL, 4.22 mmol) was added dropwise to a solution of rac-((2S,3S,4R)-2-cyclopropyl-4-(phenylamino)-1,2,3,4-tetrahydroquinolin-3-yl)methanol (for a preparation see Intermediate 390, 591 mg, 2.008 mmol) and Example 592: rac-1-((2S,3R,4R)-2-cyclopropyl-3-(hydroxymethyl)-4-(phenylamino)-3,4-dihydroquinolin-1(2H)-yl)ethanone

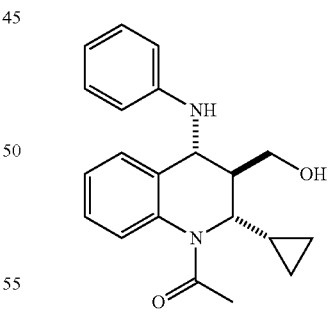

Potassium carbonate (203 mg, 1.468 mmol) was added to a solution of rac-((2S,3R,4R)-1-acetyl-2-cyclopropyl-4-(phenylamino)-1,2,3,4-tetrahydroquinolin-3-yl)methyl acetate (for a preparation see Example 591, 505 mg, 1.334 mmol) in a mixture of tetrahydrofuran (THF) (5 mL), methanol (10 mL) and water (1 mL) at 60° C. The resulting suspension was stirred for 3 h and allowed to stand over the weekend. The reaction mixture was partitioned between EtOAc and water. The aqueous layer was removed and the organic layer washed (1× brine), dried over MgSO$_4$ and evaporated in vacuo to a colourless oil. The residue was dissolved in DCM, loaded on to a 25 g silica column and eluted with cyclohexane:EtOAc (5-50%). The product containing fractions were evaporated to give the product as a white solid (203 mg). LCMS (2 min TFA): Rt=1.03 min, [MH]$^+$=337.

Example 593: rac-(2S,3R,4R)-1-acetyl-2-cyclopropyl-7-methoxy-3-methyl-4-((4-methylpyrimidin-2-yl)amino)-1,2,3,4-tetrahydroquinoline-6-carboxamide

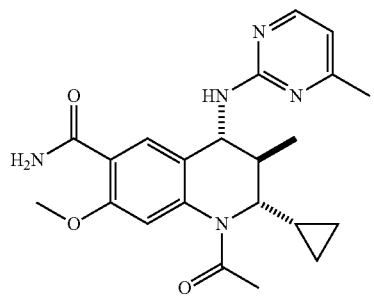 [SMILES: COc1cc2c(cc1C(N)=O)[C@H](Nc1nccc(C)n1)[C@@H](C)[C@H](C1CC1)N2C(C)=O]

To a solution of rac-(2S,3R,4R)-1-acetyl-2-cyclopropyl-7-methoxy-3-methyl-4-((4-methylpyrimidin-2-yl)amino)-1,2,3,4-tetrahydroquinoline-6-carboxylic acid (for a preparation see Intermediate 394, 82 mg, 0.200 mmol) in N,N-dimethylformamide (DMF) (1.5 mL) was added HATU (84 mg, 0.220 mmol) followed by DIPEA (0.070 ml, 0.400 mmol). The resulting reaction mixture was stirred at rt under N$_2$ for 15 min. Ammonium chloride (21.37 mg, 0.400 mmol) was then added and the reaction stirred for ~1 h. The reaction mixture was diluted to 1.8 mL and separated equally between 2 vials. The vials were purified by MDAP (HpH), the appropriate fractions were collected and concentrated in vacuo to afford the desired product as a cream glass (64 mg, 0.156 mmol, 78%).

LCMS (2 min Formic): Rt=0.67 min, [MH]$^+$=410.

Example 594: rac-(2S,3R,4R)-1-acetyl-2-cyclopropyl-7-hydroxy-3-methyl-4-((4-methylpyrimidin-2-yl)amino)-1,2,3,4-tetrahydroquinoline-6-carboxamide

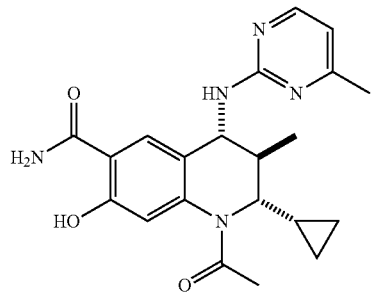 [SMILES: CC(=O)N1c2cc(O)c(C(N)=O)cc2[C@H](Nc2nccc(C)n2)[C@@H](C)[C@@H]1C1CC1]

To a solution of rac-(2S,3R,4R)-1-acetyl-2-cyclopropyl-7-methoxy-3-methyl-4-((4-methylpyrimidin-2-yl)amino)-1,2,3,4-tetrahydroquinoline-6-carboxamide (for a preparation see Example 593, 20 mg, 0.049 mmol) in dichloromethane (DCM) (1 mL) at 0° C. was added boron tribromide (1M in dichloromethane) (0.488 mL, 0.488 mmol). A suspension immediately formed. The resulting reaction mixture was stirred at rt under N$_2$ for 74 h, during which time the solvent evaporated. The reaction was diluted with DCM and methanol (0.198 mL, 4.88 mmol) and the resultant solution concentrated in vacuo. Further methanol (0.198 mL, 4.88 mmol) was added and the sample evaporated in vacuo once again. The resultant solid was taken up in DCM with a small amount of MeOH and added to a silica (10 g) column and purified by flash column purification, eluting with 0→25% (20% MeOH/DCM)/DCM. A close eluting impurity was observed, therefore the purest fractions were collected and concentrated in vacuo to afford the desired product as a white gum (6.1 mg, 0.015 mmol, 32%). LCMS (2 min Formic): Rt=0.70 min, [MH]$^+$=396.

Example 595: (2S,3R,4R)-1-acetyl-2-cyclopropyl-7-fluoro-3-methyl-4-((4-methylpyrimidin-2-yl)amino)-1,2,3,4-tetrahydroquinoline-6-carboxamide

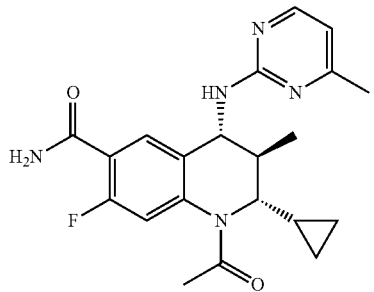 [SMILES: CC(=O)N1c2cc(F)c(C(N)=O)cc2[C@H](Nc2nccc(C)n2)[C@@H](C)[C@@H]1C1CC1]

To a solution of (2S,3R,4R)-1-acetyl-2-cyclopropyl-7-fluoro-3-methyl-4-((4-methylpyrimidin-2-yl)amino)-1,2,3,4-tetrahydroquinoline-6-carboxylic acid (for a preparation see Intermediate 399, 19.7 mg, 0.049 mmol) in N,N-Dimethylformamide (DMF) (0.7 ml) was added HATU (28.2 mg, 0.074 mmol) followed by DIPEA (0.026 ml, 0.148 mmol). The resulting reaction mixture was stirred at r.t. under N2 for 15 min. ammonium chloride (7.93 mg, 0.148 mmol) was then added and the reaction stirred for ~1 h. The reaction mixture was purified directly by MDAP (HpH) to afford a colourless oil (15.2 mg, 0.038 mmol, 77%). LCMS (2 min Formic): Rt=0.75 min, [MH]$^+$=399.

Examples 596a & 596b: 1-((2R,3S,4S)-2-ethyl-3-methyl-4-((6-methylpyridin-2-yl)amino)-3,4-dihydroquinolin-1(2H)-yl)ethanone (596a) & 1-((2S,3R,4R)-2-ethyl-3-methyl-4-((6-methylpyridin-2-yl)amino)-3,4-dihydroquinolin-1(2H)-yl)ethanone (596b)

596a

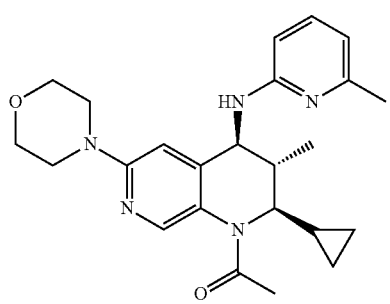

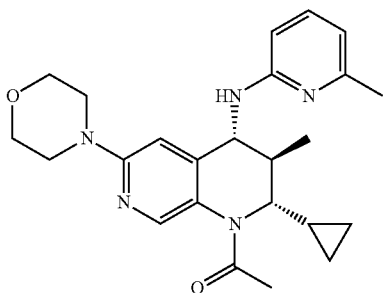

rac-1-((2S,3R,4R)-2-ethyl-3-methyl-4-((6-methylpyridin-2-yl)amino)-3,4-dihydroquinolin-1(2H)-yl)ethanone (for a preparation see Intermediate 407, ~18 mg) was submitted for chiral separation into its enantiomers (A and B) using a 250×20 mm Chiralpak AS column eluting with 20% ethanol in 80% heptane at a flow rate of 20 mL/min. Peak 1/Enantiomer A fractions were collected between 4 and 6 min. Peak 2/Enantiomer B fractions were collected between 6 and 10 min. Fraction solutions were combined then evaporated to dryness to give Enantiomer A (11 mg) and Enantiomer B (11 mg) as white solids.

Enantiomer A, Example 596a

Analytical Chiral HPLC using a 250×4.6 mm Chiralpak AS column eluting with 20% ethanol in heptane at 1 mL/min—Rt=4.6 min. 97% ee by UV.

Enantiomer B, Example 596b

Analytical Chiral HPLC using a 250×4.6 mm Chiralpak IC column eluting with 20% ethanol in heptane at 1 mL/min—Rt=7.6 min. >99% ee by UV.

Example 597: rac-(2S,3R,4R)-1-acetyl-2-cyclopropyl-3-methyl-4-(pyrimidin-2-ylamino)-1,2,3,4-tetrahydro-1,7-naphthyridine-6-carboxamide

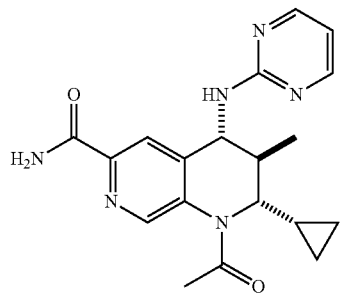

HATU (118 mg, 0.310 mmol), DIPEA (0.226 mL, 1.293 mmol) and ammonium chloride (41.5 mg, 0.776 mmol) were added to a solution of rac-(2S,3R,4R)-1-acetyl-2-cyclopropyl-3-methyl-4-(pyrimidin-2-ylamino)-1,2,3,4-tetrahydro-1,7-naphthyridine-6-carboxylic acid (for a preparation see Intermediate 413, 95 mg, 0.259 mmol) in N,N-dimethylformamide (DMF) (5 mL). The reaction mixture was stirred at rt for 3 h. The reaction mixture was concentrated under reduced pressure to give a green a residue (285 mg). The residue was loaded on a 25 g silica cartridge, purified by column chromatography, eluting with 0-8% NH$_3$(2M in MeOH) in DCM (20 CV). The appropriate fractions were combined and concentrated under reduced pressure to give the crude product (128 mg). The residue was taken up in 1:1 MeOH:DMSO (2×1 mL) and purified by MDAP (HpH). The solvent was evaporated in vacuo to give the required product (55 mg) as a yellow-white solid.

LCMS (2 min HpH): Rt=0.71 min, [MH]$^+$=367.

Example 598a & 598b: rac-1-((2S,3R,4R)-2-cyclopropyl-3-methyl-4-((4-methylpyrimidin-2-yl)amino)-3,4-dihydro-1,6-naphthyridin-1(2H)-yl)ethanone (598a) & rac-1-((2,3,4 unknown)-2-cyclopropyl-3-methyl-4-((4-methylpyrimidin-2-yl)amino)-3,4-dihydro-1,6-naphthyridin-1(2H)-yl)ethanone (598b)

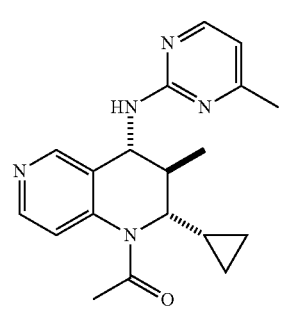

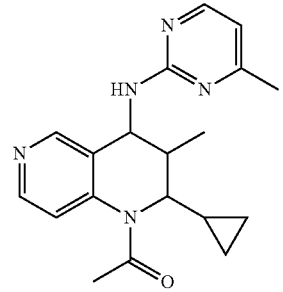

The rac-(2S,3R,4R)-1-acetyl-2-cyclopropyl-3-methyl-4-((4-methylpyrimidin-2-yl)amino)-1,2,3,4-tetrahydro-1,6-naphthyridin-5-yl trifluoromethanesulfonate compound with (2S,3R,4R)-1-acetyl-2-cyclopropyl-3-methyl-4-((4-methylpyrimidin-2-yl)amino)-1,2,3,4-tetrahydro-1,6-naphthyridin-7-yl trifluoromethanesulfonate (1:1) (for a preparation see Intermediate 419, 130 mg, 0.134 mmol) was taken up in N,N-dimethylformamide (DMF) (5 mL) and was treated with PdCl$_2$(dppf) (19.59 mg, 0.027 mmol), triethylamine (0.075 mL, 0.536 mmol) and formic acid (0.021 mL, 0.536 mmol) the reaction was allowed to stir at 60° C. under nitrogen for 16 h. The reaction was treated with further PdCl$_2$(dppf) (19.59 mg, 0.027 mmol) and formic acid (0.021 mL, 0.536 mmol) and allowed to stir at 60° C. under nitrogen for 3 days. The reaction was allowed to cool to rt and was applied directly to a pre-conditioned (MeOH) SCX SPE (5 g) elute: MeOH and 2M NH$_3$/MeOH the ammonia fraction was concentrated to a brown oil, this oil was purified using a MDAP (HpH). Two main peaks were collected; the appropriate fractions were summed and concentrated to give what was believed to be the desired product (Example 598a, 1$^{st}$ eluting isomer) (11 mg) & a second product (Example 598b 2$^{nd}$ eluting isomer) which had an unknown but alternative relative stereochemistry (16 mg).

Isomer 1: LCMS (2 min Formic): Rt=0.60 min, [MH]$^+$=338.

Isomer 2: LCMS (2 min Formic): Rt=0.62 min, [MH]$^+$=338.

Example 599: rac-1-((2S,3S,4R)-2-cyclopropyl-3-methyl-4-(phenylamino)-3,4-dihydroquinolin-1(2H)-yl)ethanone

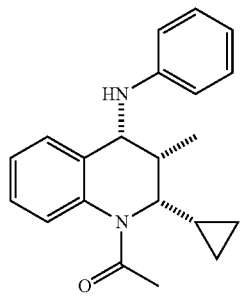

Bromobenzene (0.037 mL, 0.356 mmol) and sodium tert-butoxide (52.5 mg, 0.546 mmol) were added to a solution of rac-1-((2S,3S,4R)-4-amino-2-cyclopropyl-3-methyl-3,4-dihydroquinolin-1(2H)-yl)ethanone (for a preparation see Intermediate 422, 58 mg, 0.237 mmol) in toluene (3 mL). The resulting solution was vacuum degassed under N$_2$, Pd(QPhos)$_2$ (18.13 mg, 0.012 mmol) added, the reaction vacuum degassed under N$_2$ and heated to 50° C. under N$_2$ for 4 h. The reaction was cooled to rt, loaded directly on to a 10 g silica column and eluted with cyclohexane:EtOAc (0-25%). The product containing fractions were evaporated in vacuo to a pale brown solid (48 mg).

LCMS (2 min TFA): Rt=1.19 min, [MH]$^+$=321.

Biological Test Methods

The compounds of formula (I) may be tested in one or more of the following assays:

Time Resolved Fluorescence Resonance Energy Transfer (TR-FRET) Assay

Binding was assessed using a time resolved fluorescent resonance energy transfer binding assay.

This utilises a 6 His purification tag at the N-terminal of the proteins as an epitope for an anti-6 His antibody labeled with Europium chelate (PerkinElmer AD0111) allowing binding of the Europium to the proteins which acts as the donor fluorophore. A small molecule, high affinity binder of the bromodomains BRD2, BRD3, BRD4 and BRDT has been labeled with Alexa Fluor647 (Reference Compound X) and this acts as the acceptor in the FRET pair.

Reference Compound X: 4-((Z)-3-(6-((5-(2-((4S)-6-(4-chlorophenyl)-8-methoxy-1-methyl-4H-benzo[f][1,2,4]triazolo[4,3-a][1,4]diazepin-4-yl)acetamido)pentyl)amino)-6-oxohexyl)-2-((2E,4E)-5-(3,3-dimethyl-5-sulfo-1-(4-sulfobutyl)-3H-indol-1-ium-2-yl)penta-2,4-dien-1-ylidene)-3-methyl-5-sulfoindolin-1-yl)butane-1-sulphonate)

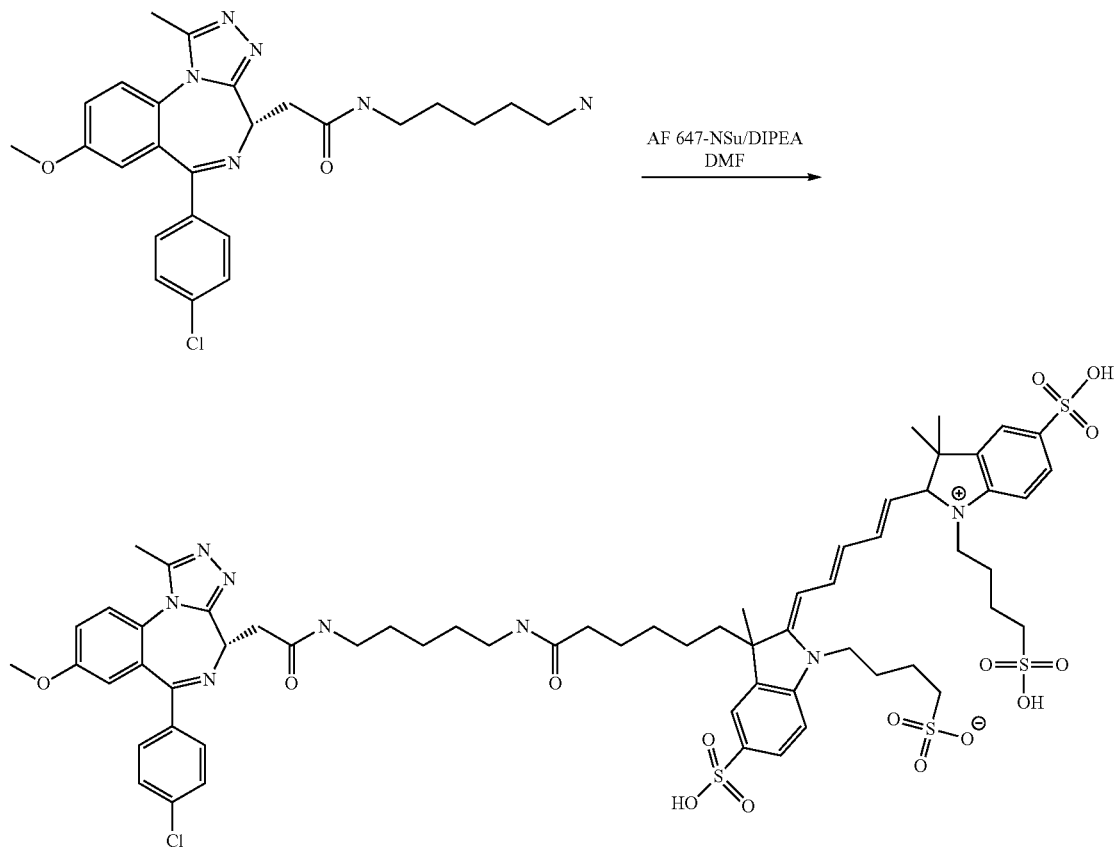

To a solution of N-(5-aminopentyl)-2-((4S)-6-(4-chlorophenyl)-8-methoxy-1-methyl-4H-benzo[f][1,2,4]triazolo[4,3-a][1,4]diazepin-4-yl)acetamide (for a preparation see Reference Compound J, WO2011/054848A1, 1.7 mg, 3.53 μmol) in DMF (100 μl) was added a solution of Alex-aFluor647-ONSu (2.16 mg, 1.966 μmol) also in DMF (100 μl). The mixture was basified with DIPEA (1 μl, 5.73 μmol) and agitated overnight on a vortex mixer.

The reaction mixture was evaporated to dryness. The solid was dissolved in acetonitrile/water/acetic acid (5/4/1, <1 ml) filtered and was applied to a Phenomenex Jupiter C18 preparative column and eluted with the following gradient (A=0.1% trifluoroacetic acid in water, B=0.1% TFA/90% acetonitrile/10% water): Flow rate=10 ml/min., AU=20/10 (214 nm):

5-35%, t=0 min: B=5%; t=10 min: B=5%; t=100 min: B=35%; t=115 min: B=100% (Sep. grad: 0.33%/min)

The major component was eluted over the range 26-28% B but appeared to be composed of two peaks. The middle fraction (F1.26) which should contain "both" components was analysed by analytical HPLC (Spherisorb ODS2, 1 to 35% over 60 min): single component eluting at 28% B. Fractions F1.25/26&27 were combined and evaporated to dryness. Transferred with DMF, evaporated to dryness, triturated with dry ether and the blue solid dried overnight at <0.2 mbar: 1.54 mg.

Analytical HPLC (Sphersisorb ODS2, 1 to 35% B over 60 min): MSM10520-1: $[M+H]^+$ (obs): 661.8/– corresponding with M-29. This equates to $[(M+2H)/2]^+$ for a calculated mass of 1320.984 which is M-29. This is a standard occurrence with the Alexa Fluor 647 dye and represents a theoretical loss of two methylene groups under the conditions of the mass spectrometer.

Assay Principle:

In the absence of a competing compound, excitation of the Europium causes the donor to emit at λ618 nm which excites the Alexa labelled bromodomain binding compound leading to an increased energy transfer that is measurable at λ647 nM. In the presence of a sufficient concentration of a compound that can bind these proteins, the interaction is disrupted leading to a quantifiable drop in fluorescent resonance energy transfer.

The binding of the compounds of formula (I) to Bromodomains BRD2, BRD3, BRD4 and BRDT was assessed using mutated proteins to detect differential binding to either Binding Domain 1 (BD1) or Binding Domain 2 (BD2) on the bromodomain. These single residue mutations in the acetyl lysine binding pocket greatly lower the affinity of the fluoroligand (Reference Compound X) for the mutated domain (>1000 fold selective for the non-mutated domain). Therefore in the final assay conditions, binding of the fluoroligand to the mutated domain cannot be detected and subsequently the assay is suitable to determine the binding of compounds to the single non-mutated bromodomain.

Protein Production:

Recombinant Human Bromodomains [(BRD2 (1-473) (Y113A) and (Y386A), BRD3 (1-435) (Y73A) and (Y348A) BRD4 (1-477) (Y97A) and (Y390A) and BRDT (1-397) (Y66A) and (Y309A)] were expressed in *E. coli* cells (in pET15b vector for BRD2/3/4 and in pET28a vector for BRDT) with a 6-His tag at the N-terminal. The His-tagged Bromodomain pellet was resuspended in 50 mM HEPES (pH7.5), 300 mM NaCl, 10 mM imidazole & 1 μl/ml protease inhibitor cocktail and extracted from the *E. coli* cells using sonication and purified using a nickel sepharose high performance column, the proteins were washed and then eluted with a linear gradient of 0-500 mM imidazole with buffer 50 mM HEPES (pH7.5), 150 mM NaCl, 500 mM imidazole, over 20 column volumes. Final purification was completed by Superdex 200 prep grade size exclusion column. Purified protein was stored at −80° C. in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3, 4 and T, BD1+BD2 Mutant Assays:

All assay components were dissolved in buffer composition of 50 mM HEPES pH7.4, 50 mM NaCl, 5% Glycerol, 1 mM DTT and 1 mM CHAPS. The final concentration of bromodomain proteins were 10 nM and the Alexa Fluor647 ligand was at Kd. These components were premixed and 5 μl of this reaction mixture was added to all wells containing 50 nl of various concentrations of test compound or DMSO vehicle (0.5% DMSO final) in Greiner 384 well black low volume microtitre plates and incubated in dark for 30 minutes at rt. 5 μl of detection mixture containing 1.5 nM final concentration anti-6His Europium chelate was added to all wells and a further dark incubation of at least 30 minutes was performed. Plates were then read on the Envision platereader, (λex=317 nm, donor λem=615 nm; acceptor λem=665 nm; Dichroic LANCE dual). Time resolved fluorescent intensity measurements were made at both emission wavelengths and the ratio of acceptor/donor was calculated and used for data analysis. All data was normalized to the mean of 16 high (inhibitor control—Example 11 of WO 2011/054846A1) and 16 low (DMSO) control wells on each plate. A four parameter curve fit of the following form was then applied:

$$y=a+((b-a)/(1+(10\textasciicircum x/10\textasciicircum c)\textasciicircum d)$$

Where 'a' is the minimum, 'b' is the Hill slope, 'c' is the $pIC_{50}$ and 'd' is the maximum.

All compounds (Examples 1-599), with the exception of Examples 122, 135 and 137, were each tested in the BRD4 BD1 and the BRD4 BD2 TR-FRET assays described above.

All tested compounds were found to have a $pIC_{50} \geq 4.0$ in at least one assay.

Examples 23, 25b, 27b, 29b, 48, 49, 50, 53, 54, 65, 67, 68, 71a, 91b, 102b, 107-113, 114b, 127, 138b, 146b, 147a, 183, 187, 188, 189b, 210, 211, 218, 220, 221, 227, 228, 239b, 298, 316, 332, 348, 387, 391, 397, 408, 422, 441, 503, 517, 519, 522, 531, 532, 533, 551a, 591, 592, 593, 596b, and 598b were found to have a $pIC_{50} \geq 4.0$ and <6.0 in the BRD4 BD2 assay.

All other tested compounds were found to have a $pIC_{50}$>6.0 in the BRD4 BD2 assay.

Examples 1-9, 12, 13, 15, 16, 20, 22, 25a, 27a, 29a, 30, 32, 57-60, 62, 69, 70, 71b, 72, 74, 77, 80, 81, 85, 87, 91a, 92, 94, 97-99, 115, 119, 124, 134, 136a, 138a, 139, 141, 143, 146a, 147b, 150, 161, 166-169, 177, 181, 189a, 192, 197, 214, 230, 231, 235, 237, 239a, 240, 243, 248, 249, 252-254, 256, 261, 262, 265-267, 269-274, 279, 283, 285, 291, 300-304, 306-311, 314, 318, 320-323, 331, 337-341, 350, 352-357, 359, 360, 362-365, 367-375, 378, 379, 381-384, 390, 392, 394-396, 399, 400, 403, 407, 411, 413, 418, 424-426, 430, 433, 436-440, 443-448, 451b, 452-467, 469, 471, 473-476, 479, 480, 484, 488, 489, 492, 493, 495-498, 501, 504, 506, 509, 518, 523, 527, 528, 540-542, 545-548, 555, 557, 559-566, 571, 575-578, 581, 582, 588 and 590 were found to have a $pIC_{50}$ 7.0 in the BRD4 BD2 assay.

Calculation of Selectivity for BRD4 BD2 Over BRD4 BD1

Selectivity for BRD4 BD2 over BRD4 BD1 was calculated as follows:

Selectivity=BRD4BD2pIC$_{50}$–BRD4BD1pIC$_{50}$ pIC$_{50}$ values are expressed as log$_{10}$ units.

With the exception of Examples 23, 24, 25b, 27b, 29b, 71a, 83, 91b, 102b, 112, 114b, 127, 138b, 140, 142, 143, 147a, 154, 166, 167, 169, 173, 174, 180, 183, 189b, 200, 202, 213, 217, 221, 230, 232, 233, 236, 237, 239b, 242, 332, 348, 397, 404, 412, 415, 422, 430, 440, 442, 460, 462, 466, 517, 532, 533, 541, 542, 544, 548, 551a, 552, 554, 591, 596b and 598b) all tested compounds were found to have selectivity for BRD4 BD1 over BRD4 BD2 of ≥1 log unit in at least one of the TR-FRET assays described above, hence are at least 10 fold selective for BRD4 BD2 over BRD4 BD1

Examples 3, 25a, 26, 27a, 28, 29a, 30-37, 55-57, 61, 63, 64, 66, 85-90, 91a, 92-96, 102a, 116, 117, 119, 124, 133, 136a, 146a, 152, 158, 161, 162, 164, 189a, 191, 192, 204, 207, 223, 224, 235, 238, 243, 245, 248-251-263, 279, 280, 281, 286, 287, 289, 290, 296, 297, 301-309, 312, 315, 318-323, 326, 337, 339, 340, 350-353, 357-360, 363, 364, 367, 368a, 368b, 371, 374, 375, 378, 382, 390, 392, 393, 416, 419, 421, 424-426, 432, 438, 480, 481, 492-496, 499, 512, 513, 516, 520, 523, 524, 539, 586, and 587 were found to have selectivity for BRD4 BD1 over BRD4 BD2 of ≥2 log unit in at least one of the TR-FRET assays described above, hence are at least 100 fold selective for BRD4 BD2 over BRD4 BD1.

The invention claimed is:

1. A compound of formula (I)

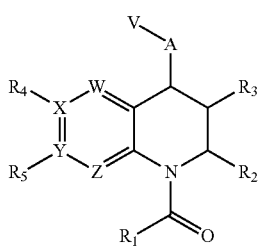

(I)

or a pharmaceutically acceptable salt thereof
wherein:
$R_1$ is $C_{1-4}$alkyl;
$R_2$ is methyl, ethyl or cyclopropyl;
$R_3$ is $C_{1-4}$alkyl;
$R_4$ when present is hydroxy, halo, cyano, —CO$_2$H, —CONH$_2$, —OSO$_2$CF$_3$, —C(O)N(R$_8$)C$_{1-4}$alkyleneOH, —C(O)N(R$_8$)C$_{1-4}$alkyleneOCH$_3$, —C(O)N(R$_8$)C$_{1-4}$alkyleneNR$_6$R$_7$, —C(O)N(R$_8$)C$_{1-4}$alkyleneSO$_2$CH$_3$, —C(O)N(R$_8$)C$_{1-4}$alkyleneCN, —C(O)NHOH, —C(O)NHCH(CH$_2$OH)$_2$ or —OCH$_2$CH$_2$OH;
$R_5$ when present is H, halo, hydroxy or $C_{1-6}$alkoxy;
A is —NH— or —O—;
V is pyrimidinyl which may be optionally substituted by 1 or 2 substituents independently selected from $C_{1-6}$alkyl, fluorine, chlorine, —OCH$_3$, —OCH(CH$_3$)$_2$, hydroxy, cyclopropyl, cyano, —CH$_2$NH$_2$, —C(O)NHCH$_3$, —CO$_2$CH$_3$, piperazinyl and morpholinyl;
$R_6$, $R_7$ and $R_8$ are each independently selected from H and $C_{1-4}$alkyl;
W is CH or N;
X is C or N;
Y is C or N; and
Z is CH or N;
subject to the proviso that no more than 2 of W, X, Y and Z are N.

2. The compound according to claim 1 which is a racemic mixture of formula (Ia)

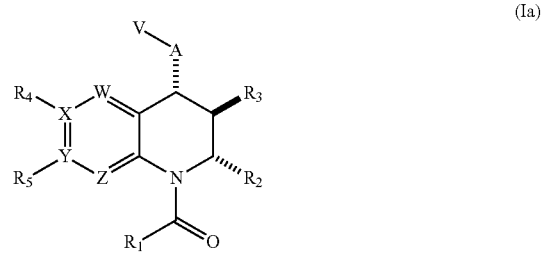

(Ia)

or a pharmaceutically acceptable salt thereof.

3. The compound or a salt thereof according to claim 2, which is an enantiomer of formula (Iaa)

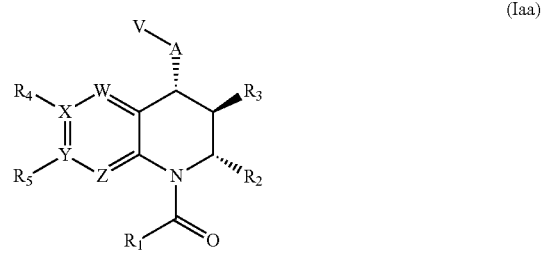

(Iaa)

or a pharmaceutically acceptable salt thereof.

4. The compound or a pharmaceutically acceptable salt thereof according to claim 3 wherein $R_1$ is methyl.

5. The compound or a pharmaceutically acceptable salt thereof according to claim 3 wherein $R_2$ is cyclopropyl.

6. The compound or a pharmaceutically acceptable salt thereof according to claim 3 wherein $R_3$ is methyl.

7. The compound or a pharmaceutically acceptable salt thereof according to claim 3 wherein $R_4$ is hydroxy, fluoro, cyano, —CO$_2$H, —CONH$_2$, —OSO$_2$CF$_3$, —C(O)NHCH$_2$CH$_2$OH, —C(O)NHCH$_2$C(CH$_3$)OH, —C(O)NHCH$_2$CH$_2$OCH$_3$, —C(O)NHCH$_2$CH$_2$NHCH$_3$, —C(O)NHCH$_2$CH$_2$SO$_2$CH$_3$, or —C(O)NHCH$_2$CN.

8. The compound or a pharmaceutically acceptable salt thereof according to claim 7 wherein $R_4$ is —CONH$_2$.

9. The compound or a pharmaceutically acceptable salt thereof according to claim 3 wherein $R_4$ is selected from:
(ii) —C(O)N(R$_8$)C$_{1-4}$alkyleneOH;
(iii) —C(O)N(R$_8$)C$_{1-4}$alkyleneOCH$_3$;
(iv) —C(O)NHCH(CH$_2$OH)$_2$;
(v) —C(O)N(R$_8$)C$_{1-4}$alkyleneNR$_6$R$_7$;
(vi) —C(O)N(R$_8$)C$_{1-4}$alkyleneSO$_2$CH$_3$; and
(vii) —C(O)N(R$_8$)C$_{1-4}$alkylene(CN).

10. The compound or a pharmaceutically acceptable salt thereof according to claim 3 wherein $R_5$ is H.

11. The compound or a pharmaceutically acceptable salt thereof according to claim 3 wherein A is —NH—.

12. The compound or a pharmaceutically acceptable salt thereof according to claim 3 wherein V is pyrimidinyl optionally substituted by 1 or 2 $C_{1-6}$alkyl groups.

13. The compound or a pharmaceutically acceptable salt thereof according to claim 3 wherein W is CH; X is C; Y is C; and Z is CH.

14. A pharmaceutical composition which comprises the compound or a pharmaceutically acceptable salt thereof as defined in claim 3 and one or more pharmaceutically acceptable carriers, diluents or excipients.

15. The compound or a pharmaceutically acceptable salt thereof according to claim 3 wherein V is

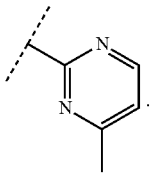

16. The compound or a pharmaceutically acceptable salt thereof according to claim 1 which is selected from:

(2S,3R,4R)-1-Acetyl-2-cyclopropyl-3-methyl-4-(pyrimidin-2-ylamino)-1,2,3,4-tetrahydroquinoline-6-carbonitrile;

(2S,3R,4R)-1-acetyl-2-cyclopropyl-3-methyl-4-(pyrimidin-2-ylamino)-1,2,3,4-tetrahydroquinoline-6-carboxamide;

(2S,3R,4R)-1-acetyl-2-cyclopropyl-N-(2-methoxyethyl)-3-methyl-4-((4-methylpyrimidin-2-yl)amino)-1,2,3,4-tetrahydroquinoline-6-carboxamide;

(2S,3R,4R)-1-acetyl-2-cyclopropyl-N-(2-hydroxyethyl)-3-methyl-4-((4-methylpyrimidin-2-yl)amino)-1,2,3,4-tetrahydroquinoline-6-carboxamide;

(2S,3R,4R)-1-acetyl-2-cyclopropyl-N-(2-methoxyethyl)-3-methyl-4-(pyrimidin-2-ylamino)-1,2,3,4-tetrahydroquinoline-6-carboxamide;

(2S,3R,4R)-1-acetyl-2-cyclopropyl-N-(2-hydroxypropyl)-3-methyl-4-(pyrimidin-2-ylamino)-1,2,3,4-tetrahydroquinoline-6-carboxamide; and (2S,3R,4R)-1-acetyl-2-cyclopropyl-3-methyl-4-((4-methylpyrimidin-2-yl)amino)-1,2,3,4-tetrahydroquinoline-6-carboxylic acid.

* * * * *